US012655106B2

(12) United States Patent
Wagner et al.

(10) Patent No.: US 12,655,106 B2
(45) Date of Patent: Jun. 16, 2026

(54) HDAC6 INHIBITORS AND USES THEREOF

(71) Applicant: Eikonizo Therapeutics, Inc., Cambridge, MA (US)

(72) Inventors: Florence Fevrier Wagner, Ashland, MA (US); Dean Hickman, Belmont, MA (US)

(73) Assignee: Eikonizo Therapeutics, Inc., Cambridge, MA (US)

( * ) Notice: Subject to any disclaimer, the term of this patent is extended or adjusted under 35 U.S.C. 154(b) by 489 days.

(21) Appl. No.: 18/275,496

(22) PCT Filed: Feb. 3, 2022

(86) PCT No.: PCT/US2022/015129
§ 371 (c)(1),
(2) Date: Aug. 2, 2023

(87) PCT Pub. No.: WO2022/169985
PCT Pub. Date: Aug. 11, 2022

(65) Prior Publication Data

US 2024/0174616 A1 May 30, 2024

Related U.S. Application Data

(60) Provisional application No. 63/145,379, filed on Feb. 3, 2021.

(51) Int. Cl.

| | |
|---|---|
| ***C07D 217/26*** | (2006.01) |
| ***C07D 209/54*** | (2006.01) |
| ***C07D 401/04*** | (2006.01) |
| ***C07D 405/04*** | (2006.01) |
| ***C07D 405/06*** | (2006.01) |
| ***C07D 409/04*** | (2006.01) |
| ***C07D 471/18*** | (2006.01) |
| ***C07D 487/08*** | (2006.01) |
| ***C07D 491/052*** | (2006.01) |
| ***C07D 493/08*** | (2006.01) |
| ***C07D 498/18*** | (2006.01) |

(52) U.S. Cl.
CPC ......... *C07D 217/26* (2013.01); *C07D 209/54* (2013.01); *C07D 401/04* (2013.01); *C07D 405/04* (2013.01); *C07D 405/06* (2013.01); *C07D 409/04* (2013.01); *C07D 471/18* (2013.01); *C07D 487/08* (2013.01); *C07D 491/052* (2013.01); *C07D 493/08* (2013.01); *C07D 498/18* (2013.01)

(58) Field of Classification Search
None
See application file for complete search history.

(56) References Cited

U.S. PATENT DOCUMENTS

| | | | |
|---|---|---|---|
| 4,205,085 | A | 5/1980 | Shepherd |
| 5,231,097 | A | 7/1993 | Klausener et al. |
| 5,272,158 | A | 12/1993 | Hartman et al. |
| 5,686,018 | A | 11/1997 | Demus et al. |
| 5,728,844 | A | 3/1998 | Muller et al. |
| 5,728,845 | A | 3/1998 | Muller et al. |
| 8,778,931 | B2 | 7/2014 | Gould |
| 9,096,518 | B2 | 8/2015 | Blackburn et al. |
| 9,145,405 | B2 | 9/2015 | Luo et al. |
| 9,650,379 | B2 | 5/2017 | Lee et al. |
| 10,357,493 | B2 | 7/2019 | Yates |
| 10,774,179 | B2 | 9/2020 | Kember et al. |
| 2005/0165015 | A1 | 7/2005 | Ncube et al. |
| 2006/0052599 | A1 | 3/2006 | Ishibashi et al. |
| 2006/0142321 | A1 | 6/2006 | Jover et al. |
| 2006/0142332 | A1 | 6/2006 | Torrens Jover et al. |
| 2008/0214603 | A1 | 9/2008 | Torrens Jover et al. |
| 2009/0036480 | A1 | 2/2009 | Torrens Jover et al. |
| 2009/0074717 | A1 | 3/2009 | Leivers et al. |
| 2009/0197880 | A1 | 8/2009 | Leivers et al. |
| 2009/0247757 | A1 | 10/2009 | Li et al. |
| 2010/0130499 | A1 | 5/2010 | Tafesse |
| 2011/0039827 | A1 | 2/2011 | Blackburn et al. |
| 2011/0212969 | A1 | 9/2011 | Blackburn et al. |
| 2011/0251184 | A1 | 10/2011 | Blackburn et al. |
| 2011/0288117 | A1 | 11/2011 | Gould et al. |
| 2012/0040953 | A1 | 2/2012 | Barba et al. |
| 2012/0053201 | A1 | 3/2012 | Blackburn et al. |
| 2012/0094997 | A1 | 4/2012 | England et al. |
| 2012/0121502 | A1 | 5/2012 | van Duzer et al. |

(Continued)

FOREIGN PATENT DOCUMENTS

| | | | |
|---|---|---|---|
| CN | 105884767 | A | 8/2016 |
| CN | 108976223 | A | 12/2018 |

(Continued)

OTHER PUBLICATIONS

Partial Supplementary European Search Report mailed Jul. 6, 2023 for European Application No. 20847655.6.
Extended European Search Report mailed Oct. 10, 2023 for European Application No. 20847655.6.
Invitation to Pay Additional Fees mailed Sep. 24, 2020 for Application No. PCT/US2020/044148.
International Search Report and Written Opinion mailed Feb. 16, 2021 for Application No. PCT/US2020/044148.
International Preliminary Report on Patentability mailed Feb. 10, 2022 for Application No. PCT/US2020/044148.
International Search Report and Written Opinion mailed May 10, 2018 for Application No. PCT/US2018/021696.

(Continued)

*Primary Examiner* — Samantha L Shterengarts
(74) *Attorney, Agent, or Firm* — Wolf, Greenfield & Sacks, P.C.

(57) ABSTRACT

Provided herein are compounds that selectively inhibit HDAC6, a protein whose activity is associated with a variety of diseases (e.g., cancer, neurological disorders). Also provided are pharmaceutical compositions and kits comprising the compounds, and methods of treating HDAC6-related diseases and disorders (e.g., Alzheimer's disease, cancer) with the compounds in a subject, by administering the compounds and/or compositions described herein.

20 Claims, 25 Drawing Sheets

(56) References Cited

U.S. PATENT DOCUMENTS

| | | | |
|---|---|---|---|
| 2012/0202834 | A1 | 8/2012 | Aspnes et al. |
| 2014/0275093 | A1 | 9/2014 | Blackburn et al. |
| 2014/0329825 | A1 | 11/2014 | Hebach et al. |
| 2015/0197497 | A1 | 7/2015 | Abeywickrama et al. |
| 2015/0359794 | A1 | 12/2015 | Benz et al. |
| 2016/0039789 | A1 | 2/2016 | England et al. |
| 2017/0096405 | A1 | 4/2017 | Song et al. |
| 2017/0183325 | A1 | 6/2017 | Chen et al. |
| 2017/0313698 | A1 | 11/2017 | Shuttleworth et al. |
| 2017/0349540 | A1 | 12/2017 | Hooker et al. |
| 2018/0215726 | A1 | 8/2018 | Holson et al. |
| 2018/0256572 | A1 | 9/2018 | Yates |
| 2019/0077786 | A1 | 3/2019 | Ueng et al. |
| 2020/0171028 | A1 | 6/2020 | Yates |
| 2021/0253555 | A1 | 8/2021 | Zheng et al. |
| 2022/0088018 | A1 | 3/2022 | Yates |
| 2022/0251043 | A1 | 8/2022 | Pan et al. |
| 2022/0281814 | A1 | 9/2022 | Wagner et al. |

FOREIGN PATENT DOCUMENTS

| | | | |
|---|---|---|---|
| CN | 109651357 | A | 4/2019 |
| CN | 110950860 | A | 4/2020 |
| CN | 112794860 | A | 5/2021 |
| DE | 3929233 | A1 | 3/1991 |
| DE | 4029466 | A1 | 3/1991 |
| DE | 540334 | A1 | 5/1993 |
| DE | 4307243 | A1 | 10/1993 |
| DE | 10312963 | A1 | 10/2004 |
| EP | 625513 | A1 | 11/1994 |
| EP | 2624832 | B1 | 9/2017 |
| JP | S58-170780 | A | 10/1983 |
| JP | H04-272989 | A | 9/1992 |
| JP | H07-206829 | A | 8/1995 |
| JP | H10-251255 | A | 9/1998 |
| JP | 2002-305083 | A | 10/2002 |
| JP | 2011-8205 | A | 1/2011 |
| JP | 2011-148714 | A | 8/2011 |
| JP | 2013-542994 | A | 11/2013 |
| JP | 2017-190296 | A | 10/2017 |
| WO | WO 1995/11228 | A1 | 4/1995 |
| WO | WO 1997/040017 | A2 | 10/1997 |
| WO | WO 1998/45268 | A1 | 10/1998 |
| WO | WO 1999/019419 | A1 | 4/1999 |
| WO | WO 2000/015637 | A1 | 3/2000 |
| WO | WO 2000/068230 | A1 | 11/2000 |
| WO | WO 2001/072712 | A1 | 10/2001 |
| WO | WO 2001/085695 | A1 | 11/2001 |
| WO | WO 2002/002530 | A1 | 1/2002 |
| WO | WO 2002/026696 | A1 | 4/2002 |
| WO | WO 2002/026703 | A1 | 4/2002 |
| WO | WO 2002/030879 | A2 | 4/2002 |
| WO | WO 2002/098426 | A1 | 12/2002 |
| WO | WO 2003/024448 | A2 | 3/2003 |
| WO | WO 2003/041641 | A2 | 5/2003 |
| WO | WO 2003/074038 | A1 | 9/2003 |
| WO | WO 2003/082288 | A1 | 10/2003 |
| WO | WO 2004/065354 | A1 | 8/2004 |
| WO | WO 2004/069823 | A1 | 8/2004 |
| WO | WO 2004/076386 | A2 | 9/2004 |
| WO | WO 2004/082638 | A2 | 9/2004 |
| WO | WO 2004/098609 | A1 | 11/2004 |
| WO | WO 2005/000300 | A1 | 1/2005 |
| WO | WO 2005/020921 | A2 | 3/2005 |
| WO | WO 2005/051300 | A2 | 6/2005 |
| WO | WO 2005/065681 | A2 | 7/2005 |
| WO | WO 2005/066151 | A2 | 7/2005 |
| WO | WO 2005/092899 | A1 | 10/2005 |
| WO | WO 2006/018308 | A1 | 2/2006 |
| WO | WO 2006/018309 | A1 | 2/2006 |
| WO | WO 2006/044958 | A1 | 4/2006 |
| WO | WO 2006/065842 | A2 | 6/2006 |
| WO | WO 2006/066133 | A2 | 6/2006 |
| WO | WO 2006/084186 | A2 | 8/2006 |
| WO | WO 2006/087309 | A1 | 8/2006 |
| WO | WO 2007/003604 | A2 | 1/2007 |
| WO | WO 2007/011626 | A2 | 1/2007 |
| WO | WO 2007/029035 | A2 | 3/2007 |
| WO | WO 2007/056593 | A2 | 5/2007 |
| WO | WO 2007/084390 | A2 | 7/2007 |
| WO | WO 2007/084455 | A1 | 7/2007 |
| WO | WO 2007/093827 | A1 | 8/2007 |
| WO | WO 2007/098608 | A1 | 9/2007 |
| WO | WO 2007/115408 | A1 | 10/2007 |
| WO | WO 2008/016123 | A1 | 2/2008 |
| WO | WO 2008/060721 | A1 | 5/2008 |
| WO | WO 2008/064265 | A2 | 5/2008 |
| WO | WO 2008/074132 | A1 | 6/2008 |
| WO | WO 2008/097428 | A2 | 8/2008 |
| WO | WO 2008/128335 | A1 | 10/2008 |
| WO | WO 2009/011787 | A1 | 1/2009 |
| WO | WO 2009/011876 | A1 | 1/2009 |
| WO | WO 2009/027349 | A2 | 3/2009 |
| WO | WO 2009/079011 | A1 | 6/2009 |
| WO | WO 2009/112550 | A1 | 9/2009 |
| WO | WO 2009/129036 | A1 | 10/2009 |
| WO | WO 2009/129335 | A2 | 10/2009 |
| WO | WO 2010/028192 | A1 | 3/2010 |
| WO | WO 2010/033906 | A2 | 3/2010 |
| WO | WO 2010/043953 | A2 | 4/2010 |
| WO | WO 2010/054278 | A2 | 5/2010 |
| WO | WO 2010/075551 | A1 | 7/2010 |
| WO | WO 2010/078449 | A2 | 7/2010 |
| WO | WO 2010/081145 | A1 | 7/2010 |
| WO | WO 2010/083141 | A1 | 7/2010 |
| WO | WO 2010/086311 | A1 | 8/2010 |
| WO | WO 2010/088414 | A2 | 8/2010 |
| WO | WO 2010/122151 | A1 | 10/2010 |
| WO | WO 2010/139966 | A1 | 12/2010 |
| WO | WO 2010/151318 | A1 | 12/2010 |
| WO | WO 2011/002520 | A2 | 1/2011 |
| WO | WO 2011/038185 | A2 | 3/2011 |
| WO | WO 2011/058582 | A1 | 5/2011 |
| WO | WO 2011/088181 | A1 | 7/2011 |
| WO | WO 2011/088187 | A1 | 7/2011 |
| WO | WO 2011/088192 | A1 | 7/2011 |
| WO | WO 2011/106632 | A1 | 9/2011 |
| WO | WO 2011/133888 | A1 | 10/2011 |
| WO | WO 2011/133920 | A1 | 10/2011 |
| WO | WO 2011/137320 | A2 | 11/2011 |
| WO | WO 2011/154374 | A1 | 12/2011 |
| WO | WO 2011/154431 | A1 | 12/2011 |
| WO | WO 2012/012320 | A1 | 1/2012 |
| WO | WO 2012/027564 | A1 | 3/2012 |
| WO | WO 2012/038438 | A1 | 3/2012 |
| WO | WO 2012/045804 | A1 | 4/2012 |
| WO | WO 2012/047852 | A2 | 4/2012 |
| WO | WO 2012/068109 | A2 | 5/2012 |
| WO | WO 2012/076898 | A1 | 6/2012 |
| WO | WO 2012/085038 | A1 | 6/2012 |
| WO | WO 2012/088015 | A2 | 6/2012 |
| WO | WO 2012/103008 | A1 | 8/2012 |
| WO | WO 2012/117027 | A1 | 9/2012 |
| WO | WO 2012/120023 | A1 | 9/2012 |
| WO | WO 2012/123916 | A2 | 9/2012 |
| WO | WO 2012/136111 | A1 | 10/2012 |
| WO | WO 2012/157984 | A2 | 11/2012 |
| WO | WO 2012/158957 | A2 | 11/2012 |
| WO | WO 2012/170867 | A1 | 12/2012 |
| WO | WO 2013/006408 | A1 | 1/2013 |
| WO | WO 2013/008162 | A1 | 1/2013 |
| WO | WO 2013/009810 | A1 | 1/2013 |
| WO | WO 2013/009812 | A1 | 1/2013 |
| WO | WO 2013/009827 | A1 | 1/2013 |
| WO | WO 2013/009830 | A1 | 1/2013 |
| WO | WO 2013/059582 | A2 | 4/2013 |
| WO | WO 2013/062344 | A1 | 5/2013 |
| WO | WO 2013/063549 | A1 | 5/2013 |
| WO | WO 2013/066831 | A1 | 5/2013 |
| WO | WO 2013/066832 | A1 | 5/2013 |
| WO | WO 2013/066833 | A1 | 5/2013 |
| WO | WO 2013/066834 | A1 | 5/2013 |
| WO | WO 2013/066835 | A2 | 5/2013 |
| WO | WO 2013/066836 | A1 | 5/2013 |

(56) References Cited

FOREIGN PATENT DOCUMENTS

WO WO 2013/066838 A1 5/2013
WO WO 2013/066839 A2 5/2013
WO WO 2013/080120 A1 6/2013
WO WO 2013/085890 A1 6/2013
WO WO 2013/101600 A1 7/2013
WO WO 2013/155262 A2 10/2013
WO WO 2013/169574 A2 11/2013
WO WO 2013/185353 A1 12/2013
WO WO 2014/014900 A1 1/2014
WO WO 2014/049107 A1 4/2014
WO WO 2014/059306 A1 4/2014
WO WO 2014/159210 A1 10/2014
WO WO 2014/159214 A1 10/2014
WO WO 2014/159218 A1 10/2014
WO WO 2014/159224 A1 10/2014
WO WO 2014/172191 A1 10/2014
WO WO 2014/178606 A1 11/2014
WO WO 2014/179528 A2 11/2014
WO WO 2014/180984 A1 11/2014
WO WO 2014/181137 A1 11/2014
WO WO 2014/194280 A2 12/2014
WO WO 2014/202827 A1 12/2014
WO WO 2015/017546 A1 2/2015
WO WO 2015/052160 A1 4/2015
WO WO 2015/058106 A1 4/2015
WO WO 2015/087151 A1 6/2015
WO WO 2015/102426 A1 7/2015
WO WO 2015/137750 A1 9/2015
WO WO 2015/154064 A2 10/2015
WO WO 2015/165960 A1 11/2015
WO WO 2015/187542 A1 12/2015
WO WO 2016/012485 A1 1/2016
WO WO 2016/018795 A1 2/2016
WO WO 2016/031815 A1 3/2016
WO WO 2016/040223 A1 3/2016
WO WO 2016/055786 A1 4/2016
WO WO 2016/087257 A1 6/2016
WO WO 2016/087265 A1 6/2016
WO WO 2016/100619 A2 6/2016
WO WO 2016/105518 A1 6/2016
WO WO 2016/120182 A1 8/2016
WO WO 2016/126721 A1 8/2016
WO WO 2016/126722 A1 8/2016
WO WO 2016/126724 A1 8/2016
WO WO 2016/126725 A1 8/2016
WO WO 2016/126726 A1 8/2016
WO WO 2016/128541 A1 8/2016
WO WO 2016/168598 A1 10/2016
WO WO 2016/168660 A1 10/2016
WO WO 2016/179550 A1 11/2016
WO WO 2016/179554 A1 11/2016
WO WO 2016/183331 A1 11/2016
WO WO 2016/190630 A1 12/2016
WO WO 2016/196771 A1 12/2016
WO WO 2017/011323 A1 1/2017
WO WO 2017/014321 A1 1/2017
WO WO 2017/018803 A1 2/2017
WO WO 2017/018804 A1 2/2017
WO WO 2017/018805 A1 2/2017
WO WO 2017/023133 A2 2/2017
WO WO 2017/024009 A1 2/2017
WO WO 2017/029514 A1 2/2017
WO WO 2017/033946 A1 3/2017
WO WO 2017/060854 A1 4/2017
WO WO 2017/065473 A1 4/2017
WO WO 2017/076757 A1 5/2017
WO WO 2017/081310 A1 5/2017
WO WO 2017/081311 A1 5/2017
WO WO 2017/083368 A1 5/2017
WO WO 2017/093019 A1 6/2017
WO WO 2017/109044 A1 6/2017
WO WO 2017/110861 A1 6/2017
WO WO 2017/110862 A1 6/2017
WO WO 2017/111152 A1 6/2017
WO WO 2017/123568 A2 7/2017
WO WO 2017/142883 A1 8/2017
WO WO 2017/156350 A1 9/2017
WO WO 2017/162834 A1 9/2017
WO WO 2017/165256 A1 9/2017
WO WO 2017/190109 A1 11/2017
WO WO 2017/193030 A1 11/2017
WO WO 2017/197046 A1 11/2017
WO WO 2017/208032 A1 12/2017
WO WO 2017/213252 A1 12/2017
WO WO 2017/222950 A1 12/2017
WO WO 2017/222951 A1 12/2017
WO WO 2017/222952 A1 12/2017
WO WO 2018/005192 A1 1/2018
WO WO 2018/050656 A2 3/2018
WO WO 2018/055135 A1 3/2018
WO WO 2018/075959 A1 4/2018
WO WO 2018/085170 A1 5/2018
WO WO 2018/129533 A1 7/2018
WO WO 2018154466 A1 8/2018
WO WO 2018/165520 A1 9/2018
WO WO 2018/187553 A1 10/2018
WO WO 2018/188962 A1 10/2018
WO WO 2018/189340 A1 10/2018
WO WO 2018/191360 A1 10/2018
WO WO 2018/202491 A1 11/2018
WO WO 2018/213364 A1 11/2018
WO WO 2018/219356 A1 12/2018
WO WO 2019/027054 A1 2/2019
WO WO 2019/060210 A1 3/2019
WO WO 2019/100735 A1 5/2019
WO WO 2019/101709 A1 5/2019
WO WO 2019/109046 A1 6/2019
WO WO 2019/110663 A1 6/2019
WO WO 2019/122323 A1 6/2019
WO WO 2019/139921 A1 7/2019
WO WO 2019/164222 A1 8/2019
WO WO 2019/166824 A1 9/2019
WO WO 2019/171234 A1 9/2019
WO WO 2019/200238 A1 10/2019
WO WO 2019/204550 A1 10/2019
WO WO 2019/212927 A1 11/2019
WO WO 2019/228289 A1 12/2019
WO WO 2020/011816 A1 1/2020
WO WO 2020/022794 A1 1/2020
WO WO 2020/028150 A1 2/2020
WO WO 2020/029908 A1 2/2020
WO WO 2020/039028 A1 2/2020
WO WO 2020/061112 A1 3/2020
WO WO 2020/061118 A1 3/2020
WO WO 2020/061216 A1 3/2020
WO WO 2020/070610 A1 4/2020
WO WO 2020/096916 A2 5/2020
WO WO 2020/106119 A1 5/2020
WO WO 2020/127974 A1 6/2020
WO WO 2020/132561 A1 6/2020
WO WO 2020/158762 A1 8/2020
WO WO 2020/194272 A1 10/2020
WO WO 2020/201773 A1 10/2020
WO WO 2020/207941 A1 10/2020
WO WO 2020/212479 A1 10/2020
WO WO 2020/219650 A1 10/2020
WO WO 2020/223136 A1 11/2020
WO WO 2020/240492 A1 12/2020
WO WO 2020/240493 A1 12/2020
WO WO 2020/245381 A1 12/2020
WO WO 2020/254494 A1 12/2020
WO WO 2020/264437 A1 12/2020
WO WO 2021/021979 A2 2/2021
WO WO 2021/022076 A1 2/2021
WO WO 2021/046183 A1 3/2021
WO WO 2021/048242 A1 3/2021
WO WO 2021/057872 A1 4/2021
WO WO 2021/060567 A1 4/2021
WO WO 2021/067859 A1 4/2021
WO WO 2021/092151 A1 5/2021
WO WO 2021/092153 A1 5/2021
WO WO 2021/092174 A1 5/2021
WO WO 2021/127643 A1 6/2021
WO WO 2021/133957 A1 7/2021

(56) References Cited

FOREIGN PATENT DOCUMENTS

| | | | |
|---|---|---|---|
| WO | WO 2021/172886 | A1 | 9/2021 |
| WO | WO 2021/172887 | A1 | 9/2021 |
| WO | WO 2021/208945 | A1 | 10/2021 |
| WO | WO 2021/210857 | A1 | 10/2021 |
| WO | WO 2021/236491 | A1 | 11/2021 |
| WO | WO 2021/263171 | A1 | 12/2021 |
| WO | WO 2022/013728 | A1 | 1/2022 |
| WO | WO 2022/029041 | A1 | 2/2022 |
| WO | WO 2022/049496 | A1 | 3/2022 |
| WO | WO 2022/081928 | A1 | 4/2022 |
| WO | WO 2022/133551 | A1 | 6/2022 |
| WO | WO 2022/169985 | A1 | 8/2022 |
| WO | WO 2022/174193 | A1 | 8/2022 |
| WO | WO 2022/187690 | A1 | 9/2022 |
| WO | WO 2022/197690 | A1 | 9/2022 |
| WO | WO 2022/215020 | A1 | 10/2022 |
| WO | WO 2022/216616 | A1 | 10/2022 |

OTHER PUBLICATIONS

International Preliminary Report on Patentability mailed Sep. 19, 2021 for Application No. PCT/US2018/021696.
Invitation to Pay Additional Fees mailed Apr. 29, 2022 for Application No. PCT/US2022/015129.
International Search Report and Written Opinion mailed Jun. 24, 2022 for Application No. PCT/US2022/015129.
International Preliminary Report on Patentability mailed Aug. 17, 2023 for Application No. PCT/US2022/015129.
Invitation to Pay Additional Fees mailed Apr. 3, 2023 for Application No. PCT/US2023/012174.
International Search Report and Written Opinion mailed Jun. 29, 2023 for Application No. PCT/US2023/012174.
[No Author Listed], Bringing NHA HDAC6 inhibitors to the clinic for cardiovascular and neurodegenerative disorders. Chong Kun Dang Pharmaceutical Corp. Nature Research Custom Media. Jun. 2022;B41.
[No Author Listed], Cancer Innovates, accelerating early cancer drug discovery. Cancer Innova. Feb. 2022. Accessed from <https://www-cancerinnova-com.translate.goog/en/cancer-innova-acelerando-el-descubrimiento-temprano-de-farmacos-en-cancer/?_x_tr_sl=auto&_x_tr_tl=en&_x_tr_hl=en&_x_tr_pto=wapp>. 10 pages.
[No Author Listed], CAS Registration No. 1332894-18-4. Registry (STN). Sep. 20, 2011. 1 page.
[No Author Listed], CAS Registration No. 1860746-44-6. Registry (STN). Feb. 5, 2016. 1 page.
[No Author Listed], CAS Registration No. 1875612-53-5. Registry (STN). Feb. 28, 2016. 1 page.
[No Author Listed], CAS Registration No. 73779-41-6. Registry (STN). Nov. 16, 1984. 1 page.
[No Author Listed], CAY10603: Catalog No. S7596; Synonyms: BML-281. Apr. 2015. 4 pages. Accessed Jul. 19, 2022 from <https://www.selleckchem.com/products/cay10603.html?gclid=CjwKCAjwoMSWBhAdEiwAVJ2ndvOI8KYzzn0XiWLIF5DRM50crFNHcVSDwVsA6XALwr0yzmIKn10muxoCgkcQAvD_B WE>.
[No Author Listed], HDAC: Inhibitory Selectivity. AdooQ Bioscience. 21 pages. Accessed May 18, 2022 from <https://www.adooq.com/epigenetics-histone-deacetylase-hdac.html?gclid=EAIaIQobChMI4K_CiJzk9AIVpQaICR2_rgPTEAMYASAAEgKHnvD_BWE>.
[No Author Listed], Highlights of Prescribing Information for Abraxane® for Injectable Suspension (paclitaxel protein-bound particles for injectable suspension). Abraxis BioScience, LLC. 2005. 24 pages.
[No Author Listed], Highlights of Prescribing Information for Qalsody® (tofersen) injection, for intrathecal use. Biogen Inc. 2023. 14 pages.
[No Author Listed], Augustine Therapeutics Showcase Presentation. Recorded at the 2022 Investival Showcase in London, England on Nov. 14, 2022. Accessed Feb. 7, 2023 from <https://www.youtube.com/watch?v=8wJXGd2CgQU>. Selected screenshots. 6 pages.
[No Author Listed], Jubilant Therapeutics Inc. receives Orphan Drug Designation for JBI-802 for Acute Myeloid Leukemia (AML) and Small Cell Lung Cancer (SCLC). Jubilant Therapeutics. Jan. 5, 2023. Accessed from <https://www.prnewswire.com/news-releases/jubilant-therapeutics-inc-receives-orphan-drug-designation-for-jbi-802-for-acute-myeloid-leukemia-aml-and-small-cell-lung-cancer-sclc-301714552.html>. 3 pages.
[No Author Listed], NCT03713892: CKD-504 in SAD and MAD in Healthy Korean and Caucasian Adult Male and Female Subjects. Last Update Posted Feb. 24, 2020. 6 pages. Accessed Feb. 7, 2023 from <https://clinicaltrials.gov/ct2/show/NCT03713892>.
[No Author Listed], NCT04746287: Evaluation of the Safety and Tolerability of CKD-510 in Healthy Subjects. Last Update Posted May 4, 2022. 8 pages. Accessed Feb. 7, 2023 from <https://clinicaltrials.gov/ct2/show/NCT04746287>.
[No Author Listed], NCT05526742: A Study to Evaluate the Relative Bioavailability of Formulations of CKD-510 and to Assess the Effect of Food on the CKD-510 Tablet Formulation in Healthy Subjects. Last Update Posted Sep. 8, 2022. 7 pages. Accessed Feb. 7, 2023 from <https://clinicaltrials.gov/ct2/show/NCT05526742>.
[No Author Listed], OnKure Expands Executive Team with the Addition of Chief Scientific Officer and Chief Development Officer. OnKure Therapeutics. Aug. 3, 2021. Accessed from <https://onkuretherapeutics.com/press-release/onkure-expands-executive-team-and-appoints-head-of-discovery-chief-financial-officer-and-general-counsel-2/>. 4 pages.
[No Author Listed], OnKure Therapeutics Appoints Jennifer R. Diamond, M.D., as Chief Medical Officer. OnKure Therapeutics. Oct. 14, 2021. Accessed from <https://onkuretherapeutics.com/year/2021/onkure-therapeutics-appoints-jennifer-r-diamond-m-d-as-chief-medical-officer/>. 3 pages.
[No Author Listed], Oryzon collaborates with the CMT Research Foundation in the US. Oryzon Press Release. Jul. 26, 2022. 2 pages.
[No Author Listed], Pharmacology review for belinostat. Center for Drug Evaluation and Research. Application No. 206256Orig1s000. May 22, 2014. 98 pages.
[No Author Listed], Pharmacology review for panobinostat. Center for Drug Evaluation and Research. Application No. 205353Orig1s000. Sep. 2, 2014. 125 pages.
[No Author Listed], Pharmacology review for vorinostat. Center for Drug Evaluation and Research. Application No. 21-991. Oct. 5, 2006. 106 pages.
[No Author Listed], Pipeline Program and Development Status. OnKure Therapeutics. May 13, 2021. Accessed from <https://web.archive.org/web/20210513123624/https:/onkuretherapeutics.com/pipeline/>. 2 pages.
[No Author Listed], Pipeline Program and Development Status. OnKure Therapeutics. Oct. 8, 2021. Accessed from <https://web.archive.org/web/20210513123624/https:/onkuretherapeutics.com/pipeline/>. 2 pages.
[No Author Listed], Precision oral medicines with enhanced therapeutic index. Jubilant Therapeutics. Corporate Presentation. Jan. 2023. 38 pages.
[No Author Listed], PubChem Substance Record for PubChem SID 227322283, SCHEMBL1075847. Accessed Sep. 21, 2020. 9 pages.
[No Author Listed], PubChem Substance Record for PubChem SID 274711921, 2-[5-(3-Nitrophenyl)furfuryl]-1,2,3,4-tetrahydroisoquinoline-7-carbohydroximic acid. Accessed Sep. 21, 2020. 8 pages.
[No Author Listed], Scaling New Heights in the Fight Against Heart Disease. Tenaya Therapeutics. Corporate Presentation. Sep. 2022. 38 pages.
[No Author Listed], Tenaya Therapeutics Announces TN-201 IND Clearance and Anticipated 2023 Milestones. GlobeNewswire. Jan. 9, 2023. Accessed from <https://www.globenewswire.com/news-release/2023/01/09/2585026/0/en/Tenaya-Therapeutics-Announces-TN-201-IND-Clearance-and-Anticipated-2023-Milestones.html>. 7 pages.
[No Author Listed], The basque-based company Quimatryx licenses a cancer drug for 92 million dollars. Basque Press. Jul. 29, 2022. Accessed from <https://basque.press/the-guipuzcoa-based-company-quimatryx-licenses-a-cancer-drug-for-92-million-dollars-la-empresa-

(56) References Cited

OTHER PUBLICATIONS guipuzcoana-quimatryx-licencia-un-farmaco-contra-el-cancer-por-92-millones-de-dolares/>. 5 pages.
[No Author Listed], The McQuade Center for Strategic Research and Development and Eikonizo Therapeutics Enter Agreement to Develop Treatments for Patients with Rare Diseases. Feb. 9, 2021.
Adalbert et al., Novel HDAC6 Inhibitors Increase Tubulin Acetylation and Rescue Axonal Transport of Mitochondria in a Model of Charcot-Marie-Tooth Type 2F. ACS Chem Neurosci. Feb. 5, 2020;11(3):258-267. doi: 10.1021/acschemneuro.9b00338. Epub Jan. 8, 2020.
Bae et al., CKD-506: A novel HDAC6-selective inhibitor that exerts therapeutic effects in a rodent model of multiple sclerosis. Sci Rep. Jul. 14, 2021;11(1):14466. doi: 10.1038/s41598-021-93232-6.
Bae et al., CKD-510, a novel non-hydroxamic acid histone deacetylase 6 (HDAC6) inhibitor for Charcot-Marie-Tooth disease type 1A. J Peripher Nerv Syst.2022;27(Suppl. 3):S4. Abstract Only.
Beshore et al., Redefining the Histone Deacetylase Inhibitor Pharmacophore: High Potency with No Zinc Cofactor Interaction. ACS Med Chem Lett. Mar. 7, 2021;12(4):540-547. doi: 10.1021/acsmedchemlett.1c00074.
Blackburn et al., Histone deacetylase inhibitors derived from 1,2,3,4-tetrahydropyrrolo[1,2-a]pyrazine and related heterocycles selective for the HDAC6 isoform. Bioorg Med Chem Lett. Dec. 1, 2014;24(23):5450-4. doi: 10.1016/j.bmcl.2014.10.022.
Blackburn et al., Potent histone deacetylase inhibitors derived from 4-(aminomethyl)-N-hydroxybenzamide with high selectivity for the HDAC6 isoform. J Med Chem. Sep. 26, 2013;56(18):7201-11. doi: 10.1021/jm400385r. Epub Sep. 4, 2013.
Bondarev et al., Recent developments of HDAC inhibitors: Emerging indications and novel molecules. Br J Clin Pharmacol. 2021; 87(12): 4577-4597. https://doi.org/10.1111/bcp.14889.
Chang et al., The Role of HDAC6 in Autophagy and NLRP3 Inflammasome. Front Immunol. Oct. 27, 2021;12:763831. doi: 10.3389/fimmu.2021.763831.
Choi et al., Acetylation changes tau interactome to degrade tau in Alzheimer's disease animal and organoid models. Aging Cell. Jan. 2020;19(1):e13081. doi: 10.1111/acel.13081. Epub Nov. 25, 2019.
Choi et al., CKD-506, a novel HDAC6-selective inhibitor, improves renal outcomes and survival in a mouse model of systemic lupus erythematosus. Sci Rep. Nov. 23, 2018;8(1):17297. doi: 10.1038/s41598-018-35602-1.
Cragin et al., A Novel Zinc Binding Group for HDAC6 Inhibition. FASEB J. May 2022;36 Suppl 1. doi: 10.1096/fasebj.2022.36.S1.R3604. Abstract Only.
Faridoon et al., Medicinal chemistry insights into non-hydroxamate HDAC6 selective inhibitors. Med Chem Res. Oct. 31, 2022;32(1):1-14. doi: 10.1007/s00044-022-02987-8.
Fazal et al., HDAC6 inhibition restores TDP-43 pathology and axonal transport defects in human motor neurons with TARDBP mutations. EMBO J. 2021;40:e106177.
Gaisina et al., Activation of Nrf2 and Hypoxic Adaptive Response Contribute to Neuroprotection Elicited by Phenylhydroxamic Acid Selective HDAC6 Inhibitors. ACS Chem Neurosci. May 16, 2018;9(5):894-900. doi: 10.1021/acschemneuro.7b00435. Epub Jan. 17, 2018.
Gajendran et al., Novel dual LSD1/HDAC6 inhibitor for the treatment of cancer. PLoS One. Jan. 3, 2023;18(1):e0279063. doi: 10.1371/journal.pone.0279063.
Ha et al., A novel histone deacetylase 6 inhibitor improves myelination of Schwann cells in a model of Charcot-Marie-Tooth disease type 1A. Br J Pharmacol. Nov. 2020; 177(22):5096-5113. doi: 10.1111/bph.15231. Epub Sep. 27, 2020.
Hendricks et al., In vivo PET imaging of histone deacetylases by 18F-suberoylanilide hydroxamic acid (18F-SAHA). J Med Chem. Aug. 11, 2011;54(15):5576-82. doi: 10.1021/jm200620f. Epub Jul. 18, 2011.
Hong et al., CKD-510, a novel selective HDAC6 inhibitor, is well-tolerated and increased acetyl-tubulin in healthy volunteers. J Peripher Nerv Syst.2022;27(Suppl. 3):S76-7. Abstract Only.
Hu et al., 3D-QSAR Studies of HDAC6 Inhibitors Using Docking-Based Alignment. Lett Drug Des Discov. Jul. 2017; 14(7):798-810. doi: 10.2174/1570180813666161028165151.
Hubbert et al., HDAC6 is a microtubule-associated deacetylase. Nature. May 23, 2002;417(6887):455-8. doi: 10.1038/417455a.
Jeong et al., Therapeutic Potential of CKD-504, a Novel Selective Histone Deacetylase 6 Inhibitor, in a Zebrafish Model of Neuromuscular Junction Disorders. Mol Cells. Apr. 30, 2022;45(4):231-242. doi: 10.14348/molcells.2022.5005.
Kattar, et al., Parallel medicinal chemistry approaches to selective HDAC1/HDAC2 inhibitor (SHI-1:2) optimization. Bioorg Med Chem Lett. Feb. 15, 2009;19(4):1168-72. doi: 10.1016/j.bmcl.2008.12.083. Epub Dec. 25, 2008.
Kim et al., HDAC6 inhibitor blocks amyloid beta-induced impairment of mitochondrial transport in hippocampal neurons. PLoS One. 2012;7(8):e42983. doi: 10.1371/journal.pone.0042983. Epub Aug. 22, 2012.
Kim et al., HDAC6 Inhibitors Rescued the Defective Axonal Mitochondrial Movement in Motor Neurons Derived from the Induced Pluripotent Stem Cells of Peripheral Neuropathy Patients with HSPB1 Mutation. Stem Cells Int. 2016;2016:9475981. doi: 10.1155/2016/9475981. Epub Dec. 26, 2016.
Kleinschek et al., Potent and Selective Non-hydroxamate Histone Deacetylase 8 Inhibitors. ChemMedChem. Dec. 6, 2016;11(23):2598-2606. doi: 10.1002/cmdc.201600528. Epub Nov. 9, 2016.
Kozikowski et al., Brain Penetrable Histone Deacetylase 6 Inhibitor SW-100 Ameliorates Memory and Learning Impairments in a Mouse Model of Fragile X Syndrome. ACS Chem Neurosci. Mar. 20, 2019;10(3):1679-1695. doi: 10.1021/acschemneuro.8b00600. Epub Dec. 14, 2018.
Kozikowski, A.P., Application for Federal Assistance for Study of the New HDAC6i SW-100 as a Treatment for Alzheimer's Disease and Other Tauopathies; Title: Study of the New HDAC6i SW-100 as a Treatment for Alzheimer's Disease and Other Tauopathies for StarWise Therapeutics LLC and University of South Florida. FOA: PAS17-065. Received Mar. 31, 2017. 62 pages.
Krukowski et al., HDAC6 inhibition effectively reverses chemotherapy-induced peripheral neuropathy. Pain. Jun. 2017;158(6):1126-1137. doi: 10.1097/j.pain.0000000000000893.
Lechner et al., Target deconvolution of HDAC pharmacopoeia reveals MBLAC2 as common off-target. Nat Chem Biol. Aug. 2022;18(8):812-820. doi: 10.1038/s41589-022-01015-5. Epub Apr. 28, 2022. Erratum in: Nat Chem Biol. Jul. 15, 2022.
Lee et al., Novel Histone Deacetylase 6 Inhibitor CKD-506 Inhibits NF-κB Signaling in Intestinal Epithelial Cells and Macrophages and Ameliorates Acute and Chronic Murine Colitis. Inflamm Bowel Dis. May 12, 2020;26(6):852-862. doi: 10.1093/ibd/izz317.
Lee et al., Novel Histone Deacetylase 6 Inhibitor Confers Anti-inflammatory Effects and Enhances Gut Barrier Function. Gut Liver. Sep. 27, 2022. doi: 10.5009/gnl220159. Epub ahead of print.
Li et al., A Novel HDAC6 Inhibitor, CKD-504, is Effective in Treating Preclinical Models of Huntington's Disease. BMB Rep. Jan. 3, 2023:5747. Epub ahead of print.
Li et al., Abstract 4441: CS3003, an HDAC6-selective inhibitor, improves anti-PD-1 immune checkpoint blockade therapy efficacy. Proceedings of the Annual Meeting of the American Association for Cancer Research. Apr. 27-28 and Jun 22-24, 2020. Philadelphia, PA. Cancer Res 2020;80(16 Suppl). Poster. 1 page.
Lipczynska-Kochany et al., Mutagenicity of pyridine- and quinoline-carbohydroxamic acid derivatives. Mutat Res. Mar. 1984; 135(3):139-48. doi: 10.1016/0165-1218(84)90114-9.
Liu et al., MiR-222-3p Inhibits Trophoblast Cell Migration and Alleviates Preeclampsia in Rats Through Inhibiting HDAC6 and Notch1 Signaling. Reprod Sci. Nov. 18, 2021. doi: 10.1007/s43032-021-00793-y. Epub ahead of print.
Mahmoud et al., Nimbolide inhibits 2D and 3D prostate cancer cells migration, affects microtubules and angiogenesis and suppresses B-RAF/p.ERK-mediated in vivo tumor growth. Phytomedicine. Jan. 2022;94:153826. doi: 10.1016/j.phymed.2021.153826. Epub Nov. 1, 2021.
Martin et al., Discovery of novel N-hydroxy-2-arylisoindoline-4-carboxamides as potent and selective inhibitors of HDAC11. Bioorg

(56) References Cited

OTHER PUBLICATIONS

Med Chem Lett. Jul. 1, 2018;28(12):2143-2147. doi: 10.1016/j.bmcl.2018.05.021. Epub May 9, 2018.
McMahon, VEGF receptor signaling in tumor angiogenesis. The Oncologist. 2000;5(suppl 1):3-10.
Mejzini et al., ALS Genetics, Mechanisms, and Therapeutics: Where Are We Now? Front Neurosci. Dec. 6, 2019;13:1310. doi: 10.3389/fnins.2019.01310.
Munakata et al., Mutagenicity of N-acylglycinohydroxamic acids and related compounds. J Pharmacobiodyn. Nov. 1980;3(11):557-61. doi: 10.1248/bpb1978.3.557.
Neidle, Cancer Drug Design and Discovery. Elsevier/Academic Press. 2008; 427-431.
Onishi et al., A novel orally active HDAC6 inhibitor T-518 shows a therapeutic potential for Alzheimer's disease and tauopathy in mice. Sci Rep. Jul. 29, 2021;11(1):15423. doi: 10.1038/s41598-021-94923-w.
Park et al., Therapeutic potential of CKD-506, a novel selective histone deacetylase 6 inhibitor, in a murine model of rheumatoid arthritis. Arthritis Res Ther. Jul. 25, 2020;22(1):176. doi: 10.1186/s13075-020-02258-0.
Pinedo et al., Translational Research: The Role of VEGF in Tumor Angiogenesis. The Oncologist. 2000;5(Suppl 1):1-2.
Rivieccio et al., HDAC6 is a target for protection and regeneration following injury in the nervous system. Proc Natl Acad Sci U S A. Nov. 17, 2009;106(46):19599-604. doi: 10.1073/pnas.0907935106. Epub Nov. 2, 2009.
Sandrone et al., Role of Fluorination in the Histone Deacetylase 6 (HDAC6) Selectivity of Benzohydroxamate-Based Inhibitors. ACS Med Chem Lett. Oct. 11, 2021;12(11):1810-1817. doi: 10.1021/acsmedchemlett.1c00425.
Selenica et al., Histone deacetylase 6 inhibition improves memory and reduces total tau levels in a mouse model of tau deposition. Alzheimers Res Ther. Feb. 27, 2014;6(1):12. doi: 10.1186/alzrt241.
Shen et al., A patent review of histone deacetylase 6 inhibitors in neurodegenerative diseases (2014-2019). Expert Opin Ther Pat. Feb. 2020;30(2):121-136. doi: 10.1080/13543776.2019.1708901. Epub Dec. 25, 2019.
Shen et al., Bicyclic-Capped Histone Deacetylase 6 Inhibitors with Improved Activity in a Model of Axonal Charcot-Marie-Tooth Disease. ACS Chem Neurosci. Feb. 17, 2016;7(2):240-58. doi: 10.1021/acschemneuro.5b00286. Epub Dec. 7, 2015.
Shen et al., Structural and in Vivo Characterization of Tubastatin A, a Widely Used Histone Deacetylase 6 Inhibitor. ACS Med Chem Lett. Jan. 15, 2020;11(5):706-712. doi: 10.1021/acsmedchemlett.9b00560.
Shen et al., Why Hydroxamates May Not Be the Best Histone Deacetylase Inhibitors—What Some May Have Forgotten or Would Rather Forget? ChemMedChem. Jan. 5, 2016;11(1):15-21. doi: 10.1002/cmdc.201500486. Epub Nov. 25, 2015.
Shukla et al., Histone Deacetylases Inhibitors in Neurodegenerative Diseases, Neuroprotection and Neuronal Differentiation. Front Pharmacol. Apr. 24, 2020;11:537. doi: 10.3389/fphar.2020.00537.
Simoes-Pires et al., HDAC6 as a target for neurodegenerative diseases: what makes it different from the other HDACs? Mol Neurodegener. Jan. 29, 2013;8:7. doi: 10.1186/1750-1326-8-7.
Sixto-Lopez et al., silico design of HDAC6 inhibitors with neuroprotective effects. J Biomol Struct Dyn. Nov. 16, 2021:1-19. doi: 10.1080/07391102.2021.2001378. Epub ahead of print.
Staff et al., Chemotherapy-induced peripheral neuropathy: A current review. Ann Neurol. Jun. 2017;81(6):772-781. doi: 10.1002/ana.24951. Epub Jun. 5, 2017. Author Manuscript, 17 pages.
Wang et al., Mutagenicity and antibacterial activity of hydroxamic acids. Antimicrob Agents Chemother. Apr. 1977;11(4):753-5. doi: 10.1128/AAC.11.4.753.
Wang, C.Y., Mutagenicity of hydroxamic acids for *Salmonella typhimurium*. Mutat Res. Sep. 1977;56(1):7-12. doi: 10.1016/0027-5107(77)90235-4.
Watson et al., Aromatic C-F Interactions Influence Binding Mode of Inhibitors in HDAC6. FAseb J. May 2022;36 Suppl 1. doi: 10.1096/fasebj.2022.36.S1.R2257. Abstract Only.
Wei et al., Mutagenicity of some monoaromatic hydroxamic acids. Toxicol Lett. Jan. 1985;24(1):111-6. doi: 10.1016/0378-4274(85)90148-1.
Xu et al., Design, Synthesis, Bioactivity Evaluation, Crystal Structures, and In Silico Studies of New α-Amino Amide Derivatives as Potential Histone Deacetylase 6 Inhibitors. Molecules. May 22, 2022;27(10):3335. doi: 10.3390/molecules27103335.
Yang et al., Phenotypic screening with deep learning identifies HDAC6 inhibitors as cardioprotective in a BAG3 mouse model of dilated cardiomyopathy. Sci Transl Med. Jul. 6, 2022;14(652):1-15. doi: 10.1126/scitranslmed.abl5654. Supplementary Materials, 44 pages.
Zhang et al., Design, synthesis, and biological evaluation of novel histone deacetylase 6 selective inhibitors. J Saudi Chem Soc. May 2022;26(3):101450. doi: 10.1016/j.jscs.2022.101450.
Zhang et al., Tubastatin A/ACY-1215 improves cognition in Alzheimer's disease transgenic mice. J Alzheimers Dis. 2014;41(4):1193-205. doi: 10.3233/JAD-140066.
Yu et al., Quinazolin-2,4-dione-Based Hydroxamic Acids as Selective Histone Deacetylase-6 Inhibitors for Treatment of Non-Small Cell Lung Cancer. J Med Chem. Jan. 24, 2019;62(2):857-874. doi: 10.1021/acs.jmedchem.8b01590. Epub Dec. 20, 2018.

| Compound | Structure | Protocol | Ames Result |
|---|---|---|---|
| 1 |  | B | Neg |
| 9 |  | B | Neg |
| 14 |  | A<br>B | Equivocal<br>Neg |
| 20 |  | B | Neg |
| 34 |  | A<br>B | Neg<br>Neg |
| 184 |  | B | Neg |
| 197 |  | B | Neg |

| Compound | Structure | Protocol | Ames Result |
|---|---|---|---|
| 201 |  | B | Neg |
| 289 |  | B | Neg |
| 301 |  | B | Neg |
| 344 |  | B | Neg |
| 352 |  | B | Neg |
| 353 |  | B | Neg |

| Compound | Structure | Protocol | Ames Result |
|---|---|---|---|
| 357 |  | B | Neg |
| 358 |  | B | Neg |
| 389 |  | B | Neg |
| 419 |  | B | Neg |
| 426 |  | B | Neg |

| Compound | Structure | Protocol | Ames Result |
|---|---|---|---|
| 435 |  | B | Neg |
| 436 |  | B | Neg |
| 437 |  | B | Neg |
| 439 |  | B | Neg |
| 440 |  | B | Neg |
| 451 |  | B | Neg |
| 453 |  | B | Neg |

| Compound | Structure | Protocol | Ames Result |
| --- | --- | --- | --- |
| 454 |  | B | Neg |
| 461 |  | B | Neg |
| 469 |  | B | Neg |
| 475 |  | B | Neg |
| 482 |  | B | Neg |
| 483 |  | B | Neg |
| 490 |  | B | Neg |

| Compound | Structure | Protocol | Ames Result |
|---|---|---|---|
| 3 |  | A | Pos |
| 4 |  | B | Pos |
| 5 |  | B | Pos |
| 6 |  | B | Pos |
| 7 |  | A | Pos |
| 15 |  | B | Bac |
| 16 |  | A<br>B<br>C | Neg<br>Neg<br>Pos |
| 21 |  | A | Bac |

| Compound | Structure | Protocol | Ames Result |
|---|---|---|---|
| 24 |  | B | Pos |
| 26 |  | A | Bac |
| 27 |  | A | Pos |
| 28 |  | A | Pos |
| 30 |  | A | Pos |
| 31 |  | A | Pos |
| 32 |  | A | Pos |
| 107 |  | A | Pos |

| Compound | Structure | Protocol | Ames Result |
|---|---|---|---|
| 108 |  | A | Pos |
| 109 |  | A | Pos |
| 110 |  | A<br>B | Bac<br>Bac |
| 174 |  | B | Pos |
| 175 |  | B | Pos |
| 177 |  | B | Pos |

| Compound | Structure | Protocol | Ames Result |
|---|---|---|---|
| 178 |  | A | Pos |
| 179 |  | B | Pos |
| 183 |  | B | Bac |
| 185 |  | B | Bac |
| 192 |  | B | Bac |
| 193 |  | B | Bac |

| Compound | Structure | Protocol | Ames Result |
|---|---|---|---|
| 194 |  | B | Bac |
| 198 |  | B | Pos |
| 199 |  | B | Equivocal |
| 291 |  | B | Pos |
| 300 |  | B | Pos |
| 302 |  | B | Equivocal |

| Compound | Structure | Protocol | Ames Result |
|---|---|---|---|
| 343 |  | B | Pos |
| 346 |  | B | Pos |
| 365 |  | B | Pos |
| 383 |  | B | Bac |
| 384 |  | B | Bac |
| 427 |  | B | Pos |
| 438 |  | B | Pos |

| Compound | Structure | Protocol | Ames Result |
|---|---|---|---|
| 463 |  | B | Pos |
| 465 |  | B | Pos |
| 466 |  | B | Pos |
| 470 |  | B | Pos |
| 474 |  | B | Pos |
| 484 |  | B | Pos |
| 607 |  | B | Pos |

| Compound | Structure | Protocol | Ames Result |
| --- | --- | --- | --- |
| 230 |  | B | Neg |
| 231 |  | B | Neg |
| 510 |  | B | Neg |
| 522 |  | B | Neg |
| 535 |  | B | Neg |
| 554 |  | B | Neg |
| 570 |  | B | Neg |

| Compound | Structure | Protocol | Ames Result |
|---|---|---|---|
| 572 |  | B | Neg |
| 573 |  | B | Neg |
| 594 |  | B | Neg |

| Compound | Structure | Protocol | Ames Result |
|---|---|---|---|
| 113 |  | A<br>B | Neg<br>Bac |
| 114 |  | A | Pos |
| 115 |  | A | Pos |
| 118 |  | A | Pos |
| 213 |  | B | Pos |
| 216 |  | B | Pos |

| Compound | Structure | Protocol | Ames Result |
|---|---|---|---|
| 233 |  | B | Bac |
| 509 |  | B | Bac |
| 518 |  | B | Bac |
| 523 |  | B | Pos |
| 553 |  | B | Pos |
| 555 |  | B | Equivocal |
| 580 |  | B | Pos |

| Compound | Structure | Protocol | Ames Result |
|---|---|---|---|
| 591 |  | B | Pos |
| 596 |  | B | Pos |
| 600 |  | B | Pos |
| 601 |  | B | Pos |

| Compound | Structure | Protocol | Ames Result |
| --- | --- | --- | --- |
| 64 |  | A<br>B | Neg<br>Neg |
| 77 |  | A<br>B | Neg<br>Neg |

| Compound | Structure | Protocol | Ames Result |
|---|---|---|---|
| 45 |  | A | Pos |
| 46 |  | A | Pos |
| 51 |  | A | Pos |
| 52 |  | A | Pos |
| 53 |  | A | Pos |
| 54 |  | A | Pos |
| 59 |  | A | Pos |

| Compound | Structure | Protocol | Ames Result |
|---|---|---|---|
| 62 |  | A | Pos |
| 63 |  | A | Pos |
| 67 |  | A | Pos |
| 72 |  | A | Pos |
| 74 |  | A | Pos |
| 75 |  | A | Pos |
| 79 |  | A | Pos |

| Compound | Structure | Protocol | Ames Result |
|---|---|---|---|
| 93 |  | A | Pos |
| 94 |  | A | Pos |
| 124 |  | A | Pos |
| 125 |  | A | Pos |
| 126 |  | A | Pos |
| 127 |  | A | Pos |
| 128 |  | A | Pos |

| Compound | Structure | Protocol | Ames Result |
|---|---|---|---|
| 134 |  | A | Pos |
| 135 |  | A | Pos |
| 137 |  | A | Pos |
| 151 |  | A | Pos |
| 152 |  | A | Pos |
| 157 |  | A | Pos |
| 158 |  | A | Pos |

| Compound | Structure | Protocol | Ames Result |
|---|---|---|---|
| 167 |  | A | Bac |
| 169 |  | A | Pos |
| 170 |  | A | Equivocal |
| 172 |  | A | Pos |
| 173 |  | A | Pos |
| 251 |  | B | Pos |
| 252 |  | B | Pos |

| Compound | Structure | Protocol | Ames Result |
|---|---|---|---|
| 253 |  | B | Pos |
| 254 |  | B | Pos |
| -- |  | A | Pos |
| -- |  | A | Pos |
| -- |  | B | Pos |
| -- |  | A | Bac |
| -- |  | A | Bac |

| Compound | Structure | Protocol | Ames Result |
|---|---|---|---|
| -- |  | A | Bac |
| -- |  | A | Bac |
| -- |  | A | Pos |
| -- |  | A | Pos |
| -- |  | A | Pos |
| -- |  | A<br>B | Bac<br>Equivocal |
| -- |  | A | Bac |

HDAC6 INHIBITORS AND USES THEREOF

RELATED APPLICATION

This application is a national stage filing under 35 U.S.C. § 371 of International PCT Application PCT/US2022/015129, filed Feb. 3, 2022, which claims priority under 35 U.S.C. § 119 (e) to U.S. Provisional Application, U.S. Ser. No. 63/145,379, filed on Feb. 3, 2021, the entire contents of each of which are incorporated herein by reference.

BACKGROUND

Histone deacetylases (HDACs) are divided into four classes based on sequence homology. HDAC6, a class IIb HDAC, is a cytoplasmic, microtubule-associated enzyme. HDAC6 has unique features among the HDAC paralogs. Unlike other HDACs, HDAC6 contains two deacetylase domains and a ubiquitin binding domain allowing HDAC6 to function in distinct cell signaling systems involving protein acetylation and ubiquitination, respectively. Importantly, it does not deacetylate histones. HDAC6 deacetylates tubulin, tau, Hsp90, cortactin, and other emerging targets. HDAC6 deacetylase function is involved in microtubule-based cargo transport, protein degradation/recycling and stress-induced glucocorticoid receptor signaling. HDAC6 deacetylase function is also involved in cell morphology, motility and migration, as well as cell growth and survival. In addition to deacetylase functions, HDAC6 forms complexes with partner proteins linked to ubiquitin-dependent functions, and influences protein aggregation, trafficking and degradation via the aggresome pathway. HDAC6 expression was shown to be elevated in postmortem brain samples from Alzheimer's disease patients. Aberrant expression of HDAC6 also correlates with tumorigenesis and is linked to the metastasis of cancer cells.

SUMMARY

The cytosolic location, distinct substrates, and structure of HDAC6 is unique among the HDAC paralogs and HDAC6-selective treatment regimens show promise to avoid many of the side effects of first-generation pan-HDAC inhibitors. However, paralog selectivity is difficult to obtain. The present disclosure stems from the recognition that the unique structure and function of HDAC6, among the HDAC paralogs, provides an opportunity for the design of selective HDAC6 inhibitors. The present disclosure also recognizes that targeting HDAC6-mediated pathways may provide improved treatments for neurological disorders. In relation to neurodegeneration, HDAC6 (1) impairs microtubule function by deacetylating tubulin, which leads to defects in axonal and mitochondrial transport; (2) promotes tau aggregation by deacetylating tau, which leads to pathological tau phosphorylation and neurofibrillary tangle formation; and (3) prevents degradation of HSP90 client proteins, including misfolded tau, by deacetylating HSP90, which stabilizes the chaperone complex associated with protein refolding/recycling. Thus, the present disclosure provides brain-penetrant, selective HDAC6 inhibitors. These compounds provide new compositions and methods for the treatment of diseases associated with HDAC6 activity (e.g., neurological disorders, such as Alzheimer's disease and other tauopathies, amyotrophic lateral sclerosis, and cancer).

In one aspect, provided are compounds of Formula (I):

(I)

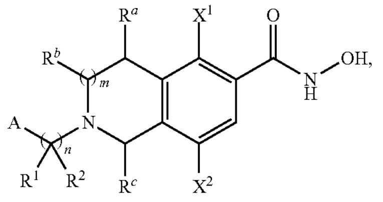

and pharmaceutically acceptable salts, co-crystals, tautomers, stereoisomers, solvates, hydrates, polymorphs, isotopically enriched derivatives, or prodrugs thereof, wherein:

$X^1$ is hydrogen or fluoro;

$X^2$ is hydrogen or fluoro; provided that at least one of $X^1$ and $X^2$ is fluoro;

A is substituted or unsubstituted alkyl, substituted or unsubstituted carbocyclyl, substituted or unsubstituted heterocyclyl, substituted or unsubstituted heteroaryl, or substituted or unsubstituted aryl;

$R^1$ is hydrogen or substituted or unsubstituted alkyl;

$R^2$ is hydrogen or substituted or unsubstituted alkyl; or $R^1$ and $R^2$ together form a substituted or unsubstituted heterocyclyl, or a substituted or unsubstituted cycloalkyl;

$R^a$ is hydrogen or is joined with $R^c$ to form a substituted or unsubstituted bridged ring;

$R^b$ is hydrogen or is joined with $R^c$ to form a substituted or unsubstituted bridged ring;

$R^c$ is hydrogen or substituted or unsubstituted alkyl or is joined with at least one of $R^a$ and $R^b$ to form a substituted or unsubstituted bridged ring;

m is 0 or 1; and n is 0 or 1, provided that the compound is not of formula:

1

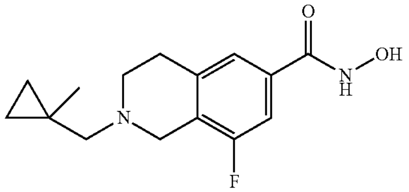

2

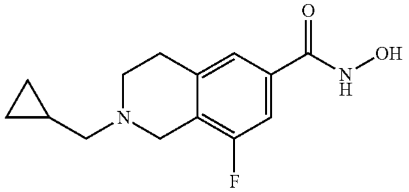

3

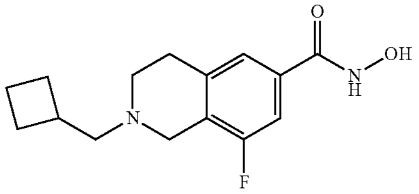

-continued
4
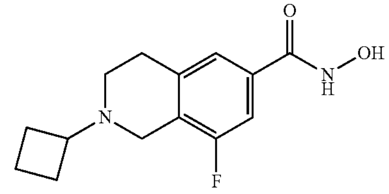
5
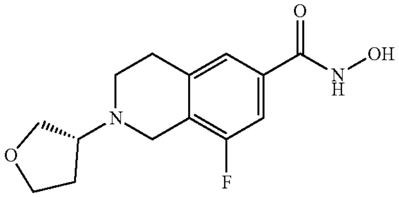
6
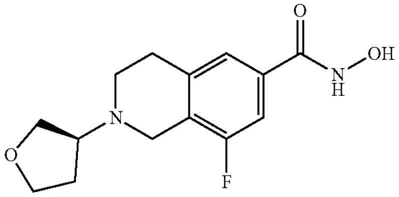
7
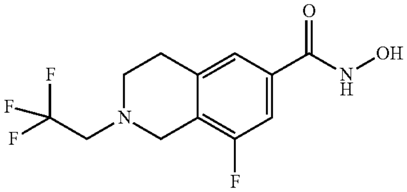
8
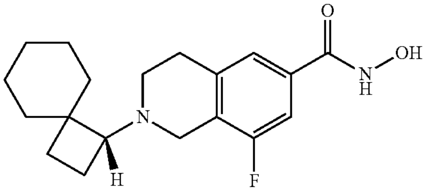
9
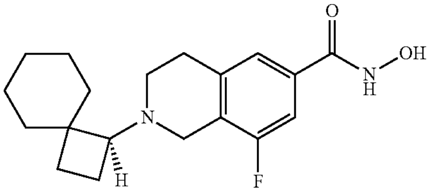
10
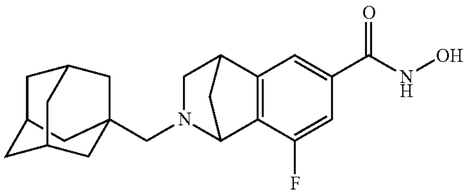
11
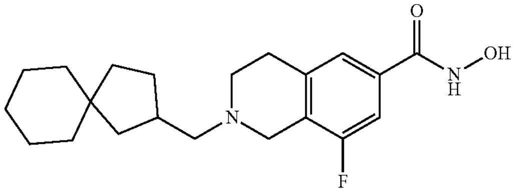
-continued
12
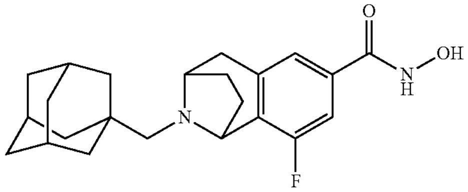
13
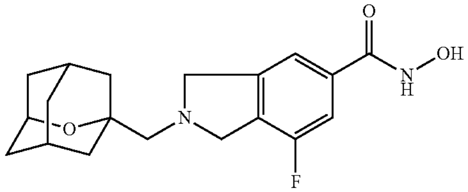
14
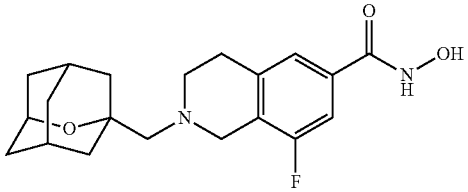
15
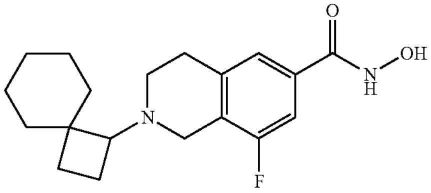
16
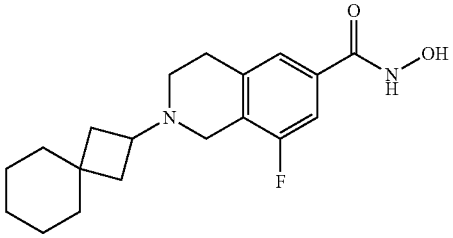
17
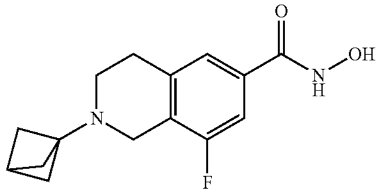
18
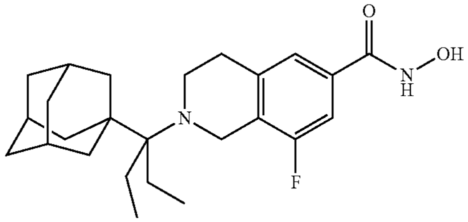

-continued
19
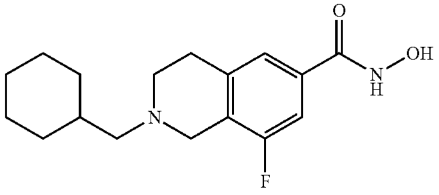
20
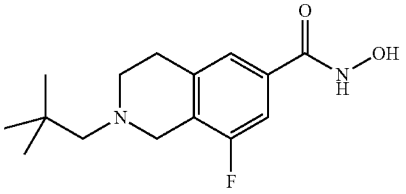
21
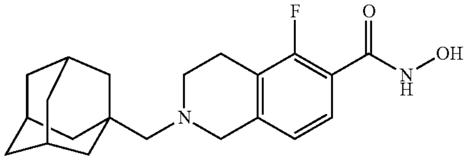
22
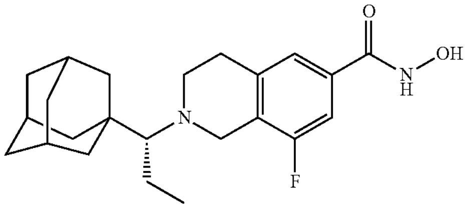
23
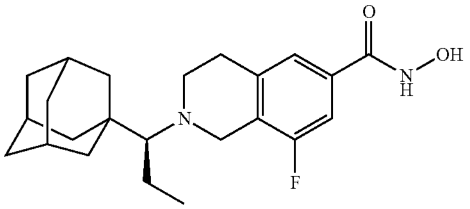
24
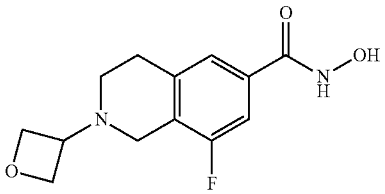
25
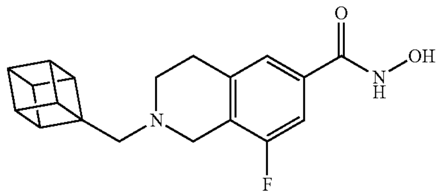
26
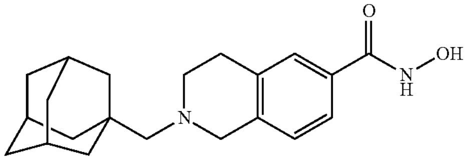
-continued
27
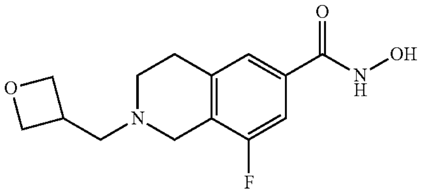
28
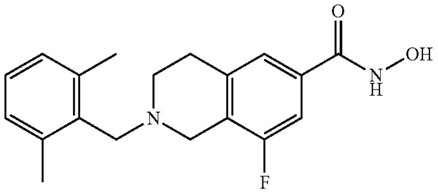
29
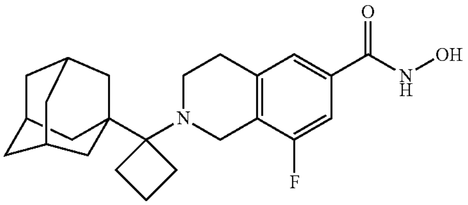
30
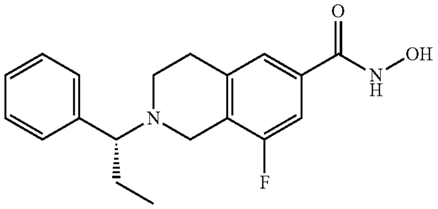
31
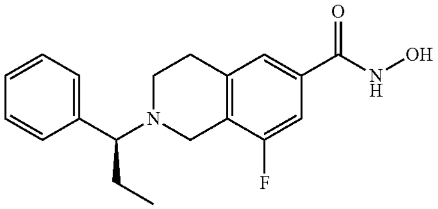
32
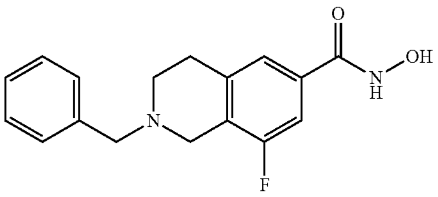
33
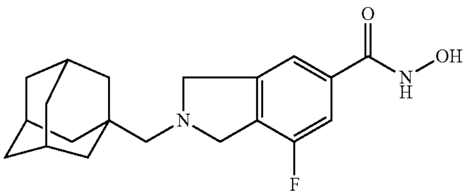

-continued
34
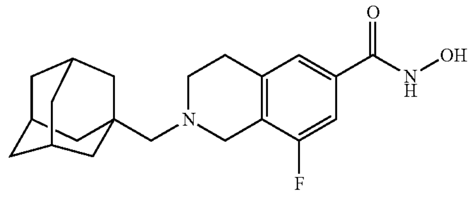
35
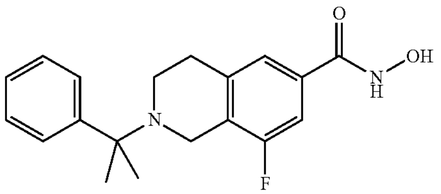
107
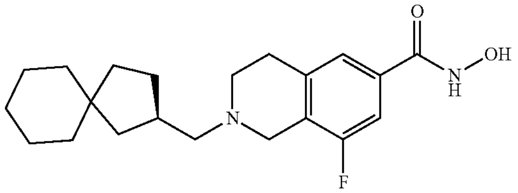
108
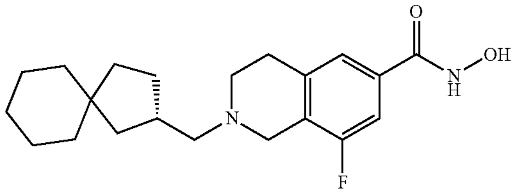
109
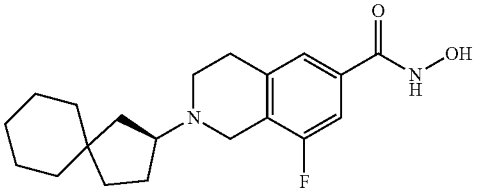
110
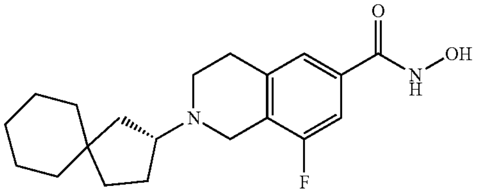
111
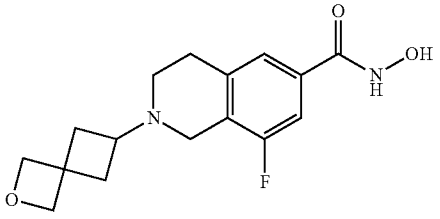
-continued
112
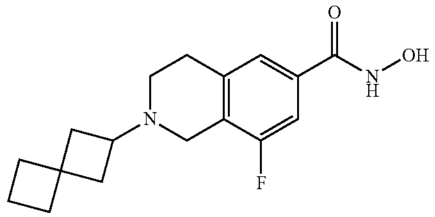
Exemplary compounds of Formula (I) include, but are not limited to:
184
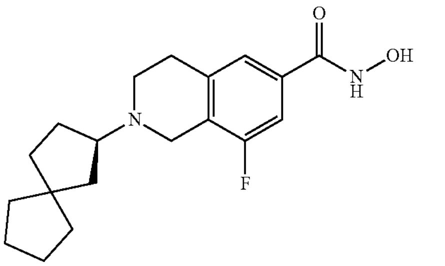
197
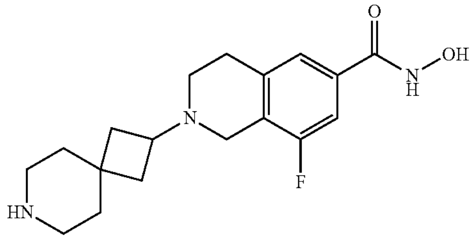
201
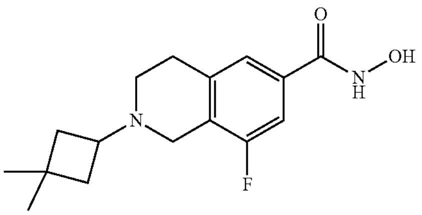
289
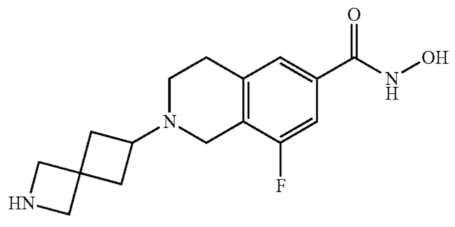
301
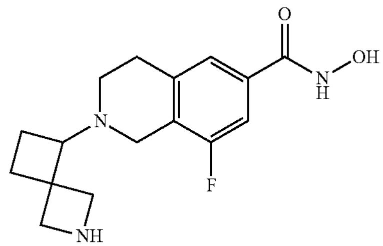

344
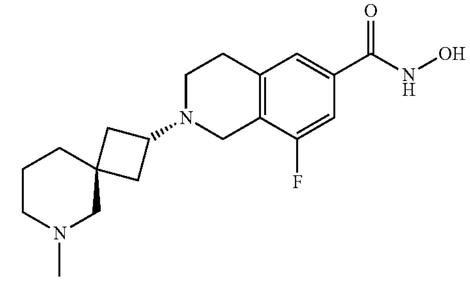
352
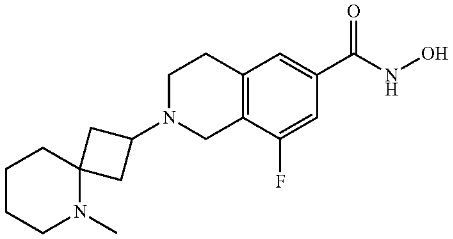
353
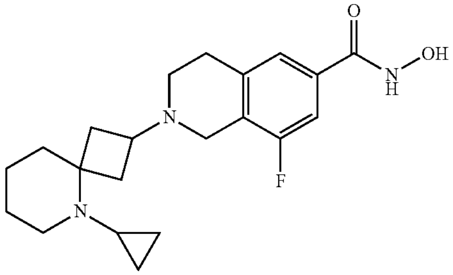
357
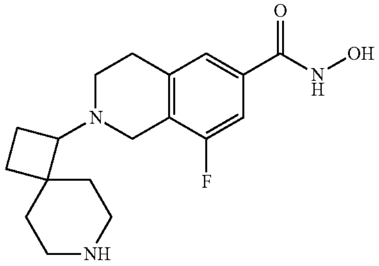
358
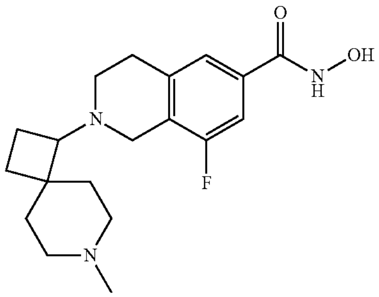
389
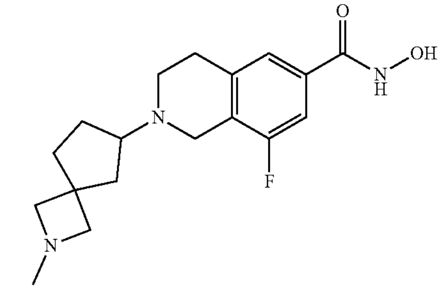
419
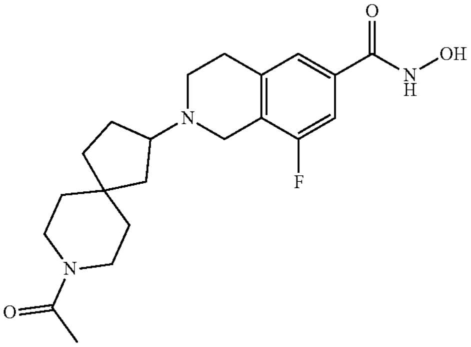
426
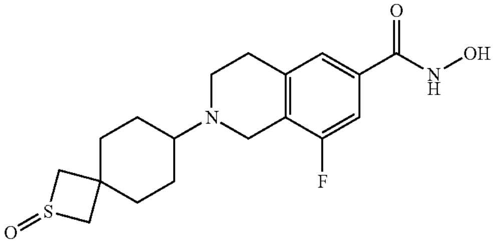
435
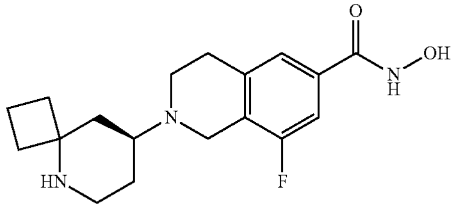
436
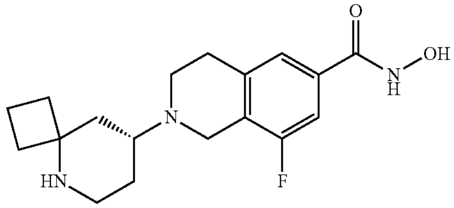
437
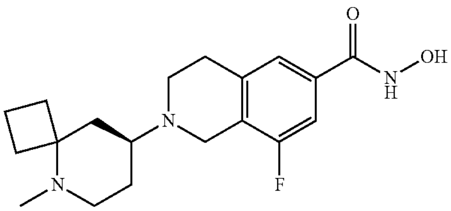

-continued
439
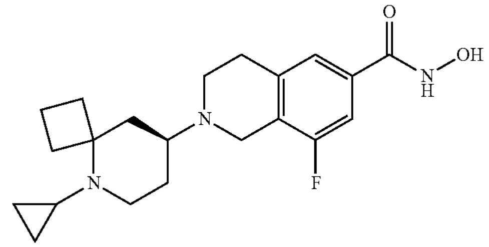
440
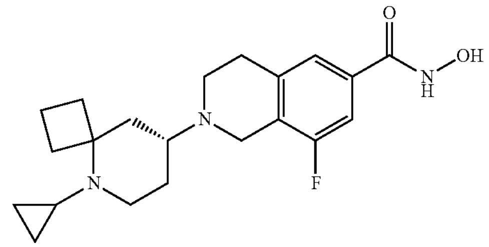
451
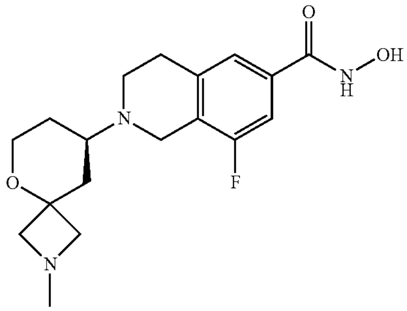
453
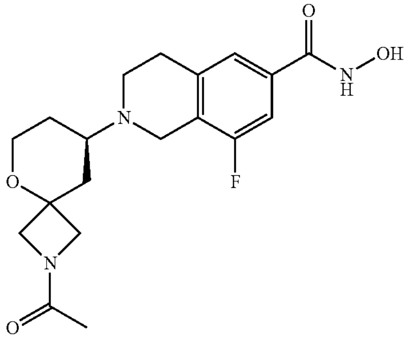
454
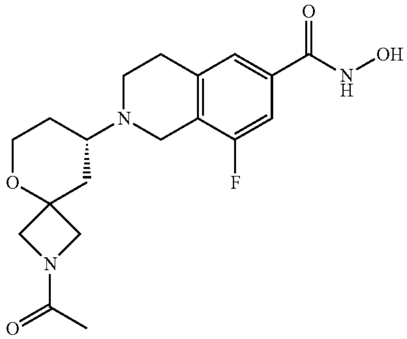
-continued
461
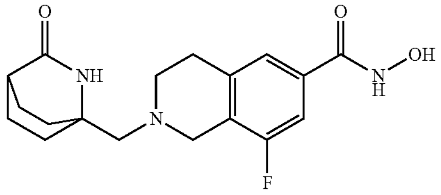
469
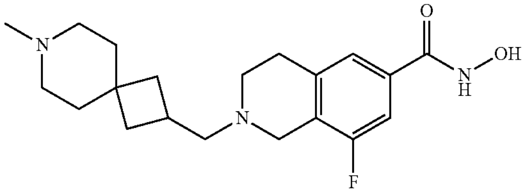
475
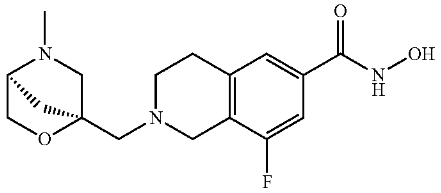
482
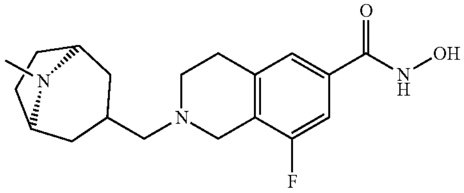
483
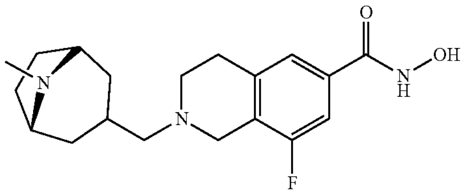
490
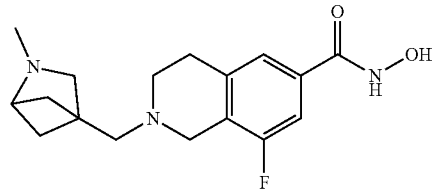
and pharmaceutically acceptable salts thereof.
Exemplary compounds of Formula (I) also include, but are not limited to:
174
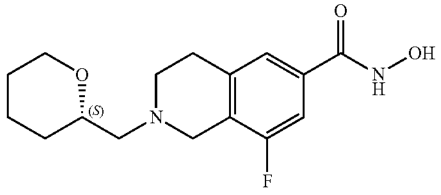

-continued
175
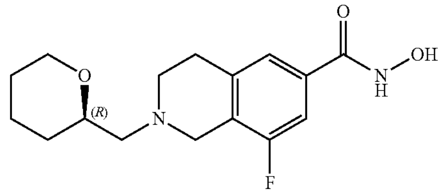
176
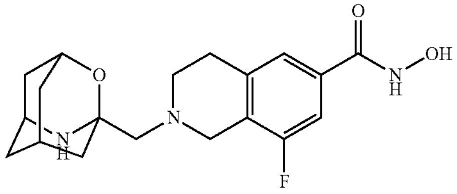
177
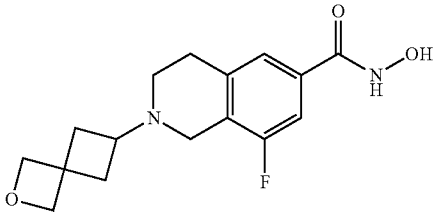
178
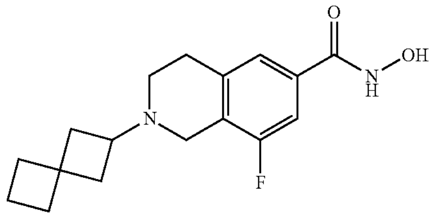
179
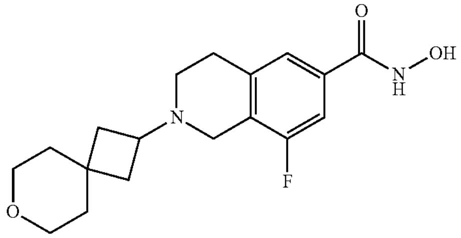
180
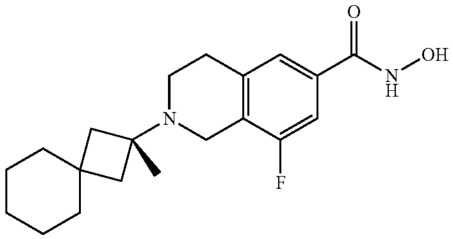
181
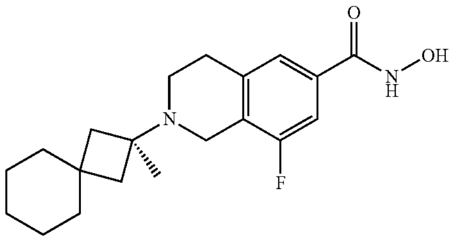
-continued
182
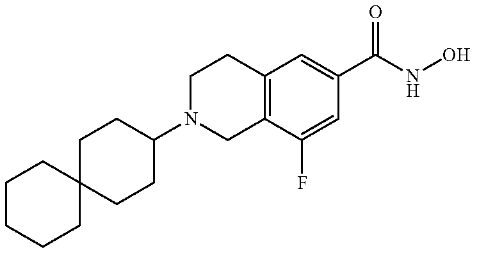
183
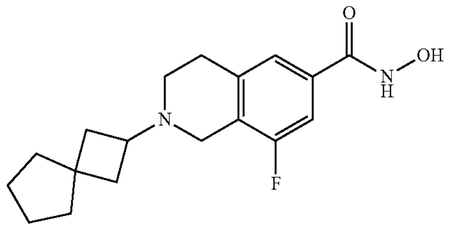
185
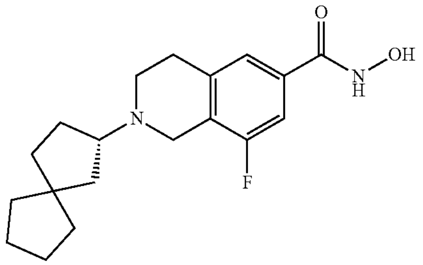
188
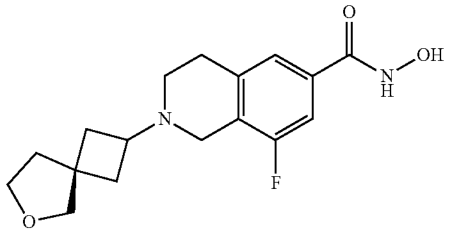
189
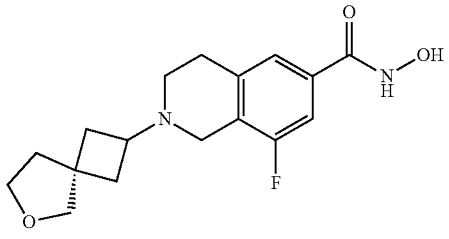
190
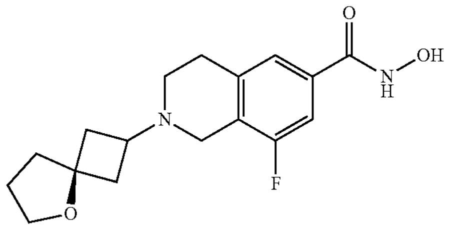

-continued
191
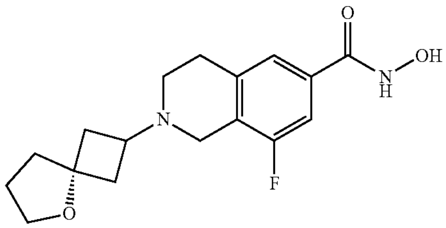
192
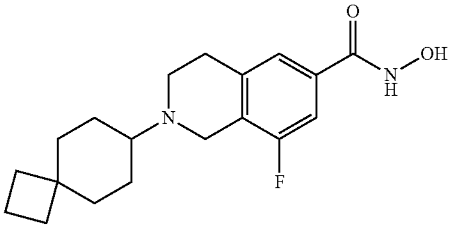
193
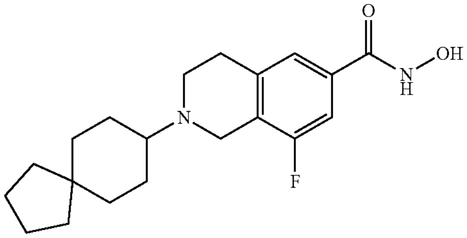
194
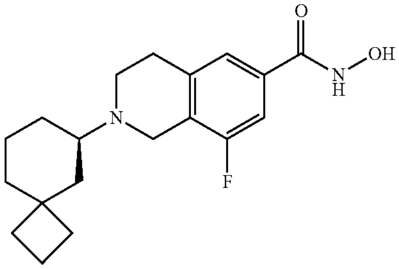
195
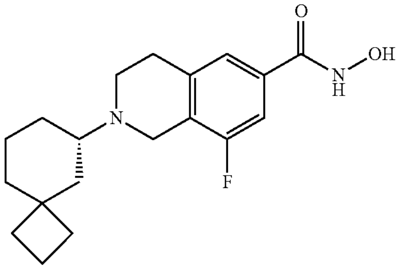
198
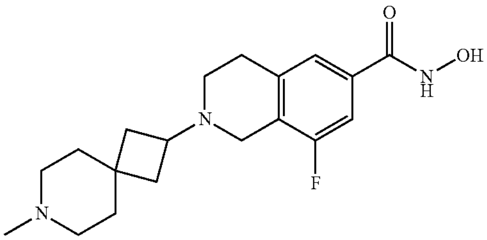
-continued
199
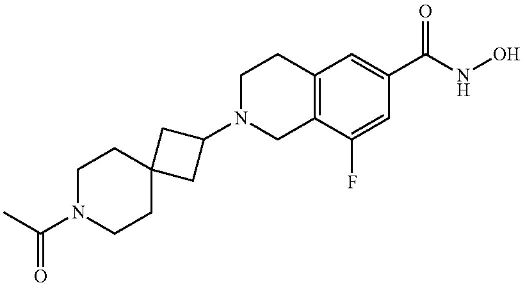
200
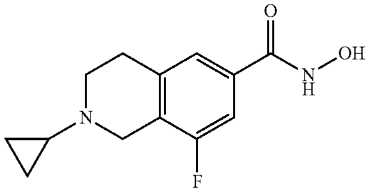
202
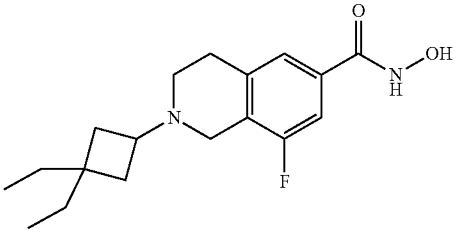
209
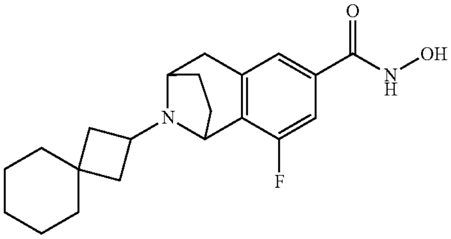
210
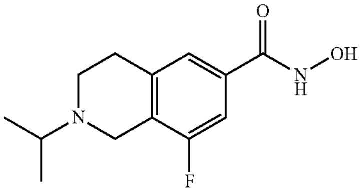
211
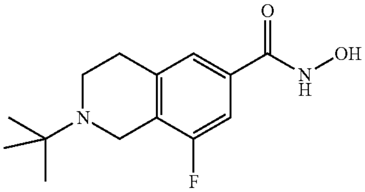
212
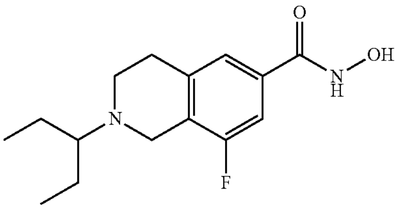

-continued
290
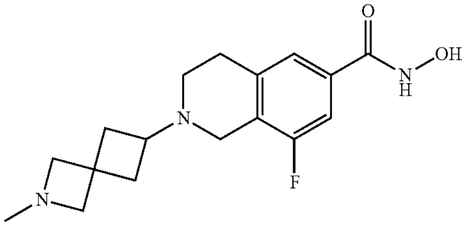
291
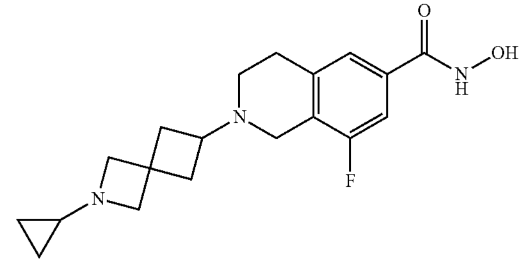
292
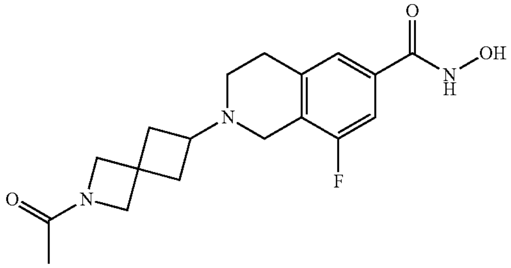
293
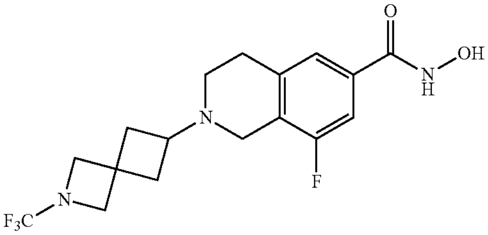
294
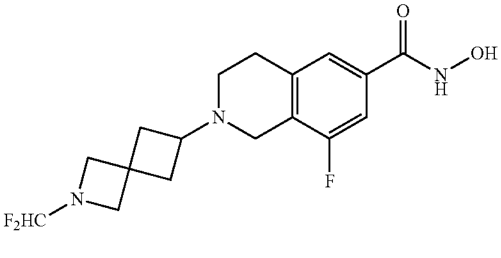
295
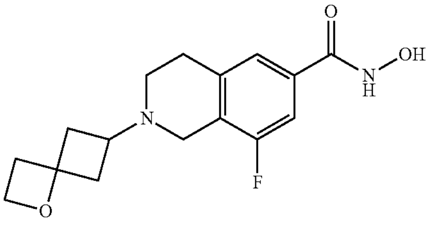
-continued
296
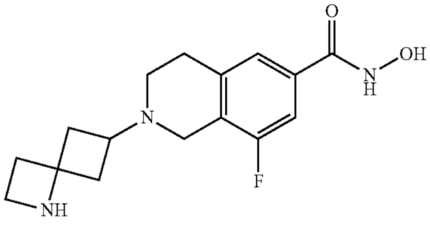
297
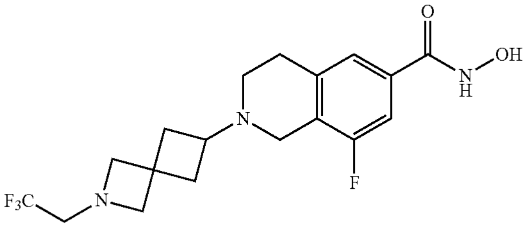
298
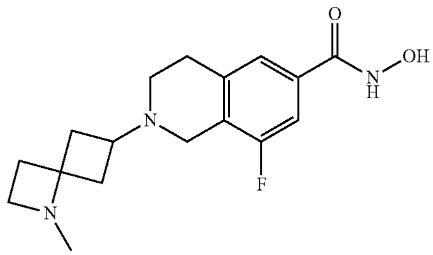
299
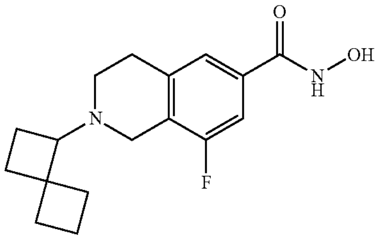
300
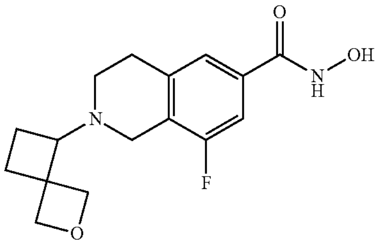
302
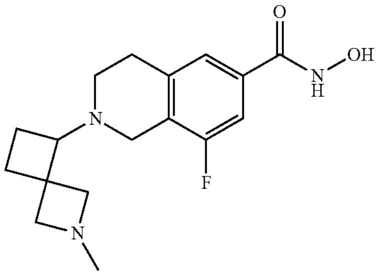

-continued
303
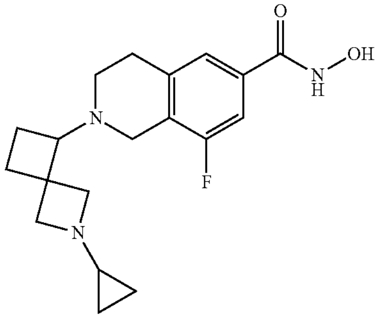
304
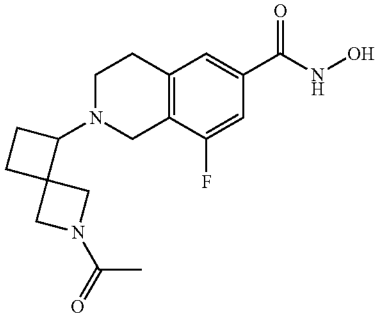
305
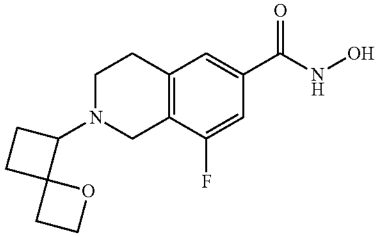
306
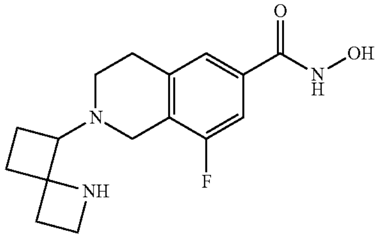
307
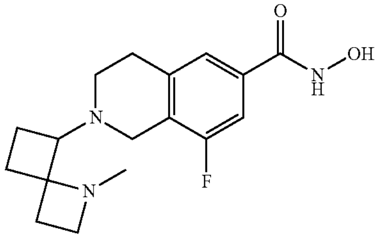
308
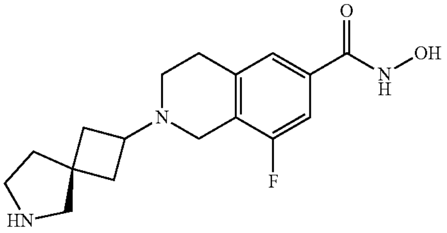
-continued
309
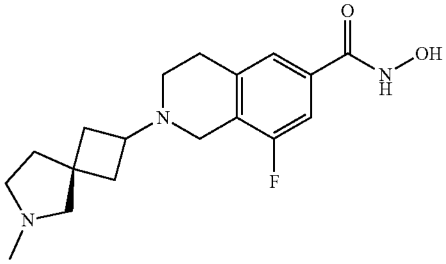
310
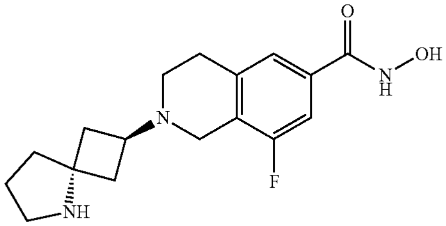
311
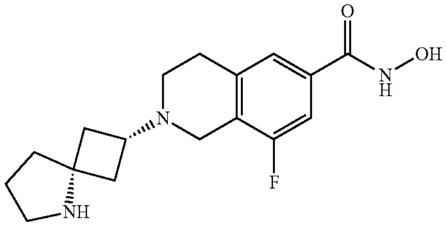
312
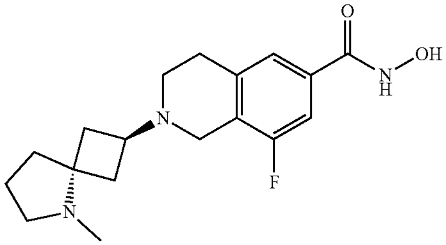
313
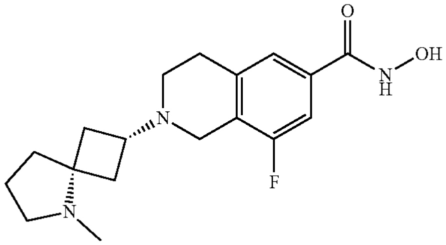
314
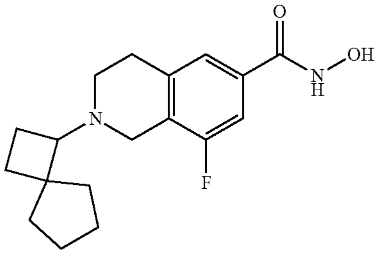

315
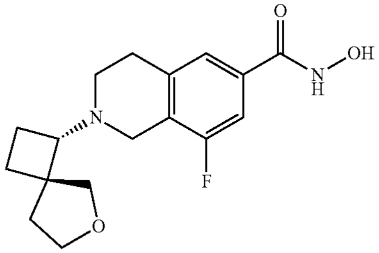
316
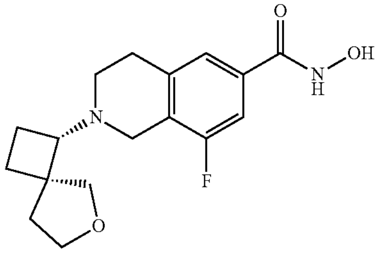
317
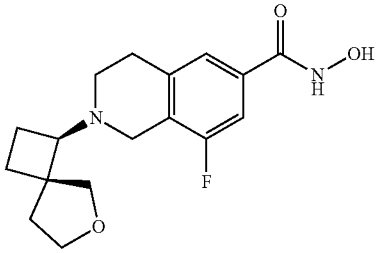
318
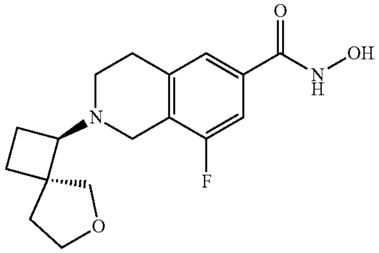
319
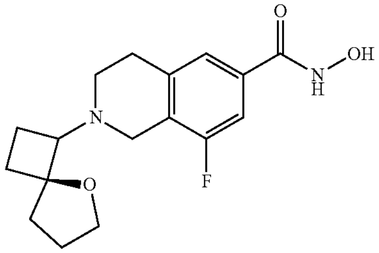
320
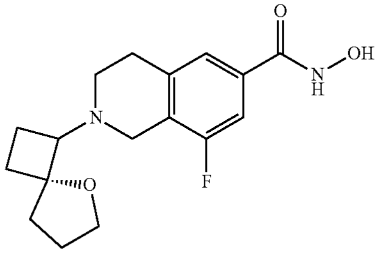
321
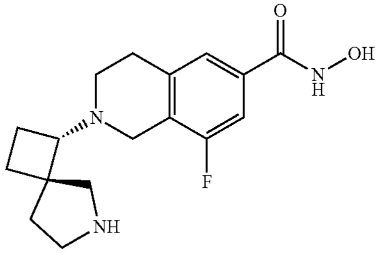
322
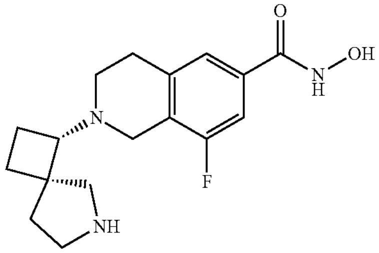
323
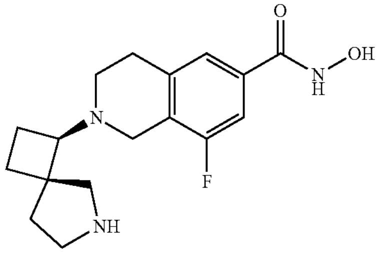
324
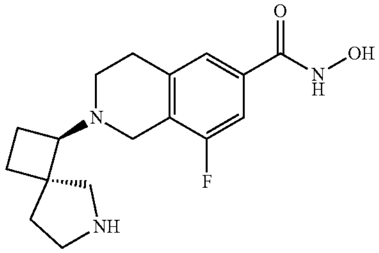
325
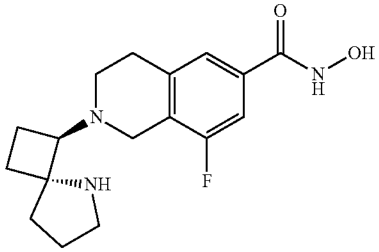
326
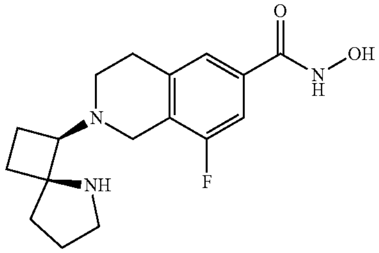

-continued
327
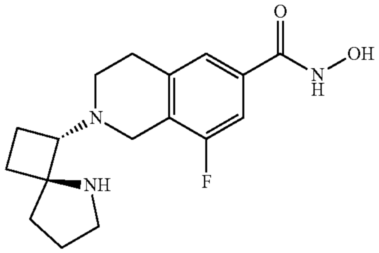
328
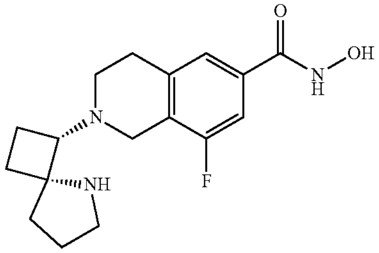
329
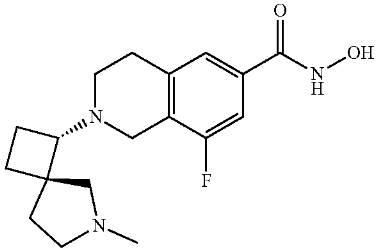
330
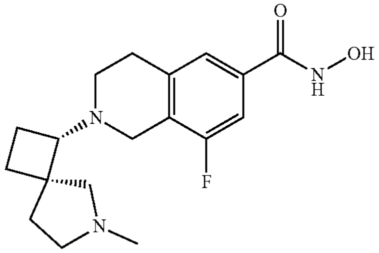
331
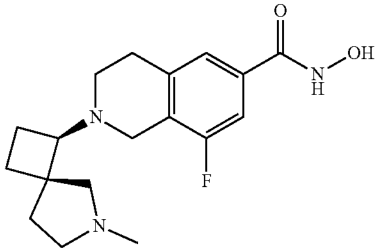
332
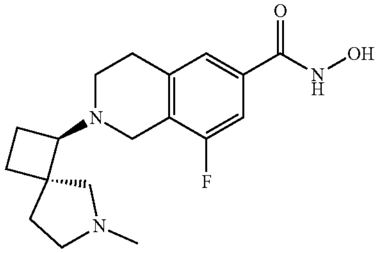
-continued
333
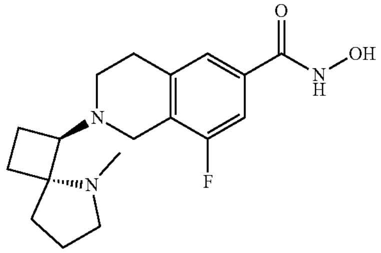
334
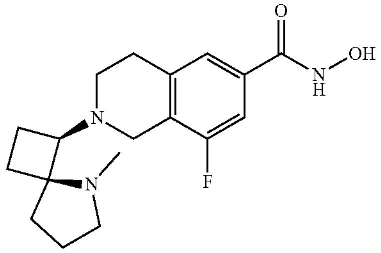
335
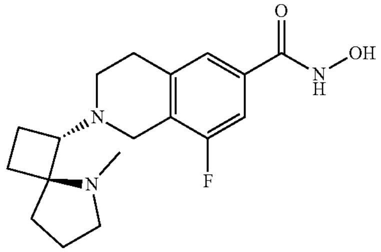
336
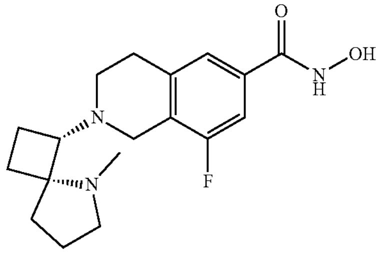
337
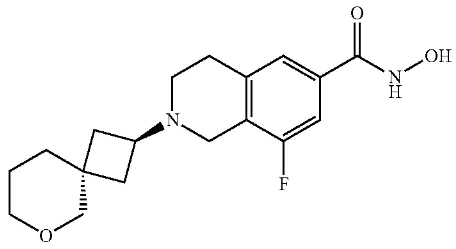
338
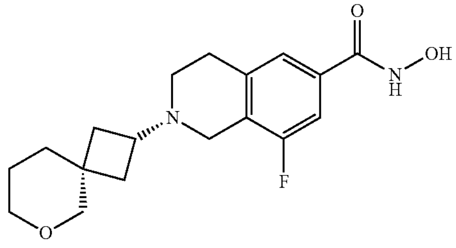

-continued
339
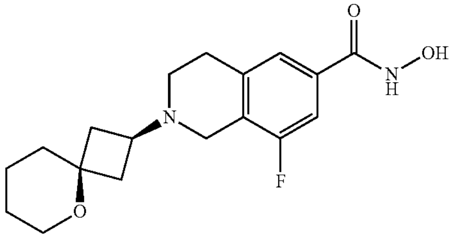
340
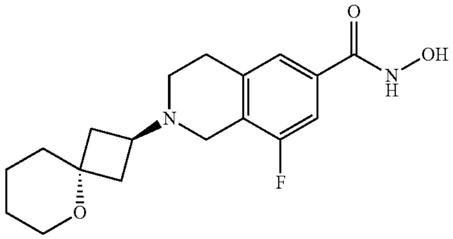
341
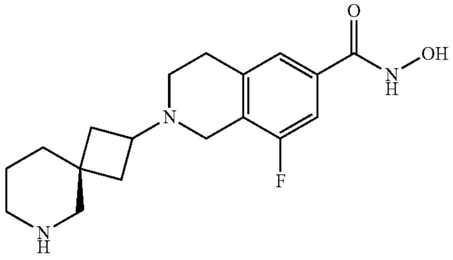
342
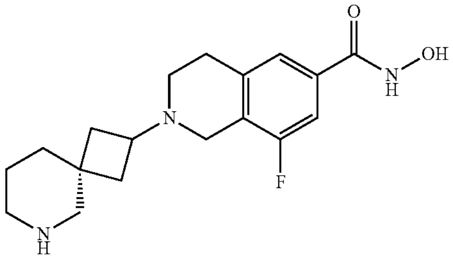
343
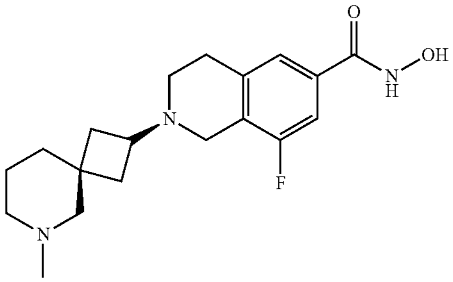
345
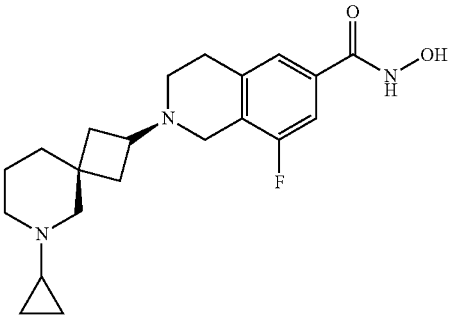
-continued
346
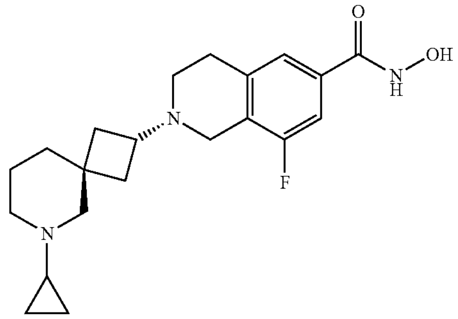
347
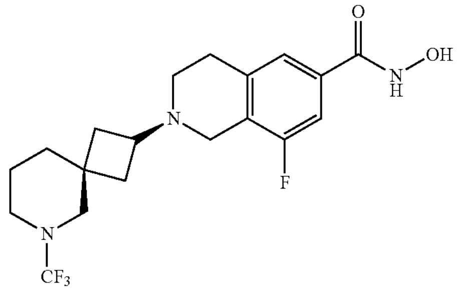
348
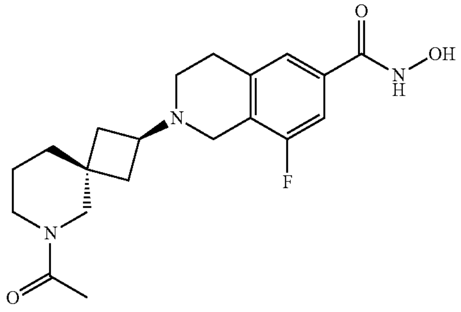
349
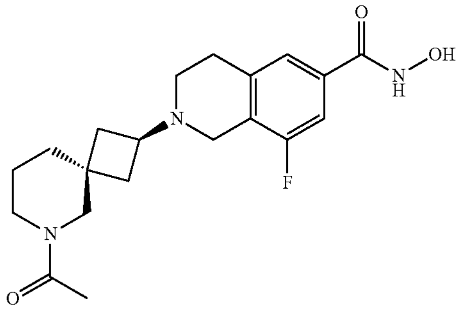
350
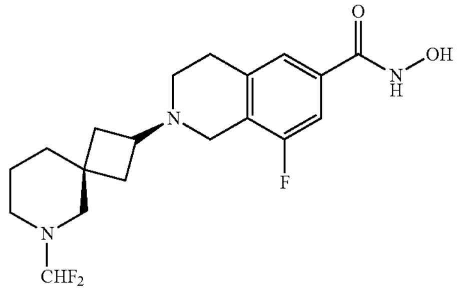

-continued
351
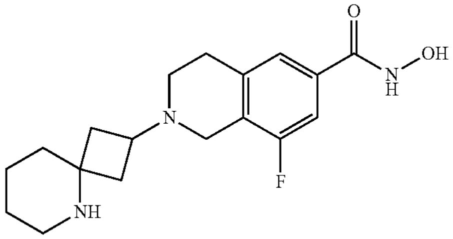
354
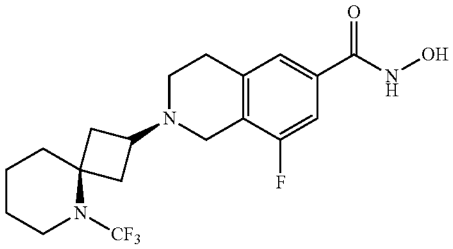
355
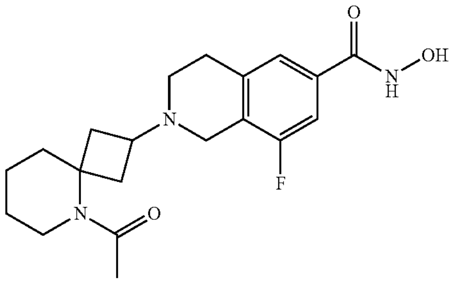
356
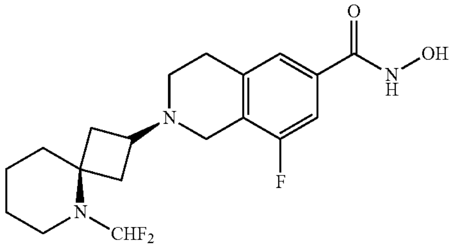
359
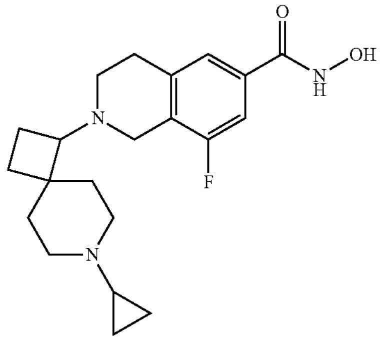
-continued
360
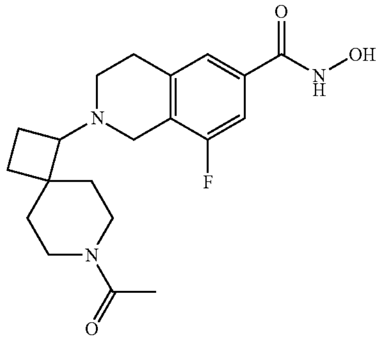
361
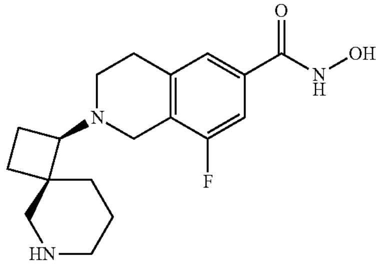
362
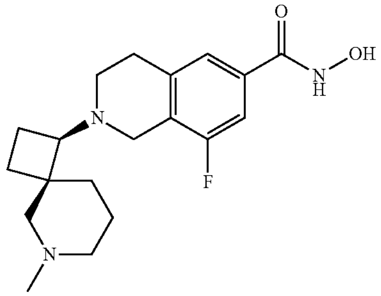
363
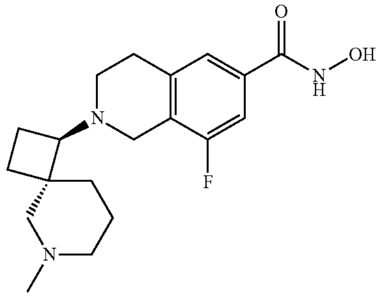
364
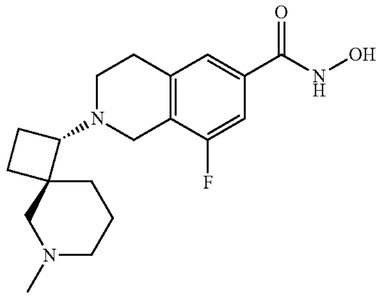

-continued
365
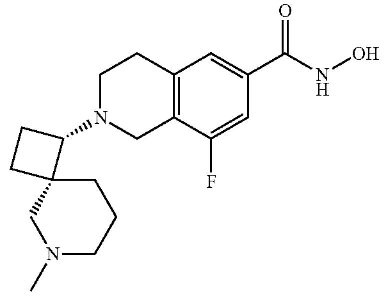
366
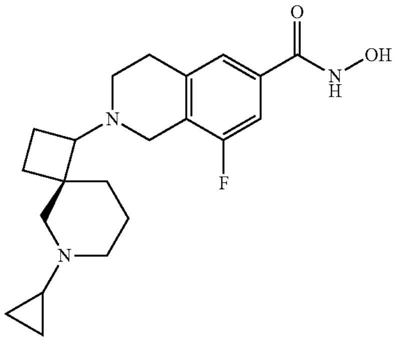
367
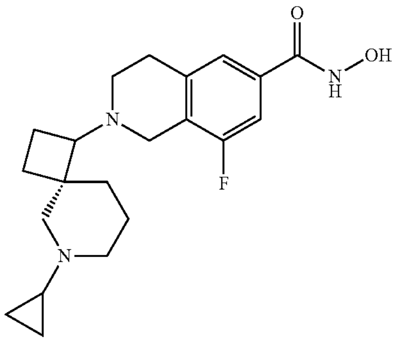
368
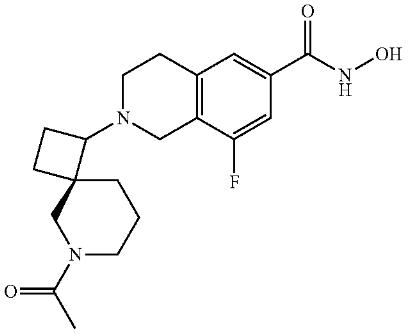
-continued
369
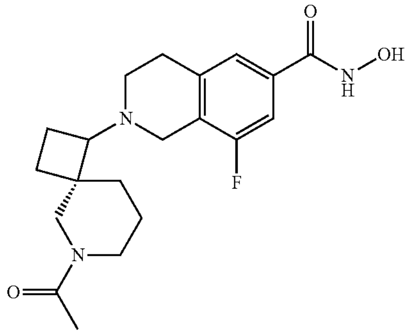
370
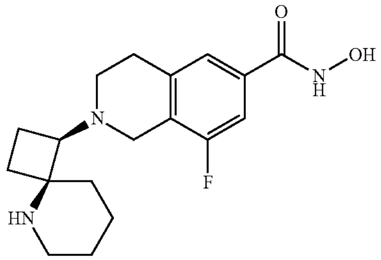
371
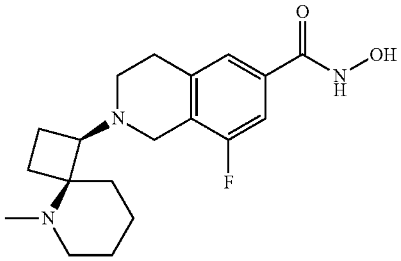
372
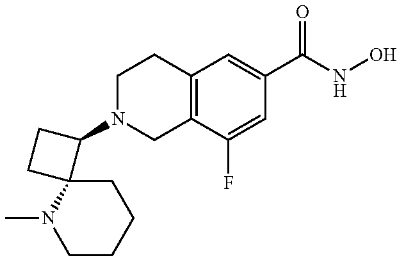
373
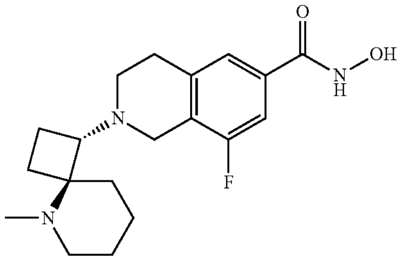

-continued
374
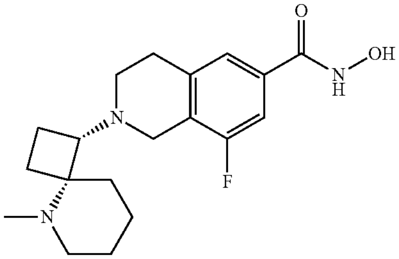
375
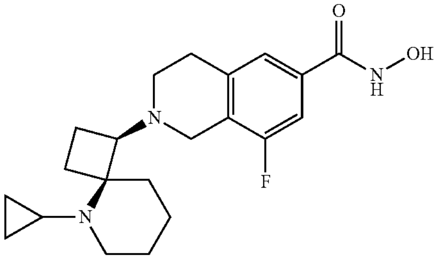
376
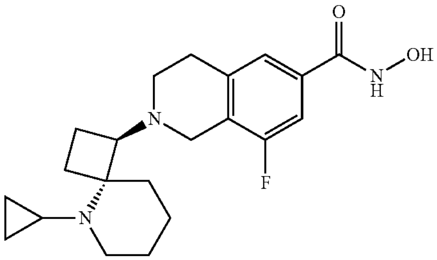
377
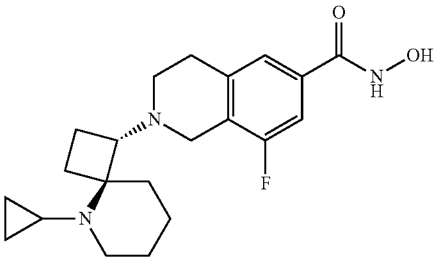
378
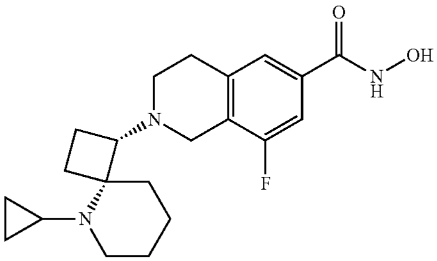
379
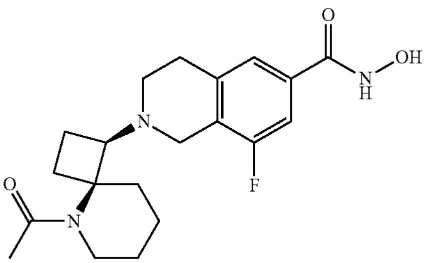
-continued
380
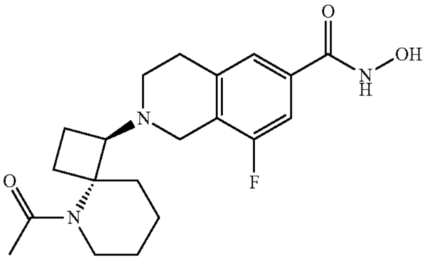
381
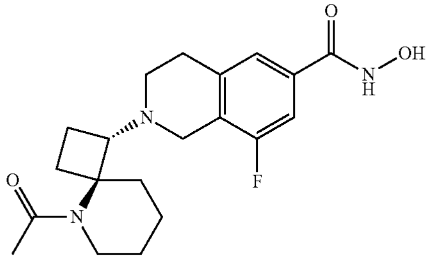
382
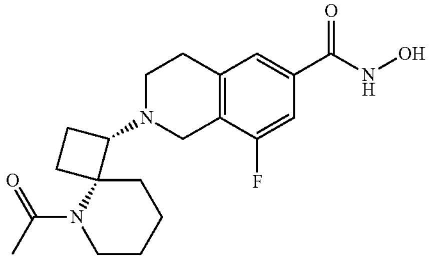
383
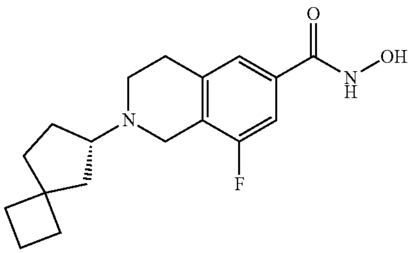
384
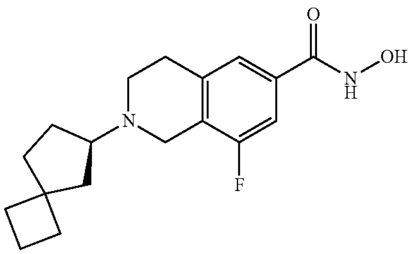
385
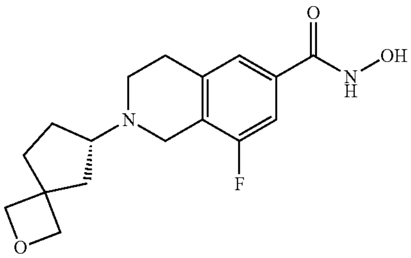

-continued
386
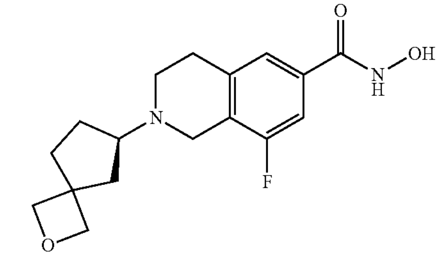
387
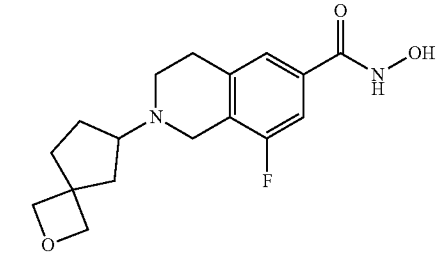
388
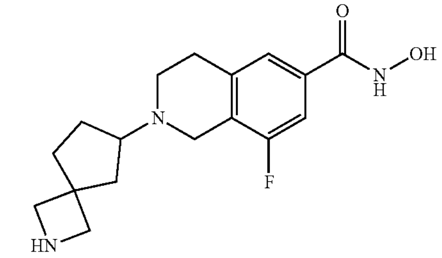
390
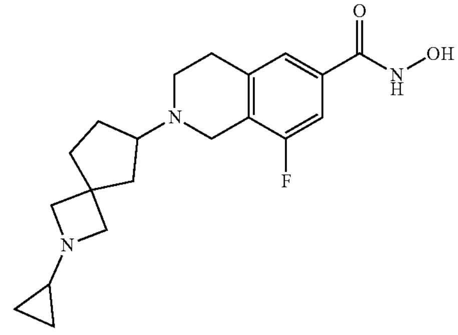
391
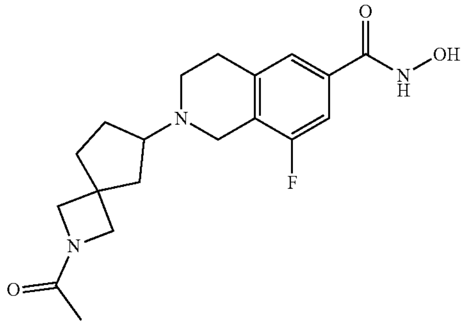
-continued
392
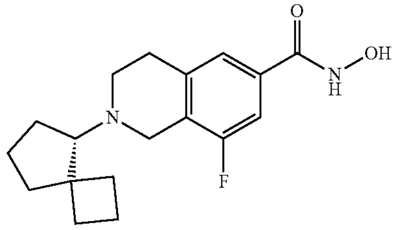
393
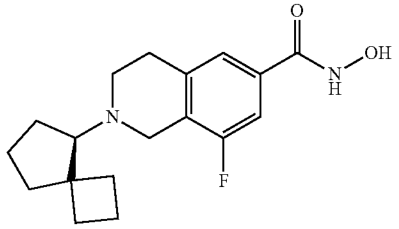
394
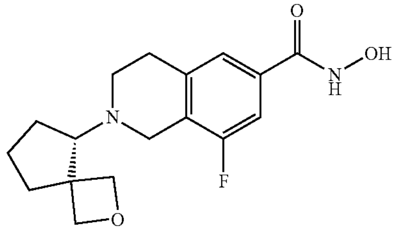
395
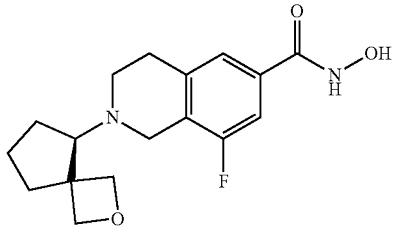
396
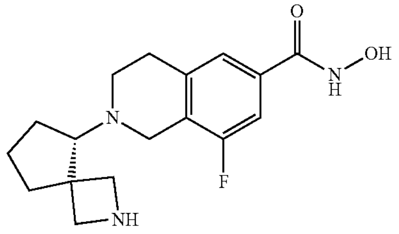
397
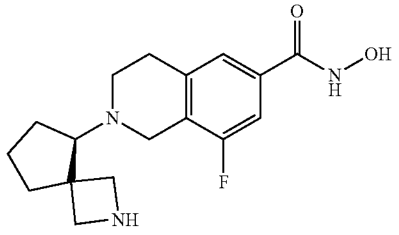

-continued
398
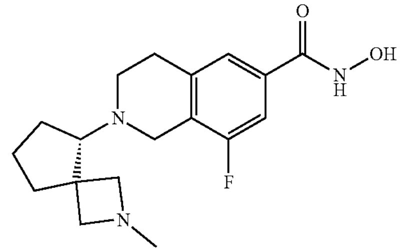
399
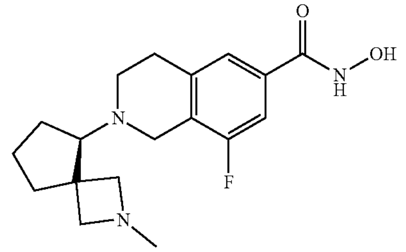
400
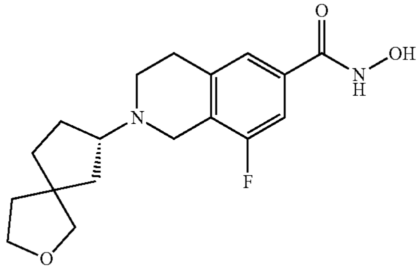
401
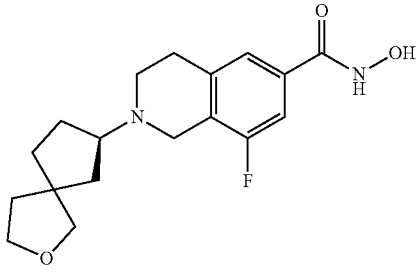
402
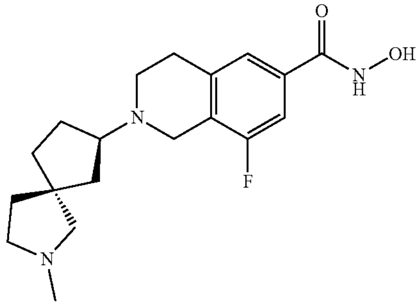
-continued
403
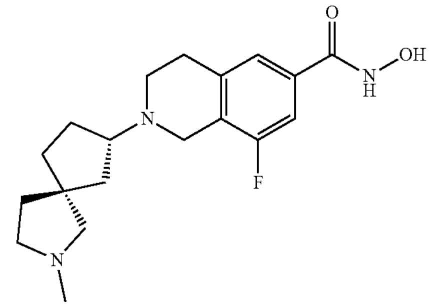
404
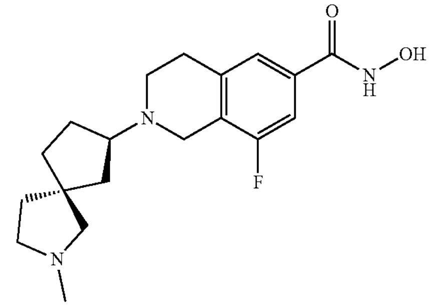
405
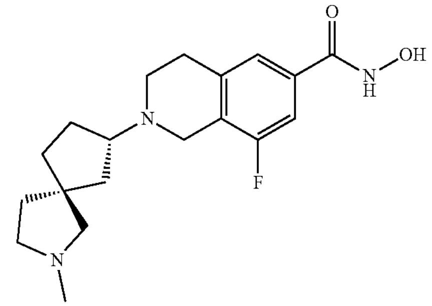
406
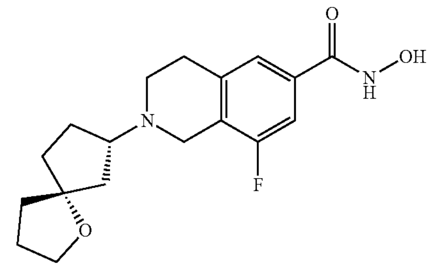
407
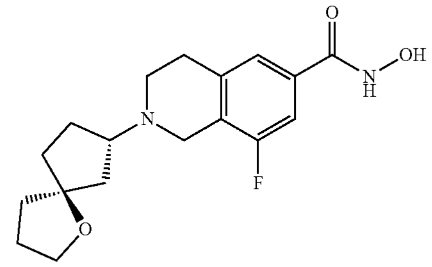

-continued
408
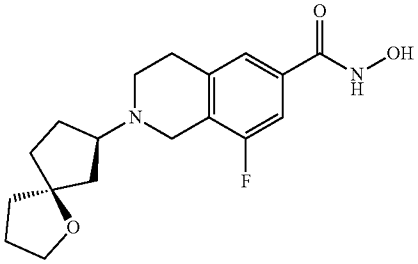
409
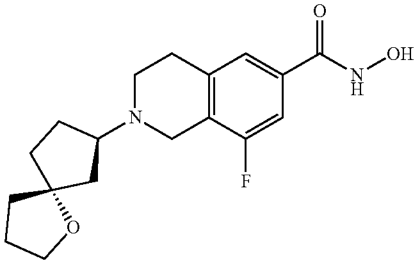
410
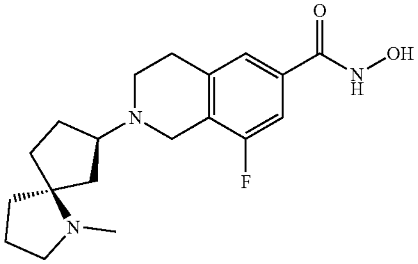
411
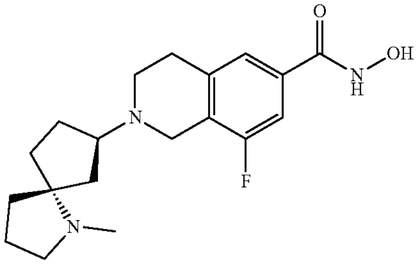
412
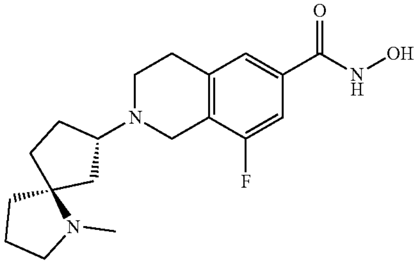
413
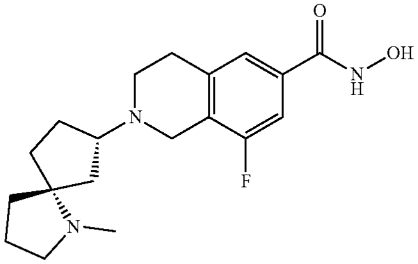
-continued
414
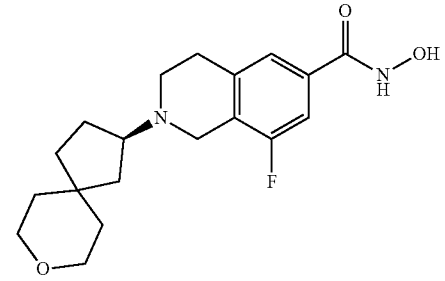
415
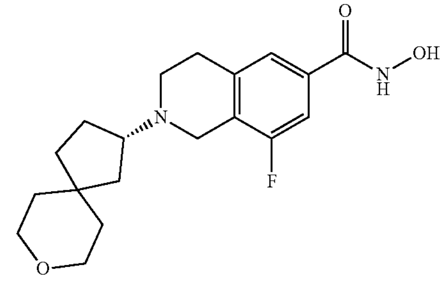
416
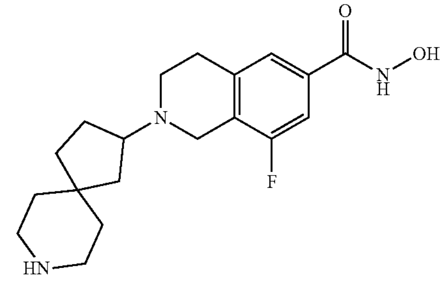
417
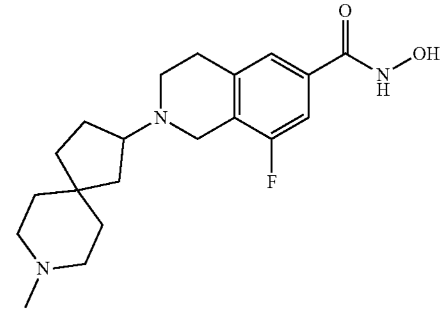
418
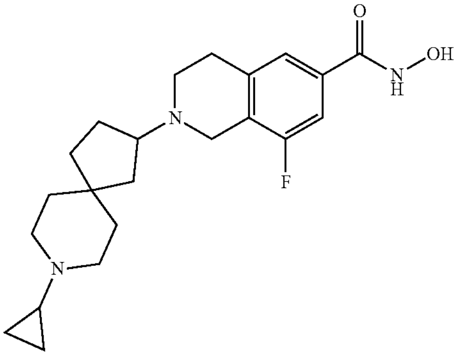

-continued
420
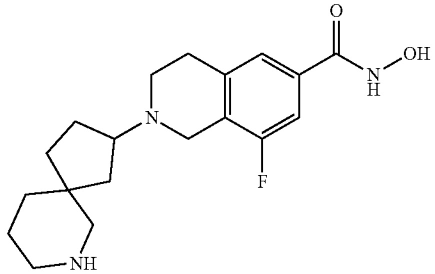
421
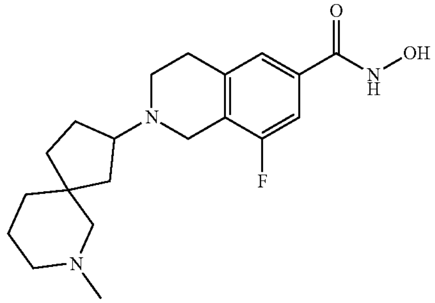
422
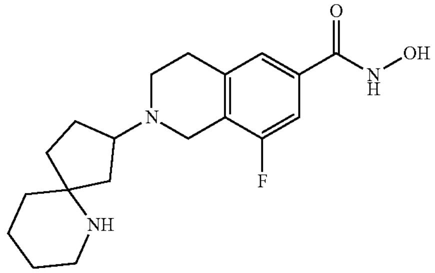
423
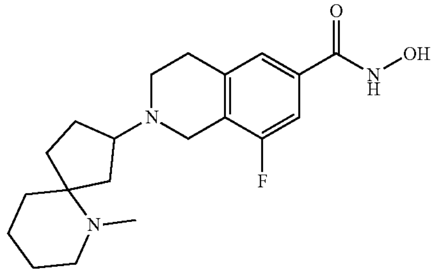
425
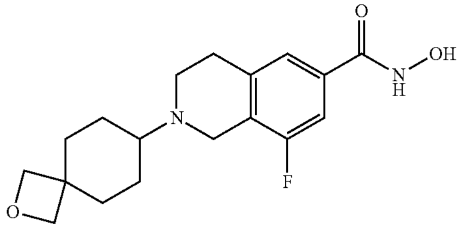
427
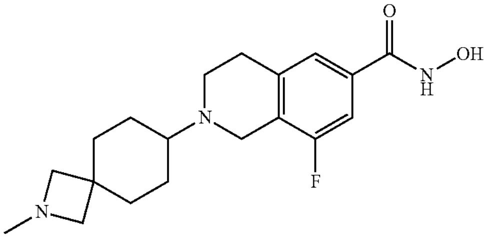
-continued
428
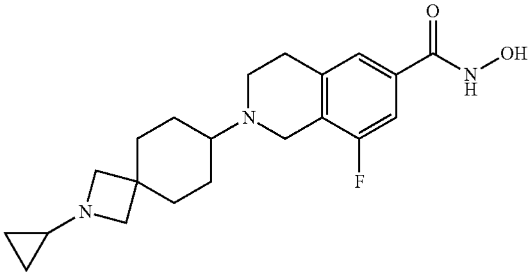
429
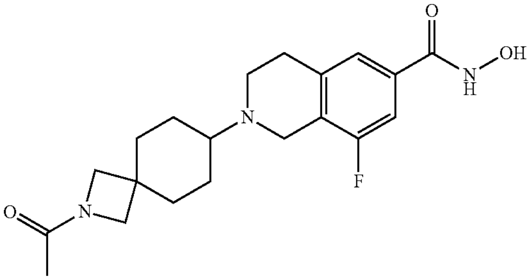
430
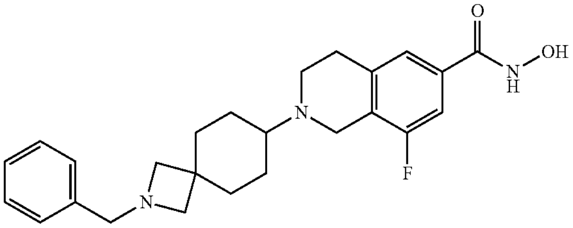
431
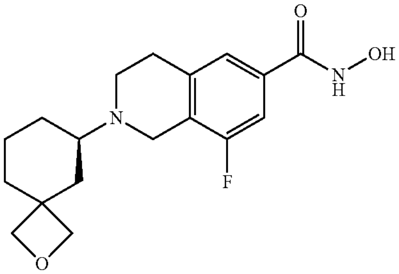
432
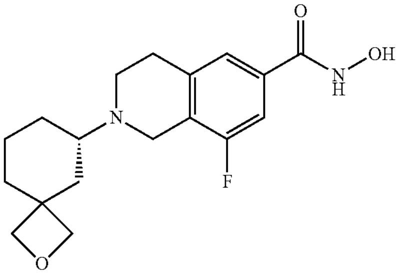

-continued
433
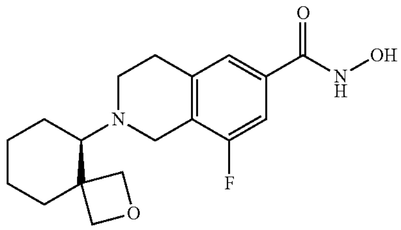
434
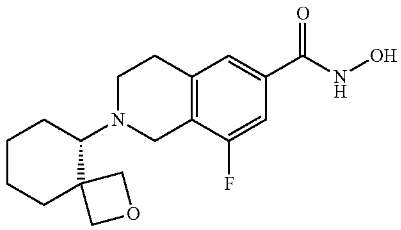
438
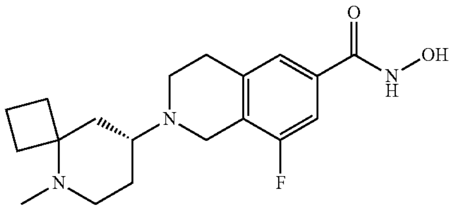
441
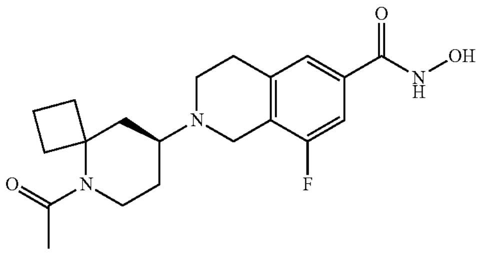
442
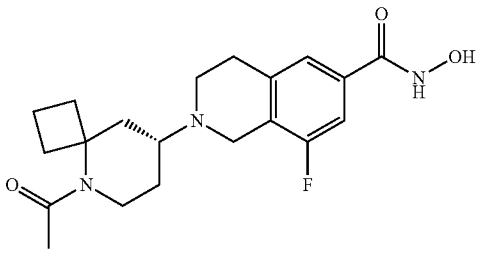
443
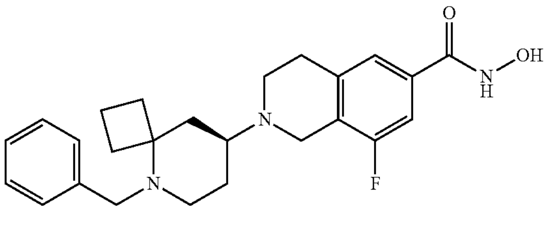
-continued
444
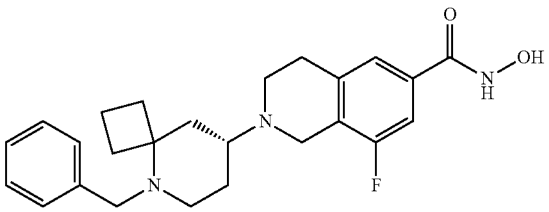
445
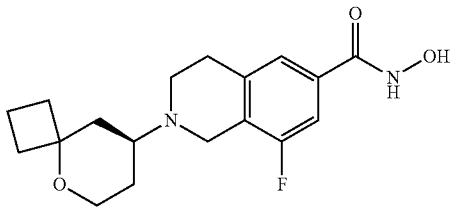
446
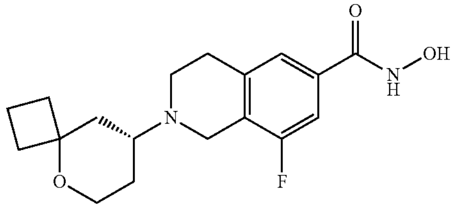
447
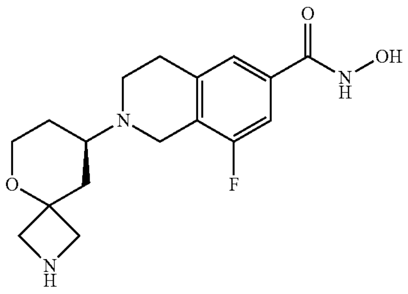
448
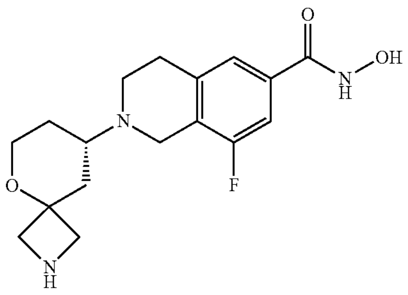
449
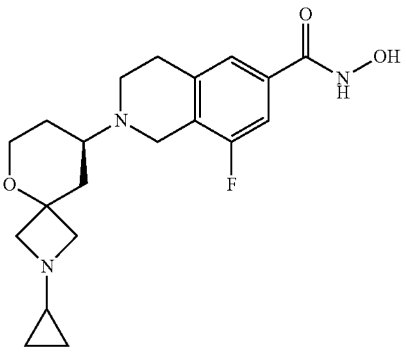

-continued
450
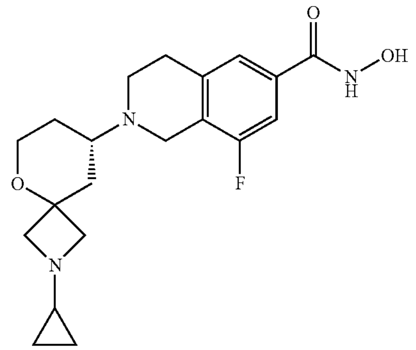
452
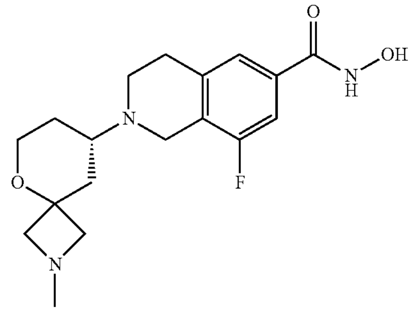
455
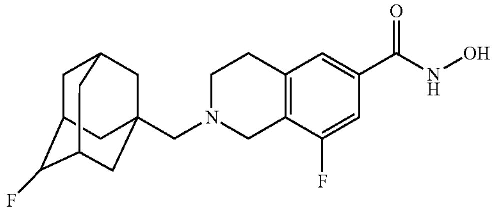
456
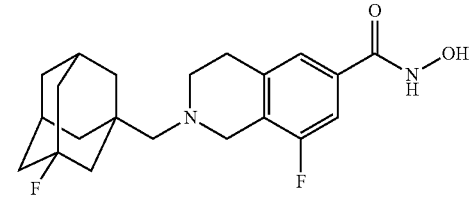
457
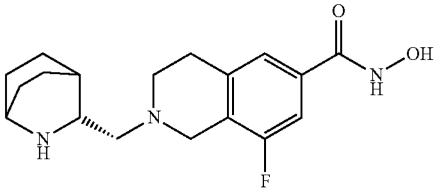
458
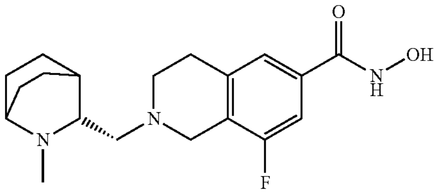
-continued
459
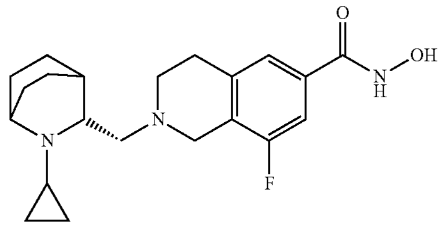
460
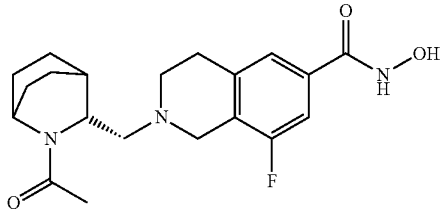
462
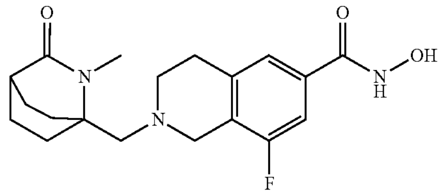
463
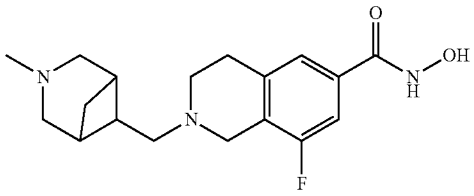
464
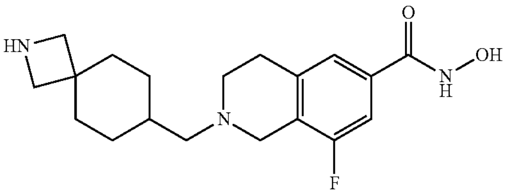
465
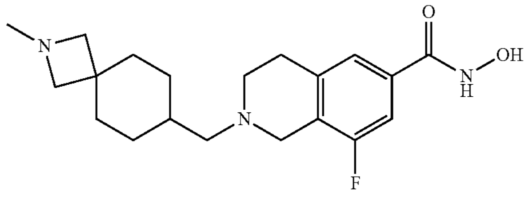
466
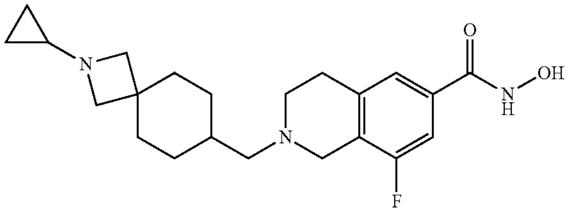

-continued
467
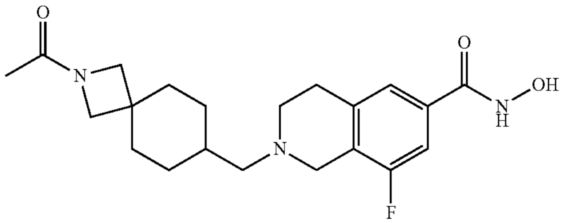
468
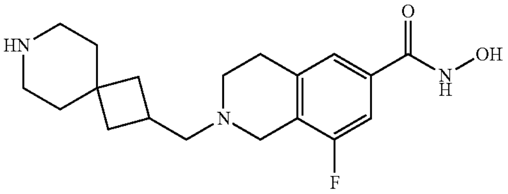
470
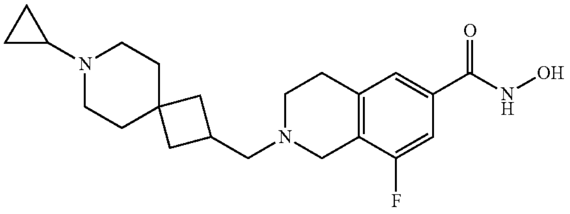
471
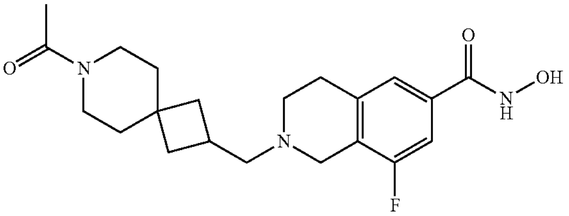
472
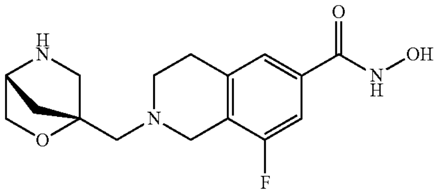
473
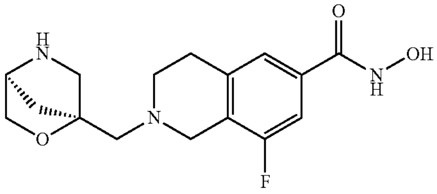
474
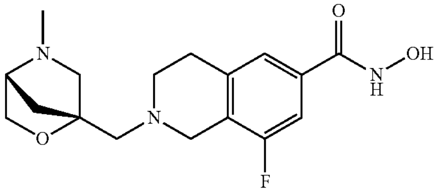
-continued
476
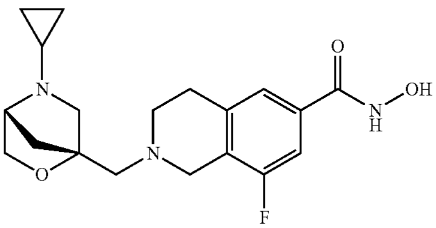
477
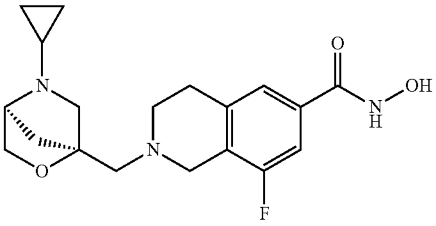
478
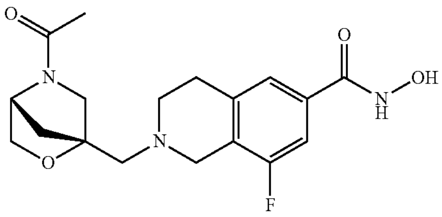
479
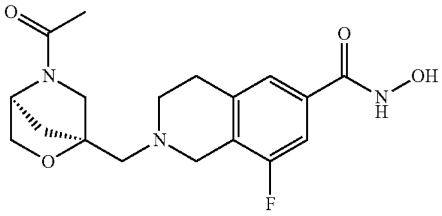
480
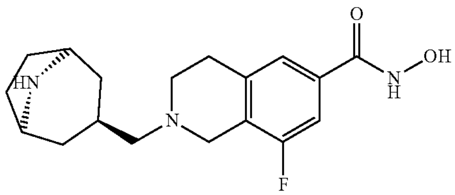
481
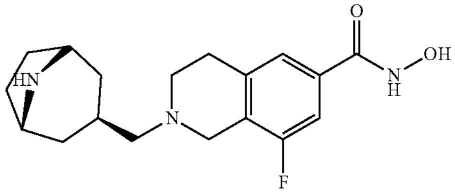
484
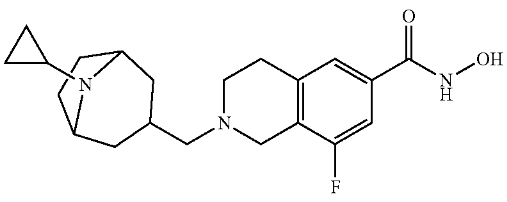

-continued
485
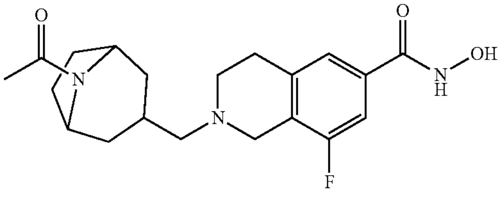
486
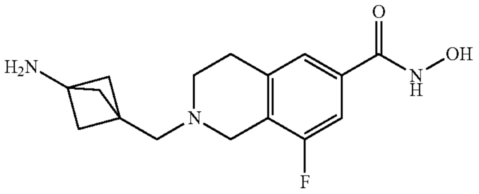
487
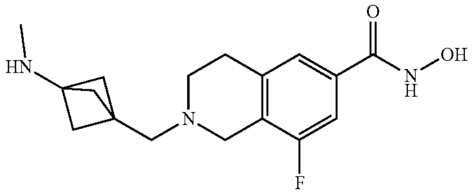
488
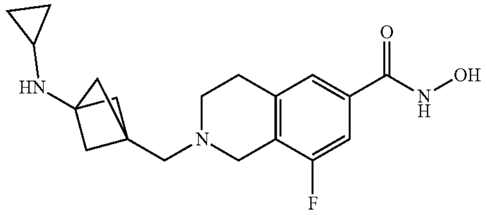
489
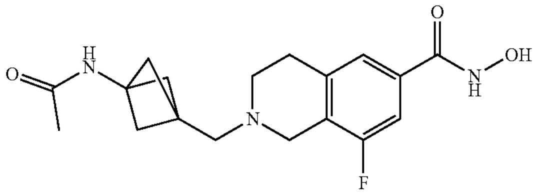
491
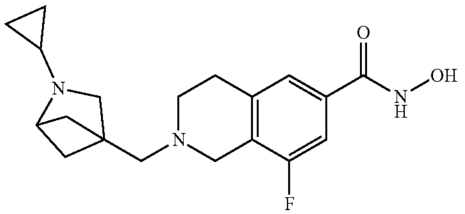
492
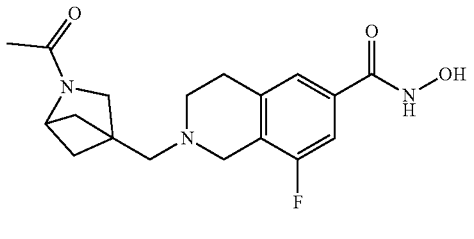
-continued
493
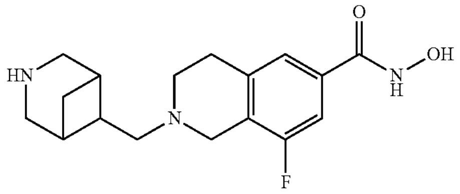
494
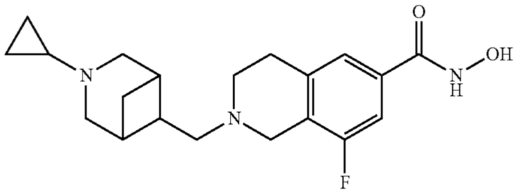
495
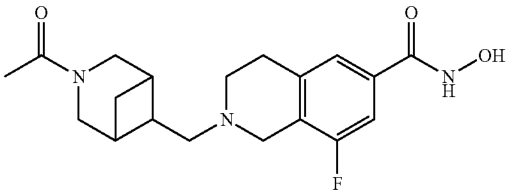
496
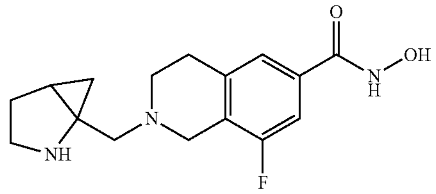
497
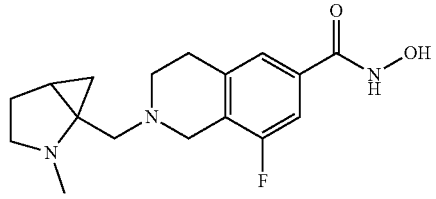
498
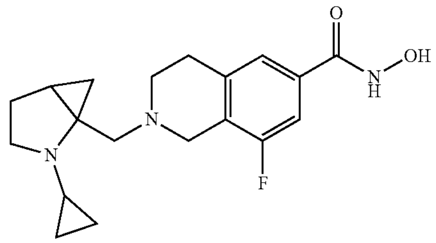
499
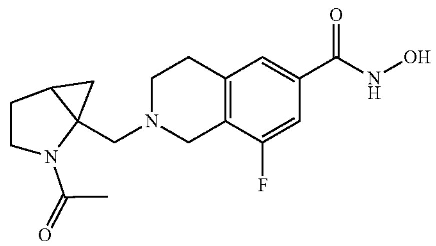

-continued
501
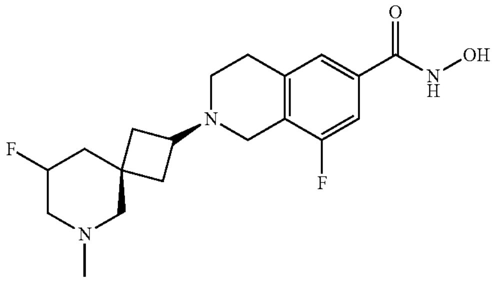
502
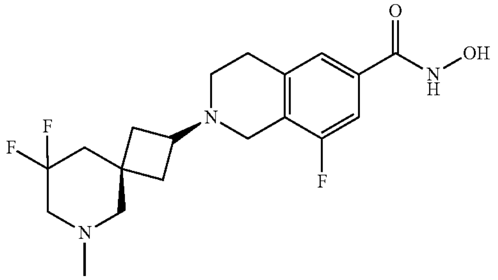
503
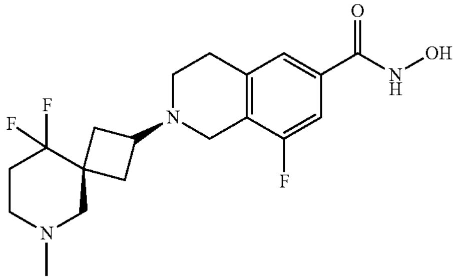
504
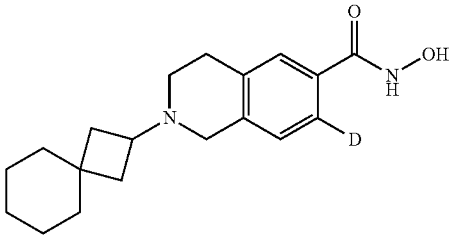
505
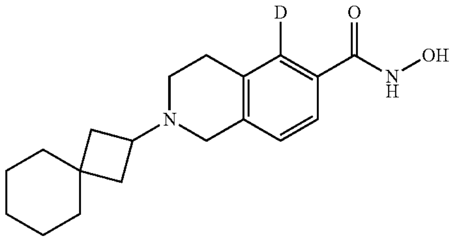
506
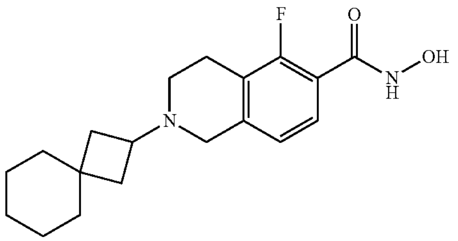
-continued
604
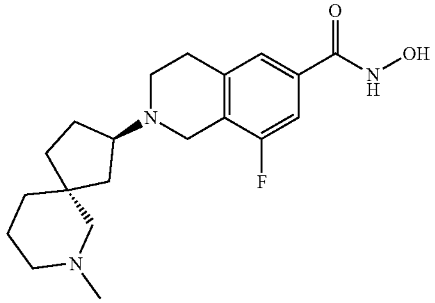
605
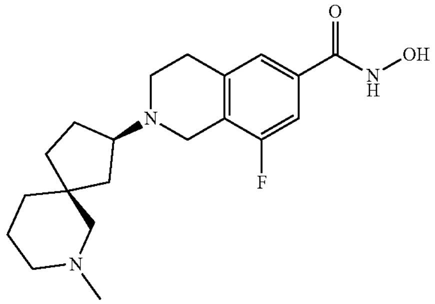
606
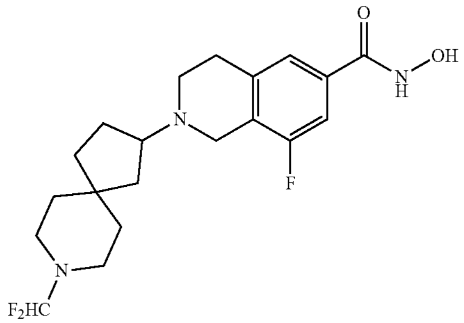
607
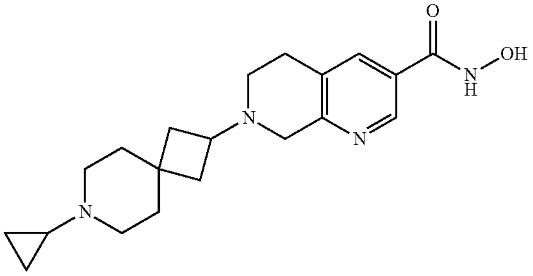
658
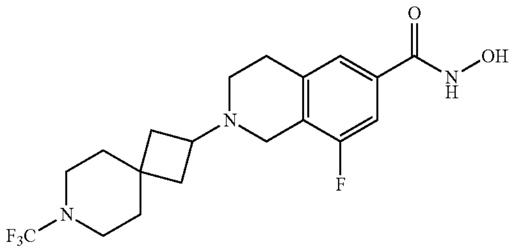

-continued

659

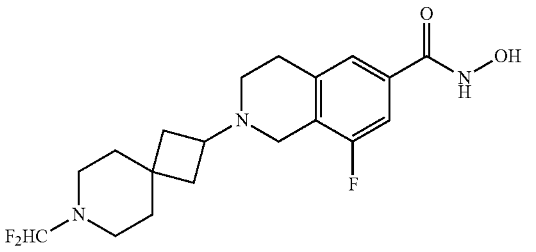

660

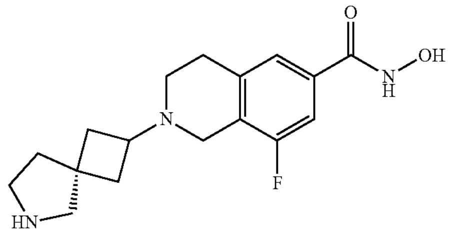

and pharmaceutically acceptable salts thereof.

In another aspect, provided are compounds of Formula (II):

(II)

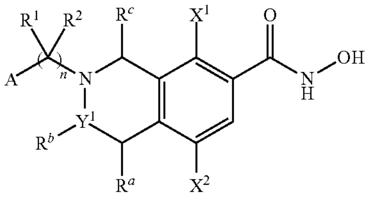

or a pharmaceutically acceptable salt thereof, wherein:

$X^1$ is hydrogen or fluoro;

$X^2$ is hydrogen or fluoro;

$Y^1$ is nitrogen or $CR^x$;

each A is independently hydrogen, substituted or unsubstituted alkyl, substituted or unsubstituted carbocyclyl, substituted or unsubstituted heterocyclyl, substituted or unsubstituted heteroaryl, or substituted or unsubstituted aryl;

each $R^1$ is independently hydrogen or substituted or unsubstituted alkyl;

each $R^2$ is independently hydrogen or substituted or unsubstituted alkyl; or $R^1$ and $R^2$ together form a substituted or unsubstituted heterocyclyl, or a substituted or unsubstituted cycloalkyl;

$R^x$ is hydrogen or substituted or unsubstituted alkyl;

$R^a$ is hydrogen or is joined with $R^c$ to form a substituted or unsubstituted bridged ring;

$R^b$ is hydrogen, substituted or unsubstituted alkyl, or $A(CR^1R^2)_n$—, or is joined with $R^c$ to form a substituted or unsubstituted bridged ring;

$R^c$ is hydrogen or substituted or unsubstituted alkyl or is joined with at least one of $R^a$ and $R^b$ to form a substituted or unsubstituted bridged ring; and each n is independently 0 or 1, provided that the compound is not of formula:

115

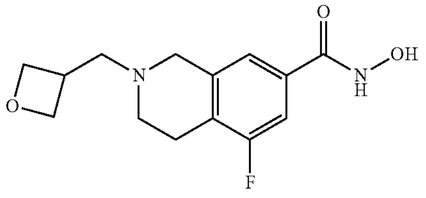

114

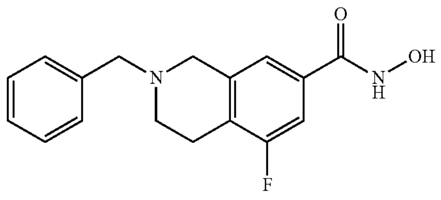

113

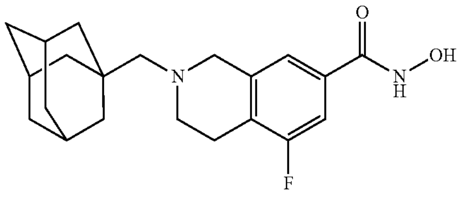

39

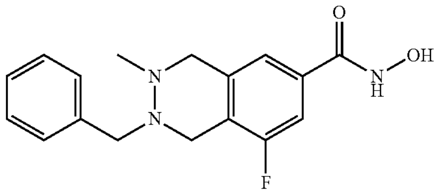

117

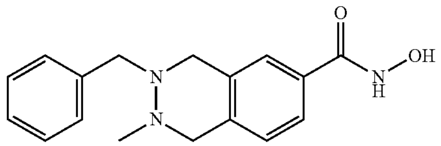

41

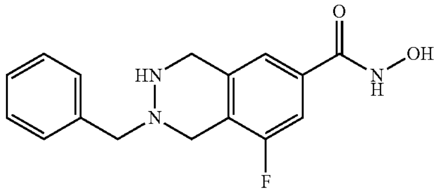

42

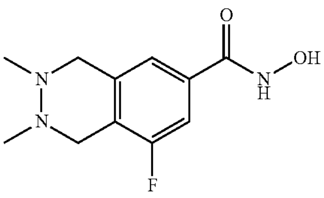

43

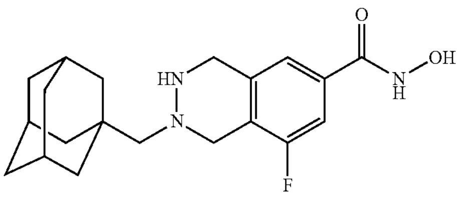

-continued
44
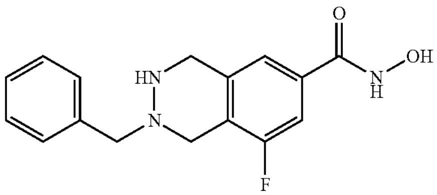
116
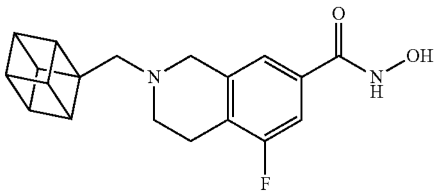
118
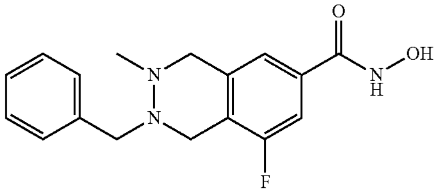
Exemplary compounds of Formula (II) include, but are not limited to:
230
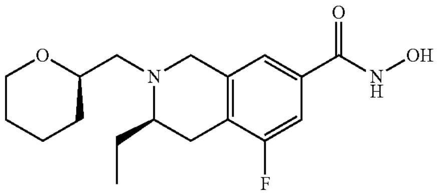
231
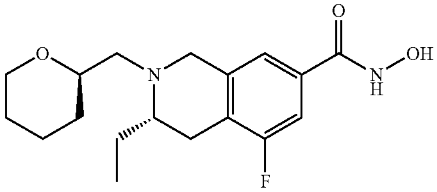
510
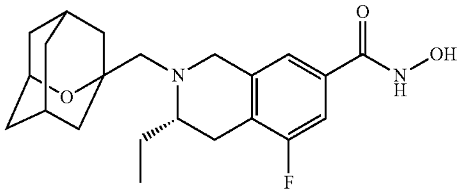
522
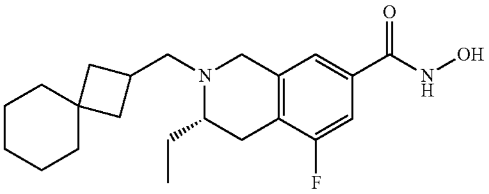
-continued
535
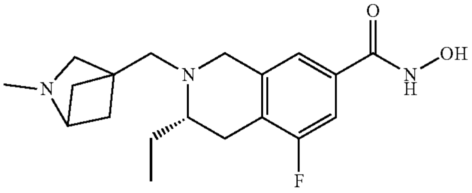
554
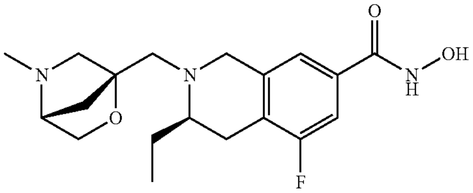
570
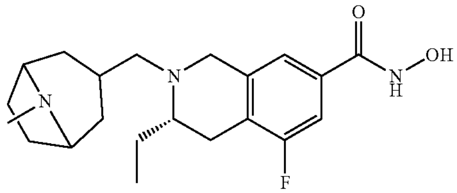
572
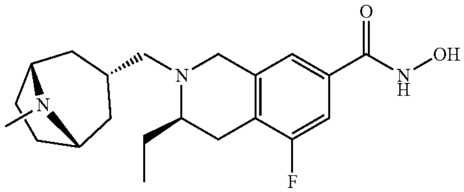
573
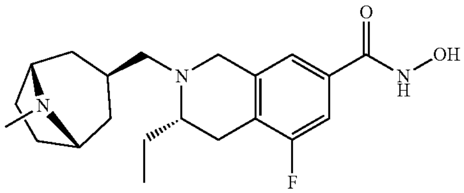
594
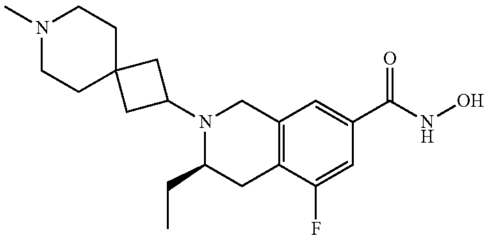
and pharmaceutically acceptable salts thereof.
Exemplary compounds of Formula (II) also include, but are not limited to:
213
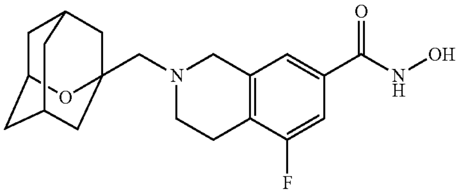

-continued
214
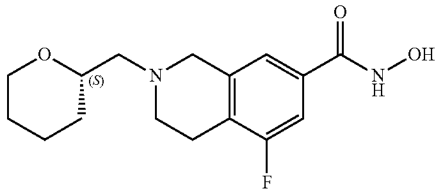
215
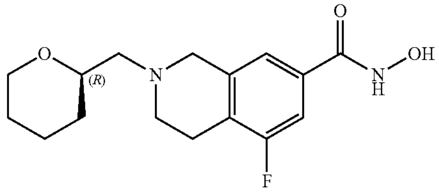
216
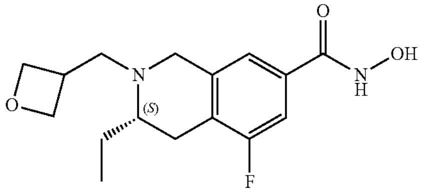
217
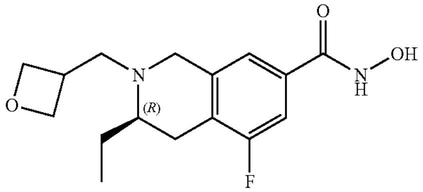
218
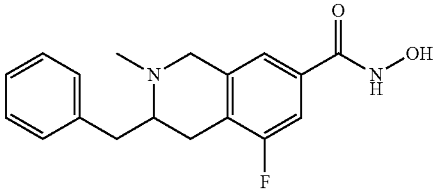
219
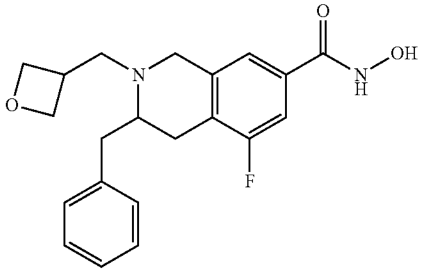
220
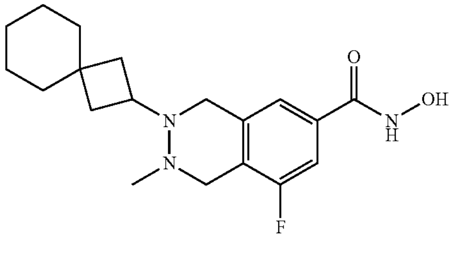
-continued
221
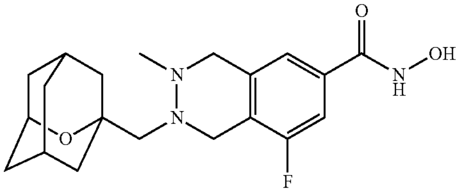
222
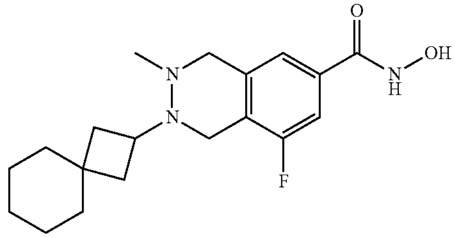
223
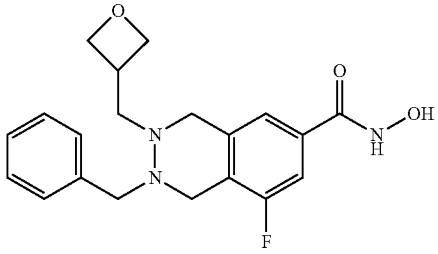
224
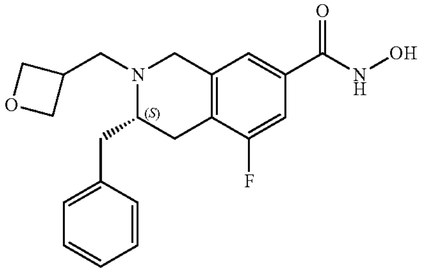
225
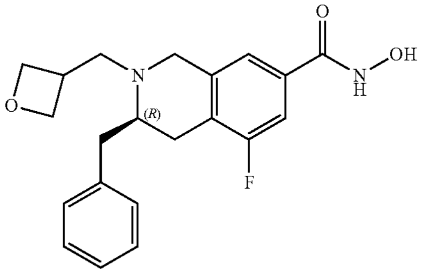
226
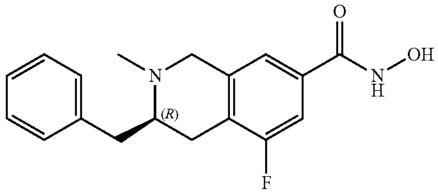

-continued
227
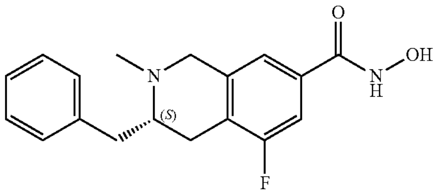
228
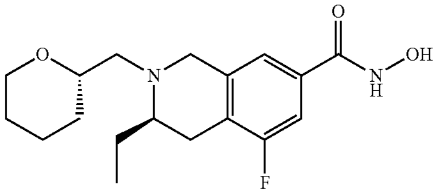
229
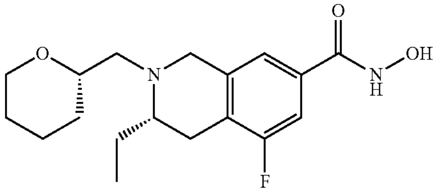
232
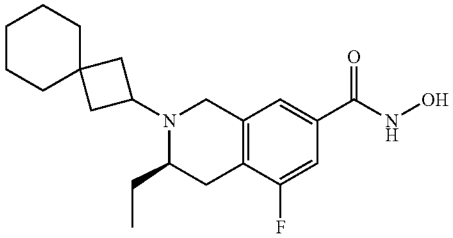
233
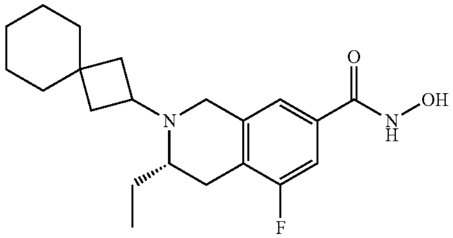
234
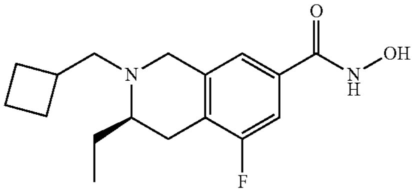
235
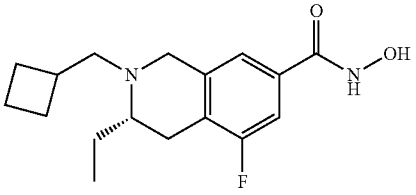
-continued
236
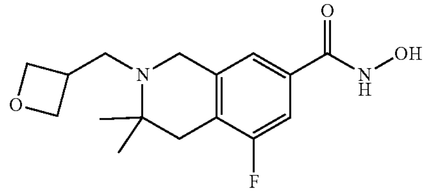
507
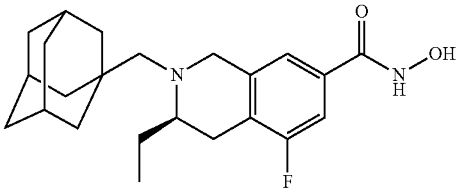
508
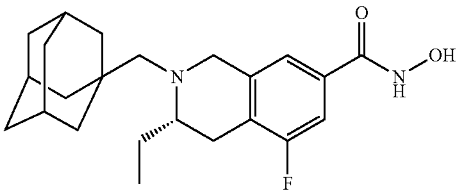
509
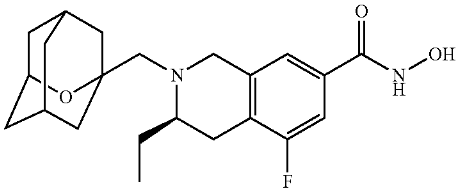
511
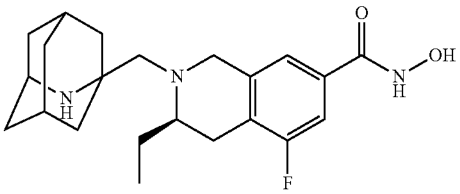
512
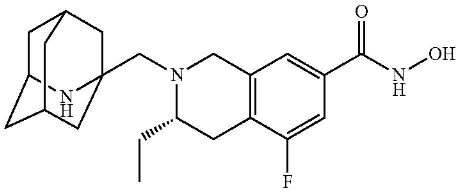
513
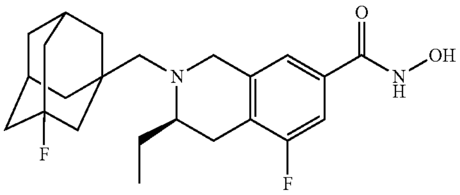
514
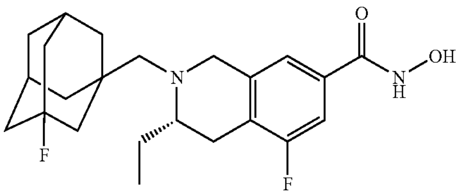

-continued
515
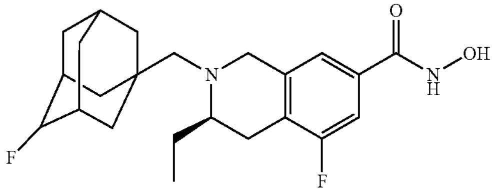
516
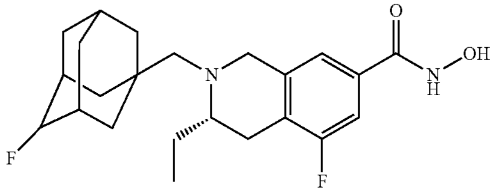
517
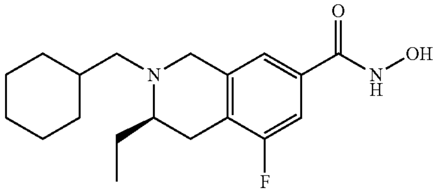
518
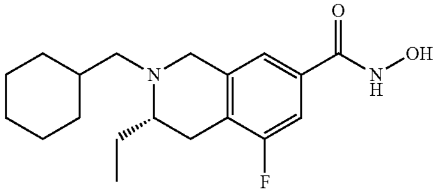
519
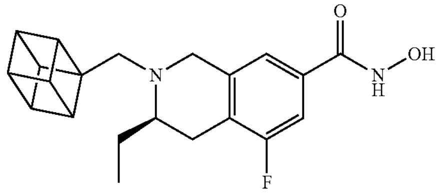
520
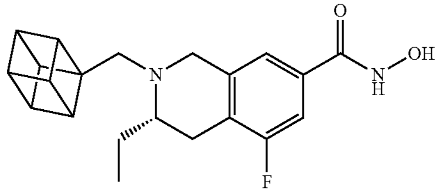
521
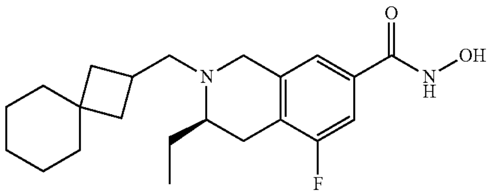
523
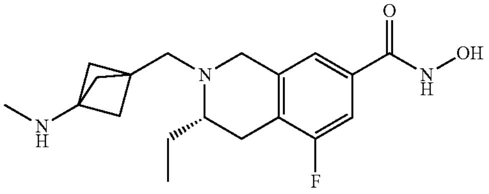
-continued
524
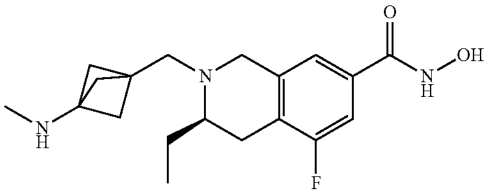
525
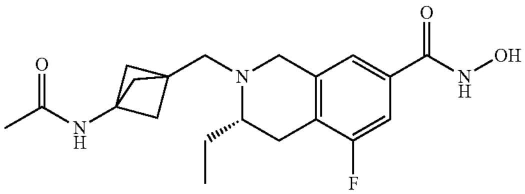
526
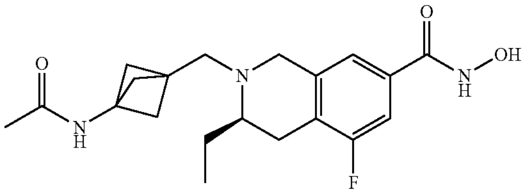
527
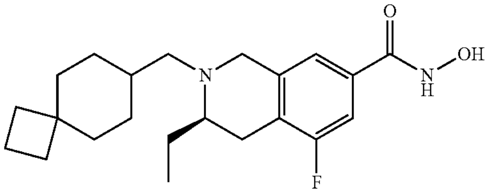
528
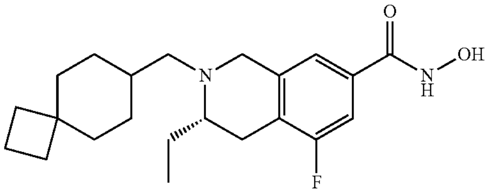
529
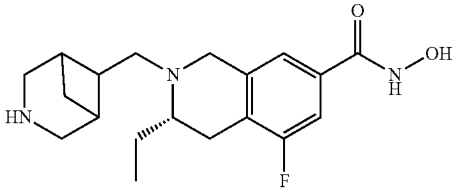
530
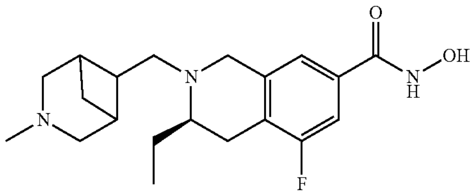

-continued
531
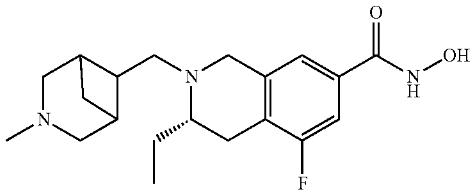
532
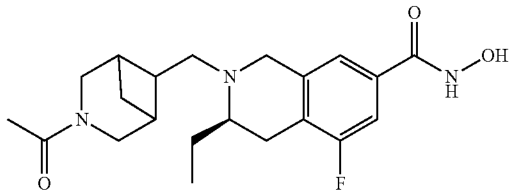
533
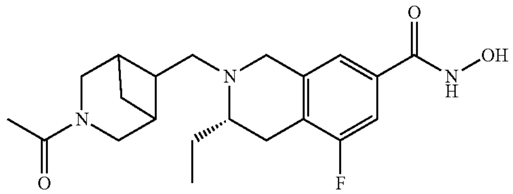
534
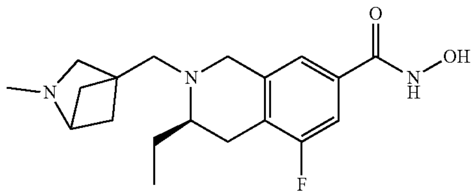
536
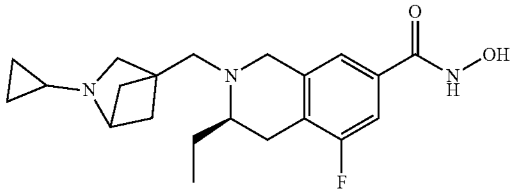
537
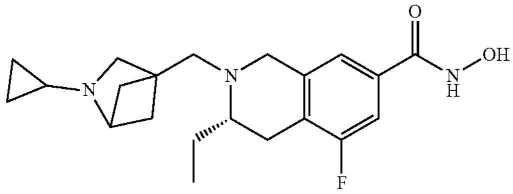
538
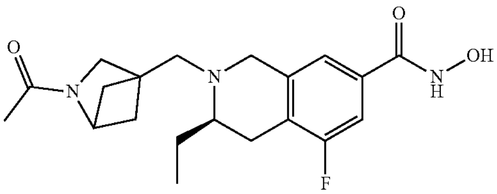
-continued
539
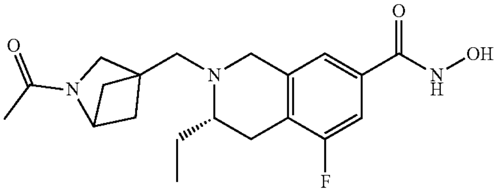
540
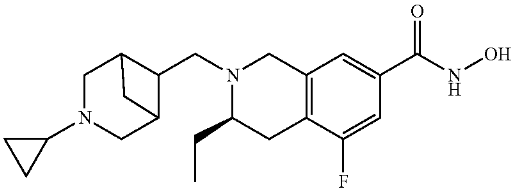
541
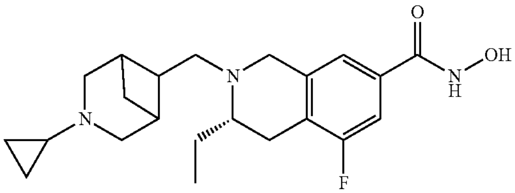
542
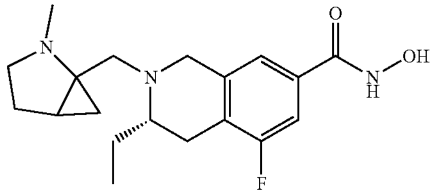
543
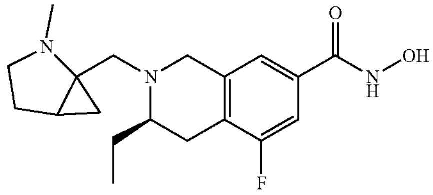
544
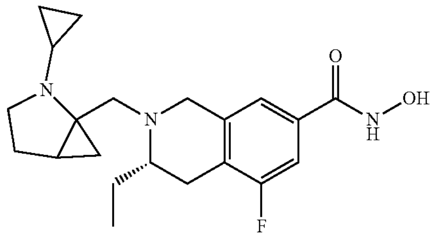
545
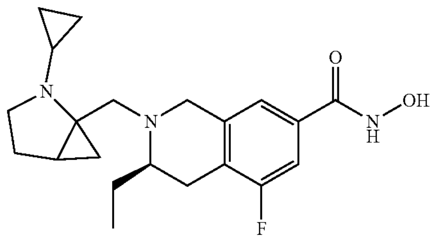

-continued
546
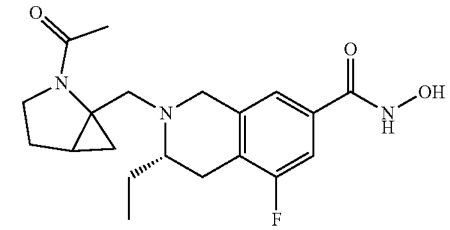
547
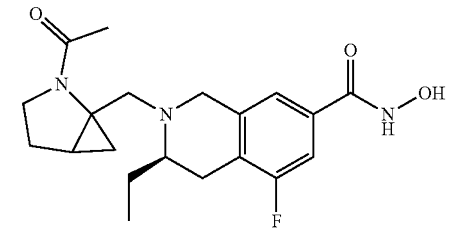
548
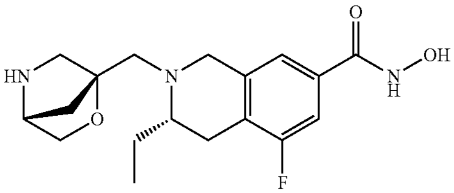
549
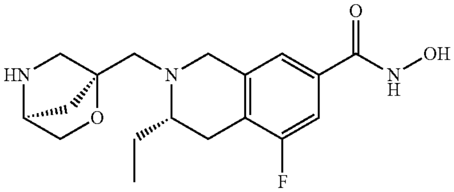
550
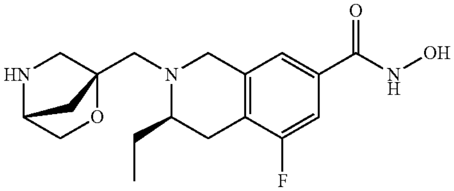
551
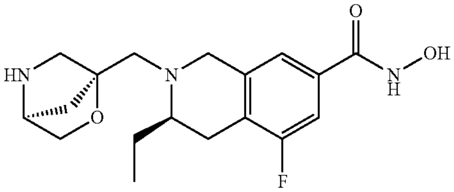
552
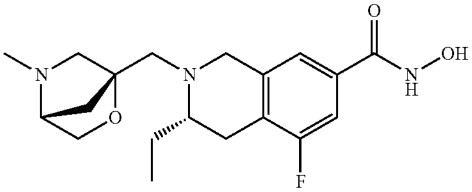
-continued
553
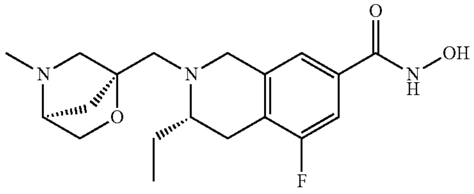
555
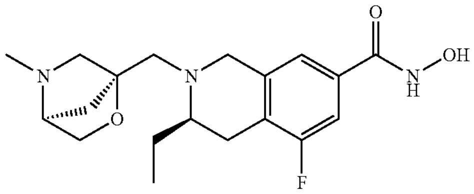
556
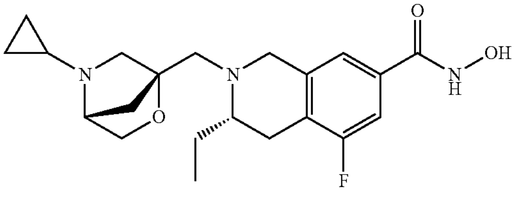
557
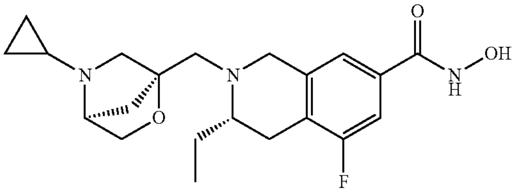
558
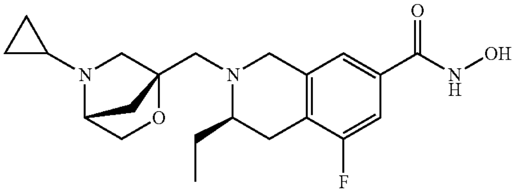
559
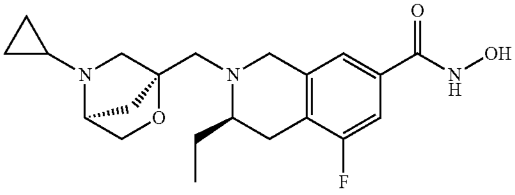
560
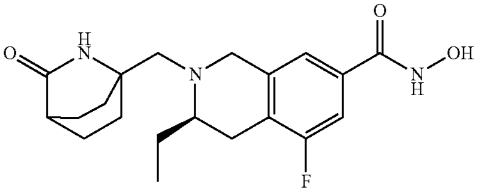

-continued
561
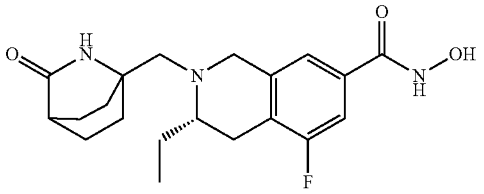
562
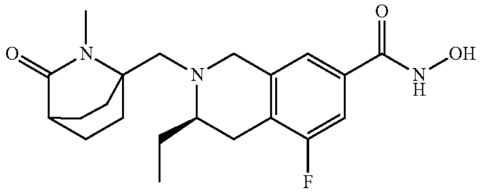
563
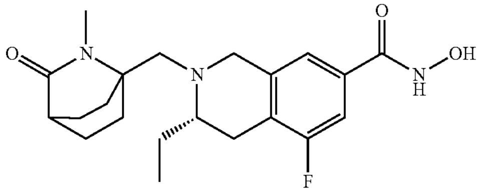
564
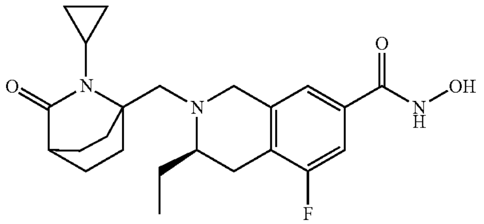
565
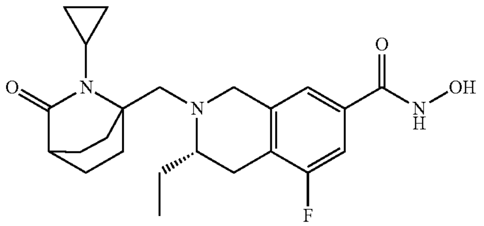
566
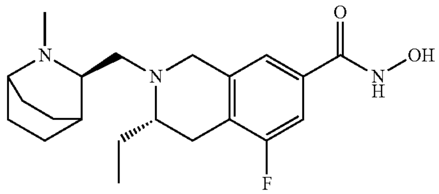
567
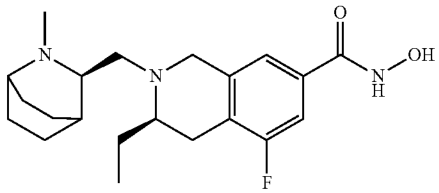
-continued
568
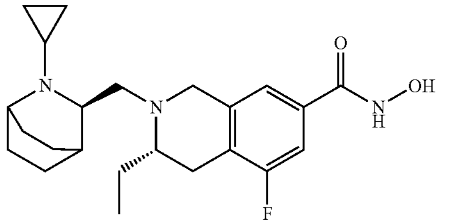
569
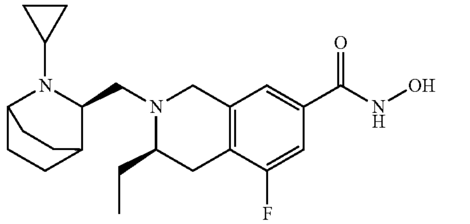
571
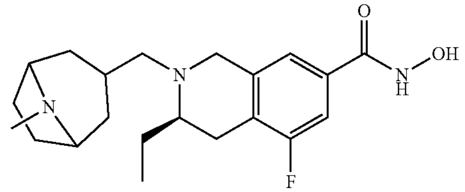
574
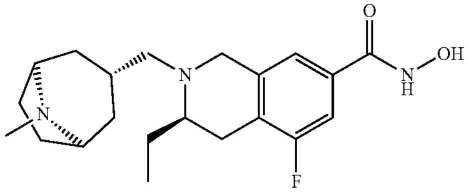
575
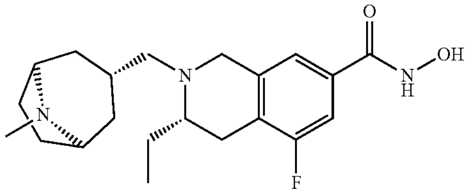
576
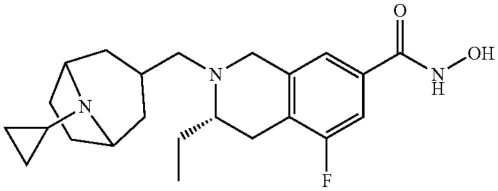
577
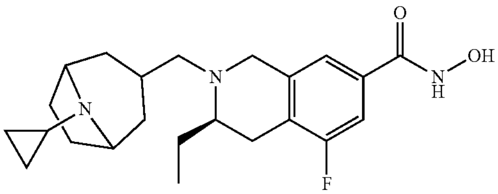

-continued
578
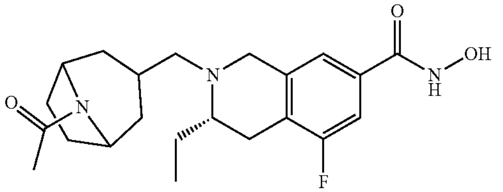
579
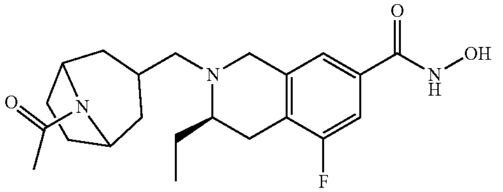
580
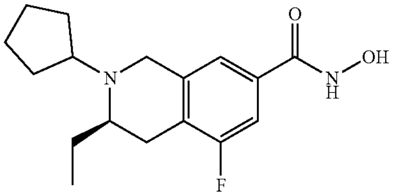
581
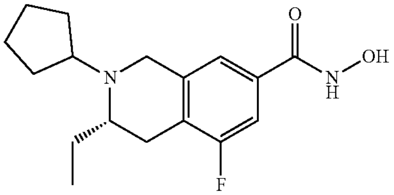
582
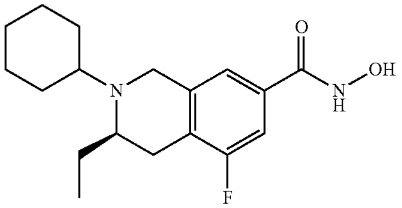
583
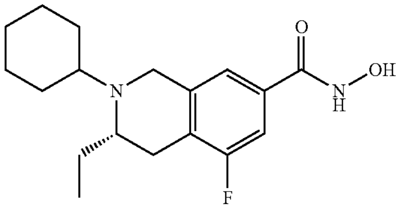
584
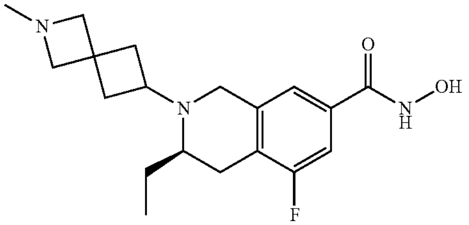
-continued
585
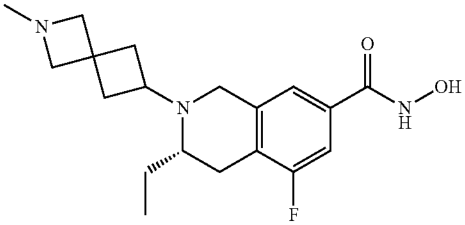
586
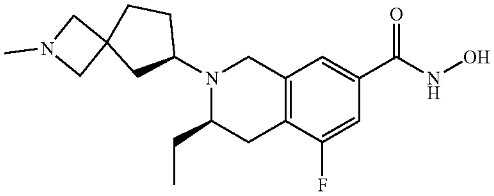
587
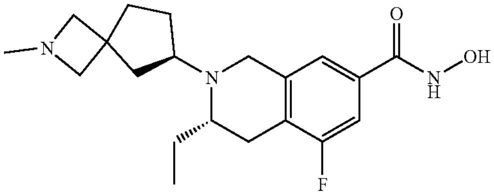
588
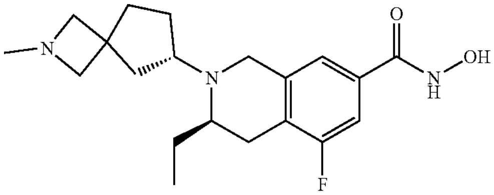
589
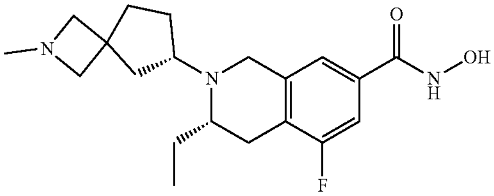
590
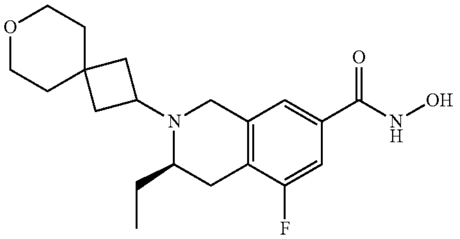
591
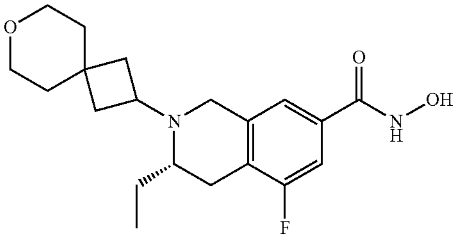

-continued
592
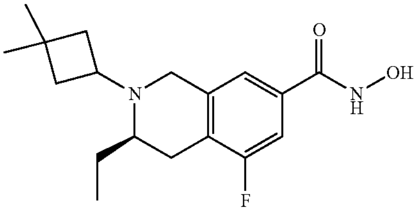
593
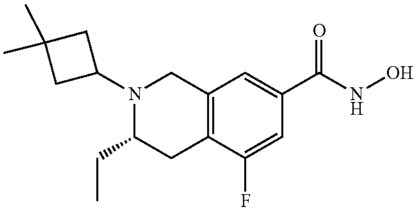
595
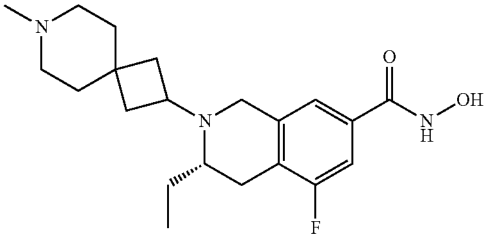
596
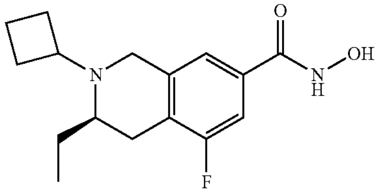
597
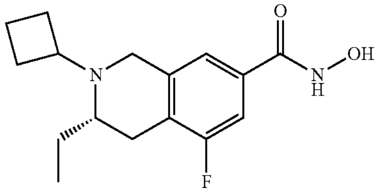
598
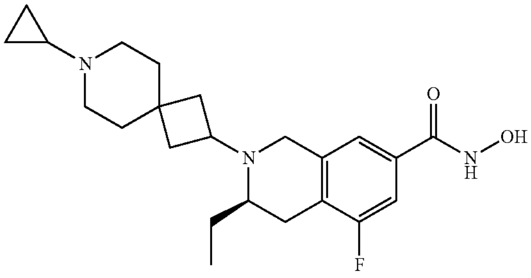
-continued
599
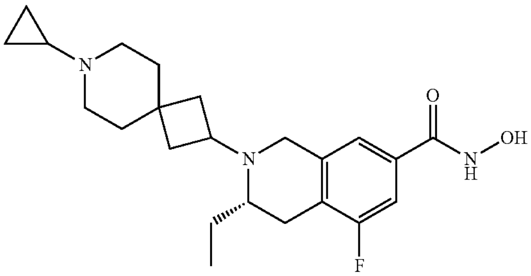
600
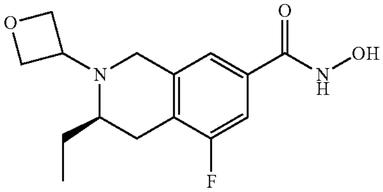
601
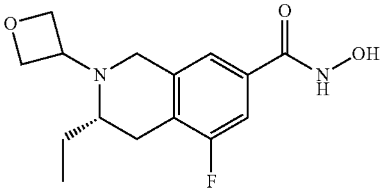
602
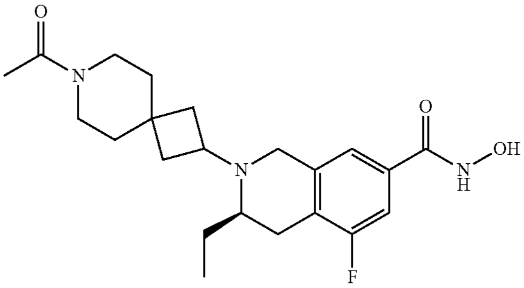
603
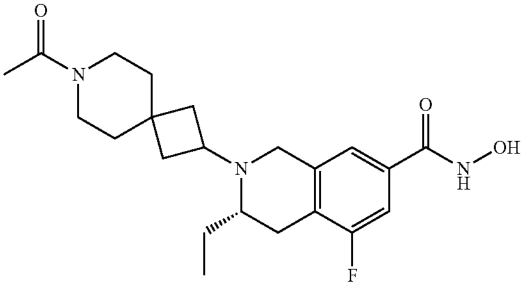
and pharmaceutically acceptable salts thereof.
In another aspect, provided are compounds of Formula (III):

(III)

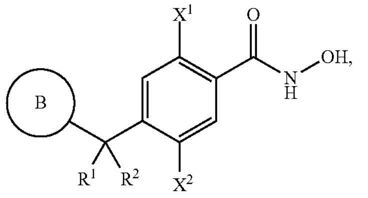

and pharmaceutically acceptable salts, co-crystals, tautomers, stereoisomers, solvates, hydrates, polymorphs, isotopically enriched derivatives, or prodrugs thereof, wherein:

$X^1$ is hydrogen or fluoro;

$X^2$ is hydrogen or fluoro;

$R^1$ is hydrogen or substituted or unsubstituted alkyl;

$R^2$ is hydrogen or substituted or unsubstituted alkyl; or $R^1$ and $R^2$ together form a substituted or unsubstituted heterocyclyl, or a substituted or unsubstituted cycloalkyl; and B is a substituted or unsubstituted polycyclic spiro ring system, a substituted or unsubstituted bridged ring system,

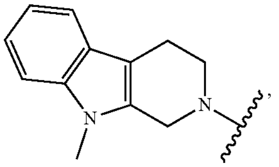
,
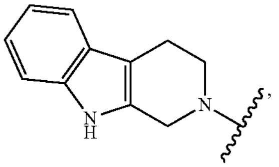
,
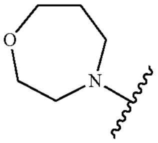
,
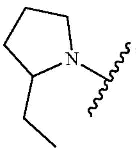
, or
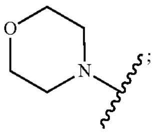
;

provided that the compound is not of formula:

45

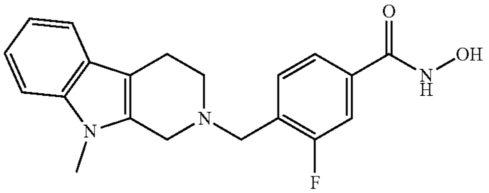

46

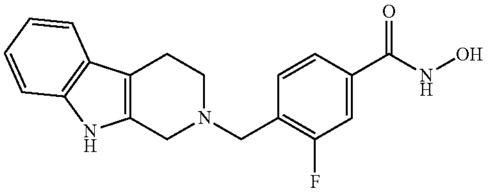

-continued

47

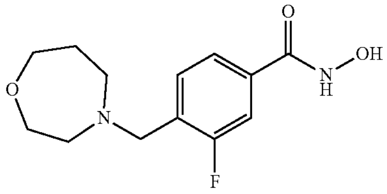

48

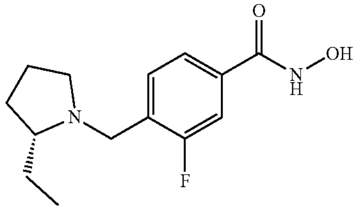

49

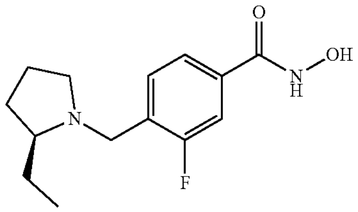

50

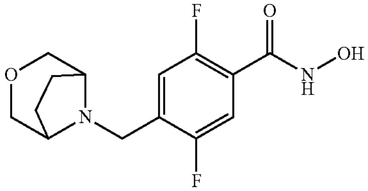

51

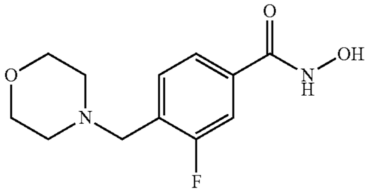

52

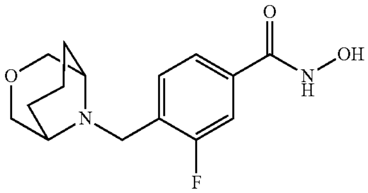

53

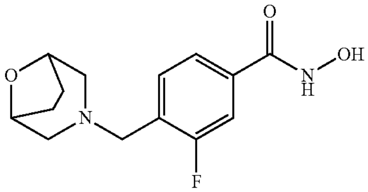

-continued
54
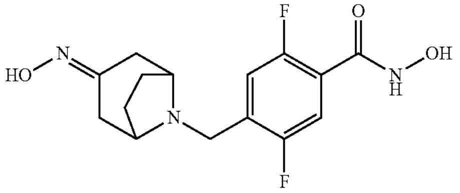
55
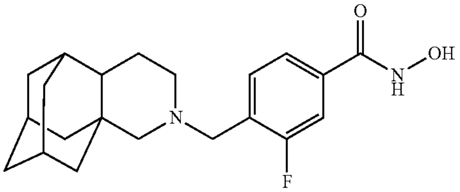
56
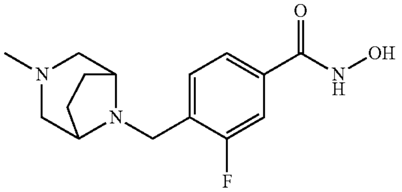
57
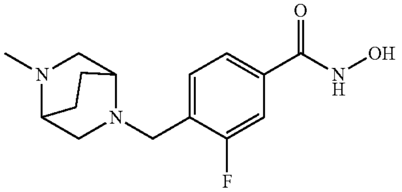
58
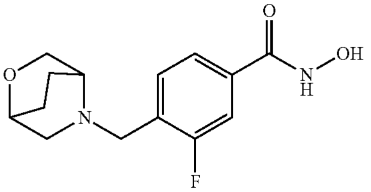
59
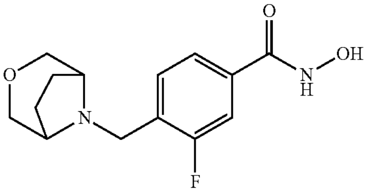
60
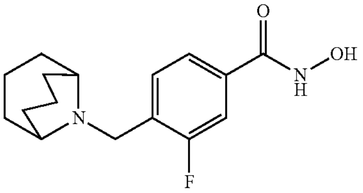
61
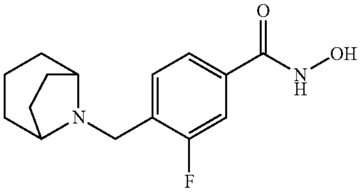
-continued
62
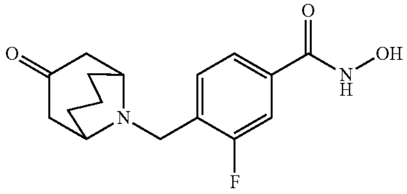
63
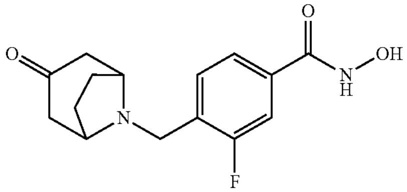
64
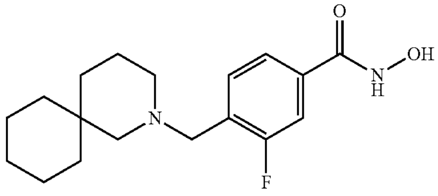
169
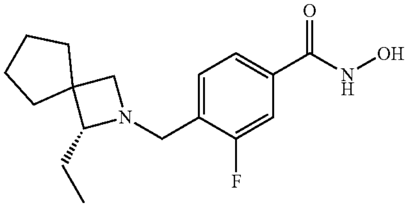
172
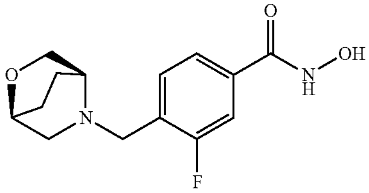
173
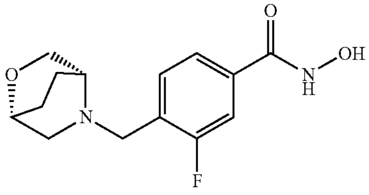
64
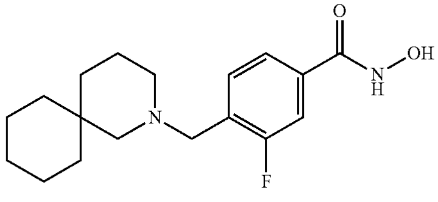

-continued
169
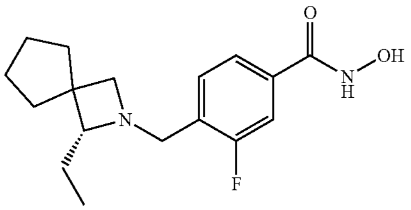
168
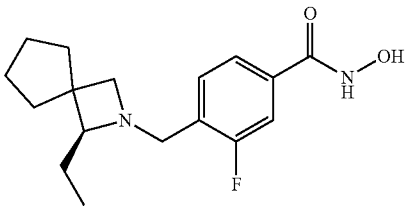
67
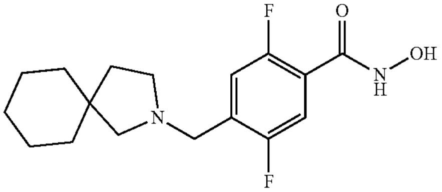
68
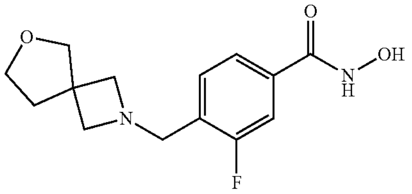
69
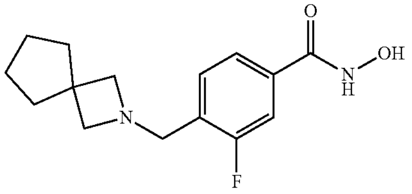
70
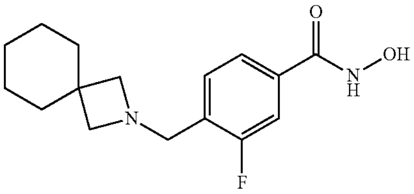
71
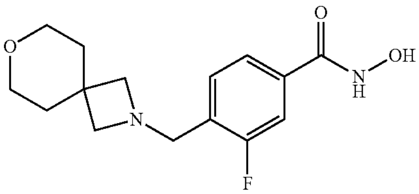
-continued
72
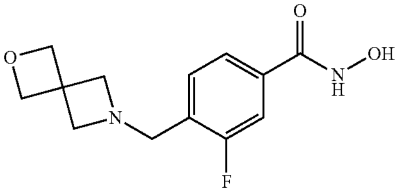
73
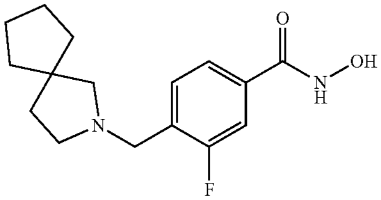
74
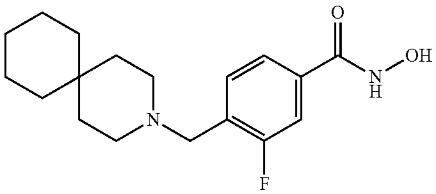
75
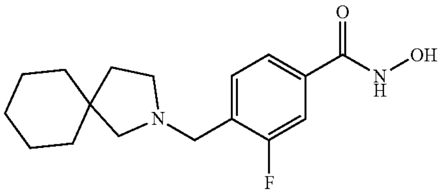
167
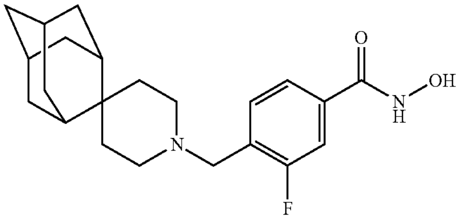
77
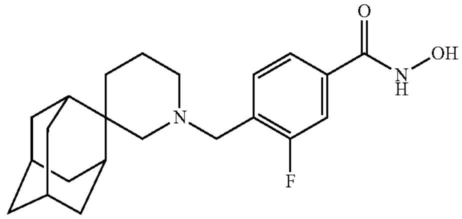
78
or
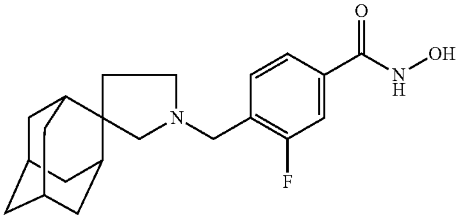
In certain embodiments, the compounds of Formula (III) are compounds of Formula (IV):

(IV)

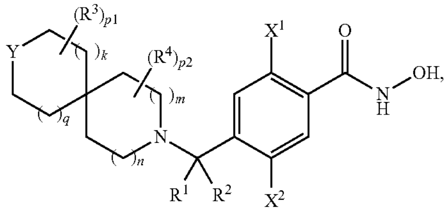

and pharmaceutically acceptable salts, co-crystals, tautomers, stereoisomers, solvates, hydrates, polymorphs, isotopically enriched derivatives, or prodrugs thereof, wherein:

$X^1$ is hydrogen or fluoro;

$X^2$ is hydrogen or fluoro;

$R^1$ is hydrogen or substituted or unsubstituted alkyl;

$R^2$ is hydrogen or substituted or unsubstituted alkyl; or $R^1$ and $R^2$ together form a substituted or unsubstituted heterocyclyl, or a substituted or unsubstituted cycloalkyl;

Y is —O—, —S—, —$NR^{a1}$—, or —($CR^3R^4$)—;

each occurrence of $R^3$ and $R^4$ is, independently, hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted heteroalkyl, —$N(R^{a1})_2$, —$OR^{b1}$, —$SR^{c1}$, or —CN; wherein two or three $R^3$ groups are optionally joined to form a substituted or unsubstituted bridged ring; wherein two or three $R^4$ groups are optionally joined to form a substituted or unsubstituted bridged ring;

each occurrence of $R^{a1}$ is, independently, hydrogen, substituted or unsubstituted acyl, substituted or unsubstituted alkyl, substituted or unsubstituted heteroalkyl, substituted or unsubstituted carbocyclyl, substituted or unsubstituted heterocyclyl, or a nitrogen protecting group, or two $R^{a1}$ groups are joined to form a substituted or unsubstituted heterocyclic ring;

each occurrence of $R^{b1}$ is, independently, hydrogen, substituted or unsubstituted acyl, substituted or unsubstituted alkyl, substituted or unsubstituted alkenyl, substituted or unsubstituted alkynyl, substituted or unsubstituted heteroalkyl, substituted or unsubstituted carbocyclyl, substituted or unsubstituted heterocyclyl, or an oxygen protecting group;

each occurrence of $R^{c1}$ is, independently, hydrogen, substituted or unsubstituted acyl, substituted or unsubstituted alkyl, substituted or unsubstituted alkenyl, substituted or unsubstituted alkynyl, substituted or unsubstituted heteroalkyl, substituted or unsubstituted carbocyclyl, substituted or unsubstituted heterocyclyl, or a sulfur protecting group;

m, n, k, and q are each independently 0, 1, or 2; and p1 and p2 are each independently 0, 1, 2, 3, or 4; provided that the compound is not of formula:

64

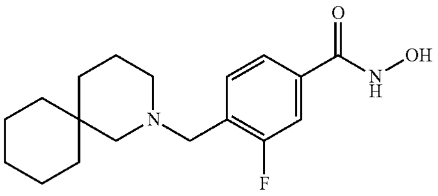

-continued

169

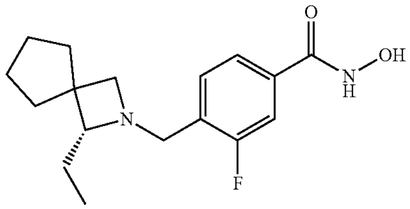

168

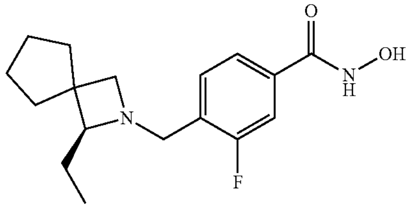

67

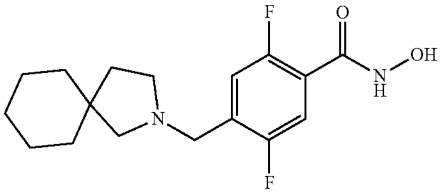

68

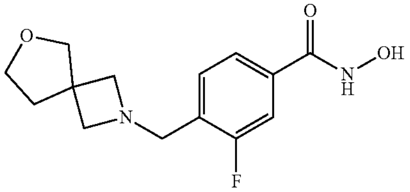

69

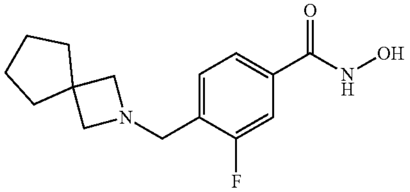

70

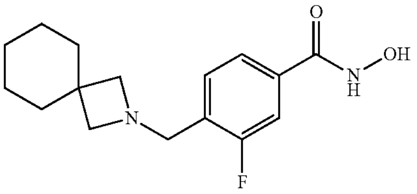

71

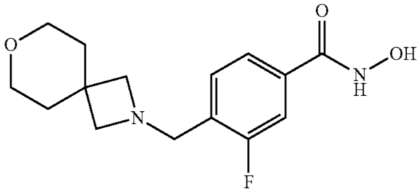

-continued

72

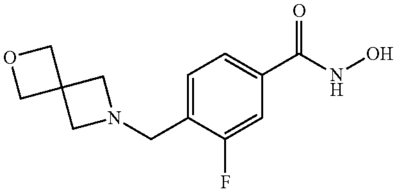

73

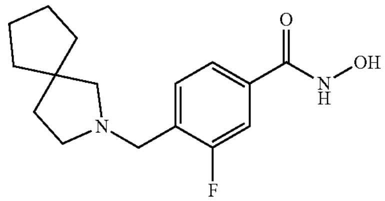

74

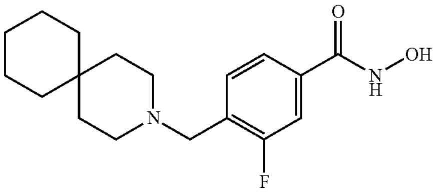

75

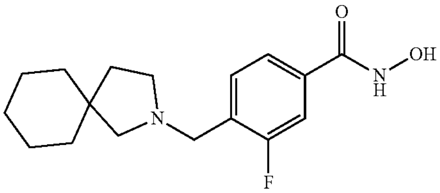

167

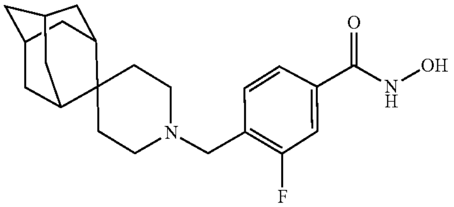

77

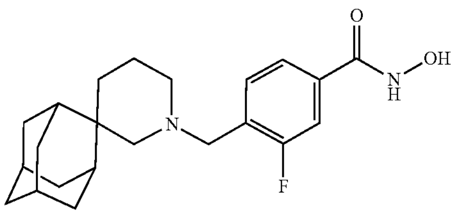

78

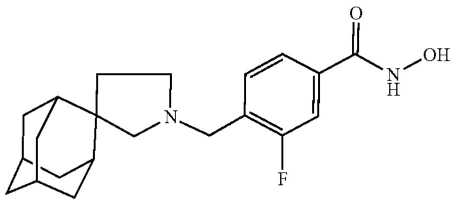

Exemplary compounds of Formula (IV) include, but are not limited to:

237

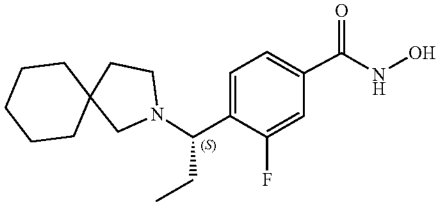

238

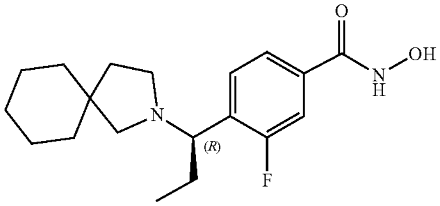

239

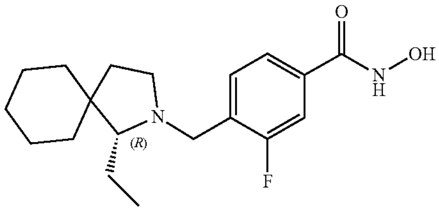

240

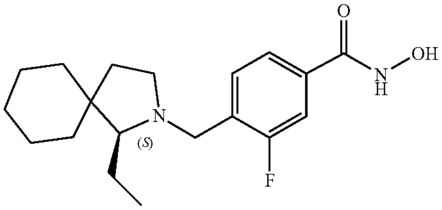

and pharmaceutically acceptable salts thereof.

In another aspect, provided are compounds of Formula (V):

(V)

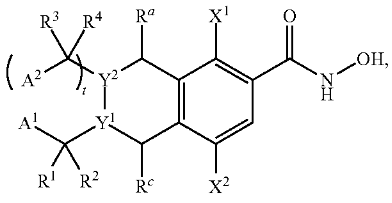

and pharmaceutically acceptable salts, co-crystals, tautomers, stereoisomers, solvates, hydrates, polymorphs, isotopically enriched derivatives, or prodrugs thereof, wherein:

$X^1$ is hydrogen or fluoro;

$X^2$ is hydrogen or fluoro;

$Y^1$ is independently nitrogen or $CR^x$;

$Y^2$ is independently nitrogen, $CR^d$, a bond, —$CH_2$—, or —NH—;

$A^1$ is joined with one of $A^2$, $R^a$, or $R^c$ to form a substituted or unsubstituted ring;

$A^2$ is hydrogen or joined with $A^1$ to form a substituted or unsubstituted ring;

$R^1$ is hydrogen or substituted or unsubstituted alkyl, or $R^1$ is joined with $R^d$, $R^3$, or $R^4$ to form a substituted or unsubstituted ring;

$R^2$ is hydrogen or substituted or unsubstituted alkyl, or $R^2$ is joined with $R^d$, $R^3$, or $R^4$ to form a substituted or unsubstituted ring; or $R^1$ and $R^2$ together form a carbonyl;

$R^3$ is hydrogen or substituted or unsubstituted alkyl, or $R^3$ is joined with $R^1$ or $R^2$ to form a substituted or unsubstituted ring;

$R^4$ is hydrogen or substituted or unsubstituted alkyl, or $R^4$ is joined with $R^1$ or $R^2$ to form a substituted or unsubstituted ring; or $R^3$ and $R^4$ together form a carbonyl;

$R^x$ is hydrogen or substituted or unsubstituted alkyl;

$R^a$ is hydrogen or is joined with $A^1$ to form a substituted or unsubstituted ring;

$R^c$ is hydrogen or is joined with $A^1$ to form a substituted or unsubstituted ring;

$R^d$ is hydrogen or is joined with $R^3$ or $R^4$ to form a substituted or unsubstituted ring; and t is 0 or 1; provided that the compound is not of formula:

79

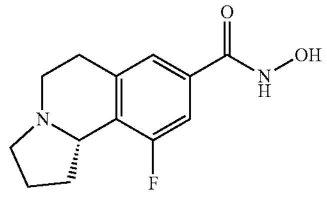

80

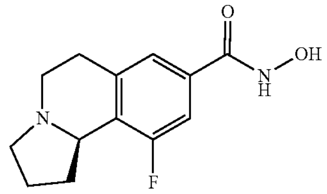

119

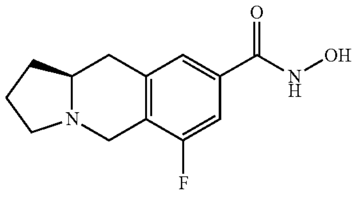

120

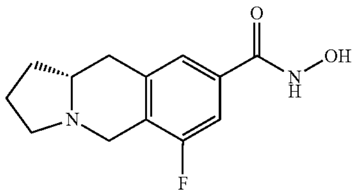

140

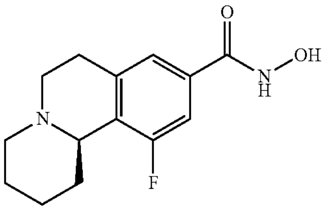

-continued

139

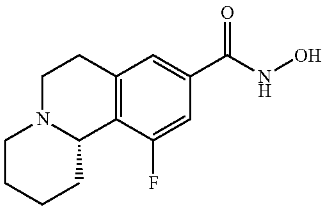

134

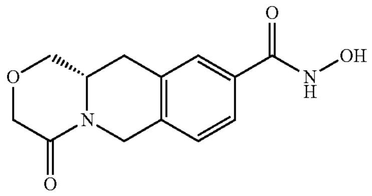

133

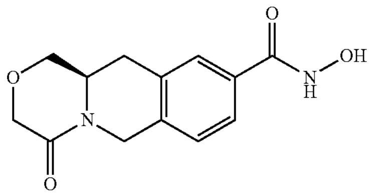

135

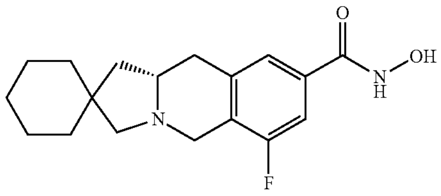

136

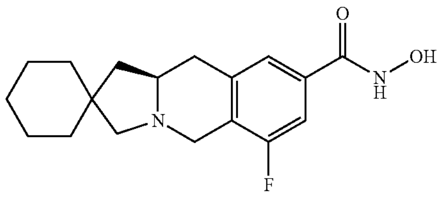

90

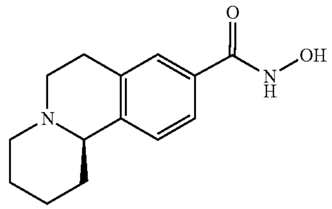

89

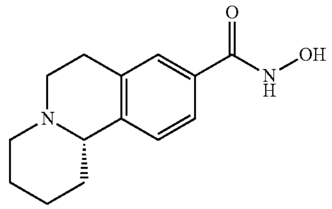

-continued
130
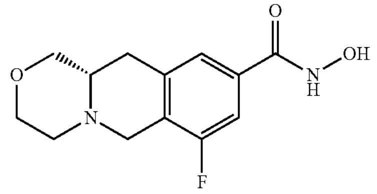
129
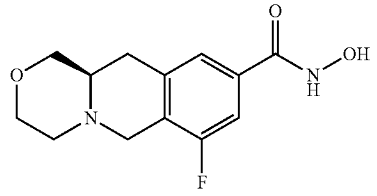
93
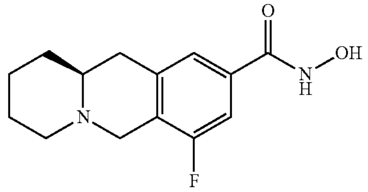
94
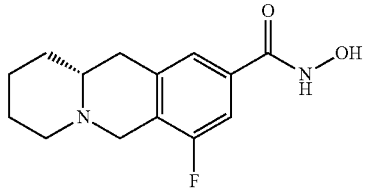
95
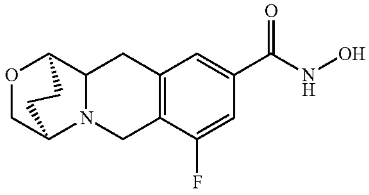
96
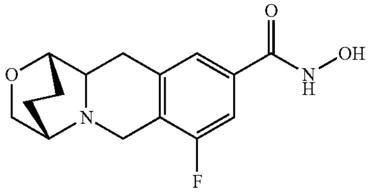
97
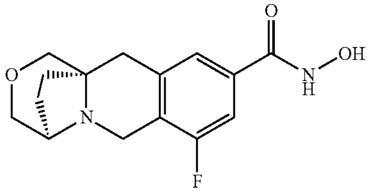
98
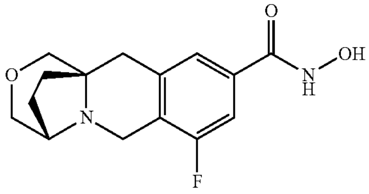
-continued
132
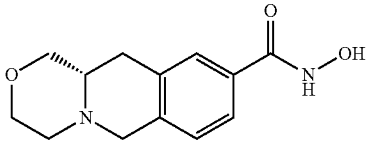
131
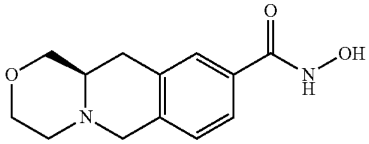
121
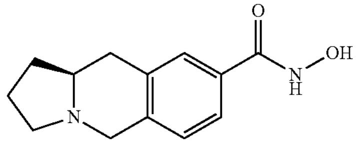
122
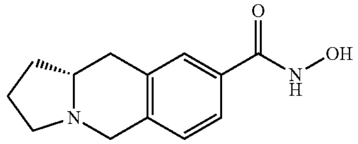
103
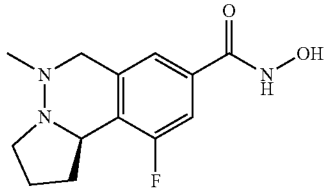
104
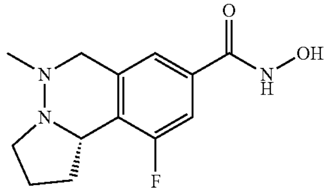
105
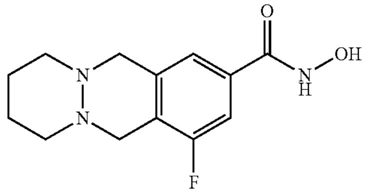
106
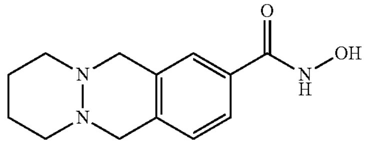
124
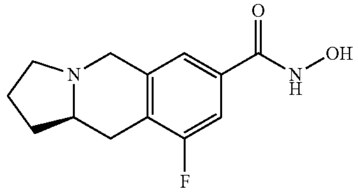

-continued
123
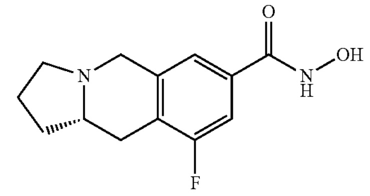
144
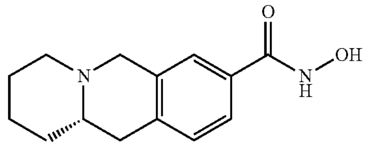
143
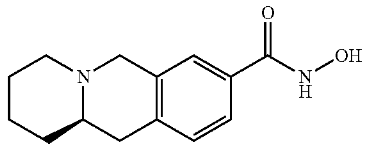
146
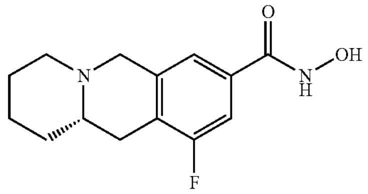
145
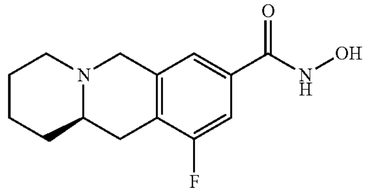
180
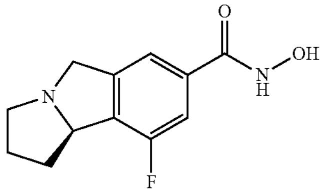
181
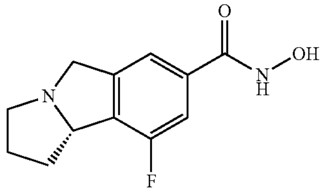
137
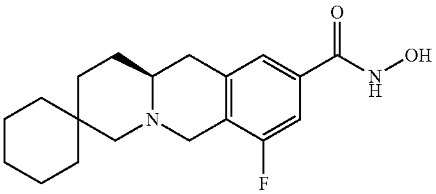
-continued
138
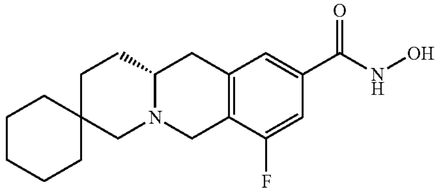
125
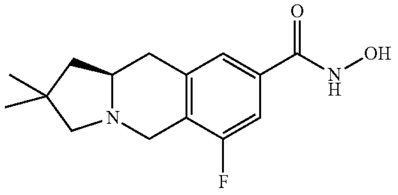
126
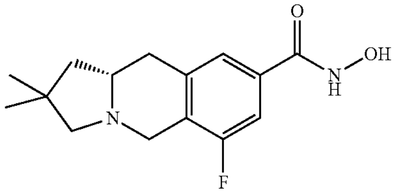
127
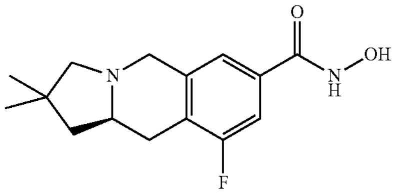
128
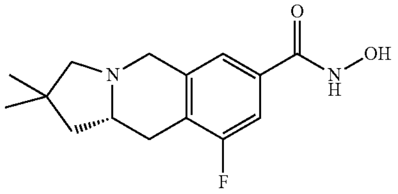
147
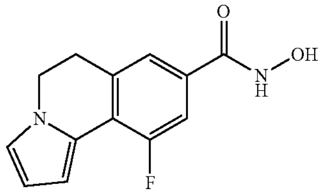
148
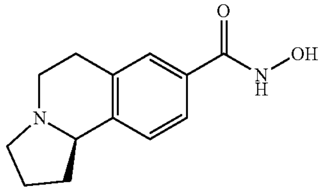
149
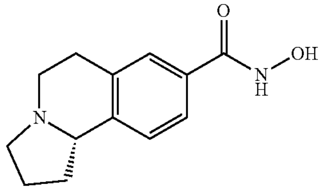

-continued
150
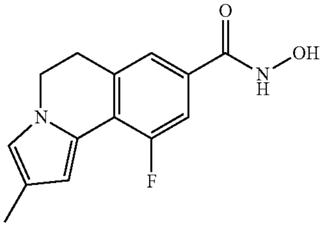
151
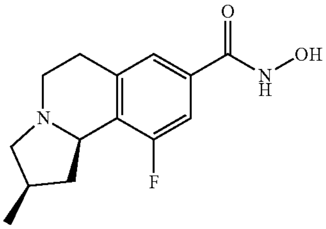
152
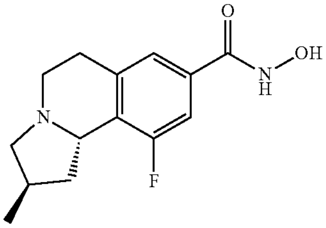
153
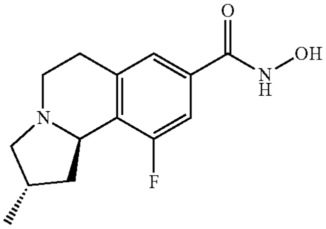
154
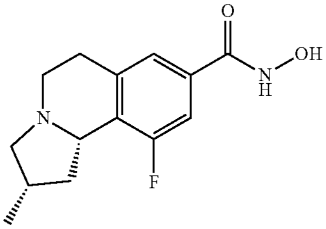
155
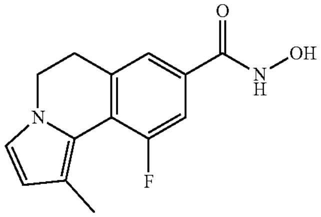
156
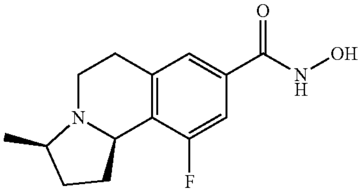
-continued
157
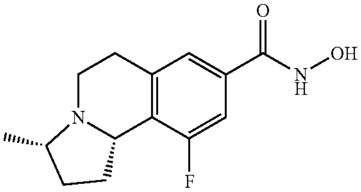
158
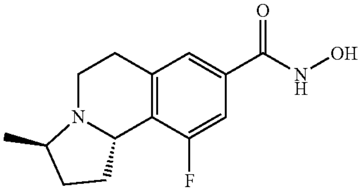
159
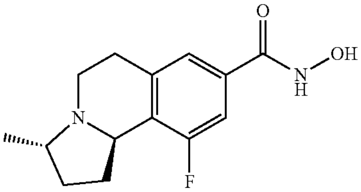
160
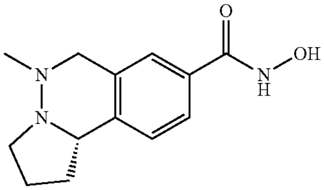
161
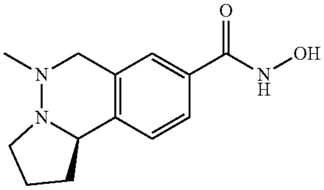
162
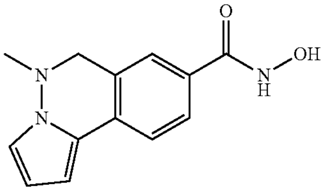
163
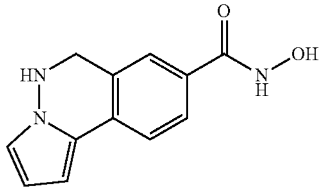
164
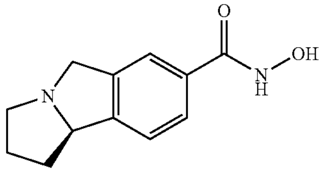

-continued
165
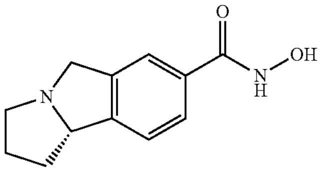
166
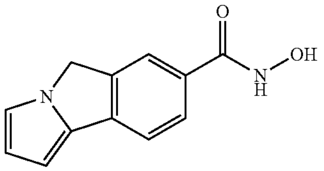
Exemplary compounds of Formula (V) include, but are not limited to:
241
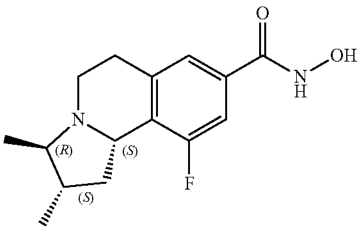
242
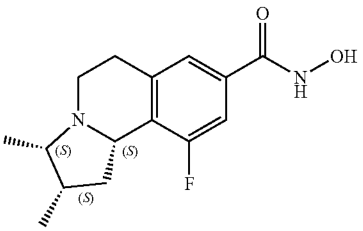
243
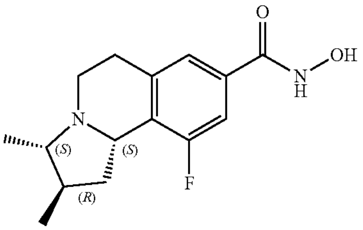
244
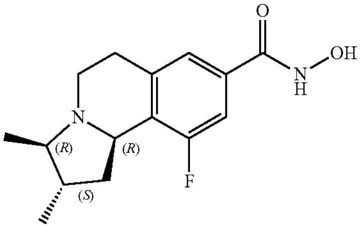
-continued
245
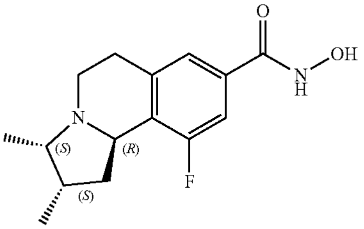
246
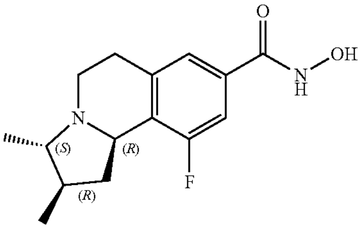
247
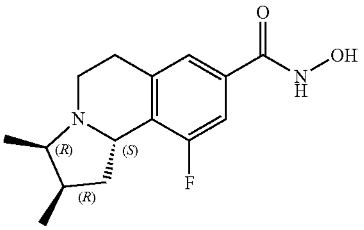
248
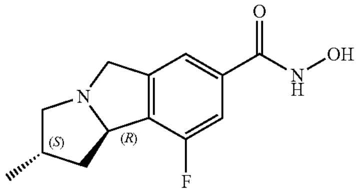
249
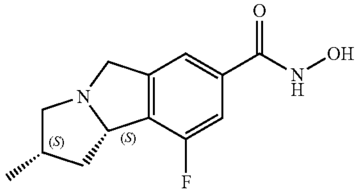
250
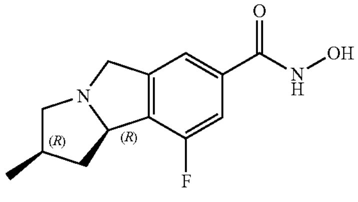
251
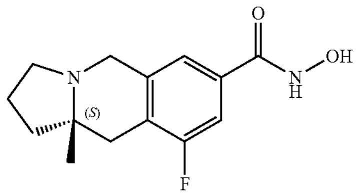

-continued
252
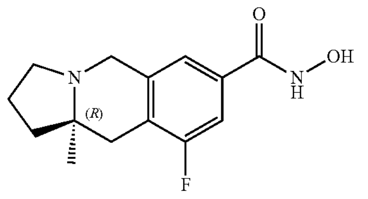
253
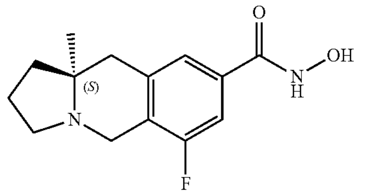
254
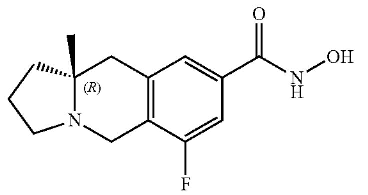
255
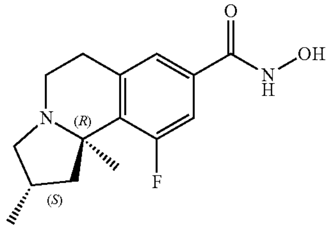
256
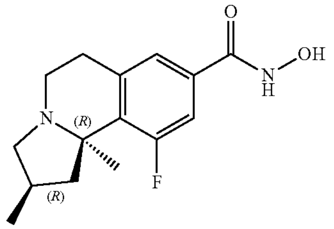
257
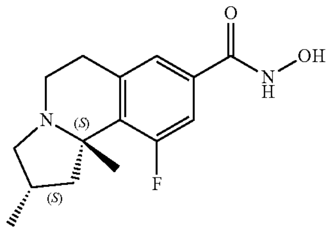
258
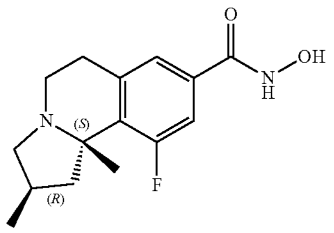
-continued
259
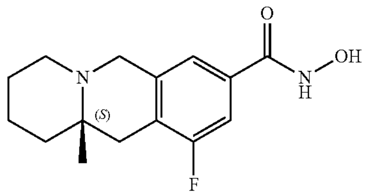
260
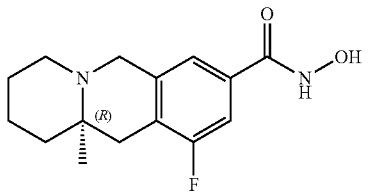
261
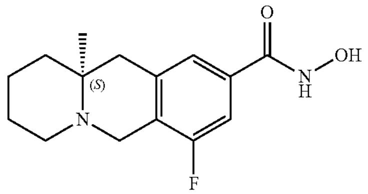
262
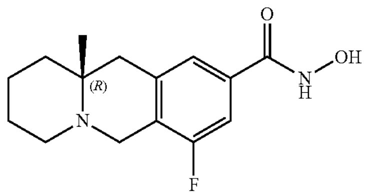
263
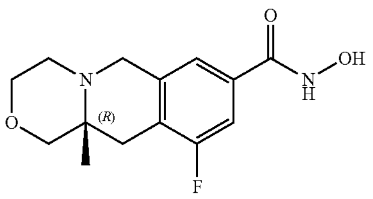
264
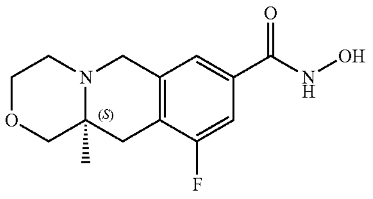
265
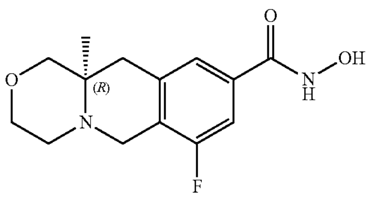
266
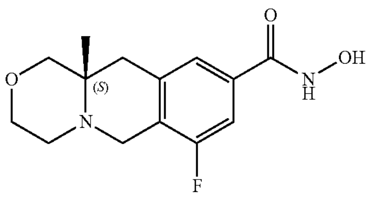

-continued

267

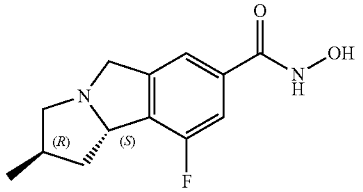

268

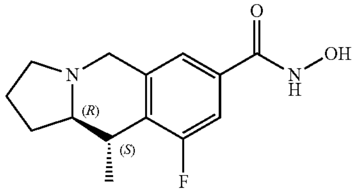

269

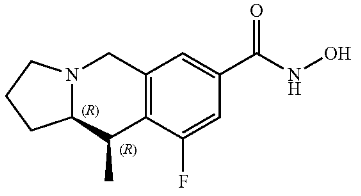

270

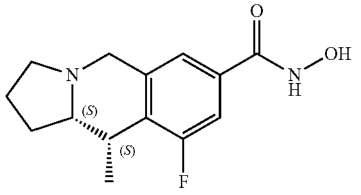

271

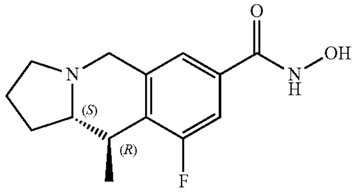

272

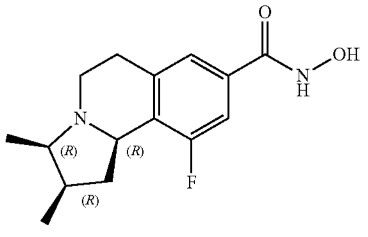

273

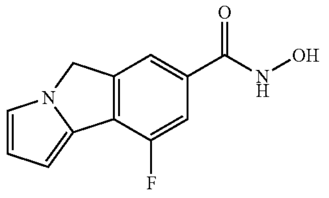

and pharmaceutically acceptable salts thereof.

In another aspect, provided are compounds of Formula (VI):

(VI)

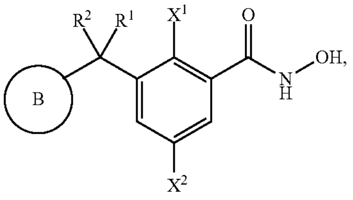

and pharmaceutically acceptable salts, co-crystals, tautomers, stereoisomers, solvates, hydrates, polymorphs, isotopically enriched derivatives, or prodrugs thereof, wherein:

$X^1$ is hydrogen or fluoro;

$X^2$ is hydrogen or fluoro;

$R^1$ is hydrogen or substituted or unsubstituted alkyl;

$R^2$ is hydrogen or substituted or unsubstituted alkyl $R^1$ and $R^2$ together form a substituted or unsubstituted heterocyclyl, or a substituted or unsubstituted cycloalkyl; and B is a substituted or unsubstituted heterocyclyl, substituted or unsubstituted carbocyclyl, a substituted or unsubstituted polycyclic spiro ring system, or a substituted or unsubstituted bridged ring system; provided that the compound is not of formula

170

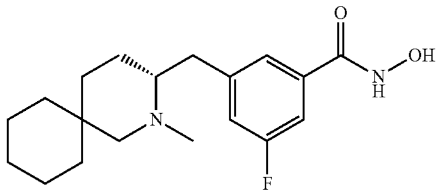

171

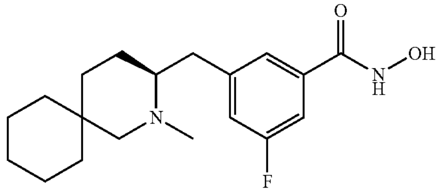

Exemplary compounds of Formula (VI) include, but are not limited to:

274

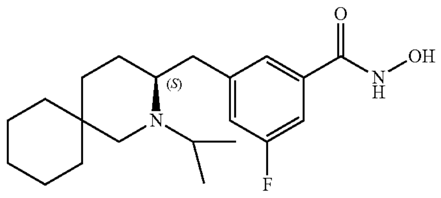

275

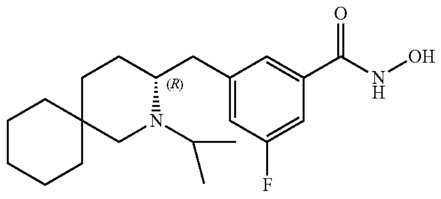

-continued

276

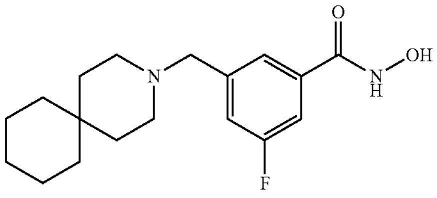

and pharmaceutically acceptable salts thereof.

In one aspect, provided are compounds of Formula (VII):

(VII)

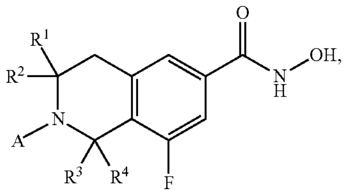

and pharmaceutically acceptable salts, co-crystals, tautomers, stereoisomers, solvates, hydrates, polymorphs, isotopically enriched derivatives, or prodrugs thereof, wherein:

A is substituted or unsubstituted carbocyclyl, or substituted or unsubstituted heterocyclyl; and $R^1$, $R^2$, $R^3$, and $R^4$ are each independently hydrogen or substituted or unsubstituted alkyl, provided that at least one of $R^1$ and $R^2$ is not hydrogen.

In certain embodiments, the compounds of Formula (VII) are compounds of Formula (VII-a), (VII-b), or (VII-c):

(VII-a)

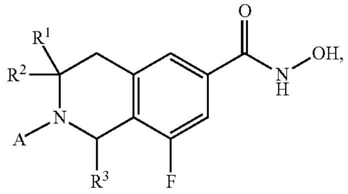

(VII-b)

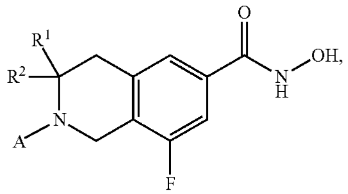

(VII-c)

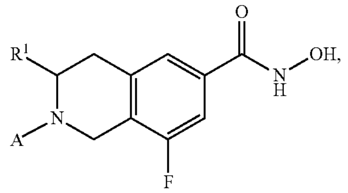

or pharmaceutically acceptable salts thereof.

Exemplary compounds of Formula (VII) include, but are not limited to:

277

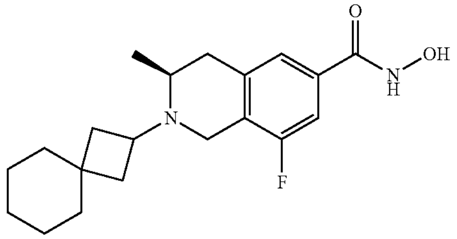

278

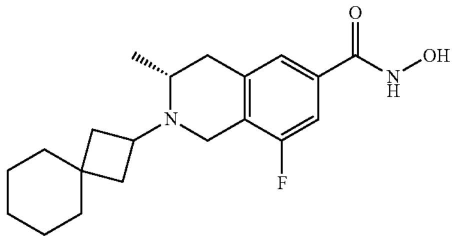

279

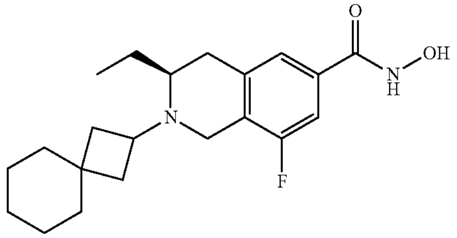

280

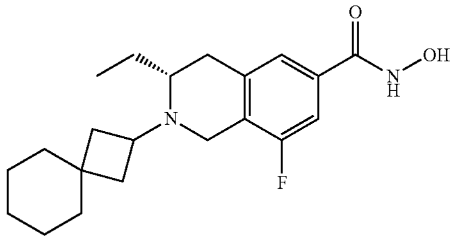

281

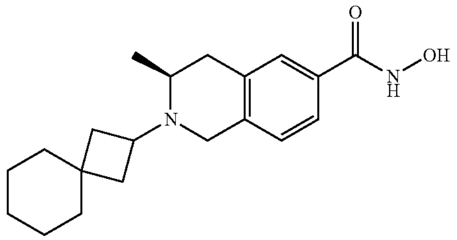

282

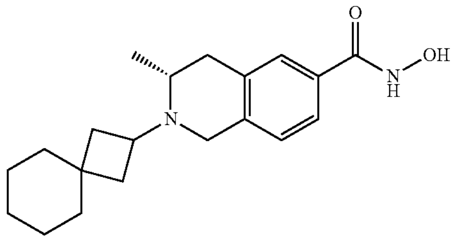

-continued

283

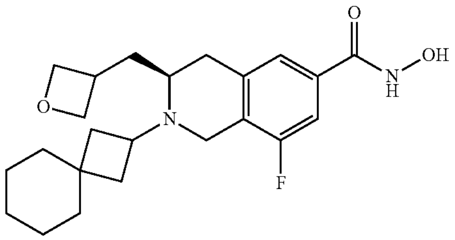

284

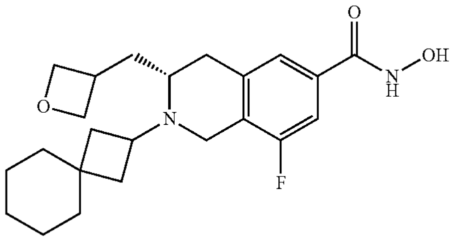

285

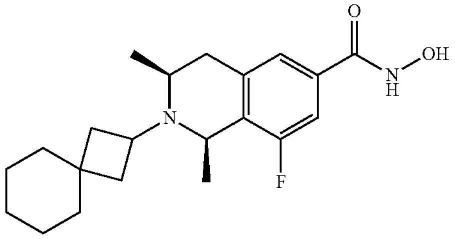

286

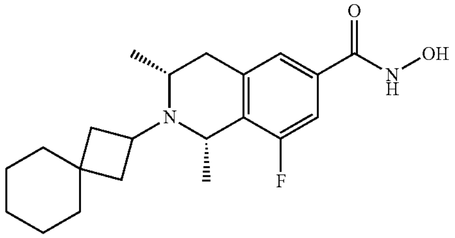

287

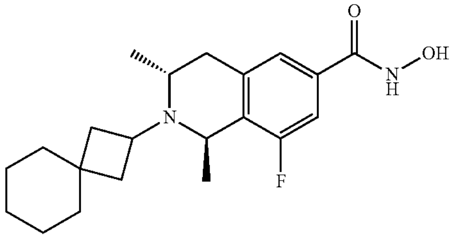

288

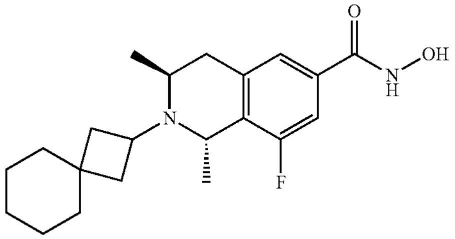

and pharmaceutically acceptable salts thereof.

In another aspect, provided are pharmaceutical compositions comprising a compound of Formula (I), (II), (Ill), (IV), (V), (VI), or (VII), or a pharmaceutically acceptable salt thereof, and optionally a pharmaceutically acceptable excipient.

In another aspect, provided are methods of treating a neurological or peripheral disease or disorder in a subject in need thereof, the method comprising administering a compound of Formula (I), (II), (Ill), (IV), (V), (VI), or (VII), or a pharmaceutically acceptable salt thereof, or a pharmaceutical composition comprising a compound of Formula (I), (II), (Ill), (IV), (V), (VI), or (VII), to the subject.

In certain embodiments, the disease or disorder being treated using a compound or composition described herein is a neurodegenerative, neurodevelopmental, neuropsychiatric, or neuropathy disease. In certain embodiments, the neurological disease or disorder is Alzheimer's disease, Fragile-X syndrome, Charcot-Marie-Tooth disease, Parkinson's disease, Huntington's disease, multiple sclerosis, amyotrophic lateral sclerosis, Rett Syndrome, major depressive disorder, chemotherapy-induced cognitive dysfunction, traumatic brain injury (TBI), chronic traumatic encephalopathy (CTE), brain cancer, or a tauopathy such as frontotemporal dementia, progressive supranuclear palsy, or corticobasal degeneration. In certain embodiments, the peripheral disease or disorder is chemotherapy-induced peripheral neuropathy, diabetic peripheral neuropathy, peripheral neuropathy, diabetic retinopathy, obesity, autosomal dominant polycystic kidney disease, cardiomyopathy, an auto-immune disease such as systemic lupus erythematosus (SLE), or cancer.

In another aspect, provided are methods of inhibiting the activity of HDAC6, the method comprising contacting HDAC6 with a compound of Formula (I), (H), (III), (IV), (V), (VI), or (VII), or a pharmaceutically acceptable salt thereof. In certain embodiments, the HDAC6 is in a cell (e.g., a human cell). In certain embodiments, the contacting is in vitro. In certain embodiments, the contacting is in vivo. In certain embodiments, the compound selectively inhibits the activity of HDAC6 over the activity of HDAC8.

In another aspect, provided are compounds of Formula (I), (II), (Ill), (IV), (V), (VI), or (VII), and pharmaceutically acceptable salts thereof, and pharmaceutical compositions comprising a compound of Formula (I), (II), (Ill), (IV), (V), (VI), or (VII), or a pharmaceutically acceptable salt thereof, for use in treating a neurological or peripheral disease or disorder in a subject in need thereof.

In another aspect, provided are kits comprising a compound of Formula (I), (II), (III), (IV), (V), (VI), or (VII), or a pharmaceutically acceptable salt thereof, or a pharmaceutical composition comprising a compound of Formula (I), (II), (Ill), (IV), (V), (VI), or (VII), or a pharmaceutically acceptable salt thereof. In certain embodiments, the kits further comprise instructions for administration (e.g., human administration).

The details of certain embodiments of the invention are set forth in the Detailed Description of Certain Embodiments, as described below. Other features, objects, and advantages of the invention will be apparent from the Definitions, Examples, and Claims.

Definitions

Chemical Definitions

Definitions of specific functional groups and chemical terms are described in more detail below. The chemical elements are identified in accordance with the Periodic Table of the Elements, CAS version, *Handbook of Chemistry and Physics,* $75^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March, *March's Advanced Organic Chemistry,* 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis,* 3$^{rd}$ Edition, Cambridge University Press, Cambridge, 1987.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., Enantiomers, Racemates and Resolutions (Wiley Interscience, New York, 1981); Wilen et al., Tetrahedron 33:2725 (1977); Eliel, E. L. Stereochemistry of Carbon Compounds (McGraw-Hill, N Y, 1962); and Wilen, S. H., Tables of Resolving Agents and Optical Resolutions p. 268 (E. L. Eliel, Ed., Univ. of Notre Dame Press, Notre Dame, IN 1972). The invention additionally encompasses compounds as individual isomers substantially free of other isomers, and alternatively, as mixtures of various isomers.

In a formula, ∿∿ is a single bond where the stereochemistry of the moieties immediately attached thereto is not specified, - - - is absent or a single bond, and ⚌ or ⚌ is a single or double bond.

Unless otherwise stated, structures depicted herein are also meant to include compounds that differ only in the presence of one or more isotopically enriched atoms. For example, compounds having the present structures except for the replacement of hydrogen by deuterium or tritium, replacement of $^{19}F$ with $^{18}F$, or the replacement of $^{12}C$ with $^{13}C$ or $^{14}C$ are within the scope of the disclosure. Such compounds are useful, for example, as analytical tools or probes in biological assays.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The term "aliphatic" refers to alkyl, alkenyl, alkynyl, and carbocyclic groups. Likewise, the term "heteroaliphatic" refers to heteroalkyl, heteroalkenyl, heteroalkynyl, and heterocyclic groups.

The term "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, iso-butyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl). Additional examples of alkyl groups include n-heptyl ($C_7$), n-octyl ($C_8$), and the like. Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is an unsubstituted $C_{1-10}$ alkyl (such as unsubstituted $C_{1-6}$ alkyl, e.g., $-CH_3$ (Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted n-butyl (n-Bu), unsubstituted tert-butyl (tert-Bu or t-Bu), unsubstituted sec-butyl (sec-Bu), unsubstituted isobutyl (i-Bu)). In certain embodiments, the alkyl group is a substituted $C_{1-10}$ alkyl (such as substituted $C_{1-6}$ alkyl, e.g., $-CF_3$, Bn).

The term "haloalkyl" is a substituted alkyl group, wherein one or more of the hydrogen atoms are independently replaced by a halogen, e.g., fluoro, bromo, chloro, or iodo. In some embodiments, the haloalkyl moiety has 1 to 8 carbon atoms ("$C_{1-8}$ haloalkyl"). In some embodiments, the haloalkyl moiety has 1 to 6 carbon atoms ("$C_{1-6}$ haloalkyl"). In some embodiments, the haloalkyl moiety has 1 to 4 carbon atoms ("$C_{1-4}$ haloalkyl"). In some embodiments, the haloalkyl moiety has 1 to 3 carbon atoms ("$C_{1-3}$ haloalkyl"). In some embodiments, the haloalkyl moiety has 1 to 2 carbon atoms ("$C_{1-2}$ haloalkyl"). Examples of haloalkyl groups include $-CHF_2$, $-CH_2F$, $-CF_3$, $-CH_2CF_3$, $-CF_2CF_3$, $-CF_2CF_2CF_3$, $-CCl_3$, $-CFCl_2$, $-CF_2Cl$, and the like.

The term "alkoxy" refers to an alkyl group, as defined herein, appended to the parent molecular moiety through an oxygen atom. In some embodiments, the alkoxy moiety has 1 to 8 carbon atoms ("$C_{1-8}$ alkoxy"). In some embodiments, the alkoxy moiety has 1 to 6 carbon atoms ("$C_{1-6}$ alkoxy"). In some embodiments, the alkoxy moiety has 1 to 4 carbon atoms ("$C_{1-4}$ alkoxy"). In some embodiments, the alkoxy moiety has 1 to 3 carbon atoms ("$C_{1-3}$ alkoxy"). In some embodiments, the alkoxy moiety has 1 to 2 carbon atoms ("$C_{1-2}$ alkoxy"). Representative examples of alkoxy include, but are not limited to, methoxy, ethoxy, propoxy, 2-propoxy, butoxy and tert-butoxy.

The term "alkoxyalkyl" is a substituted alkyl group, wherein one or more of the hydrogen atoms are independently replaced by an alkoxy group, as defined herein. In some embodiments, the alkoxyalkyl moiety has 1 to 8 carbon atoms ("$C_{1-8}$ alkoxyalkyl"). In some embodiments, the alkoxyalkyl moiety has 1 to 6 carbon atoms ("$C_{1-6}$ alkoxyalkyl"). In some embodiments, the alkoxyalkyl moiety has 1 to 4 carbon atoms ("$C_{1-4}$ alkoxyalkyl"). In some embodiments, the alkoxyalkyl moiety has 1 to 3 carbon atoms ("$C_{1-3}$ alkoxyalkyl"). In some embodiments, the alkoxyalkyl moiety has 1 to 2 carbon atoms ("$C_{1-2}$ alkoxyalkyl").

The term "heteroalkyl" refers to an alkyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkyl group refers to a saturated group having from 1 to 20 carbon atoms and 1 or more heteroatoms within the parent chain ("hetero$C_{1-20}$ alkyl"). In some embodiments, a heteroalkyl group is a saturated group having 1 to 18 carbon atoms and 1 or more heteroatoms within the parent chain ("hetero$C_{1-18}$ alkyl"). In some embodiments, a heteroalkyl group is a saturated group having 1 to 16 carbon atoms and 1 or more heteroatoms within the parent chain ("hetero$C_{1-16}$ alkyl"). In some embodiments, a heteroalkyl group is a saturated group having 1 to 14 carbon atoms and 1 or more heteroatoms within the parent chain ("hetero$C_{1-14}$ alkyl"). In some embodiments, a heteroalkyl group is a saturated group having 1 to 12 carbon atoms and 1 or more heteroatoms within the parent chain ("hetero$C_{1-12}$ alkyl"). In some embodiments, a heteroalkyl group is a saturated group having 1 to 10 carbon atoms and 1 or more heteroatoms within the parent chain ("hetero$C_{1-10}$ alkyl"). In some embodiments, a heteroalkyl group is a saturated group having 1 to 8 carbon atoms and 1 or more heteroatoms within the parent chain ("hetero$C_{1-8}$ alkyl"). In some embodiments, a heteroalkyl group is a saturated group having 1 to 6 carbon atoms and 1 or more heteroatoms within the parent chain ("hetero$C_{1-6}$ alkyl"). In some embodiments, a heteroalkyl group is a saturated group having 1 to 4 carbon atoms and 1 or 2 heteroatoms within the parent chain ("hetero$C_{1-4}$ alkyl"). In some embodiments, a heteroalkyl group is a saturated group having 1 to 3 carbon atoms and 1 heteroatom within the parent chain ("hetero$C_{1-3}$ alkyl"). In some embodiments, a heteroalkyl group is a saturated group having 1 to 2 carbon atoms and 1 heteroatom within the parent chain ("hetero$C_{1-2}$ alkyl"). In some embodiments, a heteroalkyl group is a saturated group having 1 carbon atom and 1 heteroatom ("hetero$C_1$ alkyl"). In some embodiments, the heteroalkyl group defined herein is a partially unsaturated group having 1 or more heteroatoms within the parent chain and at least one unsaturated carbon, such as a carbonyl group. For example, a heteroalkyl group may comprise an amide or ester functionality in its parent chain such that one or more carbon atoms are unsaturated carbonyl groups. Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted hetero$C_{1-20}$ alkyl. In certain embodiments, the heteroalkyl group is an unsubstituted hetero$C_{1-10}$ alkyl. In certain embodiments, the heteroalkyl group is a substituted hetero$C_{1-20}$ alkyl. In certain embodiments, the heteroalkyl group is an unsubstituted hetero$C_{1-10}$ alkyl.

The term "alkenyl" refers to a radical of a straight-chain or branched hydrocarbon group having from 2 to 10 carbon atoms and one or more carbon-carbon double bonds (e.g., 1, 2, 3, or 4 double bonds). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted $C_{2-10}$ alkenyl. In certain embodiments, the alkenyl group is a substituted $C_{2-10}$ alkenyl. In an alkenyl group, a C═C double bond for which the stereochemistry is not specified (e.g., —CH═$CHCH_3$ or

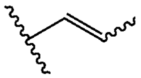

)

may be an (E)- or (Z)-double bond.

The term "heteroalkenyl" refers to an alkenyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkenyl group refers to a group having from 2 to 10 carbon atoms, at least one double bond, and 1 or more heteroatoms within the parent chain ("hetero$C_{2-10}$ alkenyl"). In some embodiments, a heteroalkenyl group has 2 to 9 carbon atoms at least one double bond, and 1 or more heteroatoms within the parent chain ("hetero$C_{2-9}$ alkenyl"). In some embodiments, a heteroalkenyl group has 2 to 8 carbon atoms, at least one double bond, and 1 or more heteroatoms within the parent chain ("hetero$C_{2-6}$ alkenyl"). In some embodiments, a heteroalkenyl group has 2 to 7 carbon atoms, at least one double bond, and 1 or more heteroatoms within the parent chain ("hetero$C_{2-7}$ alkenyl"). In some embodiments, a heteroalkenyl group has 2 to 6 carbon atoms, at least one double bond, and 1 or more heteroatoms within the parent chain ("hetero$C_{2-6}$ alkenyl"). In some embodiments, a heteroalkenyl group has 2 to 5 carbon atoms, at least one double bond, and 1 or 2 heteroatoms within the parent chain ("hetero$C_{2-5}$ alkenyl"). In some embodiments, a heteroalkenyl group has 2 to 4 carbon atoms, at least one double bond, and 1 or 2 heteroatoms within the parent chain ("hetero$C_{2-4}$ alkenyl"). In some embodiments, a heteroalkenyl group has 2 to 3 carbon atoms, at least one double bond, and 1 heteroatom within the parent chain ("hetero$C_{2-3}$ alkenyl"). In some embodiments, a heteroalkenyl group has 2 to 6 carbon atoms, at least one double bond, and 1 or 2 heteroatoms within the parent chain ("hetero$C_{2-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted hetero$C_{2-10}$ alkenyl. In certain embodiments, the heteroalkenyl group is a substituted hetero$C_{2-10}$ alkenyl.

The term "alkynyl" refers to a radical of a straight-chain or branched hydrocarbon group having from 2 to 10 carbon atoms and one or more carbon-carbon triple bonds (e.g., 1, 2, 3, or 4 triple bonds) ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted $C_{2-10}$ alkynyl. In certain embodiments, the alkynyl group is a substituted $C_{2-10}$ alkynyl.

The term "heteroalkynyl" refers to an alkynyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkynyl group refers to a group having from 2 to 10 carbon atoms, at least one triple bond, and 1 or more heteroatoms within the parent chain ("hetero$C_{2-10}$ alkynyl"). In some embodiments, a heteroalkynyl group has 2 to 9 carbon atoms, at least one triple bond, and 1 or more heteroatoms within the parent chain ("hetero$C_{2-9}$ alkynyl"). In some embodiments, a heteroalkynyl group has 2 to 8 carbon atoms, at least one triple bond, and 1 or more heteroatoms within the parent chain ("hetero$C_{2-8}$ alkynyl"). In some embodiments, a heteroalkynyl group has 2 to 7 carbon atoms, at least one triple bond, and 1 or more heteroatoms within the parent chain ("hetero$C_{2-7}$ alkynyl"). In some embodiments, a heteroalkynyl group has 2 to 6 carbon atoms, at least one triple bond, and 1 or more heteroatoms within the parent chain ("hetero$C_{2-6}$ alkynyl"). In some embodiments, a heteroalkynyl group has 2 to 5 carbon atoms, at least one triple bond, and 1 or 2 heteroatoms within the parent chain ("hetero$C_{2-5}$ alkynyl"). In some embodiments, a heteroalkynyl group has 2 to 4 carbon atoms, at least one triple bond, and 1 or 2 heteroatoms within the parent chain ("hetero$C_{2-4}$ alkynyl"). In some embodiments, a heteroalkynyl group has 2 to 3 carbon atoms, at least one triple bond, and 1 heteroatom within the parent chain ("hetero$C_{2-3}$ alkynyl"). In some embodiments, a heteroalkynyl group has 2 to 6 carbon atoms, at least one triple bond, and 1 or 2 heteroatoms within the parent chain ("hetero$C_{2-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted hetero$C_{2-10}$ alkynyl. In certain embodiments, the heteroalkynyl group is a substituted hetero$C_{2-10}$ alkynyl.

The term "carbocyclyl" or "carbocyclic" refers to a radical of a non-aromatic cyclic hydrocarbon group having from 3 to 14 ring carbon atoms ("$C_{3-14}$ carbocyclyl") and zero heteroatoms in the non-aromatic ring system. In some embodiments, a carbocyclyl group has 3 to 10 ring carbon atoms ("$C_{3-10}$ carbocyclyl"). In some embodiments, a carbocyclyl group has 3 to 8 ring carbon atoms ("$C_{3-8}$ carbocyclyl"). In some embodiments, a carbocyclyl group has 3 to 7 ring carbon atoms ("$C_{3-7}$ carbocyclyl"). In some embodiments, a carbocyclyl group has 3 to 6 ring carbon atoms ("$C_{3-6}$ carbocyclyl"). In some embodiments, a carbocyclyl group has 4 to 6 ring carbon atoms ("$C_{4-6}$ carbocyclyl"). In some embodiments, a carbocyclyl group has 5 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_7$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted $C_{3-14}$ carbocyclyl. In certain embodiments, the carbocyclyl group is a substituted $C_{3-14}$ carbocyclyl.

In some embodiments, "carbocyclyl" is a monocyclic, saturated carbocyclyl group having from 3 to 14 ring carbon atoms ("$C_{3-14}$ cycloalkyl"). In some embodiments, a cycloalkyl group has 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 4 to 6 ring carbon atoms ("$C_{4-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5\_6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted $C_{3-14}$ cycloalkyl. In certain embodiments, the cycloalkyl group is a substituted $C_{3-14}$ cycloalkyl.

The term "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

Exemplary 3-membered heterocyclyl groups containing 1 heteroatom include, without limitation, azirdinyl, oxiranyl, and thiiranyl. Exemplary 4-membered heterocyclyl groups containing 1 heteroatom include, without limitation, azetidinyl, oxetanyl, and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, and dioxanyl. Exemplary 6-membered heterocyclyl groups containing 3 heteroatoms include, without limitation, triazinyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

The term "aryl" refers to a radical of a monocyclic or polycyclic (e.g., bicyclic or tricyclic) 4n+2 aromatic ring system (e.g., having 6, 10, or 14 n electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-14}$ aryl.

"Aralkyl" is a subset of "alkyl" and refers to an alkyl group substituted by an aryl group, wherein the point of attachment is on the alkyl moiety.

The term "heteroaryl" refers to a radical of a 5-14 membered monocyclic or polycyclic (e.g., bicyclic, tricyclic) 4n+2 aromatic ring system (e.g., having 6, 10, or 14 n electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include, without limitation, pyrrolyl, furanyl, and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl, and phenazinyl.

"Heteroaralkyl" is a subset of "alkyl" and refers to an alkyl group substituted by a heteroaryl group, wherein the point of attachment is on the alkyl moiety.

The term "polycyclic spiro ring system" refers to ring systems having two or more rings linked by one common atom. The common atom is known as a spiro atom. The ring systems may be fully carbocyclic (all carbon) or heterocyclic (having one or more non-carbon atom). A ring system is considered heterocyclic if the spiro atom or any atom in either ring are not carbon atoms.

The term "bridged ring system" refers to ring systems having two or more rings that contain a bridge—a single atom or an unbranched chain of atoms (or even just a valence bond) that connect two "bridgehead" atoms. The bridgehead atoms are defined as any atom that is not a hydrogen, and that is part of the skeletal framework of the molecule that is bonded to three or more other skeletal atoms. The ring systems may be fully carbocyclic (all carbon) or heterocyclic (having one or more non-carbon atoms). A ring system is considered heterocyclic if any atom is not a carbon atom.

The term "unsaturated bond" refers to a double or triple bond.

The term "unsaturated" or "partially unsaturated" refers to a moiety that includes at least one double or triple bond.

The term "saturated" refers to a moiety that does not contain a double or triple bond, i.e., the moiety only contains single bonds.

Affixing the suffix "-ene" to a group indicates the group is a divalent moiety, e.g., alkylene is the divalent moiety of alkyl, alkenylene is the divalent moiety of alkenyl, alkynylene is the divalent moiety of alkynyl, heteroalkylene is the divalent moiety of heteroalkyl, heteroalkenylene is the divalent moiety of heteroalkenyl, heteroalkynylene is the divalent moiety of heteroalkynyl, carbocyclylene is the divalent moiety of carbocyclyl, heterocyclylene is the divalent moiety of heterocyclyl, arylene is the divalent moiety of aryl, and heteroarylene is the divalent moiety of heteroaryl.

A group is optionally substituted unless expressly provided otherwise. The term "optionally substituted" refers to being substituted or unsubstituted. In certain embodiments, alkyl, alkenyl, alkynyl, heteroalkyl, heteroalkenyl, heteroalkynyl, carbocyclyl, heterocyclyl, aryl, and heteroaryl groups are optionally substituted. "Optionally substituted" refers to a group which may be substituted or unsubstituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, and includes any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety. The invention is not intended to be limited in any manner by the exemplary substituents described herein.

Exemplary carbon atom substituents include, but are not limited to, halogen, —CN, —$NO_2$, —$N_3$, —$SO_2H$, —$SO_3H$, —OH, —$OR^{aa}$, —$ON(R^{bb})_2$, —$N(R^{bb})_2$, —$N(R^{bb})_3{}^+X^-$, —$N(OR^{cc})R^{bb}$, —SH, —$SR^{aa}$, —$SSR^{cc}$, —$C(=O)R^{aa}$, —$CO_2H$, —CHO, —$C(OR^{cc})_3$, —$CO_2R^{aa}$, —$OC(=O)R^{aa}$, —$OCO_2R^{aa}$, —$C(=O)N(R^{bb})_2$, —$OC(=O)N(R^{bb})_2$, —$NR^{bb}C(=O)R^{aa}$, —$NR^{bb}CO_2R^{aa}$, —$NR^{bb}C(=O)N(R^{bb})_2$, —$C(=NR^{bb})R^{aa}$, —$C(=NR^{bb})OR^{aa}$, —$OC(=NR^{bb})R^{aa}$, —$OC(=NR^{bb})OR^{aa}$, —$C(=NR^{bb})N(R^{bb})_2$, —$OC(=NR^{bb})N(R^{bb})_2$, —$NR^{bb}C(=NR^{bb})N(R^{bb})_2$, —$C(=O)NR^{bb}SO_2R^{aa}$, —$NR^{bb}SO_2R^{aa}$, —$SO_2N(R^{bb})_2$, —$SO_2R^{aa}$, —$SO_2OR^{aa}$, —$OSO_2R^{aa}$, —$S(=O)R^{aa}$, —$OS(=O)R^{aa}$, —$Si(R^{aa})_3$, —$OSi(R^{aa})_3$, —$C(=S)N(R^{bb})_2$, —$C(=O)SR^{aa}$, —$C(=S)SR^{aa}$, —$SC(=S)SR^{aa}$, —$SC(=O)SR^{aa}$, —$OC(=O)SR^{aa}$, —$SC(=O)OR^{aa}$, —$SC(=O)R^{aa}$, —$P(=O)(R^{aa})_2$, —$P(=O)(OR^{cc})_2$, —$OP(=O)(R^{aa})_2$, —$OP(=O)(OR^{cc})_2$, —$P(=O)(N(R^{bb})_2)_2$, —$OP(=O)(N(R^{bb})_2)_2$, —$NR^{bb}P(=O)(R^{aa})_2$, —$NR^{bb}P(=O)(OR^{cc})_2$, —$NR^{bb}P(=O)(N(R^{bb})_2)_2$, —$P(R^{cc})_2$, —$P(OR^{cc})_2$, —$P(R^{cc})_3{}^+X^-$, —$P(OR^{cc})_3{}^+X^-$, —$P(R^{cc})_4$, —$P(OR^{cc})_4$, —$OP(R^{cc})_2$, —$OP(R^{cc})_3{}^+X^-$, —$OP(OR^{cc})_2$, —$OP(OR^{cc})_3{}^+X^-$, —$OP(R^{cc})_4$, —$OP(OR^{cc})_4$, —$B(R^{aa})_2$, —$B(OR^{cc})_2$, —$BR^{aa}(OR^{cc})$, $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups; wherein $X^-$ is a counterion;

or two geminal hydrogens on a carbon atom are replaced with the group =O, =S, =$NN(R^{bb})_2$, =$NNR^{bb}C(=O)R^{aa}$, =$NNR^{bb}C(=O)OR^{aa}$, =$NNR^{bb}S(=O)_2R^{aa}$, =$NR^{bb}$, or =$NOR^{cc}$;

each instance of $R^{aa}$ is, independently, selected from $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl, or two $R^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{bb}$ is, independently, selected from hydrogen, —OH, —$OR^{aa}$, —$N(R^{cc})_2$, —CN, —$C(=O)R^{aa}$, —$C(=O)N(R^{cc})_2$, —$CO_2R^{aa}$, —$SO_2R^{aa}$, —$C(=NR^{cc})OR^{aa}$, —$C(=NR^{cc})N(R^{cc})_2$, —$SO_2N(R^{cc})_2$, —$SO_2R^{cc}$, —$SO_2OR^{cc}$, —$SOR^{aa}$, —$C(=S)N(R^{cc})_2$, —$C(=O)SR^{cc}$, —$C(=S)SR^{cc}$, —$P(=O)(R^{aa})_2$, —$P(=O)(OR^{cc})_2$, —$P(=O)(N(R^{cc})_2)_2$, $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$ alkenyl, hetero$C_{2-10}$alkynyl, $C_{3-10}$ carbocyclyl, 3-14 membered heterocyclyl, $C_{6-14}$ aryl, and 5-14 membered heteroaryl, or two $R^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups; wherein $X^-$ is a counterion;

each instance of $R^{cc}$ is, independently, selected from hydrogen, $C_{1-10}$ alkyl, $C_{1-10}$ perhaloalkyl, $C_{2-10}$ alkenyl, $C_{2-10}$ alkynyl, hetero$C_{1-10}$alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{dd}$ is, independently, selected from halogen, —CN, —$NO_2$, —$N_3$, —$SO_2H$, —$SO_3H$, —OH, —$OR^{ee}$, —$ON(R^{ff})_2$, —$N(R^{ff})_2$, —$N(R^{ff})_3{}^+X^-$, —$N(OR^{ee})R^{ff}$, —SH, —$SR^{ee}$, —$SSR^{ee}$, —$C(=O)R^{ee}$, —$CO_2H$, —$CO_2R^{ee}$, —$OC(=O)R^{ee}$, —$OCO_2R^{ee}$, —$C(=O)N(R^{ff})_2$, —$OC(=O)N(R^{ff})_2$, —$NR^{ff}C(=O)R^{ee}$, —$NR^{ff}CO_2R^{ee}$, —$NR^{ff}C(=O)N(R^{ff})_2$, —$C(=NR^{ff})OR^{ee}$, —$OC(=NR^{ff})R^{ee}$, —$OC(=NR^{ff})OR^{ee}$, —$C(=NR^{ff})N(R^{ff})_2$, —$OC(=NR^{ff})N(R^{ff})_2$, —$NR^{ff}C(=NR^{ff})N(R^{ff})_2$, —$NR^{ff}SO_2R^{ee}$, —$SO_2N(R^{ff})_2$, —$SO_2R_{ee}$, —$SO_2OR^{ee}$, —$OSO_2R^{ee}$, —$S(=O)R^{ee}$, —$Si(R^{ee})_3$, —$OSi(R^{ee})_3$, —$C(=S)N(R^{ff})_2$, —$C(=O)SR^{ee}$, —$C(=S)SR^{ee}$, —$SC(=S)SR^{ee}$, —$P(=O)(OR^{ee})_2$, —$P(=O)(R^{ee})_2$, —$OP(=O)(R^{ee})_2$, —$OP(=O)(OR^{ee})_2$, $C_{1-6}$ alkyl, $C_{1-6}$ perhaloalkyl, $C_{2-6}$ alkenyl, $C_{2-6}$ alkynyl, hetero$C_{1-6}$ alkyl, hetero$C_{2-6}$ alkenyl, hetero$C_{2-6}$ alkynyl, $C_{3-10}$ carbocyclyl, 3-10 membered heterocyclyl, $C_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form =O or =S; wherein $X^-$ is a counterion;

each instance of $R^{ee}$ is, independently, selected from $C_{1-6}$ alkyl, $C_{1-6}$ perhaloalkyl, $C_{2-6}$ alkenyl, $C_{2-6}$ alkynyl, hetero$C_{1-6}$ alkyl, hetero$C_{2-6}$ alkenyl, hetero$C_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, hetero$C_{1-6}$ alkyl, hetero$C_{2-6}$ alkenyl, hetero$C_{2-6}$ alkynyl, $C_{3-10}$ carbocyclyl, 3-10 membered heterocyclyl, $C_{6-10}$ aryl and 5-10 membered heteroaryl, or two $R^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —$NO_2$, —$N_3$, —$SO_2H$, —$SO_3H$, —OH, —$OC_{1-6}$ alkyl, —$ON(C_{1-6}$ alkyl), —$N(C_{1-6}$ alkyl), —$N(C_{1-6}$ alkyl$)_3{}^+X^-$, —$NH(C_{1-6}$ alkyl)+$X^-$, —$NH_2(C_{1-6}$ alkyl$)^+X^-$, —$NH_3{}^+X^-$, —$N(OC_{1-6}$ alkyl)($C_{1-6}$ alkyl), —$N(OH)(C_{1-6}$ alkyl), —NH(OH), —SH, —$SC_{1-6}$ alkyl, —SS($C_{1-6}$ alkyl), —C(=O)($C_{1-6}$ alkyl), —$CO_2$H, —$CO_2$($C_{1-6}$ alkyl), —OC(=O)($C_{1-6}$ alkyl), —$CCO_2$($C_{1-6}$ alkyl), —C(=O)$NH_2$, —C(=O)N($C_{1-6}$ alkyl), —OC(=O)NH($C_{1-6}$ alkyl), —NHC(=O)($C_{1-6}$ alkyl), —N($C_{1-6}$ alkyl)C(=O)($C_{1-6}$ alkyl), —$NHCO_2$($C_{1-6}$ alkyl), —NHC(=O)N($C_{1-6}$ alkyl), —NHC(=O)NH($C_{1-6}$ alkyl), —NHC(=O)$NH_2$, —C(=NH)O($C_{1-6}$ alkyl), —OC(=NH)($C_{1-6}$ alkyl), —OC(=NH)O$C_{1-6}$ alkyl, —C(=NH)N($C_{1-6}$ alkyl), —C(=NH)NH($C_{1-6}$ alkyl), —C(=NH)$NH_2$, —OC(=NH)N($C_{1-6}$ alkyl), —OC(=NH)NH($C_{1-6}$ alkyl), —OC(=NH)$NH_2$, —NHC(=NH)N($C_{1-6}$ alkyl), —NHC(=NH)$NH_2$, —$NHSO_2$($C_{1-6}$ alkyl), —$SO_2$N($C_{1-6}$ alkyl), —$SO_2$NH($C_{1-6}$ alkyl), —$SO_2NH_2$, —$SO_2$($C_{1-6}$ alkyl), —$SO_2$O($C_{1-6}$ alkyl), —$OSO_2$($C_{1-6}$ alkyl), —SO($C_{1-6}$ alkyl), —Si($C_{1-6}$ $alkyl)_3$, —OSi($C_{1-6}$ $alkyl)_3$—C(=S)N($C_{1-6}$ alkyl), C(=S)NH($C_{1-6}$ alkyl), C(=S)$NH_2$, —C(=O)S($C_{1-6}$ alkyl), —C(=S)S$C_{1-6}$ alkyl, —SC(=S)S$C_{1-6}$ alkyl, —P(=O)(O$C_{1-6}$ alkyl), —P(=O)($C_{1-6}$ alkyl), —OP(=O)($C_{1-6}$ alkyl), —OP(=O)(O$C_{1-6}$ alkyl), $C_{1-6}$ alkyl, $C_{1-6}$ perhaloalkyl, $C_{2-6}$ alkenyl, $C_{2-6}$ alkynyl, hetero$C_{1-6}$ alkyl, hetero$C_{2-6}$ alkenyl, hetero$C_{2-6}$ alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form =O or =S; wherein $X^-$ is a counterion.

The term "halo" or "halogen" refers to fluorine (fluoro, —F), chlorine (chloro, —Cl), bromine (bromo, —Br), or iodine (iodo, —I).

The term "hydroxyl" or "hydroxy" refers to the group —OH. The term "substituted hydroxyl" or "substituted hydroxyl," by extension, refers to a hydroxyl group wherein the oxygen atom directly attached to the parent molecule is substituted with a group other than hydrogen, and includes groups selected from —$OR^{aa}$, —ON$(R^{bb})_2$, —OC(=O)$SR^{aa}$, —OC(=O)$R^{aa}$, —$OCO_2R^{aa}$, —OC(=O)N$(R^{bb})_2$, —OC(=$NR^{bb}$)$R^{aa}$, —OC(=$NR^{bb}$)$OR^{aa}$, —OC(=$NR^{bb}$)N$(R^{bb})_2$, —OS(=O)$R^{aa}$, —$OSO_2R^{aa}$, —OSi$(R^{aa})_3$, —OP$(R^{cc})_2$, —OP$(R^{cc})_3^+X^-$, —OP$(OR^{cc})_2$, —OP$(OR^{cc})_3^+X^-$, —OP(=O)$(R^{aa})_2$, —OP(=O)$(OR^{cc})_2$, and —OP(=O)(N$(R^{bb})_2)_2$, wherein $X^-$, $R^{aa}$, $R^{bb}$, and $R^{cc}$ are as defined herein.

The term "amino" refers to the group —$NH_2$. The term "substituted amino," by extension, refers to a monosubstituted amino, a disubstituted amino, or a trisubstituted amino. In certain embodiments, the "substituted amino" is a monosubstituted amino or a disubstituted amino group.

The term "monosubstituted amino" refers to an amino group wherein the nitrogen atom directly attached to the parent molecule is substituted with one hydrogen and one group other than hydrogen, and includes groups selected from —NH$(R^{bb})$, —NHC(=O)$R^{aa}$, —$NHCO_2R^{aa}$, —NHC(=O)N$(R^{bb})_2$, —NHC(=$NR^{bb}$)N$(R^{bb})_2$, —$NHSO_2R^{aa}$, —NHP(=O)$(OR^{cc})_2$, and —NHP(=O)(N$(R^{bb})_2)_2$, wherein $R^{aa}$, $R^{bb}$ and $R^{cc}$ are as defined herein, and wherein $R^{bb}$ of the group —NH$(R^{bb})$ is not hydrogen.

The term "disubstituted amino" refers to an amino group wherein the nitrogen atom directly attached to the parent molecule is substituted with two groups other than hydrogen, and includes groups selected from —N$(R^{bb})_2$, —$NR^{bb}$C(=O)$R^{aa}$, —$NR^{bb}CO_2R^{aa}$, —$NR^{bb}$C(=O)N$(R^{bb})_2$, —$NR^{bb}$C(=$NR^{bb}$)N$(R^{bb})_2$, —$NR^{bb}SO_2R^{aa}$, —$NR^{bb}$P(=O)$(OR^{cc})_2$, and —$NR^{bb}$P(=O)(N$(R^{bb})_2)_2$, wherein $R^{aa}$, $R^{bb}$, and $R^{cc}$ are as defined herein, with the proviso that the nitrogen atom directly attached to the parent molecule is not substituted with hydrogen.

The term "trisubstituted amino" refers to an amino group wherein the nitrogen atom directly attached to the parent molecule is substituted with three groups, and includes groups selected from —N$(R^{bb})_3$ and —N$(R^{bb})_3^+X^-$, wherein $R^{bb}$ and $X^-$ are as defined herein.

The term "sulfonyl" refers to a group selected from —$SO_2$N$(R^{bb})_2$, —$SO_2R^{aa}$, and —$SO_2OR^{aa}$, wherein $R^{aa}$ and $R^{bb}$ are as defined herein.

The term "sulfinyl" refers to the group —S(=O)$R^{aa}$, wherein $R^{aa}$ is as defined herein.

The term "acyl" refers to a group having the general formula: —C(=O)$R^{X1}$, —C(=O)$OR^{X1}$, —C(=O)—O—C(=O)$R^{X1}$, —C(=O)$SR^{X1}$, —C(=O)N$(R^{X1})_2$, —C(=S)$R^{X1}$, —C(=S)N$(R^{X1})_2$, —C(=S)O$(R^{X1})$, —C(=S)S$(R^{X1})$, —C(=$NR^{X1}$)$R^{X1}$, —C(=$NR^{X1}$)$OR^{X1}$, —C(=$NR^{X1}$)$SR^{X1}$, or —C(=$NR^{X1}$)N$(R^{X1})_2$, wherein $R^{X1}$ is hydrogen; halogen; substituted or unsubstituted hydroxyl; substituted or unsubstituted thiol; substituted or unsubstituted amino; substituted or unsubstituted acyl, cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl; substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two $R^{X1}$ groups taken together form a 5- to 6-membered heterocyclic ring. Exemplary acyl groups include aldehydes (—CHO), carboxylic acids (—$CO_2$H), ketones, acyl halides, esters, amides, imines, carbonates, carbamates, and ureas. Acyl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "oxo" refers to the group =O, and the term "thiooxo" refers to the group =S.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —$OR^{aa}$, —N$(R^{cc})_2$, —CN, —C(=O)$R^{aa}$, —C(=O)N$(R^{cc})_2$, —$CO_2R^{aa}$, —$SO_2R^{aa}$, —C(=$NR^{bb}$)$R^{aa}$, —C(=$NR^{cc}$)$OR^{aa}$, —C(=$NR^{cc}$)N$(R^{cc})_2$, —$SO_2$N$(R^{cc})_2$, —$SO_2R^{cc}$, —$SO_2OR^{cc}$, —$SOR^{aa}$, —C(=S)N$(R^{cc})_2$, —C(=O)$SR^{cc}$, —C(=S)$SR^{cc}$, —P(=O)$(OR^{cc})_2$, —P(=O)$(R^{aa})_2$, —P(=O)N$(R^{cc})_2)_2$, $C_{1-10}$ alkyl, $C_{1-10}$ perhaloalkyl, $C_{2-10}$ alkenyl, $C_{2-10}$ alkynyl, hetero$C_{1-10}$alkyl, hetero$C_{2-10}$alkenyl, hetero$C_{2-10}$alkynyl, $C_{3-10}$ carbocyclyl, 3-14 membered heterocyclyl, $C_{6-14}$ aryl, and 5-14 membered heteroaryl, or two $R^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined herein.

In certain embodiments, the substituent present on the nitrogen atom is an nitrogen protecting group (also referred to herein as an "amino protecting group"). Nitrogen protecting groups include, but are not limited to, —OH, —$OR^{aa}$, —$N(R^{cc})_2$, —$C(=O)R^{aa}$, —$C(=O)N(R^{cc})_2$, —$CO_2R^{aa}$, —$SO_2R^{aa}$, —$C(=NR^{cc})R^{aa}$, —$C(=NR^{cc})OR^{aa}$, —$C(=NR^{cc})N(R^{cc})_2$, —$SO_2N(R^{cc})_2$, —$SO_2R^{cc}$, —$SO_2OR^{cc}$, —$SOR^{aa}$, —$C(=S)N(R^{cc})_2$, —$C(=O)SR^{cc}$, —$C(=S)SR^{cc}$, $C_{1-10}$ alkyl (e.g., aralkyl, heteroaralkyl), $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined herein. Nitrogen protecting groups are well known in the art and include those described in detail in *Protecting Groups in Organic Synthesis*, T. W. Greene and P. G. M. Wuts, 3rd edition, John Wiley & Sons, 1999, incorporated herein by reference.

For example, nitrogen protecting groups such as amide groups (e.g., —$C(=O)R^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups (e.g., —$C(=O)OR^{aa}$) include, but are not limited to, methyl carbamate, ethyl carbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —$S(=O)_2R^{aa}$) include, but are not limited to, p-toluenesulfonamide (Ts), benzenesulfonamide, 2,3,6-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), p-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5- chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys). In certain embodiments, a nitrogen protecting group is benzyl (Bn), tert-butyloxycarbonyl (BOC), carbobenzyloxy (Cbz), 9-flurenylmethyloxycarbonyl (Fmoc), trifluoroacetyl, triphenylmethyl, acetyl (Ac), benzoyl (Bz), p-methoxybenzyl (PMB), 3,4-dimethoxybenzyl (DMPM), p-methoxyphenyl (PMP), 2,2,2-trichloroethyloxycarbonyl (Troc), triphenylmethyl (Tr), tosyl (Ts), brosyl (Bs), nosyl (Ns), mesyl (Ms), triflyl (Tf), or dansyl (Ds).

In certain embodiments, the substituent present on an oxygen atom is an oxygen protecting group (also referred to herein as an "hydroxyl protecting group"). Oxygen protecting groups include, but are not limited to, $—R^{aa}$, $—N(R^{bb})_2$, $—C(=O)SR^{aa}$, $—C(=O)R^{aa}$, $—CO_2R^{aa}$, $—C(=O)N(R^{bb})_2$, $—C(=NR^{bb})R^{aa}$, $—C(=NR^{bb})OR^{aa}$, $—C(=NR^{bb})N(R^{bb})_2$, $—S(=O)R^{aa}$, $—SO_2R^{aa}$, $—Si(R^{aa})_3$, $—P(R^{aa})_2$, $—P(R^{aa})_3^+X^-$, $—P(OR^{aa})_2$, $—P(OR^{cc})_3^+X^-$, $—P(=O)(R^{aa})_2$, $—P(=O)(OR^{cc})_2$, and $—P(=O)(N(R^{bb})_2)_2$, wherein $X^-$, $R^{aa}$, $R^{bb}$, and $R^{cc}$ are as defined herein. Oxygen protecting groups are well known in the art and include those described in detail in *Protecting Groups in Organic Synthesis*, T. W. Greene and P. G. M. Wuts, 3rd edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl) methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl) ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, a-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris (levulinoyloxyphenyl)methyl, 4,4',4"-tris (benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, t-butyl carbonate (BOC or Boc), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, a-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). In certain embodiments, an oxygen protecting group is silyl. In certain embodiments, an oxygen protecting group is t-butyldiphenylsilyl (TBDPS), t-butyldimethylsilyl (TBDMS), triisoproylsilyl (TIPS), triphenylsilyl (TPS), triethylsilyl (TES), trimethylsilyl (TMS), triisopropylsiloxymethyl (TOM), acetyl (Ac), benzoyl (Bz), allyl carbonate, 2,2,2-trichloroethyl carbonate (Troc), 2-trimethylsilylethyl carbonate, methoxymethyl (MOM), 1-ethoxyethyl (EE), 2-methyoxy-2-propyl (MOP), 2,2,2-trichloroethoxyethyl, 2-methoxyethoxymethyl (MEM), 2-trimethylsilylethoxymethyl (SEM), methylthiomethyl (MTM), tetrahydropyranyl (THP), tetrahydrofuranyl (THF), p-methoxyphenyl (PMP), triphenylmethyl (Tr), methoxytrityl (MMT), dimethoxytrityl (DMT), allyl, p-methoxybenzyl (PMB), t-butyl, benzyl (Bn), allyl, or pivaloyl (Piv).

In certain embodiments, the substituent present on a sulfur atom is a sulfur protecting group (also referred to as a "thiol protecting group"). Sulfur protecting groups include, but are not limited to, $—R^{aa}$, $—N(R^{bb})_2$, $—C(=O)SR^{aa}$, $—C(=O)R^{aa}$, $—CO_2R^{aa}$, $—C(=O)N(R^{bb})_2$, $—C(=NR^{bb})R^{aa}$, $—C(=NR^{bb})OR^{aa}$, $—C(=NR^{bb})N(R^{bb})_2$, $—S(=O)R^{aa}$, $—SO_2R^{aa}$, $—Si(R^{aa})_3$, $—P(R^{cc})_2$, $—P(R^{cc})_3^+X^-$, $—P(OR^{cc})_2$, $—P(OR^{cc})_3^+X^-$, $—P(=O)(R^{aa})_2$, $—P(=O)(OR^{cc})_2$, and $—P(=O)(N(R^{bb})_2)_2$, wherein $R^{aa}$, $R^{bb}$, and $R^{cc}$ are as defined herein. Sulfur protecting groups are well known in the art and include those described in detail in

*Protecting Groups in Organic Synthesis*, T. W. Greene and P. G. M. Wuts, $3^{rd}$ edition, John Wiley & Sons, 1999, incorporated herein by reference. In certain embodiments, a sulfur protecting group is acetamidomethyl, t-Bu, 3-nitro-2-pyridine sulfenyl, 2-pyridine-sulfenyl, or triphenylmethyl.

A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., $F^-$, $Cl^-$, $Br^-$, $I^-$), $NO_3^-$, $ClO_4^-$, $OH^-$, $H_2PO_4^-$, $HCO_3^-$, $HSO_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), $BF_4^-$, $PF_4^-$, $PF_6^-$, $AsF_6^-$, $SbF_6^-$, $B[3,5-(CF_3)_2C_6H_3]_4]^-$, $B(C_6F_5)_4^-$, $BPh_4^-$, $Al(OC(CF_3)_3)_4^-$, and carborane anions (e.g., $CB_{11}H_{12}^-$ or $(HCB_{11}Me_5Br_6)^-$). Exemplary counterions which may be multivalent include $CO_3^{2-}$, $HPO_4^{2-}$, $PO_4^{3-}$, $B_4O_7^{2-}$, $SO_4^{2-}$, $S_2O_3^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

These and other exemplary substituents are described in more detail in the Detailed Description, Examples, and Claims. The invention is not intended to be limited in any manner by the above exemplary listing of substituents.

Other Definitions

The following definitions are more general terms used throughout the present application.

As used herein, the term "salt" refers to any and all salts, and encompasses pharmaceutically acceptable salts.

The term "pharmaceutically acceptable salt" refers to those salts which are, within the scope of sound medical judgment, suitable for use in contact with the tissues of humans and/or animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in J. Pharmaceutical Sciences, 1977, 66, 1-19, incorporated herein by reference. Pharmaceutically acceptable salts of the compounds of this disclosure include those derived from suitable inorganic and organic acids and bases. Examples of pharmaceutically acceptable, nontoxic acid addition salts are salts of an amino group formed with inorganic acids, such as hydrochloric acid, hydrobromic acid, phosphoric acid, sulfuric acid, and perchloric acid or with organic acids, such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium, and $N^+(C_{1-4}\ alkyl)_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "solvate" refers to forms of the compound, or a salt thereof, that are associated with a solvent, usually by a solvolysis reaction. This physical association may include hydrogen bonding. Conventional solvents include water, methanol, ethanol, acetic acid, DMSO, THF, diethyl ether, and the like. The compounds described herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolatable solvates. Representative solvates include hydrates, ethanolates, and methanolates.

The term "hydrate" refers to a compound that is associated with water molecules. Typically, the number of the water molecules contained in a hydrate of a compound is in a definite ratio to the number of the compound molecules in the hydrate. Therefore, a hydrate of a compound may be represented, for example, by the general formula R-x $H_2O$, wherein R is the compound, and x is a number greater than 0. A given compound may form more than one type of hydrate, including, e.g., monohydrates (x is 1), lower hydrates (x is a number greater than 0 and smaller than 1, e.g., hemihydrates ($R\cdot0.5\ H_2O$)), and polyhydrates (x is a number greater than 1, e.g., dihydrates ($R\cdot2\ H_2O$) and hexahydrates ($R\cdot6\ H_2O$)).

The term "tautomers" or "tautomeric" refers to two or more interconvertible compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol, amide-to-imide, lactam-to-lactim, enamine-to-imine, and enamine-to-(a different enamine) tautomerizations.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "polymorph" refers to a crystalline form of a compound (or a salt, hydrate, or solvate thereof). Many compounds can adopt a variety of different crystal forms (i.e., different polymorphs). Typically, such different crystalline forms have different X-ray diffraction patterns, infrared spectra, and/or can vary in some or all properties such as melting points, density, hardness, crystal shape, optical and electrical properties, stability, solubility, and bioavailability. Recrystallization solvent, rate of crystallization, storage temperature, and other factors may cause one crystal form to dominate a given preparation. Various polymorphs of a compound can be prepared by crystallization under different conditions.

The term "co-crystal" refers to a crystalline structure composed of at least two components. In certain embodiments, a co-crystal contains a compound of the present disclosure and one or more other component(s), including, but not limited to, atoms, ions, molecules, or solvent molecules. In certain embodiments, a co-crystal contains a compound of the present disclosure and one or more solvent molecules. In certain embodiments, a co-crystal contains a compound of the present disclosure and one or more acid or base. In certain embodiments, a co-crystal contains a compound of the present disclosure and one or more components related to said compound, including, but not limited to, an isomer, tautomer, salt, solvate, hydrate, synthetic precursor, synthetic derivative, fragment, or impurity of said compound.

The term "prodrugs" refers to compounds that have cleavable groups that are removed, by solvolysis or under physiological conditions, to provide the compounds described herein, which are pharmaceutically active in vivo. Such examples include, but are not limited to, choline ester derivatives and the like, N-alkylmorpholine esters and the like. Other derivatives of the compounds described herein have activity in both their acid and acid derivative forms, but in the acid sensitive form often offer advantages of solubility, tissue compatibility, or delayed release in the mammalian organism (see, Bundgard, H., *Design of Prodrugs*, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides, and anhydrides derived from acidic groups pendant on the compounds described herein are particular prodrugs. In some cases it is desirable to prepare double ester type prodrugs such as (acyloxy)alkyl esters or ((alkoxycarbonyl)oxy)alkylesters. $C_{1-8}$ alkyl, $C_{2-8}$ alkenyl, $C_{2-8}$ alkynyl, aryl, $C_{7-12}$ substituted aryl, and $C_{7-12}$ arylalkyl esters of the compounds described herein may be preferred.

The terms "composition" and "formulation" are used interchangeably.

A "subject" to which administration is contemplated refers to a human (i.e., male or female of any age group, e.g., pediatric subject (e.g., infant, child, or adolescent) or adult subject (e.g., young adult, middle-aged adult, or senior adult)) or non-human animal. In certain embodiments, the non-human animal is a mammal (e.g., primate (e.g., cynomolgus monkey or rhesus monkey), commercially relevant mammal (e.g., cattle, pig, horse, sheep, goat, cat, or dog), or bird (e.g., commercially relevant bird, such as chicken, duck, goose, or turkey)). In certain embodiments, the non-human animal is a fish, reptile, or amphibian. The non-human animal may be a male or female at any stage of development. The non-human animal may be a transgenic animal or genetically engineered animal. The term "patient" refers to a human subject in need of treatment of a disease. The subject may also be a plant. In certain embodiments, the plant is a land plant. In certain embodiments, the plant is a non-vascular land plant. In certain embodiments, the plant is a vascular land plant. In certain embodiments, the plant is a seed plant. In certain embodiments, the plant is a cultivated plant. In certain embodiments, the plant is a dicot. In certain embodiments, the plant is a monocot. In certain embodiments, the plant is a flowering plant. In some embodiments, the plant is a cereal plant, e.g., maize, corn, wheat, rice, oat, barley, rye, or millet. In some embodiments, the plant is a legume, e.g., a bean plant, e.g., soybean plant. In some embodiments, the plant is a tree or shrub.

The term "biological sample" refers to any sample including tissue samples (such as tissue sections and needle biopsies of a tissue); cell samples (e.g., cytological smears (such as Pap or blood smears) or samples of cells obtained by microdissection); samples of whole organisms (such as samples of yeasts or bacteria); or cell fractions, fragments or organelles (such as obtained by lysing cells and separating the components thereof by centrifugation or otherwise). Other examples of biological samples include blood, serum, urine, semen, fecal matter, cerebrospinal fluid, interstitial fluid, mucous, tears, sweat, pus, biopsied tissue (e.g., obtained by a surgical biopsy or needle biopsy), nipple aspirates, milk, vaginal fluid, saliva, swabs (such as buccal swabs), or any material containing biomolecules that is derived from a first biological sample.

The term "administer," "administering," or "administration" refers to implanting, absorbing, ingesting, injecting, inhaling, or otherwise introducing a compound described herein, or a composition thereof, in or on a subject.

The terms "treatment," "treat," and "treating" refer to reversing, alleviating, delaying the onset of, or inhibiting the progress of a disease described herein. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms). Treatment may also be continued after symptoms have resolved, for example, to delay or prevent recurrence.

The terms "condition," "disease," and "disorder" are used interchangeably.

An "effective amount" of a compound described herein refers to an amount sufficient to elicit the desired biological response. An effective amount of a compound described herein may vary depending on such factors as the desired biological endpoint, the pharmacokinetics of the compound, the condition being treated, the mode of administration, and the age and health of the subject. In certain embodiments, an effective amount is a therapeutically effective amount. In certain embodiments, an effective amount is a prophylactic treatment. For example, in treating cancer, an effective amount of an inventive composition may prevent tumor regrowth, reduce the tumor burden, or stop the growth or spread of a tumor. In certain embodiments, an effective amount is the amount of a compound described herein in a single dose. In certain embodiments, an effective amount is the combined amounts of a compound described herein in multiple doses.

A "therapeutically effective amount" of a compound described herein is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent. In certain embodiments, a therapeutically effective amount is an amount sufficient for HDAC6 inhibition (e.g., at least 5%, at least 10%, at least 20%, at least 30%, at least 40%, at least 50%, at least 60%, at least 70%, at least 80%, at least 90%, at least 95%, or at least 99% inhibition of the activity of HDAC6). In certain embodiments, a therapeutically effective amount is an amount sufficient for treating a disease or disorder (e.g., neurological disorder, cancer). In certain embodiments, a therapeutically effective amount is an amount sufficient for HDAC6 inhibition and treating a disease or disorder (e.g., neurological disorder, cancer).

A "prophylactically effective amount" of a compound described herein is an amount sufficient to prevent a condition, or one or more signs or symptoms associated with the condition, or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent. In certain embodiments, a prophylactically effective amount is an amount sufficient for HDAC6 inhibition. In certain embodiments, a prophylactically effective amount is an amount sufficient for treating a disease or disorder (e.g., neurological disorder, cancer). In certain embodiments, a prophylactically effective amount is an amount sufficient for HDAC6 inhibition and treating a disease or disorder (e.g., neurological disorder, cancer).

As used herein, the term "inhibit" or "inhibition" in the context of enzymes, for example, in the context of HDAC6, refers to a reduction in the activity of the enzyme. In some embodiments, the term refers to a reduction of the level of enzyme activity, e.g., HDAC6 activity, to a level that is statistically significantly lower than an initial level, which may, for example, be a baseline level of enzyme activity. In some embodiments, the term refers to a reduction of the level of enzyme activity, e.g., HDAC6 activity, to a level that is less than 75%, less than 50%, less than 40%, less than 30%, less than 25%, less than 20%, less than 10%, less than 9%, less than 8%, less than 7%, less than 6%, less than 5%, less than 4%, less than 3%, less than 2%, less than 1%, less than 0.5%, less than 0.1%, less than 0.01%, less than 0.001%, or less than 0.0001% of an initial level, which may, for example, be a baseline level of enzyme activity.

A "proliferative disease" refers to a disease that occurs due to abnormal growth or extension by the multiplication of cells (Walker, *Cambridge Dictionary of Biology*; Cambridge University Press: Cambridge, UK, 1990). A proliferative disease may be associated with: 1) the pathological proliferation of normally quiescent cells; 2) the pathological migration of cells from their normal location (e.g., metastasis of neoplastic cells); 3) the pathological expression of proteolytic enzymes such as matrix metalloproteinases (e.g., collagenases, gelatinases, and elastases); or 4) pathological angiogenesis as in proliferative retinopathy and tumor metastasis. Exemplary proliferative diseases include cancers (i.e., "malignant neoplasms"), benign neoplasms, angiogenesis or diseases associated with angiogenesis, inflammatory diseases, autoinflammatory diseases, and autoimmune diseases.

The terms "neoplasm" and "tumor" are used herein interchangeably and refer to an abnormal mass of tissue wherein the growth of the mass surpasses and is not coordinated with the growth of a normal tissue. A neoplasm or tumor may be "benign" or "malignant," depending on the following characteristics: degree of cellular differentiation (including morphology and functionality), rate of growth, local invasion, and metastasis. A "benign neoplasm" is generally well differentiated, has characteristically slower growth than a malignant neoplasm, and remains localized to the site of origin. In addition, a benign neoplasm does not have the capacity to infiltrate, invade, or metastasize to distant sites. Exemplary benign neoplasms include, but are not limited to, lipoma, chondroma, adenomas, acrochordon, senile angiomas, seborrheic keratoses, lentigos, and sebaceous hyperplasias. In some cases, certain "benign" tumors may later give rise to malignant neoplasms, which may result from additional genetic changes in a subpopulation of the tumor's neoplastic cells, and these tumors are referred to as "pre-malignant neoplasms." An example of a pre-malignant neoplasm is a teratoma. In contrast, a "malignant neoplasm" is generally poorly differentiated (anaplasia) and has characteristically rapid growth accompanied by progressive infiltration, invasion, and destruction of the surrounding tissue. Furthermore, a malignant neoplasm generally has the capacity to metastasize to distant sites.

The term "metastasis," "metastatic," or "metastasize" refers to the spread or migration of cancerous cells from a primary or original tumor to another organ or tissue and is typically identifiable by the presence of a "secondary tumor" or "secondary cell mass" of the tissue type of the primary or original tumor and not of that of the organ or tissue in which the secondary (metastatic) tumor is located. For example, a prostate cancer that has migrated to bone is said to be metastasized prostate cancer and includes cancerous prostate cancer cells growing in bone tissue.

The term "cancer" refers to a malignant neoplasm (*Stedman's Medical Dictionary,* 25th ed.; Hensyl ed.; Williams & Wilkins: Philadelphia, 1990). Exemplary cancers include, but are not limited to, acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; eye cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); hematological cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma such as Hodgkin lymphoma (HL) (e.g., B-cell HL, T-cell HL) and non-Hodgkin lymphoma (NHL) (e.g., diffuse large B-cell lymphoma (DLBCL)), follicular lymphoma, chronic lymphocytic leukemia/small lymphocytic lymphoma (CLUSLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenstrom's macroglobulinemia), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungiodes, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); a mixture of one or more leukemia/lymphoma as described above; and multiple myeloma), heavy chain disease (e.g., alpha chain disease, gamma chain disease, mu chain disease); hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendocrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

The term "immunotherapy" refers to a therapeutic agent that promotes the treatment of disease by inducing, enhancing, or suppressing an immune response. Immunotherapies designed to elicit or amplify an immune response are classified as activation immunotherapies, while immunotherapies that reduce or suppress are classified as suppression immunotherapies. Immunotherapies are typically, but not always, biotherapeutic agents. Numerous immunotherapies are used to treat cancer. These include, but are not limited to, monoclonal antibodies, adoptive cell transfer, cytokines, chemokines, vaccines, and small molecule inhibitors.

The terms "biologic," "biologic drug," and "biological product" refer to a wide range of products such as vaccines, blood and blood components, allergenics, somatic cells, gene therapy, tissues, nucleic acids, and proteins. Biologics may include sugars, proteins, or nucleic acids, or complex combinations of these substances, or may be living entities, such as cells and tissues. Biologics may be isolated from a variety of natural sources (e.g., human, animal, microorganism) and may be produced by biotechnological methods and other technologies.

The term "small molecule" or "small molecule therapeutic" refers to molecules, whether naturally occurring or artificially created (e.g., via chemical synthesis) that have a relatively low molecular weight. Typically, a small molecule is an organic compound (i.e., it contains carbon). The small molecule may contain multiple carbon-carbon bonds, stereocenters, and other functional groups (e.g., amines, hydroxyl, carbonyls, and heterocyclic rings, etc.). In certain embodiments, the molecular weight of a small molecule is not more than about 1,000 g/mol, not more than about 900 g/mol, not more than about 800 g/mol, not more than about 700 g/mol, not more than about 600 g/mol, not more than about 500 g/mol, not more than about 400 g/mol, not more than about 300 g/mol, not more than about 200 g/mol, or not more than about 100 g/mol. In certain embodiments, the molecular weight of a small molecule is at least about 100 g/mol, at least about 200 g/mol, at least about 300 g/mol, at least about 400 g/mol, at least about 500 g/mol, at least about 600 g/mol, at least about 700 g/mol, at least about 800 g/mol, or at least about 900 g/mol, or at least about 1,000 g/mol. Combinations of the above ranges (e.g., at least about 200 g/mol and not more than about 500 g/mol) are also possible. In certain embodiments, the small molecule is a therapeutically active agent such as a drug (e.g., a molecule approved by the U.S. Food and Drug Administration as provided in the Code of Federal Regulations (C.F.R.)). The small molecule may also be complexed with one or more metal atoms and/or metal ions. In this instance, the small molecule is also referred to as a "small organometallic molecule." Preferred small molecules are biologically active in that they produce a biological effect in animals, preferably mammals, more preferably humans. Small molecules include, but are not limited to, radionuclides and imaging agents. In certain embodiments, the small molecule is a drug. Preferably, though not necessarily, the drug is one that has already been deemed safe and effective for use in humans or animals by the appropriate governmental agency or regulatory body. For example, drugs approved for human use are listed by the FDA under 21 C.F.R. §§ 330.5, 331 through 361, and 440 through 460, incorporated herein by reference; drugs for veterinary use are listed by the FDA under 21 C.F.R. §§ 500 through 589, incorporated herein by reference. All listed drugs are considered acceptable for use in accordance with the present invention.

The term "therapeutic agent" refers to any substance having therapeutic properties that produce a desired, usually beneficial, effect. For example, therapeutic agents may treat, ameliorate, and/or prevent disease. Therapeutic agents, as disclosed herein, may be biologics or small molecule therapeutics, or combinations thereof.

The term "chemotherapeutic agent" refers to a therapeutic agent known to be of use in chemotherapy for cancer.

A "hematological cancer" includes a cancer which affects a hematopoietic cell or tissue. Hematological cancers include cancers associated with aberrant hematological content and/or function. Examples of hematological cancers include, but are nor limited to, leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), chronic lymphocytic leukemia (CLL) (e.g., B-cell CLL, T-cell CLL)), lymphoma such as Hodgkin's lymphoma (HL) (e.g., B-cell HL, T-cell HL), non-Hodgkin's lymphoma (NHL) (e.g., diffuse large B-cell lymphoma (DLBCL)), follicular lymphoma, chronic lymphocytic leukemia/small lymphocytic lymphoma (CLUSLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenstrom's macroglobulinemia), hairy cell leukemia (HCL), immunoblastic large cell lymphoma, precursor B-lymphoblastic lymphoma, primary central nervous system (CNS) lymphoma, T-cell NHL such as precursor T-lymphoblastic lymphoma/leukemia, peripheral T-cell lymphoma (PTCL) (e.g., cutaneous T-cell lymphoma (CTCL) (e.g., mycosis fungiodes, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma), a mixture of one or more leukemia/lymphoma as described above, multiple myeloma, heavy chain disease (e.g., alpha chain disease, gamma chain disease, mu chain disease) acute non-lymphocytic leukemia (ANLL), acute promyelocytic leukemia (APL), acute myelomonocytic leukemia (AMMoL), polycythemia vera, Wilm's tumor, and Ewing's sarcoma.

The term "heteroimmune disease" refers to a state in which an immune response to an exogenous antigen (e.g., drug, pathogen) results in immunopathological changes. The immune response is triggered by an antigen from a different species (heteroimmune), thus it differs from an infectious disease because the emphasis is on the immune response, not the foreign species (infectious pathogen) causing the disease.

DETAILED DESCRIPTION OF CERTAIN EMBODIMENTS

Figure 1A:
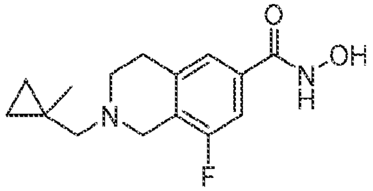
FIG. 1A is a chart of exemplary compounds of Formula (I) assayed as negative using the microplate Ames fluctuation assay (A) or the microAmes protocol (B).

Provided herein are compounds that are HDAC inhibitors (e.g., HDAC6 inhibitors). The compounds described herein possess advantageous properties, such as selective inhibition of HDAC6 and/or the ability to cross the blood-brain-barrier, that allow the compounds to be useful as therapeutic agents. In one aspect, the provided HDAC6 inhibitors are compounds of Formula (I), (II), (III), (IV), (V), (VI), and (VII), and pharmaceutically acceptable salts, solvates, hydrates, polymorphs, co-crystals, tautomers, stereoisomers, isotopically labeled derivatives, prodrugs, and pharmaceutical compositions thereof. Accordingly, the compounds are useful for the treatment and/or prevention of diseases and disorders associated with HDAC6 activity (e.g., proliferative disease, inflammatory disease, infectious disease, autoimmune disease, heteroimmune disease, neurological disorder, metabolic disease, cystic fibrosis, polycystic kidney disease, pulmonary hypertension, cardiac dysfunction, or disease or disorder mediated by or linked to T-cell dysregulation) in a subject in need thereof.

The compounds described herein interact with HDAC6. As described herein, the therapeutic effect may be a result of inhibition, modulation, binding, and/or modification of HDAC6 by the compounds described herein. The compounds may be provided for use in any composition, kit, or method described herein as a pharmaceutically acceptable salt, co-crystal, tautomer, stereoisomer, solvate, hydrate, polymorph, isotopically enriched derivative, or prodrug thereof.

Compounds of Formula (I)

In one aspect, disclosed is a compound of Formula (I):

(I)

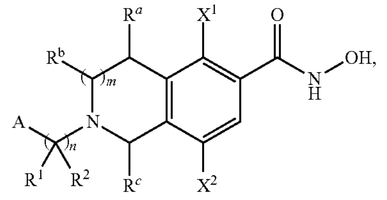

or a pharmaceutically acceptable salt, co-crystal, tautomer, stereoisomer, solvate, hydrate, polymorph, isotopically enriched derivative, or prodrug thereof, wherein:

$X^1$ is hydrogen or fluoro;

$X^2$ is hydrogen or fluoro; provided that at least one of $X^1$ and $X^2$ is fluorine;

A is substituted or unsubstituted alkyl, substituted or unsubstituted carbocyclyl, substituted or unsubstituted heterocyclyl, substituted or unsubstituted heteroaryl, or substituted or unsubstituted aryl;

$R^1$ is hydrogen or substituted or unsubstituted alkyl;

$R^2$ is hydrogen or substituted or unsubstituted alkyl; or $R^1$ and $R^2$ together form a substituted or unsubstituted heterocyclyl, or a substituted or unsubstituted cycloalkyl;

$R^a$ is hydrogen or is joined with $R^c$ to form a substituted or unsubstituted bridged ring;

$R^b$ is hydrogen or is joined with $R^c$ to form a substituted or unsubstituted bridged ring;

$R^c$ is hydrogen or substituted or unsubstituted alkyl or is joined with at least one of $R^a$ and $R^b$ to form a substituted or unsubstituted bridged ring;

m is 0 or 1; and n is 0 or 1; provided that the compound is not of formula:

1

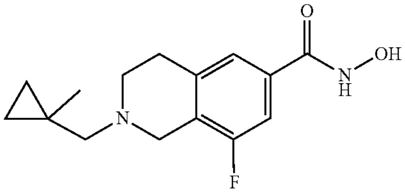

2

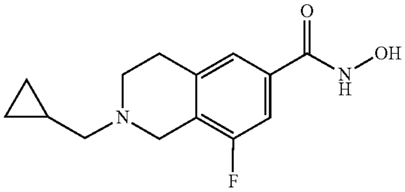

3

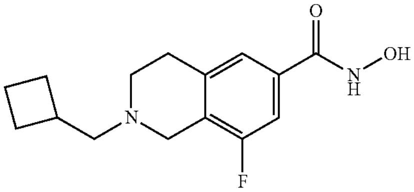

4

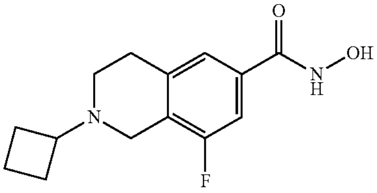

5

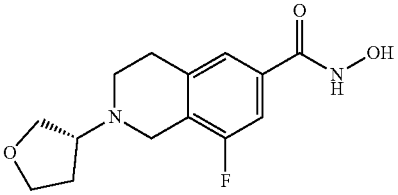

-continued

6

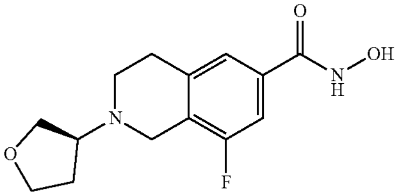

7

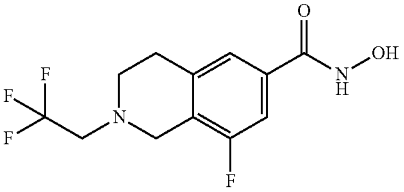

8

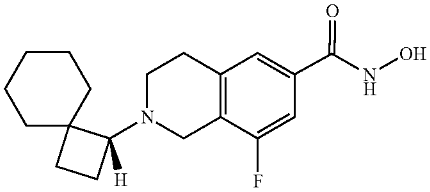

9

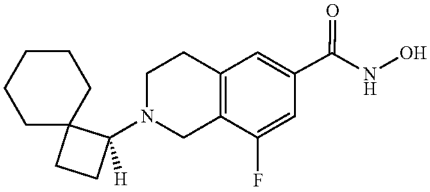

10

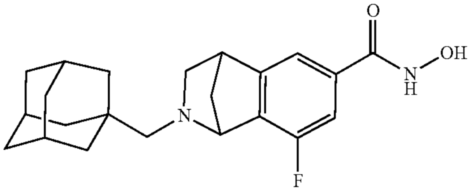

11

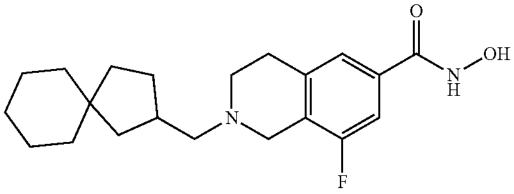

12

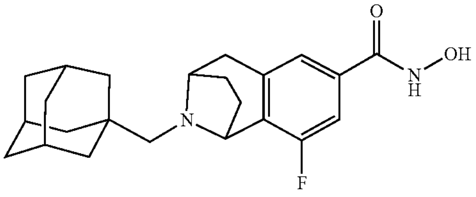

13

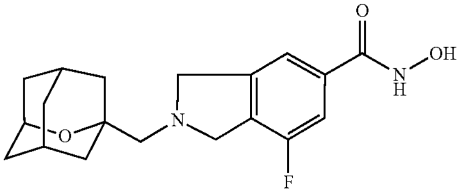

-continued
14
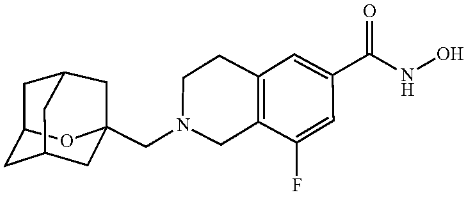
15
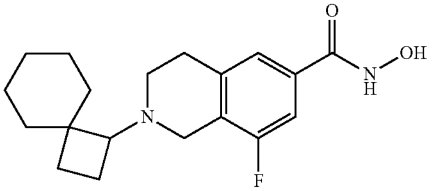
16
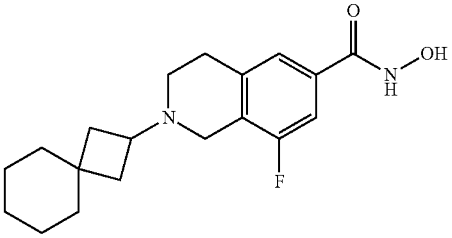
17
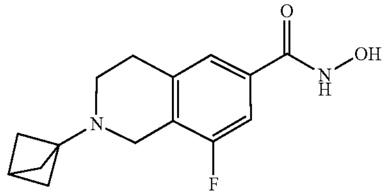
18
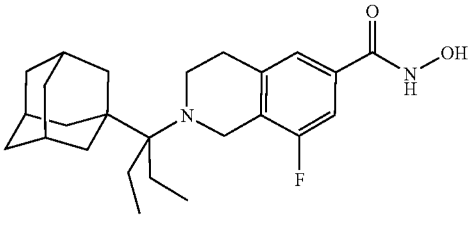
19
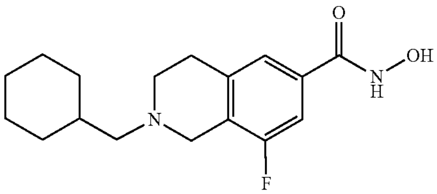
20
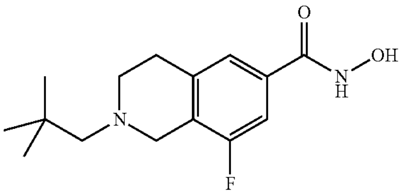
-continued
21
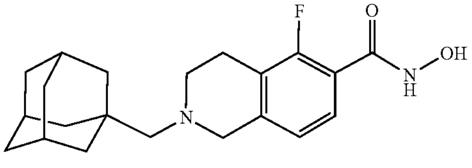
22
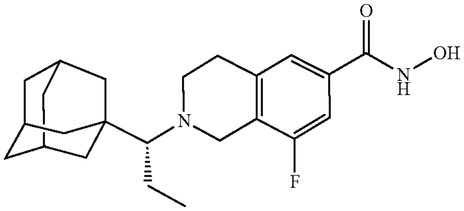
23
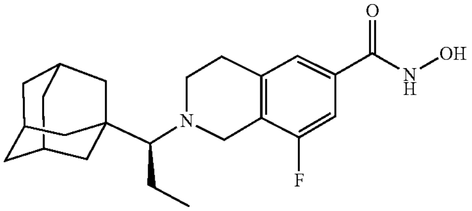
24
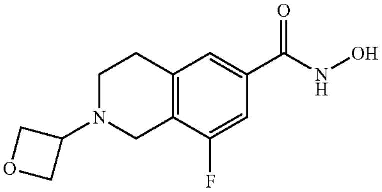
25
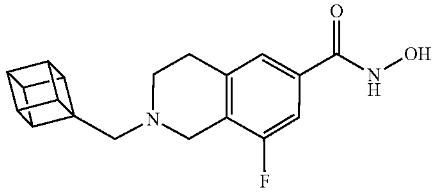
26
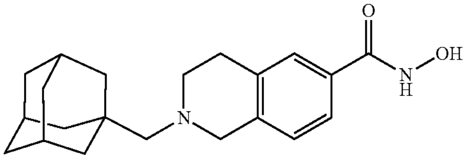
27
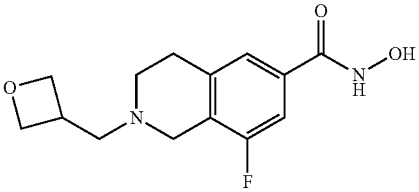
28
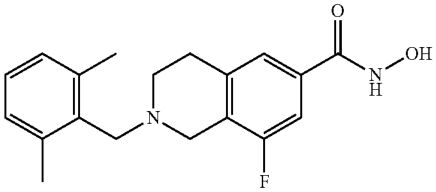

-continued
29
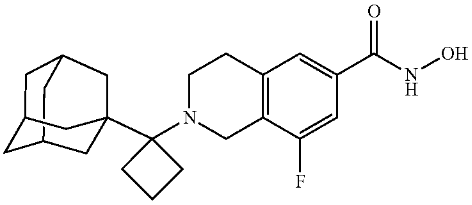
30
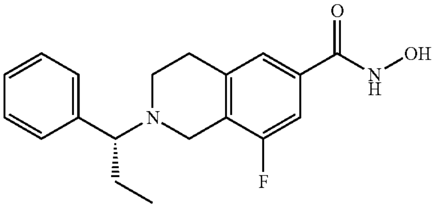
31
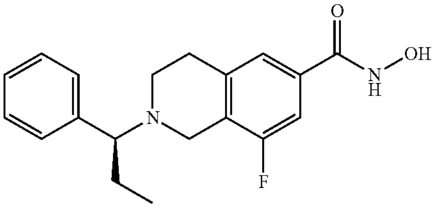
32
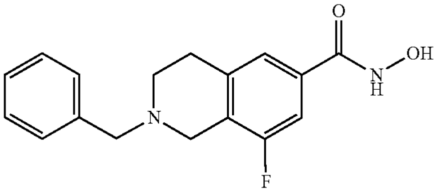
33
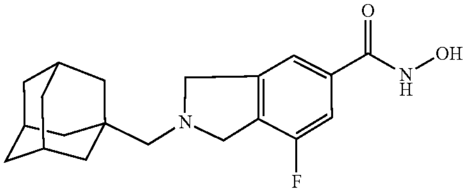
34
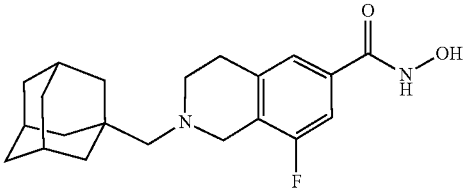
35
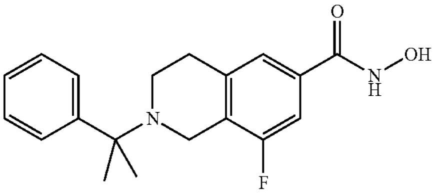
-continued
107
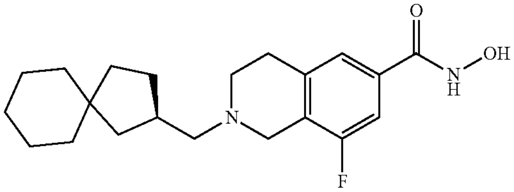
108
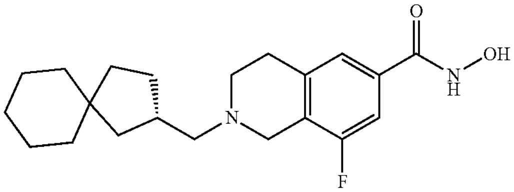
109
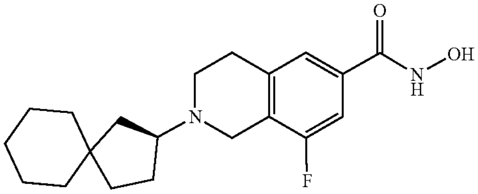
110
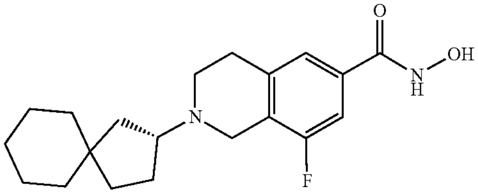
111
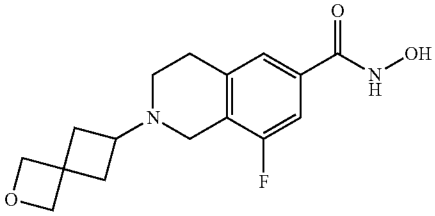
112
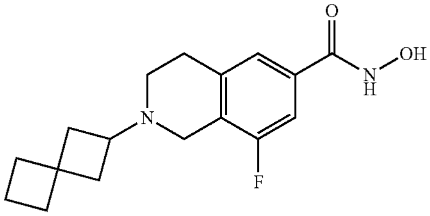
In certain embodiments, the compound of Formula (I) is not of formula:

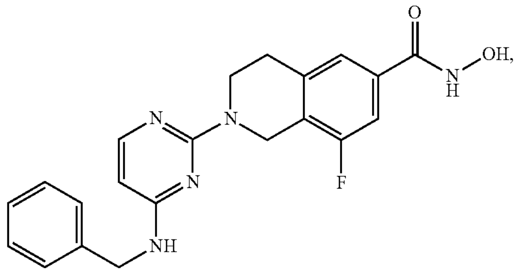

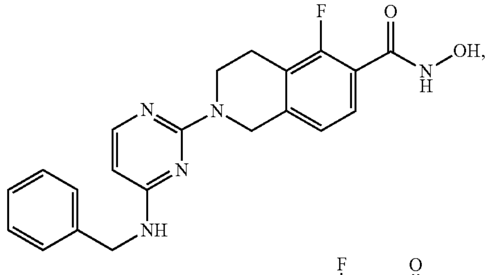

or

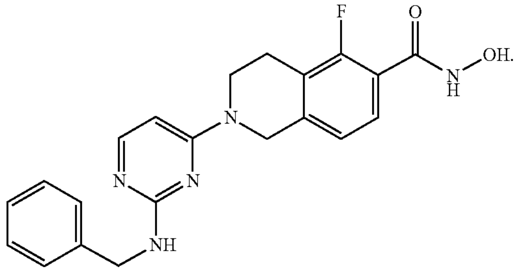

X[1] and X[2]

As described herein, $X^1$ is hydrogen or fluoro; and $X^2$ is hydrogen or fluoro; provided that at least one of $X^1$ and $X^2$ is fluorine. In certain embodiments, $X^1$ is hydrogen; and $X^2$ is fluoro. In certain embodiments, $X^1$ is fluoro; and $X^2$ is hydrogen. In certain embodiments, $X^1$ is fluoro; and $X^2$ is fluoro.

A

As described herein, A is substituted or unsubstituted alkyl, substituted or unsubstituted carbocyclyl, substituted or unsubstituted heterocyclyl, substituted or unsubstituted heteroaryl, or substituted or unsubstituted aryl.

In certain embodiments, A is unsubstituted $C_{1-4}$ alkyl, $C_{1-4}$ haloalkyl, substituted or unsubstituted cycloalkyl, substituted or unsubstituted heterocyclyl, substituted or unsubstituted heteroaryl, or substituted or unsubstituted aryl.

In certain embodiments, A is substituted or unsubstituted cycloalkyl, substituted or unsubstituted heterocyclyl, or substituted or unsubstituted aryl.

In certain embodiments, A is substituted or unsubstituted cycloalkyl. In certain embodiments, A is substituted or unsubstituted $C_{3-10}$ cycloalkyl. In certain embodiments, A is a substituted or unsubstituted $C_{5-10}$ bridged cycloalkyl, substituted or unsubstituted $C_{5-10}$ spirocyclic cycloalkyl, or substituted or unsubstituted $C_{3-8}$ monocyclic cycloalkyl. In certain embodiments, A is a substituted or unsubstituted $C_{5-10}$ bridged cycloalkyl. In certain embodiments, A is a substituted or unsubstituted $C_{5-10}$ spirocyclic cycloalkyl. In certain embodiments, A is a substituted or unsubstituted $C_{8-10}$ spirocyclic cycloalkyl. In certain embodiments, A is substituted or unsubstituted $C_{3-8}$ monocyclic cycloalkyl. In certain embodiments, A is substituted or unsubstituted $C_{3-6}$ monocyclic cycloalkyl.

In certain embodiments, A is cyclopropyl, cyclobutyl, cyclopentyl, cyclohexyl, adamantyl,

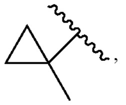, 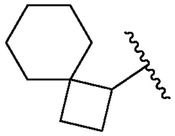, 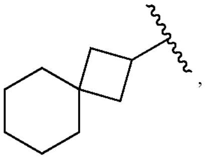, 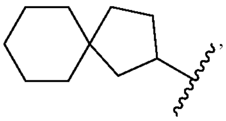, 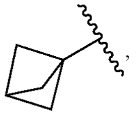, or 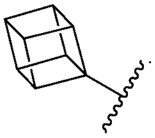.

In certain embodiments, A is cyclopropyl, cyclobutyl, cyclopentyl, cyclohexyl, adamantyl,

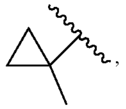, 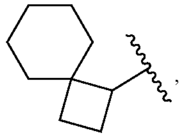, 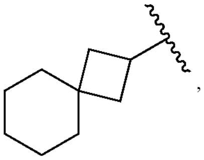, 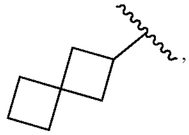, 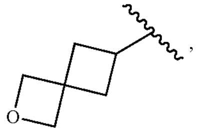, 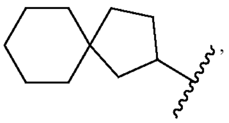, 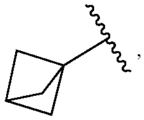, or 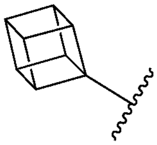.

In certain embodiments, A is substituted or unsubstituted heterocyclyl. In certain embodiments, A is substituted or unsubstituted 4-10 membered heterocyclyl. In certain embodiments, A is substituted or unsubstituted monocyclic 4-7 membered heterocyclyl or substituted or unsubstituted 5-10 membered bridged heterocyclyl. In certain embodiments, A is substituted or unsubstituted monocyclic 4-7 membered heterocyclyl. In certain embodiments, A is substituted or unsubstituted monocyclic 4-6 membered heterocyclyl. In certain embodiments, A is substituted or unsubstituted monocyclic 4-5 membered heterocyclyl. In certain embodiments, A is substituted or unsubstituted monocyclic 5-6 membered heterocyclyl. In certain embodiments, A is substituted or unsubstituted 5-10 membered bridged heterocyclyl. In certain embodiments, A is substituted or unsubstituted 6-10 membered bridged heterocyclyl. In certain embodiments, A is substituted or unsubstituted 8-10 membered bridged heterocyclyl. In certain embodiments, A is substituted or unsubstituted 10-membered bridged heterocyclyl.

In certain embodiments, A is substituted or unsubstituted oxetanyl, substituted or unsubstituted tetrahydrofuranyl, substituted or unsubstituted pyranyl, substituted or unsubstituted dihydropyranyl, substituted or unsubstituted tetrahydropyranyl, substituted or unsubstituted dioxanyl, substituted or unsubstituted oxepanyl, substituted or unsubstituted azetidinyl, substituted or unsubstituted pyrrolidinyl, substituted or unsubstituted piperidinyl, substituted or unsubstituted piperazinyl, substituted or unsubstituted azepanyl, substituted or unsubstituted diazepanyl, substituted or unsubstituted morpholinyl, substituted or unsubstituted oxazepanyl, or oxaadamantanyl. In certain embodiments, A is tetrahydrofuranyl, oxetanyl, or

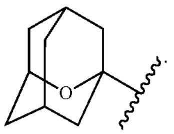 [SMILES: *C12CC3CC(CC(C3)O1)C2].

In certain embodiments, A is substituted or unsubstituted aryl. In certain embodiments, A is substituted or unsubstituted phenyl. In certain embodiments, A is unsubstituted phenyl. In certain embodiments, A is phenyl substituted with 1-5 substituents selected from halogen, cyano, alkyl, haloalkyl, alkenyl, alkynyl, alkoxy, haloalkoxy, or alkoxyalkyl. In certain embodiments, A is 2,6-dimethylphenyl.

In certain embodiments, A is unsubstituted $C_{1-4}$ alkyl or $C_{1-4}$ haloalkyl. In certain embodiments, A is unsubstituted $C_{1-4}$ alkyl. In certain embodiments, A is methyl, ethyl, n-propyl, isopropyl, n-butyl, sec-butyl, t-butyl, or isobutyl. In certain embodiments, A is t-butyl. In certain embodiments, A is $C_{1-4}$ haloalkyl. In certain embodiments, A is $—CF_3$, $—CHF_2$, or $—CH_2F$. In certain embodiments, A is $—CF_3$. In certain embodiments, A is $—CF_3$ or t-butyl.

In certain embodiments, A is unsubstituted $C_{1-4}$ alkyl, $C_{1-4}$ haloalkyl, substituted or unsubstituted $C_{8-10}$ spirocyclic cycloalkyl, substituted or unsubstituted $C_{3-6}$ monocyclic cycloalkyl, substituted or unsubstituted monocyclic 4-7 membered heterocyclyl, substituted or unsubstituted 8-10 membered bridged heterocyclyl, or substituted or unsubstituted phenyl.

In certain embodiments, A is $—CF_3$, $—C(CH_3)_3$, phenyl, 2,6-dimethylphenyl, tetrahydrofuranyl, oxetanyl, cyclopropyl, cyclobutyl, cyclopentyl, cyclohexyl, adamantyl,

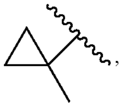, 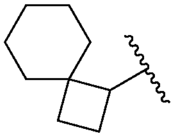, 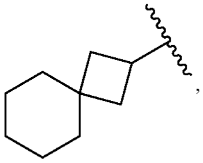, 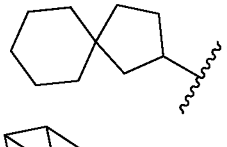, 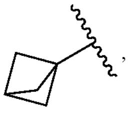, 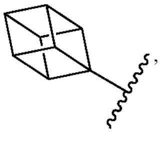, or 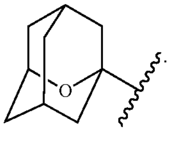.

In certain embodiments, A is $—CF_3$, $—C(CH_3)_3$, phenyl, 2,6-dimethylphenyl, tetrahydrofuranyl, oxetanyl, cyclopropyl, cyclobutyl, cyclopentyl, cyclohexyl, adamantyl,

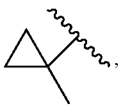, 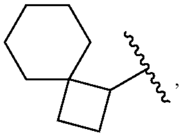, 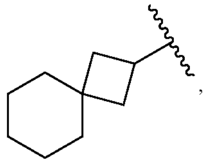, 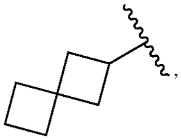, 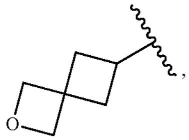, 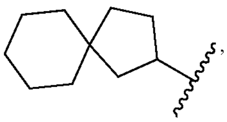, 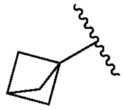, 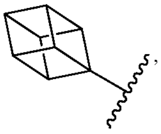, or 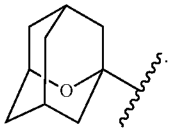.

In certain embodiments, A is a 7-11 membered bicyclic spirocyclic heterocyclyl, a $C_{7-11}$ substituted or unsubstituted bicyclic spirocyclic carbocyclyl, a $C_{4-7}$ bridged cycloalkyl, a 4-7 membered heterocyclyl; or a $C_{3-6}$ monocyclic cycloalkyl ring, each optionally substituted with methyl, acyl, oxo or cyclopropyl; or a substituted or unsubstituted $C_{1-6}$ alkyl. In certain embodiments, each A is optionally substituted with $(C_1\text{-}C_4)$alkyl or $(C_3\text{-}C_6)$cycloalkyl each optionally further substituted with one or more halogen; amino optionally further substituted with one or more $(C_1\text{-}C_4)$alkyl; halogen; oxo; acyl; $(C_1\text{-}C_4)$alkylamino or amino optionally substituted with $(C_1\text{-}C_4)$alkyl.

In certain embodiments, A is a 7-11 membered bicyclic spirocyclic heterocyclyl or 7-11 carbon bicyclic spirocyclic carbocyclyl, each optionally substituted with one or more: $(C_1\text{-}C_4)$alkyl optionally further substituted with one or more fluoro; amino optionally further substituted with one or more $(C_1\text{-}C_4)$alkyl; halogen; oxo; acyl; cyclopropyl; or benzyl.

In certain embodiments, A is

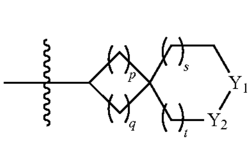 or 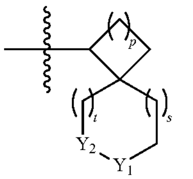

wherein: p and q are each independently 1 or 2; s and t are each independently 0, 1, or 2, provided that the sum of s and t is 0, 1, or 2; $Y_1$ and $Y_2$ are each independently selected from S(═O), $CR_{s1}R_{s2}$, $NR_s$ and O, provided that at least one of $Y_1$ and $Y_2$ is $CR_{s1}R_{s2}$; $R_{s1}$ and $R_{s2}$ are each independently hydrogen, or $(C_1\text{-}C_4)$alkyl optionally substituted with one or more halogen; and $R_s$ is hydrogen, $(C_1\text{-}C_4)$alkyl optionally substituted with one or more halogen, acyl, $(C_3\text{-}C_6)$cycloalkyl or 3- to 6-member heterocycloalkyl comprising one or more heteroatoms selected from the group consisting of O and N.

In certain embodiments, p and q are each independently 1 or 2; s and t are each independently 0, 1, or 2, provided that the sum of s and t is 0, 1, or 2; $Y_1$ and $Y_2$ are each independently S(=O), $CR_{s1}R_{s2}$, or $NR_s$, provided that at least one of $Y_1$ and $Y_2$ is $CR_{s1}R_{s2}$; $R_{s1}$ and $R_{s2}$ are each hydrogen; and $R_s$ is hydrogen, $(C_1$-$C_4)$alkyl, acyl, or $(C_3$-$C_6)$cycloalkyl In certain embodiments, A is

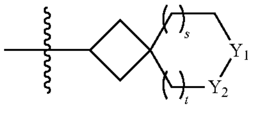
or
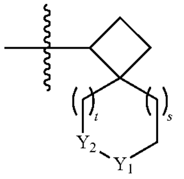
, wherein: s and t are each independently 0, 1, or 2, provided that the sum of s and t is 0, 1, or 2; $Y_1$ and $Y_2$ are each independently selected from S(=O), $CR_{s1}R_{s2}$, $NR_s$ and O, provided that at least one of $Y_1$ and $Y_2$ is $CR_{s1}R_{s2}$; $R_{s1}$ and $R_{s2}$ are each independently hydrogen, or $(C_1$-$C_4)$alkyl optionally substituted with one or more halogen; and $R_s$ is hydrogen, $(C_1$-$C_4)$alkyl optionally substituted with one or more halogen, acyl, $(C_3$-$C_6)$cycloalkyl or 3- to 6-member heterocycloalkyl comprising one or more heteroatoms selected from the group consisting of O and N.

In certain embodiments, $R_{s1}$ and $R_{s2}$ are each independently hydrogen, or methyl optionally substituted with one or more F; and $R_s$ is hydrogen, methyl optionally substituted with one or more F, acyl, or cyclopropyl. In certain embodiments, $R_{s1}$ and $R_{s2}$ are each hydrogen; and $R_s$ is hydrogen, methyl optionally substituted with one or more F, acyl, and cyclopropyl.

In certain embodiments, s and t are each independently 0, 1, or 2, provided that the sum of s and t is 0, 1, or 2; $Y_1$ and $Y_2$ are each independently $CR_{s1}R_{s2}$ or $NR_s$, provided that at least one of $Y_1$ and $Y_2$ is $CR_{s1}R_{s2}$; $R_{s1}$ and $R_{s2}$ are each hydrogen; and $R_s$ is hydrogen, $(C_1$-$C_4)$alkyl, acyl, or $(C_3$-$C_6)$cycloalkyl.

In certain embodiments, A is A is selected from the group consisting of:

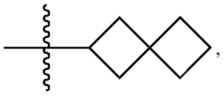
,
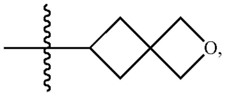
,
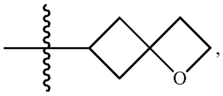
,
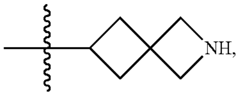
,
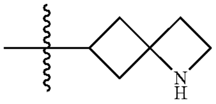
,
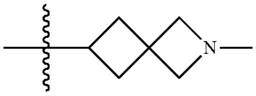
,
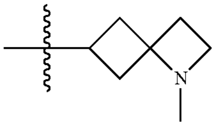
,
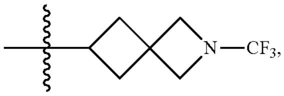
,
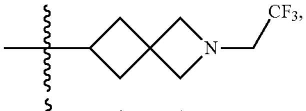
,
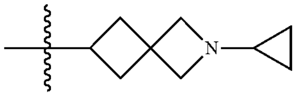
, -continued

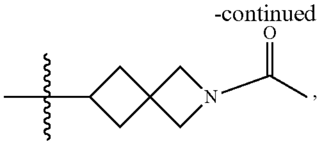
,
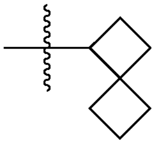
,
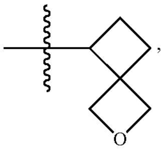
,
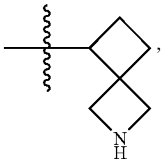
,
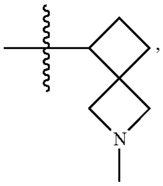
,
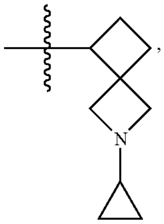
,
and
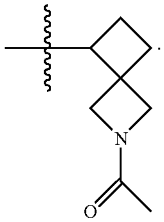
.

In certain embodiments, A is

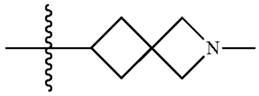
,
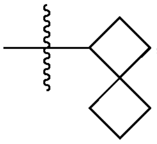
,
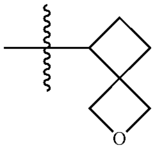
or
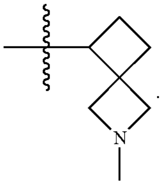
.

In certain embodiments, A is

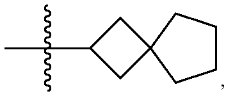
,
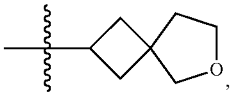
,
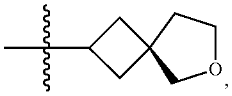
,
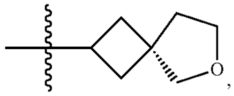
,
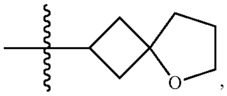
,
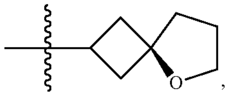
,
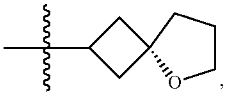
,
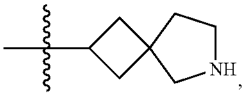
,
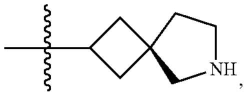
,
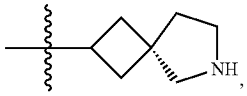
,
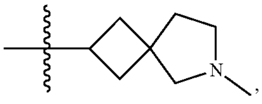
,
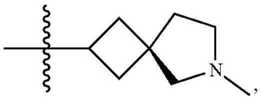
, -continued
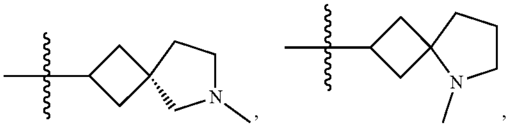
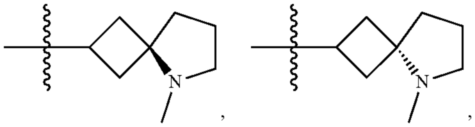
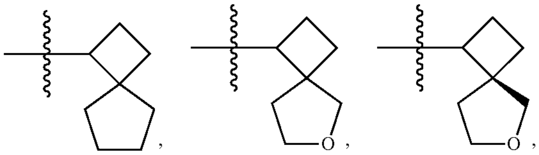
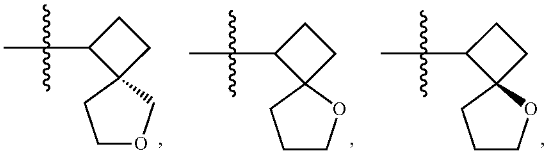
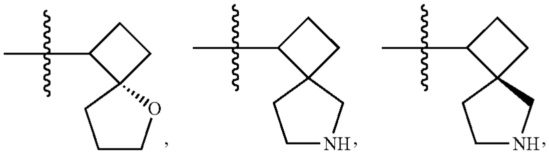
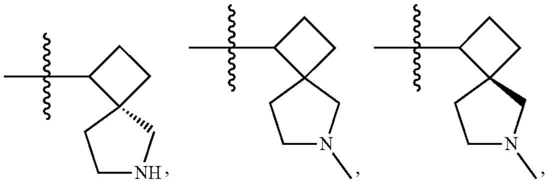
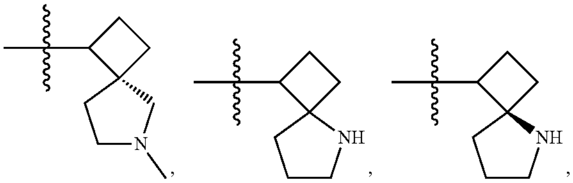
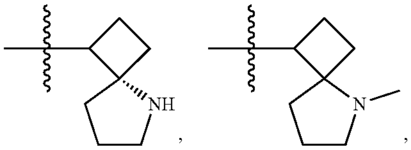
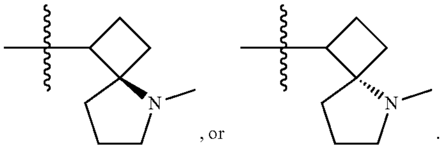
, or
In certain embodiments, A is
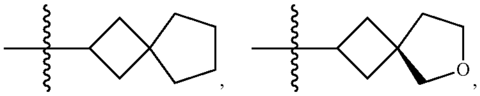
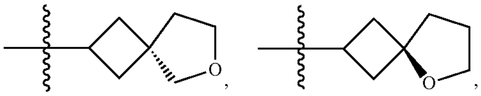
-continued
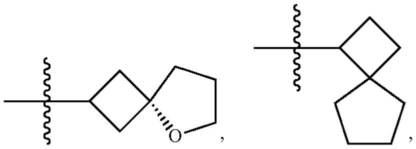
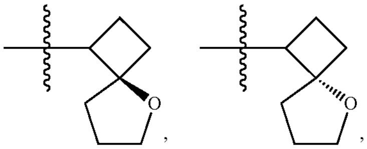
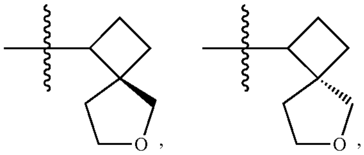
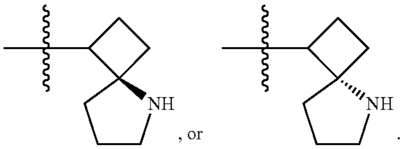
, or
In certain embodiments, A is
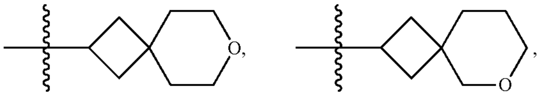
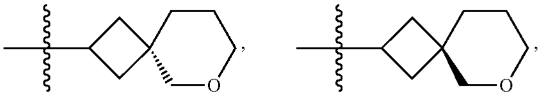
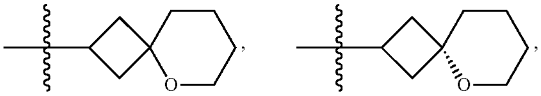
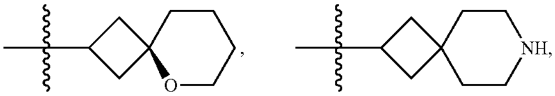
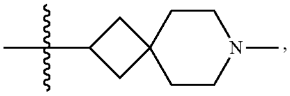
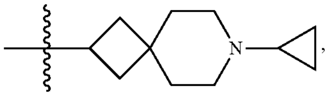
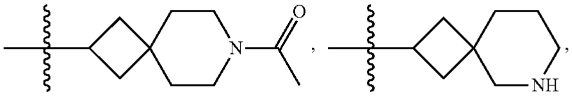
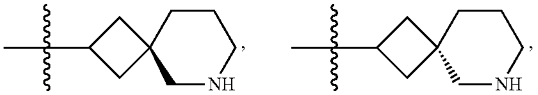
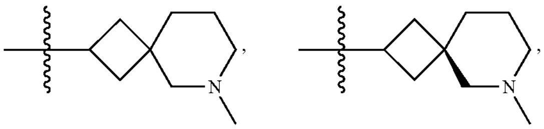

-continued
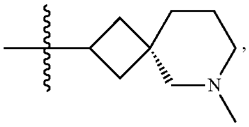
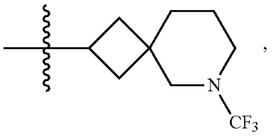
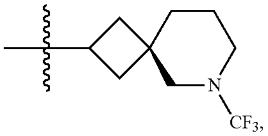
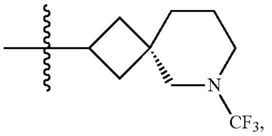
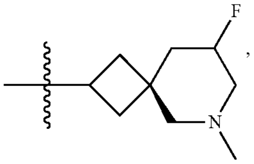
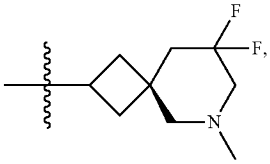
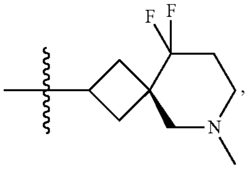
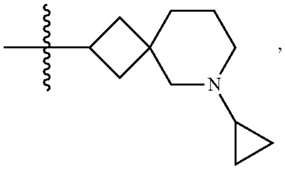
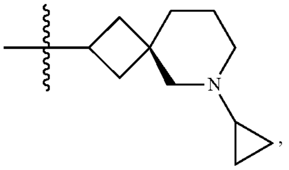
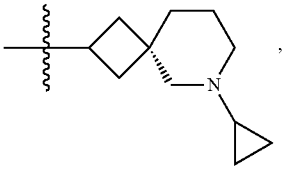
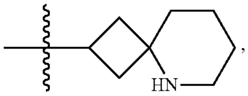
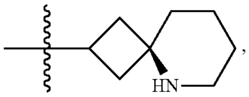
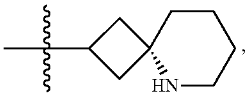
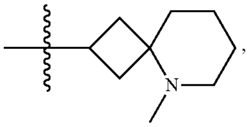
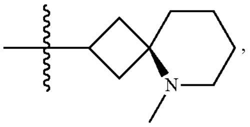
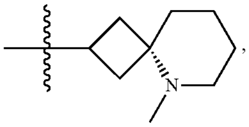
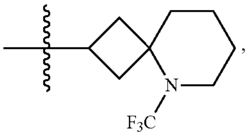
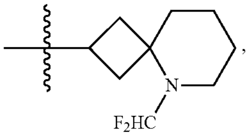
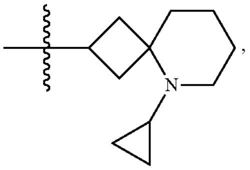
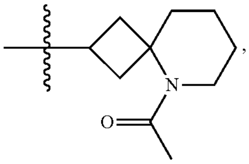
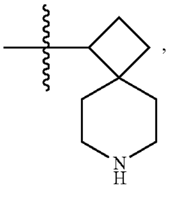
-continued
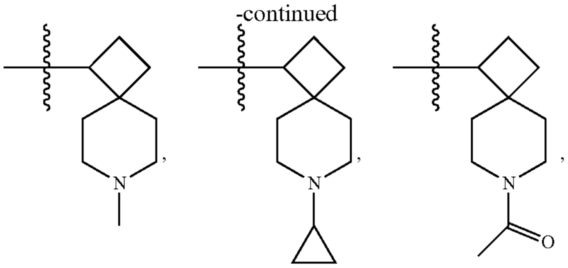
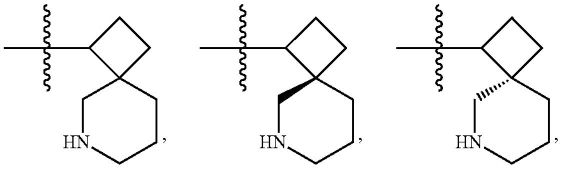
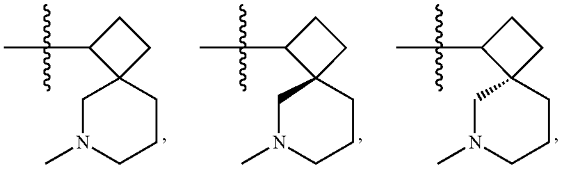
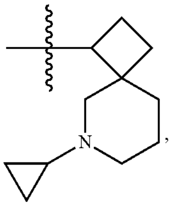
or
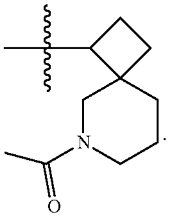
In certain embodiments, A is
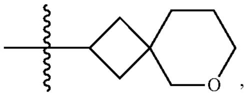
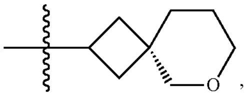
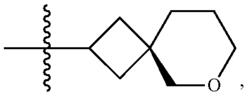
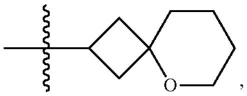
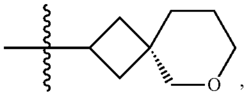
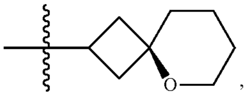
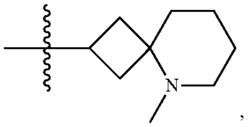
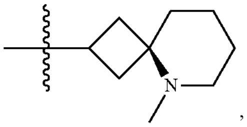
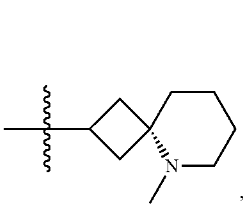
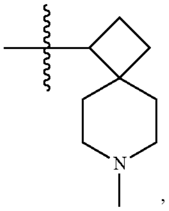
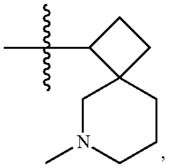
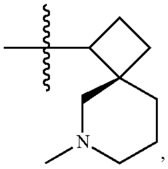
, or
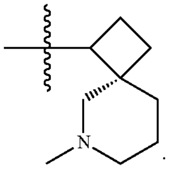

In certain embodiments, A is

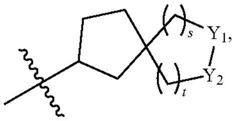

wherein: s and t are each independently 0, 1 or 2 provided that the sum of s and t is 1, 2 or 3; $Y_1$ and $Y_2$ are each independently selected from $CR_{s1}R_{s2}$, $NR_s$ and O, provided that at least one of $Y_1$ and $Y_2$ is $CR_{s1}R_{s2}$; $R_{s1}$ and $R_{s2}$ are each independently hydrogen, or $(C_1$-$C_4)$alkyl optionally substituted with one or more halogen; and $R_s$ is hydrogen, $(C_1$-$C_4)$alkyl optionally substituted with one or more halogen, acyl, $(C_3$-$C_6)$cycloalkyl or 3- to 6-member heterocycloalkyl comprising one or more heteroatoms selected from the group consisting of O and N.

In certain embodiments, s and t are each independently 0, 1, or 2, provided that the sum of s and t is 1, 2, or 3; $Y_1$ and $Y_2$ are each independently $CR_{s1}R_{s2}$ or $NR_s$, provided that at least one of $Y_1$ and $Y_2$ is $CR_{s1}R_{s2}$; $R_{s1}$ and $R_{s2}$ are each hydrogen; and $R_s$ is hydrogen, $(C_1$-$C_4)$alkyl, or acyl.

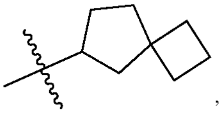 , 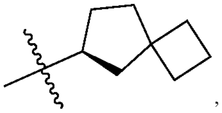 ,

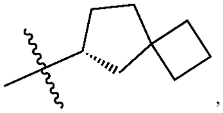 , 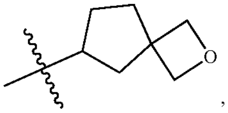 ,

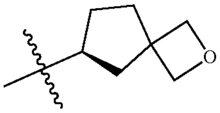 , 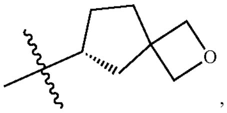 ,

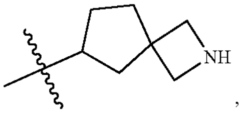 , 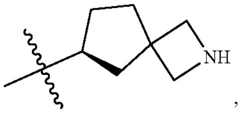 ,

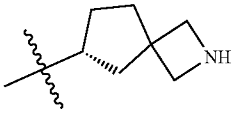 , 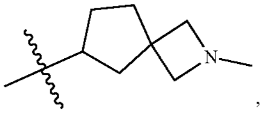 ,

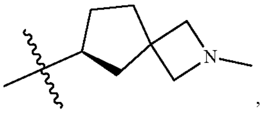 , 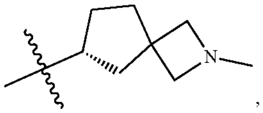 ,

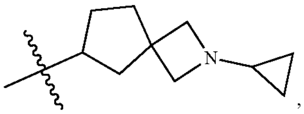 ,

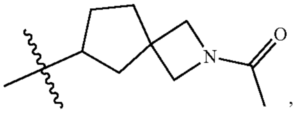 , 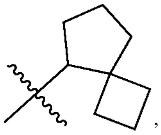 ,

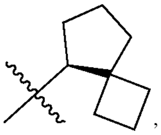 , 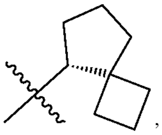 , 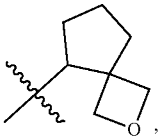 ,

-continued

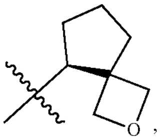 , 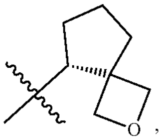 , 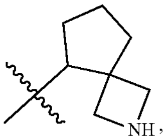 ,

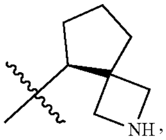 , 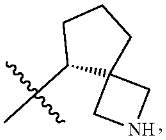 ,

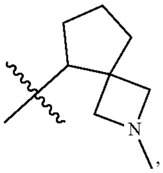 , 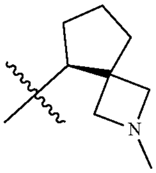 or 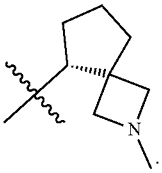 .

In certain embodiments, A is

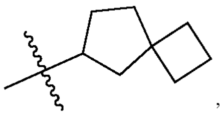 , 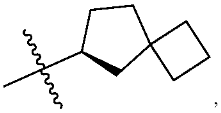 ,

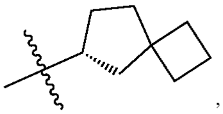 , 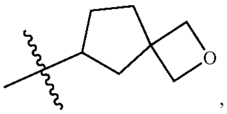 ,

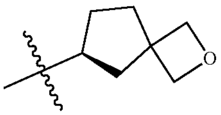 , 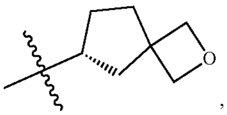 ,

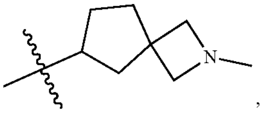 , 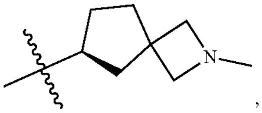 ,

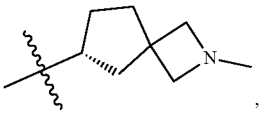 ,

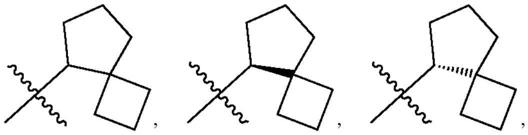

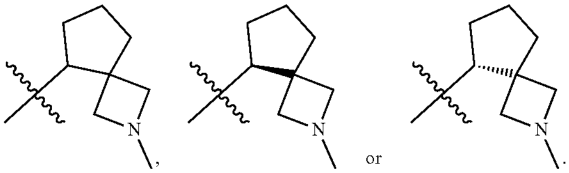

In certain embodiments, A is

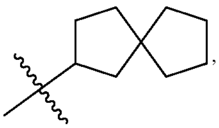 , 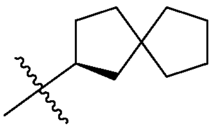 ,

-continued

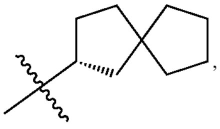,
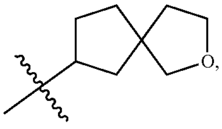
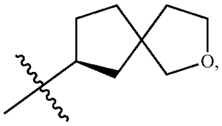
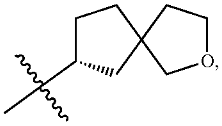
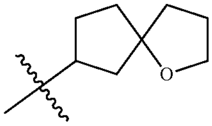,
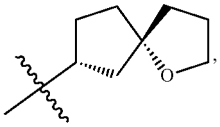,
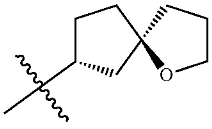,
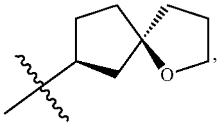,
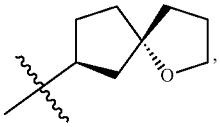,
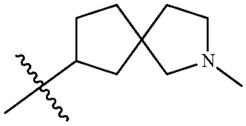,
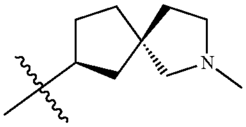,
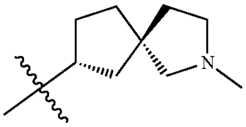,
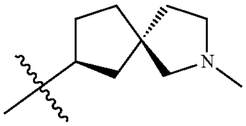,
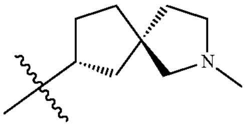,
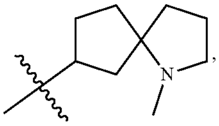,
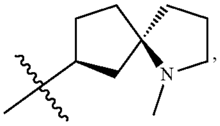,
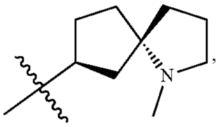,
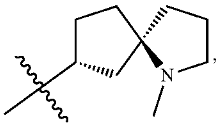, or
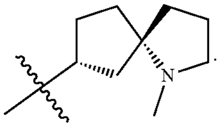.

In certain embodiments, A is

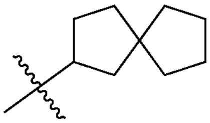,
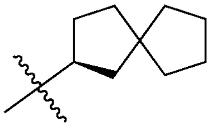, or
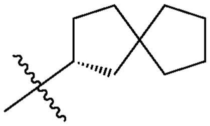.

In certain embodiments, A is

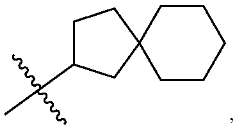,
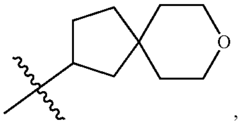,
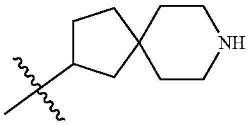,
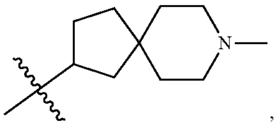,
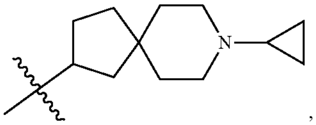,
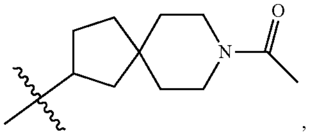,
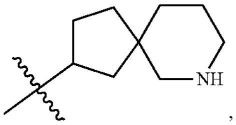,
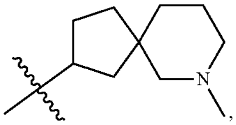,
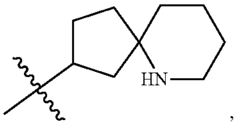, or
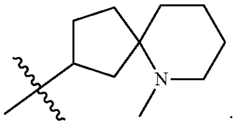.

In certain embodiments, A is

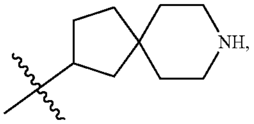
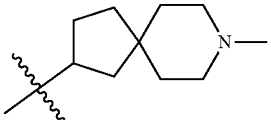, or
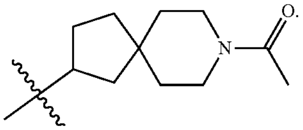

In certain embodiments, A is

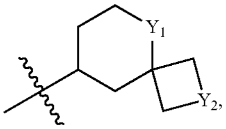

wherein: $Y_1$ is selected from $NR_s$ and O; $Y_2$ are each independently selected from $CR_{t1}R_{t2}$, $NR_s$ and O; $R_{t1}$ and $R_{t2}$ are each independently hydrogen, or $(C_1\text{-}C_4)$alkyl optionally substituted with one or more halogen; and $R_s$ is hydrogen, acyl, $(C_3\text{-}C_6)$cycloalkyl or $(C_1\text{-}C_4)$alkyl optionally substituted with one or more halogen or aryl. In certain embodiments, $Y_1$ is selected from $NR_s$ and O; $Y_2$ is $CH_2$; and $R_s$ is hydrogen, acyl, cyclopropyl or $(C_1-C_4)$alkyl optionally substituted with one or more halogen or phenyl.

In certain embodiments, $Y_1$ is selected from $NR_s$ and O; $Y_2$ is $CR_{t1}R_{t2}$ or $NR_s$; $R_{t1}$ and $R_{t2}$ are each hydrogen; and $R_s$ is hydrogen, acyl, $(C_3-C_6)$cycloalkyl or $(C_1-C_4)$alkyl.

In certain embodiments, A is

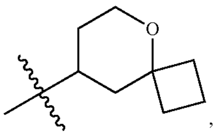,
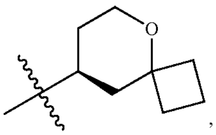,
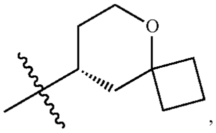,
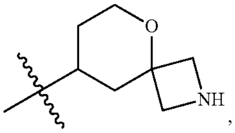,
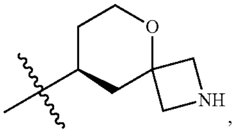,
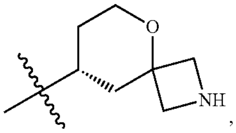,
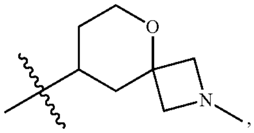,
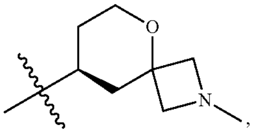,
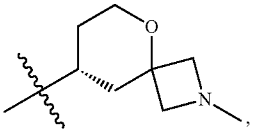,
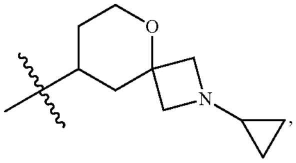,
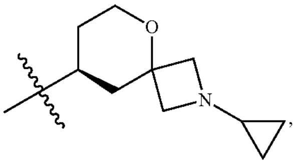,
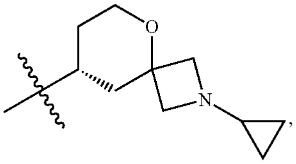,
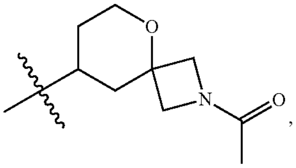,
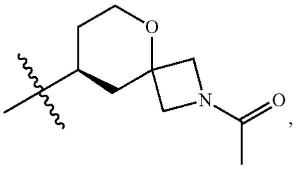,
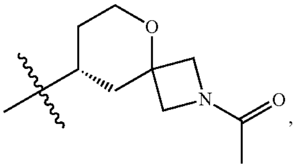, -continued

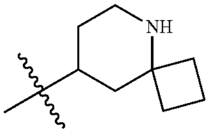,
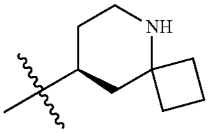,
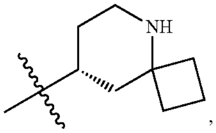,
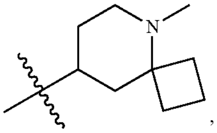,
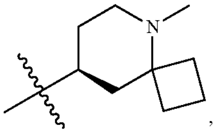,
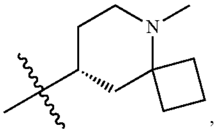,
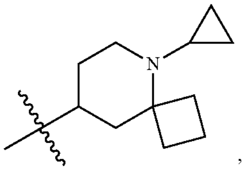,
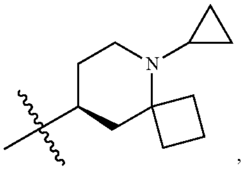,
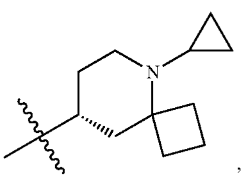,
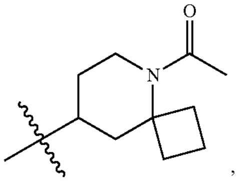,
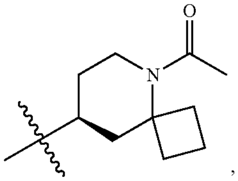,
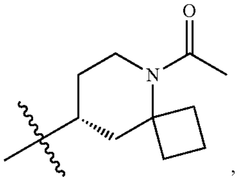,
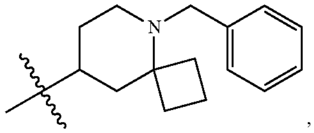,
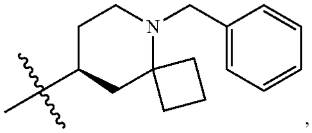, or
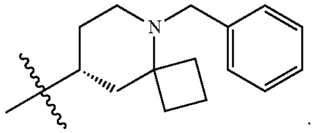.

In certain embodiments, A is

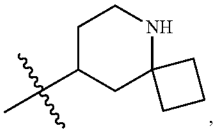,
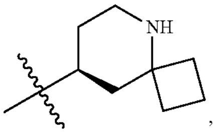,
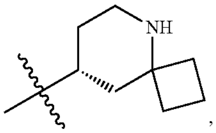,
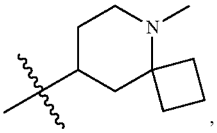,

-continued

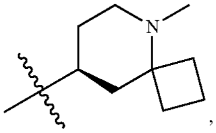 , 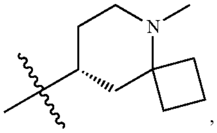 ,

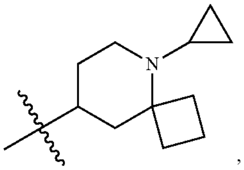 , 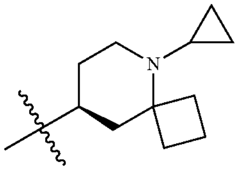 ,

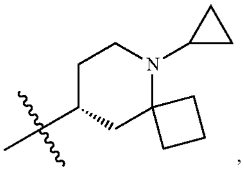 , 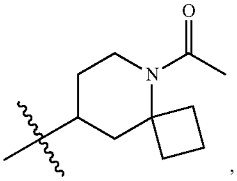 ,

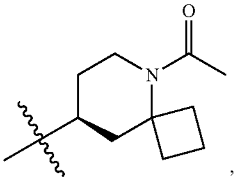 , 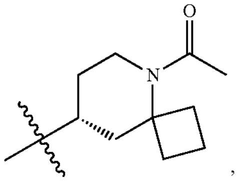 ,

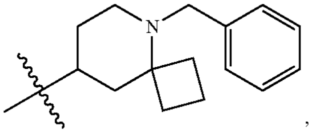 ,

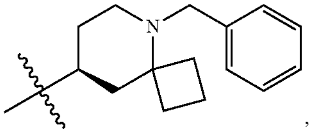 ,

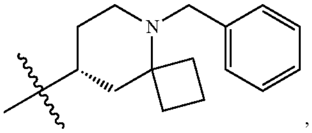 ,

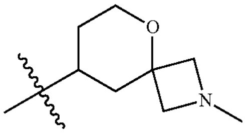 , 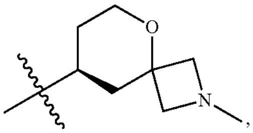 , or

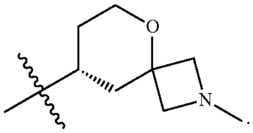 .

In certain embodiments, n is 1 and m is 1; and A is a 4-10 membered bridged, spirocyclic or fused bicyclic heterocyclyl comprising one or more heteroatoms selected from N and O, optionally substituted with ($C_1$-$C_4$)alkyl, halogen, oxo, ($C_3$-$C_6$)cycloalkyl, acyl, and amino optionally substituted with one or more methyl or cyclopropyl.

In certain embodiments, n is 1 and m is 1; and A is a 4-10 membered bridged heterocyclyl comprising one or more heteroatoms selected from N and O, optionally substituted with ($C_1$-$C_4$)alkyl, halogen, oxo, ($C_3$-$C_6$)cycloalkyl, acyl, and amino optionally substituted with one or more methyl or cyclopropyl.

In certain embodiments, A is

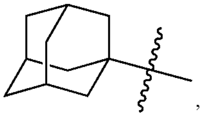 , 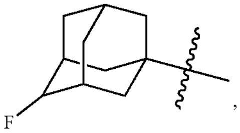 ,

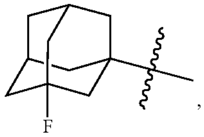 , 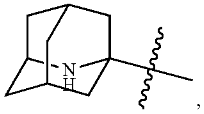 ,

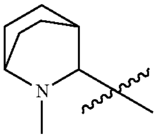 , 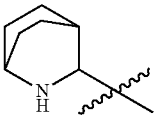 , 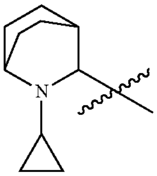 ,

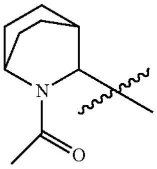 , 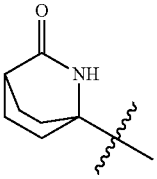 , 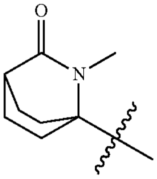 ,

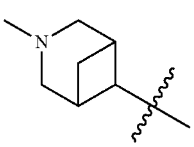 , 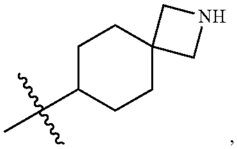 ,

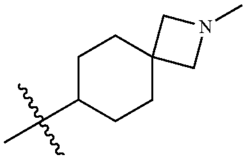 , 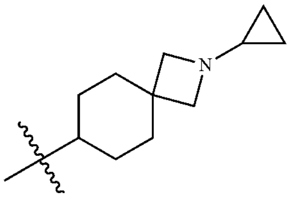 ,

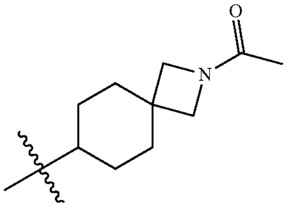 , 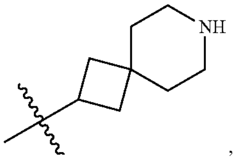 ,

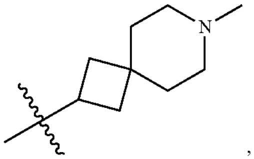 , 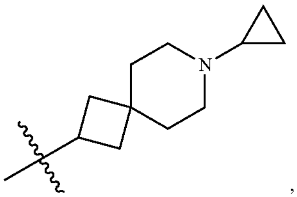 ,

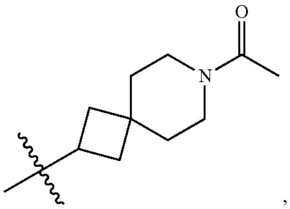 , 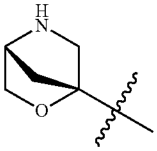 ,

-continued

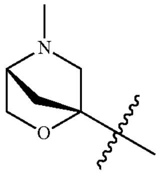,
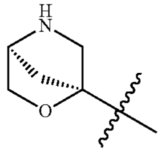,
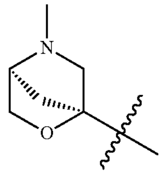,
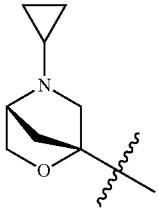,
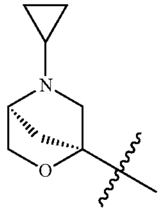,
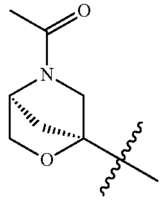,
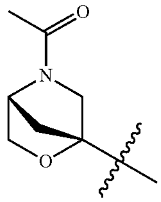,
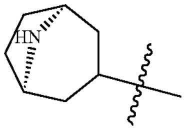,
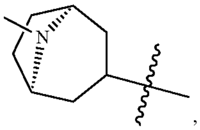,
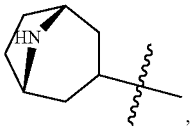,
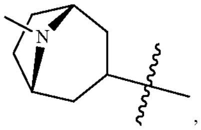,
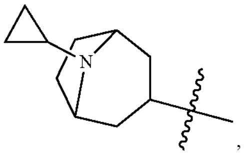,
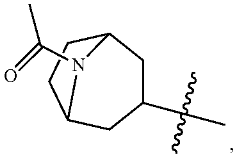,
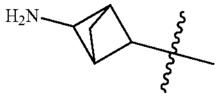,
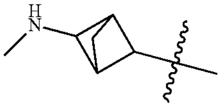,
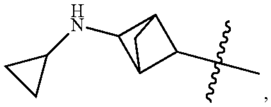,
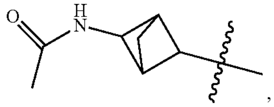,
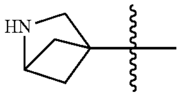,
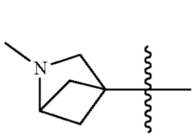,
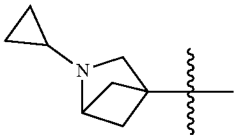,
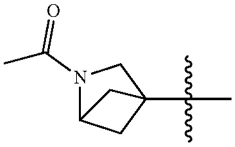,
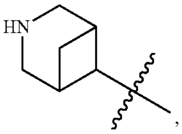,
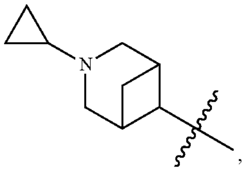,
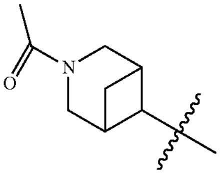, -continued

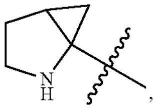,
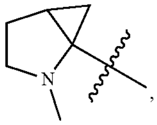,
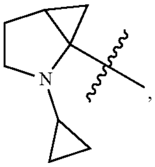, or
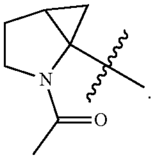.

In certain embodiments, A is

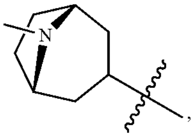,
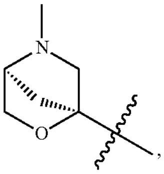,
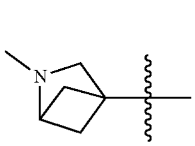,
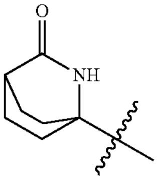,
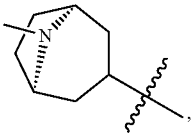, or
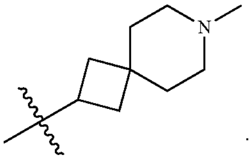.

In certain embodiments, n is 0 and m is 1; and A is a monocyclic 4-6 membered heterocyclyl ring or a $C_{4-6}$ cycloalkyl ring optionally substituted with one or more methyl or ethyl.

In certain embodiments, A is

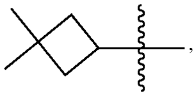, or
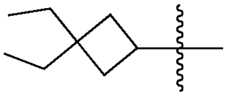.

In certain embodiments, n is 1 and m is 1; and A is a monocyclic 4-6 membered heterocyclyl ring or a $C_{4-6}$ cycloalkyl ring optionally substituted with one or more methyl.

In certain embodiments, A is

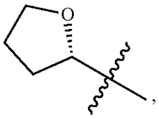,
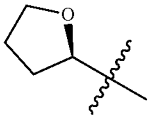,

-continued
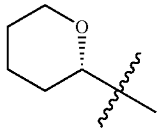, or 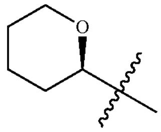.
In certain embodiments, A is substituted or unsubstituted 7-11 membered polycyclic spiro ring system, a substituted or unsubstituted $C_{4-6}$ cycloalkyl, or a 4-10 membered bridged heterocyclyl.
In certain embodiments, A is
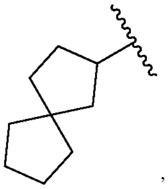, 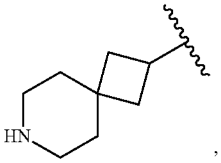, 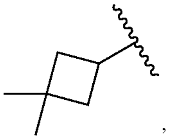,
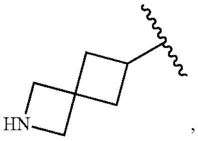, 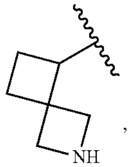, 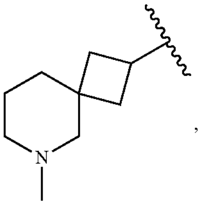,
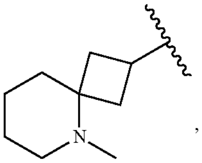, 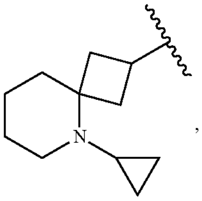, 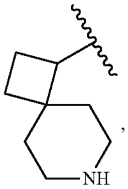,
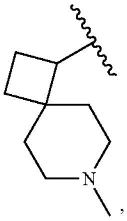, 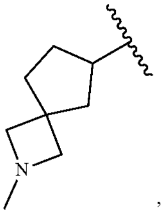, 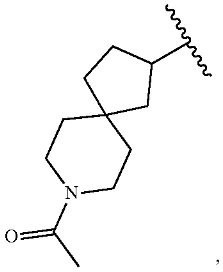,
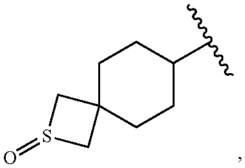, 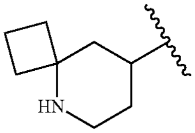,
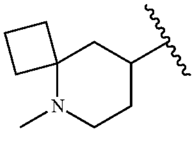, 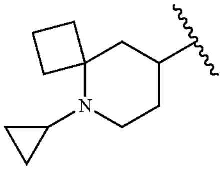,
-continued
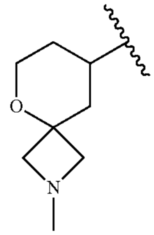, 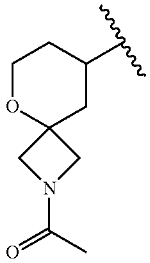, 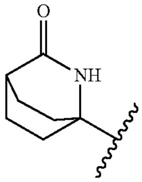,
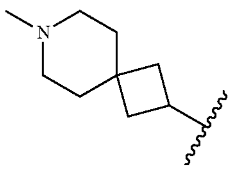, 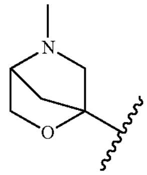,
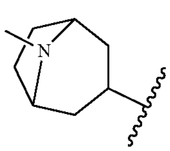, or 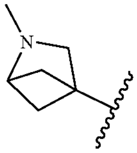.
In certain embodiments, A is
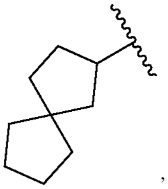, 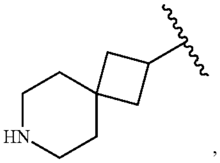, 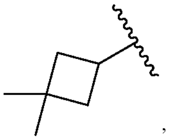,
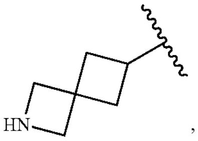, 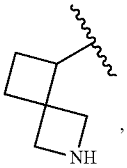,
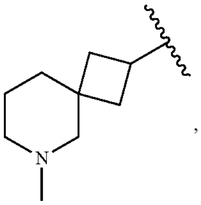, 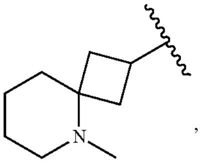,
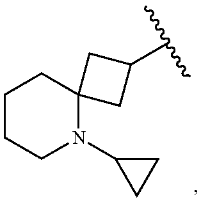, 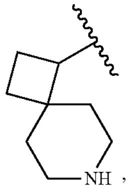, -continued
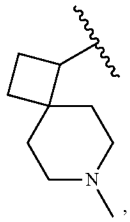, 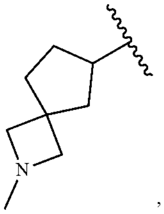, 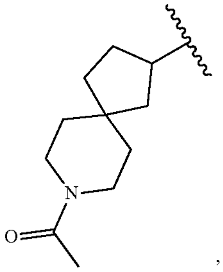, 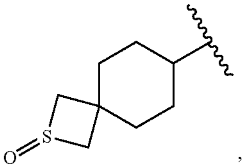, 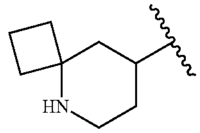, 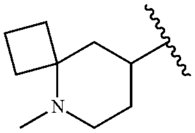, 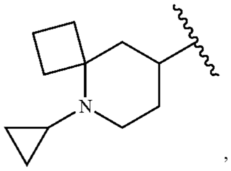, 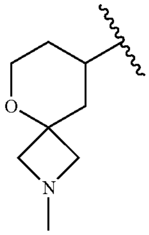, or 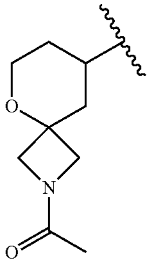.
In certain embodiments, A is
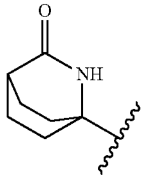, 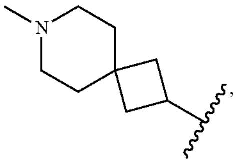, 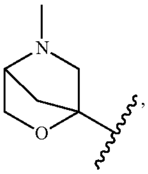, 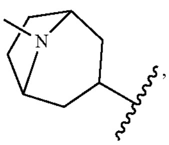, or 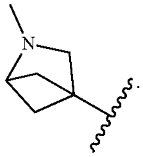.
In certain embodiments, A is
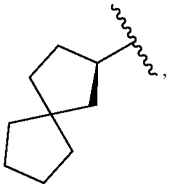, 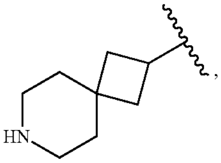,
-continued
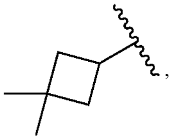, 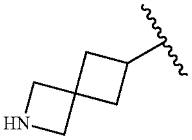, 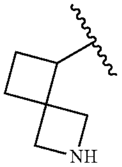, 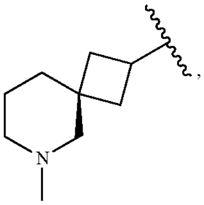, 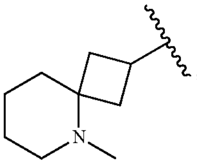, 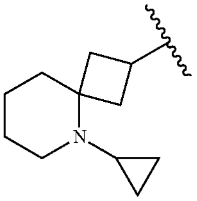, 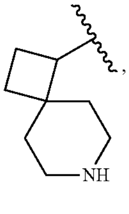, 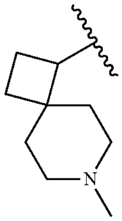, 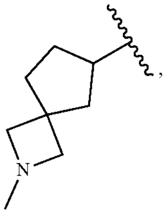, 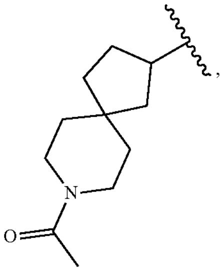, 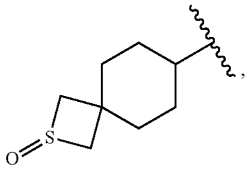, 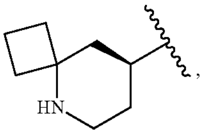, 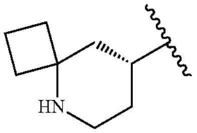, 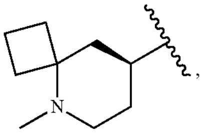, 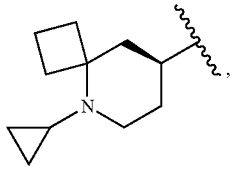, 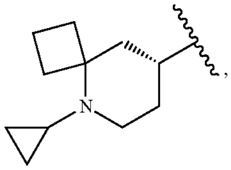, 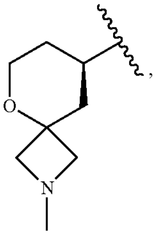, 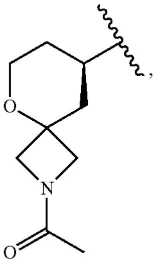, 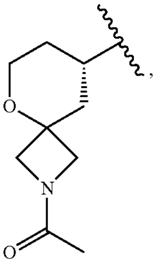, -continued

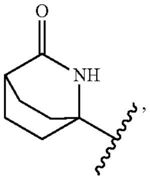,
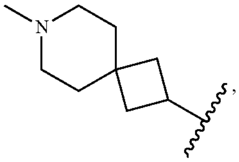,
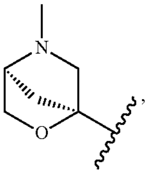,
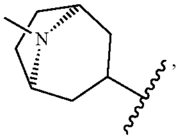,
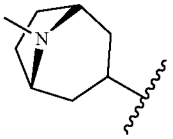, or
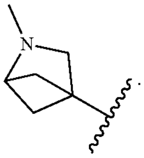.

In certain embodiments, A is

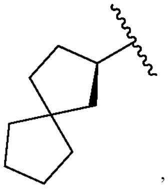,
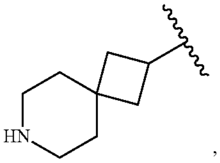,
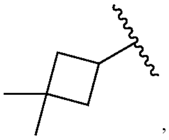,
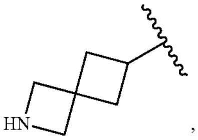,
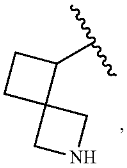,
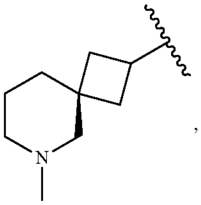,
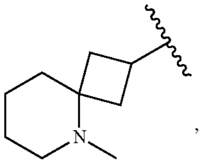,
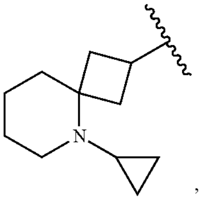,
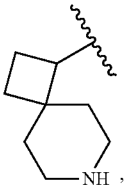,
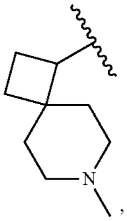,
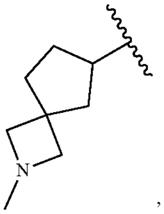,
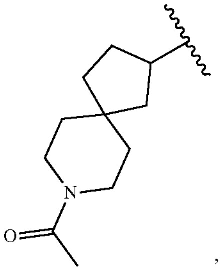, -continued

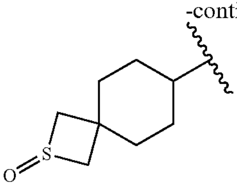,
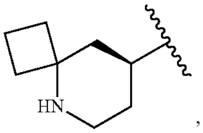,
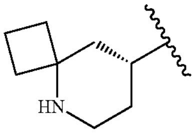,
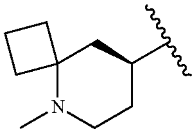,
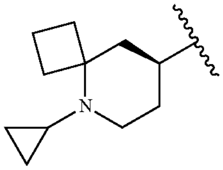,
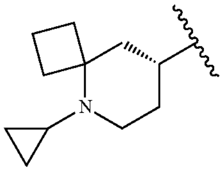,
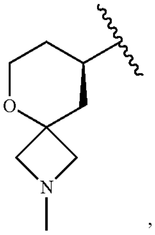,
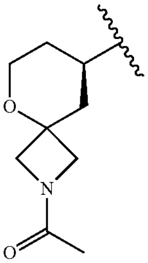, or
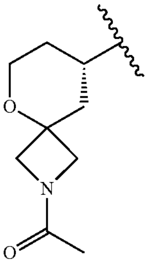.

In certain embodiments, A is

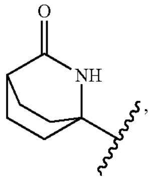,
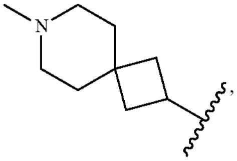,
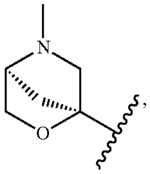,
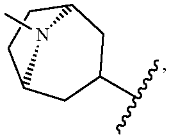,
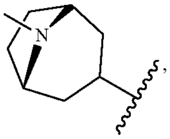, or
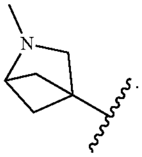.

In certain embodiments, A is not one or more of the following: unsubstituted or substituted $C_{1-6}$ aliphatic, unsubstituted or substituted 3-10-membered cycloaliphatic, unsubstituted or substituted 4-10-membered heterocyclyl having 1-4 heteroatoms independently selected from nitrogen, oxygen, and sulfur, unsubstituted or substituted 6-10-membered aryl, or unsubstituted or substituted 5-10-membered heteroaryl having 1-4 heteroatoms independently selected from nitrogen, oxygen, and sulfur.

In certain embodiments, A is not one or more of the following: methyl, ethyl, propyl, isopropyl, tert-butyl, butyl, iso-butyl, pentyl, hexyl, butenyl, propenyl, pentenyl, hexenyl, furanyl, thienyl, pyrrolyl, oxazolyl, thiazolyl, imidazolyl, pyrazolyl, isoxazolyl, isothiazolyl, oxadiazolyl, triazolyl, thiadiazolyl, phenyl, naphthyl, pyranyl, pyridyl, pyridazinyl, pyrimidinyl, pyrazinyl, triazinyl, indolizinyl, indolyl, isoindolyl, indazolyl, benzimidazolyl, benzthiazolyl, benzothienyl, benzofuranyl, benzoxazolyl, benzo[c][1,2,5]oxadiazolyl, benzo[c][1,2,5]thiadiazolyl, benzo[d]oxazol-2(3H)-one, 2,3-dihydrobenzo[b][1,4]dioxinyl, benzo[d][1,3]dioxolyl, 2,3-dihydrobenzofuranyl, 4H-furo[3,2-b]pyrrolyl, purinyl, quinolyl, isoquinolyl, tetrahydroquinolinyl, tetrahydroisoquinolinyl, cinnolinyl, phthalazinyl, quinazolinyl, quinoxalinyl, naphthyridinyl, pteridinyl, imidazopyridyl, benzodioxolyl, benzthiadiazolyl, pyrazolopyrimidinyl, tetrahydronaphthyridinyl, tetrahydrofuranyl, tetrahydropyranyl, tetrahydrothienyl, indanyl, tetrahydroindazolyl, pyrrolidinyl, pyrrolidonyl, piperidinyl, pyrrolinyl, decahydroquinolinyl, oxazolidinyl, piperazinyl, dioxanyl, diazepinyl, oxazepinyl, thiazepinyl, morpholinyl, thiomoφpholinyl, quinuclidinyl, phenanthridinyl, tetrahydronaphthyl, indolinyl, benzodioxanyl, chromanyl, cyclopropyl, cyclobutyl, cyclopentyl, cyclohexyl, cycloheptyl, cyclooctyl, cyclopentenyl, cyclohexenyl, cycloheptenyl, cyclooctenyl, bicycloheptanyl, bicyclooctanyl, or adamantyl, wherein each of the foregoing groups are unsubstituted or substituted.

In certain embodiments, A is not one or more of the following:

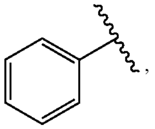
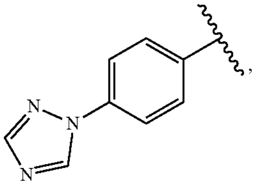
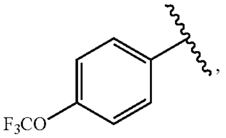
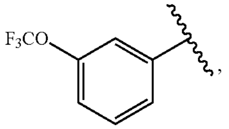
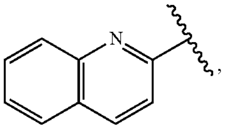
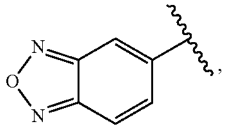
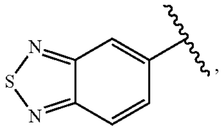
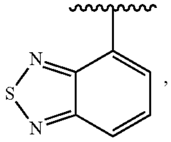
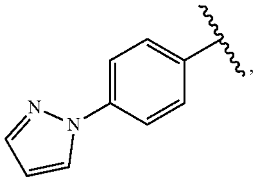
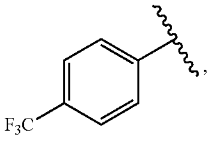
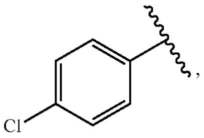
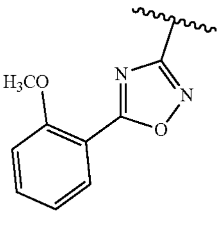
, -continued

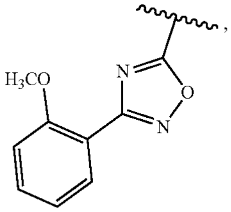
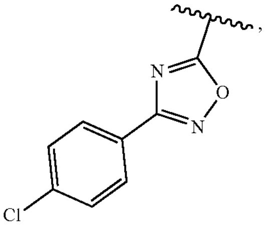
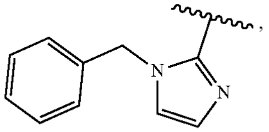
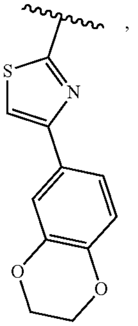
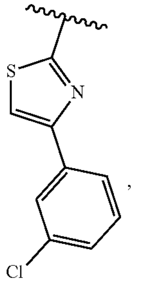
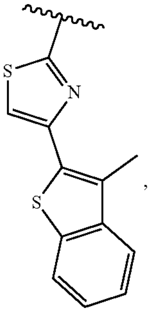
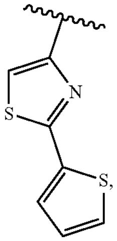
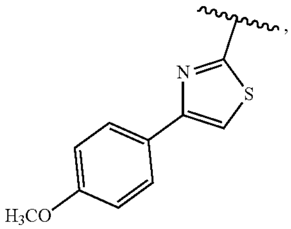
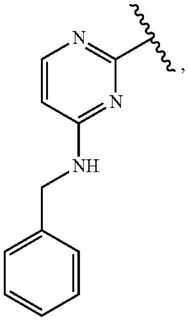
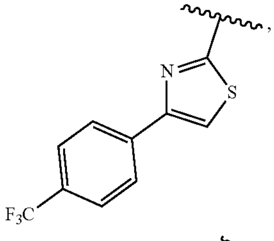
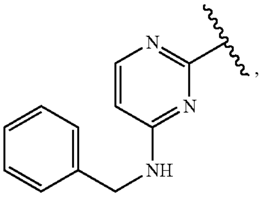
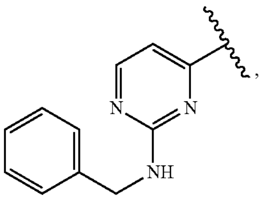
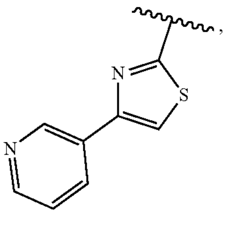

-continued

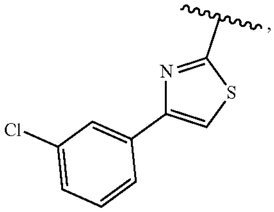, or 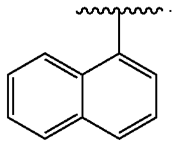.

In certain embodiments, A is not a 6-membered aromatic ring containing 0-2 nitrogen atoms which is unsubstituted or substituted with 1-2 independent occurrences of chloro, fluoro, cyano, hydroxy, methoxy, ethoxy, trifluoromethoxy, trifluoromethyl, methyl, or ethyl; wherein the 6-membered aromatic ring is substituted with a substituted or unsubstituted 4-7 membered heterocyclic ring containing one nitrogen atom.

In certain embodiments, A is not a phenyl or pyridyl unsubstituted or substituted with 1-2 independent occurrences of chloro, fluoro, cyano, hydroxy, methoxy, ethoxy, trifluoromethoxy, trifluoromethyl, methyl, or ethyl; wherein the phenyl or pyridyl is substituted with a substituted or unsubstituted 4-7 membered heterocyclic ring containing one nitrogen atom.

In certain embodiments, A is not a phenyl or pyridyl unsubstituted or substituted with 1-2 independent occurrences of chloro, fluoro, cyano, hydroxy, methoxy, ethoxy, trifluoromethoxy, trifluoromethyl, methyl, or ethyl; wherein the phenyl or pyridyl is substituted with a substituted or unsubstituted pyrrolidinyl or substituted or unsubstituted piperidinyl. In certain embodiments, A is not a phenyl or pyridyl unsubstituted or substituted with 1-2 independent occurrences of chloro, fluoro, cyano, hydroxy, methoxy, ethoxy, trifluoromethoxy, trifluoromethyl, methyl, or ethyl; wherein the phenyl or pyridyl is substituted with a substituted or unsubstituted pyrrolidinyl. In certain embodiments, A is not a phenyl or pyridyl unsubstituted or substituted with 1-2 independent occurrences of chloro, fluoro, cyano, hydroxy, methoxy, ethoxy, trifluoromethoxy, trifluoromethyl, methyl, or ethyl; wherein the phenyl or pyridyl is substituted with a substituted or unsubstituted piperidinyl.

In certain embodiments, A is not a substituted or unsubstituted 4-7 membered heterocyclic ring containing one nitrogen atom.

In certain embodiments, A is not a substituted or unsubstituted piperidinyl. In certain embodiments, A is not a substituted or unsubstituted pyrrolidinyl. In certain embodiments, A is not a substituted or unsubstituted pyrrolidinyl or substituted or unsubstituted piperidinyl.

In certain embodiments, A is not one or more of the following:

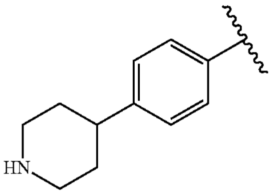,

-continued

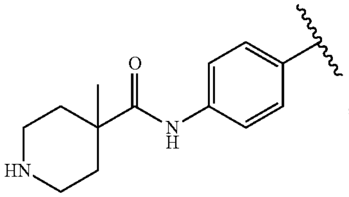,

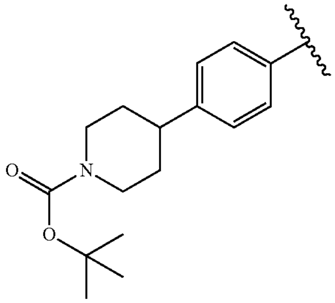,

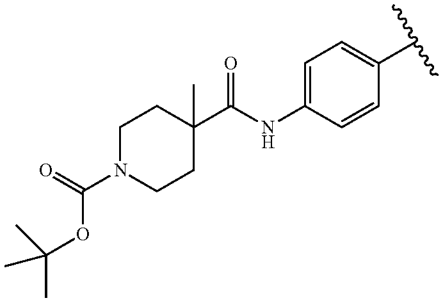,

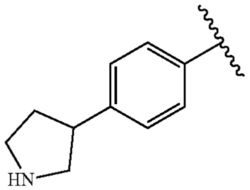,

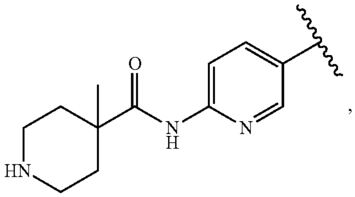,

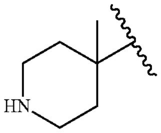, or 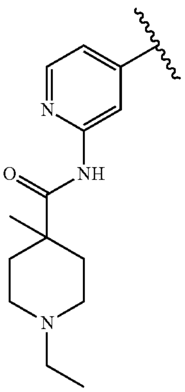.

R$^1$ and R$^2$

As described herein, R$^1$ is hydrogen or substituted or unsubstituted alkyl; and R$^2$ is hydrogen or substituted or unsubstituted alkyl; or $R^1$ and $R^2$ together form a substituted or unsubstituted heterocyclyl, or a substituted or unsubstituted cycloalkyl.

In certain embodiments, $R^1$ is hydrogen; and $R^2$ is unsubstituted $C_{1-4}$ alkyl; or $R^1$ and $R^2$ together form an unsubstituted cycloalkyl. In certain embodiments, $R^1$ is hydrogen; and $R^2$ is unsubstituted $C_{1-4}$ alkyl; or $R^1$ and $R^2$ together form an unsubstituted $C_{3-6}$ cycloalkyl. In certain embodiments, $R^1$ is hydrogen; and $R^2$ is methyl or ethyl; or $R^1$ and $R^2$ together form an unsubstituted $C_{3-6}$ cycloalkyl. In certain embodiments, $R^1$ is hydrogen; and $R^2$ is methyl or ethyl; or $R^1$ and $R^2$ together form an unsubstituted cyclobutyl. In certain embodiments, $R^1$ is hydrogen; and $R^2$ is unsubstituted $C_{1-4}$ alkyl. In certain embodiments, $R^1$ is hydrogen; and $R^2$ is methyl or ethyl. In certain embodiments, $R^1$ is hydrogen; and $R^2$ is methyl. In certain embodiments, $R^1$ is hydrogen; and $R^2$ is ethyl.

In certain embodiments, $R^1$ is unsubstituted $C_{1-4}$ alkyl; and $R^2$ is hydrogen; or $R^1$ and $R^2$ together form an unsubstituted cycloalkyl. In certain embodiments, $R^1$ is unsubstituted $C_{1-4}$ alkyl; and $R^2$ is hydrogen; or $R^1$ and $R^2$ together form an unsubstituted $C_{3-6}$ cycloalkyl. In certain embodiments, $R^1$ is methyl or ethyl; and $R^2$ is hydrogen; or $R^1$ and $R^2$ together form an unsubstituted $C_{3-6}$ cycloalkyl. In certain embodiments, $R^1$ is methyl or ethyl; and $R^2$ is hydrogen; or $R^1$ and $R^2$ together form an unsubstituted cyclobutyl.

In certain embodiments, $R^1$ is unsubstituted $C_{1-4}$ alkyl; and $R^2$ is hydrogen. In certain embodiments, $R^1$ is methyl or ethyl; and $R^2$ is hydrogen. In certain embodiments, $R^1$ is methyl; and $R^2$ is hydrogen. In certain embodiments, $R^1$ is ethyl; and $R^2$ is hydrogen.

In certain embodiments, $R^1$ is hydrogen; and $R^2$ is unsubstituted $C_{1-4}$ alkyl. In certain embodiments, $R^1$ is hydrogen; and $R^2$ is methyl or ethyl. In certain embodiments, $R^1$ is hydrogen; and $R^2$ is methyl. In certain embodiments, $R^1$ is hydrogen; and $R^2$ is ethyl.

In certain embodiments, $R^1$ and $R^2$ together form a substituted or unsubstituted cycloalkyl. In certain embodiments, $R^1$ and $R^2$ together form an unsubstituted cycloalkyl. In certain embodiments, $R^1$ and $R^2$ together form an unsubstituted $C_{3-6}$ cycloalkyl. In certain embodiments, $R^1$ and $R^2$ together form an unsubstituted cyclopropyl. In certain embodiments, $R^1$ and $R^2$ together form an unsubstituted cyclobutyl. In certain embodiments, $R^1$ and $R^2$ together form an unsubstituted cyclopentyl. In certain embodiments, $R^1$ and $R^2$ together form an unsubstituted cyclohexyl.

In certain embodiments, $R^1$ is hydrogen; and $R^2$ is hydrogen.

$R^a$, $R^b$, $R^c$, m, and n

As described herein, $R^a$ is hydrogen or is joined with $R^c$ to form a substituted or unsubstituted bridged ring; $R^b$ is hydrogen or is joined with $R^c$ to form a substituted or unsubstituted bridged ring; and $R^c$ is hydrogen or substituted or unsubstituted alkyl or is joined with at least one of $R^a$ and $R^b$ to form a substituted or unsubstituted bridged ring.

In certain embodiments, $R^a$ is joined with $R^c$ to form a substituted or unsubstituted bridged ring. In certain embodiments, $R^a$ is joined with $R^c$ to form a substituted or unsubstituted bridged ring; and $R^b$ is hydrogen. In certain embodiments, $R^a$ is joined with $R^c$ to form an unsubstituted bridged ring; and $R^b$ is hydrogen. In certain embodiments, $R^a$ is joined with $R^c$ to form an unsubstituted carbocyclic bridged ring; and $R^b$ is hydrogen. In certain embodiments, $R^a$ is joined with $R^c$ to form an unsubstituted heterocyclic bridged ring; and $R^b$ is hydrogen.

In certain embodiments, $R^b$ is joined with $R^c$ to form a substituted or unsubstituted bridged ring. In certain embodiments, $R^b$ is joined with $R^c$ to form a substituted or unsubstituted bridged ring; and $R^a$ is hydrogen. In certain embodiments, $R^b$ is joined with $R^c$ to form an unsubstituted bridged ring; and $R^a$ is hydrogen. In certain embodiments, $R^b$ is joined with $R^c$ to form an unsubstituted carbocyclic bridged ring; and $R^a$ is hydrogen. In certain embodiments, $R^b$ is joined with $R^c$ to form an unsubstituted heterocyclic bridged ring; and $R^a$ is hydrogen.

In certain embodiments, $R^a$ is hydrogen; $R^b$ is hydrogen; and $R^c$ is hydrogen or substituted or unsubstituted alkyl. In certain embodiments, $R^a$ is hydrogen; $R^b$ is hydrogen; and $R^c$ is hydrogen or unsubstituted alkyl. In certain embodiments, $R^a$ is hydrogen; $R^b$ is hydrogen; and $R^c$ is hydrogen or unsubstituted $C_{1-4}$ alkyl. In certain embodiments, $R^a$ is hydrogen; $R^b$ is hydrogen; and $R^c$ is hydrogen. In certain embodiments, $R^a$ is hydrogen; $R^b$ is hydrogen; and $R^c$ is unsubstituted $C_{1-4}$ alkyl.

As described herein, m is 0 or 1. In certain embodiments, m is 0. In certain embodiments, m is 1. As described herein, n is 0 or 1. In certain embodiments, n is 0. In certain embodiments, n is 1.

In certain embodiments, m is 0 or 1; and n is 0. In certain embodiments, m is 0 or 1; and n is 1. In certain embodiments, m is 0; and n is 0 or 1. In certain embodiments, m is 1; and n is 0 or 1. In certain embodiments, m is 0; and n is 1. In certain embodiments, m is 0; and n is 0. In certain embodiments, m is 1; and n is 0.

Certain Embodiments

In certain embodiments, the compound of Formula (I) is of Formula (I-a):

(I-a)

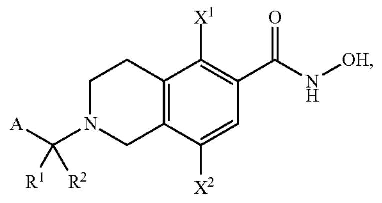

or a pharmaceutically acceptable salt, co-crystal, tautomer, stereoisomer, solvate, hydrate, polymorph, isotopically enriched derivative, or prodrug thereof; wherein A, $R^1$, $R^2$, $X^1$, and $X^2$ are as defined herein.

In certain embodiments of Formula (I-a), A is

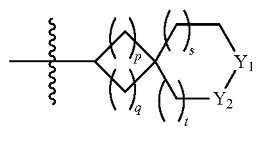

or

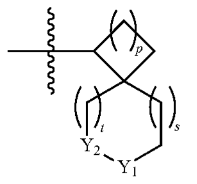

wherein: p and q are each independently 1 or 2; s and t are each independently 0, 1, or 2, provided that the sum of s and t is 0, 1, or 2; $Y_1$ and $Y_2$ are each independently selected from S(=O), $CR_{s1}R_{s2}$, $NR_s$ and O, provided that at least one of $Y_1$ and $Y_2$ is $CR_{s1}R_{s2}$; $R_{S1}$ and $R_{s2}$ are each independently hydrogen, or $(C_1$-$C_4)$alkyl optionally substituted with one or more halogen; and $R_s$ is hydrogen, $(C_1$-$C_4)$alkyl optionally substituted with one or more halogen, acyl, $(C_3$-$C_6)$cycloalkyl or 3-6-membered heterocycloalkyl comprising one or more heteroatoms selected from the group consisting of O and N.

In certain embodiments of Formula (I-a), A is

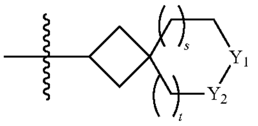 or 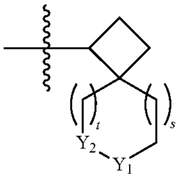 , wherein: s and t are each independently 0, 1, or 2, provided that the sum of s and t is 0, 1, or 2; $Y_1$ and $Y_2$ are each independently selected from S(═O), $CR_{s1}R_{s2}$, $NR_s$ and O, provided that at least one of $Y_1$ and $Y_2$ is $CR_{s1}R_{s2}$; $R_{s1}$ and $R_{s2}$ are each independently hydrogen, or $(C_1$-$C_4)$alkyl optionally substituted with one or more halogen; and $R_s$ is hydrogen, $(C_1$-$C_4)$alkyl optionally substituted with one or more halogen, acyl, $(C_3$-$C_6)$cycloalkyl or 3- to 6-member heterocycloalkyl comprising one or more heteroatoms selected from the group consisting of O and N.

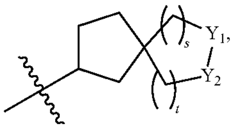

In certain embodiments of Formula (I-a), A is t, wherein: s and t are each independently 0, 1 or 2 provided that the sum of s and t is 1, 2 or 3; $Y_1$ and $Y_2$ are each independently selected from $CR_{s1}R_{s2}$, $NR_s$ and O, provided that at least one of $Y_1$ and $Y_2$ is $CR_{s1}R_{s2}$; $R_{s1}$ and $R_{s2}$ are each independently hydrogen, or $(C_1$-$C_4)$alkyl optionally substituted with one or more halogen; and $R_s$ is hydrogen, $(C_1$-$C_4)$alkyl optionally substituted with one or more halogen, acyl, $(C_3$-$C_6)$cycloalkyl or 3- to 6-member heterocycloalkyl comprising one or more heteroatoms selected from the group consisting of O and N.

In certain embodiments of Formula (I-a), A is 2,

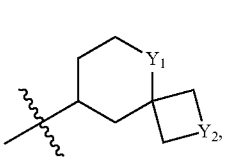

wherein: $Y_1$ is selected from $NR_s$ and O; $Y_2$ are each independently selected from $CR_{t1}R_{t2}$, $NR_s$ and O; $R_{t1}$ and $R_{t2}$ are each independently hydrogen, or $(C_1$-$C_4)$alkyl optionally substituted with one or more halogen; and $R_s$ is hydrogen, acyl, $(C_3$-$C_6)$cycloalkyl or $(C_1$-$C_4)$alkyl optionally substituted with one or more halogen or aryl.

In certain embodiments of Formula (I-a), A is a 4-10 membered bridged heterocyclyl comprising one or more heteroatoms selected from N and O, optionally substituted with $(C_1$-$C_4)$alkyl, halogen, oxo, $(C_3$-$C_6)$cycloalkyl, acyl, and/or amino optionally substituted with one or more methyl or cyclopropyl.

In certain embodiments of Formula (I-a), A is substituted or unsubstituted 7-11 membered polycyclic spiro ring system, a substituted or unsubstituted $C_{4-6}$ cycloalkyl, or a substituted or unsubstituted 4-10 membered bridged heterocyclyl.

In certain embodiments of Formula (I-a), A is substituted or unsubstituted 7-11 membered polycyclic spiro ring system, a substituted or unsubstituted $C_{4-6}$ cycloalkyl, or a substituted or unsubstituted 4-10 membered bridged heterocyclyl; wherein each is unsubstituted or substituted with oxo, $(C_1$-$C_4)$alkyl, acyl, or $(C_3$-$C_6)$cycloalkyl.

In certain embodiments of Formula (I-a), A is

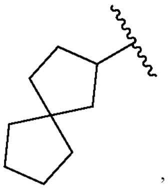 , 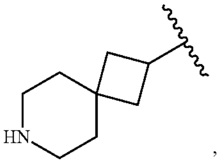 , 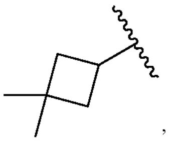 ,

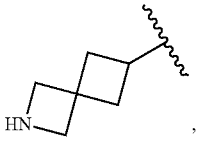 , 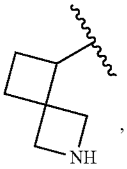 ,

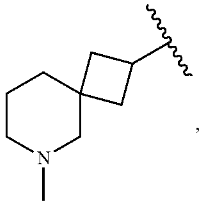 , 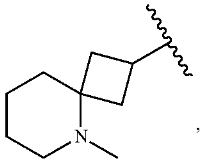 ,

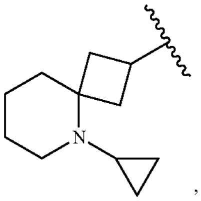 , 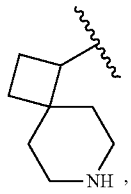 ,

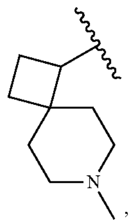 , 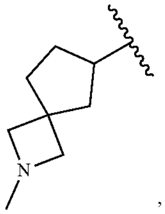 , 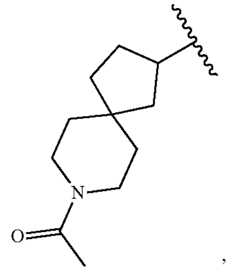 ,

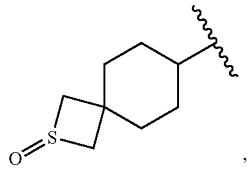 , 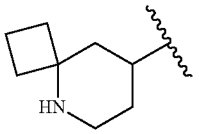 ,

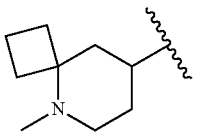 , 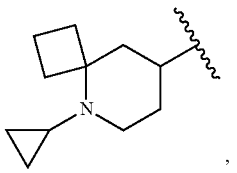 ,

-continued
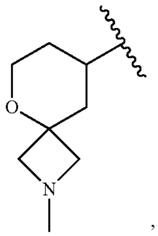,
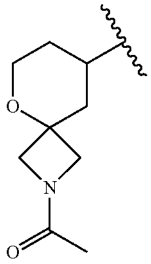,
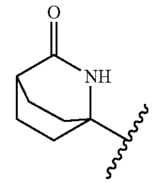,
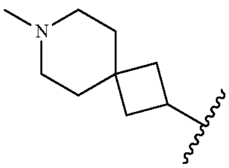,
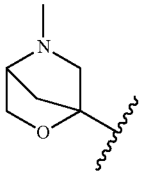,
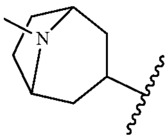, or
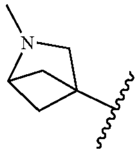.
In certain embodiments of Formula (I-a), A is
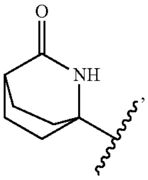,
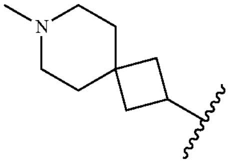,
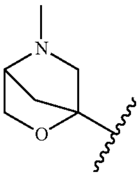,
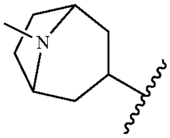, or
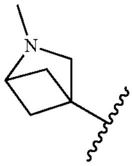.
In certain embodiments of Formula (I-a), A is
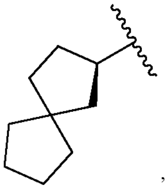,
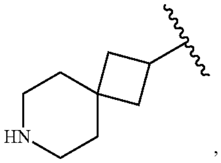,
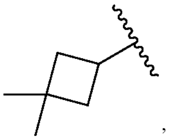,
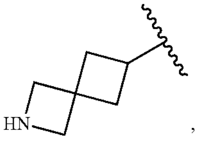,
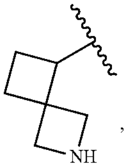,
-continued
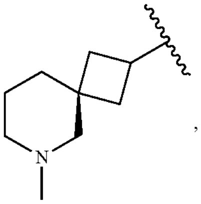,
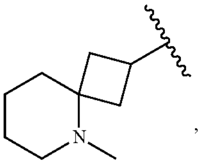,
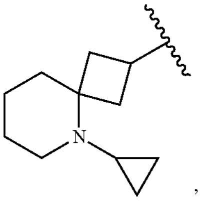,
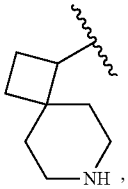,
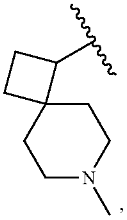,
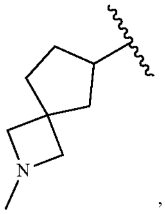,
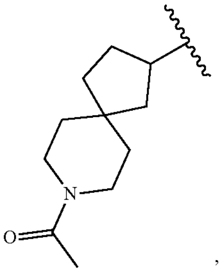,
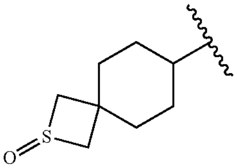,
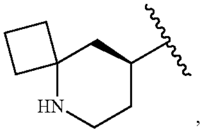,
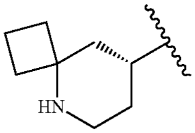,
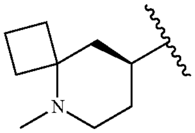,
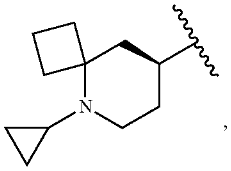,
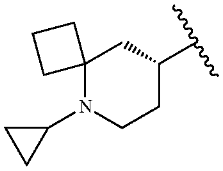,
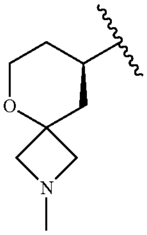,
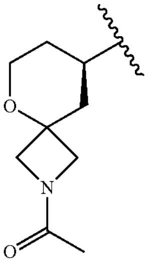,
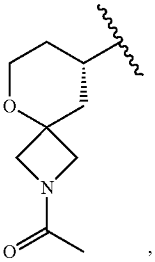,
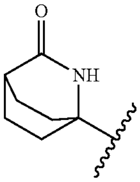,
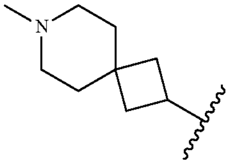,
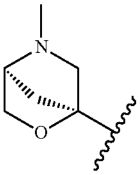, -continued

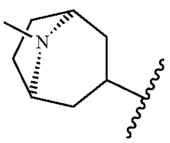
,
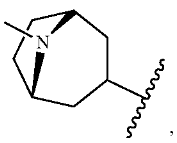
, or
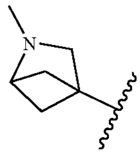
.

In certain embodiments of Formula (I-a), A is

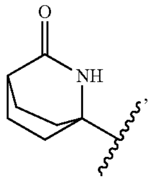
,
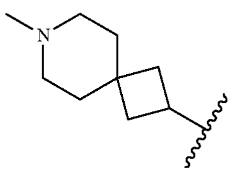
,
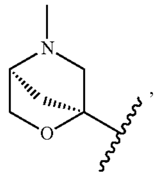
,
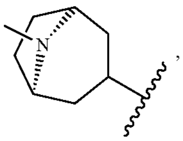
,
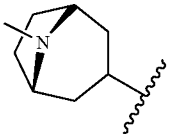
, or
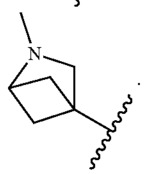
.

In certain embodiments, the compound of Formula (I) is of Formula (I-b):

(I-b)

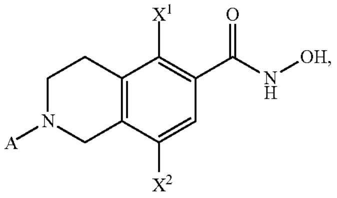

or a pharmaceutically acceptable salt, co-crystal, tautomer, stereoisomer, solvate, hydrate, polymorph, isotopically enriched derivative, or prodrug thereof; wherein A, $X^1$, and $X^2$ are as defined herein.

In certain embodiments of Formula (I-b), A is

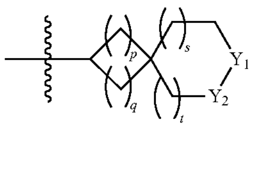
or
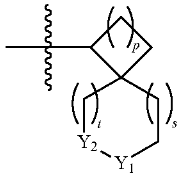

wherein: p and q are each independently 1 or 2; s and t are each independently 0, 1, or 2, provided that the sum of s and t is 0, 1, or 2; $Y_1$ and $Y_2$ are each independently selected from S(=O), $CR_{s1}R_{s2}$, $NR_s$ and O, provided that at least one of $Y_1$ and $Y_2$ is $CR_{s1}R_{s2}$; $R_{S1}$ and $R_S2$ are each independently hydrogen, or ($C_1$-$C_4$)alkyl optionally substituted with one or more halogen; and $R_s$ is hydrogen, ($C_1$-$C_4$)alkyl optionally substituted with one or more halogen, acyl, ($C_3$-$C_6$)cycloalkyl or 3- to 6-member heterocycloalkyl comprising one or more heteroatoms selected from the group consisting of O and N.

In certain embodiments of Formula (I-b), A is

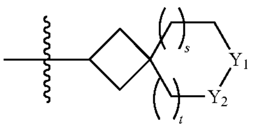
or
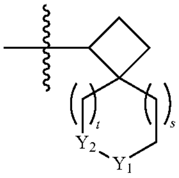
, wherein: s and t are each independently 0, 1, or 2, provided that the sum of s and t is 0, 1, or 2; $Y_1$ and $Y_2$ are each independently selected from S(=O), $CR_{s1}R_{s2}$, $NR_s$ and O, provided that at least one of $Y_1$ and $Y_2$ is $CR_{s1}R_{s2}$; $R_{s1}$ and $R_{s2}$ are each independently hydrogen, or ($C_1$-$C_4$)alkyl optionally substituted with one or more halogen; and $R_s$ is hydrogen, ($C_1$-$C_4$)alkyl optionally substituted with one or more halogen, acyl, ($C_3$-$C_6$)cycloalkyl or 3- to 6-member heterocycloalkyl comprising one or more heteroatoms selected from the group consisting of O and N.

In certain embodiments of Formula (I-b), A is

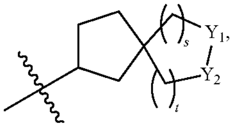

wherein: s and t are each independently 0, 1 or 2 provided that the sum of s and t is 1, 2 or 3; $Y_1$ and $Y_2$ are each independently selected from $CR_{s1}R_{s2}$, $NR_s$ and O, provided that at least one of $Y_1$ and $Y_2$ is $CR_{s1}R_{s2}$; $R_{s1}$ and $R_{s2}$ are each independently hydrogen, or ($C_1$-$C_4$)alkyl optionally substituted with one or more halogen; and $R_s$ is hydrogen, ($C_1$-$C_4$)alkyl optionally substituted with one or more halogen, acyl, ($C_3$-$C_6$)cycloalkyl or 3- to 6-member heterocycloalkyl comprising one or more heteroatoms selected from the group consisting of O and N.

In certain embodiments of Formula (I-b), A is

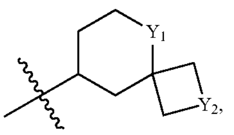

wherein: $Y_1$ is selected from $NR_s$ and O; $Y_2$ are each independently selected from $CR_{t1}R_{t2}$, $NR_s$ and O; $R_{t1}$ and $R_{t2}$ are each independently hydrogen, or ($C_1$-$C_4$)alkyl optionally substituted with one or more halogen; and $R_s$ is hydrogen, acyl, ($C_3$-$C_6$)cycloalkyl or ($C_1$-$C_4$)alkyl optionally substituted with one or more halogen or aryl.

In certain embodiments of Formula (I-b), A is a 4-10 membered bridged heterocyclyl comprising one or more heteroatoms selected from N and O, optionally substituted with ($C_1$-$C_4$)alkyl, halogen, oxo, ($C_3$-$C_6$)cycloalkyl, acyl, and amino optionally substituted with one or more methyl or cyclopropyl.

In certain embodiments of Formula (I-b), A is substituted or unsubstituted 7-11 membered polycyclic spiro ring system, a substituted or unsubstituted $C_{4-6}$ cycloalkyl, or a substituted or unsubstituted 4-10 membered bridged heterocyclyl.

In certain embodiments of Formula (I-b), A is substituted or unsubstituted 7-11 membered polycyclic spiro ring system, a substituted or unsubstituted $C_{4-6}$ cycloalkyl, or a substituted or unsubstituted 4-10 membered bridged heterocyclyl; wherein each is unsubstituted or substituted with oxo, $(C_1-C_4)$alkyl, acyl, or $(C_3-C_6)$cycloalkyl.

In certain embodiments of Formula (I-b), A is

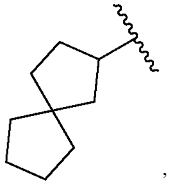 , 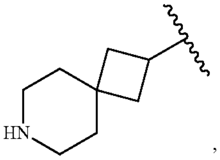 , 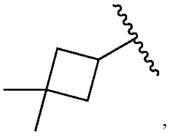 ,

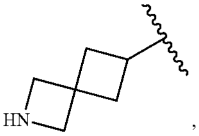 , 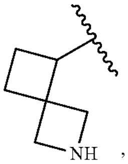 , 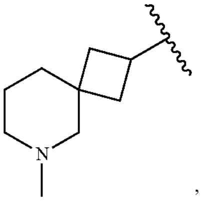 ,

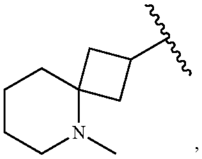 , 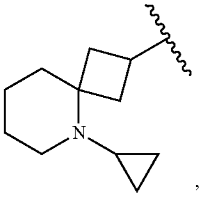 ,

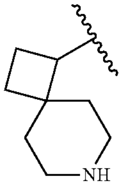 , 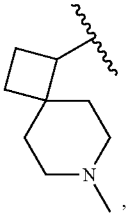 , 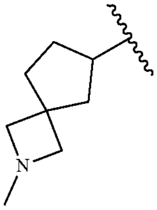 ,

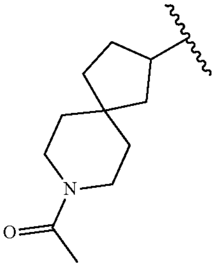 , 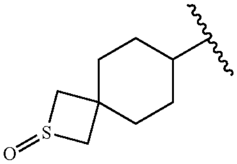 ,

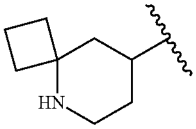 , 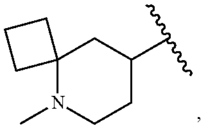 ,

-continued

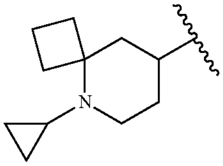 , 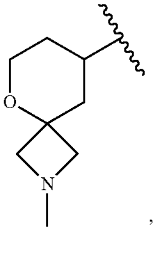 , 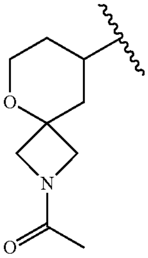 ,

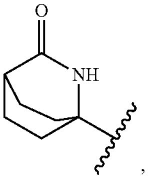 , 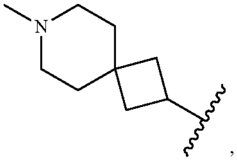 ,

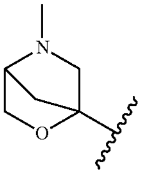 , 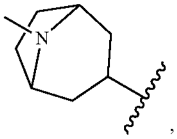 , or 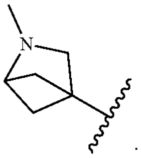 .

In certain embodiments of Formula (I-b), A is

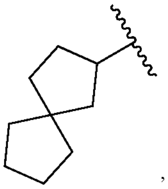 , 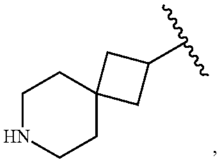 , 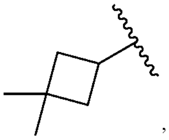 ,

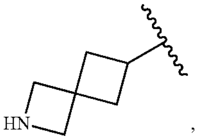 , 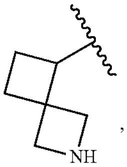 ,

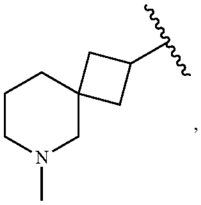 , 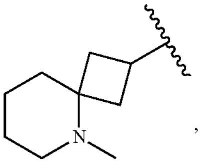 ,

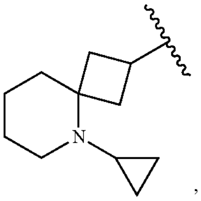 , 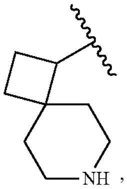 ,

-continued
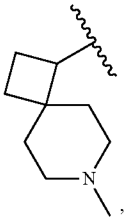,
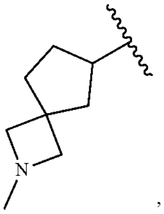,
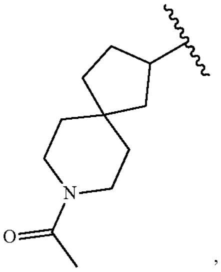,
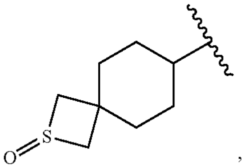,
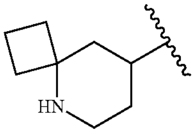,
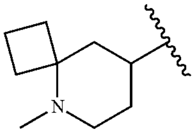,
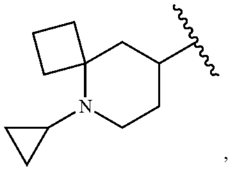,
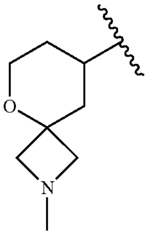, or
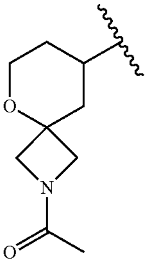.
In certain embodiments of Formula (I-b), A is
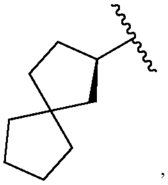,
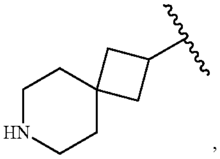,
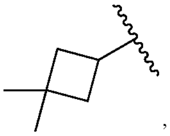,
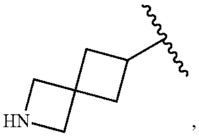,
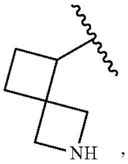,
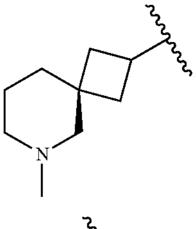,
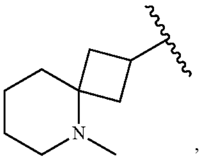,
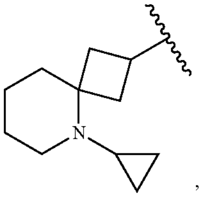,
-continued
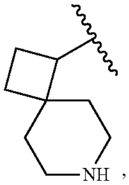,
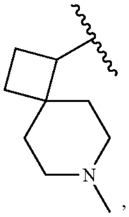,
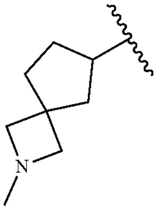,
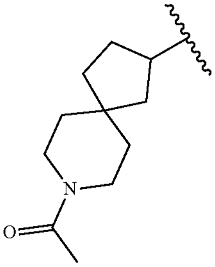,
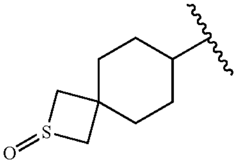,
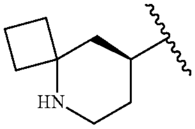,
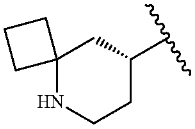,
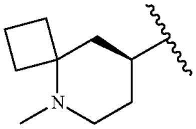,
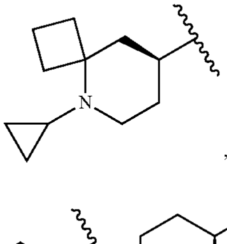,
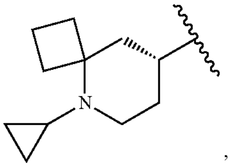,
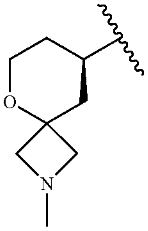,
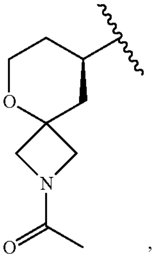,
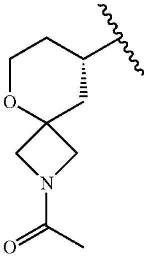,
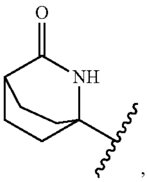,
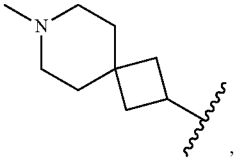,
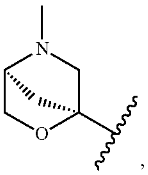,
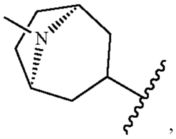,
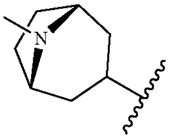, or
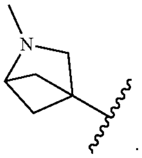.

In certain embodiments of Formula (I-b), A is

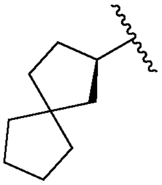,
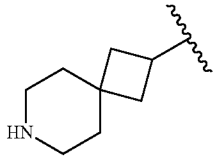,
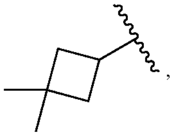,
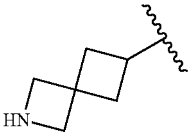,
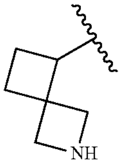,
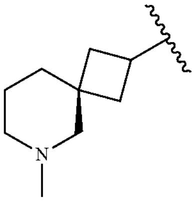,
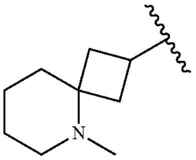,
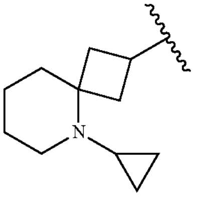,
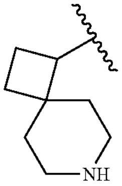,
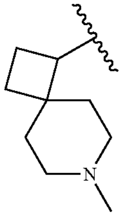,
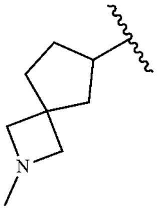,
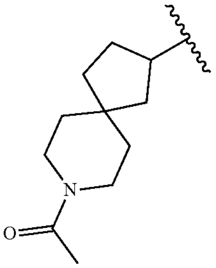,
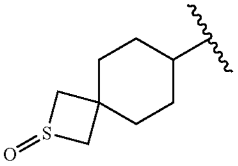,
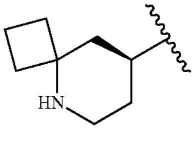,
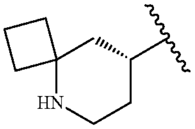,
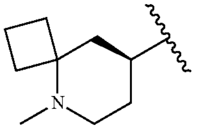,
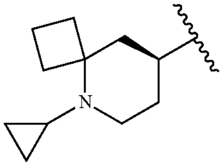,
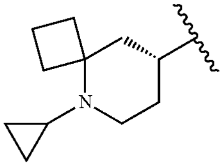, -continued

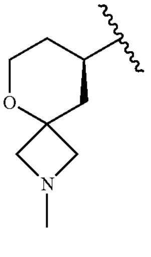,
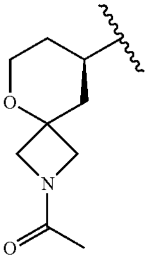, or
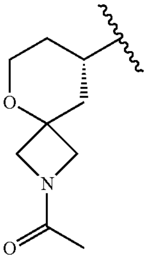.

In certain embodiments, the compound of Formula I is of Formula (I-c):

(I-c)

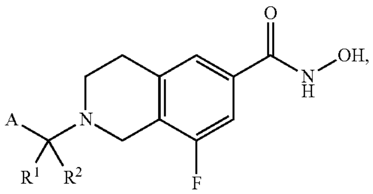

or a pharmaceutically acceptable salt, co-crystal, tautomer, stereoisomer, solvate, hydrate, polymorph, isotopically enriched derivative, or prodrug thereof; wherein A, $R^1$, and $R^2$ are as defined herein.

In certain embodiments of Formula (I-c), A is

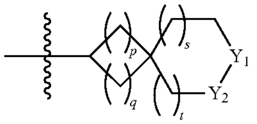
or
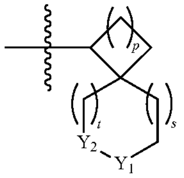

wherein: p and q are each independently 1 or 2; s and t are each independently 0, 1, or 2, provided that the sum of s and t is 0, 1, or 2; $Y_1$ and $Y_2$ are each independently selected from S(=O), $CR_{s1}R_{s2}$, $NR_s$ and O, provided that at least one of $Y_1$ and $Y_2$ is $CR_{s1}R_{s2}$; $R_{s1}$ and $R_{s2}$ are each independently hydrogen, or $(C_1\text{-}C_4)$alkyl optionally substituted with one or more halogen; and $R_s$ is hydrogen, $(C_1\text{-}C_4)$alkyl optionally substituted with one or more halogen, acyl, $(C_3\text{-}C_6)$cycloalkyl or 3- to 6-member heterocycloalkyl comprising one or more heteroatoms selected from the group consisting of O and N.

In certain embodiments of Formula (I-c), A is

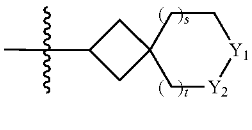
or
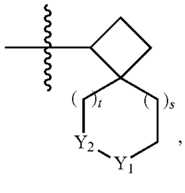, wherein: s and t are each independently 0, 1, or 2, provided that the sum of s and t is 0, 1, or 2; $Y_1$ and $Y_2$ are each independently selected from S(=O), $CR_{s1}R_{s2}$, $NR_s$ and O, provided that at least one of $Y_1$ and $Y_2$ is $CR_{s1}R_{s2}$; $R_{s1}$ and $R_{s2}$ are each independently hydrogen, or $(C_1\text{-}C_4)$alkyl optionally substituted with one or more halogen; and $R_s$ is hydrogen, $(C_1\text{-}C_4)$alkyl optionally substituted with one or more halogen, acyl, $(C_3\text{-}C_6)$cycloalkyl or 3- to 6-member heterocycloalkyl comprising one or more heteroatoms selected from the group consisting of O and N.

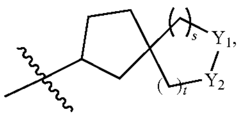

In certain embodiments of Formula (I-c), A is II, wherein: s and t are each independently 0, 1 or 2 provided that the sum of s and t is 1, 2 or 3; $Y_1$ and $Y_2$ are each independently selected from $CR_{s1}R_{s2}$, $NR_s$ and O, provided that at least one of $Y_1$ and $Y_2$ is $CR_{s1}R_{s2}$; $R_{s1}$ and $R_{s2}$ are each independently hydrogen, or $(C_1\text{-}C_4)$alkyl optionally substituted with one or more halogen; and $R_s$ is hydrogen, $(C_1\text{-}C_4)$alkyl optionally substituted with one or more halogen, acyl, $(C_3\text{-}C_6)$cycloalkyl or 3- to 6-member heterocycloalkyl comprising one or more heteroatoms selected from the group consisting of O and N.

In certain embodiments of Formula (I-c), A is

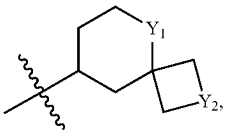

wherein: $Y_1$ is selected from $NR_s$ and O; $Y_2$ are each independently selected from $CR_{t1}R_{t2}$, $NR_s$ and O; $R_{t1}$ and $R_{t2}$ are each independently hydrogen, or $(C_1\text{-}C_4)$alkyl optionally substituted with one or more halogen; and $R_s$ is hydrogen, acyl, $(C_3\text{-}C_6)$cycloalkyl or $(C_1\text{-}C_4)$alkyl optionally substituted with one or more halogen or aryl.

In certain embodiments of Formula (I-c), A is a 4-10 membered bridged heterocyclyl comprising one or more heteroatoms selected from N and O, optionally substituted with $(C_1\text{-}C_4)$alkyl, halogen, oxo, $(C_3\text{-}C_6)$cycloalkyl, acyl, and amino optionally substituted with one or more methyl or cyclopropyl.

In certain embodiments of Formula (I-c), A is substituted or unsubstituted 7-11 membered polycyclic spiro ring system, a substituted or unsubstituted $C_{4-6}$ cycloalkyl, or a substituted or unsubstituted 4-10 membered bridged heterocyclyl.

In certain embodiments of Formula (I-c), A is substituted or unsubstituted 7-11 membered polycyclic spiro ring system, a substituted or unsubstituted $C_{4-6}$ cycloalkyl, or a substituted or unsubstituted 4-10 membered bridged heterocyclyl; wherein each is unsubstituted or substituted with oxo, $(C_1\text{-}C_4)$alkyl, acyl, or $(C_3\text{-}C_6)$cycloalkyl.

In certain embodiments of Formula (I-c), A is

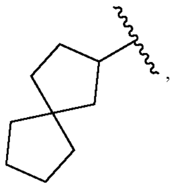,
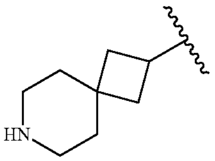,

-continued

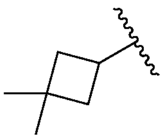,
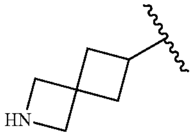,
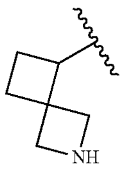,

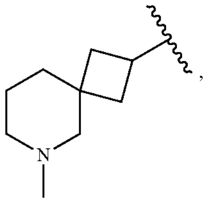,
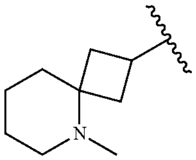,

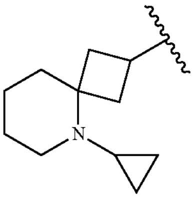,
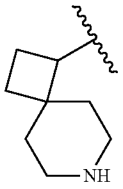,
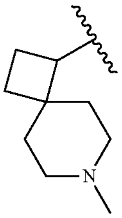,

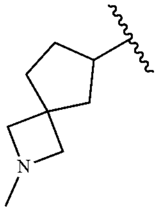,
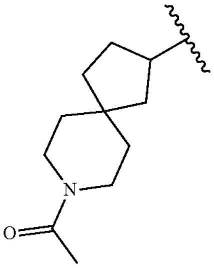,

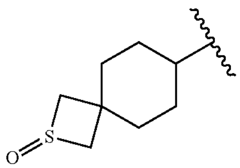,
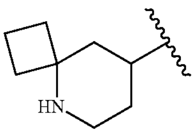,

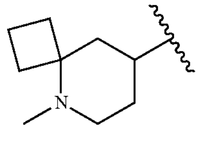,
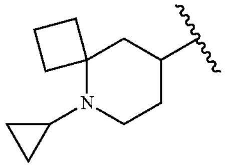,

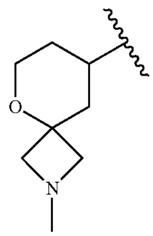,
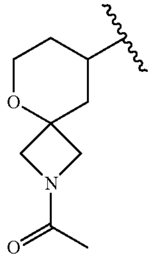,
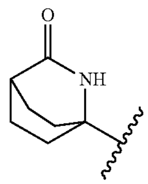,

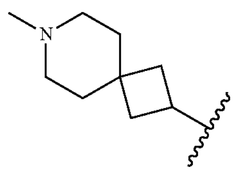,
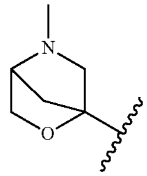,

-continued
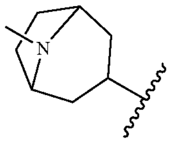, or 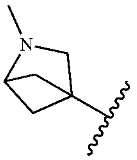.
In certain embodiments of Formula (I-c), A is
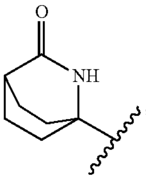, 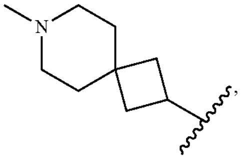,
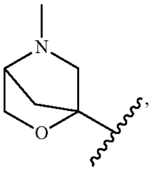, 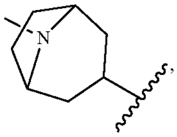, or 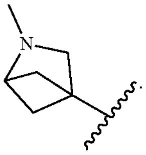.
In certain embodiments of Formula (I-c), A is
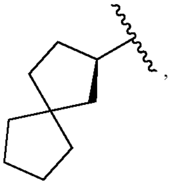, 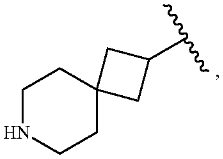,
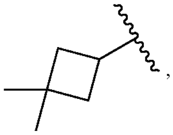, 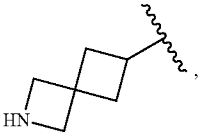, 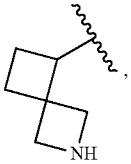,
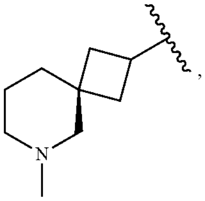, 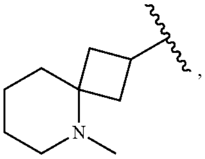,
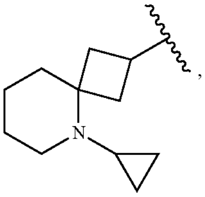, 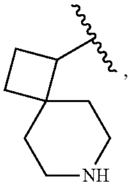, 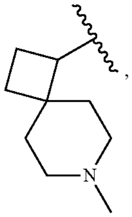,
-continued
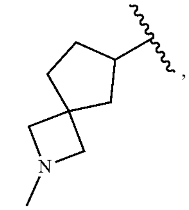, 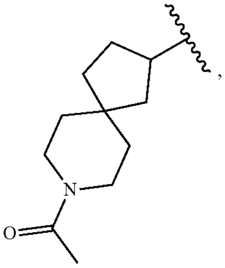,
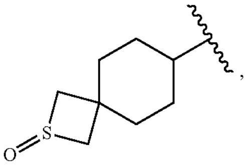, 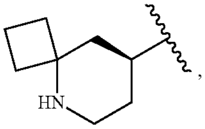,
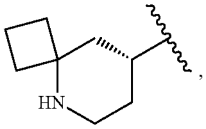, 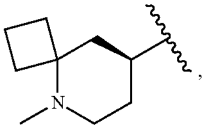,
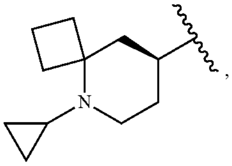, 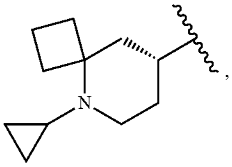,
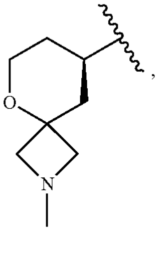, 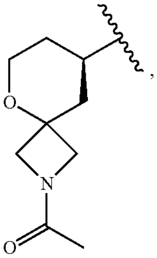, 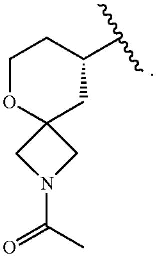.
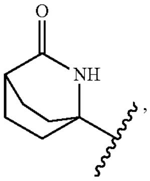, 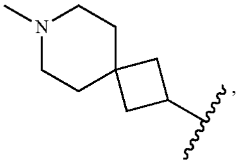, 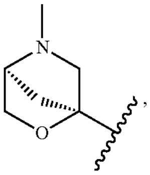,
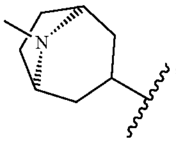, 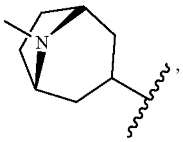, or 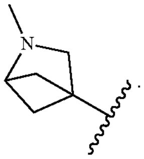.
In certain embodiments of Formula (I-c), A is
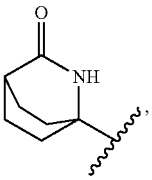, 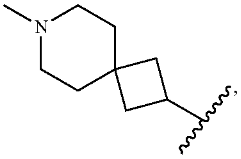, -continued

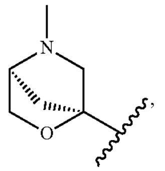, 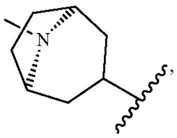, 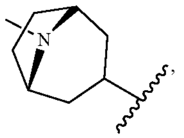, or

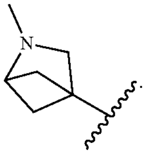.

In certain embodiments, the compound of Formula (I) is of Formula (I-c-1):

(I-c-1)

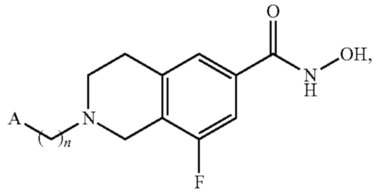

or a pharmaceutically acceptable salt, co-crystal, tautomer, stereoisomer, solvate, hydrate, polymorph, isotopically enriched derivative, or prodrug thereof; wherein A is as defined herein; and n is 0 or 1.

In certain embodiments of Formula (I-c-1), A is

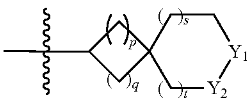 or 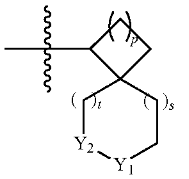

wherein: p and q are each independently 1 or 2; s and t are each independently 0, 1, or 2, provided that the sum of s and t is 0, 1, or 2; $Y_1$ and $Y_2$ are each independently selected from S(═O), $CR_{s1}R_{s2}$, $NR_s$ and O, provided that at least one of $Y_1$ and $Y_2$ is $CR_{s1}R_{s2}$; $R_{s1}$ and $R_{s2}$ are each independently hydrogen, or ($C_1$-$C_4$)alkyl optionally substituted with one or more halogen; and $R_s$ is hydrogen, ($C_1$-$C_4$)alkyl optionally substituted with one or more halogen, acyl, ($C_3$-$C_6$)cycloalkyl or 3- to 6-member heterocycloalkyl comprising one or more heteroatoms selected from the group consisting of O and N.

In certain embodiments of Formula (I-c-1), A is

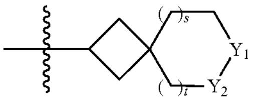 or 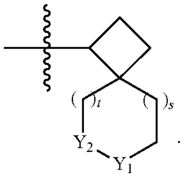.

wherein: s and t are each independently 0, 1, or 2, provided that the sum of s and t is 0, 1, or 2; $Y_1$ and $Y_2$ are each independently selected from S(═O), $CR_{s1}R_{s2}$, $NR_s$ and O, provided that at least one of $Y_1$ and $Y_2$ is $CR_{s1}R_{s2}$; $R_{s1}$ and $R_{s2}$ are each independently hydrogen, or ($C_1$-$C_4$)alkyl optionally substituted with one or more halogen; and $R_s$ is hydrogen, ($C_1$-$C_4$)alkyl optionally substituted with one or more halogen, acyl, ($C_3$-$C_6$)cycloalkyl or 3- to 6-member heterocycloalkyl comprising one or more heteroatoms selected from the group consisting of O and N.

In certain embodiments of Formula (I-c-1), A is

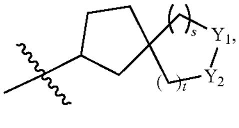

wherein: s and t are each independently 0, 1 or 2 provided that the sum of s and t is 1, 2 or 3; $Y_1$ and $Y_2$ are each independently selected from $CR_{s1}R_{s2}$, $NR_s$ and O, provided that at least one of $Y_1$ and $Y_2$ is $CR_{s1}R_{s2}$; $R_1$ and $R_{s2}$ are each independently hydrogen, or ($C_1$-$C_4$)alkyl optionally substituted with one or more halogen; and $R_s$ is hydrogen, ($C_1$-$C_4$)alkyl optionally substituted with one or more halogen, acyl, ($C_3$-$C_6$)cycloalkyl or 3- to 6-member heterocycloalkyl comprising one or more heteroatoms selected from the group consisting of O and N.

In certain embodiments of Formula (I-c-1), A is

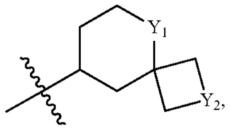

wherein: $Y_1$ is selected from $NR_s$ and O; $Y_2$ are each independently selected from $CR_t1R_t2$, $NR_s$ and O; $R_{t1}$ and $R_{t2}$ are each independently hydrogen, or ($C_1$-$C_4$)alkyl optionally substituted with one or more halogen; and $R_s$ is hydrogen, acyl, ($C_3$-$C_6$)cycloalkyl or ($C_1$-$C_4$)alkyl optionally substituted with one or more halogen or aryl.

In certain embodiments of Formula (I-c-1), A is a 4-10 membered bridged heterocyclyl comprising one or more heteroatoms selected from N and O, optionally substituted with ($C_1$-$C_4$)alkyl, halogen, oxo, ($C_3$-$C_6$)cycloalkyl, acyl, and amino optionally substituted with one or more methyl or cyclopropyl.

In certain embodiments of Formula (I-c-1), A is substituted or unsubstituted 7-11 membered polycyclic spiro ring system, a substituted or unsubstituted $C_{4-6}$ cycloalkyl, or a substituted or unsubstituted 4-10 membered bridged heterocyclyl.

In certain embodiments of Formula (I-c-1), A is substituted or unsubstituted 7-11 membered polycyclic spiro ring system, a substituted or unsubstituted $C_{4-6}$ cycloalkyl, or a substituted or unsubstituted 4-10 membered bridged heterocyclyl; wherein each is unsubstituted or substituted with oxo, ($C_1$-$C_4$)alkyl, acyl, or ($C_3$-$C_6$)cycloalkyl.

In certain embodiments of Formula (I-c-1), A is
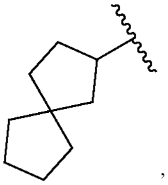, 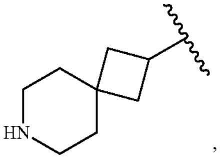, 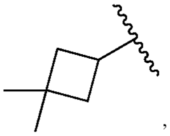, 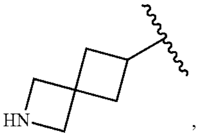, 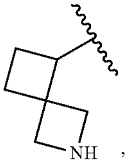, 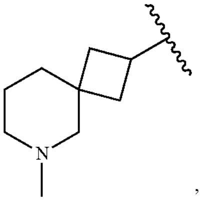, 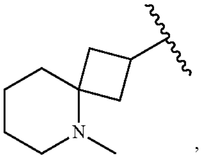, 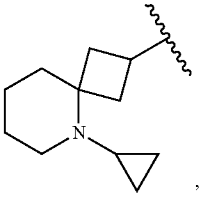, 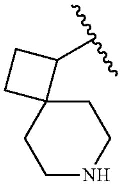, 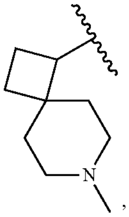, 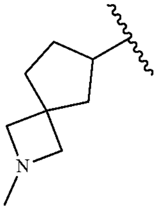, 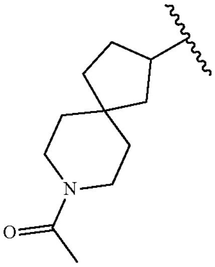, 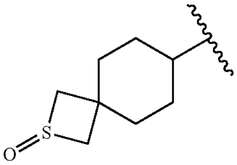, 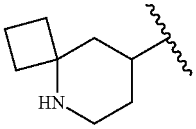, 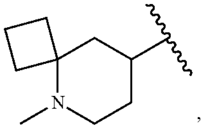, 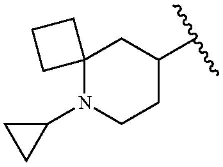, 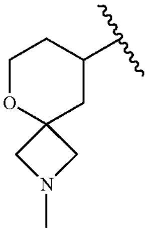, 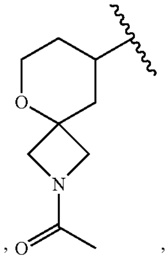, 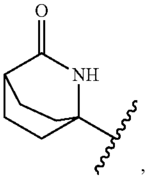, 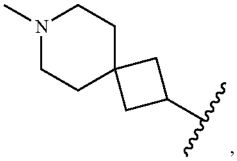,
-continued
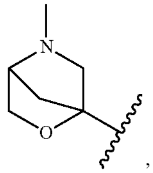, 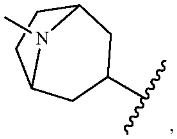, or 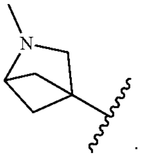.
In certain embodiments of Formula (I-c-1), A is
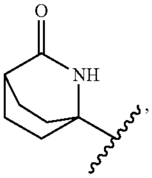, 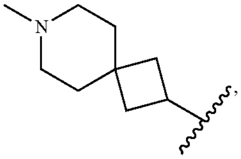, 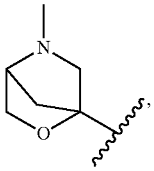, 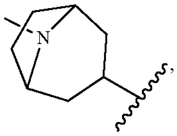, or 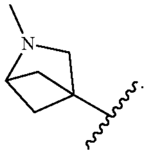.
In certain embodiments of Formula (I-c-1), A is
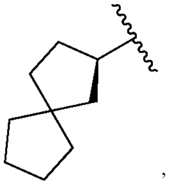, 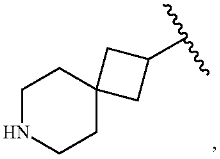, 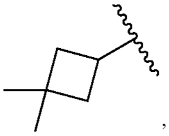, 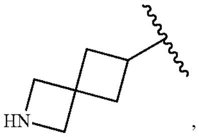, 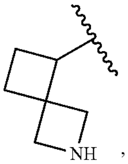, 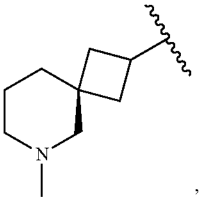, 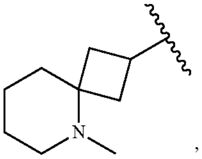, 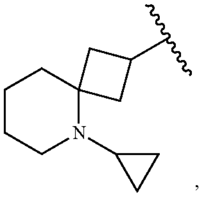, 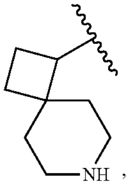, 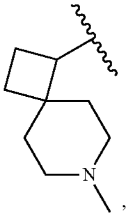, 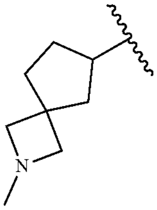, -continued

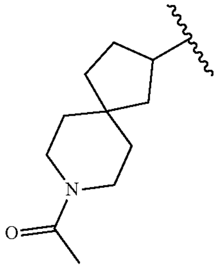,

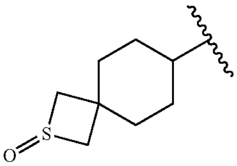,

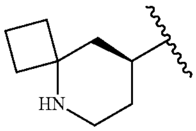,

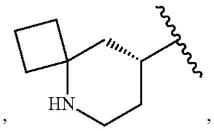,

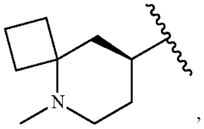,

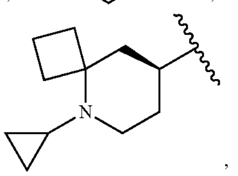,

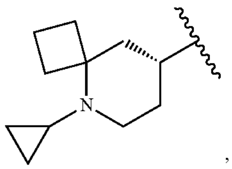,

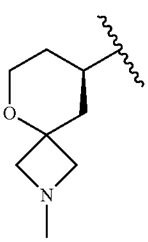,

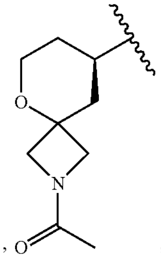,

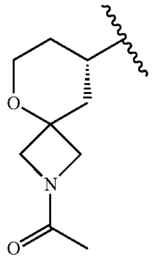,

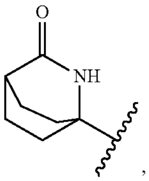,

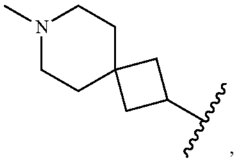,

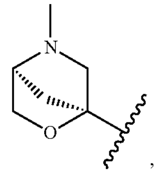,

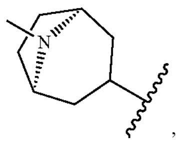,

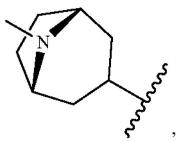, or

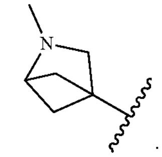.

In certain embodiments of Formula (I-c-1), A is

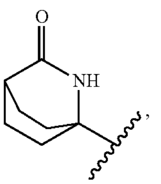,

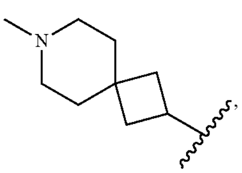,

-continued

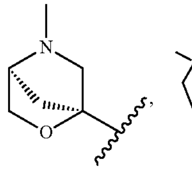,

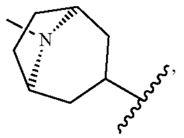,

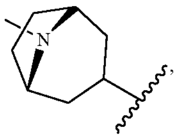, or

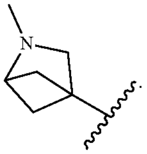.

In certain embodiments, the compound of Formula (I) is of Formula (I-c-2):

(I-c-2)

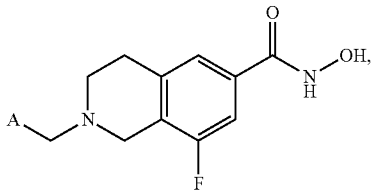

or a pharmaceutically acceptable salt, co-crystal, tautomer, stereoisomer, solvate, hydrate, polymorph, isotopically enriched derivative, or prodrug thereof; wherein A is as defined herein.

In certain embodiments of Formula (I-c-2), A is

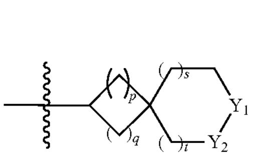

or

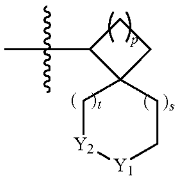

wherein: p and q are each independently 1 or 2; s and t are each independently 0, 1, or 2, provided that the sum of s and t is 0, 1, or 2; $Y_1$ and $Y_2$ are each independently selected from S(=O), $CR_{s1}R_{s2}$, $NR_s$ and O, provided that at least one of $Y_1$ and $Y_2$ is $CR_{s1}R_{s2}$; $R_{s1}$ and $R_{s2}$ are each independently hydrogen, or $(C_1$-$C_4)$alkyl optionally substituted with one or more halogen; and $R_s$ is hydrogen, $(C_1$-$C_4)$alkyl optionally substituted with one or more halogen, acyl, $(C_3$-$C_6)$cycloalkyl or 3- to 6-member heterocycloalkyl comprising one or more heteroatoms selected from the group consisting of O and N.

In certain embodiments of Formula (I-c-2), A is

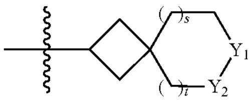

or

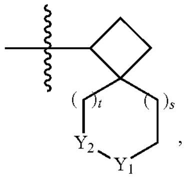, wherein: s and t are each independently 0, 1, or 2, provided that the sum of s and t is 0, 1, or 2; $Y_1$ and $Y_2$ are each independently selected from S(═O), $CR_{s1}R_{s2}$, $NR_s$ and O, provided that at least one of $Y_1$ and $Y_2$ is $CR_{s1}R_{s2}$; $R_{s1}$ and $R_{s2}$ are each independently hydrogen, or ($C_1$-$C_4$)alkyl optionally substituted with one or more halogen; and $R_s$ is hydrogen, ($C_1$-$C_4$)alkyl optionally substituted with one or more halogen, acyl, ($C_3$-$C_6$)cycloalkyl or 3- to 6-member heterocycloalkyl comprising one or more heteroatoms selected from the group consisting of O and N.

In certain embodiments of Formula (I-c-2), A is

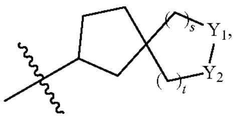

wherein: s and t are each independently 0, 1 or 2 provided that the sum of s and t is 1, 2 or 3; $Y_1$ and $Y_2$ are each independently selected from $CR_{s1}R_{s2}$, $NR_s$ and O, provided that at least one of $Y_1$ and $Y_2$ is $CR_{s1}R_{s2}$; $R_{s1}$ and $R_{s2}$ are each independently hydrogen, or ($C_1$-$C_4$)alkyl optionally substituted with one or more halogen; and $R_s$ is hydrogen, ($C_1$-$C_4$)alkyl optionally substituted with one or more halogen, acyl, ($C_3$-$C_6$)cycloalkyl or 3- to 6-member heterocycloalkyl comprising one or more heteroatoms selected from the group consisting of O and N.

In certain embodiments of Formula (I-c-2), A is

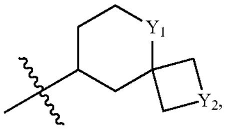

wherein: $Y_1$ is selected from $NR_s$ and O; $Y_2$ are each independently selected from $CR_{t1}R_{t2}$, $NR_s$ and O; $R_{t1}$ and $R_{t2}$ are each independently hydrogen, or ($C_1$-$C_4$)alkyl optionally substituted with one or more halogen; and $R_s$ is hydrogen, acyl, ($C_3$-$C_6$)cycloalkyl or ($C_1$-$C_4$)alkyl optionally substituted with one or more halogen or aryl.

In certain embodiments of Formula (I-c-2), A is a 4-10 membered bridged heterocyclyl comprising one or more heteroatoms selected from N and O, optionally substituted with ($C_1$-$C_4$)alkyl, halogen, oxo, ($C_3$-$C_6$)cycloalkyl, acyl, and amino optionally substituted with one or more methyl or cyclopropyl.

In certain embodiments of Formula (I-c-2), A is substituted or unsubstituted 7-11 membered polycyclic spiro ring system, a substituted or unsubstituted $C_{4-6}$ cycloalkyl, or a substituted or unsubstituted 4-10 membered bridged heterocyclyl.

In certain embodiments of Formula (I-c-2), A is substituted or unsubstituted 7-11 membered polycyclic spiro ring system, a substituted or unsubstituted $C_{4-6}$ cycloalkyl, or a substituted or unsubstituted 4-10 membered bridged heterocyclyl; wherein each is unsubstituted or substituted with oxo, ($C_1$-$C_4$)alkyl, acyl, or ($C_3$-$C_6$)cycloalkyl.

In certain embodiments of Formula (I-c-2), A is

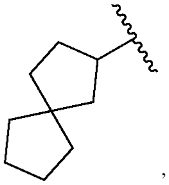 , 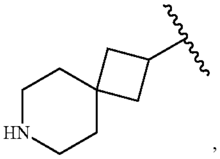 , 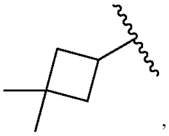 ,

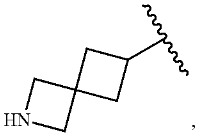 , 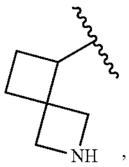 , 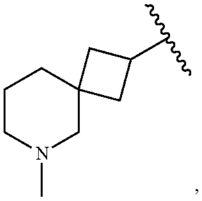 ,

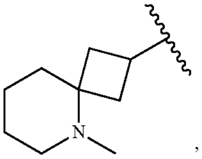 , 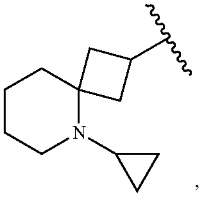 ,

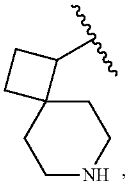 , 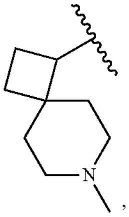 , 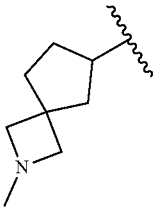 ,

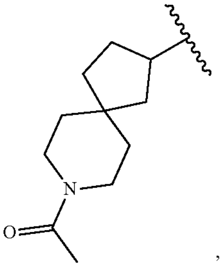 , 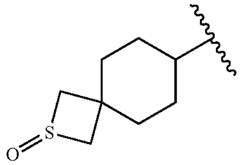 ,

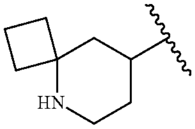 , 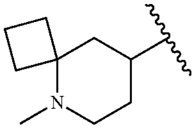 ,

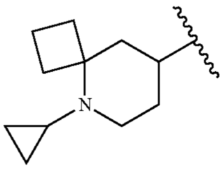 , 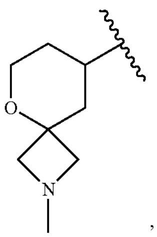 , 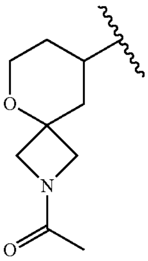 ,

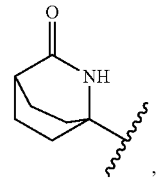 , 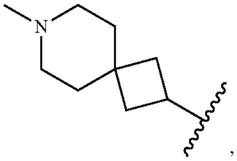 ,

-continued
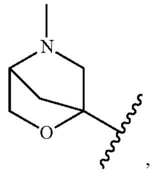, 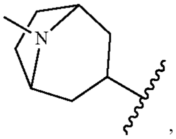, or 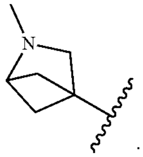.
In certain embodiments of Formula (I-c-2), A is
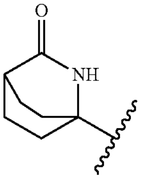, 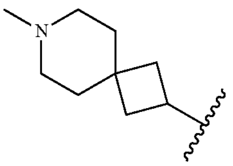, 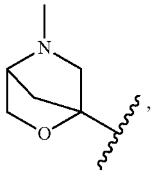,
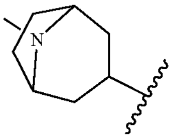, or 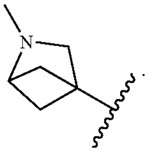.
In certain embodiments of Formula (I-c-2) A is
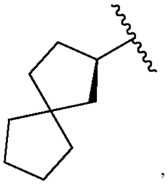, 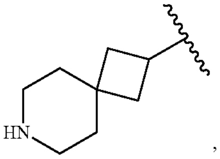, 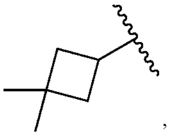,
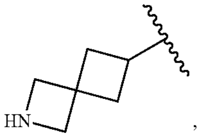, 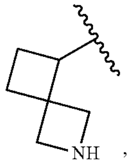, 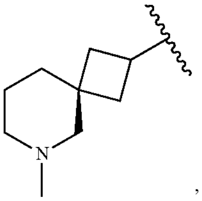,
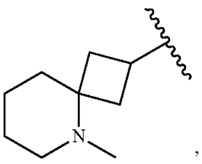, 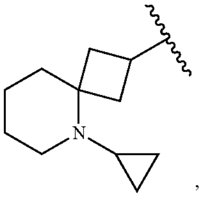,
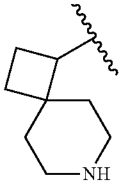, 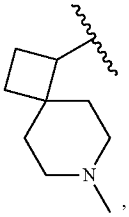, 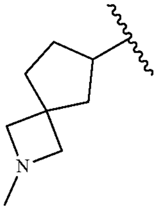,
-continued
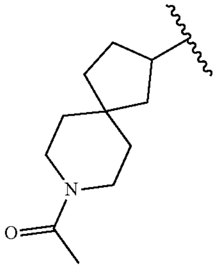, 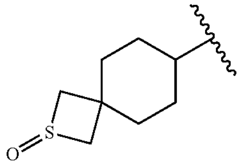,
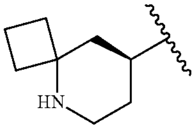, 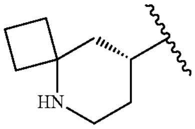,
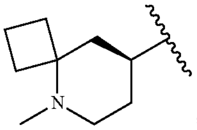, 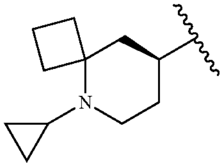,
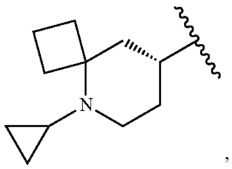, 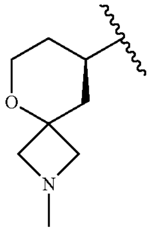, 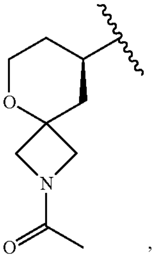,
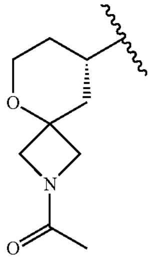, 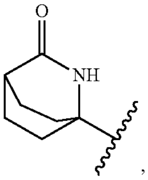, 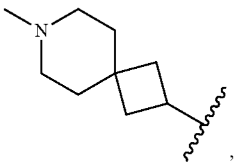,
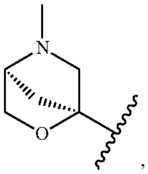, 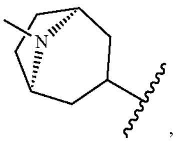, 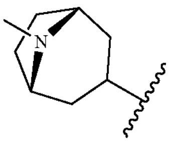, or
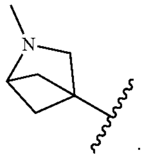.
In certain embodiments of Formula (I-c-2), A is
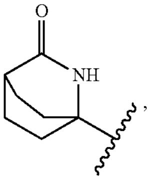, 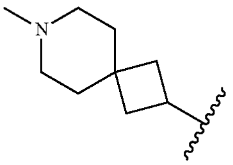, 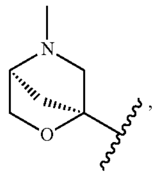, -continued

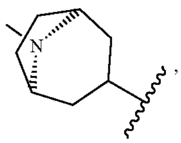, 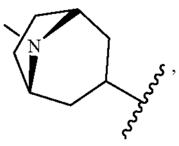, or 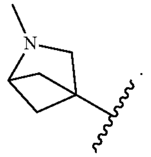.

In certain embodiments, the compound of Formula (I) is of Formula (I-d):

(I-d)

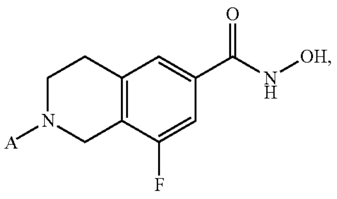

or a pharmaceutically acceptable salt, co-crystal, tautomer, stereoisomer, solvate, hydrate, polymorph, isotopically enriched derivative, or prodrug thereof; wherein A is as defined herein.

In certain embodiments of Formula (I-d), A is

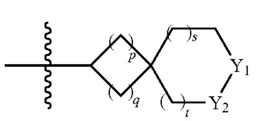 or 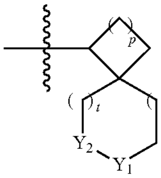

wherein: p and q are each independently 1 or 2; s and t are each independently 0, 1, or 2, provided that the sum of s and t is 0, 1, or 2; $Y_1$ and $Y_2$ are each independently selected from S(=O), $CR_{s1}R_{s2}$, $NR_s$ and O, provided that at least one of $Y_1$ and $Y_2$ is $CR_{s1}R_{s2}$; $R_{s1}$ and $R_{s2}$ are each independently hydrogen, or $(C_1\text{-}C_4)$alkyl optionally substituted with one or more halogen; and $R_s$ is hydrogen, $(C_1\text{-}C_4)$alkyl optionally substituted with one or more halogen, acyl, $(C_3\text{-}C_6)$cycloalkyl or 3- to 6-member heterocycloalkyl comprising one or more heteroatoms selected from the group consisting of O and N.

In certain embodiments of Formula (I-d). A is

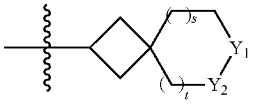 or 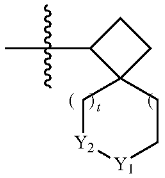

wherein: s and t are each independently 0, 1, or 2, provided that the sum of s and t is 0, 1, or 2; $Y_1$ and $Y_2$ are each independently selected from S(=O), $CR_{s1}R_{s2}$, $NR_s$ and O, provided that at least one of $Y_1$ and $Y_2$ is $CR_{s1}R_{s2}$; $R_{s1}$ and $R_{s2}$ are each independently hydrogen, or $(C_1\text{-}C_4)$alkyl optionally substituted with one or more halogen; and $R_s$ is hydrogen, $(C_1\text{-}C_4)$alkyl optionally substituted with one or more halogen, acyl, $(C_3\text{-}C_6)$cycloalkyl or 3- to 6-member heterocycloalkyl comprising one or more heteroatoms selected from the group consisting of O and N.

In certain embodiments of Formula (I-d), A is

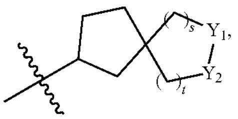

wherein: s and t are each independently 0, 1 or 2 provided that the sum of s and t is 1, 2 or 3; $Y_1$ and $Y_2$ are each independently selected from $CR_{s1}R_{s2}$, $NR_s$ and O, provided that at least one of $Y_1$ and $Y_2$ is $CR_{s1}R_{s2}$; $R_1$ and $R_s2$ are each independently hydrogen, or $(C_1\text{-}C_4)$alkyl optionally substituted with one or more halogen; and $R_s$ is hydrogen, $(C_1\text{-}C_4)$alkyl optionally substituted with one or more halogen, acyl, $(C_3\text{-}C_6)$cycloalkyl or 3- to 6-member heterocycloalkyl comprising one or more heteroatoms selected from the group consisting of O and N.

In certain embodiments of Formula (I-d), A is

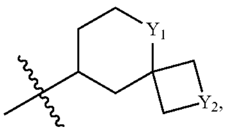

wherein: $Y_1$ is selected from $NR_s$ and O; $Y_2$ are each independently selected from $CR_{t1}R_{t2}$, $NR_s$ and O; $R_{t1}$ and $R_{t2}$ are each independently hydrogen, or $(C_1\text{-}C_4)$alkyl optionally substituted with one or more halogen; and $R_s$ is hydrogen, acyl, $(C_3\text{-}C_6)$cycloalkyl or $(C_1\text{-}C_4)$alkyl optionally substituted with one or more halogen or aryl.

In certain embodiments of Formula (I-d), A is a 4-10 membered bridged heterocyclyl comprising one or more heteroatoms selected from N and O, optionally substituted with $(C_1\text{-}C_4)$alkyl, halogen, oxo, $(C_3\text{-}C_6)$cycloalkyl, acyl, and amino optionally substituted with one or more methyl or cyclopropyl.

In certain embodiments of Formula (I-d), A is substituted or unsubstituted 7-11 membered polycyclic spiro ring system, a substituted or unsubstituted $C_{4\text{-}6}$ cycloalkyl, or a substituted or unsubstituted 4-10 membered bridged heterocyclyl.

In certain embodiments of Formula (I-d), A is substituted or unsubstituted 7-11 membered polycyclic spiro ring system, a substituted or unsubstituted $C_{4\text{-}6}$ cycloalkyl, or a substituted or unsubstituted 4-10 membered bridged heterocyclyl; wherein each is unsubstituted or substituted with oxo, $(C_1\text{-}C_4)$alkyl, acyl, or $(C_3\text{-}C_6)$cycloalkyl.

In certain embodiments of Formula (I-d), A is

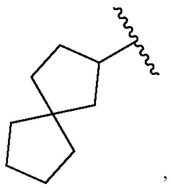, 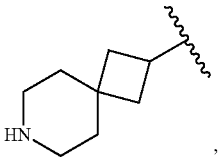, 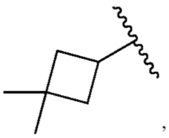,

-continued
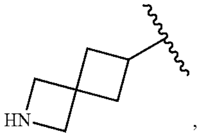, 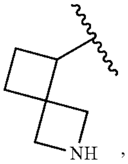, 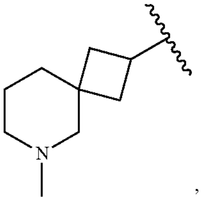,
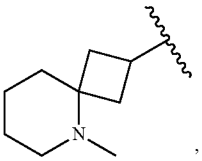, 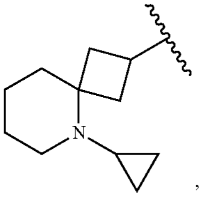,
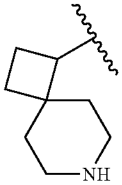, 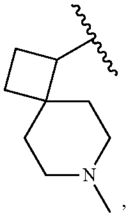, 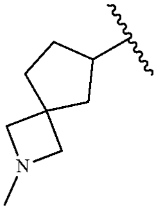,
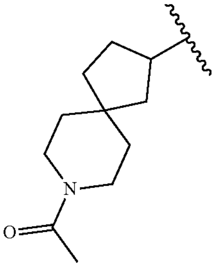, 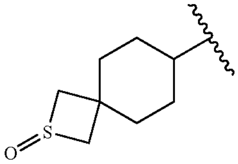,
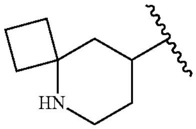, 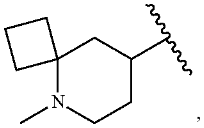,
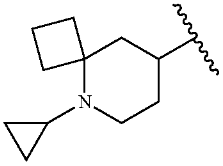, 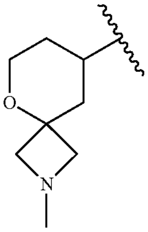, 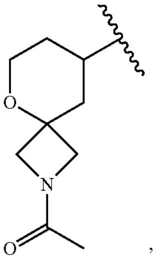,
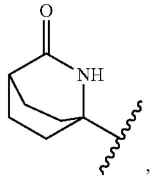, 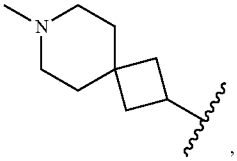,
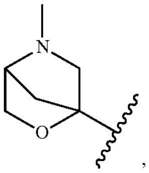, 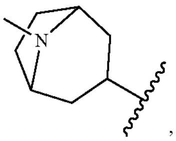, or 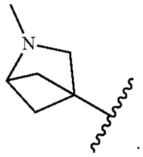.
In certain embodiments of Formula (I), A is
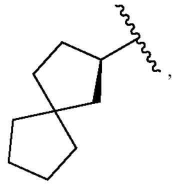, 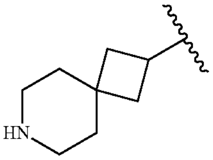,
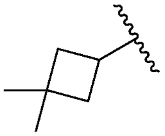, 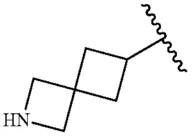, 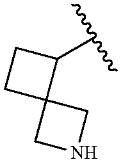,
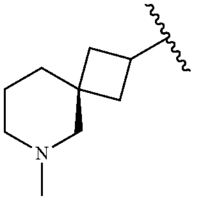, 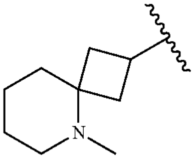,
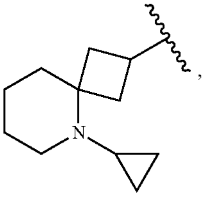, 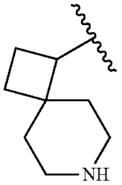, 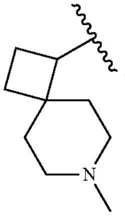,
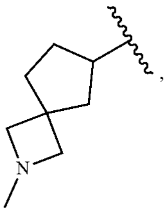, 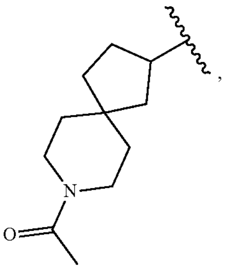,
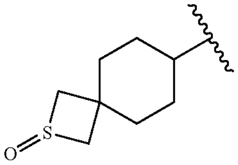, 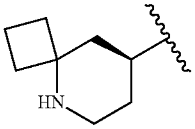,
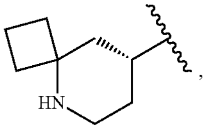, 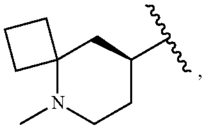,
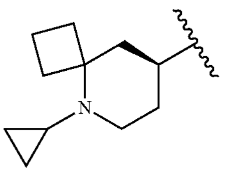, 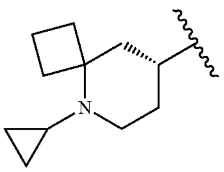, -continued

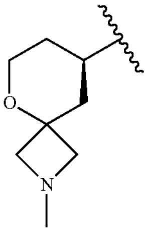,
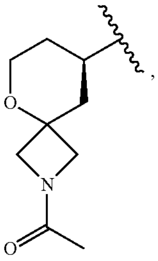,
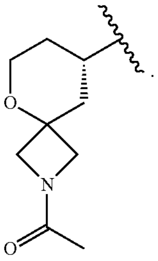.
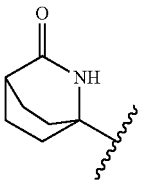,
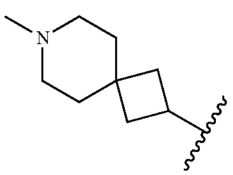,
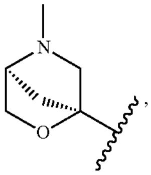,
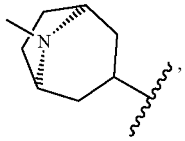,
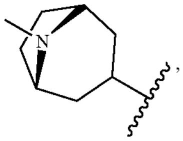, or
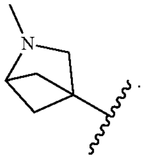.

In certain embodiments, the compound of Formula (I) is of Formula (I-e):

(I-e)

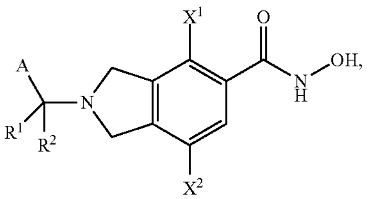

or a pharmaceutically acceptable salt, co-crystal, tautomer, stereoisomer, solvate, hydrate, polymorph, isotopically enriched derivative, or prodrug thereof; wherein A, $R^1$, $R^2$, $X^1$, and $X^2$ are as defined herein.

In certain embodiments, the compound of Formula (I) is of Formula (I-f):

(I-f)

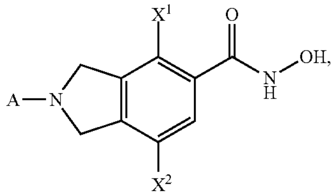

or a pharmaceutically acceptable salt, co-crystal, tautomer, stereoisomer, solvate, hydrate, polymorph, isotopically enriched derivative, or prodrug thereof; wherein A, $X^1$, and $X^2$ are as defined herein.

In certain embodiments, the compound of Formula (I) is of Formula (I-g):

(I-g)

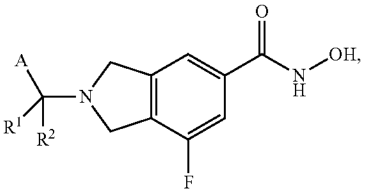

or a pharmaceutically acceptable salt, co-crystal, tautomer, stereoisomer, solvate, hydrate, polymorph, isotopically enriched derivative, or prodrug thereof; wherein A, $R^1$, and $R^2$ are as defined herein.

In certain embodiments, the compound of Formula (I) is of Formula (I-h):

(I-h)

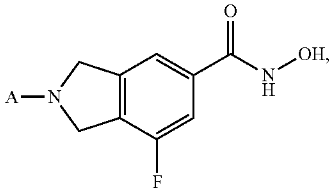

or a pharmaceutically acceptable salt, co-crystal, tautomer, stereoisomer, solvate, hydrate, polymorph, isotopically enriched derivative, or prodrug thereof; wherein A is as defined herein.

In certain embodiments, the compound of Formula (I) is one of the following compounds, or a pharmaceutically acceptable salt, co-crystal, tautomer, stereoisomer, solvate, hydrate, polymorph, isotopically enriched derivative, or prodrug thereof:

184

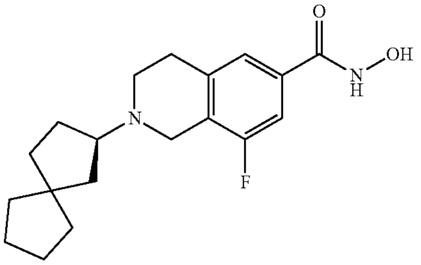

197

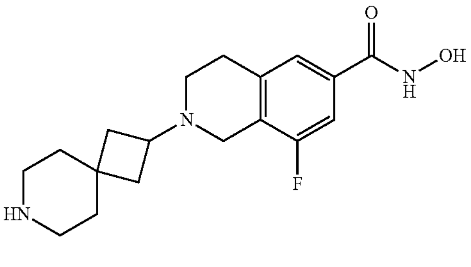

-continued
201
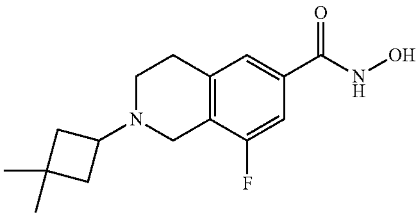
289
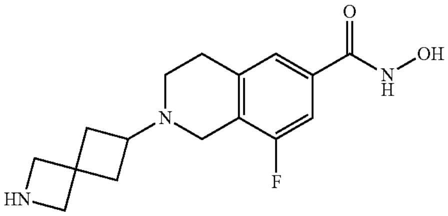
301
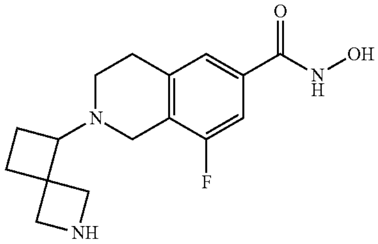
344
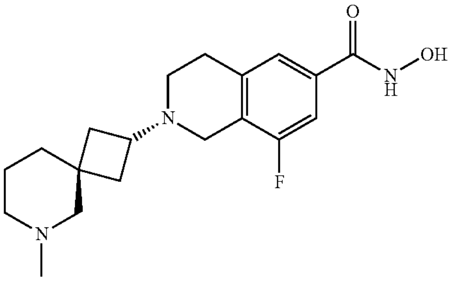
352
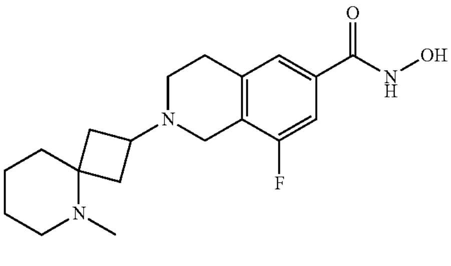
353
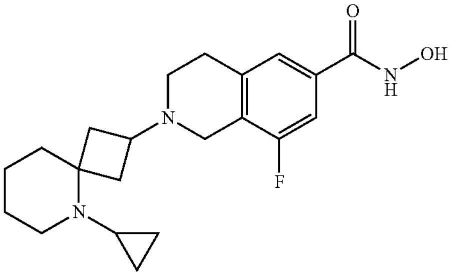
-continued
357
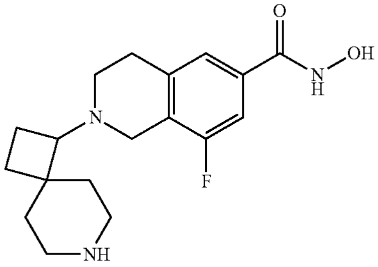
358
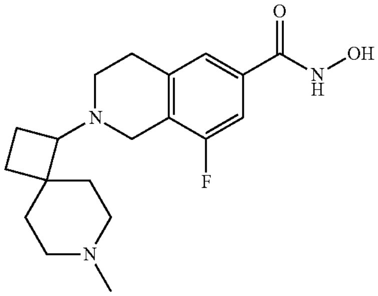
389
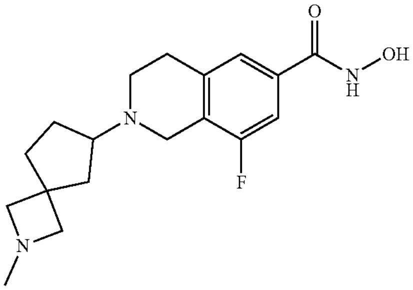
419
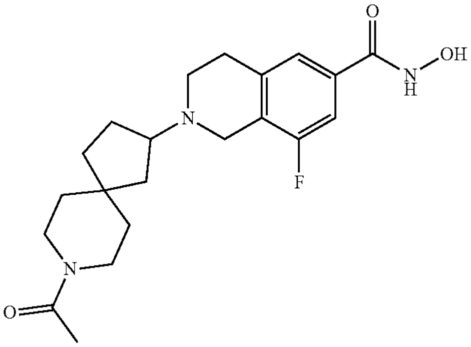
426
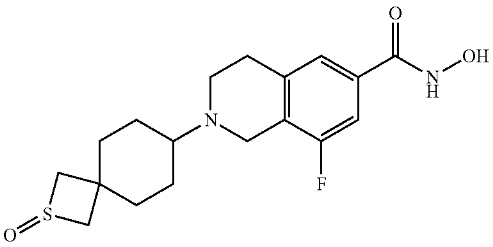

-continued
435
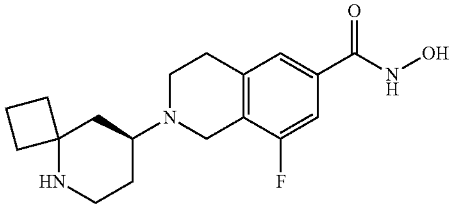
436
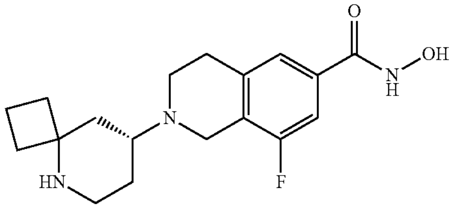
437
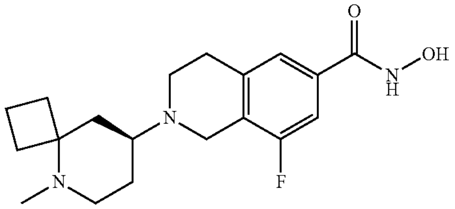
439
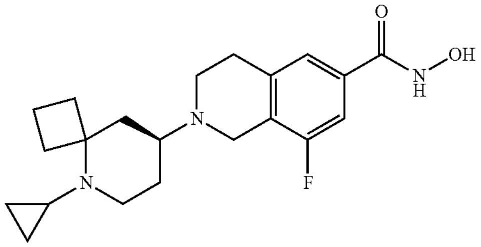
440
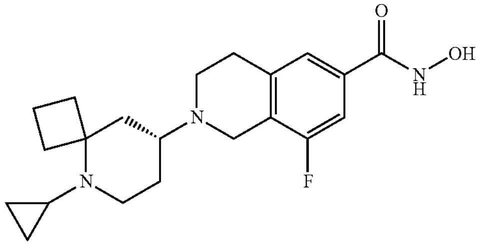
451
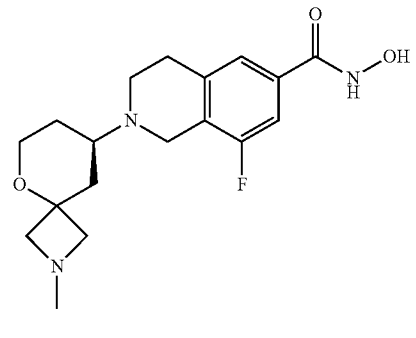
-continued
453
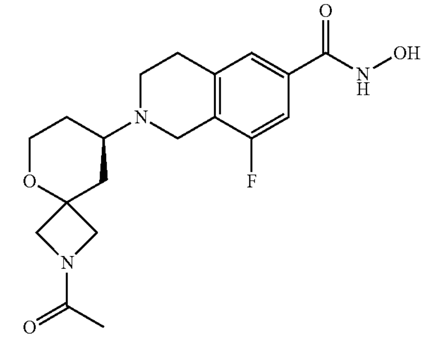
454
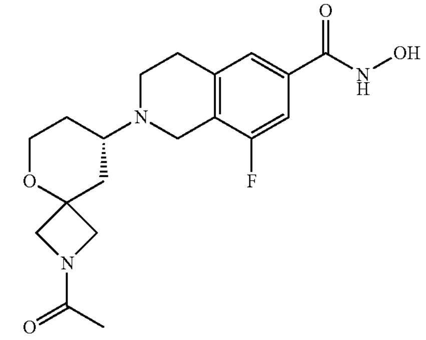
461
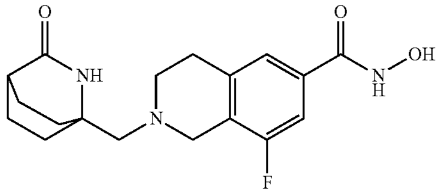
469
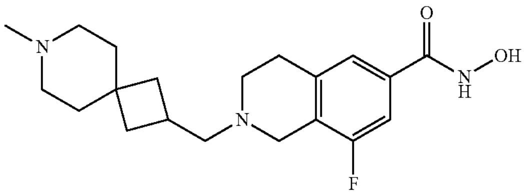
475
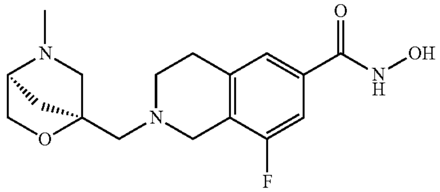
482
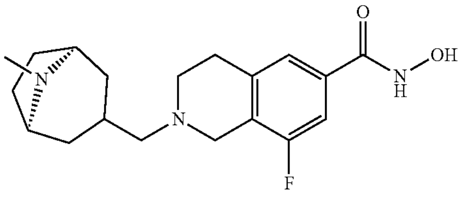

-continued

483

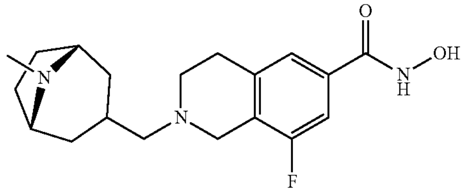

490

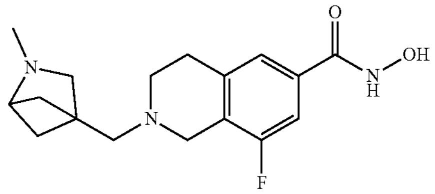

In certain embodiments, the compound of Formula (I) is one of the following compounds, or a pharmaceutically acceptable salt, co-crystal, tautomer, stereoisomer, solvate, hydrate, polymorph, isotopically enriched derivative, or prodrug thereof:

184

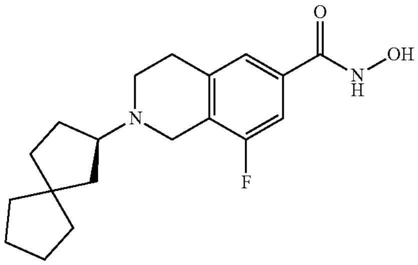

197

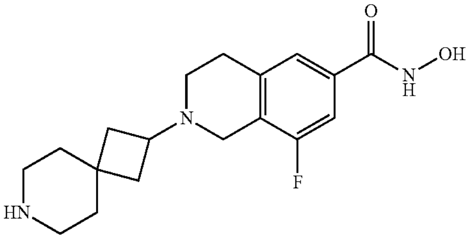

201

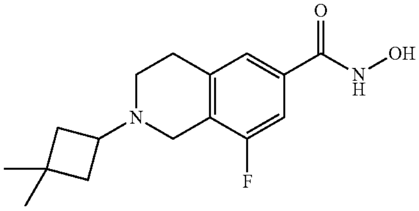

In certain embodiments, the compound of Formula (I) is one of the following compounds, or a pharmaceutically acceptable salt, co-crystal, tautomer, stereoisomer, solvate, hydrate, polymorph, isotopically enriched derivative, or prodrug thereof:

174

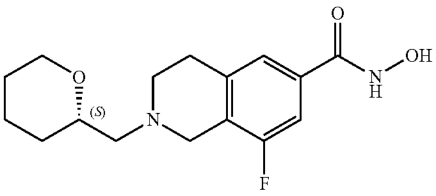

175

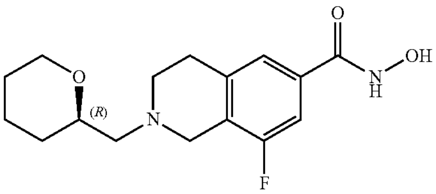

176

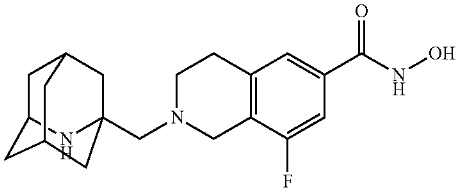

177

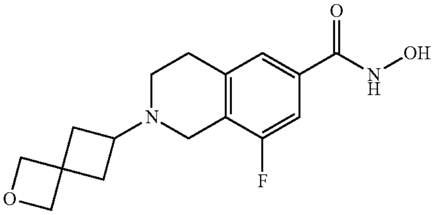

178

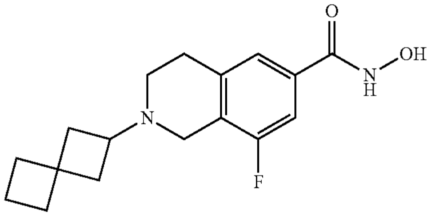

179

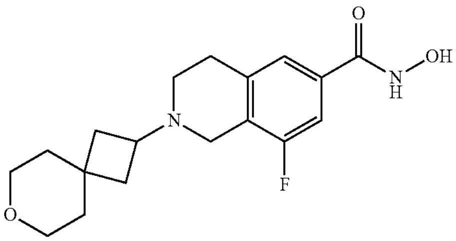

180

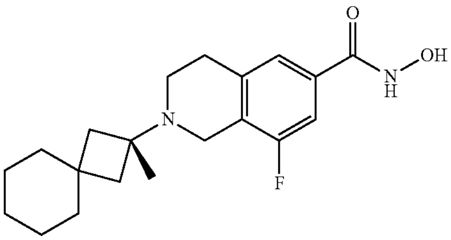

-continued
181
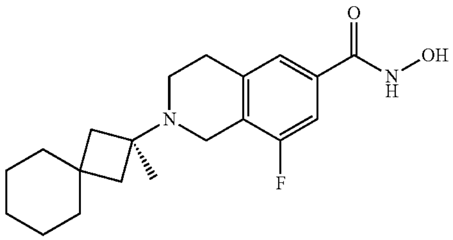
182
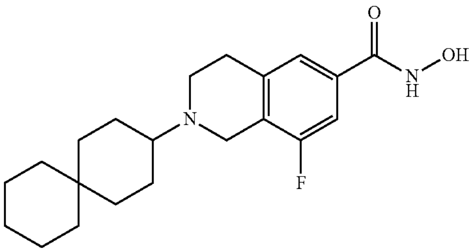
183
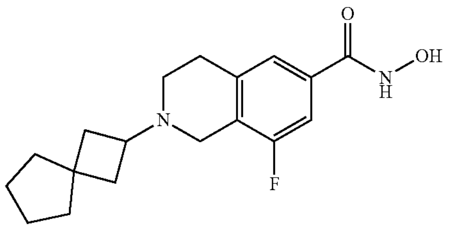
185
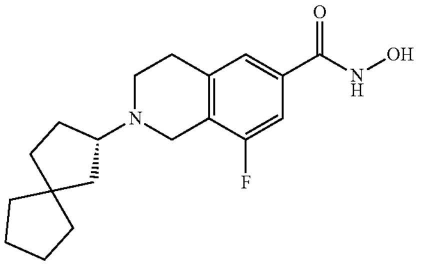
188
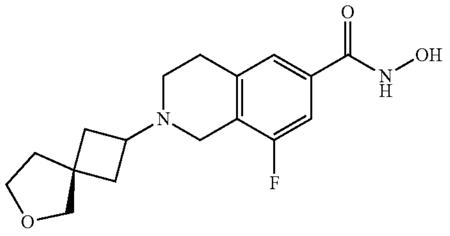
189
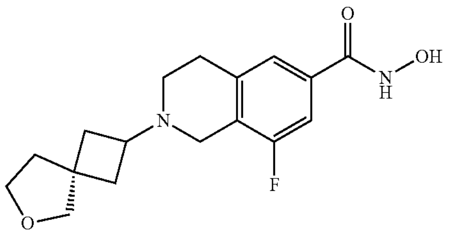
-continued
190
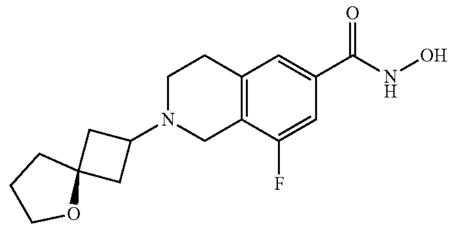
191
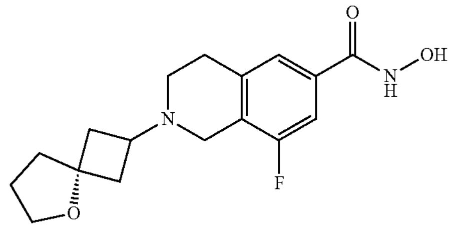
192
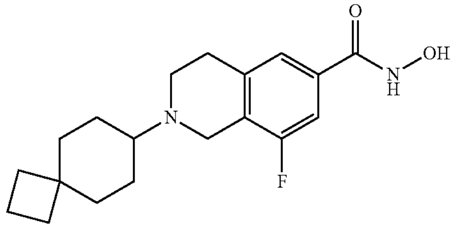
193
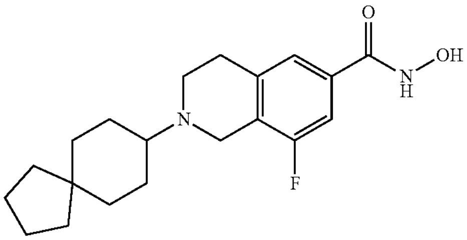
194
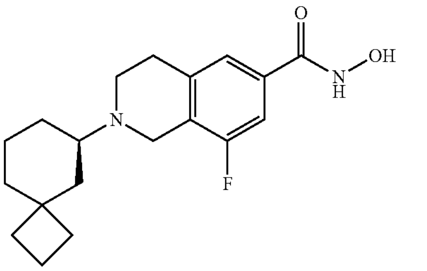
195
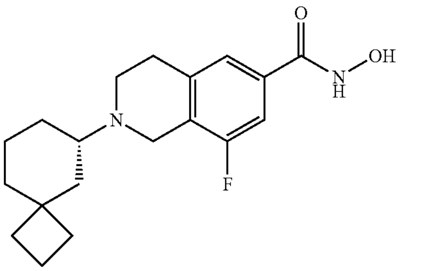

-continued
198
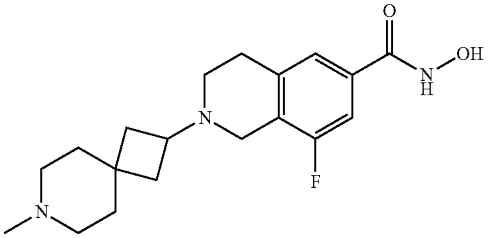
199
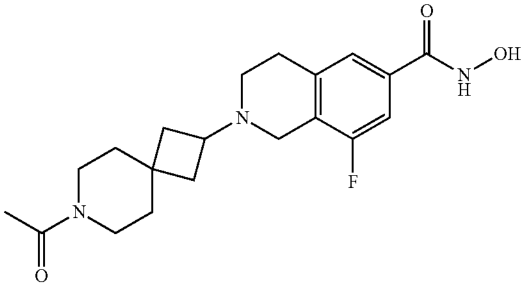
200
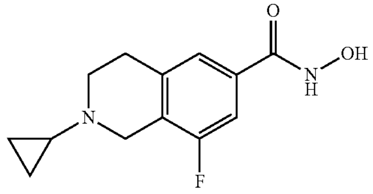
202
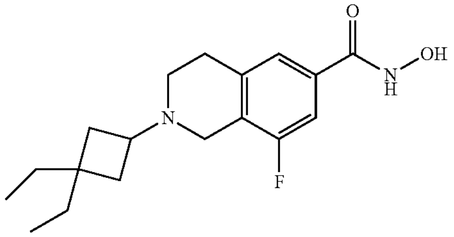
209
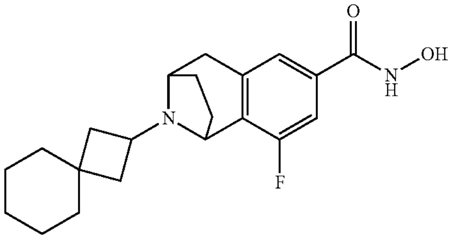
210
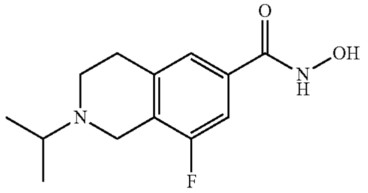
-continued
211
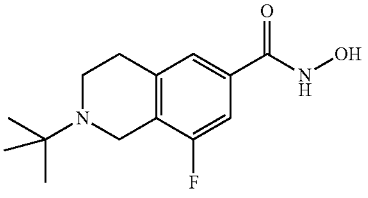
212
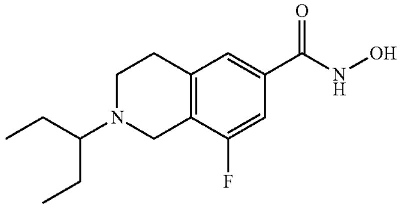
290
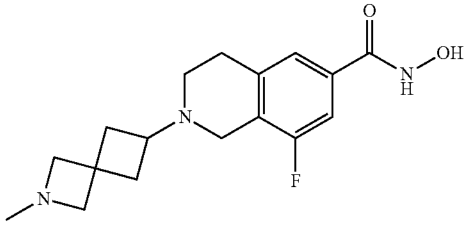
291
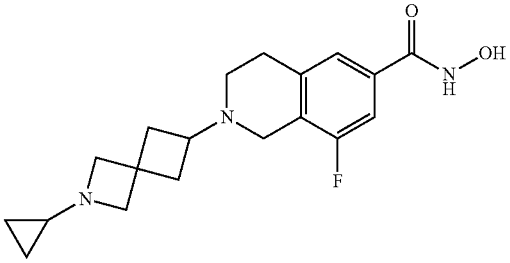
292
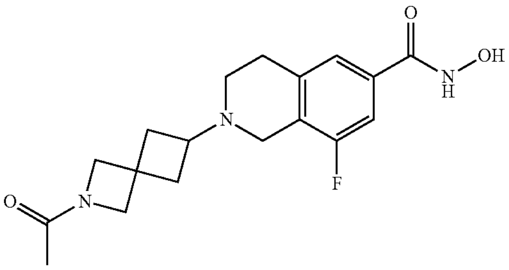
293
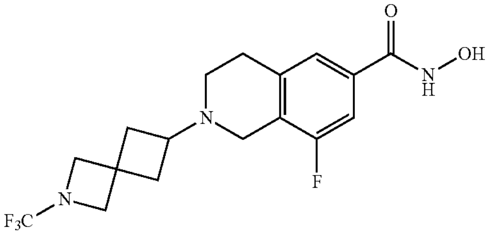

-continued
294
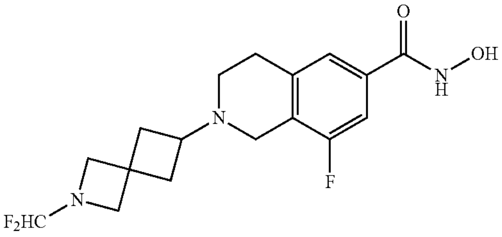
295
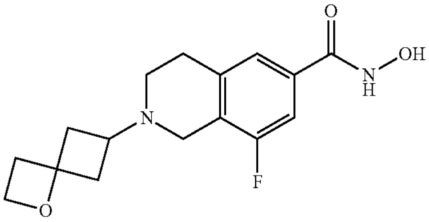
296
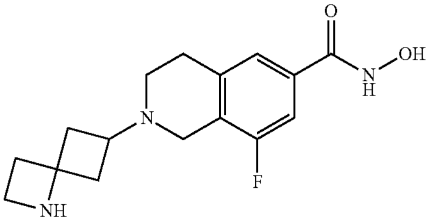
297
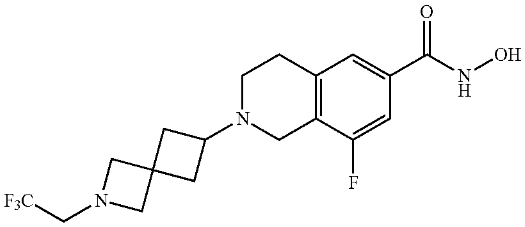
298
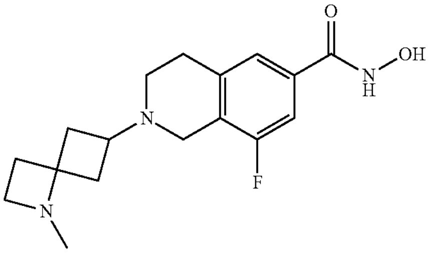
299
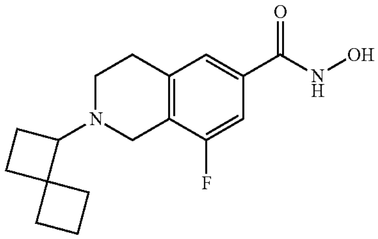
-continued
300
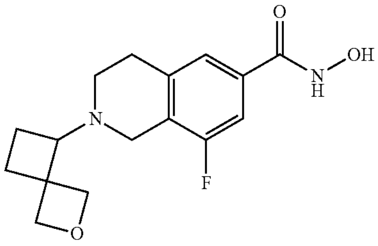
302
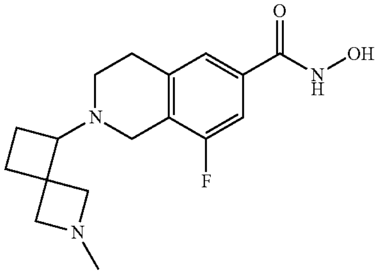
303
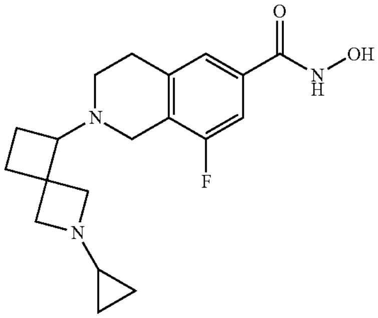
304
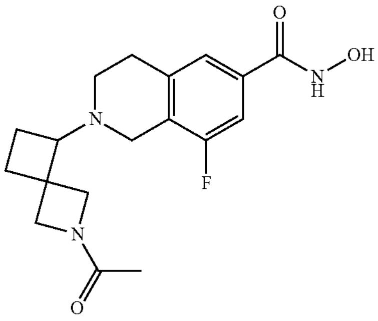
305
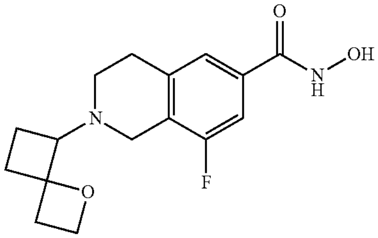

-continued
306
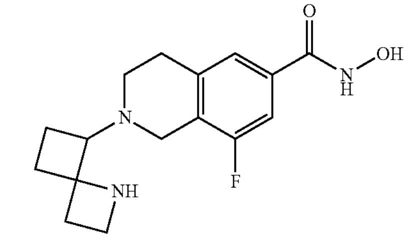
307
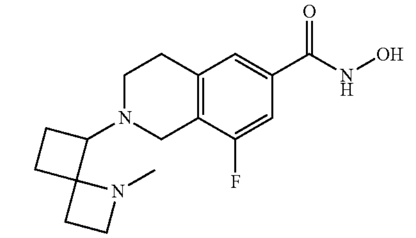
308
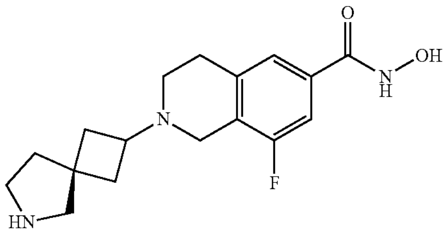
309
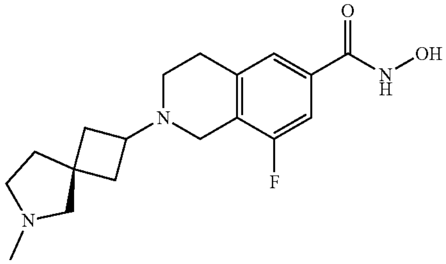
310
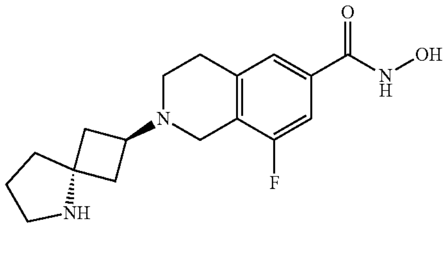
311
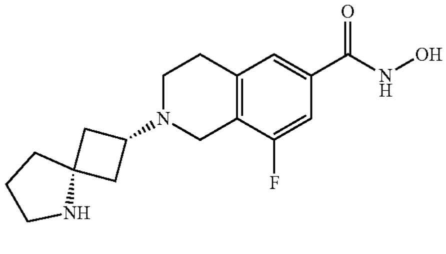
-continued
312
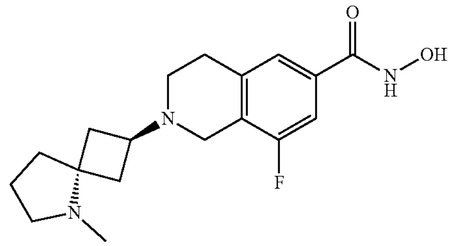
313
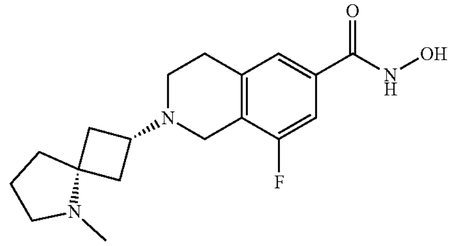
314
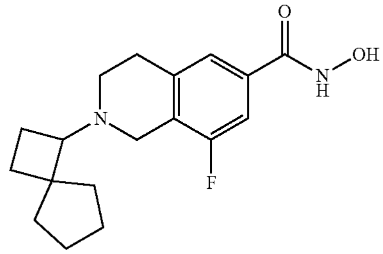
315
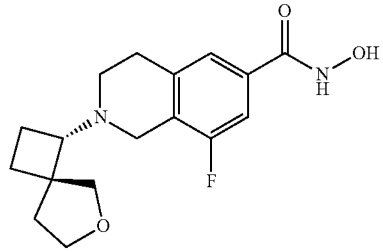
316
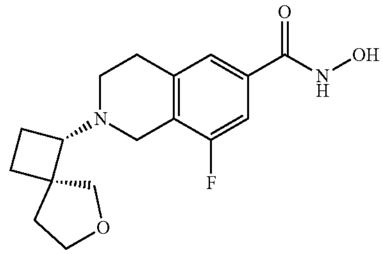
317
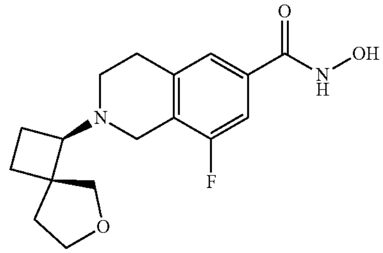

-continued
318
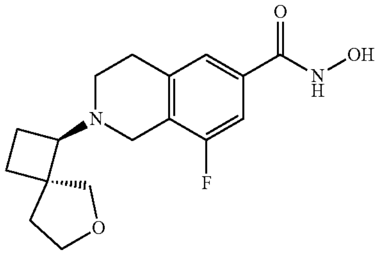
319
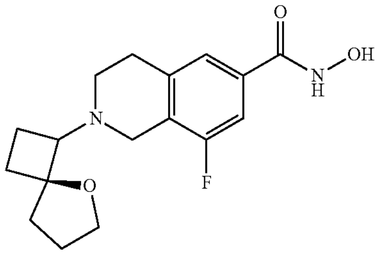
320
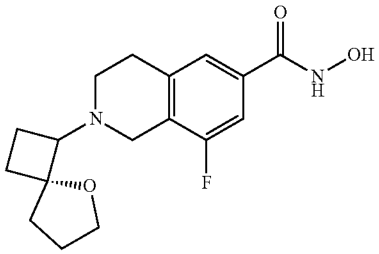
321
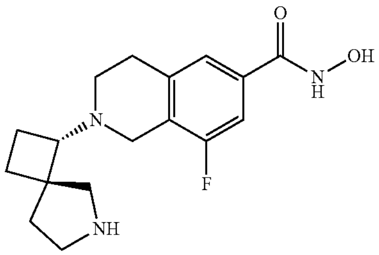
322
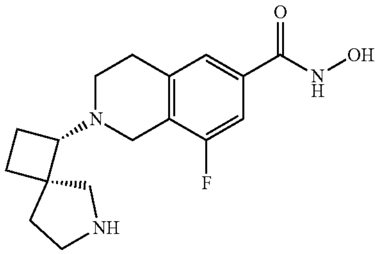
323
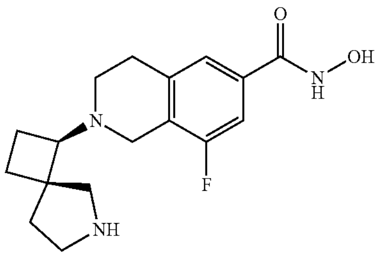
-continued
324
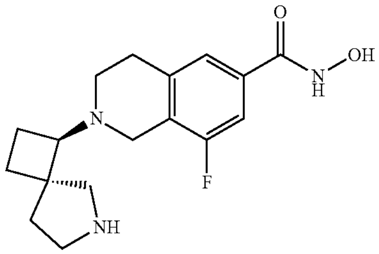
325
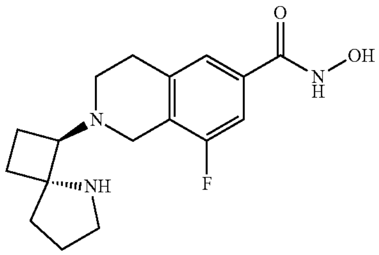
326
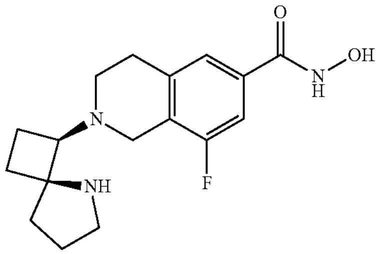
327
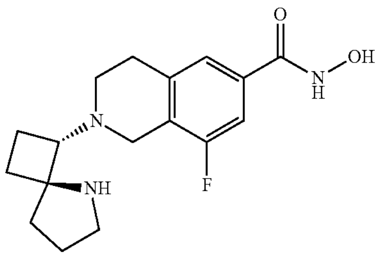
328
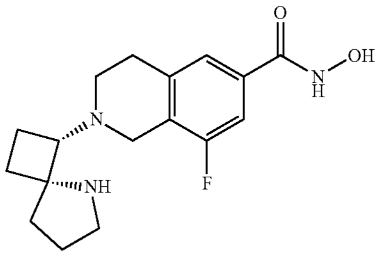
329
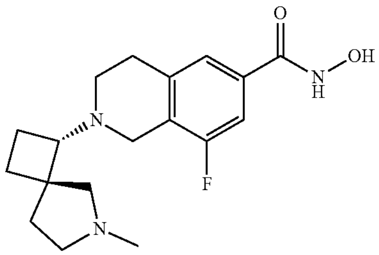

-continued
330
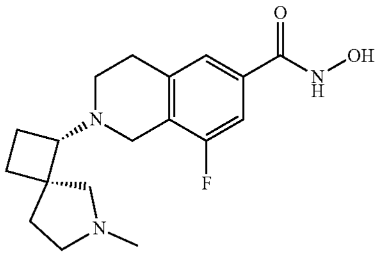
331
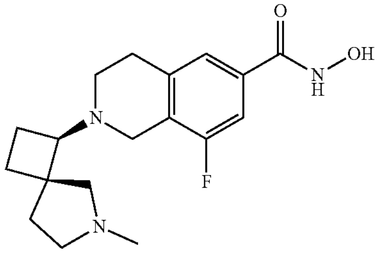
332
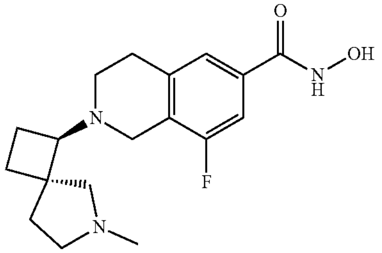
333
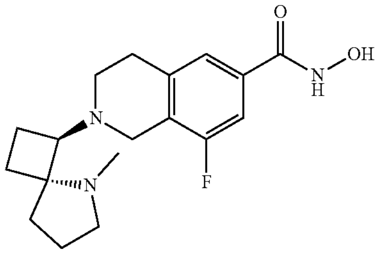
334
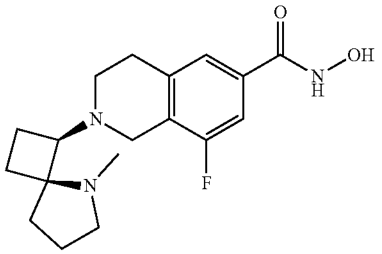
335
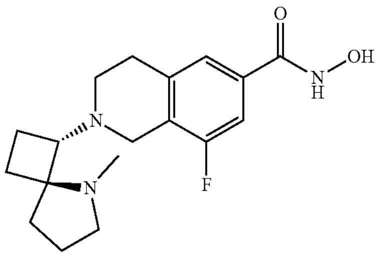
-continued
336
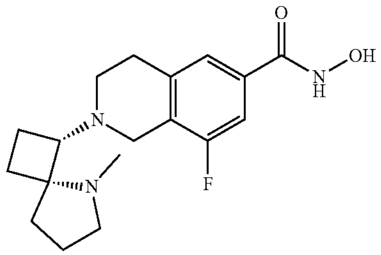
337
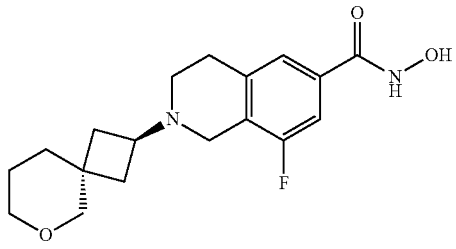
338
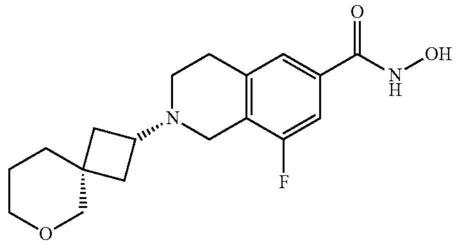
339
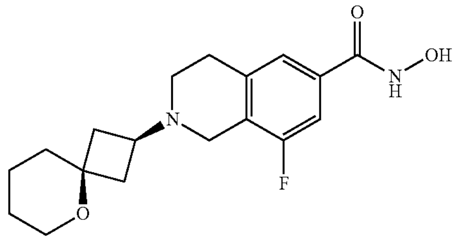
340
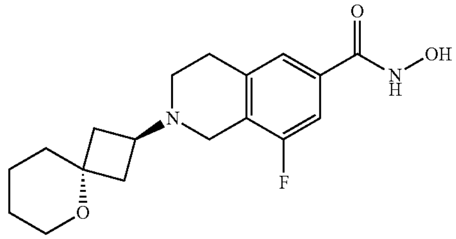
341
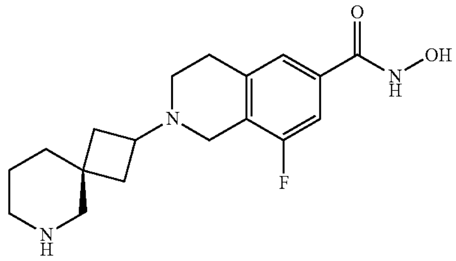

-continued
342
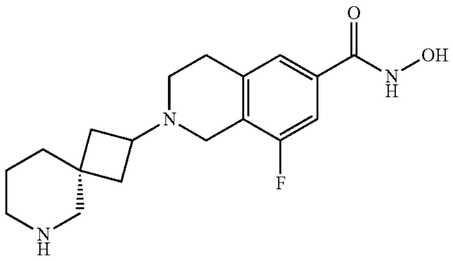
343
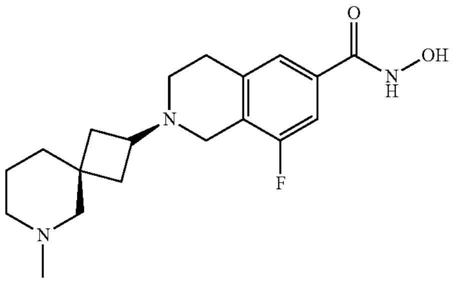
345
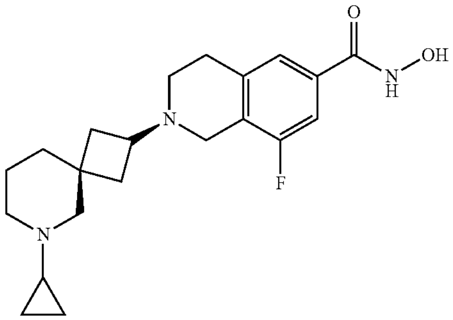
346
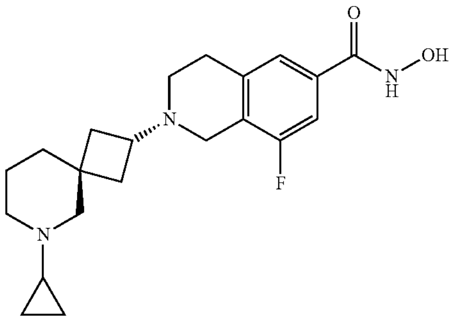
347
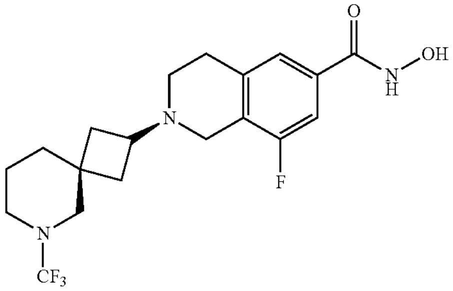
-continued
348
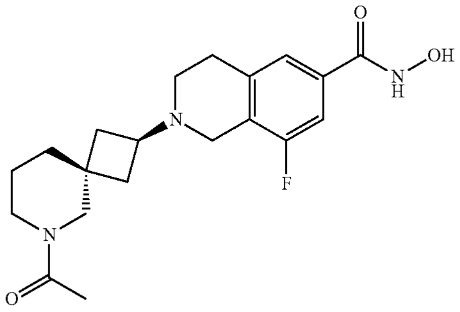
349
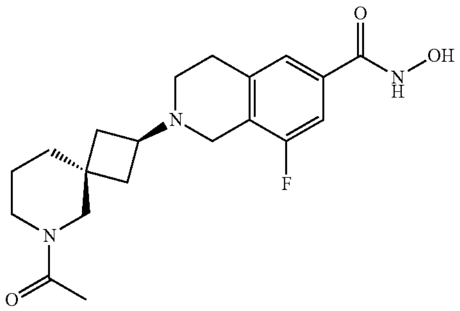
350
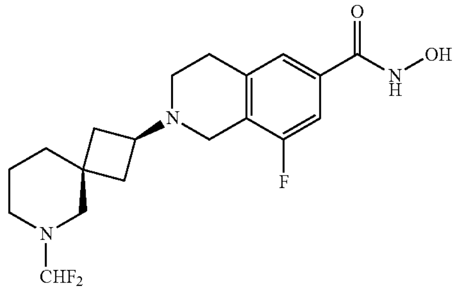
351
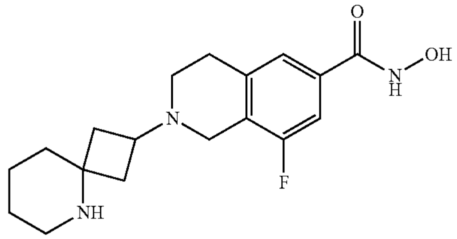
354
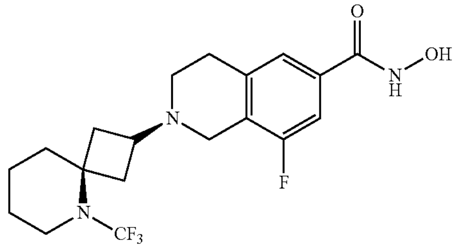

-continued
355
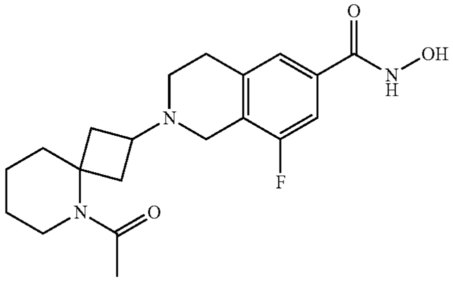
356
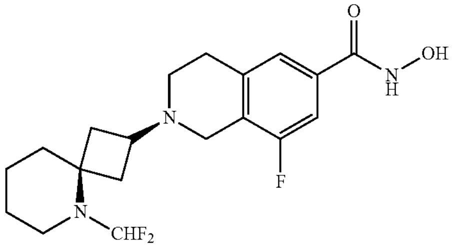
359
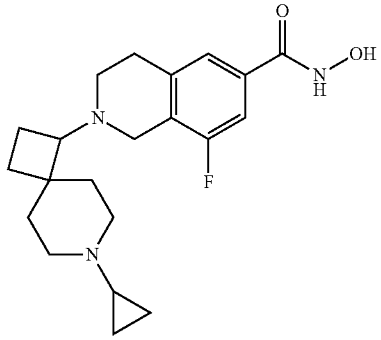
360
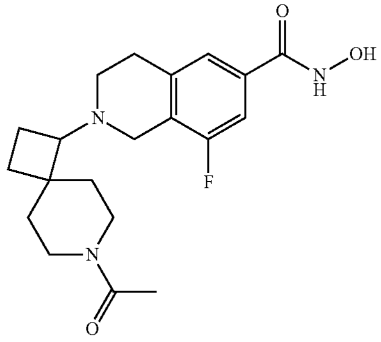
361
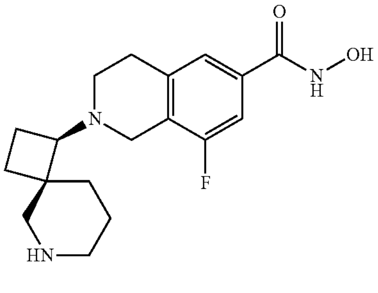
-continued
362
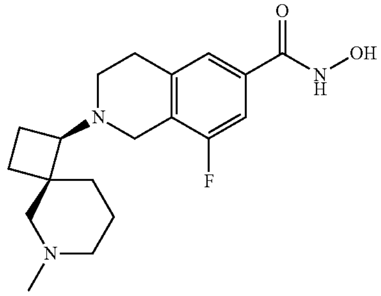
363
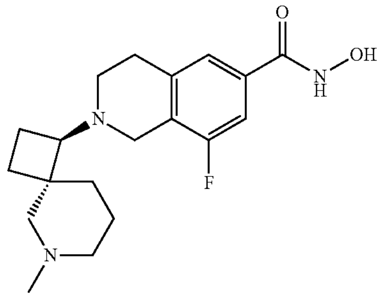
364
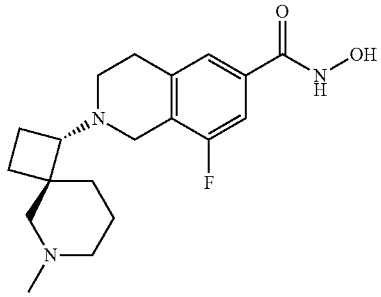
365
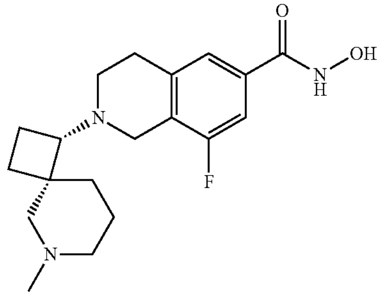
366
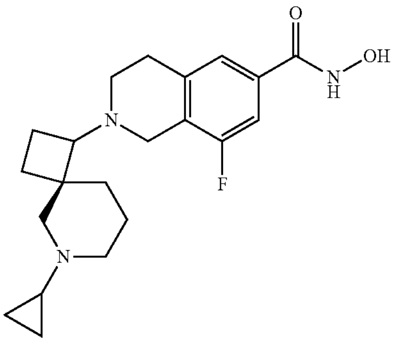

-continued
367
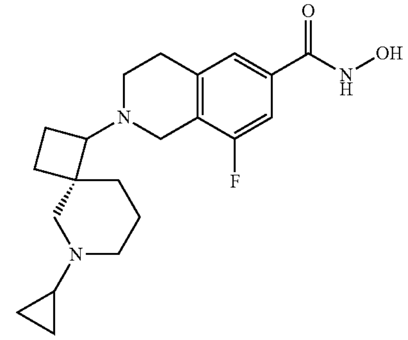
368
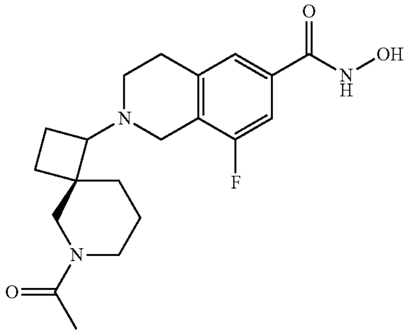
369
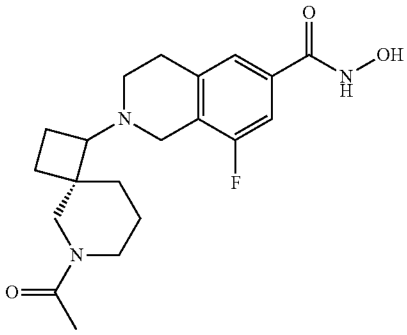
370
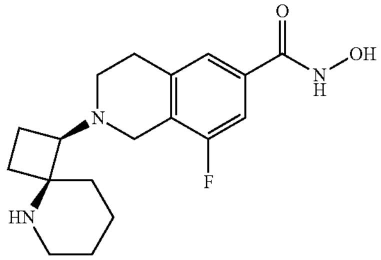
371
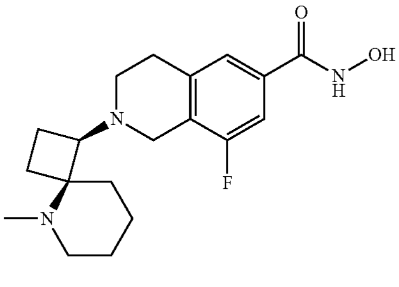
-continued
372
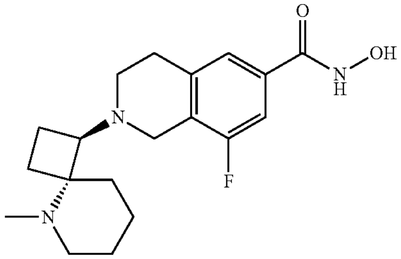
373
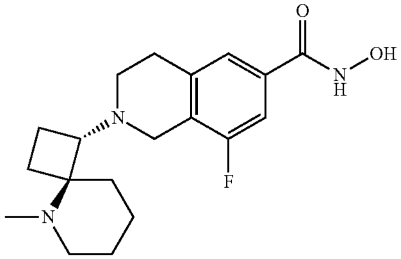
374
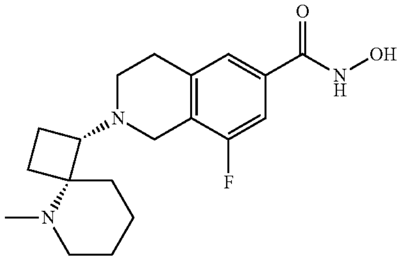
375
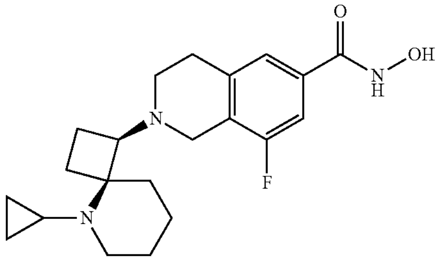
376
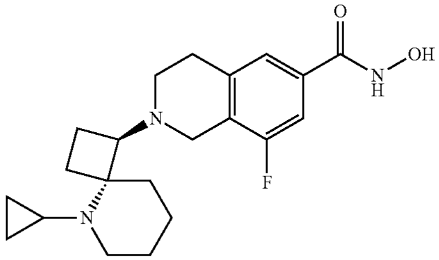
377
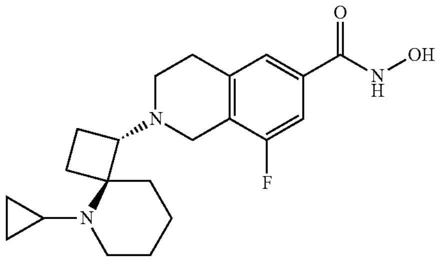

-continued
378
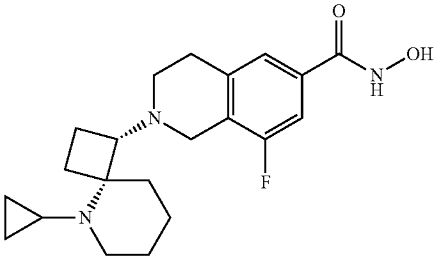
379
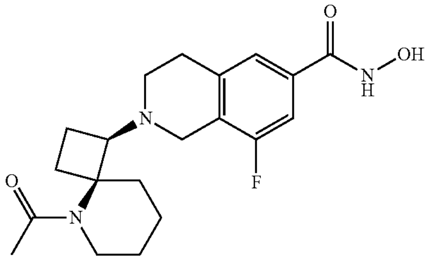
380
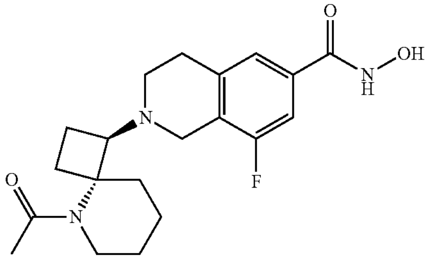
381
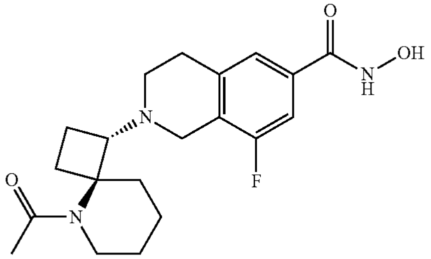
382
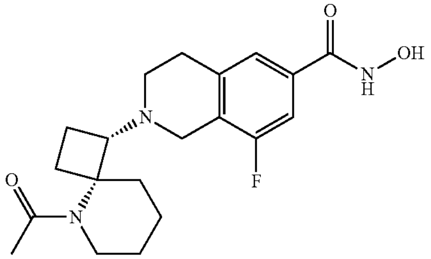
383
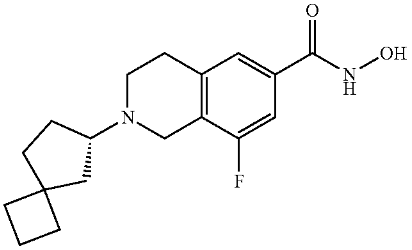
-continued
384
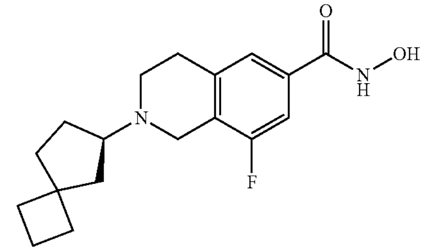
385
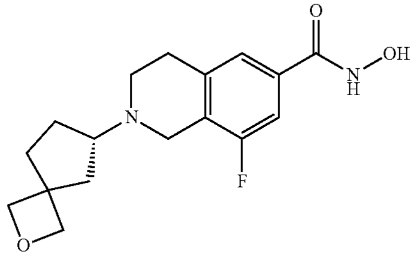
386
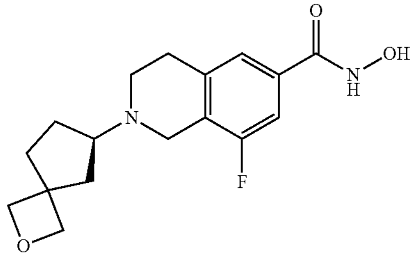
387
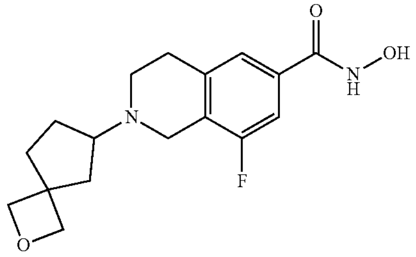
388
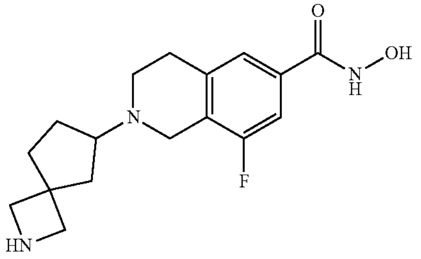

-continued
390
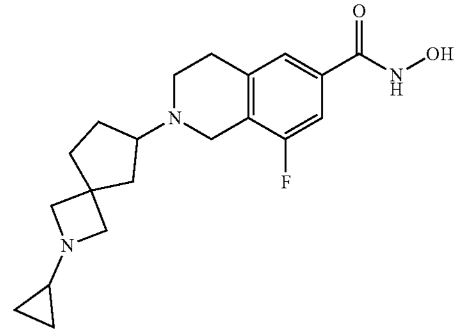
391
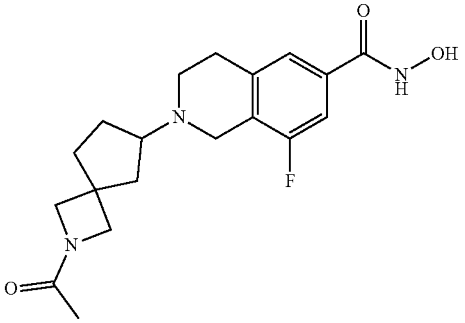
392
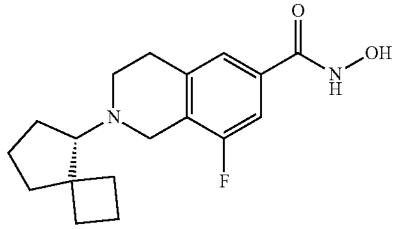
393
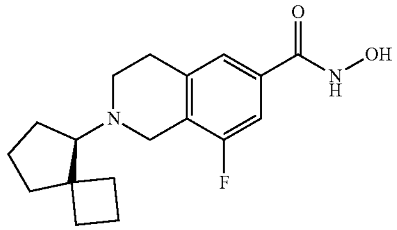
394
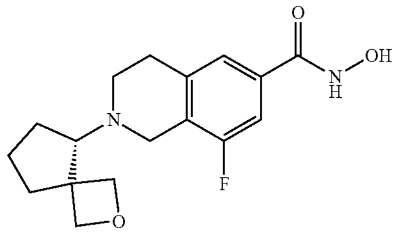
395
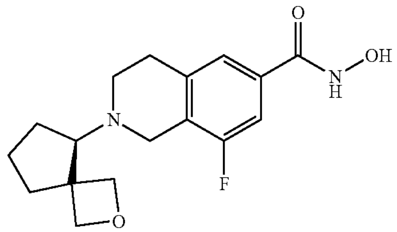
-continued
396
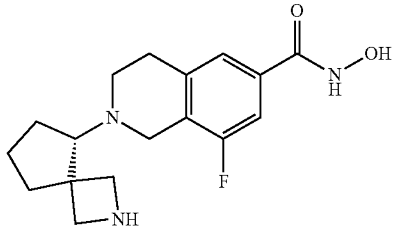
397
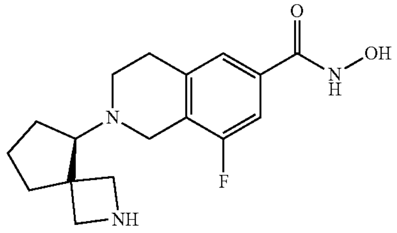
398
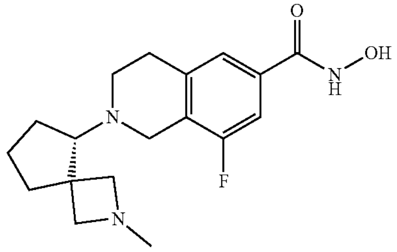
399
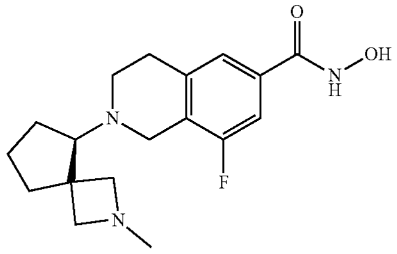
400
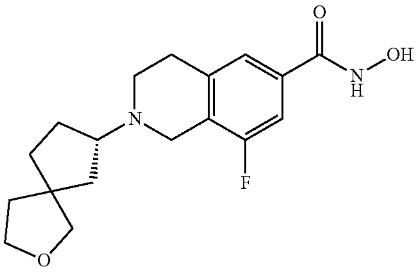
401
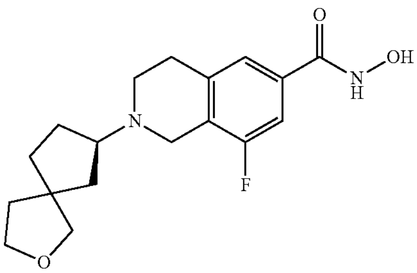

-continued
402
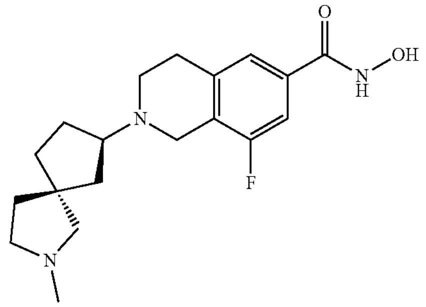
403
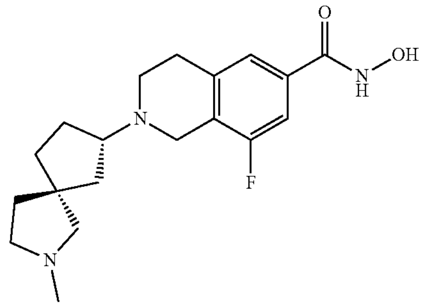
404
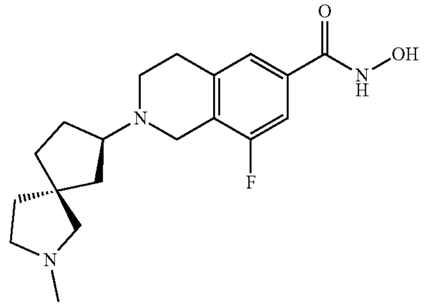
405
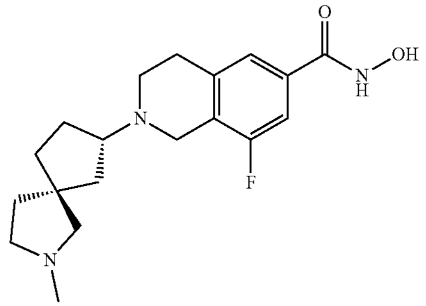
406
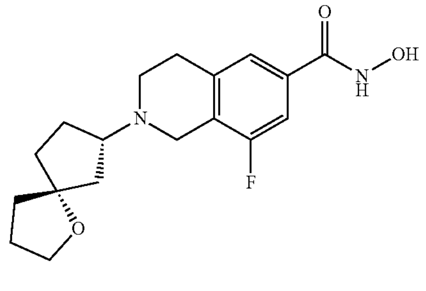
-continued
407
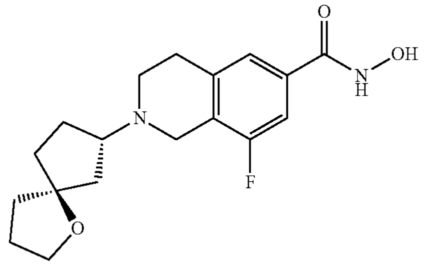
408
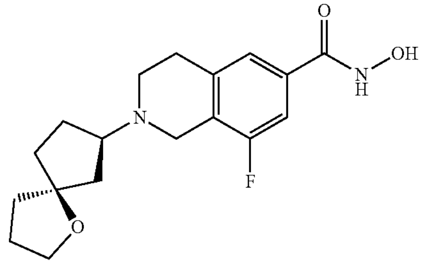
409
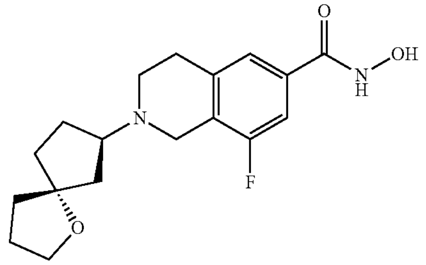
410
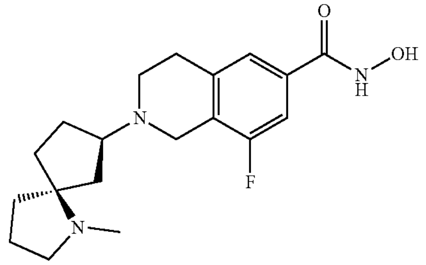
411
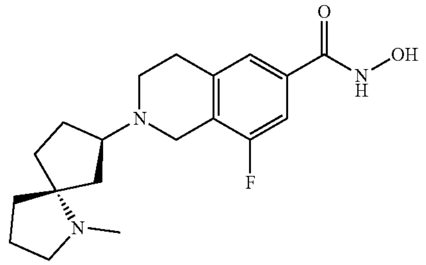
412
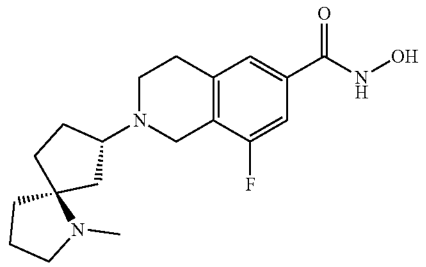

-continued
413
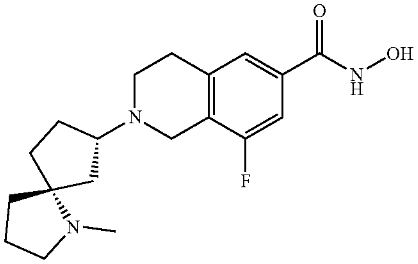
141
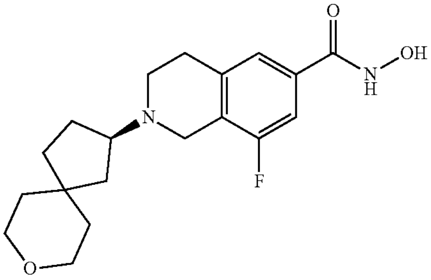
415
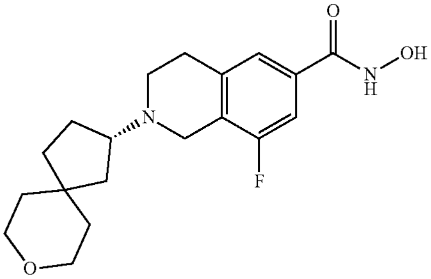
416
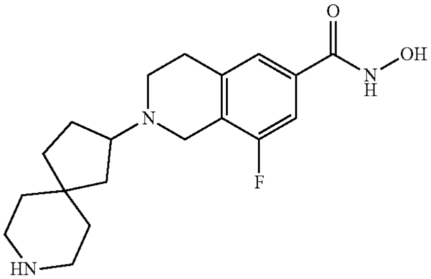
417
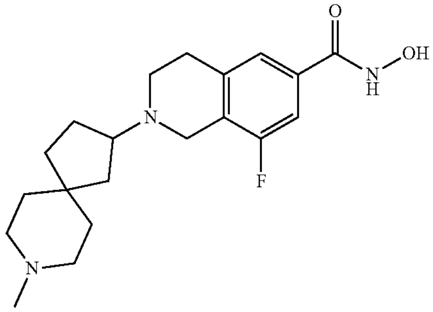
-continued
418
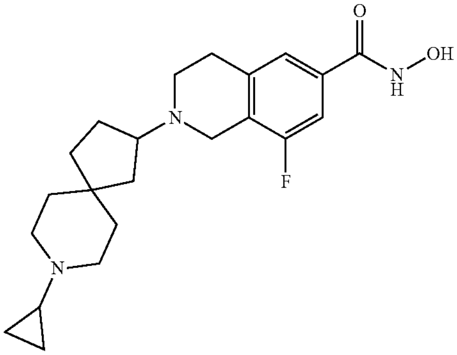
420
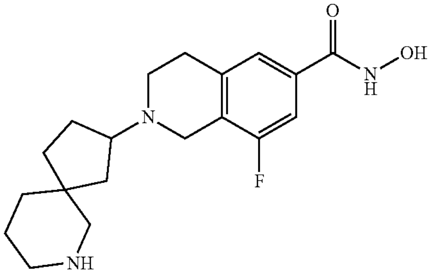
421
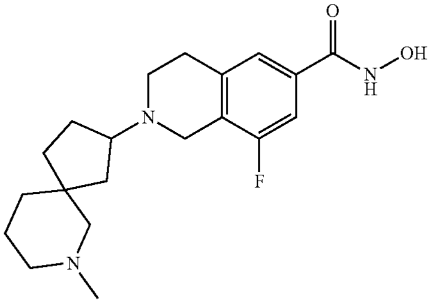
422
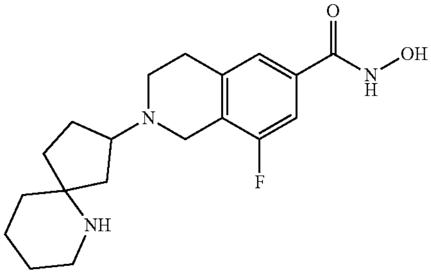
423
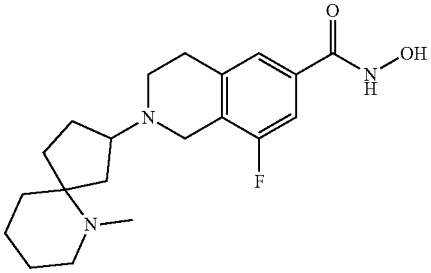

-continued
425
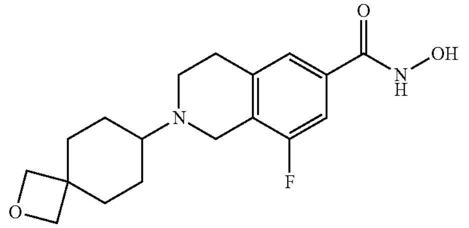
427
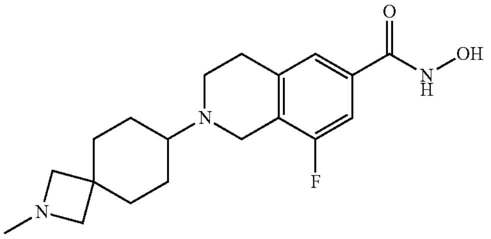
428
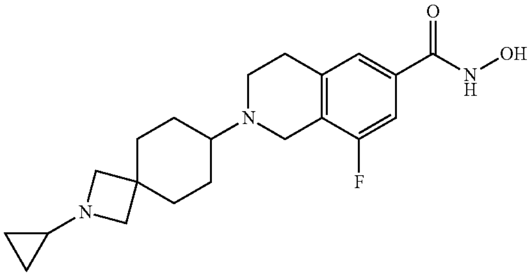
429
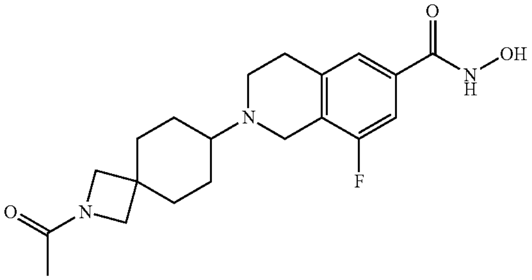
430
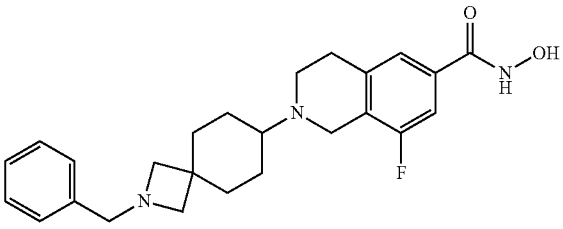
431
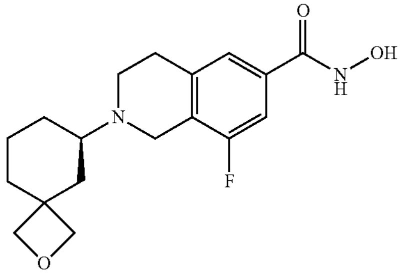
-continued
432
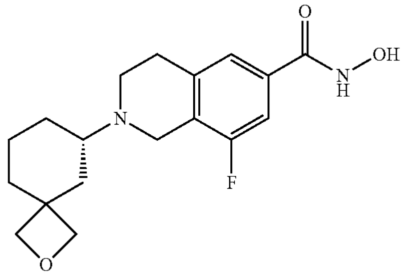
433
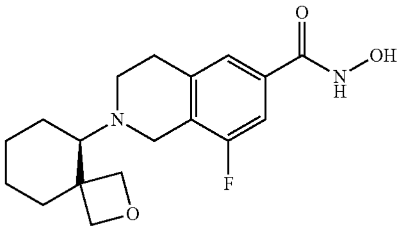
434
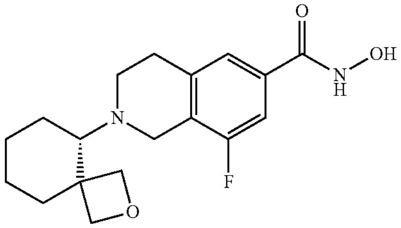
438
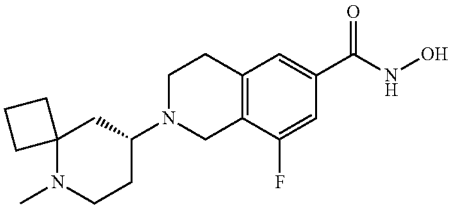
441
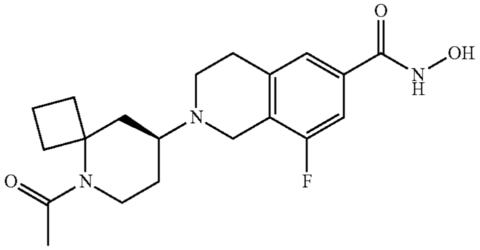
442
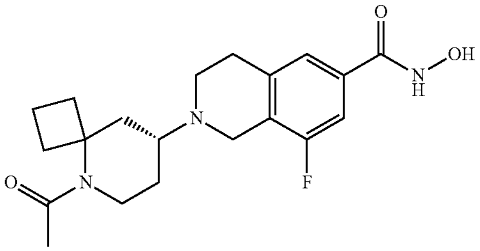

-continued
443
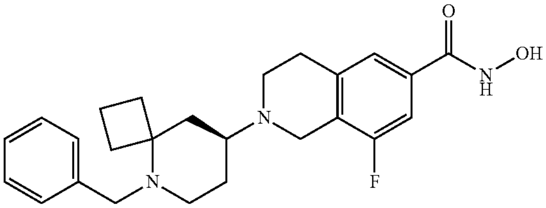
444
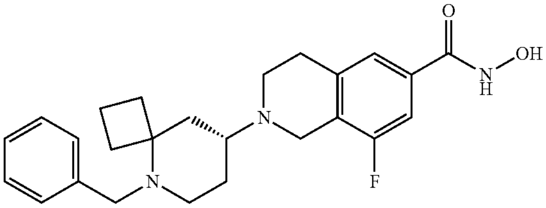
445
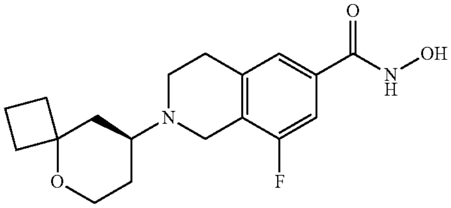
446
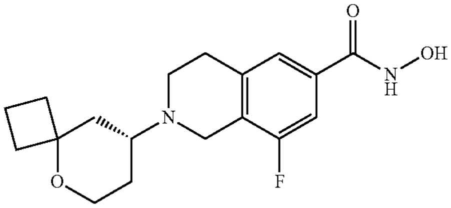
447
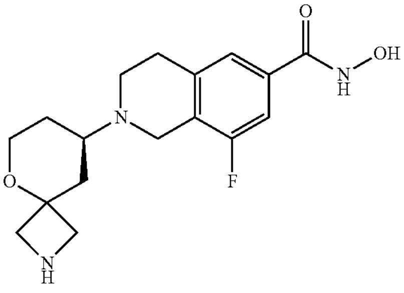
448
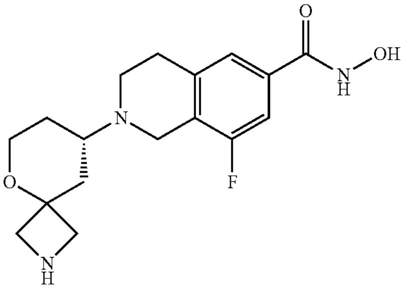
-continued
449
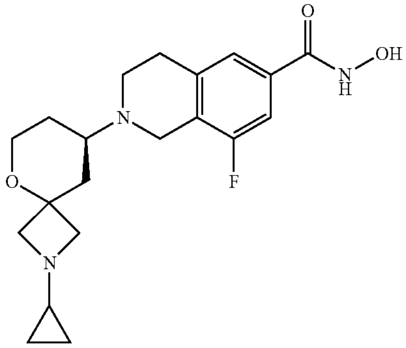
450
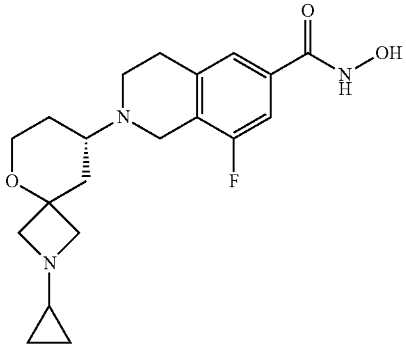
452
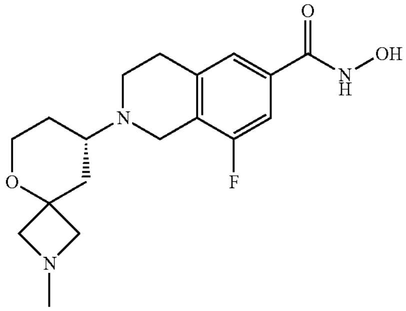
455
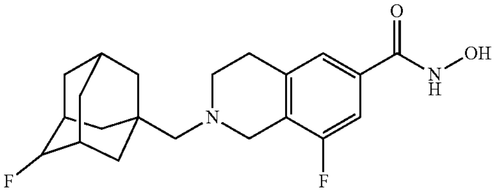
456
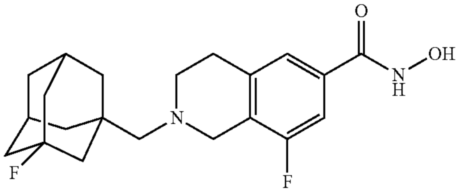
457
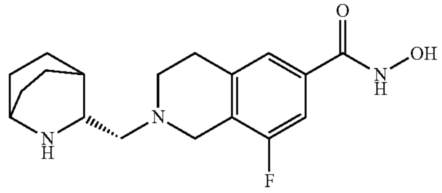

-continued
458
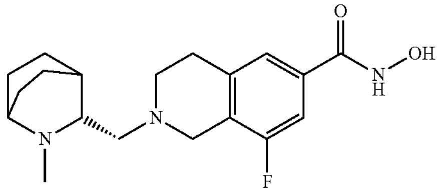
459
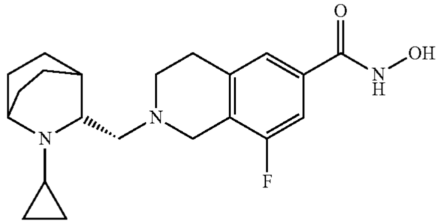
460
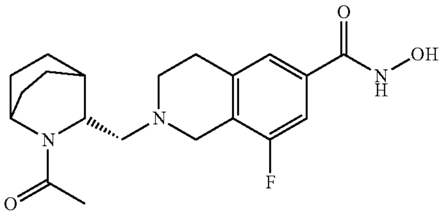
462
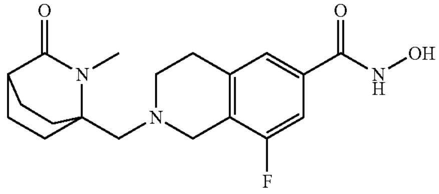
463
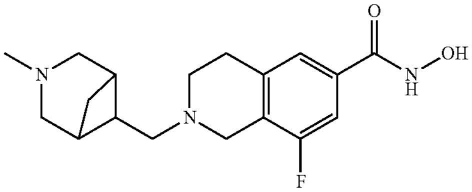
464
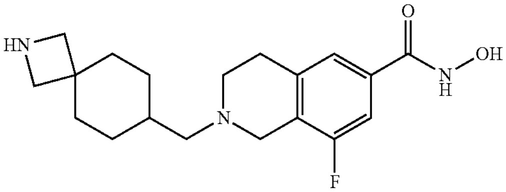
465
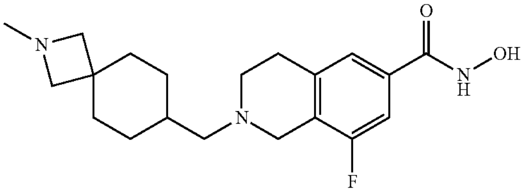
-continued
466
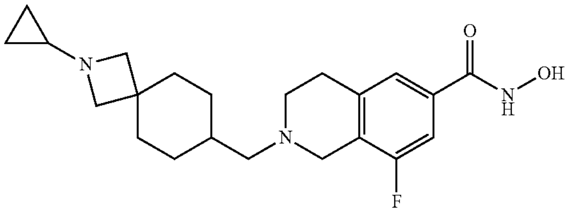
467
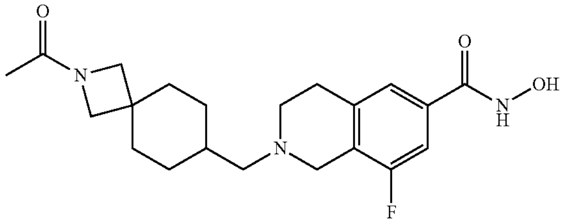
468
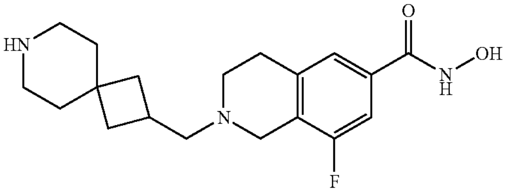
470
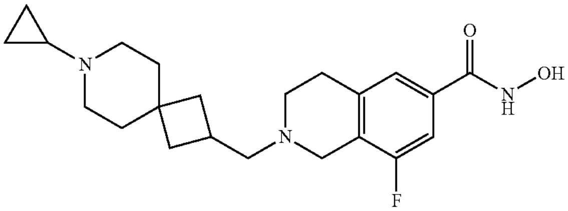
471
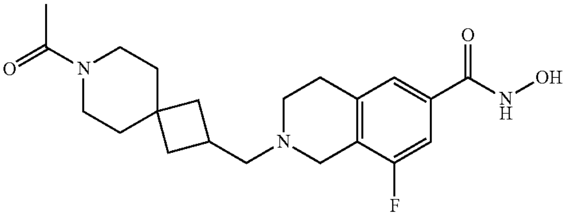
472
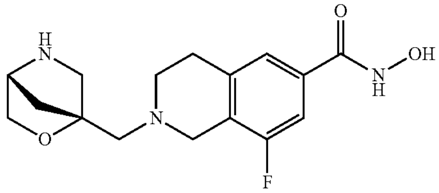
473
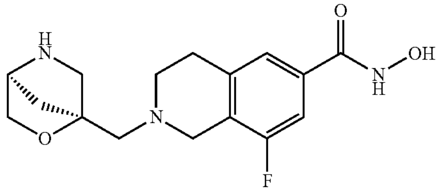

474
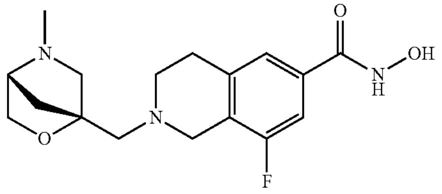
476
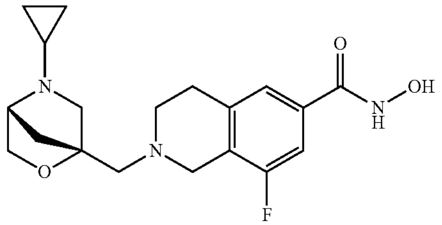
477
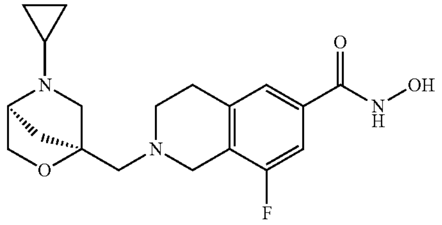
478
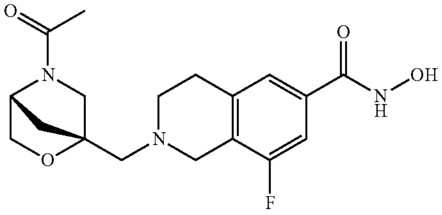
479
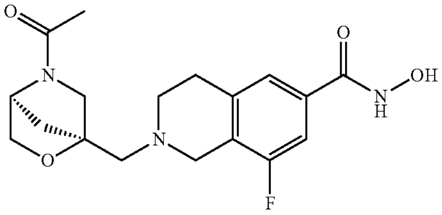
480
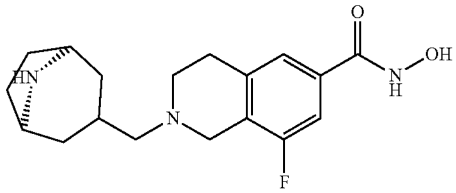
481
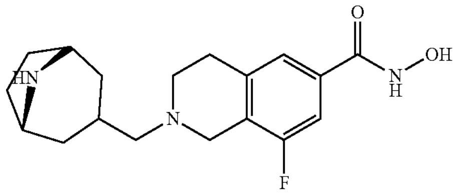
484
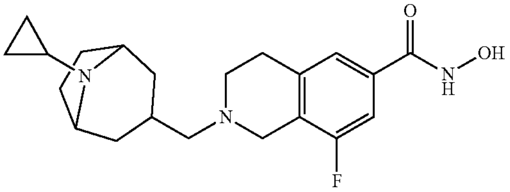
485
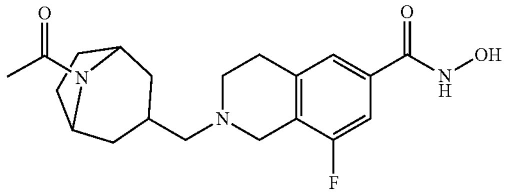
486
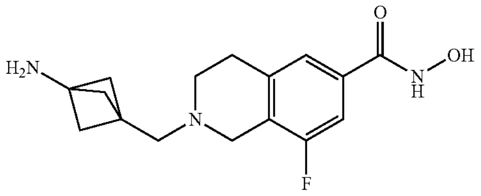
487
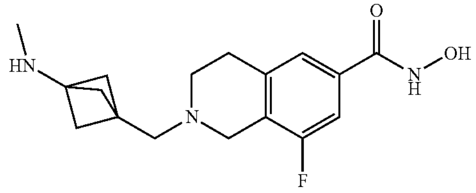
488
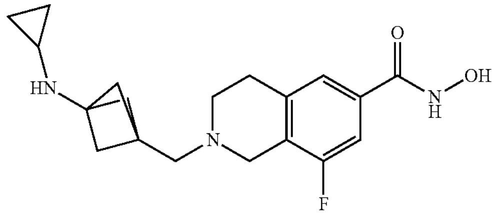
489
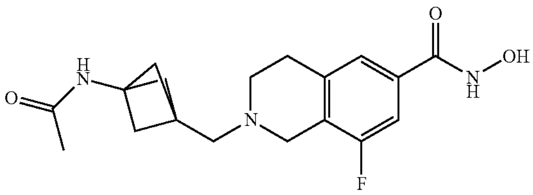
491
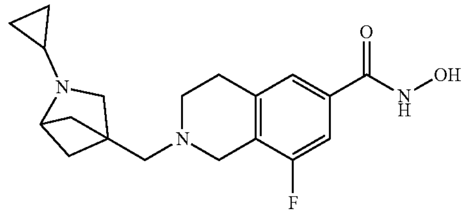

-continued
492
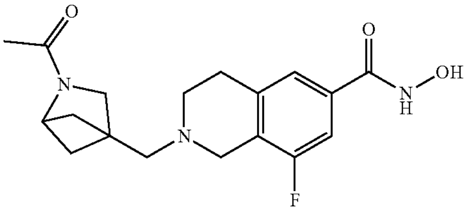
493
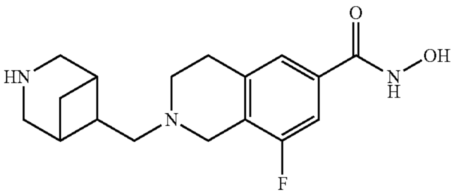
494
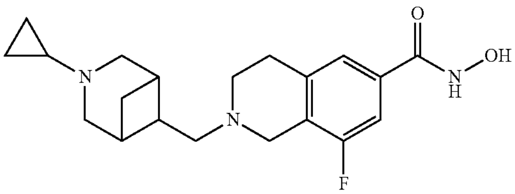
495
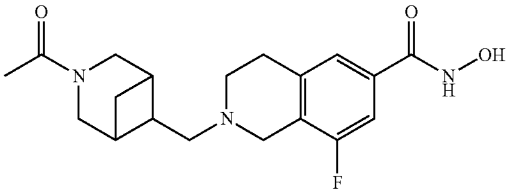
496
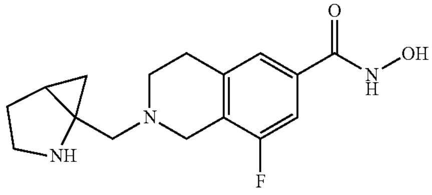
497
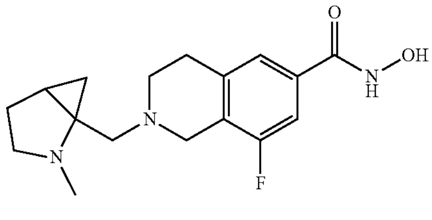
498
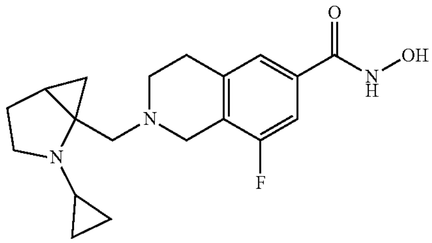
-continued
499
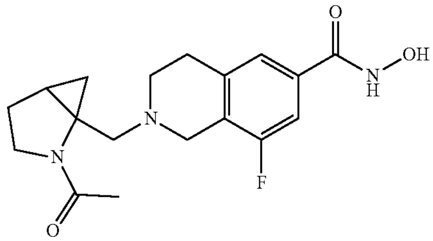
501
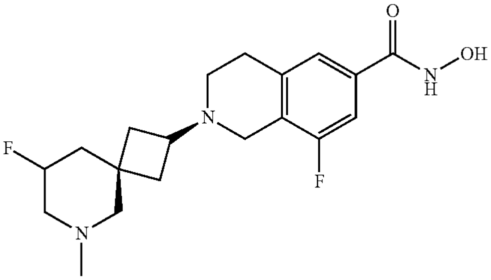
502
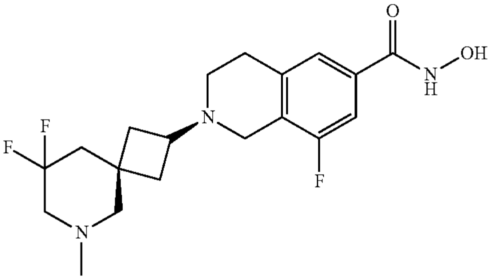
503
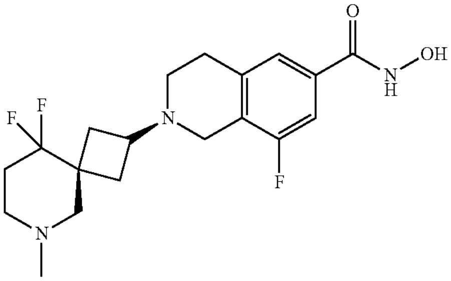
504
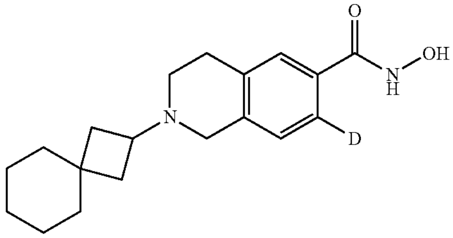

-continued
505
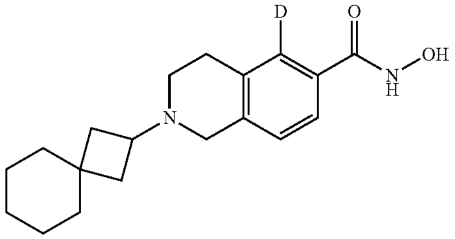
506
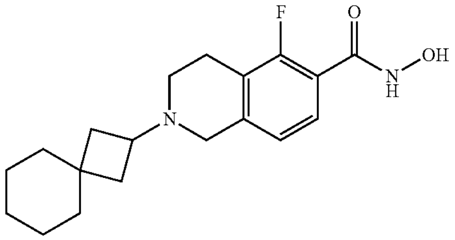
604
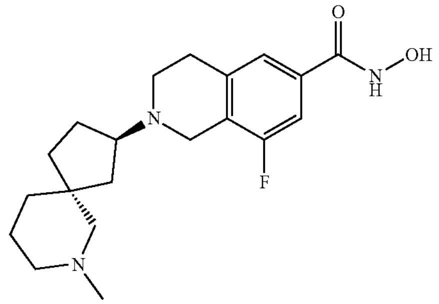
605
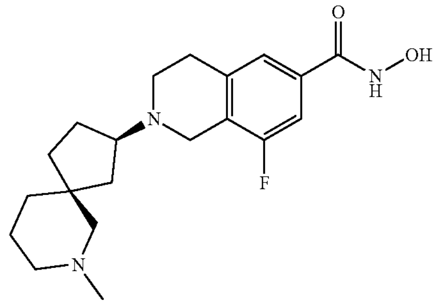
606
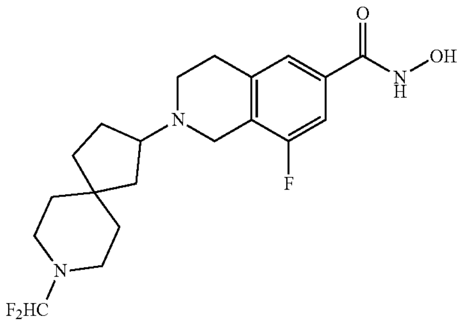
-continued
607
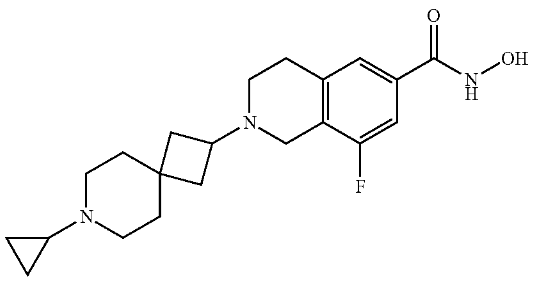
658
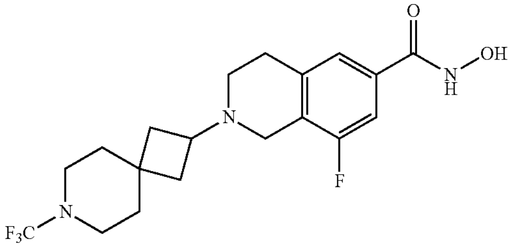
659
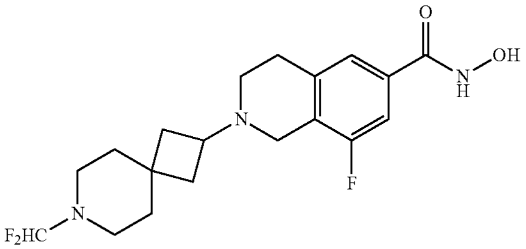
660
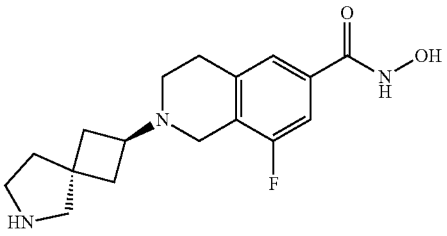
Compounds of Formula (II)
In another aspect, disclosed is a compound of Formula (II):
(II)
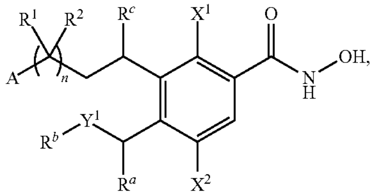
or a pharmaceutically acceptable salt, co-crystal, tautomer, stereoisomer, solvate, hydrate, polymorph, isotopically enriched derivative, or prodrug thereof, wherein:
$X^1$ is hydrogen or fluoro;
$X^2$ is hydrogen or fluoro;
$Y^1$ is nitrogen or $CR^x$;

each A is independently hydrogen, substituted or unsubstituted alkyl, substituted or unsubstituted carbocyclyl, substituted or unsubstituted heterocyclyl, substituted or unsubstituted heteroaryl, or substituted or unsubstituted aryl;

each $R^1$ is independently hydrogen or substituted or unsubstituted alkyl;

each $R^2$ is independently hydrogen or substituted or unsubstituted alkyl; or $R^1$ and $R^2$ together form a substituted or unsubstituted heterocyclyl, or a substituted or unsubstituted cycloalkyl;

$R^x$ is hydrogen or substituted or unsubstituted alkyl;

$R^a$ is hydrogen or is joined with $R^c$ to form a substituted or unsubstituted bridged ring;

$R^b$ is hydrogen, substituted or unsubstituted alkyl, or $A(CR^1R^2)_n$—, or is joined with $R^c$ to form a substituted or unsubstituted bridged ring;

$R^c$ is hydrogen or substituted or unsubstituted alkyl or is joined with at least one of $R^a$ and $R^b$ to form a substituted or unsubstituted bridged ring; and each n is independently 0 or 1; provided the compound is not of formula:

115

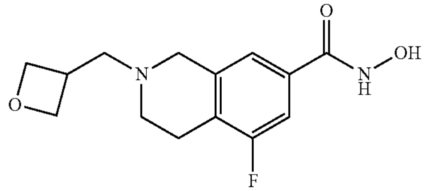

114

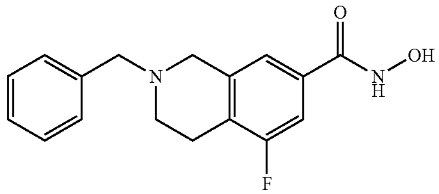

113

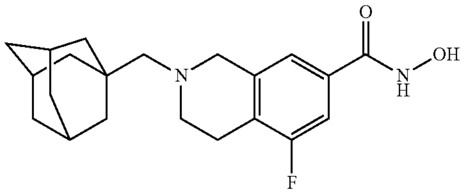

39

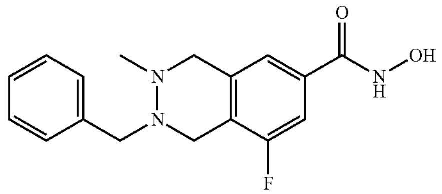

117

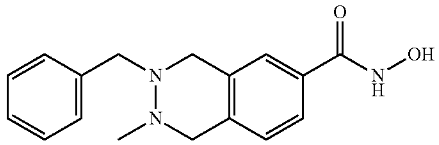

-continued

41

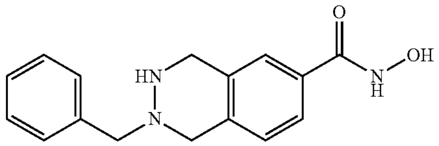

42

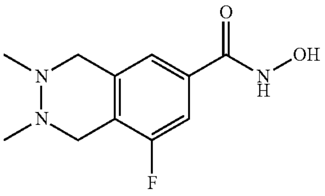

43

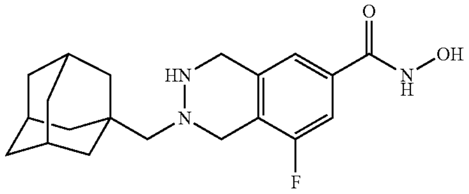

44

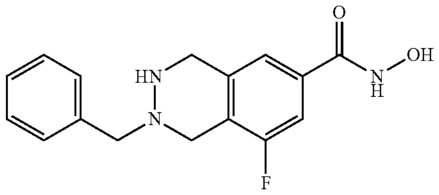

116

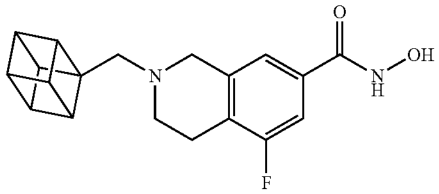

118

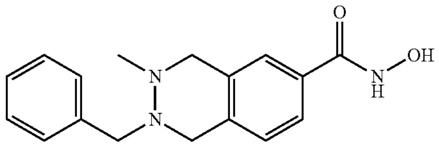

$X^1$ and $X^2$

As described herein, $X^1$ is hydrogen or fluoro; and $X^2$ is hydrogen or fluoro. In certain embodiments, $X^1$ is hydrogen or fluoro; and $X^2$ is hydrogen or fluoro; provided that at least one of $X^1$ and $X^2$ is fluoro. In certain embodiments, $X^1$ is hydrogen; and $X^2$ is fluoro. In certain embodiments, $X^1$ is fluoro; and $X^2$ is hydrogen. In certain embodiments, $X^1$ is hydrogen; and $X^2$ is hydrogen. In certain embodiments, $X^1$ is fluoro; and $X^2$ is fluoro.

$Y^1$

As described herein, $Y^1$ is nitrogen or CH. In certain embodiments, $Y^1$ is nitrogen. In certain embodiments, $Y^1$ is CH.

A

As described herein, each A is independently hydrogen, substituted or unsubstituted alkyl, substituted or unsubstituted carbocyclyl, substituted or unsubstituted heterocyclyl, substituted or unsubstituted heteroaryl, or substituted or unsubstituted aryl. In certain embodiments, A is substituted or unsubstituted alkyl, substituted or unsubstituted carbocyclyl, substituted or unsubstituted heterocyclyl, substituted or unsubstituted heteroaryl, or substituted or unsubstituted aryl.

In certain embodiments, A is unsubstituted $C_{1-4}$ alkyl, $C_{1-4}$ haloalkyl, substituted or unsubstituted cycloalkyl, substituted or unsubstituted heterocyclyl, substituted or unsubstituted heteroaryl, or substituted or unsubstituted aryl.

In certain embodiments, A is substituted or unsubstituted cycloalkyl, substituted or unsubstituted heterocyclyl, or substituted or unsubstituted aryl.

In certain embodiments, A is substituted or unsubstituted cycloalkyl. In certain embodiments, A is substituted or unsubstituted $C_{3-10}$ cycloalkyl. In certain embodiments, A is a substituted or unsubstituted $C_{5-10}$ bridged cycloalkyl, substituted or unsubstituted $C_{5-10}$ spirocyclic cycloalkyl, or substituted or unsubstituted $C_{3-8}$ monocyclic cycloalkyl. In certain embodiments, A is a substituted or unsubstituted $C_{5-10}$ bridged cycloalkyl. In certain embodiments, A is a substituted or unsubstituted $C_{5-10}$ spirocyclic cycloalkyl. In certain embodiments, A is a substituted or unsubstituted $C_{8-10}$ spirocyclic cycloalkyl. In certain embodiments, A is substituted or unsubstituted $C_{3-8}$ monocyclic cycloalkyl. In certain embodiments, A is substituted or unsubstituted $C_{3-6}$ monocyclic cycloalkyl.

In certain embodiments, A is cyclopropyl, cyclobutyl, cyclopentyl, cyclohexyl, adamantyl,

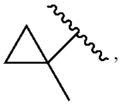, 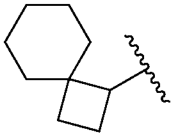, 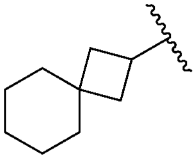, 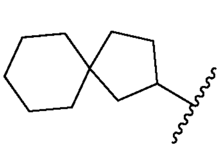, 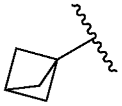, or 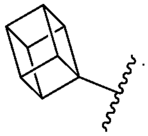.

In certain embodiments, A is adamantyl.

In certain embodiments, A is substituted or unsubstituted heterocyclyl. In certain embodiments, A is substituted or unsubstituted 4-10 membered heterocyclyl. In certain embodiments, A is substituted or unsubstituted monocyclic 4-7 membered heterocyclyl or substituted or unsubstituted 5-10 membered bridged heterocyclyl. In certain embodiments, A is substituted or unsubstituted monocyclic 4-7 membered heterocyclyl. In certain embodiments, A is substituted or unsubstituted monocyclic 4-6 membered heterocyclyl. In certain embodiments, A is substituted or unsubstituted monocyclic 4-5 membered heterocyclyl. In certain embodiments, A is substituted or unsubstituted monocyclic 5-6 membered heterocyclyl. In certain embodiments, A is substituted or unsubstituted 5-10 membered bridged heterocyclyl. In certain embodiments, A is substituted or unsubstituted 6-10 membered bridged heterocyclyl. In certain embodiments, A is substituted or unsubstituted 8-10 membered bridged heterocyclyl. In certain embodiments, A is substituted or unsubstituted 10-membered bridged heterocyclyl.

In certain embodiments, A is substituted or unsubstituted oxetanyl, substituted or unsubstituted tetrahydrofuranyl, substituted or unsubstituted pyranyl, substituted or unsubstituted dihydropyranyl, substituted or unsubstituted tetrahydropyranyl, substituted or unsubstituted dioxanyl, substituted or unsubstituted oxepanyl, substituted or unsubstituted azetidinyl, substituted or unsubstituted pyrrolidinyl, substituted or unsubstituted piperidinyl, substituted or unsubstituted piperazinyl, substituted or unsubstituted azepanyl, substituted or unsubstituted diazepanyl, substituted or unsubstituted morpholinyl, substituted or unsubstituted oxazepanyl, or oxaadamantanyl. In certain embodiments, A is tetrahydrofuranyl, oxetanyl, or

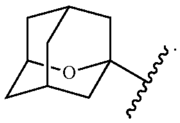 [SMILES: *C12CC3CC(CC(C3)O1)C2].

In certain embodiments, A is oxetanyl.

In certain embodiments, A is substituted or unsubstituted aryl. In certain embodiments, A is substituted or unsubstituted phenyl. In certain embodiments, A is unsubstituted phenyl. In certain embodiments, A is phenyl substituted with 1-5 substituents selected from halogen, cyano, alkyl, haloalkyl, alkenyl, alkynyl, alkoxy, haloalkoxy, or alkoxyalkyl. In certain embodiments, A is 2,6-dimethylphenyl.

In certain embodiments, A is hydrogen, unsubstituted $C_{1-4}$ alkyl, or $C_{1-4}$ haloalkyl. In certain embodiments, A is hydrogen or unsubstituted $C_{1-4}$ alkyl. In certain embodiments, A is unsubstituted $C_{1-4}$ alkyl or $C_{1-4}$ haloalkyl. In certain embodiments, A is unsubstituted $C_{1-4}$ alkyl. In certain embodiments, A is methyl, ethyl, n-propyl, isopropyl, n-butyl, sec-butyl, t-butyl, or isobutyl. In certain embodiments, A is t-butyl. In certain embodiments, A is $C_{1-4}$ haloalkyl. In certain embodiments, A is $—CF_3$, $—CHF_2$, or $—CH_2F$. In certain embodiments, A is $—CF_3$. In certain embodiments, A is $—CF_3$ or t-butyl. In certain embodiments, A is methyl or hydrogen. In certain embodiments, A is methyl or hydrogen, and n is 0. In certain embodiments, A is methyl. In certain embodiments, A is methyl, and n is 0. In certain embodiments, A is hydrogen. In certain embodiments, A is hydrogen, and n is 0.

In certain embodiments, A is unsubstituted $C_{1-4}$ alkyl, $C_{14}$ haloalkyl, substituted or unsubstituted $C_{8-10}$ spirocyclic cycloalkyl, substituted or unsubstituted $C_{3-6}$ monocyclic cycloalkyl, substituted or unsubstituted monocyclic 4-7 membered heterocyclyl, substituted or unsubstituted 8-10 membered bridged heterocyclyl, or substituted or unsubstituted phenyl.

In certain embodiments, A is $—CF_3$, $—C(CH_3)_3$, phenyl, 2,6-dimethylphenyl, tetrahydrofuranyl, oxetanyl, cyclopropyl, cyclobutyl, cyclopentyl, cyclohexyl, adamantyl,

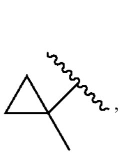, 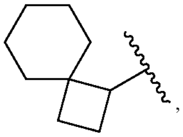, 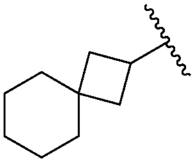, 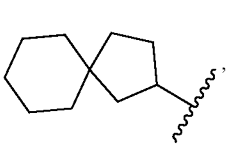, 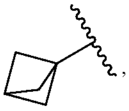, 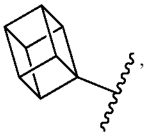, or -continued

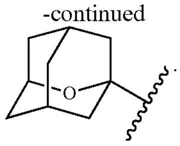

In certain embodiments, A is $—CF_3$, $—C(CH_3)_3$, phenyl, 2,6-dimethylphenyl, tetrahydrofuranyl, oxetanyl, cyclopropyl, cyclobutyl, cyclopentyl, cyclohexyl, adamant 1

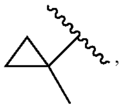, 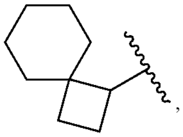, 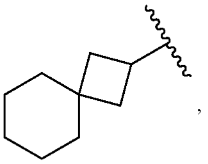,

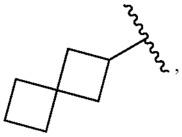, 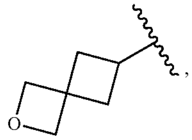,

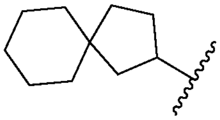, 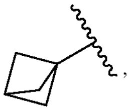, 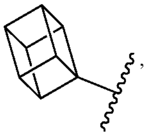 [SMILES: *C12C3C4C5C3C1C5C42], or

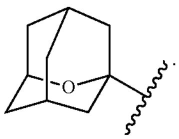

In certain embodiments, A is phenyl, oxetanyl, or adamantyl. In certain embodiments, A is

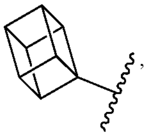, phenyl, oxetanyl, or adamantyl.

In certain embodiments, A is $C_{1-4}$ alkyl; $Y^1$ is $NR^b$ and $R^b$ is a 7-11 membered bicyclic spirocyclic heterocyclyl; a $C_{7-11}$ substituted or unsubstituted bicyclic spirocyclic carbocyclyl; or $C_{1-4}$ alkyl substituted with a 4-10 membered bridged heterocyclyl or a $C_{4-10}$ membered bridged cycloalkyl.

In certain embodiments, A is methyl and $R^b$ is

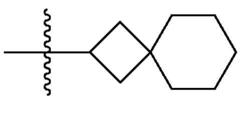 or 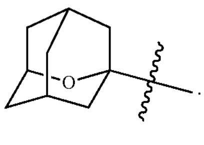.

In certain embodiments, A is a substituted or unsubstituted 7-11 membered bicyclic spirocyclic heterocyclyl; or a substituted or unsubstituted $C_{7-11}$ substituted or unsubstituted bicyclic spirocyclic carbocyclyl.

In certain embodiments, n is 0, A is

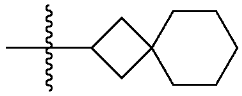

and $R^b$ is methyl.

In certain embodiments, A is a substituted or unsubstituted 4-7 membered heterocyclyl ring or $C_{1-4}$ alkyl; $R^b$ is benzyl; and $R^x$ is hydrogen.

In certain embodiments, n is 1 and A is

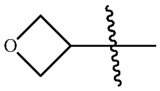;

or n is 0 and A is methyl. In certain embodiments, n is 1 and A is

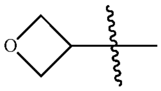.

In certain embodiments, n is 0 and A is methyl.

In certain embodiments, A is a substituted or unsubstituted 4-10 membered bridged heterocyclyl, a substituted or unsubstituted 4-6 membered heterocyclyl, or a substituted or unsubstituted $C_{4-10}$ membered bridged cycloalkyl. In certain embodiments, A is a substituted or unsubstituted 4-10 membered bridged heterocyclyl or a substituted or unsubstituted 4-6 membered heterocyclyl.

In certain embodiments, A is 4 or

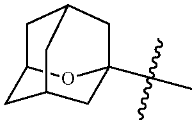 or 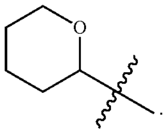.

In certain embodiments, n is 0 and A is $C_{1-4}$ alkyl.

In certain embodiments, A is substituted or unsubstituted $C_{3-6}$ carbocyclyl; or substituted or unsubstituted 4-6 membered heterocyclyl.

In certain embodiments, A is

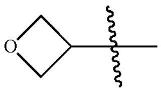.

In certain embodiments, A is a 7-11 membered bicyclic spirocyclic heterocyclyl, or a $C_{7-11}$ substituted or unsubstituted bicyclic spirocyclic carbocyclyl; wherein A is optionally substituted with $(C_1-C_4)$alkyl or $(C_3-C_6)$cycloalkyl. In certain embodiments, A is optionally substituted with methyl or cyclopropyl.

In certain embodiments, A is

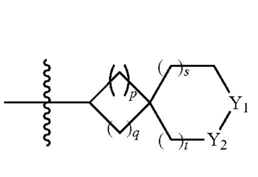

or

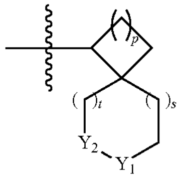

wherein: p and q are each independently 1 or 2; s and t are each independently 0, 1, or 2, provided that the sum of s and t is 0, 1, or 2; $Y_1$ and $Y_2$ are each independently selected from S(=O), $CR_{s1}R_{s2}$, $NR_s$ and O, provided that at least one of $Y_1$ and $Y_2$ is $CR_{s1}R_{s2}$; $R_{s1}$ and $R_{s2}$ are each independently hydrogen, or ($C_1$-$C_4$)alkyl optionally substituted with one or more halogen; and $R_s$ is hydrogen, ($C_1$-$C_4$)alkyl optionally substituted with one or more halogen, acyl, ($C_3$-$C_6$)cycloalkyl or 3- to 6-member heterocycloalkyl comprising one or more heteroatoms selected from the group consisting of O and N.

In certain embodiments A is

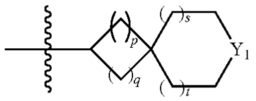

wherein: p and q are each independently 1 or 2; s and t are each independently 0 or 1; $Y_1$ is selected from $CH_2$, O, and $NR_s$, where $R_s$ is hydrogen, methyl or cyclopropyl.

In certain embodiments, A is

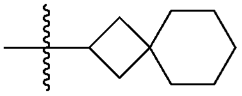 [SMILES: *C1CC2(CCCCC2)C1],
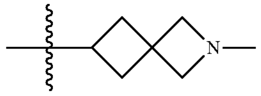,
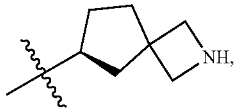
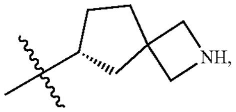
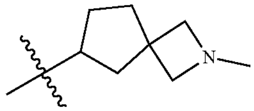,
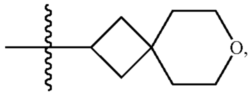
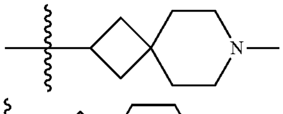,
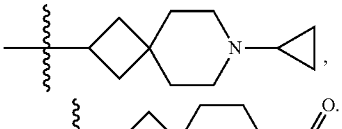, or
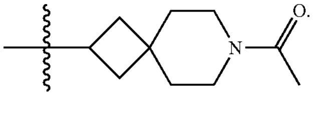

In certain embodiments, A is 4-6 membered heterocyclyl, or a $C_{3-6}$ carbocyclyl; wherein A is optionally substituted with ($C_1$-$C_4$)alkyl.

In certain embodiments, A is cyclobutyl, cyclopentyl or cyclohexyl optionally substituted with one or more methyl.

In certain embodiments, A is

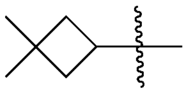

or

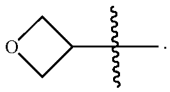.

In certain embodiments, A is adamantyl or a 10-membered bridged heterocyclyl comprising an oxygen or nitrogen heteroatom and optionally substituted with one or more fluoro.

In certain embodiments, A is

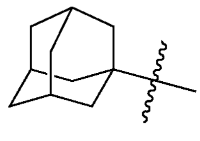,
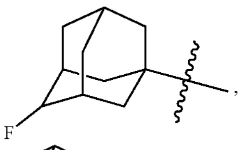,
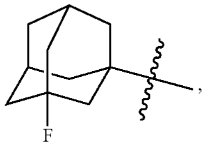,
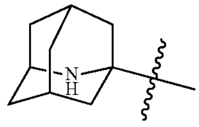, or
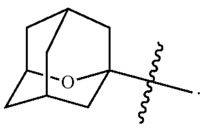.

In certain embodiments, A is

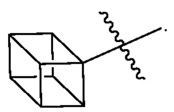 [SMILES: *C12C3C4C5C3C1C5C42].

In certain embodiments, A is a 4-10 membered bridged, spirocyclic or fused bicyclic heterocyclyl comprising one or more heteroatoms selected from N and O, optionally substituted with ($C_1$-$C_4$)alkyl, halogen, oxo, ($C_3$-$C_6$)cycloalkyl, acyl, and amino optionally substituted with one or more methyl, acyl or cyclopropyl.

In certain embodiments, A is a 4-membered bridged carbocyclic optionally substituted with amino, the amino optionally further substituted with one or more methyl or cyclopropyl.

In certain embodiments, A is

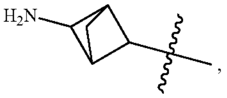,
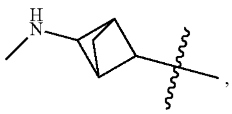,
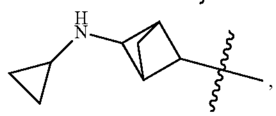, or

-continued

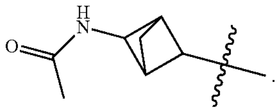.

In certain embodiments, A is a 5-membered bridged carbocyclic or 6-member heterocyclyl comprising an oxygen heteroatom, each optionally substituted with amino, the amino optionally further substituted with one or more methyl or cyclopropyl.

In certain embodiments, A is

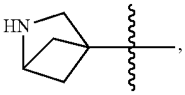,

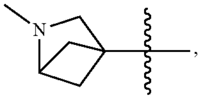,

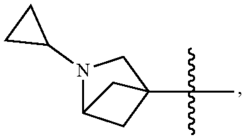, or

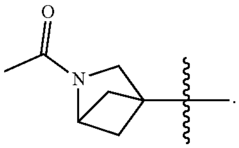.

In certain embodiments, A is a 6-8 membered bridged carbocyclic or 6-8 membered heterocyclyl comprising one or more of an oxygen and a nitrogen heteroatom, each optionally substituted with one or more of an oxo, and an amino wherein the amino is optionally further substituted with one or more methyl or cyclopropyl.

In certain embodiments, A is

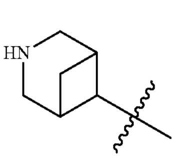, 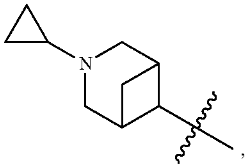,

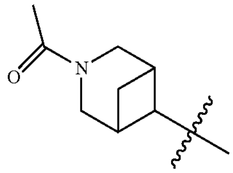, 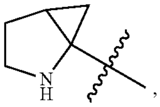,

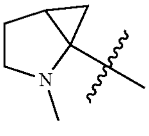, 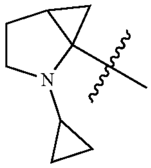, 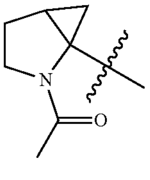

-continued

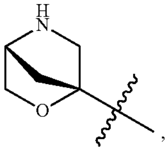, 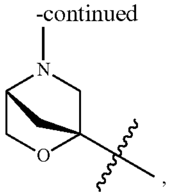, 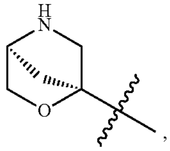,

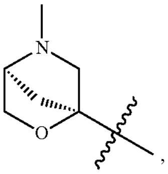, 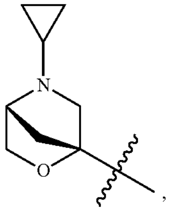, 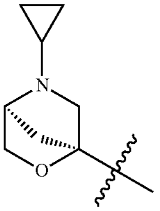,

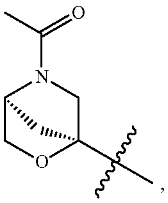, 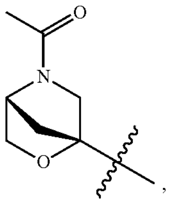, 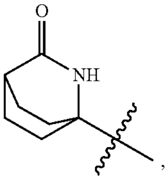,

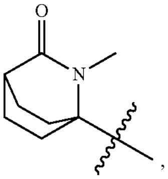, 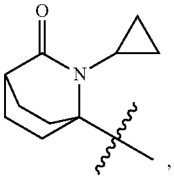, 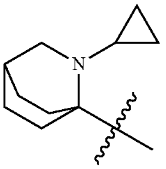,

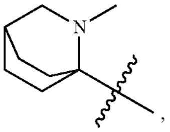, 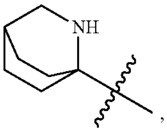, 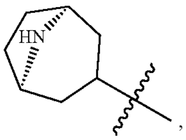,

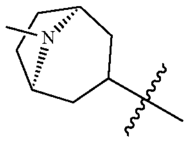, 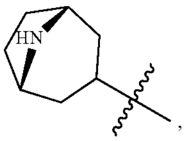,

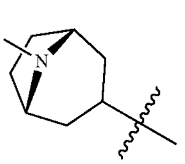, 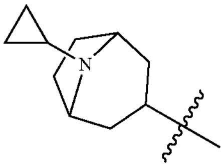, or

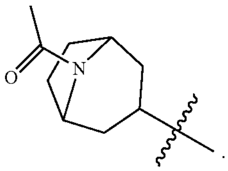.

In certain embodiments, A is

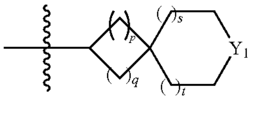

wherein: p and q are each independently 1 or 2; s and t are each independently 0 or 1; $Y_1$ is selected from $CH_2$, O and $NR_s$, where $R_s$ is hydrogen, methyl or cyclopropyl.

In certain embodiments, A is

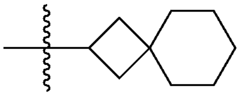
,

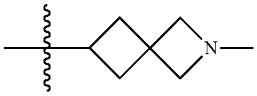
,

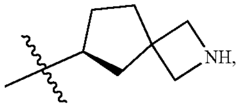
,

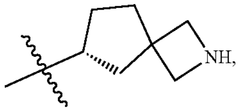
,

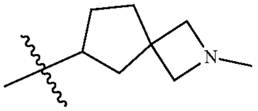
,

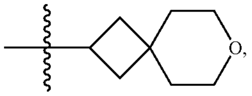
,

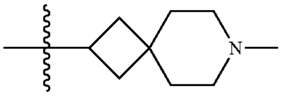
,

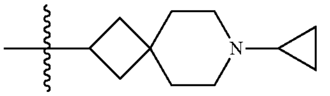
, or

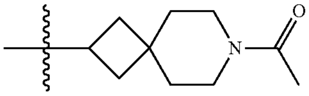
.

In certain embodiments, A is

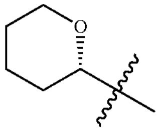
or
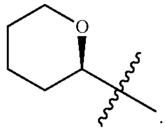
.

In certain embodiments, A is a substituted or unsubstituted spirocyclic heterocyclyl, or a substituted or unsubstituted spirocyclic carbocyclyl. In certain embodiments, A is a substituted or unsubstituted 7-11 membered bicyclic spirocyclic carbocyclyl.

In certain embodiments, A is

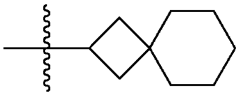
.

In certain embodiments, A is

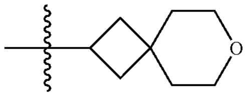
or

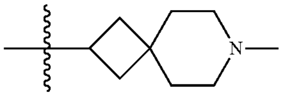
.

In certain embodiments, A is a substituted or unsubstituted $C_{5-10}$ bridged cycloalkyl, or a substituted or unsubstituted $C_{5-10}$ bridged heterocycloalkyl. In certain embodiments, A is a substituted or unsubstituted $C_{5-10}$ bridged heterocycloalkyl. In certain embodiments, A is a substituted or unsubstituted $C_{5-10}$ bridged cycloalkyl. In certain embodiments, A is adamantyl.

In certain embodiments, A is a substituted or unsubstituted 4-10 membered bridged heterocyclyl, a substituted or unsubstituted 4-6 membered heterocyclyl, a substituted or unsubstituted a 7-11 membered spirocyclic heterocyclyl, or a substituted or unsubstituted $C_{7-11}$ bicyclic spirocyclic carbocyclyl.

In certain embodiments, A is a substituted or unsubstituted 6-10 membered bridged heterocyclyl, a substituted or unsubstituted 6-membered heterocyclyl, a substituted or unsubstituted 9-membered spirocyclic heterocyclyl, or a substituted or unsubstituted $C_9$ bicyclic spirocyclic carbocyclyl.

In certain embodiments, A is a 6-10 membered bridged heterocyclyl, a 6-membered heterocyclyl, a 9-membered spirocyclic heterocyclyl, or a $C_9$ bicyclic spirocyclic carbocyclyl; wherein each is unsubstituted or substituted with a $C_{1-4}$ alkyl.

In certain embodiments, A is a 6-10 membered bridged heterocyclyl, a 6-membered heterocyclyl having at least one oxygen atom in the ring, a 9-membered spirocyclic heterocyclyl, or a $C_9$ bicyclic spirocyclic carbocyclyl; wherein each is unsubstituted or substituted with a $C_{1-4}$ alkyl.

In certain embodiments, A is

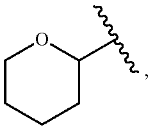
,

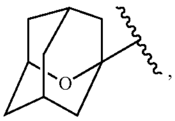
,

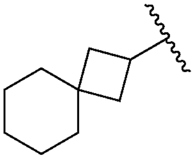
,

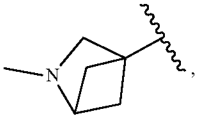
,

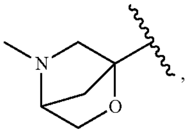
,

-continued

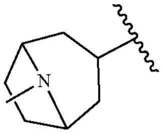

, or

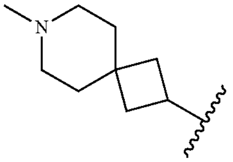

.

In certain embodiments, A is

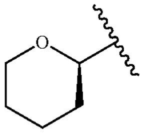

,

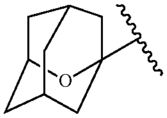

,

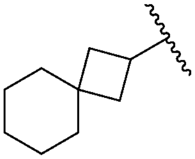

,

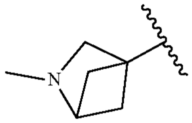

,

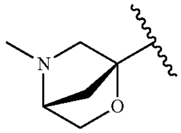

,

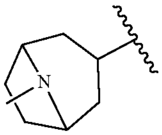

,

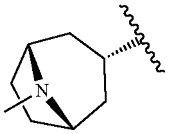

,

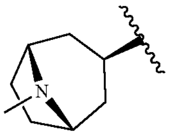

, or

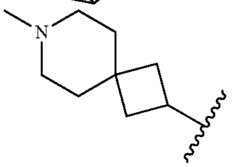

.

In certain embodiments, A is not one or more of the following: unsubstituted or substituted $C_{1-6}$ aliphatic, unsubstituted or substituted 3-10-membered cycloaliphatic, unsubstituted or substituted 4-10-membered heterocyclyl having 1-4 heteroatoms independently selected from nitrogen, oxygen, and sulfur, unsubstituted or substituted 6-10-membered aryl, or unsubstituted or substituted 5-10-membered heteroaryl having 1-4 heteroatoms independently selected from nitrogen, oxygen, and sulfur.

In certain embodiments, A is not one or more of the following: methyl, ethyl, propyl, isopropyl, tert-butyl, butyl, iso-butyl, pentyl, hexyl, butenyl, propenyl, pentenyl, hexenyl, furanyl, thienyl, pyrrolyl, oxazolyl, thiazolyl, imidazolyl, pyrazolyl, isoxazolyl, isothiazolyl, oxadiazolyl, triazolyl, thiadiazolyl, phenyl, naphthyl, pyranyl, pyridyl, pyridazinyl, pyrimidinyl, pyrazinyl, triazinyl, indolizinyl, indolyl, isoindolyl, indazolyl, benzimidazolyl, benzthiazolyl, benzothienyl, benzofuranyl, benzoxazolyl, benzo[c][1,2,5]oxadiazolyl, benzo[c][1,2,5]thiadiazolyl, benzo[d]oxazol-2(3H)-one, 2,3-dihydrobenzo[b][1,4]dioxinyl, benzo[d][1,3]dioxolyl, 2,3-dihydrobenzofuranyl, 4H-furo[3,2-b]pyrrolyl, purinyl, quinolyl, isoquinolyl, tetrahydroquinolinyl, tetrahydroisoquinolinyl, cinnolinyl, phthalazinyl, quinazolinyl, quinoxalinyl, naphthyridinyl, pteridinyl, imidazopyridyl, benzodioxolyl, benzthiadiazolyl, pyrazolopyrimidinyl, tetrahydronaphthyridinyl, tetrahydrofuranyl, tetrahydropyranyl, tetrahydrothienyl, indanyl, tetrahydroindazolyl, pyrrolidinyl, pyrrolidonyl, piperidinyl, pyrrolinyl, decahydroquinolinyl, oxazolidinyl, piperazinyl, dioxanyl, diazepinyl, oxazepinyl, thiazepinyl, morpholinyl, thiomoφholinyl, quinuclidinyl, phenanthridinyl, tetrahydronaphthyl, indolinyl, benzodioxanyl, chromanyl, cyclopropyl, cyclobutyl, cyclopentyl, cyclohexyl, cycloheptyl, cyclooctyl, cyclopentenyl, cyclohexenyl, cycloheptenyl, cyclooctenyl, bicycloheptanyl, bicyclooctanyl, or adamantyl, wherein each of the foregoing groups are unsubstituted or substituted.

In certain embodiments, A is not one or more of the following:

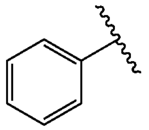

,

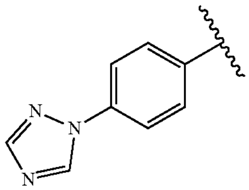

,

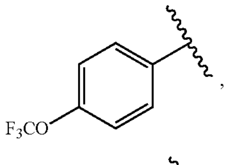

,

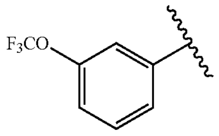

,

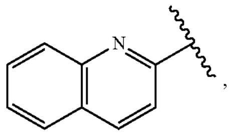

,

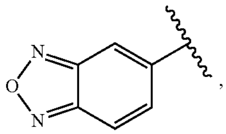

,

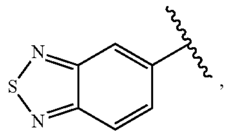

,

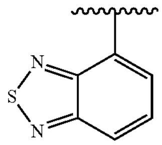

,

-continued

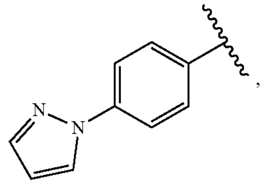,
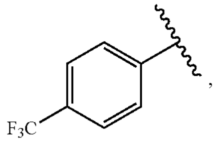,
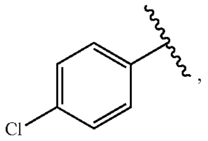,
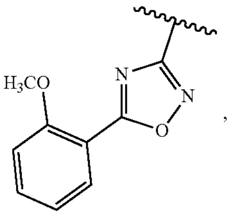,
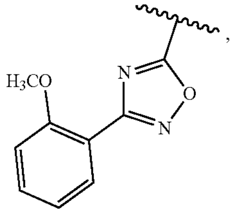,
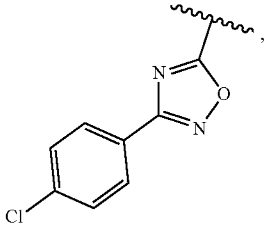,
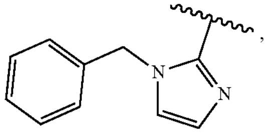,
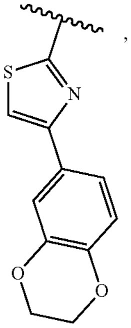,
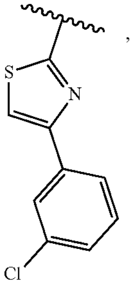,
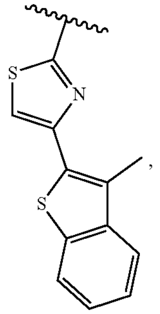,
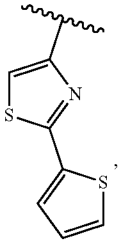,
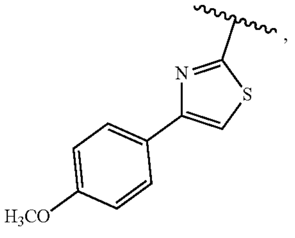,
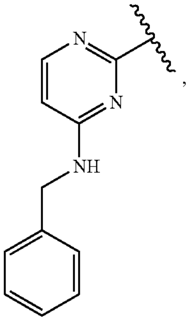, -continued

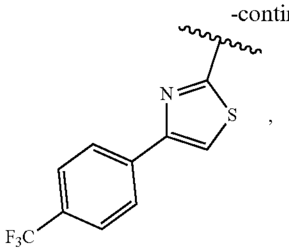,
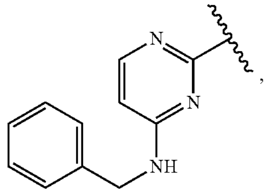,
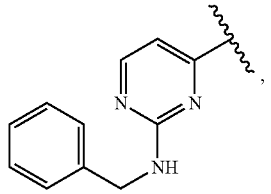,
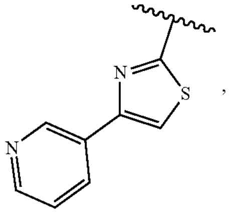,
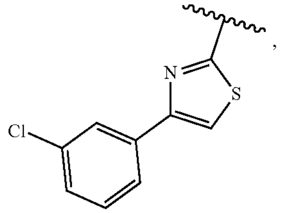, or
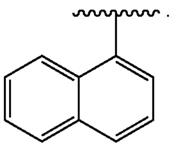.

In certain embodiments, A is not a 6-membered aromatic ring containing 0-2 nitrogen atoms which is unsubstituted or substituted with 1-2 independent occurrences of chloro, fluoro, cyano, hydroxy, methoxy, ethoxy, trifluoromethoxy, trifluoromethyl, methyl, or ethyl; wherein the 6-membered aromatic ring is substituted with a substituted or unsubstituted 4-7 membered heterocyclic ring containing one nitrogen atom.

In certain embodiments, A is not a phenyl or pyridyl unsubstituted or substituted with 1-2 independent occurrences of chloro, fluoro, cyano, hydroxy, methoxy, ethoxy, trifluoromethoxy, trifluoromethyl, methyl, or ethyl; wherein the phenyl or pyridyl is substituted with a substituted or unsubstituted 4-7 membered heterocyclic ring containing one nitrogen atom.

In certain embodiments, A is not a phenyl or pyridyl unsubstituted or substituted with 1-2 independent occurrences of chloro, fluoro, cyano, hydroxy, methoxy, ethoxy, trifluoromethoxy, trifluoromethyl, methyl, or ethyl; wherein the phenyl or pyridyl is substituted with a substituted or unsubstituted pyrrolidinyl or substituted or unsubstituted piperidinyl. In certain embodiments, A is not a phenyl or pyridyl unsubstituted or substituted with 1-2 independent occurrences of chloro, fluoro, cyano, hydroxy, methoxy, ethoxy, trifluoromethoxy, trifluoromethyl, methyl, or ethyl; wherein the phenyl or pyridyl is substituted with a substituted or unsubstituted pyrrolidinyl. In certain embodiments, A is not a phenyl or pyridyl unsubstituted or substituted with 1-2 independent occurrences of chloro, fluoro, cyano, hydroxy, methoxy, ethoxy, trifluoromethoxy, trifluoromethyl, methyl, or ethyl; wherein the phenyl or pyridyl is substituted with a substituted or unsubstituted piperidinyl.

In certain embodiments, A is not a substituted or unsubstituted 4-7 membered heterocyclic ring containing one nitrogen atom.

In certain embodiments, A is not a substituted or unsubstituted piperidinyl. In certain embodiments, A is not a substituted or unsubstituted pyrrolidinyl. In certain embodiments, A is not a substituted or unsubstituted pyrrolidinyl or substituted or unsubstituted piperidinyl.

In certain embodiments, A is not one or more of the following:

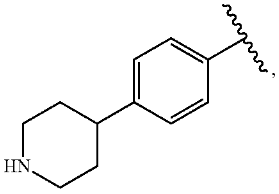
,

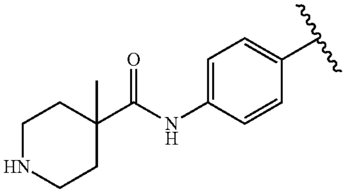
,

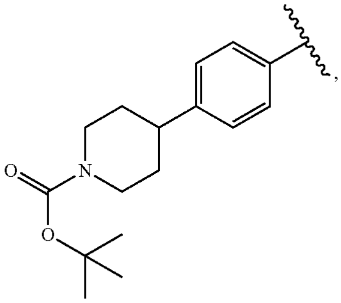
,

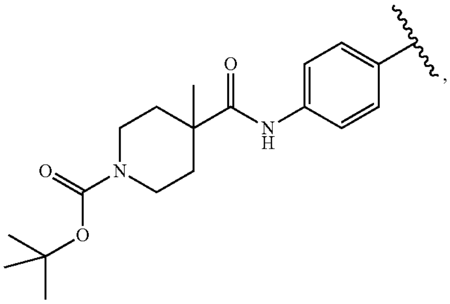
,

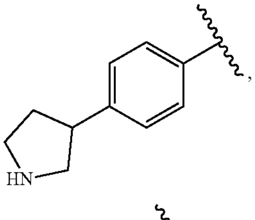
,

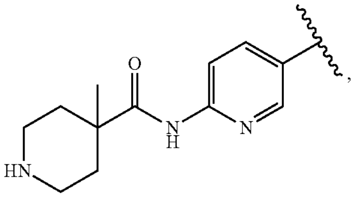
,

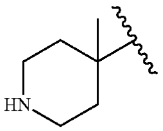
,

-continued

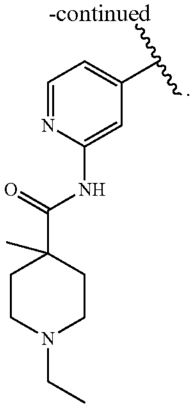
.

R$^1$ and R$^2$

As described herein, each R$^1$ is independently hydrogen or substituted or unsubstituted alkyl; and each R$^2$ is independently hydrogen or substituted or unsubstituted alkyl; or R$^1$ and R$^2$ together form a substituted or unsubstituted heterocyclyl, or a substituted or unsubstituted cycloalkyl.

In certain embodiments, R$^1$ is hydrogen; and R$^2$ is unsubstituted $C_{1-4}$ alkyl; or R$^1$ and R$^2$ together form an unsubstituted cycloalkyl. In certain embodiments, R$^1$ is hydrogen; and R$^2$ is unsubstituted $C_{1-4}$ alkyl; or R$^1$ and R$^2$ together form an unsubstituted $C_{3-6}$ cycloalkyl. In certain embodiments, R$^1$ is hydrogen; and R$^2$ is methyl or ethyl; or R$^1$ and R$^2$ together form an unsubstituted $C_{3-6}$ cycloalkyl. In certain embodiments, R$^1$ is hydrogen; and R$^2$ is methyl or ethyl; or R$^1$ and R$^2$ together form an unsubstituted cyclobutyl. In certain embodiments, R$^1$ is hydrogen; and R$^2$ is unsubstituted $C_{1-4}$ alkyl. In certain embodiments, R$^1$ is hydrogen; and R$^2$ is methyl or ethyl. In certain embodiments, R$^1$ is hydrogen; and R$^2$ is methyl. In certain embodiments, R$^1$ is hydrogen; and R$^2$ is ethyl.

In certain embodiments, R$^1$ is unsubstituted $C_{1-4}$ alkyl; and R$^2$ is hydrogen; or R$^1$ and R$^2$ together form an unsubstituted cycloalkyl. In certain embodiments, R$^1$ is unsubstituted $C_{1-4}$ alkyl; and R$^2$ is hydrogen; or R$^1$ and R$^2$ together form an unsubstituted $C_{3-6}$ cycloalkyl. In certain embodiments, R$^1$ is methyl or ethyl; and R$^2$ is hydrogen; or R$^1$ and R$^2$ together form an unsubstituted $C_{3-6}$ cycloalkyl. In certain embodiments, R$^1$ is methyl or ethyl; and R$^2$ is hydrogen; or R$^1$ and R$^2$ together form an unsubstituted cyclobutyl.

In certain embodiments, R$^1$ is unsubstituted $C_{1-4}$ alkyl; and R$^2$ is hydrogen. In certain embodiments, R$^1$ is methyl or ethyl; and R$^2$ is hydrogen. In certain embodiments, R$^1$ is methyl; and R$^2$ is hydrogen. In certain embodiments, R$^1$ is ethyl; and R$^2$ is hydrogen.

In certain embodiments, R$^1$ is hydrogen; and R$^2$ is unsubstituted $C_{1-4}$ alkyl. In certain embodiments, R$^1$ is hydrogen; and R$^2$ is methyl or ethyl. In certain embodiments, R$^1$ is hydrogen; and R$^2$ is methyl. In certain embodiments, R$^1$ is hydrogen; and R$^2$ is ethyl.

In certain embodiments, R$^1$ and R$^2$ together form a substituted or unsubstituted cycloalkyl. In certain embodiments, R$^1$ and R$^2$ together form an unsubstituted cycloalkyl. In certain embodiments, R$^1$ and R$^2$ together form an unsubstituted $C_{3-6}$ cycloalkyl. In certain embodiments, R$^1$ and R$^2$ together form an unsubstituted cyclopropyl. In certain embodiments, R$^1$ and R$^2$ together form an unsubstituted cyclobutyl. In certain embodiments, R$^1$ and R$^2$ together form an unsubstituted cyclopentyl. In certain embodiments, R$^1$ and R$^2$ together form an unsubstituted cyclohexyl.

In certain embodiments, $R^1$ is hydrogen; and $R^2$ is hydrogen.

$R^a$, $R^b$, $R^c$, $R^x$, and n

As described herein, $R^x$ is hydrogen or substituted or unsubstituted alkyl; $R^a$ is hydrogen or is joined with $R^c$ to form a substituted or unsubstituted bridged ring; $R^b$ is hydrogen, substituted or unsubstituted alkyl, or $A(CR^1R^2)_n$—, or is joined with $R^c$ to form a substituted or unsubstituted bridged ring; and $R^c$ is hydrogen or substituted or unsubstituted alkyl or is joined with at least one of $R^a$ and $R^b$ to form a substituted or unsubstituted bridged ring.

In certain embodiments, $R^x$ is hydrogen. In certain embodiments, $R^x$ is substituted or unsubstituted alkyl. In certain embodiments, $R^x$ is substituted or unsubstituted $C_{1-6}$ alkyl. In certain embodiments, $R^x$ is substituted or unsubstituted $C_{1-4}$ alkyl. In certain embodiments, $R^x$ is substituted or unsubstituted $C_{1-3}$ alkyl. In certain embodiments, $R^x$ is substituted alkyl. In certain embodiments, $R^x$ is substituted $C_{1-6}$ alkyl. In certain embodiments, $R^x$ is substituted $C_{1-4}$ alkyl. In certain embodiments, $R^x$ is substituted $C_{1-3}$ alkyl. In certain embodiments, $R^x$ is unsubstituted alkyl. In certain embodiments, $R^x$ is unsubstituted $C_{1-6}$ alkyl. In certain embodiments, $R^x$ is unsubstituted $C_{1-4}$ alkyl. In certain embodiments, $R^x$ is unsubstituted $C_{1-3}$ alkyl.

In certain embodiments, $R^a$ is joined with $R^c$ to form a substituted or unsubstituted bridged ring. In certain embodiments, $R^a$ is joined with $R^c$ to form a substituted or unsubstituted bridged ring; and $R^b$ is hydrogen. In certain embodiments, $R^a$ is joined with $R^c$ to form an unsubstituted bridged ring; and $R^b$ is hydrogen. In certain embodiments, $R^a$ is joined with $R^c$ to form an unsubstituted carbocyclic bridged ring; and $R^b$ is hydrogen. In certain embodiments, $R^a$ is joined with $R^c$ to form an unsubstituted heterocyclic bridged ring; and $R^b$ is hydrogen.

In certain embodiments, $R^b$ is hydrogen. In certain embodiments, $R^b$ is substituted or unsubstituted alkyl. In certain embodiments, $R^b$ is unsubstituted alkyl. In certain embodiments, $R^b$ is unsubstituted $C_{1-4}$ alkyl. In certain embodiments, $R^b$ is $A(CR^1R^2)_n$—, and n is 1. In certain embodiments, $R^b$ is $A(CR^1R^2)_n$—, and n is 0. In certain embodiments, $R^b$ is joined with $R^c$ to form a substituted or unsubstituted bridged ring. In certain embodiments, $R^b$ is joined with $R^c$ to form a substituted or unsubstituted bridged ring; and $R^a$ is hydrogen. In certain embodiments, $R^b$ is joined with $R^c$ to form an unsubstituted bridged ring; and $R^a$ is hydrogen. In certain embodiments, $R^b$ is joined with $R^c$ to form an unsubstituted carbocyclic bridged ring; and $R^a$ is hydrogen. In certain embodiments, $R^b$ is joined with $R^c$ to form an unsubstituted heterocyclic bridged ring; and $R^a$ is hydrogen.

In certain embodiments, $R^a$ is hydrogen; $R^b$ is hydrogen; and $R^c$ is hydrogen or substituted or unsubstituted alkyl. In certain embodiments, $R^a$ is hydrogen; $R^b$ is hydrogen; and $R^c$ is hydrogen or unsubstituted alkyl. In certain embodiments, $R^a$ is hydrogen; $R^b$ is hydrogen; and $R^c$ is hydrogen or unsubstituted $C_{1-4}$ alkyl. In certain embodiments, $R^a$ is hydrogen; $R^b$ is hydrogen; and $R^c$ is hydrogen. In certain embodiments, $R^a$ is hydrogen; $R^b$ is hydrogen; and $R^c$ is unsubstituted $C_{1-4}$ alkyl.

In certain embodiments, n is 0. In certain embodiments, n is 1.

Certain Embodiments

In certain embodiments, the compound of Formula (II) is of Formula (II-a):

(II-a)

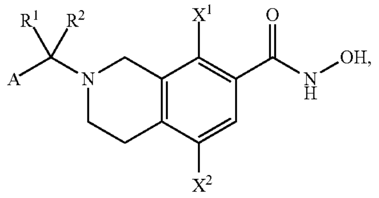

or a pharmaceutically acceptable salt, co-crystal, tautomer, stereoisomer, solvate, hydrate, polymorph, isotopically enriched derivative, or prodrug thereof; wherein A, $R^1$, $R^2$, $X^1$, and $X^2$ are as defined herein.

In certain embodiments, the compound of Formula (II) is of Formula (II-b):

(II-b)

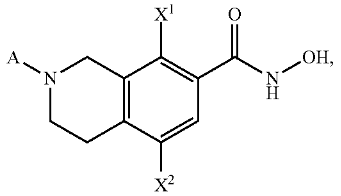

or a pharmaceutically acceptable salt, co-crystal, tautomer, stereoisomer, solvate, hydrate, polymorph, isotopically enriched derivative, or prodrug thereof; wherein A, $X^1$, and $X^2$ are as defined herein.

In certain embodiments, the compound of Formula (II) is of Formula (II-c):

(II-c)

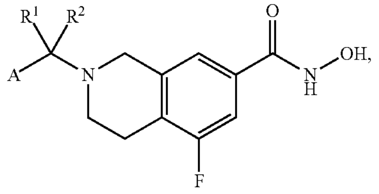

or a pharmaceutically acceptable salt, co-crystal, tautomer, stereoisomer, solvate, hydrate, polymorph, isotopically enriched derivative, or prodrug thereof; wherein A, $R^1$, and $R^2$ are as defined herein.

In certain embodiments, the compound of Formula (II) is of Formula (II-d):

(II-d)

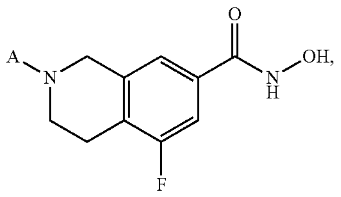

or a pharmaceutically acceptable salt, co-crystal, tautomer, stereoisomer, solvate, hydrate, polymorph, isotopically enriched derivative, or prodrug thereof; wherein A is as defined herein.

In certain embodiments, the compound of Formula (II) is of Formula (II-e):

(II-e)

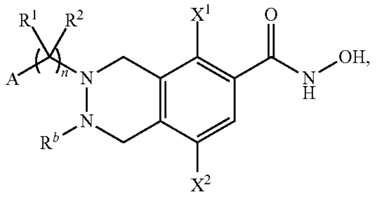

or a pharmaceutically acceptable salt, co-crystal, tautomer, stereoisomer, solvate, hydrate, polymorph, isotopically enriched derivative, or prodrug thereof; wherein A, $R^1$, $R^2$, $X^1$, $X^2$, $R^b$, and n are as defined herein.

In certain embodiments of the compound of Formula (II-e), $R^b$ is hydrogen or unsubstituted alkyl. In certain embodiments of the compound of Formula (II-e), $R^b$ is hydrogen. In certain embodiments of the compound of Formula (II-e), $R^b$ is methyl.

In certain embodiments, the compound of Formula (II-e) is of Formula (II-e-1):

(II-e-1)

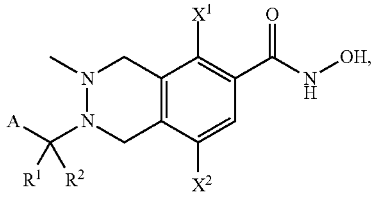

or a pharmaceutically acceptable salt, co-crystal, tautomer, stereoisomer, solvate, hydrate, polymorph, isotopically enriched derivative, or prodrug thereof; wherein A, $R^1$, $R^2$, $X^1$, and $X^2$ are as defined herein.

In certain embodiments, the compound of Formula (II-e) is of Formula (II-e-2):

(II-e-2)

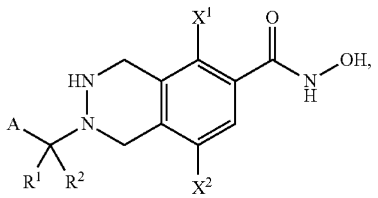

or a pharmaceutically acceptable salt, co-crystal, tautomer, stereoisomer, solvate, hydrate, polymorph, isotopically enriched derivative, or prodrug thereof; wherein A, $R^1$, $R^2$, $X^1$, and $X^2$ are as defined herein.

In certain embodiments, the compound of Formula (II) is of Formula (I-f):

(II-f)

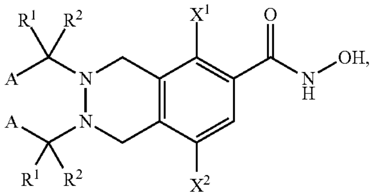

or a pharmaceutically acceptable salt, co-crystal, tautomer, stereoisomer, solvate, hydrate, polymorph, isotopically enriched derivative, or prodrug thereof; wherein A, $R^1$, $R^2$, $X^1$, and $X^2$ are as defined herein.

In certain embodiments, the compound of Formula (H) is of Formula (II-g):

(II-g)

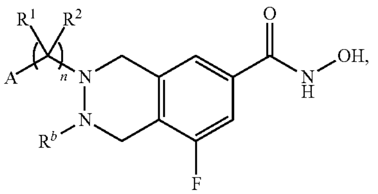

or a pharmaceutically acceptable salt, co-crystal, tautomer, stereoisomer, solvate, hydrate, polymorph, isotopically enriched derivative, or prodrug thereof; wherein A, $R^1$, $R^2$, $R^b$, and n are as defined herein.

In certain embodiments of the compound of Formula (II-g), $R^b$ is hydrogen or unsubstituted alkyl. In certain embodiments of the compound of Formula (II-g), $R^b$ is hydrogen. In certain embodiments of the compound of Formula (II-g), $R^b$ is methyl.

In certain embodiments, the compound of Formula (II-g) is of Formula (II-g-1):

(II-g-1)

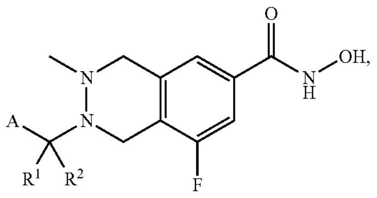

or a pharmaceutically acceptable salt, co-crystal, tautomer, stereoisomer, solvate, hydrate, polymorph, isotopically enriched derivative, or prodrug thereof; wherein A, $R^1$, and $R^2$ are as defined herein.

In certain embodiments, the compound of Formula (II-g) is of Formula (II-g-2):

(II-g-2)

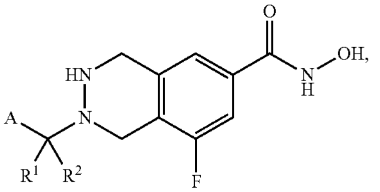

or a pharmaceutically acceptable salt, co-crystal, tautomer, stereoisomer, solvate, hydrate, polymorph, isotopically enriched derivative, or prodrug thereof; wherein A, $R^1$, and $R^2$ are as defined herein.

In certain embodiments, the compound of Formula (II) is of Formula (II-h):

(II-h)

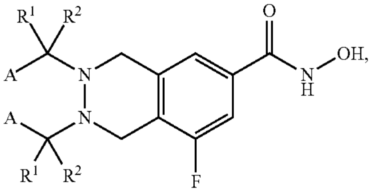

or a pharmaceutically acceptable salt, co-crystal, tautomer, stereoisomer, solvate, hydrate, polymorph, isotopically enriched derivative, or prodrug thereof; wherein A, $R^1$, and $R^2$ are as defined herein.

In certain embodiments the compound of Formula II) is of Formula (I-i):

(II-i)

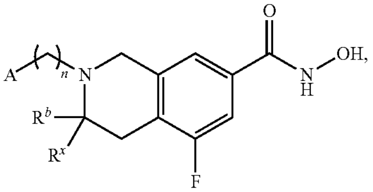

or a pharmaceutically acceptable salt, co-crystal, tautomer, stereoisomer, solvate, hydrate, polymorph, isotopically enriched derivative, or prodrug thereof; wherein:

A is substituted or unsubstituted carbocyclyl, or substituted or unsubstituted heterocyclyl;

n is 0 or 1; and $R^b$ and $R^x$ are each independently hydrogen or substituted or unsubstituted alkyl; provided that at least one of $R^b$ and $R^x$ is not hydrogen.

In certain embodiments of the compounds of Formula (II-i), A is cyclopropyl, cyclobutyl,

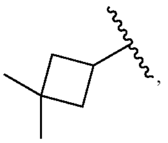 [SMILES: *C1CC(C)(C)C1]

, oxetanyl,

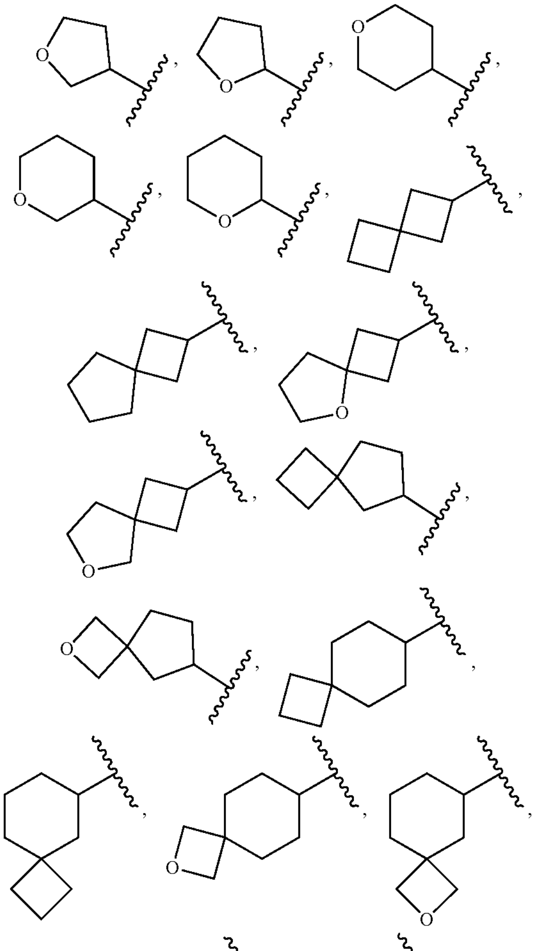

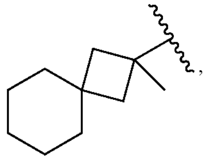

, or

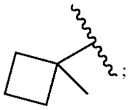

;

and $R^b$ and $R^x$ are each independently hydrogen, methyl, ethyl, propyl, isopropyl, t-butyl, cyclopropyl,

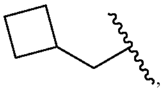

,

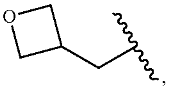

, benzyl,

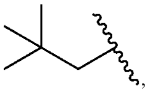

, or

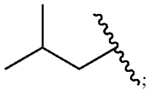

;

provided that at least one of $R^b$ and $R^x$ is not hydrogen.

In certain embodiments of the compounds of Formula (II-i), A is

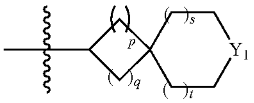

wherein: p and q are each independently 1 or 2; s and t are each independently 0 or 1; $Y_1$ is selected from $CH_2$, O, and $NR_s$, where $R_s$ is hydrogen, methyl or cyclopropyl; and $R^b$ and $R^x$ are each independently hydrogen, methyl, or ethyl; provided that at least one of $R^b$ and $R^x$ is not hydrogen.

In certain embodiments of Formula (II-i), A is a substituted or unsubstituted 4-10 membered bridged heterocyclyl, a substituted or unsubstituted 4-6 membered heterocyclyl, a substituted or unsubstituted a 7-11 membered spirocyclic heterocyclyl, or a substituted or unsubstituted $C_{7-11}$ bicyclic spirocyclic carbocyclyl; and $R^b$ and $R^x$ are each independently hydrogen, methyl, or ethyl; provided that at least one of $R^b$ and $R^x$ is not hydrogen.

In certain embodiments of Formula (II-i), A is a substituted or unsubstituted 6-10 membered bridged heterocyclyl, a substituted or unsubstituted 6-membered heterocyclyl, a substituted or unsubstituted 9-membered spirocyclic heterocyclyl, or a substituted or unsubstituted $C_9$ bicyclic spirocyclic carbocyclyl; and $R^b$ and $R^x$ are each independently hydrogen, methyl, or ethyl; provided that at least one of $R^b$ and $R^x$ is not hydrogen.

In certain embodiments of Formula (II-i), A is a 6-10 membered bridged heterocyclyl, a 6-membered heterocyclyl, a 9-membered spirocyclic heterocyclyl, or a $C_9$ bicyclic spirocyclic carbocyclyl; wherein each is unsubstituted or substituted with a $C_{1-4}$ alkyl; and $R^b$ and $R^x$ are each independently hydrogen, methyl, or ethyl; provided that at least one of $R^b$ and $R^x$ is not hydrogen.

In certain embodiments of Formula (II-i), A is a 6-10 membered bridged heterocyclyl, a 6-membered heterocyclyl having at least one oxygen atom in the ring, a 9-membered spirocyclic heterocyclyl, or a $C_9$ bicyclic spirocyclic carbocyclyl; wherein each is unsubstituted or substituted with a $C_{1-4}$ alkyl; and $R^b$ and $R^x$ are each independently hydrogen, methyl, or ethyl; provided that at least one of $R^b$ and $R^x$ is not hydrogen.

In certain embodiments of Formula (II-i), A is

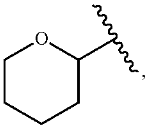,
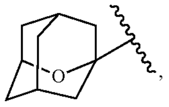,
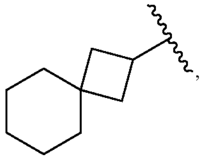,
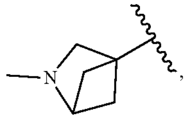,
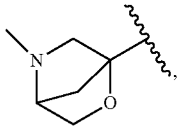,
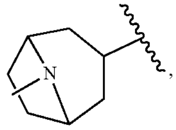, or
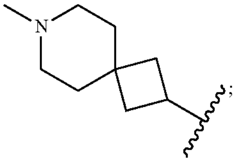;

and $R^b$ and $R^x$ are each independently hydrogen, methyl, or ethyl; provided that at least one of $R^b$ and $R^x$ is not hydrogen.

In certain embodiments of Formula (II-i), A is

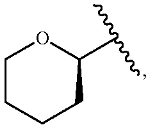,
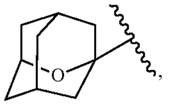,
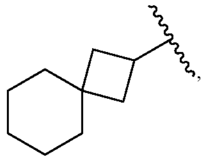,
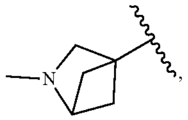,
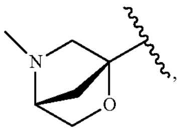,
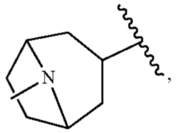,
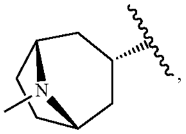,
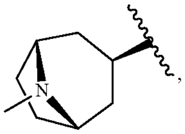, or
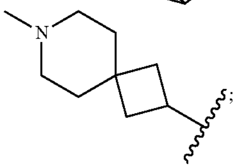;

and $R^b$ and $R^x$ are each independently hydrogen, methyl, or ethyl; provided that at least one of $R^b$ and $R^x$ is not hydrogen.

In certain embodiments, the compound of Formula (II) is of Formula (II-i-1):

(II-i-1)

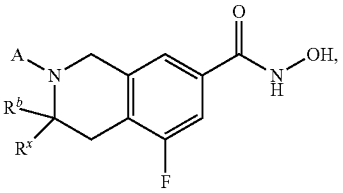

or a pharmaceutically acceptable salt, co-crystal, tautomer, stereoisomer, solvate, hydrate, polymorph, isotopically enriched derivative, or prodrug thereof; wherein:

A is substituted or unsubstituted carbocyclyl, or substituted or unsubstituted heterocyclyl; and $R^b$ and $R^x$ are each independently hydrogen or substituted or unsubstituted alkyl; provided that at least one of $R^b$ and $R^x$ is not hydrogen.

In certain embodiments of the compounds of Formula (II-i-1), A is cyclopropyl, cyclobutyl,

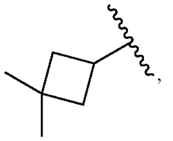 [SMILES: *C1CC(C)(C)C1], oxetanyl,

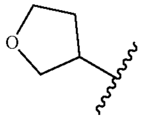, 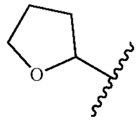, 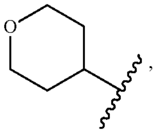, 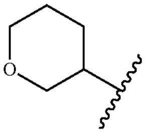, 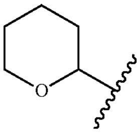, 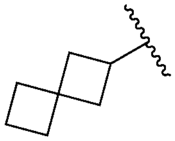, 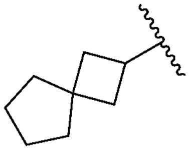, 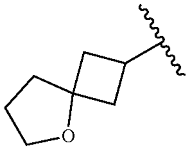, 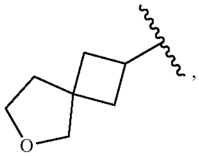, 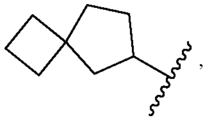, 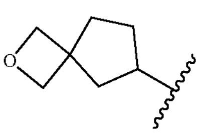, 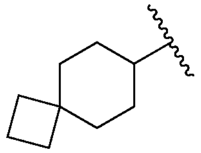, 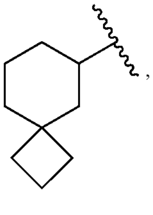, 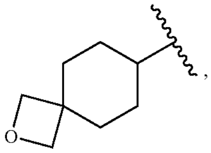, 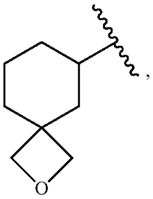, 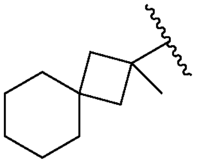, or 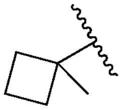;

and $R^b$ and $R^x$ are each independently hydrogen, methyl, ethyl, propyl, isopropyl, t-butyl, cyclopropyl,

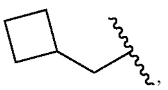, 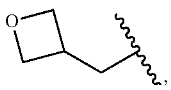, benzyl,

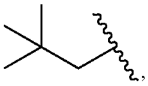, or 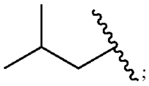;

provided that at least one of $R^b$ and $R^x$ is not hydrogen.

In certain embodiments of the compounds of Formula (II-i-1), A is

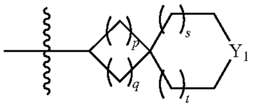

wherein: p and q are each independently 1 or 2; s and t are each independently 0 or 1; $Y_1$ is selected from $CH_2$, O, and $NR_s$, where $R_s$ is hydrogen, methyl or cyclopropyl; and $R^b$ and $R^x$ are each independently hydrogen, methyl, or ethyl; provided that at least one of $R^b$ and $R^x$ is not hydrogen.

In certain embodiments of Formula (II-i-1), A is a substituted or unsubstituted 4-10 membered bridged heterocyclyl, a substituted or unsubstituted 4-6 membered heterocyclyl, a substituted or unsubstituted a 7-11 membered spirocyclic heterocyclyl, or a substituted or unsubstituted $C_{7-11}$ bicyclic spirocyclic carbocyclyl; and $R^b$ and $R^x$ are each independently hydrogen, methyl, or ethyl; provided that at least one of $R^b$ and $R^x$ is not hydrogen.

In certain embodiments of Formula (II-i-1), A is a substituted or unsubstituted 6-10 membered bridged heterocyclyl, a substituted or unsubstituted 6-membered heterocyclyl, a substituted or unsubstituted 9-membered spirocyclic heterocyclyl, or a substituted or unsubstituted $C_9$ bicyclic spirocyclic carbocyclyl; and $R^b$ and $R^x$ are each independently hydrogen, methyl, or ethyl; provided that at least one of $R^b$ and $R^x$ is not hydrogen.

In certain embodiments of Formula (I-i-1), A is a 6-10 membered bridged heterocyclyl, a 6-membered heterocyclyl, a 9-membered spirocyclic heterocyclyl, or a $C_9$ bicyclic spirocyclic carbocyclyl; wherein each is unsubstituted or substituted with a $C_{1-4}$ alkyl; and $R^b$ and $R^x$ are each independently hydrogen, methyl, or ethyl; provided that at least one of $R^b$ and $R^x$ is not hydrogen.

In certain embodiments of Formula (I-i-1), A is a 6-10 membered bridged heterocyclyl, a 6-membered heterocyclyl having at least one oxygen atom in the ring, a 9-membered spirocyclic heterocyclyl, or a $C_9$ bicyclic spirocyclic carbocyclyl; wherein each is unsubstituted or substituted with a $C_{1-4}$ alkyl; and $R^b$ and $R^x$ are each independently hydrogen, methyl, or ethyl; provided that at least one of $R^b$ and $R^x$ is not hydrogen.

In certain embodiments of Formula (II-i-1), A is

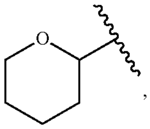, 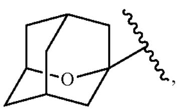, 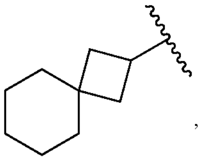, 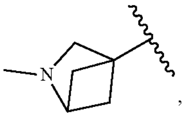, 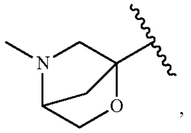, 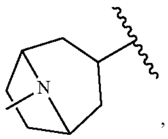, or 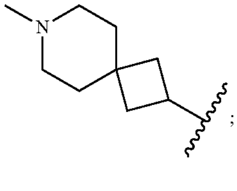;

and $R^b$ and $R^x$ are each independently hydrogen, methyl, or ethyl; provided that at least one of $R^b$ and $R^x$ is not hydrogen.

In certain embodiments of Formula (I-i-1), A is

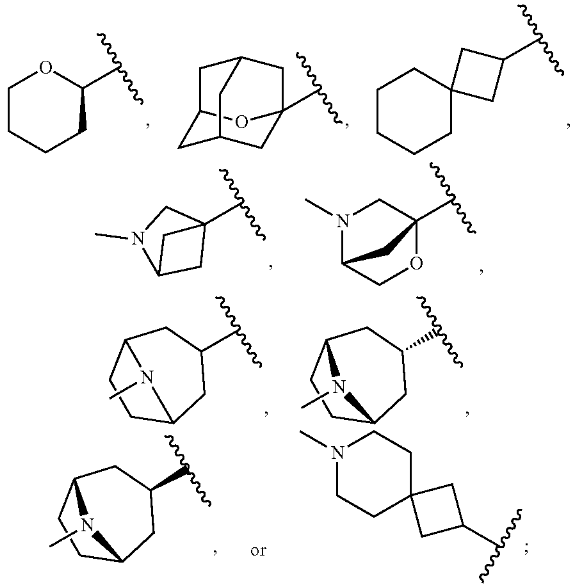

and $R^b$ and $R^x$ are each independently hydrogen, methyl, or ethyl; provided that at least one of $R^b$ and $R^x$ is not hydrogen.

In certain embodiments, the compound of Formula (II) is of Formula (II-j):

(II-j)

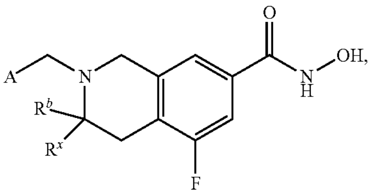

or a pharmaceutically acceptable salt, co-crystal, tautomer, stereoisomer, solvate, hydrate, polymorph, isotopically enriched derivative, or prodrug thereof; wherein:

A is substituted or unsubstituted carbocyclyl, or substituted or unsubstituted heterocyclyl; and $R^b$ and $R^x$ are each independently hydrogen or substituted or unsubstituted alkyl; provided that at least one of $R^b$ and $R^x$ is not hydrogen.

In certain embodiments of the compounds of Formula (II-j), A is

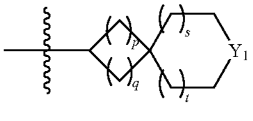

wherein: p and q are each independently 1 or 2; s and t are each independently 0 or 1; $Y_1$ is selected from $CH_2$, O, and $NR_s$, where $R_s$ is hydrogen, methyl or cyclopropyl; and $R^b$ and $R^x$ are each independently hydrogen, methyl, or ethyl; provided that at least one of $R^b$ and $R^x$ is not hydrogen.

In certain embodiments of Formula (II-j), A is a substituted or unsubstituted 4-10 membered bridged heterocyclyl, a substituted or unsubstituted 4-6 membered heterocyclyl, a substituted or unsubstituted a 7-11 membered spirocyclic heterocyclyl, or a substituted or unsubstituted $C_{7-11}$ bicyclic spirocyclic carbocyclyl; and $R^b$ and $R^x$ are each independently hydrogen, methyl, or ethyl; provided that at least one of $R^b$ and $R^x$ is not hydrogen.

In certain embodiments of Formula (II-j), A is a substituted or unsubstituted 6-10 membered bridged heterocyclyl, a substituted or unsubstituted 6-membered heterocyclyl, a substituted or unsubstituted 9-membered spirocyclic heterocyclyl, or a substituted or unsubstituted $C_9$ bicyclic spirocyclic carbocyclyl; and $R^b$ and $R^x$ are each independently hydrogen, methyl, or ethyl; provided that at least one of $R^b$ and $R^x$ is not hydrogen.

In certain embodiments of Formula (II-j), A is a 6-10 membered bridged heterocyclyl, a 6-membered heterocyclyl, a 9-membered spirocyclic heterocyclyl, or a $C_9$ bicyclic spirocyclic carbocyclyl; wherein each is unsubstituted or substituted with a $C_{1-4}$ alkyl; and $R^b$ and $R^x$ are each independently hydrogen, methyl, or ethyl; provided that at least one of $R^b$ and $R^x$ is not hydrogen.

In certain embodiments of Formula (II-j), A is a 6-10 membered bridged heterocyclyl, a 6-membered heterocyclyl having at least one oxygen atom in the ring, a 9-membered spirocyclic heterocyclyl, or a $C_9$ bicyclic spirocyclic carbocyclyl; wherein each is unsubstituted or substituted with a $C_{1-4}$ alkyl; and $R^b$ and $R^x$ are each independently hydrogen, methyl, or ethyl; provided that at least one of $R^b$ and $R^x$ is not hydrogen.

In certain embodiments of Formula (II-j), A is

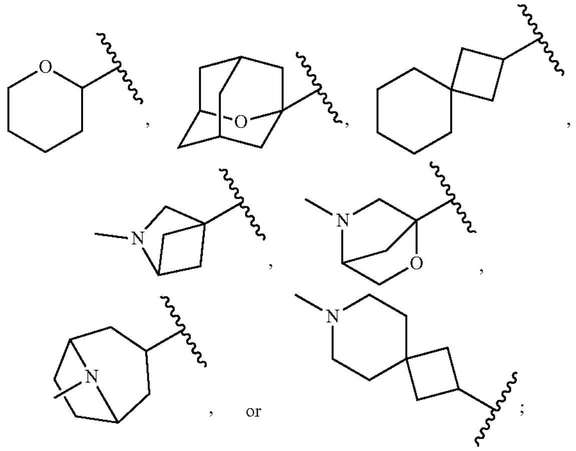

and $R^b$ and $R^x$ are each independently hydrogen, methyl, or ethyl; provided that at least one of $R^b$ and $R^x$ is not hydrogen.

In certain embodiments of Formula (II-j), A is

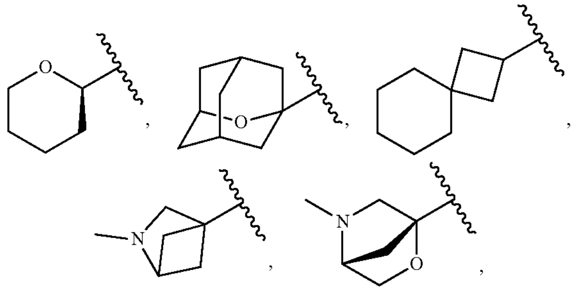

-continued

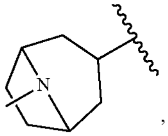,

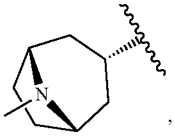,

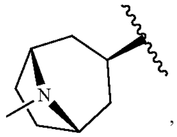, or

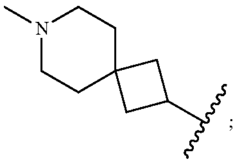;

and $R^b$ and $R^x$ are each independently hydrogen, methyl, or ethyl; provided that at least one of $R^b$ and $R^x$ is not hydrogen.

In certain embodiments the compound of Formula (II) is of Formula (II-k):

(II-k)

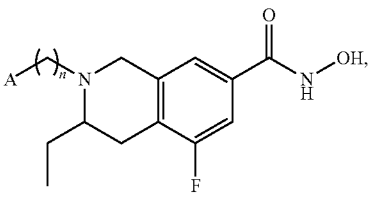

or a pharmaceutically acceptable salt, co-crystal, tautomer, stereoisomer, solvate, hydrate, polymorph, isotopically enriched derivative, or prodrug thereof; wherein A is as defined herein; and is 0 or 1.

In certain embodiments of the compounds of Formula (II-k), A is substituted or unsubstituted carbocyclyl, or substituted or unsubstituted heterocyclyl.

In certain embodiments of the compounds of Formula (II-k), A is

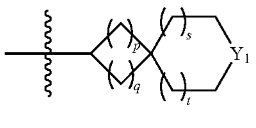

wherein: p and q are each independently 1 or 2; s and t are each independently 0 or 1; $Y_1$ is selected from $CH_2$, O, and $NR_s$, where $R_s$ is hydrogen, methyl or cyclopropyl.

In certain embodiments of Formula (II-k), A is a substituted or unsubstituted 4-10 membered bridged heterocyclyl, a substituted or unsubstituted 4-6 membered heterocyclyl, a substituted or unsubstituted a 7-11 membered spirocyclic heterocyclyl, or a substituted or unsubstituted $C_{7-11}$ bicyclic spirocyclic carbocyclyl.

In certain embodiments of Formula (II-k), A is a substituted or unsubstituted 6-10 membered bridged heterocyclyl, a substituted or unsubstituted 6-membered heterocyclyl, a substituted or unsubstituted 9-membered spirocyclic heterocyclyl, or a substituted or unsubstituted $C_9$ bicyclic spirocyclic carbocyclyl.

In certain embodiments of Formula (II-k), A is a 6-10 membered bridged heterocyclyl, a 6-membered heterocyclyl, a 9-membered spirocyclic heterocyclyl, or a $C_9$ bicyclic spirocyclic carbocyclyl; wherein each is unsubstituted or substituted with a $C_{1-4}$ alkyl.

In certain embodiments of Formula (II-k), A is a 6-10 membered bridged heterocyclyl, a 6-membered heterocyclyl having at least one oxygen atom in the ring, a 9-membered spirocyclic heterocyclyl, or a $C_9$ bicyclic spirocyclic carbocyclyl; wherein each is unsubstituted or substituted with a $C_{1-4}$ alkyl.

In certain embodiments of Formula (I-k) A is

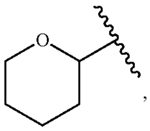, 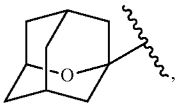, 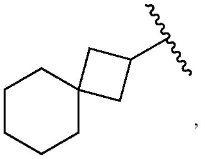,

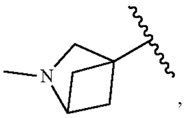, 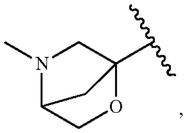,

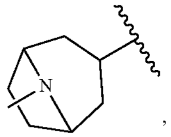, or 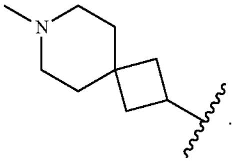.

In certain embodiments of Formula (II-k), A is

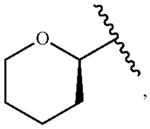, 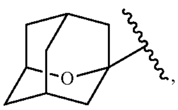, 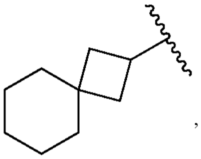,

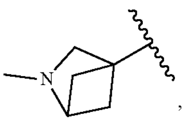, 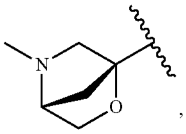,

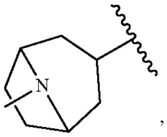, 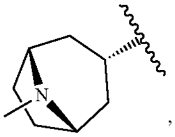,

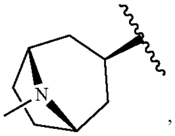, or 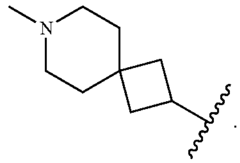.

In certain embodiments, the compound of Formula (II) is of Formula (II-l):

(II-1)

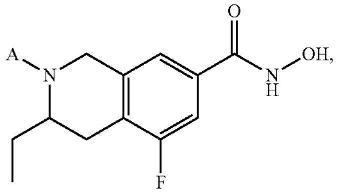

or a pharmaceutically acceptable salt, co-crystal, tautomer, stereoisomer, solvate, hydrate, polymorph, isotopically enriched derivative, or prodrug thereof; wherein A is as defined herein.

In certain embodiments of the compounds of Formula (II-l), A is substituted or unsubstituted carbocyclyl, or substituted or unsubstituted heterocyclyl.

In certain embodiments of the compounds of Formula (II-l), A is

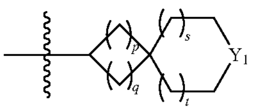

wherein: p and q are each independently 1 or 2; s and t are each independently 0 or 1; $Y_1$ is selected from $CH_2$, O, and $NR_s$, where $R_s$ is hydrogen, methyl or cyclopropyl.

In certain embodiments of Formula (II-l), A is a substituted or unsubstituted 4-10 membered bridged heterocyclyl, a substituted or unsubstituted 4-6 membered heterocyclyl, a substituted or unsubstituted a 7-11 membered spirocyclic heterocyclyl, or a substituted or unsubstituted $C_{7-11}$ bicyclic spirocyclic carbocyclyl.

In certain embodiments of Formula (II-l), A is a substituted or unsubstituted 6-10 membered bridged heterocyclyl, a substituted or unsubstituted 6-membered heterocyclyl, a substituted or unsubstituted 9-membered spirocyclic heterocyclyl, or a substituted or unsubstituted $C_9$ bicyclic spirocyclic carbocyclyl.

In certain embodiments of Formula (II-l), A is a 6-10 membered bridged heterocyclyl, a 6-membered heterocyclyl, a 9-membered spirocyclic heterocyclyl, or a $C_9$ bicyclic spirocyclic carbocyclyl; wherein each is unsubstituted or substituted with a $C_{1-4}$ alkyl.

In certain embodiments of Formula (II-l), A is a 6-10 membered bridged heterocyclyl, a 6-membered heterocyclyl having at least one oxygen atom in the ring, a 9-membered spirocyclic heterocyclyl, or a $C_9$ bicyclic spirocyclic carbocyclyl; wherein each is unsubstituted or substituted with a $C_{1-4}$ alkyl.

In certain embodiments of Formula (II-l), A is

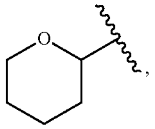, 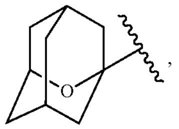,

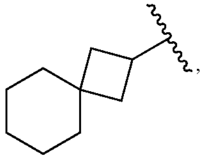, 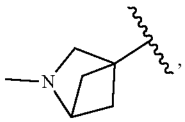,

-continued

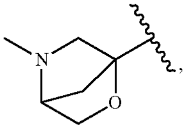, 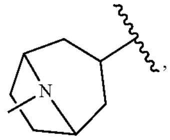, or

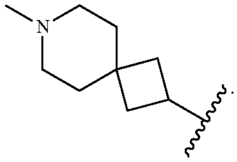.

In certain embodiments of Formula (II-l), A is

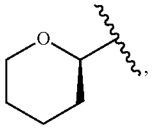, 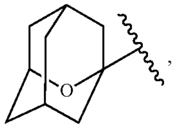,

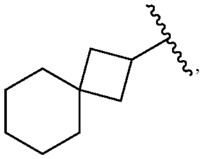, 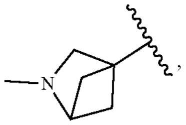,

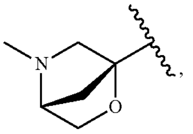, 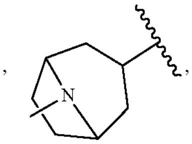,

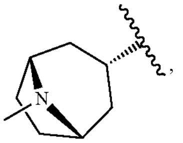, 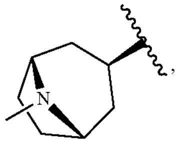, or

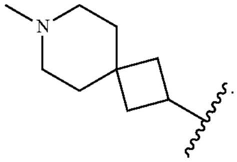.

In certain embodiments, the compound of Formula (II) is of Formula (II-m):

(II-m)

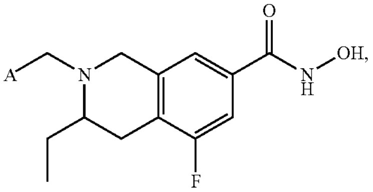

or a pharmaceutically acceptable salt, co-crystal, tautomer, stereoisomer, solvate, hydrate, polymorph, isotopically enriched derivative, or prodrug thereof; wherein A is as defined herein.

In certain embodiments of the compounds of Formula (II-m), A is substituted or unsubstituted carbocyclyl, or substituted or unsubstituted heterocyclyl.

In certain embodiments of the compounds of Formula (II-m), A is

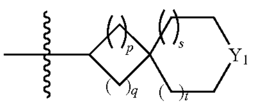

wherein: p and q are each independently 1 or 2; s and t are each independently 0 or 1; $Y_1$ is selected from $CH_2$, O, and $NR_s$, where $R_s$ is hydrogen, methyl or cyclopropyl.

In certain embodiments of Formula (II-m), A is a substituted or unsubstituted 4-10 membered bridged heterocyclyl, a substituted or unsubstituted 4-6 membered heterocyclyl, a substituted or unsubstituted a 7-11 membered spirocyclic heterocyclyl, or a substituted or unsubstituted $C_{7-11}$ bicyclic spirocyclic carbocyclyl.

In certain embodiments of Formula (II-m), A is a substituted or unsubstituted 6-10 membered bridged heterocyclyl, a substituted or unsubstituted 6-membered heterocyclyl, a substituted or unsubstituted 9-membered spirocyclic heterocyclyl, or a substituted or unsubstituted $C_9$ bicyclic spirocyclic carbocyclyl.

In certain embodiments of Formula (II-m), A is a 6-10 membered bridged heterocyclyl, a 6-membered heterocyclyl, a 9-membered spirocyclic heterocyclyl, or a $C_9$ bicyclic spirocyclic carbocyclyl; wherein each is unsubstituted or substituted with a $C_{1-4}$ alkyl.

In certain embodiments of Formula (II-m), A is a 6-10 membered bridged heterocyclyl, a 6-membered heterocyclyl having at least one oxygen atom in the ring, a 9-membered spirocyclic heterocyclyl, or a $C_9$ bicyclic spirocyclic carbocyclyl; wherein each is unsubstituted or substituted with a $C_{1-4}$ alkyl.

In certain embodiments of Formula (II-m), A is

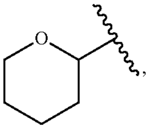,
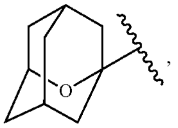,
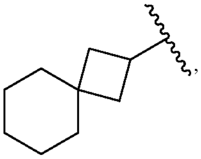,
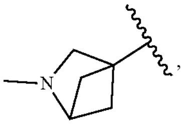,
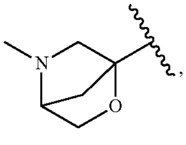,
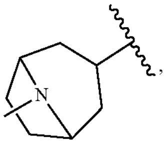, or
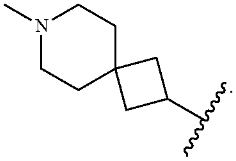.

In certain embodiments of Formula (II-m), A is

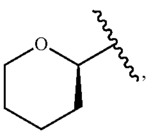,
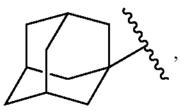,
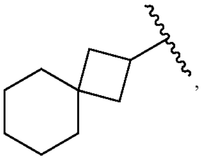,
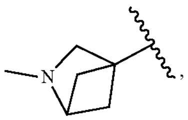,
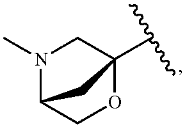,
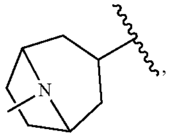,
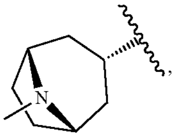,
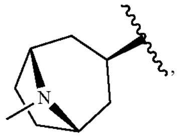, and
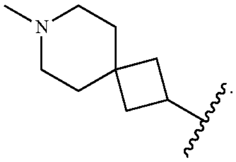.

In certain embodiments, the compound of Formula (II) is one of the following compounds, or a pharmaceutically acceptable salt, co-crystal, tautomer, stereoisomer, solvate, hydrate, polymorph, isotopically enriched derivative, or prodrug thereof:

230

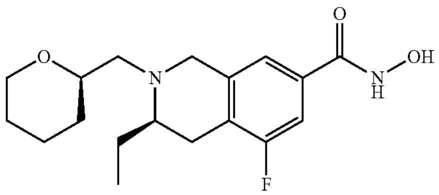

231

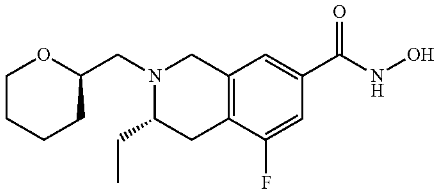

510

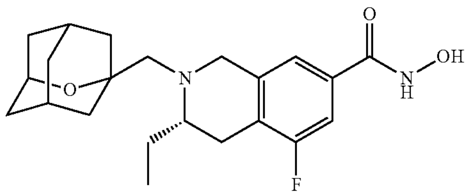

522

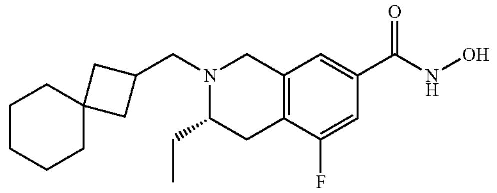

-continued

535

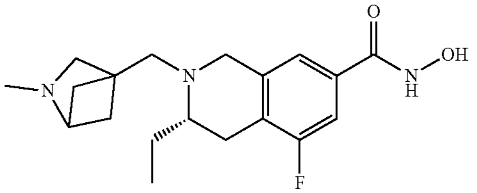

554

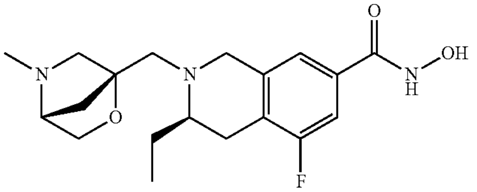

570

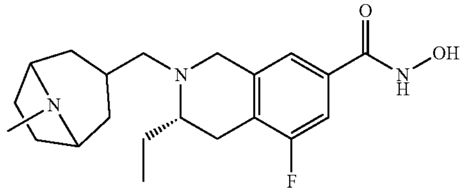

572

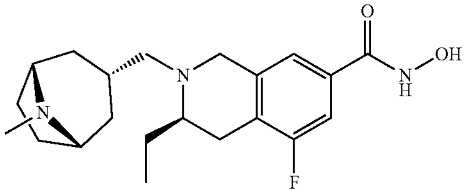

573

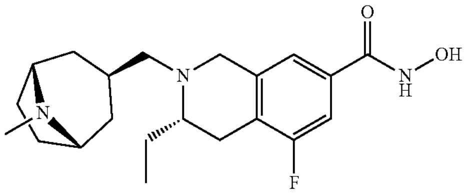

594

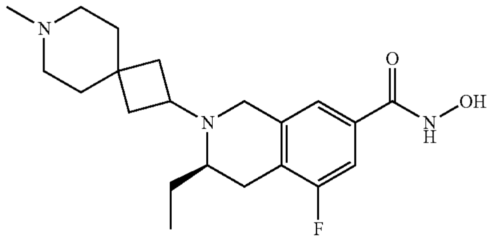

In certain embodiments, the compound of Formula (II) is one of the following compounds, or a pharmaceutically acceptable salt, co-crystal, tautomer, stereoisomer, solvate, hydrate, polymorph, isotopically enriched derivative, or prodrug thereof:

230

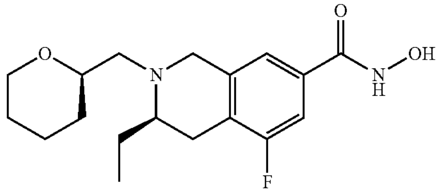

231

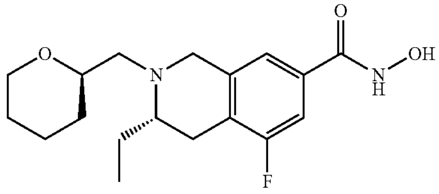

In certain embodiments, the compound of Formula (II) is one of the following compounds, or a pharmaceutically acceptable salt, co-crystal, tautomer, stereoisomer, solvate, hydrate, polymorph, isotopically enriched derivative, or prodrug thereof:

213

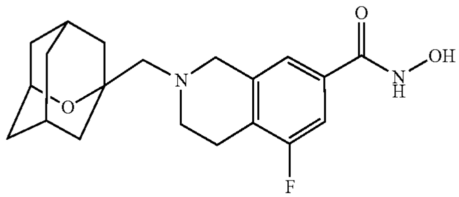

214

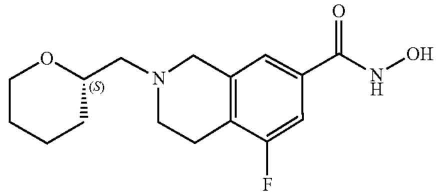

215

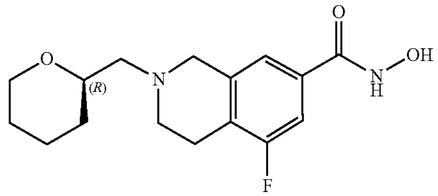

216

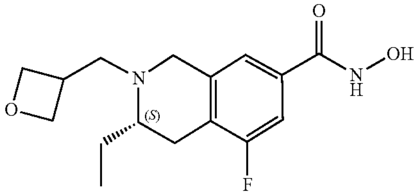

217

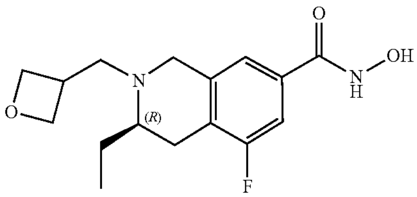

-continued
218
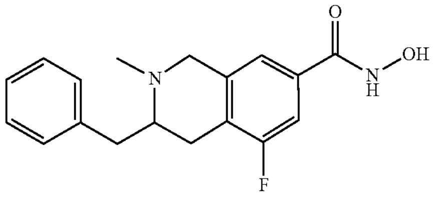
219
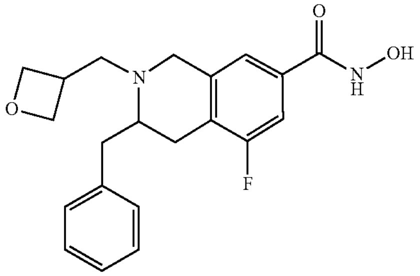
220
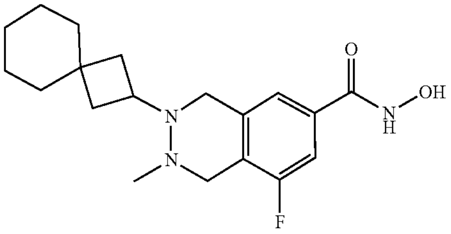
221
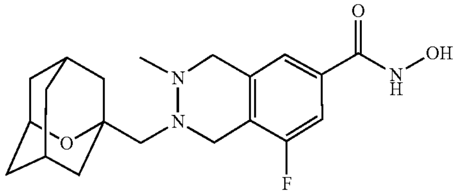
222
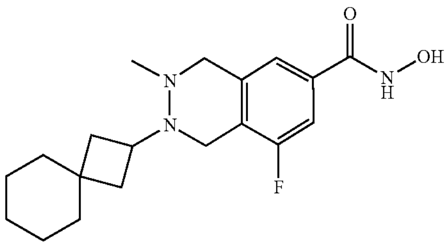
223
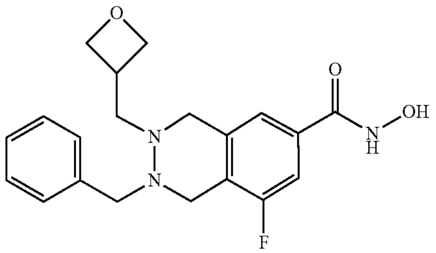
-continued
224
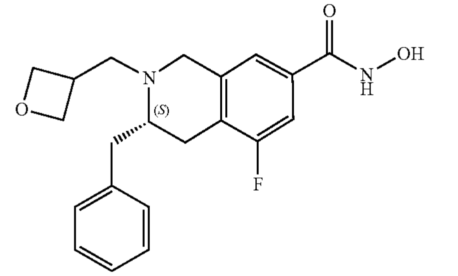
225
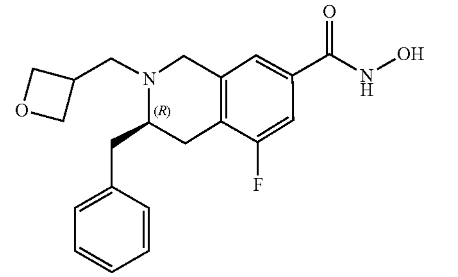
226
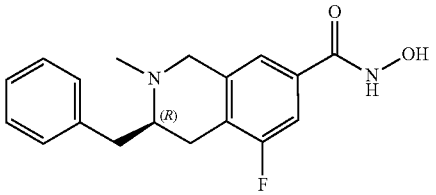
227
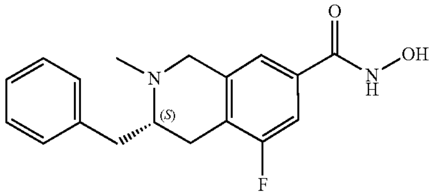
228
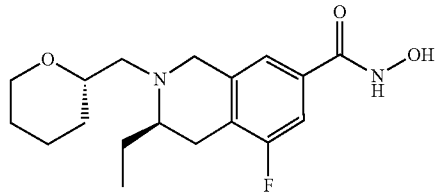
229
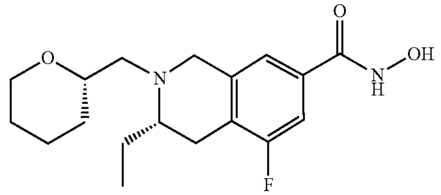
232
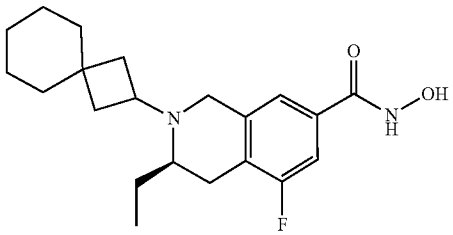

-continued
233
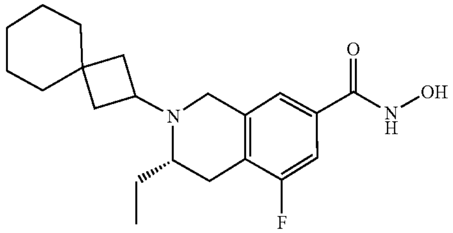
234
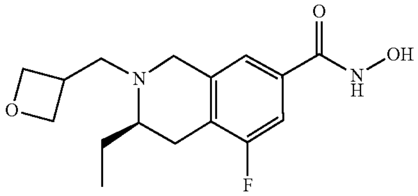
235
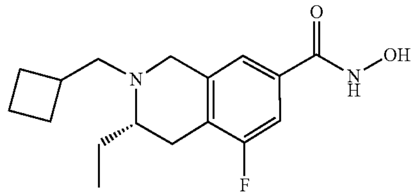
236
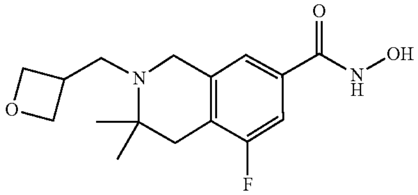
507
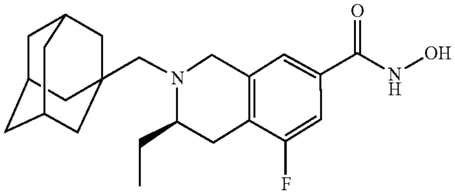
508
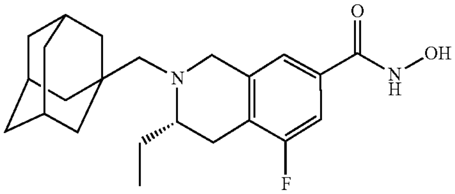
509
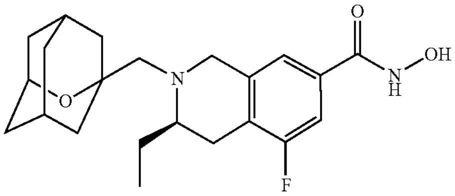
-continued
511
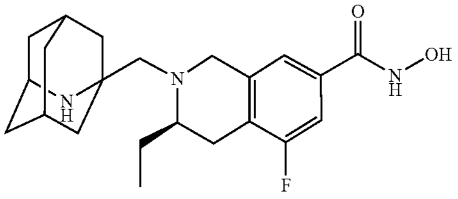
512
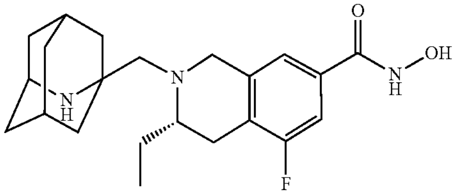
513
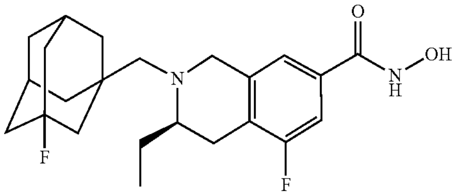
514
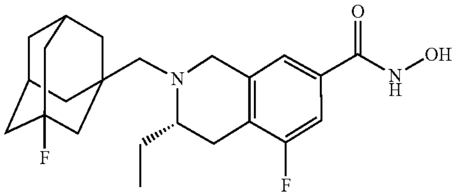
515
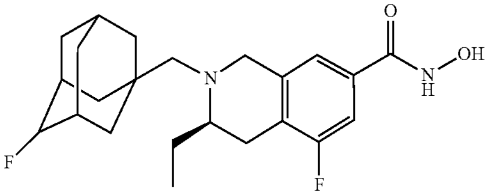
516
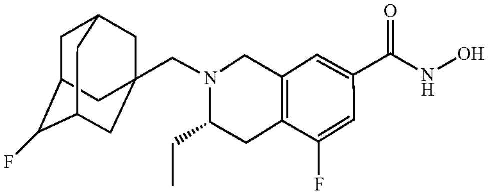
517
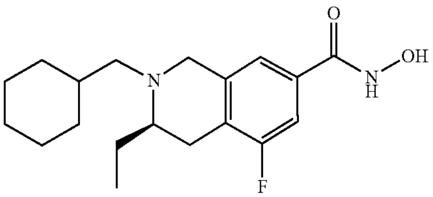

-continued
518
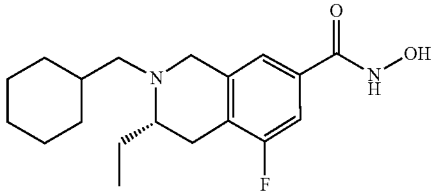
519
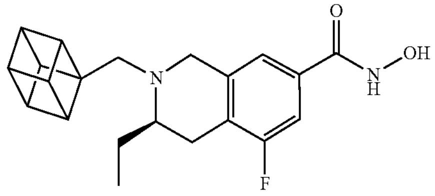
520
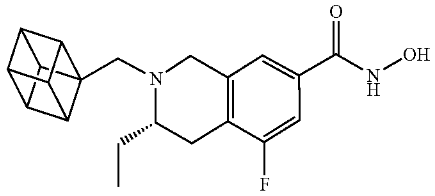
521
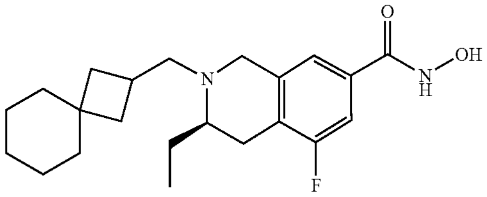
523
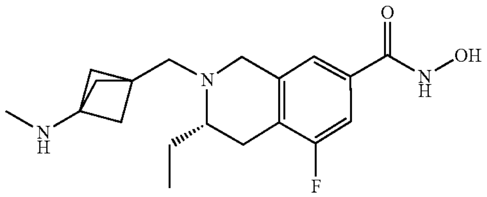
524
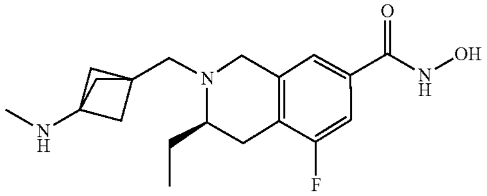
525
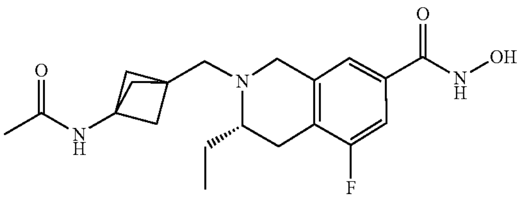
-continued
526
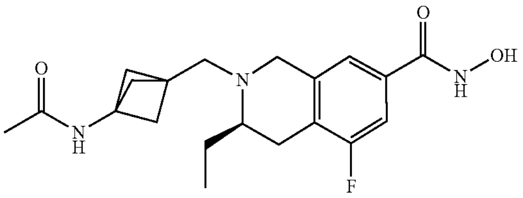
527
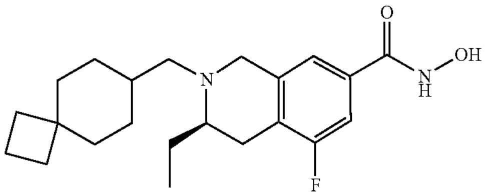
528
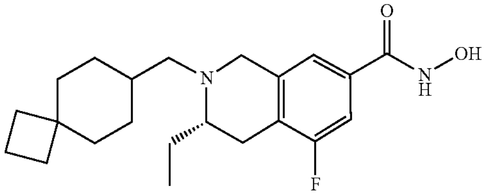
529
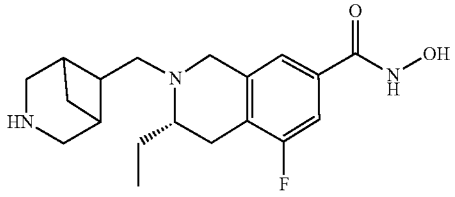
530
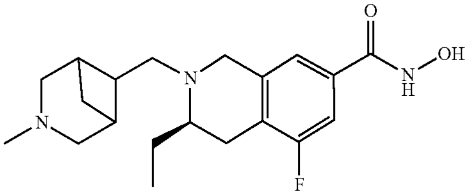
531
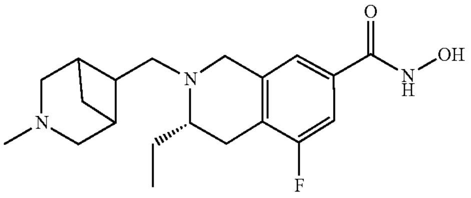
532
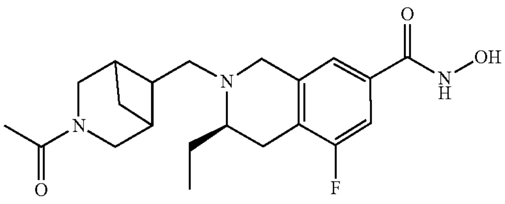

-continued
533
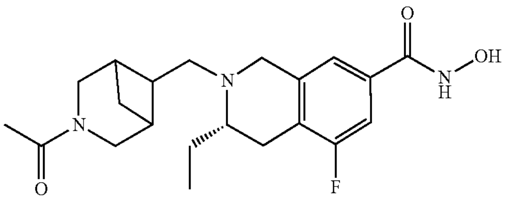
534
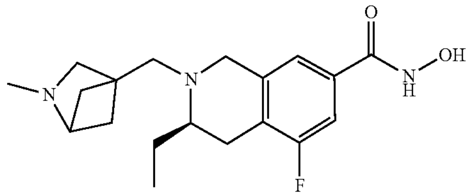
536
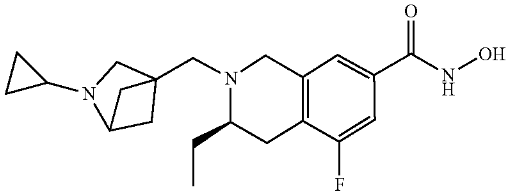
537
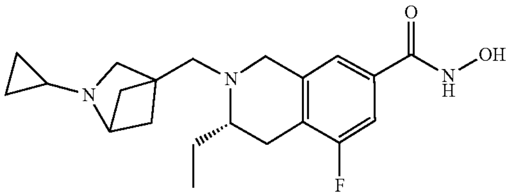
538
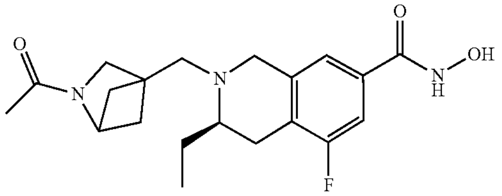
539
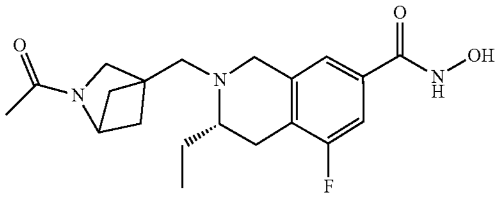
540
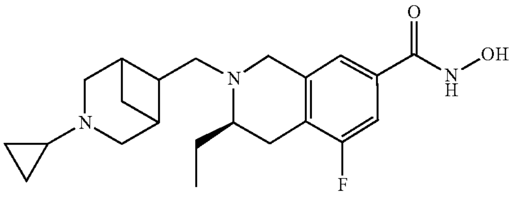
-continued
541
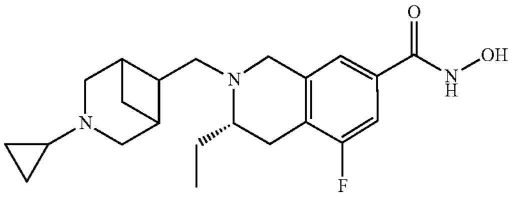
542
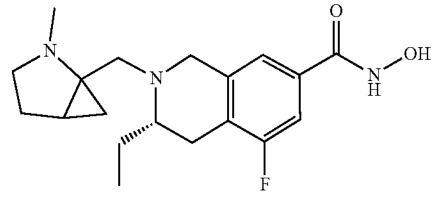
543
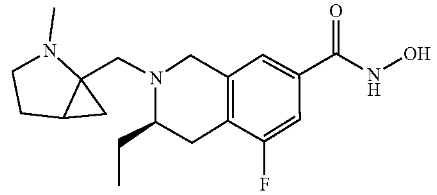
544
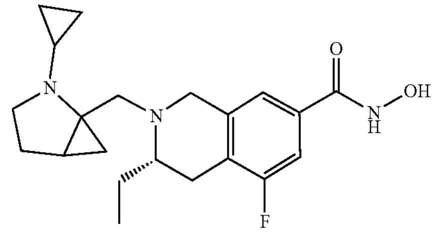
545
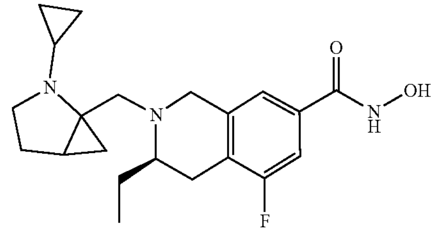
546
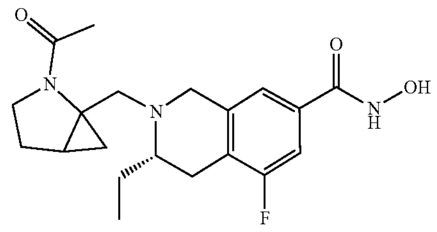
547
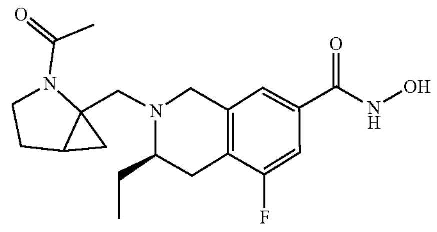

-continued
548
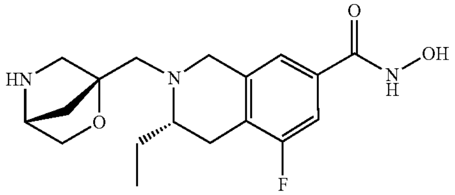
549
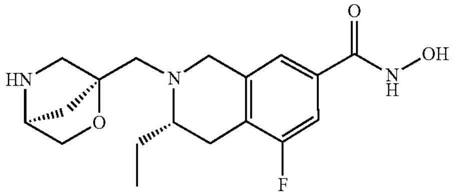
550
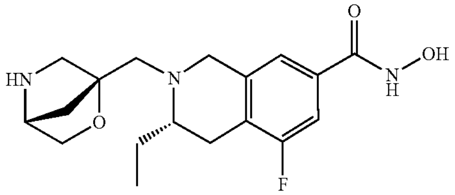
551
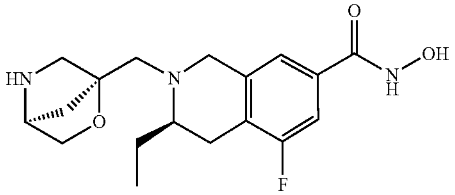
552
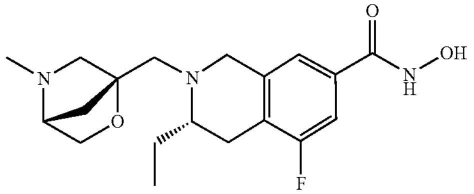
553
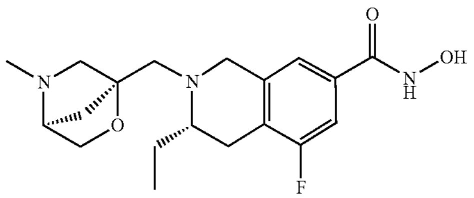
555
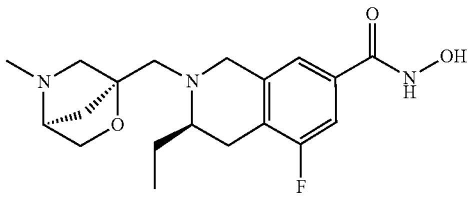
-continued
556
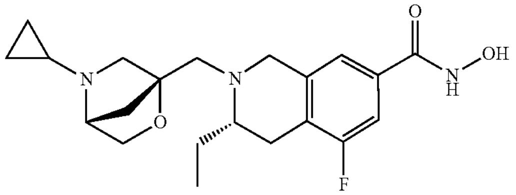
557
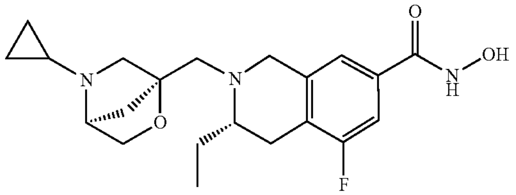
558
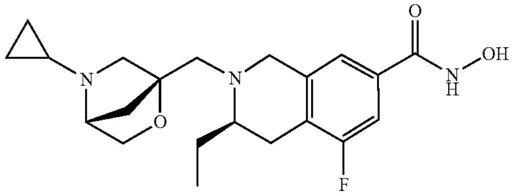
559
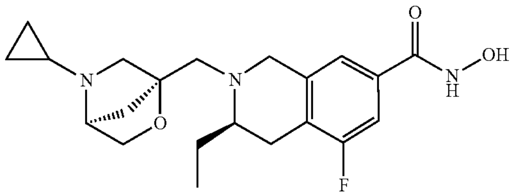
560
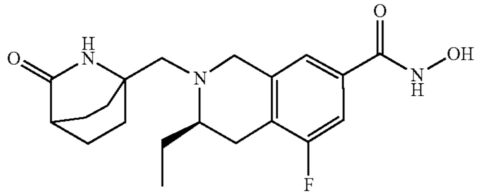
561
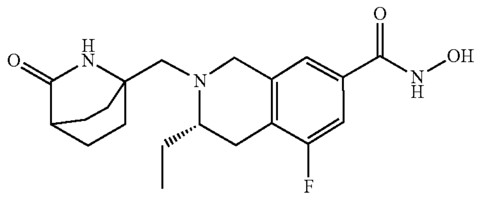
562
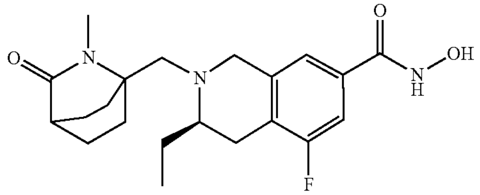

-continued
563
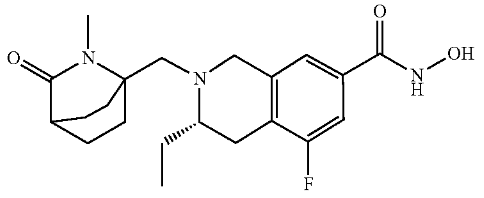
564
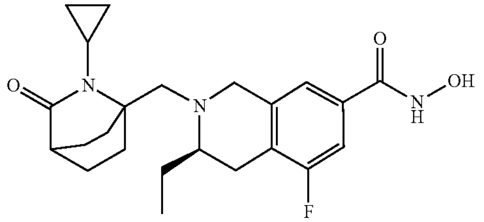
565
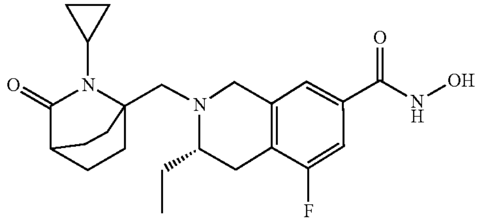
566
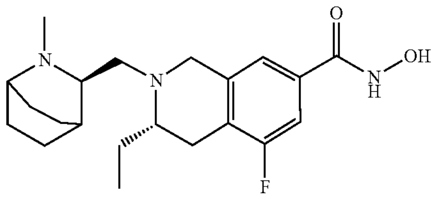
567
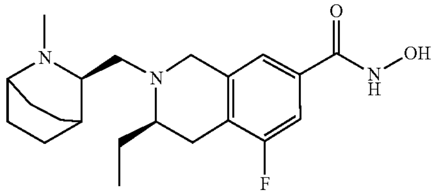
568
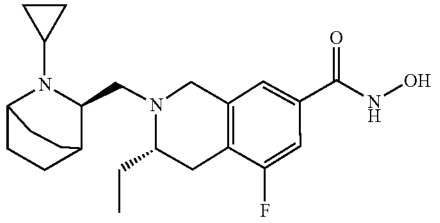
569
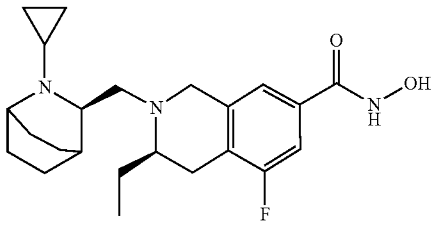
-continued
571
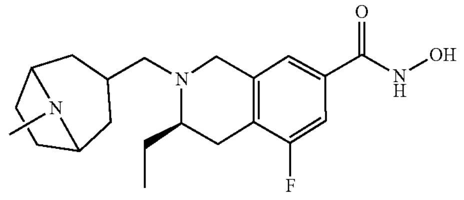
574
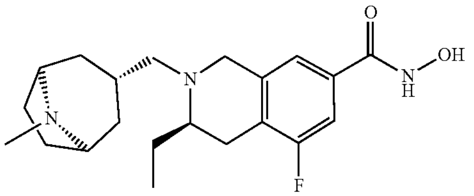
575
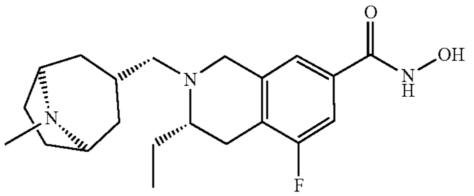
576
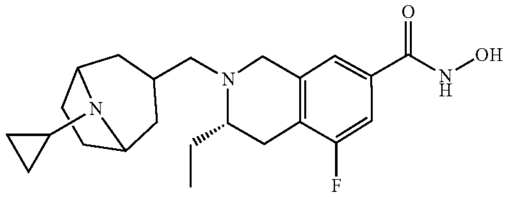
577
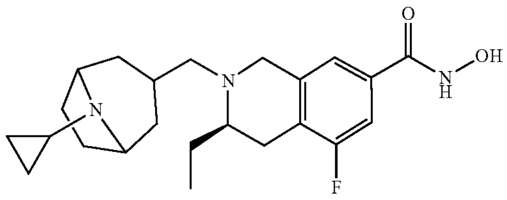
578
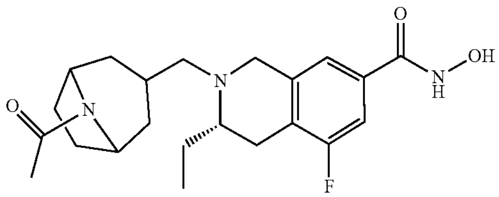
579
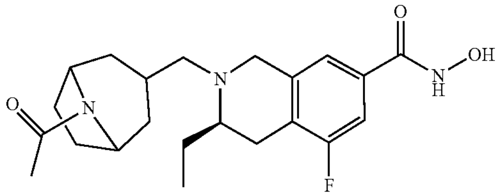

580
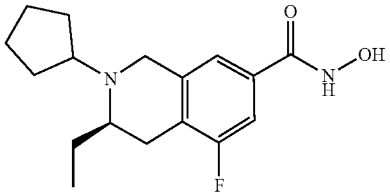
581
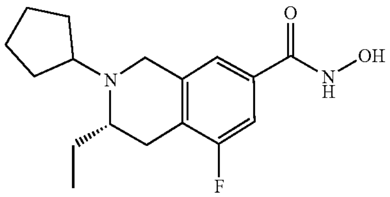
582
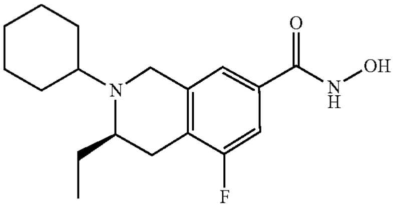
583
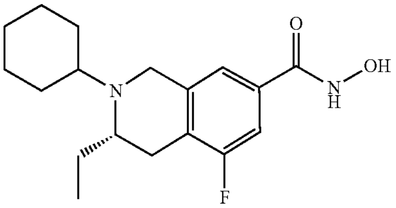
584
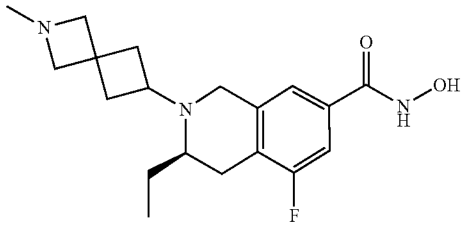
585
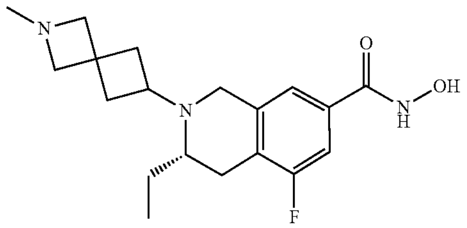
586
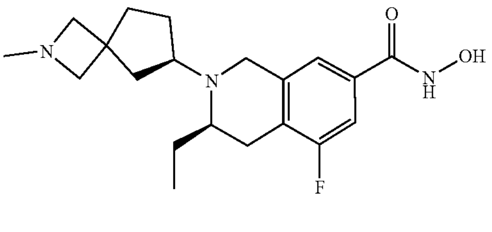
587
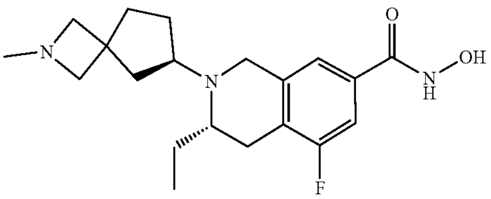
588
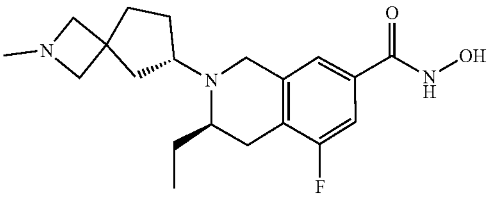
589
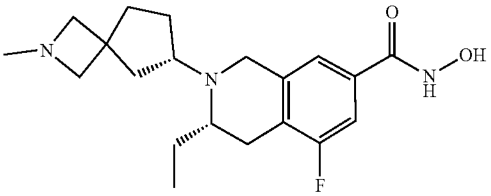
590
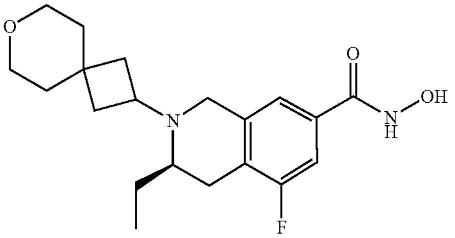
591
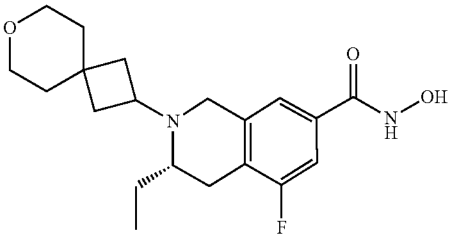
592
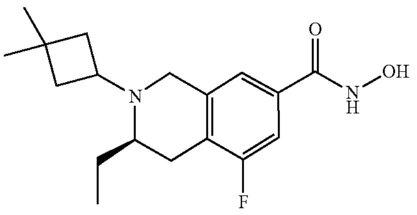
593
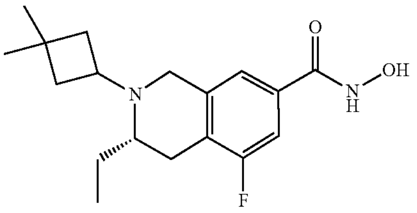

-continued

595

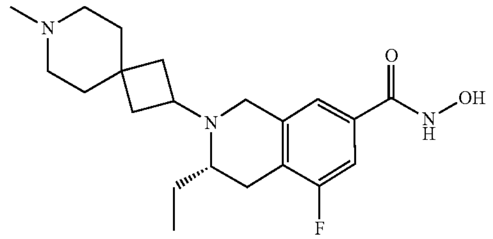

596

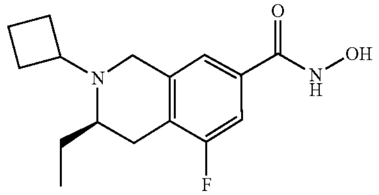

597

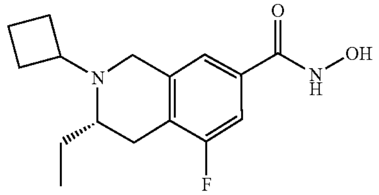

598

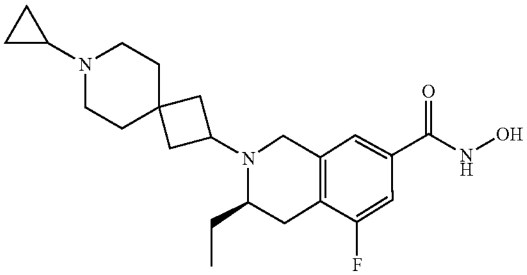

599

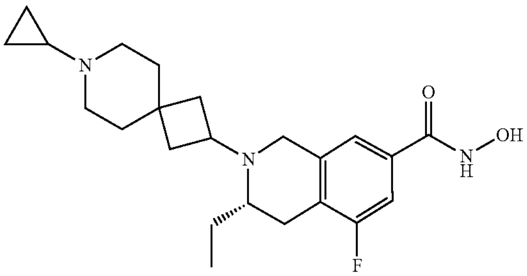

600

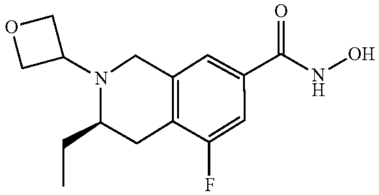

-continued

601

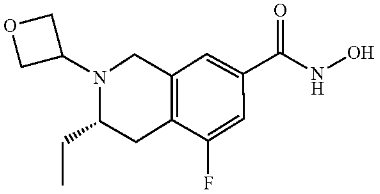

602

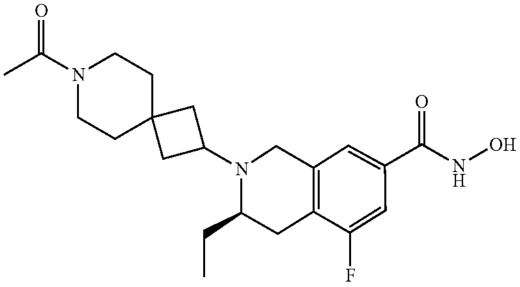

603

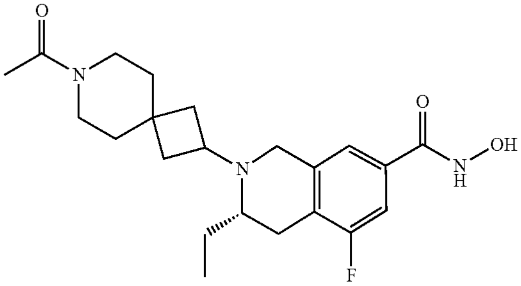

Compounds of Formula (III)

In another aspect, disclosed is a compound of Formula (III):

(III)

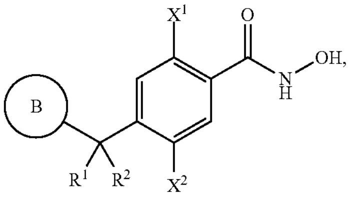

or a pharmaceutically acceptable salt, co-crystal, tautomer, stereoisomer, solvate, hydrate, polymorph, isotopically enriched derivative, or prodrug thereof, wherein:

$X^1$ is hydrogen or fluoro;

$X^2$ is hydrogen or fluoro;

$R^1$ is hydrogen or substituted or unsubstituted alkyl;

$R^2$ is hydrogen or substituted or unsubstituted alkyl; or $R^1$ and $R^2$ together form a substituted or unsubstituted heterocyclyl, or a substituted or unsubstituted cycloalkyl; and B is a substituted or unsubstituted polycyclic spiro ring system, a bridged ring system,

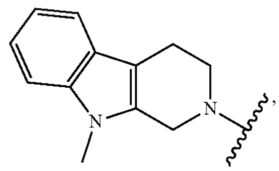,
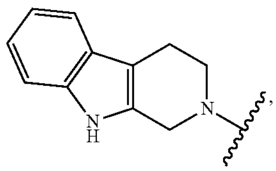,
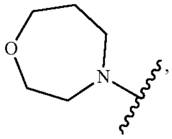,
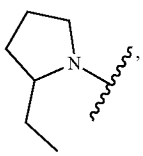, or
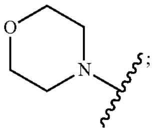;
provided the compound is not of formula:
45
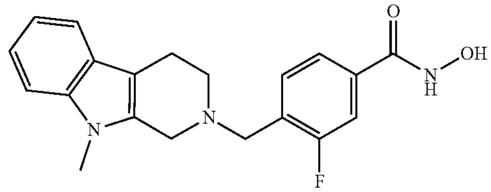
46
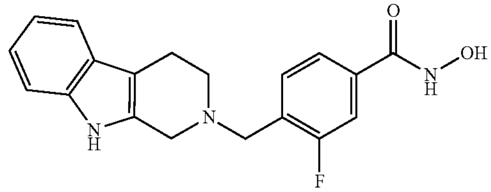
47
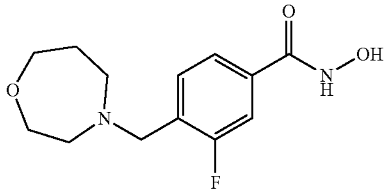
48
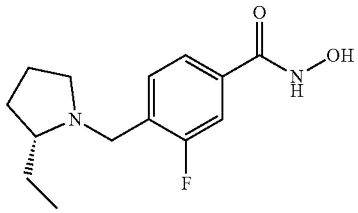
49
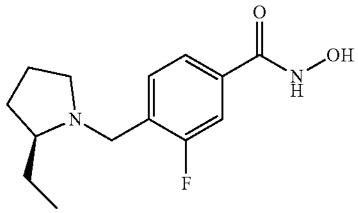
-continued
50
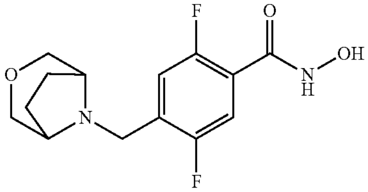
51
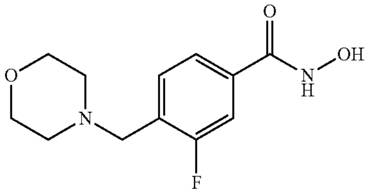
52
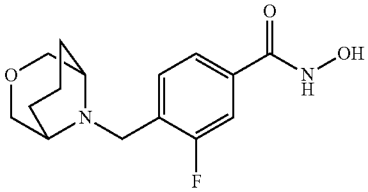
53
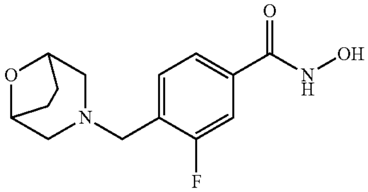
54
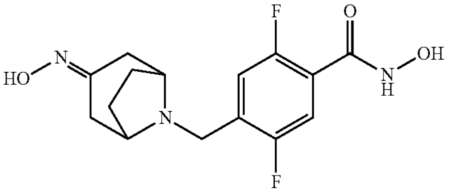
55
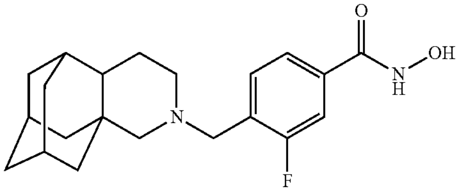
56
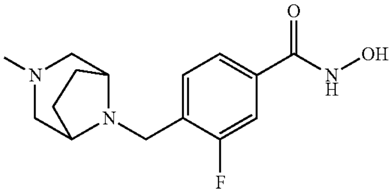
57
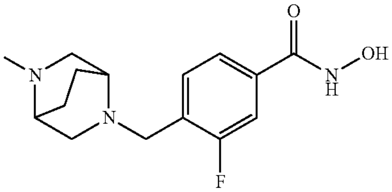

-continued
58
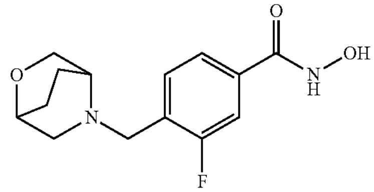
59
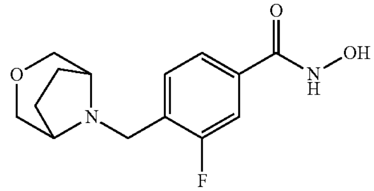
60
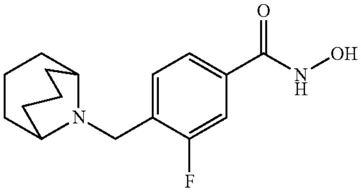
61
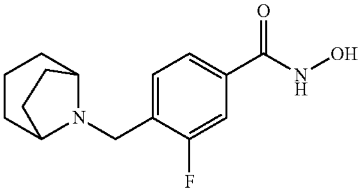
62
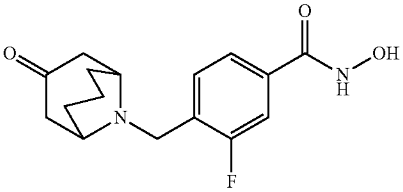
63
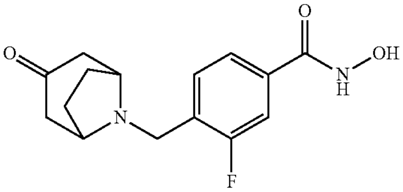
64
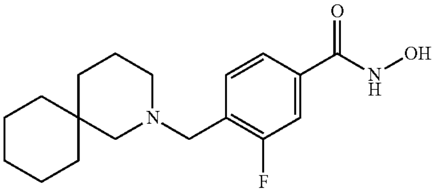
169
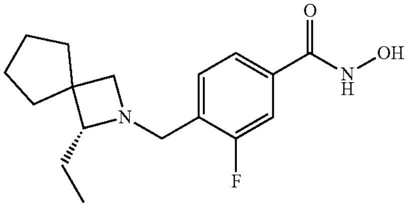
-continued
172
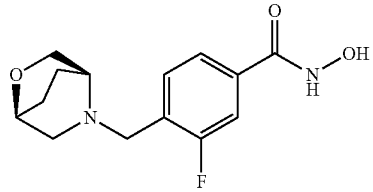
173
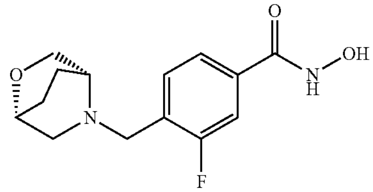
64
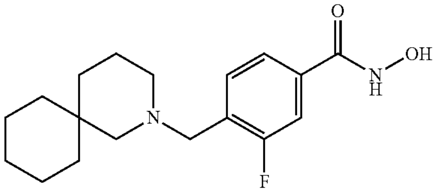
169
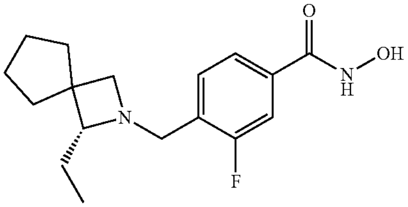
168
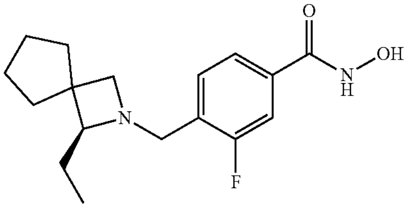
67
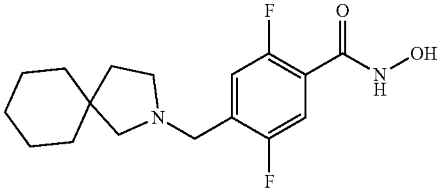
68
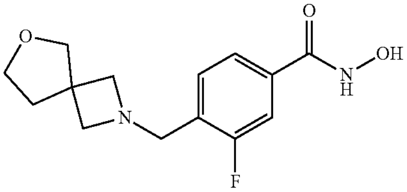

-continued

69

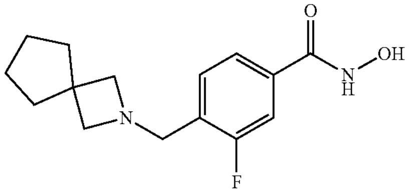

70

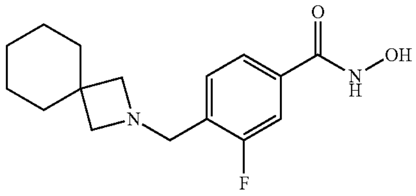

71

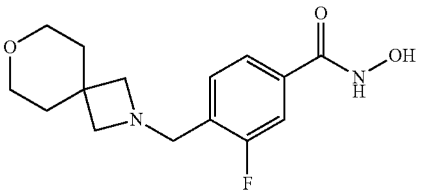

72

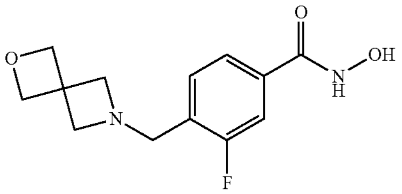

73

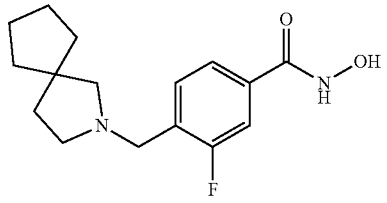

74

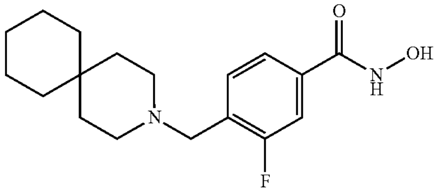

75

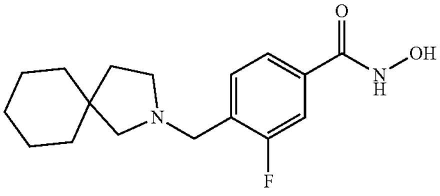

167

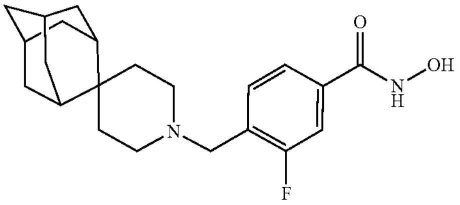

-continued

77

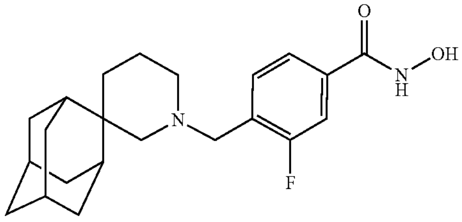

or

78

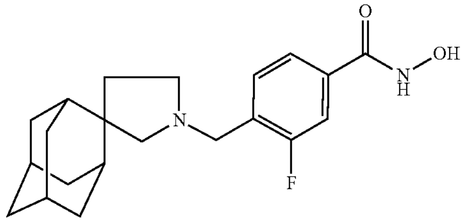

$X^1$ and $X^2$

As described herein, $X^1$ is hydrogen or fluoro; and $X^2$ is hydrogen or fluoro. In certain embodiments, $X^1$ is hydrogen or fluoro; and $X^2$ is hydrogen or fluoro; provided that at least one of $X^1$ and $X^2$ is fluoro. In certain embodiments, $X^1$ is hydrogen; and $X^2$ is fluoro. In certain embodiments, $X^1$ is fluoro; and $X^2$ is hydrogen. In certain embodiments, $X^1$ is fluoro; and $X^2$ is fluoro. In certain embodiments, $X^1$ is hydrogen; and $X^2$ is hydrogen.

B

As described herein, B is a substituted or unsubstituted polycyclic spiro ring system, a substituted or unsubstituted bridged ring system,

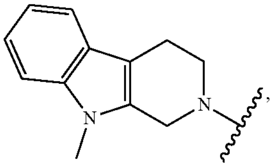,

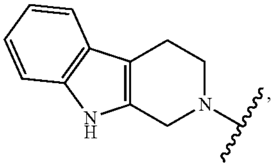,

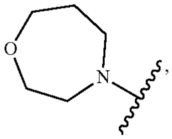,

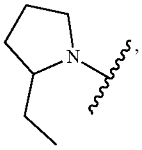, or

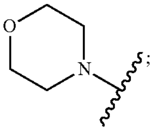;

In certain embodiments, B is a substituted or unsubstituted bridged ring system. In certain embodiments, B is a substituted or unsubstituted heterocyclic bridged ring system.

In certain embodiments, B is of formula:

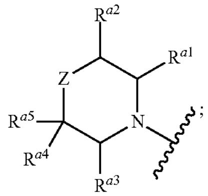

wherein Z is —O—, —$NCH_3$—, —C(═O)—, —C(═NOH)—, or —$CHR^6$—; $R^{a1}$ is hydrogen or is joined with $R^{a3}$ or $R^{a4}$ to form a 1-4 carbon bridge; $R^{a2}$ is hydrogen or is joined with $R^{a3}$ or $R^{a4}$ to form a 1-4 carbon bridge; $R^{a3}$ is hydrogen or is joined with $R^{a1}$ or $R^{a2}$ to form a 1-4 carbon bridge; $R^{a4}$ is hydrogen or is joined with $R^{a1}$ or $R^{a2}$ to form a 1-4 carbon bridge; RV is hydrogen or is joined with $R^{a5}$ to form a substituted or unsubstituted cycloalkyl; and $R^{a5}$ is hydrogen or is joined with $R^{a5}$ to form a substituted or unsubstituted cycloalkyl.

In certain embodiments, B is of formula:

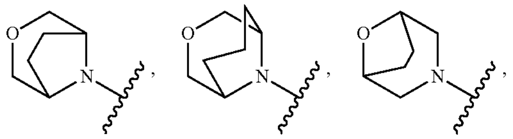

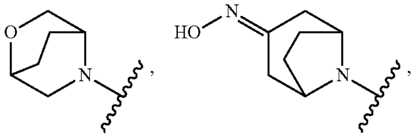

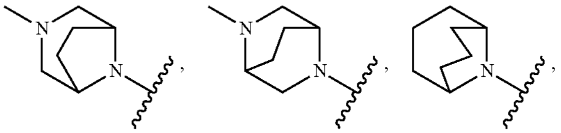

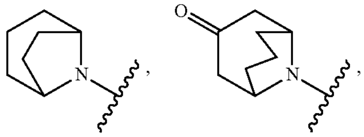

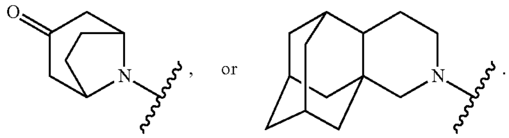

In certain embodiments, B is of formula:

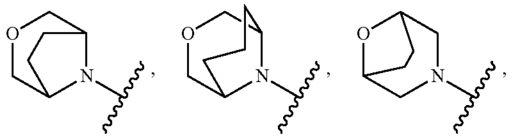

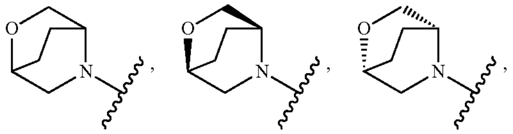

-continued

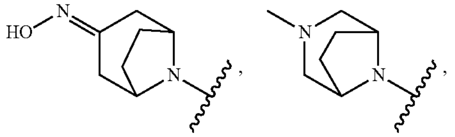

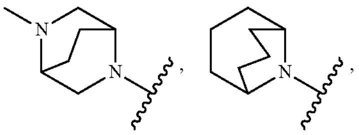

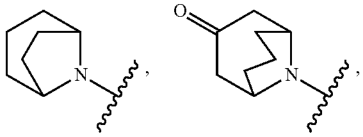

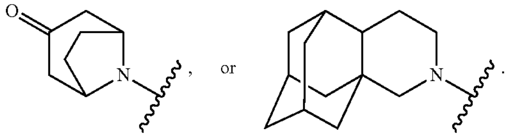

In certain embodiments, B is of formula:

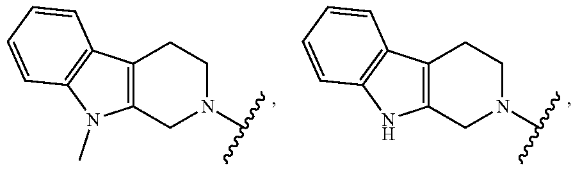

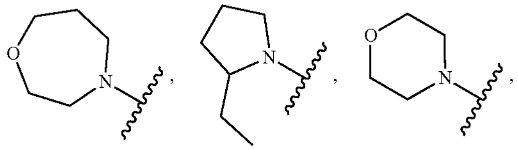

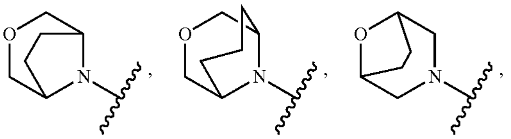

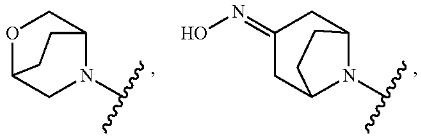

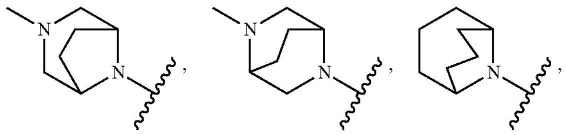

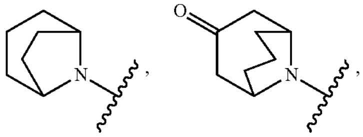

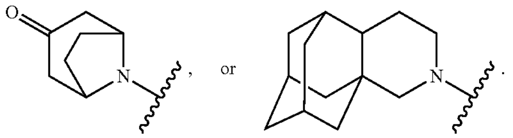

In certain embodiments, B is of formula:
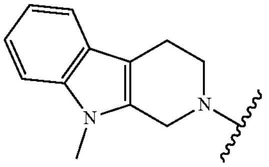, 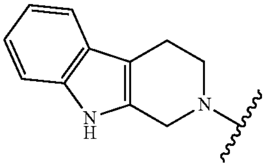,
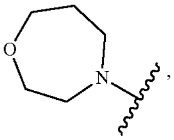, 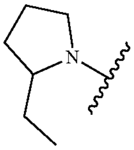, 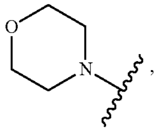,
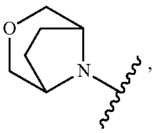, 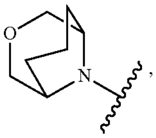, 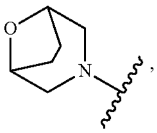,
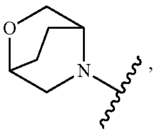, 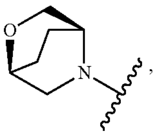, 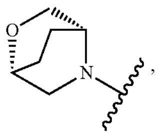,
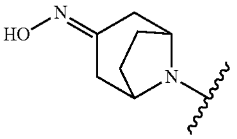, 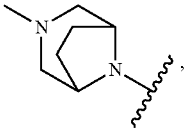,
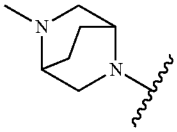, 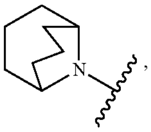, 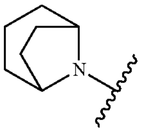,
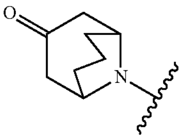, 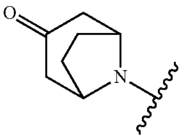, or
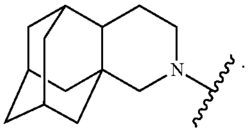.
In certain embodiments, B is of formula:
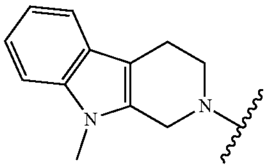 or
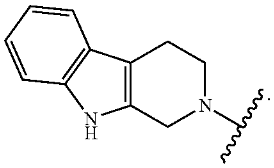.
In certain embodiments, B is of formula:
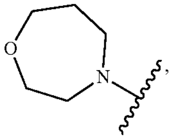, 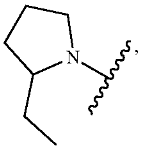, or
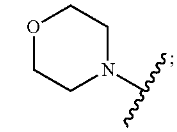;
In certain embodiments, B is of formula:
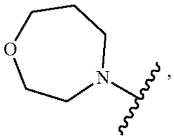, 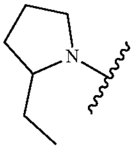, 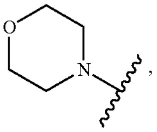,
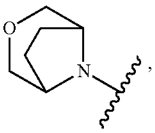, 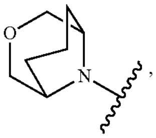, 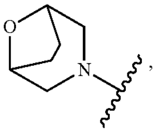,
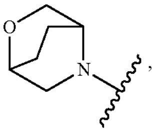, 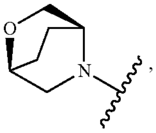, 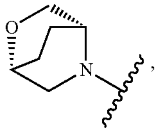,
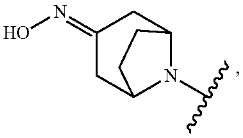, 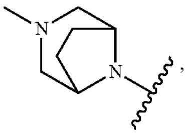,
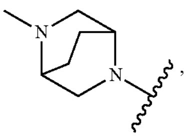, 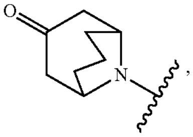, or
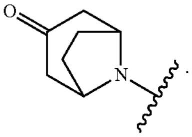.
In certain embodiments, B is of formula:
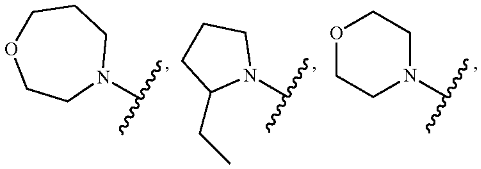
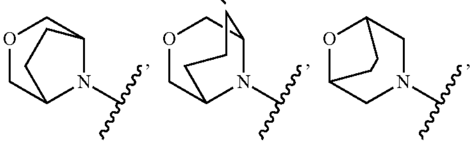

-continued

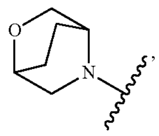

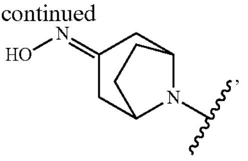

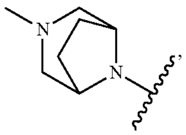

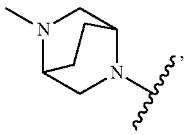

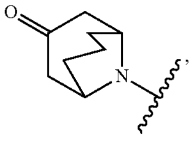

or

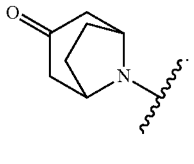

$R^1$ and $R^2$

As described herein, $R^1$ is hydrogen or substituted or unsubstituted alkyl; and $R^2$ is hydrogen or substituted or unsubstituted alkyl; or $R^1$ and $R^2$ together form a substituted or unsubstituted heterocyclyl, or a substituted or unsubstituted cycloalkyl.

In certain embodiments, $R^1$ is hydrogen; and $R^2$ is unsubstituted $C_{1-4}$ alkyl; or $R^1$ and $R^2$ together form an unsubstituted cycloalkyl. In certain embodiments, $R^1$ is hydrogen; and $R^2$ is unsubstituted $C_{1-4}$ alkyl; or $R^1$ and $R^2$ together form an unsubstituted $C_{3-6}$ cycloalkyl. In certain embodiments, $R^1$ is hydrogen; and $R^2$ is methyl or ethyl; or $R^1$ and $R^2$ together form an unsubstituted $C_{3-6}$ cycloalkyl. In certain embodiments, $R^1$ is hydrogen; and $R^2$ is methyl or ethyl; or $R^1$ and $R^2$ together form an unsubstituted cyclobutyl. In certain embodiments, $R^1$ is hydrogen; and $R^2$ is unsubstituted $C_{1-4}$ alkyl. In certain embodiments, $R^1$ is hydrogen; and $R^2$ is methyl or ethyl. In certain embodiments, $R^1$ is hydrogen; and $R^2$ is methyl. In certain embodiments, $R^1$ is hydrogen; and $R^2$ is ethyl.

In certain embodiments, $R^1$ is unsubstituted $C_{1-4}$ alkyl; and $R^2$ is hydrogen; or $R^1$ and $R^2$ together form an unsubstituted cycloalkyl. In certain embodiments, $R^1$ is unsubstituted $C_{1-4}$ alkyl; and $R^2$ is hydrogen; or $R^1$ and $R^2$ together form an unsubstituted $C_{3-6}$ cycloalkyl. In certain embodiments, $R^1$ is methyl or ethyl; and $R^2$ is hydrogen; or $R^1$ and $R^2$ together form an unsubstituted $C_{3-6}$ cycloalkyl. In certain embodiments, $R^1$ is methyl or ethyl; and $R^2$ is hydrogen; or $R^1$ and $R^2$ together form an unsubstituted cyclobutyl.

In certain embodiments, $R^1$ is unsubstituted $C_{1-4}$ alkyl; and $R^2$ is hydrogen. In certain embodiments, $R^1$ is methyl or ethyl; and $R^2$ is hydrogen. In certain embodiments, $R^1$ is methyl; and $R^2$ is hydrogen. In certain embodiments, $R^1$ is ethyl; and $R^2$ is hydrogen.

In certain embodiments, $R^1$ is hydrogen; and $R^2$ is unsubstituted $C_{1-4}$ alkyl. In certain embodiments, $R^1$ is hydrogen; and $R^2$ is methyl or ethyl. In certain embodiments, $R^1$ is hydrogen; and $R^2$ is methyl. In certain embodiments, $R^1$ is hydrogen; and $R^2$ is ethyl.

In certain embodiments, $R^1$ and $R^2$ together form a substituted or unsubstituted cycloalkyl. In certain embodiments, $R^1$ and $R^2$ together form an unsubstituted cycloalkyl. In certain embodiments, $R^1$ and $R^2$ together form an unsubstituted $C_{3-6}$ cycloalkyl. In certain embodiments, $R^1$ and $R^2$ together form an unsubstituted cyclopropyl. In certain embodiments, $R^1$ and $R^2$ together form an unsubstituted cyclobutyl. In certain embodiments, $R^1$ and $R^2$ together form an unsubstituted cyclopentyl. In certain embodiments, $R^1$ and $R^2$ together form an unsubstituted cyclohexyl.

In certain embodiments, $R^1$ is hydrogen; and $R^2$ is hydrogen.

Certain Embodiments

In certain embodiments, the compound of Formula (III) is of Formula (III-a):

(III-a)

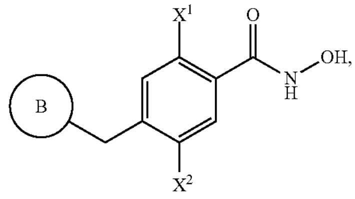

or a pharmaceutically acceptable salt, co-crystal, tautomer, stereoisomer, solvate, hydrate, polymorph, isotopically enriched derivative, or prodrug thereof; wherein B, $X^1$, and $X^2$ are as defined herein.

In certain embodiments, the compound of Formula (III) is of Formula (III-b):

(III-b)

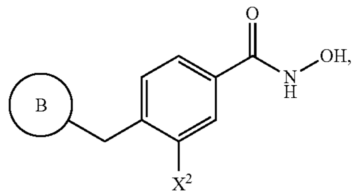

or a pharmaceutically acceptable salt, co-crystal, tautomer, stereoisomer, solvate, hydrate, polymorph, isotopically enriched derivative, or prodrug thereof; wherein B and $X^2$ are as defined herein.

In certain embodiments, the compound of Formula (III) is of Formula (III-c):

(III-c)

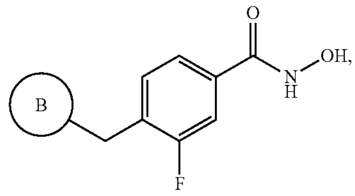

or a pharmaceutically acceptable salt, co-crystal, tautomer, stereoisomer, solvate, hydrate, polymorph, isotopically enriched derivative, or prodrug thereof; wherein B is as defined herein.

Compounds of Formula (IV)

In certain embodiments of the compound of Formula (III), B is a substituted or unsubstituted polycyclic spiro ring system. In certain embodiments, the compound of Formula (III) is of Formula (IV):

(IV)

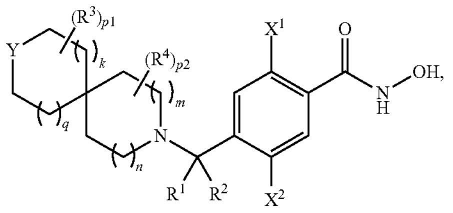

or a pharmaceutically acceptable salt, co-crystal, tautomer, stereoisomer, solvate, hydrate, polymorph, isotopically enriched derivative, or prodrug thereof, wherein:

$X^1$ is hydrogen or fluoro;

$X^2$ is hydrogen or fluoro;

$R^1$ is hydrogen or substituted or unsubstituted alkyl;

$R^2$ is hydrogen or substituted or unsubstituted alkyl; or $R^1$ and $R^2$ together form a substituted or unsubstituted heterocyclyl, or a substituted or unsubstituted cycloalkyl;

Y is —O—, —S—, —$NR^{a1}$—, or —($CR^3R^4$)—;

each occurrence of $R^3$ and $R^4$ is, independently, hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted heteroalkyl, —$N(R^{a1})_2$, —$OR^{b1}$, —$SR^{c1}$, or —CN; wherein two or three $R^3$ groups are optionally joined to form a substituted or unsubstituted bridged ring; wherein two or three $R^4$ groups are optionally joined to form a substituted or unsubstituted bridged ring;

each occurrence of $R^{a1}$ is, independently, hydrogen, substituted or unsubstituted acyl, substituted or unsubstituted alkyl, substituted or unsubstituted heteroalkyl, substituted or unsubstituted carbocyclyl, substituted or unsubstituted heterocyclyl, or a nitrogen protecting group, or two $R^{a1}$ groups are joined to form a substituted or unsubstituted heterocyclic ring;

each occurrence of $R^{b1}$ is, independently, hydrogen, substituted or unsubstituted acyl, substituted or unsubstituted alkyl, substituted or unsubstituted alkenyl, substituted or unsubstituted alkynyl, substituted or unsubstituted heteroalkyl, substituted or unsubstituted carbocyclyl, substituted or unsubstituted heterocyclyl, or an oxygen protecting group;

each occurrence of $R^{c1}$ is, independently, hydrogen, substituted or unsubstituted acyl, substituted or unsubstituted alkyl, substituted or unsubstituted alkenyl, substituted or unsubstituted alkynyl, substituted or unsubstituted heteroalkyl, substituted or unsubstituted carbocyclyl, substituted or unsubstituted heterocyclyl, or a sulfur protecting group;

m, n, k, and q are each independently 0, 1, or 2; and p1 and p2 are each independently 0, 1, 2, 3, or 4; provided the compound is not of formula:

64

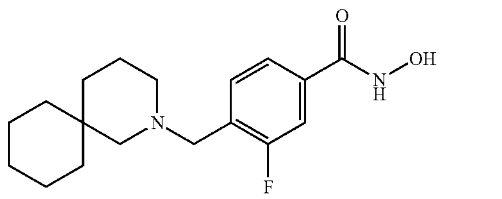

-continued

169

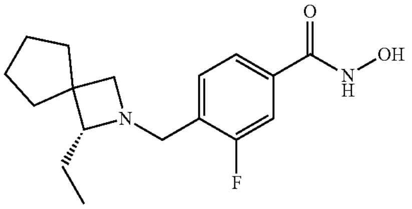

168

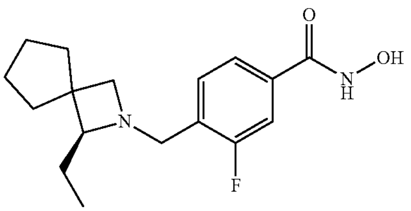

67

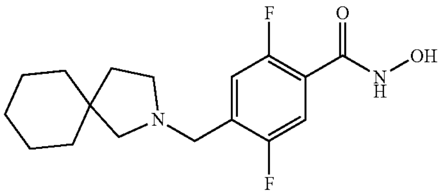

68

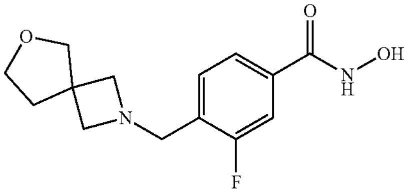

69

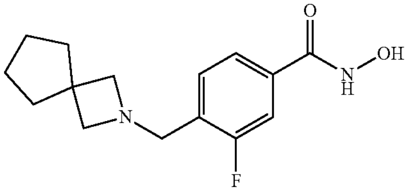

70

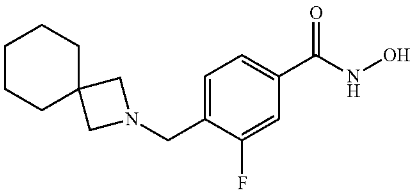

71

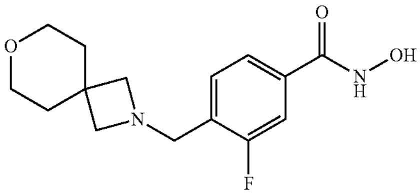

-continued

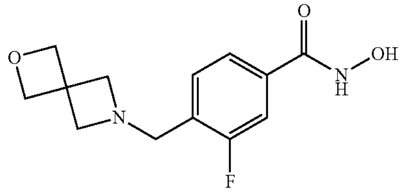

72

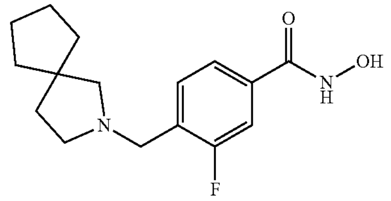

73

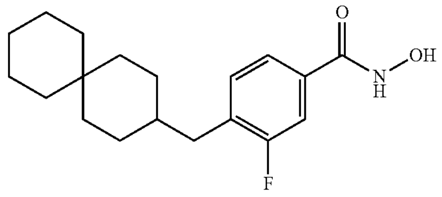

74

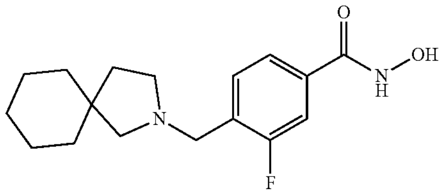

75

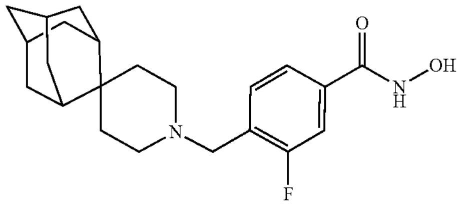

167

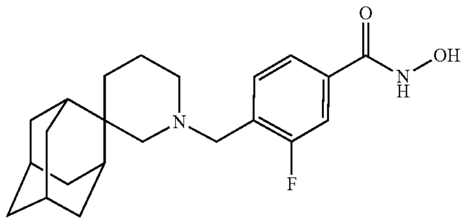

77 or

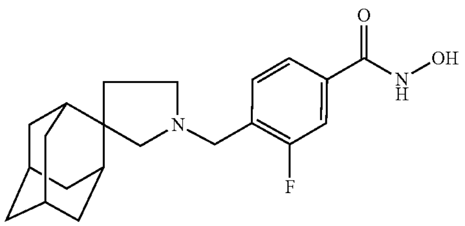

78

$X^1$ and $X^2$

In certain embodiments, $X^1$ is hydrogen or fluoro; and $X^2$ is hydrogen or fluoro; provided that at least one of $X^1$ and $X^2$ is fluoro. In certain embodiments, $X^1$ is hydrogen; and $X^2$ is fluoro. In certain embodiments, $X^1$ is fluoro; and $X^2$ is hydrogen. In certain embodiments, $X^1$ is fluoro; and $X^2$ is fluoro. In certain embodiments, $X^1$ is hydrogen; and $X^2$ is hydrogen.

$R^1$ and $R^2$

In certain embodiments, $R^1$ is hydrogen; and $R^2$ is unsubstituted $C_{1-4}$ alkyl; or $R^1$ and $R^2$ together form an unsubstituted cycloalkyl. In certain embodiments, $R^1$ is hydrogen; and $R^2$ is unsubstituted $C_{1-4}$ alkyl; or $R^1$ and $R^2$ together form an unsubstituted $C_{3-6}$ cycloalkyl. In certain embodiments, $R^1$ is hydrogen; and $R^2$ is methyl or ethyl; or $R^1$ and $R^2$ together form an unsubstituted $C_{3-6}$ cycloalkyl. In certain embodiments, $R^1$ is hydrogen; and $R^2$ is methyl or ethyl; or $R^1$ and $R^2$ together form an unsubstituted cyclobutyl. In certain embodiments, $R^1$ is hydrogen; and $R^2$ is unsubstituted $C_{1-4}$ alkyl. In certain embodiments, $R^1$ is hydrogen; and $R^2$ is methyl or ethyl. In certain embodiments, $R^1$ is hydrogen; and $R^2$ is methyl. In certain embodiments, $R^1$ is hydrogen; and $R^2$ is ethyl.

In certain embodiments, $R^1$ is unsubstituted $C_{1-4}$ alkyl; and $R^2$ is hydrogen; or $R^1$ and $R^2$ together form an unsubstituted cycloalkyl. In certain embodiments, $R^1$ is unsubstituted $C_{1-4}$ alkyl; and $R^2$ is hydrogen; or $R^1$ and $R^2$ together form an unsubstituted $C_{3-6}$ cycloalkyl. In certain embodiments, $R^1$ is methyl or ethyl; and $R^2$ is hydrogen; or $R^1$ and $R^2$ together form an unsubstituted $C_{3-6}$ cycloalkyl. In certain embodiments, $R^1$ is methyl or ethyl; and $R^2$ is hydrogen; or $R^1$ and $R^2$ together form an unsubstituted cyclobutyl.

In certain embodiments, $R^1$ is unsubstituted $C_{1-4}$ alkyl; and $R^2$ is hydrogen. In certain embodiments, $R^1$ is methyl or ethyl; and $R^2$ is hydrogen. In certain embodiments, $R^1$ is methyl; and $R^2$ is hydrogen. In certain embodiments, $R^1$ is ethyl; and $R^2$ is hydrogen.

In certain embodiments, $R^1$ is hydrogen; and $R^2$ is unsubstituted $C_{1-4}$ alkyl. In certain embodiments, $R^1$ is hydrogen; and $R^2$ is methyl or ethyl. In certain embodiments, $R^1$ is hydrogen; and $R^2$ is methyl. In certain embodiments, $R^1$ is hydrogen; and $R^2$ is ethyl.

In certain embodiments, $R^1$ and $R^2$ together form a substituted or unsubstituted cycloalkyl. In certain embodiments, $R^1$ and $R^2$ together form an unsubstituted cycloalkyl. In certain embodiments, $R^1$ and $R^2$ together form an unsubstituted $C_{3-6}$ cycloalkyl. In certain embodiments, $R^1$ and $R^2$ together form an unsubstituted cyclobutyl.

In certain embodiments, $R^1$ is hydrogen; and $R^2$ is hydrogen.

B

As described herein, Y is —O—, —S—, —$NR^{a1}$—, or —($CR^3R^4$)—;

- each occurrence of $R^3$ and $R^4$ is, independently, hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted heteroalkyl, —$N(R^{a1})_2$, —$OR^{b1}$, —$SR^{c1}$, or —CN; wherein two or three $R^3$ groups are optionally joined to form a substituted or unsubstituted bridged ring; wherein two or three $R^4$ groups are optionally joined to form a substituted or unsubstituted bridged ring;
- each occurrence of $R^{a1}$ is, independently, hydrogen, substituted or unsubstituted acyl, substituted or unsubstituted alkyl, substituted or unsubstituted heteroalkyl, substituted or unsubstituted carbocyclyl, substituted or unsubstituted heterocyclyl, or a nitrogen protecting group, or two $R^{a1}$ groups are joined to form a substituted or unsubstituted heterocyclic ring;

each occurrence of $R^{b1}$ is, independently, hydrogen, substituted or unsubstituted acyl, substituted or unsubstituted alkyl, substituted or unsubstituted alkenyl, substituted or unsubstituted alkynyl, substituted or unsubstituted heteroalkyl, substituted or unsubstituted carbocyclyl, substituted or unsubstituted heterocyclyl, or an oxygen protecting group;

each occurrence of $R^{c1}$ is, independently, hydrogen, substituted or unsubstituted acyl, substituted or unsubstituted alkyl, substituted or unsubstituted alkenyl, substituted or unsubstituted alkynyl, substituted or unsubstituted heteroalkyl, substituted or unsubstituted carbocyclyl, substituted or unsubstituted heterocyclyl, or a sulfur protecting group;

m, n, k, and q are each independently 0, 1, or 2; and p1 and p2 are each independently 0, 1, 2, 3, or 4.

In certain embodiments, Y is —O—, —($CR^3R^4$)—, or —$NR^{a1}$—; and $R^3$, $R^4$, and $R^{a1}$ are as defined herein. In certain embodiments, Y is —O—. In certain embodiments, Y is —($CR^3R^4$)—; and $R^3$, $R^4$, and $R^{a1}$ are as defined herein. In certain embodiments, Y is —$NR^{a1}$—; and $R^{a1}$ is as defined herein.

In certain embodiments, Y is —O—, —($CR^3R^4$)—, or —$NR^{a1}$—; each occurrence of $R^3$ and $R^4$ is, independently, hydrogen, halogen, substituted or unsubstituted alkyl; wherein two or three $R^3$ groups are optionally joined to form a substituted or unsubstituted bridged ring; wherein two or three $R^4$ groups are optionally joined to form a substituted or unsubstituted bridged ring; and each occurrence of $R^{a1}$ is, independently, hydrogen, substituted or unsubstituted acyl, substituted or unsubstituted alkyl, substituted or unsubstituted heteroalkyl, substituted or unsubstituted carbocyclyl, substituted or unsubstituted heterocyclyl, or a nitrogen protecting group.

In certain embodiments, Y is —O—, —($CR^3R^4$)—, or —$NR^{a1}$—; each occurrence of $R^3$ and $R^4$ is, independently, hydrogen, halogen, substituted or unsubstituted alkyl; wherein two or three $R^3$ groups are optionally joined to form a substituted or unsubstituted bridged ring; wherein two or three $R^4$ groups are optionally joined to form a substituted or unsubstituted bridged ring; each occurrence of $R^{a1}$ is, independently, hydrogen, substituted or unsubstituted acyl, substituted or unsubstituted alkyl, substituted or unsubstituted heteroalkyl, substituted or unsubstituted carbocyclyl, substituted or unsubstituted heterocyclyl, or a nitrogen protecting group; the sum of m and n is 0, 1, or 2; and the sum of k and q is 0, 1, or 2.

In certain embodiments, Y is —O—, —($CR^3R^4$)—, or —$NR^{a1}$—; each occurrence of $R^3$ and $R^4$ is, independently, hydrogen, halogen, substituted or unsubstituted alkyl; wherein two or three $R^3$ groups are optionally joined to form a substituted or unsubstituted bridged ring; wherein two or three $R^4$ groups are optionally joined to form a substituted or unsubstituted bridged ring; and each occurrence of $R^{a1}$ is, independently, hydrogen, substituted or unsubstituted acyl, substituted or unsubstituted alkyl, or a nitrogen protecting group.

In certain embodiments, Y is —O—, —($CR^3R^4$)—, or —$NR^{a1}$—; each occurrence of $R^3$ and $R^4$ is, independently, hydrogen, halogen, substituted or unsubstituted alkyl; wherein two or three $R^3$ groups are optionally joined to form a substituted or unsubstituted bridged ring; wherein two or three $R^4$ groups are optionally joined to form a substituted or unsubstituted bridged ring; each occurrence of $R^{a1}$ is, independently, hydrogen, substituted or unsubstituted acyl, substituted or unsubstituted alkyl, or a nitrogen protecting group; the sum of m and n is 0, 1, or 2; and the sum of k and q is 0, 1, or 2.

In certain embodiments, Y is —O—, —($CR^3R^4$)—, or —$NR^{a1}$—; each occurrence of $R^3$ and $R^4$ is, independently, hydrogen, or substituted or unsubstituted alkyl; wherein two or three $R^3$ groups are optionally joined to form a substituted or unsubstituted bridged ring; and each occurrence of $R^{a1}$ is, independently, hydrogen, substituted or unsubstituted acyl, substituted or unsubstituted alkyl, or a nitrogen protecting group.

In certain embodiments, Y is —O—, —($CR^3R^4$)—, or —$NR^{a1}$—; each occurrence of $R^3$ and $R^4$ is, independently, hydrogen, or substituted or unsubstituted alkyl; wherein two or three $R^3$ groups are optionally joined to form a substituted or unsubstituted bridged ring; each occurrence of $R^{a1}$ is, independently, hydrogen, substituted or unsubstituted acyl, substituted or unsubstituted alkyl, or a nitrogen protecting group; the sum of m and n is 0, 1, or 2; and the sum of k and q is 0, 1, or 2.

In certain embodiments, Y is —$NR^{a1}$—; each occurrence of $R^3$ and $R^4$ is, independently, hydrogen, or substituted or unsubstituted alkyl; wherein two or three $R^3$ groups are optionally joined to form a substituted or unsubstituted bridged ring; and each occurrence of $R^{a1}$ is, independently, hydrogen, substituted or unsubstituted acyl, substituted or unsubstituted alkyl, or a nitrogen protecting group.

In certain embodiments, Y is —$NR^{a1}$—; each occurrence of $R^3$ and $R^4$ is, independently, hydrogen, or substituted or unsubstituted alkyl; wherein two or three $R^3$ groups are optionally joined to form a substituted or unsubstituted bridged ring; each occurrence of $R^{a1}$ is, independently, hydrogen, substituted or unsubstituted acyl, substituted or unsubstituted alkyl, or a nitrogen protecting group; the sum of m and n is 0, 1, or 2; and the sum of k and q is 0, 1, or 2.

In certain embodiments, Y is —O— or —($CR^3R^4$)—; and each occurrence of $R^3$ and $R^4$ is, independently, hydrogen, halogen, or substituted or unsubstituted alkyl; wherein two or three $R^3$ groups are optionally joined to form a substituted or unsubstituted bridged ring; wherein two or three $R^4$ groups are optionally joined to form a substituted or unsubstituted bridged ring.

In certain embodiments, Y is —O— or —($CR^3R^4$)—; each occurrence of $R^3$ and $R^4$ is, independently, hydrogen, halogen, or substituted or unsubstituted alkyl; wherein two or three $R^3$ groups are optionally joined to form a substituted or unsubstituted bridged ring; wherein two or three $R^4$ groups are optionally joined to form a substituted or unsubstituted bridged ring; the sum of m and n is 0, 1, or 2; and the sum of k and q is 0, 1, or 2.

In certain embodiments, Y is —O— or —($CR^3R^4$)—; and each occurrence of $R^3$ and $R^4$ is, independently, hydrogen, or substituted or unsubstituted alkyl; wherein two or three $R^3$ groups are optionally joined to form a substituted or unsubstituted bridged ring.

In certain embodiments, Y is —O— or —($CR^3R^4$)—; each occurrence of $R^3$ and $R^4$ is, independently, hydrogen, or substituted or unsubstituted alkyl; wherein two or three $R^3$ groups are optionally joined to form a substituted or unsubstituted bridged ring; the sum of m and n is 0, 1, or 2; and the sum of k and q is 0, 1, or 2.

In certain embodiments, Y is —O—; and each occurrence of $R^3$ and $R^4$ is, independently, hydrogen, halogen, or substituted or unsubstituted alkyl; wherein two or three $R^3$ groups are optionally joined to form a substituted or unsubstituted bridged ring; wherein two or three $R^4$ groups are optionally joined to form a substituted or unsubstituted bridged ring.

In certain embodiments, Y is —O—; each occurrence of $R^3$ and $R^4$ is, independently, hydrogen, halogen, or substituted or unsubstituted alkyl; wherein two or three $R^3$ groups are optionally joined to form a substituted or unsubstituted bridged ring; wherein two or three $R^4$ groups are optionally joined to form a substituted or unsubstituted bridged ring; the sum of m and n is 0, 1, or 2; and the sum of k and q is 0, 1, or 2.

In certain embodiments, Y is —O—; and each occurrence of $R^3$ and $R^4$ is, independently, hydrogen, or substituted or unsubstituted alkyl; wherein two or three $R^3$ groups are optionally joined to form a substituted or unsubstituted bridged ring.

In certain embodiments, Y is —O—; and each occurrence of $R^3$ and $R^4$ is, independently, hydrogen, or substituted or unsubstituted alkyl; wherein two or three $R^3$ groups are optionally joined to form a substituted or unsubstituted bridged ring; the sum of m and n is 0, 1, or 2; and the sum of k and q is 0, 1, or 2.

In certain embodiments, Y is —$(CR^3R^4)$—; and each occurrence of $R^3$ and $R^4$ is, independently, hydrogen, halogen, or substituted or unsubstituted alkyl; wherein two or three $R^3$ groups are optionally joined to form a substituted or unsubstituted bridged ring; wherein two or three $R^4$ groups are optionally joined to form a substituted or unsubstituted bridged ring.

In certain embodiments, Y is —$(CR^3R^4)$—; each occurrence of $R^3$ and $R^4$ is, independently, hydrogen, halogen, or substituted or unsubstituted alkyl; wherein two or three $R^3$ groups are optionally joined to form a substituted or unsubstituted bridged ring; wherein two or three $R^4$ groups are optionally joined to form a substituted or unsubstituted bridged ring; the sum of m and n is 0, 1, or 2; and the sum of k and q is 0, 1, or 2.

In certain embodiments, Y is —$(CR^3R^4)$—; and each occurrence of $R^3$ and $R^4$ is, independently, hydrogen, or substituted or unsubstituted alkyl; wherein two or three $R^3$ groups are optionally joined to form a substituted or unsubstituted bridged ring.

In certain embodiments, Y is —$(CR^3R^4)$—; each occurrence of $R^3$ and $R^4$ is, independently, hydrogen, or substituted or unsubstituted alkyl; wherein two or three $R^3$ groups are optionally joined to form a substituted or unsubstituted bridged ring; the sum of m and n is 0, 1, or 2; and the sum of k and q is 0, 1, or 2.

In certain embodiments, Y is —$(CHR^3)$—; and each occurrence of $R^3$ and $R^4$ is, independently, hydrogen, halogen, or substituted or unsubstituted alkyl; wherein two or three $R^3$ groups are optionally joined to form a substituted or unsubstituted bridged ring; wherein two or three $R^4$ groups are optionally joined to form a substituted or unsubstituted bridged ring.

In certain embodiments, Y is —$(CHR^3)$—; each occurrence of $R^3$ and $R^4$ is, independently, hydrogen, halogen, or substituted or unsubstituted alkyl; wherein two or three $R^3$ groups are optionally joined to form a substituted or unsubstituted bridged ring; wherein two or three $R^4$ groups are optionally joined to form a substituted or unsubstituted bridged ring; the sum of m and n is 0, 1, or 2; and the sum of k and q is 0, 1, or 2.

In certain embodiments, Y is —$(CHR^3)$—; and each occurrence of $R^3$ and $R^4$ is, independently, hydrogen, or substituted or unsubstituted alkyl; wherein two or three $R^3$ groups are optionally joined to form a substituted or unsubstituted bridged ring.

In certain embodiments, Y is —$(CHR^3)$—; and each occurrence of $R^3$ and $R^4$ is, independently, hydrogen, or substituted or unsubstituted alkyl; wherein two or three $R^3$ groups are optionally joined to form a substituted or unsubstituted bridged ring; the sum of m and n is 0, 1, or 2; and the sum of k and q is 0, 1, or 2.

In certain embodiments, the sum of m and n is 0, 1, or 2. In certain embodiments, m is 0; and n is 0. In certain embodiments, m is 1; and n is 0. In certain embodiments, m is 2; and n is 0. In certain embodiments, m is 0; and n is 1. In certain embodiments, m is 1; and n is 1. In certain embodiments, m is 0; and n is 2.

In certain embodiments, the sum of k and q is 0, 1, or 2. In certain embodiments, k is 0; and q is 0. In certain embodiments, k is 1; and q is 0. In certain embodiments, k is 2; and q is 0. In certain embodiments, k is 0; and q is 1. In certain embodiments, k is 1; and q is 1. In certain embodiments, k is 0; and q is 2.

In certain embodiments, B is of formula:

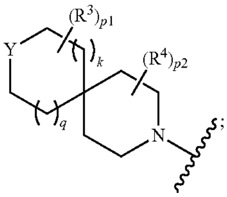
;
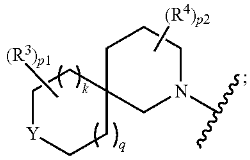
;
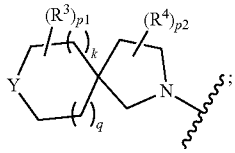
;
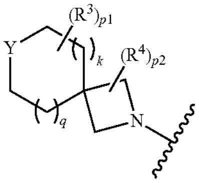
; or
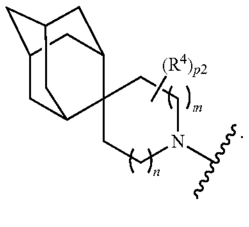
.

In certain embodiment, B is of formula:

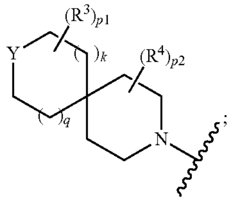
;
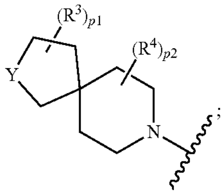
;
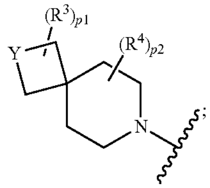
;
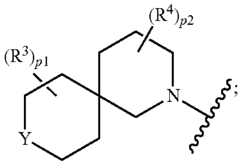
;

-continued

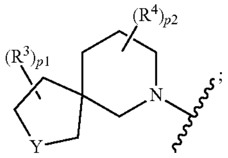

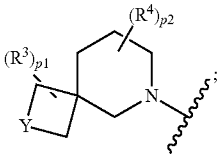

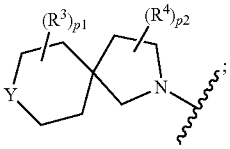

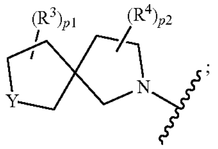

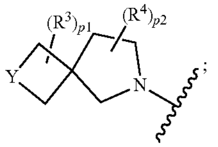

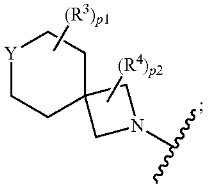

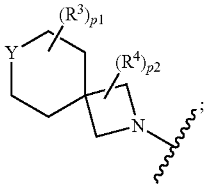

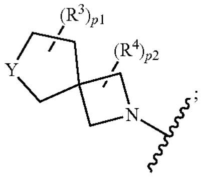

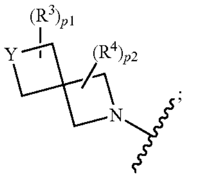

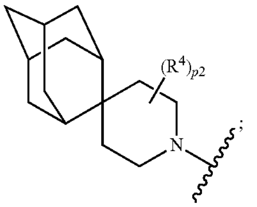

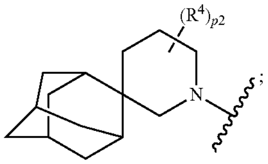

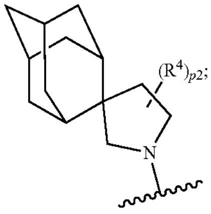

or

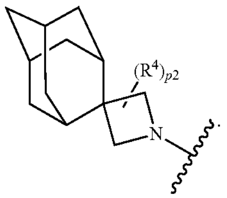

Certain Embodiments

In certain embodiments, the compound of Formula (IV) is of Formula (IV-a):

(IV-a)

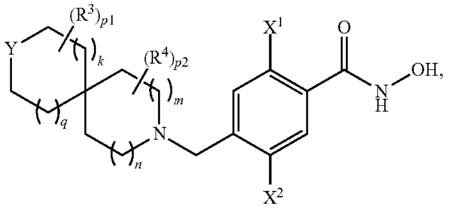

or a pharmaceutically acceptable salt, co-crystal, tautomer, stereoisomer, solvate, hydrate, polymorph, isotopically enriched derivative, or prodrug thereof; wherein $X^1$, $X^2$, $R^3$, $R^4$, Y, p1, p2, m, n, k, and q are as defined herein.

In certain embodiments, the compound of Formula (IV) is of Formula (IV-b):

(IV-b)

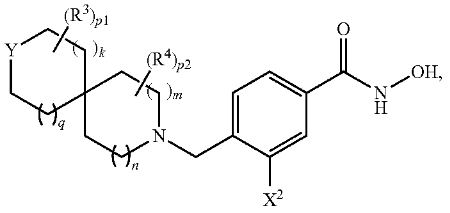

or a pharmaceutically acceptable salt, co-crystal, tautomer, stereoisomer, solvate, hydrate, polymorph, isotopically enriched derivative, or prodrug thereof; wherein $X^2$, $R^3$, $R^4$, Y, p1, p2, m, n, k, and q are as defined herein.

In certain embodiments, the compound of Formula (V) is of Formula (V-c):

(IV-c)

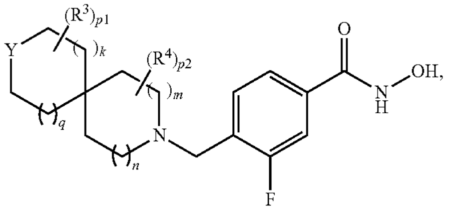

or a pharmaceutically acceptable salt, co-crystal, tautomer, stereoisomer, solvate, hydrate, polymorph, isotopically enriched derivative, or prodrug thereof; wherein $R^3$, $R^4$, Y, p1, p2, m, n, k, and q are as defined herein.

In certain embodiments, the compound of Formula (V) is of Formula (V-d):

(IV-d)

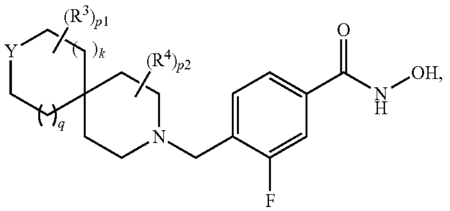

or a pharmaceutically acceptable salt, co-crystal, tautomer, stereoisomer, solvate, hydrate, polymorph, isotopically enriched derivative, or prodrug thereof; wherein $R^3$, $R^4$, Y, p1, p2, k, and q are as defined herein.

In certain embodiments, the compound of Formula (IV) is of Formula (IV-e):

(IV-e)

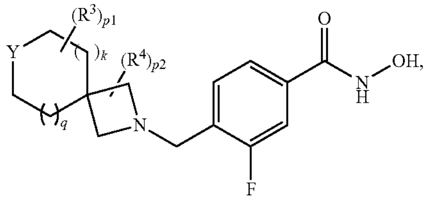

or a pharmaceutically acceptable salt, co-crystal, tautomer, stereoisomer, solvate, hydrate, polymorph, isotopically enriched derivative, or prodrug thereof; wherein $R^3$, $R^4$, Y, p1, p2, k, and q are as defined herein.

In certain embodiments, the compound of Formula (V) is of Formula (IV-f):

(IV-f)

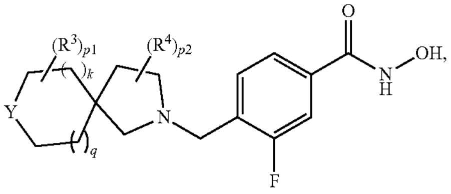

or a pharmaceutically acceptable salt, co-crystal, tautomer, stereoisomer, solvate, hydrate, polymorph, isotopically enriched derivative, or prodrug thereof; wherein $R^3$, $R^4$, Y, p1, p2, k, and q are as defined herein.

In certain embodiments, the compound of Formula (V) is of Formula (IV-g):

(IV-g)

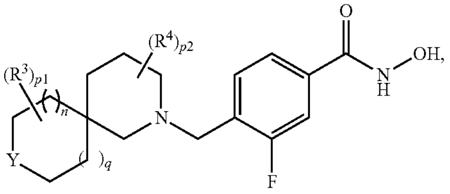

or a pharmaceutically acceptable salt, co-crystal, tautomer, stereoisomer, solvate, hydrate, polymorph, isotopically enriched derivative, or prodrug thereof; wherein $R^3$, $R^4$, Y, p1, p2, k, and q are as defined herein.

In certain embodiments the compound of Formula IV is of Formula (IV-h):

(IV-h)

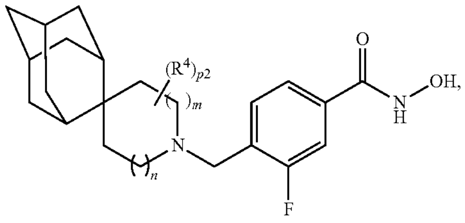

or a pharmaceutically acceptable salt, co-crystal, tautomer, stereoisomer, solvate, hydrate, polymorph, isotopically enriched derivative, or prodrug thereof; wherein $R^4$, p2, m, and n are as defined herein.

In certain embodiments, the compound of Formula (IV) is one of the following compounds, or a pharmaceutically acceptable salt, co-crystal, tautomer, stereoisomer, solvate, hydrate, polymorph, isotopically enriched derivative, or prodrug thereof:

237

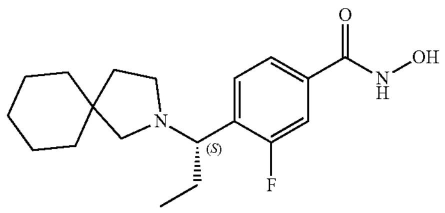

238

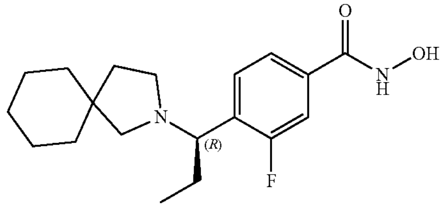

239

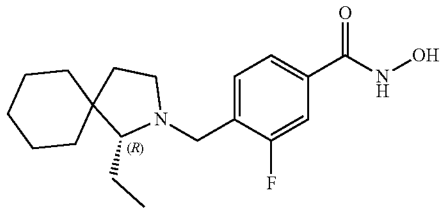

240

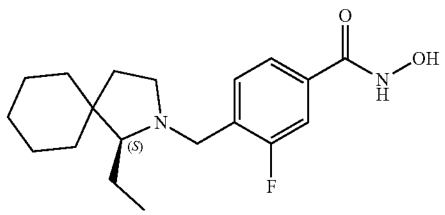

Compounds of Formula (V)

In another aspect, disclosed is a compound of Formula (V):

(V-a)

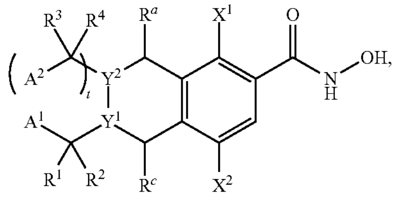

or a pharmaceutically acceptable salt, co-crystal, tautomer, stereoisomer, solvate, hydrate, polymorph, isotopically enriched derivative, or prodrug thereof, wherein:

$X^1$ is hydrogen or fluoro;

$X^2$ is hydrogen or fluoro;

$Y^1$ is nitrogen or $CR^x$;

$Y^2$ is nitrogen, $CR^d$, a bond, —$CH_2$—, or —NH—;

$A^1$ is joined with one of $A^2$, $R^a$, and $R^c$ to form a substituted or unsubstituted ring;

$A^2$ is hydrogen or joined with $A^1$ to form a substituted or unsubstituted ring;

$R^1$ is hydrogen or substituted or unsubstituted alkyl, or $R^1$ is joined with $R^d$, $R^3$, or $R^4$ to form a substituted or unsubstituted ring;

$R^2$ is hydrogen or substituted or unsubstituted alkyl, or $R^2$ is joined with $R^d$, $R^3$, or $R^4$ to form a substituted or unsubstituted ring; or $R^1$ and $R^2$ together form a carbonyl;

$R^3$ is hydrogen or substituted or unsubstituted alkyl, or $R^3$ is joined with $R^1$ or $R^2$ to form a substituted or unsubstituted ring;

$R^4$ is hydrogen or substituted or unsubstituted alkyl, or $R^4$ is joined with $R^1$ or $R^2$ to form a substituted or unsubstituted ring; or $R^3$ and $R^4$ together form a carbonyl;

$R^x$ is hydrogen or substituted or unsubstituted alkyl;

$R^a$ is hydrogen or is joined with $A^1$ to form a substituted or unsubstituted ring;

$R^c$ is hydrogen or is joined with $A^1$ to form a substituted or unsubstituted ring;

$R^d$ is hydrogen or is joined with $R^1$ or $R^2$ to form a substituted or unsubstituted ring; and t is 0 or 1; provided the compound is not of formula:

79

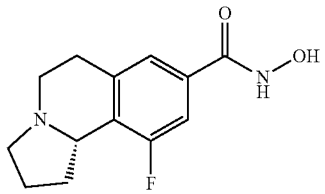

80

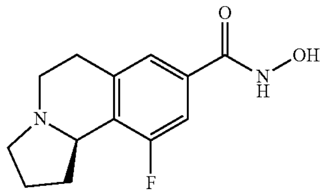

-continued

119

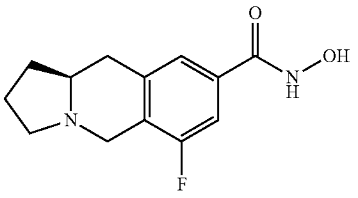

120

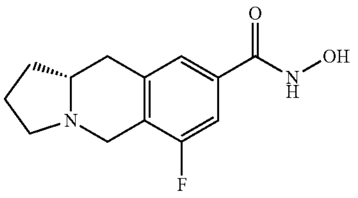

140

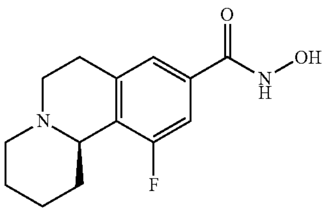

139

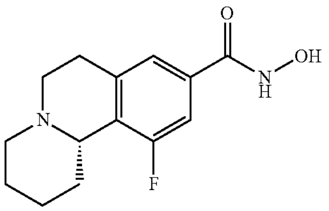

134

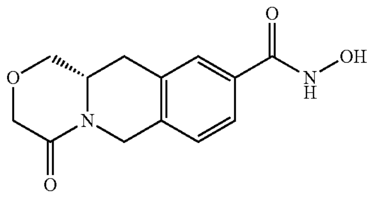

133

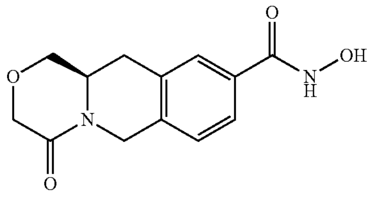

135

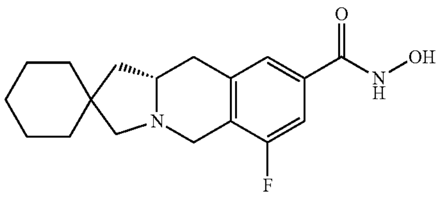

-continued
136
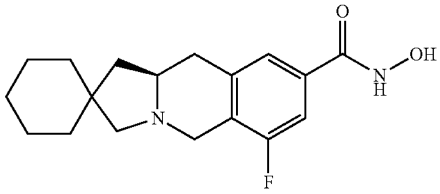
90
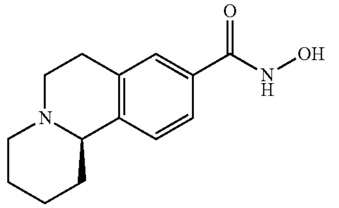
89
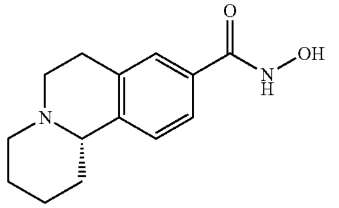
130
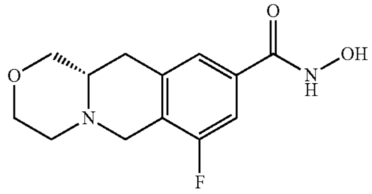
129
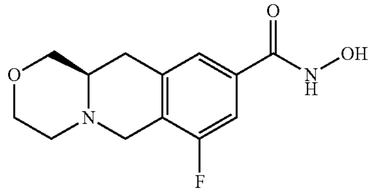
93
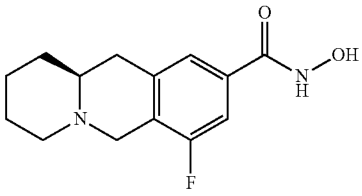
94
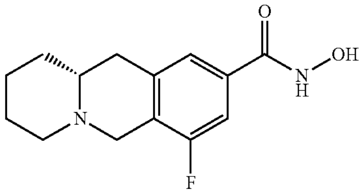
-continued
95
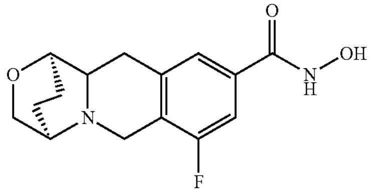
96
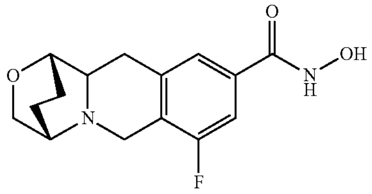
97
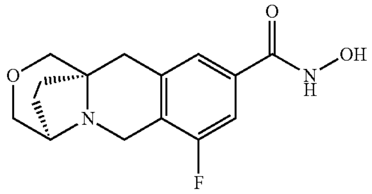
98
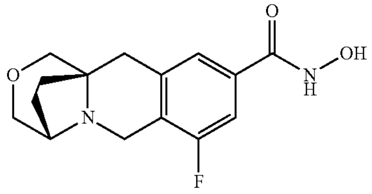
132
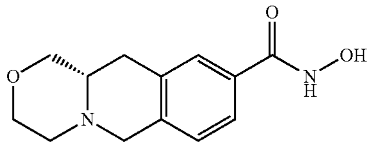
131
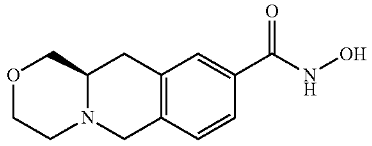
121
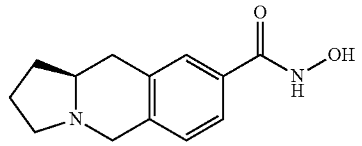
122
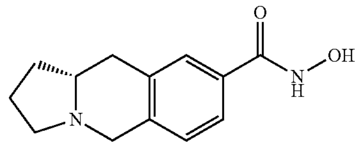
103
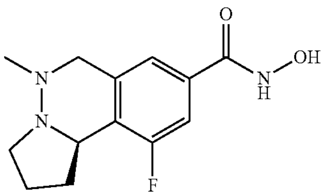

-continued
104
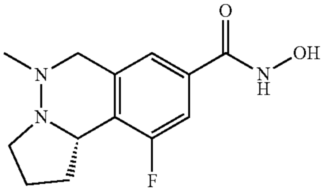
105
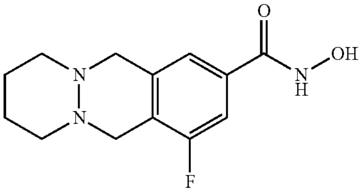
106
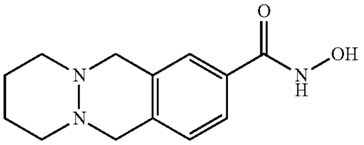
124
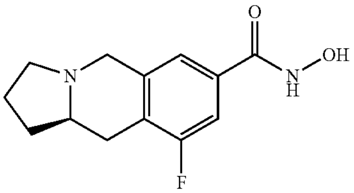
123
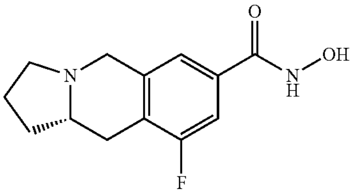
144
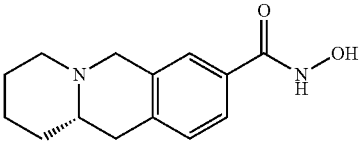
143
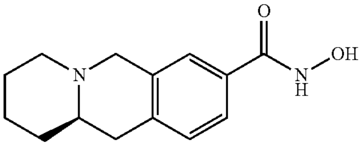
146
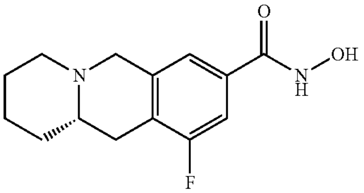
-continued
145
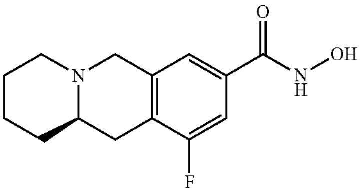
180
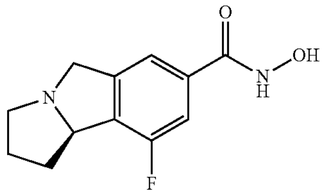
181
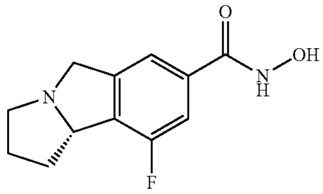
137
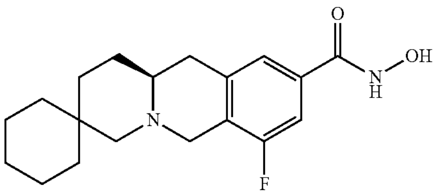
138
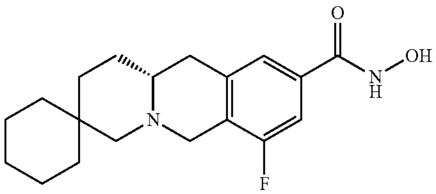
125
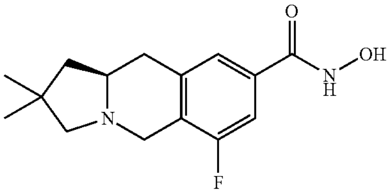
126
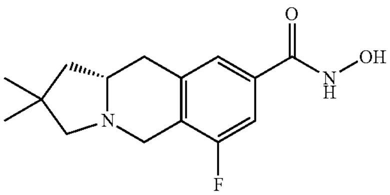
127
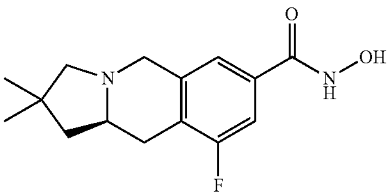

128
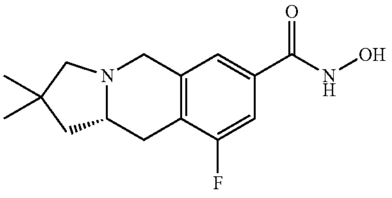
147
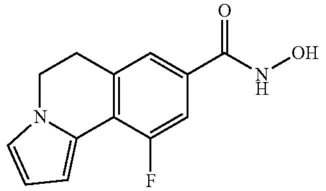
148
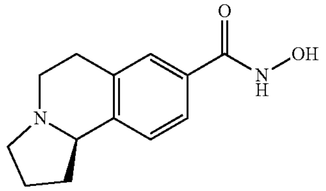
149
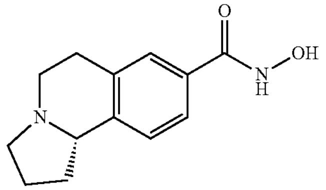
150
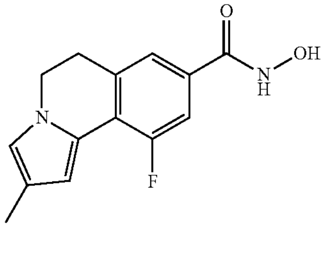
151
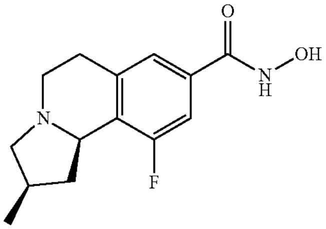
152
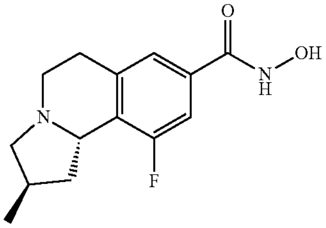
153
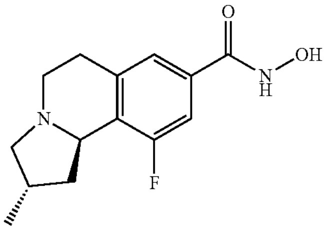
154
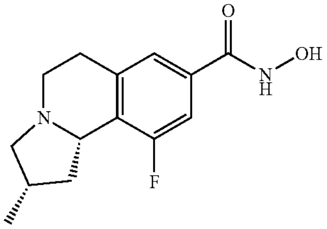
155
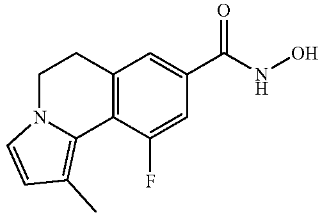
156
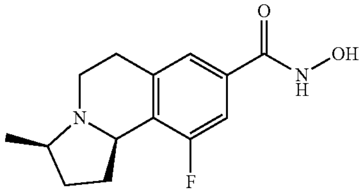
157
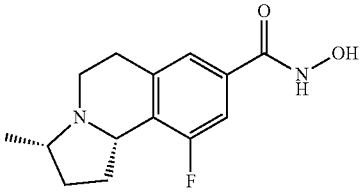
158
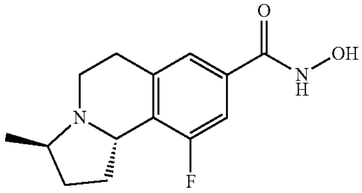
159
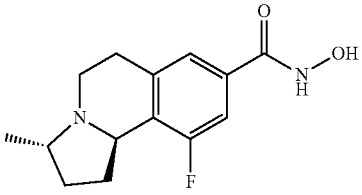

-continued

160

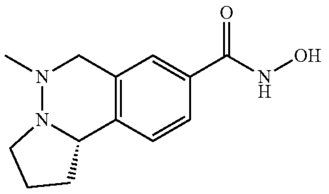

161

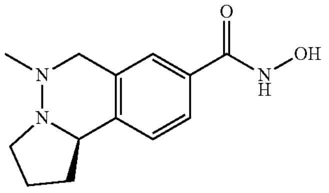

162

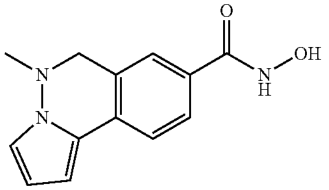

163

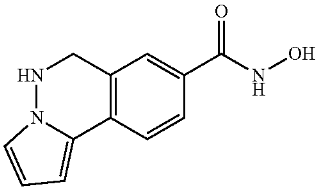

164

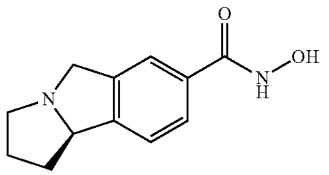

165

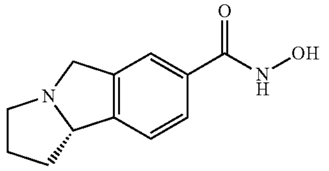

166

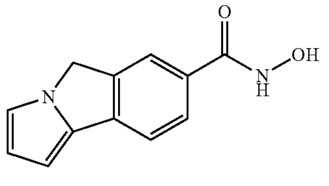

$X^1$ and $X^2$

As described herein, $X^1$ is hydrogen or fluoro; and $X^2$ is hydrogen or fluoro. In certain embodiments, $X^1$ is hydrogen or fluoro; and $X^2$ is hydrogen or fluoro; provided that at least one of $X^1$ and $X^2$ is fluoro. In certain embodiments, $X^1$ is hydrogen; and $X^2$ is fluoro. In certain embodiments, $X^1$ is fluoro; and $X^2$ is hydrogen. In certain embodiments, $X^1$ is fluoro; and $X^2$ is fluoro. In certain embodiments, $X^1$ is hydrogen; and $X^2$ is hydrogen.

$Y^1$ and $Y_2$

As described herein, $Y^1$ is nitrogen or CH. In certain embodiments, $Y^1$ is nitrogen. In certain embodiments, $Y^1$ is CH.

As described herein, $Y^2$ is nitrogen, $CR^d$, a bond, —$CH_2$—, or —NH—; and $R^d$ is hydrogen or is joined with $R^3$ or $R^4$ to form a substituted or unsubstituted ring. In certain embodiments, $Y^2$ is nitrogen, CH, or a bond; or $Y^2$ is —$CH_2$— or —NH— when t is 0. In certain embodiments, $Y^2$ is nitrogen, CH, or a bond. In certain embodiments, $Y^2$ is nitrogen or CH. In certain embodiments, $Y^2$ is nitrogen or a bond. In certain embodiments, $Y^2$ is CH or a bond. In certain embodiments, $Y^2$ is nitrogen. In certain embodiments, $Y^2$ is nitrogen; and $A^2$, $R^3$, and $R^4$ are each substituted or unsubstituted alkyl. In certain embodiments, $Y^2$ is nitrogen; and $A^2$, $R^3$, and $R^4$ are each hydrogen. In certain embodiments, $Y^2$ is a bond. In certain embodiments, $Y^2$ is —$CH_2$— when t is 0. In certain embodiments, $Y^2$ is —NH— when t is 0. In certain embodiments, $Y^2$ is $CR^d$; and $R^d$ is hydrogen or is joined with $R^3$ or $R^4$ to form a substituted or unsubstituted ring. In certain embodiments, $Y^2$ is $CR^d$; and Rd is joined with $R^3$ or $R^4$ to form a substituted or unsubstituted ring. In certain embodiments, $Y^2$ is $CR^d$; and $R^d$ is joined with $R^3$ or $R^4$ to form a substituted or unsubstituted bridged ring.

In certain embodiments, $Y^1$ is nitrogen; and $Y^2$ is nitrogen, $CR^d$, a bond, —$CH_2$—, or —NH—; and $R^d$ is hydrogen or is joined with $R^3$ or $R^4$ to form a substituted or unsubstituted ring. In certain embodiments, $Y^1$ is nitrogen; and $Y^2$ is nitrogen, $CR^d$, a bond, —$CH_2$—, or —NH—. In certain embodiments, $Y^1$ is nitrogen; and $Y^2$ is nitrogen, CH, or a bond. In certain embodiments, $Y^1$ is nitrogen; and $Y^2$ is nitrogen. In certain embodiments, $Y^1$ is nitrogen; and $Y^2$ is CH. In certain embodiments, $Y^1$ is nitrogen; and $Y^2$ is a bond. In certain embodiments, $Y^1$ is nitrogen; and $Y^2$ is —$CH_2$— or —NH— when t is 0. In certain embodiments, $Y^1$ is nitrogen; and $Y^2$ is —$CH_2$— when t is 0. In certain embodiments, $Y^1$ is nitrogen; $Y^2$ is $CR^d$; and $R^d$ is joined with $R^3$ or $R^4$ to form a substituted or unsubstituted ring. In certain embodiments, $Y^1$ is nitrogen; $Y^2$ is $CR^d$; and $R^d$ is joined with $R^3$ or $R^4$ to form a substituted or unsubstituted bridged ring.

$A^1$ and $A^2$

As described herein, $A^1$ is joined with one of $A^2$, $R^a$, and $R^c$ to form a substituted or unsubstituted ring. In certain embodiments, $A^1$ is joined with one of $A^2$, $R^a$, and $R^c$ to form a substituted or unsubstituted 5 or 6-membered ring. In certain embodiments, $A^1$ is joined with one of $A^2$, $R^a$, and $R^c$ to form a substituted or unsubstituted 5 or 6-membered heteroaryl, heterocyclyl, or cycloalkyl ring. In certain embodiments, $A^1$ is joined with one of $A^2$, $R^a$, and $R^c$ to form a substituted or unsubstituted 5 or 6-membered heterocyclyl or cycloalkyl ring. In certain embodiments, $A^1$ is joined with one of $A^2$, $R^a$, and $R^c$ to form a substituted or unsubstituted 5 or 6-membered heteroaryl ring. In certain embodiments, $A^1$ is joined with one of $A^2$, $R^a$, and $R^c$ to form a substituted or unsubstituted 5 or 6-membered heterocyclyl ring. In certain embodiments, $A^1$ is joined with one of $A^2$, $R^a$, and $R^c$ to form a substituted or unsubstituted 5 or 6-membered cycloalkyl ring.

In certain embodiments, $A^1$ is joined with $A^2$ to form a substituted or unsubstituted ring. In certain embodiments, $A^1$ is joined with $A^2$ to form a substituted or unsubstituted 5 or 6-membered ring. In certain embodiments, $A^1$ is joined with $A^2$ to form a substituted or unsubstituted 5 or 6-membered heterocyclyl ring. In certain embodiments, $A^1$ is joined with $A^2$ to form a substituted or unsubstituted 5-membered heterocyclyl ring. In certain embodiments, $A^1$ is joined with $A^2$ to form a substituted or unsubstituted 6-membered heterocyclyl ring. In certain embodiments, $A^1$ is joined with $A^2$ to form a substituted or unsubstituted pyrrolidine. In certain embodiments, $A^1$ is joined with $A^2$ to form a substituted or unsubstituted piperidine. In certain embodiments, $A^1$ is joined with $A^2$ to form a substituted or unsubstituted morpholine. In certain embodiments, $A^1$ is joined with $A^2$ to form a substituted or unsubstituted hexahydropyridazine.

In certain embodiments, $A^1$ is joined with $R^a$ to form a substituted or unsubstituted ring. In certain embodiments, $A^1$ is joined with $R^a$ to form a substituted or unsubstituted 5 or 6-membered ring. In certain embodiments, $A^1$ is joined with $R^a$ to form a substituted or unsubstituted 5 or 6-membered heterocyclyl ring. In certain embodiments, $A^1$ is joined with $R^a$ to form a substituted or unsubstituted 5-membered heterocyclyl ring. In certain embodiments, $A^1$ is joined with $R^a$ to form a substituted or unsubstituted 6-membered heterocyclyl ring. In certain embodiments, $A^1$ is joined with $R^a$ to form a substituted or unsubstituted pyrrolidine. In certain embodiments, $A^1$ is joined with $R^a$ to form a substituted or unsubstituted piperidine.

In certain embodiments, $A^1$ is joined with $R^c$ to form a substituted or unsubstituted ring. In certain embodiments, $A^1$ is joined with $R^c$ to form a substituted or unsubstituted 5 or 6-membered ring. In certain embodiments, $A^1$ is joined with $R^c$ to form a substituted or unsubstituted 5 or 6-membered heterocyclyl or heteroaryl ring. In certain embodiments, $A^1$ is joined with $R^c$ to form a substituted or unsubstituted 5 or 6-membered heterocyclyl ring. In certain embodiments, $A^1$ is joined with $R^c$ to form a substituted or unsubstituted 5-membered heterocyclyl ring. In certain embodiments, $A^1$ is joined with $R^c$ to form a substituted or unsubstituted 6-membered heterocyclyl ring. In certain embodiments, $A^1$ is joined with $R^c$ to form a substituted or unsubstituted pyrrolidine. In certain embodiments, $A^1$ is joined with $R^c$ to form a substituted or unsubstituted piperidine. In certain embodiments, $A^1$ is joined with $R^c$ to form a substituted or unsubstituted 5 or 6-membered heteroaryl ring. In certain embodiments, $A^1$ is joined with $R^c$ to form a substituted or unsubstituted 5-membered heteroaryl ring. In certain embodiments, $A^1$ is joined with $R^c$ to form a substituted or unsubstituted 6-membered heteroaryl ring. In certain embodiments, $A^1$ is joined with $R^c$ to form a substituted or unsubstituted pyrrole.

As described herein, $A^2$ is hydrogen or joined with $A^1$ to form a substituted or unsubstituted ring. In certain embodiments, $A^2$ is hydrogen. In certain embodiments, $A^2$ is joined with $A^1$ to form a substituted or unsubstituted ring. In certain embodiments, $A^2$ is joined with $A^1$ to form a substituted or unsubstituted 5 or 6-membered ring. In certain embodiments, $A^2$ is joined with $A^1$ to form a substituted or unsubstituted 5 or 6-membered heterocyclyl ring. In certain embodiments, $A^2$ is joined with $A^1$ to form a substituted or unsubstituted 5-membered heterocyclyl ring. In certain embodiments, $A^2$ is joined with $A^1$ to form a substituted or unsubstituted 6-membered heterocyclyl ring. In certain embodiments, $A^2$ is joined with $A^1$ to form a substituted or unsubstituted pyrrolidine. In certain embodiments, $A^2$ is joined with $A^1$ to form a substituted or unsubstituted piperidine. In certain embodiments, $A^2$ is joined with $A^1$ to form a substituted or unsubstituted morpholine. In certain embodiments, $A^2$ is joined with $A^1$ to form a substituted or unsubstituted hexahydropyridazine.

$R^1$ and $R^2$

As described herein, $R^1$ is hydrogen or substituted or unsubstituted alkyl, or $R^1$ is joined with $R^d$, $R^3$, or $R^4$ to form a substituted or unsubstituted ring. In certain embodiments, $R^1$ is substituted or unsubstituted alkyl. In certain embodiments, $R^1$ is unsubstituted alkyl. In certain embodiments, $R^1$ is unsubstituted $C_{1-6}$ alkyl. In certain embodiments, $R^1$ is unsubstituted $C_{1-4}$ alkyl. In certain embodiments, $R^1$ is hydrogen. In certain embodiments, $R^1$ is joined with $R^d$, $R^3$, or $R^4$ to form a substituted or unsubstituted ring. In certain embodiments, $R^1$ is joined with $R^d$, $R^3$, or $R^4$ to form a substituted or unsubstituted bridged ring. In certain embodiments, $R^1$ is joined with $R^d$, $R^3$, or $R^4$ to form a substituted or unsubstituted 5 or 6-membered bridged ring. In certain embodiments, $R^1$ is joined with $R^d$, $R^3$, or $R^4$ to form a substituted or unsubstituted 5-membered bridged ring. In certain embodiments, $R^1$ is joined with $R^d$, $R^3$, or $R^4$ to form a substituted or unsubstituted 6-membered bridged ring. In certain embodiments, $R^1$ is joined with $R^d$ to form a substituted or unsubstituted ring. In certain embodiments, $R^1$ is joined with $R^d$ to form a substituted or unsubstituted bridged ring. In certain embodiments, $R^1$ is joined with $R^d$ to form a substituted or unsubstituted 5 or 6-membered bridged ring. In certain embodiments, $R^1$ is joined with $R^d$ to form a substituted or unsubstituted 5-membered bridged ring. In certain embodiments, $R^1$ is joined with $R^d$ to form a substituted or unsubstituted 6-membered bridged ring. In certain embodiments, $R^1$ is joined with $R^3$ to form a substituted or unsubstituted ring. In certain embodiments, $R^1$ is joined with $R^3$ to form a substituted or unsubstituted bridged ring. In certain embodiments, $R^1$ is joined with $R^3$ to form a substituted or unsubstituted 5 or 6-membered bridged ring. In certain embodiments, $R^1$ is joined with $R^3$ to form a substituted or unsubstituted 5-membered bridged ring. In certain embodiments, $R^1$ is joined with $R^3$ to form a substituted or unsubstituted 6-membered bridged ring. In certain embodiments, $R^1$ is joined with $R^4$ to form a substituted or unsubstituted ring. In certain embodiments, $R^1$ is joined with $R^4$ to form a substituted or unsubstituted bridged ring. In certain embodiments, $R^1$ is joined with $R^4$ to form a substituted or unsubstituted 5 or 6-membered bridged ring. In certain embodiments, $R^1$ is joined with $R^4$ to form a substituted or unsubstituted 5-membered bridged ring. In certain embodiments, $R^1$ is joined with $R^4$ to form a substituted or unsubstituted 6-membered bridged ring.

As described herein, $R^2$ is hydrogen or substituted or unsubstituted alkyl, or $R^2$ is joined with $R^d$, $R^3$, or $R^4$ to form a substituted or unsubstituted ring. In certain embodiments, $R^2$ is substituted or unsubstituted alkyl. In certain embodiments, $R^2$ is unsubstituted alkyl. In certain embodiments, $R^2$ is unsubstituted $C_{1-6}$ alkyl. In certain embodiments, $R^2$ is unsubstituted $C_{1-4}$ alkyl. In certain embodiments, $R^2$ is hydrogen. In certain embodiments, $R^2$ is joined with $R^d$, $R^3$, or $R^4$ to form a substituted or unsubstituted ring. In certain embodiments, $R^2$ is joined with $R^d$, $R^3$, or $R^4$ to form a substituted or unsubstituted bridged ring. In certain embodiments, $R^2$ is joined with $R^d$, $R^3$, or $R^4$ to form a substituted or unsubstituted 5 or 6-membered bridged ring. In certain embodiments, $R^2$ is joined with $R^d$, $R^3$, or $R^4$ to form a substituted or unsubstituted 5-membered bridged ring. In certain embodiments, $R^2$ is joined with $R^d$, $R^3$, or $R^4$ to form a substituted or unsubstituted 6-membered bridged ring. In certain embodiments, $R^2$ is joined with $R^d$ to form a substituted or unsubstituted ring. In certain embodiments, $R^2$ is joined with $R^d$ to form a substituted or unsubstituted bridged ring. In certain embodiments, $R^2$ is joined with $R^d$ to form a substituted or unsubstituted 5 or 6-membered bridged ring. In certain embodiments, $R^2$ is joined with $R^d$ to form a substituted or unsubstituted 5-membered bridged ring. In certain embodiments, $R^2$ is joined with $R^d$ to form a substituted or unsubstituted 6-membered bridged ring. In certain embodiments, $R^2$ is joined with $R^3$ to form a substituted or unsubstituted ring. In certain embodiments, $R^2$ is joined with $R^3$ to form a substituted or unsubstituted bridged ring. In certain embodiments, $R^2$ is joined with $R^3$ to form a substituted or unsubstituted 5 or 6-membered bridged ring. In certain embodiments, $R^2$ is joined with $R^3$ to form a substituted or unsubstituted 5-membered bridged ring. In certain embodiments, $R^2$ is joined with $R^3$ to form a substituted or unsubstituted 6-membered bridged ring. In certain embodiments, $R^2$ is joined with $R^4$ to form a substituted or unsubstituted ring. In certain embodiments, $R^2$ is joined with $R^4$ to form a substituted or unsubstituted bridged ring. In certain embodiments, $R^2$ is joined with $R^4$ to form a substituted or unsubstituted 5 or 6-membered bridged ring. In certain embodiments, $R^2$ is joined with $R^4$ to form a substituted or unsubstituted 5-membered bridged ring. In certain embodiments, $R^2$ is joined with $R^4$ to form a substituted or unsubstituted 6-membered bridged ring.

In certain embodiments, $R^1$ and $R^2$ together form a carbonyl. In certain embodiments, $R^1$ is hydrogen; and $R^2$ is hydrogen.

$R^3$ and $R^4$

As described herein, $R^3$ is hydrogen or substituted or unsubstituted alkyl, or $R^3$ is joined with $R^1$ or $R^2$ to form a substituted or unsubstituted ring. In certain embodiments, $R^3$ is substituted or unsubstituted alkyl. In certain embodiments, $R^3$ is unsubstituted alkyl. In certain embodiments, $R^3$ is unsubstituted $C_{1-6}$ alkyl. In certain embodiments, $R^3$ is unsubstituted $C_{1-4}$ alkyl. In certain embodiments, $R^3$ is hydrogen. In certain embodiments, $R^3$ is joined with $R^1$ or $R^2$ to form a substituted or unsubstituted ring. In certain embodiments, $R^3$ is joined with $R^1$ or $R^2$ to form a substituted or unsubstituted bridged ring. In certain embodiments, $R^3$ is joined with $R^1$ or $R^2$ to form a substituted or unsubstituted 5 or 6-membered bridged ring. In certain embodiments, $R^3$ is joined with $R^1$ or $R^2$ to form a substituted or unsubstituted 5-membered bridged ring. In certain embodiments, $R^3$ is joined with $R^1$ or $R^2$ to form a substituted or unsubstituted 6-membered bridged ring. In certain embodiments, $R^3$ is joined with $R^1$ to form a substituted or unsubstituted ring. In certain embodiments, $R^3$ is joined with $R^1$ to form a substituted or unsubstituted bridged ring. In certain embodiments, $R^3$ is joined with $R^1$ to form a substituted or unsubstituted 5 or 6-membered bridged ring. In certain embodiments, $R^3$ is joined with $R^1$ to form a substituted or unsubstituted 5-membered bridged ring. In certain embodiments, $R^3$ is joined with $R^1$ to form a substituted or unsubstituted 6-membered bridged ring. In certain embodiments, $R^3$ is joined with $R^1$ to form a substituted or unsubstituted ring. In certain embodiments, $R^3$ is joined with $R^1$ to form a substituted or unsubstituted bridged ring. In certain embodiments, $R^3$ is joined with $R^1$ to form a substituted or unsubstituted 5 or 6-membered bridged ring. In certain embodiments, $R^3$ is joined with $R^1$ to form a substituted or unsubstituted 5-membered bridged ring. In certain embodiments, $R^3$ is joined with $R^1$ to form a substituted or unsubstituted 6-membered bridged ring. In certain embodiments, $R^3$ is joined with $R^2$ to form a substituted or unsubstituted ring. In certain embodiments, $R^3$ is joined with $R^2$ to form a substituted or unsubstituted bridged ring. In certain embodiments, $R^3$ is joined with $R^2$ to form a substituted or unsubstituted 5 or 6-membered bridged ring. In certain embodiments, $R^3$ is joined with $R^2$ to form a substituted or unsubstituted 5-membered bridged ring. In certain embodiments, $R^3$ is joined with $R^2$ to form a substituted or unsubstituted 6-membered bridged ring.

As described herein, $R^2$ is hydrogen or substituted or unsubstituted alkyl, or $R^2$ is joined with $R^d$, $R^3$, or $R^4$ to form a substituted or unsubstituted ring. In certain embodiments, $R^2$ is substituted or unsubstituted alkyl. In certain embodiments, $R^2$ is unsubstituted alkyl. In certain embodiments, $R^2$ is unsubstituted $C_{1-6}$ alkyl. In certain embodiments, $R^2$ is unsubstituted $C_{1-4}$ alkyl. In certain embodiments, $R^2$ is hydrogen. In certain embodiments, $R^2$ is joined with $R^d$, $R^3$, or $R^4$ to form a substituted or unsubstituted ring. In certain embodiments, $R^2$ is joined with $R^d$, $R^3$, or $R^4$ to form a substituted or unsubstituted bridged ring. In certain embodiments, $R^2$ is joined with $R^d$, $R^3$, or $R^4$ to form a substituted or unsubstituted 5 or 6-membered bridged ring. In certain embodiments, $R^2$ is joined with $R^d$, $R^3$, or $R^4$ to form a substituted or unsubstituted 5-membered bridged ring. In certain embodiments, $R^2$ is joined with $R^d$, $R^3$, or $R^4$ to form a substituted or unsubstituted 6-membered bridged ring. In certain embodiments, $R^2$ is joined with $R^d$ to form a substituted or unsubstituted ring. In certain embodiments, $R^2$ is joined with $R^d$ to form a substituted or unsubstituted bridged ring. In certain embodiments, $R^2$ is joined with $R^d$ to form a substituted or unsubstituted 5 or 6-membered bridged ring. In certain embodiments, $R^2$ is joined with $R^d$ to form a substituted or unsubstituted 5-membered bridged ring. In certain embodiments, $R^2$ is joined with $R^d$ to form a substituted or unsubstituted 6-membered bridged ring. In certain embodiments, $R^2$ is joined with $R^3$ to form a substituted or unsubstituted ring. In certain embodiments, $R^2$ is joined with $R^3$ to form a substituted or unsubstituted bridged ring. In certain embodiments, $R^2$ is joined with $R^3$ to form a substituted or unsubstituted 5 or 6-membered bridged ring. In certain embodiments, $R^2$ is joined with $R^3$ to form a substituted or unsubstituted 5-membered bridged ring. In certain embodiments, $R^2$ is joined with $R^3$ to form a substituted or unsubstituted 6-membered bridged ring. In certain embodiments, $R^2$ is joined with $R^4$ to form a substituted or unsubstituted ring. In certain embodiments, $R^2$ is joined with $R^4$ to form a substituted or unsubstituted bridged ring. In certain embodiments, $R^2$ is joined with $R^4$ to form a substituted or unsubstituted 5 or 6-membered bridged ring. In certain embodiments, $R^2$ is joined with $R^4$ to form a substituted or unsubstituted 5-membered bridged ring. In certain embodiments, $R^2$ is joined with $R^4$ to form a substituted or unsubstituted 6-membered bridged ring.

In certain embodiments, $R^3$ and $R^4$ together form a carbonyl. In certain embodiments, $R^3$ is hydrogen; and $R^4$ is hydrogen.

$R^a$, $R^b$, $R^d$, $R^x$, and t

As described herein, $R^x$ is hydrogen or substituted or unsubstituted alkyl; $R^a$ is hydrogen or is joined with $A^1$ to form a substituted or unsubstituted ring. In certain embodiments, $R^a$ is hydrogen. In certain embodiments, $R^a$ is joined with $A^1$ to form a substituted or unsubstituted ring. In certain embodiments, $R^a$ is joined with $A^1$ to form a substituted or unsubstituted 5 or 6-membered ring. In certain embodiments, $R^a$ is joined with $A^1$ to form a substituted or unsubstituted 5 or 6-membered heterocyclyl ring. In certain embodiments, $R^a$ is joined with $A^1$ to form a substituted or unsubstituted 5-membered heterocyclyl ring. In certain embodiments, $R^a$ is joined with $A^1$ to form a substituted or unsubstituted 6-membered heterocyclyl ring. In certain embodiments, $R^a$ is joined with $A^1$ to form a substituted or unsubstituted pyrrolidine. In certain embodiments, $R^a$ is joined with $A^1$ to form a substituted or unsubstituted piperidine.

In certain embodiments, $R^x$ is hydrogen. In certain embodiments, $R^x$ is substituted or unsubstituted alkyl. In certain embodiments, $R^x$ is substituted or unsubstituted $C_{1-6}$ alkyl. In certain embodiments, $R^x$ is substituted or unsubstituted $C_{1-4}$ alkyl. In certain embodiments, $R^x$ is substituted or unsubstituted $C_{1-3}$ alkyl. In certain embodiments, $R^x$ is substituted alkyl. In certain embodiments, $R^x$ is substituted $C_{1-6}$ alkyl. In certain embodiments, $R^x$ is substituted $C_{1-4}$ alkyl. In certain embodiments, $R^x$ is substituted $C_{1-3}$ alkyl. In certain embodiments, $R^x$ is unsubstituted alkyl. In certain embodiments, $R^x$ is unsubstituted $C_{1-6}$ alkyl. In certain embodiments, $R^x$ is unsubstituted $C_{1-4}$ alkyl. In certain embodiments, $R^x$ is unsubstituted $C_{1-3}$ alkyl.

As described herein, $R^c$ is hydrogen or is joined with $A^1$ to form a substituted or unsubstituted ring. In certain embodiments, $R^c$ is hydrogen. In certain embodiments, $R^c$ is joined with $A^1$ to form a substituted or unsubstituted ring. In certain embodiments, $R^c$ is joined with $A^1$ to form a substituted or unsubstituted 5 or 6-membered ring. In certain embodiments, $R^c$ is joined with $A^1$ to form a substituted or unsubstituted 5 or 6-membered heterocyclyl ring. In certain embodiments, $R^c$ is joined with $A^1$ to form a substituted or unsubstituted 5-membered heterocyclyl ring. In certain embodiments, $R^c$ is joined with $A^1$ to form a substituted or unsubstituted 6-membered heterocyclyl ring. In certain embodiments, $R^c$ is joined with $A^1$ to form a substituted or unsubstituted pyrrolidine. In certain embodiments, $R^c$ is joined with $A^1$ to form a substituted or unsubstituted piperidine.

In certain embodiments, $R^d$ is joined with $R^1$ to form a substituted or unsubstituted ring. In certain embodiments, $R^d$ is joined with $R^1$ to form a substituted or unsubstituted bridged ring. In certain embodiments, $R^d$ is joined with $R^1$ to form a substituted or unsubstituted 5 or 6-membered bridged ring. In certain embodiments, $R^d$ is joined with $R^1$ to form a substituted or unsubstituted 5-membered bridged ring. In certain embodiments, $R^d$ is joined with $R^1$ to form a substituted or unsubstituted 6-membered bridged ring.

In certain embodiments, $R^d$ is joined with $R^2$ to form a substituted or unsubstituted ring. In certain embodiments, $R^d$ is joined with $R^2$ to form a substituted or unsubstituted bridged ring. In certain embodiments, $R^d$ is joined with $R^2$ to form a substituted or unsubstituted 5 or 6-membered bridged ring. In certain embodiments, $R^d$ is joined with $R^2$ to form a substituted or unsubstituted 5-membered bridged ring. In certain embodiments, $R^d$ is joined with $R^2$ to form a substituted or unsubstituted 6-membered bridged ring.

As described herein, t is 0 or 1. In certain embodiments, t is 0. In certain embodiments, t is 1.

Certain Embodiments

In certain embodiments, the compound of Formula (V) is of Formula (V-a):

(V-a)

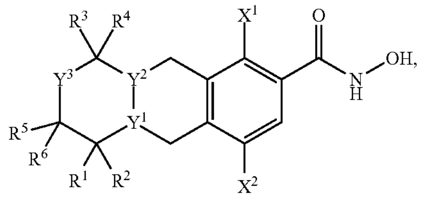

or a pharmaceutically acceptable salt, co-crystal, tautomer, stereoisomer, solvate, hydrate, polymorph, isotopically enriched derivative, or prodrug thereof; wherein $R^1$, $R^2$, $R^3$, $R^4$, $Y^1$, $Y^2$, $X^1$, and $X^2$ are as defined herein;

$Y^3$ is a bond, —$CH_2$—, —O—, —S—, or —$NR^e$—;

$R^e$ is hydrogen, substituted or unsubstituted alkyl, or a protecting group; and $R^5$ and $R^6$ are each independently hydrogen, substituted or unsubstituted alkyl, or together form a substituted or unsubstituted cycloalkyl.

In certain embodiments of the compound of Formula (V-a), $Y^3$ is a bond, —$CH_2$—, or —O—. In certain embodiments of the compound of Formula (V-a), $Y^3$ is —$CH_2$— or —O—. In certain embodiments of the compound of Formula (V-a), $Y^3$ is —$CH_2$—. In certain embodiments of the compound of Formula (V-a), $Y^3$ is —O—. In certain embodiments of the compound of Formula (V-a), $Y^3$ is —O—; and $R^1$ and $R^2$ together form a carbonyl.

In certain embodiments of the compound of Formula (V-a), $Y^3$ is a bond, —$CH_2$—, or —O—; and $R^5$ and $R^6$ are each independently hydrogen, or together form a substituted or unsubstituted cycloalkyl. In certain embodiments of the compound of Formula (V-a), $Y^3$ is —$CH_2$— or —O—; and $R^5$ and $R^6$ are each independently hydrogen, or together form a substituted or unsubstituted cycloalkyl. In certain embodiments of the compound of Formula (V-a), $Y^3$ is —$CH_2$—; and $R^5$ and $R^6$ are each independently hydrogen, or together form a substituted or unsubstituted cycloalkyl. In certain embodiments of the compound of Formula (V-a), $Y^3$ is —O—; and $R^5$ and $R^6$ are each independently hydrogen, or together form a substituted or unsubstituted cycloalkyl.

In certain embodiments, the compound of Formula (V-a) is of Formula (V-a-1):

(V-a-1)

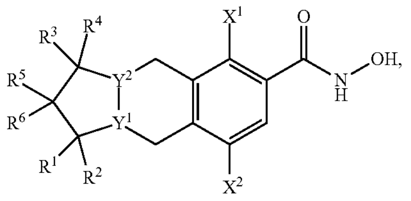

or a pharmaceutically acceptable salt, co-crystal, tautomer, stereoisomer, solvate, hydrate, polymorph, isotopically enriched derivative, or prodrug thereof; wherein $R^1$, $R^2$, $R^3$, $R^4$, $Y^1$, $Y^2$, $X^1$, and $X^2$ are as defined herein; and $R^5$ and $R^6$ are each independently hydrogen, substituted or unsubstituted alkyl, or together form a substituted or unsubstituted cycloalkyl.

In certain embodiments, the compound of Formula (V) is of Formula (V-b):

(V-b)

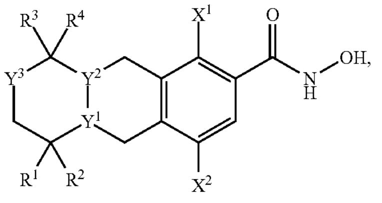

or a pharmaceutically acceptable salt, co-crystal, tautomer, stereoisomer, solvate, hydrate, polymorph, isotopically enriched derivative, or prodrug thereof; wherein $R^1$, $R^2$, $R^3$, $R^4$, $Y^1$, $Y^2$, $X^1$, and $X^2$ are as defined herein;

$Y^3$ is a bond, —$CH_2$—, —O—, —S—, or —$NR^e$—; and $R^e$ is hydrogen, substituted or unsubstituted alkyl, or a protecting group.

In certain embodiments of the compound of Formula (V-b), $Y^3$ is a bond, —$CH_2$—, or —O—. In certain embodiments of the compound of Formula (V-b), $Y^3$ is —$CH_2$— or —O—. In certain embodiments of the compound of Formula (V-b), $Y^3$ is —$CH_2$—. In certain embodiments of the compound of Formula (V-b), $Y^3$ is —O—. In certain embodiments of the compound of Formula (V-b), $Y^3$ is —O—; and $R^1$ and $R^2$ together form a carbonyl.

In certain embodiments, the compound of Formula (V) is of Formula (V-c):

(V-c)

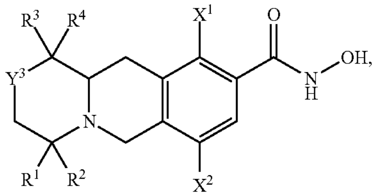

or a pharmaceutically acceptable salt, co-crystal, tautomer, stereoisomer, solvate, hydrate, polymorph, isotopically enriched derivative, or prodrug thereof; wherein $R^1$, $R^2$, $R^3$, $R^4$, $X^1$, and $X^2$ are as defined herein;

$Y^3$ is a bond, —$CH_2$—, —O—, —S—, or —$NR^e$—; and $R^e$ is hydrogen, substituted or unsubstituted alkyl, or a protecting group.

In certain embodiments of the compound of Formula (V-c), $Y^3$ is a bond, —$CH_2$—, or —O—. In certain embodiments of the compound of Formula (V-c), $Y^3$ is —$CH_2$— or —O—. In certain embodiments of the compound of Formula (V-c), $Y^3$ is —$CH_2$—. In certain embodiments of the compound of Formula (V-c), $Y^3$ is —O—. In certain embodiments of the compound of Formula (V-c), $Y^3$ is —O—; and $R^1$ and $R^2$ together form a carbonyl.

In certain embodiments, the compound of Formula (V) is of Formula (V-d):

(V-d)

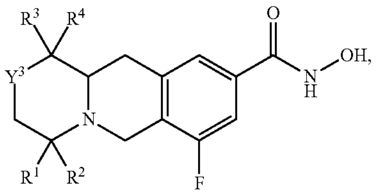

or a pharmaceutically acceptable salt, co-crystal, tautomer, stereoisomer, solvate, hydrate, polymorph, isotopically enriched derivative, or prodrug thereof; wherein $R^1$, $R^2$, $R^3$, and $R^4$ are as defined herein;

$Y^3$ is a bond, —$CH_2$—, —O—, —S—, or —$NR^e$—; and $R^e$ is hydrogen, substituted or unsubstituted alkyl, or a protecting group.

In certain embodiments of the compound of Formula (V-d), $Y^3$ is a bond, —$CH_2$—, or —O—. In certain embodiments of the compound of Formula (V-d), $Y^3$ is —$CH_2$— or —O—. In certain embodiments of the compound of Formula (V-d), $Y^3$ is —$CH_2$—. In certain embodiments of the compound of Formula (V-d), $Y^3$ is —O—. In certain embodiments of the compound of Formula (V-d), $Y^3$ is —O—; and $R^1$ and $R^2$ together form a carbonyl.

In certain embodiments, the compound of Formula (V) is of Formula (V-e):

(V-e)

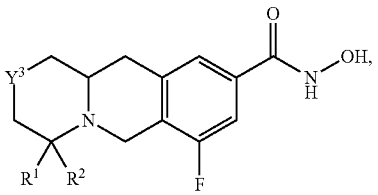

or a pharmaceutically acceptable salt, co-crystal, tautomer, stereoisomer, solvate, hydrate, polymorph, isotopically enriched derivative, or prodrug thereof; wherein $R^1$ and $R^2$ are as defined herein;

$Y^3$ is a bond, —$CH_2$—, —O—, —S—, or —$NR^e$—; and $R^e$ is hydrogen, substituted or unsubstituted alkyl, or a protecting group.

In certain embodiments of the compound of Formula (V-e), $Y^3$ is a bond, —$CH_2$—, or —O—. In certain embodiments of the compound of Formula (V-e), $Y^3$ is —$CH_2$— or —O—. In certain embodiments of the compound of Formula (V-e), $Y^3$ is —$CH_2$—. In certain embodiments of the compound of Formula (V-e), $Y^3$ is —O—. In certain embodiments of the compound of Formula (V-e), $Y^3$ is —O—; and $R^1$ and $R^2$ together form a carbonyl.

In certain embodiments, the compound of Formula (V) is of Formula (V-f):

(V-f)

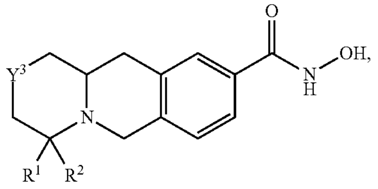

or a pharmaceutically acceptable salt, co-crystal, tautomer, stereoisomer, solvate, hydrate, polymorph, isotopically enriched derivative, or prodrug thereof; wherein $R^1$ and $R^2$ are as defined herein;

$Y^3$ is a bond, —$CH_2$—, —O—, —S—, or —$NR^e$—; and $R^e$ is hydrogen, substituted or unsubstituted alkyl, or a protecting group.

In certain embodiments of the compound of Formula (V-f), $Y^3$ is a bond, —$CH_2$—, or —O—. In certain embodiments of the compound of Formula (V-f), $Y^3$ is —$CH_2$— or —O—. In certain embodiments of the compound of Formula (V-f), $Y^3$ is —$CH_2$—. In certain embodiments of the compound of Formula (V-f), $Y^3$ is —O—. In certain embodiments of the compound of Formula (V-f), $Y^3$ is —O—; and $R^1$ and $R^2$ together form a carbonyl.

In certain embodiments, the compound of Formula (V) is of Formula (V-g):

(V-g)

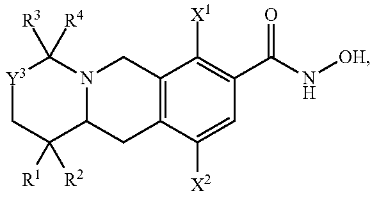

or a pharmaceutically acceptable salt, co-crystal, tautomer, stereoisomer, solvate, hydrate, polymorph, isotopically enriched derivative, or prodrug thereof; wherein $R^1$, $R^2$, $R^3$, $R^4$, $X^1$, and $X^2$ are as defined herein;

$Y^3$ is a bond, —$CH_2$—, —O—, —S—, or —$NR^e$—; and $R^e$ is hydrogen, substituted or unsubstituted alkyl, or a protecting group.

In certain embodiments of the compound of Formula (V-g), $Y^3$ is a bond or —$CH_2$—. In certain embodiments of the compound of Formula (V-g), $Y^3$ is a bond. In certain embodiments of the compound of Formula (V-g), $Y^3$ is —$CH_2$—.

In certain embodiments, the compound of Formula (V) is of Formula (V-h):

(V-i)

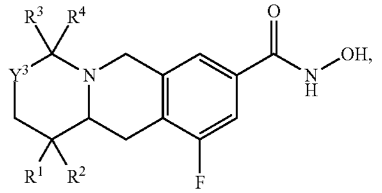

or a pharmaceutically acceptable salt, co-crystal, tautomer, stereoisomer, solvate, hydrate, polymorph, isotopically enriched derivative, or prodrug thereof; wherein $R^1$, $R^2$, $R^3$, and $R^4$ are as defined herein;

$Y^3$ is a bond, —$CH_2$—, —O—, —S—, or —$NR^e$—; and $R^e$ is hydrogen, substituted or unsubstituted alkyl, or a protecting group.

In certain embodiments of the compound of Formula (V-h), $Y^3$ is a bond or —$CH_2$—. In certain embodiments of the compound of Formula (V-h), $Y^3$ is a bond. In certain embodiments of the compound of Formula (V-h), $Y^3$ is —$CH_2$—.

In certain embodiments, the compound of Formula (V) is of Formula (V-i):

(V-j)

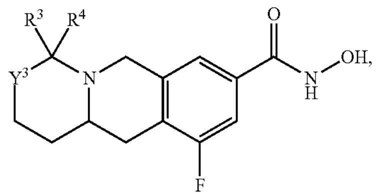

or a pharmaceutically acceptable salt, co-crystal, tautomer, stereoisomer, solvate, hydrate, polymorph, isotopically enriched derivative, or prodrug thereof; wherein $R^3$ and $R^4$ are as defined herein;

$Y^3$ is a bond, —$CH_2$—, —O—, —S—, or —$NR^e$—; and $R^e$ is hydrogen, substituted or unsubstituted alkyl, or a protecting group.

In certain embodiments of the compound of Formula (V-i), $Y^3$ is a bond or —$CH_2$—. In certain embodiments of the compound of Formula (V-i), $Y^3$ is a bond. In certain embodiments of the compound of Formula (V-i), $Y^3$ is —$CH_2$—.

In certain embodiments, the compound of Formula (V) is of Formula (V-j):

(V-j)

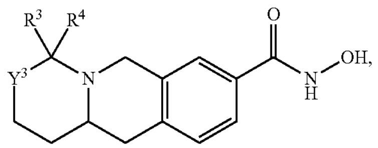

or a pharmaceutically acceptable salt, co-crystal, tautomer, stereoisomer, solvate, hydrate, polymorph, isotopically enriched derivative, or prodrug thereof; wherein $R^3$ and $R^4$ are as defined herein;

$Y^3$ is a bond, —$CH_2$—, —O—, —S—, or —$NR^e$—; and $R^e$ is hydrogen, substituted or unsubstituted alkyl, or a protecting group.

In certain embodiments of the compound of Formula (V-j), $Y^3$ is a bond or —$CH_2$—. In certain embodiments of the compound of Formula (V-j), $Y^3$ is a bond. In certain embodiments of the compound of Formula (V-j), $Y^3$ is —$CH_2$—.

In certain embodiments, the compound of Formula (V) is of Formula (V-k):

(V-k)

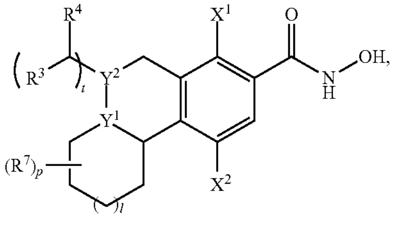

or a pharmaceutically acceptable salt, co-crystal, tautomer, stereoisomer, solvate, hydrate, polymorph, isotopically enriched derivative, or prodrug thereof; wherein $R^3$, $R^4$, t, $Y^1$, $Y^2$, $X^1$, and $X^2$ are as defined herein; each $R^7$ is independently substituted or unsubstituted alkyl, halogen, or two instances of $R^7$ together form a substituted or unsubstituted cycloalkyl, or substituted or unsubstituted heterocyclyl; p is 0, 1, 2, or 3; and 1 is 0 or 1.

In certain embodiments, the compound of Formula (V) is of Formula (V-l):

(V-l)

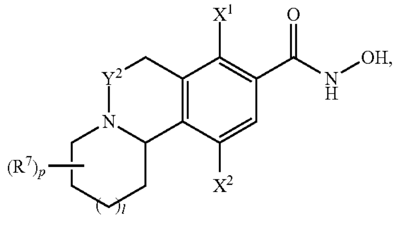

or a pharmaceutically acceptable salt, co-crystal, tautomer, stereoisomer, solvate, hydrate, polymorph, isotopically enriched derivative, or prodrug thereof; wherein $Y^2$, $X^1$, and $X^2$ are as defined herein; each $R^7$ is independently substituted or unsubstituted alkyl, halogen, or two instances of $R^7$ together form a substituted or unsubstituted cycloalkyl, or substituted or unsubstituted heterocyclyl; p is 0, 1, 2, or 3; and 1 is 0 or 1.

In certain embodiments, the compound of Formula (V-l) is of Formula (V-l-1):

(V-l-1)

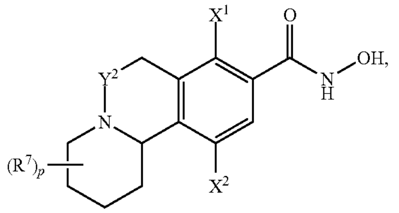

or a pharmaceutically acceptable salt, co-crystal, tautomer, stereoisomer, solvate, hydrate, polymorph, isotopically enriched derivative, or prodrug thereof; wherein $Y^2$, $X^1$, and $X^2$ are as defined herein; each $R^7$ is independently substituted or unsubstituted alkyl, halogen, or two instances of $R^7$ together form a substituted or unsubstituted cycloalkyl, or substituted or unsubstituted heterocyclyl; and p is 0, 1, 2, or 3.

In certain embodiments, the compound of Formula (V-l) is of Formula (V-l-2):

(V-l-2)

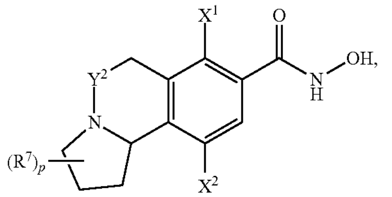

or a pharmaceutically acceptable salt, co-crystal, tautomer, stereoisomer, solvate, hydrate, polymorph, isotopically enriched derivative, or prodrug thereof; wherein $Y^2$, $X^1$, and $X^2$ are as defined herein; each $R^7$ is independently substituted or unsubstituted alkyl, halogen, or two instances of $R^7$ together form a substituted or unsubstituted cycloalkyl, or substituted or unsubstituted heterocyclyl; and p is 0, 1, 2, or 3.

In certain embodiments, the compound of Formula V-l is of Formula (V-l-3):

(V-l-3)

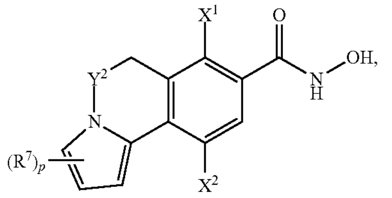

or a pharmaceutically acceptable salt, co-crystal, tautomer, stereoisomer, solvate, hydrate, polymorph, isotopically enriched derivative, or prodrug thereof; wherein $Y^2$, $X^1$, and $X^2$ are as defined herein; each $R^7$ is independently substituted or unsubstituted alkyl, halogen, or two instances of $R^7$ together form a substituted or unsubstituted cycloalkyl, or substituted or unsubstituted heterocyclyl; and p is 0, 1, 2, or 3.

In certain embodiments of the compound of Formula (V-l), $Y^2$ is —NH—, —NMe-, —$CH_2$—, or a bond. In certain embodiments of the compound of Formula (V-l), $Y^2$ is —NMe-, —$CH_2$—, or a bond. In certain embodiments of the compound of Formula (V-l), $Y^2$ is —NMe-. In certain embodiments of the compound of Formula (V-l), $Y^2$ is —$CH_2$—. In certain embodiments of the compound of Formula (V-l), $Y^2$ is a bond.

In certain embodiments, the compound of Formula (V) is of Formula (V-m):

(V-m)

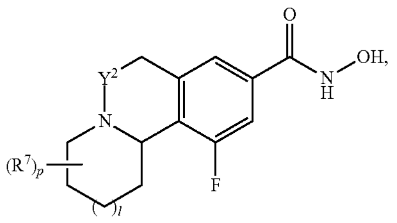

or a pharmaceutically acceptable salt, co-crystal, tautomer, stereoisomer, solvate, hydrate, polymorph, isotopically enriched derivative, or prodrug thereof; wherein $Y^2$ is as defined herein; each $R^7$ is independently substituted or unsubstituted alkyl, halogen, or two instances of $R^7$ together form a substituted or unsubstituted cycloalkyl, or substituted or unsubstituted heterocyclyl; p is 0, 1, 2, or 3; and 1 is 0 or 1.

In certain embodiments, the compound of Formula (V-m) is of Formula (V-m-1):

(V-m-1)

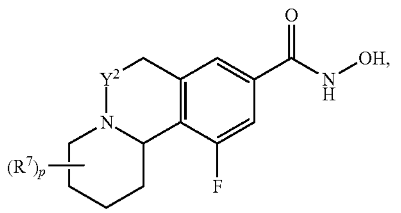

or a pharmaceutically acceptable salt, co-crystal, tautomer, stereoisomer, solvate, hydrate, polymorph, isotopically enriched derivative, or prodrug thereof; wherein $Y^2$, $R^7$, and p are as defined herein.

In certain embodiments, the compound of Formula (V-m) is of Formula (V-m-2):

(V-m-2)

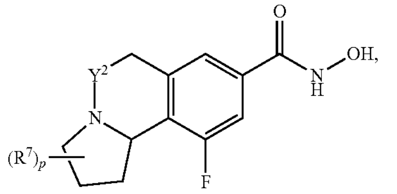

or a pharmaceutically acceptable salt, co-crystal, tautomer, stereoisomer, solvate, hydrate, polymorph, isotopically enriched derivative, or prodrug thereof; wherein $Y^2$, $R^7$, and p are as defined herein.

In certain embodiments the compound of Formula (V-m) is of Formula (V-m-3):

(V-m-3)

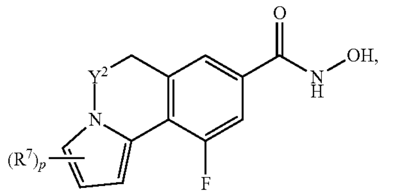

or a pharmaceutically acceptable salt, co-crystal, tautomer, stereoisomer, solvate, hydrate, polymorph, isotopically enriched derivative, or prodrug thereof; wherein $Y^2$, $R^7$, and p are as defined herein.

In certain embodiments of the compound of Formula (V-m), $Y^2$ is —NH—, —NMe-, —$CH_2$—, or a bond. In certain embodiments of the compound of Formula (V-m), $Y^2$ is —NMe-, —$CH_2$—, or a bond. In certain embodiments of the compound of Formula (V-m), $Y^2$ is —NMe-. In certain embodiments of the compound of Formula (V-m), $Y^2$ is —$CH_2$—. In certain embodiments of the compound of Formula (V-m), $Y^2$ is a bond.

In certain embodiments, the compound of Formula (V) is of Formula (V-n):

(V-n)

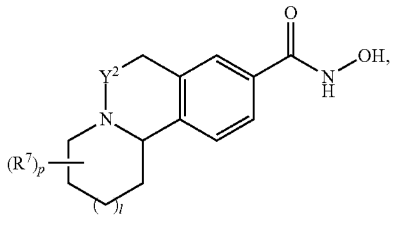

or a pharmaceutically acceptable salt, co-crystal, tautomer, stereoisomer, solvate, hydrate, polymorph, isotopically enriched derivative, or prodrug thereof; wherein $Y^2$ is as defined herein; each $R^7$ is independently substituted or unsubstituted alkyl, halogen, or two instances of $R^7$ together form a substituted or unsubstituted cycloalkyl, or substituted or unsubstituted heterocyclyl; p is 0, 1, 2, or 3; and 1 is 0 or 1.

In certain embodiments, the compound of Formula (V) is of Formula (V-n-1):

(V-n-1)

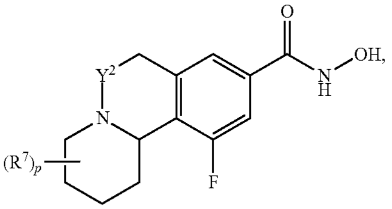

or a pharmaceutically acceptable salt, co-crystal, tautomer, stereoisomer, solvate, hydrate, polymorph, isotopically enriched derivative, or prodrug thereof; wherein $Y^2$ is as defined herein.

In certain embodiments, the compound of Formula (V) is of Formula (V-n-2):

(V-n-2)

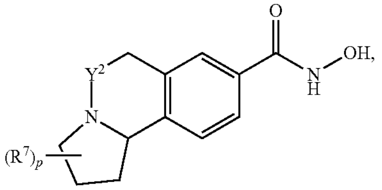

or a pharmaceutically acceptable salt, co-crystal, tautomer, stereoisomer, solvate, hydrate, polymorph, isotopically enriched derivative, or prodrug thereof; wherein $Y^2$, $R^7$, and p are as defined herein.

In certain embodiments, the compound of Formula (V) is of Formula (V-n-3):

(V-n-3)

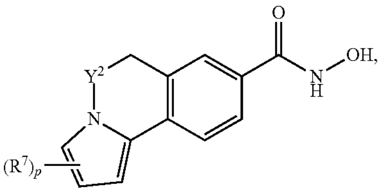

or a pharmaceutically acceptable salt, co-crystal, tautomer, stereoisomer, solvate, hydrate, polymorph, isotopically enriched derivative, or prodrug thereof; wherein $Y^2$, $R^7$, and p are as defined herein.

In certain embodiments of the compound of Formula (V-n), $Y^2$ is —NH—, —NMe-, —$CH_2$—, or a bond. In certain embodiments of the compound of Formula (V-n), $Y^2$ is —NMe-, —$CH_2$—, or a bond. In certain embodiments of the compound of Formula (V-n), $Y^2$ is —NMe-. In certain embodiments of the compound of Formula (V-n), $Y^2$ is —$CH_2$—. In certain embodiments of the compound of Formula (V-n), $Y^2$ is a bond.

In certain embodiments, the compound of Formula (V) is one of the following compounds, or a pharmaceutically acceptable salt, co-crystal, tautomer, stereoisomer, solvate, hydrate, polymorph, isotopically enriched derivative, or prodrug thereof:

-continued
241
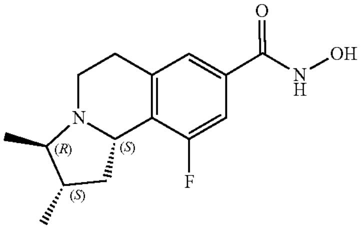
242
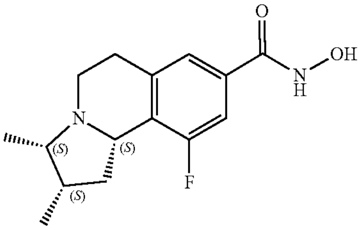
243
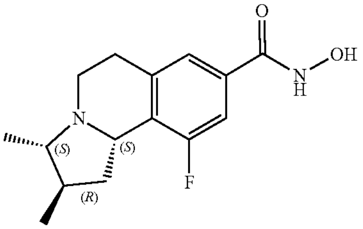
244
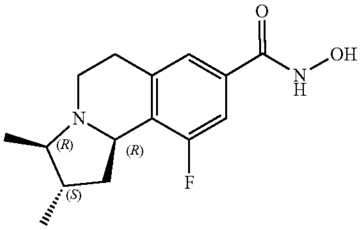
245
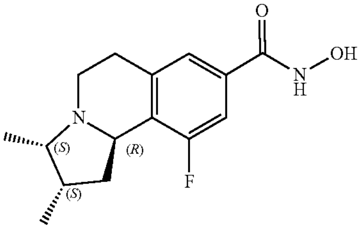
246
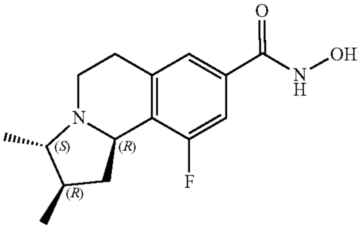
247
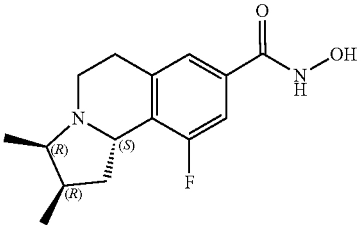
248
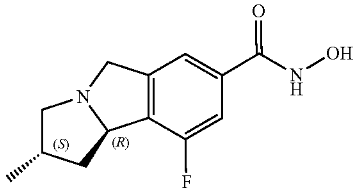
249
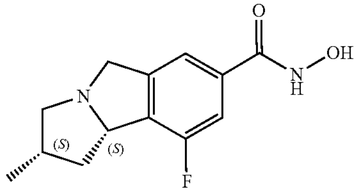
250
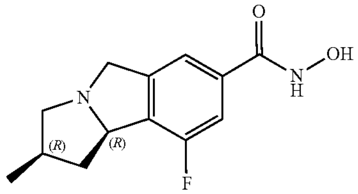
251
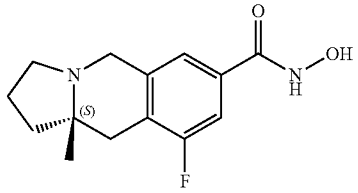
252
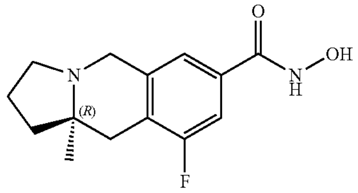
253
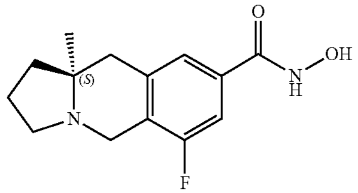

-continued
254
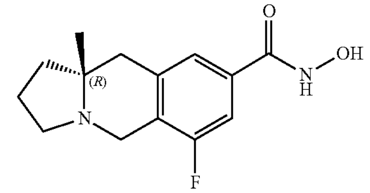
255
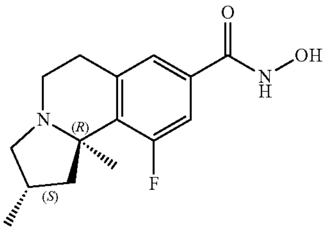
256
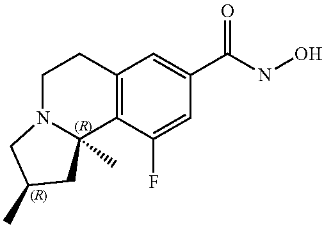
257
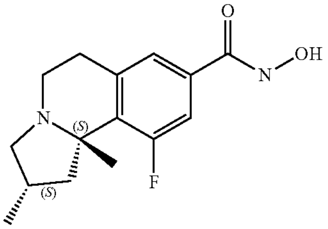
258
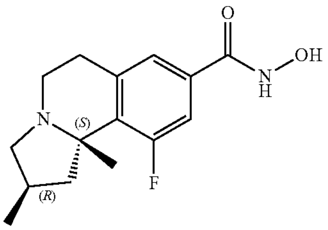
259
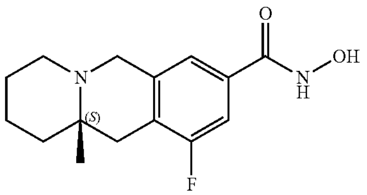
260
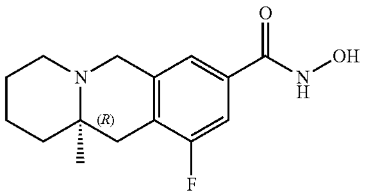
-continued
261
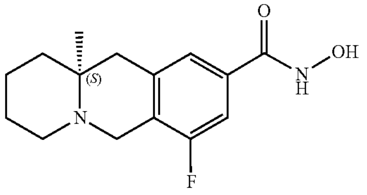
262
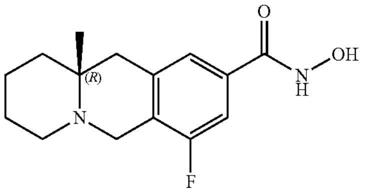
263
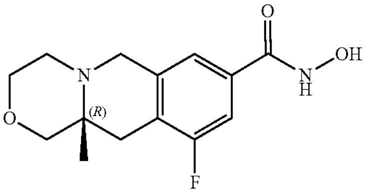
264
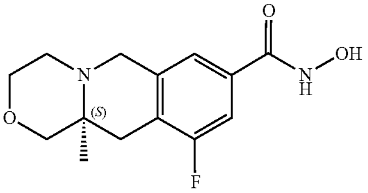
265
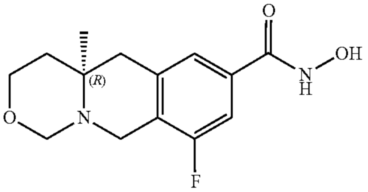
266
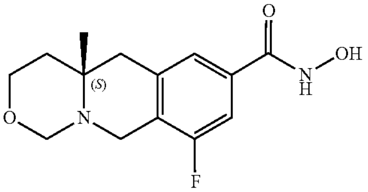
267
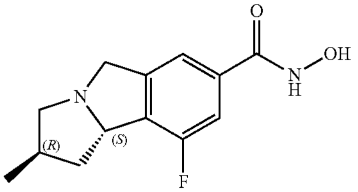
268
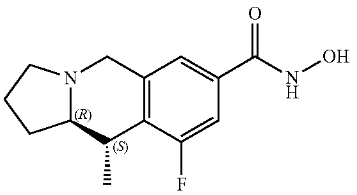

-continued

269

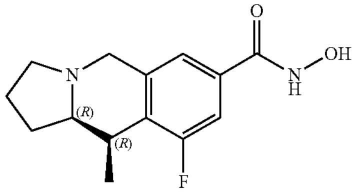

270

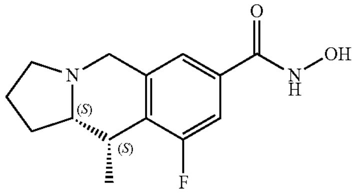

271

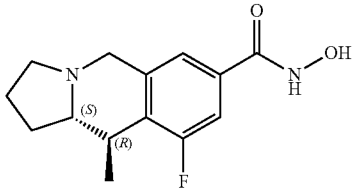

272

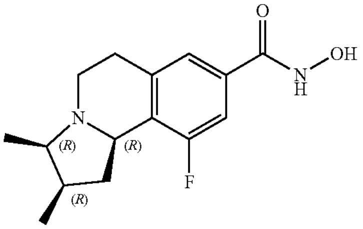

273

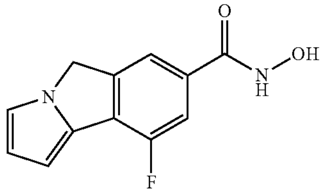

Compound of Formula (VI)

In another aspect, disclosed is a compound of Formula (VI):

(VI)

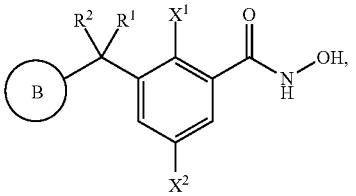

or a pharmaceutically acceptable salt, co-crystal, tautomer, stereoisomer, solvate, hydrate, polymorph, isotopically enriched derivative, or prodrug thereof, wherein:

$X^1$ is hydrogen or fluoro;

$X^2$ is hydrogen or fluoro;

$R^1$ is hydrogen or substituted or unsubstituted alkyl;

$R^2$ is hydrogen or substituted or unsubstituted alkyl; or $R^1$ and $R^2$ together form a substituted or unsubstituted heterocyclyl, or a substituted or unsubstituted cycloalkyl; and B is a substituted or unsubstituted heterocyclyl, substituted or unsubstituted carbocyclyl, a substituted or unsubstituted polycyclic spiro ring system, or a substituted or unsubstituted bridged ring system; provided the compound is not of formula:

170

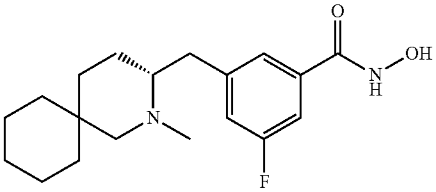

171

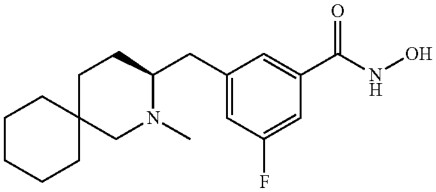

$X^1$ and $X^2$

As described herein, $X^1$ is hydrogen or fluoro; and $X^2$ is hydrogen or fluoro. In certain embodiments, $X^1$ is hydrogen or fluoro; and $X^2$ is hydrogen or fluoro; provided that at least one of $X^1$ and $X^2$ is fluoro. In certain embodiments, $X^1$ is hydrogen; and $X^2$ is fluoro. In certain embodiments, $X^1$ is fluoro; and $X^2$ is hydrogen. In certain embodiments, $X^1$ is fluoro; and $X^2$ is fluoro. In certain embodiments, $X^1$ is hydrogen; and $X^2$ is hydrogen.

$R^1$ and $R^2$

In certain embodiments, $R^1$ is hydrogen; and $R^2$ is unsubstituted $C_{1-4}$ alkyl; or $R^1$ and $R^2$ together form an unsubstituted cycloalkyl. In certain embodiments, $R^1$ is hydrogen; and $R^2$ is unsubstituted $C_{1-4}$ alkyl; or $R^1$ and $R^2$ together form an unsubstituted $C_{3-6}$ cycloalkyl. In certain embodiments, $R^1$ is hydrogen; and $R^2$ is methyl or ethyl; or $R^1$ and $R^2$ together form an unsubstituted $C_{3-6}$ cycloalkyl. In certain embodiments, $R^1$ is hydrogen; and $R^2$ is methyl or ethyl; or $R^1$ and $R^2$ together form an unsubstituted cyclobutyl. In certain embodiments, $R^1$ is hydrogen; and $R^2$ is unsubstituted $C_{1-4}$ alkyl. In certain embodiments, $R^1$ is hydrogen; and $R^2$ is methyl or ethyl. In certain embodiments, $R^1$ is hydrogen; and $R^2$ is methyl. In certain embodiments, $R^1$ is hydrogen; and $R^2$ is ethyl.

In certain embodiments, $R^1$ is unsubstituted $C_{1-4}$ alkyl; and $R^2$ is hydrogen; or $R^1$ and $R^2$ together form an unsubstituted cycloalkyl. In certain embodiments, $R^1$ is unsubstituted $C_{1-4}$ alkyl; and $R^2$ is hydrogen; or $R^1$ and $R^2$ together form an unsubstituted $C_{3-6}$ cycloalkyl. In certain embodiments, $R^1$ is methyl or ethyl; and $R^2$ is hydrogen; or $R^1$ and $R^2$ together form an unsubstituted $C_{3-6}$ cycloalkyl. In certain embodiments, $R^1$ is methyl or ethyl; and $R^2$ is hydrogen; or $R^1$ and $R^2$ together form an unsubstituted cyclobutyl.

In certain embodiments, $R^1$ is unsubstituted $C_{1-4}$ alkyl; and $R^2$ is hydrogen. In certain embodiments, $R^1$ is methyl or ethyl; and $R^2$ is hydrogen. In certain embodiments, $R^1$ is methyl; and $R^2$ is hydrogen. In certain embodiments, $R^1$ is ethyl; and $R^2$ is hydrogen.

In certain embodiments, $R^1$ is hydrogen; and $R^2$ is unsubstituted $C_{1-4}$ alkyl. In certain embodiments, $R^1$ is hydrogen; and $R^2$ is methyl or ethyl. In certain embodiments, $R^1$ is hydrogen; and $R^2$ is methyl. In certain embodiments, $R^1$ is hydrogen; and $R^2$ is ethyl.

In certain embodiments, $R^1$ and $R^2$ together form a substituted or unsubstituted cycloalkyl. In certain embodiments, $R^1$ and $R^2$ together form an unsubstituted cycloalkyl. In certain embodiments, $R^1$ and $R^2$ together form an unsubstituted $C_{3-6}$ cycloalkyl. In certain embodiments, $R^1$ and $R^2$ together form an unsubstituted cyclobutyl.

In certain embodiments, $R^1$ is hydrogen; and $R^2$ is hydrogen.

B

As described herein, B is a substituted or unsubstituted heterocyclyl, substituted or unsubstituted carbocyclyl, a substituted or unsubstituted polycyclic spiro ring system, or a substituted or unsubstituted bridged ring system.

In certain embodiments, B is a substituted or unsubstituted polycyclic spiro ring system, a substituted or unsubstituted bridged ring system,

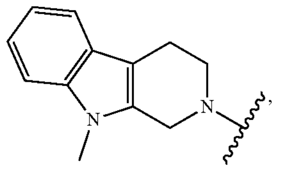
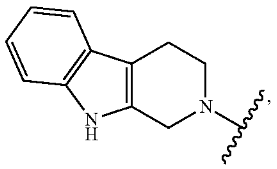
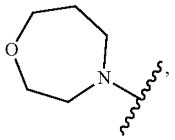
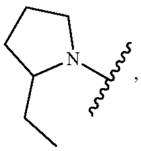
and
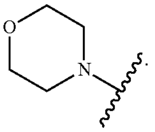

In certain embodiments, B is a substituted or unsubstituted bridged ring system. In certain embodiments, B is a substituted or unsubstituted heterocyclic bridged ring system.

In certain embodiments, B is of formula:

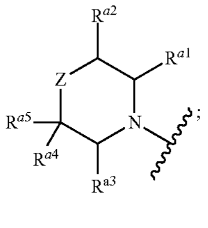

wherein Z is —O—, —$NCH_3$—, —C(=O)—, —C(=NOH)—, or —$CHR^6$—; $R^{a1}$ is hydrogen or is joined with $R^{a3}$ or $R^{a4}$ to form a 1-4 carbon bridge; $R^{a2}$ is hydrogen or is joined with $R^{a3}$ or $R^{a4}$ to form a 1-4 carbon bridge; $R^{a3}$ is hydrogen or is joined with $R^{a1}$ or $R^{a2}$ to form a 1-4 carbon bridge; $R^{a4}$ is hydrogen or is joined with $R^{a1}$ or $R^{a2}$ to form a 1-4 carbon bridge; RV is hydrogen or is joined with $R^6$ to form a substituted or unsubstituted cycloalkyl; and $R^6$ is hydrogen or is joined with $R^a$ to form a substituted or unsubstituted cycloalkyl.

In certain embodiments, B is of formula:

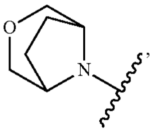
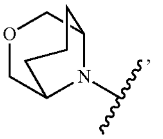
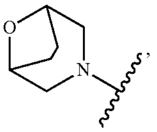
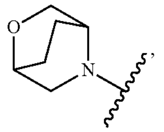
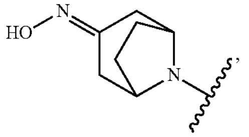
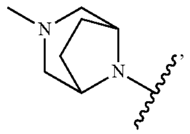
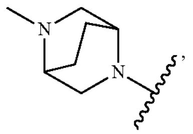
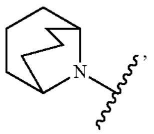
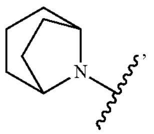
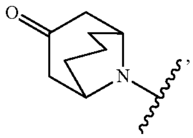
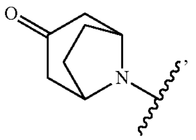
or
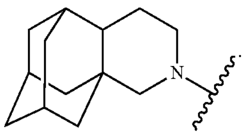

In certain embodiments, B is of formula:

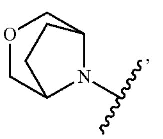
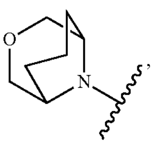
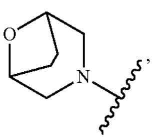
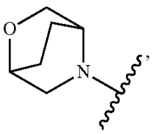
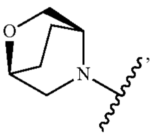
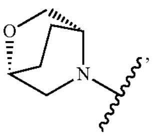
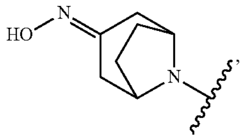
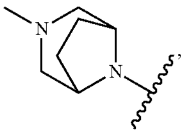
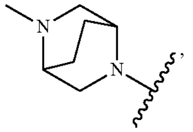
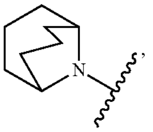
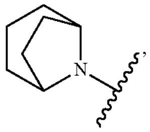
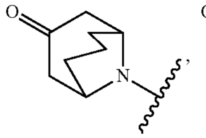
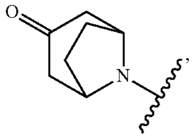
or
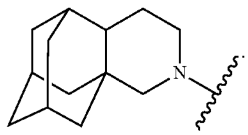

In certain embodiments, B is of formula:
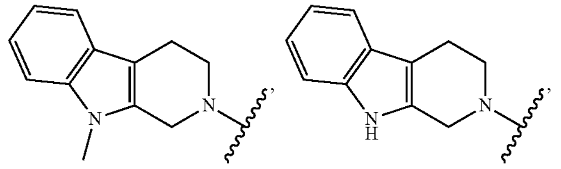
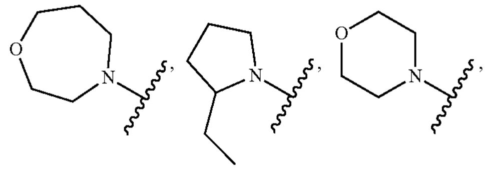
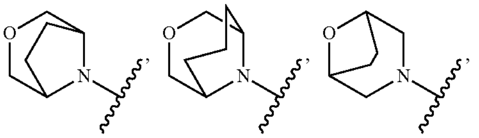
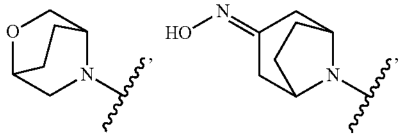
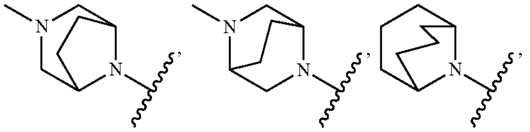
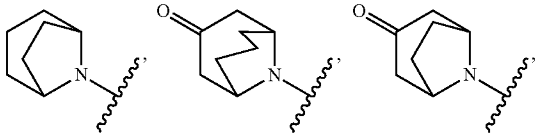
or
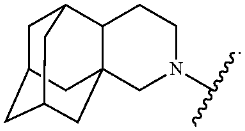
In certain embodiments, B is of formula:
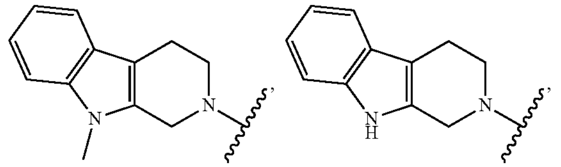
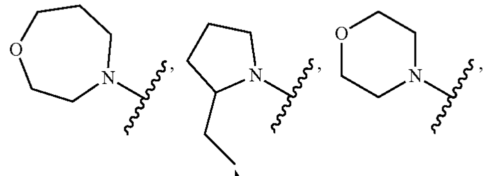
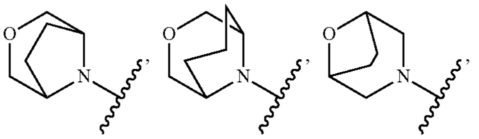
-continued
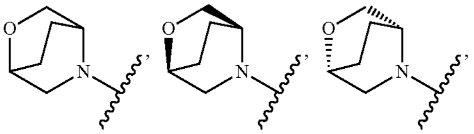
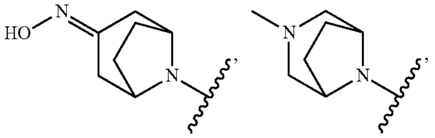
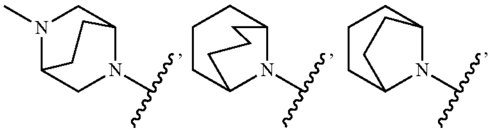
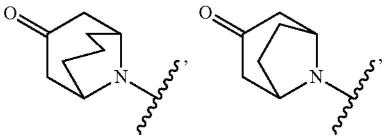
or
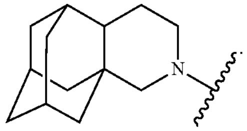
In certain embodiments, B is of formula:
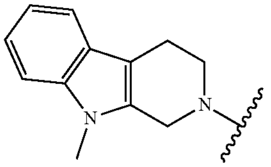
or
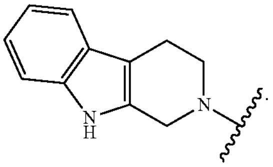
In certain embodiments, B is of formula:
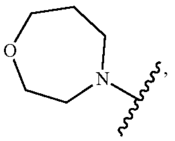
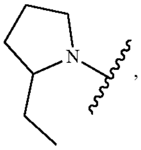
, or
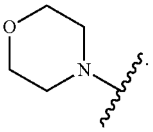
In certain embodiments, B is a substituted or unsubstituted polycyclic spiro ring system.

In certain embodiments,

B is

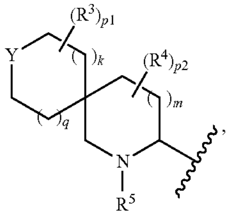

wherein

Y is —O—, —S—, —$NR^{a1}$—, or —($CR^3R^4$)—;

each occurrence of $R^3$ and $R^4$ is, independently, hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted heteroalkyl, —$N(R^{a1})_2$, —$OR^{b1}$, —$SR^{c1}$, or —CN; wherein two or three $R^3$ groups are optionally joined to form a substituted or unsubstituted bridged ring; wherein two or three $R^4$ groups are optionally joined to form a substituted or unsubstituted bridged ring;

$R^5$ is hydrogen, substituted or unsubstituted acyl, substituted or unsubstituted alkyl, or a nitrogen protecting group;

each occurrence of $R^{a1}$ is, independently, hydrogen, substituted or unsubstituted acyl, substituted or unsubstituted alkyl, substituted or unsubstituted heteroalkyl, substituted or unsubstituted carbocyclyl, substituted or unsubstituted heterocyclyl, or a nitrogen protecting group, or two $R^{a1}$ groups are joined to form a substituted or unsubstituted heterocyclic ring;

each occurrence of $R^{b1}$ is, independently, hydrogen, substituted or unsubstituted acyl, substituted or unsubstituted alkyl, substituted or unsubstituted alkenyl, substituted or unsubstituted alkynyl, substituted or unsubstituted heteroalkyl, substituted or unsubstituted carbocyclyl, substituted or unsubstituted heterocyclyl, or an oxygen protecting group;

each occurrence of $R^{c1}$ is, independently, hydrogen, substituted or unsubstituted acyl, substituted or unsubstituted alkyl, substituted or unsubstituted alkenyl, substituted or unsubstituted alkynyl, substituted or unsubstituted heteroalkyl, substituted or unsubstituted carbocyclyl, substituted or unsubstituted heterocyclyl, or a sulfur protecting group;

m, k, and q are each independently 0, 1, or 2; and p1 and p2 are each independently 0, 1, 2, 3, or 4.

In certain embodiments, Y is —O—, —($CR^3R^4$)—, or —$NR^{a1}$—; and $R^3$, $R^4$, and $R^{a1}$ are as defined herein. In certain embodiments, Y is —O—. In certain embodiments, Y is —($CR^3R^4$)—; and $R^3$, $R^4$, and $R^{a1}$ are as defined herein. In certain embodiments, Y is —$NR^{a1}$—; and $R^{a1}$ is as defined herein.

In certain embodiments, Y is —O—, —($CR^3R^4$)—, or —$NR^{a1}$—; each occurrence of $R^3$ and $R^4$ is, independently, hydrogen, halogen, substituted or unsubstituted alkyl; wherein two or three $R^3$ groups are optionally joined to form a substituted or unsubstituted bridged ring; wherein two or three $R^4$ groups are optionally joined to form a substituted or unsubstituted bridged ring; and each occurrence of $R^{a1}$ is, independently, hydrogen, substituted or unsubstituted acyl, substituted or unsubstituted alkyl, substituted or unsubstituted heteroalkyl, substituted or unsubstituted carbocyclyl, substituted or unsubstituted heterocyclyl, or a nitrogen protecting group.

In certain embodiments, Y is —O—, —($CR^3R^4$)—, or —$NR^{a1}$—; each occurrence of $R^3$ and $R^4$ is, independently, hydrogen, halogen, substituted or unsubstituted alkyl; wherein two or three $R^3$ groups are optionally joined to form a substituted or unsubstituted bridged ring; wherein two or three $R^4$ groups are optionally joined to form a substituted or unsubstituted bridged ring; each occurrence of $R^{a1}$ is, independently, hydrogen, substituted or unsubstituted acyl, substituted or unsubstituted alkyl, substituted or unsubstituted heteroalkyl, substituted or unsubstituted carbocyclyl, substituted or unsubstituted heterocyclyl, or a nitrogen protecting group; the sum of m and n is 0, 1, or 2; and the sum of k and q is 0, 1, or 2.

In certain embodiments, Y is —O—, —($CR^3R^4$)—, or —$NR^{a1}$—; each occurrence of $R^3$ and $R^4$ is, independently, hydrogen, halogen, substituted or unsubstituted alkyl; wherein two or three $R^3$ groups are optionally joined to form a substituted or unsubstituted bridged ring; wherein two or three $R^4$ groups are optionally joined to form a substituted or unsubstituted bridged ring; and each occurrence of $R^{a1}$ is, independently, hydrogen, substituted or unsubstituted acyl, substituted or unsubstituted alkyl, or a nitrogen protecting group.

In certain embodiments, Y is —O—, —($CR^3R^4$)—, or —$NR^{a1}$—; each occurrence of $R^3$ and $R^4$ is, independently, hydrogen, halogen, substituted or unsubstituted alkyl; wherein two or three $R^3$ groups are optionally joined to form a substituted or unsubstituted bridged ring; wherein two or three $R^4$ groups are optionally joined to form a substituted or unsubstituted bridged ring; each occurrence of $R^{a1}$ is, independently, hydrogen, substituted or unsubstituted acyl, substituted or unsubstituted alkyl, or a nitrogen protecting group; the sum of m and n is 0, 1, or 2; and the sum of k and q is 0, 1, or 2.

In certain embodiments, Y is —O—, —($CR^3R^4$)—, or —$NR^{a1}$—; each occurrence of $R^3$ and $R^4$ is, independently, hydrogen, or substituted or unsubstituted alkyl; wherein two or three $R^3$ groups are optionally joined to form a substituted or unsubstituted bridged ring; and each occurrence of $R^{a1}$ is, independently, hydrogen, substituted or unsubstituted acyl, substituted or unsubstituted alkyl, or a nitrogen protecting group.

In certain embodiments, Y is —O—, —($CR^3R^4$)—, or —$NR^{a1}$—; each occurrence of $R^3$ and $R^4$ is, independently, hydrogen, or substituted or unsubstituted alkyl; wherein two or three $R^3$ groups are optionally joined to form a substituted or unsubstituted bridged ring; each occurrence of $R^{a1}$ is, independently, hydrogen, substituted or unsubstituted acyl, substituted or unsubstituted alkyl, or a nitrogen protecting group; the sum of m and n is 0, 1, or 2; and the sum of k and q is 0, 1, or 2.

In certain embodiments, Y is —$NR^{a1}$—; each occurrence of $R^3$ and $R^4$ is, independently, hydrogen, or substituted or unsubstituted alkyl; wherein two or three $R^3$ groups are optionally joined to form a substituted or unsubstituted bridged ring; and each occurrence of $R^{a1}$ is, independently, hydrogen, substituted or unsubstituted acyl, substituted or unsubstituted alkyl, or a nitrogen protecting group.

In certain embodiments, Y is —$NR^{a1}$—; each occurrence of $R^3$ and $R^4$ is, independently, hydrogen, or substituted or unsubstituted alkyl; wherein two or three $R^3$ groups are optionally joined to form a substituted or unsubstituted bridged ring; each occurrence of $R^{a1}$ is, independently, hydrogen, substituted or unsubstituted acyl, substituted or unsubstituted alkyl, or a nitrogen protecting group; the sum of m and n is 0, 1, or 2; and the sum of k and q is 0, 1, or 2.

In certain embodiments, Y is —O— or —($CR^3R^4$)—; and each occurrence of $R^3$ and $R^4$ is, independently, hydrogen, halogen, or substituted or unsubstituted alkyl; wherein two or three $R^3$ groups are optionally joined to form a substituted or unsubstituted bridged ring; wherein two or three $R^4$ groups are optionally joined to form a substituted or unsubstituted bridged ring.

In certain embodiments, Y is —O— or —($CR^3R^4$)—; each occurrence of $R^3$ and $R^4$ is, independently, hydrogen, halogen, or substituted or unsubstituted alkyl; wherein two or three $R^3$ groups are optionally joined to form a substituted or unsubstituted bridged ring; wherein two or three $R^4$ groups are optionally joined to form a substituted or unsubstituted bridged ring; the sum of m and n is 0, 1, or 2; and the sum of k and q is 0, 1, or 2.

In certain embodiments, Y is —O— or —($CR^3R^4$)—; and each occurrence of $R^3$ and $R^4$ is, independently, hydrogen, or substituted or unsubstituted alkyl; wherein two or three $R^3$ groups are optionally joined to form a substituted or unsubstituted bridged ring.

In certain embodiments, Y is —O— or —($CR^3R^4$)—; each occurrence of $R^3$ and $R^4$ is, independently, hydrogen, or substituted or unsubstituted alkyl; wherein two or three $R^3$ groups are optionally joined to form a substituted or unsubstituted bridged ring; the sum of m and n is 0, 1, or 2; and the sum of k and q is 0, 1, or 2.

In certain embodiments, Y is —O—; and each occurrence of $R^3$ and $R^4$ is, independently, hydrogen, halogen, or substituted or unsubstituted alkyl; wherein two or three $R^3$ groups are optionally joined to form a substituted or unsubstituted bridged ring; wherein two or three $R^4$ groups are optionally joined to form a substituted or unsubstituted bridged ring.

In certain embodiments, Y is —O—; each occurrence of $R^3$ and $R^4$ is, independently, hydrogen, halogen, or substituted or unsubstituted alkyl; wherein two or three $R^3$ groups are optionally joined to form a substituted or unsubstituted bridged ring; wherein two or three $R^4$ groups are optionally joined to form a substituted or unsubstituted bridged ring; the sum of m and n is 0, 1, or 2; and the sum of k and q is 0, 1, or 2.

In certain embodiments, Y is —O—; and each occurrence of $R^3$ and $R^4$ is, independently, hydrogen, or substituted or unsubstituted alkyl; wherein two or three $R^3$ groups are optionally joined to form a substituted or unsubstituted bridged ring.

In certain embodiments, Y is —O—; and each occurrence of $R^3$ and $R^4$ is, independently, hydrogen, or substituted or unsubstituted alkyl; wherein two or three $R^3$ groups are optionally joined to form a substituted or unsubstituted bridged ring; the sum of m and n is 0, 1, or 2; and the sum of k and q is 0, 1, or 2.

In certain embodiments, Y is —($CR^3R^4$)—; and each occurrence of $R^3$ and $R^4$ is, independently, hydrogen, halogen, or substituted or unsubstituted alkyl; wherein two or three $R^3$ groups are optionally joined to form a substituted or unsubstituted bridged ring; wherein two or three $R^4$ groups are optionally joined to form a substituted or unsubstituted bridged ring.

In certain embodiments, Y is —($CR^3R^4$)—; each occurrence of $R^3$ and $R^4$ is, independently, hydrogen, halogen, or substituted or unsubstituted alkyl; wherein two or three $R^3$ groups are optionally joined to form a substituted or unsubstituted bridged ring; wherein two or three $R^4$ groups are optionally joined to form a substituted or unsubstituted bridged ring; the sum of m and n is 0, 1, or 2; and the sum of k and q is 0, 1, or 2.

In certain embodiments, Y is —($CR^3R^4$)—; and each occurrence of $R^3$ and $R^4$ is, independently, hydrogen, or substituted or unsubstituted alkyl; wherein two or three $R^3$ groups are optionally joined to form a substituted or unsubstituted bridged ring.

In certain embodiments, Y is —($CR^3R^4$)—; each occurrence of $R^3$ and $R^4$ is, independently, hydrogen, or substituted or unsubstituted alkyl; wherein two or three $R^3$ groups are optionally joined to form a substituted or unsubstituted bridged ring; the sum of m and n is 0, 1, or 2; and the sum of k and q is 0, 1, or 2.

In certain embodiments, Y is —($CHR^3$)—; and each occurrence of $R^3$ and $R^4$ is, independently, hydrogen, halogen, or substituted or unsubstituted alkyl; wherein two or three $R^3$ groups are optionally joined to form a substituted or unsubstituted bridged ring; wherein two or three $R^4$ groups are optionally joined to form a substituted or unsubstituted bridged ring.

In certain embodiments, Y is —($CHR^3$)—; each occurrence of $R^3$ and $R^4$ is, independently, hydrogen, halogen, or substituted or unsubstituted alkyl; wherein two or three $R^3$ groups are optionally joined to form a substituted or unsubstituted bridged ring; wherein two or three $R^4$ groups are optionally joined to form a substituted or unsubstituted bridged ring; the sum of m and n is 0, 1, or 2; and the sum of k and q is 0, 1, or 2.

In certain embodiments, Y is —($CHR^3$)—; and each occurrence of $R^3$ and $R^4$ is, independently, hydrogen, or substituted or unsubstituted alkyl; wherein two or three $R^3$ groups are optionally joined to form a substituted or unsubstituted bridged ring.

In certain embodiments, Y is —($CHR^3$)—; and each occurrence of $R^3$ and $R^4$ is, independently, hydrogen, or substituted or unsubstituted alkyl; wherein two or three $R^3$ groups are optionally joined to form a substituted or unsubstituted bridged ring; the sum of m and n is 0, 1, or 2; and the sum of k and q is 0, 1, or 2.

In certain embodiments, the sum of m and n is 0, 1, or 2. In certain embodiments, m is 0; and n is 0. In certain embodiments, m is 1; and n is 0. In certain embodiments, m is 2; and n is 0. In certain embodiments, m is 0; and n is 1. In certain embodiments, m is 1; and n is 1. In certain embodiments, m is 0; and n is 2.

In certain embodiments, the sum of k and q is 0, 1, or 2. In certain embodiments, k is 0; and q is 0. In certain embodiments, k is 1; and q is 0. In certain embodiments, k is 2; and q is 0. In certain embodiments, k is 0; and q is 1. In certain embodiments, k is 1; and q is 1. In certain embodiments, k is 0; and q is 2.

In certain embodiments, B is of formula:

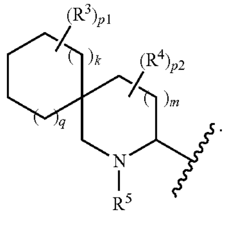

In certain embodiments, B is of formula:

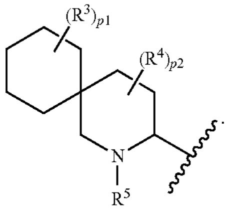

In certain embodiments, B is of formula:

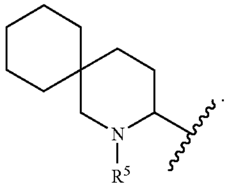

In certain embodiments, B is of formula:

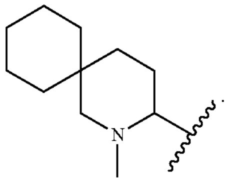 [SMILES: *C1CCC2(CCCCC2)CN1C]

In certain embodiments, B is of formula:

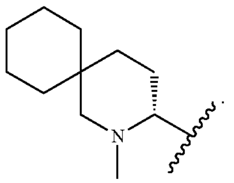 [SMILES: *[C@H]1CCC2(CCCCC2)CN1C]

In certain embodiments, B is of formula:

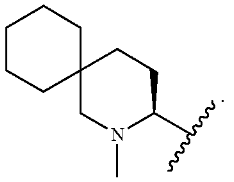 [SMILES: *[C@@H]1CCC2(CCCCC2)CN1C]

In certain embodiments, B is of formula:

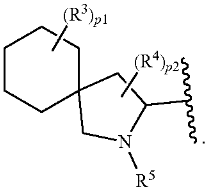

In certain embodiments, B is of formula:

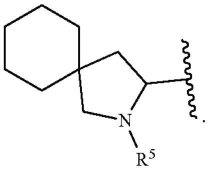

In certain embodiments, B is of formula:

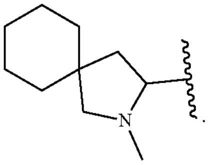 [SMILES: *C1CC2(CCCCC2)CN1C]

In certain embodiments, B is of formula:

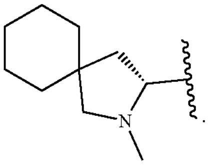 [SMILES: *[C@H]1CC2(CCCCC2)CN1C]

In certain embodiments, B is of formula:

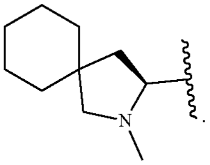 [SMILES: *[C@@H]1CC2(CCCCC2)CN1C]

Certain Embodiments

In certain embodiments, the compound of Formula (VI) is of Formula (VI-a):

(VI-a)

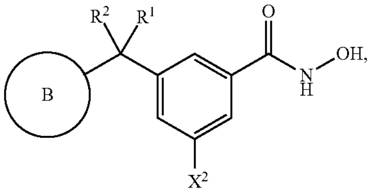

or a pharmaceutically acceptable salt, co-crystal, tautomer, stereoisomer, solvate, hydrate, polymorph, isotopically enriched derivative, or prodrug thereof; wherein $X^2$, $R^1$, $R^2$, and B are as defined herein.

In certain embodiments, the compound of Formula (VI) is of Formula (VI-b):

(VI-b)

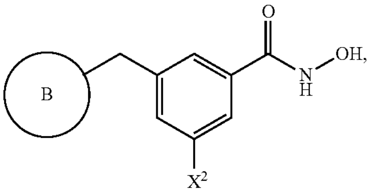

or a pharmaceutically acceptable salt, co-crystal, tautomer, stereoisomer, solvate, hydrate, polymorph, isotopically enriched derivative, or prodrug thereof; wherein $X^2$ and B are as defined herein.

In certain embodiments, the compound of Formula (VI) is of Formula (VI-c):

(VI-c)

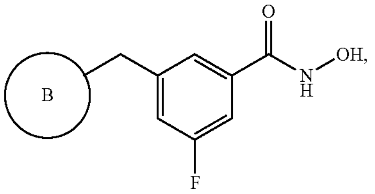

or a pharmaceutically acceptable salt, co-crystal, tautomer, stereoisomer, solvate, hydrate, polymorph, isotopically enriched derivative, or prodrug thereof; wherein B is as defined herein.

In certain embodiments, the compound of Formula (VI) is one of the following compounds, or a pharmaceutically acceptable salt, co-crystal, tautomer, stereoisomer, solvate, hydrate, polymorph, isotopically enriched derivative, or prodrug thereof:

274

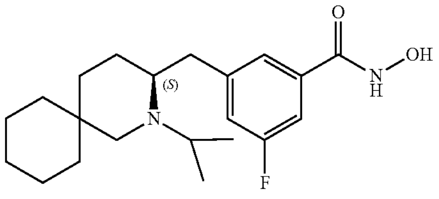

-continued

275

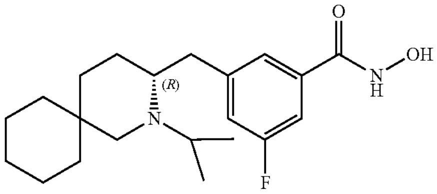

276

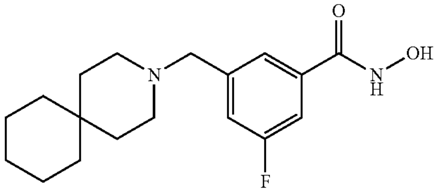

Compound of Formula (VII)

In another aspect, disclosed is a compound of Formula (VII):

(VII)

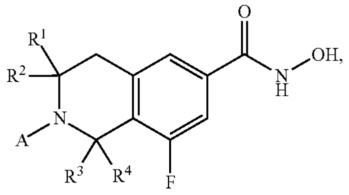

or a pharmaceutically acceptable salt, co-crystal, tautomer, stereoisomer, solvate, hydrate, polymorph, isotopically enriched derivative, or prodrug thereof, wherein:

A is substituted or unsubstituted carbocyclyl, or substituted or unsubstituted heterocyclyl; and $R^1$, $R^2$, $R^3$, and $R^4$ are each independently hydrogen or substituted or unsubstituted alkyl; provided that at least one of $R^1$ and $R^2$ is not hydrogen.

A

As described herein, A is substituted or unsubstituted carbocyclyl, or substituted or unsubstituted heterocyclyl. In certain embodiments, A is substituted or unsubstituted cycloalkyl, or substituted or unsubstituted heterocyclyl.

In certain embodiments, A is substituted or unsubstituted cycloalkyl. In certain embodiments, A is substituted or unsubstituted $C_{3-10}$ cycloalkyl. In certain embodiments, A is a substituted or unsubstituted $C_{5-10}$ bridged cycloalkyl, substituted or unsubstituted $C_{5-10}$ spirocyclic cycloalkyl, or substituted or unsubstituted $C_{3-8}$ monocyclic cycloalkyl. In certain embodiments, A is a substituted or unsubstituted $C_{5-10}$ bridged cycloalkyl. In certain embodiments, A is a substituted or unsubstituted $C_{5-10}$ spirocyclic cycloalkyl. In certain embodiments, A is a substituted or unsubstituted $C_{8-10}$ spirocyclic cycloalkyl. In certain embodiments, A is substituted or unsubstituted $C_{3-8}$ monocyclic cycloalkyl. In certain embodiments, A is substituted or unsubstituted $C_{3-6}$ monocyclic cycloalkyl.

In certain embodiments, A is substituted or unsubstituted heterocyclyl. In certain embodiments, A is substituted or unsubstituted 4-10 membered heterocyclyl. In certain embodiments, A is substituted or unsubstituted monocyclic 4-7 membered heterocyclyl. In certain embodiments, A is substituted or unsubstituted monocyclic 4-6 membered heterocyclyl. In certain embodiments, A is substituted or unsubstituted monocyclic 4-5 membered heterocyclyl. In certain embodiments, A is substituted or unsubstituted monocyclic 5-6 membered heterocyclyl. In certain embodiments, A is a substituted or unsubstituted $C_{5-10}$ spirocyclic heterocyclyl. In certain embodiments, A is a substituted or unsubstituted $C_{7-10}$ spirocyclic heterocyclyl. In certain embodiments, A is a substituted or unsubstituted $C_{5-10}$ polycyclic spiro ring system comprising a heterocyclyl ring. In certain embodiments, A is a substituted or unsubstituted $C_{7-10}$ polycyclic spiro ring system comprising a heterocyclyl ring.

In certain embodiments, A is substituted or unsubstituted oxetanyl, substituted or unsubstituted tetrahydrofuranyl, substituted or unsubstituted pyranyl, substituted or unsubstituted dihydropyranyl, substituted or unsubstituted tetrahydropyranyl, substituted or unsubstituted dioxanyl, substituted or unsubstituted oxepanyl, substituted or unsubstituted azetidinyl, substituted or unsubstituted pyrrolidinyl, substituted or unsubstituted piperidinyl, substituted or unsubstituted piperazinyl, substituted or unsubstituted azepanyl, substituted or unsubstituted diazepanyl, substituted or unsubstituted morpholinyl, substituted or unsubstituted oxazepanyl, or oxaadamantanyl.

In certain embodiments, A is a substituted or unsubstituted $C_{7-10}$ polycyclic spiro ring system comprising a heterocycle, substituted or unsubstituted $C_{5-10}$ spirocyclic cycloalkyl, substituted or unsubstituted $C_{3-6}$ monocyclic cycloalkyl, or substituted or unsubstituted monocyclic 4-7 membered heterocyclyl.

In certain embodiments, A is cyclopropyl, cyclobutyl,

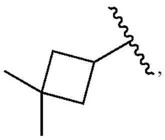 [SMILES: *C1CC(C)(C)C1], oxetanyl,

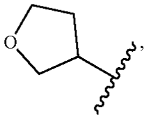, 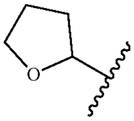, 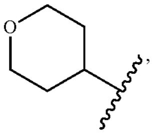,

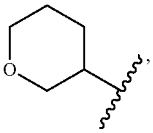, 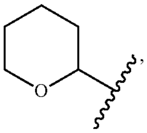, 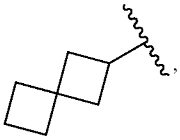,

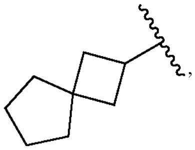, 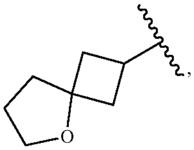,

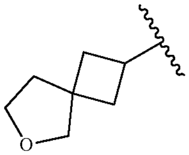, 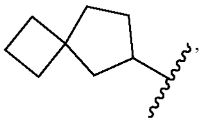,

-continued

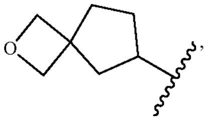, 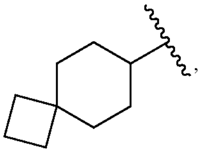,

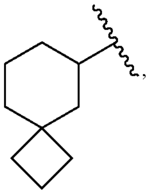, 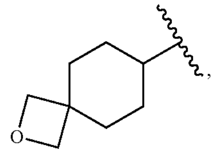, 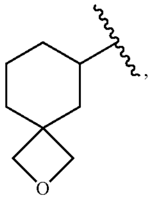,

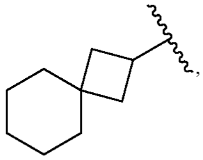, 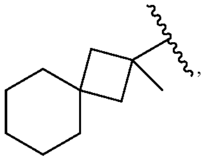, or

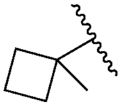

$R^1$, $R^2$, $R^3$, and $R^4$

As described herein, $R^1$, $R^2$, $R^3$, and $R^4$ are each independently hydrogen or substituted or unsubstituted alkyl; provided that at least one of $R^1$ and $R^2$ is not hydrogen. In certain embodiments, $R^1$, $R^2$, $R^3$, and $R^4$ are each independently hydrogen or substituted or unsubstituted $C_{1-4}$ alkyl; provided that at least one of $R^1$ and $R^2$ is not hydrogen. In certain embodiments, $R^1$, $R^2$, $R^3$, and $R^4$ are each independently hydrogen or substituted or unsubstituted $C_{1-2}$ alkyl; provided that at least one of $R^1$ and $R^2$ is not hydrogen.

In certain embodiments, $R^1$, $R^2$, $R^3$, and $R^4$ are each independently hydrogen, methyl, ethyl, propyl, isopropyl, t-butyl, cyclopropyl,

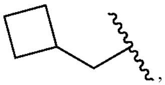, 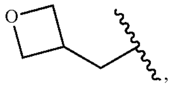, benzyl,

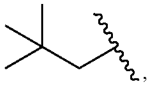, or 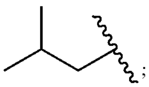;

provided that at least one of $R^1$ and $R^2$ is not hydrogen.

Certain Embodiments

In certain embodiments of the compounds of Formula (V), A is cyclopropyl, cyclobutyl,

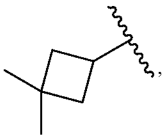 [SMILES: *C1CC(C)(C)C1], oxetanyl,

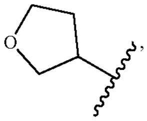, 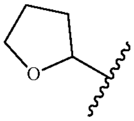, 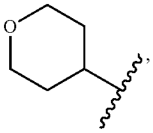,

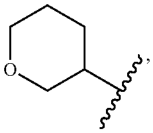, 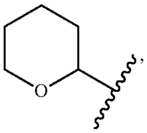, 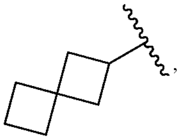,

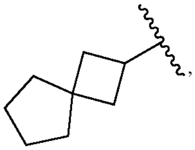, 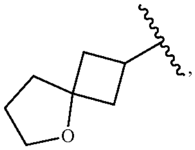,

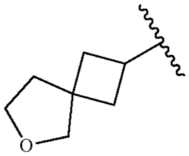, 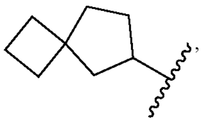,

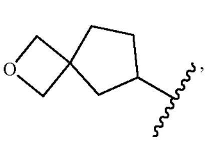, 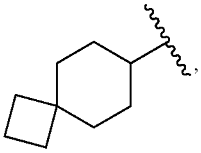,

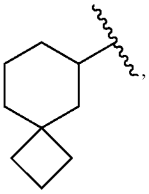, 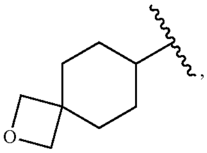, 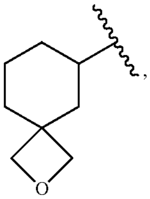,

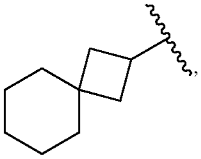, 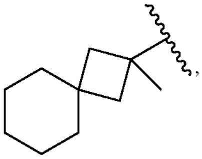, or

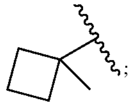;

and $R^1$, $R^2$, $R^3$, and $R^4$ are each independently hydrogen, methyl, ethyl, propyl, isopropyl, t-butyl, cyclopropyl,

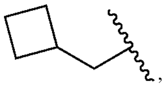, 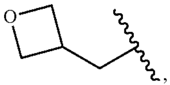, benzyl,

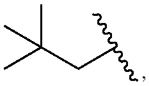, or 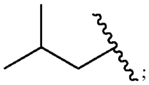;

provided that at least one of $R^1$, $R^2$, $R^3$, and $R^4$ is not hydrogen.

In certain embodiments, the compound of Formula (VII) is of Formula (VII-a):

(VII-a)

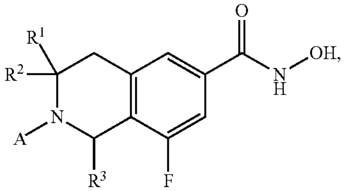

or a pharmaceutically acceptable salt, co-crystal, tautomer, stereoisomer, solvate, hydrate, polymorph, isotopically enriched derivative, or prodrug thereof; wherein A, $R^1$, $R^2$, and $R^3$ are as defined herein.

In certain embodiments of the compounds of Formula (VII-a), A is cyclopropyl, cyclobutyl,

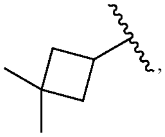 [SMILES: *C1CC(C)(C)C1], oxetanyl,

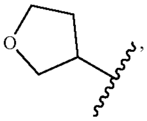, 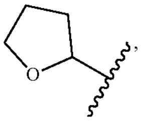, 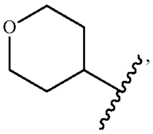,

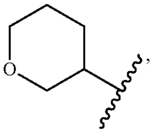, 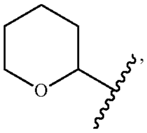, 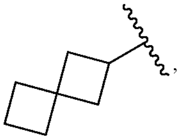,

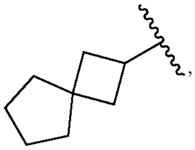, 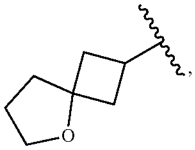,

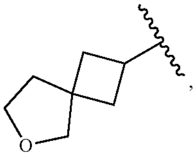, 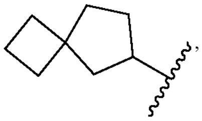,

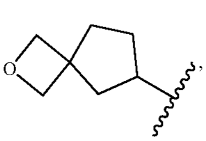, 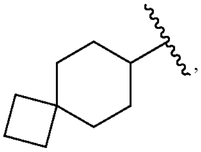,

-continued

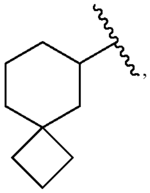 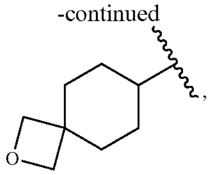 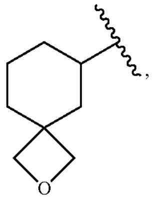

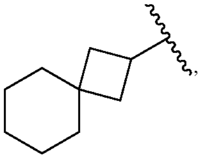 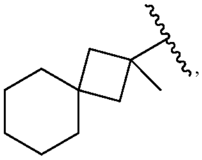 or

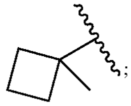

and $R^1$, $R^2$, and $R^3$ are each independently hydrogen, methyl, ethyl, propyl, isopropyl, t-butyl, cyclopropyl,

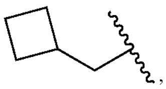 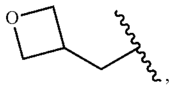

benzyl,

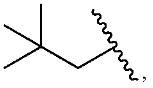 or 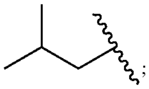

provided that at least one of $R^1$, $R^2$, and $R^3$ is not hydrogen.

In certain embodiments, the compound of Formula (VII) is of Formula (VII-b):

(VII-b)

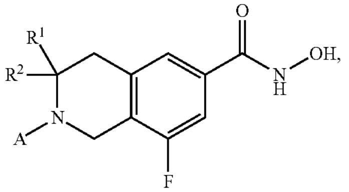

or a pharmaceutically acceptable salt, co-crystal, tautomer, stereoisomer, solvate, hydrate, polymorph, isotopically enriched derivative, or prodrug thereof; wherein A, $R^1$, and $R^2$ are as defined herein.

In certain embodiments of the compounds of Formula (VII-b), A is cyclopropyl, cyclobutyl,

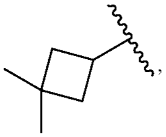 [SMILES: *C1CC(C)(C)C1]

oxetanyl,

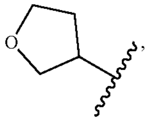 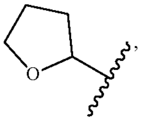 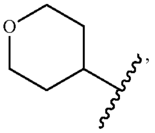

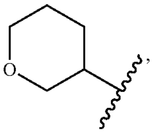 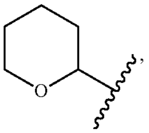 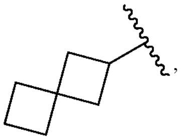

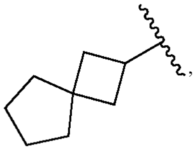 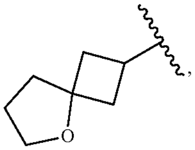

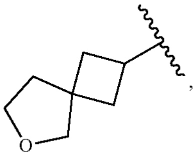 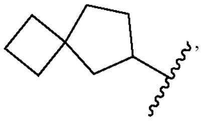

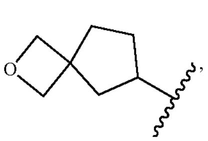 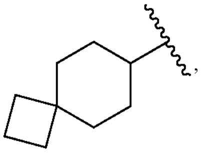

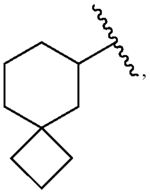 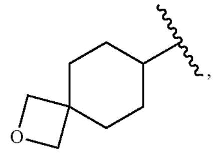 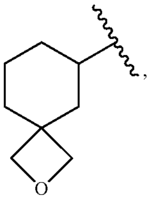

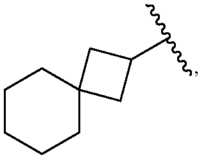 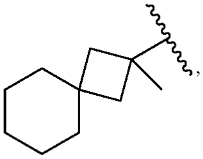 or

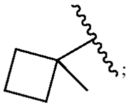

and $R^1$ and $R^2$ are each independently hydrogen, methyl, ethyl, propyl, isopropyl, t-butyl, cyclopropyl,

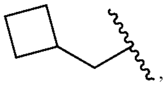 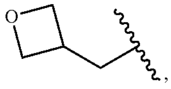

benzyl,

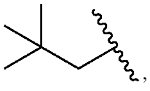 or 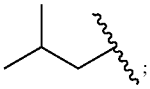

provided that at least one of $R^1$ and $R^2$ is not hydrogen.

In certain embodiments, the compound of Formula (VII) is of Formula (VII-c):

(VII-c)

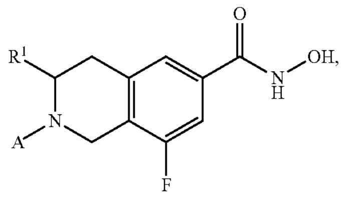

or a pharmaceutically acceptable salt, co-crystal, tautomer, stereoisomer, solvate, hydrate, polymorph, isotopically enriched derivative, or prodrug thereof; wherein A and $R^1$ are as defined herein.

In certain embodiments of the compounds of Formula (VII-c), A is cyclopropyl, cyclobutyl,

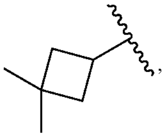 [SMILES: *C1CC(C)(C)C1], oxetanyl,

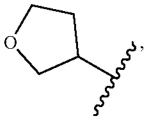, 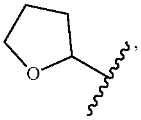, 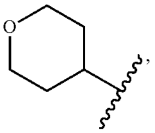,

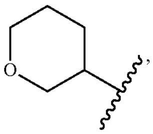, 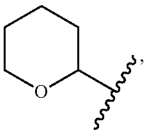, 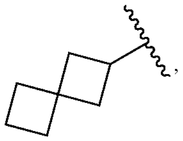,

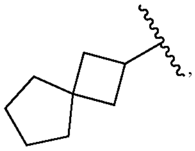, 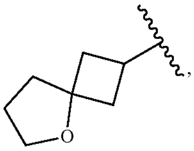,

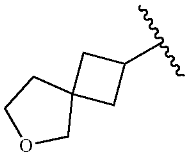, 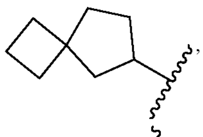,

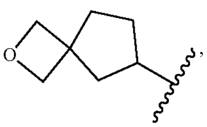, 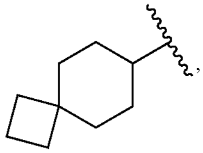,

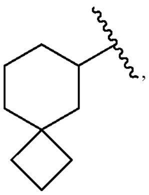, 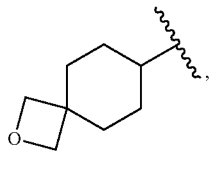, 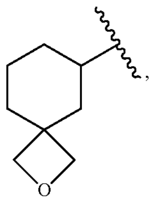,

-continued

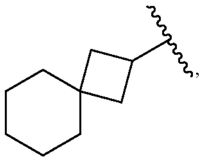, 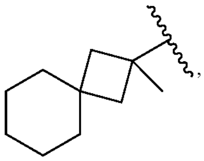, or

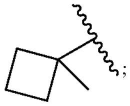;

and $R^1$ is methyl, ethyl, propyl, isopropyl, t-butyl, cyclopropyl,

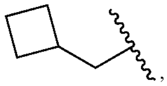, 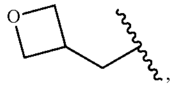, benzyl,

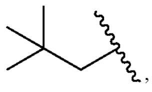, or 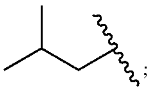;

In certain embodiments, the compound of Formula (VII) is one of the following compounds, or a pharmaceutically acceptable salt, co-crystal, tautomer, stereoisomer, solvate, hydrate, polymorph, isotopically enriched derivative, or prodrug thereof:

277

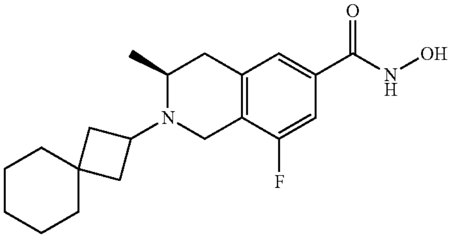

278

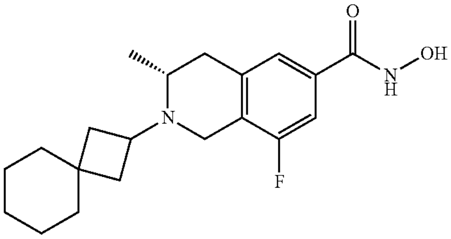

-continued

279

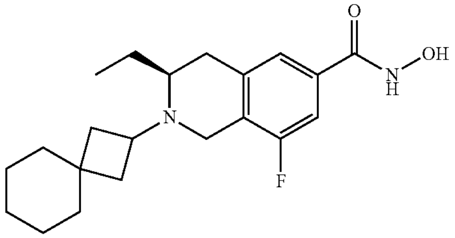

280

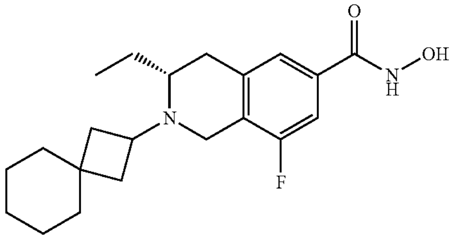

281

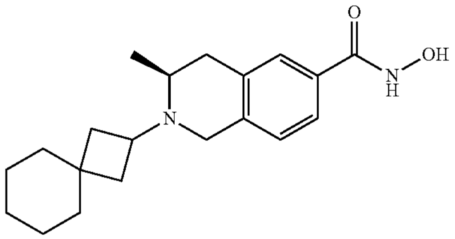

282

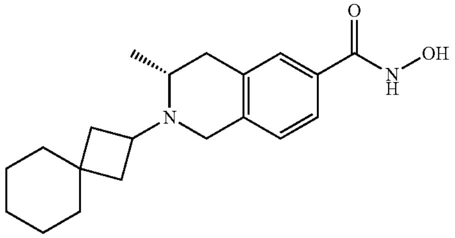

283

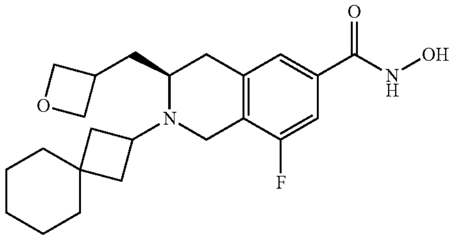

284

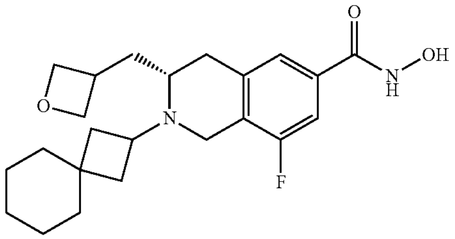

-continued

285

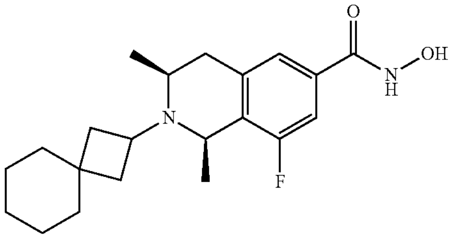

286

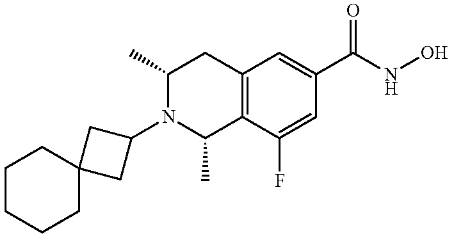

287

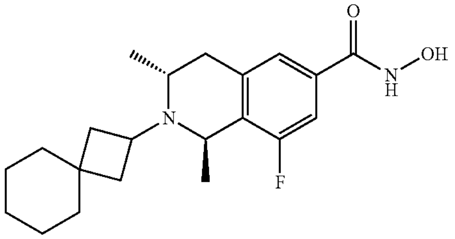

288

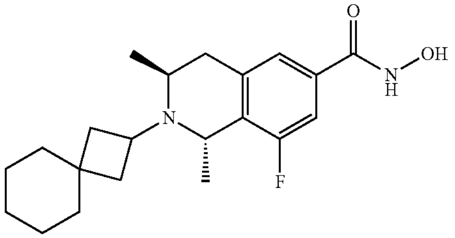

In certain embodiments, the provided compounds (e.g., compounds of Formula (I), (II), (III), (IV), (V), (VI), and (VII)) inhibit HDAC6 with an $IC_{50}$ of less than 100,000 nM, less than 50,000 nM, less than 20,000 nM, less than 10,000 nM, less than 5,000 nM, less than 2,500 nM, less than 1,000 nM, less than 900 nM, less than 800 nM, less than 700 nM, less than 600 nM, less than 500 nM, less than 400 nM, less than 300 nM, less than 200 nM, less than 100 nM, less than 90 nM, less than 80 nM, less than 70 nM, less than 60 nM, less than 50 nM, less than 40 nM, less than 30 nM, less than 20 nM, less than 10 nM, less than 5 nM, less than 4 nM, less than 3 nM, less than 2 nM, or less than 1 nM.

In certain embodiments, the provided compounds (e.g., compounds of Formula (I), (II), (III), (IV), (V), (VI), and (VII)) selectively inhibit HDAC6 over any of HDAC1, HDAC2, HDAC3, HDAC4, HDAC5, HDAC7, HDAC8, HDAC9, HDAC10, and HDAC11. In certain embodiments, the compounds selectively inhibit HDAC6 over each of HDAC1, HDAC2, HDAC3, HDAC4, HDAC5, HDAC7, HDAC8, HDAC9, HDAC10, and HDAC11. In certain embodiments, the compounds are 5-fold, 10-fold, 20-fold, 30-fold, 40-fold, 50-fold, 60-fold, 70-fold, 80-fold, 90-fold, 100-fold, 1,000-fold, or 10,000-fold, more selective inhibitors of HDAC6 over any of HDAC1, HDAC2, HDAC3, HDAC4, HDAC5, HDAC7, HDAC8, HDAC9, HDAC10, and HDAC11. In certain embodiments, the compounds are 5-fold, 10-fold, 20-fold, 30-fold, 40-fold, 50-fold, 60-fold, 70-fold, 80-fold, 90-fold, 100-fold, 1,000-fold, or 10,000-fold, more selective inhibitors of HDAC6 over each of HDAC1, HDAC2, HDAC3, HDAC4, HDAC5, HDAC7, HDAC8, HDAC9, HDAC10, and HDAC11. In certain embodiments, the compounds are 5-fold, 10-fold, 20-fold, 30-fold, 40-fold, 50-fold, 60-fold, 70-fold, 80-fold, 90-fold, 100-fold, 1,000-fold, or 10,000-fold, more selective inhibitors of HDAC6 over HDAC8.

Pharmaceutical Compositions, Kits, and Administration

The present disclosure provides pharmaceutical compositions comprising a disclosed compound (e.g., a compound of Formula (I), (II), (III), (IV), (V), (VI), or (VII)), or a pharmaceutically acceptable salt, co-crystal, tautomer, stereoisomer, solvate, hydrate, polymorph, isotopically enriched derivative, or prodrug thereof, and optionally a pharmaceutically acceptable excipient. In certain embodiments, the pharmaceutical composition described herein comprises a compound of Formula (I), (II), (III), (IV), (V), (VI), or (VII), or a pharmaceutically acceptable salt thereof, and a pharmaceutically acceptable excipient.

In certain embodiments, the compound of Formula (I), (II), (III), (IV), (V), (VI), or (VII) is provided in an effective amount in the pharmaceutical composition. In certain embodiments, the effective amount is a therapeutically effective amount. In certain embodiments, the effective amount is a prophylactically effective amount. In certain embodiments, the effective amount is an amount effective for treating a proliferative disease in a subject in need thereof. In certain embodiments, the effective amount is an amount effective for treating cancer in a subject in need thereof. In certain embodiments, the effective amount is an amount effective for preventing cancer in a subject in need thereof. In certain embodiments, the effective amount is an amount effective for treating a hematological cancer in a subject in need thereof. In certain embodiments, the effective amount is an amount effective for treating a cancer comprising a solid tumor in a subject in need thereof. In certain embodiments, the effective amount is an amount effective for treating inflammatory disease in a subject in need thereof. In certain embodiments, the effective amount is an amount effective for preventing inflammatory disease in a subject in need thereof. In certain embodiments, the effective amount is an amount effective for treating an infectious disease in a subject in need thereof. In certain embodiments, the effective amount is an amount effective for preventing an infectious disease in a subject in need thereof. In certain embodiments, the effective amount is an amount effective for treating a cardiovascular disease in a subject in need thereof. In certain embodiments, the effective amount is an amount effective for treating a neurological disorder in a subject in need thereof. In certain embodiments, the effective amount is an amount effective for preventing a neurological disorder in a subject in need thereof. In certain embodiments, the effective amount is an amount effective for treating a neurodegenerative, neurodevelopmental, neuropsychiatric, or neuropathy disease in a subject in need thereof. In certain embodiments, the effective amount is an amount effective for treating a peripheral disorder in a subject in need thereof. In certain embodiments, the effective amount is an amount effective for preventing a peripheral disorder in a subject in need thereof. In certain embodiments, the effective amount is an amount effective for treating a chemotherapy-induced peripheral neuropathy, diabetic peripheral neuropathy, peripheral neuropathy, diabetic retinopathy, obesity, autosomal dominant polycystic kidney disease, cardiomyopathy, an auto-immune disease such as systemic lupus erythematosus (SLE), or cancer in a subject in need thereof.

In certain embodiments, the effective amount is an amount effective for reducing the risk of developing a disease (e.g., proliferative disease, inflammatory disease, infectious disease, a neurological disorder, a peripheral disorder, or cardiovascular disease) in a subject in need thereof.

In certain embodiments, the effective amount is an amount effective for inhibiting the activity (e.g., aberrant activity, such as increased activity) of HDAC6 in a subject, tissue, biological sample, or cell.

In certain embodiments, the subject being treated or administered a compound described herein is an animal. The animal may be of either sex and may be at any stage of development. In certain embodiments, the subject described herein is a human. In certain embodiments, the subject is a non-human animal. In certain embodiments, the subject is a mammal. In certain embodiments, the subject is a non-human mammal. In certain embodiments, the subject is a domesticated animal, such as a dog, cat, cow, pig, horse, sheep, or goat. In certain embodiments, the subject is a companion animal, such as a dog or cat. In certain embodiments, the subject is a livestock animal, such as a cow, pig, horse, sheep, or goat. In certain embodiments, the subject is a zoo animal. In another embodiment, the subject is a research animal, such as a rodent (e.g., mouse, rat), dog, pig, or non-human primate. In certain embodiments, the animal is a genetically engineered animal. In certain embodiments, the animal is a transgenic animal (e.g., transgenic mice and transgenic pigs). In certain embodiments, the subject is a fish or reptile.

In certain embodiments, the effective amount is an amount effective for inhibiting the activity of HDAC6 by at least about 10%, at least about 20%, at least about 30%, at least about 40%, at least about 50%, at least about 60%, at least about 70%, at least about 80%, at least about 90%, at least about 95%, at least about 98%, or at least about 99%. In certain embodiments, the effective amount is an amount effective for inhibiting the activity of HDAC6 by a range between a percentage described in this paragraph and another percentage described in this paragraph, inclusive.

The present disclosure provides pharmaceutical compositions comprising a compound that interacts with (e.g., inhibits) HDAC6 for use in treating a HDAC6-related disease or disorder in a subject in need thereof. The present disclosure provides pharmaceutical compositions comprising a compound that interacts with (e.g., inhibits) HDAC6 for use in treating a disease or disorder associated with aberrant activity of HDAC6 in a subject in need thereof. The present disclosure provides pharmaceutical compositions comprising a compound that interacts with (e.g., inhibits) HDAC6 for use in treating a disease or disorder associated with increased activity of HDAC6 in a subject in need thereof.

In certain embodiments, the composition is for use in treating a proliferative disease in a subject in need thereof. In certain embodiments, the composition is for use in treating cancer in a subject in need thereof. In certain embodiments, the composition is for use in treating a hematological cancer. In certain embodiments, the composition is for use in treating a leukemia, T-cell lymphoma, Hodgkin's Disease, non-Hodgkin's lymphoma, or multiple myeloma. In certain embodiments, the composition is for use in treating a cancer comprising a solid tumor. In certain embodiments, the composition is for use in treating glioma, glioblastoma, non-small cell lung cancer, brain tumor, neuroblastoma, bone tumor, soft-tissue sarcoma, head and neck cancer, genitourinary cancer, lung cancer, breast cancer, pancreatic cancer, melanoma, stomach cancer, brain cancer, liver cancer, thyroid cancer, clear cell carcinoma, uterine cancer, or ovarian cancer.

In certain embodiments, the composition is for use in treating an inflammatory disease. In certain embodiments, the composition is for use in treating osteoarthritis, rheumatoid arthritis, lupus, inflammatory bowel disease, Crohn's Disease, ulcerative colitis, anemia, leukocytosis, asthma, chronic obstructive pulmonary disease, appendicitis, bronchitis, bursitis, conjunctivitis, dermatitis, encephalitis, myelitis myocarditis, sinusitis, dermatitis, psoriasis, eczema, or acne.

In certain embodiments, the composition is for use in treating an infectious disease. In certain embodiments, the composition is for use in treating bacterial, fungal, or protozoal infections.

In certain embodiments, the composition is for use in treating autoimmune disease. In certain embodiments, the composition is for use in treating diabetes, thyroiditis, Graves' disease, Guillain-Barre syndrome, Addison's disease, scleroderma, primary biliary cirrhosis, Reiter's syndrome, psoriasis, chronic fatigue, or endometriosis.

In certain embodiments, the composition is for use in treating heteroimmune disease. In certain embodiments, the composition is for use in treating graft versus host disease, transplantation, transfusion, anaphylaxis, allergic conjunctivitis, or allergic rhinitis.

In certain embodiments, the composition is for use in treating a neurological disorder. In certain embodiments, the composition is for use in treating a neurodegenerative, neurodevelopmental, neuropsychiatric, or neuropathy disease. In certain embodiments, the composition is for use in treating Fragile-X syndrome, Charcot-Marie-Tooth disease, Alzheimer's disease, Parkinson's diseases, Huntington's disease, multiple sclerosis, amyotrophic lateral sclerosis, Creutzfeldt-Jakob disease, Lewy body dementia, vascular dementia, muscular atrophy, seizure induced memory loss, schizophrenia, Rubinstein Taybi syndrome, Rett Syndrome, attention deficit hyperactivity disorder, dyslexia, bipolar disorder, social, cognitive and learning disorders associated with autism, attention deficit disorder, schizophrenia, major depressive disorder, peripheral neuropathy, diabetic retinopathy, diabetic peripheral neuropathy, chemotherapy-induced peripheral neuropathy, traumatic brain injury (TBI), chronic traumatic encephalopathy (CTE), or a tauopathy. In certain embodiments, the composition is for use in treating primary age-related tauopathy (PART)/neurofibrillary tangle-predominant senile dementia, chronic traumatic encephalopathy, dementia pugilistica, progressive supranuclear palsy, corticobasal degeneration, Pick's disease, frontotemporal dementia, frontotemporal dementia and parkinsonism linked to chromosome 17, Lytico-Bodig disease, ganglioglioma, gangliocytoma, meningioangiomatosis, postencephalitic parkinsonism, subacute sclerosing panencephalitis, lead encephalopathy, tuberous sclerosis, lipofuscinosis, Alzheimer's disease, or argyrophilic grain disease.

In certain embodiments, the composition is for use in treating a neurological or peripheral disease or disorder. In certain embodiments, the composition is for use in treating a neurodegenerative, neurodevelopmental, neuropsychiatric, or neuropathy disease. In certain embodiments, the composition is for use in treating Alzheimer's disease, Fragile-X syndrome, Charcot-Marie-Tooth disease, Parkinson's disease, Huntington's disease, multiple sclerosis, amyotrophic lateral sclerosis, Rett Syndrome, major depressive disorder, chemotherapy-induced cognitive dysfunction, traumatic brain injury (TBI), chronic traumatic encephalopathy (CTE), brain cancer, or a tauopathy such as frontotemporal dementia, progressive supranuclear palsy, or corticobasal degeneration. In certain embodiments, the composition is for use in treating chemotherapy-induced peripheral neuropathy, diabetic peripheral neuropathy, peripheral neuropathy, diabetic retinopathy, obesity, autosomal dominant polycystic kidney disease, cardiomyopathy, an auto-immune disease such as systemic lupus erythematosus (SLE), or cancer.

In certain embodiments, the composition is for use in treating a disease or disorder mediated by or linked to T-cell dysregulation. In certain embodiments, the composition is for use in treating arthritis, colitis, allograft rejection, lupus, asthma, psoriasis, inflammation, allergy, allergic encephalomyelitis, autoimmune lymphoproliferative disorder, autoimmune polyglandular syndrome type II, type I diabetes, lymphoma, Wiskott-Aldrich syndrome, or myasthenia gravis.

A compound or composition, as described herein, can be administered in combination with one or more additional pharmaceutical agents (e.g., therapeutically and/or prophylactically active agents). The compounds or compositions can be administered in combination with additional pharmaceutical agents that improve their activity (e.g., activity (e.g., potency and/or efficacy) in treating a disease in a subject in need thereof, in preventing a disease in a subject in need thereof, and/or in reducing the risk to develop a disease in a subject in need thereof), improve bioavailability, improve safety, reduce drug resistance, reduce and/or modify metabolism, inhibit excretion, and/or modify distribution in a subject or cell. It will also be appreciated that the therapy employed may achieve a desired effect for the same disorder, and/or it may achieve different effects. In certain embodiments, a pharmaceutical composition described herein including a compound described herein and an additional pharmaceutical agent exhibit a synergistic effect that is absent in a pharmaceutical composition including one of the compound and the additional pharmaceutical agent, but not both.

The compound or composition can be administered concurrently with, prior to, or subsequent to one or more additional pharmaceutical agents, which may be useful as, e.g., combination therapies. Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is a pharmaceutical agent useful for treating and/or preventing a disease (e.g., proliferative disease, hematological cancer, chemo-induced neuropathy, neurological disorder, autoimmune disease, and/or inflammatory disease). Each additional pharmaceutical agent may be administered at a dose and/or on a time schedule determined for that pharmaceutical agent. The additional pharmaceutical agents may also be administered together with each other and/or with the compound or composition described herein in a single dose or administered separately in different doses. The particular combination to employ in a regimen will take into account compatibility of the compound described herein with the additional pharmaceutical agent(s) and/or the desired therapeutic and/or prophylactic effect to be achieved. In general, it is expected that the additional pharmaceutical agent(s) in combination be utilized at levels that do not exceed the levels at which they are utilized individually. In some embodiments, the levels utilized in combination will be lower than those utilized individually.

The additional pharmaceutical agents include, but are not limited to, anti-proliferative agents, anti-cancer agents, anti-angiogenesis agents, anti-inflammatory agents, and immunosuppressants. In certain embodiments, the additional pharmaceutical agent is an anti-inflammatory agent. In certain embodiments, the additional pharmaceutical agent is an immunotherapy. In certain embodiments, the additional pharmaceutical agent is an anti-proliferative agent. In certain embodiments, the additional pharmaceutical agent is an anti-cancer agent. In certain embodiments, the anti-cancer agents include, but are not limited to, epigenetic or transcriptional modulators (e.g., DNA methyltransferase inhibitors, HDAC inhibitors, lysine methyltransferase inhibitors), antimitotic drugs (e.g., taxanes and *vinca* alkaloids), cell signaling pathway inhibitors (e.g., tyrosine protein kinase inhibitors), modulators of protein stability (e.g., proteasome inhibitors), Hsp90 inhibitors, glucocorticoids, all-trans retinoic acids, anti-estrogens (e.g., tamoxifen, raloxifene, and megestrol), LHRH agonists (e.g., goscrclin and leuprolide), anti-androgens (e.g. flutamide and bicalutamide), photodynamic therapies (e.g., vertoporfin (BPD-MA), phthalocyanine, photosensitizer Pc4, and demethoxy-hypocrellin A (2BA-2-DMHA)), nitrogen mustards (e.g., cyclophosphamide, ifosfamide, trofosfamide, chlorambucil, estramustine, and melphalan), nitrosoureas (e.g., carmustine (BCNU) and lomustine (CCNU)), alkylsulphonates (e.g., busulfan and treosulfan), triazenes (e.g. dacarbazine, temozolomide), platinum containing compounds (e.g. cisplatin, carboplatin, oxaliplatin), *vinca* alkaloids (e.g. vincristine, vinblastine, vindesine, and vinorelbine), taxoids (e.g. paclitaxel or a paclitaxel equivalent such as nanoparticle albumin-bound paclitaxel (ABRAXANE), docosahexaenoic acid bound-paclitaxel (DHA-paclitaxel, Taxoprexin), polyglutamate bound-paclitaxel (PG-paclitaxel, paclitaxel poliglumex, CT-2103, XYOTAX), the tumor-activated prodrug (TAP) ANG1005 (Angiopep-2 bound to three molecules of paclitaxel), paclitaxel-EC-1 (paclitaxel bound to the erbB2-recognizing peptide EC-1), and glucose-conjugated paclitaxel, e.g., 2'-paclitaxel methyl 2-glucopyranosyl succinate; docetaxel, taxol), epipodophyllins (e.g. etoposide, etoposide phosphate, teniposide, topotecan, 9-aminocamptothecin, camptoirinotecan, irinotecan, crisnatol, mytomycin C), antimetabolites, DHFR inhibitors (e.g., methotrexate, dichloromethotrexate, trimetrexate, edatrexate), IMP dehydrogenase inhibitors (e.g., mycophenolic acid, tiazofurin, ribavirin, and EICAR), ribonuclotide reductase inhibitors (e.g., hydroxyurea and deferoxamine), uracil analogs (e.g., 5-fluorouracil (5-FU), floxuridine, doxifluridine, ratitrexed, tegafur-uracil, capecitabine), cytosine analogs (e.g., cytarabine (ara C), cytosine arabinoside, and fludarabine), purine analogs (e.g., mercaptopurine and Thioguanine), Vitamin D3 analogs (e.g., EB 1089, CB 1093, and KH 1060), isoprenylation inhibitors (e.g., lovastatin), dopaminergic neurotoxins (e.g., 1-methyl-4-phenylpyridinium ion), cell cycle inhibitors (e.g., staurosporine), actinomycin (e.g., actinomycin D, dactinomycin), bleomycin (e.g., bleomycin A2, bleomycin B2, peplomycin), anthracycline (e.g., daunorubicin, doxorubicin, pegylated liposomal doxorubicin, idarubicin, epirubicin, pirarubicin, zorubicin, mitoxantrone), MDR inhibitors (e.g., verapamil), $Ca^{2+}$ ATPase inhibitors (e.g., thapsigargin), thalidomide, lenalidomide, pomalidomide, tyrosine kinase inhibitors (e.g., axitinib, bosutinib, cediranib (RECENTIN™), dasatinib (SPRYCEL®), erlotinib (TARCEVA®), gefitinib (IRESSA®), imatinib (Gleevec®), lapatinib (TYKERB®, TYVERB®), lestaurtinib, neratinib, nilotinib (TASIGNA®), semaxanib, sunitinib (SUTENT®), toceranib (PALLADIA®), vandetanib (ZACTIMA®, ZD6474), vatalanib (PTK787), nilotinib (TASIGNA®), sorafenib (NEXAVAR®), everolimus (AFINITOR®), gemtuzumab ozogamicin (MYLOTARG®), temsirolimus (TORISEL®), ENMD-2076, PCI-32765, AC220, dovitinib lactate (TKI258, CHIR-258), BIBW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, and/or XL228), proteasome inhibitors (e.g., bortezomib (VELCADE)), mTOR inhibitors (e.g., rapamycin, temsirolimus (CCI-779), everolimus (RAD-001), ridaforolimus, AP23573 (Ariad), AZD8055 (AstraZeneca), BEZ235 (Novartis), BGT226 (Norvartis), XL765 (Sanofi Aventis), PF-4691502 (Pfizer), GDC0980 (Genetech), SF1126 (Semafoe) and OSI-027 (OSI)), oblimersen, gemcitabine, carminomycin, leucovorin, pemetrexed, cyclophosphamide, dacarbazine, procarbizine, prednisolone, dexamethasone, campathecin, plicamycin, asparaginase, aminopterin, methopterin, porfiromycin, melphalan, leurosidine, leurosine, chlorambucil, trabectedin, procarbazine, discodermolide, carminomycin, aminopterin, and hexamethyl melamine. In certain embodiments, the additional pharmaceutical agent is cisplatin. In certain embodiments, the additional pharmaceutical agent is paclitaxel. In certain embodiments, the additional pharmaceutical agent is vincristine.

In certain embodiments, the additional pharmaceutical agent is an immunotherapy. In certain embodiments, the immunotherapy is useful in the treatment of a cancer. Exemplary immunotherapies include, but are not limited to, T-cell therapies, interferons, cytokines (e.g., tumor necrosis factor, interferon $\alpha$, interferon $\gamma$), vaccines, hematopoietic growth factors, monoclonal serotherapy, immunostimulants and/or immunodulatory agents (e.g., IL-1, 2, 4, 6, or 12), immune cell growth factors (e.g., GM-CSF) and antibodies. In certain embodiments, the immunotherapy is a T-cell therapy. In certain embodiments, the T-cell therapy is chimeric antigen receptor T cells (CAR-T). In certain embodiments, the immunotherapy is an antibody. In certain embodiments, the antibody is an anti-PD-1 antibody, an anti-PD-L1 antibody, an anti-CTLA-4 antibody, an anti-TIM3 antibody, an anti-OX40 antibody, an anti-GITR antibody, an anti-LAG-3 antibody, an anti-CD137 antibody, an anti-CD27 antibody, an anti-CD28 antibody, an anti-CD28H antibody, an anti-CD30 antibody, an anti-CD39 antibody, an anti-CD40 antibody, an anti-CD47 antibody, an anti-CD48 antibody, an anti-CD70 antibody, an anti-CD73 antibody, an anti-CD96 antibody, an anti-CD160 antibody, an anti-CD200 antibody, an anti-CD244 antibody, an anti-ICOS antibody, an anti-TNFRSF25 antibody, an anti-TMIGD2 antibody, an anti-DNAM1 antibody, an anti-BTLA antibody, an anti-LIGHT antibody, an anti-TIGIT antibody, an anti-VISTA antibody, an anti-HVEM antibody, an anti-Siglec antibody, an anti-GAL1 antibody, an anti-GAL3 antibody, an anti-GAL9 antibody, an anti-BTNL2 (butrophylins) antibody, an anti-B7-H3 antibody, an anti-B7-H4 antibody, an anti-B7-H5 antibody, an anti-B7-H6 antibody, an anti-KIR antibody, an anti-LIR antibody, an anti-ILT antibody, an anti-MICA antibody, an anti-MICB antibody, an anti-NKG2D antibody, an anti-NKG2A antibody, an anti-TGFβ antibody, an anti-TGFpR antibody, an anti-CXCR4 antibody, an anti-CXCL12 antibody, an anti-CCL2 antibody, an anti-IL-10 antibody, an anti-IL-13 antibody, an anti-IL-23 antibody, an anti-phosphatidylserine antibody, an anti-neuropilin antibody, an anti-GalCer antibody, an anti-HER2 antibody, an anti-VEGFA antibody, an anti-VEGFR antibody, an anti-EGFR antibody, or an anti-Tie2 antibody. In certain embodiments, the antibody is pembrolizumab, nivolumab, pidilizumab, ipilimumab, tremelimumab, durvalumab, atezolizumab, avelumab, PF-06801591, utomilumab, PDR001, PBF-509, MGB453, LAG525, AMP-224, INCSHR1210, INCAGN1876, INCAGN1949, samalizumab, PF-05082566, urelumab, lirilumab, lulizumab, BMS-936559, BMS-936561, BMS-986004, BMS-986012, BMS-986016, BMS-986178, IMP321, IPH2101, IPH2201, varilumab, ulocuplumab, monalizumab, MEDI0562, MEDIO680, MEDI1873, MEDI6383, MEDI6469, MEDI9447, AMG228, AMG820, CC-90002, CDX-1127, CGEN15001T, CGEN15022, CGEN15029, CGEN15049, CGEN15027, CGEN15052, CGEN15092, CX-072, CX-2009, CP-870893, lucatumumab, dacetuzumab, Chi Lob 7/4, RG6058, RG7686, RG7876, RG7888, TRX518, MK-4166, MGA271, IMC-CS4, emactuzumab, pertuzumab, obinutuzumab, cabiralizumab, margetuximab, enoblituzumab, mogamulizumab, carlumab, bevacizumab, trastuzumab (HERCEPTIN®), bevacizumab (AVASTIN®), rituximab (RITUXAN®), cetuximab (ERBITUX®), panitumumab (VECTIBIX®), alemtuzumab (CAMPATH®), or ranibizumab (Lucentis®).

In certain embodiments, the additional pharmaceutical agent is a symptomatic drug, such as cholinesterase inhibitors (e.g., ARICEPT®, EXELON®, RAZADYNE®, donepezil, rivastigmine, and galantamine) and glutamate regulators (e.g., NAMENDA®, memantine). In certain embodiments, the additional pharmaceutical agent is riluzole. In certain embodiments, the additional pharmaceutical agent is edaravone. In certain embodiments, the additional pharmaceutical agent is an anti-amyloid or anti-tau antibody. In certain embodiments, the additional pharmaceutical agent is any agent useful in the treatment of Alzheimer's disease (e.g., small molecule, antibody, polypeptide, antisense oligo, RNA).

In certain embodiments, the compounds or pharmaceutical compositions described herein can be administered in combination with an anti-cancer therapy including, but not limited to, surgery, radiation therapy, and transplantation (e.g., stem cell transplantation, bone marrow transplantation).

In certain embodiments, the compound or pharmaceutical composition is a solid. In certain embodiments, the compound or pharmaceutical composition is a powder. In certain embodiments, the compound or pharmaceutical composition can be dissolved in a liquid to make a solution. In certain embodiments, the compound or pharmaceutical composition is dissolved in water to make an aqueous solution. In certain embodiments, the pharmaceutical composition is a liquid for parental injection. In certain embodiments, the pharmaceutical composition is a liquid for oral administration (e.g., ingestion). In certain embodiments, the pharmaceutical composition is a liquid (e.g., aqueous solution) for intravenous injection. In certain embodiments, the pharmaceutical composition is a liquid (e.g., aqueous solution) for subcutaneous injection.

After formulation with an appropriate pharmaceutically acceptable excipient in a desired dosage, the pharmaceutical compositions of the present disclosure can be administered to humans and other animals orally, parenterally, intracisternally, intraperitoneally, topically, bucally, or the like, depending on the disease or condition being treated.

In certain embodiments, a pharmaceutical composition comprising a compound of Formula (I), (II), (III), (IV), (V), (VI), or (VII) is administered, orally or parenterally, at dosage levels of each pharmaceutical composition sufficient to deliver from about 0.001 mg/kg to about 200 mg/kg in one or more dose administrations for one or several days (depending on the mode of administration). In certain embodiments, the effective amount per dose varies from about 0.001 mg/kg to about 200 mg/kg, about 0.001 mg/kg to about 100 mg/kg, about 0.01 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, of subject body weight per day, one or more times a day, to obtain the desired therapeutic and/or prophylactic effect. In certain embodiments, the compounds described herein may be at dosage levels sufficient to deliver from about 0.001 mg/kg to about 200 mg/kg, from about 0.001 mg/kg to about 100 mg/kg, from about 0.01 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic and/or prophylactic effect. The desired dosage may be delivered three times a day, two times a day, once a day, every other day, every third day, every week, every two weeks, every three weeks, or every four weeks. In certain embodiments, the desired dosage may be delivered using multiple administrations (e.g., two, three, four, five, six, seven, eight, nine, ten, eleven, twelve, thirteen, fourteen, or more administrations). In certain embodiments, the composition described herein is administered at a dose that is below the dose at which the agent causes non-specific effects.

In certain embodiments, the pharmaceutical composition is administered at a dose of about 0.001 mg to about 1000 mg per unit dose. In certain embodiments, the pharmaceutical composition is administered at a dose of about 0.01 mg to about 200 mg per unit dose. In certain embodiments, the pharmaceutical composition is administered at a dose of about 0.01 mg to about 100 mg per unit dose. In certain embodiments, pharmaceutical composition is administered at a dose of about 0.01 mg to about 50 mg per unit dose. In certain embodiments, the pharmaceutical composition is administered at a dose of about 0.01 mg to about 10 mg per unit dose. In certain embodiments, the pharmaceutical composition is administered at a dose of about 0.1 mg to about 10 mg per unit dose.

Pharmaceutical compositions described herein can be prepared by any method known in the art of pharmacology. In general, such preparatory methods include the steps of bringing the composition comprising a compound of Formula (I), (II), (III), (IV), (V), (VI), or (VII) into association with a carrier and/or one or more other accessory ingredients, and then, if necessary and/or desirable, shaping and/or packaging the product into a desired single- or multi-dose unit.

Pharmaceutical compositions can be prepared, packaged, and/or sold in bulk, as a single unit dose, and/or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage, such as, for example, one-half or one-third of such a dosage.

Relative amounts of the active ingredient, the pharmaceutically acceptable excipient, and/or any additional ingredients in a pharmaceutical composition of the invention will vary, depending upon the identity, size, and/or condition of the subject treated and further depending upon the route by which the composition is to be administered. By way of example, the composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite (aluminum silicate) and Veegum (magnesium aluminum silicate)), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate (Tween 20), polyoxyethylene sorbitan (Tween 60), polyoxyethylene sorbitan monooleate (Tween 80), sorbitan monopalmitate (Span 40), sorbitan monostearate (Span 60), sorbitan tristearate (Span 65), glyceryl monooleate, sorbitan monooleate (Span 80)), polyoxyethylene esters (e.g. polyoxyethylene monostearate (Myrj 45), polyoxyethylene hydrogenated castor oil, polyethoxylated castor oil, polyoxymethylene stearate, and Solutol), sucrose fatty acid esters, polyethylene glycol fatty acid esters (e.g. Cremophor™), polyoxyethylene ethers, (e.g. polyoxyethylene lauryl ether (Brij 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F-68, Poloxamer-188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, *eucalyptus*, evening primrose, fish, flaxseed, geraniol, gourd, grape seed, hazelnut, hyssop, isopropyl myristate, jojoba, kukui nut, lavandin, lavender, lemon, *Litsea cubeba*, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include, but are not limited to, pharmaceutically acceptable emulsions, microemulsions, solutions, suspensions, syrups, and elixirs. In addition to the active agents, the liquid dosage forms may contain inert diluents commonly used in the art such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, oral compositions can also include adjuvants such as wetting agents, emulsifying and suspending agents, sweetening, flavoring, and perfuming agents. In certain embodiments for parenteral administration, agents of the invention are mixed with solubilizing agents such CREMOPHOR EL® (polyethoxylated castor oil), alcohols, oils, modified oils, glycols, polysorbates, cyclodextrins, polymers, and combinations thereof.

Injectable preparations, for example, sterile injectable aqueous or oleaginous suspensions, may be formulated according to the known art using suitable dispersing or wetting agents and suspending agents. Sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

Solid dosage forms for oral administration include capsules, tablets, pills, powders, and granules. In such solid dosage forms, the active agent is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active agents can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active agent may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets, and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Formulations suitable for topical administration include liquid or semi-liquid preparations such as liniments, lotions, gels, applicants, oil-in-water or water-in-oil emulsions such as creams, ointments, or pastes; or solutions or suspensions such as drops. Formulations for topical administration to the skin surface can be prepared by dispersing the drug with a dermatologically acceptable carrier such as a lotion, cream, ointment, or soap. Useful carriers are capable of forming a film or layer over the skin to localize application and inhibit removal. For topical administration to internal tissue surfaces, the agent can be dispersed in a liquid tissue adhesive or other substance known to enhance adsorption to a tissue surface. For example, hydroxypropylcellulose or fibrinogen/thrombin solutions can be used to advantage. Alternatively, tissue-coating solutions, such as pectin-containing formulations can be used. Ophthalmic formulation, ear drops, and eye drops are also contemplated as being within the scope of this invention. Additionally, the present disclosure contemplates the use of transdermal patches, which have the added advantage of providing controlled delivery of an agent to the body. Such dosage forms can be made by dissolving or dispensing the agent in the proper medium. Absorption enhancers can also be used to increase the flux of the agent across the skin. The rate can be controlled by either providing a rate controlling membrane or by dispersing the agent in a polymer matrix or gel.

Additionally, the carrier for a topical formulation can be in the form of a hydroalcoholic system (e.g., liquids and gels), an anhydrous oil or silicone based system, or an emulsion system, including, but not limited to, oil-in-water, water-in-oil, water-in-oil-in-water, and oil-in-water-in-silicone emulsions. The emulsions can cover a broad range of consistencies including thin lotions (which can also be suitable for spray or aerosol delivery), creamy lotions, light creams, heavy creams, and the like. The emulsions can also include microemulsion systems. Other suitable topical carriers include anhydrous solids and semisolids (such as gels and sticks); and aqueous based mousse systems.

Also encompassed by the disclosure are kits (e.g., pharmaceutical packs). The kits provided may comprise a pharmaceutical composition or compound described herein and a container (e.g., a vial, ampule, bottle, syringe, and/or dispenser package, or other suitable container). In some embodiments, provided kits may optionally further include a second container comprising a pharmaceutical excipient for dilution or suspension of a pharmaceutical composition or compound described herein. In some embodiments, the pharmaceutical composition or compound described herein provided in the first container and the second container are combined to form one unit dosage form.

Thus, in one aspect, provided are kits including a first container comprising a compound or pharmaceutical composition described herein. In certain embodiments, the kits are useful for treating a disease (e.g., proliferative disease, inflammatory disease, infectious disease, autoimmune disease, heteroimmune disease, neurological disorder, peripheral disorder, metabolic disease, cystic fibrosis, polycystic kidney disease, pulmonary hypertension, cardiac dysfunction, or disease or disorder mediated by or linked to T-cell dysregulation) in a subject in need thereof. In certain embodiments, the kits are useful for preventing a disease (e.g., proliferative disease, inflammatory disease, infectious disease, autoimmune disease, heteroimmune disease, neurological disorder, peripheral disorder, metabolic disease, cystic fibrosis, polycystic kidney disease, pulmonary hypertension, cardiac dysfunction, or disease or disorder mediated by or linked to T-cell dysregulation) in a subject in need thereof. In certain embodiments, the kits are useful for reducing the risk of developing a disease (e.g., proliferative disease, inflammatory disease, infectious disease, autoimmune disease, heteroimmune disease, neurological disorder, peripheral disorder, metabolic disease, cystic fibrosis, polycystic kidney disease, pulmonary hypertension, cardiac dysfunction, or disease or disorder mediated by or linked to T-cell dysregulation) in a subject in need thereof. In certain embodiments, the kits are useful for inhibiting the activity (e.g., aberrant activity, such as increased activity) of HDAC6 in a subject or cell.

In certain embodiments, a kit described herein further includes instructions for using the kit. A kit described herein may also include information as required by a regulatory agency such as the U.S. Food and Drug Administration (FDA). In certain embodiments, the information included in the kits is prescribing information. In certain embodiments, the kits and instructions provide for treating a disease (e.g., proliferative disease, inflammatory disease, infectious disease, autoimmune disease, heteroimmune disease, neurological disorder, peripheral disorder, metabolic disease, cystic fibrosis, polycystic kidney disease, pulmonary hypertension, cardiac dysfunction, or disease or disorder mediated by or linked to T-cell dysregulation) in a subject in need thereof. In certain embodiments, the kits and instructions provide for preventing a disease (e.g., proliferative disease, inflammatory disease, infectious disease, autoimmune disease, heteroimmune disease, neurological disorder, peripheral disorder, metabolic disease, cystic fibrosis, polycystic kidney disease, pulmonary hypertension, cardiac dysfunction, or disease or disorder mediated by or linked to T-cell dysregulation) in a subject in need thereof. In certain embodiments, the kits and instructions provide for reducing the risk of developing a disease (e.g., proliferative disease, inflammatory disease, infectious disease, autoimmune disease, heteroimmune disease, neurological disorder, peripheral disorder, metabolic disease, cystic fibrosis, polycystic kidney disease, pulmonary hypertension, cardiac dysfunction, or disease or disorder mediated by or linked to T-cell dysregulation) in a subject in need thereof. In certain embodiments, the kits and instructions provide for inhibiting the activity (e.g., aberrant activity, such as increased activity) of HDAC6 in a subject or cell. A kit described herein may include one or more additional pharmaceutical agents described herein as a separate composition.

Methods of Treatment

HDAC6 is unique in structure and function among all HDAC paralogs. In particular, it possesses two catalytic (deacetylase) domains and a zinc finger ubiquitin-binding domain. HDAC6 does not deacetylate histones, yet interacts with multiple substrates that affect disease-relevant pathways including microtubule stability, axonal and mitochondrial transport, protein aggregation, and autophagy. For example, HDAC6's direct substrates (e.g., tau, tubulin, and HSP90) engage key mechanisms in Alzheimer's disease. As a result of its unique structure and function, selectively targeting and inhibiting HDAC6 activity may avoid the side effects that are typical of existing FDA-approved HDAC inhibitors that result in clinical toxicity due to broad inhibition of multiple HDAC paralogs an/or inhibition of HDACs 1 and/or 2 (which has been shown to cause thrombocytopenia, a dose-limiting toxicity of most FDA-approved pan-HDAC inhibitors). Thus, treatment of HDAC6-related diseases with HDAC6-selective inhibitors may be particularly effective.

The present disclosure provides methods for treating HDAC6-related diseases and disorders. In certain embodiments, the application provides a method of treating a proliferative disease. In certain embodiments, the application provides a method of treating cancer. In certain embodiments, the application provides a method of treating a hematological cancer. In certain embodiments, the application provides a method of treating leukemia, T-cell lymphoma, Hodgkin's Disease, non-Hodgkin's lymphoma, or multiple myeloma. In certain embodiments, the application provides a method of treating a cancer comprising a solid tumor. In certain embodiments, the application provides a method of treating glioma, glioblastoma, non-small cell lung cancer, brain tumor, neuroblastoma, bone tumor, soft-tissue sarcoma, head and neck cancer, genitourinary cancer, lung cancer, breast cancer, pancreatic cancer, melanoma, stomach cancer, brain cancer, liver cancer, thyroid cancer, clear cell carcinoma, uterine cancer, or ovarian cancer.

In certain embodiments, the application provides a method of treating an inflammatory disease. In certain embodiments, the application provides a method of treating osteoarthritis, rheumatoid arthritis, lupus, inflammatory bowel disease, Crohn's Disease, ulcerative colitis, anemia, leukocytosis, asthma, chronic obstructive pulmonary disease, appendicitis, bronchitis, bursitis, conjunctivitis, dermatitis, encephalitis, myelitis myocarditis, sinusitis, dermatitis, psoriasis, eczema, or acne.

In certain embodiments, the application provides a method of treating an infectious disease. In certain embodiments, the application provides a method of treating bacterial, fungal, or protozoal infections.

In certain embodiments, the application provides a method of treating an autoimmune disease. In certain embodiments, the application provides a method of treating diabetes, thyroiditis, Graves' disease, Guillain-Barre syndrome, Addison's disease, scleroderma, primary biliary cirrhosis, Reiter's syndrome, psoriasis, chronic fatigue, or endometriosis.

In certain embodiments, the application provides a method of treating a heteroimmune disease. In certain embodiments, the application provides a method of treating graft versus host disease, transplantation, transfusion, anaphylaxis, allergic conjunctivitis, or allergic rhinitis.

In certain embodiments, the application provides a method of treating a neurological disorder. In certain embodiments, the application provides a method of treating a neurodegenerative, neurodevelopmental, neuropsychiatric, or neuropathy disease. In certain embodiments, the application provides a method of treating Fragile-X syndrome, Charcot-Marie-Tooth disease, Alzheimer's disease, Parkinson's diseases, Huntington's disease, multiple sclerosis, amyotrophic lateral sclerosis, Creutzfeldt-Jakob disease, Lewy body dementia, vascular dementia, muscular atrophy, seizure induced memory loss, schizophrenia, Rubinstein Taybi syndrome, Rett Syndrome, attention deficit hyperactivity disorder, dyslexia, bipolar disorder, social, cognitive and learning disorders associated with autism, attention deficit disorder, schizophrenia, major depressive disorder, peripheral neuropathy, diabetic retinopathy, diabetic peripheral neuropathy, chemotherapy-induced peripheral neuropathy, traumatic brain injury (TBI), chronic traumatic encephalopathy (CTE), or a tauopathy. In certain embodiments, the application provides a method of treating primary age-related tauopathy (PART)/neurofibrillary tangle-predominant senile dementia, chronic traumatic encephalopathy, dementia pugilistica, progressive supranuclear palsy, corticobasal degeneration, Pick's disease, frontotemporal dementia, frontotemporal dementia and parkinsonism linked to chromosome 17, Lytico-Bodig disease, ganglioglioma, gangliocytoma, meningioangiomatosis, postencephalitic parkinsonism, subacute sclerosing panencephalitis, lead encephalopathy, tuberous sclerosis, lipofuscinosis, Alzheimer's disease, or argyrophilic grain disease. In certain embodiments, the application provides a method of treating Alzheimer's disease.

In certain embodiments, the application provides a method of treating a neurological or peripheral disease or disorder. In certain embodiments, the application provides a method of treating a neurodegenerative, neurodevelopmental, neuropsychiatric, or neuropathy disease. In certain embodiments, the application provides a method of treating Alzheimer's disease, Fragile-X syndrome, Charcot-Marie-Tooth disease, Parkinson's disease, Huntington's disease, multiple sclerosis, amyotrophic lateral sclerosis, Rett Syndrome, major depressive disorder, chemotherapy-induced cognitive dysfunction, traumatic brain injury (TBI), chronic traumatic encephalopathy (CTE), brain cancer, or a tauopathy such as frontotemporal dementia, progressive supranuclear palsy, or corticobasal degeneration.

In certain embodiments, the application provides a method of treating a peripheral disease or disorder. In certain embodiments, the application provides a method of treating chemotherapy-induced peripheral neuropathy, diabetic peripheral neuropathy, peripheral neuropathy, diabetic retinopathy, obesity, autosomal dominant polycystic kidney disease, cardiomyopathy, an auto-immune disease such as systemic lupus erythematosus (SLE), or cancer In certain embodiments, the application provides a method of treating cystic fibrosis. In certain embodiments, the application provides a method of treating polycystic kidney disease. In certain embodiments, the application provides a method of treating pulmonary hypertension. In certain embodiments, the application provides a method of treating cardiac dysfunction.

The present disclosure provides methods of inhibiting the activity of HDAC. In certain embodiments, the application provides a method of inhibiting the activity of HDAC6. In certain embodiments, the application provides a method of inhibiting the activity of HDAC6 in vitro. In certain embodiments, the application provides a method of inhibiting the activity of HDAC6 in vivo. In certain embodiments, the application provides a method of inhibiting the activity of HDAC6 in a cell. In certain embodiments, the application provides a method of inhibiting the activity of HDAC6 in a human cell.

In certain embodiments, the methods comprise administering to a subject in need thereof (e.g., a subject with a neurological disorder) a compound that interacts with HDAC6, for example, a compound that is an inhibitor of HDAC6, a modulator of HDAC6, a binder of HDAC6, or a compound that modifies HDAC6. In certain embodiments, the methods comprise administering a compound of the disclosure (e.g., a compound of Formula (I), (II), (III), (IV), (V), (VI), or (VII)), or a pharmaceutically acceptable salt, co-crystal, tautomer, stereoisomer, solvate, hydrate, polymorph, isotopically enriched derivative, or prodrug, or composition thereof, to a subject in need thereof. In some embodiments, the method comprises administering a pharmaceutical composition comprising a compound of the disclosure (e.g., a compound of Formula (I), (II), (Ill), (IV), (V), (VI), or (VII)), or a pharmaceutically acceptable salt, co-crystal, tautomer, stereoisomer, solvate, hydrate, polymorph, isotopically enriched derivative, or prodrug, or composition thereof, to a subject in need thereof.

ADDITIONAL EMBODIMENTS

For reasons of completeness, various aspects of the present disclosure are set out in the following numbered embodiments and clauses:

Embodiments

1. A compound of Formula (I), or a pharmaceutically acceptable salt thereof, (I)

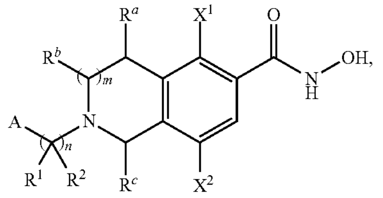

wherein:

$X^1$ is hydrogen;

$X^2$ is fluoro;

A is a substituted or unsubstituted spirocyclic heterocyclyl, a substituted or unsubstituted spirocyclic carbocyclyl, a substituted or unsubstituted bridged cycloalkyl, a substituted or unsubstituted bridged heterocycloalkyl, a substituted or unsubstituted monocyclic heterocyclyl ring; a substituted or unsubstituted monocyclic cycloalkyl ring; or a substituted or unsubstituted alkyl;

$R^1$ is hydrogen or substituted or unsubstituted alkyl;

$R^2$ is hydrogen or substituted or unsubstituted alkyl; or $R^1$ and $R^2$ together form a substituted or unsubstituted heterocyclyl, or a substituted or unsubstituted cycloalkyl;

$R^a$ is hydrogen or is joined with $R^c$ to form a substituted or unsubstituted bridged ring;

$R^b$ is hydrogen or is joined with $R^c$ to form a substituted or unsubstituted bridged ring;

$R^c$ is hydrogen or substituted or unsubstituted alkyl or is joined with at least one of $R^a$ and $R^b$ to form a substituted or unsubstituted bridged ring;

m is 0 or 1; and n is 0 or 1; and provided that the compound is not any of the following compounds:

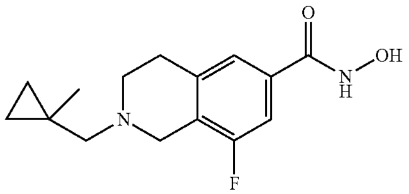

1

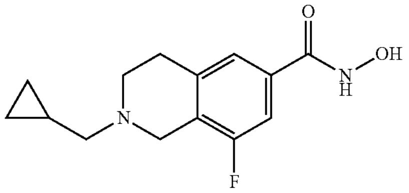

2

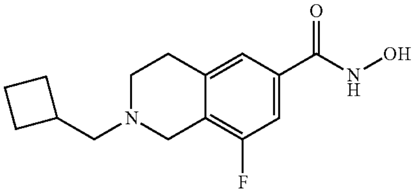

3

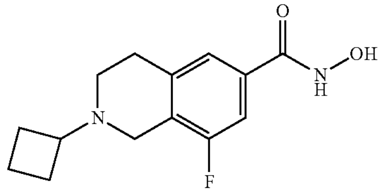

4

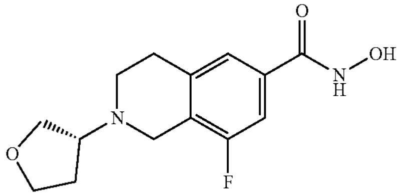

5

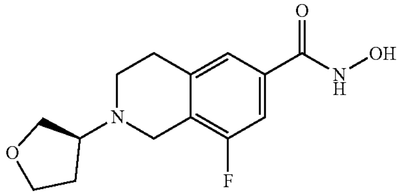

6

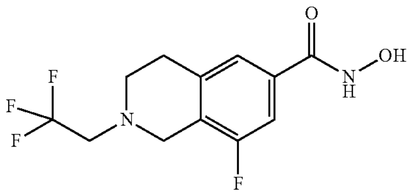

7

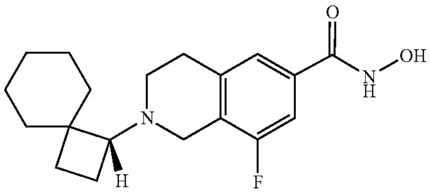

8

-continued
9
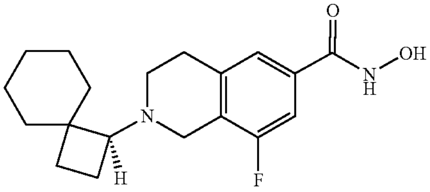
10
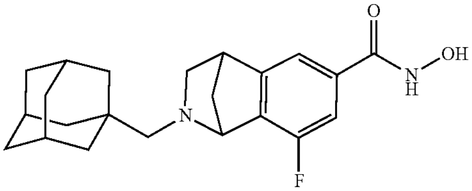
11
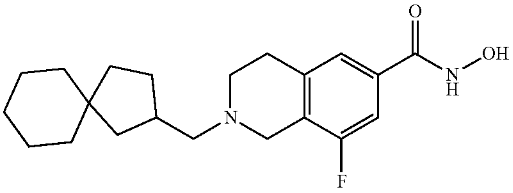
12
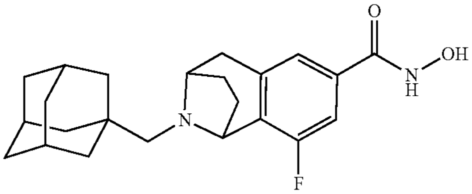
13
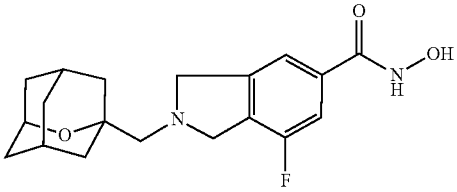
14
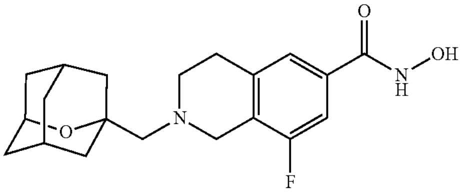
15
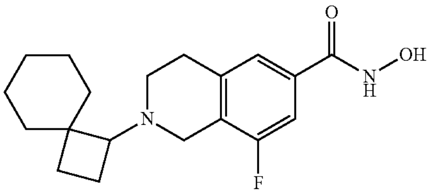
-continued
16
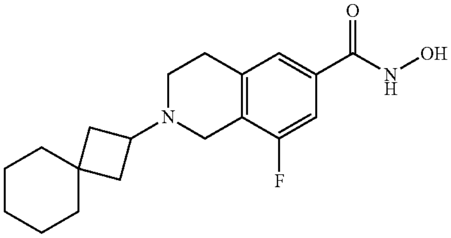
17
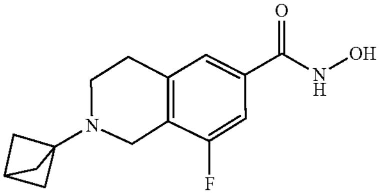
18
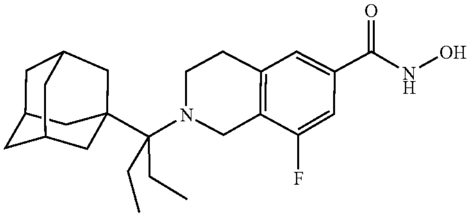
19
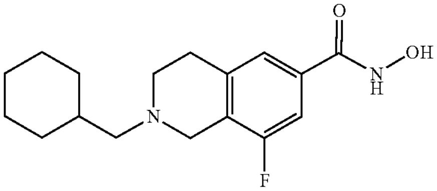
20
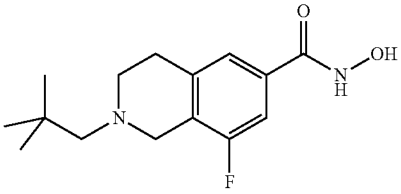
21
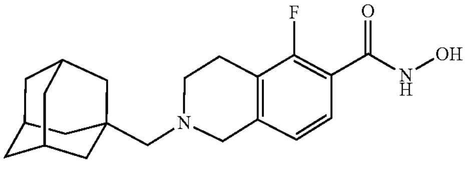
22
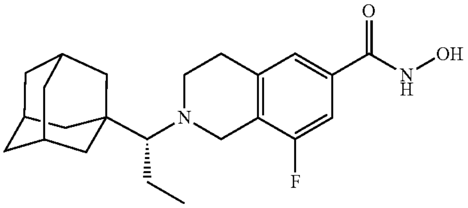

-continued
23
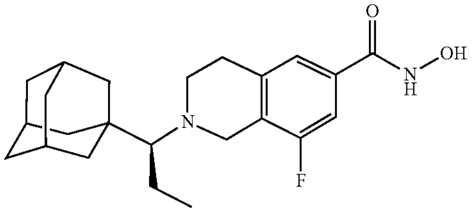
24
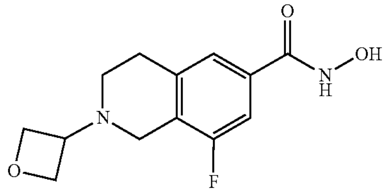
25
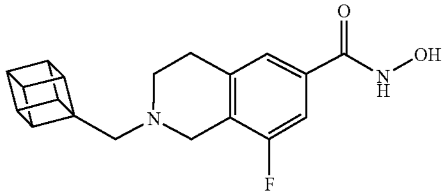
26
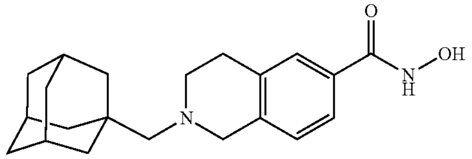
27
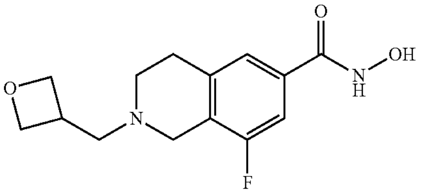
28
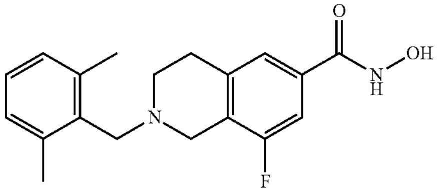
29
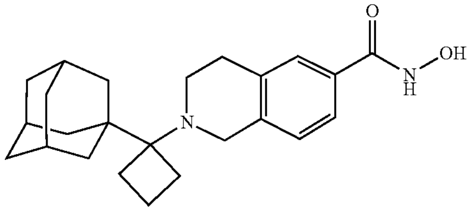
30
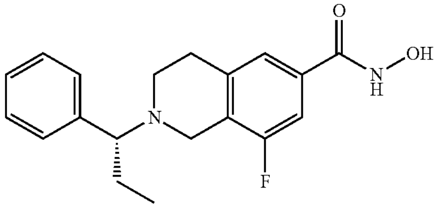
-continued
31
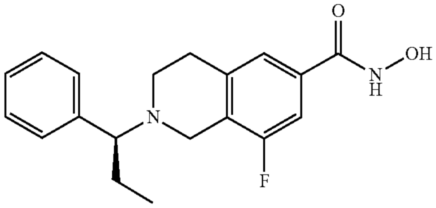
32
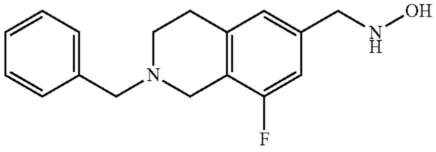
33
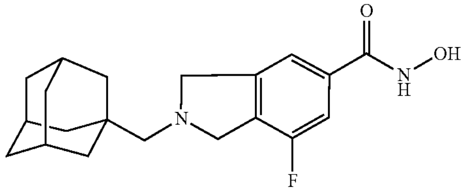
34
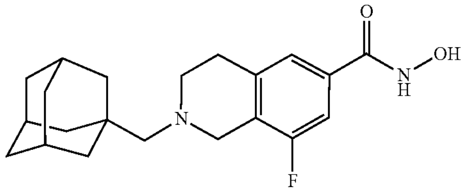
35
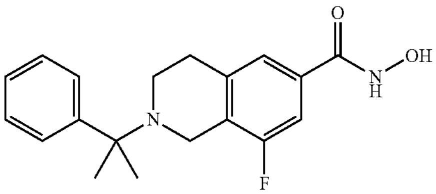
107
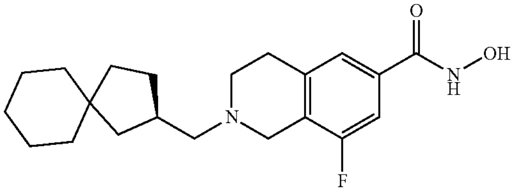
108
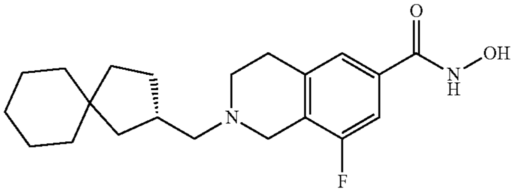
109
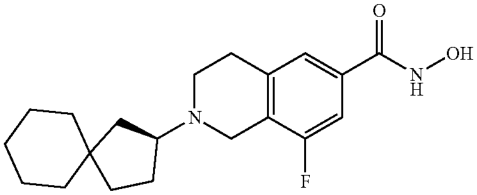

-continued

110

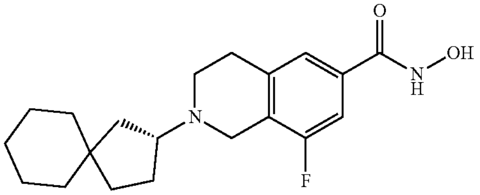

111

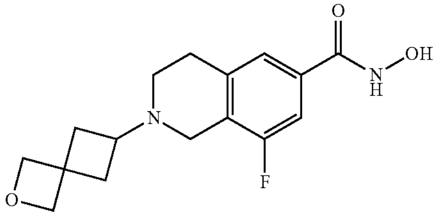

112

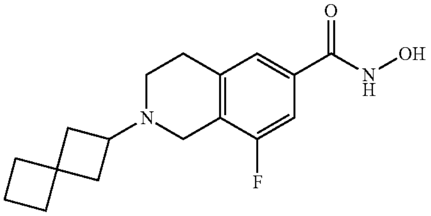

2. The compound of embodiment 1, wherein
   a. $R^1$ is hydrogen $C_{1-4}$ alkyl optionally substituted with one or more halogen;
   b. $R^2$ is hydrogen or substituted or unsubstituted $C_{1-4}$ alkyl; or $R^1$ and $R^2$ together form a substituted or unsubstituted 3-6 member heterocyclyl, or a substituted or unsubstituted $C_{3-6}$ cycloalkyl;
   c. $R^a$ is hydrogen;
   d. $R^b$ is hydrogen;
   e. $R^c$ is hydrogen; and
   f. A is selected from the group consisting of:
      i. a 7-11 member bicyclic spirocyclic heterocyclyl, or a $C_{7-11}$ substituted or unsubstituted bicyclic spirocyclic carbocyclyl;
      ii. a $C_{4-7}$ bridged cycloalkyl, or a bridged 4-7 member heterocycloalkyl, or a 4-7 member heterocyclyl ring; or a $C_{3-6}$ monocyclic cycloalkyl ring, each optionally substituted with methyl, acyl, oxo or cyclopropyl; and
      iii. a substituted or unsubstituted $C_{1-6}$ alkyl; and wherein each A is optionally substituted with ($C_1$-$C_4$) alkyl or ($C_3$-$C_6$)cycloalkyl each optionally further substituted with one or more halogen; amino optionally further substituted with one or more ($C_1$-$C_4$) alkyl; halogen; oxo; acyl; and ($C_1$-$C_4$)alkylamino or amino optionally substituted with ($C_1$-$C_4$)alkyl.
3. The compound of embodiment 2, wherein
   a. n is 0 and m is 1; and
   b. A is a 7-11 member bicyclic spirocyclic heterocyclyl or 7-11 carbon bicyclic spirocyclic carbocyclyl, each optionally substituted with one or more: ($C_1$-$C_4$) alkyl optionally further substituted with one or more fluoro; amino optionally further substituted with one or more ($C_1$-$C_4$)alkyl; halogen; oxo; acyl; cyclopropyl; or benzyl.
4. The compound of any one of embodiments 1-3, wherein A is

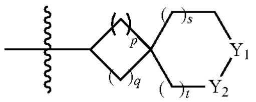 or 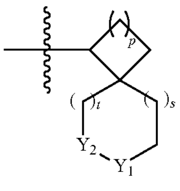

wherein
   p and q are each independently 1 or 2;
   s and t are each independently 0, 1, or 2, provided that the sum of s and t is 0, 1, or 2;
   $Y_1$ and $Y_2$ are each independently selected from S(═O), $CR_{s1}R_{s2}$, $NR_s$ and O, provided that at least one of $Y_1$ and $Y_2$ is $CR^{s1}R_{s2}$;
   $R_{s1}$ and $R_{s2}$ are each independently hydrogen, or ($C_1$-$C_4$)alkyl optionally substituted with one or more halogen; and
   $R_s$ is hydrogen, ($C_1$-$C_4$)alkyl optionally substituted with one or more halogen, acyl, ($C_3$-$C_6$)cycloalkyl or 3- to 6-member heterocycloalkyl comprising one or more heteroatoms selected from the group consisting of O and N.
5. The compound of embodiment 3, wherein A is

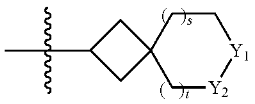 or 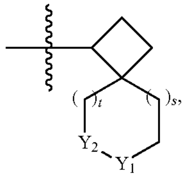, wherein
   s and t are each independently 0, 1, or 2, provided that the sum of s and t is 0, 1, or 2; and
   $Y_1$ and $Y_2$ are each independently selected from S(═O), $CR_{s1}R_{s2}$, $NR_s$ and O, provided that at least one of $Y_1$ and $Y_2$ is $CR_{s1}R_{s2}$;
   $R_{s1}$ and $R_{s2}$ are each independently hydrogen, or ($C_1$-$C_4$)alkyl optionally substituted with one or more halogen; and
   $R_s$ is hydrogen, ($C_1$-$C_4$)alkyl optionally substituted with one or more halogen, acyl, ($C_3$-$C_6$)cycloalkyl or 3- to 6-member heterocycloalkyl comprising one or more heteroatoms selected from the group consisting of O and N.
6. The compound of embodiment 5, wherein
   a. $R_{s1}$ and $R_{s2}$ are each independently hydrogen, or methyl optionally substituted with one or more F; and
   b. $R_s$ is hydrogen, methyl optionally substituted with one or more F, acyl, or cyclopropyl.
7. The compound of embodiment 5, wherein $R_{s1}$ and $R_{s2}$ are each hydrogen; and $R_s$ is hydrogen, methyl optionally substituted with one or more F, acyl, and cyclopropyl.
8. The compound of embodiment 3, wherein A is selected from the group consisting of:

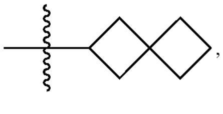, 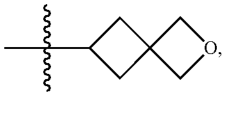,

-continued
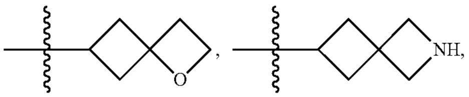
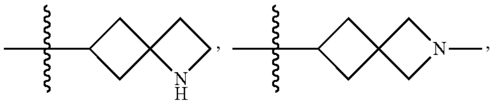
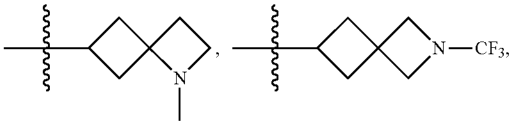
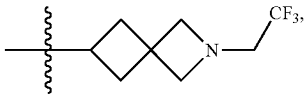
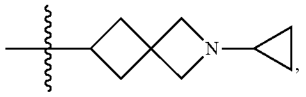
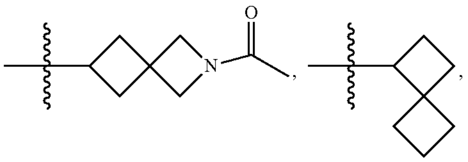
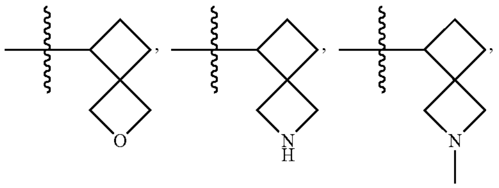
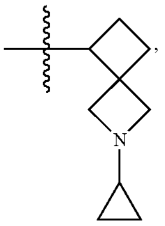
, and
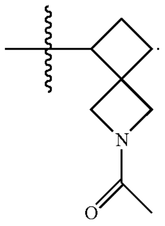
.
9. The compound of embodiment 3, wherein A is
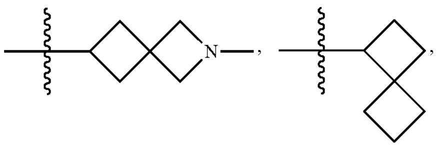
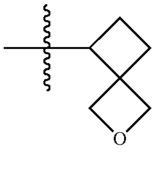
or
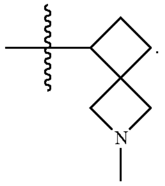
.
10. The compound of embodiment 3, wherein A is selected from the group consisting of:
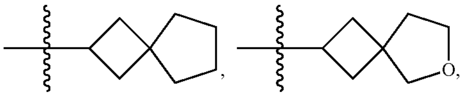
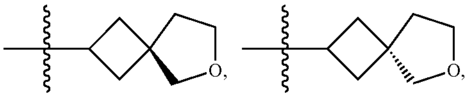
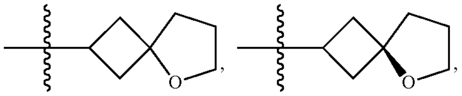
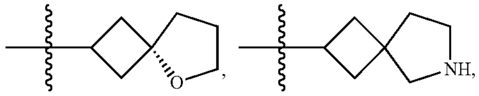
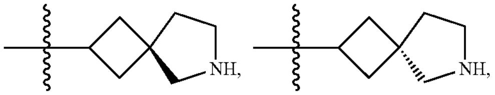
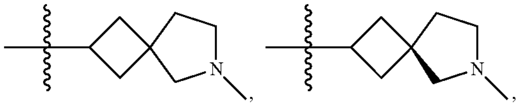
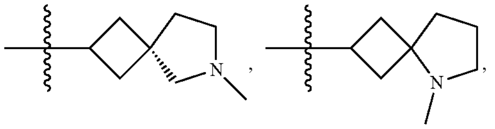
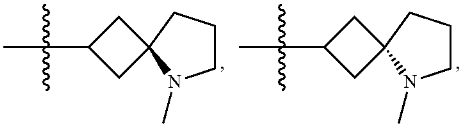
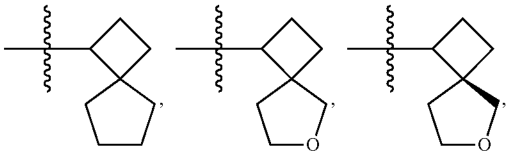
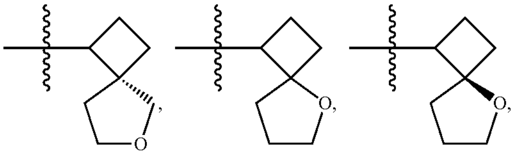
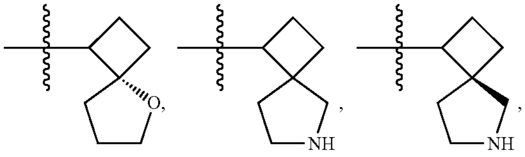
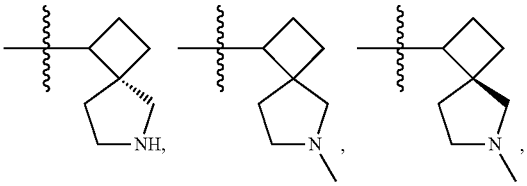
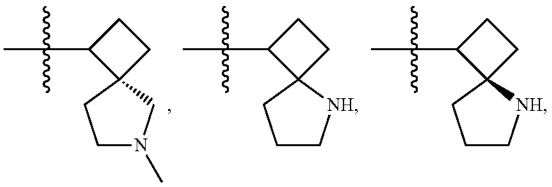

-continued
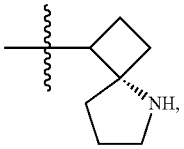
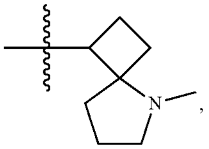
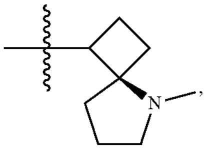
and
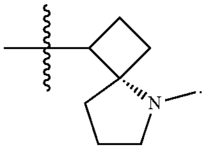
11. The compound of embodiment 3, wherein A is selected from the group consisting of:
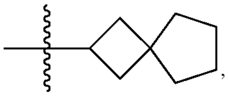
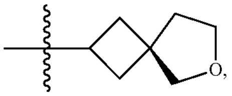
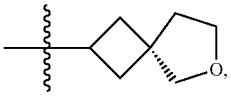
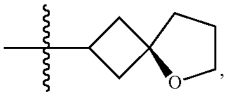
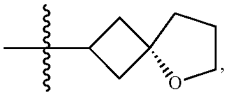
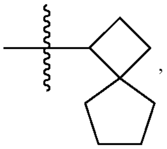
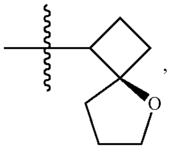
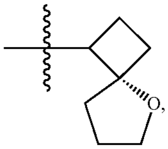
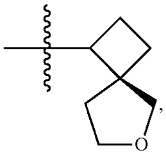
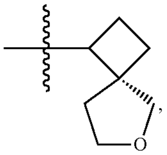
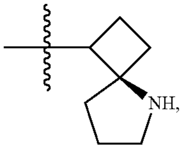
and
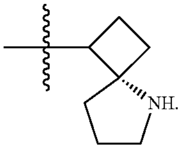
12. The compound of embodiment 3, wherein A is selected from the group consisting of:
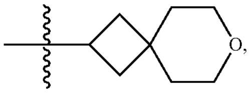
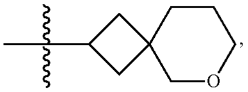
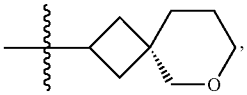
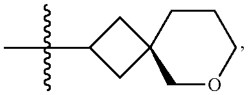
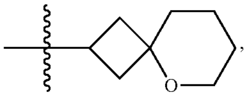
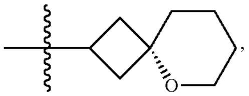
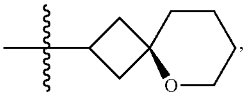
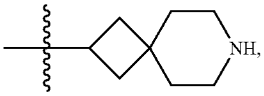
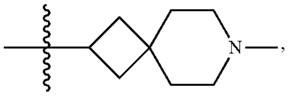
-continued
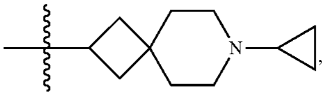
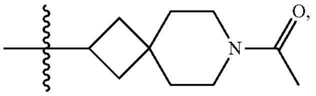
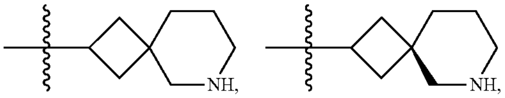
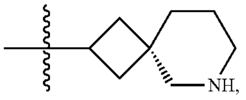
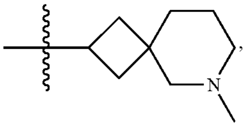
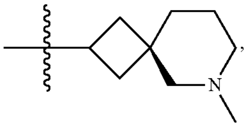
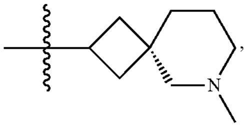
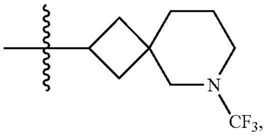
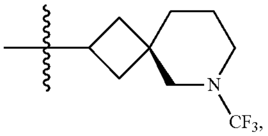
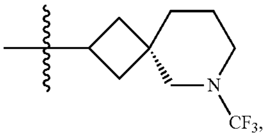
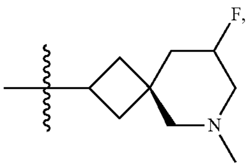
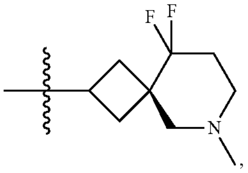
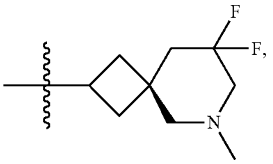
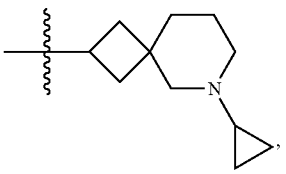
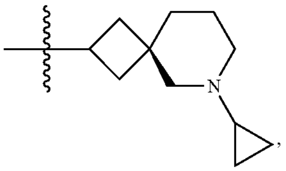

-continued
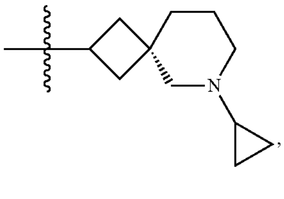,
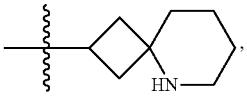,
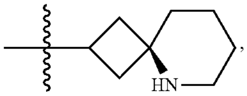,
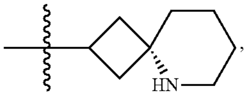,
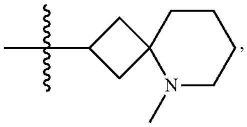,
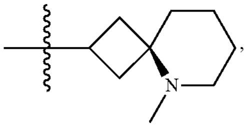,
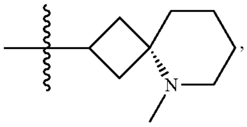,
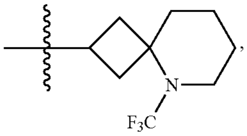,
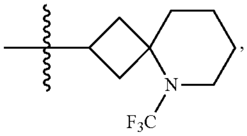,
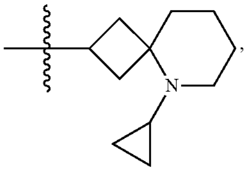,
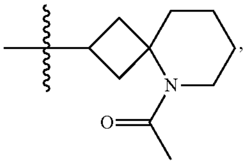,
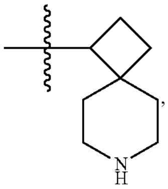,
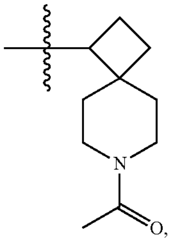
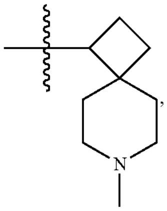,
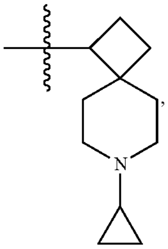,
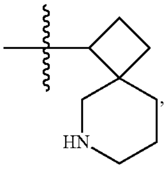,
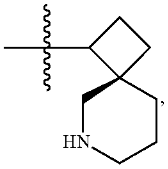,
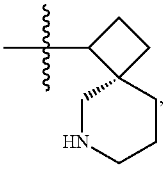,
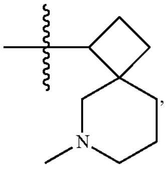,
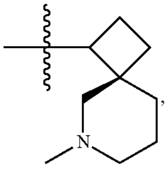,
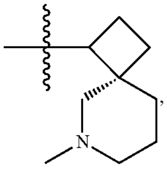,
-continued
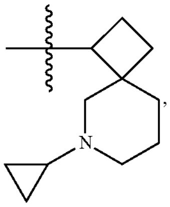, and 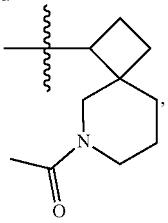,
13. The compound of embodiment 3, wherein A is selected from the group consisting of:
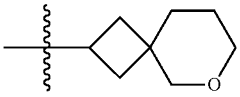,
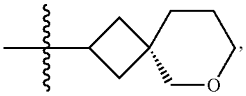,
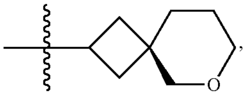,
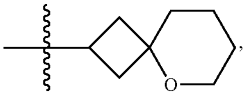,
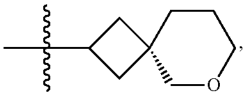,
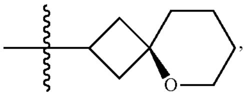,
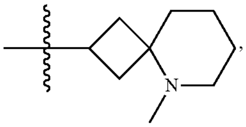,
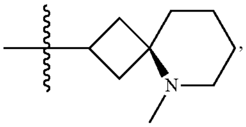,
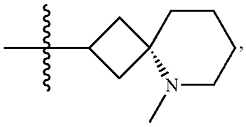,
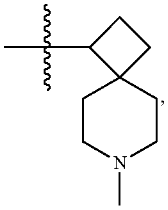,
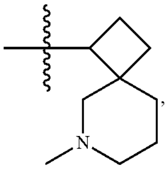,
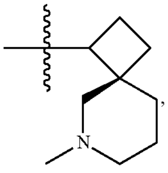, and
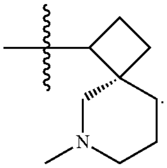.
14. The compound of embodiment 3, wherein A is
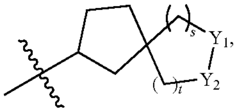
wherein
s and t are each independently 0, 1 or 2 provided that the sum of s and t is 1, 2 or 3;
$Y_1$ and $Y_2$ are each independently selected from $CR_{s1}R_{s2}$, $NR_s$ and O, provided that at least one of $Y_1$ and $Y_2$ is $CR_{s1}R_{s2}$;

$R_{s1}$ and $R_{s2}$ are each independently hydrogen, or $(C_1\text{-}C_4)$alkyl optionally substituted with one or more halogen; and $R_s$ is hydrogen, $(C_1\text{-}C_4)$alkyl optionally substituted with one or more halogen, acyl, $(C_3\text{-}C_6)$cycloalkyl or 3- to 6-member heterocycloalkyl comprising one or more heteroatoms selected from the group consisting of O and N.

15. The compound of embodiment 3, wherein A is selected from the group consisting of:

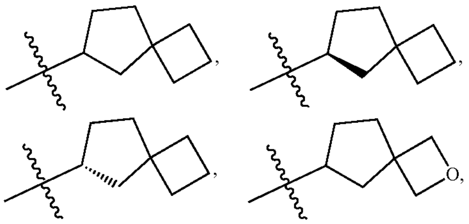
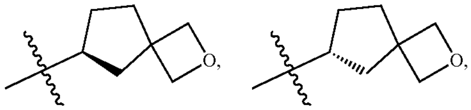
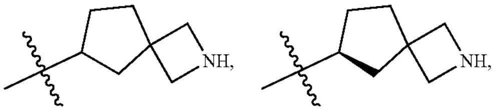
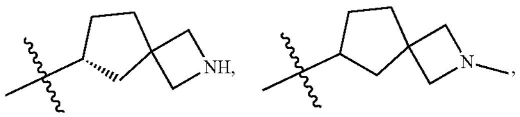
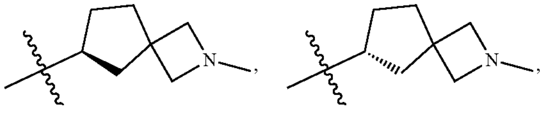
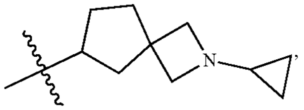
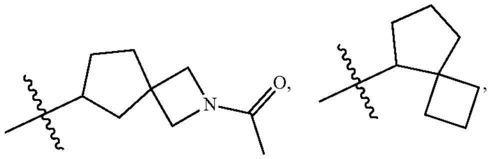
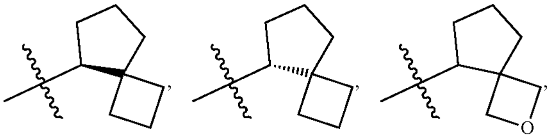
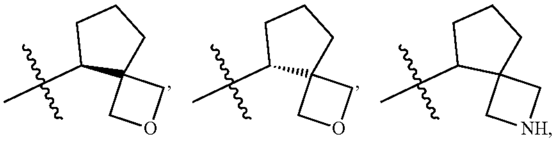
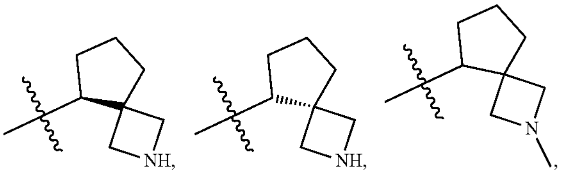

-continued

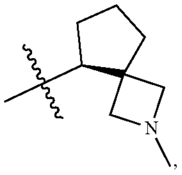
and
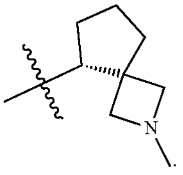

16. The compound of embodiment 3, wherein A is selected from the group consisting of:

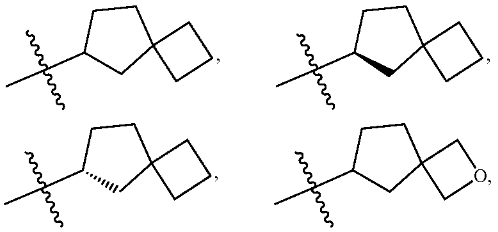
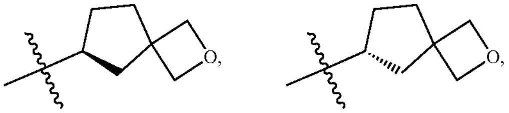
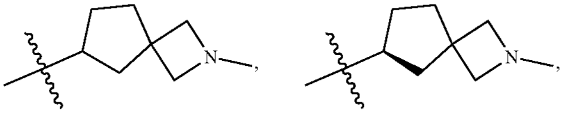
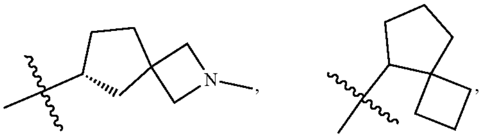
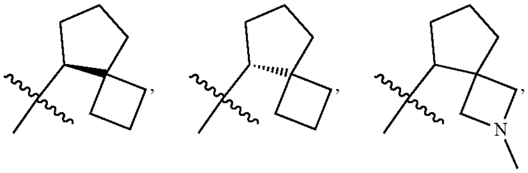
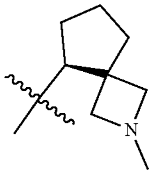
and
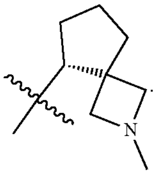

17. The compound of embodiment 3, wherein A is selected from the group consisting of:

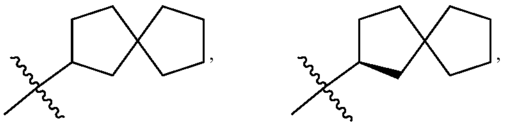
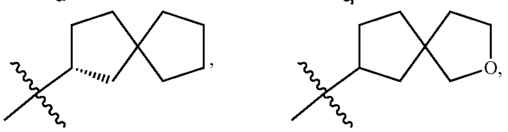

-continued

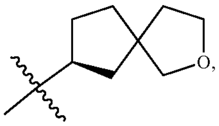,
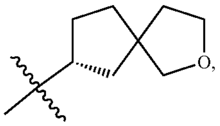,
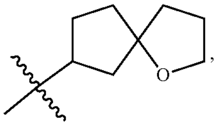,
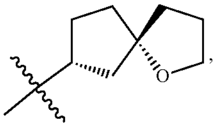,
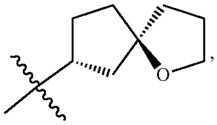,
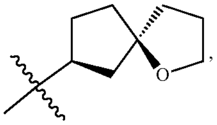,
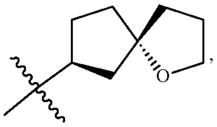,
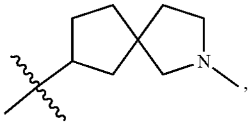,
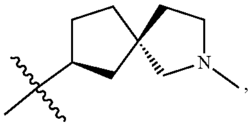,
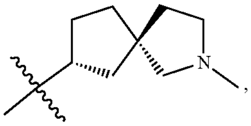,
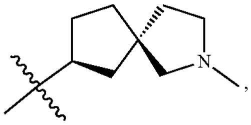,
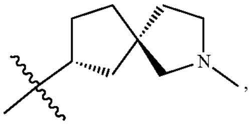,
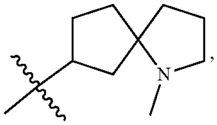,
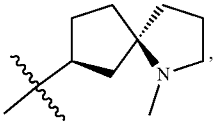,
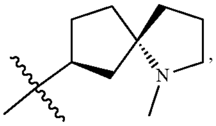,
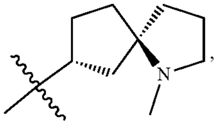, and
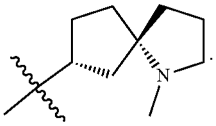.

18. The compound of embodiment 3, wherein A is selected from the group consisting of:

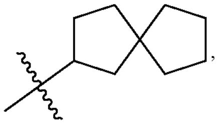,
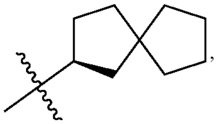, and
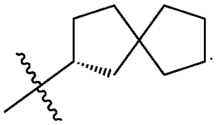.

19. The compound of embodiment 3, wherein A is selected from the group consisting of:

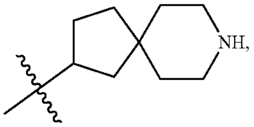,
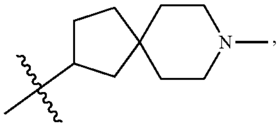, and
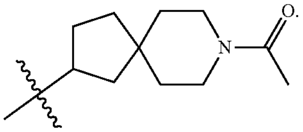.

20. The compound of embodiment 16, wherein A is selected from the group consisting of:

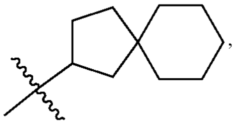,
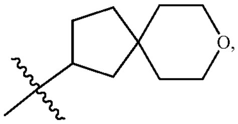,
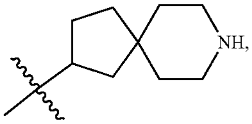,
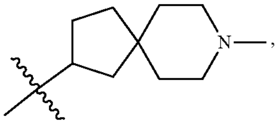,
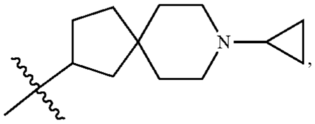,
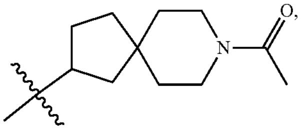,
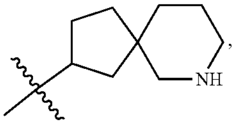,
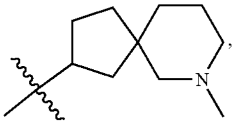,
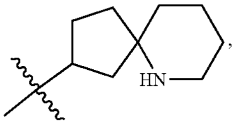, and
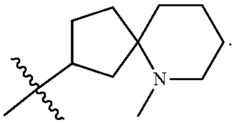.

21. The compound of embodiment 3, wherein A is

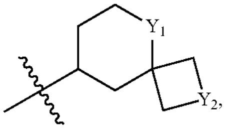, wherein $Y_1$ is selected from $NR_s$ and O;

$Y_2$ are each independently selected from $CR_{t1}R_{t2}$, $NR_s$ and O;

$R_{t1}$ and $R_{t2}$ are each independently hydrogen, or $(C_1-C_4)$alkyl optionally substituted with one or more halogen; and $R_s$ is hydrogen, acyl, $(C_3-C_6)$cycloalkyl or $(C_1-C_4)$ alkyl optionally substituted with one or more halogen or aryl.

22. The compound of embodiment 21, wherein $Y_1$ is selected from $NR_s$ and O;

$Y_2$ is $CH_2$; and $R_s$ is hydrogen, acyl, cyclopropyl or $(C_1-C_4)$alkyl optionally substituted with one or more halogen or phenyl.

23. The compound of embodiment 3, wherein A is selected from the group consisting of:

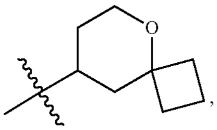,
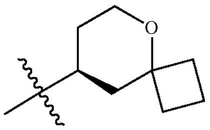,
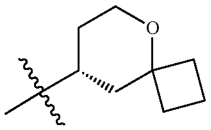,
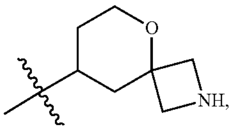,
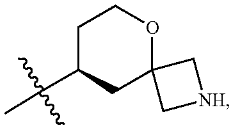,
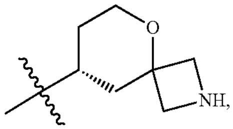,
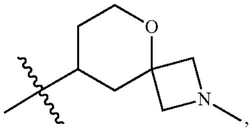,
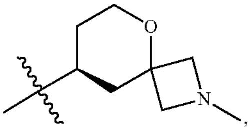,
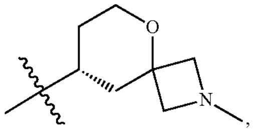,
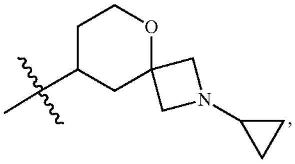,
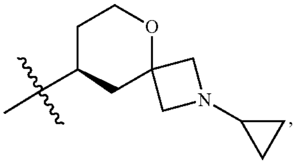,
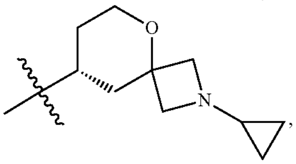,
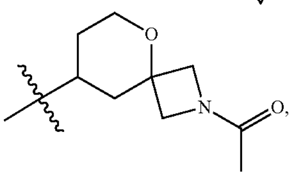,
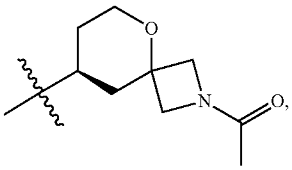

-continued

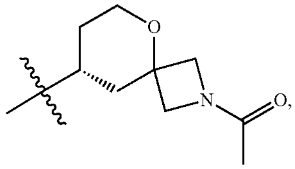,
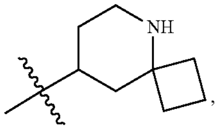,
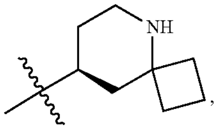,
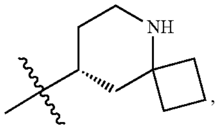,
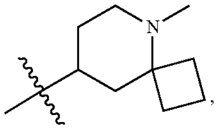,
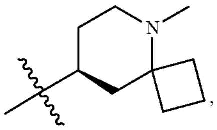,
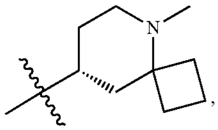,
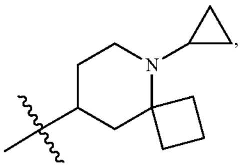,
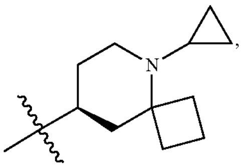,
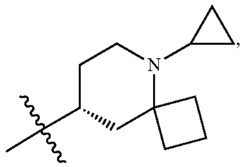,
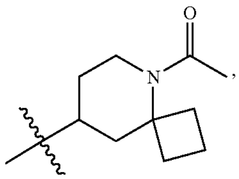,
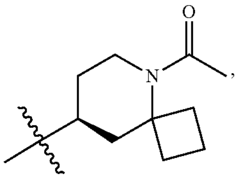,
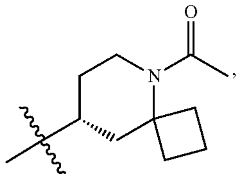,
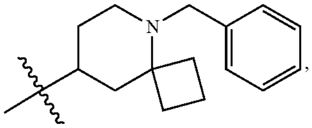,
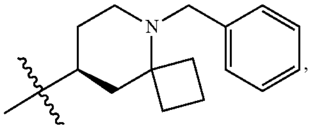, and
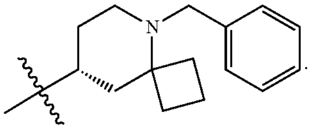.

24. The compound of embodiment 3, wherein A is selected from the group consisting of:

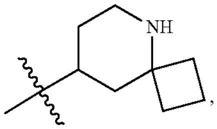
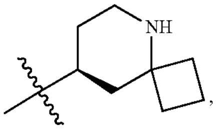
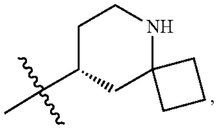
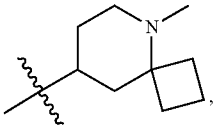
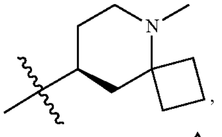
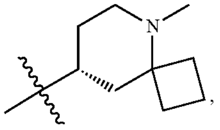
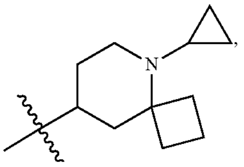
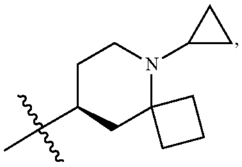
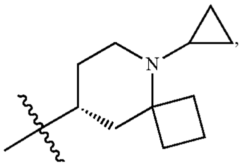
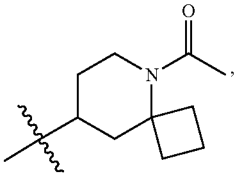
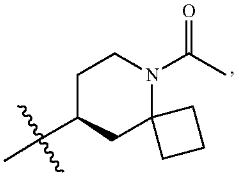
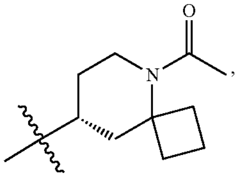
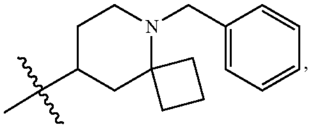
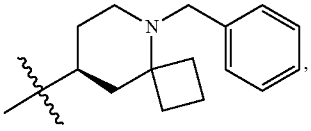
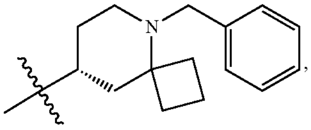
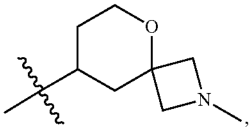
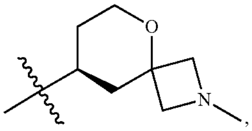
and
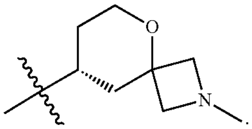

25. The compound of embodiment 2, wherein:

a. n is 1 and m is 1; and b. A is a 4-10 membered bridged, spirocyclic or fused bicyclic heterocyclyl comprising one or more heteroatoms selected from N and O, optionally substituted with ($C_1$-$C_4$)alkyl, halogen, oxo, ($C_3$-$C_6$)cycloalkyl, acyl, and amino optionally substituted with one or more methyl or cyclopropyl.

26. The compound of embodiment 25, wherein $R^1$ is hydrogen and $R^2$ is hydrogen.

27. The compound of embodiment 26, wherein A is

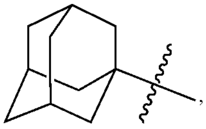
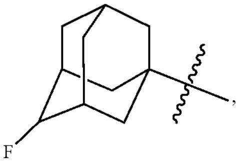
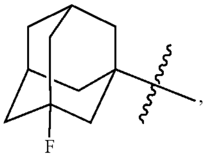
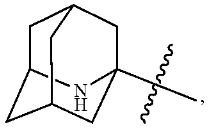
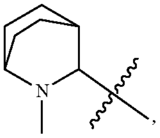
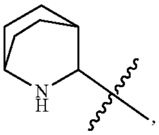
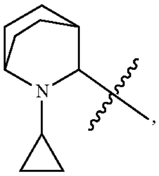
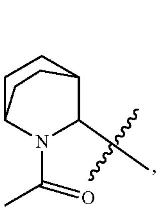
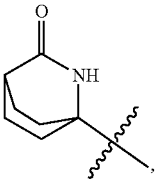
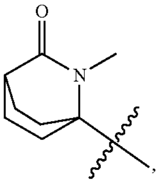
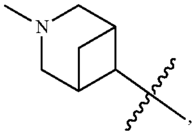
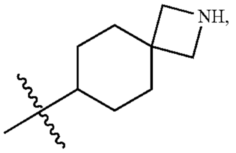
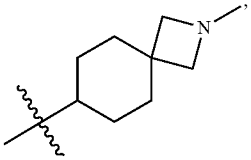
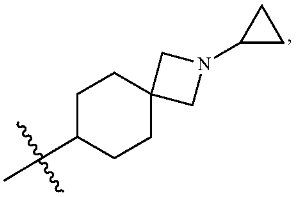
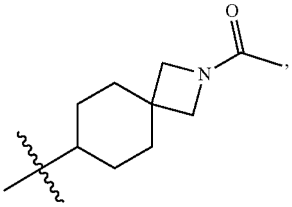
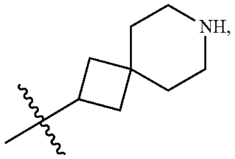

-continued
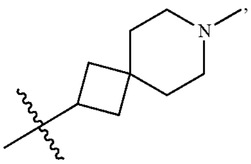,
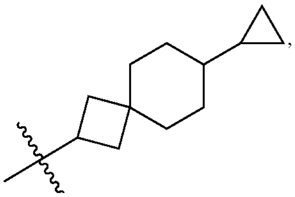,
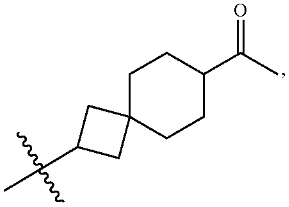,
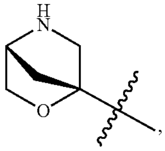,
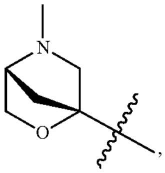,
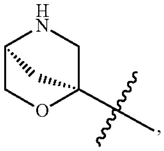,
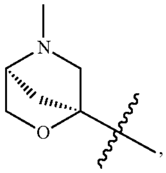,
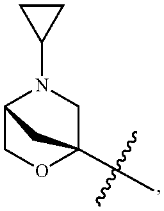,
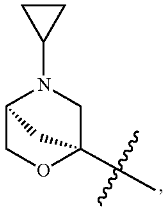,
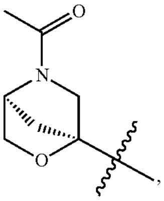,
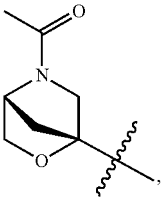,
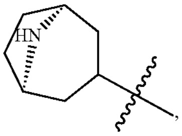,
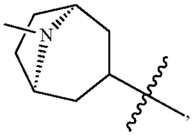,
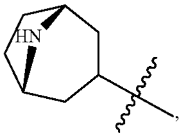,
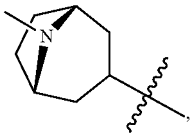,
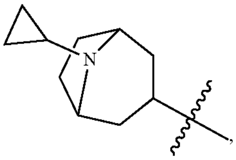,
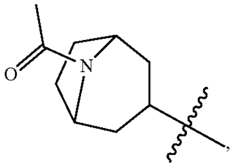,
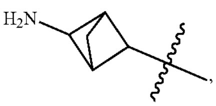,
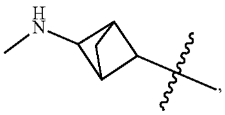,
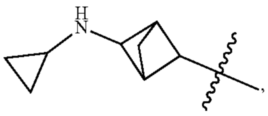,
-continued
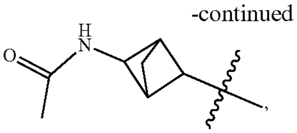,
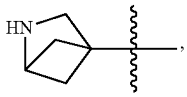,
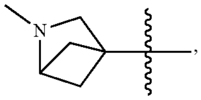,
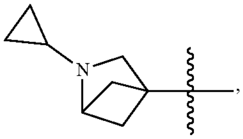,
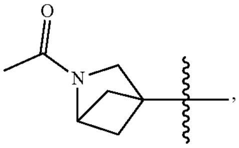,
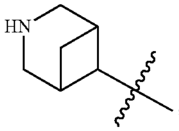,
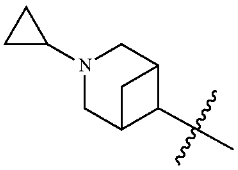,
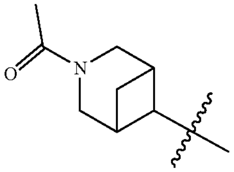,
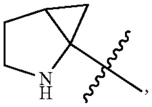,
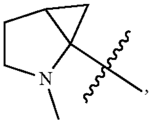,
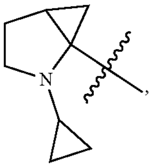, or
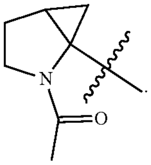.
28. The compound of embodiment 27, wherein A is
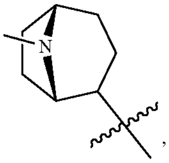,
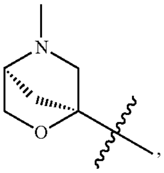,
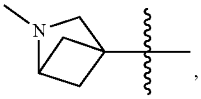,
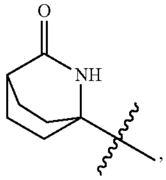,
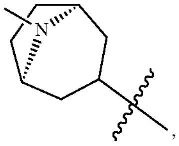, and
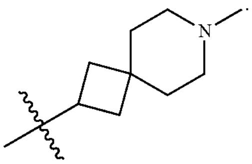.
29. The compound of embodiment 2, wherein
a. n is 0 and m is 1; and
b. A is a monocyclic 4-6 membered heterocyclyl ring or a $C_{4-6}$ cycloalkyl ring optionally substituted with one or more methyl or ethyl.

30. The compound of embodiment 29, wherein A is
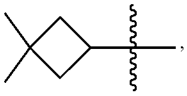, or 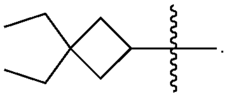.
31. The compound of embodiment 2, wherein
a. n is 1 and m is 1; and
b. A is a monocyclic 4-6 membered heterocyclyl ring or a $C_{4-6}$cycloalkyl ring optionally substituted with one or more methyl.
32. The compound of embodiment 31, wherein A is
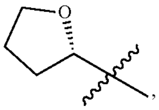, 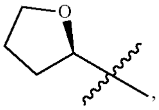, 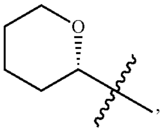, or 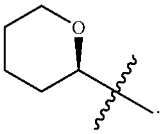.
33. The compound of embodiment 1, selected from the group consisting of:
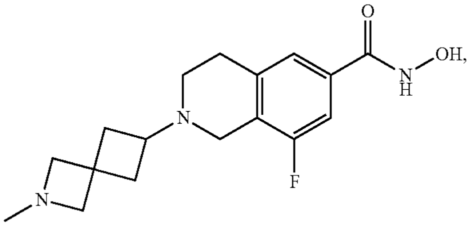
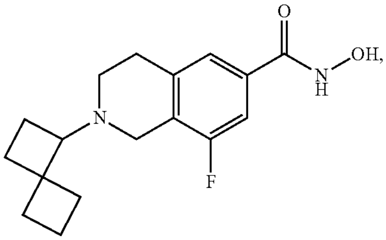
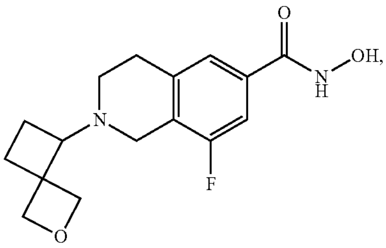
-continued
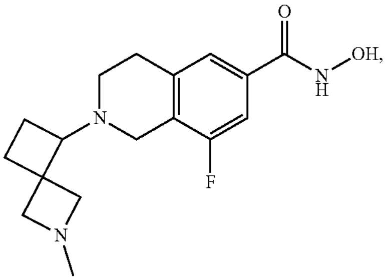
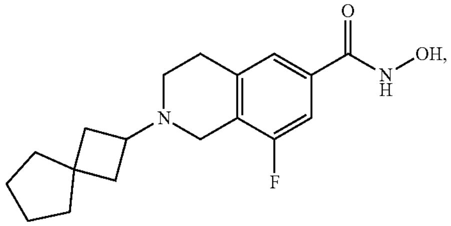
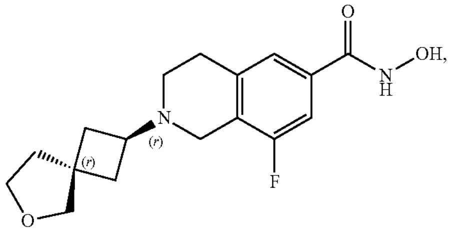
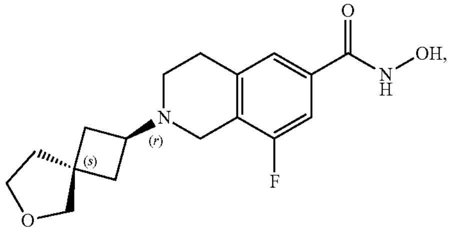
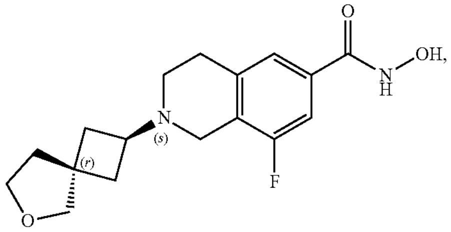
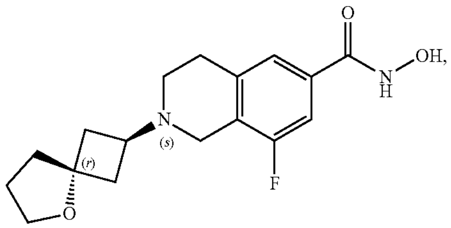
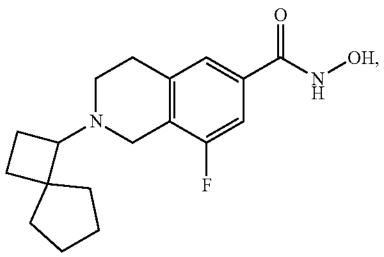

-continued
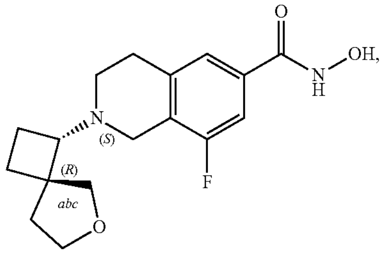
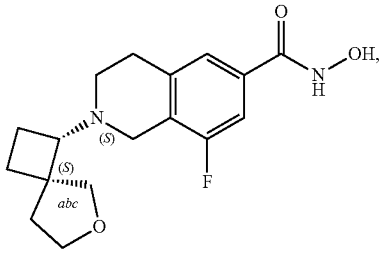
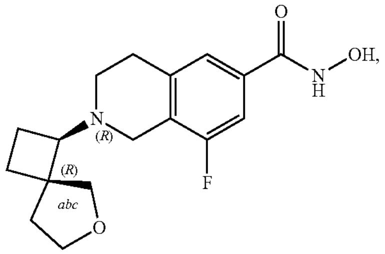
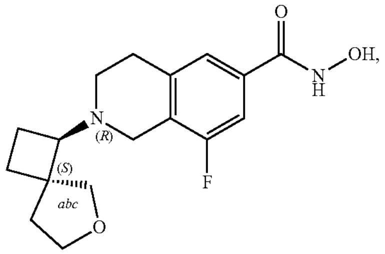
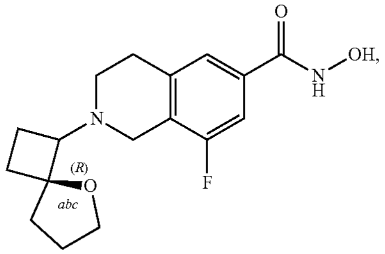
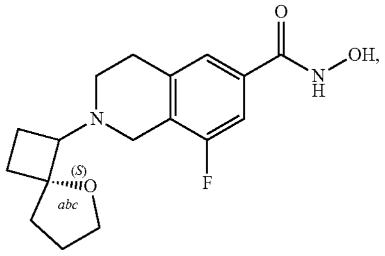
-continued
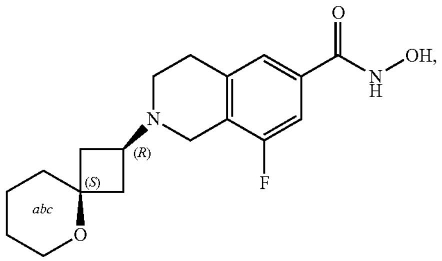
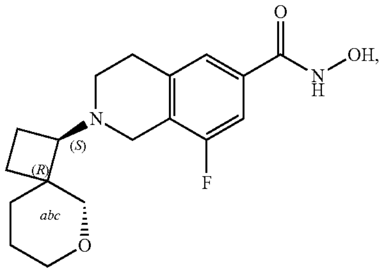
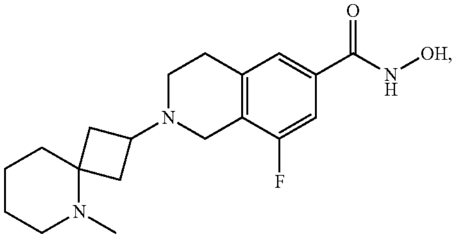
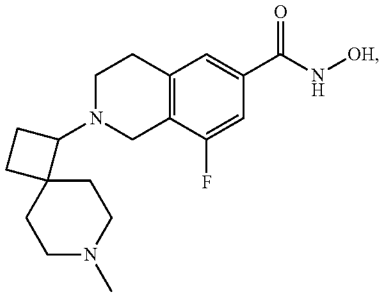
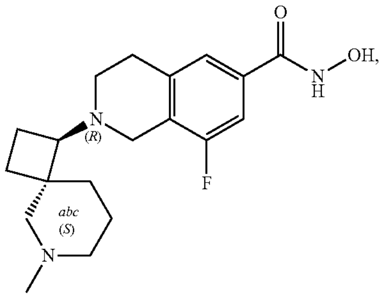
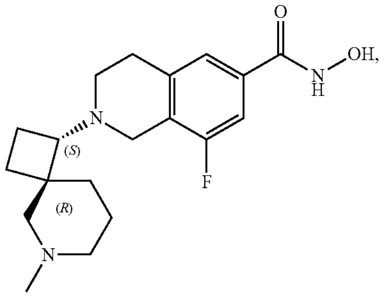

-continued
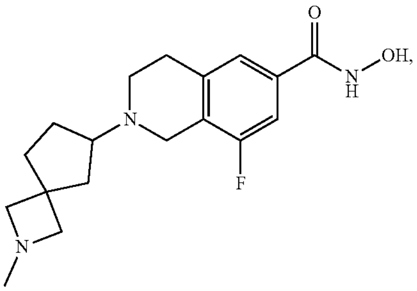
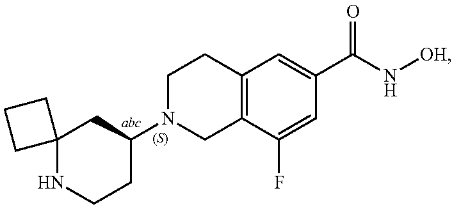
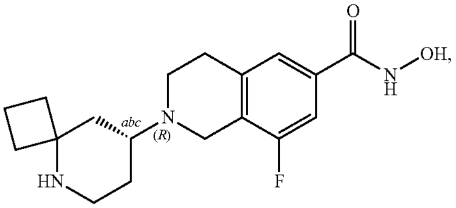
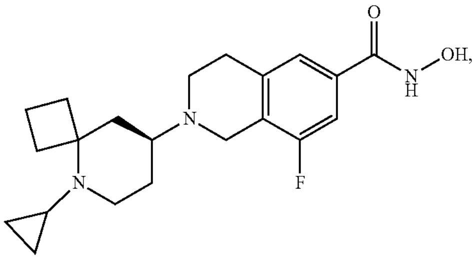
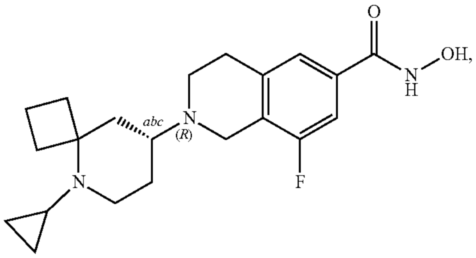
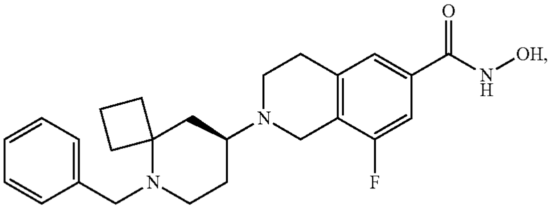
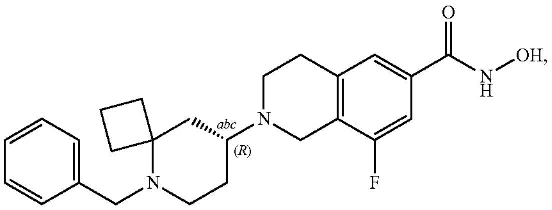
-continued
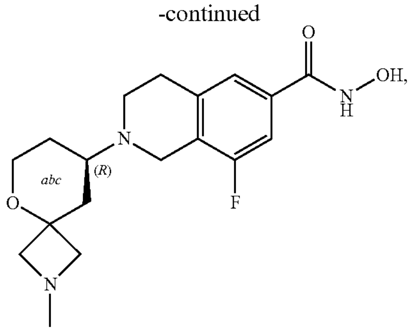
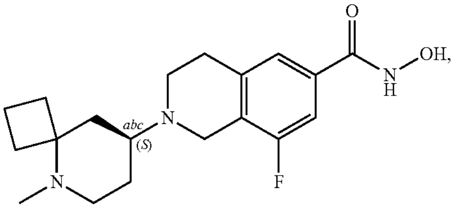
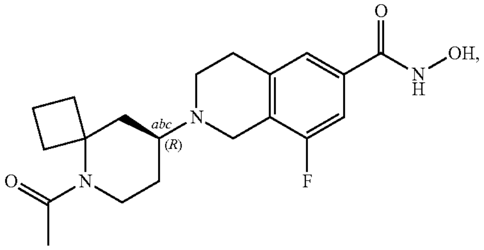
and
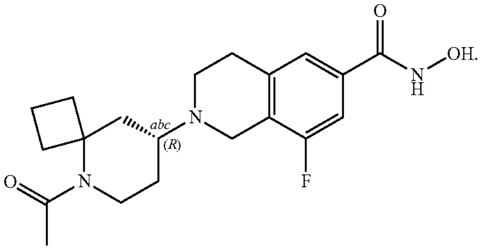
34. The compound of embodiment 1, selected from the group consisting of:
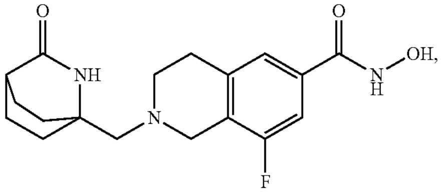
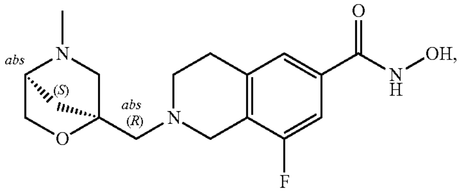
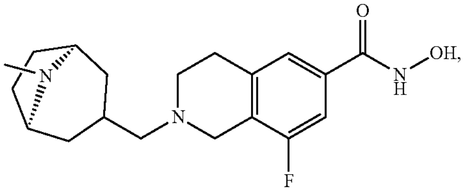

-continued

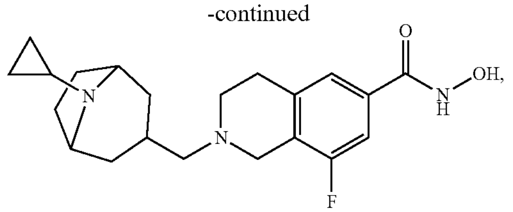

,

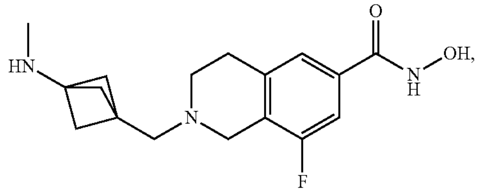

,

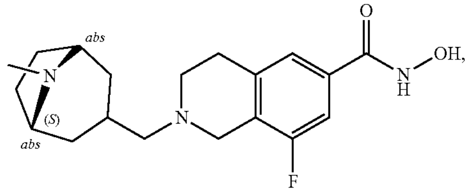

,

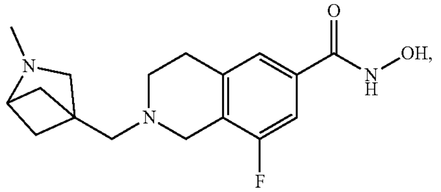

and

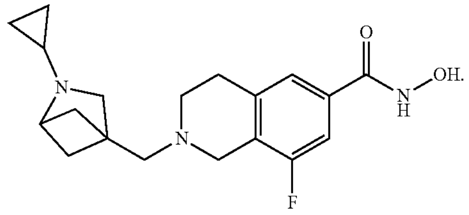

.

35. The compound of embodiment 1, wherein the compound is:

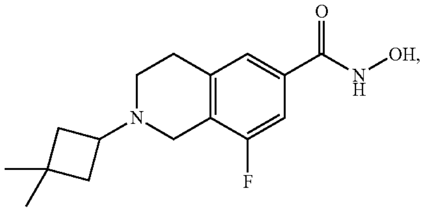 [SMILES: CC1(C)CC(N2CCc3cc(C(=O)NO)cc(F)c3C2)C1]

,

36. A compound of Formula (II-m):

(II-m)

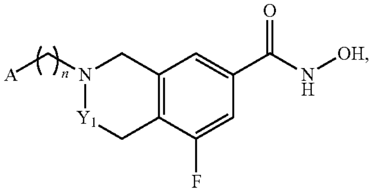

, or a pharmaceutically acceptable salt thereof, wherein:

$Y^1$ is $NR^b$ or $CR^bR^x$;

A is substituted or unsubstituted alkyl; substituted or unsubstituted carbocyclyl; or substituted or unsubstituted heterocyclyl;

$R^x$ is hydrogen or substituted or unsubstituted alkyl;

$R^a$ is hydrogen;

$R^b$ is hydrogen, substituted or unsubstituted alkyl, substituted or unsubstituted carbocyclyl: substituted or unsubstituted heterocyclyl; or benzyl; and n is 0 or 1;

provided that the compound is not any of the following compounds:

115

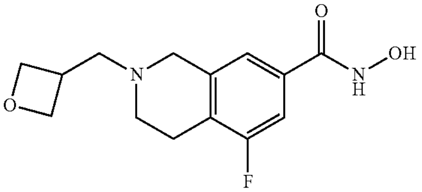

114

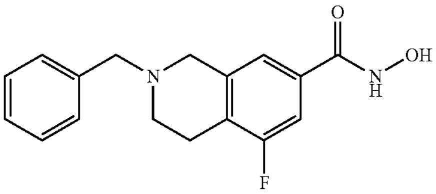

113

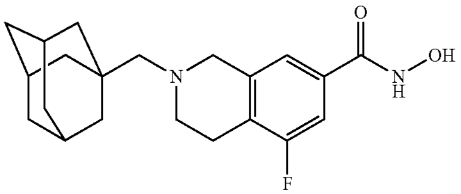

39

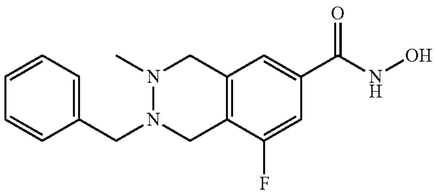

117

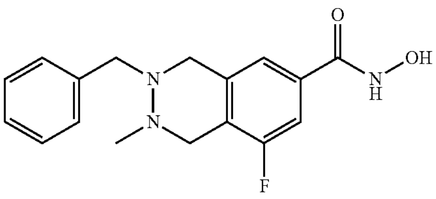

41

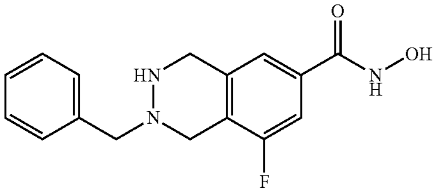

-continued

42

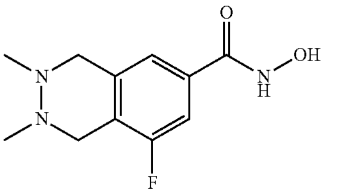

43

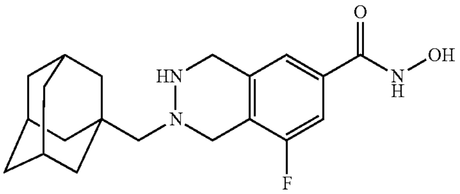

44

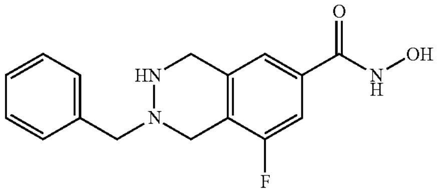

116

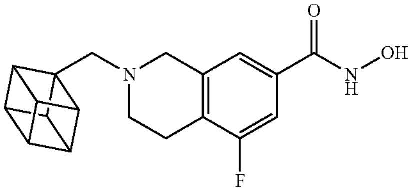

118

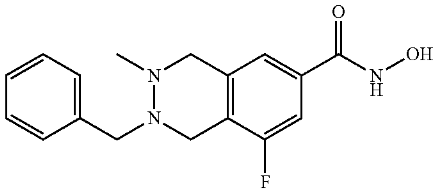

37. The compound of embodiment 36, wherein
   a. A is $C_{1-4}$ alkyl; and
   b. $Y^1$ is $NR^b$ and $R^b$ is a 7-11 member bicyclic spirocyclic heterocyclyl; a $C_{7-11}$ substituted or unsubstituted bicyclic spirocyclic carbocyclyl; or $C_{1-4}$ alkyl substituted with a 4-10 member bridged heterocyclyl or a $C_{4-10}$ member bridged cycloalkyl.
38. The compound of embodiment 37, wherein n is 0, A is methyl and Rb is

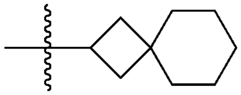 [SMILES: *C1CC2(CCCCC2)C1]

or

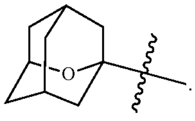

.

39. The compound of embodiment 36, wherein
   a. A is a 7-11 member bicyclic spirocyclic heterocyclyl; or a $C_{7-11}$ substituted or unsubstituted bicyclic spirocyclic carbocyclyl; and
   b. $Y^1$ is $NR^b$ and $R^b$ is $C_{1-4}$ alkyl
40. The compound of embodiment 39, wherein n is 0, A is

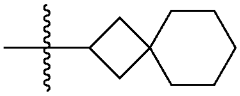

and $R^b$ is methyl.
41. The compound of embodiment 36, wherein
   a. A is a 4-7 member heterocyclyl ring or $C_{1-4}$ alkyl;
   b. $R^b$ is benzyl; and
   c. $R^x$ is hydrogen.
42. The compound of embodiment 41, wherein n is 1 and A is
32. The compound of embodiment 31 wherein

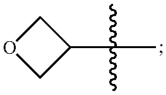 [SMILES: *C1COC1]

;

or n is 0 and A is methyl.
43. The compound of embodiment 36, wherein $Y^1$ is $CR^bR^x$.
44. The compound of embodiment 43, wherein $R^b$ and $R^x$ are each independently hydrogen.
45. The compound of embodiment 44, wherein n is 1.
46. The compound of embodiment 45, wherein A is a 4-10 member bridged heterocyclyl, a 4-6 member heterocyclyl, or a $C_{4-10}$ member bridged cycloalkyl.
47. The compound of embodiment 46, wherein A is

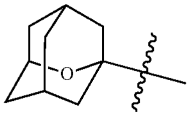

or

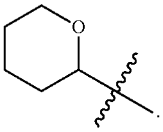

.

48. The compound of embodiment 43, wherein $R^x$ is hydrogen and $R^b$ is benzyl.
49. The compound of embodiment 48, wherein n is 0 and A is $C_{1-4}$ alkyl.
50. The compound of embodiment 43, wherein $R^x$ is methyl or ethyl and $R^b$ is hydrogen or methyl.
51. The compound of embodiment 50, wherein A is $C_{3-6}$ carbocyclyl; or 4-6 member heterocyclyl.
52. The compound of embodiment 51, wherein n is 1 and A is

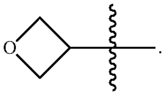

.

53. The compound of embodiment 43, wherein $R^x$ is ethyl and $R^b$ is hydrogen.

54. The compound of embodiment 53, wherein n is 0.

55. The compound of embodiment 54, wherein A is a 7-11 member bicyclic spirocyclic heterocyclyl, or a $C_{7-11}$ substituted or unsubstituted bicyclic spirocyclic carbocyclyl; wherein A is optionally substituted with $(C_1$-$C_4)$alkyl or $(C_3$-$C_6)$cycloalkyl.

56. The compound of embodiment 55, wherein A is optionally substituted with methyl or cyclopropyl.

57. The compound of any one of embodiments 53-56, wherein A is

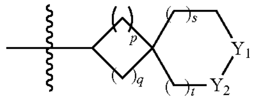 or

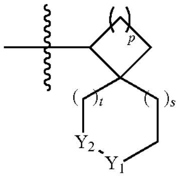

wherein p and q are each independently 1 or 2;

s and t are each independently 0, 1, or 2, provided that the sum of s and t is 0, 1, or 2;

$Y_1$ and $Y_2$ are each independently selected from S(═O), $CR_{s1}R_{s2}$, $NR_s$ and O, provided that at least one of $Y_1$ and $Y_2$ is $CR_{s1}R_{s2}$;

$R_{s1}$ and $R_{s2}$ are each independently hydrogen, or $(C_1$-$C_4)$alkyl optionally substituted with one or more halogen; and $R_s$, is hydrogen, $(C_1$-$C_4)$alkyl optionally substituted with one or more halogen, acyl, $(C_3$-$C_6)$cycloalkyl or 3- to 6-member heterocycloalkyl comprising one or more heteroatoms selected from the group consisting of O and N.

58. The compound of any one of embodiments 53-57, wherein A is

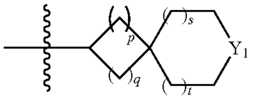

wherein p and q are each independently 1 or 2;

s and t are each independently 0 or 1;

$Y_1$ is selected from $CH_2$, O, and $NR_s$, where $R_s$ is hydrogen, methyl or cyclopropyl.

59. The compound of embodiment 54, wherein A is selected from the group consisting of

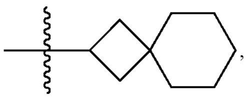, 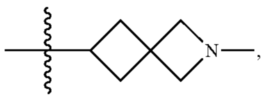,

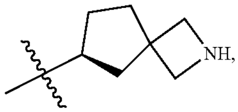, 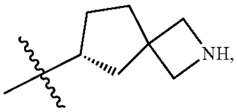,

-continued

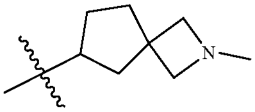, 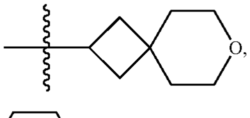,

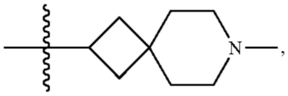,

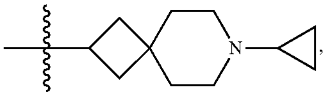, and

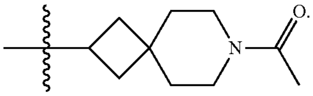

60. The compound of embodiment 55, wherein A is 4-6 member heterocyclyl, or a $C_{3-6}$ carbocyclyl; wherein A is optionally substituted with $(C_1$-$C_4)$alkyl.

61. The compound of embodiment 60, wherein A is cyclobutyl, cyclopentyl or cyclohexyl optionally substituted with one or more methyl.

62. The compound of embodiment 60, wherein A is

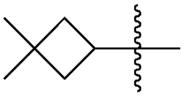 or 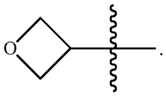 [SMILES: *C1COC1].

63. The compound of embodiment 53, wherein n is 1.

64. The compound of embodiment 63, wherein A is adamantyl or a 10-member bridged heterocyclyl comprising an oxygen or nitrogen heteroatom and optionally substituted with one or more fluoro.

65. The compound of embodiment 64, wherein A is

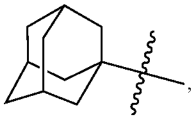, 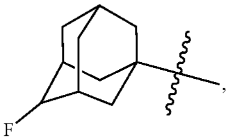,

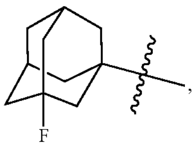, 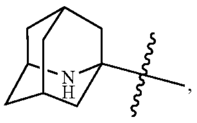, or

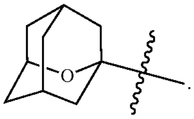.

66. The compound of embodiment 63, wherein A is

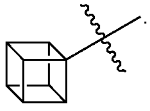 [SMILES: *C12C3C4C5C3C1C5C42].

67. The compound of embodiment 63, wherein A is a 4-10 membered bridged, spirocyclic or fused bicyclic heterocyclyl comprising one or more heteroatoms selected from N and O, optionally substituted with ($C_1$-$C_4$) alkyl, halogen, oxo, ($C_3$-$C_6$)cycloalkyl, acyl, and amino optionally substituted with one or more methyl, acyl or cyclopropyl.

68. The compound of embodiment 67, wherein A is a 4-member bridged carbocyclic optionally substituted with amino, the amino optionally further substituted with one or more methyl or cyclopropyl.

69. The compound of embodiment 68, wherein A is

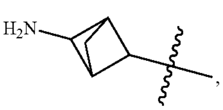, 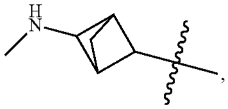,

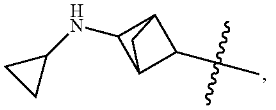, or

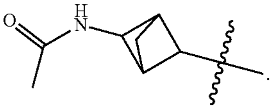.

70. The compound of embodiment 67, wherein A is a 5-member bridged carbocyclic or 6-member heterocyclyl comprising an oxygen heteroatom, each optionally substituted with amino, the amino optionally further substituted with one or more methyl or cyclopropyl.

71. The compound of embodiment 70, wherein A is

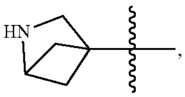, 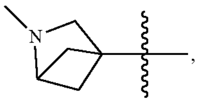,

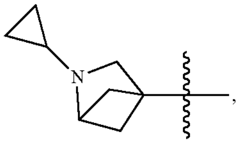, or 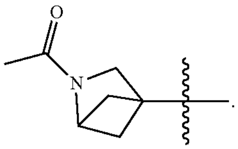.

72. The compound of embodiment 67, wherein A is a 6-8 member bridged carbocyclic or 6-8 member heterocyclyl comprising one or more of an oxygen and a nitrogen heteroatom, each optionally substituted with one or more of an oxo, and an amino wherein the amino is optionally further substituted with one or more methyl or cyclopropyl.

73. The compound of embodiment 72, wherein A is

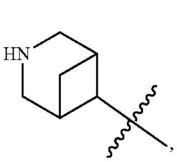, 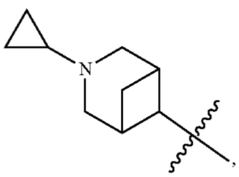,

-continued

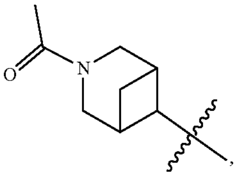, 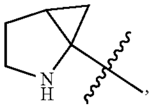,

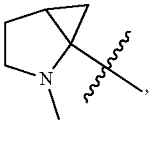, 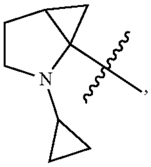, 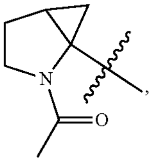,

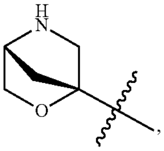, 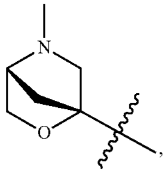, 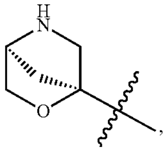,

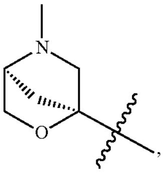, 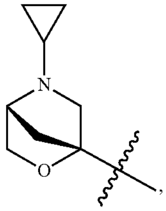, 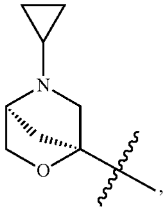,

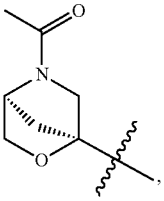, 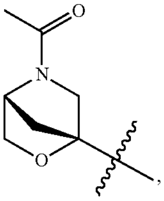, 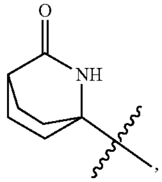,

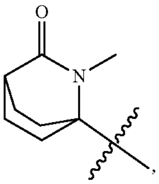, 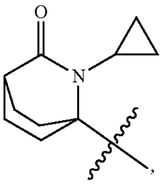, 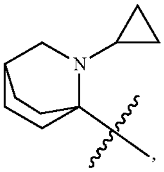,

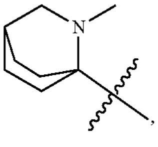, 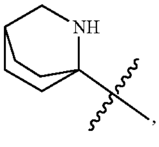, 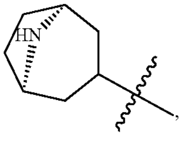,

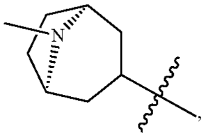, 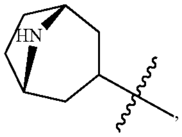,

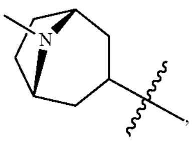, 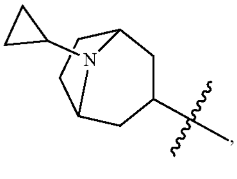, or

-continued

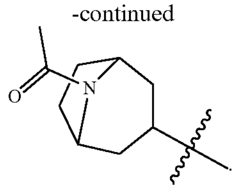

74. The compound of embodiment 53, wherein n is 1 and A is

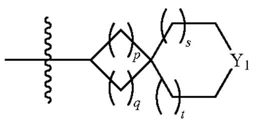

wherein p and q are each independently 1 or 2;

s and t are each independently 0 or 1;

$Y_1$ is selected from $CH_2$, O, and $NR_s$, where $R_s$ is hydrogen, methyl or cyclopropyl.

75. The compound of embodiment 54, wherein A is selected from the group consisting of:

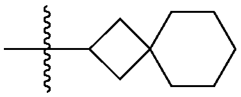 , 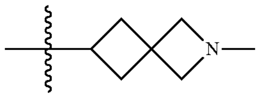 ,

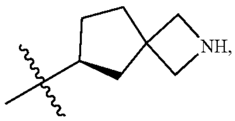 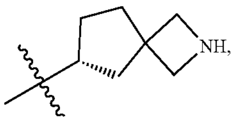

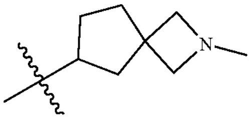 , 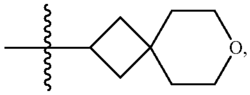 [SMILES: *C1CC2(CCCCC2)C1]

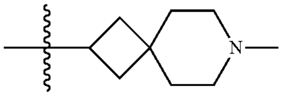 ,

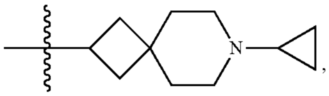 , and

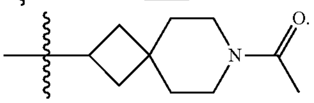

76. The compound of embodiment 36, wherein A is

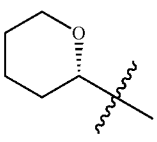 or 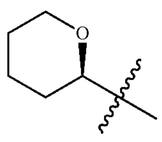 .

77. The compound of embodiment 36, wherein A is a substituted or unsubstituted spirocyclic heterocyclyl, or a substituted or unsubstituted spirocyclic carbocyclyl.

78. The compound of embodiment 36, wherein A is a substituted or unsubstituted 7-11 member bicyclic spirocyclic carbocyclyl.

79. The compound of embodiment 36, wherein A is

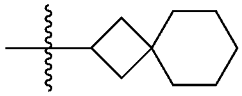

80. The compound of embodiment 36, wherein A is

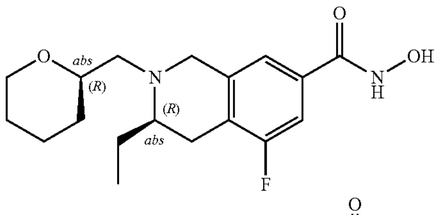 or

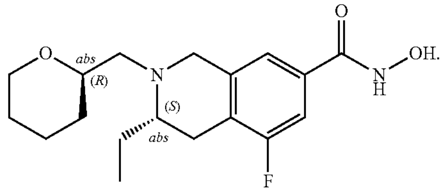

81. The compound of embodiment 36, wherein the compound is

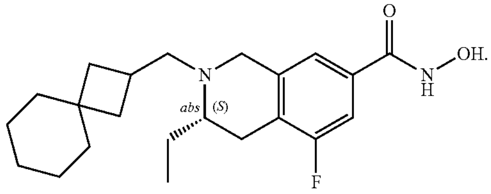

82. The compound of embodiment 36, wherein A is a substituted or unsubstituted 7-11 member bicyclic spirocyclic heterocyclyl.

83. The compound of embodiment 36, wherein A is

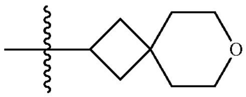 or 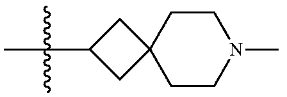

84. The compound of embodiment 36, wherein the compound is

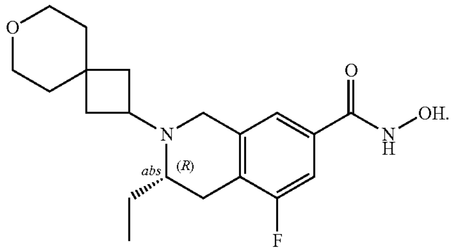

85. The compound of embodiment 36, wherein the compound is

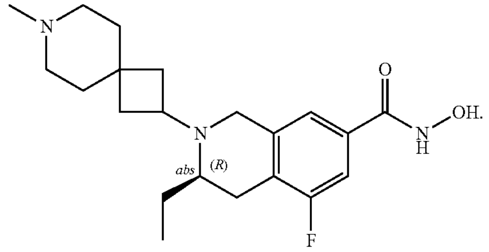

86. The compound of embodiment 36, wherein A is a substituted or unsubstituted $C_{5-10}$ bridged cycloalkyl, or a substituted or unsubstituted $C_{5-10}$ bridged heterocycloalkyl.

87. The compound of embodiment 36, wherein A is a substituted or unsubstituted $C_{5-10}$ bridged hetercycloalkyl.

88. The compound of embodiment 36, wherein the compound is

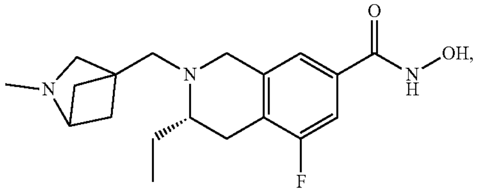

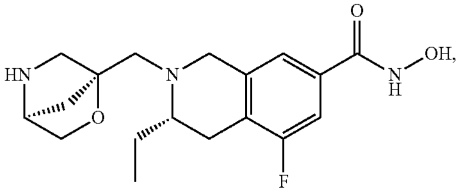

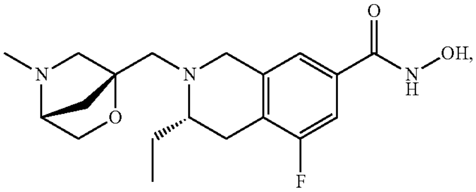

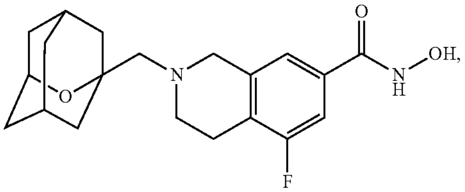

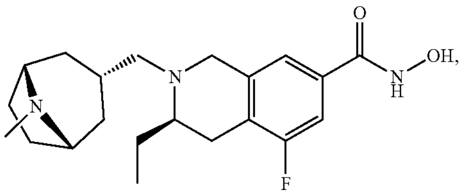

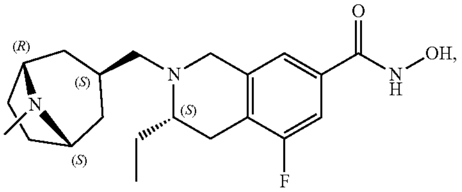

or

-continued

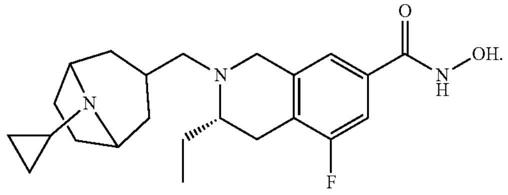

89. The compound of embodiment 36, wherein A is a substituted or unsubstituted $C_{5-10}$ bridged cycloalkyl.

90. The compound of embodiment 36, wherein A is adamantyl.

91. A compound selected from the group consisting of the following compounds, or a pharmaceutically acceptable salt thereof:

174

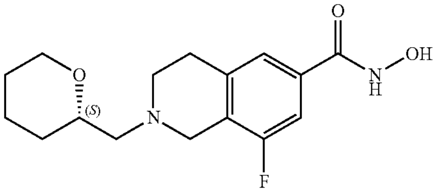

175

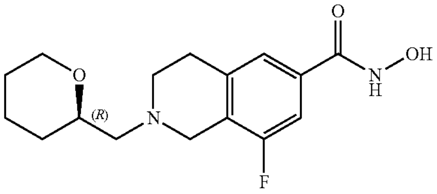

176

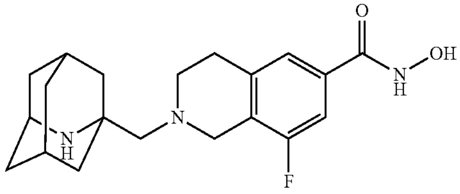

177

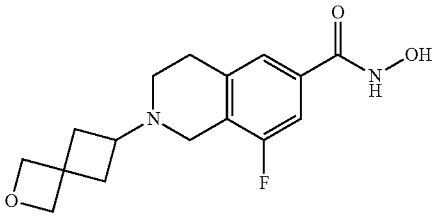

178

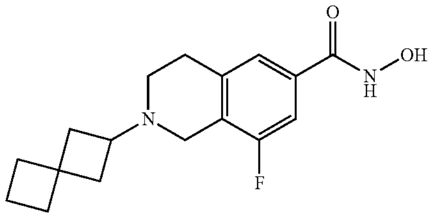

-continued
179
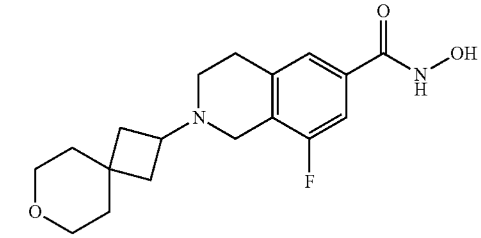
180
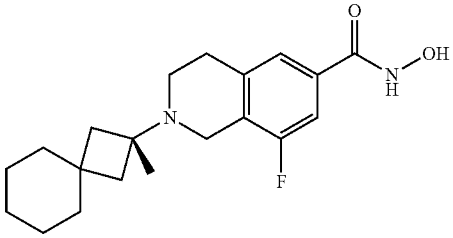
181
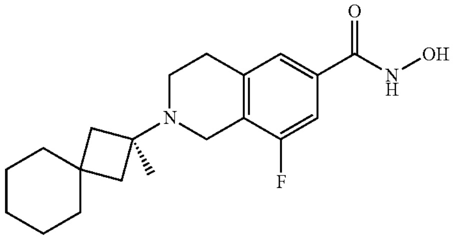
182
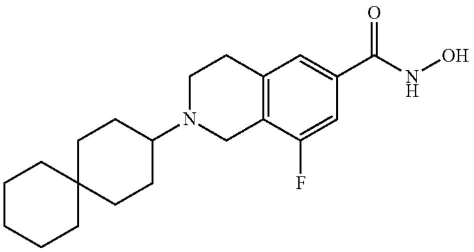
183
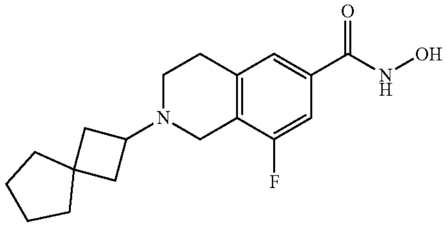
184
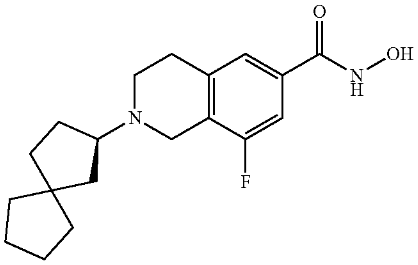
-continued
185
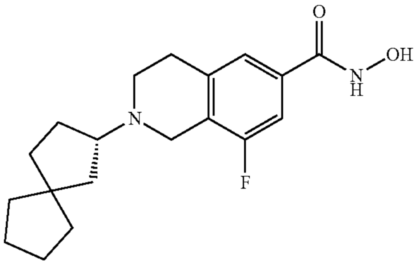
188
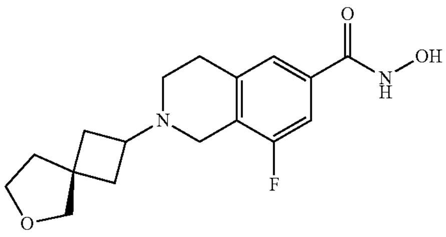
189
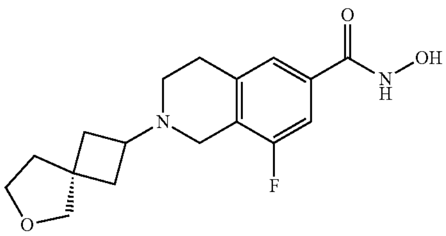
190
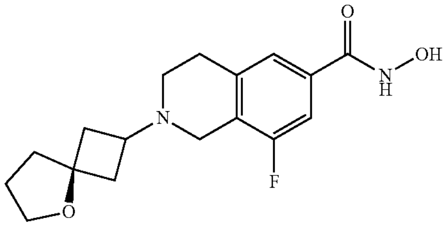
191
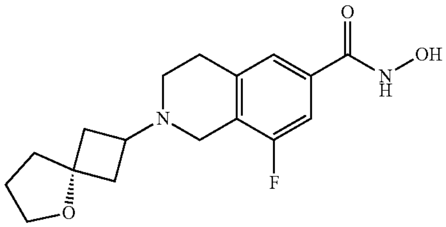
192
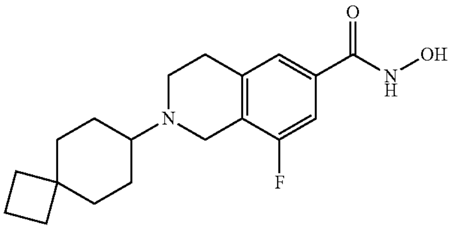

-continued
193
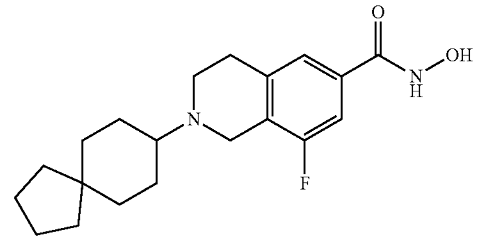
194
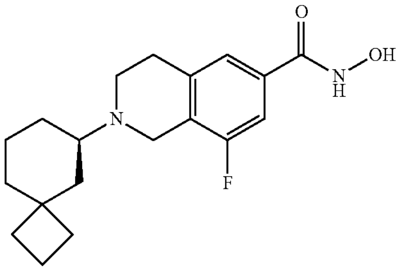
195
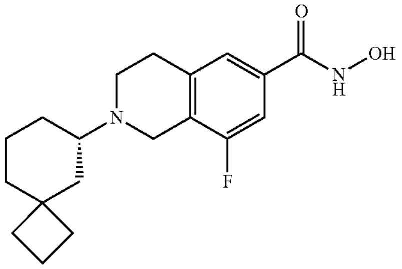
197
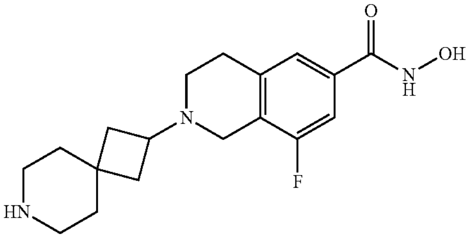
198
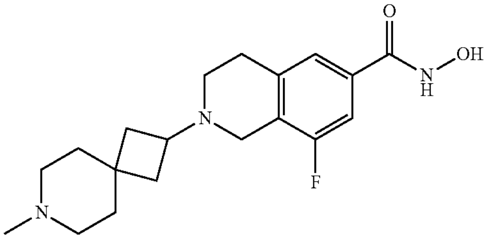
199
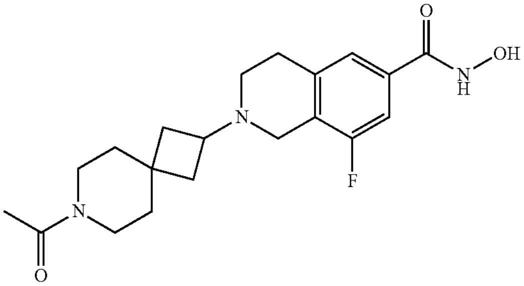
-continued
200
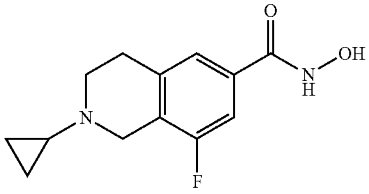
201
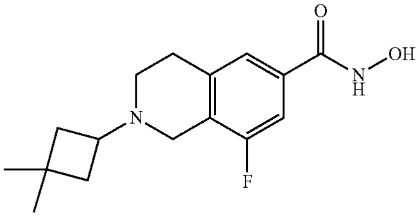
202
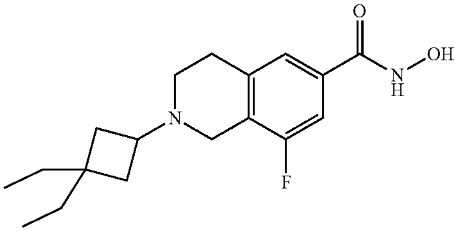
208
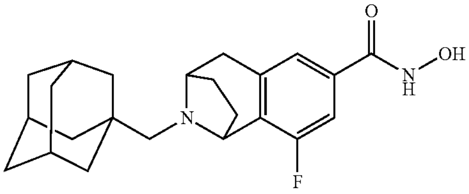
209
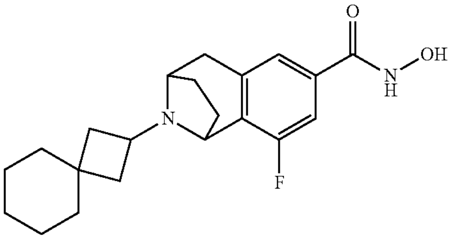
210
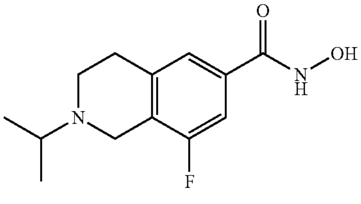
211
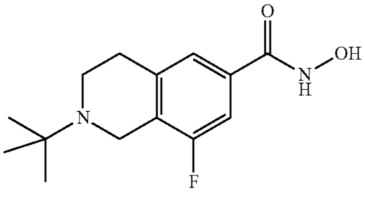

212
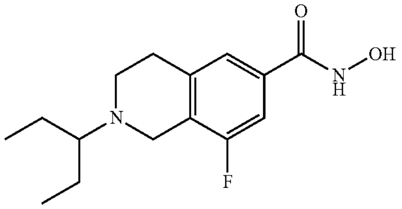
92. A compound selected from the group consisting of the following compounds, or a pharmaceutically acceptable salt thereof:
289
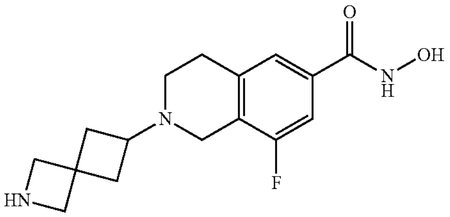
290
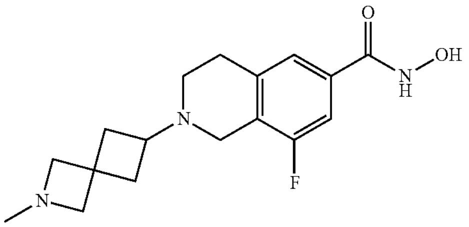
291
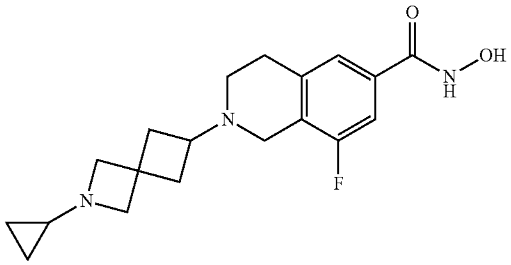
292
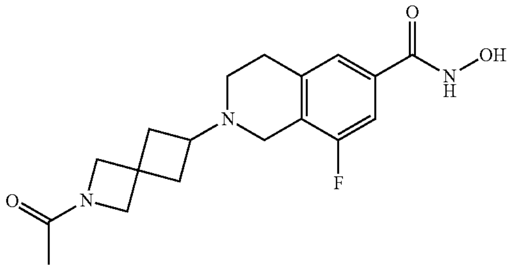
293
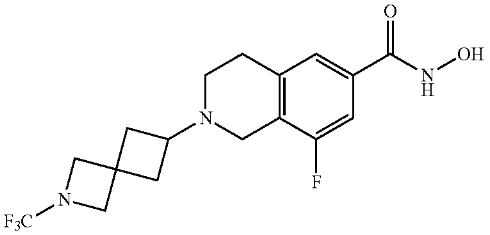
294
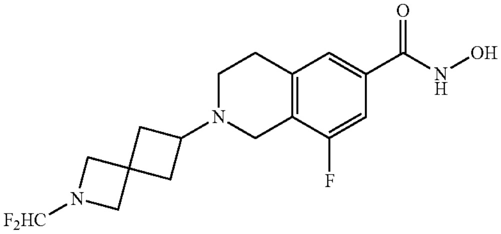
295
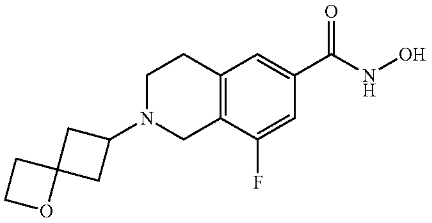
296
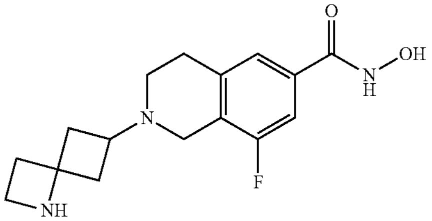
297
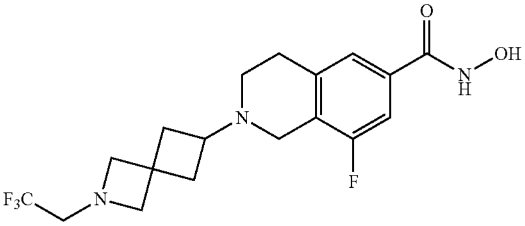
298
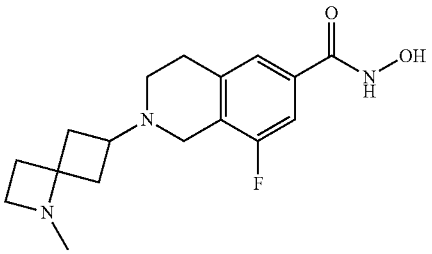

-continued
299
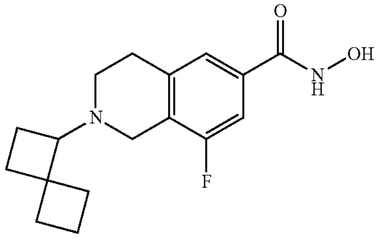
300
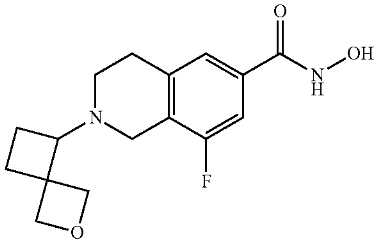
301
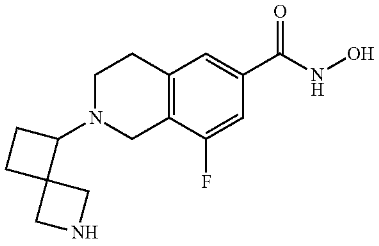
302
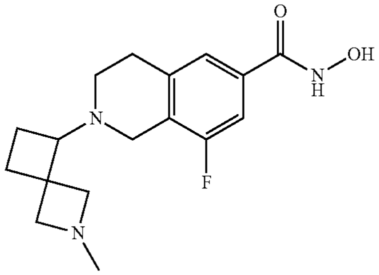
303
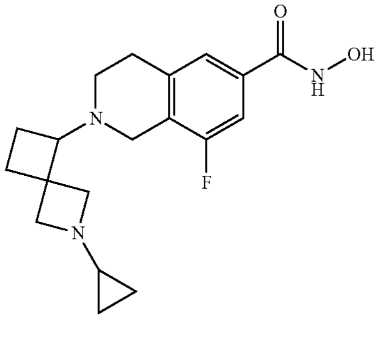
-continued
304
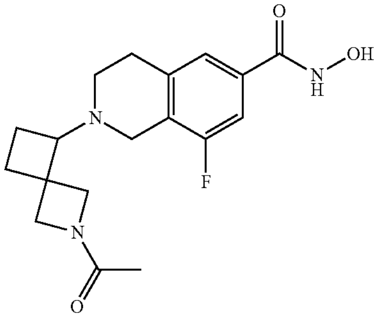
305
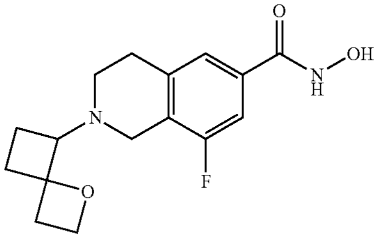
306
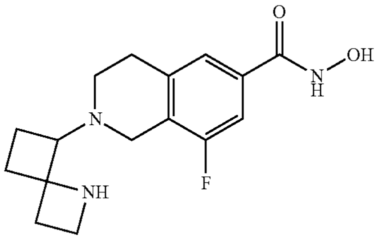
307
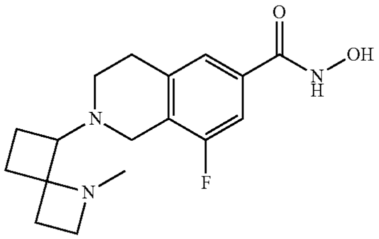
308
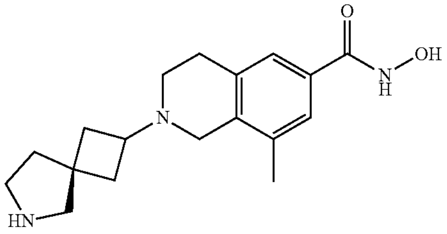

-continued
309
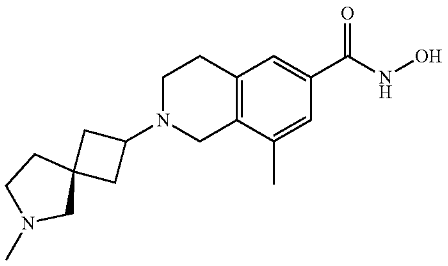
310
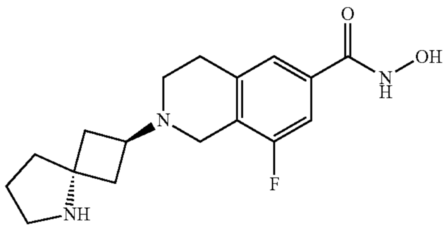
311
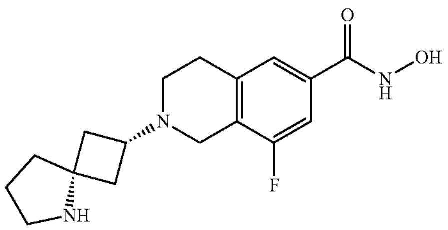
312
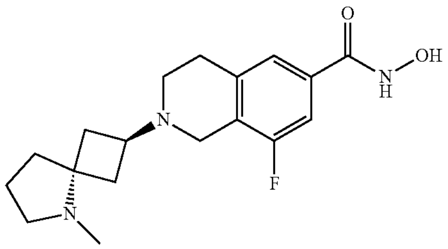
313
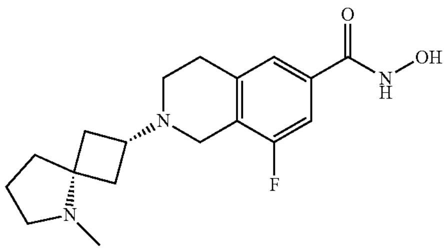
314
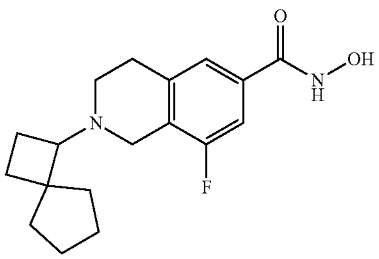
-continued
315
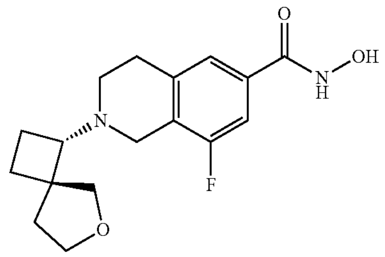
316
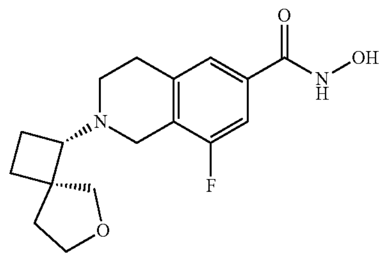
317
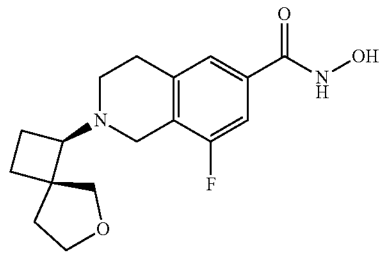
318
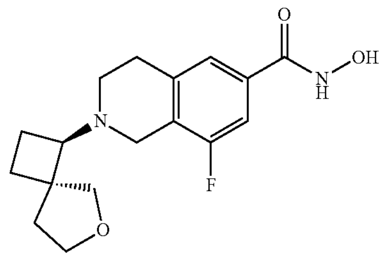
319
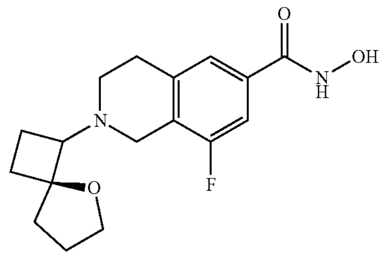
320
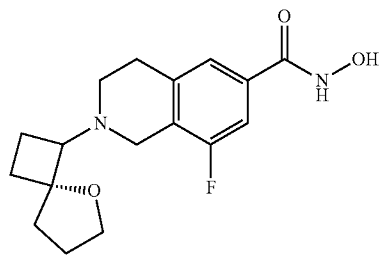

-continued
321
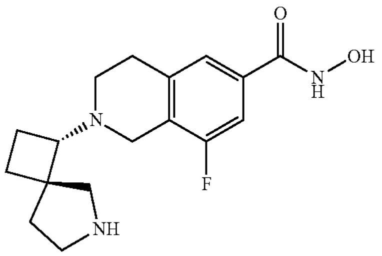
322
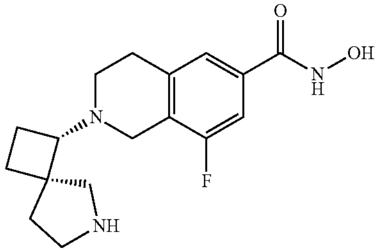
323
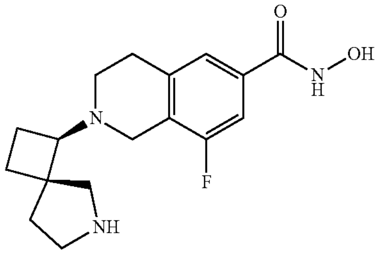
324
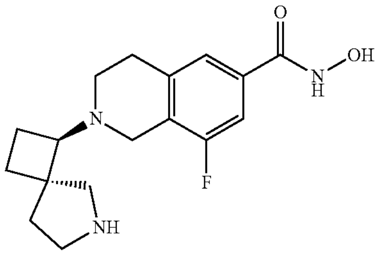
325
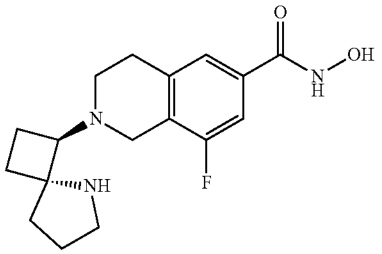
326
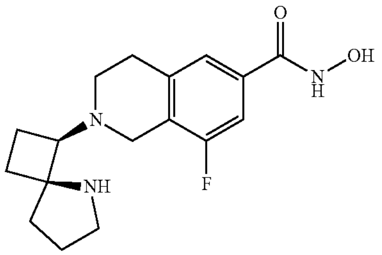
-continued
327
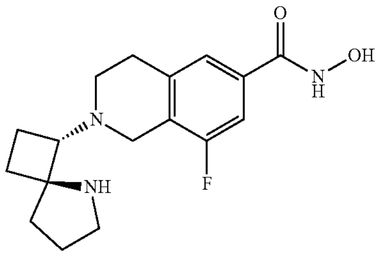
328
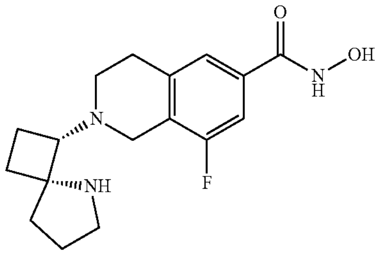
329
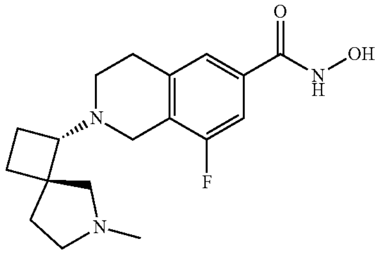
330
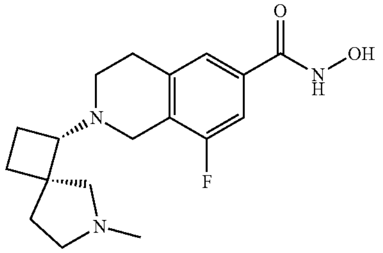
331
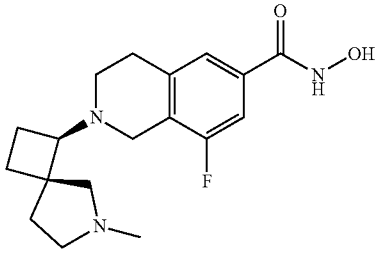
332
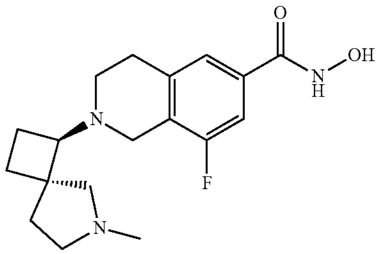

-continued
333
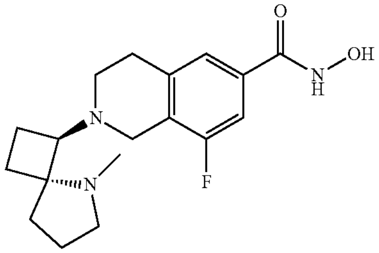
334
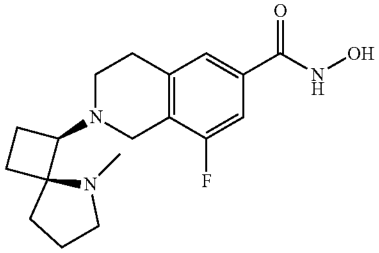
335
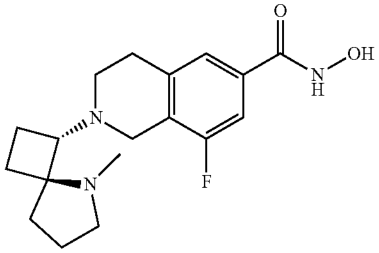
336
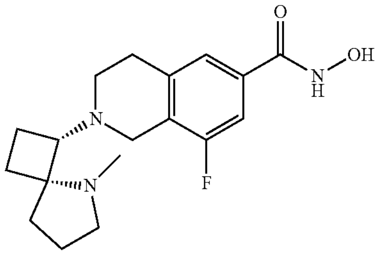
337
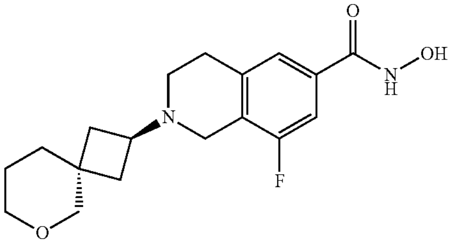
338
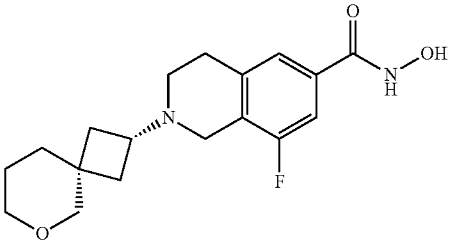
-continued
339
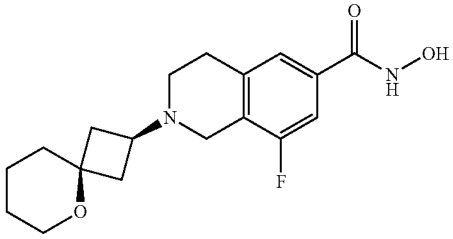
340
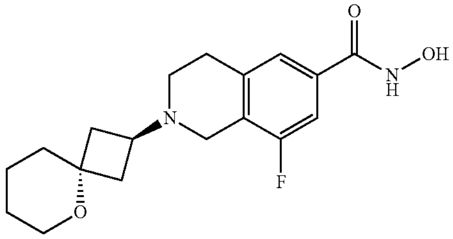
341
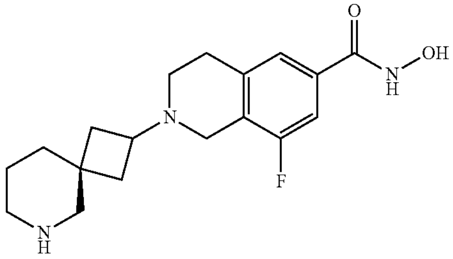
342
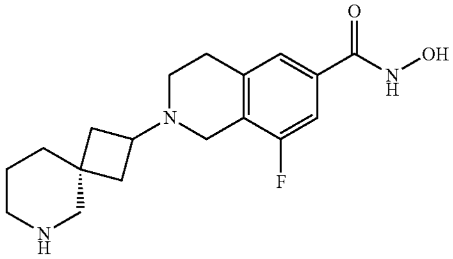
343
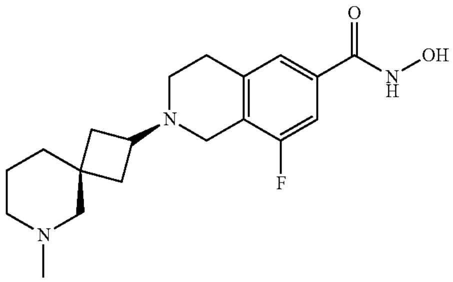
344
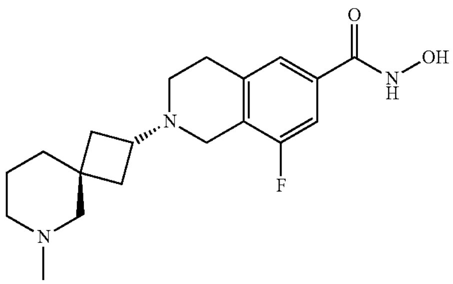

-continued
345
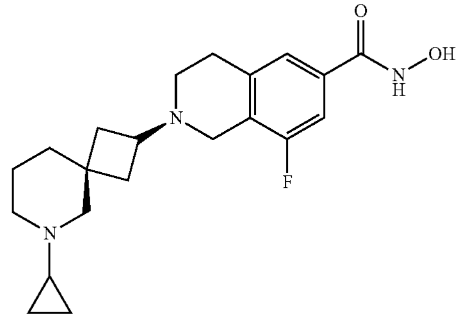
346
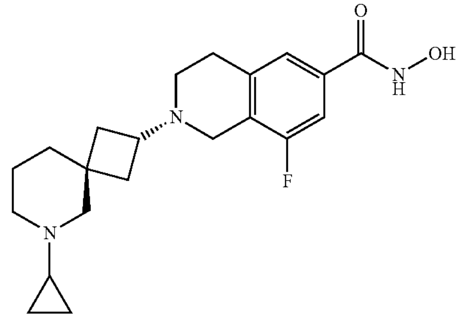
347
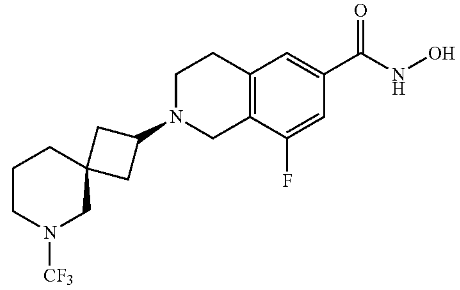
348
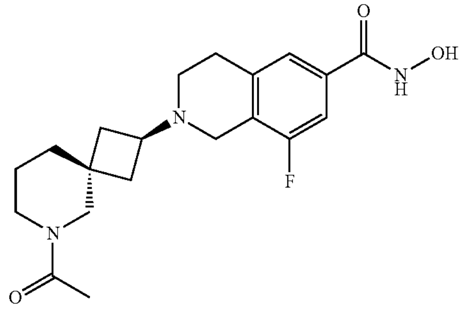
349
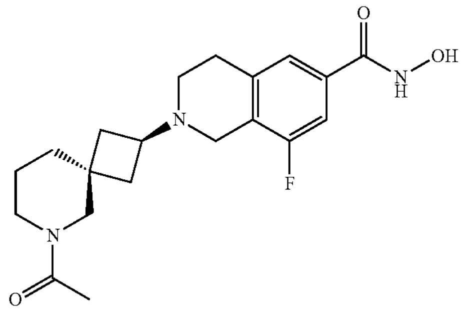
-continued
350
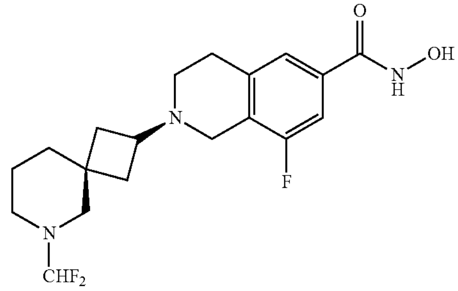
351
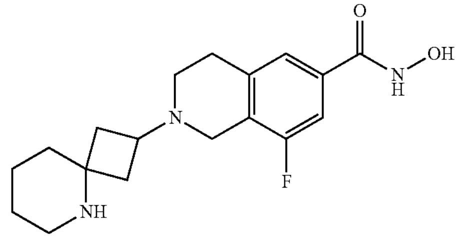
352
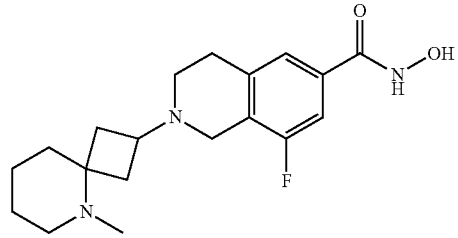
353
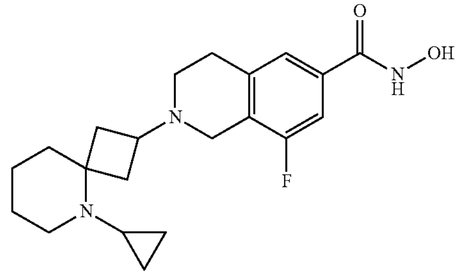
354
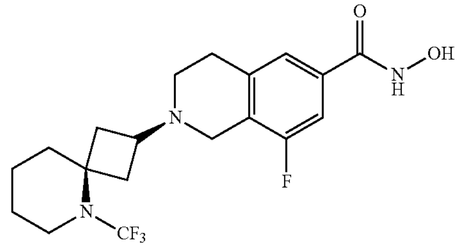
355
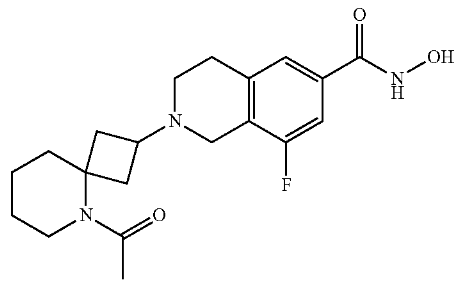

-continued
356
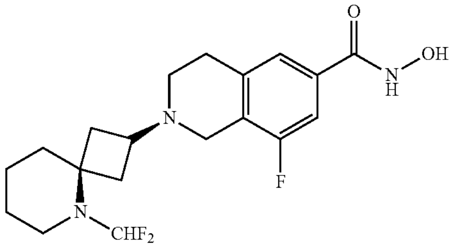
357
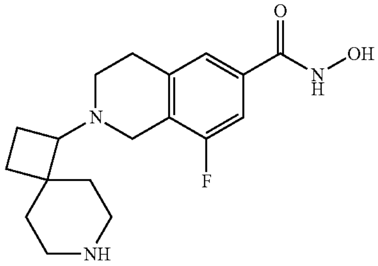
358
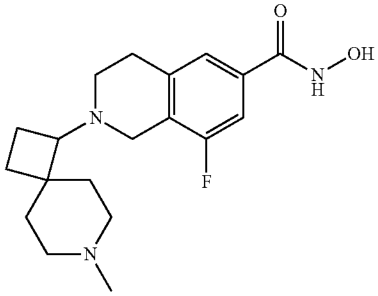
359
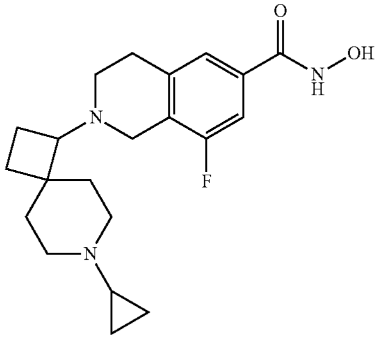
360
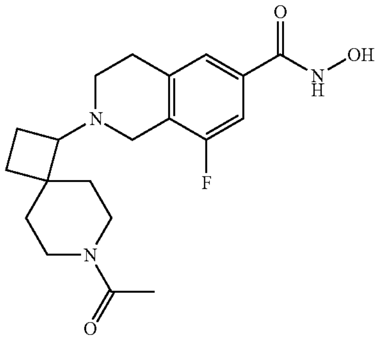
-continued
361
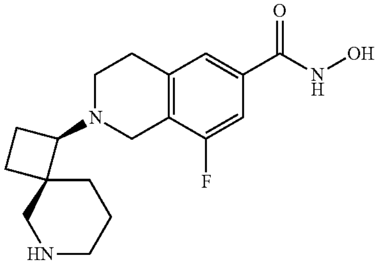
362
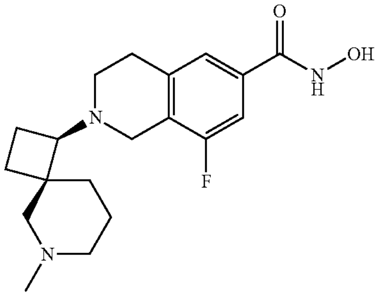
363
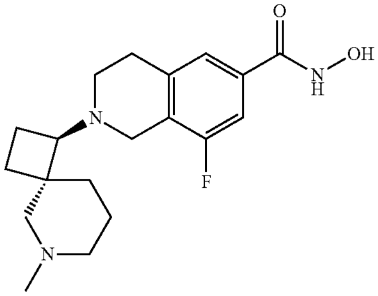
364
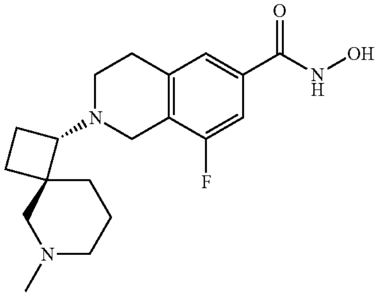
365
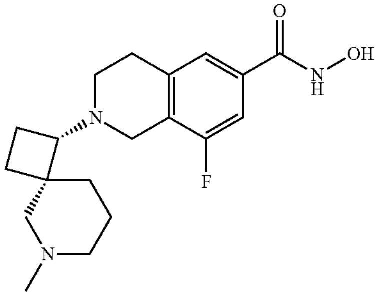

-continued
366
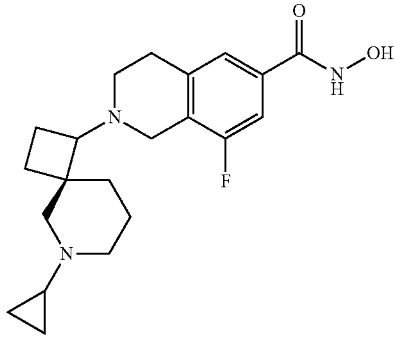
367
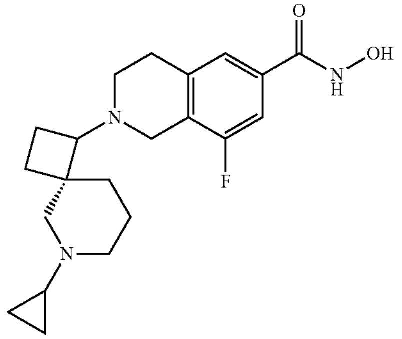
368
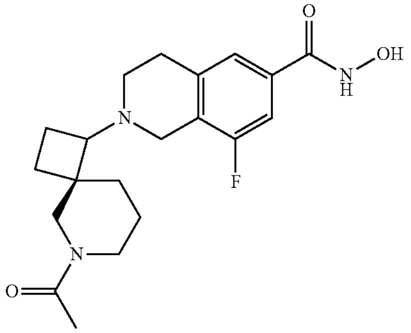
369
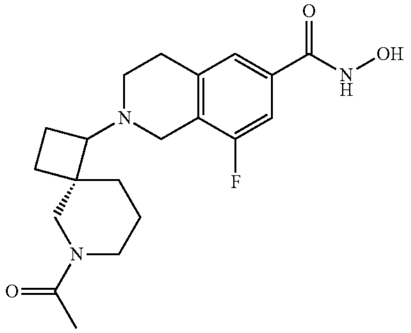
370
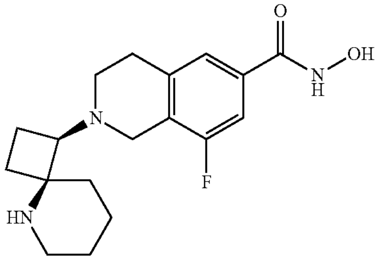
-continued
371
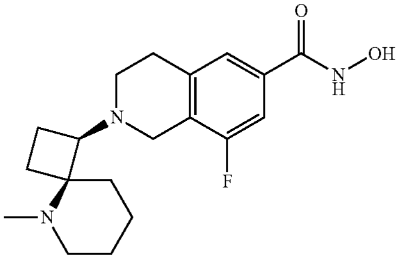
372
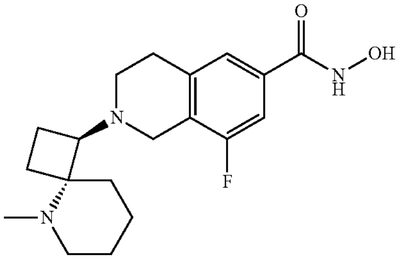
373
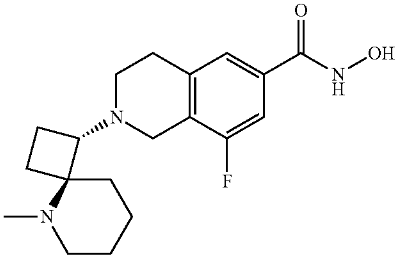
374
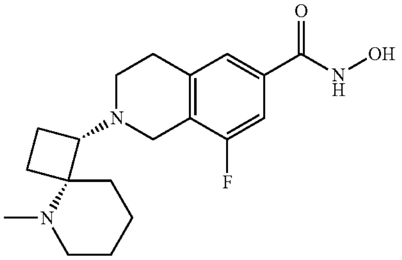
375
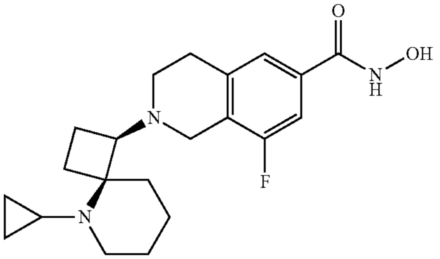
376
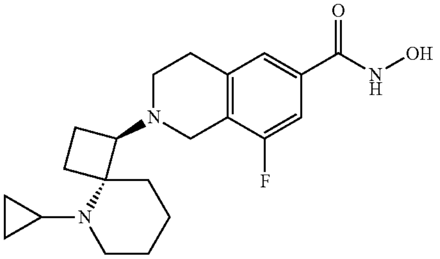

-continued
377
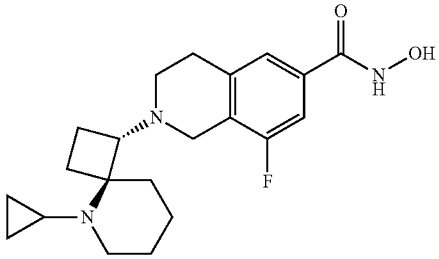
378
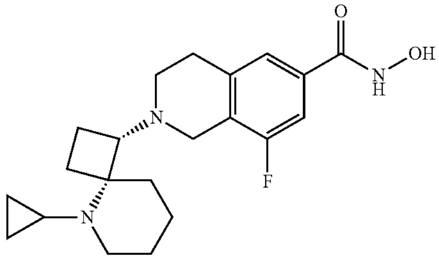
379
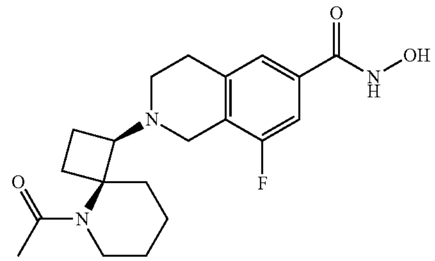
380
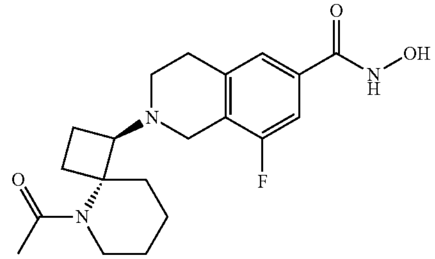
381
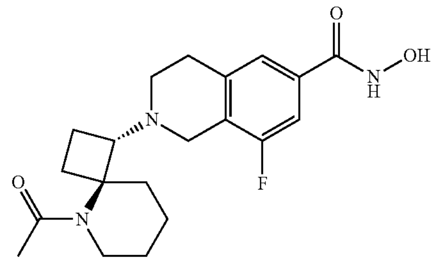
382
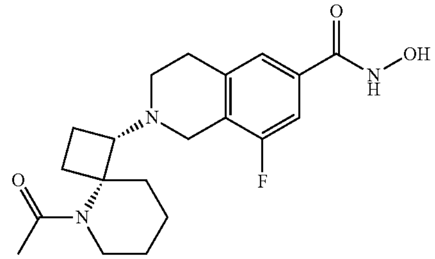
-continued
383
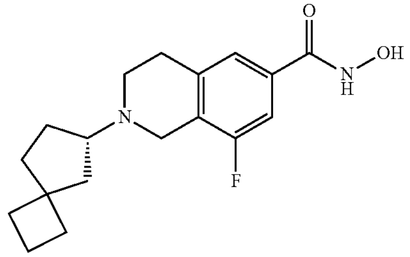
384
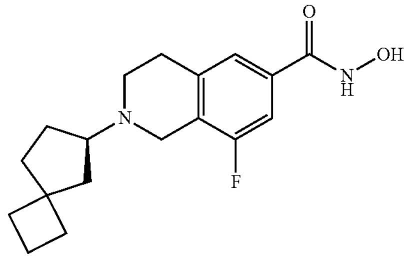
385
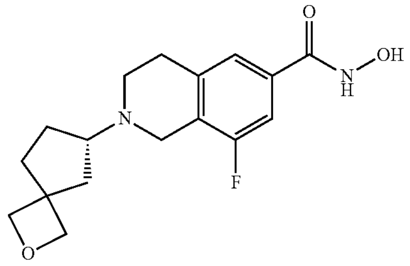
386
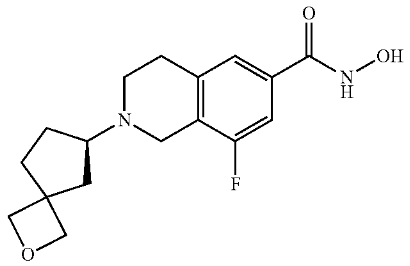
387
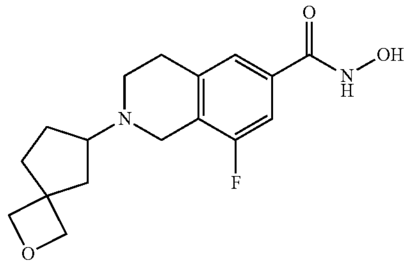
388
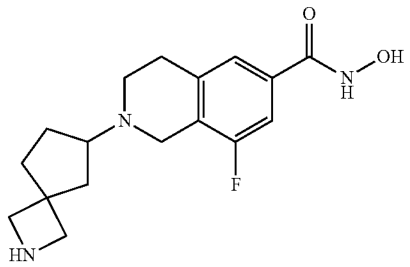

389
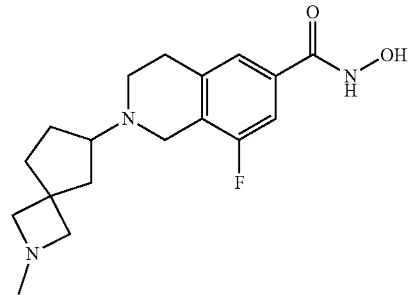
390
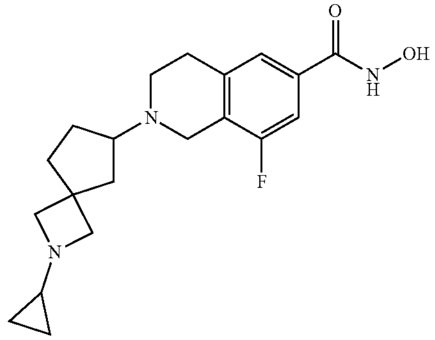
391
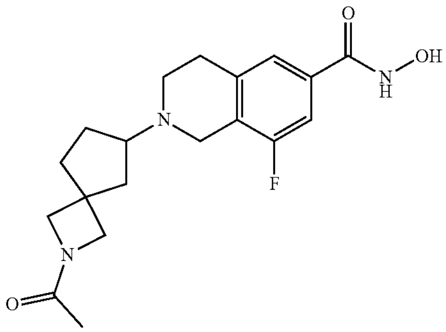
392
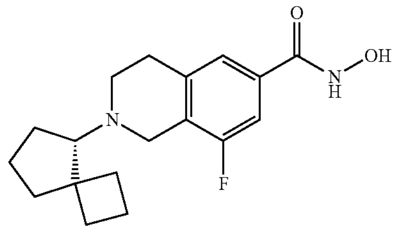
393
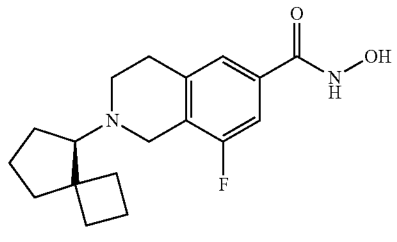
394
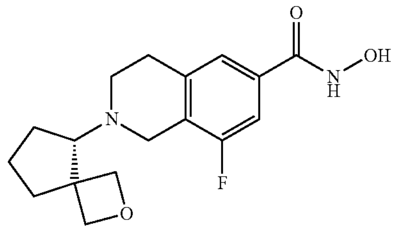
395
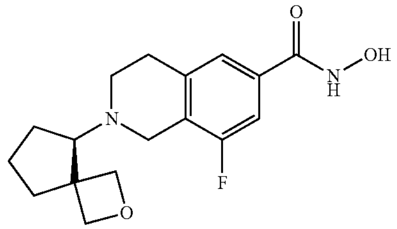
396
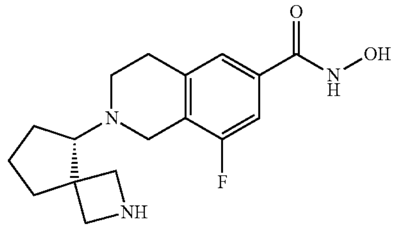
397
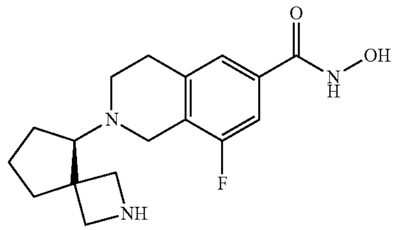
398
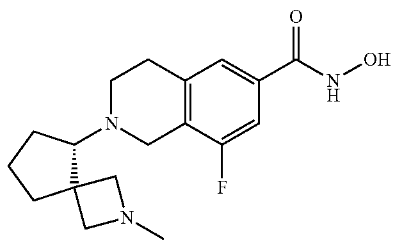
399
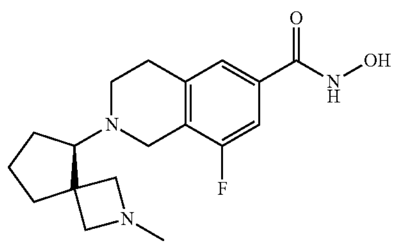

-continued
400
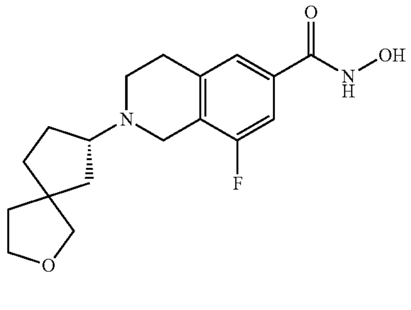
401
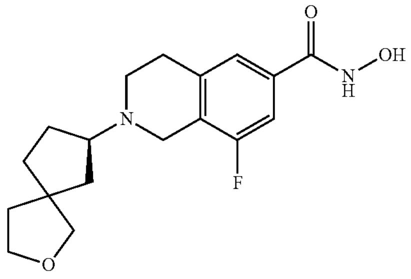
402
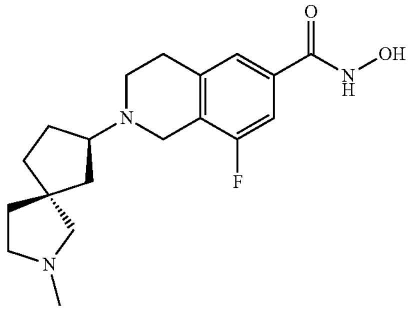
403
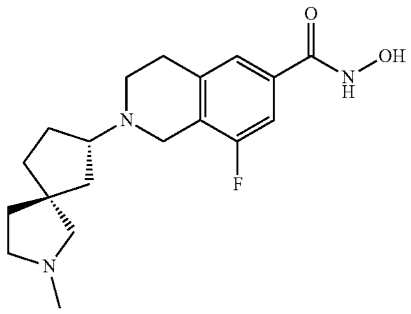
404
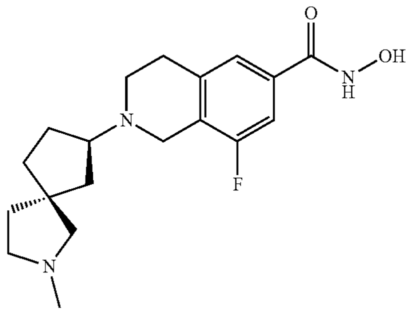
-continued
405
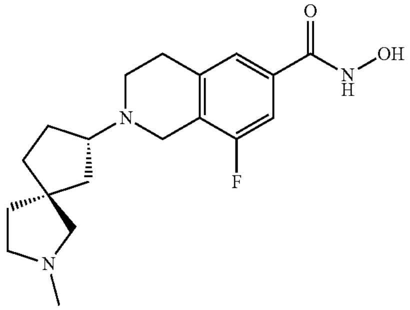
406
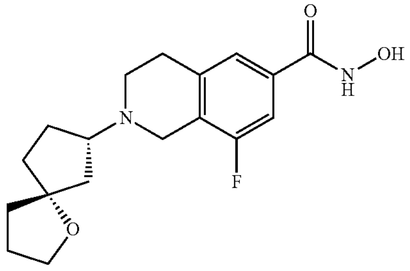
407
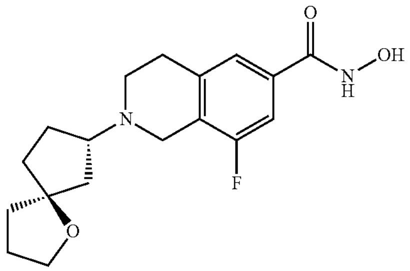
408
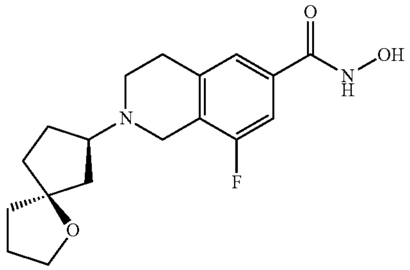
409
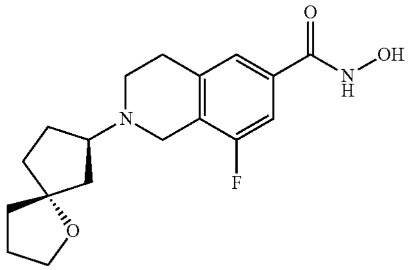

-continued
410
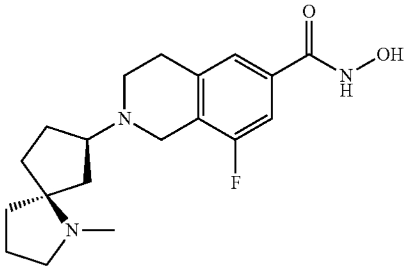
411
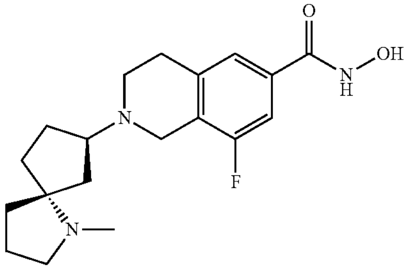
412
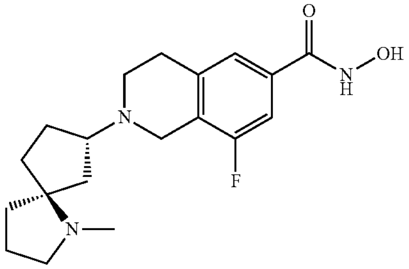
413
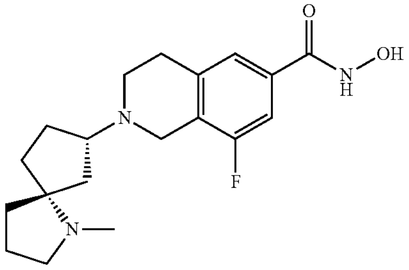
414
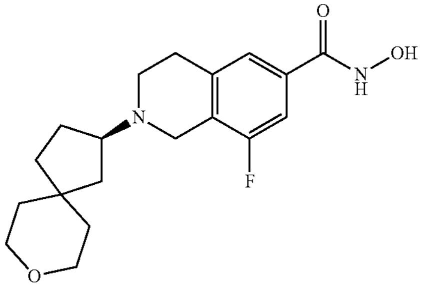
-continued
415
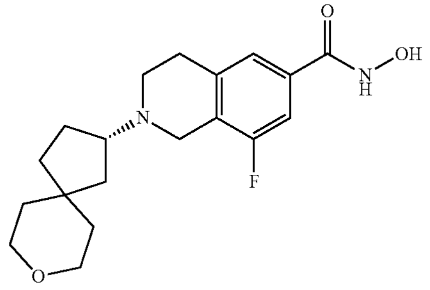
416
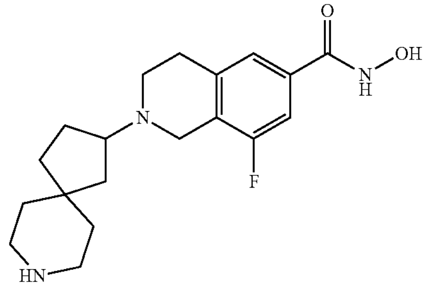
417
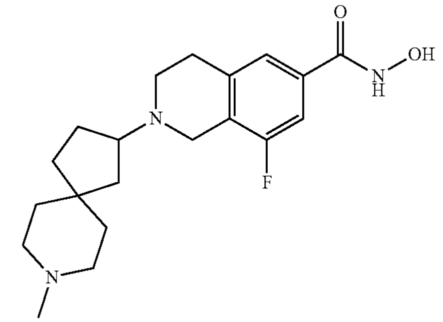
418
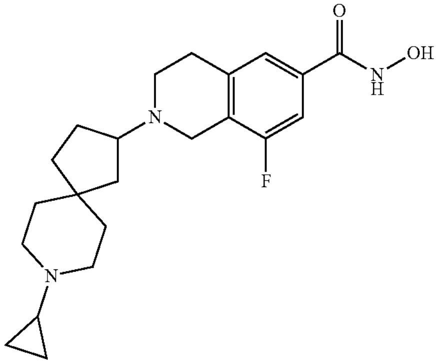
419
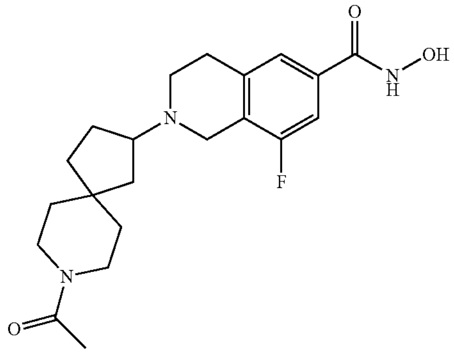

-continued
420
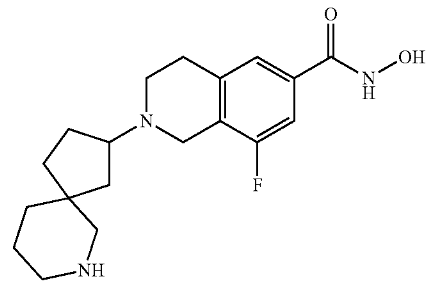
421
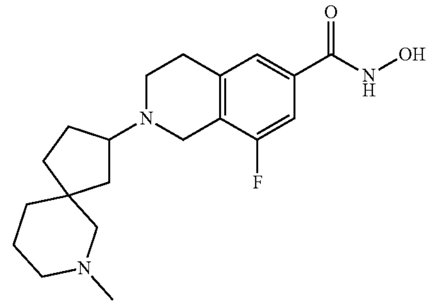
422
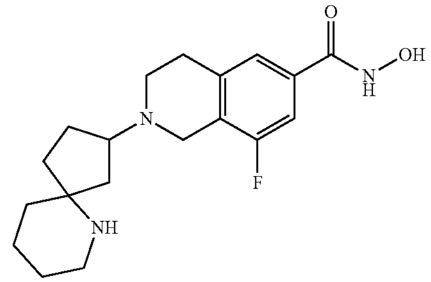
423
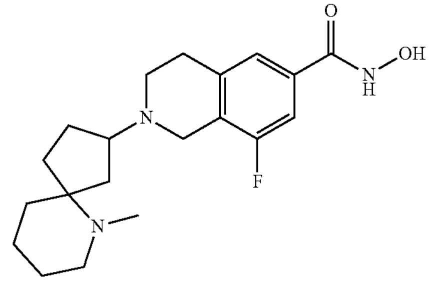
425
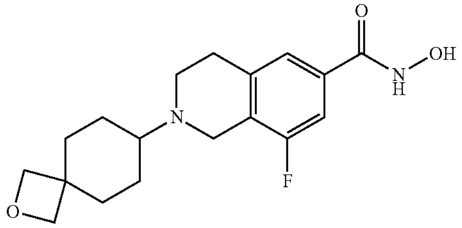
-continued
426
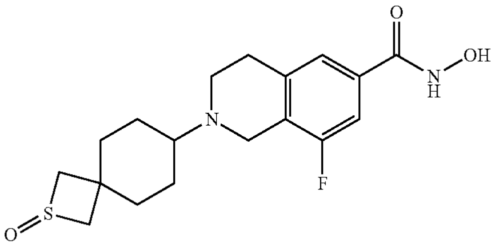
427
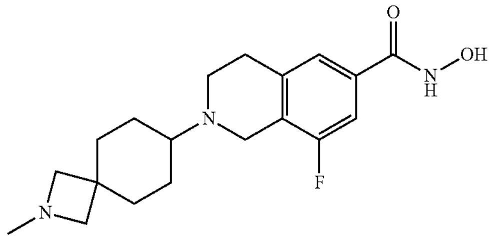
428
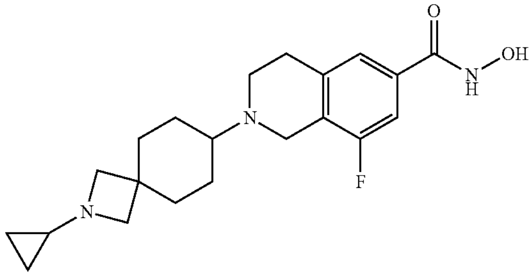
429
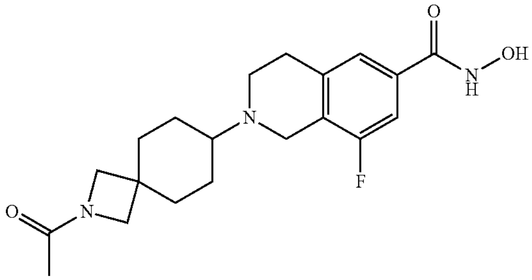
430
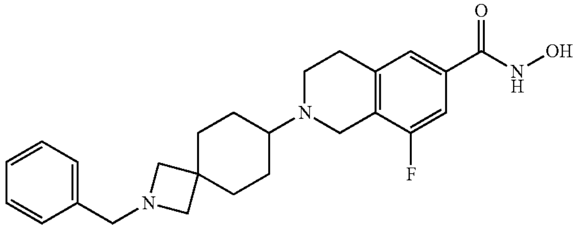

-continued
431
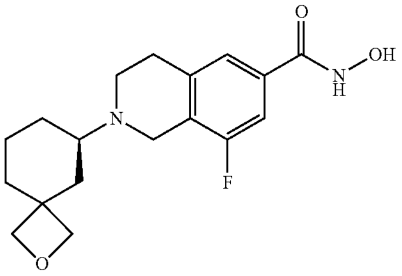
432
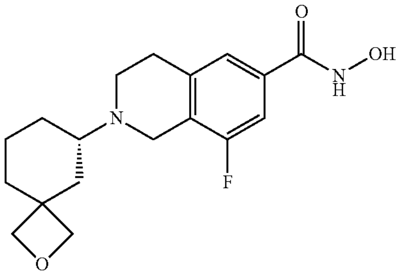
433
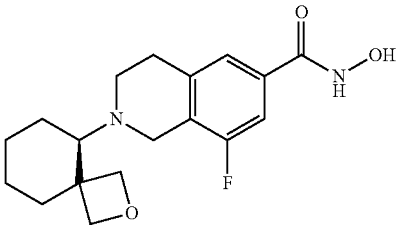
434
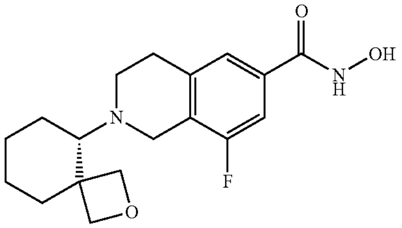
435
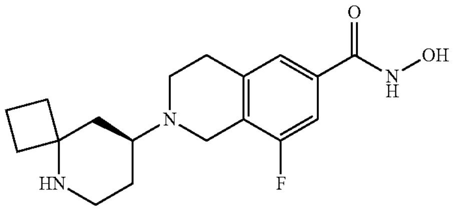
436
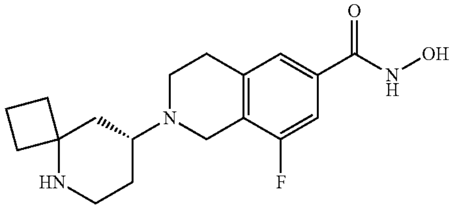
-continued
437
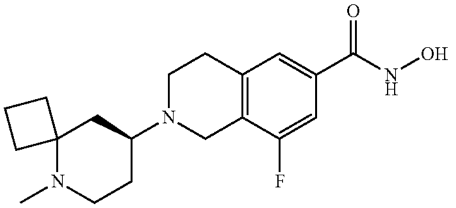
438
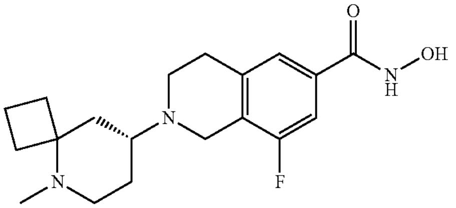
439
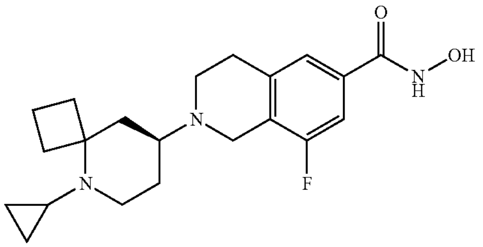
440
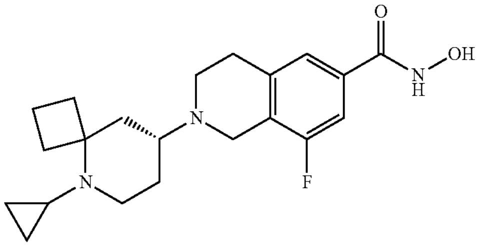
441
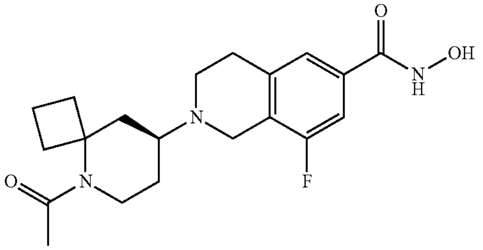
442
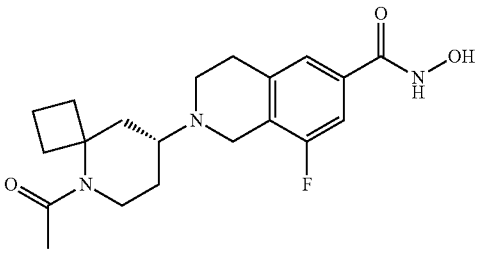

-continued
443
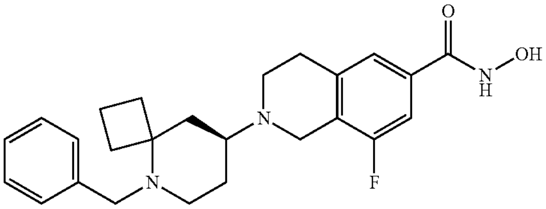
444
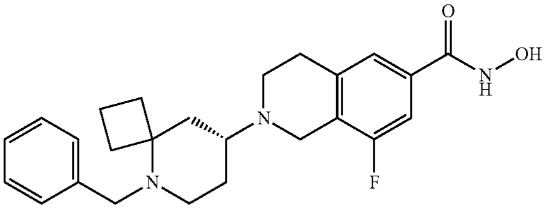
445
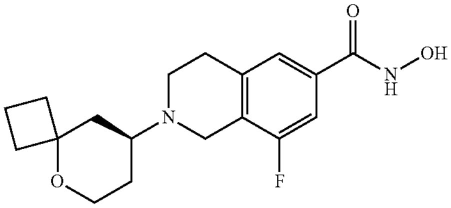
446
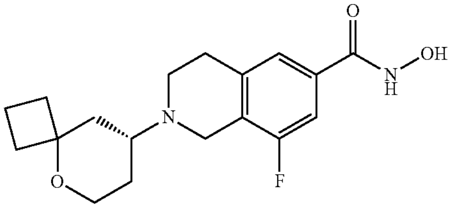
447
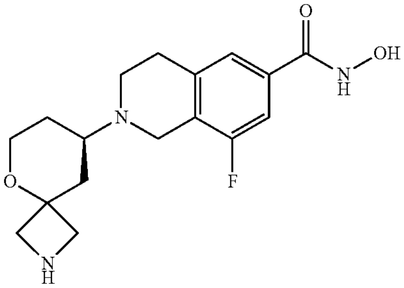
448
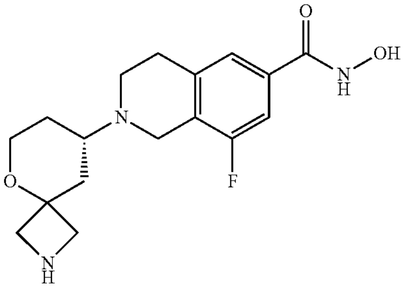
-continued
449
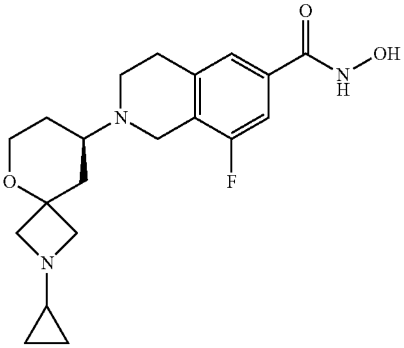
450
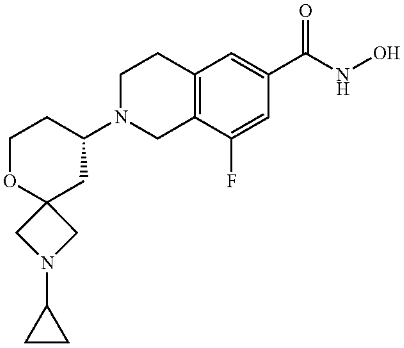
451
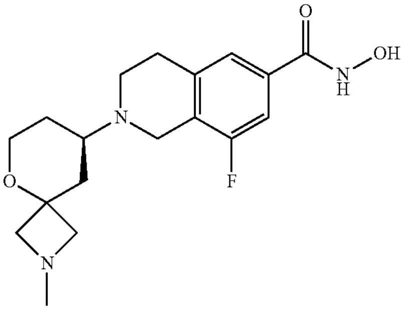
452
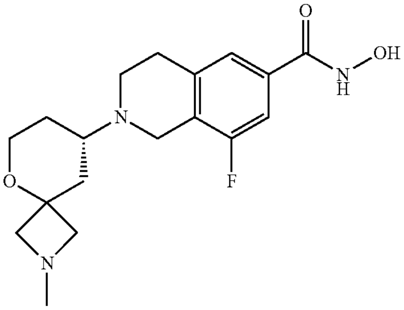

453
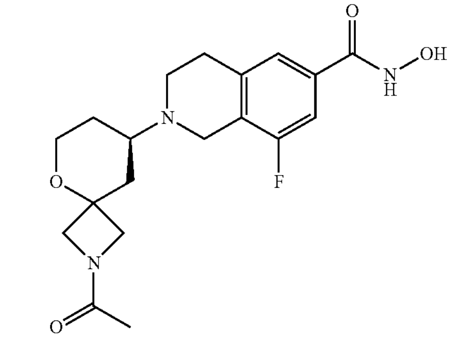
454
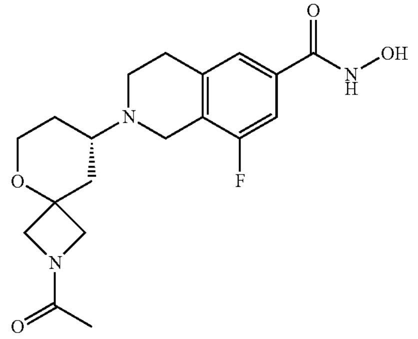
455
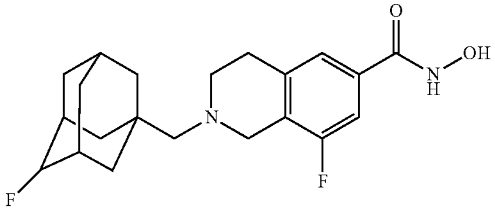
456
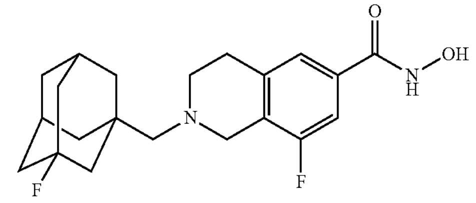
457
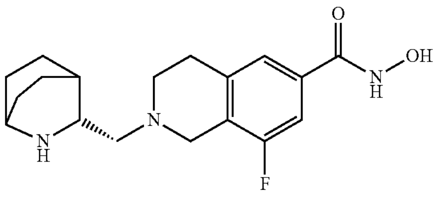
458
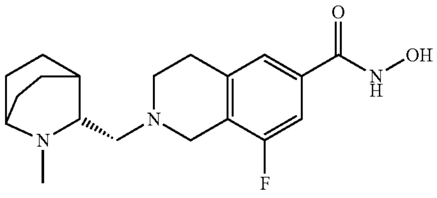
459
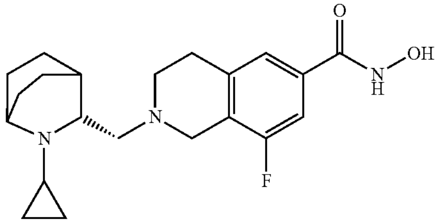
460
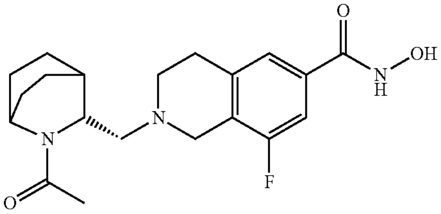
461
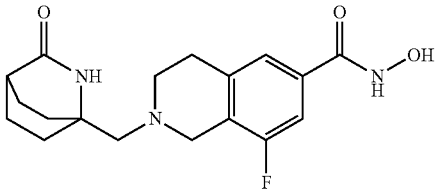
462
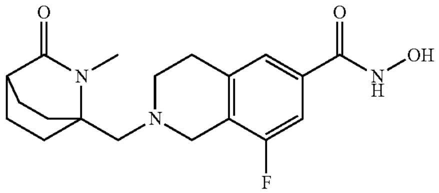
463
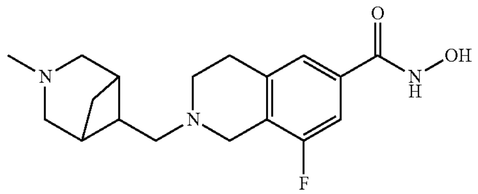
464
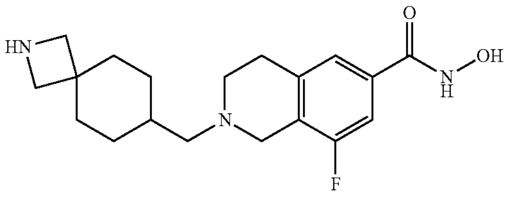
465
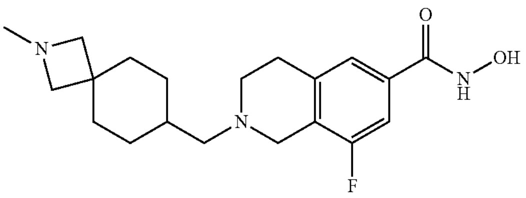

-continued
466
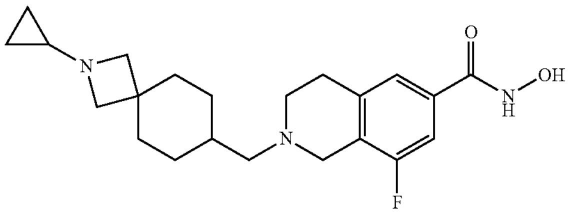
467
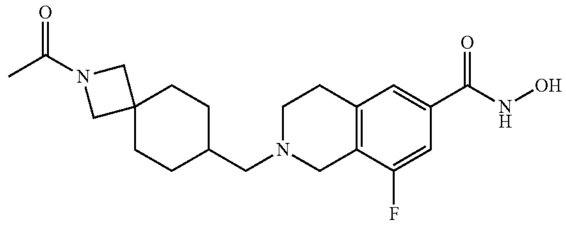
468
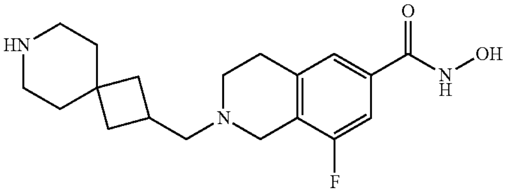
469
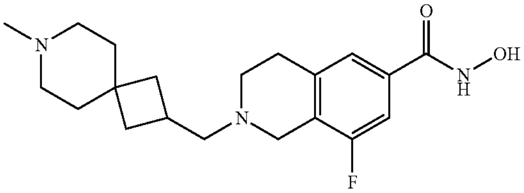
470
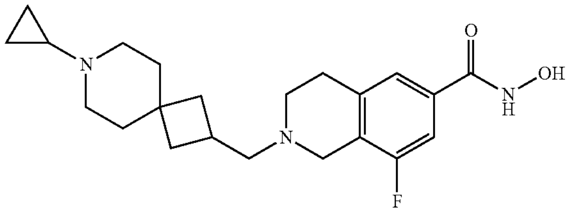
471
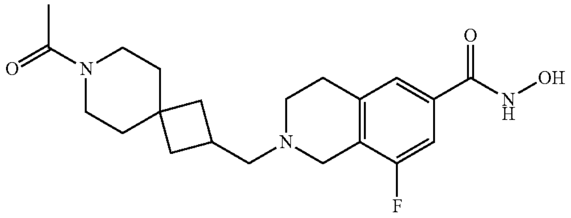
472
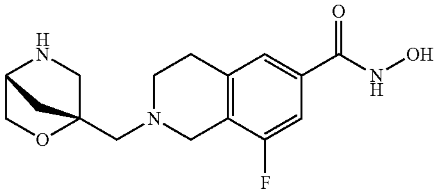
-continued
473
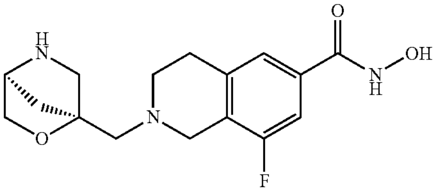
474
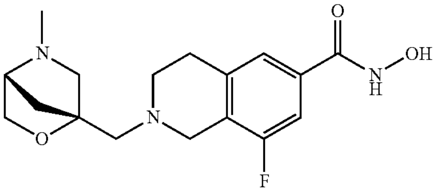
475
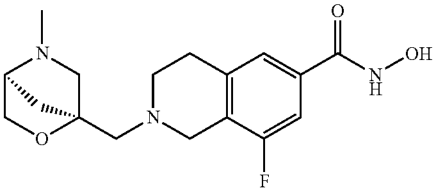
476
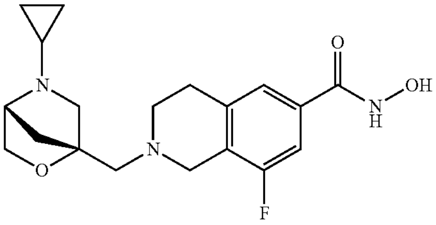
477
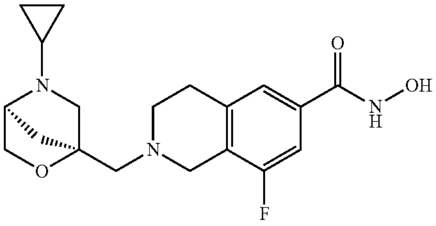
478
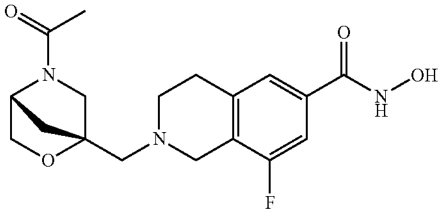
479
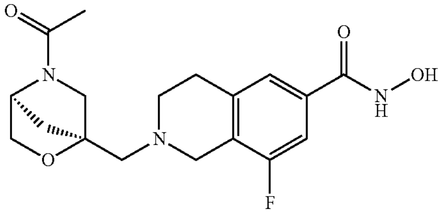

480
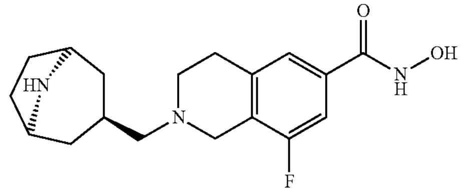
481
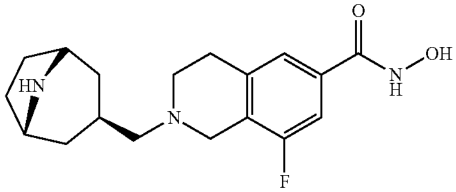
482
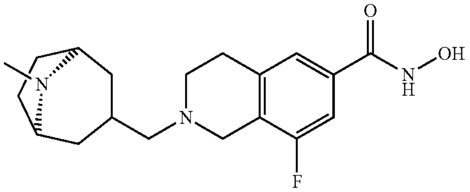
483
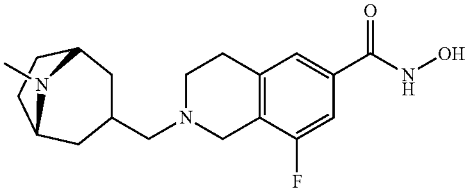
484
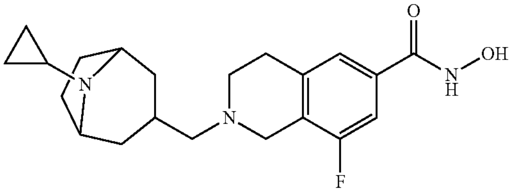
485
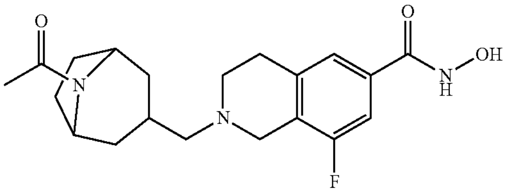
486
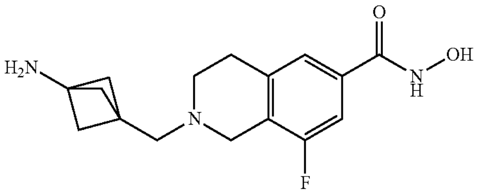
487
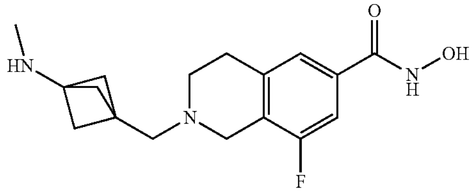
488
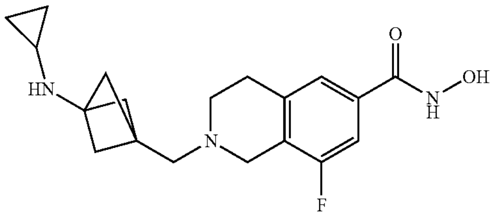
489
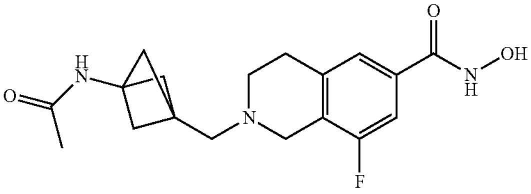
490
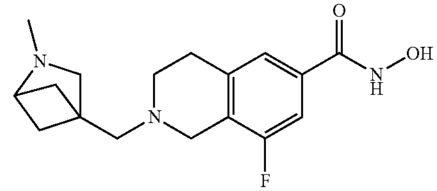
491
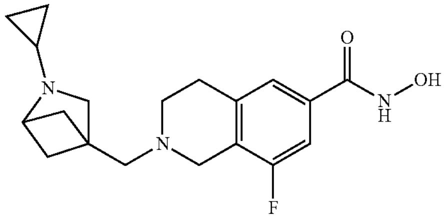
492
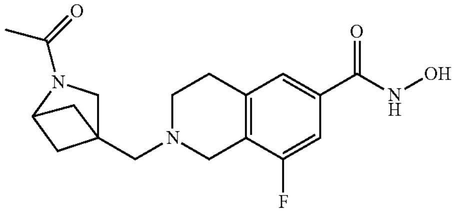
493
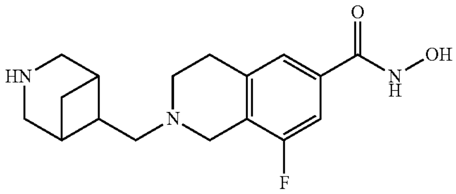

-continued
494
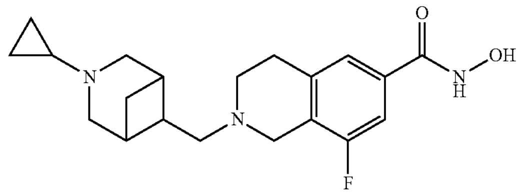
495
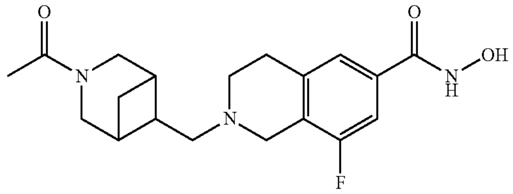
496
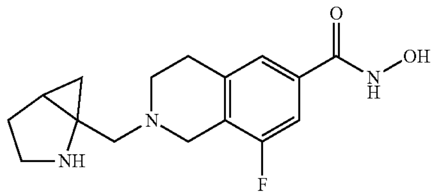
497
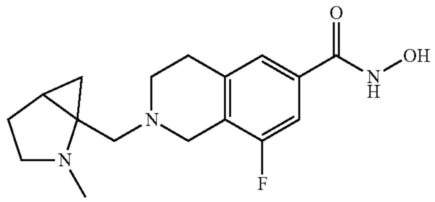
498
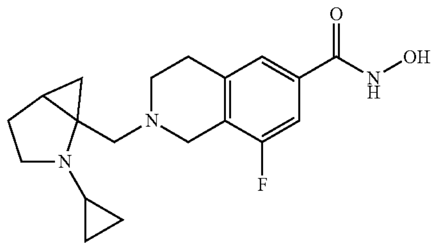
499
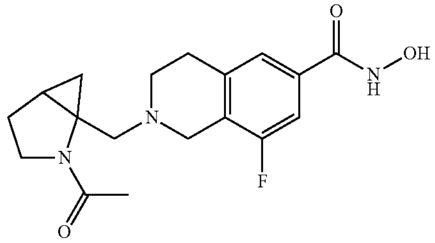
-continued
501
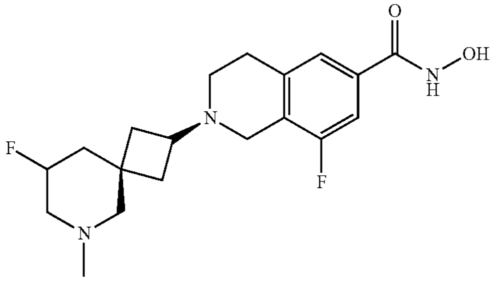
502
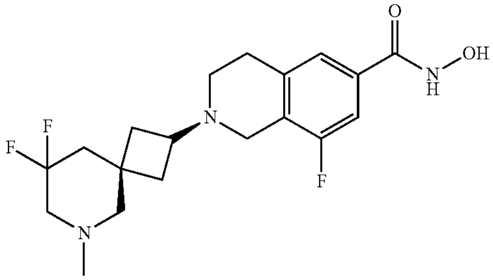
503
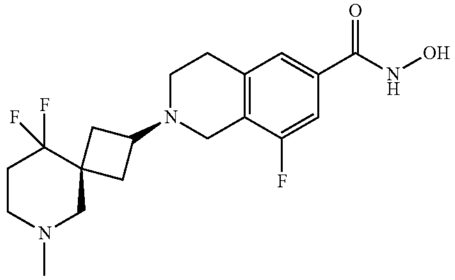
504
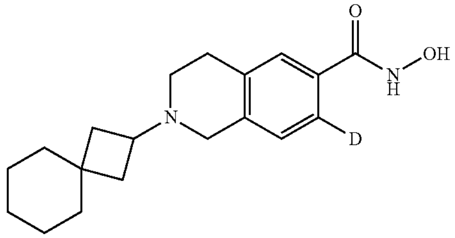
505
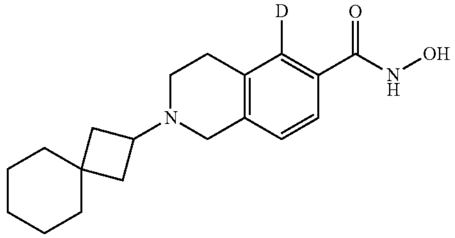
506
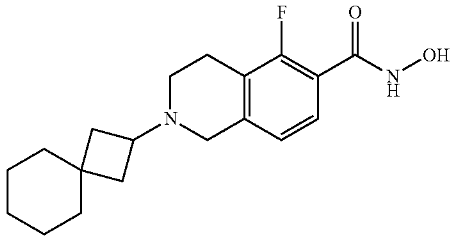

-continued
604
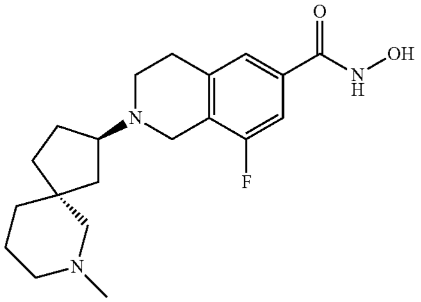
605
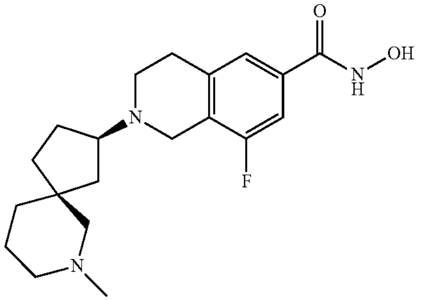
606
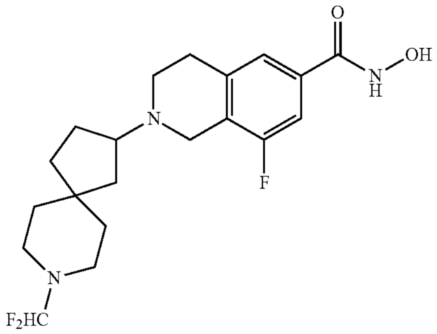
607
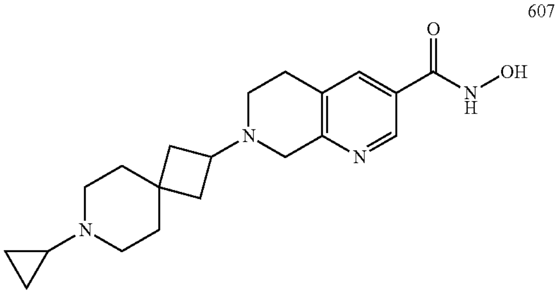
658
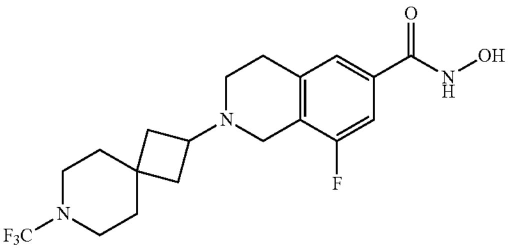
-continued
659
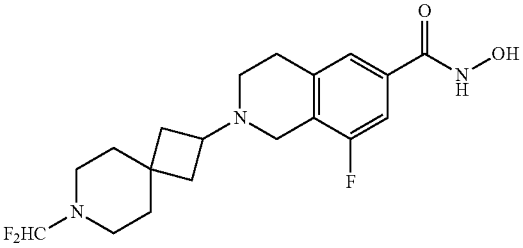
660
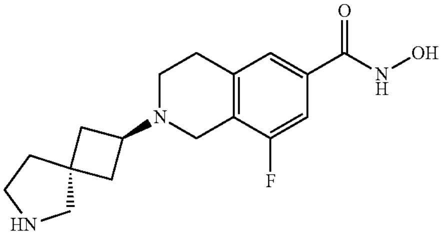
93. A compound selected from the following compounds, or a pharmaceutically acceptable salt thereof:
213
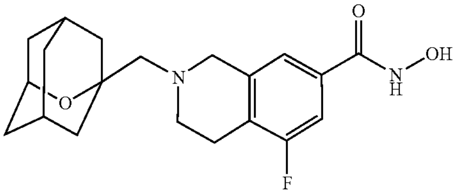
214
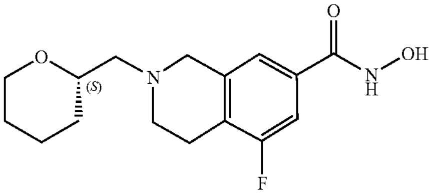
215
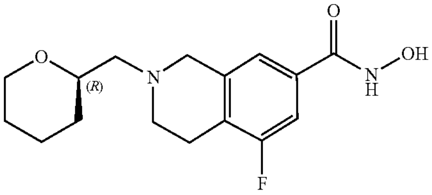
216
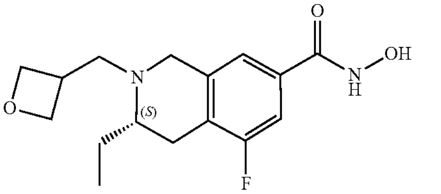

-continued
217
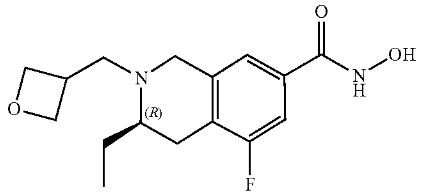
218
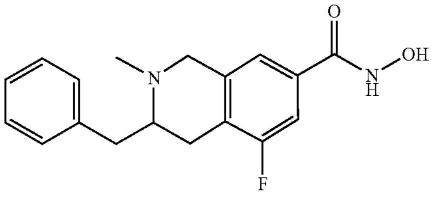
219
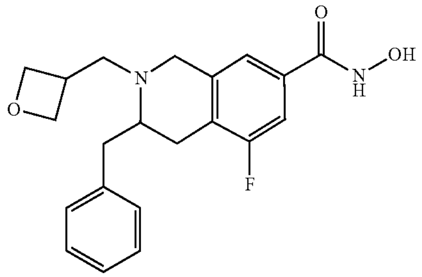
220
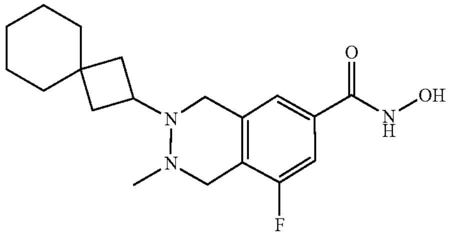
221
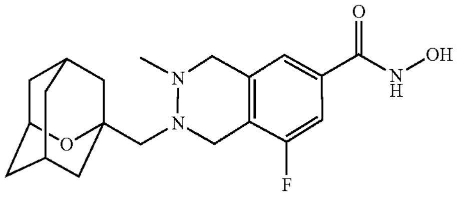
222
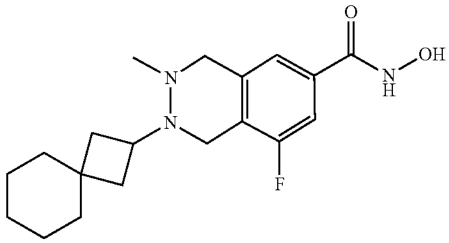
-continued
223
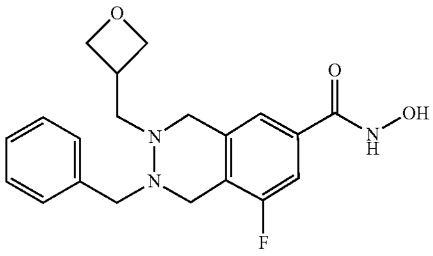
224
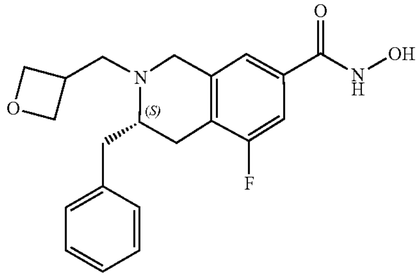
225
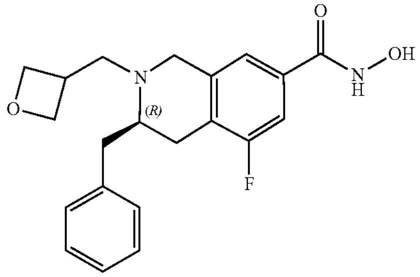
226
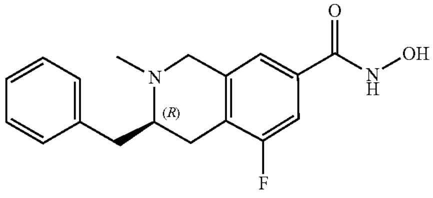
227
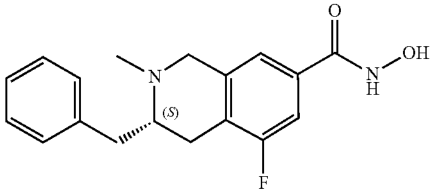
228
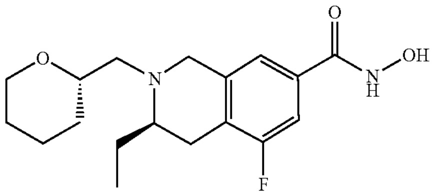

-continued
229
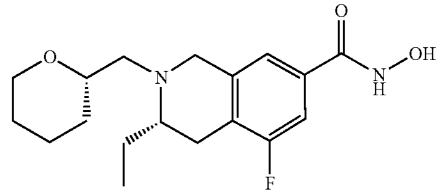
230
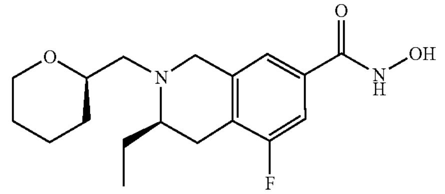
231
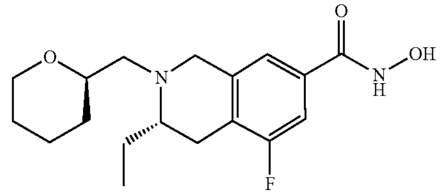
232
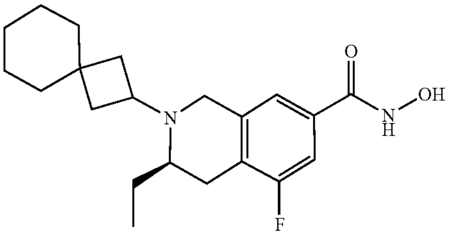
233
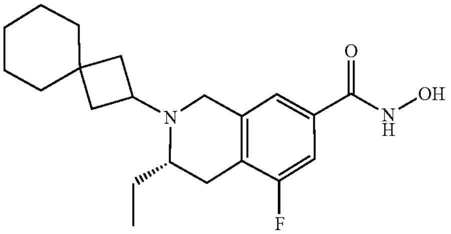
234
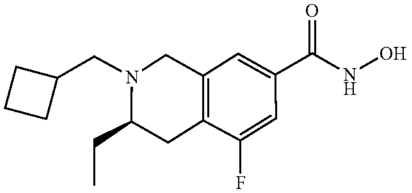
235
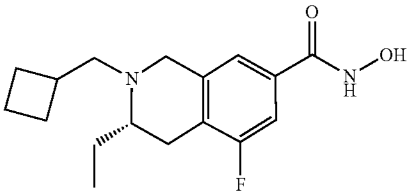
-continued
236
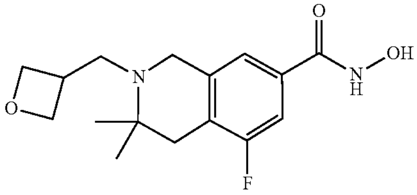
94. A compound selected from the following compounds or a pharmaceutically acceptable salt thereof:
510
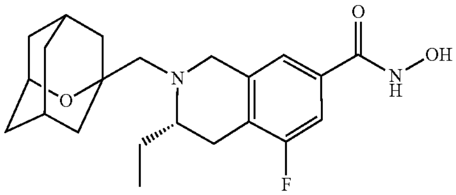
511
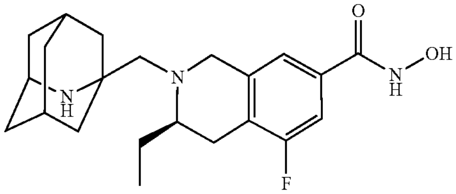
512
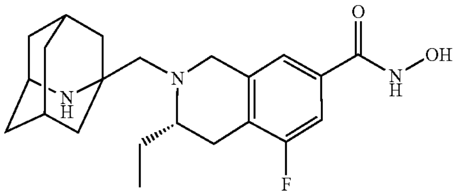
513
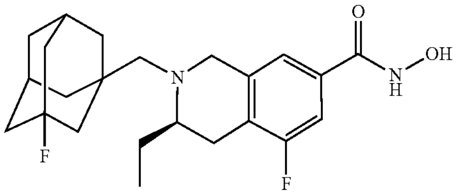
514
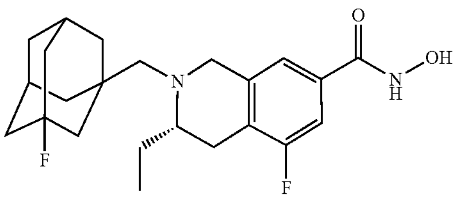

-continued
515
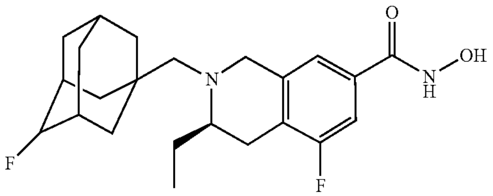
516
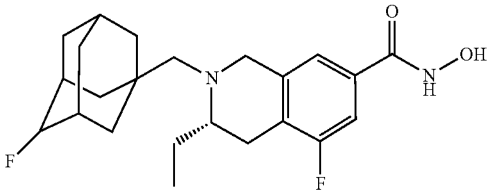
517
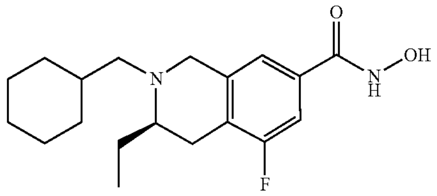
518
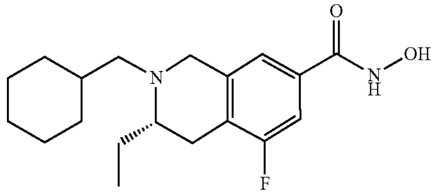
519
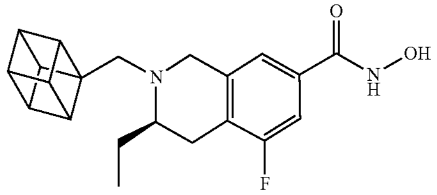
520
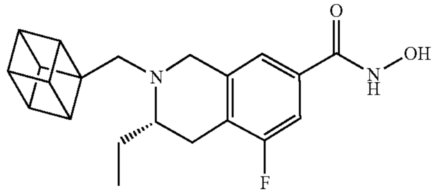
521
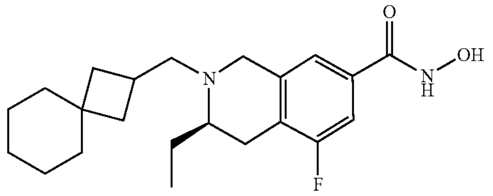
-continued
522
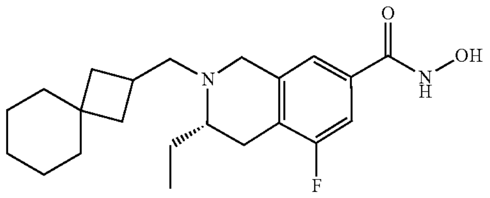
523
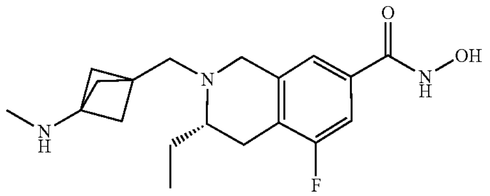
524
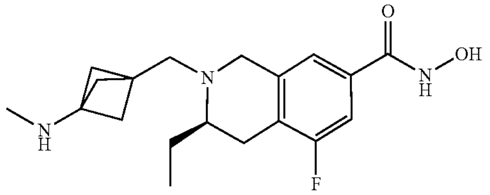
525
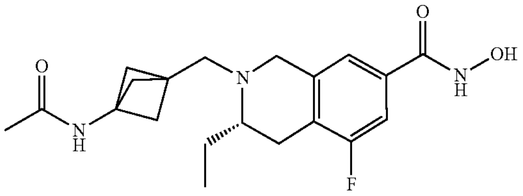
526
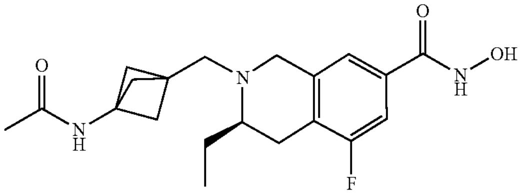
527
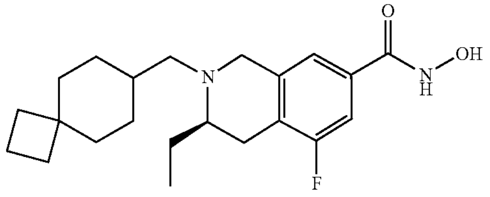
528
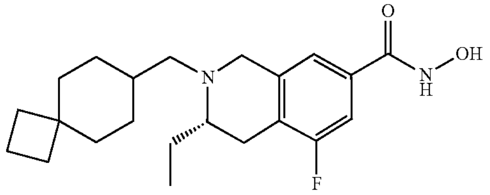

-continued
529
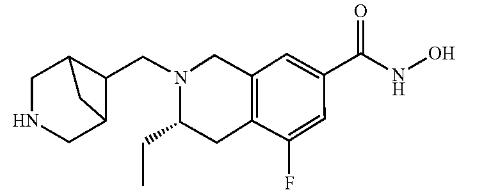
530
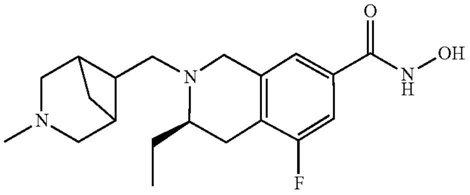
531
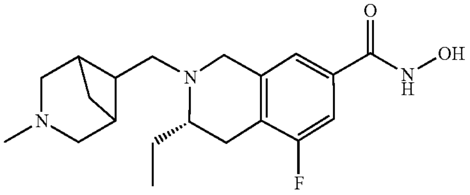
532
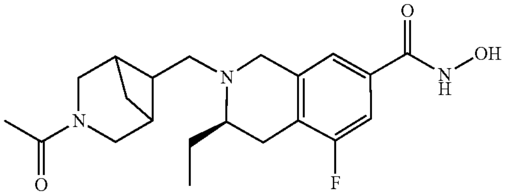
533
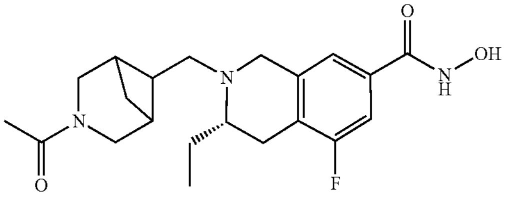
534
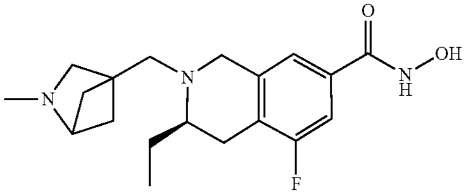
535
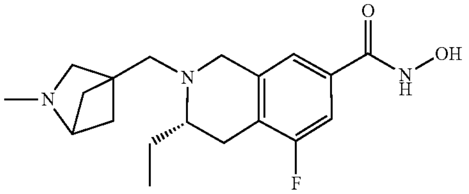
536
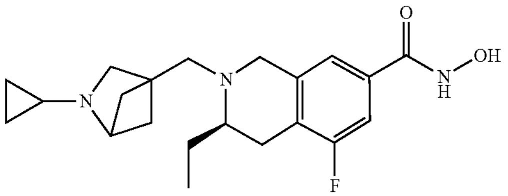
-continued
537
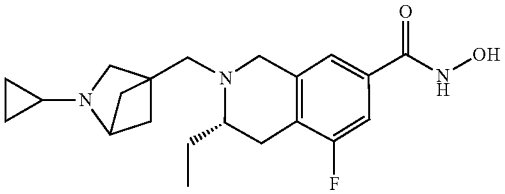
538
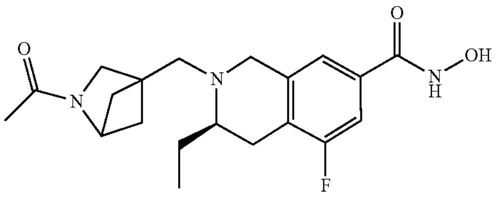
539
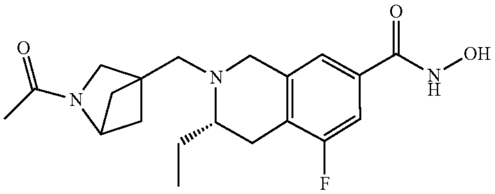
540
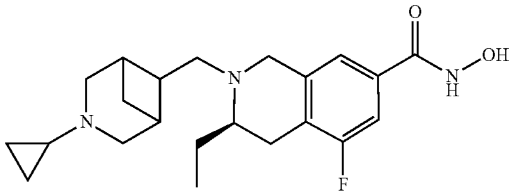
541
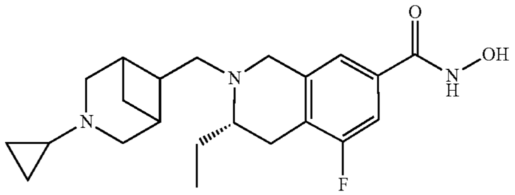
542
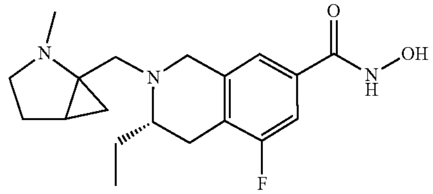
543
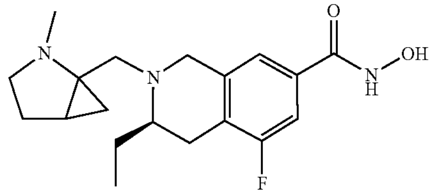

-continued
544
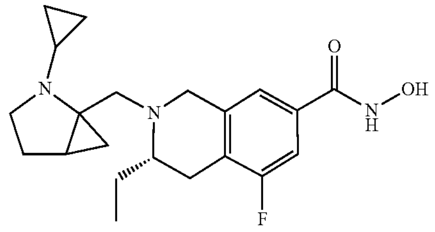
545
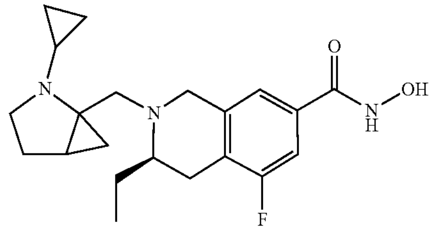
546
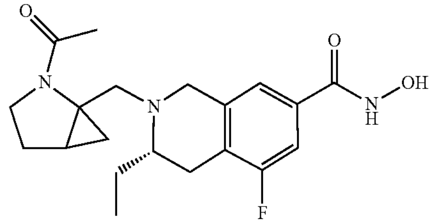
547
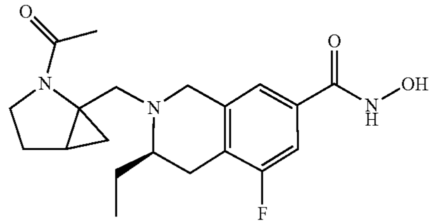
548
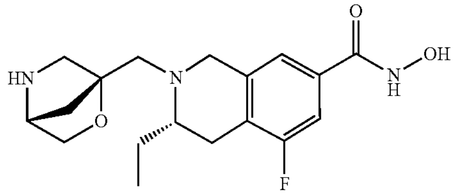
549
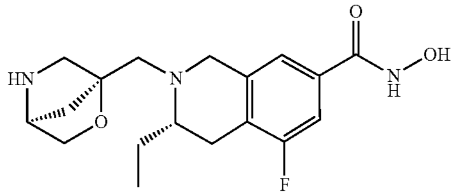
550
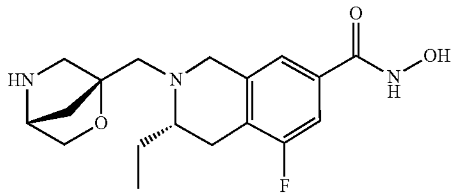
-continued
551
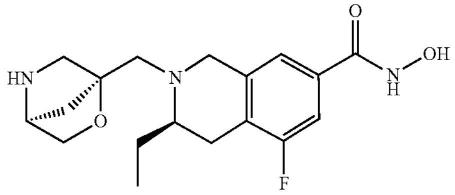
552
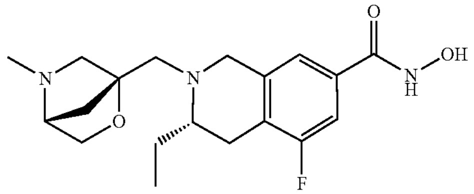
553
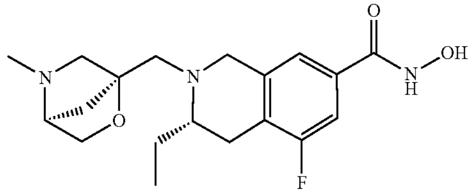
554
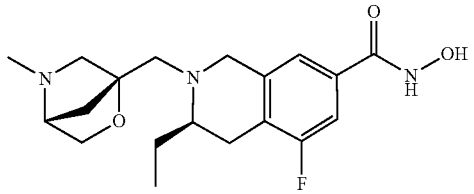
555
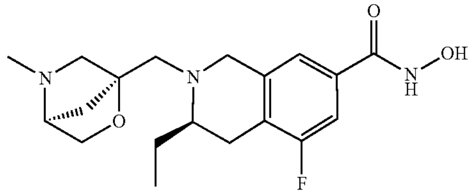
556
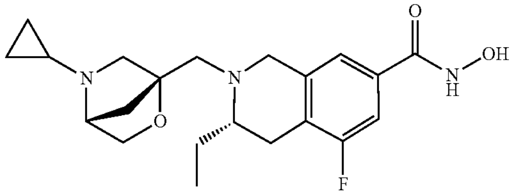
557
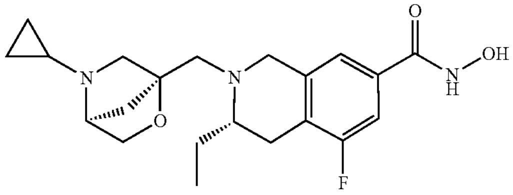

-continued
558
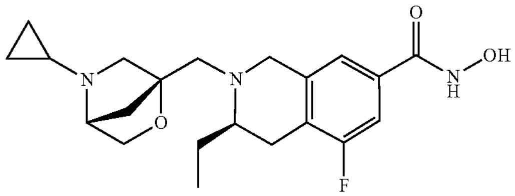
559
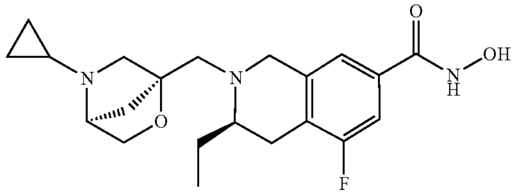
560
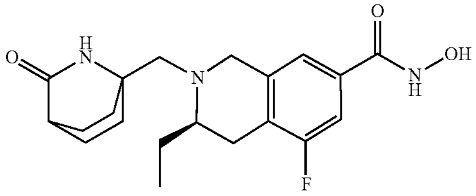
561
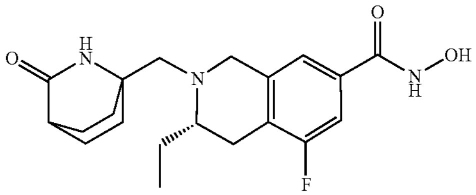
562
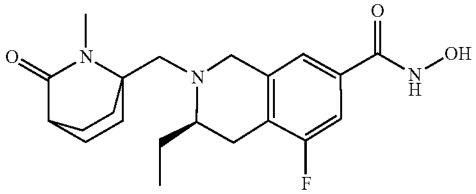
563
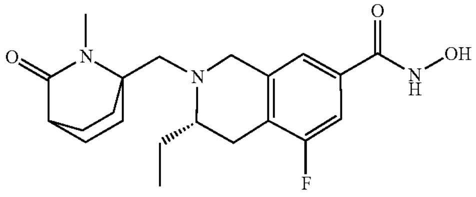
564
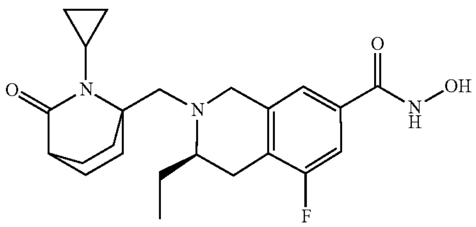
-continued
565
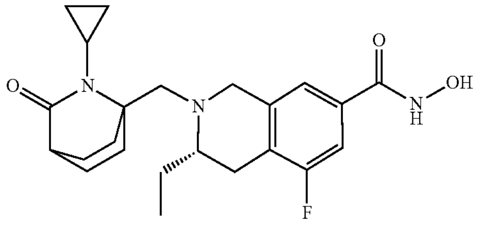
566
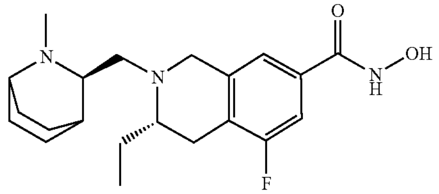
567
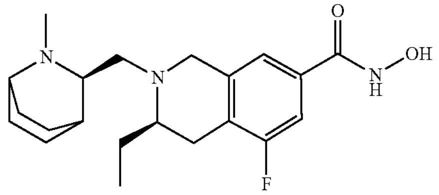
568
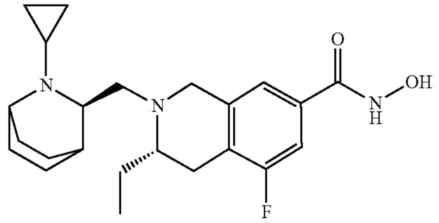
569
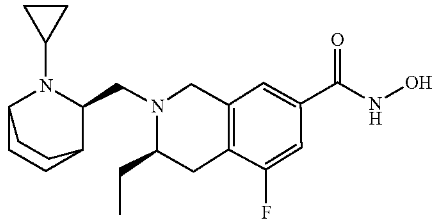
570
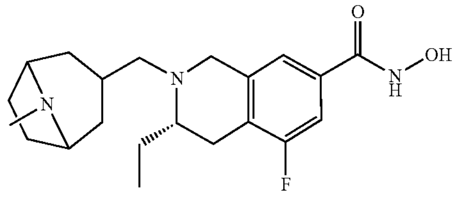
571
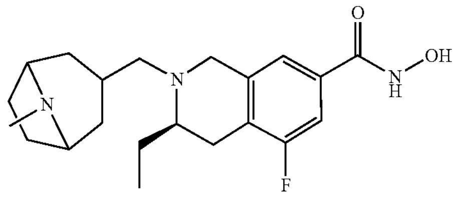

-continued
572
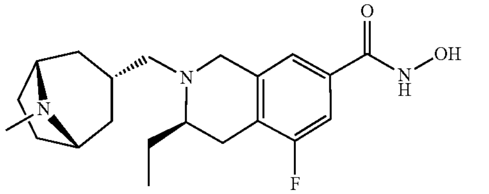
573
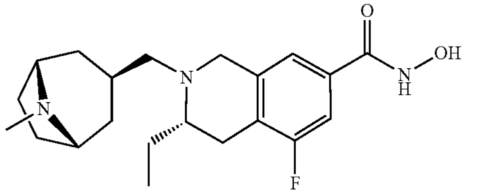
574
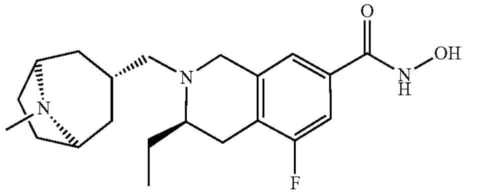
575
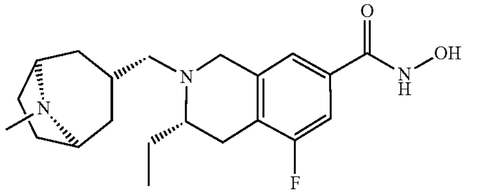
576
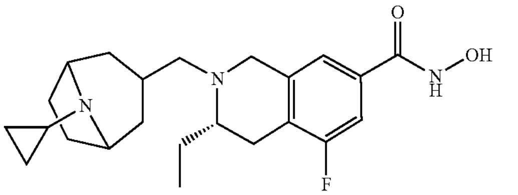
577
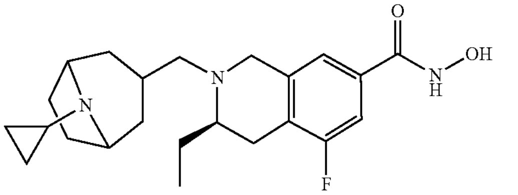
578
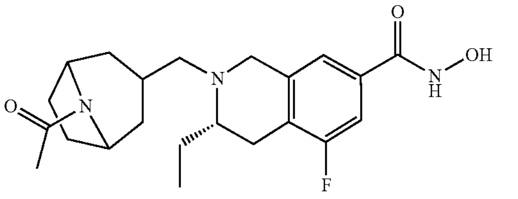
579
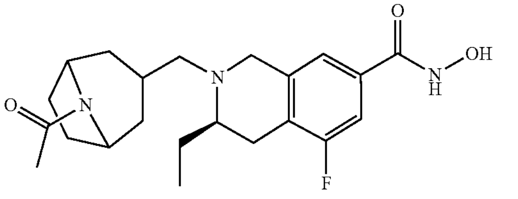
-continued
580
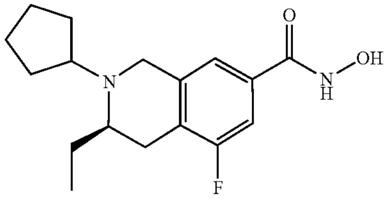
581
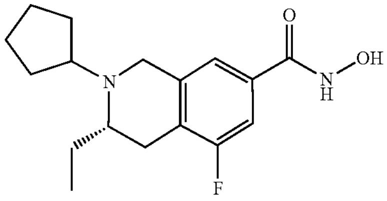
582
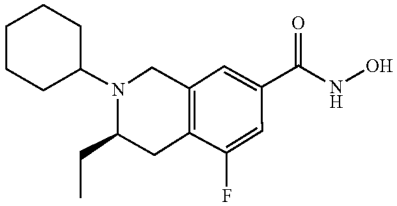
583
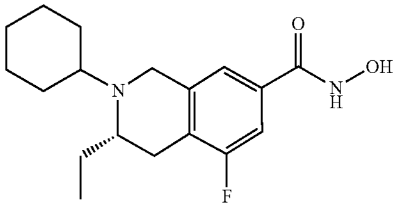
584
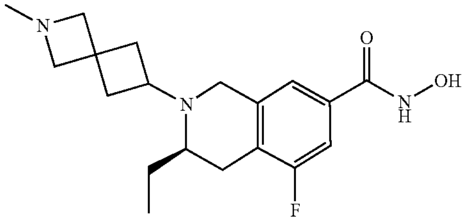
585
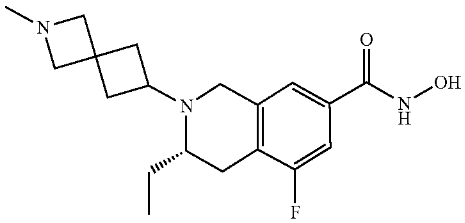
586
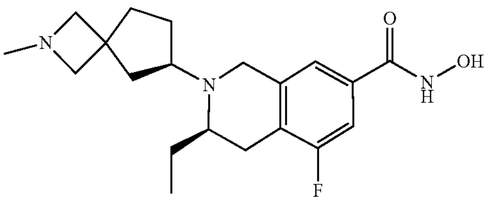

-continued
587
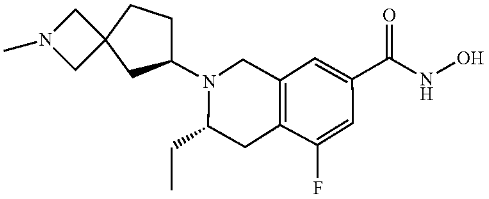
588
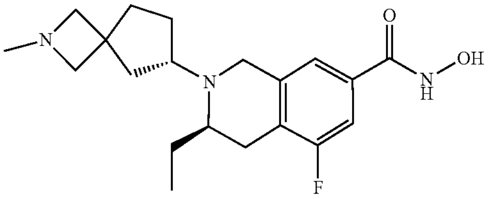
589
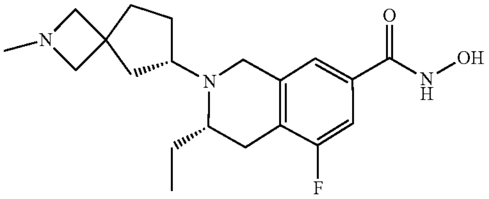
590
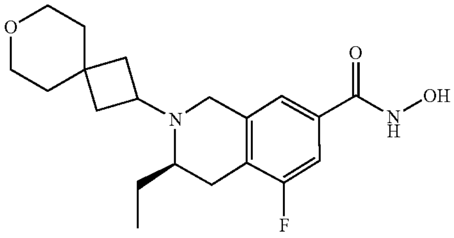
591
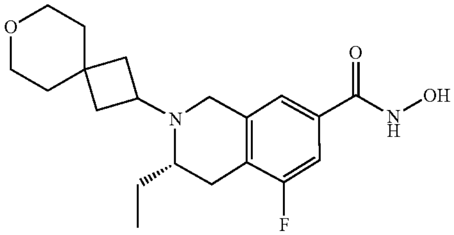
592
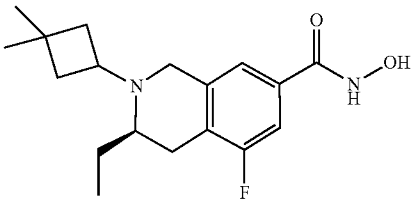
593
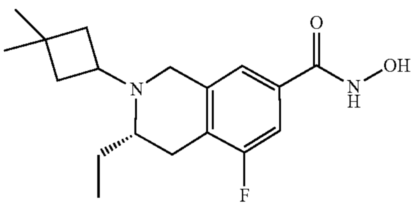
-continued
594
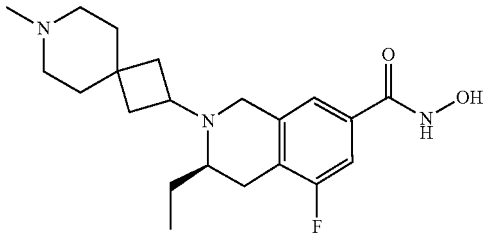
595
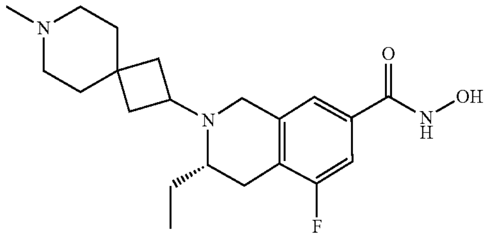
596
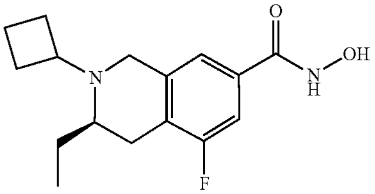
597
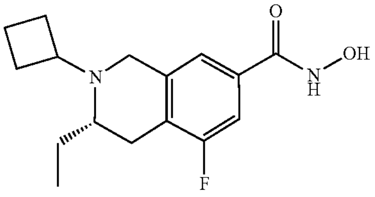
598
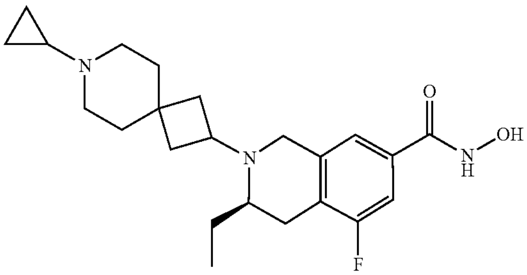
599
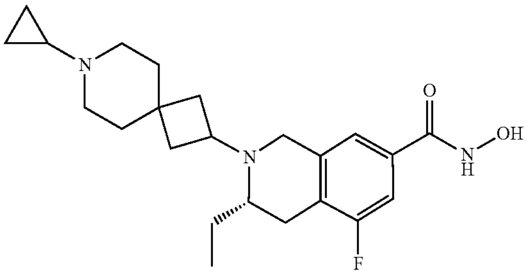

-continued

600

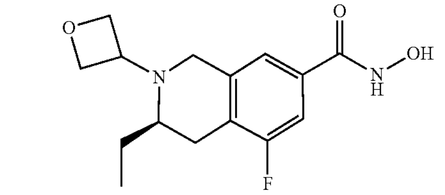

601

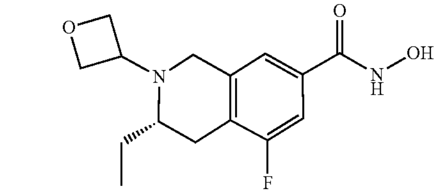

602

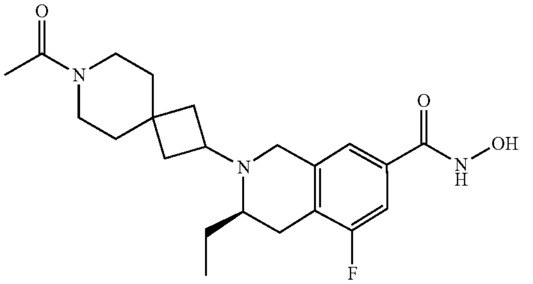

603

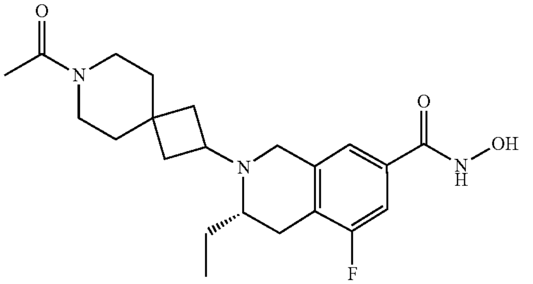

95. A compound of Formula (III), or a pharmaceutically acceptable salt thereof, (III)

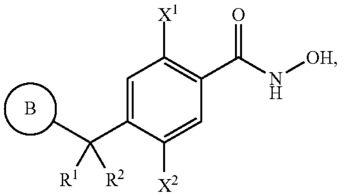

and pharmaceutically acceptable salts, co-crystals, tautomers, stereoisomers, solvates, hydrates, polymorphs, isotopically enriched derivatives, or prodrugs thereof, wherein:

$X^1$ is hydrogen or fluoro;

$X^2$ is hydrogen or fluoro;

$R^1$ is hydrogen or substituted or unsubstituted alkyl;

$R^2$ is hydrogen or substituted or unsubstituted alkyl; or $R^1$ and $R^2$ together form a substituted or unsubstituted heterocyclyl, or a substituted or unsubstituted cycloalkyl; and B is a substituted or unsubstituted polycyclic spiro ring system, a substituted or unsubstituted bridged ring system,

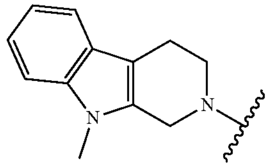, 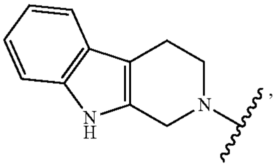,

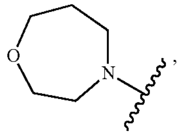, 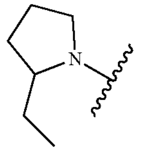, or 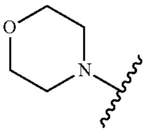;

provided that the compound is not of formula:

45

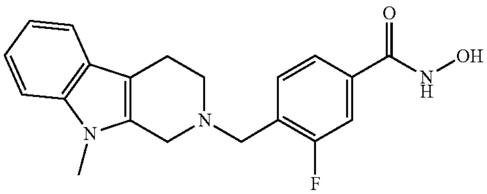

46

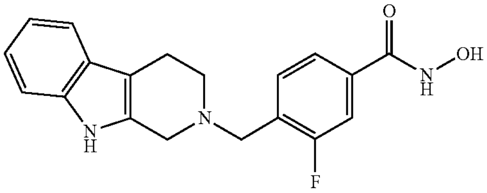

47

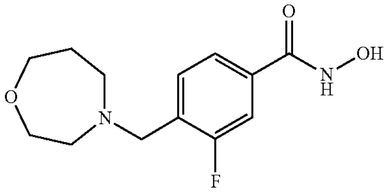

48

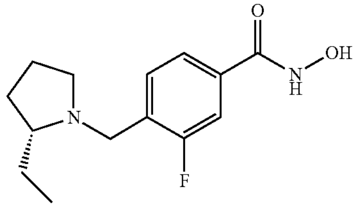

49

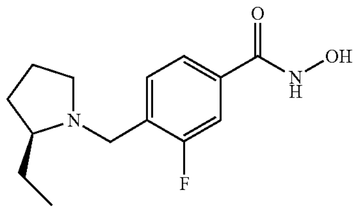

-continued
50
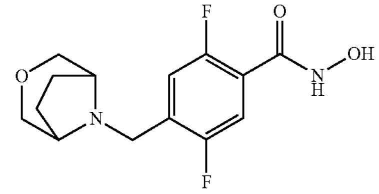
51
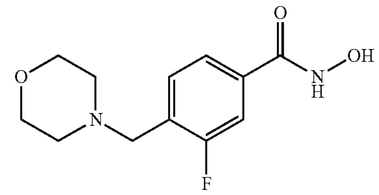
52
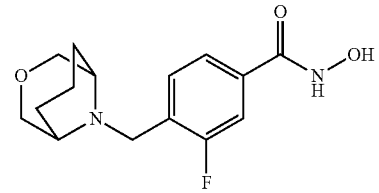
53
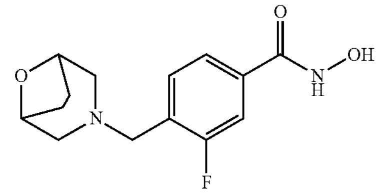
54
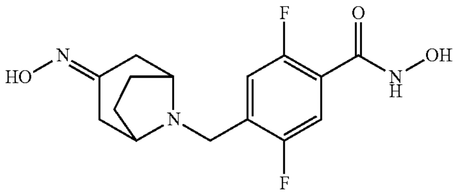
55
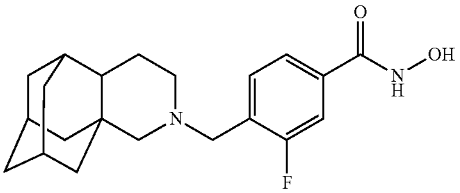
56
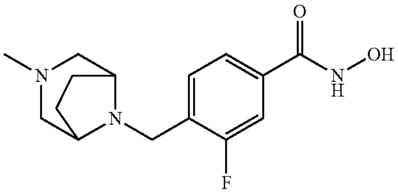
57
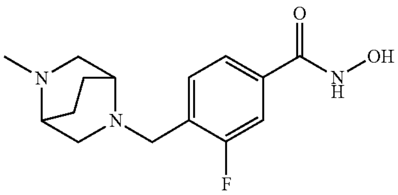
-continued
58
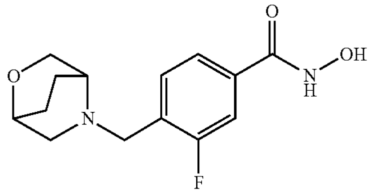
59
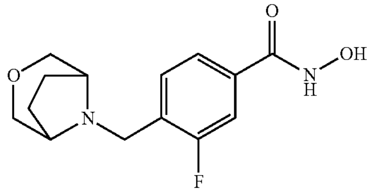
60
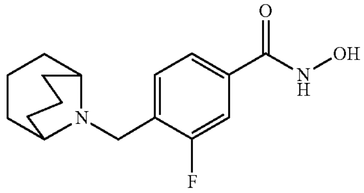
61
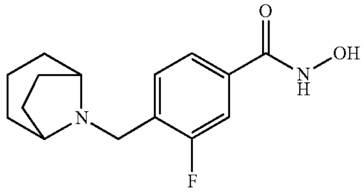
62
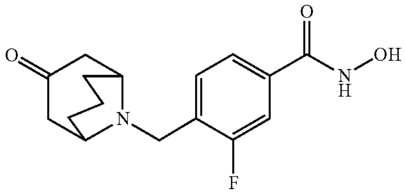
63
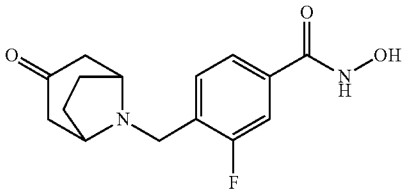
64
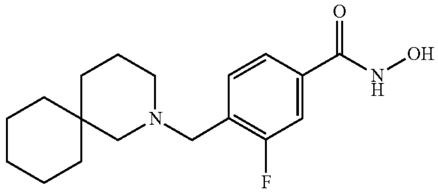
169
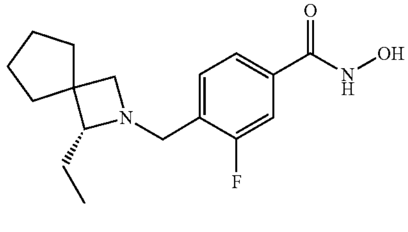

-continued
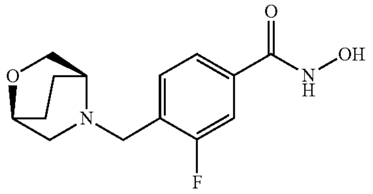
172
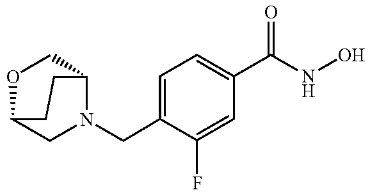
173
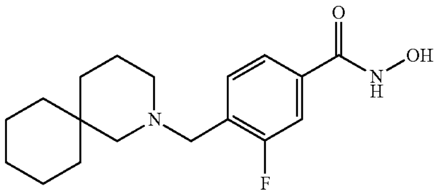
64
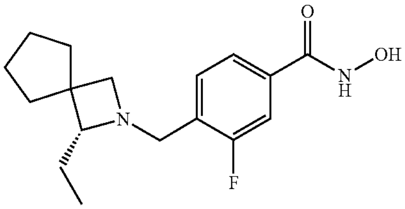
169
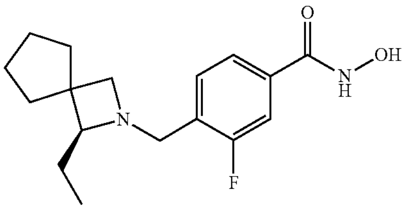
168
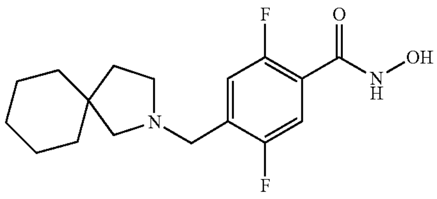
67
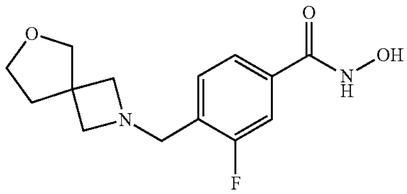
68
-continued
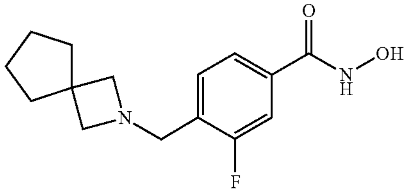
69
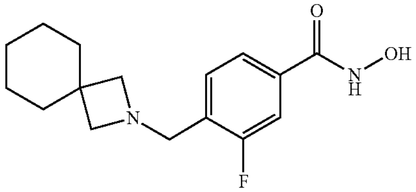
70
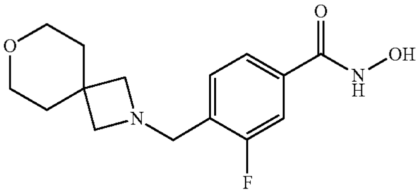
71
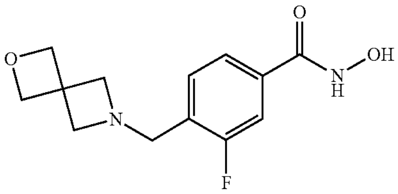
72
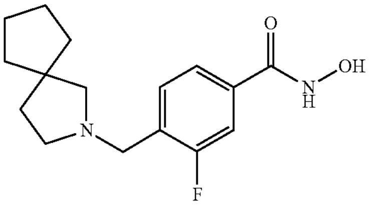
73
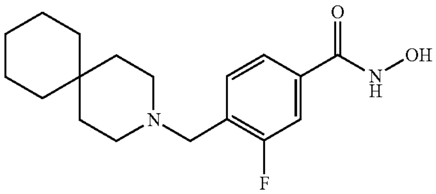
74
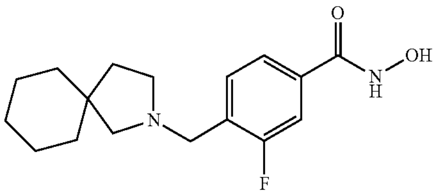
75

-continued

167

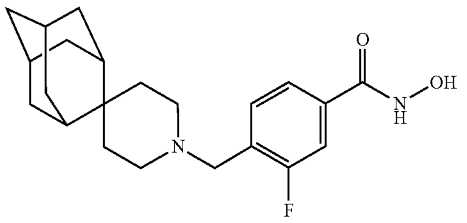

77

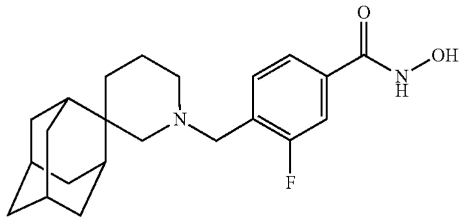

or

78

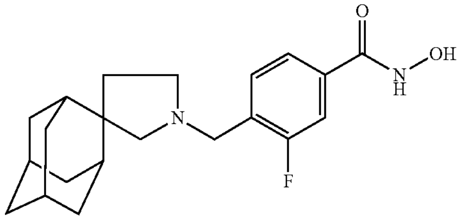

96. A compound of Formula (IV), or a pharmaceutically acceptable salt thereof (IV)

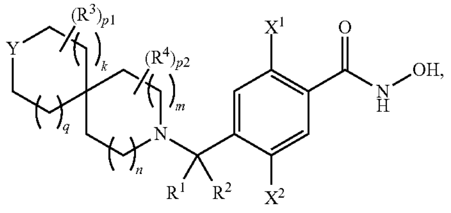

and pharmaceutically acceptable salts, co-crystals, tautomers, stereoisomers, solvates, hydrates, polymorphs, isotopically enriched derivatives, or prodrugs thereof, wherein:

$X^1$ is hydrogen or fluoro;

$X^2$ is hydrogen or fluoro;

$R^1$ is hydrogen or substituted or unsubstituted alkyl;

$R^2$ is hydrogen or substituted or unsubstituted alkyl; or $R^1$ and $R^2$ together form a substituted or unsubstituted heterocyclyl, or a substituted or unsubstituted cycloalkyl;

Y is —O—, —S—, —$NR^{a1}$—, or —$(CR^3R^4)$—;

each occurrence of $R^3$ and $R^4$ is, independently, hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted heteroalkyl, —$N(R^{a1})_2$, —$OR^{b1}$, —$SR^{c1}$, or —CN; wherein two or three $R^3$ groups are optionally joined to form a substituted or unsubstituted bridged ring; wherein two or three $R^4$ groups are optionally joined to form a substituted or unsubstituted bridged ring;

each occurrence of $R^{a1}$ is, independently, hydrogen, substituted or unsubstituted acyl, substituted or unsubstituted alkyl, substituted or unsubstituted heteroalkyl, substituted or 2% unsubstituted carbocyclyl, substituted or unsubstituted heterocyclyl, or a nitrogen protecting group, or two $R^{a1}$ groups are joined to form a substituted or unsubstituted heterocyclic ring;

each occurrence of $R^{b1}$ is, independently, hydrogen, substituted or unsubstituted acyl, substituted or unsubstituted alkyl, substituted or unsubstituted alkenyl, substituted or unsubstituted alkynyl, substituted or unsubstituted heteroalkyl, substituted or unsubstituted carbocyclyl, substituted or unsubstituted heterocyclyl, or an oxygen protecting group;

each occurrence of $R^{c1}$ is, independently, hydrogen, substituted or unsubstituted acyl, substituted or unsubstituted alkyl, substituted or unsubstituted alkenyl, substituted or unsubstituted alkynyl, substituted or unsubstituted heteroalkyl, substituted or unsubstituted carbocyclyl, substituted or unsubstituted heterocyclyl, or a sulfur protecting group;

m, n, k, and q are each independently 0, 1, or 2; and p1 and p2 are each independently 0, 1, 2, 3, or 4; provided that the compound is not of formula:

64

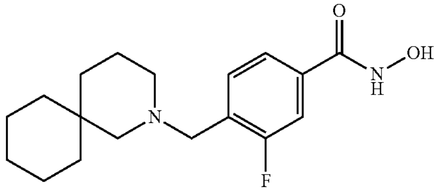

169

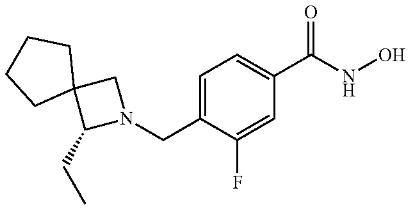

168

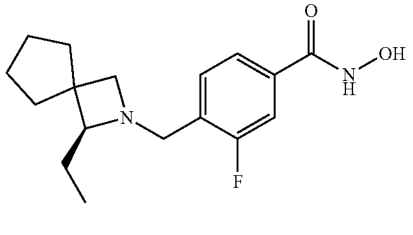

67

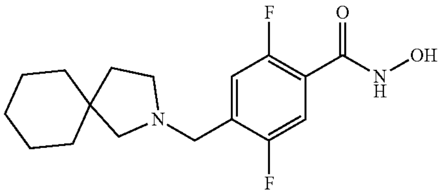

-continued
68
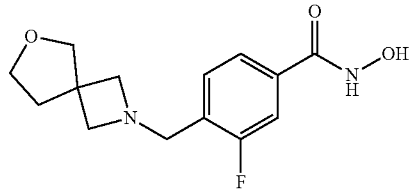
69
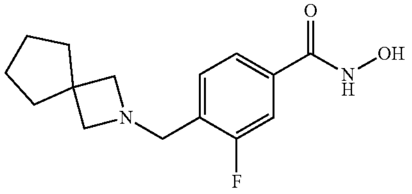
70
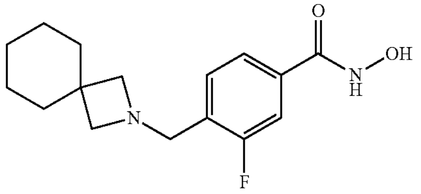
71
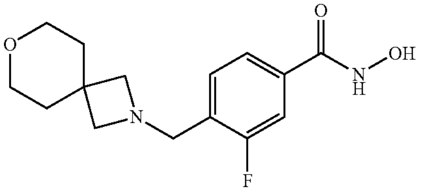
72
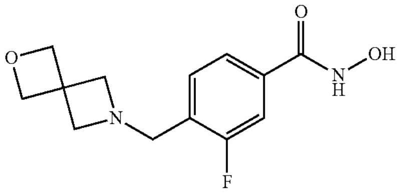
73
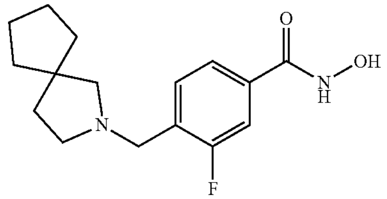
74
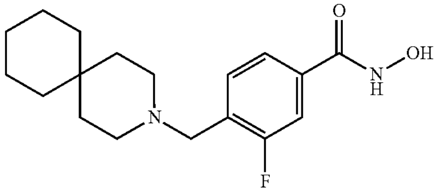
75
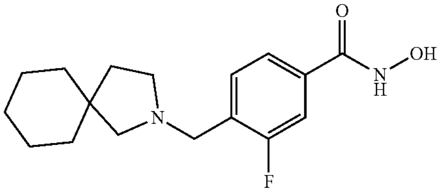
-continued
167
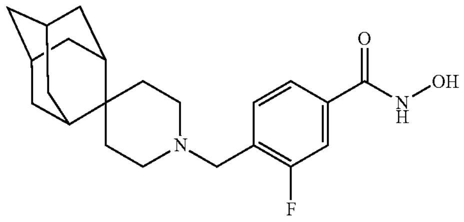
77
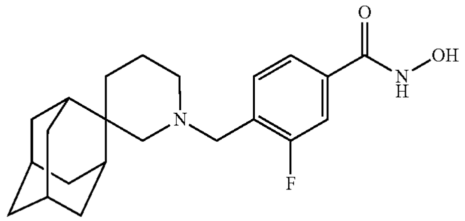
78
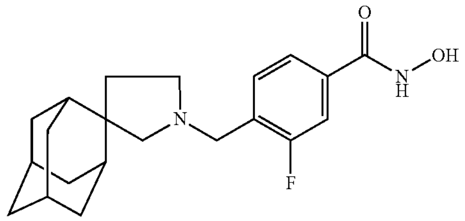
97. A compound selected from the following compounds or a pharmaceutically acceptable salt thereof:
237
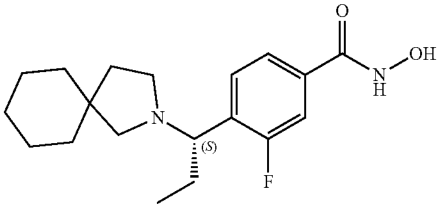
238
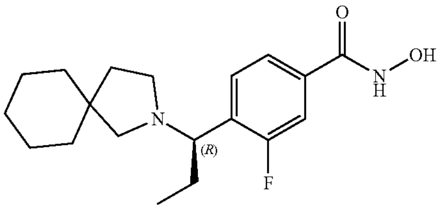
239
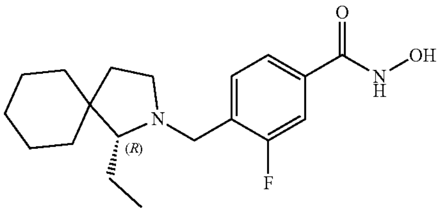

-continued

240

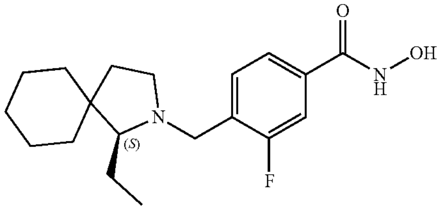

98. A compound of Formula (V), or a pharmaceutically acceptable salt thereof (V)

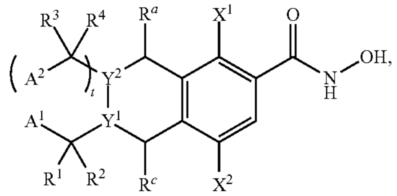

and pharmaceutically acceptable salts, co-crystals, tautomers, stereoisomers, solvates, hydrates, polymorphs, isotopically enriched derivatives, or prodrugs thereof, wherein:

$X^1$ is hydrogen or fluoro;

$X^2$ is hydrogen or fluoro;

$Y^1$ is independently nitrogen or $CR^x$;

$Y^2$ is independently nitrogen, $CR^d$, a bond, —$CH_2$—, or —NH—;

$A^1$ is joined with one of $A^2$, $R^a$, or $R^c$ to form a substituted or unsubstituted ring;

$A^2$ is hydrogen or joined with $A^1$ to form a substituted or unsubstituted ring;

$R^1$ is hydrogen or substituted or unsubstituted alkyl, or $R^1$ is joined with $R^d$, $R^3$, or $R^4$ to form a substituted or unsubstituted ring;

$R^2$ is hydrogen or substituted or unsubstituted alkyl, or $R^2$ is joined with $R^d$, $R^3$, or R to form a substituted or unsubstituted ring; or $R^1$ and $R^2$ together form a carbonyl;

$R^3$ is hydrogen or substituted or unsubstituted alkyl, or $R^3$ is joined with $R^1$ or $R^2$ to form a substituted or unsubstituted ring;

$R^4$ is hydrogen or substituted or unsubstituted alkyl, or $R^4$ is joined with $R^1$ or $R^2$ to form a substituted or unsubstituted ring; or $R^3$ and $R^4$ together form a carbonyl;

$R^x$ is hydrogen or substituted or unsubstituted alkyl;

$R^a$ is hydrogen or is joined with $A^1$ to form a substituted or unsubstituted ring;

$R^c$ is hydrogen or is joined with $A^1$ to form a substituted or unsubstituted ring;

$R^d$ is hydrogen or is joined with $R^3$ or $R^4$ to form a substituted or unsubstituted ring; and t is 0 or 1; provided that the compound is not of formula:

79

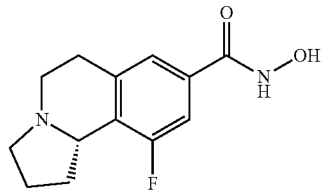

80

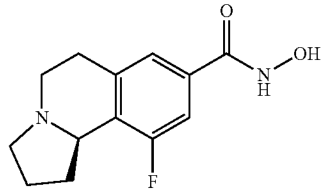

119

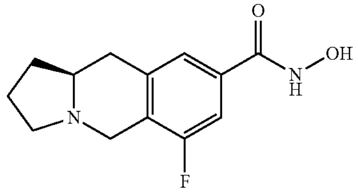

120

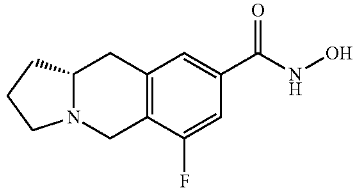

140

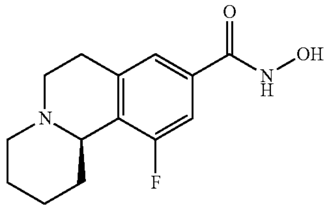

139

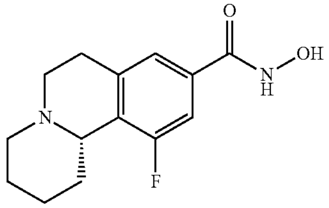

134

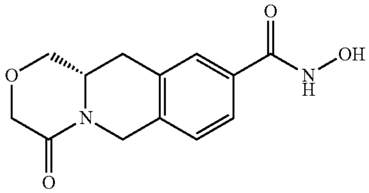

-continued
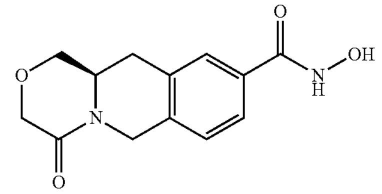
133
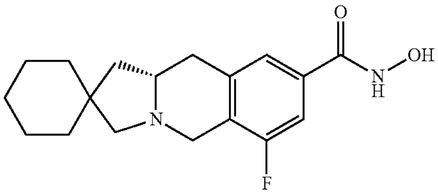
135
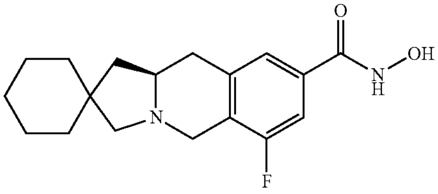
136
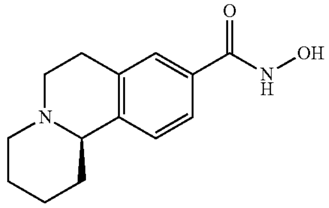
90
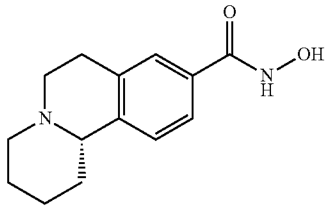
89
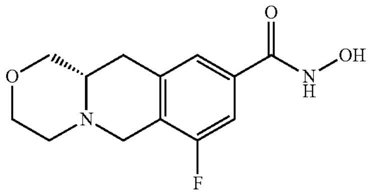
130
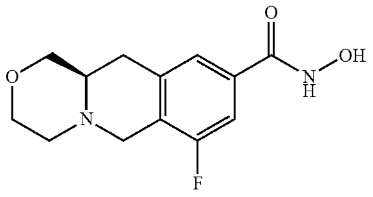
129
-continued
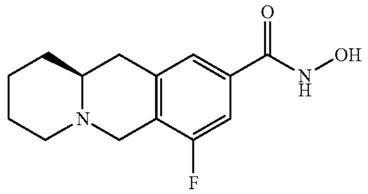
93
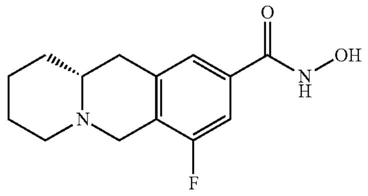
94
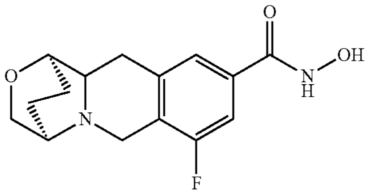
95
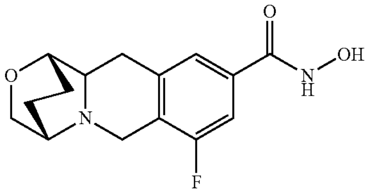
96
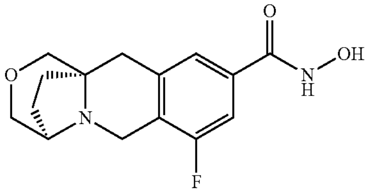
97
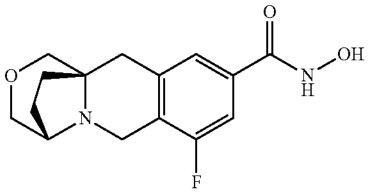
98
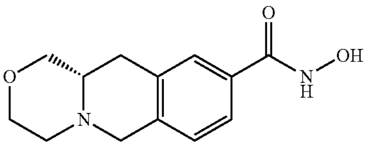
132
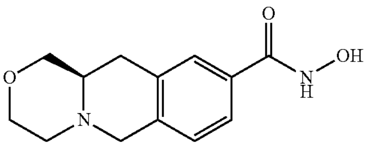
131

-continued
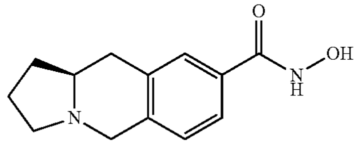
121
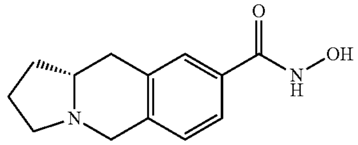
122
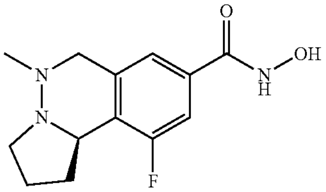
103
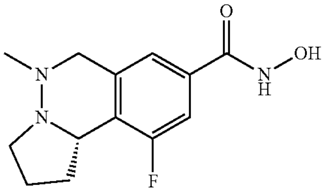
104
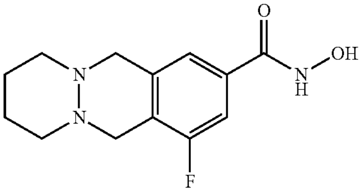
105
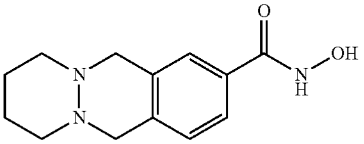
106
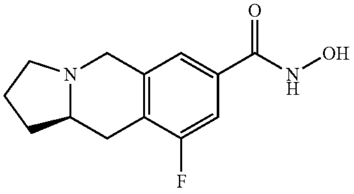
124
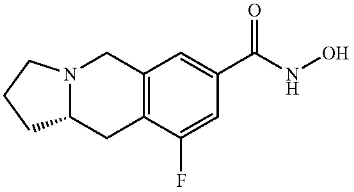
123
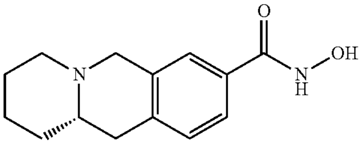
144
-continued
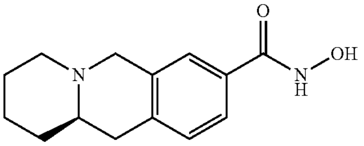
143
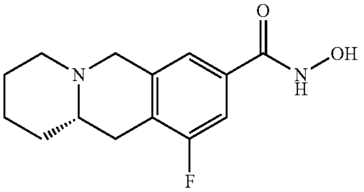
146
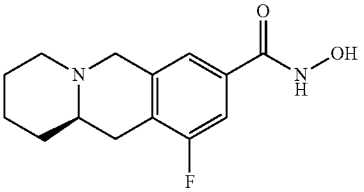
145
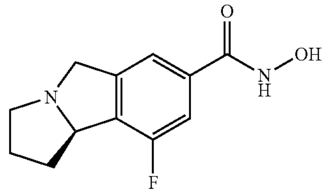
180
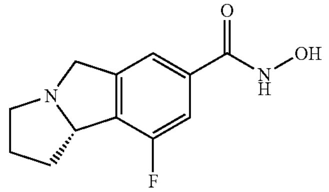
181
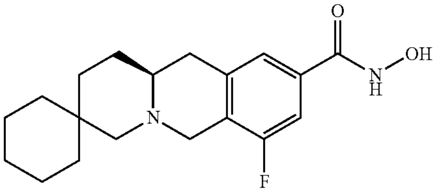
137
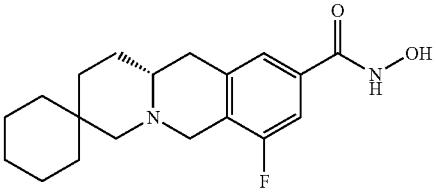
138
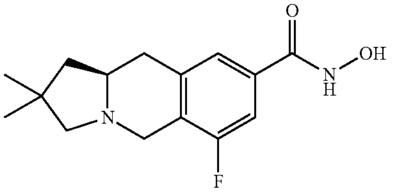
125

-continued
126
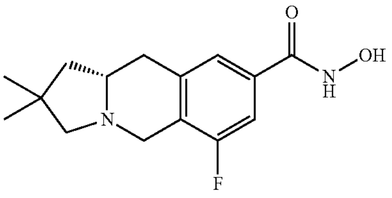
127
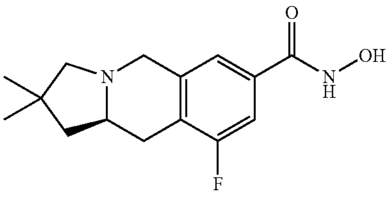
128
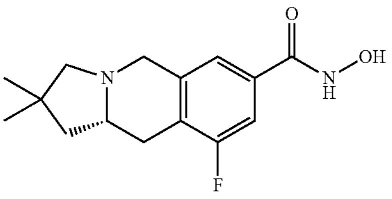
147
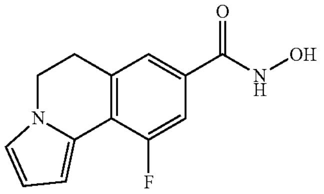
148
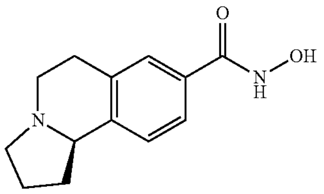
149
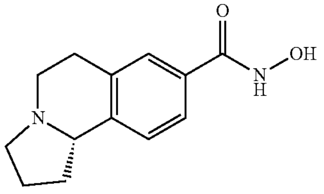
150
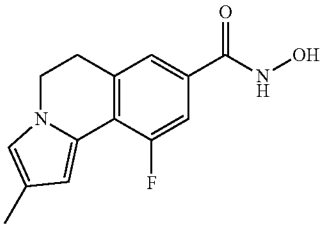
-continued
151
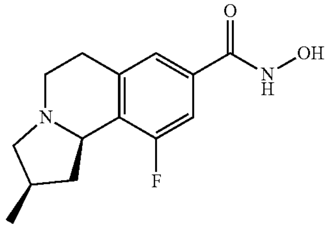
152
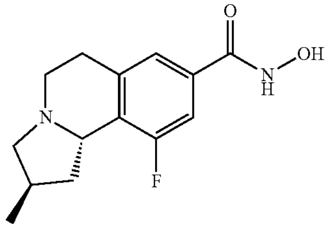
153
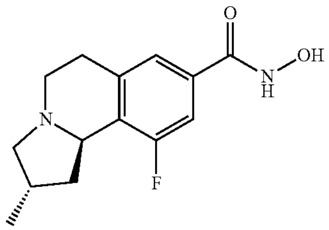
154
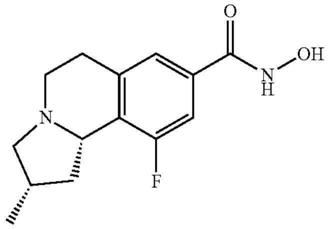
155
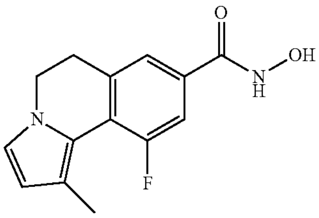
156
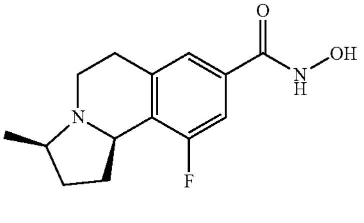
157
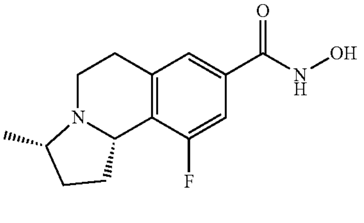

-continued
158
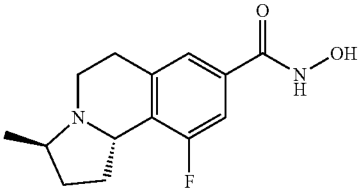
159
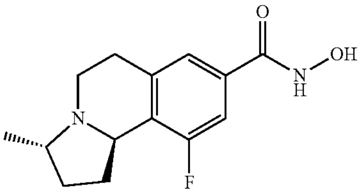
160
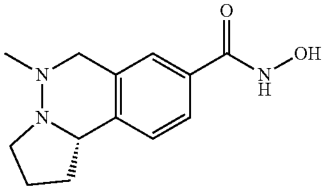
161
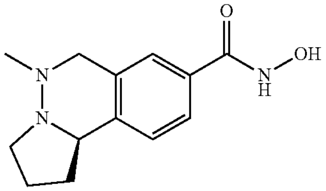
162
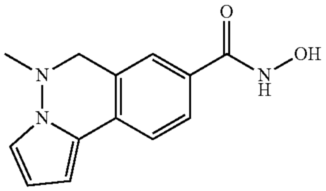
163
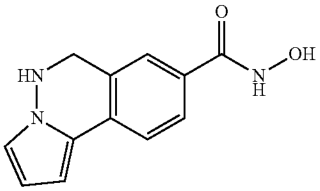
164
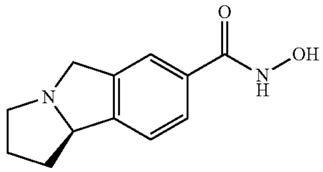
165
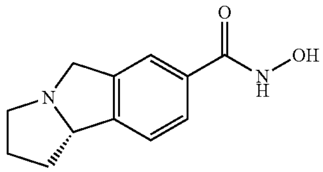
-continued
166
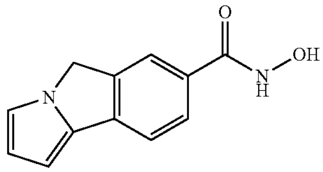
99. A compound selected from the following compounds, or a pharmaceutically acceptable salt thereof:
241
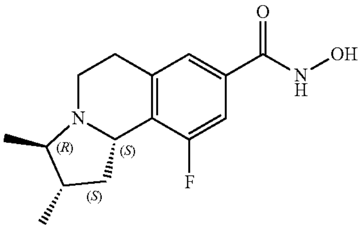
242
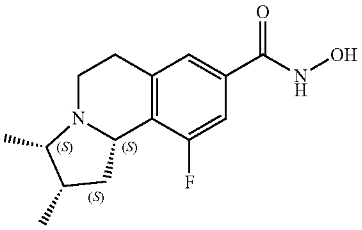
243
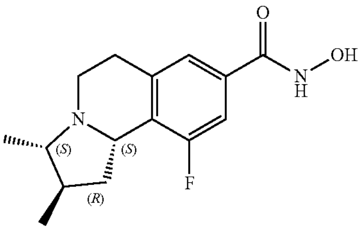
244
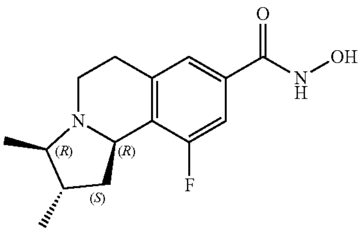
245
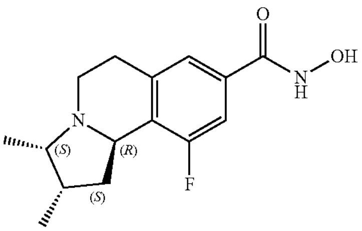

-continued
246
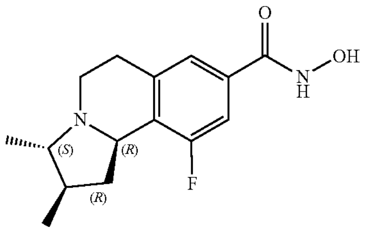
247
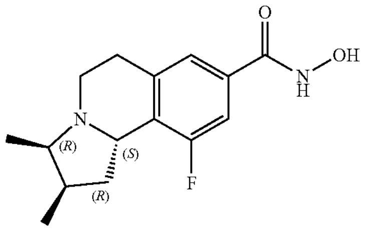
248
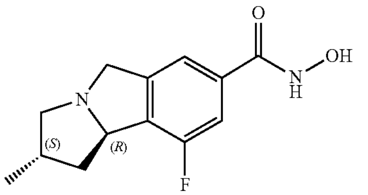
249
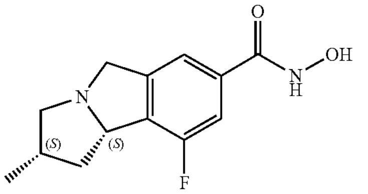
250
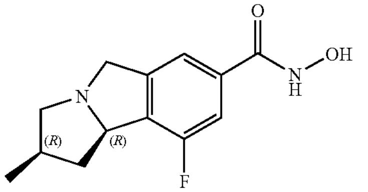
251
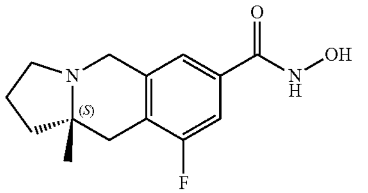
252
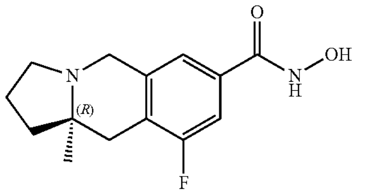
-continued
253
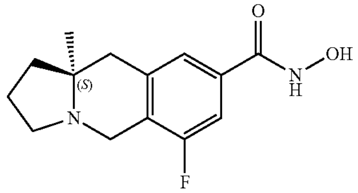
254
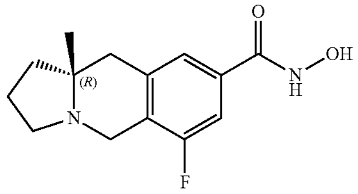
255
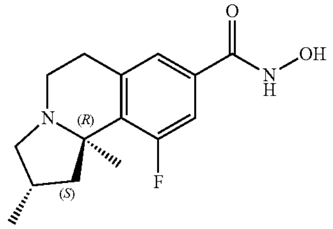
256
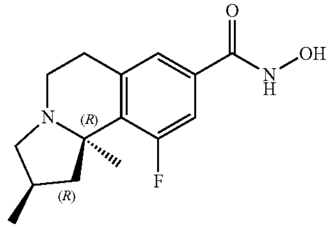
257
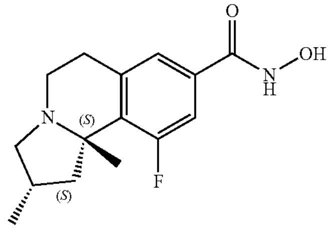
258
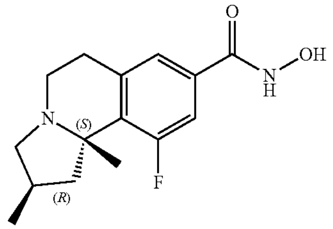
259
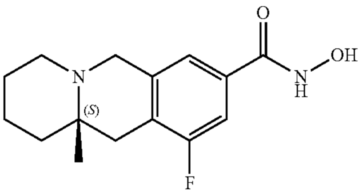

-continued
260
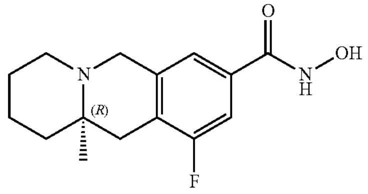
261
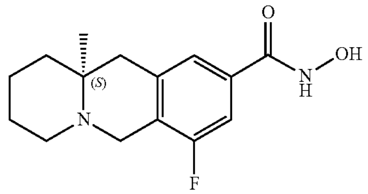
262
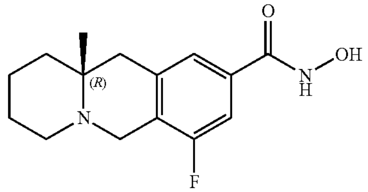
263
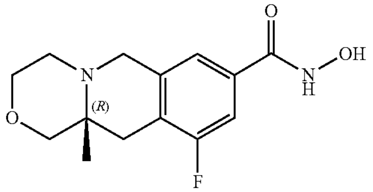
264
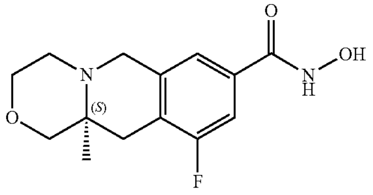
265
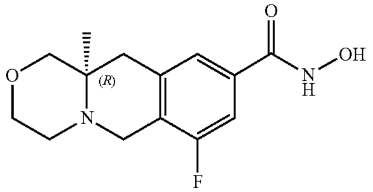
266
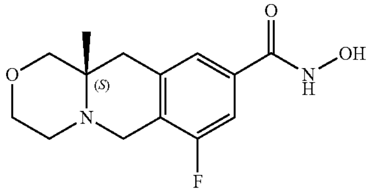
267
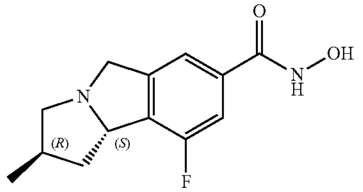
-continued
268
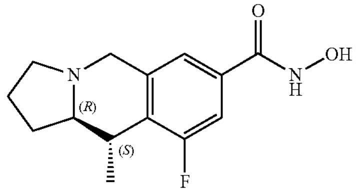
269
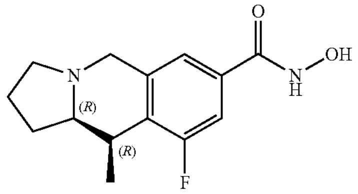
270
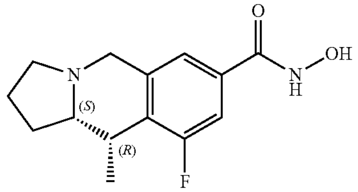
271
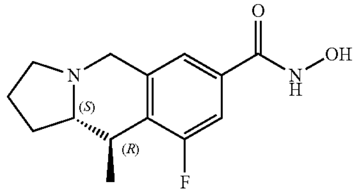
272
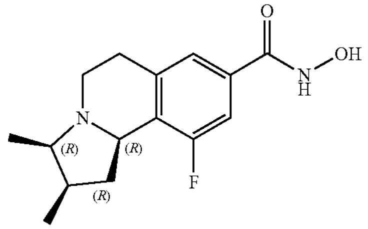
273
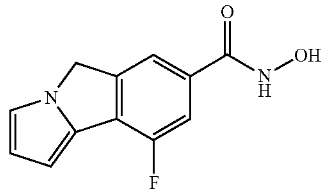
100. A compound of Formula (VI), or a pharmaceutically acceptable salt thereof
(VI)
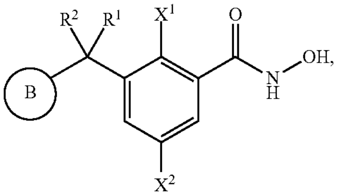

and pharmaceutically acceptable salts, co-crystals, tautomers, stereoisomers, solvates, hydrates, polymorphs, isotopically enriched derivatives, or prodrugs thereof, wherein:

$X^1$ is hydrogen or fluoro;

$X^2$ is hydrogen or fluoro;

$R^1$ is hydrogen or substituted or unsubstituted alkyl;

$R^2$ is hydrogen or substituted or unsubstituted alkyl; or $R^1$ and $R^2$ together form a substituted or unsubstituted heterocyclyl, or a substituted or unsubstituted cycloalkyl; and B is a substituted or unsubstituted heterocyclyl, substituted or unsubstituted carbocyclyl, a substituted or unsubstituted polycyclic spiro ring system, or a substituted or unsubstituted bridged ring system; provided that the compound is not of formula

170

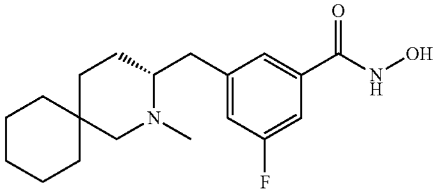

171

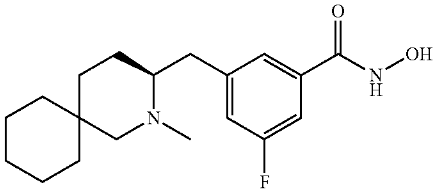

101. A compound selected from the following compounds, or a pharmaceutically acceptable salt thereof:

274

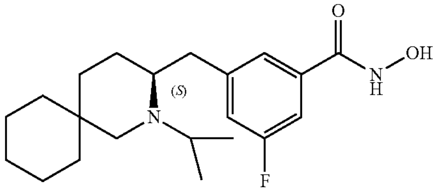

275

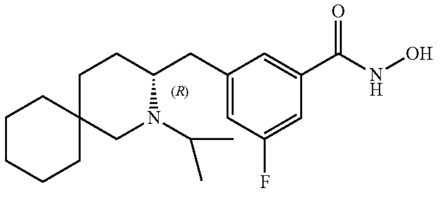

276

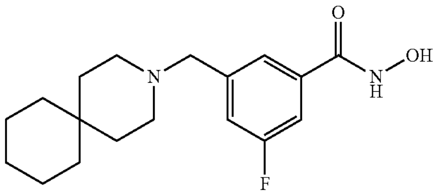

102. A compound selected from the following compounds, or a pharmaceutically acceptable salt thereof:

277

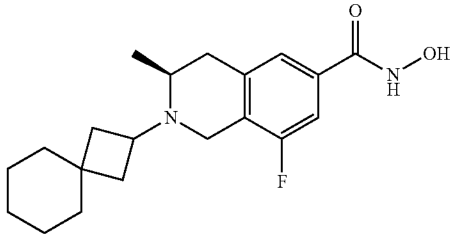

278

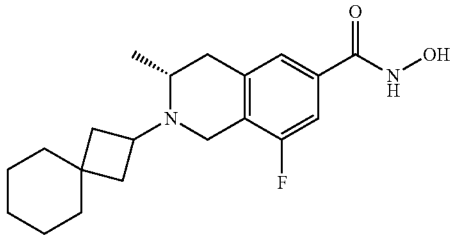

279

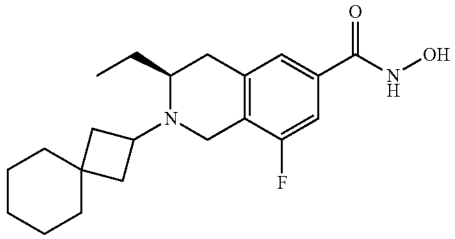

280

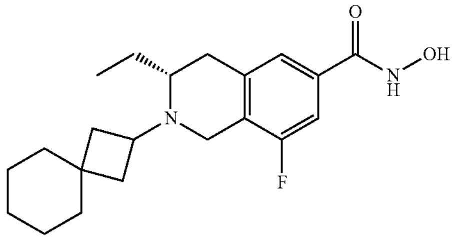

281

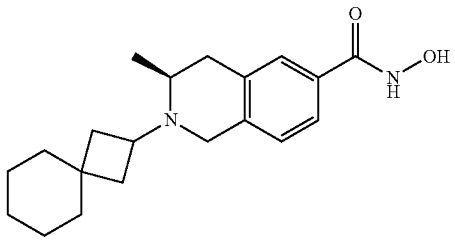

282

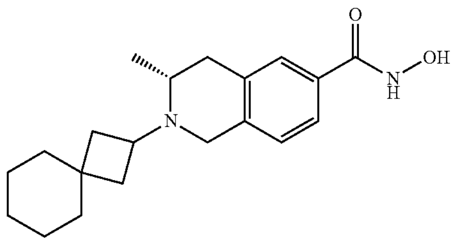

-continued

283

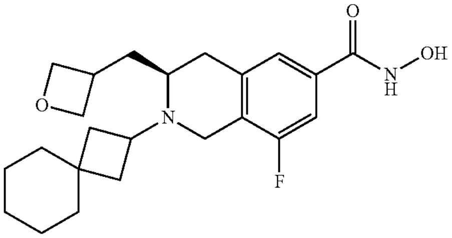

284

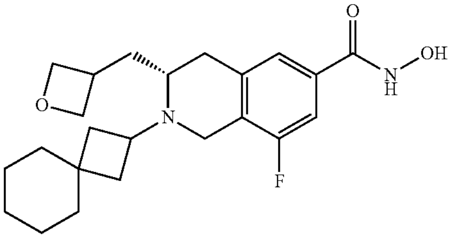

285

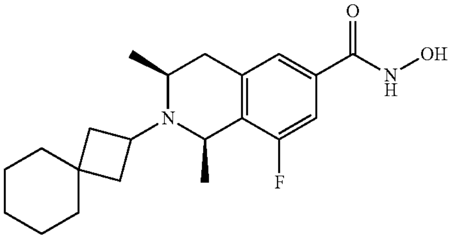

286

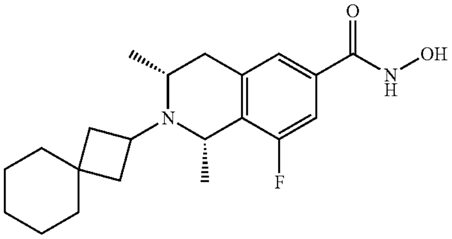

287

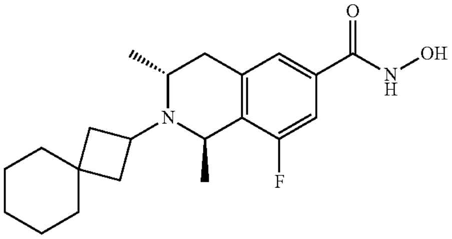

288

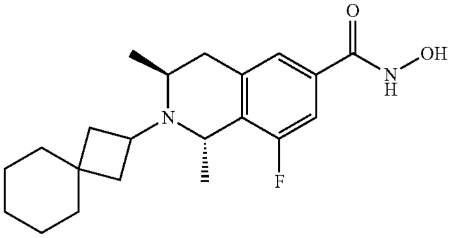

103. A compound of Formula (VIII), or a pharmaceutically acceptable salt thereof, (VIII)

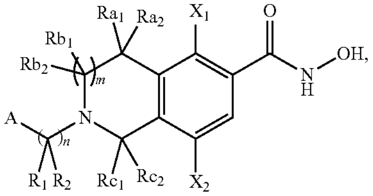

wherein:

$X^1$ is hydrogen or fluoro;

$X^2$ is hydrogen or fluoro; provided that at least one of $X^1$ and $X^2$ is fluoro;

A is substituted or unsubstituted alkyl, substituted or unsubstituted carbocyclyl, substituted or unsubstituted heterocyclyl, substituted or unsubstituted heteroaryl, or substituted or unsubstituted aryl;

$R^1$ is hydrogen or substituted or unsubstituted alkyl;

$R^2$ is hydrogen or substituted or unsubstituted alkyl; or $R^1$ and $R^2$ together form a substituted or unsubstituted heterocyclyl, or a substituted or unsubstituted cycloalkyl;

$R^{a1}$ and $R^{a2}$ are each independently hydrogen, or is joined with $R^c$ to form a substituted or unsubstituted bridged ring;

$R^{b1}$ and $R^{b2}$ are joined together by an alkyl to form a substituted or unsubstituted spirocyclic cycloalkyl ring;

$R^{c1}$ and $R^{c2}$ are hydrogen or substituted or unsubstituted alkyl or is joined with at least one of $R^a$ and $R^b$ to form a substituted or unsubstituted bridged ring;

m is 1; and n is 0 or 1' provided that the compound of Formula (VIII) is not any of the following compounds:

1

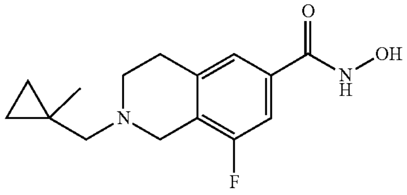

2

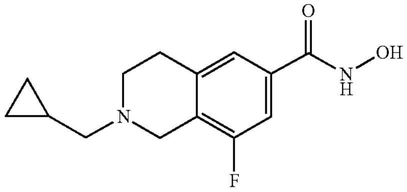

3

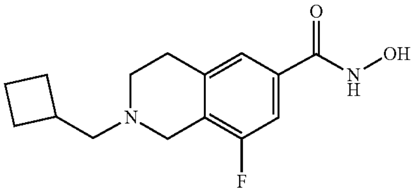

-continued
4
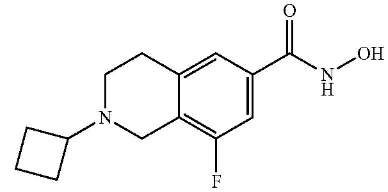
5
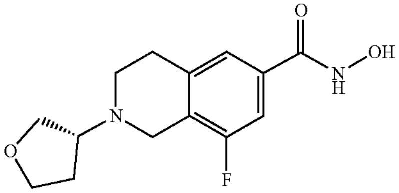
6
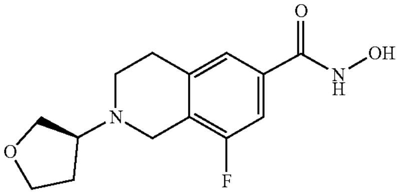
7
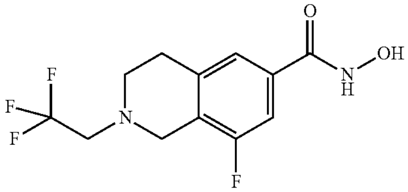
8
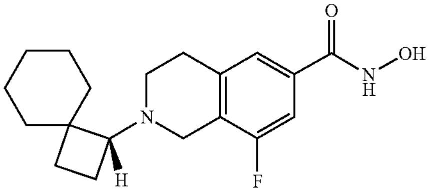
9
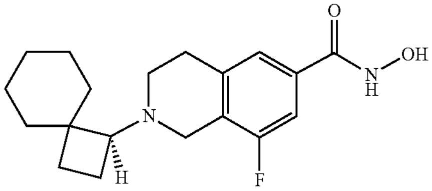
10
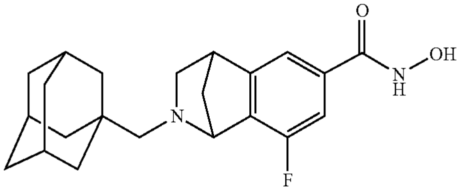
11
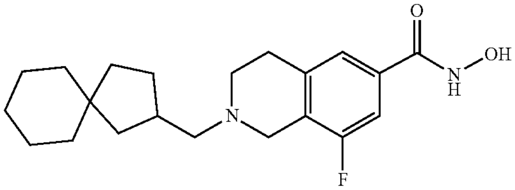
-continued
12
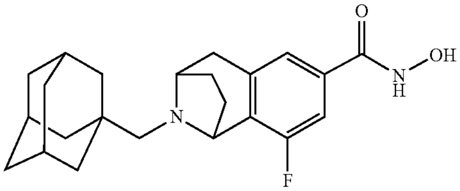
13
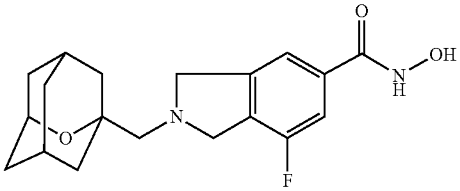
14
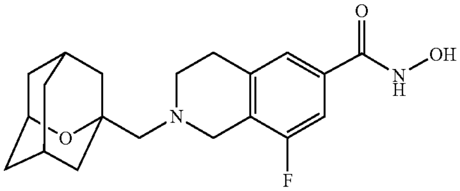
15
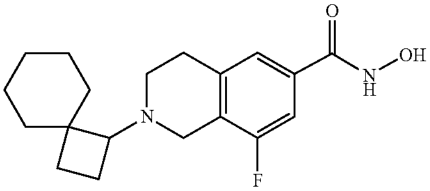
16
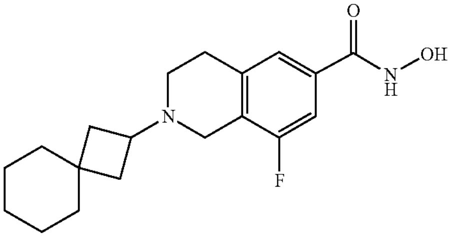
17
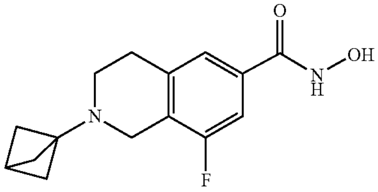
18
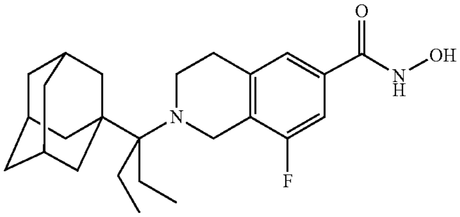

19
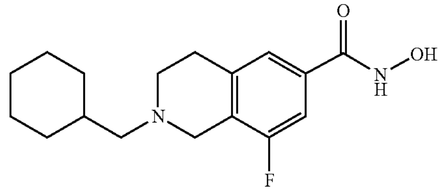
20
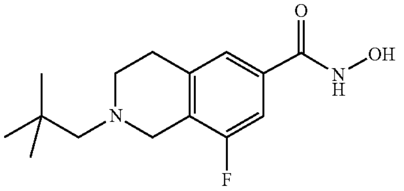
21
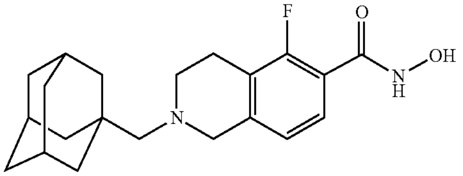
22
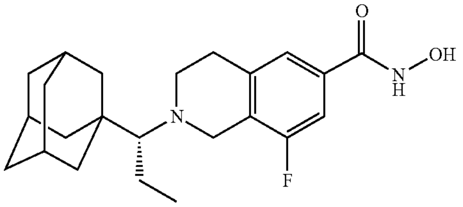
23
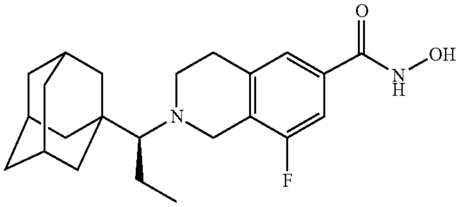
24
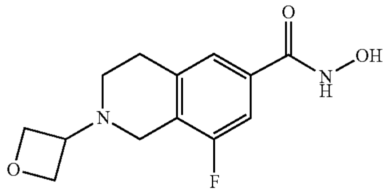
25
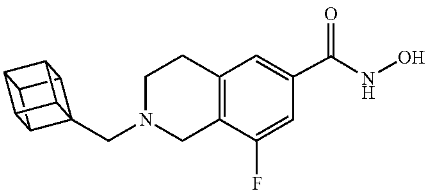
26
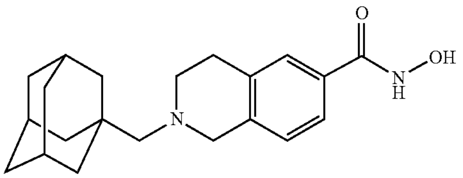
27
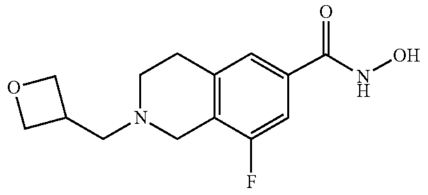
28
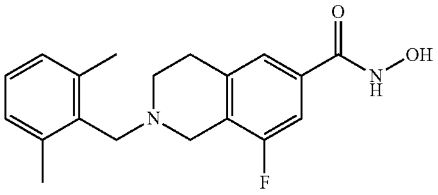
29
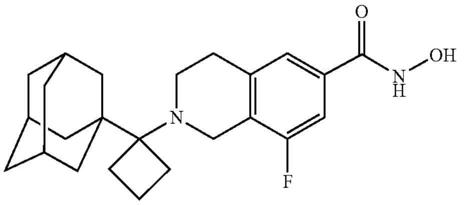
30
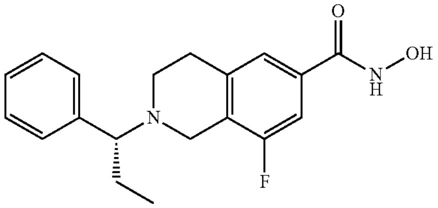
31
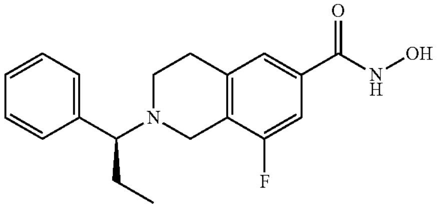
32
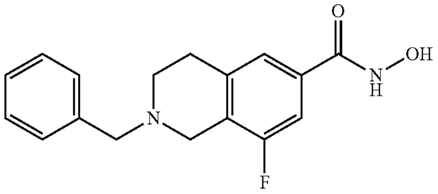
33
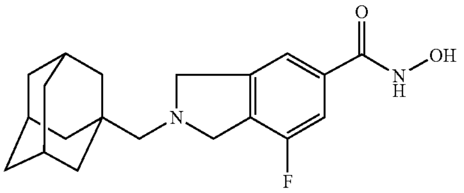

-continued

34

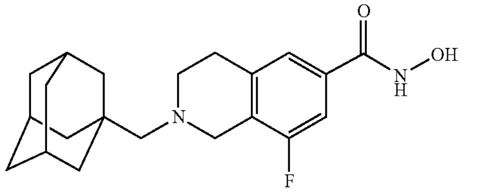

35

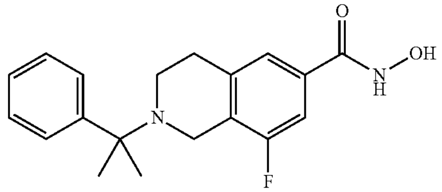

107

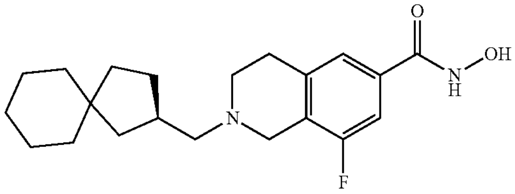

108

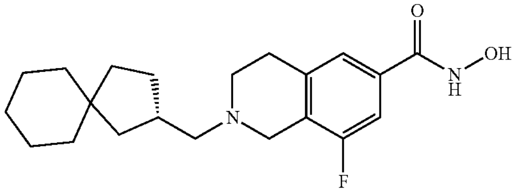

109

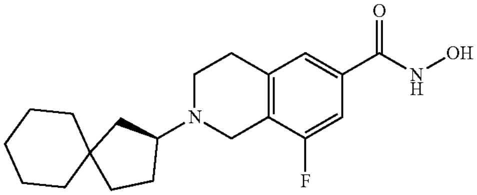

110

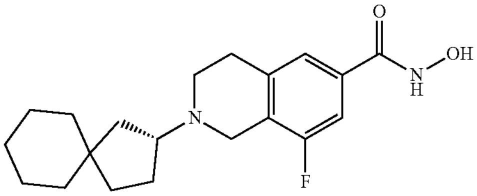

111

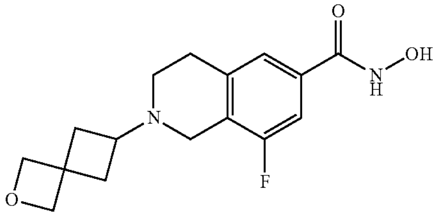

-continued

112

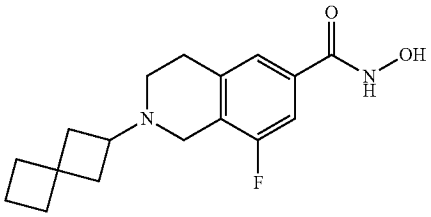

104. A compound of Formula (IX), or a pharmaceutically acceptable salt thereof, (IX)

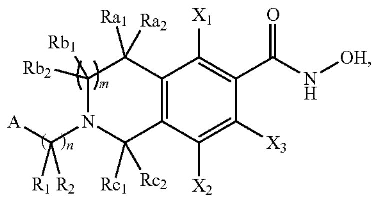

wherein:

$X^1$ is hydrogen, fluoro or deuterium;

$X^2$ is hydrogen or fluoro;

$X^3$ is hydrogen or deuterium;

A is a substituted or unsubstituted spirocyclic heterocyclyl, a substituted or unsubstituted spirocyclic carbocyclyl, a substituted or unsubstituted bridged cycloalkyl, a substituted or unsubstituted bridged heterocycloalkyl, a substituted or unsubstituted monocyclic heterocyclyl ring; a substituted or unsubstituted monocyclic cycloalkyl ring; or a substituted or unsubstituted alkyl;

$R^1$ is hydrogen or substituted or unsubstituted alkyl;

$R^2$ is hydrogen or substituted or unsubstituted alkyl; or $R^1$ and $R^2$ together form a substituted or unsubstituted heterocyclyl, or a substituted or unsubstituted cycloalkyl;

$R^a$ is hydrogen or is joined with $R^c$ to form a substituted or unsubstituted bridged ring;

$R^b$ is hydrogen or is joined with $R^c$ to form a substituted or unsubstituted bridged ring;

$R^c$ is hydrogen or substituted or unsubstituted alkyl or is joined with at least one of $R^a$ and $R^b$ to form a substituted or unsubstituted bridged ring;

m is 0 or 1; and n is 0 or 1;

provided that the compound of Formula (IX) is not any of the following compounds:

1

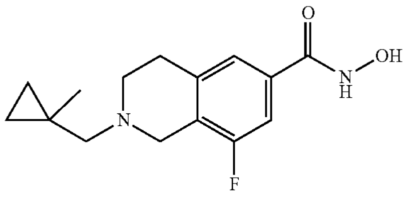

-continued
2
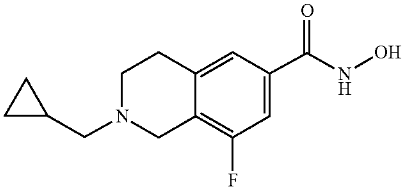
3
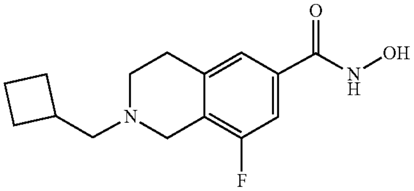
4
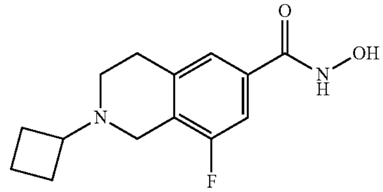
5
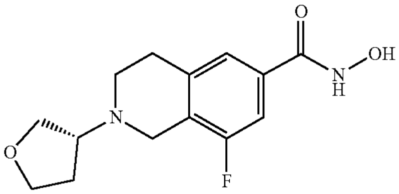
6
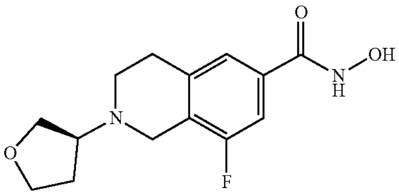
7
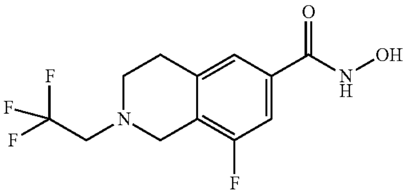
8
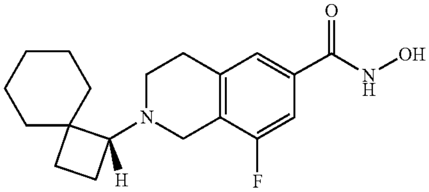
9
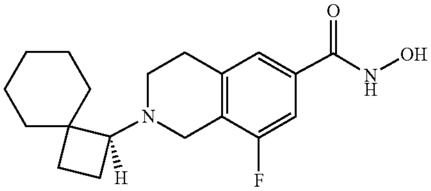
-continued
10
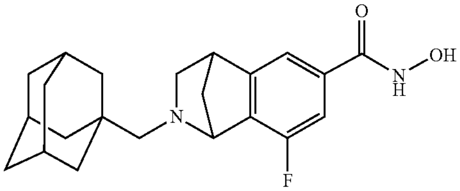
11
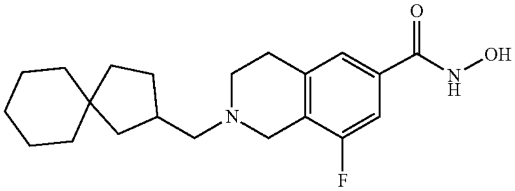
12
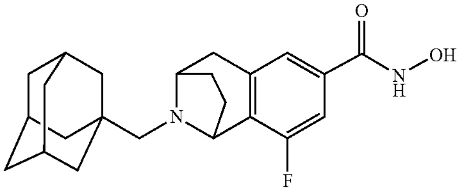
13
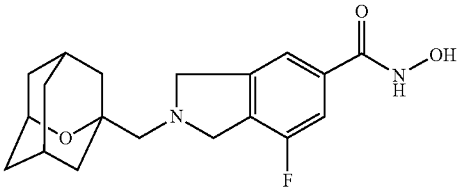
14
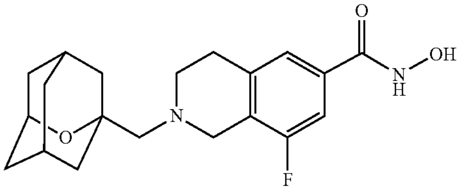
15
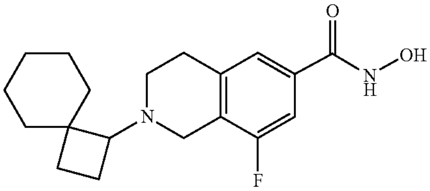
16
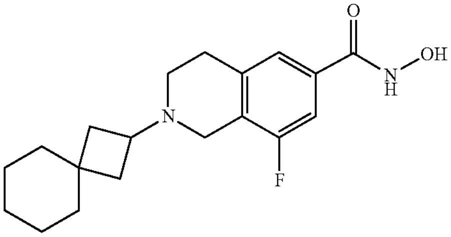

-continued
17
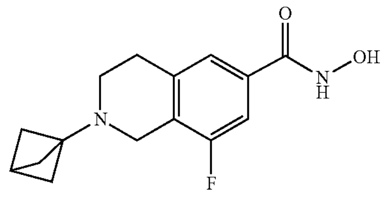
18
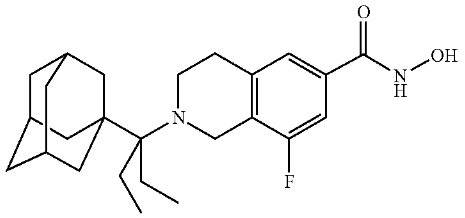
19
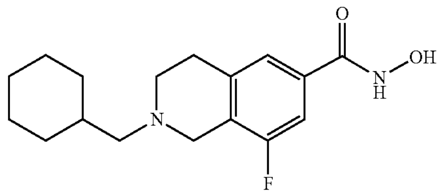
20
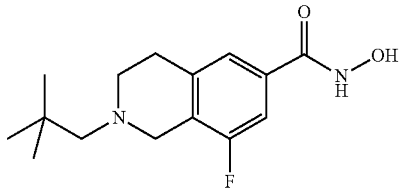
21
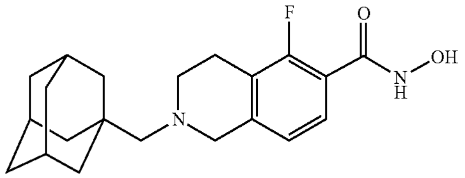
22
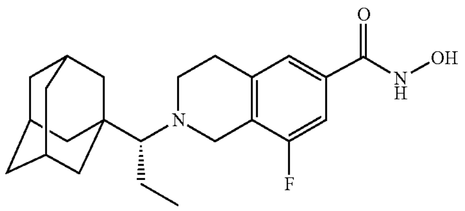
23
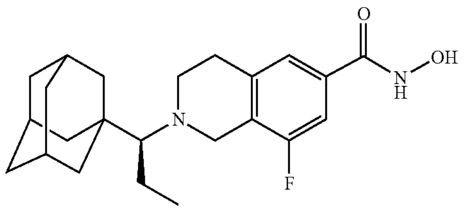
-continued
24
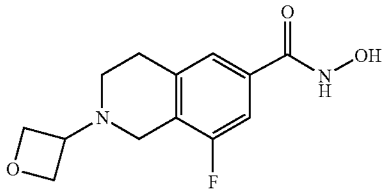
25
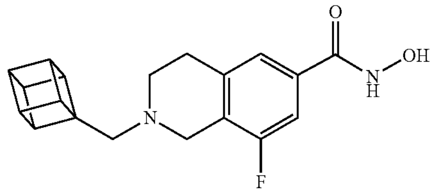
26
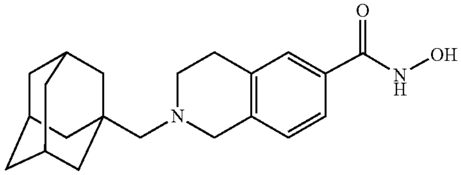
27
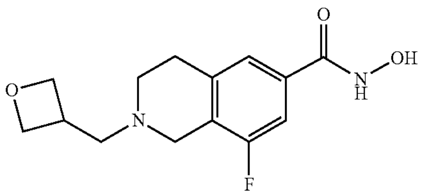
28
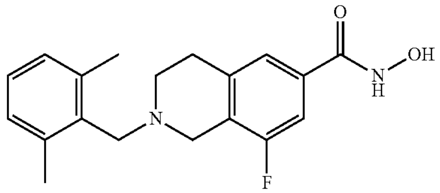
29
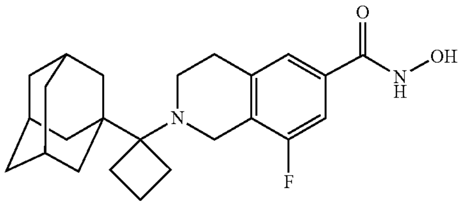
30
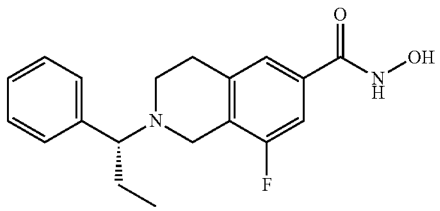
31
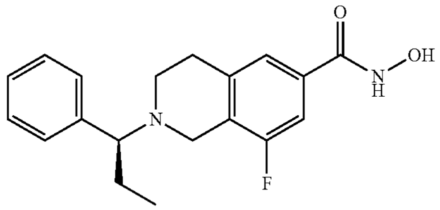

-continued
32
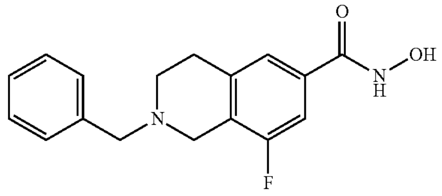
33
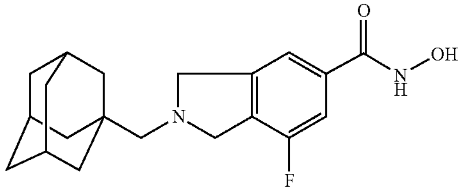
34
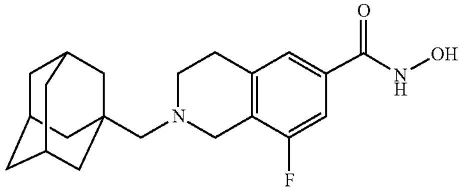
35
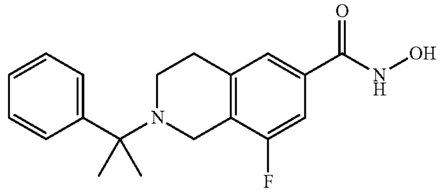
107
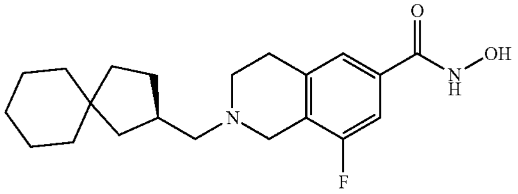
108
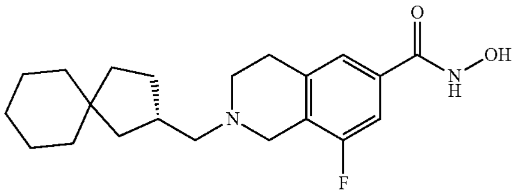
109
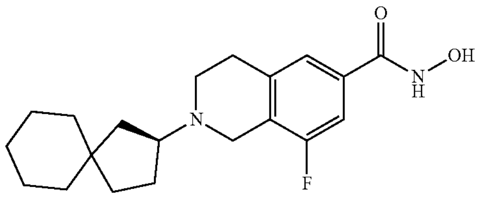
110
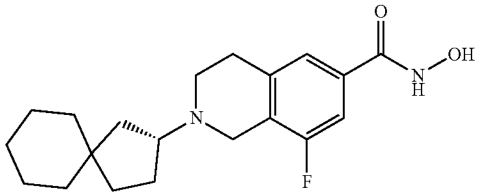
-continued
111
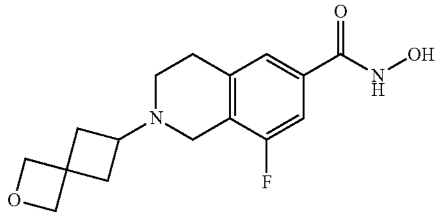
112
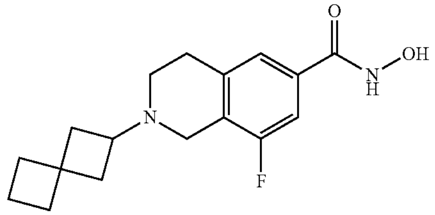
Clauses
1. A compound of formula
174
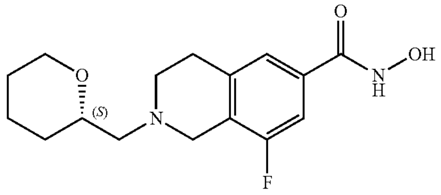
175
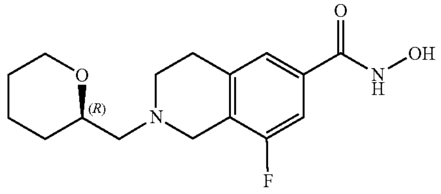
176
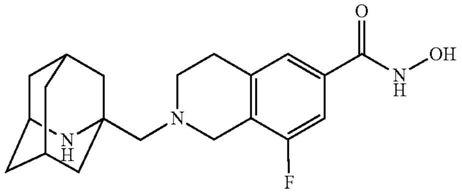
177
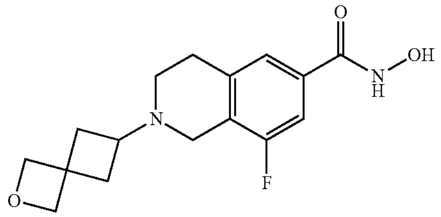

-continued
178
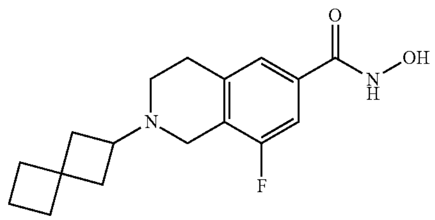
179
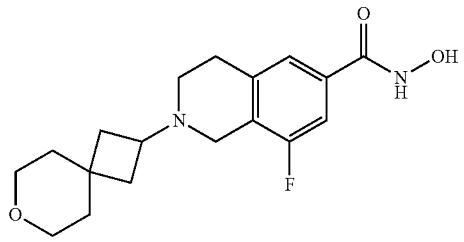
180
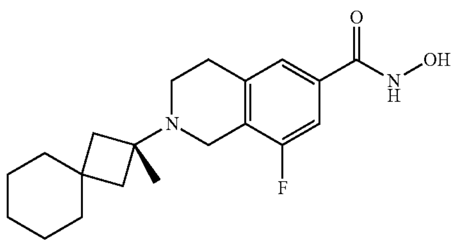
181
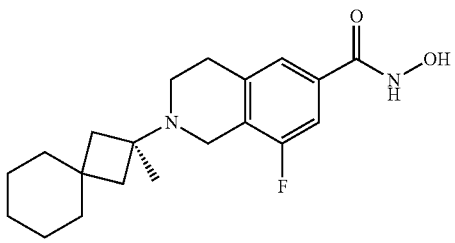
182
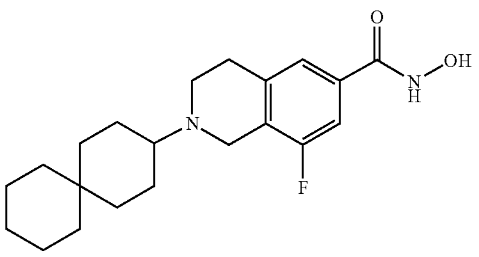
183
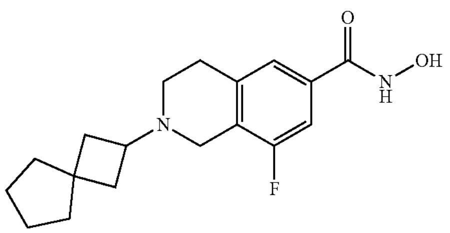
-continued
184
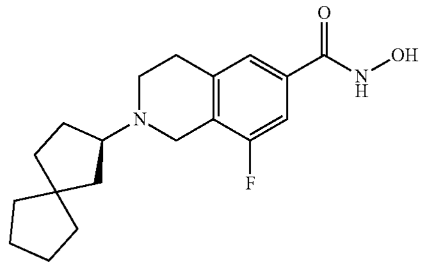
185
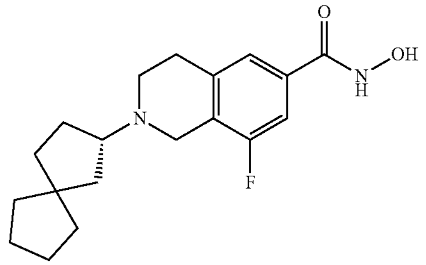
188
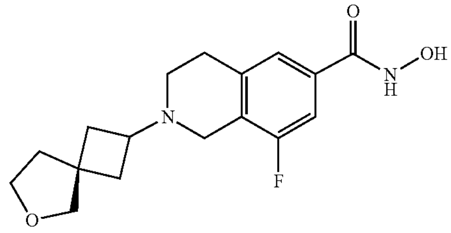
189
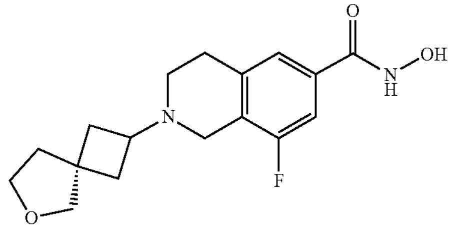
190
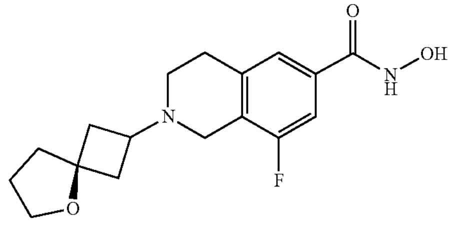
191
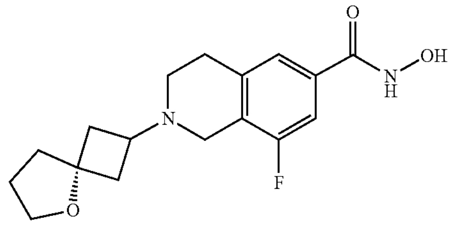

-continued
192
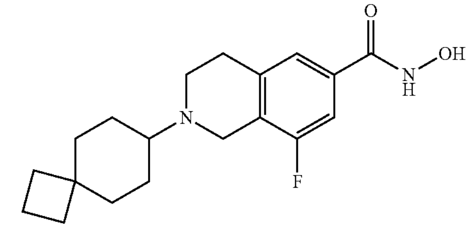
193
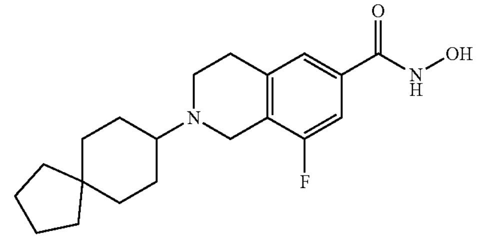
194
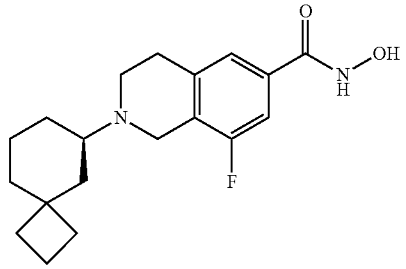
195
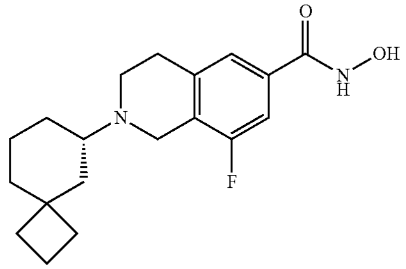
197
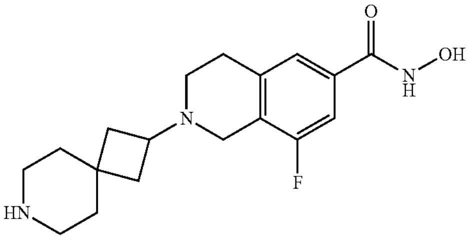
198
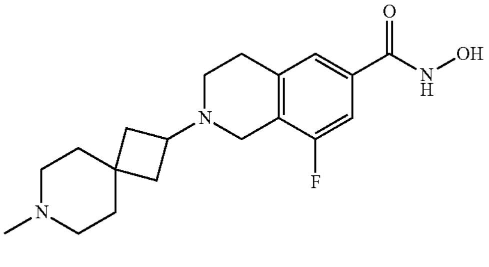
-continued
199
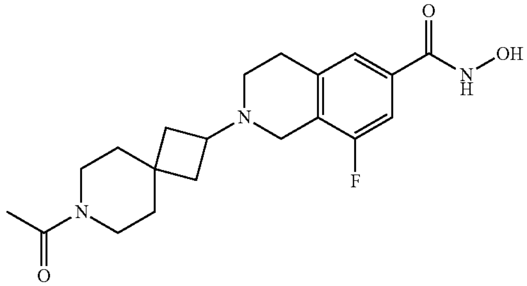
200
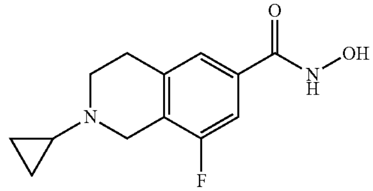
201
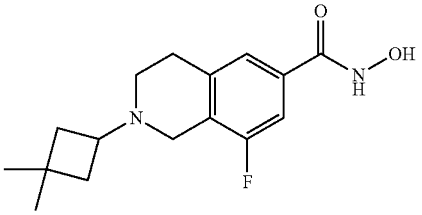
202
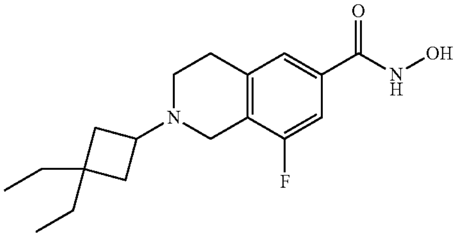
208
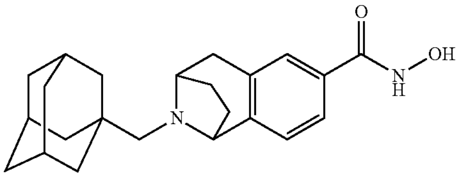
209
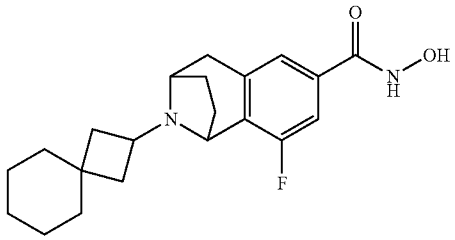
210
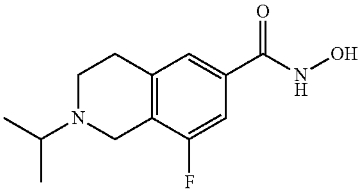

-continued
211
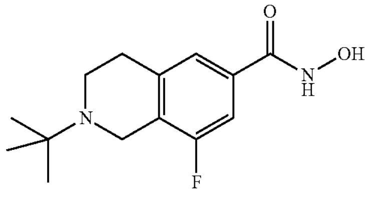
212
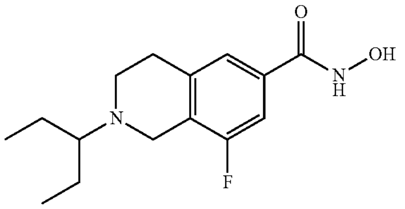
or a pharmaceutically acceptable salt thereof.
2. The compound of clause 1, wherein the compound is of formula
174
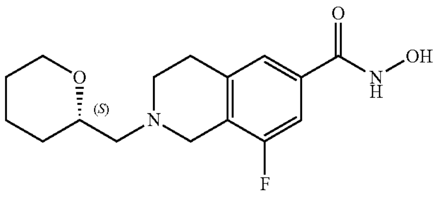
175
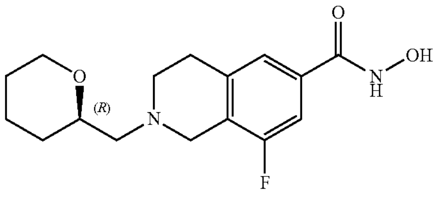
176
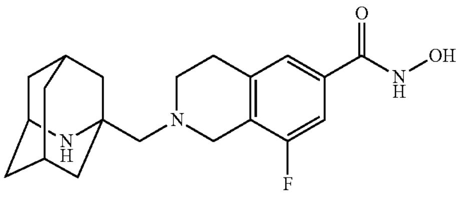
177
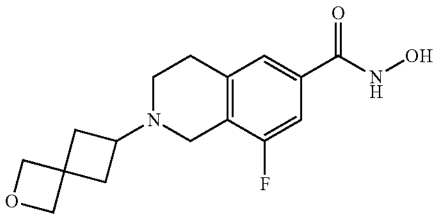
-continued
178
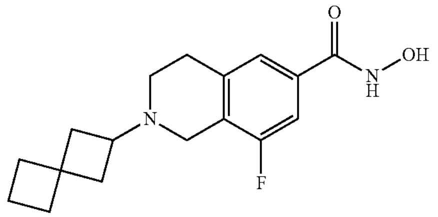
or a pharmaceutically acceptable salt thereof.
3. A compound of formula:
213
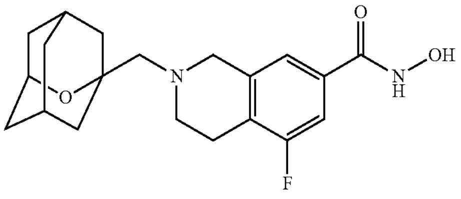
214
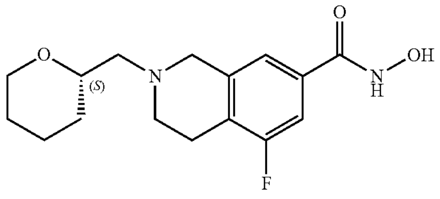
215
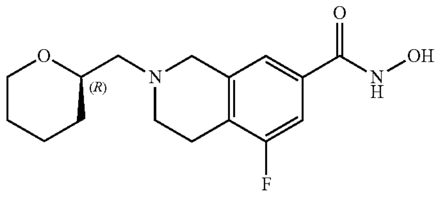
216
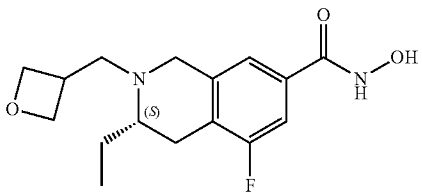
217
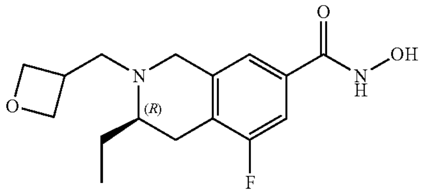
218
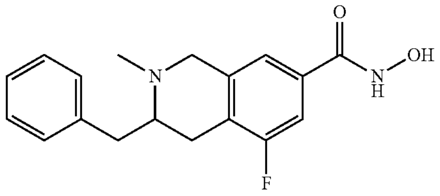

-continued
219
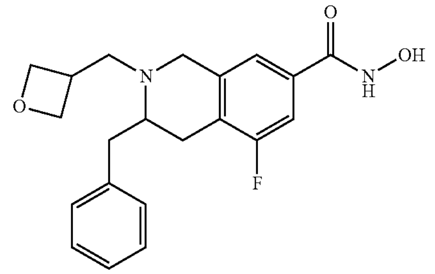
220
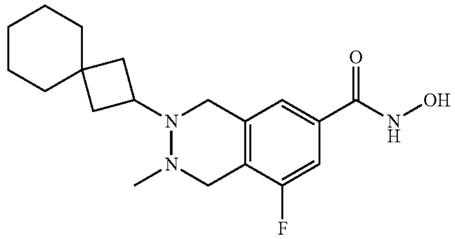
221
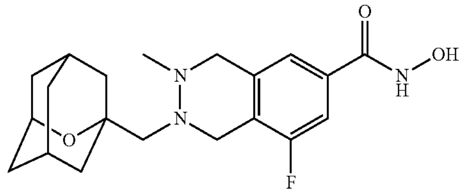
222
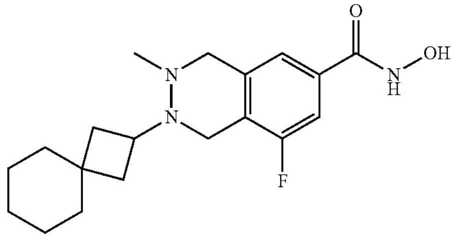
223
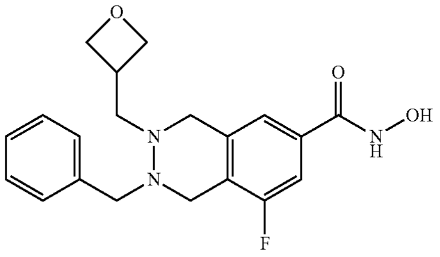
224
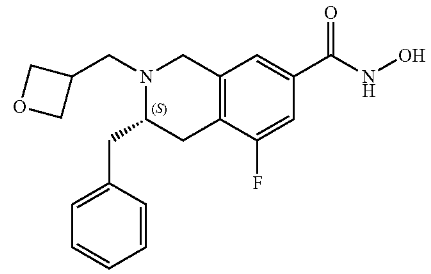
-continued
225
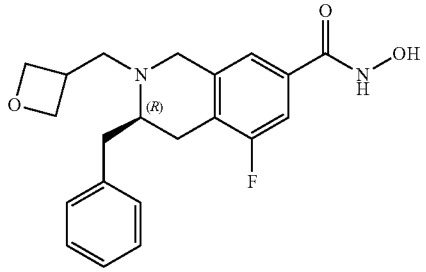
226
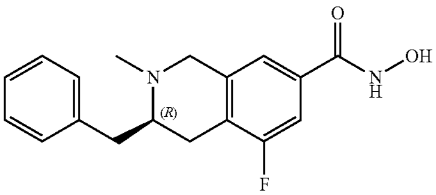
227
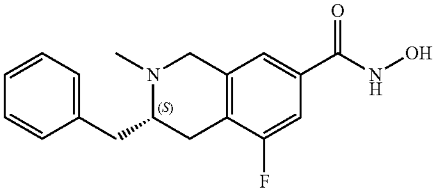
228
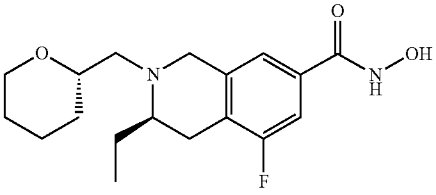
229
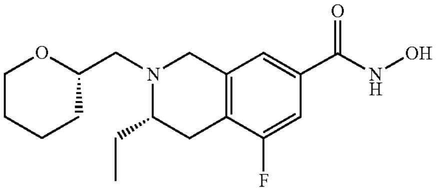
230
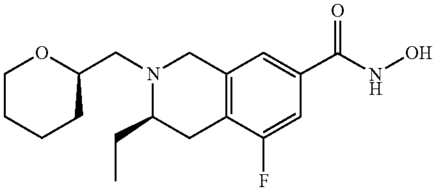
231
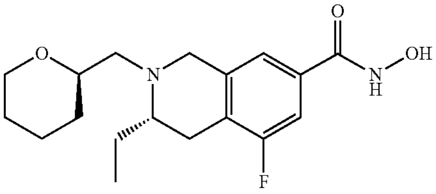

-continued
232
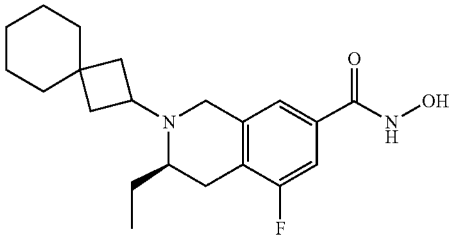
233
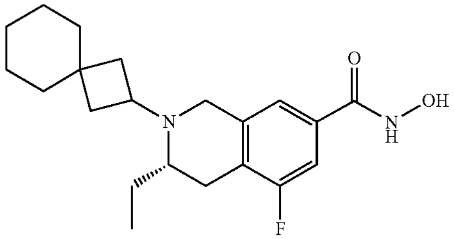
234
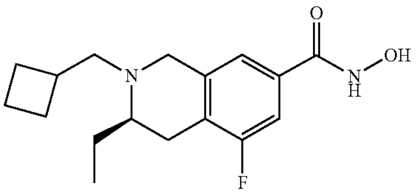
235
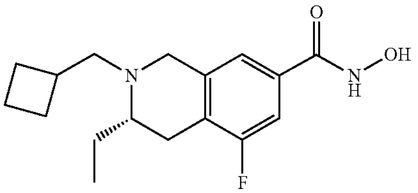
236
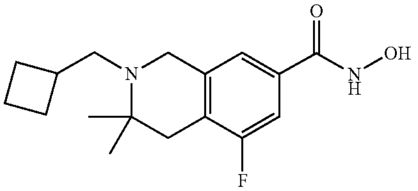
or a pharmaceutically acceptable salt thereof.
4. The compound of clause 3, wherein the compound is of formula
213
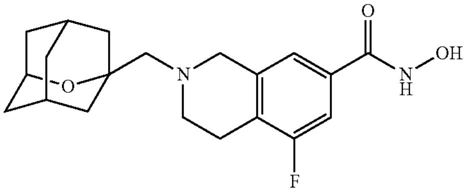
-continued
214
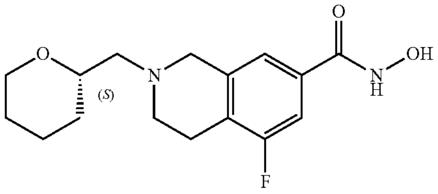
215
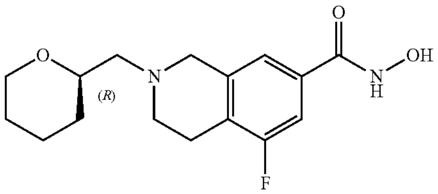
216
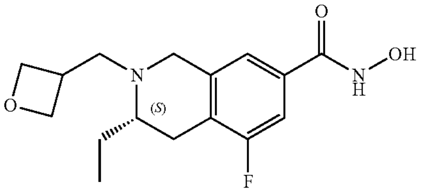
217
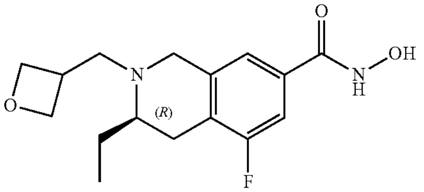
218
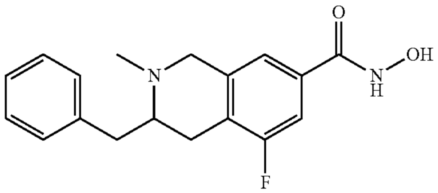
or a pharmaceutically acceptable salt thereof.
5. The compound of clause 3, wherein the compound is of formula
213
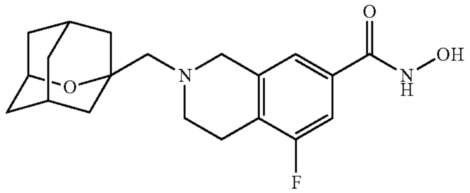
214
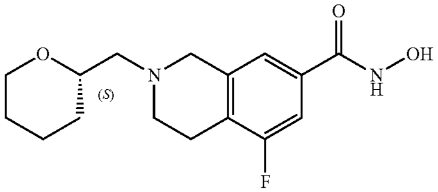

-continued
215
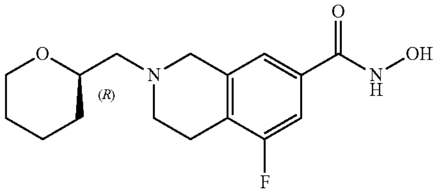
216
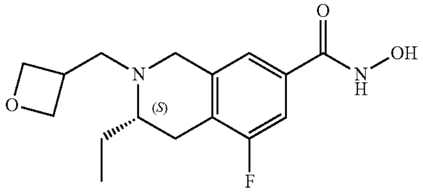
217
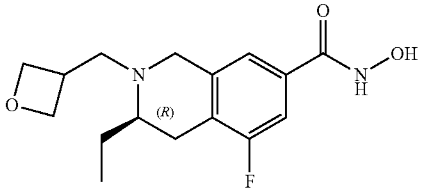
or a pharmaceutically acceptable salt thereof.
6. A compound of formula:
237
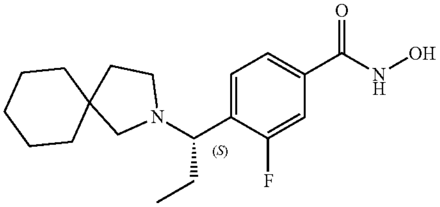
238
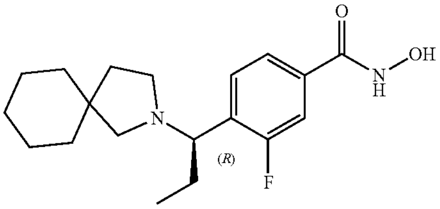
239
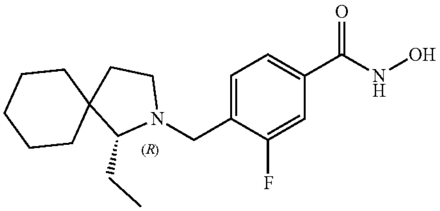
240
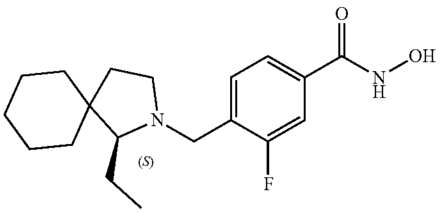
or a pharmaceutically acceptable salt thereof.
7. The compound of clause 6, wherein the compound is of formula
237
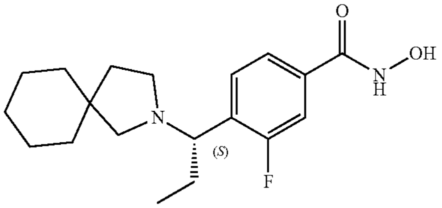
238
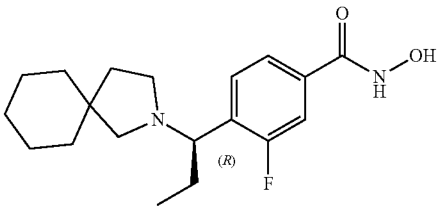
or a pharmaceutically acceptable salt thereof.
8. A compound of formula:
241
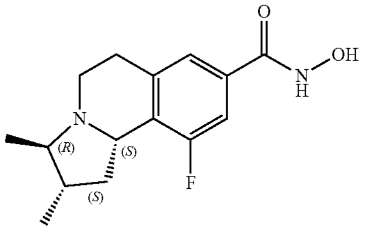
242
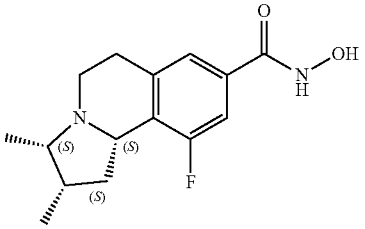
243
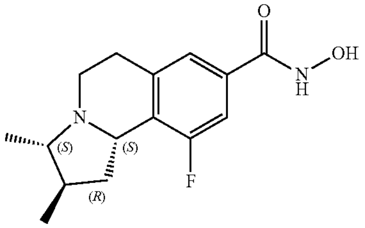
244
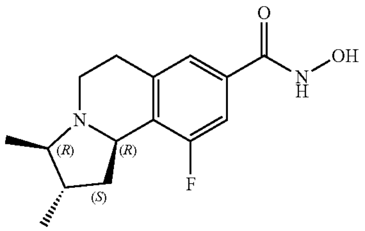

-continued
245
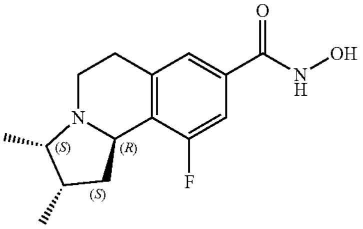
246
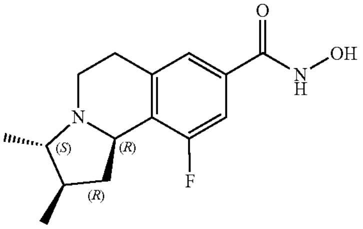
247
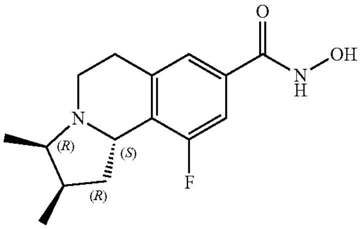
248
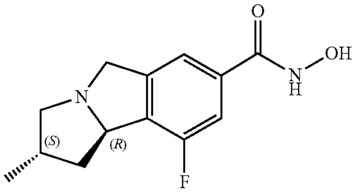
249
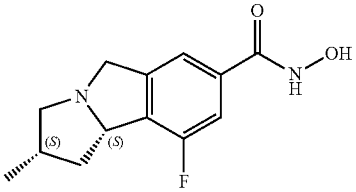
250
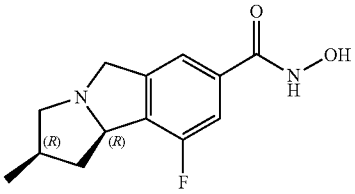
251
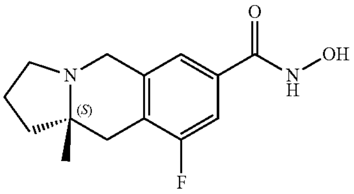
-continued
252
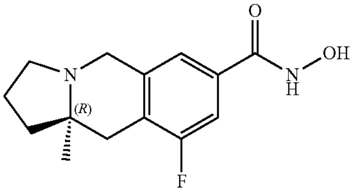
253
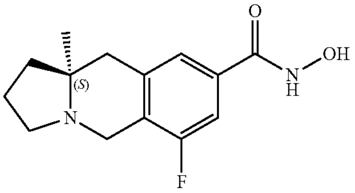
254
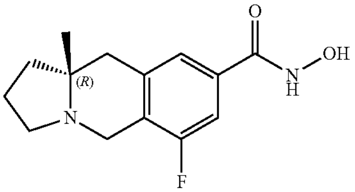
255
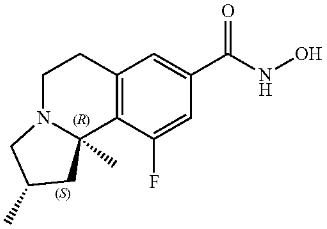
256
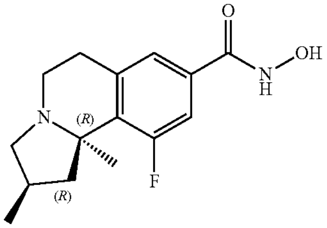
257
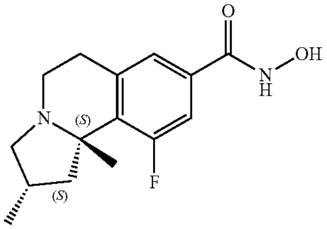
258
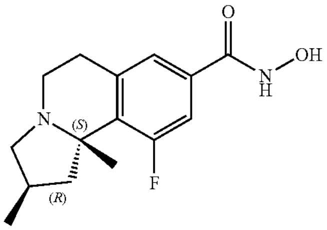

-continued
259
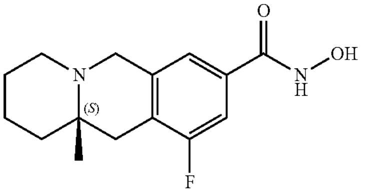
260
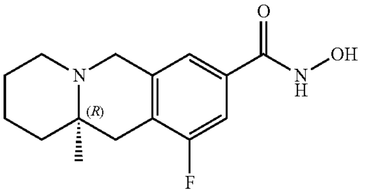
261
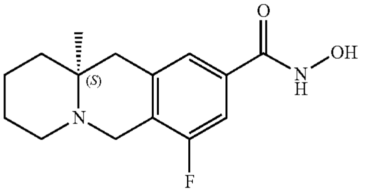
262
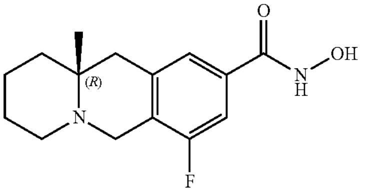
263
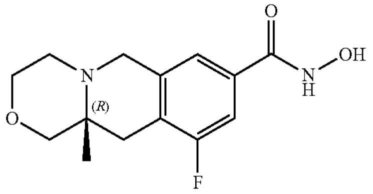
264
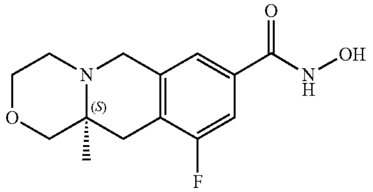
265
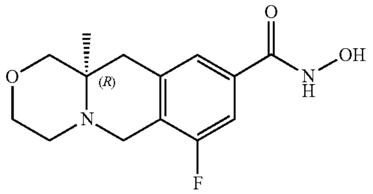
266
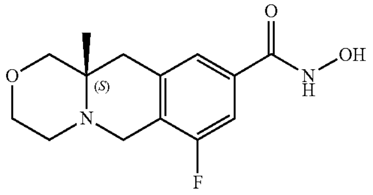
-continued
267
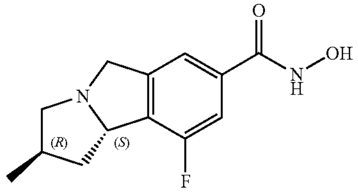
268
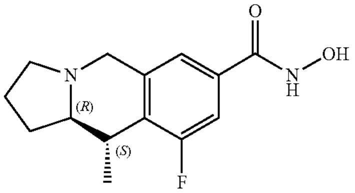
269
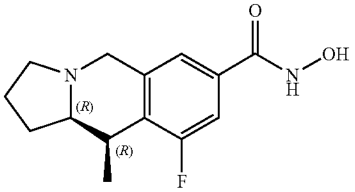
270
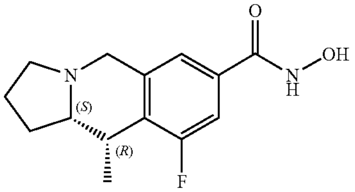
271
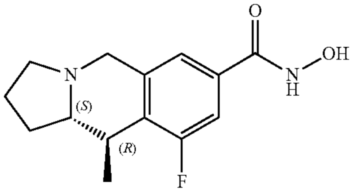
272
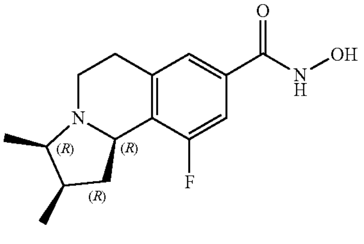
273
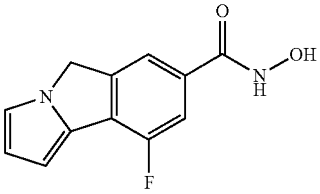
or a pharmaceutically acceptable salt thereof.

9. A compound of formula:

274

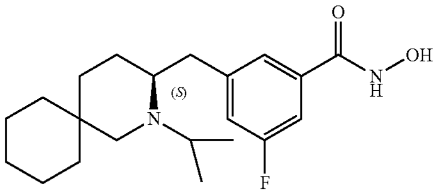

275

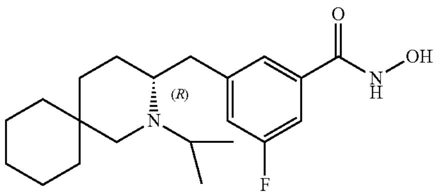

276

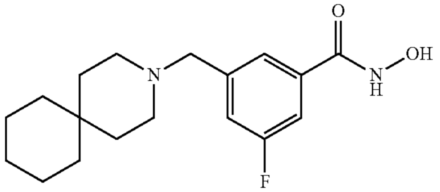

or a pharmaceutically acceptable salt thereof.

10. A compound of Formula (VII):

(VII)

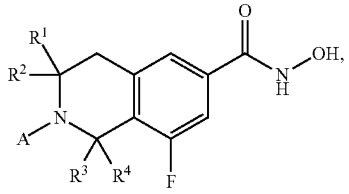

or a pharmaceutically acceptable salt thereof, wherein:

A is substituted or unsubstituted carbocyclyl or substituted or unsubstituted heterocyclyl; and $R^1$, $R^2$, $R^3$, and $R^4$ are each independently hydrogen or substituted or unsubstituted alkyl; provided that at least one of $R^1$ and $R^2$ is not hydrogen.

11. The compound of clause 10, or a pharmaceutically acceptable salt thereof, wherein: A is a substituted or unsubstituted $C_7$0.10 polycyclic spiro ring system comprising a heterocycle, substituted or unsubstituted $C_{5-10}$ spirocyclic cycloalkyl, substituted or unsubstituted $C_{3-6}$ monocyclic cycloalkyl, or substituted or unsubstituted monocyclic 4-7 membered heterocyclyl.

12. The compound of clause 10 or 11, or a pharmaceutically acceptable salt thereof, wherein: A is cyclopropyl, cyclobutyl,

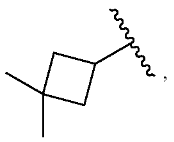 [SMILES: *C1CC(C)(C)C1], oxetanyl,

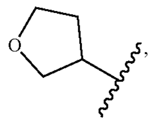, 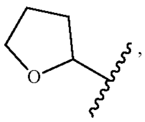, 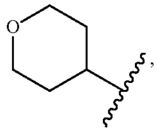, 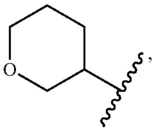, 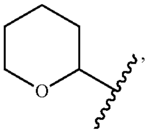, 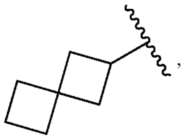, 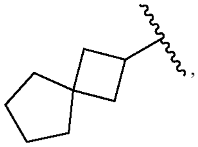, 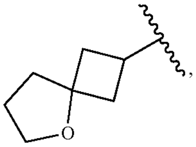, 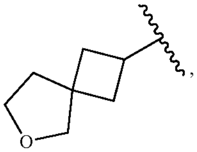, 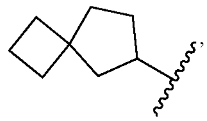, 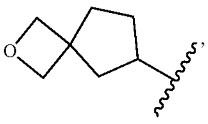, 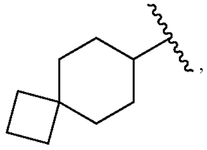, 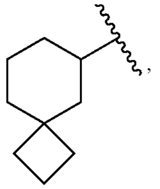, 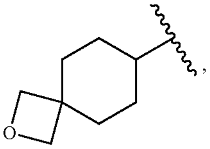, 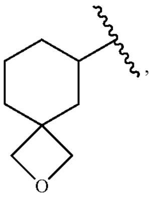, 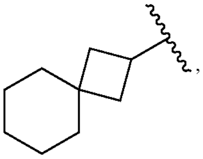, 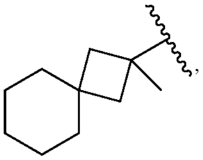, or 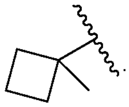.

13. The compound of any of clauses 10-12, or a pharmaceutically acceptable salt thereof, wherein: A is

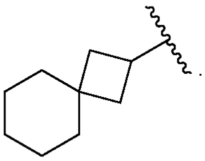 [SMILES: *C1CC2(CCCCC2)C1].

14. The compound of any of clauses 10-13, or a pharmaceutically acceptable salt thereof, wherein: $R^1$, $R^2$, $R^3$, and $R^4$ are each independently hydrogen or substituted or unsubstituted $C_{1-4}$ alkyl; provided that at least one of $R^1$ and $R^2$ is not hydrogen.

15. The compound of any of clauses 10-13, or a pharmaceutically acceptable salt thereof, wherein: $R^1$, $R^2$, $R^3$, and $R^4$ are each independently hydrogen or substituted or unsubstituted $C_{1-2}$ alkyl; provided that at least one of $R^1$ and $R^2$ is not hydrogen.

16. The compound of any of clauses 10-13, or a pharmaceutically acceptable salt thereof, wherein: $R^1$, $R^2$, $R^3$, and $R^4$ are each independently hydrogen, methyl, ethyl, propyl, isopropyl, t-butyl, cyclopropyl,

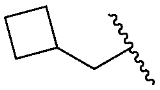,
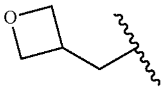, benzyl,

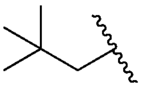, or 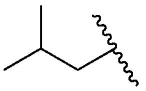;

provided that at least one of $R^1$ and $R^2$ is not hydrogen.

17. The compound of clause 10, wherein the compound is of Formula (VII-a):

(VII-a)

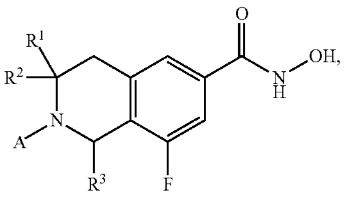

or a pharmaceutically acceptable salt thereof.

18. The compound of clause 10, wherein the compound is of Formula (VII-b):

(VII-b)

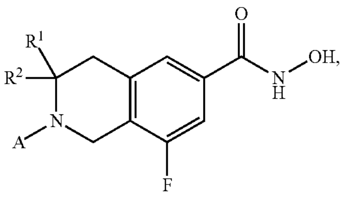

or a pharmaceutically acceptable salt thereof.

19. The compound of clause 10, wherein the compound is of Formula (VII-c):

(VII-c)

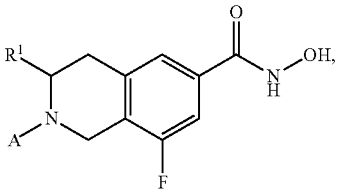

or a pharmaceutically acceptable salt thereof.

20. The compound of clause 10, wherein the compound is of formula

277

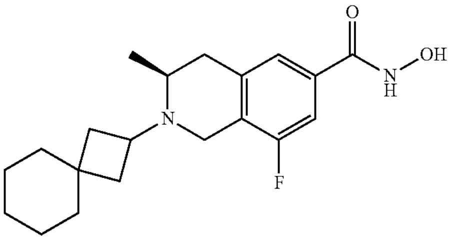

278

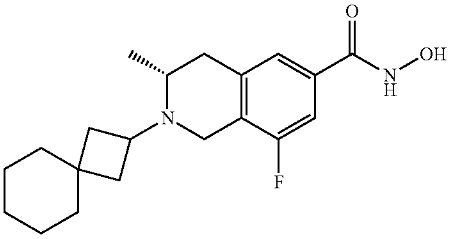

279

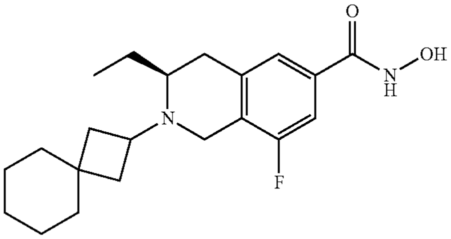

280

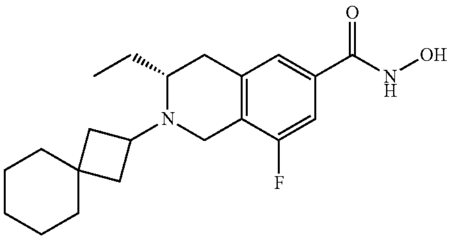

281

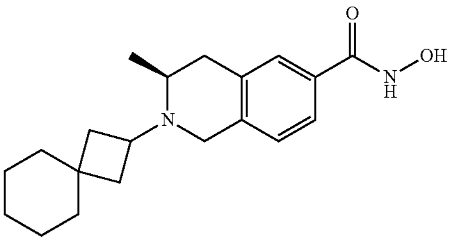

-continued

282

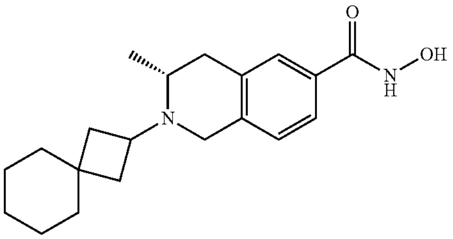

283

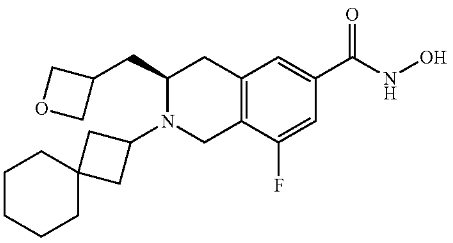

284

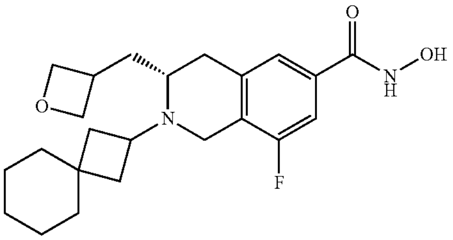

285

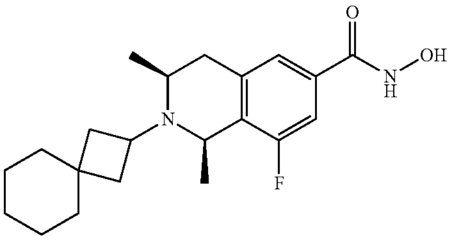

286

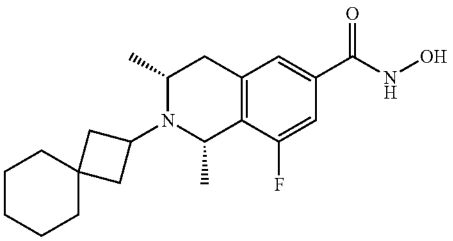

287

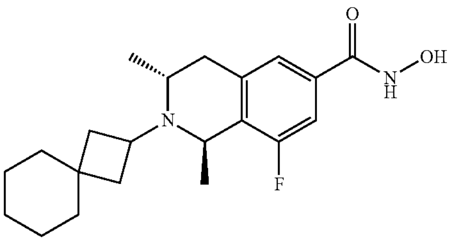

-continued

288

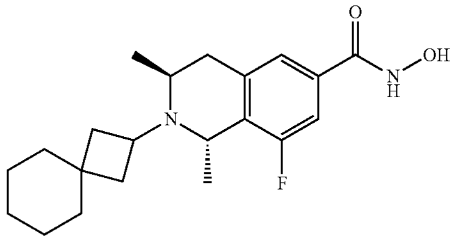

or a pharmaceutically acceptable salt thereof.

21. A pharmaceutical composition comprising a compound of any one of clauses 1-20, or a pharmaceutically acceptable salt thereof, and a pharmaceutically acceptable excipient.

22. A method of treating a disease or disorder in a subject in need thereof, wherein the disease or disorder is a proliferative disease, inflammatory disease, infectious disease, autoimmune disease, heteroimmune disease, neurological disorder, metabolic disease, cystic fibrosis, polycystic kidney disease, pulmonary hypertension, cardiac dysfunction, or disease or disorder mediated by or linked to T-cell dysregulation, the method comprising administering a compound of any one of clauses 1-20, or a pharmaceutically acceptable salt thereof, or a pharmaceutical composition of clause 21 to the subject.

23. The method of clause 22, wherein the disease or disorder is a neurodegenerative, neurodevelopmental, neuropsychiatric, or neuropathy disease.

24. The method of clause 23, wherein the neurodegenerative, neurodevelopmental, neuropsychiatric, or neuropathy disease is Fragile-X syndrome, Charcot-Marie-Tooth disease, Alzheimer's disease, Parkinson's diseases, Huntington's disease, multiple sclerosis, amyotrophic lateral sclerosis, Creutzfeldt-Jakob disease, Lewy body dementia, vascular dementia, muscular atrophy, seizure induced memory loss, schizophrenia, Rubinstein Taybi syndrome, Rett Syndrome, attention deficit hyperactivity disorder, dyslexia, bipolar disorder, social, cognitive and learning disorders associated with autism, attention deficit disorder, schizophrenia, major depressive disorder, peripheral neuropathy, diabetic retinopathy, diabetic peripheral neuropathy, chemotherapy-induced peripheral neuropathy, traumatic brain injury (TBI), chronic traumatic encephalopathy (CTE), or a tauopathy.

25. The method of clause 24, wherein the tauopathy is primary age-related tauopathy (PART)/neurofibrillary tangle-predominant senile dementia, chronic traumatic encephalopathy, dementia pugilistica, progressive supranuclear palsy, corticobasal degeneration, Pick's disease, frontotemporal dementia and parkinsonism linked to chromosome 17, Lytico-Bodig disease, ganglioglioma, gangliocytoma, meningioangiomatosis, postencephalitic parkinsonism, subacute sclerosing panencephalitis, lead encephalopathy, tuberous sclerosis, lipofuscinosis, Alzheimer's disease, or argyrophilic grain disease.

26. The method of clause 22, wherein the disease or disorder is cancer.

27. The method of clause 26, wherein the cancer is a hematological cancer.

28. The method of clause 27, wherein the cancer is a leukemia, T-cell lymphoma, Hodgkin's Disease, non-Hodgkin's lymphoma, or multiple myeloma.

29. The method of clause 22, wherein the cancer comprises a solid tumor.
30. The method of clause 29, wherein the cancer is glioma, glioblastoma, non-small cell lung cancer, brain tumor, neuroblastoma, bone tumor, soft-tissue sarcoma, head and neck cancer, genitourinary cancer, lung cancer, breast cancer, pancreatic cancer, melanoma, stomach cancer, brain cancer, liver cancer, thyroid cancer, clear cell carcinoma, uterine cancer, or ovarian cancer.
31. The method of any one of clauses 22-30, further comprising administering an additional therapeutic agent.
32. The compound of any one of clauses 1-20 for use in the treatment of a disease or disorder in a subject in need thereof, wherein the disease or disorder is a proliferative disease, inflammatory disease, infectious disease, autoimmune disease, heteroimmune disease, neurological disorder, metabolic disease, cystic fibrosis, polycystic kidney disease, pulmonary hypertension, cardiac dysfunction, or disease or disorder mediated by or linked to T-cell dysregulation.
33. The compound of clause 32, wherein the disease or disorder is a neurodegenerative, neurodevelopmental, neuropsychiatric, or neuropathy disease.
34. The compound of clause 33, wherein the neurodegenerative, neurodevelopmental, neuropsychiatric, or neuropathy disease is Fragile-X syndrome, Charcot-Marie-Tooth disease, Alzheimer's disease, Parkinson's diseases, Huntington's disease, multiple sclerosis, amyotrophic lateral sclerosis, Creutzfeldt-Jakob disease, Lewy body dementia, vascular dementia, muscular atrophy, seizure induced memory loss, schizophrenia, Rubinstein Taybi syndrome, Rett Syndrome, attention deficit hyperactivity disorder, dyslexia, bipolar disorder, social, cognitive and learning disorders associated with autism, attention deficit disorder, schizophrenia, major depressive disorder, peripheral neuropathy, diabetic retinopathy, diabetic peripheral neuropathy, chemotherapy-induced peripheral neuropathy, traumatic brain injury (TBI), chronic traumatic encephalopathy (CTE), or a tauopathy.
35. The compound of clause 34, wherein the tauopathy is primary age-related tauopathy (PART)/neurofibrillary tangle-predominant senile dementia, chronic traumatic encephalopathy, dementia pugilistica, progressive supranuclear palsy, corticobasal degeneration, Pick's disease, frontotemporal dementia and parkinsonism linked to chromosome 17, Lytico-Bodig disease, ganglioglioma, gangliocytoma, meningioangiomatosis, postencephalitic parkinsonism, subacute sclerosing panencephalitis, lead encephalopathy, tuberous sclerosis, lipofuscinosis, Alzheimer's disease, or argyrophilic grain disease.
36. The compound of clause 32, wherein the disease or disorder is cancer.
37. The compound of clause 36, wherein the cancer is a hematological cancer.
38. The compound of clause 37, wherein the cancer is a leukemia, T-cell lymphoma, Hodgkin's Disease, non-Hodgkin's lymphoma, or multiple myeloma.
39. The compound of clause 36, wherein the cancer comprises a solid tumor.
40. The compound of clause 39, wherein the cancer is glioma, glioblastoma, non-small cell lung cancer, brain tumor, neuroblastoma, bone tumor, soft-tissue sarcoma, head and neck cancer, genitourinary cancer, lung cancer, breast cancer, pancreatic cancer, melanoma, stomach cancer, brain cancer, liver cancer, thyroid cancer, clear cell carcinoma, uterine cancer, or ovarian cancer.
41. A kit comprising a compound of any one of clauses 1-20, or a pharmaceutically acceptable salt thereof, or a pharmaceutical composition of clause 21; and instructions for administering the compound, the pharmaceutically acceptable salt thereof, or the pharmaceutical composition to a subject.

EXAMPLES

In order that the invention described herein may be more fully understood, the following examples are set forth. The examples described in this application are offered to illustrate the compounds, pharmaceutical compositions, and methods provided herein and are not to be construed in any way as limiting their scope.

Synthetic Methods

General details. All oxygen and/or moisture-sensitive reactions were carried out under nitrogen ($N_2$) atmosphere in glassware that had been flame-dried under vacuum (approximately 0.5 mm Hg) and purged with $N_2$ prior to use. All reagents and solvents were purchased from commercial vendors and used as received, or synthesized according to methods already reported. NMR spectra were recorded on a Bruker 300 (300 MHz $^1$H, 75 MHz $^{13}$C) or Varian UNITY INOVA 500 (500 MHz $^1$H, 125 MHz $^{13}$C) spectrometer. Proton and carbon chemical shifts are reported in ppm (δ) referenced to the NMR solvent. Data are reported as follows: chemical shifts, multiplicity (br=broad, s=singlet, d=doublet, t=triplet, q=quartet, m=multiplet; coupling constant(s) in Hz). Unless otherwise indicated, NMR data were collected at 25° C. Flash chromatography was performed using 40-60 μm Silica Gel (60 Å mesh) on a Teledyne Isco Combiflash $R_f$. Tandem Liquid Chromatography/Mass Spectrometry (LC/MS) was performed on a Waters 2795 separations module and 3100 mass detector. Analytical thin layer chromatography (TLC) was performed on EM Reagent 0.25 mm silica gel 60-F plates.

In the below examples, certain compounds are designated as having absolute stereochemistry at chiral centers in their chemical structures. Where this stereochemistry is defined in the chemical structures, the compounds are pure stereoisomers as each stereoisomer was prepared and isolated. However, the absolute stereochemistry of these compounds are unknown. For compounds having chiral centers that were not isolated as single stereoisomers, the compounds are mixtures of stereoisomers.

Compounds of Formula (I) were prepared following the synthetic schemes and procedures described in detail below.

General Scheme

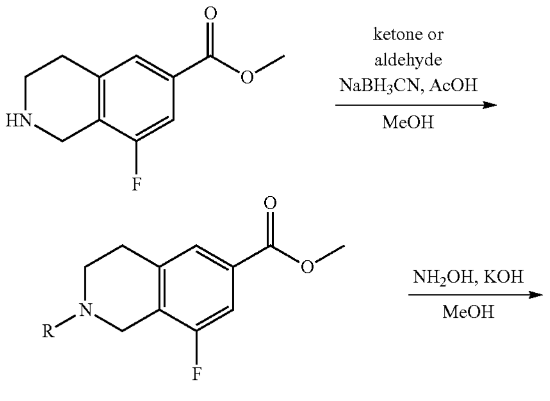

-continued

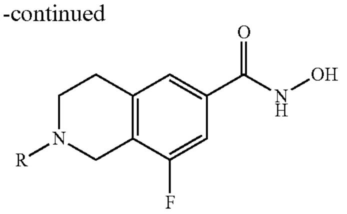

In general, compounds of Formula (I) can be prepared via reductive amination of the above fluorinated tetrahydroisoquinoline followed by conversion of the ester to the hydroxamic acid employing reaction methods well known to one of ordinary skill in the art and as described in more detail below.

8-Fluoro-N-hydroxy-2-(7-oxaspiro[3.5]nonan-2-yl)-1,2,3,4-tetrahydroisoquinoline-6-carboxamide (179)

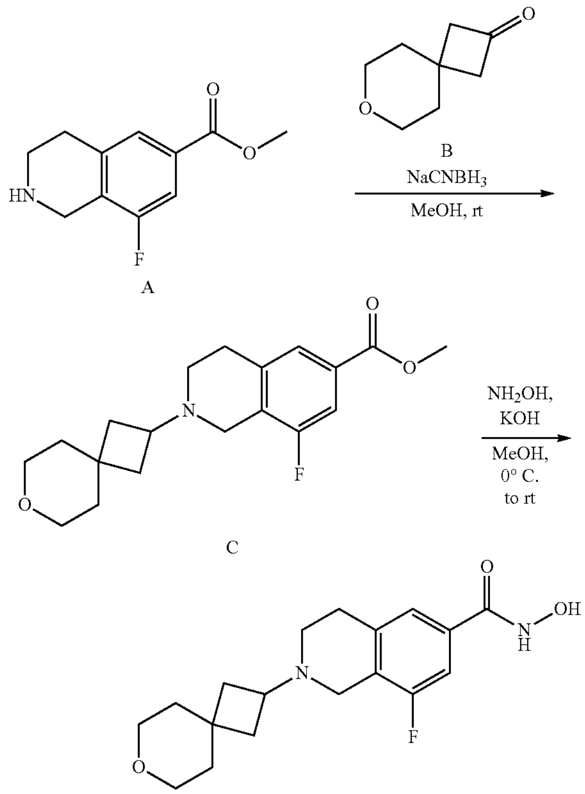

To a mixture of methyl 8-fluoro-1,2,3,4-tetrahydroisoquinoline-6-carboxylate (A, 200 mg, 0.9564 mmol, 1.0 equiv.) in MeOH (10 mL) was added 7-oxaspiro[3.5]nonan-2-one (2, 160.9 mg, 1.1477 mmol, 1.2 equiv.) and the pH adjusted to ~6 with AcOH at room temperature. After 1 h, $NaCNBH_3$ (120 mg, 1.9128 mmol, 2.0 equiv.) was added and the reaction allowed to stir at room temperature for 5 h. After the completion of the reaction, the reaction mixture was concentrated to get the crude residue which was diluted with $H_2O$ (20 mL). The mixture was then extracted with ethyl acetate (20 mL×3) and the organic layer was dried over $Na_2SO_4$, concentrated and purified over column chromatography. using ethyl acetate and hexane to give methyl 8-fluoro-2-(7-oxaspiro[3.5]nonan-2-yl)-1,2,3,4-tetrahydroisoquinoline-6-carboxylate (C, 100 mg, 0.2999 mmol, 31%) MS (ESI): 334 $[M+H]^+$.

To an ice cold solution of methyl 8-fluoro-2-(7-oxaspiro[3.5]nonan-2-yl)-1,2,3,4-tetrahydroisoquinoline-6-carboxylate (C, 100 mg, 0.2999 mmol, 1.0 equiv) in MeOH (2 mL) was added 50% aq. $NH_2OH$ soln (0.37 mL, 5.9988 mmol, 20.0 equiv.) at 0° C. and KOH (42 mg, 0.7497 mmol, 2.5 equiv) and was allowed to stir for 30 minutes at room temperature. After the completion of the reaction, the reaction mixture was concentrated to get the crude residue which was diluted with $H_2O$ (2 mL) and neutralized by the addition of AcOH. The precipitate formed was filtered, washed with water (10 mL) and n-hexane to obtain crude product as residue. The crude compound was purified by prep HPLC method using 0.1% TFA in water and $CH_3CN$ as a mobile phase to give 8-fluoro-N-hydroxy-2-(7-oxaspiro[3.5]nonan-2-yl)-1,2,3,4-tetrahydroisoquinoline-6-carboxamide (179, 9.603 mg, 0.02871 mmol, 9.57%). MS (ESI): 335 $[M+H]^+$. $^1H$ NMR (400 MHz, DMSO-$d_6$) δ 11.1 (bs, 1H), 9.11 (bs, 1H), 7.40 (s, 1H), 7.31 (d, J=12.0 Hz, 1H), 3.54-3.30 (m, 6H), 2.92-2.60 (m, 3H), 2.10-2.05 (m, 2H), 1.66-1.44 (m, 6H).

N-hydroxy-2-(spiro[3.5]nonan-2-yl)-1,2,3,4-tetrahydroisoquinoline-7-d-6-carboxamide (504)

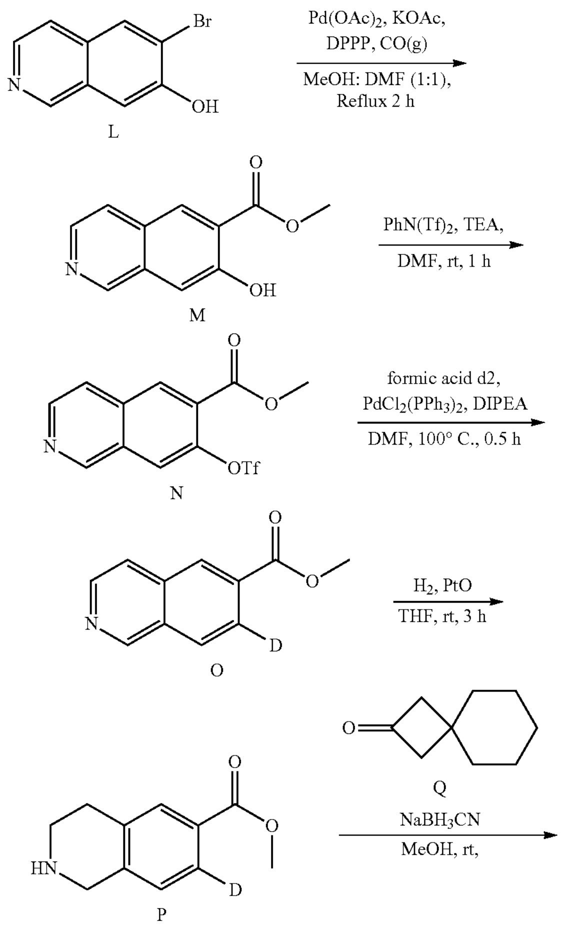

-continued

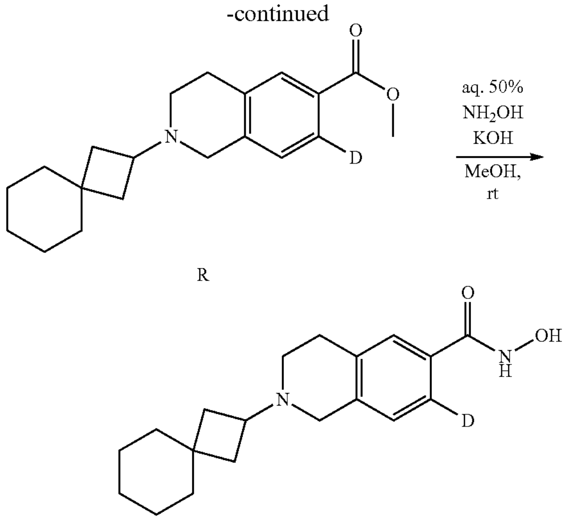

R

504

To a solution of 6-bromoisoquinolin-7-ol (L, 1.3 g, 5.803 mmol, 1.0 equiv.) in MeOH:DMF (16 mL, 1:1) was added KOAc (1.7 g, 17.409 mmol, 3.0 equiv.) and the mixture was degassed for 20 mins. DPPP (359 mg, 0.870 mmol, 0.15 equiv.) and $Pd(OAc)_2$ (130 mg, 0.580 mmol, 0.1 equiv.) were then added at room temperature and heated to 100° C. under CO atmosphere (400 psi) for 16 h. Completion of reaction was monitored by TLC and LCMS. The reaction mixture was filtered through celite and concentrated in vacuo. The crude compound was purified by column chromatography using hexane and ethyl acetate (22%) to get methyl 7-hydroxyisoquinoline-6-carboxylate (M, 235 mg, 1.157 mmol, 20%) as a white solid. MS (ESI): 204 [M+H]+

To a stirred solution of methyl 7-hydroxyisoquinoline-6-carboxylate (M, 235 mg, 1.157 mmol, 1.0 equiv.) in DCM (2.0 mL) at 0° C. were added TEA (0.4 mL, 2.894 mmol, 2.5 equiv.) and $PhN(Tf)_2$ (620 mg, 1.736 mmol, 1.5 equiv.). The reaction mixture was stiffed at room temperature for 1 h. Completion of reaction was monitored by TLC. The reaction mass was concentrated, basified using aq. $NaHCO_3$, extracted twice with DCM (20 mL×2). The organic layers were combined, dried over $Na_2SO_4$ and concentrated. The resulting crude mass was purified by column chromatography using hexane and ethyl acetate (27%) to obtain methyl 7-(((trifluoromethyl)sulfonyl)oxy)isoquinoline-6-carboxylate (N, 204 mg, 0.6085 mmol, 52%). MS (ESI): 336 $[M+H]^+$ To a solution of methyl 7-(trifluoromethyl)sulfonyl)oxy) isoquinoline-6-carboxylate (N, 204 mg, 0.621 mmol, 1.0 equiv.) in DMF (3.0 mL) were added DIPEA (0.3 mL, 1.801 mmol, 2.9 equiv.), $PdCl_2(PPh_3)_2$ (22 mg, 0.031 mmol, 0.05 equiv.), and formic acid-$d_2$ (0.04 mL, 1.242 mmol, 2.0 equiv). The reaction mixture was stiffed at 100° C. for 30 min. Completion of reaction was monitored by TLC and LCMS. Upon completion, the reaction mixture was concentrated and the crude compound was purified by column chromatography using hexane and ethyl acetate (27%) to get methyl isoquinoline-6-carboxylate-7-d (0, 130 mg, 0.6907 mmol, quantitative). MS (ESI): 189 $[M+H]^+$.

To a stirred solution of methyl isoquinoline-6-carboxylate-7-d (0, 130 mg, 0.6907 mmol, 1 equiv.) in THF (5.0 mL) were added 1N HCl (cat.) and $PtO_2$ (39 mg, 0.069 mmol, 0.25 equiv.) under $H_2$ atmosphere (200 psi) in a 50 mL autoclave. The mixture was stirred room temperature for 3 h and the reaction mixture was filtered through celite and washed with THF (10.0 mL). The mixture was concentrated under vacuum to give methyl 1,2,3,4-tetrahydroisoquinoline-6-carboxylate-7-d as a yellow oil (P, 50 mg, 0.260 mmol, 37%).

Compound R was prepared in a manner analogous to that used for preparation of compound C in the synthesis of compound 179. MS (ESI): 315 $[M+H]^+$.

To a stirred solution of methyl 2-(spiro[3.5]nonan-2-yl)-1,2,3,4-tetrahydroisoquinoline-6-carboxylate-7-d (R, 90 mg, 0.325 mmol, 1 equiv.) in methanol (2.0 mL) were added 50% aq.$NH_2OH$ (214.4 mg, 6.498 mmol, 20 equiv; 50% aq solution of in $H_2O$) and KOH (35.6 mg, 0.648 mmol, 2.0 equiv.) at 0° C. for 15 mins. Completion of reaction was confirmed by TLC. Reaction mixture was evaporated to dryness; the crude material was purified by Prep HPLC purification using (1) 0.1% TFA in water (2) 100% acetonitrile. The solvents were lyophilized to give N-hydroxy-2-(spiro[3.5]nonan-2-yl)-1,2,3,4-tetrahydroisoquinoline-7-d-6-carboxamide (504) (~3 mg, 0.009510 mmol, 6%). MS (ESI): 279 $[M+H]^+$.

The following compounds were prepared in a manner analogous to that used for preparing compound 179. Although certain compound pairs below are designated as having absolute stereochemistry as each stereoisomer was prepared and isolated, the absolute stereochemistry of each is unknown.

| Compound | Structure/Name | Characterization |
|---|---|---|
| 174 | 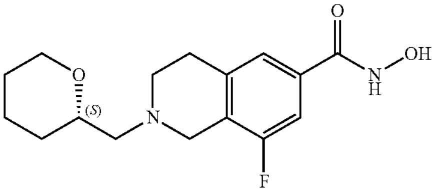 (S)-8-fluoro-N-hydroxy-2-((tetrahydro-2H-pyran-2-yl)methyl)-1,2,3,4-tetrahydroisoquinoline-6-carboxamide | $^1H$ NMR (400 MHz, DMSO-$d_6$) δ 11.18 (s, 1H), 9.09 (s, 1H), 7.40 (s, 1H), 7.31 (d, J = 10.5Hz, 1H), 3.92 - 3.79 (m, 1H), 3.62 (s, 2H), 3.51 (dt, J = 11.8, 4.8 Hz, 1H), 2.84 (t, J = 5.7 Hz, 2H), 2.73 (dd, J = 16.1, 5.6 Hz, 2H), 2.57 (dd, J = 13.1, 6.6 Hz, 2H), 1.77 (d, J = 10.3 Hz, 1H), 1.60 (d, J = 13.3 Hz, 1H), 1.46 (dt, J = 9.4, 4.9 Hz, 3H), 1.26 - 1.13 (m, 1H). MS (ESI): 309 $[M + H]^+$ Note: absolute stereochemistry is unknown |

-continued

| Compound | Structure/Name | Characterization |
|---|---|---|
| 175 | 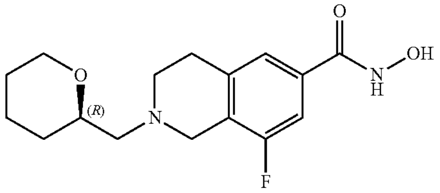<br>(R)-8-fluoro-N-hydroxy-2-((tetrahydro-2H-pyran-2-yl)methyl)-1,2,3,4-tetrahydroisoquinoline-6-carboxamide | $^{1}$H NMR (400 MHz, DMSO-$d_6$) δ 11.18 (s, 1H), 9.09 (s, 1H), 7.40 (s, 1H), 7.35 − 7.22 (m, 1H), 3.92 − 3.78 (m, 1H), 3.62 (s, 2H), 3.56 − 3.47 (m, 1H), 2.83 (d, J = 5.8 Hz, 2H), 2.73 (ddd, J = 22.3, 11.6, 5.6 Hz, 2H), 2.57 (dd, J = 13.0, 6.5 Hz, 2H), 1.77 (d, J = 10.6 Hz, 1H), 1.60 (d, J = 12.8 Hz, 1H), 1.52 − 1.38 (m, 3H), 1.29 − 1.12 (m, 1H). MS (ESI): 309 [M + H]$^{+}$<br>Note: absolute stereochemistry is unknown |
| 177 | 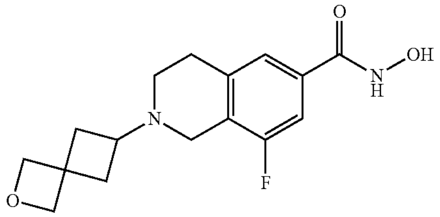 [SMILES: O=C(NO)c1cc(F)c2c(c1)CCN(C1CC3(COC3)C1)C2]<br>8-fluoro-N-hydroxy-2-(2-oxaspiro[3.3]heptan-6-yl)-1,2,3,4-tetrahydroisoquinoline-6-carboxamide | $^{1}$HNMR (400 MHz, Methanol-d4) δ 7.36 (s, 1H), 7.26 (d, J = 10.2 Hz, 1H), 4.74 (s, 2H), 4.60 (s, 2H), 3.53 (s, 2H), 2.93 (t, J = 5.9 Hz, 2H), 2.81 (q, J = 7.8 Hz, 1H), 2.63 (t, J = 6.0 Hz, 2H), 2.53 (ddd, J = 9.9, 7.0, 3.1 Hz, 2H), 2.13 (td, J = 8.8, 3.0 Hz, 2H).<br>LC-MS: m/z 307 [M + H] |
| 176 | 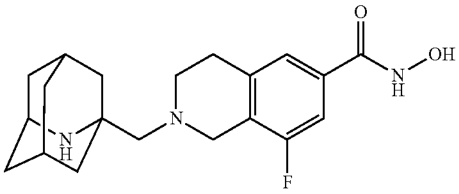 [SMILES: O=C(NO)c1cc(F)c2c(c1)CCN(CC13CC4CC(CC(C4)N1)C3)C2] | LC-MS: m/z 360 [M + H] |
| 178 | 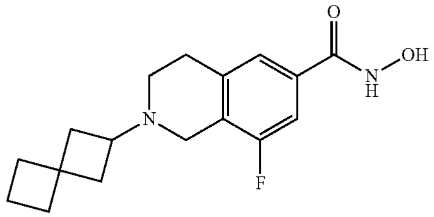 [SMILES: O=C(NO)c1cc(F)c2c(c1)CCN(C1CC3(CCC3)C1)C2] | $^{1}$HNMR (400 MHz, Methanol-d4) δ 7.38 (s, 1H), 7.28 (d, J = 10.2Hz, 1H), 3.54 (s, 2H), 2.96 (t, 6.0Hz, 2H), 2.86 (q, J = 7.9 Hz, 1H), 2.65 (t, J = 5.9Hz, 2H), 2.30 (s, 2H), 2.10 (t, J = 7.3Hz, 2H), 2.00-1.84 (m, 6H)<br>LC-MS: m/z 305 [M + H] |
| 183 | 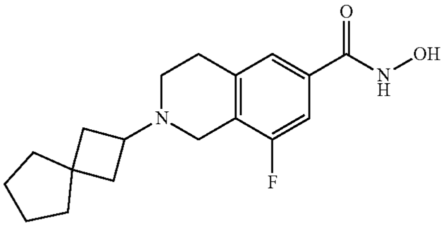 [SMILES: O=C(NO)c1cc(F)c2c(c1)CCN(C1CC3(CCCC3)C1)C2]<br>8-fluoro-N-hydroxy-2-(spiro[3.4]octan-2-yl)-1,2,3,4-tetrahydroisoquinoline-6-carboxamide | $^{1}$H NMR (400 MHz, Methanol-$d_4$) δ 7.40 (s, 1H), 7.30 (d, J = 10.2 Hz, 1H), 3.57 (s, 2H), 2.97 (q, J = 4.7, 3.0 Hz, 3H), 2.68 (t, J = 6.0 Hz, 2H), 2.15 (td, J = 8.3, 7.5, 2.8 Hz, 2H), 1.97 − 1.84 (m, 2H), 1.68 (h, J = 6.7, 6.2 Hz, 4H), 1.60 (d, J = 3.6 Hz, 4H). MS (ESI): 319 [M + H]$^{+}$ |
| 188 | 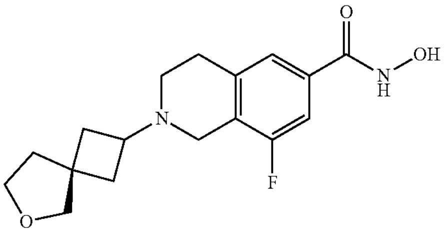 | MS (ESI): 321 [M + H]$^{+}$<br>Note: absolute stereochemistry is unknown |

-continued

| Compound | Structure/Name | Characterization |
|---|---|---|
| | 8-fluoro-N-hydroxy-2-(6-oxaspiro[3.4]octan-2-yl)-1,2,3,4-tetrahydroisoquinoline-6-carboxamide | |
| 189 | 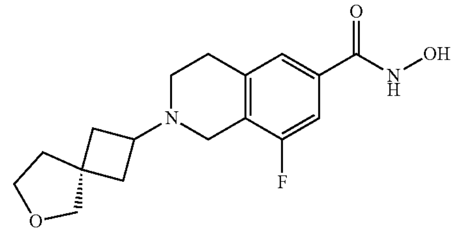 8-fluoro-N-hydroxy-2-(6-oxaspiro[3.4]octan-2-yl)-1,2,3,4-tetrahydroisoquinoline-6-carboxamide | $^1$H NMR (400 MHz, DMSO-$d_6$) δ 1.97 (d, J = 6.9 Hz, 1H), 2.38 (s, 2H), 3.17 (s, 2H), 3.59 (s, 1H), 3.74 (t, J = 6.8 Hz, 1H), 3.94 (s, 1H), 4.21 (s, OH), 4.57 (s, OH), 7.50 (d, J = 10.2 Hz, OH), 7.59 (s, 1H), 9.24 (s, OH), 10.33 (s, 1H), 11.38 (s, 1H). MS (ESI): 321 $[M + H]^+$ Note: absolute stereochemistry is unknown |
| 198 | 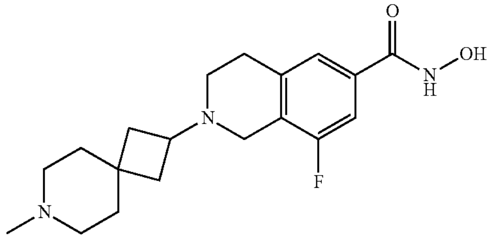 [SMILES: CN1CCC2(CC1)CC(N1CCc3cc(C(=O)NO)cc(F)c3C1)C2] 8-fluoro-N-hydroxy-2-(7-methyl-7-azaspiro[3.5]nonan-2-yl)-1,2,3,4-tetrahydroisoquinoline-6-carboxamide | 1H NMR (400 MHz, DMSO-d6) δ 11.37 (s, 1H), 10.86 (s, 1H), 9.48 (s, 1H), 9.22 (s, 1H), 7.57 (s, 1H), 7.48 (d, J = 10.4 Hz, 1H), 4.15 (s, 1H), 3.86 (s, OH), 3.34 (t, J = 15.0 Hz, 1H), 3.15 (s, 2H), 2.76(d, J = 4.3 Hz, 2H), 2.45 (s, 6H), 2.21 (s, 1H), 2.09 (s, 1H), 1.91 (d, J = 14.4 Hz, 1H), 1.73 (s, 2H),1.73 – 1.64 (m, 0H), 1.01 (s, 2H). MS (ESI): 348 $[M + H]^+$ |
| 199 | 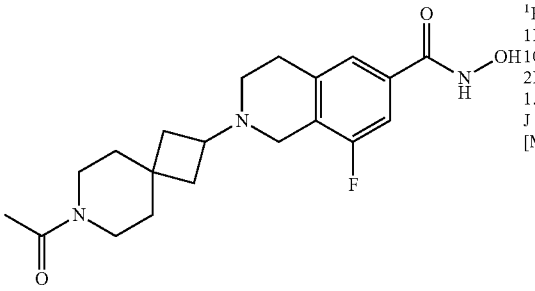 2-(7-acetyl-7-azaspiro[3.5]nonan-2-yl)-8-fluoro-N-hydroxy-1,2,3,4-tetrahydroisoquinoline-6-carboxamide | $^1$H NMR (400 MHz, DMSO-$d_6$) δ 11.23 (s, 1H), 9.11 (s, 1H), 7.42 (s, 1H), 7.33 (d, J = 10.5Hz, 1H), 3.45 (s, 4H), 2.85 (d, J = 5.9 Hz, 2H), 2.08 (s, 2H), 1.98 (d, J = 7.1 Hz, 3H), 1.64 (d, J = 9.5Hz, 2H), 1.58 (s, 1H), 1.49 (d, J = 5.8 Hz, 2H), 1.39 (s, 1H). MS (ESI): 376 [M + H]+ |
| 292 | 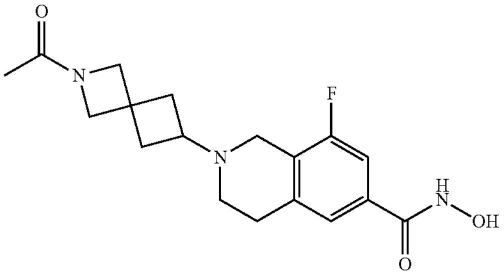 [SMILES: CC(=O)N1CC2(CC(N3CCc4cc(C(=O)NO)cc(F)c4C3)C2)C1] 2-(2-acetyl-2-azaspiro[3.3]heptan-6-yl)-8-fluoro-N-hydroxy-1,2,3,4-tetrahydroisoquinoline-6-carboxamide | $^1$H NMR (400 MHz, DMSO-$d_6$) δ 7.38 (s, 1H), 7.29 (d, J = 10.5Hz, 1H), 4.14 (s, 1H), 4.01 (s, 1H), 3.86 (s, 1H), 3.73 (s, 1H), 3.42 (s, 2H), 2.82 (s, 3H), 2.05 (d, J = 10.2 Hz, 2H), 1.72 (d, J = 6.6 Hz, 3H). MS (ESI): 348 $[M + H]^+$ |

-continued

| Compound | Structure/Name | Characterization |
|---|---|---|
| 391 | 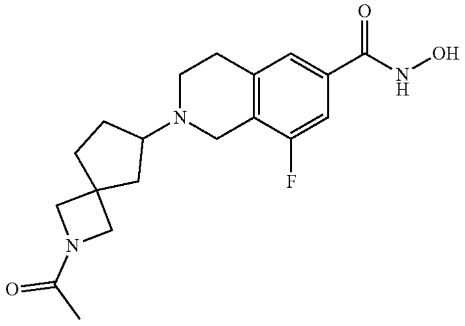 [SMILES: CC(=O)N1CC2(CCC(N3CCc4cc(C(=O)NO)cc(F)c4C3)C2)C1] 2-(2-acetyl-2-azaspiro[3.4]octan-6-yl)-8-fluoro-N-hydroxy-1,2,3,4-tetrahydroisoquinoline-6-carboxamide | $^{1}$H NMR (400 MHz, DMSO-d6) δ 11.36 (s, 1H), 10.26 (s, 1H), 9.22 (s, 1H), 7.56 (s, 1H), 7.48 (d, J = 10.2 Hz, 1H), 4.59 (s, 1H), 4.35 (s, 1H), 4.10 – 3.90 (m, 3H), 3.80 – 3.66 (m, 4H), 3.16 (s, 2H), 2.14 (s, 2H), 2.01 – 1.81 (m, 4H), 1.74 (d, J = 2.8 Hz, 3H). MS (ESI): 362 [M + H]+ |
| 506 | 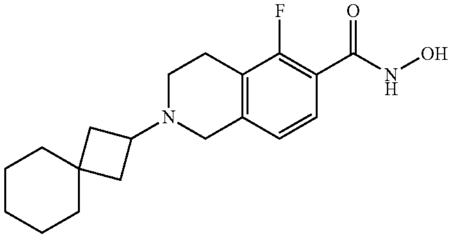 [SMILES: O=C(NO)c1ccc2c(c1F)CCN(C1CC3(CCCCC3)C1)C2] 5-fluoro-N-hydroxy-2-(spiro[3.5]nonan-2-yl)-1,2,3,4-tetrahydroisoquinoline-6-carboxamide | $^{1}$H NMR (400 MHz, DMSO-$d_6$) δ 11.05 (s, 1H), 10.38 (s, 1H), 9.29 (s, 1H), 7.45 (t, J = 7.4 Hz, 1H), 7.14 (d, J = 8.0 Hz, 1H), 4.57 (d, J = 16.1 Hz, 1H), 4.17 (dd, J = 16.5, 7.2 Hz, 1H), 3.80 (q, J = 8.2 Hz, 1H), 3.63 (s, 1H), 3.23 – 3.04 (m, 2H), 2.98 (q, J = 10.7, 9.0 Hz, 1H), 2.26 – 2.10 (m, 2H), 2.02 – 1.89 (m, 2H), 1.48 – 1.31 (m, 8H). MS (ESI): 333 [M + H]$^{+}$ |

8-fluoro-N-hydroxy-2-((2s,4r)-6-azaspiro[3.5]nonan-2-yl)-1,2,3,4-tetrahydr quinoline-6-carboxamide (341)

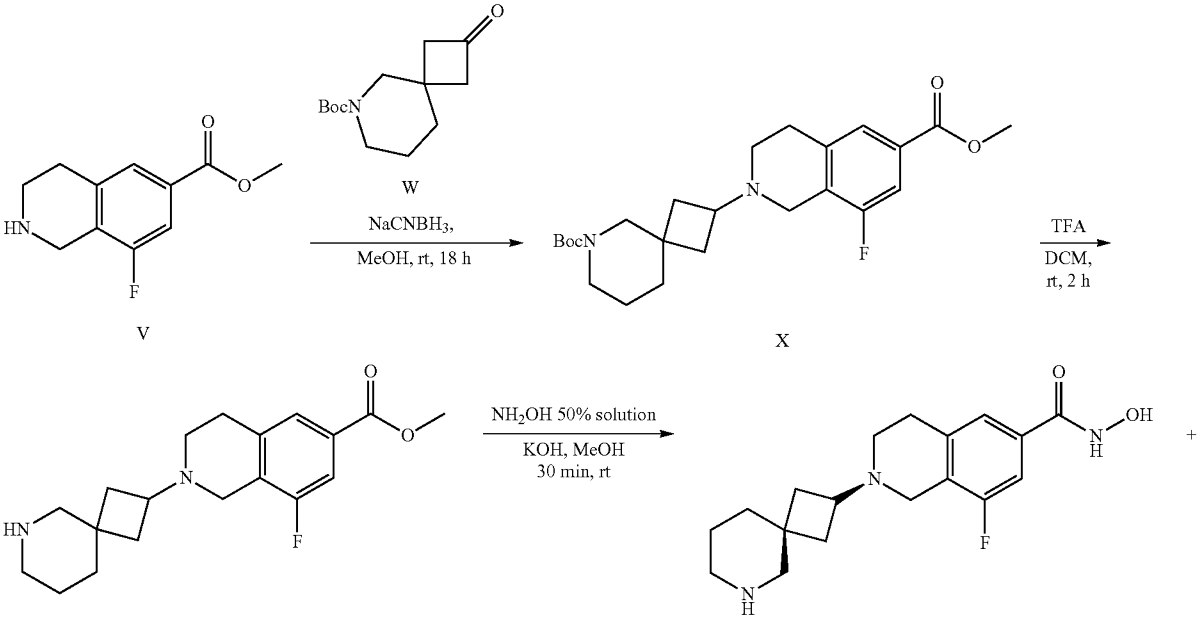

V X Y 341

-continued
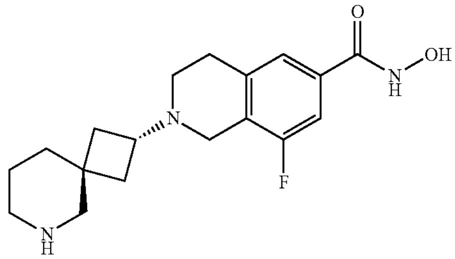
342
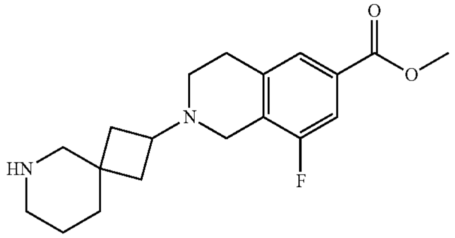
Y
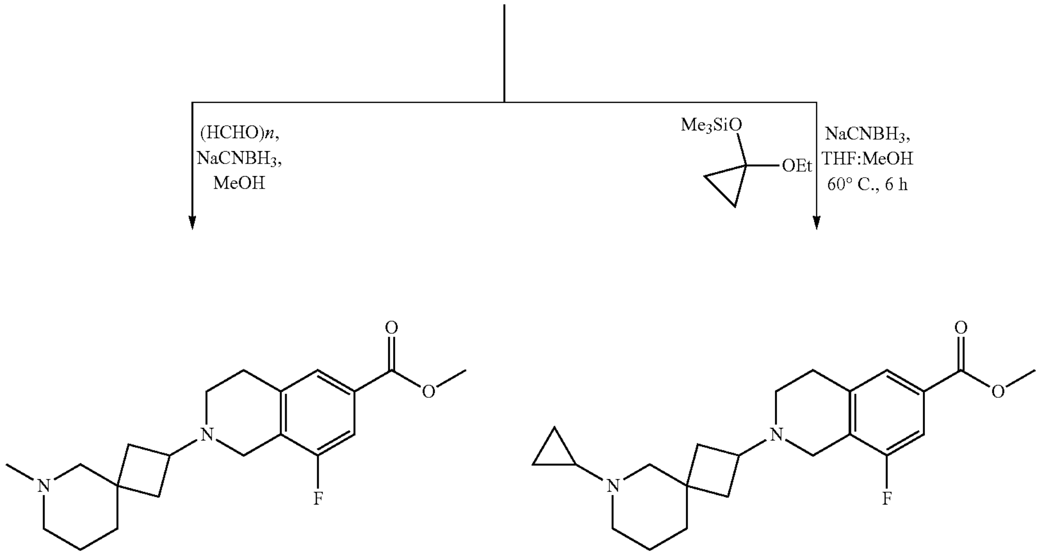
Z
Aa
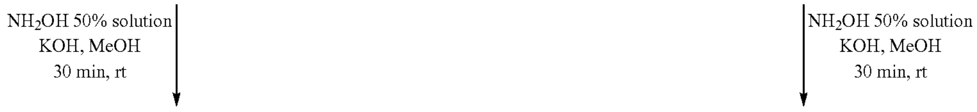
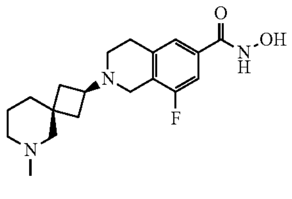
343
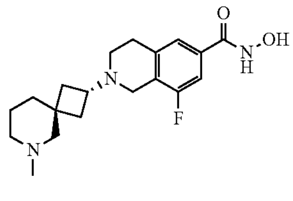
344
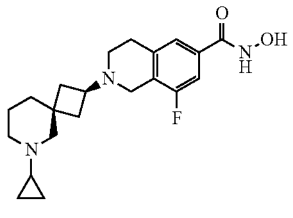
345
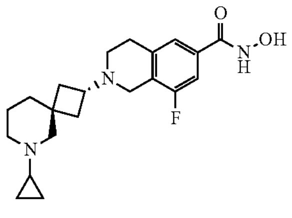
346

Intermediate X was prepared in a manner analogous to that used for preparation of compound C in the synthesis of compound 179. MS (ESI): 433 $[M+H]^+$.

Intermediate Y was prepared by removal of the Boc protecting group under standard deprotection conditions with administration of TFA. MS (ESI): 333 $[M+H]^+$.

Intermediate Z was prepared by administration of paraformaldehyde and sodium cyanoborohydride under standard reductive amination conditions. MS (ESI): 347 $[M+H]^+$.

Intermediate Aa was prepared by administration of cyclopropanone ethyl trimethylsilyl acetal and sodium cyanoborohydride under standard reductive amination conditions. MS (ESI): 373 $[M+H]^+$.

The hydroxamic acid moieties were installed to prepare compounds 341, 342, 345, and 346 in a manner analogous to that used for preparing compounds 179 and 504 by administration of $NH_2OH$ in the presence of KOH to convert the ester to the hydroxamic acid. The following compounds were prepared in an analogous manner. Although certain compounds below are designated as having absolute stereochemistry as each stereoisomer was prepared and isolated, the absolute stereochemistry of each is unknown.

| Compound | Structure/Name | Characterization |
| --- | --- | --- |
| 341 | 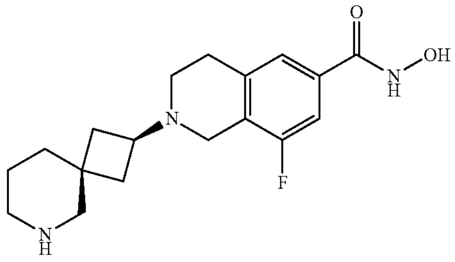 [SMILES: O=C(NO)c1cc(F)c2c(c1)CCN([C@H]1C[C@]3(CCCNC3)C1)C2] 8-fluoro-N-hydroxy-2-((2r,4s)-6-azaspiro[3.5]nonan-2-yl)-1,2,3,4-tetrahydroisoquinoline-6-carboxamide | $^1H$ NMR (400 MHz, DMSO-$d_6$) δ 11.35 (s, 1H), 10.94 (s, 1H), 9.19 (s, 1H), 8.61 (s, 2H), 7.65 - 7.37 (m, 2H), 4.14 (s, 2H), 3.15 (s, 2H), 3.00 (s, 3H), 2.24 (s, 4H), 1.70 (s, 4H), 1.26 (d, J = 6.4 Hz, 2H). MS (ESI): 334 $[M + H]^+$ Note: absolute stereochemistry is unknown |
| 342 | 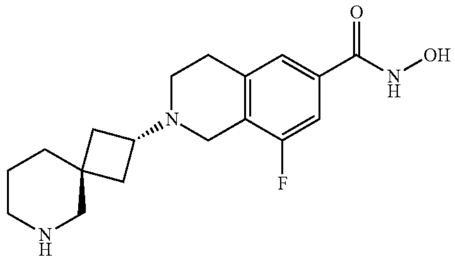 [SMILES: O=C(NO)c1cc(F)c2c(c1)CCN([C@H]1C[C@@]3(CCCNC3)C1)C2] 8-fluoro-N-hydroxy-2-((2s,4r)-6-azaspiro[3.5]nonan-2-yl)-1,2,3,4-tetrahydroisoquinoline-6-carboxamide | $^1H$ NMR (400 MHz, DMSO-$d_6$) δ 11.35 (s, 1H), 9.20 (s, 1H), 8.82 - 8.52 (m, 2H), 7.65 - 7.40 (m, 2H), 4.54 (s, 1H), 4.13 (s, 2H), 3.85 (s, 1H), 3.13 (s, 3H), 2.99 (s, 2H), 2.14 (s, 2H), 1.64 (s, 4H). MS (ESI): 334 $[M + H]^+$ Note: absolute stereochemistry is unknown. |
| 345 | 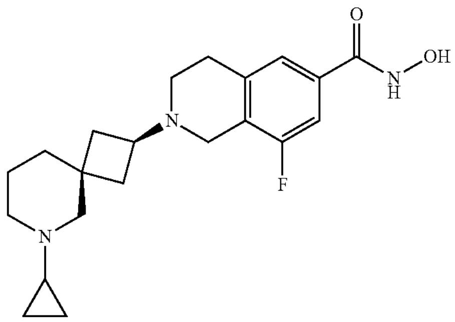 [SMILES: O=C(NO)c1cc(F)c2c(c1)CCN([C@H]1C[C@]3(CCCN(C4CC4)C3)C1)C2] 2-((2r,4s)-6-cyclopropyl-6-azaspiro[3.5]nonan-2-yl)-8-fluoro-N-hydroxy-1,2,3,4-tetrahydroisoquinoline-6-carboxamide | MS (ESI): 374 $[M + H]^+$ Note: absolute stereochemistry is unknown. |

-continued

| Compound | Structure/Name | Characterization |
| --- | --- | --- |
| 346 | 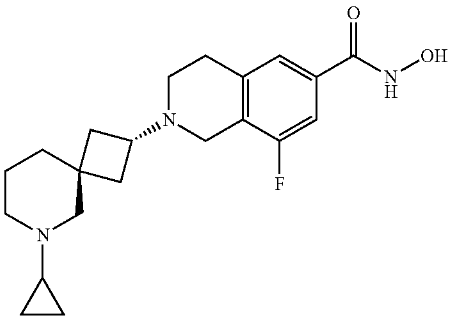 [SMILES: O=C(NO)c1cc(F)c2c(c1)CCN([C@H]1C[C@@]3(CCCN(C4CC4)C3)C1)C2] 2-((2s,4r)-6-cyclopropyl-6-azaspiro[3.5]nonan-2-yl)-8-fluoro-N-hydroxy-1,2,3,4-tetrahydroisoquinoline-6-carboxamide | MS (ESI): 374 [M + H]+ Note: absolute stereochemistry is unknown. |
| 416 | 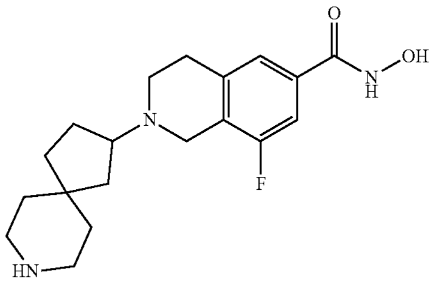 [SMILES: O=C(NO)c1cc(F)c2c(c1)CCN(C1CCC3(CCNCC3)C1)C2] 8-fluoro-N-hydroxy-2-(8-azaspiro[4.5]decan-2-yl)-1,2,3,4-tetrahydroisoquinoline-6-carboxamide | $^1$H NMR (400 MHz, DMSO-$d_6$) δ 11.36 (s, 1H), 10.58 (s, 1H), 9.21 (s, 1H), 8.52 (d, J = 33.2 Hz, 2H), 7.63 - 7.38 (m, 2H), 4.60 (s, 1H), 4.34 (s, 1H), 3.78 (s, 2H), 3.11 (d, J = 41.4 Hz, 6H), 2.20 (s, 2H), 1.92 (s, 1H), 1.78 - 1.30 (m, 7H). MS (ESI) 348 [M + H]+ |
| 417 | 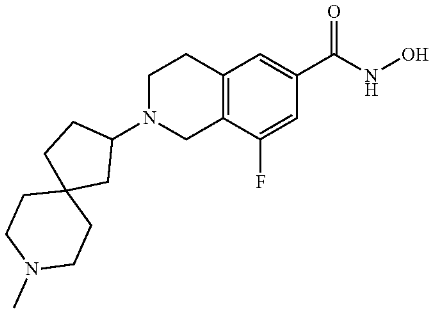 [SMILES: CN1CCC2(CCC(N3CCc4cc(C(=O)NO)cc(F)c4C3)C2)CC1] 8-fluoro-N-hydroxy-2-(8-methyl-8-azaspiro[4.5]decan-2-yl)-1,2,3,4-tetrahydroisoquinoline-6-carboxamide | $^1$H NMR (400 MHz, DMSO-$d_6$) δ 11.36 (s, 1H), 10.37 (s, 1H), 9.28 (d, J = 49.4 Hz, 2H), 7.58 - 7.42 (m, 2H), 4.35 (s, 2H), 3.81 (s, 4H), 3.17 (s, 3H), 2.98 (s, 2H), 2.77 (d, J = 3.8 Hz, 3H), 1.80 - 1.53 (m, 10H). MS (ESI): 362 [M + H]+ |
| 418 | 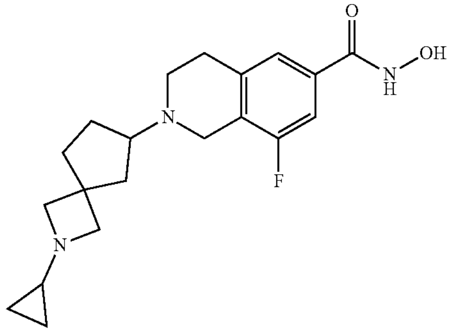 [SMILES: O=C(NO)c1cc(F)c2c(c1)CCN(C1CCC3(C1)CN(C1CC1)C3)C2] N- 2-(8-cyclopropyl-8-azaspiro[4.5]decan-2-yl)-8-fluoro-N-hydroxy-1,2,3,4-tetrahydroisoquinoline-6-carboxamide | $^1$H NMR (400 MHz, DMSO-$d_6$) δ 11.37 (s, 1H), 10.73 (s, 1H), 9.15 (s, 1H), 7.65 - 7.40 (m, 2H), 4.59 (s, 1H), 4.36 (s, 1H), 3.46 - 3.29 (m, 3H), 3.18 (s, 3H), 2.86 (s, 1H), 2.23 (s, 2H), 1.96 (s, 1H), 1.85 - 1.48 (m, 7H), 1.00 - 0.72 (m, 4H). MS (ESI): 388 [M + H]+ |

-continued

| Compound | Structure/Name | Characterization |
|---|---|---|
| 388 | 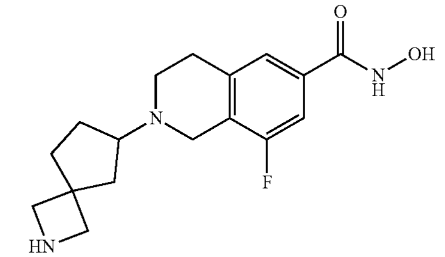 [SMILES: O=C(NO)c1cc(F)c2c(c1)CCN(C1CCC3(CNC3)C1)C2] 8-fluoro-N-hydroxy-2-(2-azaspiro[3.4]octan-6-yl)-1,2,3,4-tetrahydroisoquinoline-6-carboxamide | MS (ESI): 320 $[M + H]^+$ |
| 290 | 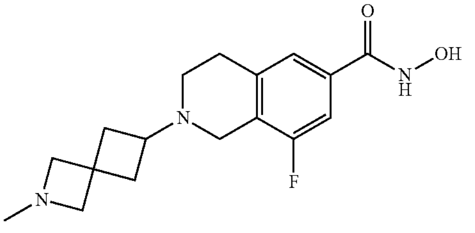 [SMILES: CN1CC2(CC(N3CCc4cc(C(=O)NO)cc(F)c4C3)C2)C1] 8-fluoro-N-hydroxy-2-(2-methyl-2-azaspiro[3.3]heptan-6-yl)-1,2,3,4-tetrahydroisoquinoline-6-carboxamide | $^1H$ NMR (400 MHz, DMSO-$d_6$) δ 11.34 (s, 1H), 10.37 (s, 1H), 9.21 (s, 1H), 7.51 (d, J = 30.4 Hz, 2H), 4.53 (s, 2H), 3.97 - 3.89 (m, 4H), 3.79 - 3.72 (m, 3H), 3.12 (s, 2H), 2.77 - 2.71 (m, 5H), 1.87 - 1.70 (m, 2H). MS (ESI): 320 $[M - H]^-$ |
| 291 | 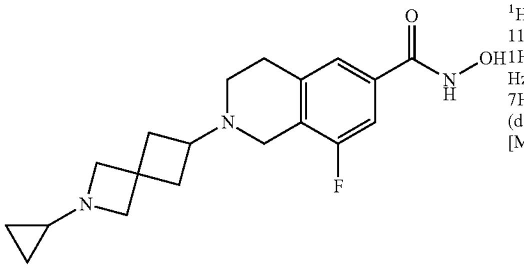 2-(2-cyclopropyl-2-azaspiro[3.3]heptan-6-yl)-8-fluoro-N-hydroxy-1,2,3,4-tetrahydroisoquinoline-6-carboxamide | $^1H$ NMR (400 MHz, DMSO-$d_6$) δ 11.35 (s, 1H), 10.33 (s, 1H), 9.22 (s, 1H), 7.55 (s, 1H), 7.46 (d, J = 10.4 Hz, 1H), 4.15 (dd, J = 36.7, 11.6 Hz, 7H), 3.10 (s, 3H), 3.01 (s, 2H), 0.75 (d, J = 5.4 Hz, 4H). MS (ESI): 346 $[M - H]^-$ |

8-fluoro-N-hydroxy-2-(8-methyl-8-azaspiro[4.5]decan-2-yl)-1,2,3,4-tetrahydroisoquinoline-6-carboxamide (344)

-continued

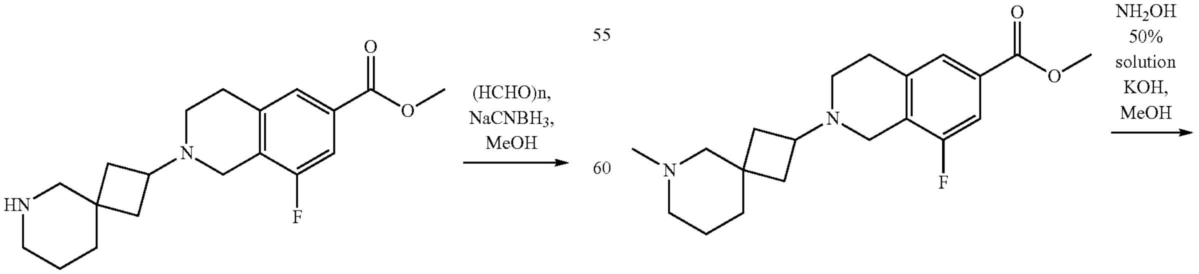

-continued

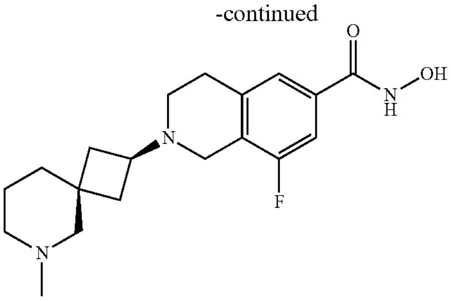

+

343

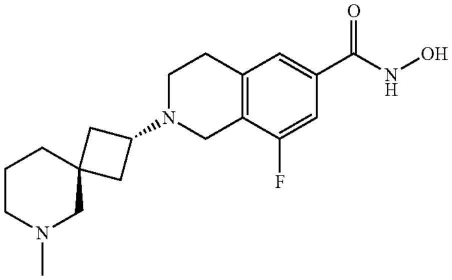 [SMILES: CN1CCC[C@]2(C1)C[C@H](N1CCc3cc(C(=O)NO)cc(F)c3C1)C2]

344

To a solution of methyl 2-(6-azaspiro[3.5]nonan-2-yl)-8-fluoro-3,4-dihydro-1H-isoquinoline-6-carboxylate (900 mg, 2.22 mmol, 1 eq, 2HCl) in MeOH (10 mL) was added HCHO (270.28 mg, 3.33 mmol, 247.97 uL, 37% purity, 1.5 eq) and AcOH (266.68 mg, 4.44 mmol, 253.98 uL, 2 eq) and NaBH3CN (209.30 mg, 3.33 mmol, 1.5 eq). The mixture was stirred at 25° C. for 12 hr. The reaction mixture was concentrated under reduced pressure to remove solvent. The residue was purified by flash silica gel chromatography (20 g, Silica Flash Column, Eluent of 0-80% Ethylacetate/Petroleum Ethergradient® 40 mL/min). Compound methyl 8-fluoro-2-(6-methyl-6-azaspiro[3.5]nonan-2-yl)-3,4-dihydro-1H-isoquinoline-6-carboxylate (900 mg, 2.18 mmol, 98.28% yield, 84% purity) was obtained as a white solid. MS(ESI): 347.1[M+H]+

To a solution of methyl 8-fluoro-2-(6-methyl-6-azaspiro[3.5]nonan-2-yl)-3,4-dihydro-1H-isoquinoline-6-carboxylate (900 mg, 2.18 mmol, 84% purity, 1 eq) in MeOH (8 mL) was added KOH (244.87 mg, 4.36 mmol, 2 eq) and hydroxylamine (2.88 g, 43.64 mmol, 50% purity, 20 eq). The mixture was stirred at 25° C. for 12 hr. The reaction mixture was concentrated under reduced pressure to remove solvent. The residue was purified by prep-HPLC (column: Waters Atlantis T3 150*30 mm*5 um; mobile phase: [water (TFA)-ACN]; B %: 0%-20%, 20 min). Compound 8-fluoro-2-(6-methyl-6-azaspiro[3.5]nonan-2-yl)-3,4-dihydro-1H-isoquinoline-6-carbohydroxamic acid (361.67 mg, 1.04 mmol, 47.66% yield, 99.9% purity) was obtained as an orange solid.

8-fluoro-N-hydroxy-2-((2s,4r)-6-methyl-6-azaspiro[3.5]nonan-2-yl)-1,2,3,4-tetrahydroisoquinoline-6-carboxamide (343) was prepared in an analogous manner.

| | | |
|---|---|---|
| 343 | 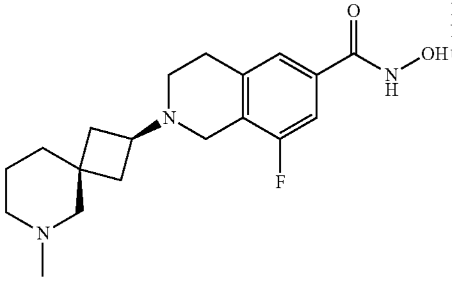<br>8-fluoro-N-hydroxy-2-((2r,4s)-6-methyl-6-azaspiro[3.5]nonan-2-yl)-1,2,3,4-tetrahydroisoquinoline-6-carboxamide | MS (ESI): 348 [M − H]$^+$<br>Note: absolute stereochemistry is unknown |
| 344 | 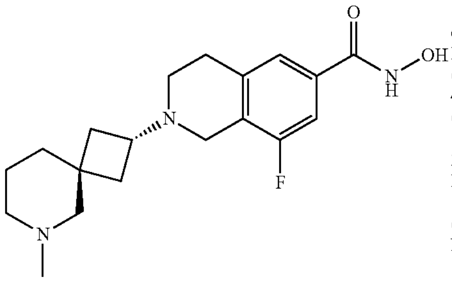<br>8-fluoro-N-hydroxy-2-((2s,4r)-6-methyl-6-azaspiro[3.5]nonan-2-yl)-1,2,3,4-tetrahydroisoquinoline-6-carboxamide | 1H NMR (400 MHz, METHANOL-d4) δ = 7.53 (s, 1H), 7.45 (d, J = 10.1 Hz, 1H), 4.48 − 4.32 (m, 2H), 4.00 (quin, J = 8.2 Hz, 1H), 3.55 − 3.42 (m, 4H), 3.29 (bt, J = 5.7 Hz, 2H), 3.03 (bd, J = 12.5Hz, 1H), 2.96 − 2.89 (m, 1H), 2.87 (s, 3H), 2.60 − 2.51 (m, 1H), 2.49 − 2.43 (m, 1H), 2.39 (bd, J = 8.3 Hz, 2H), 2.06 − 1.95 (m, 2H), 1.92 − 1.82 (m, 1H), 1.70 − 1.60 (m, 1H). MS (ESI): 348 [M + H]$^+$<br>Note: absolute stereochemistry is unknown. |

8-fluoro-N-hydroxy-2-((2s,4r)-6-oxaspiro[3.5]nonan-2-yl)-1,2,3,4-tetrahydroisoquinoline-6-carboxamide (338) and 8-fluoro-N-hydroxy-2-((2r,4s)-6-oxaspiro[3.5]nonan-2-yl)-1,2,3,4-tetrahydroisoquinoline-6-carboxamide (337)

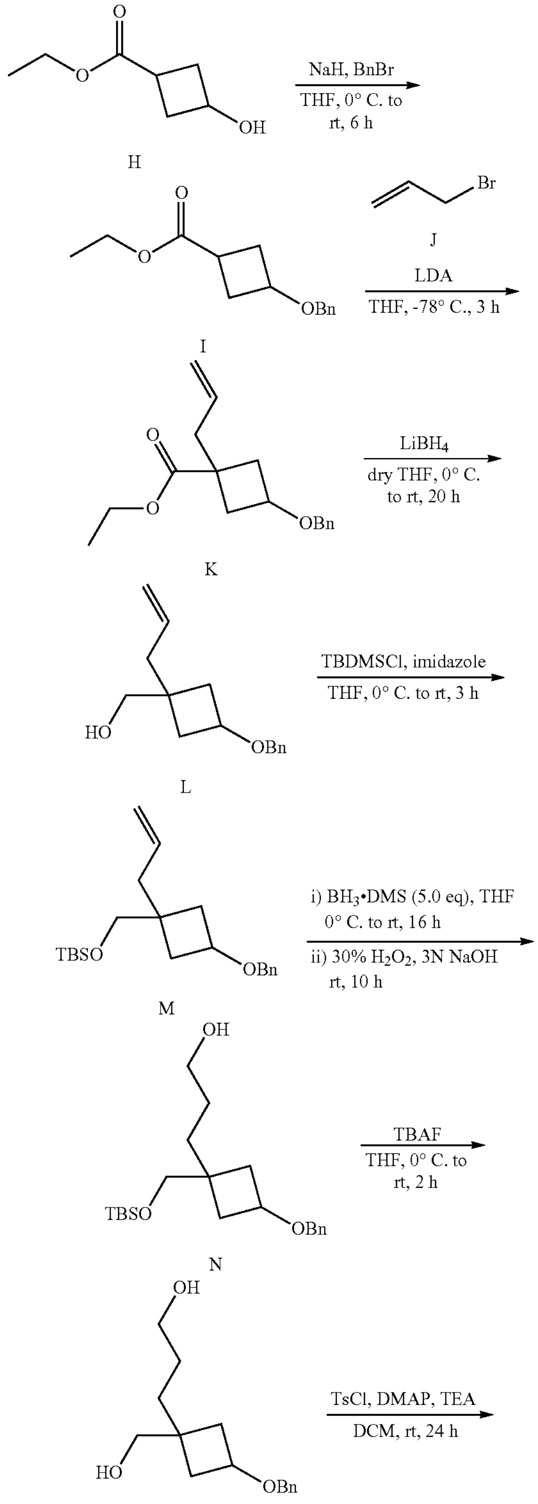

-continued

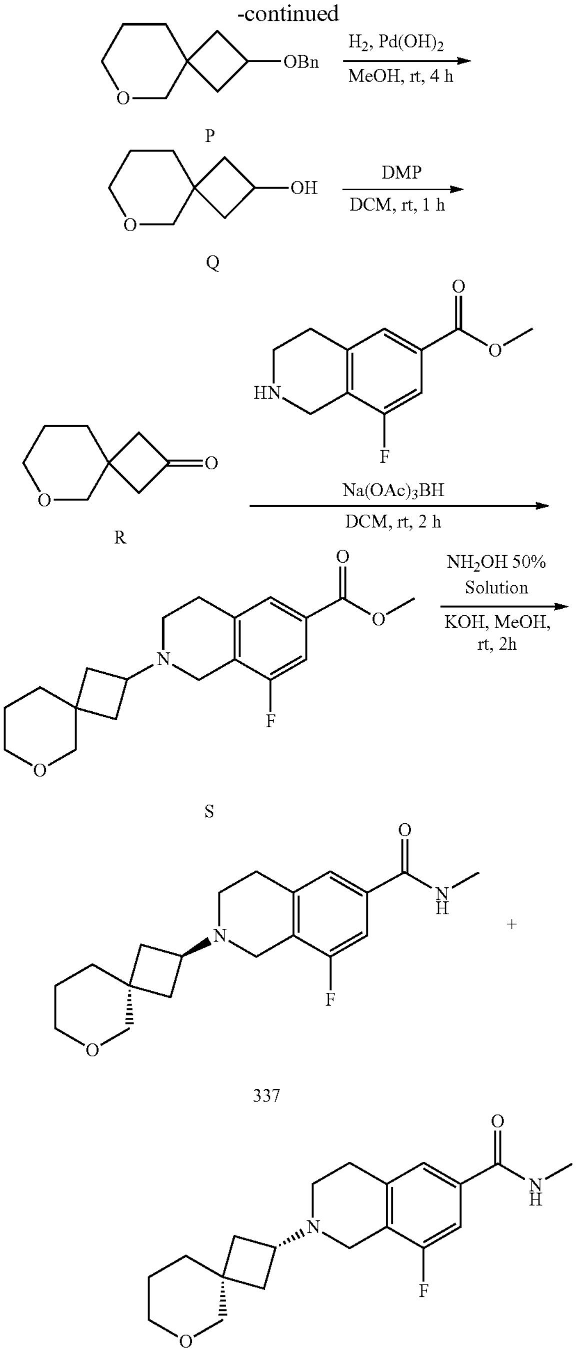

337

338

To a solution of ethyl 3-hydroxycyclobutane-1-carboxylate (H, 15 g, 104.04 mmol, 1.0 equiv.) in THF (150 mL) at 0° C. was added NaH (4.99 g, 124.85 mmol, 1.2 equiv.) portion wise and the reaction was stirred at 0° C. for 0.5 h followed by the addition of benzyl bromide (18.5 mL, 156.06 mmol, 1.5 equiv.) and the reaction was allowed to stir at room temperature for 6 h. The reaction mass was then diluted with water (200 mL) and extracted with ethyl acetate (3×200 mL). The combined organic layer was dried over $Na_2SO_4$, concentrated and the residual mass was purified by silica gel column chromatography. Compound was eluted at 10% EtOAc in hexanes to get ethyl 3-(benzyloxy)cyclobutane-1-carboxylate (I, 9.8 g, 41.826 mmol, 40.2%). $^{1}$H NMR (400 MHz, DMSO-$d_6$) δ 7.35-7.28 (m, 5H), 4.45 (s, 2H), 4.18-4.12 (m, 2H), 3.98 (t, J=5.2 Hz, 1H), 2.62-2.60 (m, 1H), 2.53-2.50 (m, 2H), 2.30-2.24 (m, 2H), 1.28 (t, J=8 Hz, 3H).

To a solution of ethyl 3-(benzyloxy)cyclobutane-1-carboxylate (I, 9.8 g, 41.826 mmol, 1.0 equiv.) in THF (50 mL) at −78° C. was added LDA (1.0 M in THF Solution) (50 mL, 50.1920 mmol, 1.2 equiv.) drop wise and the reaction was stirred at −78° C. for 40 min followed by the addition of allyl bromide (J, 5.42 mL, 62.739 mmol, 1.5 equiv.) and the reaction mixture was stirred at −78° C. for 2.5 h. The reaction mass was then diluted with water (80 mL) and extracted with ethyl acetate (3×80 mL). The combined organic layer was dried over $Na_2SO_4$, concentrated and the residual mass was purified by silica gel column chromatography. Compound was eluted at 2.1% EtOAc in hexanes to get ethyl 1-allyl-3-(benzyloxy)cyclobutane-1-carboxylate (K, 7.0 g, 25.51 mmol, 61%). MS (ESI): 275 $[M+H]^+$.

To a solution of ethyl 1-allyl-3-(benzyloxy)cyclobutane-1-carboxylate (K, 7.0 g, 25.519 mmol, 1.0 equiv.) in THF (50 mL) at 0° C. was added $LiBH_4$ (2.0 M in THF Solution) (15.3 mL, 30.623 mmol, 1.2 equiv.) drop wise and the reaction was stirred at 0° C. to room temperature for 20 h. The reaction mass was then diluted with water (50 mL) and extracted with ethyl acetate (3×50 mL). The combined organic layer was dried over $Na_2SO_4$, concentrated and the residual mass was purified by silica gel column chromatography. Compound was eluted at 27% EtOAc in hexanes to get (1-allyl-3-(benzyloxy)cyclobutyl)methanol (L, 3.1 g, 13.3436 mmol, 52.2%). MS (ESI): 233 $[M+H]^+$.

To a solution of (1-allyl-3-(benzyloxy)cyclobutyl)methanol (L, 3.1 g, 13.3436 mmol, 1.0 equiv.), in a THF (20 mL) were added imidazole (2.27 g, 33.359 mmol, 2.5 equiv.) and DMAP (0.814 g, 6.672 mmol, 0.5 equiv) at 0° C. followed by the addition of TBDMSCl (4.02 g, 26.6873 mmol, 2.0 equiv.) at room temperature. The reaction mixture was stirred at room temperature for 3 h. Completion of reaction was confirmed by TLC. The reaction mixture was poured in to ice water (100 mL) and extracted with ethyl acetate (100 mL×3). The combined organic layer was dried over $Na_2SO_4$ and evaporated. The residue was purified by column chromatography using hexane/ethyl acetate to give ((1-allyl-3-(benzyloxy)cyclobutyl)methoxy)(tert-butyl)dimethylsilane (M, 2.7 g, 7.790 mmol, 58%). $^{1}$H NMR (400 MHz, DMSO-$d_6$) δ 7.35-7.30 (m, 5H), 5.77-5.75 (m, 1H), 5.08-5.01 (m, 2H), 4.33 (s, 2H), 4.03-3.97 (m, 1H), 3.40 (d, J=6.8 Hz, 2H), 2.16 (t, J=5.6 Hz, 2H), 2.09 (t, J=9.6 Hz, 1H), 2.0-1.95 (m, 1H), 1.83-1.79 (m, 1H), 1.73-1.70 (m, 1H), 0.89 (s, 9H), 0.04 (s, 6H).

To a solution of ((1-allyl-3-(benzyloxy)cyclobutyl)methoxy)(tert-butyl)dimethylsilane (M, 2.7 g, 7.790 mmol, 1.0 equiv.), in THF (25 mL) at 0° C. was added $BH_3$-DMS (2.0 M in THF Solution) (19.5 mL, 38.951 mmol, 5.0 equiv.) drop wise and the reaction was allowed to stir at room temperature for 16 h. 2.7 mL of $H_2O$, 8.1 mL of 3 N NaOH, and 2.7 mL of 30% $H_2O_2$ were then added. The reaction mixture was stirred at room temperature for 10 h. Completion of reaction was confirmed by TLC. The reaction mixture was poured in to water (50 mL) and extracted with ethyl acetate (50 mL×3). The combined organic layer was dried over $Na_2SO_4$ and evaporated. The residue was purified by column chromatography using haxane/ethyl acetate (15.5%) to give 3-(3-(benzyloxy)-1-(((tert-butyldimethylsilyl)oxy)methyl)cyclobutyl)propan-1-ol (N, 1.5 g, 4.1140 mmol, 52.81%). MS (ESI): 365 $[M+H]^+$.

To a solution of 3-(3-(benzyloxy)-1-(((tert-butyldimethylsilyl)oxy)methyl)cyclobutyl)propan-1-ol (N, 1.5 g, 4.114 mmol, 1.0 equiv) in THF (10 mL) at 0° C. was added TBAF (1.0 M in THF Solution) (10 mL, 10.285 mmol, 2.5 equiv.) drop wise and the reaction was allowed to stir at room temperature for 2 h. Completion of reaction was confirmed by TLC. The reaction mixture was poured in to water (10 mL) and extracted with ethyl acetate (10 mL×3). The combined organic layer was dried over $Na_2SO_4$ and evaporated to afford 3-(3-(benzyloxy)-1-(hydroxymethyl)cyclobutyl)propan-1-ol (0, 0.83 g, 3.3160 mmol, 81%) which was used as such for the next step.

The remaining steps in the synthesis were carried out in a manner analogous to that used for preparation of 179. Although 337/338 are designated as having absolute stereochemistry as each stereoisomer was prepared and isolated, the absolute stereochemistry of each is unknown.

8-fluoro-N-hydroxy-2-((2s,4r)-6-oxaspiro[3.5]nonan-2-yl)-1,2,3,4-tetrahydroisoquinoline-6-carboxamide. (338). $^{1}$H NMR (400 MHz, DMSO-$d_6$) δ 11.37 (s, 1H), 10.64 (s, 1H), 9.22 (s, 1H), 7.58-7.48 (m, 2H), 4.56 (bs, 1H), 4.15 (bs, 1H), 3.86 (bs, 1H), 3.52 (bs, 3H), 3.46 (bs, 3H), 3.18 (bs, 2H), 2.27 (bs, 2H), 2.05 (bs, 2H), 1.62 (bs, 2H), 1.48 (bs, 2H). MS (ESI): 335 $[M+H]^+$.

8-fluoro-N-hydroxy-2-((2r,4s)-6-oxaspiro[3.5]nonan-2-yl)-1,2,3,4-tetrahydroisoquinoline-6-carboxamide (337). $^{1}$H NMR (400 MHz, DMSO-$d_6$) δ 11.37 (s, 1H), 10.20 (s, 1H), 9.22 (s, 1H), 7.59-7.50 (m, 2H), 4.57 (bs, 1H), 4.18 (bs, 1H), 3.91 (bs, 1H), 3.62 (bs, 3H), 3.51 (bs, 3H), 3.18 (bs, 2H), 2.18 (bs, 2H), 2.05 (bs, 2H), 1.67 (bs, 2H), 1.53 (bs, 2H). MS (ESI): 335 $[M+H]^+$.

8-fluoro-2-spiro[3.4]octan-2-yl-3,4-dihydro-1H-isoquinoline-6-carbohydroxamic acid (183)

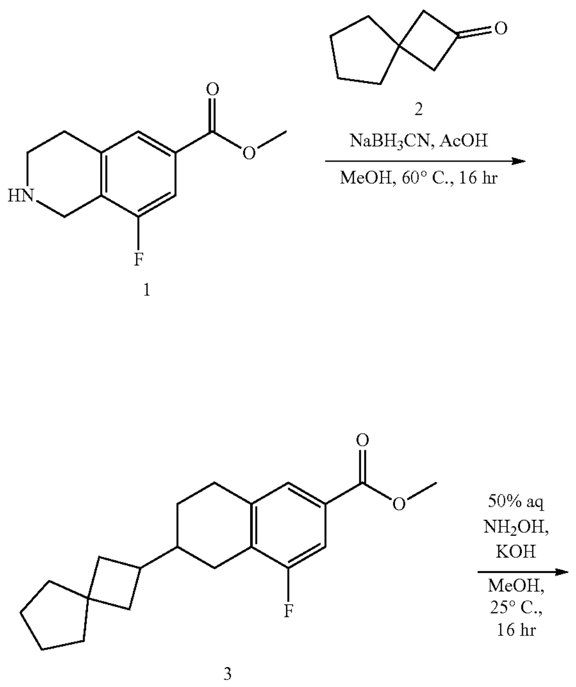

-continued

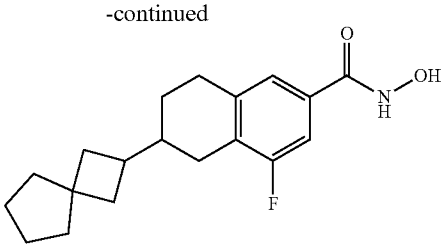

183

To a solution of methyl 8-fluoro-1,2,3,4-tetrahydroisoquinoline-6-carboxylate (185.33 mg, 885.81 umol, 1.1 eq), spiro[3.4]octan-2-one (100 mg, 805.28 umol, 1 eq) in MeOH (5 mL) was added AcOH (96.72 mg, 1.61 mmol, 92.11 uL, 2 eq) and NaBH3CN (65.79 mg, 1.05 mmol, 1.3 eq). The mixture was stiffed at 60° C. for 16 hr. The mixture was concentrated under reduced pressure and purified by prep-TLC to obtain methyl 8-fluoro-2-spiro[3.4]octan-2-yl-3,4-dihydro-1H-isoquinoline-6-carboxylate (170 mg, 482.05 umol, 59.86% yield, 90% purity) as a yellow oil. LCMS (ESI): 318.2 $[M+H]^+$.

To a solution of methyl 8-fluoro-2-spiro[3.4]octan-2-yl-3,4-dihydro-1H-isoquinoline-6-carboxylate (170 mg, 482.05 umol, 90% purity, 1 eq) in MeOH (10 mL) was added hydroxylamine (636.88 mg, 9.64 mmol, 50% purity, 20 eq) and KOH (54.09 mg, 964.09 umol, 2 eq). The mixture was stirred at 25° C. for 16 hr. The mixture was concentrated under reduced pressure and purified by prep-HPLC(TFA) to obtain 8-fluoro-2-spiro[3.4]octan-2-yl-3,4-dihydro-1H-isoquinoline-6-carbohydroxamic acid (83.49 mg, 257.51 umol, 53.42% yield, 98.2% purity) as a white solid. 1H NMR (400 MHz, METHANOL-d4) δ=7.37 (s, 1H), 7.27 (d, J=10.1 Hz, 1H), 3.55 (s, 2H), 2.99-2.92 (m, 3H), 2.66 (t, J=6.0 Hz, 2H), 2.16-2.09 (m, 2H), 1.93-1.87 (m, 2H), 1.71-1.63 (m, 4H), 1.61-1.56 (m, 4H). LCMS (ESI): 319.2 $[M+H]^+$.

8-fluoro-2-[spiro[3.4]octan-7-yl]-3,4-dihydro-1H-isoquinoline-6-carbohydroxamic acid (383 and 384)

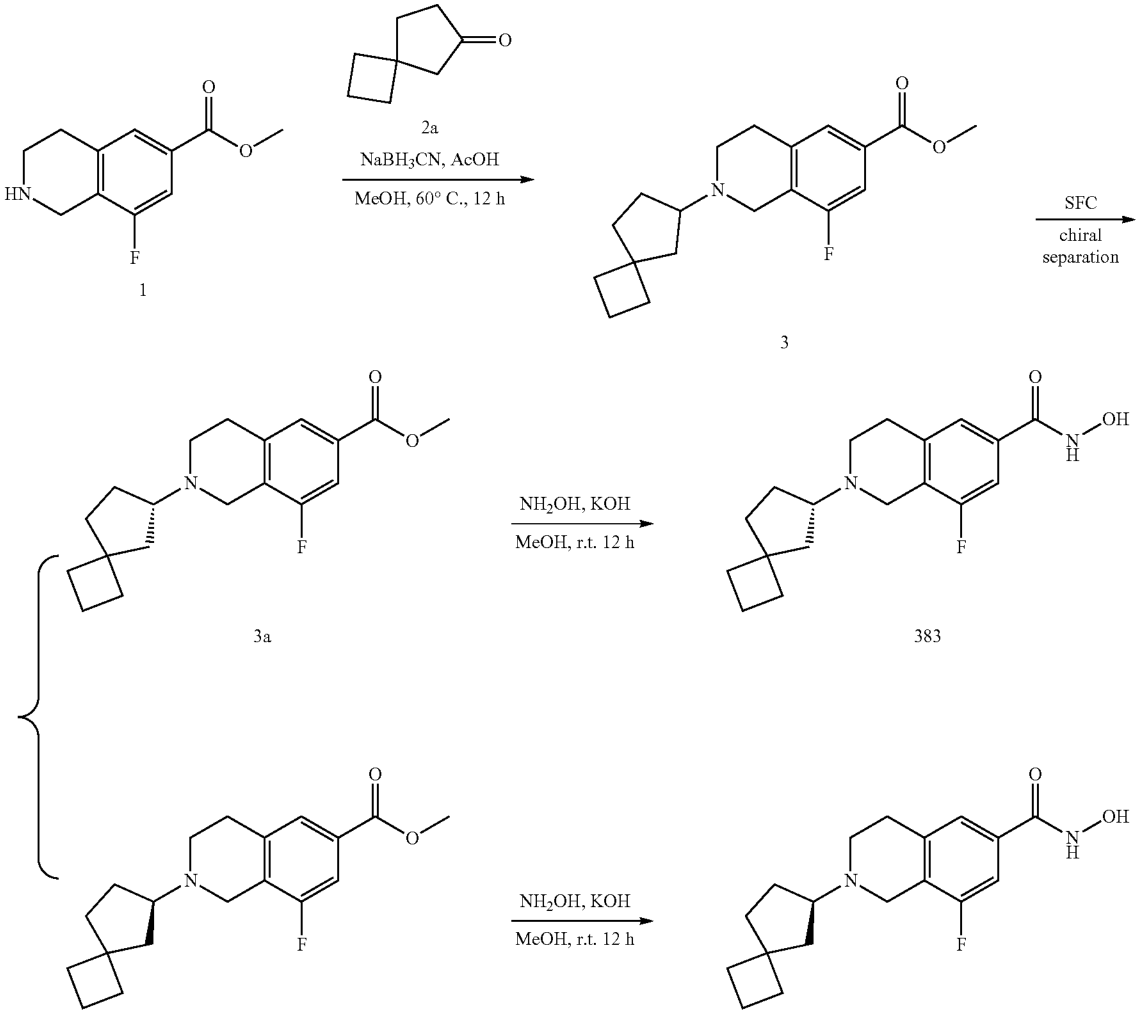

383 and 384 were prepared in a manner analogous to that used in the preparation of compound 183. The enantiomers of ester 3 were resolved by supercritical fluid chromatography (SFC), and then used to prepare the final analogs separately. The absolute stereochemistry of each is unknown.

8-fluoro-2-[(7S)-spiro[3.4]octan-7-yl]-3,4-dihydro-1H-isoquinoline-6-carbohydroxamic acid (383): $^1$H NMR (400 MHz, METHANOL-d4) δ ppm 7.52-7.59 (s, 1H) 7.47 (d, J=10.1 Hz, 1H) 4.35-4.76 (m, 2H) 3.76-3.99 (m, 2H) 3.29 (br s, 2H) 2.47-2.38 (m, 1H) 2.24-2.36 (m, 1H) 2.10-2.18 (m, 1H) 1.79-2.10 (m, 10H)MS (ESI): 319.1 [M+H]$^+$.

8-fluoro-2-[(7R)-spiro[3.4]octan-7-yl]-3,4-dihydro-1H-isoquinoline-6-carbohydroxamic acid (384): $^1$H NMR (400 MHz, METHANOL-d4) δ=7.55 (s, 1H), 7.47 (d, J=10.1 Hz, 1H), 4.76-4.60 (m, 1H), 4.52-4.30 (m, 1H), 3.95-3.73 (m, 2H), 3.28 (bs, 2H), 2.48-2.36 (m, 1H), 2.34-2.23 (m, 1H), 2.17-2.09 (m, 1H), 2.06-1.98 (m, 2H), 1.97-1.81 (m, 8H). MS(ESI) 319.2 [M+H]+.

8-fluoro-2-(2-methyl-2-azaspiro[3.5]nonan-7-yl)-3,4-dihydro-1H-isoquinoline-6-carbohydroxamic acid (427)

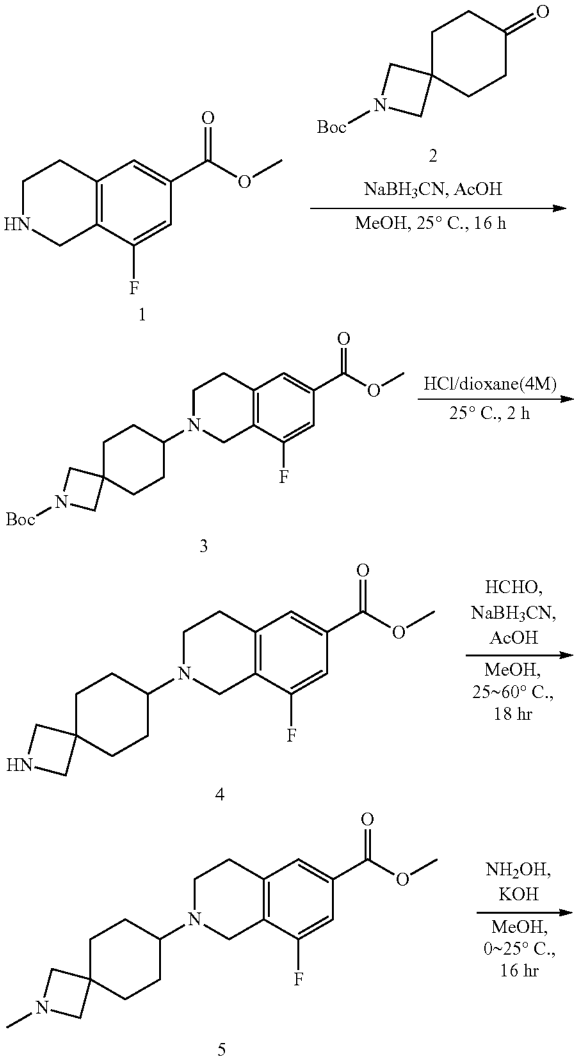

-continued

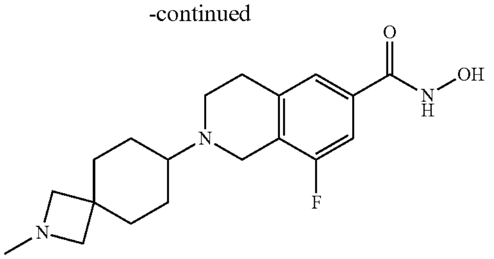

427

To a solution of tert-butyl 7-oxo-2-azaspiro[3.5]nonane-2-carboxylate (900 mg, 3.76 mmol, 1 eq) in MeOH(15 mL) was added methyl 8-fluoro-1,2,3,4-tetrahydroisoquinoline-6-carboxylate (865 mg, 4.14 mmol, 1.1 eq), AcOH (451.67 mg, 7.52 mmol, 430.17 uL, 2 eq). The mixture was stiffed at 25° C. for 2 hr. Then NaBH3CN (307.23 mg, 4.89 mmol, 1.3 eq) was added. The mixture was stirred at 25° C. for 16 hr. The mixture was concentrated under reduced pressure and purified by prep-TLC to obtain methyl 2-(2-tert-butoxycarbonyl-2-azaspiro[3.5]nonan-7-yl)-8-fluoro-3,4-dihydro-1H-isoquinoline-6-carboxylate (1.1 g, 2.47 mmol, 65.59% yield, 97% purity) as white solid. 1H NMR (400 MHz, CHLOROFORM-d) δ=7.61 (s, 1H), 7.50 (s, 1H), 3.90 (s, 3H), 3.81 (bs, 2H), 3.64 (s, 2H), 3.59 (s, 2H), 2.94 (br s, 2H), 2.83 (bs, 2H), 2.52 (bs, 1H), 2.01 (br d, J=12.4 Hz, 2H), 1.92 (bd, J=11.6 Hz, 2H), 1.56-1.48 (m, 2H), 1.45 (s, 9H), 1.43-1.33 (m, 2H). LCMS: MS(ESI): 433.2 [M+H]+.

The solution of methyl methyl 2-(2-tert-butoxycarbonyl-2-azaspiro[3.5]nonan-7-yl)-8-fluoro-3,4-dihydro-1H-isoquinoline-6-carboxylate (600 mg, 1.35 mmol, 97% purity, 1 eq) in HCl/dioxane (4 M, 8 mL, 23.78 eq) was stirred at 25° C. for 1.5 hr. The mixture was concentrated under reduced pressure to obtain methyl 2-(2-azaspiro[3.5]nonan-7-yl)-8-fluoro-3,4-dihydro-1H-isoquinoline-6-carboxylate (400 mg, crude, HCl) as white solid was used into the next step without further purification. 1H NMR (400 MHz, METHANOL-d4) δ=7.80 (s, 1H), 7.65 (bd, J=10.2 Hz, 1H), 4.61-4.52 (m, 2H), 3.96 (s, 2H), 3.92 (s, 3H), 3.82 (s, 2H), 3.66 (s, 2H), 3.54-3.49 (m, 1H), 3.35 (s, 2H), 2.32 (bd, J=9.4 Hz, 2H), 2.25-2.18 (m, 2H), 1.78-1.68 (m, 4H). LCMS: MS(ESI): 333.1 [M+H]+.

To a solution of methyl 2-(2-azaspiro[3.5]nonan-7-yl)-8-fluoro-3,4-dihydro-1H-isoquinoline-6-carboxylate (200 mg, 553.53 umol, 92% purity, 1 eq) in MeOH(5 mL) was added formaldehyde formaldehyde (97.65 mg, 1.20 mmol, 89.59 uL, 37% purity, 1.5 eq), AcOH (72.26 mg, 1.20 mmol, 68.82 uL, 2 eq). The mixture was stirred at 25° C. for 2 hr. NaBH3CN (49.15 mg, 782.12 umol, 1.5 eq) was added. The mixture was stirred at 25° C. for 16 hr. The mixture was concentrated under reduced pressure. The residue was purified by prep-TLC (SiO2) to obtain methyl 8-fluoro-2-(2-methyl-2-azaspiro[3.5]nonan-7-yl)-3,4-dihydro-1H-isoquinoline-6-carboxylate (160 mg, 452.61 umol, 81.77% yield, 98% purity) as a colorless liquid. 1H NMR (400 MHz, METHANOL-d4) δ=7.66 (s, 1H), 7.50 (dd, J=1.2, 10.2 Hz, 1H), 4.30 (s, 2H), 4.00 (bs, 2H), 3.93 (d, J=1.8 Hz, 2H), 3.90 (s, 3H), 3.88 (br s, 2H), 3.35 (s, 2H), 2.99 (br d, J=2.0 Hz, 2H), 2.93 (s, 3H), 2.75-2.65 (m, 1H), 2.19 (bd, J=13.0 Hz, 2H), 1.65 (dt, J=3.1, 13.2 Hz, 2H), 1.52-1.40 (m, 2H). LCMS(ESI): 347.3 [M+H]+.

To a solution of methyl 8-fluoro-2-(2-methyl-2-azaspiro[3.5]nonan-7-yl)-3,4-dihydro-1H-isoquinoline-6-carboxylate (160 mg, 452.61 umol, 98% purity, 1 eq) in MeOH (5 mL) was added hydroxylamine (597.98 mg, 9.05 mmol, 50% purity, 20 eq) and KOH (50.79 mg, 905.21 umol, 2 eq) at 0° C. The mixture was stiffed at 25° C. for 16 hr. The mixture was concentrated under reduced pressure and purified by prep-HPLC(TFA) to obtain 8-fluoro-2-(2-methyl-2-azaspiro[3.5]nonan-7-yl)-3,4-dihydro-1H-isoquinoline-6-carbohydroxamic acid (427) (36.73 mg, 79.26 umol, 17.51% yield, 99.573% purity, TFA) as a yellow solid. 1H NMR (400 MHz, METHANOL-d4) δ=7.55 (s, 1H), 7.48 (d, J=10.1 Hz, 1H), 4.56 (s, 2H), 4.26-4.24 (m, 1H), 4.05-4.00 (m, 1H), 3.95-3.82 (m, 2H), 3.64-3.60 (m, 2H), 3.55-3.47 (m, 1H), 3.30-3.28 (m, 2H), 2.97 (s, 3H), 2.41-2.16 (m, 4H), 1.83-1.63 (m, 4H). MS(ESI): 348.2 [M+H]+.

2-[(7-cyclopropyl-7-azaspiro[3.5]nonan-2-yl)methyl]-8-fluoro-3,4-dihydro-1H-isoquinoline-6-carbohydroxamic acid (607)

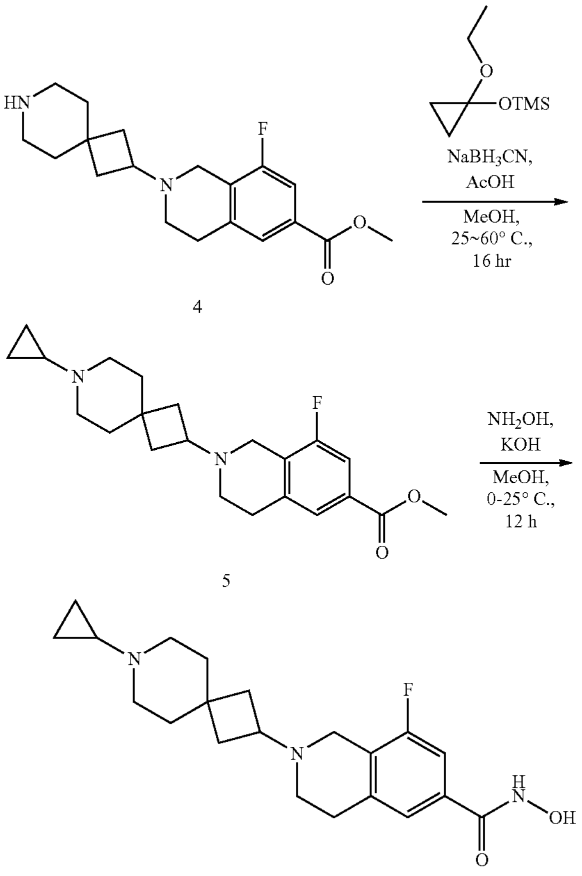

4

5

607

To a solution of methyl 2-(7-azaspiro[3.5]nonan-2-yl)-8-fluoro-3,4-dihydro-1H-isoquinoline-6-carboxylate (350 mg, 1.05 mmol, 1 eq) in MeOH(10 mL) was added (1-ethoxycyclopropoxy)-trimethyl-silane (240.89 mg, 1.36 mmol, 232.86 uL, 1.5 eq), AcOH (126.46 mg, 2.11 mmol, 120.44 uL, 2 eq). The mixture was stirred at 25° C. for 2 hr. $NaBH_3CN$ (99.25 mg, 1.58 mmol, 1.5 eq) was added. The mixture was stirred at 25° C. for 16 hr. The mixture was concentrated under reduced pressure. The residue was purified by prep-TLC (SiO2) to obtain methyl 2-(7-cyclopropyl-7-azaspiro[3.5]nonan-2-yl)-8-fluoro-3,4-dihydro-1H-isoquinoline-6-carboxylate (180 mg, 444.59 umol, 42.23% yield, 92% purity) as a colorless liquid. $^1$H NMR (400 MHz, METHANOL-d4) δ ppm 7.65-7.69 (m, 1H) 7.48-7.53 (m, 1H) 3.91 (s, 3H) 3.59 (s, 2H) 2.97-3.03 (m, 3H) 2.62-2.71 (m, 4H) 2.17 (br t, J=8.50 Hz, 2H) 1.58-1.77 (m, 8H) 0.48-0.52 (m, 2H) 0.42-0.46 (m, 2H), LCMS(ESI): 373.2 [M+H]+.

To a solution of methyl 2-(7-cyclopropyl-7-azaspiro[3.5]nonan-2-yl)-8-fluoro-3,4-dihydro-1H-isoquinoline-6-carboxylate (160 mg, 429.56 umol, 1 eq) in MeOH (5 mL) was added hydroxylamine (283.76 mg, 8.59 mmol, 20 eq) and KOH (48.21 mg, 859.12 umol, 2 eq) at 0° C. The mixture was stirred at 25° C. for 16 hr. The mixture was concentrated under reduced pressure and purified by prep-HPLC ($NH_3H_2O$) to obtain 2-(7-cyclopropyl-7-azaspiro[3.5]nonan-2-yl)-8-fluoro-3,4-dihydro-1H-isoquinoline-6-carbohydroxamic acid (607) (57 mg, 149.57 umol, 34.82% yield, 98% purity) as a yellow solid. $^1$H NMR (400 MHz, METHANOL-d4) δ ppm 7.51 (s, 1H) 7.41 (d, J=10.1 Hz, 1H) 3.57-3.60 (m, 2H) 2.97-3.04 (m, 3H) 2.68-2.71 (m, 6H) 2.14-2.23 (m, 2H) 1.79 (s, 5H) 1.61-1.66 (m, 2H) 0.54-0.60 (m, 2H) 0.44-0.52 (m, 2H). MS (ESI): 374.2 [M+H]+.

2-(2-acetyl-2-azaspiro[3.5]nonan-7-yl)-8-fluoro-3,4-dihydro-1H-isoquinoline-6-carbohydroxamic acid (429)

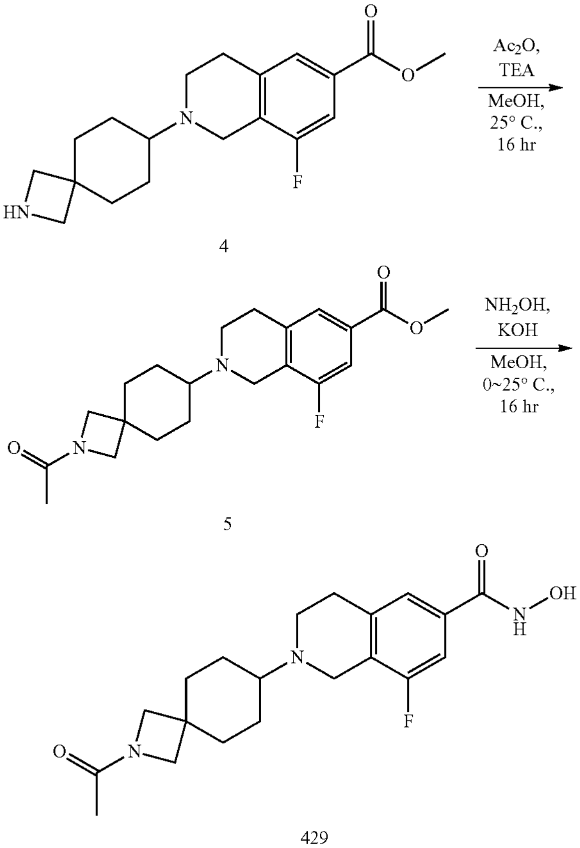

4

5

429

To a solution of methyl 2-(2-azaspiro[3.5]nonan-7-yl)-8-fluoro-3,4-dihydro-1H-isoquinoline-6-carboxylate(200 mg, 498.82 umol, 92% purity, 1 eq, HCl) in DCM (4 mL) was added $Ac_2O$ (61.11 mg, 598.58 umol, 56.06 uL, 1.2 eq) and TEA (100.95 mg, 997.63 umol, 138.86 uL, 2.0 eq). The mixture was stirred at 25° C. for 16 hr. The mixture was concentrated under reduced pressure to give residue and then was purified by prep-TLC (SiO2) to obtain methyl 2-(2-acetyl-2-azaspiro[3.5]nonan-7-yl)-8-fluoro-3,4-dihydro-1H-isoquinoline-6-carboxylate (112 mg, 278.17 umol, 55.77% yield, 93% purity) as a colorless oil. 1H NMR (400 MHz, METHANOL-d4) δ=7.64 (s, 1H), 7.48 (d, J=10.3 Hz, 1H), 3.94 (s, 1H), 3.89 (s, 3H), 3.85 (d, J=5.5 Hz, 3H), 3.71 (s, 1H), 3.62-3.59 (m, 1H), 2.96 (bd, J=5.4 Hz, 2H), 2.93-2.87 (m, 2H), 2.61 (tdd, J=3.6, 7.6, 11.2 Hz, 1H), 2.03 (bd, J=13.1 Hz, 2H), 1.99-1.95 (m, 2H), 1.88 (d, J=8.4 Hz, 3H), 1.65-1.55 (m, 2H), 1.51-1.41 (m, 2H). LCMS: MS(ESI): 375.2 [M+H]+

To a solution of methyl 2-(2-acetyl-2-azaspiro[3.5]nonan-7-yl)-8-fluoro-3,4-dihydro-1H-isoquinoline-6-carboxylate (112 mg, 278.17 umol, 93% purity, 1 eq) in MeOH (5 mL) was added hydroxylamine (367.52 mg, 5.56 mmol, 50% purity, 20 eq) and KOH (31.21 mg, 556.34 umol, 2 eq) at 0° C. The mixture was stirred at 25° C. for 16 hr. Then the mixture was concentrated under reduced pressure and purified by prep-HPLC(TFA) to obtain 2-(2-acetyl-2-azaspiro[3.5]nonan-7-yl)-8-fluoro-3,4-dihydro-1H-isoquinoline-6-carbohydroxamic acid (429) (39.93 mg, 80.27 umol, 28.86% yield, 98.393% purity, TFA) as a yellow solid. 1H NMR (400 MHz, METHANOL-d4) δ=7.54 (s, 1H), 7.45 (d, J=10.1 Hz, 1H), 4.56 (bs, 2H), 3.99 (s, 1H), 3.89 (s, 1H), 3.78-3.64 (m, 3H), 3.57-3.42 (m, 1H), 3.30-3.25 (m, 3H), 2.16 (bd, J=8.3 Hz, 4H), 1.89 (d, J=7.5 Hz, 3H), 1.70 (bd, J=8.4 Hz, 4H). MS(ESI): 376.1 [M+H]+.

2-(2-benzyl-2-azaspiro[3.5]nonan-7-yl)-8-fluoro-3,4-dihydro-1H-isoquinoline-6-carbohydroxamic acid (430)

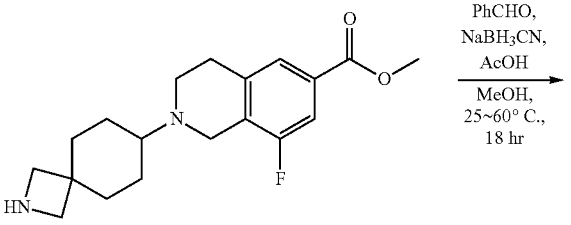

4

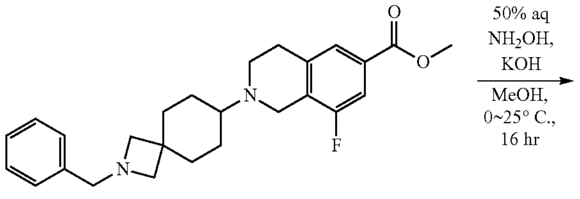

5

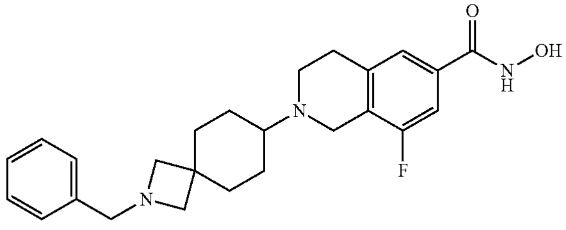

430

To a solution of methyl 2-(2-azaspiro[3.5]nonan-7-yl)-8-fluoro-3,4-dihydro-1H-isoquinoline-6-carboxylate (200 mg, 601.66 umol, 1 eq) in MeOH (3 mL) was added benzaldehyde (63.85 mg, 601.66 umol, 60.81 uL, 1 eq), AcOH (72.26 mg, 1.20 mmol, 68.82 uL, 2 eq). The mixture was stirred at 25° C. for 2 hr. Then the mixture was added NaBH3CN (49.15 mg, 782.16 umol, 1.3 eq). The mixture was stirred at 60° C. for 16 hr. The mixture was concentrated under reduced pressure. The residue was purified by prep-TLC (SiO2) to obtain methyl 2-(2-benzyl-2-azaspiro[3.5]nonan-7-yl)-8-fluoro-3,4-dihydro-1H-isoquinoline-6-carboxylate (60 mg, 127.80 umol, 21.24% yield, 90% purity) as a colorless liquid. $^1$H NMR (400 MHz, METHANOL-d4) δ=7.63 (s, 1H), 7.47 (d, J=10.3 Hz, 1H), 7.42-7.35 (m, 5H), 4.05-3.99 (m, 2H), 3.89 (s, 3H), 3.82 (s, 2H), 3.59-3.53 (m, 2H), 3.49-3.42 (m, 2H), 2.98-2.92 (m, 2H), 2.90-2.84 (m, 2H), 2.60-2.50 (m, 1H), 2.15-2.06 (m, 2H), 1.94 (bs, 2H), 1.56 (dt, J=2.4, 13.1 Hz, 2H), 1.46-1.37 (m, 2H). LCMS (ESI): 423.4 $[M+H]^+$.

To a solution of methyl 2-(2-benzyl-2-azaspiro[3.5]nonan-7-yl)-8-fluoro-3,4-dihydro-1H-isoquinoline-6-carboxylate (60 mg, 127.80 umol, 90% purity, 1 eq) in MeOH (1 mL) was added hydroxylamine (168.85 mg, 2.56 mmol, 50% purity, 20 eq) and KOH (14.34 mg, 255.60 umol, 2 eq) at 0° C. The mixture was stirred at 25° C. for 16 hr. The mixture was concentrated under reduced pressure and purified by prep-HPLC(TFA) to obtain 2-(2-benzyl-2-azaspiro[3.5]nonan-7-yl)-8-fluoro-3,4-dihydro-1H-isoquinoline-6-carbohydroxamic acid (430) (16.43 mg, 29.95 umol, 23.44% yield, 98% purity, TFA) as a yellow solid. $^1$H NMR (400 MHz, METHANOL-d4) δ=7.51 (s, 1H), 7.49 (s, 5H), 7.44 (d, J=10.3 Hz, 1H), 4.53 (bs, 2H), 4.41 (s, 2H), 4.05 (bs, 2H), 4.00-3.87 (m, 2H), 3.70-3.57 (m, 1H), 3.56-3.40 (m, 2H), 3.27-3.26 (m, 2H), 2.40-2.23 (m, 2H), 2.18-2.16 (m, 2H), 1.79-1.64 (m, 4H). MS(ESI): 424.2 $[M+H]^+$.

(S)-8-fluoro-N-hydroxy-2-(5-oxaspiro[3.5]nonan-8-yl)-1,2,3,4-tetrahydroisoquinoline-6-carboxamide (445) and (R)-8-fluoro-N-hydroxy-2-(5-oxaspiro[3.5]nonan-8-yl)-1,2,3,4-tetrahydroisoquinoline-6-carboxamide (446)

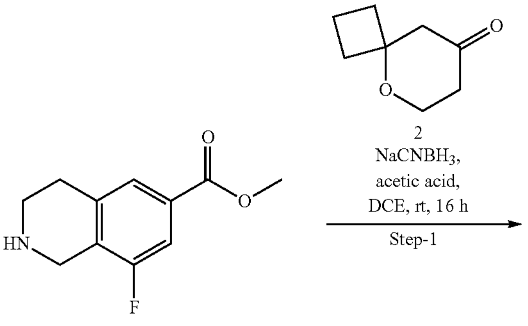

1

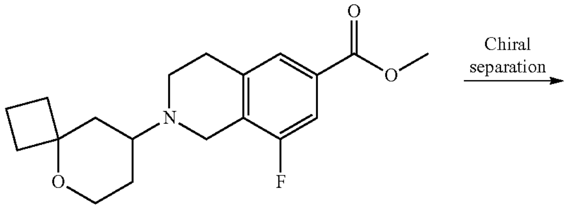

3

-continued

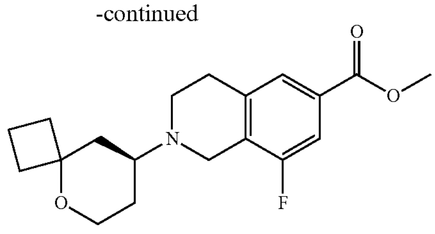

4a (Peak-1)

+

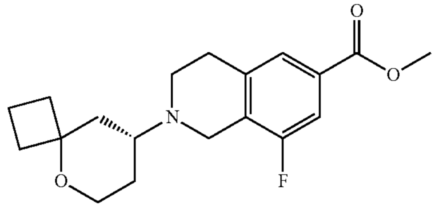

4b (Peak-2)

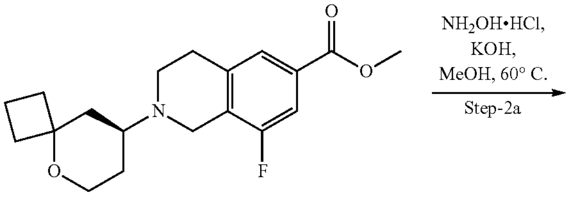

4a (Peak-1)

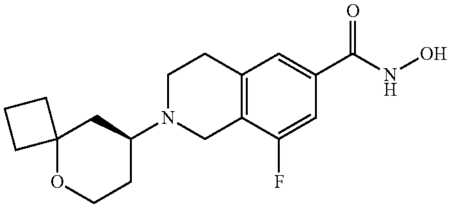

445

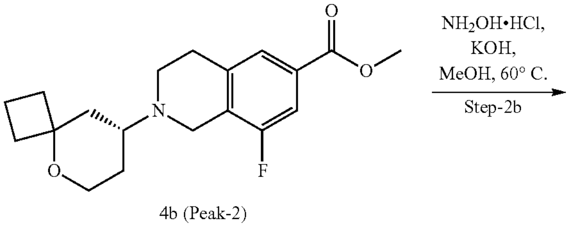

4b (Peak-2)

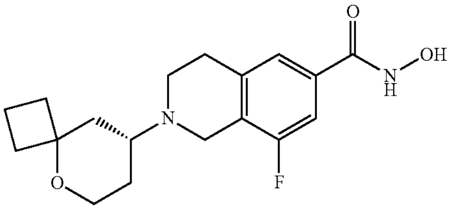

446

To a stirred solution of methyl 8-fluoro-1,2,3,4-tetrahydroisoquinoline-6-carboxylate (1, 0.500 g, 2.389 mmol, 1.0 equiv.) and 5-oxaspiro[3.5]nonan-8-one (2, 0.335 g, 2.389 mmol, 1.0 equiv.) in DCE (10 mL) was added acetic acid (1.5 mL, 3.0 Volume) at room temperature and stirred for 3 h. To the resulting reaction mixture was added $NaCNBH_3$ (1.50 g, 7.167 mmol, 3 equiv.) at room temperature and stiffed for 16 h. Progress of the reaction was monitored by TLC. After completion, reaction mixture was quenched with water (10 mL) and extracted with DCM (2×50 mL). The combined organic layer was washed with aq. $NaHCO_3$ (13 mL) followed by brine (20 mL), dried over anhydrous $Na_2SO_4$, filtered and concentrated under reduced pressure to get crude product. The crude product was purified by CombiFlash column chromatography using ethyl acetate: n-heptane (40%) to afford racemic mixture of methyl 8-fluoro-2-(5-oxaspiro[3.5]nonan-8-yl)-1,2,3,4-tetrahydroisoquinoline-6-carboxylate (3, 0.600 g, 75%) as white solid. MS (ESI): 333.95 $[M+H]^+$. Chiral HPLC: Peak-1_HPLC=63.29%, Rt=7.422 min. Peak-2_HPLC=36.71%, Rt=9.199 min.

(S)-8-fluoro-N-hydroxy-2-(5-oxaspiro[3.5]nonan-8-yl)-1,2,3,4-tetrahydroisoquinoline-6-carboxamide (45): The obtained racemic mixture of methyl 8-fluoro-2-(5-oxaspiro[3.5]nonan-8-yl)-1,2,3,4-tetrahydroisoquinoline-6-carboxylate (3, 0.600 g) was subjected to chiral prep-HPLC separation to afford 4a (Peak-1, 0.250 g) and 4b (Peak-2, 0.280 g) respectively. To a solution of Hydroxylamine hydrochloride (2.0 g, 28.77 mmol, 38.0 equiv.) in methanol (10 mL) was added potassium hydroxide solution in methanol (2.85 g, 50.79 mmol, 68 equiv, 6.0 mL methanol) at room temperature and stirred the reaction mixture under inert atmosphere at 90° C. temperature for 30 min. After 30 min., reaction mixture was cooled to room temperature, resulting organic layer of hydroxylamine potassium salt (2.0 mL, 1.7 M) was added to a reaction mixture of methyl (S)-8-fluoro-2-(5-oxaspiro[3.5]nonan-8-yl)-1,2,3,4-tetrahydroisoquinoline-6-carboxylate (4a_Peak-1, 0.250 g, 0.7498 mmol, 1.0 equiv.) in DMF (0.5 mL) at room temperature. Reaction mixture was stirred for 3 h at room temperature and progress of reaction was monitored by TLC. After completion of reaction, reaction mixture was quenched with acetic acid and concentrated under reduced pressure to obtain crude product. The crude product was purified by Prep HPLC to afford (S)-8-fluoro-N-hydroxy-2-(5-oxaspiro[3.5]nonan-8-yl)-1,2,3,4-tetrahydroisoquinoline-6-carboxamide (445, 0.080 g, 32%) as an off white solid. $^1H$ NMR (400 MHz, DMSO-$d_6$) δ ppm 10.23 (br. s, 1H), 8.64 (s, 1H), 7.39 (s, 1H), 7.32 (d, J=7.98 Hz, 1H), 3.65-3.75 (m, 3H), 3.30-3.40 (m, 1H), 2.83 (d, J=8.01 Hz, 2H), 2.65-2.75 (m, 3H), 1.98-2.10 (m, 3H), 1.80-1.90 (m, 2H), 1.60-1.65 (m, 3H), 1.30-1.50 (m, 2H). $^{19}F$ NMR (400 MHz, DMSO-d.): 6-121.11. MS (ESI): 335.00 $[M+H]^+$. HPLC=96.86%, $R_t$=6.366 min.

(R)-8-fluoro-N-hydroxy-2-(5-oxaspiro[3.5]nonan-8-yl)-1,2,3,4-tetrahydroisoquinoline-6-carboxamide (446): To a solution of Hydroxylamine hydrochloride (2.0 g, 28.77 mmol, 35.0 equiv.) in methanol (10 mL) was added potassium hydroxide solution in methanol (2.85 g, 50.79 mmol, 61 equiv, 6.0 mL methanol) at room temperature and stirred the reaction mixture under inert atmosphere at 90° C. temperature for 30 min. After 30 min., reaction mixture was cooled to room temperature, resulting organic layer of hydroxylamine potassium salt (2.0 mL, 1.7 M) was added to a reaction mixture of methyl (R)-8-fluoro-2-(5-oxaspiro[3.5]nonan-8-yl)-1,2,3,4-tetrahydroisoquinoline-6-carboxylate (4a_Peak-2, 0.280 g, 0.8398 mmol, 1.0 equiv.) in DMF (0.56 mL) at room temperature. Reaction mixture was stirred for 3 h at room temperature and progress of reaction was monitored by TLC. After completion of reaction, reaction mixture was quenched with acetic acid and concentrated under reduced pressure to obtain crude product. The crude product was purified by Prep HPLC to afford (R)-8-fluoro-N-hydroxy-2-(5-oxaspiro[3.5]nonan-8-yl)-1,2,3,4-tetrahydroisoquinoline-6-carboxamide (446, 0.090 g, 3%) as an off white solid. $^1H$ NMR (400 MHz, DMSO-$d_6$) δ ppm 11.20 (br. s, 1H), 9.05 (br. s, 1H), 7.39 (s, 1H), 7.32 (d, J=7.98 Hz, 1H), 3.65-3.75 (m, 3H), 3.30-3.40 (m, 1H), 2.83 (d, J=8.01

Hz, 2H), 2.65-2.75 (m, 3H), 1.97-2.06 (m, 3H), 1.82-1.92 (m, 2H), 1.59-1.71 (m, 3H), 1.31-1.47 (m, 2H). $^{19}$F NMR (400 MHz, DMSO-$d_6$): −121.08. MS (ESI): 335.00 $[M+H]^+$. HPLC=96.98%, $R_t$=6.372 min.

LCMS_Condition_01: Column: X-Bridge BEH C-18 (3.0×50 mm, 2.5 μm), Mobile Phase: A-0.025% FA in Water, Mobile Phase: B-ACN, Flow Rate: 1.2 mL/min (Gradient).

LCMS Condition_02: Column: X-Select CSH C-18 (150×4.6 mm, 3.5μ), Mobile Phase: A-0.025% Aq FORMIC ACID, Mobile Phase: B-ACN, Flow Rate: 1.0 mlmin (Gradient)

HPLC_Condition_01: Column: XSELECT CSH C18 (150×4.6 mm, 3.5μ), Mobile Phase-A: 0.05% TFA: ACETONITRILE (95:05), Mobile Phase-B: ACETONITRILE: 0.05% TFA (95:05), Flow: 1.0 mL/min, Diluent: ACN: Water HPLC_Condition_02: Column: XSELECT CSH C18 (150×4.6 mm, 3.5μ), Mobile Phase-A: 5 mM Ammonium acetate, Mobile Phase—ACN, Flow: 1.0 mlmin, Diluent: ACN: Water Chiral prep-HPLC separation method: Chiral pak IC (250*4.6 mm, 5 um); Mobile phase::0.1% DEA in n-Hexane; Mobile phase::B::DCM:Methanol (50:50); A:B: 85:15; Flow:1.0 ml/min.

Absolute stereochemistry is unknown for 445 and 446.

8-fluoro-2-[(3R)-spiro[4.4]nonan-3-yl]-3,4-dihydro-1H-isoquinoline-6-carbohydroxamic acid (184)

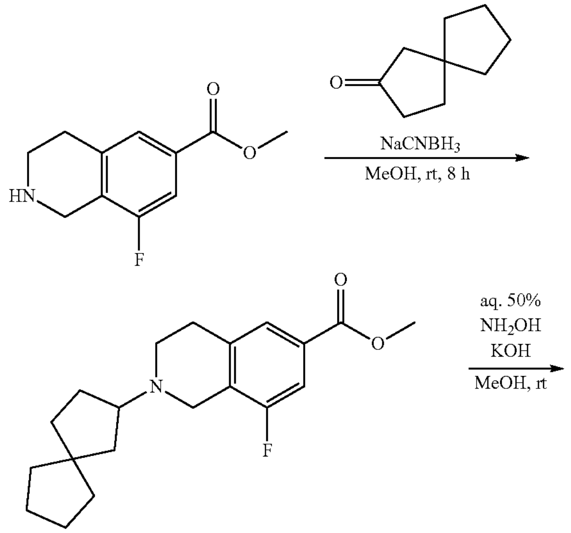

-continued

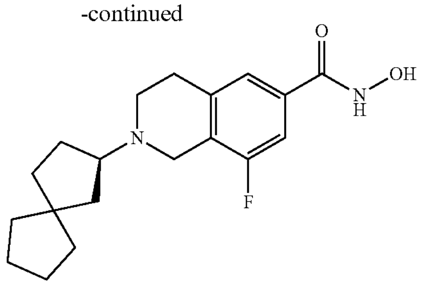

184

To a solution of methyl 8-fluoro-1,2,3,4-tetrahydroisoquinoline-6-carboxylate (605.52 mg, 2.89 mmol, 1 eq), spiro[4.4]nonan-3-one (400 mg, 2.89 mmol, 1 eq) in MeOH (15 mL) was added AcOH (347.61 mg, 5.79 mmol, 331.06 uL, 2 eq) and NaBH3CN (236.44 mg, 3.76 mmol, 1.3 eq). The mixture was stiffed at 60° C. for 16 hr. The mixture was concentrated under reduced pressure. The mixture was purified by flash silica gel chromatography (ISCO®; 20 g SepaFlash® Silica Flash Column, Eluent of 0-30% Ethyl acetate/Petroleum ether gradient @ 70 mL/min) and then was further separated by SFC (column: DAICEL CHIRALCEL OD (250 mm*30 mm, 10 um); mobile phase: [Neu-IPA]; B %: 10%-10%, 12; 360 min). Methyl 8-fluoro-2-spiro[4.4]nonan-3-yl-3,4-dihydro-1H-isoquinoline-6-carboxylate (130 mg, 292.27 umol, 10.10% yield, 74.512% purity) was obtained as a colorless oil. Methyl 8-fluoro-2-[(3S)-spiro[4.4]nonan-3-yl]-3,4-dihydro-1H-isoquinoline-6-carboxylate (130 mg, 298.98 umol, 10.33% yield, 76.223% purity) was obtained as a colorless oil.

To a solution of methyl 8-fluoro-2-[(3R)-spiro[4.4]nonan-3-yl]-3,4-dihydro-1H-isoquinoline-6-carboxylate (130 mg, 290.26 umol, 74% purity, 1 eq) in MeOH (10 mL) was added hydroxylamine (383.49 mg, 5.81 mmol, 50% purity, 20 eq) and KOH (32.57 mg, 580.53 umol, 2 eq).The mixture was stirred at 25° C. for 16 hr. The mixture was concentrated under reduced pressure. The residue was purified by prep-HPLC (column: Phenomenex Luna C18 150*25 mm*10 um; mobile phase: [water(TFA)-ACN]; B %: 5%-35%, 10 min). Compound 8-fluoro-2-[(3R)-spiro[4.4]nonan-3-yl]-3,4-dihydro-1H-isoquinoline-6-carbohydroxamic acid (20 mg, 44.58 umol, 15.36% yield, 99.5% purity, TFA) was obtained as a white solid.

8-fluoro-2-[(3S)-spiro[4.4]nonan-3-yl]-3,4-dihydro-1H-isoquinoline-6-carbohydroxamic acid (185) was prepared in an analogous manner.

| | | |
|---|---|---|
| 184 | 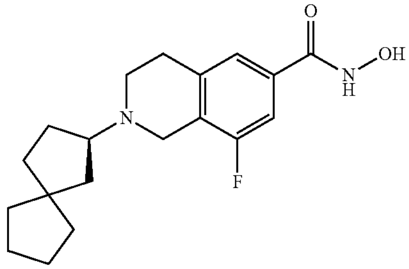 [SMILES: O=C(NO)c1cc(F)c2c(c1)CCN([C@@H]1CCC3(CCCC3)C1)C2]<br>8-fluoro-2-[(3R)-spiro[4.4]nonan-3-yl]-3,4-dihydro-1H-isoquinoline-6-carbohydroxamic acid | 1H NMR (400 MHz, METHANOL-d4) δ = 7.53 (s, 1H), 7.44 (d, J = 10.1 Hz, 1H), 4.75 − 4.24 (m, 2H), 3.97 − 3.77 (m, 2H), 3.27 (bs, 2H), 2.41 − 2.29 (m, 1H), 2.25 − 2.15 (m, 1H), 2.04 − 1.92 (m, 1H), 1.88 − 1.75 (m, 2H), 1.75 − 1.57 (m, 8H), 1.57 − 1.47 (m, 2H). MS(ESI): 333.2 [M + H]+. Absolute stereochemistry is unknown. |

-continued

| | | |
|---|---|---|
| 185 | 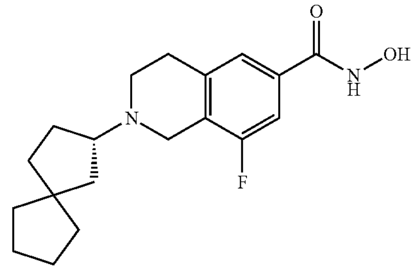 [SMILES: O=C(NO)c1cc(F)c2c(c1)CCN([C@H]1CCC3(CCCC3)C1)C2] 8-fluoro-2-[(3S)-spiro[4.4]nonan-3-yl]-3,4-dihydro-1H-isoquinoline-6-carbohydroxamic acid | 1H NMR (400 MHz, METHANOL-d4) δ = 7.53 (s, 1H), 7.45 (d, J = 10.1 Hz, 1H), 4.77 - 4.28 (m, 2H), 3.96 - 3.76 (m, 2H), 3.50 - 3.36 (m, 1H), 3.27 (bs, 2H), 2.40 - 2.29 (m, 1H), 2.27 - 2.11 (m, 1H), 2.04 - 1.91 (m, 1H), 1.88 - 1.61 (m, 10H), 1.60 - 1.49 (m, 2H). MS(ESI): 333.2 [M + H]+. Absolute stereochemistry is unknown. |

2-(7-azaspiro[3.5]nonan-2-yl)-8-fluoro-3,4-dihydro-1H-isoquinoline-6-carbohydroxamic acid (197)

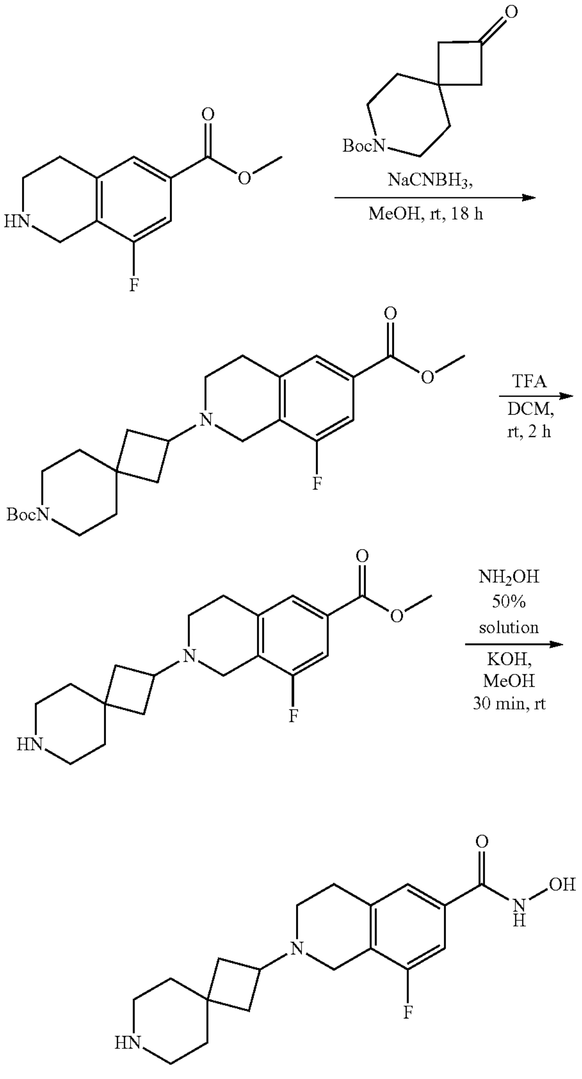

197

To a solution of tert-butyl 2-oxo-7-azaspiro[3.5]nonane-7-carboxylate (150 mg, 626.80 umol, 1 eq), methyl 8-fluoro-1,2,3,4-tetrahydroisoquinoline-6-carboxylate (131.14 mg, 626.80 umol, 1 eq) in MeOH (3 mL) was added AcOH (75.28 mg, 1.25 mmol, 71.70 uL, 2 eq) and NaBH3CN (59.08 mg, 940.20 umol, 1.5 eq). The mixture was stiffed at 25° C. for 16 hr. The reaction mixture was concentrated under reduced pressure to remove solvent. The residue was purified by prep-TLC(Petroleum ether: Ethyl acetate=3:1). Compound methyl 2-(7-tert-butoxycarbonyl-7-azaspiro[3.5]nonan-2-yl)-8-fluoro-3,4-dihydro-1H-isoquinoline-6-carboxylate (140 mg, crude) was obtained as a yellow solid. MS(ESI)=433.2[M+H]+

To a solution of methyl 2-(7-tert-butoxycarbonyl-7-azaspiro[3.5]nonan-2-yl)-8-fluoro-3,4-dihydro-1H-isoquinoline-6-carboxylate (140 mg, 323.68 umol, 1 eq) in HCl/dioxane (10 mL).The mixture was stirred at 25° C. for 2 hr. The reaction mixture was concentrated under reduced pressure to remove solvent. The crude product was used into the next step without further purification. Compound methyl 2-(7-azaspiro[3.5]nonan-2-yl)-8-fluoro-3,4-dihydro-1H-isoquinoline-6-carboxylate (110 mg, crude, HCl) was obtained as a yellow solid. MS(ESI)=333.1[M+H]+

To a solution of methyl 2-(7-azaspiro[3.5]nonan-2-yl)-8-fluoro-3,4-dihydro-1H-isoquinoline-6-carboxylate (110 mg, 298.21 umol, 1 eq, HCl) in MeOH (5 mL) was added KOH (41.83 mg, 745.52 umol, 2.5 eq) and hydroxylamine (393.99 mg, 5.96 mmol, 50% purity, 20 eq).The mixture was stirred at 25° C. for 5 hr. [Monitoring]LC-MS (EC2898-13-P1A1) showed EC2898-13-R1 was consumed completely and one main peak with desired mass was detected. The reaction mixture was concentrated under reduced pressure to remove solvent. The residue was purified by prep-HPLC (column: Waters Atlantis T3 150*30 mm*5 um; mobile phase: [water (TFA)-ACN]; B %:0%-20%, 10 min). Compound 2-(7-azaspiro[3.5]nonan-2-yl)-8-fluoro-3,4-dihydro-1H-isoquinoline-6-carbohydroxamic acid (25 mg, 55.64 umol, 18.66% yield, 99.58% purity, TFA) was obtained as a yellow solid. MS(ESI)=334.2[M+H]+; 1H NMR (400 MHz, METHANOL-d4) δ=7.51 (s, 1H), 7.43 (d, J=10.1 Hz, 1H), 4.47-4.29 (m, 2H), 3.91 (quin, J=8.4 Hz, 1H), 3.47 (bdd, J=1.5, 3.1 Hz, 2H), 3.26 (bt, J=5.7 Hz, 2H), 3.22-3.18 (m, 2H), 3.15-3.11 (m, 2H), 2.54-2.47 (m, 2H), 2.29-2.21 (m, 2H), 1.95-1.90 (m, 2H), 1.89-1.84 (m, 2H)

2-(3,3-dimethylcyclobutyl)-8-fluoro-3,4-dihydro-1H-isoquinoline-6-carbohydroxamic acid (201)

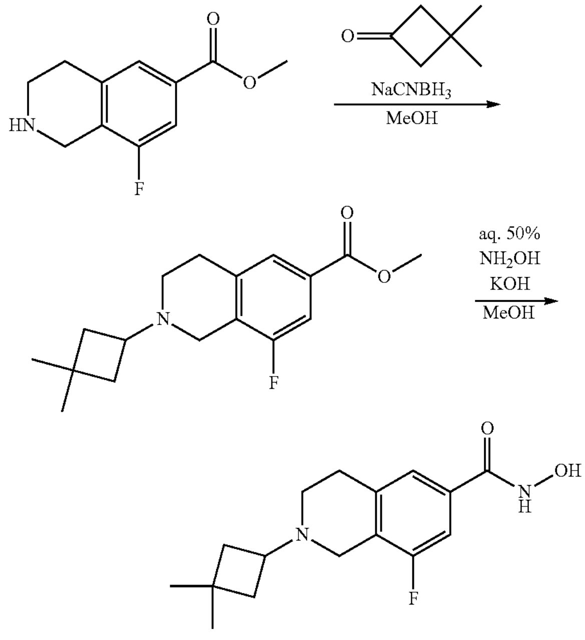

201

To a solution of methyl 8-fluoro-1,2,3,4-tetrahydroisoquinoline-6-carboxylate (300 mg, 1.43 mmol, 1 eq) in MeOH (3 mL) was added AcOH (172.22 mg, 2.87 mmol, 164.02 uL, 2 eq) and 3,3-dimethylcyclobutanone (154.80 mg, 1.58 mmol, 1.1 eq) at 25° C., the mixture was stirred at this temperature for 1 hr, and then NaBH3CN (135.17 mg, 2.15 mmol, 1.5 eq) was added at 25° C. The resulting mixture was stirred at 60° C. for 11 hr. The mixture was filtered and concentrated under reduced pressure. The residue was purified by prep-HPLC (column: Phenomenex Luna C18 150*25 mm*10 um; mobile phase: [water (FA)-ACN]; B %: 3%-33%, 10 min). Compound methyl 2-(3,3-dimethylcyclobutyl)-8-fluoro-3,4-dihydro-1H-isoquinoline-6-carboxylate (214 mg, 577.20 umol, 40.25% yield, 91% purity, FA) was obtained as a yellow solid.

To a solution of methyl 2-(3,3-dimethylcyclobutyl)-8-fluoro-3,4-dihydro-1H-isoquinoline-6-carboxylate (214 mg, 734.49 umol, 1 eq) in MeOH (5 mL) was added hydroxylamine (970.40 mg, 14.69 mmol, 50% purity, 20 eq) and KOH (82.42 mg, 1.47 mmol, 2 eq) at 0° C. The mixture was stirred at 25° C. for 16 hr. The mixture was filtered and concentrated under reduced pressure. The residue was purified by prep-HPLC (column: Welch Xtimate C18 150*25 mm*5 um; mobile phase: [water (TFA)-ACN]; B %:0%-30%, 10 min). Compound 2-(3,3-dimethylcyclobutyl)-8-fluoro-3,4-dihydro-1H-isoquinoline-6-carbohydroxamic acid (110.92 mg, 272.41 umol, 37.09% yield, 99.8% purity, TFA) was obtained as a white solid. MS(ESI): 293.1 [M+H]+; 1H NMR (400 MHz, METHANOL-d4) δ=7.53 (s, 1H), 7.44 (d, J=10.1 Hz, 1H), 4.67-4.44 (m, 1H), 4.34-4.13 (m, 1H), 3.91 (t, J=8.2 Hz, 1H), 3.81-3.54 (m, 1H), 3.30-3.21 (m, 3H), 2.35-2.29 (m, 2H), 2.16-2.10 (m, 2H), 1.25 (s, 3H), 1.22 (s, 3H).

2-(2-azaspiro[3.3]heptan-6-yl)-8-fluoro-3,4-dihydro-1H-isoquinoline-6-carbohydroxamic acid (289)

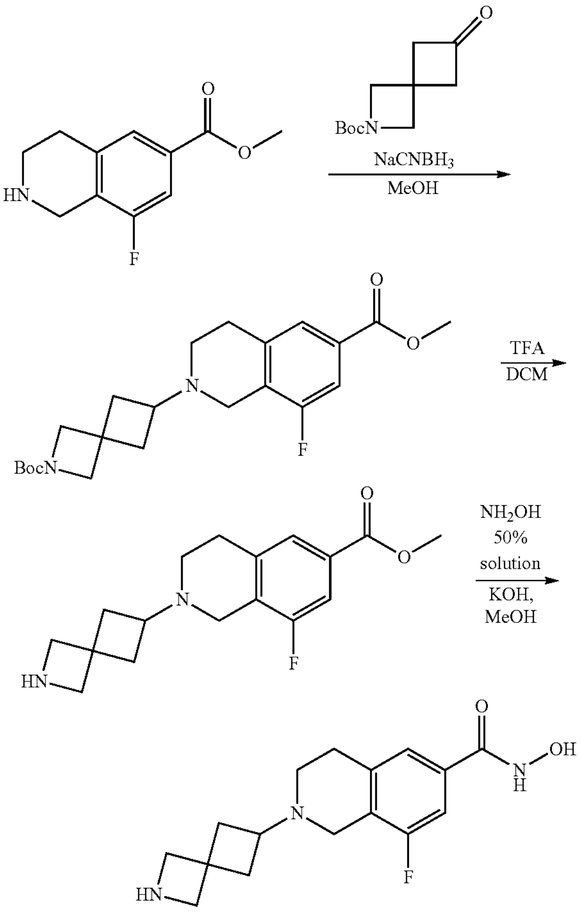

289

To a solution of methyl 8-fluoro-1,2,3,4-tetrahydroisoquinoline-6-carboxylate (990.34 mg, 4.73 mmol, 1 eq), tert-butyl 6-oxo-2-azaspiro[3.3]heptane-2-carboxylate (1 g, 4.73 mmol, 1 eq) in MeOH (20 mL) was added AcOH (568.52 mg, 9.47 mmol, 541.45 uL, 2 eq) and NaBH3CN (297.47 mg, 4.73 mmol, 1 eq) at 25° C. The mixture was stiffed at 60° C. for 16 hr. The mixture was concentrated under reduced pressure. The residue was purified by flash silica gel chromatography (20 g Silica Flash Column, Eluent of 25-30% Ethylacetate/Petroleum ether gradient @ 45 mL/min). Compound methyl 2-(2-tert-butoxycarbonyl-2-azaspiro[3.3]heptan-6-yl)-8-fluoro-3,4-dihydro-1H-isoquinoline-6-carboxylate (1.2 g, 2.28 mmol, 48.26% yield, 77% purity) was obtained as a light-yellow gum. MS(ESI): 405.2 [M+H]+

To a solution of methyl 2-(2-tert-butoxycarbonyl-2-azaspiro[3.3]heptan-6-yl)-8-fluoro-3,4-dihydro-1H-isoquinoline-6-carboxylate (1.2 g, 2.97 mmol, 1 eq) was added HCl/dioxane (4 M, 741.70 uL, 1 eq). The mixture was stirred at 25° C. for 1 hr. The mixture was concentrated under reduce pressure. Compound methyl 2-(2-azaspiro[3.3]heptan-6-yl)-8-fluoro-3,4-dihydro-1H-isoquinoline-6-carboxylate (1.3 g, crude) was obtained as a light yellow gum was used into the next step without further purification. MS(ESI): 305.2[M+H]+

To a solution of methyl 2-(2-azaspiro[3.3]heptan-6-yl)-8-fluoro-3,4-dihydro-1H-isoquinoline-6-carboxylate (1.3 g, 4.27 mmol, 1 eq) in MeOH (15 mL) was added KOH (958.57 mg, 17.09 mmol, 4 eq) and hydroxylamine (7.05 g, 106.78 mmol, 50% purity, 25 eq). The mixture was stirred at 25° C. for 4 hr. The mixture was concentrated under reduce pressure. The residue was purified by prep-HPLC (column: Waters Atlantis T3 150*30 mm*5 um; mobile phase: [water (TFA)-ACN]; B %: 0%-5%, 10 min). Compound 2-(2-azaspiro[3.3]heptan-6-yl)-8-fluoro-3,4-dihydro-1H-isoquinoline-6-carbohydroxamic acid (211.13 mg, 501.43 umol, 11.74% yield, 99.6% purity, TFA) was obtained as a orange solid. MS(ESI): 306.1[M+H]+; 1H NMR (400 MHz, METHANOL-d4) δ=7.53 (s, 1H), 7.45 (d, J=10.0 Hz, 1H), 4.35 (br s, 2H), 4.23 (s, 2H), 4.12 (s, 2H), 3.87-3.73 (m, 1H), 3.44 (br s, 2H), 3.28-3.22 (m, 2H), 2.91-2.80 (m, 2H), 2.74-2.62 (m, 2H)

2-(2-azaspiro[3.3]heptan-7-yl)-8-fluoro-3,4-dihydro-1H-isoquinoline-6-carbohydroxamic acid (301)

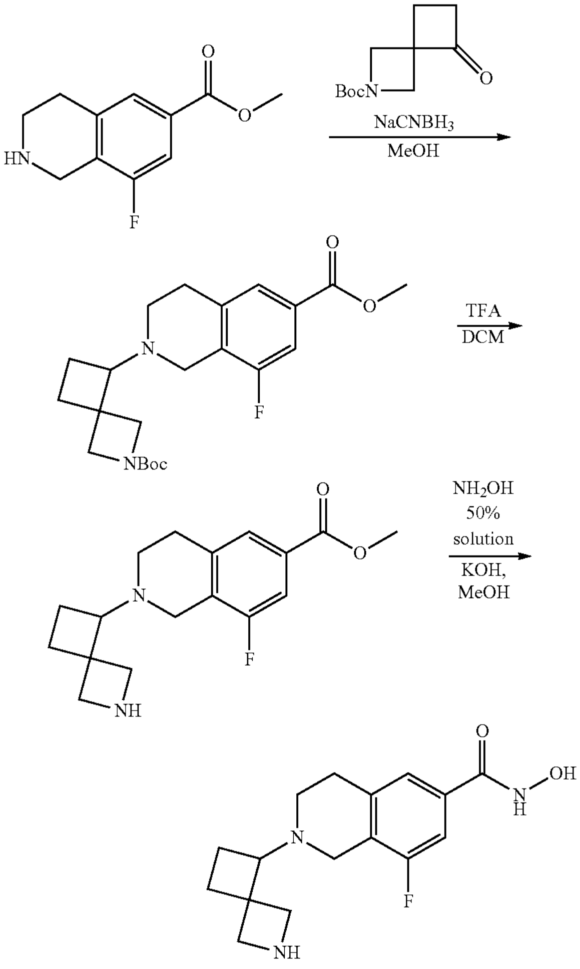

301

To a solution of methyl 8-fluoro-1,2,3,4-tetrahydroisoquinoline-6-carboxylate (970.53 mg, 4.64 mmol, 1 eq), tert-butyl 7-oxo-2-azaspiro[3.3]heptane-2-carboxylate (980 mg, 4.64 mmol, 1 eq) in MeOH (10 mL) was added AcOH (557.15 mg, 9.28 mmol, 530.62 uL, 2 eq) and NaBH3CN (437.28 mg, 6.96 mmol, 1.5 eq) at 25° C. The mixture was stirred at 80° C. for 12 hr. The reaction mixture was concentrated under reduced pressure to remove solvent. The residue was purified by prep-HPLC (column: Phenomenex Luna C18 200*40 mm*10 um; mobile phase: [water (FA)-ACN]; B %: 18%-48%, 10 min). [Result]Compound methyl 2-(2-tert-butoxycarbonyl-2-azaspiro[3.3]heptan-7-yl)-8-fluoro-3,4-dihydro-1H-isoquinoline-6-carboxylate (1.1 g, 2.39 mmol, 51.59% yield, 88% purity) was obtained as a off-white solid. MS(ESI): 405.2[M+H]+

To a solution of methyl 2-(2-tert-butoxycarbonyl-2-azaspiro[3.3]heptan-7-yl)-8-fluoro-3,4-dihydro-1H-isoquinoline-6-carboxylate (1.1 g, 2.39 mmol, 88% purity, 1 eq) in dioxane (2 mL) was added HCl/dioxane (4 M, 10 mL, 16.71 eq). The mixture was stirred at 25° C. for 3 hr. The reaction mixture was concentrated under reduced pressure to remove solvent. Compound methyl 2-(2-azaspiro[3.3]heptan-7-yl)-8-fluoro-3,4-dihydro-1H-isoquinoline-6-carboxylate (1 g, crude, HCl) was obtained as a white solid and used into the next step without further purification. MS(ESI): 305.2[M+H]+

To a solution of methyl 2-(2-azaspiro[3.3]heptan-7-yl)-8-fluoro-3,4-dihydro-1H-isoquinoline-6-carboxylate (60 mg, 176.05 umol, 1 eq, HCl) in MeOH (5 mL) was added hydroxylamine (232.59 mg, 3.52 mmol, 50% purity, 20 eq) and KOH (19.75 mg, 352.09 umol, 2 eq). The mixture was stirred at 25° C. for 12 hr. The reaction mixture was concentrated under reduced pressure to remove solvent. The residue was purified by prep-HPLC (column: Waters Atlantis T3 150*30 mm*5 um; mobile phase: [water (TFA)-ACN]; B %: 0%-10%, 10 min). [Result]Compound 2-(2-azaspiro[3.3]heptan-7-yl)-8-fluoro-3,4-dihydro-1H-isoquinoline-6-carbohydroxamic acid (4.39 mg, 14.16 umol, 8.04% yield, 98.5% purity) was obtained as a orange solid. MS(ESI): 306.1[M+H]$^+$; 1H NMR (400 MHz, METHANOL-d4) δ=7.49 (s, 1H), 7.40 (d, J=10.1 Hz, 1H), 4.71 (bs, 1H), 4.34 (bd, J=11.8 Hz, 1H), 4.25-3.95 (m, 4H), 3.61-3.49 (m, 1H), 3.36 (bd, J=6.4 Hz, 1H), 3.27-3.09 (m, 3H), 2.38-2.23 (m, 2H), 2.22-2.02 (m, 2H).

8-fluoro-2-(5-methyl-5-azaspiro[3.5]nonan-2-yl)-3,4-dihydro-1H-isoquinoline-6-carbohydroxamic acid (352)

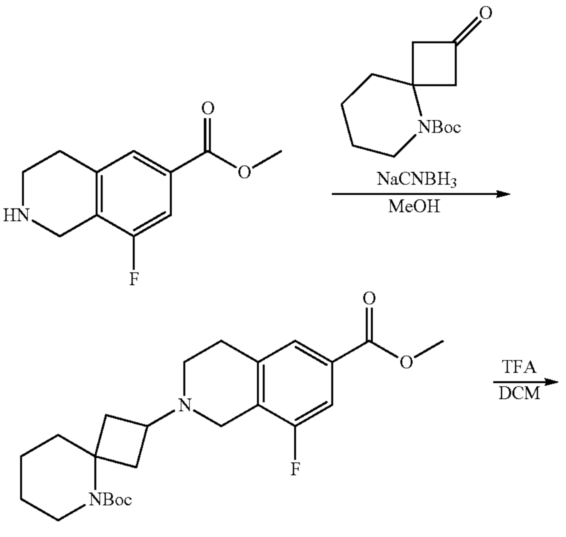

-continued

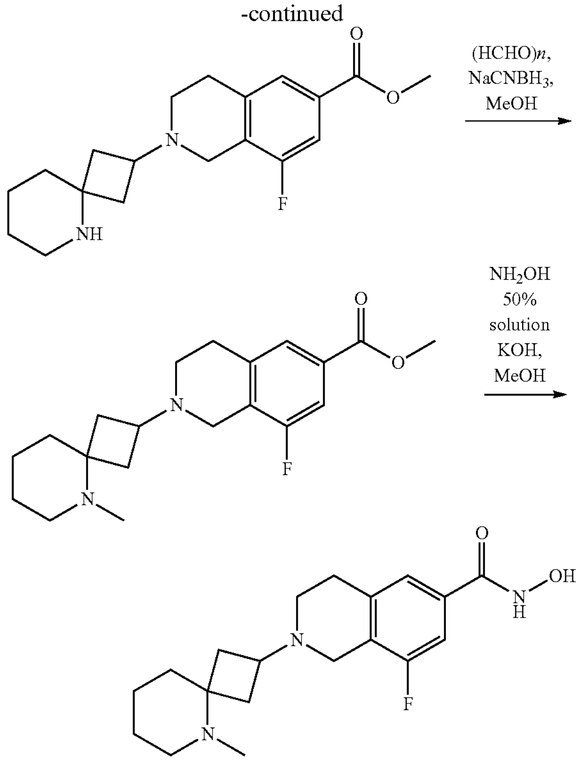

352

To a solution of methyl 8-fluoro-1,2,3,4-tetrahydroisoquinoline-6-carboxylate (300 mg, 1.43 mmol, 1 eq) in MeOH (3 mL) was added AcOH (172.22 mg, 2.87 mmol, 164.02 uL, 2 eq) and tert-butyl 2-oxo-5-azaspiro[3.5]nonane-5-carboxylate (343.15 mg, 1.43 mmol, 1 eq) at 25° C. for 2 hr. and then NaBH3CN (135.17 mg, 2.15 mmol, 1.5 eq) was added dropwise at 25° C. The resulting mixture was stirred at 25° C. for 12 hr. The reaction mixture was concentrated under reduced pressure to remove solvent. The residue was purified by prep-HPLC column: Phenomenex Luna C18 150*25 mm*10 um; mobile phase: [water (0.225% FA)-ACN]; B %: 18%-48%, 10 min. Compound methyl 2-(5-tert-butoxycarbonyl-5-azaspiro[3.5]nonan-2-yl)-8-fluoro-3,4-dihydro-1H-isoquinoline-6-carboxylate (400 mg, 850.81 umol, 59.33% yield, 92% purity) was obtained as a yellow solid. MS (ESI): 433.3 [M+H]+

A mixture of methyl 2-(5-tert-butoxycarbonyl-5-azaspiro[3.5]nonan-2-yl)-8-fluoro-3,4-dihydro-1H-isoquinoline-6-carboxylate(280 MG, 647.36 umol, 1 eq), in HCl/dioxane (10 mL) was degassed and purged with $N_2$ for 3 times, and then the mixture was stirred at 25° C. for 2 hr under $N_2$ atmosphere. The reaction mixture was concentrated under reduced pressure to remove solvent. The residue was taken to the next step without purification. Compound methyl 2-(5-azaspiro[3.5]nonan-2-yl)-8-fluoro-3,4-dihydro-1H-isoquinoline-6-carboxylate (260 mg, 634.37 umol, 97.99% yield, 90% purity, HCl) was obtained as a yellow solid. MS (ESI): 333.1 [M+H]+

To a solution of methyl 2-(5-azaspiro[3.5]nonan-2-yl)-8-fluoro-3,4-dihydro-1H-isoquinoline-6-carboxylate (260 mg, 782.16 umol, 1 eq) in MeOH (2 mL) was added AcOH (93.94 mg, 1.56 mmol, 89.47 uL, 2 eq) and HCHO (126.95 mg, 1.56 mmol, 116.47 uL, 37% purity, 2 eq) NaBH3CN (73.73 mg, 1.17 mmol, 1.5 eq).The mixture was stirred at 25° C. for 12 hr. The reaction mixture was concentrated under reduced pressure to remove solvent. The residue was purified by prep-HPLC column: Phenomenex luna C18 150*25 mm*10 um; mobile phase: [water (FA)-ACN]; B %: 1%-26%, 10.5 min. Compound methyl 8-fluoro-2-(5-methyl-5-azaspiro[3.5]nonan-2-yl)-3,4-dihydro-1H-isoquinoline-6-carboxylate (150 mg, 402.67 umol, 51.48% yield, 93% purity) was obtained as a yellow solid. MS (ESI): 347.1 [M+H]+

To a solution of methyl 8-fluoro-2-(5-methyl-5-azaspiro[3.5]nonan-2-yl)-3,4-dihydro-1H-isoquinoline-6-carboxylate (150 mg, 432.98 umol, 1 eq) in MeOH (2 mL) was added KOH (48.58 mg, 865.96 umol, 2 eq) and hydroxylamine (572.05 mg, 8.66 mmol, 50% purity, 20 eq). The mixture was stirred at 25° C. for 12 hr. The reaction mixture was concentrated under reduced pressure to remove solvent. The residue was purified by prep-HPLC column: Waters Atlantis T3 150*30 mm*5 um; mobile phase: [water (TFA)-ACN]; B %: 0%-20%, 8 min. Compound 8-fluoro-2-(5-methyl-5-azaspiro[3.5]nonan-2-yl)-3,4-dihydro-1H-isoquinoline-6-carbohydroxamic acid (79 mg, 167.78 umol, 38.75% yield, 98% purity, TFA) was obtained as a yellow solid. MS (ESI): 348.1 $[M+H]^+$ 1H NMR (400 MHz, METHANOL-d4) δ ppm 7.52 (s, 1H) 7.40-7.47 (m, 1H) 4.34 (br s, 2H) 3.71 (br d, J=5.00 Hz, 1H) 3.40 (br s, 2H) 3.26 (br d, J=5.50 Hz, 4H) 2.90 (s, 3H) 2.66-2.87 (m, 4H) 1.73-2.10 (m, 6H)

2-(5-cyclopropyl-5-azaspiro[3.5]nonan-2-yl)-8-fluoro-3,4-dihydro-1H-isoquinoline-6-carbohydroxamic acid (353)

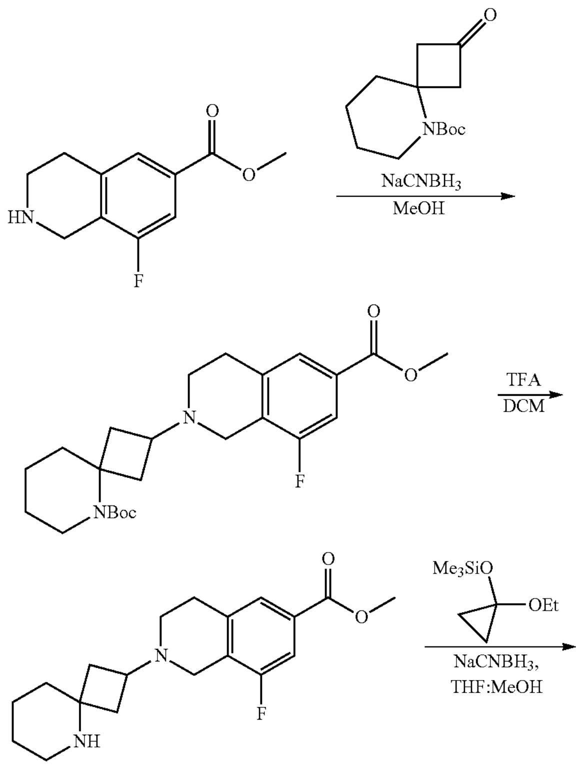

-continued

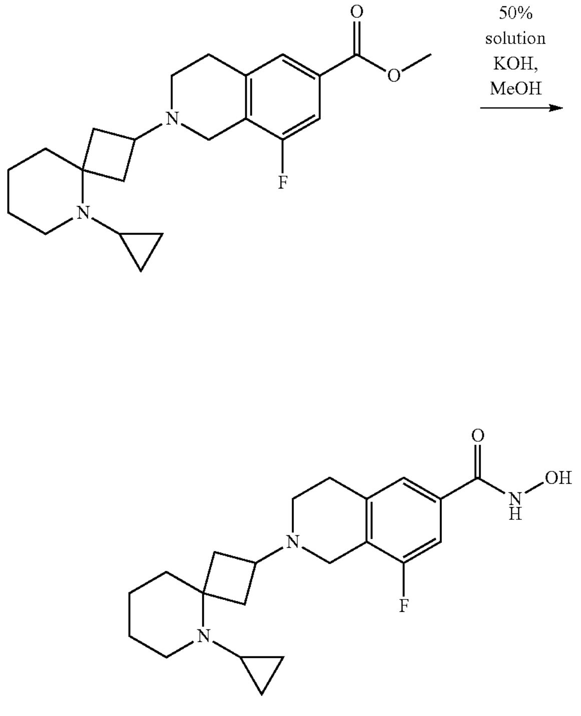

353

To a solution of methyl 2-(5-azaspiro[3.5]nonan-2-yl)-8-fluoro-3,4-dihydro-1H-isoquinoline-6-carboxylate (100 mg, 300.83 umol, 1 eq) in MeOH (3 mL) was added AcOH (36.13 mg, 601.66 umol, 34.41 uL, 2 eq) and (1-ethoxycyclopropoxy)-trimethyl-silane (57.68 mg, 330.92 umol, 66.53 uL, 1.1 eq) NaBH3CN (28.36 mg, 451.25 umol, 1.5 eq).The mixture was stirred at 60° C. for 12 hr. The reaction mixture was concentrated under reduced pressure to remove solvent. The residue was purified by prep-HPLC column: Phenomenex luna C18 150*25 mm*10 um; mobile phase: [water (FA)-ACN]; B %: 1%-23%, 10 min. Compound methyl 2-(5-cyclopropyl-5-azaspiro[3.5]nonan-2-yl)-8-fluoro-3,4-dihydro-1H-isoquinoline-6-carboxylate (60 mg, 153.03 umol, 50.87% yield, 95% purity) was obtained as a yellow solid. MS (ESI): 373.1 [M+H]+

To a solution of methyl 2-(5-cyclopropyl-5-azaspiro[3.5]nonan-2-yl)-8-fluoro-3,4-dihydro-1H-isoquinoline-6-carboxylate (60 mg, 161.08 umol, 1 eq) in MeOH (3 mL) was added KOH (18.08 mg, 322.17 umol, 2 eq) and hydroxylamine (212.82 mg, 3.22 mmol, 50% purity, 20 eq).The mixture was stirred at 25° C. for 12 hr. The reaction mixture was concentrated under reduced pressure to remove solvent. The residue was purified by prep-HPLC column: Waters Atlantis T3 150*30 mm*5 um; mobile phase: [water (TFA)-ACN]; B %: 0%-30%, 10 min. Compound 2-(5-cyclopropyl-5-azaspiro[3.5]nonan-2-yl)-8-fluoro-3,4-dihydro-1H-isoquinoline-6-carbohydroxamic acid (28 mg, 56.29 umol, 34.94% yield, 98% purity, TFA) was obtained as a white solid. MS (ESI): 374.1 [M+H]+; 1H NMR (400 MHz, METHANOL-d4) δ ppm 7.51 (s, 1H) 7.42 (d, J=10.51 Hz, 1H) 4.23 (br s, 2H) 3.86-3.97 (m, 1H) 3.36-3.44 (m, 2H) 3.18-3.31 (m, 6H) 3.05-3.12 (m, 1H) 2.55-2.65 (m, 2H) 2.11 (brs, 2H) 1.79-1.90 (m, 2H) 1.66-1.74 (m, 2H) 1.03-1.28 (m, 4H)

2-(7-azaspiro[3.5]nonan-3-yl)-8-fluoro-3,4-dihydro-1H-isoquinoline-6-carbohydroxamic acid (357)

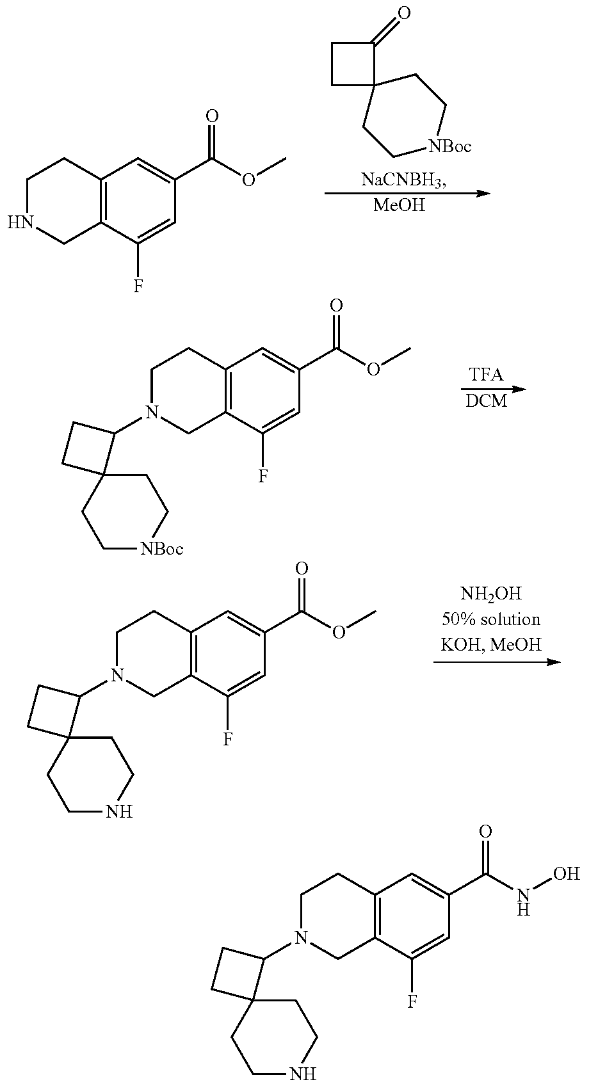

357

A mixture of tert-butyl 3-oxo-7-azaspiro[3.5]nonane-7-carboxylate (200 mg, 835.74 umol, 1 eq), methyl 8-fluoro-1,2,3,4-tetrahydroisoquinoline-6-carboxylate (192.33 mg, 919.31 umol, 1.1 eq), AcOH (100.38 mg, 1.67 mmol, 95.60 uL, 2 eq) in MeOH (5 mL) was stirred at 25° C. After 15 mins NaBH3CN (78.78 mg, 1.25 mmol, 1.5 eq) was added at 25° C., and then the mixture was stirred at 60° C. for 12 hr. The reaction mixture was concentrated under reduced pressure to remove MeOH. The residue was purified by prep-TLC (SiO2, Petroleum ether/Ethyl acetate=5/1)). Compound methyl 2-(7-tert-butoxycarbonyl-7-azaspiro[3.5]nonan-3-yl)-8-fluoro-3,4-dihydro-1H-isoquinoline-6-carboxylate (280 mg, 637.65 umol, 76.30% yield, 98.5% purity) was obtained as yellow liquid. MS(ESI): 433.4 [M+H]+

To a solution of methyl 2-(7-tert-butoxycarbonyl-7-azaspiro[3.5]nonan-3-yl)-8-fluoro-3,4-dihydro-1H-isoquinoline-6-carboxylate (280 mg, 637.65 umol, 98.5% purity, 1 eq) in dioxane (1 mL) was added HCl/dioxane (4 M, 4 mL, 25.09 eq).The mixture was stirred at 25° C. for 1 hr. The reaction mixture was concentrated under reduced pressure to remove HCl/dioxane. The reaction was used into the next step without further purification. Compound methyl 2-(7-azaspiro[3.5]nonan-3-yl)-8-fluoro-3,4-dihydro-1H-isoquinoline-6-carboxylate (265 mg, 634.17 umol, 99.45% yield, 97% purity, 2HCl) was obtained as a white solid. MS(ESI): 333.2[M+H]+

To a solution of methyl 2-(7-azaspiro[3.5]nonan-3-yl)-8-fluoro-3,4-dihydro-1H-isoquinoline-6-carboxylate (265 mg, 634.17 umol, 97% purity, 1 eq, 2HCl) in MeOH (5 mL) was added KOH (106.75 mg, 1.90 mmol, 3 eq) and hydroxylamine (837.86 mg, 12.68 mmol, 50% purity, 20 eq).The mixture was stirred at 25° C. for 12 hr. The reaction mixture was concentrated under reduced pressure to remove MeOH. The crude product was purified by reversed-phase HPLC (column: Waters Atlantis T3 150*30 mm*5 um; mobile phase: [water (TFA)-ACN]; B %: 0%-20%, 10 min). Compound 2-(7-azaspiro[3.5]nonan-3-yl)-8-fluoro-3,4-dihydro-1H-isoquinoline-6-carbohydroxamic acid (135.27 mg, 302.03 umol, 47.63% yield, 99.9% purity, TFA) was obtained as an off-white solid. MS(ESI): 334.2[M+H]+; 1H NMR (400 MHz, METHANOL-d4) δ=7.51 (s, 1H), 7.44 (d, J=10.1 Hz, 1H), 4.51-4.27 (m, 2H), 3.75 (br t, J=9.0 Hz, 1H), 3.58-3.45 (m, 3H), 3.42-3.34 (m, 1H), 3.32-3.25 (m, 2H), 3.19 (dt, J=2.9, 13.0 Hz, 1H), 2.98 (dt, J=2.9, 13.1 Hz, 1H), 2.54-2.44 (m, 1H), 2.41-2.32 (m, 1H), 2.31-2.09 (m, 4H), 2.04-1.96 (m, 1H), 1.84-1.73 (m, 1H)

8-fluoro-2-(7-methyl-7-azaspiro[3.5]nonan-3-yl)-3,4-dihydro-1H-isoquinoline-6-carbohydroxamic acid (358)

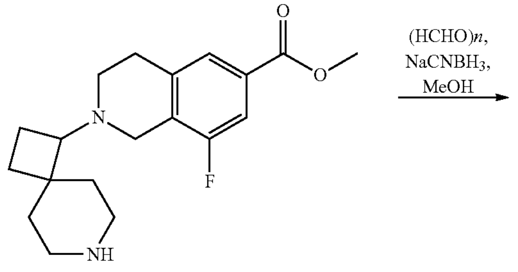

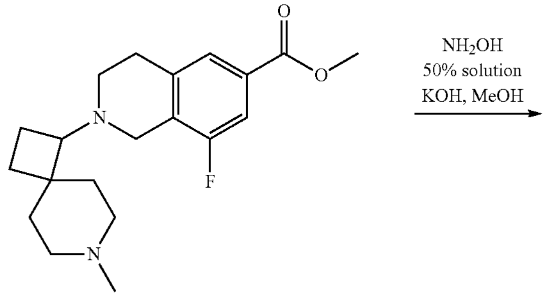

-continued

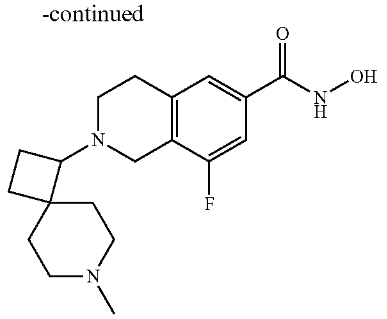

358

To a solution of methyl 2-(7-azaspiro[3.5]nonan-3-yl)-8-fluoro-3,4-dihydro-1H-isoquinoline-6-carboxylate (150 mg, 406.64 umol, 1 eq, HCl) in MeOH (5 mL) was added AcOH (24.42 mg, 406.64 umol, 23.26 uL, 1 eq) and HCHO (66.01 mg, 813.29 umol, 60.56 uL, 37% purity, 2 eq) at 25° C., the mixture was stirred at this temperature for 1 hr, then NaBH3CN (38.33 mg, 609.97 umol, 1.5 eq) was added at 25° C. The resulting mixture was stirred at 25° C. for 15 hr. The reaction was filtered and concentrated under reduced pressure. The residue was purified by prep-HPLC(column: Phenomenex Luna C18 150*25 mm*10 um; mobile phase: [water(FA)-ACN]; B %: 0%-14%, 8 min). Compound methyl 8-fluoro-2-(7-methyl-7-azaspiro[3.5]nonan-3-yl)-3,4-dihydro-1H-isoquinoline-6-carboxylate (130 mg, 360.24 umol, 88.59% yield, 96% purity) was obtained as a yellow solid. MS(ESI): 347.2 [M+H]+

To a solution of methyl 8-fluoro-2-(7-methyl-7-azaspiro[3.5]nonan-3-yl)-3,4-dihydro-1H-isoquinoline-6-carboxylate (130 mg, 375.25 umol, 1 eq) in MeOH (2 mL) was added hydroxylamine (495.78 mg, 7.50 mmol, 50% purity, 20 eq) and KOH (42.11 mg, 750.50 umol, 2 eq) at 0° C. The mixture was stirred at 25° C. for 16 hr. The reaction as filtered and concentrated under reduced pressure. The residue was purified by prep-HPLC (column: Waters Atlantis T3 150*30 mm*5 um; mobile phase: [water (TFA)-ACN]; B %: 0%-20%, 10 min). Compound 8-fluoro-2-(7-methyl-7-azaspiro[3.5]nonan-3-yl)-3,4-dihydro-1H-isoquinoline-6-carbohydroxamic acid (28.74 mg, 59.79 umol, 15.93% yield, 96% purity, TFA) was obtained as a yellow gum. MS(ESI): 348.2 [M+H]+; 1H NMR (400 MHz, CHLOROFORM-d) δ=7.50 (s, 1H), 7.42 (d, J=10.1 Hz, 1H), 4.39-4.31 (m, 1H), 4.27-4.16 (m, 1H), 3.67 (br t, J=8.7 Hz, 1H), 3.61-3.53 (m, 1H), 3.48-3.37 (m, 3H), 3.26-3.15 (m, 3H), 3.02-2.93 (m, 1H), 2.88 (s, 3H), 2.49-2.41 (m, 1H), 2.36-2.20 (m, 3H), 2.20-2.14 (m, 1H), 2.10 (br s, 1H), 2.05-1.99 (m, 1H), 1.75 (q, J=10.1 Hz, 1H)

8-fluoro-2-(2-methyl-2-azaspiro[3.4]octan-6-yl)-3,4-dihydro-1H-isoquinoline-6-carbohydroxamic acid (389)

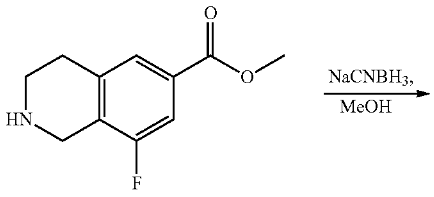

-continued

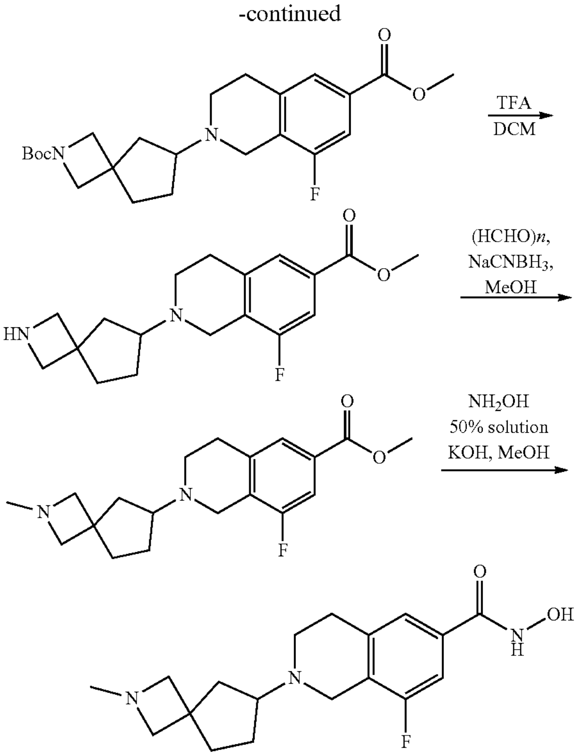

389

To a solution of methyl 8-fluoro-1,2,3,4-tetrahydroisoquinoline-6-carboxylate (1 g, 4.78 mmol, 1 eq), tert-butyl 6-oxo-2-azaspiro[3.4]octane-2-carboxylate (1.08 g, 4.78 mmol, 1 eq) in MeOH (25 mL) was added AcOH (574.07 mg, 9.56 mmol, 546.73 uL, 2 eq) and NaBH3CN (450.55 mg, 7.17 mmol, 1.5 eq) at 25° C. The mixture was stirred at 60° C. for 16 hr. The mixture was concentrated under reduce pressure. The residue was purified by flash silica gel chromatography (25 g Silica Flash Column, Eluent of 0~50% Ethylacetate/Petroleum ether gradient 70 mL/min). Compound methyl 2-(2-tert-butoxycarbonyl-2-azaspiro[3.4]octan-6-yl)-8-fluoro-3,4-dihydro-1H-isoquinoline-6-carboxylate (1.04 g, 2.31 mmol, 48.31% yield, 93% purity) was obtained as a yellow oil. MS(ESI): 419.2 [M+H]+

To a solution of methyl 2-(2-tert-butoxycarbonyl-2-azaspiro[3.4]octan-6-yl)-8-fluoro-3,4-dihydro-1H-isoquinoline-6-carboxylate (1.04 g, 2.31 mmol, 93% purity, 1 eq) in dioxane (1 mL) was added HCl/dioxane (4 M, 1.73 mL, 3 eq). The mixture was stirred at 25° C. for 2 hr. The mixture was concentrated under reduce pressure. Compound methyl 2-(2-azaspiro[3.4]octan-6-yl)-8-fluoro-3,4-dihydro-1H-isoquinoline-6-carboxylate (1.29 g, crude, 2HCl) was obtained as a yellow gum. MS(ESI): 319.1 [M+H]+

To a solution of methyl 2-(2-azaspiro[3.4]octan-6-yl)-8-fluoro-3,4-dihydro-1H-isoquinoline-6-carboxylate (250 mg, 638.88 umol, 1 eq, 2HCl) in MeOH (10 mL) was added, formaldehyde (57.03 mg, 702.77 umol, 52.32 uL, 37% purity, 1.1 eq), Pd/C (15 mg, 638.88 umol, 10% purity, 1 eq) under $N_2$. The suspension was degassed and purged with H2 for 3times. The mixture was stirred under H2 (15 Psi) at 25° C. for 16 hr. The mixture was filtered and concentrated under reduced pressure. The residue was purified by prep-HPLC (column: Waters Atlantis T3 150*30 mm*5 um; mobile phase: [water (TFA)-ACN]; B %: 0%-30%, 10 min). Compound methyl 8-fluoro-2-(2-methyl-2-azaspiro[3.4]octan-6-yl)-3,4-dihydro-1H-isoquinoline-6-carboxylate (137 mg, 412.14 umol, 64.51% yield, 100% purity) was obtained as a white solid. MS(ESI): 333.2 [M+H]+

To a solution of methyl 8-fluoro-2-(2-methyl-2-azaspiro[3.4]octan-6-yl)-3,4-dihydro-1H-isoquinoline-6-carboxylate (137 mg, 412.14 umol, 1 eq) in MeOH (3 mL) was added HYDROXYLAMINE (544.52 mg, 8.24 mmol, 50% purity, 20 eq) and KOH (34.69 mg, 618.21 umol, 1.5 eq).The mixture was stiffed at 25° C. for 12 hr. The mixture was concentrated under reduce pressure. The residue was purified by prep-HPLC (column: Waters Atlantis T3 150*30 mm*5 um; mobile phase: [water (TFA)-ACN]; B %: 0%-10%, 10 min). Compound 8-fluoro-2-(2-methyl-2-azaspiro[3.4]octan-6-yl)-3,4-dihydro-1H-isoquinoline-6-carbohydroxamic acid (27.30 mg, 80.71 umol, 19.58% yield, 98.57% purity) was obtained as a yellow gum.

MS(ESI): 334.1 [M+H]+; 1H NMR (400 MHz, METHANOL-d4) δ=7.38 (s, 1H), 7.31 (br d, J=10.1 Hz, 1H), 4.44 (br s, 2H), 4.28-4.07 (m, 2H), 4.02-3.84 (m, 2H), 3.81-3.69 (m, 1H), 3.54 (br s, 2H), 3.20-3.12 (m, 2H), 2.84 (s, 3H), 2.72-2.50 (m, 1H), 2.30-2.10 (m, 3H), 2.05-1.86 (m, 2H)

2-(8-acetyl-8-azaspiro[4.5]decan-3-yl)-8-fluoro-3,4-dihydro-1H-isoquinoline-6-carbohydroxamic acid (419)

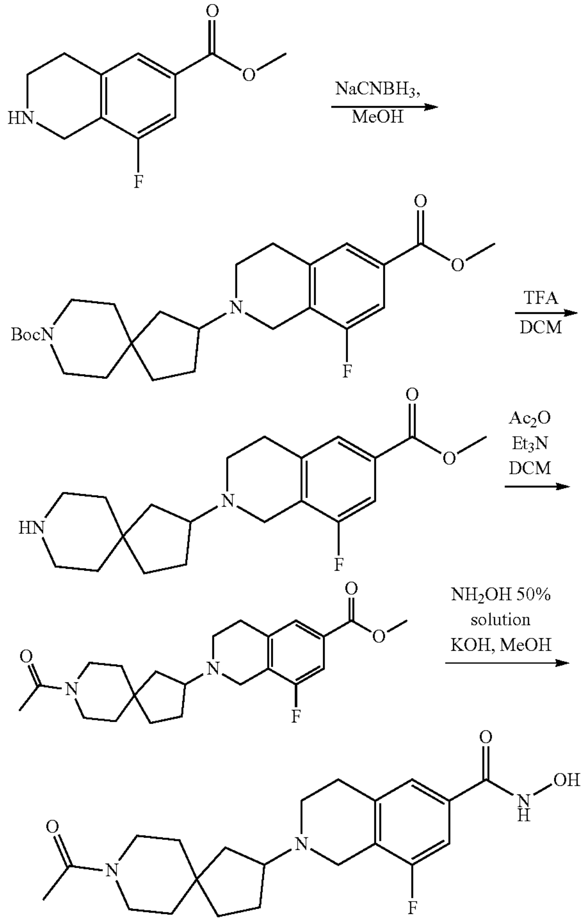

419

To a solution of tert-butyl 3-oxo-8-azaspiro[4.5]decane-8-carboxylate (508.57 mg, 2.01 mmol, 1 eq) in MeOH (5 mL) was added dropwise AcOH (180.83 mg, 3.01 mmol, 172.22 uL, 1.5 eq) and methyl 8-fluoro-1,2,3,4-tetrahydroisoquinoline-6-carboxylate (420 mg, 2.01 mmol, 1 eq) at 25° C., the mixture was stirred at this temperature for 2 hr, and then NaBH3CN (189.23 mg, 3.01 mmol, 1.5 eq) was added dropwise at 25° C. The resulting mixture was stirred at 25° C. for 14 hr. The reaction was filtered and concentrated under reduced pressure. The residue was purified by (20 g Silica Flash Column, Eluent of 0-40% Ethyl acetate/Petroleum ether @ 80 mL/min). Compound methyl 2-(8-tert-butoxycarbonyl-8-azaspiro[4.5]decan-3-yl)-8-fluoro-3,4-dihydro-1H-isoquinoline-6-carboxylate (840 mg, 1.23 mmol, 61.21% yield, 82% purity, TFA) was obtained as a yellow solid. MS(ESI): 447.3 [M+H]+

To a solution of methyl 2-(8-tert-butoxycarbonyl-8-azaspiro[4.5]decan-3-yl)-8-fluoro-3,4-dihydro-1H-isoquinoline-6-carboxylate (840 mg, 1.88 mmol, 1 eq) was added HCl/dioxane (4 M, 940.54 uL, 2 eq). The mixture was stirred at 25° C. for 2 hr. The reaction was filtered and concentrated under reduced pressure. The crude product was used for next step directly without purification. Compound methyl 2-(8-azaspiro[4.5]decan-3-yl)-8-fluoro-3,4-dihydro-1H-isoquinoline-6-carboxylate (520 mg, 1.50 mmol, 79.79% yield) was obtained as a white solid. MS(ESI): 347.1 [M+H]+

To a solution of methyl 2-(8-azaspiro[4.5]decan-3-yl)-8-fluoro-3,4-dihydro-1H-isoquinoline-6-carboxylate (520 mg, 1.36 mmol, 1 eq, HCl) in DCM (6 mL) was added Ac2O (166.37 mg, 1.63 mmol, 152.63 uL, 1.2 eq) and TEA (274.84 mg, 2.72 mmol, 378.05 uL, 2 eq).The mixture was stirred at 25° C. for 16 hr. The reaction was filtered and concentrated under reduced pressure. The residue was purified by Silica Flash Column, Eluent of 0-40% Ethyl acetate/Petroleum ether @ 80 mL/min). Compound methyl 2-(8-acetyl-8-azaspiro[4.5]decan-3-yl)-8-fluoro-3,4-dihydro-1H-isoquinoline-6-carboxylate (460 mg, 959.14 umol, 70.63% yield, 81% purity) was obtained as a yellow solid. MS(ESI): 389.2 [M+H]+

To a solution of methyl 2-(8-acetyl-8-azaspiro[4.5]decan-3-yl)-8-fluoro-3,4-dihydro-1H-isoquinoline-6-carboxylate (400 mg, 1.03 mmol, 1 eq) in MeOH (6 mL) was added hydroxylamine (1.36 g, 20.59 mmol, 50% purity, 20 eq) and KOH (115.54 mg, 2.06 mmol, 2 eq) at 0° C. The mixture was stirred at 25° C. for 16 hr. The reaction was filtered and concentrated under reduced pressure. The residue was purified by prep-HPLC (column: Welch Xtimate C18 150*25 mm*5 um; mobile phase: [water (TFA)-ACN]; B %: 0%-25%, 10 min). Compound 2-(8-acetyl-8-azaspiro[4.5]decan-3-yl)-8-fluoro-3,4-dihydro-1H-isoquinoline-6-carbohydroxamic acid (183.60 mg, 360.65 umol, 35.03% yield, 98.9% purity, TFA) was obtained as a orange solid. MS(ESI): 390.1 [M+H]+ 1H NMR (400 MHz, METHANOL-d4) δ=7.54 (br s, 1H), 7.50-7.43 (m, 1H), 4.75-4.41 (m, 2H), 3.94 (br t, J=8.9 Hz, 1H), 3.66-3.48 (m, 5H), 3.30 (br s, 2H), 2.44-2.32 (m, 2H), 2.12 (s, 3H), 2.07-1.97 (m, 1H), 1.90-1.69 (m, 4H), 1.69-1.48 (m, 4H)

8-fluoro-2-(2-oxo-2MA-thiaspiro[3.5]nonan-7-yl)-3,4-dihydro-1H-isoquinoline-6-carbohydroxamic acid (426)

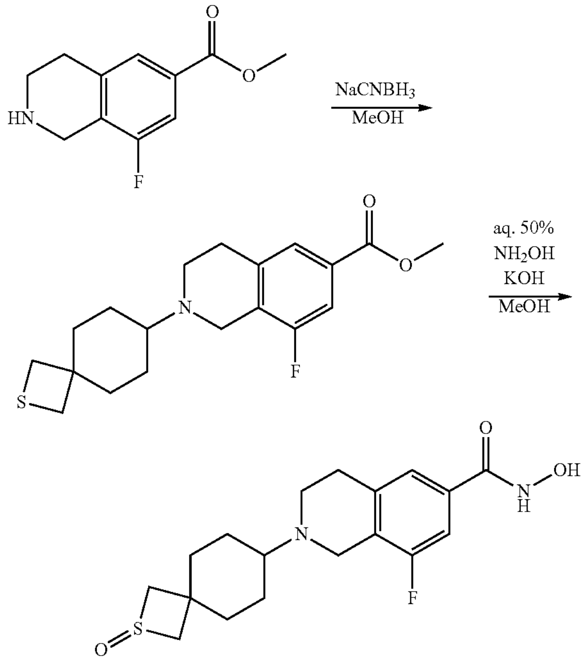

426

To a solution of 2-thiaspiro[3.5]nonan-7-one (298.72 mg, 1.91 mmol, 1 eq) in MeOH (4 mL) was added $CH_3COOH$ (172.21 mg, 2.87 mmol, 164.01 uL, 1.5 eq) and methyl 8-fluoro-1,2,3,4-tetrahydroisoquinoline-6-carboxylate (400 mg, 1.91 mmol, 1 eq) at 25° C., the mixture was stiffed at this temperature for 1 hr, and then NaBH3CN (180.22 mg, 2.87 mmol, 1.5 eq) was added at 25° C. The resulting mixture was stiffed at 25° C. for 15 hr. The reaction mixture was quenched by addition $NaHCO_3$ (2 ml) at 25° C., filtered and concentrated under reduced pressure. The residue was purified by flash silica gel chromatography (20 g Silica Flash Column, Eluent of 0-50% Ethyl acetate/Petroleum ether gradient @ 80 mL/min). Compound methyl 8-fluoro-2-(2-thiaspiro[3.5]nonan-7-yl)-3,4-dihydro-1H-isoquinoline-6-carboxylate (420 mg, 997.53 umol, 52.18% yield, 83% purity) was obtained as a yellow solid. MS(ESI): 350.0 [M+H]+

To a solution of methyl 8-fluoro-2-(2-thiaspiro[3.5]nonan-7-yl)-3,4-dihydro-1H-isoquinoline-6-carboxylate (420 mg, 1.20 mmol, 1 eq) in MeOH (8 mL) was added KOH (134.86 mg. 2.40 mmol, 2 eq) and hydroxylamine (793.94 mg. 24.04 mmol, 20 eq) at 0° C. then the mixture was stirred at 25° C. for 16 hr. The reaction mixture was quenched by addition $NaHCO_3$ (1 mL) at 25° C., filtered and concentrated under reduced pressure. The residue was purified by prep-HPLC (column: Phenomenex luna C18 150*25 mm*10 um; mobile phase: [water (0.1% TFA)-ACN]; B %: 1%-25%, 10 min). Compound 8-fluoro-2-(2-oxo-2.4-thiaspiro[3.5]nonan-7-yl)-3,4-dihydro-1H-isoquinoline-6-carbohydroxamic acid (86.6 mg, 173.03 umol, 14.40% yield, 96% purity, TFA) was obtained as a pink solid. MS(ESI): 367.1 $[M+H]^+$; 1H NMR (400 MHz, METHANOL-d4) o=7.54 (s, 1H), 7.46 (d, J=10.1 Hz, 1H), 4.57 (br s, 2H), 3.92 (dd, J=5.1, 11.9 Hz. 1H), 3.62 (dd, J=4.9, 11.7 Hz, 2H), 3.52-3.46 (m, 1H), 3.30 (br s, 2H), 3.11-2.93 (m, 3H), 2.23-2.08 (m, 3H), 1.99 (br dd, J=2.8, 13.3 Hz, 1H), 1.83-1.75 (m, 2H). 1.72 (br d, J=10.3 Hz, 2H).

2-[(8S)-5-azaspiro[3.5]non-8-yl]-8-fluoro-3,4-dihydro-1H-isoquinoline-6-carbohydroxamic acid (435) and 2-[(8R)-5-azaspiro[3.5]nonan-8-yl]-8-fluoro-3,4-dihydro-1H-isoquinoline-6-carbohydroxamic acid (436)

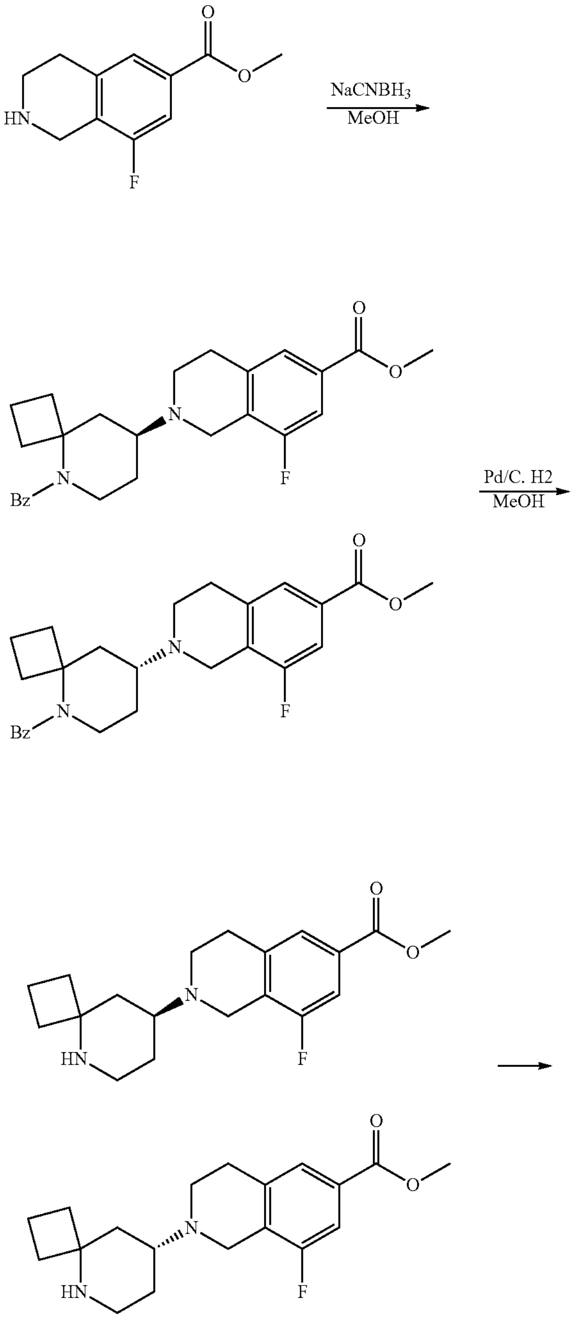

-continued

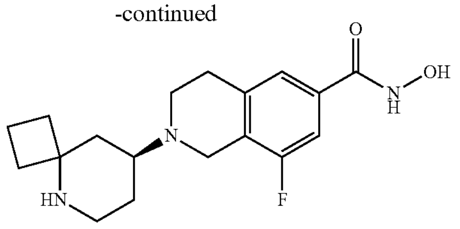

435

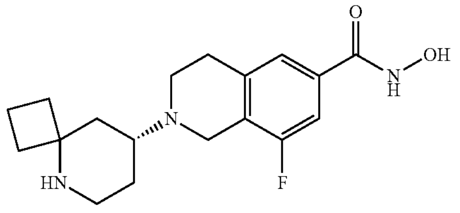

436

To a solution of methyl 8-fluoro-1,2,3,4-tetrahydroisoquinoline-6-carboxylate (912.35 mg, 4.36 mmol, 1 eq), 5-benzyl-5-azaspiro[3.5]nonan-8-one (1 g, 4.36 mmol, 1 eq) in MeOH (10 mL) was added AcOH (523.75 mg, 8.72 mmol, 498.81 uL, 2 eq) and NaBH3CN (356.25 mg, 5.67 mmol, 1.3 eq). The mixture was stirred at 60° C. for 16 hr. The mixture was concentrated under reduced pressure. The residue was purified by flash silica gel chromatography (ISCO®; 20 g SepaFlash® Silica Flash Column, Eluent of 30-100% Ethylacetate/Petroleum ether gradient @ 70 mL/min) to give 1.4 g crude(97% purity), monitored by HPLC(EC2084-157-P1B1), which was further separated by SFC(column: DAICEL CHIRALPAK AD(250 mm*30 mm, 10 um); mobile phase: [0.1% NH3H2O MEOH]; B %: 50%-50%, 5; 80 min). Compound methyl 2-[(8S)-5-benzyl-5-azaspiro[3.5]nonan-8-yl]-8-fluoro-3,4-dihydro-1H-isoquinoline-6-carboxylate (480 mg, 1.11 mmol, 25.53% yield. 98% purity) was obtained as a colorless oil. MS(ESI): 423.2 [M+H]+; Compound methyl 2-[(8R)-5-benzyl-5-azaspiro[3S]nonan-8-yl]-8-fluoro-3,4-dihydro-1H-isoquinoline-6-carboxylate (400 mg, 946.67 umol, 21.71% yield, 100% purity) was obtained as a colorless oil. MS(ESI): 423.3 [M+H]+

To a solution of methyl 2-[(8R)-5-benzyl-5-azaspiro[3.5]nonan-8-yl]-8-fluoro-3,4-dihydro-1H-isoquinoline-6-carboxylate (400 mg, 946.67 umol, 100% purity, 1 eq) in MeOH (15 mL) was added Pd/C(10%, 30 mg)under N2 atmosphere. The suspension was degassed and purged with H2 for three times. The mixture was stirred under H2 (15 Psi) at 25° C. for 16 hr. The mixture was filtered and concentrated under reduced pressure. The crude product methyl 2-[(8R)-5-azaspiro[3.5]nonan-8-yl]-8-fluoro-3,4-dihydro-1H-isoquinoline-6-carboxylate (350 mg, crude) as yellow solid was used into the next step without further purification. MS(ES+): 333.2 [M+H]+

To a solution of methyl 2-[(8S)-5-azaspiro[3.5]nonan-8-yl]-8-fluoro-3,4-dihydro-1H-isoquinoline-6-carboxylate (400 mg, 1.20 mmol, 1 eq) in MeOH (10 mL) was added KOH (67.51 mg, 1.20 mmol, 1 eq) and hydroxylamine (1.59 g, 24.07 mmol, 50% purity, 20 eq). The mixture was stirred at 25° C. for 3 hr. The mixture was concentrated under reduced pressure. The residue was purified by prep-HPLC (column: Waters Atlantis T3 150*30 mm*5 um; mobile phase: [water(TFA)-ACN]; B %: 0%-20%, 10 min). Compound 2-[(8S)-5-azaspiro[3.5]nonan-8-yl]-8-fluoro-3,4-dihydro-1H-isoquinoline-6-carbohydroxamic acid (435)

(93.89 mg, 208.80 umol, 17.35% yield, 99.5% purity, TFA) was obtained as a brown solid. MS(ES+): 334.1 [M+H]+; 1H NMR (400 MHz, METHANOL-d4) δ=7.51 (s, 1H), 7.43 (d, J=10.1 Hz, 1H), 4.49 (s, 2H), 3.71-3.60 (m, 1H), 3.59-3.47 (m, 3H), 3.26 (bs, 2H), 3.16-3.05 (m, 1H), 2.70 (bd, J=12.0 Hz, 1H), 2.45-2.30 (m, 4H), 2.27-2.17 (m, 1H), 2.14-1.91 (m, 4H)

To a solution of methyl 2-[(8R)-5-azaspiro[3.5]nonan-8-yl]-8-fluoro-3,4-dihydro-1H-isoquinoline-6-carboxylate (350 mg, 1.05 mmol, 1 eq) in MeOH (8 mL) was added hydroxylamine (1.39 g, 21.06 mmol, 50% purity, 20 eq) and KOH (118.15 mg, 2.11 mmol, 2 eq).The mixture was stirred at 25° C. for 3 hr. The mixture was concentrated under reduced pressure. The residue was purified by prep-HPLC (column: Waters Atlantis T3 150*30 mm*5 um; mobile phase: [water (TFA)-ACN]; B %: 0%-20%, 10 min). Compound 2-[(8R)-5-azaspiro[3.5]nonan-8-yl]-8-fluoro-3,4-dihydro-1H-isoquinoline-6-carbohydroxamic acid (436) (154.13 mg, 343.45 umol, 32.62% yield, 99.7% purity, TFA) was obtained as a red solid. MS(ES+): 334.1 [M+H]+; 1H NMR (400 MHz, METHANOL-d4) δ=7.56-7.35 (m, 2H), 4.74-4.48 (m, 2H), 3.92-3.45 (m, 4H), 3.37-3.32 (m, 1H), 3.30-3.24 (m, 1H), 3.22-3.03 (m, 1H), 2.76 (bs, 1H), 2.52-1.96 (m, 9H). Absolute stereochemistry is unknown for these compounds 435 and 436.

8-fluoro-2-[(8S)-5-methyl-5-azaspiro[3.5]nonan-8-yl]-3,4-dihydro-1H-isoquinoline-6-carbohydroxamic acid (437)

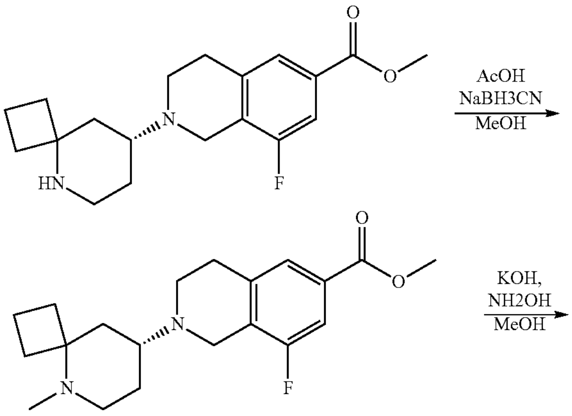

-continued

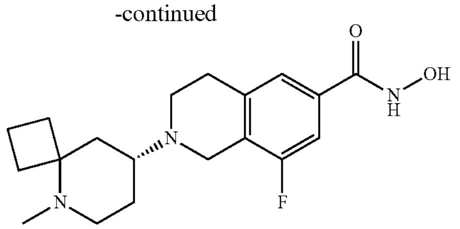

437

To a solution of methyl 2-[(8S)-5-azaspiro[3.5]nonan-8-yl]-8-fluoro-3,4-dihydro-1H-isoquinoline-6-carboxylate (300 mg, 740.13 umol, 1 eq, 2HCl), HCHO (44.45 mg, 1.48 mmol, 40.78 uL, 2 eq) in MeOH (5 mL) was added AcOH (88.89 mg, 1.48 mmol, 84.66 uL, 2 eq) and NaBH3CN (69.77 mg, 1.11 mmol, 1.5 eq), The mixture was stiffed at 25° C. for 16 hr. The reaction mixture was concentrated under reduced pressure to remove solvent. The residue was purified by prep-HPLC (column: Phenomenex luna C18 150*25 mm*10 um; mobile phase: [water(FA)-ACN]; B %: 1%-15%, 10.5 min). [Result]Compound methyl 8-fluoro-2-[(8S)-5-methyl-5-azaspiro[3.5]nonan-8-yl]-3,4-dihydro-1H-isoquinoline-6-carboxylate (210 mg, 594.05 umol, 80.26% yield, 98% purity) was obtained as a white solid. MS(ESI): 347.3[M+H]+

To a solution of methyl 8-fluoro-2-[(8S)-5-methyl-5-azaspiro[3.5]nonan-8-yl]-3,4-dihydro-1H-isoquinoline-6-carboxylate (210 mg, 594.05 umol, 98% purity, 1 eq) in MeOH (5 mL) was added KOH (66.66 mg, 1.19 mmol, 2 eq) and hydroxylamine (784.85 mg, 11.88 mmol, 50% purity, 20 eq). The mixture was stirred at 25° C. for 16 hr. The reaction mixture was concentrated under reduced pressure to remove solvent. The residue was purified by prep-HPLC (column: Waters Atlantis T3 150*30 mm*5 um; mobile phase: [water (TFA)-ACN]; B %: 0%-20%, 10 min). Compound 8-fluoro-2-[(8S)-5-methyl-5-azaspiro[3.5]nonan-8-yl]-3,4-dihydro-1H-isoquinoline-6-carbohydroxamic acid (119 mg, 255.30 umol, 42.98% yield, 99% purity, TFA) was obtained as a yellow gum. MS(ESI): 348.1[M+H]+; 1H NMR (400 MHz, METHANOL-d4) δ=7.53 (s, 1H), 7.46 (d, J=10.5 Hz, 1H), 4.60 (s, 2H), 3.86-3.76 (m, 1H), 3.66 (bt, J=5.6 Hz, 2H), 3.46 (bd, J=1.4 Hz, 2H), 3.30 (bs, 2H), 2.93 (bs, 3H), 2.71-2.45 (m, 3H), 2.33 (bt, J=12.5 Hz, 4H), 2.16-2.00 (m, 3H)

8-fluoro-2-[(8R)-5-methyl-5-azaspiro[3.5]nonan-8-yl]-3,4-dihydro-1H-isoquinoline-6-carbohydroxamic acid (438) was prepared in an analogous manner.

| | | |
|---|---|---|
| 437 | 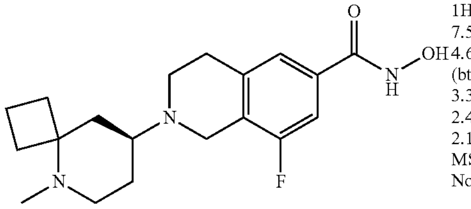<br>8-fluoro-2-[(8S)-5-methyl-5-azaspiro[3.5]nonan-8-yl]-3,4-dihydro-1H-isoquinoline-6-carbohydroxamic acid | 1H NMR (400 MHz, METHANOL-d4) δ = 7.53 (s, 1H), 7.46 (d, J = 10.5Hz, 1H), 4.60 (s, 2H), 3.86 – 3.76 (m, 1H), 3.66 (bt, J = 5.6 Hz, 2H), 3.52 – 3.46 (m, 2H), 3.30 – 3.28 (m, 2H), 2.93 (bs, 3H), 2.71 – 2.45 (m, 3H), 2.33 (bt, J = 12.5Hz, 4H), 2.16 – 2.00 (m, 3H).<br>MS(ESI): 348.3[M + H]+<br>Note: absolute stereochemistry is unknown. |

-continued

| | | |
|---|---|---|
| 438 | 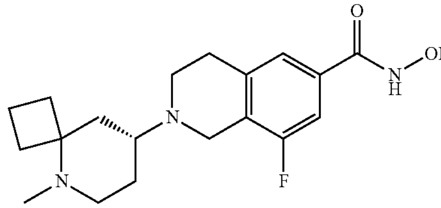 8-fluoro-2-[(8R)-5-methyl-5-azaspiro[3.5]nonan-8-yl]-3,4-dihydro-1H-isoquinoline-6-carbohydroxamic acid | 1H NMR (400 MHz, METHANOL-d4) δ = 7.50 (s, 1H), 7.43 (d, J = 10.0 Hz, 1H), 4.64 (b s, 2H), 3.88 (br s, 1H), 3.71 (b s, 2H), 3.57 - 3.32 (m, 3H), 3.31 - 3.26 (m, 1H), 2.91 (b s, 3H), 2.81 - 2.22 (m, 7H), 2.16 - 1.89 (m, 3H). MS(ESI): 348.2 [M + H]+. Absolute stereochemistry is unknown. |

2-[(8S)-5-cyclopropyl-5-azaspiro[3.5]nonan-8-yl]-8-fluoro-3,4-dihydro-1H-isoquinoline-6-carbohydroxamic acid (439) and 2-[(8R)-5-cyclopropyl-5-azaspiro[3.5]nonan-8-yl]-8-fluoro-3 4-dihydro-1H-isoquinoline-6-carbohydroxamic acid (440)

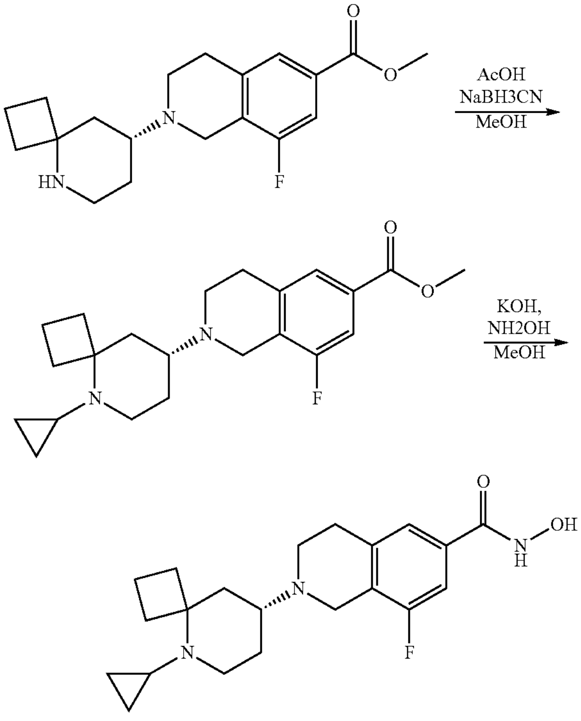

440

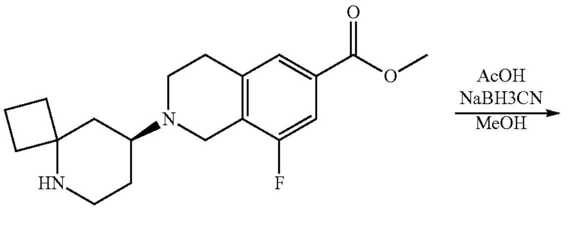

-continued

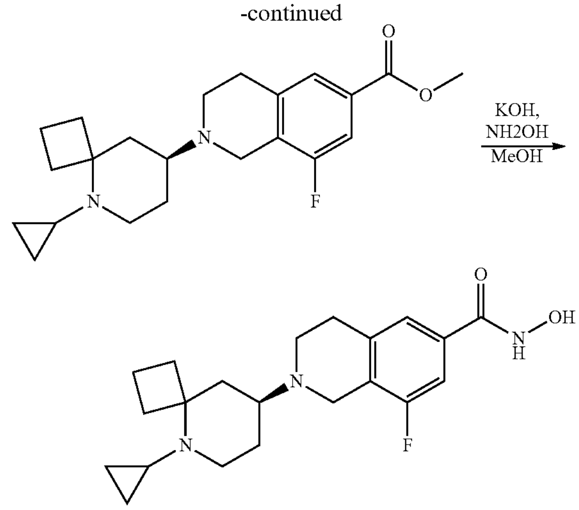

439

To a solution of methyl 2-[(8R)-5-azaspiro[3.5]nonan-8-yl]-8-fluoro-3,4-dihydro-1H-isoquinoline-6-carboxylate (300.00 mg, 740.13 umol, 1 eq, 2HCl), (1-ethoxycyclopropoxy)-trimethyl-silane (154.82 mg, 888.16 umol, 178.57 uL, 1.2 eq) in MeOH (8 mL) was added AcOH (88.89 mg, 1.48 mmol, 84.66 uL, 2 eq) and NaBH3CN (69.76 mg, 1.11 mmol, 1.5 eq).The mixture was stiffed at 60° C. for 16 hr. The mixture was filtered and concentrated under reduced pressure. The residue was purified by prep-TLC (SiO2, DCM:MeOH=10:1). Compound methyl 2-[(8R)-5-cyclopropyl-5-azaspiro[3.5]nonan-8-yl]-8-fluoro-3,4-dihydro-1H-isoquinoline-6-carboxylate (200 mg, 445.67 umol, 60.21% yield, 83% purity) was obtained as a yellow oil. MS(ESI): 373.2 [M+H]+

To a solution of methyl 2-[(8S)-5-cyclopropyl-5-azaspiro[3.5]nonan-8-yl]-8-fluoro-3,4-dihydro-1H-isoquinoline-6-carboxylate (150 mg, 374.52 umol, 93% purity, 1 eq) in MeOH (5 mL) was added hydroxylamine (494.82 mg, 7.49 mmol, 50% purity, 20 eq) and KOH (42.03 mg, 749.04 umol, 2 eq).The mixture was stirred at 25° C. for 16 hr. The mixture was concentrated under reduced pressure. The residue was purified by prep-HPLC (column: Waters Atlantis T3 150*30 mm*5 um; mobile phase: [water(TFA)-ACN]; B %: 0%-20%, 10 min). Compound 2-[(8S)-5-cyclopropyl-5-azaspiro[3.5]nonan-8-yl]-8-fluoro-3,4-dihydro-1H-isoquinoline-6-carbohydroxamic acid (58.13 mg, 119.24 umol, 31.84% yield, 100% purity, TFA) was obtained as a yellow gum. 1H NMR (400 MHz, METHANOL-d4) δ=7.52 (s, 1H), 7.43 (b d, J=10.3 Hz, 1H), 4.71-4.47 (m, 2H), 3.80-3.50

(m, 4H), 3.29-3.21 (m, 2H), 3.18-3.04 (m, 1H), 2.98-2.81 (m, 1H), 2.79-2.64 (m, 1H), 2.62-2.19 (m, 6H), 2.16-1.95 (m, 3H), 1.31-0.95 (m, 4H). MS(ESI): 374.2 [M+H]+

To a solution of methyl 2-[(8R)-5-cyclopropyl-5-azaspiro [3.5]nonan-8-yl]-8-fluoro-3,4-dihydro-1H-isoquinoline-6-carboxylate (200 mg, 536.95 umol, 1 eq) in MeOH (8 mL) was added hydroxylamine (709.41 mg, 10.74 mmol, 50% purity, 20 eq) and KOH (60.25 mg, 1.07 mmol, 2 eq).The mixture was stirred at 25° C. for 16 hr. The mixture was concentrated under reduced pressure. The residue was purified by prep-HPLC(column: Waters Atlantis T3 150*30 mm*5 um; mobile phase: [water(TFA)-ACN]; B %: 0%-20%, 10 min). Compound 2-[(8R)-5-cyclopropyl-5-azaspiro[3.5]nonan-8-yl]-8-fluoro-3,4-dihydro-1H-isoquinoline-6-carbohydroxamic acid (103.84 mg, 210.88 umol, 39.27% yield, 99% purity, TFA) was obtained as a yellow gum. 1H NMR (400 MHz, METHANOL-d4) δ=7.52 (s, 1H), 7.44 (b d, J=10.3 Hz, 1H), 4.70-4.50 (m, 2H), 3.84-3.53 (m, 4H), 3.28 (brs, 2H), 3.18-3.04 (m, 1H), 2.97-2.79 (m, 1H), 2.77-2.66 (m, 1H), 2.60-2.20 (m, 6H), 2.15-1.98 (m, 3H), 1.32-1.15 (m, 1H), 1.14-0.94 (m, 3H). MS(ESI): 374.2 [M+H]+. Absolute stereochemistry is unknown for these compounds 439 and 440.

8-fluoro-2-[(8S)-2-methyl-5-oxa-2-azaspiro[3.5] nonan-8-yl]-3,4-dihydro-1H-isoquinoline-6-carbohydroxamic acid (451) and 8-fluoro-2-[(8R)-2-methyl-5-oxa-2-azaspiro[3.5]nonan-8-yl]-3,4-dihydro-1H-isoquinoline-6-carbohydroxamic acid (452)

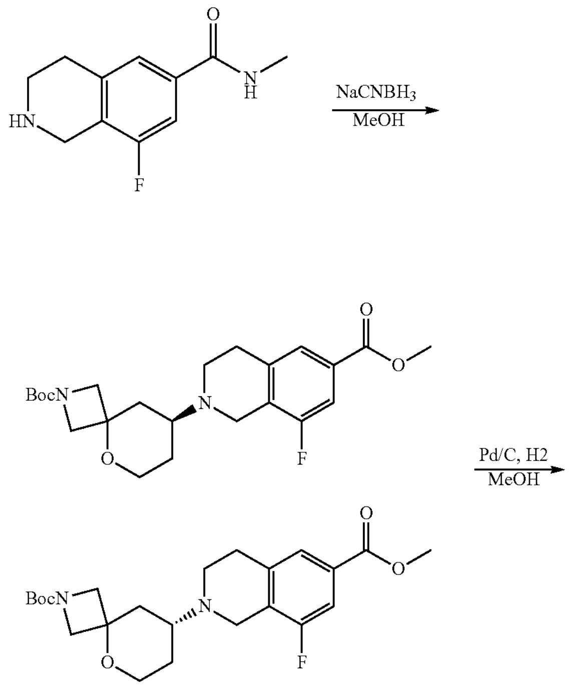

-continued

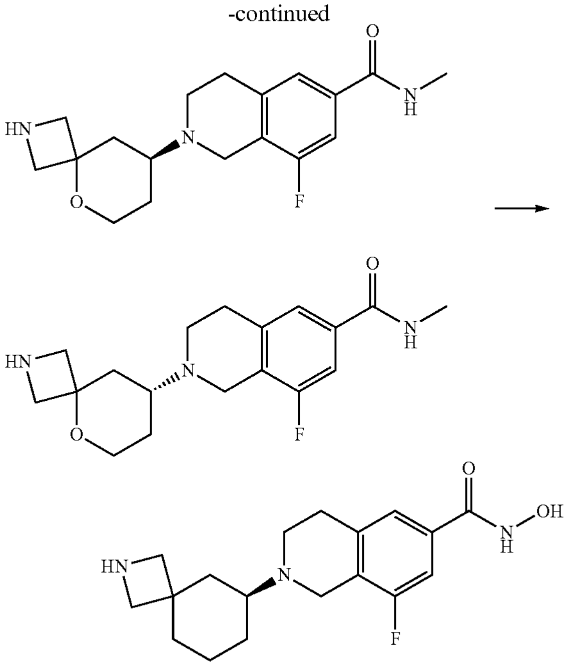

451

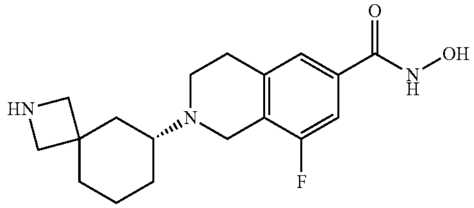

452

To a solution of methyl 8-fluoro-1,2,3,4-tetrahydroisoquinoline-6-carboxylate (0.9 g, 4.30 mmol, 1.04 eq) in MeOH (5 mL) was added AcOH (497.77 mg, 8.29 mmol, 474.07 uL, 2 eq) and tert-butyl 8-oxo-5-oxa-2-azaspiro[3.5]nonane-2-carboxylate (1.00 g, 4.14 mmol, 1 eq) NaBH3CN (390.67 mg, 6.22 mmol, 1.5 eq). The mixture was stirred at 80° C. for 12 hr. The reaction mixture was concentrated under reduced pressure to remove solvent. The residue was purified by prep-HPLC column: YMC Triart C18 250*50 mm*7 um; mobile phase: [water(FA)-ACN]; B %: 22%-52%, 12 min. Compound tert-butyl 8-(8-fluoro-6-methoxycarbonyl-3,4-dihydro-1H-isoquinolin-2-yl)-5-oxa-2-azaspiro[3.5] nonane-2-carboxylate (0.9 g, 1.97 mmol, 47.48% yield, 95% purity) was obtained as a yellow solid. MS (ESI): 435.1 [M+H]+

The residue was further separated by SFC column: DAICEL CHIRALPAK AD(250 mm*30 mm, 10 um); mobile phase: [Neu-MeOH]; B %: 30%-30%, 9.5; 180 min).

tert-butyl (8S)-8-(8-fluoro-6-methoxycarbonyl-3,4-dihydro-1H-isoquinolin-2-yl)-5-oxa-2-azaspiro[3.5]nonane-2-carboxylate (360 mg, 787.11 umol, 38.00% yield, 95% purity) was obtained as a white solid. tert-butyl (8R)-8-(8-fluoro-6-methoxycarbonyl-3,4-dihydro-1H-isoquinolin-2-yl)-5-oxa-2-azaspiro[3.5]nonane-2-carboxylate (270 mg, 590.33 umol, 28.50% yield, 95% purity) was obtained as a white solid.

To a solution of tert-butyl (8S)-8-(8-fluoro-6-methoxycarbonyl-3,4-dihydro-1H-isoquinolin-2-yl)-5-oxa-2- azaspiro[3.5]nonane-2-carboxylate (360 mg, 828.54 umol, 1 eq) in dioxane (1 ml) was added HCl/dioxane (4 M, 207.13 uL, 1 eq). The mixture was stirred at 25° C. for 2 hr. The mixture was concentrated under reduced pressure to give a residue. The crude product EC2819-1-P1 was used into the next step without further purification. The crude product methyl 8-fluoro-2-[(8S)-5-oxa-2-azaspiro[3.5]nonan-8-yl]-3,4-dihydro-1H-isoquinoline-6-carboxylate (320 mg, 722.80 umol, 87.24% yield, 92% purity, 2HCl) was obtained as a white solid, and was used into the next step without further purification.

To a solution of methyl 8-fluoro-2-[(8S)-5-oxa-2-azaspiro[3.5]nonan-8-yl]-3,4-dihydro-1H-isoquinoline-6-carboxylate (160 mg, 392.82 umol, 1 eq, 2HC) in MeOH (3 mL) was added HCHO (77.66 mg, 956.98 umol, 71.25 uL, 37% purity, 2.44 eq) and AcOH (57.47 mg, 957.00 umol, 54.73 uL, 2.44 eq) and NaBH3CN (45.10 mg, 717.67 umol, 1.83 eq).The mixture was stirred at 25° C. for 16 hr. The mixture was concentrated under reduced pressure to give a residue. The residue was purified by prep-HPLC (column: Welch Xtimate C18 150*25 mm*5 um; mobile phase: [water(FA)-ACN]; B %: 0%-10%, 10 min). The crude product methyl 8-fluoro-2-[(8S)-2-methyl-5-oxa-2-azaspiro[3.5]nonan-8-yl]-3,4-dihydro-1H-isoquinoline-6-carboxylate (70 mg, 196.89 umol, 50.12% yield, 98% purity) was obtained as a yellow oil. MS(ESI): 349.0 [M+H]+; To a solution of methyl 8-fluoro-2-[(8S)-2-methyl-5-oxa-2-azaspiro[3.5]nonan-8-yl]-3,4-dihydro-1H-isoquinoline-6-carboxylate (70 mg, 200.91 umol, 1 eq) in MeOH (2 mL) was added KOH (22.54 mg, 401.82 umol, 2 eq) and hydroxylamine (265.44 mg, 4.02 mmol, 50% purity, 20 eq). The mixture was stirred at 25° C. for 16 hr. The mixture was concentrated under reduced pressure. The residue was purified by prep-HPLC (column: Waters Atlantis T3 150*30 mm*5 um; mobile phase: [water(TFA)-ACN]; B %: 0%-15%, 10 min). The product 8-fluoro-2-[(8S)-2-methyl-5-oxa-2-azaspiro[3.5]nonan-8-yl]-3,4-dihydro-1H-isoquinoline-6-carbohydroxamic acid (13 mg, 27.49 umol, 13.68% yield, 98% purity, TFA) was obtained as a yellow gum. MS(ESI): 350.0 [M+H]+; 1H NMR (400 MHz, METHANOL-d4) δ ppm 1.91-2.16 (m, 3H) 2.58-2.65 (m, 1H) 2.98-3.07 (m, 3H) 3.28 (br d, J=5.25 Hz, 3H) 3.52-3.71 (m, 4H) 3.99-4.25 (m, 4H) 4.49 (br s, 2H) 7.46 (d, J=10.38 Hz, 1H) 7.54 (s, 1H).

8-fluoro-2-[(8R)-2-methyl-5-oxa-2-azaspiro[3.5]nonan-8-yl]-3,4-dihydro-1H-isoquinoline-6-carbohydroxamic acid (452) was prepared in analogous fashion. 1H NMR (400 MHz, METHANOL-d4) δ=7.54 (s, 1H), 7.46 (d, J=10.3 Hz, 1H), 4.53 (bs, 2H), 4.46-3.86 (m, 5H), 3.82-3.51 (m, 4H), 3.29-3.27 (m, 2H), 3.02 (s, 3H), 2.75-2.61 (m, 1H), 2.15-2.13 (m, 1H), 2.07-1.88 (m, 2H). MS(ESI): 350.1 [M+H]+. Absolute stereochemistry is unknown for compounds 451 and 452.

2-[(8S)-2-acetyl-5-oxa-2-azaspiro[3.5]nonan-8-yl]-8-fluoro-3,4-dihydro-1H-isoquinoline-6-carbohydroxamic acid (453) and 2-[(8R)-2-acetyl-5-oxa-2-azaspiro[3.5]nonan-8-yl]-8-fluoro-3,4-dihydro-1H-isoquinoline-6-carbohydroxamic acid (454)

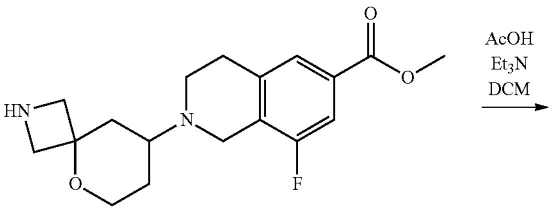

-continued

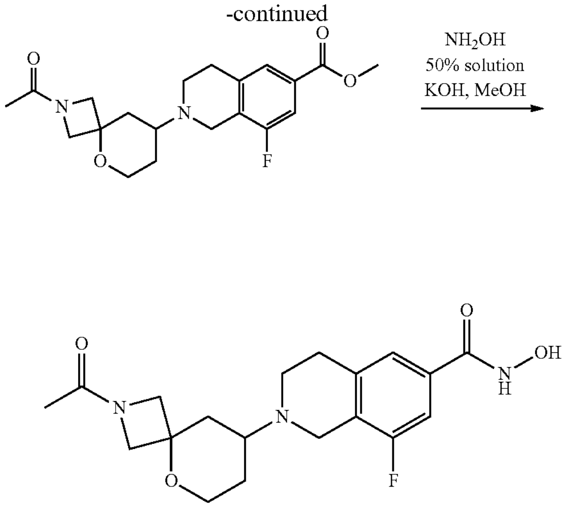

453/454

To a solution of methyl 8-fluoro-2-[(8S)-5-oxa-2-azaspiro[3.5]nonan-8-yl]-3,4-dihydro-1H-isoquinoline-6-carboxylate (250 mg, 633.69 umol, 94% purity, 1 eq, HCl) in DCM (10 mL) was added $Ac_2O$ (107.62 mg, 1.05 mmol, 98.73 uL, 1.66 eq) and TEA (142.23 mg, 1.41 mmol, 195.64 uL, 2.22 eq) at 25° C. The mixture was stirred at 25° C. for 16 hr. The reaction mixture was concentrated under reduced pressure to remove solvent. The residue was purified by prep-HPLC (column: Phenomenex Luna C18 150*25 mm*10 um; mobile phase: [water(FA)-ACN]; B %: 1%-28%, 10 min). Compound methyl 2-[(8S)-2-acetyl-5-oxa-2-azaspiro[3.5]nonan-8-yl]-8-fluoro-3,4-dihydro-1H-isoquinoline-6-carboxylate (140 mg, 364.49 umol, 57.52% yield, 98% purity) was obtained as a white solid. MS(ESI)=377.2[M+H]+

To a solution of methyl 2-[(8S)-2-acetyl-5-oxa-2-azaspiro[3.5]nonan-8-yl]-8-fluoro-3,4-dihydro-1H-isoquinoline-6-carboxylate (140 mg, 364.49 umol, 98% purity, 1 eq) in MeOH (3 mL) was added hydroxylamine (481.56 mg, 7.29 mmol, 50% purity, 20 eq) and KOH (40.90 mg, 728.97 umol, 2 eq) at 25° C. The mixture was stirred at 25° C. for 16 hr. The reaction mixture was concentrated under reduced pressure to remove solvent. The residue was purified by prep-HPLC (column: Waters Atlantis T3 150*30 mm*5 um; mobile phase: [water(TFA)-ACN]; B %: 0%-20%, 10 min). Compound 2-[(8S)-2-acetyl-5-oxa-2-azaspiro[3.5]nonan-8-yl]-8-fluoro-3,4-dihydro-1H-isoquinoline-6-carbohydroxamic acid (453) (54 mg, 109.36 umol, 30.00% yield, 99.52% purity, TFA) was obtained as an orange solid To a solution of methyl 2-[(8R)-2-acetyl-5-oxa-2-azaspiro[3.5]nonan-8-yl]-8-fluoro-3,4-dihydro-1H-isoquinoline-6-carboxylate (160 mg, 420.81 umol, 99% purity, 1 eq) in MeOH (4 mL) was added KOH (70.83 mg, 1.26 mmol, 3 eq) and hydroxylamine (555.96 mg, 8.42 mmol, 50% purity, 20 eq).The mixture was stirred at 25° C. for 12 hr. The reaction mixture was concentrated under reduced pressure to remove MeOH. The crude product was purified by reversed-phase HPLC (column: Waters Atlantis T3 150*30 mm*5 um; mobile phase: [water(TFA)-ACN]; B %: 0%-20%, 10 min). Compound 2-[(8R)-2-acetyl-5-oxa-2-azaspiro[3.5]nonan-8-yl]-8-fluoro-3,4-dihydro-1H-isoquinoline-6-carbohydroxamic acid (454) (16.68 mg, 33.87 umol, 8.05% yield, 99.8% purity, TFA) was obtained as a yellow solid.

| | | |
|---|---|---|
| 453 | 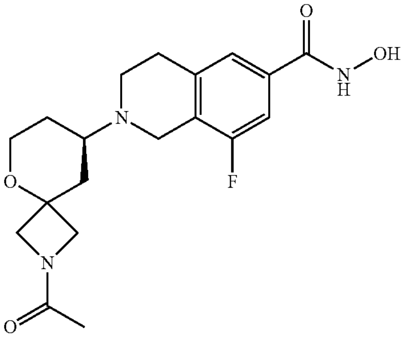 [SMILES: CC(=O)N1CC2(C[C@H](N3CCc4cc(C(=O)NO)cc(F)c4C3)CCO2)C1]<br>2-[(8S)-2-acetyl-5-oxa-2-azaspiro[3.5]nonan-8-yl]-8-fluoro-3,4-dihydro-1H-isoquinoline-6-carbohydroxamic acid | 1H NMR (400 MHz, METHANOL-d4) δ = 7.54 (s, 1H), 7.46 (d, J = 10.3 Hz, 1H), 4.60 (bs, 2H), 4.21 - 4.15 (m, 2H), 4.11 - 4.05 (m, 1H), 3.98 - 3.87 (m, 2H), 3.81 - 3.55 (m, 5H), 2.57 - 2.56 (m, 1H), 2.13 - 2.11 (m, 1H), 2.05 - 1.87 (m, 6H). MS(ESI): 378.2 [M + H]+.<br>Absolute stereochemistry is unknown. |
| 454 | 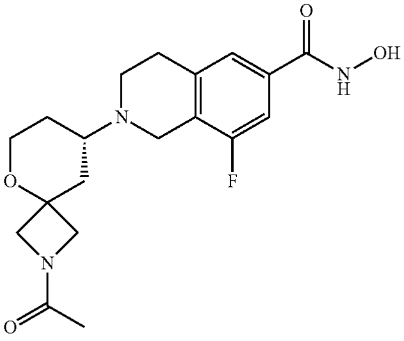 [SMILES: CC(=O)N1CC2(C[C@@H](N3CCc4cc(C(=O)NO)cc(F)c4C3)CCO2)C1]<br>N 2-[(8R)-2-acetyl-5-oxa-2-azaspiro[3.5]nonan-8-yl]-8-fluoro-3,4-dihydro-1H-isoquinoline-6-carbohydroxamic acid | 1H NMR (400 MHz, METHANOL-d4) δ = 7.56 (s, 1H), 7.48 (d, J = 10.3 Hz, 1H), 4.60 (br s, 2H), 4.19 (br d, J = 11.8 Hz, 2H), 4.14 - 4.07 (m, 1H), 4.00 - 3.90 (m, 2H), 3.81 - 3.54 (m, 5H), 2.58 - 2.56 (m, 1H), 2.14 - 2.13 (m, 1H), 2.05 - 1.98 (m, 1H), 1.94 - 1.93 (m, 5H). MS(ESI): 378.1 [M + H]+.<br>Absolute stereochemistry is unknown. |

8-fluoro-2-[(3-oxo-2-azabicyclo[2.2.2]octan-1-yl)methyl]-3,4-dihydro-1H-isoquinoline-6-carbohydroxamic acid (461)

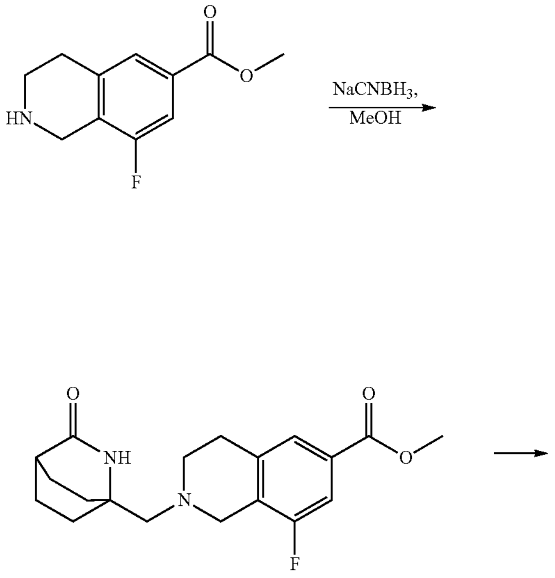

-continued

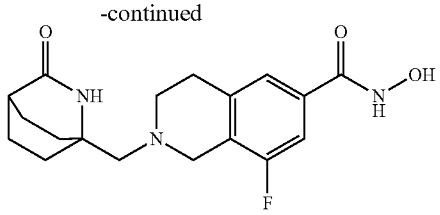

461

To a solution of 3-oxo-2-azabicyclo[2.2.2]octane-1-carbaldehyde (14.85 mg, 96.97 umol, 1 eq) in MeOH (4 mL) was added AcOH (11.65 mg, 193.94 umol, 11.09 uL, 2 eq) methyl 8-fluoro-1,2,3,4-tetrahydroisoquinoline-6-carboxylate (20.29 mg, 96.97 umol, 1 eq) NaBH3CN (9.14 mg, 145.45 umol, 1.5 eq). The mixture was stirred at 60° C. for 12 hr. The reaction mixture was concentrated under reduced pressure to remove solvent. After purification, compound methyl 8-fluoro-2-[(3-oxo-2-azabicyclo[2.2.2]octan-1-yl)methyl]-3,4-dihydro-1H-isoquinoline-6-carboxylate (150 mg, crude) was obtained as a yellow oil.

To a solution of methyl 8-fluoro-2-[(3-oxo-2-azabicyclo[2.2.2]octan-1-yl)methyl]-3,4-dihydro-1H-isoquinoline-6-carboxylate (150 mg, 433.03 umol, 1 eq) in MeOH (5 mL) was added KOH (48.59 mg, 866.06 umol, 2 eq) hydroxylamine (572.12 mg, 8.66 mmol, 50% purity, 20 eq). The mixture was stirred at 25° C. for 12 hr. The reaction mixture was concentrated under reduced pressure to remove solvent.

The residue was purified by prep-HPLC (column: Welch Xtimate C18 150*25 mm*5 um; mobile phase: [water (TFA)-ACN]; B %: 0%-25%, 10 min). Compound 8-fluoro-2-[(3-oxo-2-azabicyclo[2.2.2]octan-1-yl)methyl]-3,4-dihydro-1H-isoquinoline-6-carbohydroxamic acid (44.13 mg, 126.91 umol, 29.31% yield, 99.9% purity) was obtained as a white solid. MS (ESI): 348.2 [M+H]+; 1H NMR (400 MHz, METHANOL-d4) o ppm 7.53 (s, 1H) 7.45 (br d, J=10.26 Hz, 1H) 4.61 (br s, 2H) 3.70 (br d. J=1.75 Hz, 2H) 3.47-3.60 (m, 2H) 3.31 (br d, J=1.25 Hz, 2H) 2.54 (br s, 1H) 1.78-1.99 (m, 8H)

8-fluoro-2-[(7-methyl-7-azaspiro[35]nonan-2-yl) methyl]-34dihydro-1H-isoquinoline-6-carbohydroxamic acid (469)

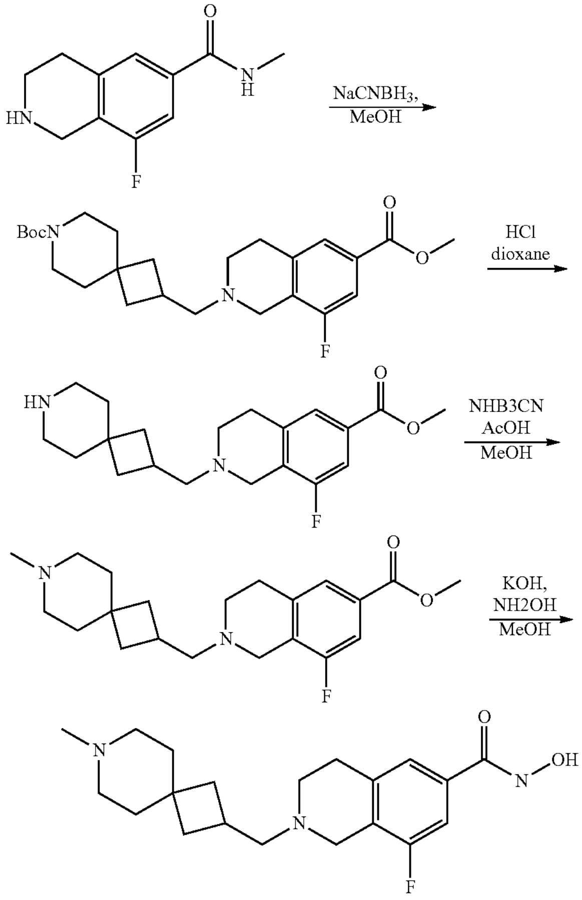

469

To a solution of methyl 8-fluoro-1,2,3,4-tetrahydroisoquinoline-6-carboxylate (817.59 mg, 3.91 mmol, 1.1 eq) in MeOH (10 mL) was added tert-butyl 2-formyl-7-azaspiro[3.5]nonane-7-carboxylate (900 mg, 3.55 mmol, 1 eq), AcOH (426.68 mg, 7.11 mmol, 406.36 uL, 2 eq). The mixture was stirred at 25° C. for 2 hr. Then the mixture was added NaBH3CN (290.23 mg, 4.62 mmol, 1.3 eq). The mixture was stirred at 25° C. for 16 hr. The mixture was concentrated under reduced pressure. The residue was purified by flash silica gel chromatography (ISCO®; 25 g SepaFlash® Silica Flash Column. Eluent of 30-100% Ethylacetate/Petroleum ether gradient @ 60 mL/min). Compound methyl 2-[(7-tert-butoxycarbonyl-7-azaspiro[3.5]nonan-2-yl)methyl]-8-fluoro-3,4-dihydro-1H-isoquinoline-6-carboxylate (1.1 g, 2.07 mmol, 58.24% yield, 84% purity) was obtained as a yellow oil. MS(ESI): 447.4 [M+H]+

A solution of methyl 2-[(7-tert-butoxycarbonyl-7-azaspiro[3.5]nonan-2-yl)methyl]-8-fluoro-3,4-dihydro-1H-isoquinoline-6-carboxylate (1.1 g, 2.07 mmol, 84% purity, 1 eq) was added HCl/dioxane (4 M, 8.40 mL, 16.24 eq). The mixture was stirred at 25° C. for 1 hr. The mixture was concentrated under reduced pressure to give residue. The crude product methyl 2-(7-azaspiro[3.5]nonan-2-ylmethyl)-8-fluoro-3,4-dihydro-1H-isoquinoline-6-carboxylate (1.1 g, crude, HCl) as white solid was used into the next step without further purification.

To a solution of methyl 2-(7-azaspiro[3.5]nonan-2-ylmethyl)-8-fluoro-3,4-dihydro-1H-isoquinoline-6-carboxylate (250 mg, 721.63 umol, 1 eq) in MeOH (3 mL) was added formaldehyde (87.84 mg, 1.08 mmol, 80.59 uL, 37% purity, 1.5 eq), AcOH (86.67 mg, 1.44 mmol, 82.54 uL, 2 eq). The mixture was stirred at 25° C. for 2 hr. Then the mixture was added NaBH3CN (58.95 mg, 938.12 umol, 1.3 eq). The mixture was stirred at 60° C. for 16 hr. The mixture was diluted with H2O 20 mL and extracted with EtOAc (20 mL*3). The combined organic layers were washed with brine(20 mL), dried over [Na2SO4], filtered and concentrated under reduced pressure to give a residue. The residue was purified by prep-TLC (SiO2, Dichloromethane: Methanol=10:1). Compound methyl 8-fluoro-2-[(7-methyl-7-azaspiro[3.5]nonan-2-yl)methyl]-3,4-dihydro-1H-isoquinoline-6-carboxylate (130 mg, 339.01 umol, 46.98% yield, 94% purity) was obtained as a colorless liquid. MS(ESI): 361.4 [M+H]+

To a solution of methyl 8-fluoro-2-[(7-methyl-7-azaspiro[3.5]nonan-2-yl)methyl]-3,4-dihydro-1H-isoquinoline-6-carboxylate (130 mg, 339.01 umol, 94% purity, 1 eq) in MeOH (3 mL) was added hydroxylamine (471.72 mg, 7.14 mmol, 50% purity, 21.06 eq) and KOH (40.06 mg, 714.01 umol, 2.11 eq) at 0° C. The mixture was stirred at 25° C. for 4 hr. The mixture was concentrated under reduced pressure. The residue was purified by prep-HPLC (column: Waters Atlantis T3 150*30 mm*5 um; mobile phase: [water (0.1% TFA)-ACN]; B %: 0%-20%, 10 min). Compound 8-fluoro-2-[(7-methyl-7-azaspiro[3.5]nonan-2-yl)methyl]-3,4-dihydro-1H-isoquinoline-6-carbohydroxamic acid. (40.56 mg, 84.83 umol, 25.02% yield, 99.443% purity, TFA) was obtained as a yellow solid. MS(ESI): 362.2 [M+H]+; 1H NMR (400 MHz, METHANOL-d4) δ=7.51 (bs, 1H), 7.44 (bd, J=10.3 Hz, 1H), 4.58-4.35 (m, 2H), 3.68-3.49 (m, 2H), 3.46 (d, J=7.0 Hz, 2H), 3.45-3.33 (m, 2H), 3.27 (bs, 2H), 3.09-2.99 (m, 1H), 2.96-2.88 (m, 2H), 2.85 (s, 3H), 2.39-2.31 (m, 1H), 2.21-2.10 (m, 2H), 1.93-1.83 (m, 3H), 1.82-1.75 (m, 2H).

8-fluoro-2-[[(1R,4S)-5-methyl-2-oxa-5-azabicyclo[2.2.1]heptan-1-yl]methyl]-3,4-dihydro-1H-isoquinoline-6-carbohydroxamic acid (475)

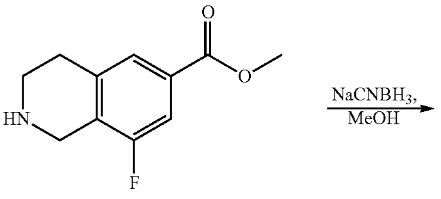

-continued

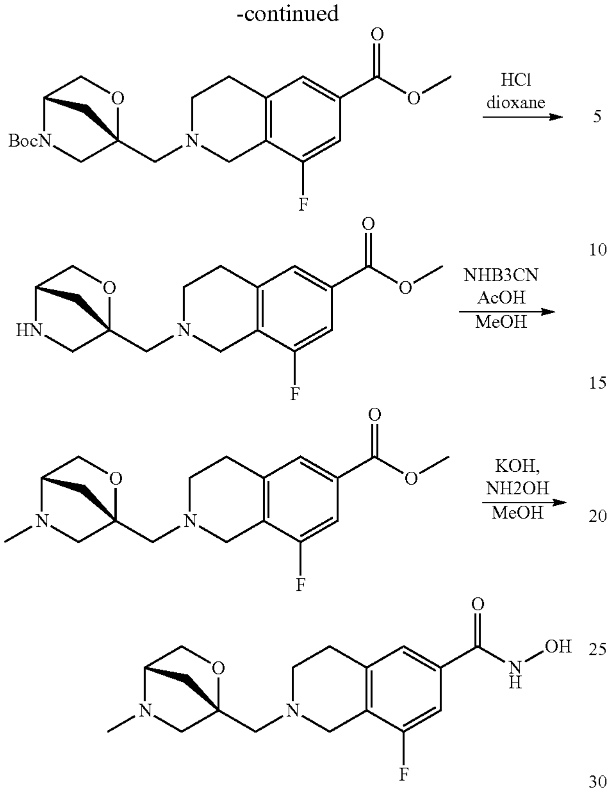

475

To a solution of tert-butyl (1S,4S)-1-formyl-2-oxa-5-azabicyclo[2.2.1]heptane-5-carboxylate (300 mg, 1.32 mmol, 1 eq), methyl 8-fluoro-1,2,3,4-tetrahydroisoquinoline-6-carboxylate (276.19 mg, 1.32 mmol, 1 eq) in MeOH (10 mL) was added NaBH3CN (107.84 mg, 1.72 mmol, 1.3 eq) and AcOH (158.55 mg, 2.64 mmol, 151.00 uL, 2 eq).The mixture was stirred at 60° C. for 16 hr. The mixture was concentrated under reduced pressure. The residue was purified by prep-TLC (SiO2, Petroleum ether: Ethyl acetate=3: 1). Compound tert-butyl (1R,4S)-1-[(8-fluoro-6-methoxycarbonyl-3,4-dihydro-1H-isoquinolin-2-yl)methyl]-2-oxa-5-azabicyclo[2.2.1]heptane-5-carboxylate (160 mg, 371.77 umol, 28.16% yield, 97.7% purity) was obtained as a colorless oil. MS(ES+): 421.5 [M+H]+

The solution of tert-butyl (1R,4S)-1-[(8-fluoro-6-methoxycarbonyl-3,4-dihydro-1H-isoquinolin-2-yl) methyl]-2-oxa-5-azabicyclo[2.2.1]heptane-5-carboxylate (160 mg, 369.11 umol, 97% purity, 1 eq) in HCl/dioxane (4 M, 92.28 uL, 1 eq) was stirred at 25° C. for 2 hr. The mixture was concentrated under reduced pressure. The crude product methyl 8-fluoro-2-[[(1S,4S)-2-oxa-5-azabicyclo[2.2.1]heptan-1-yl]methyl]-3,4-dihydro-1H-isoquinoline-6-carboxylate (160 mg, crude) as white solid was used into the next step without further purification. MS(ES+): 321.1 [M+H]+

To a solution of methyl 8-fluoro-2-[[(1S,4S)-2-oxa-5-azabicyclo[2.2.1]heptan-1-yl]methyl]-3,4-dihydro-1H-isoquinoline-6-carboxylate (160 mg, 448.41 umol, 1 eq, HCl), formaldehyde (54.58 mg, 672.61 umol, 50.08 uL, 37% purity, 1.5 eq) in MeOH (8 mL) was added AcOH (53.86 mg, 896.81 umol, 51.29 uL, 2 eq) and NaBH3CN (36.63 mg, 582.93 umol, 1.3 eq). The mixture was stirred at 60° C. for 16 hr. The mixture was concentrated under reduced pressure. The residue was purified by prep-HPLC (column: Phenomenex luna C18 150*25 mm*10 um; mobile phase: [water (FA)-ACN]; B %: 0%-20%, 10.5 min). Compound methyl 8-fluoro-2-[[(1R,4S)-5-methyl-2-oxa-5-azabicyclo[2.2.1]heptan-1-yl]methyl]-3,4-dihydro-1H-isoquinoline-6-carboxylate (100 mg, 244.47 umol, 54.52% yield, 93% purity, FA) was obtained as a yellow oil. MS(ES+): 335.1 [M+H]+

To a solution of methyl 8-fluoro-2-[[(1R,4S)-5-methyl-2-oxa-5-azabicyclo[2.2.1]heptan-1-yl]methyl]-3,4-dihydro-1H-isoquinoline-6-carboxylate (100.00 mg, 244.47 umol, 93% purity, 1 eq, FA) in MeOH (3 mL) was added KOH (27.43 mg, 488.95 umol, 2 eq) and hydroxylamine (323.00 mg, 4.89 mmol, 50% purity, 20 eq). The mixture was stirred at 25° C. for 3 hr. The mixture was concentrated under reduced pressure. The residue was purified by prep-HPLC (column: Waters Atlantis T3 150*30 mm*5 um; mobile phase: [water(TFA)-ACN]; B %: 0%-20%, 10 min). Compound 8-fluoro-2-[[(1R,4S)-5-methyl-2-oxa-5-azabicyclo[2.2.1]heptan-1-yl]methyl]-3,4-dihydro-1H-isoquinoline-6-carbohydroxamic acid (76.84 mg, 168.89 umol, 69.08% yield, 98.776% purity, TFA) was obtained as a yellow oil. MS(ESI): 336.1 $[M+H]^+$; 1H NMR (400 MHz, METHANOL-d4) δ=7.47 (s, 1H), 7.38 (d, J=10.3 Hz, 1H), 4.45-4.31 (m, 3H), 4.30-4.13 (m, 1H), 4.08 (dd, J=1.8, 10.1 Hz, 1H), 4.00-3.75 (m, 1H), 3.67-3.56 (m, 2H), 3.54-3.35 (m, 3H), 3.17 (bt, J=5.9 Hz, 2H), 3.02 (s, 3H), 2.52-2.34 (m, 2H).

8-fluoro-N-hydroxy-2-(((1R,5S)-8-methyl-8-azabicyclo[3.2.1]octan-3-yl)methyl)-1,2,3,4-tetrahydroisoquinoline-6-carboxamide (482) and 8-fluoro-2-[[(1S,5R)-8-methyl-8-azabicyclo[3.2.1]octan-3-yl]methyl]-3,4-dihydro-1H-isoquinoline-6-carbohydroxamic acid (483)

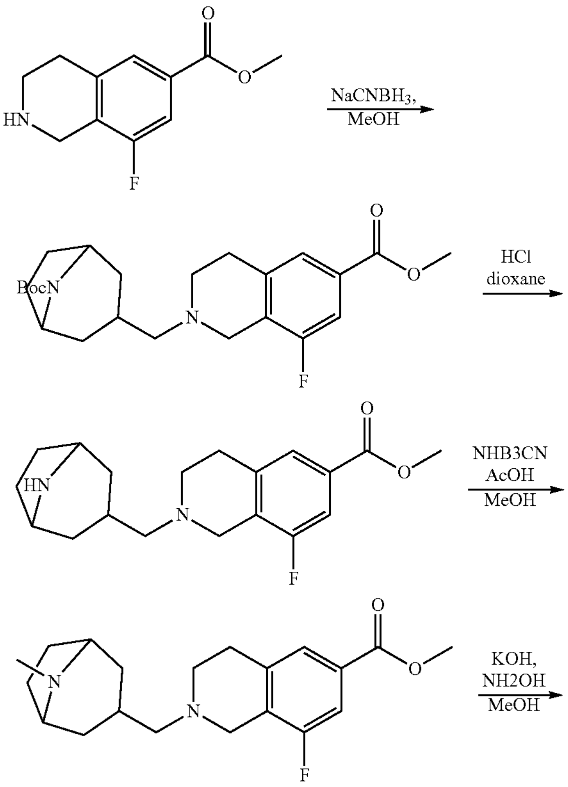

-continued

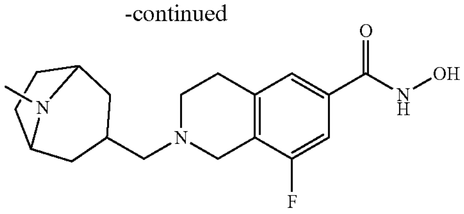

482/483

A mixture of tert-butyl 3-formyl-8-azabicyclo[3.2.1]octane-8-carboxylate (316 mg, 1.32 mmol, 1 eq), methyl 8-fluoro-1,2,3,4-tetrahydroisoquinoline-6-carboxylate (303.89 mg, 1.45 mmol, 1.1 eq), AcOH (158.59 mg, 2.64 mmol, 151.04 uL, 2 eq) in MeOH (4 mL) was stirred at 25° C. After 10 mins NaBH3CN (124.47 mg, 1.98 mmol, 1.5 eq) was added at 25° C., and then the mixture was stirred at 60° C. for 12 hr. The reaction mixture was concentrated under reduced pressure to remove MeOH. The crude product was purified by reversed-phase HPLC (column: Phenomenex luna C18 150*25 mm*10 um; mobile phase: [water (FA)-ACN]; B %: 17%-47%, 10.5 min). Compound methyl 2-[(8-tert-butoxycarbonyl-8-azabicyclo[3.2.1]octan-3-yl) methyl]-8-fluoro-3,4-dihydro-1H-isoquinoline-6-carboxylate (120 mg, 260.79 umol, 19.75% yield, 94% purity) was obtained as colorless liquid.

A solution of methyl 2-[(8-tert-butoxycarbonyl-8-azabicyclo[3.2.1]octan-3-yl)methyl]-8-fluoro-3,4-dihydro-1H-isoquinoline-6-carboxylate (120 mg, 277.44 umol, 1 eq) in HCl/dioxane (6 mL). The mixture was stirred at 25° C. for 3 hr. The reaction mixture was concentrated under reduced pressure to remove HCL/dioxane[Purification] The reaction was used into the next step without further purification. The crude product methyl 2-(8-azabicyclo[3.2.1]octan-3-ylmethyl)-8-fluoro-3,4-dihydro-1H-isoquinoline-6-carboxylate (120 mg, 233.59 umol, 84.20% yield, 86% purity, 3HCl) was obtained white solid, used into the next step without further purification.

A mixture of methyl 2-(8-azabicyclo[3.2.1]octan-3-ylmethyl)-8-fluoro-3,4-dihydro-1H-isoquinoline-6-carboxylate (120 mg, 271.62 umol, 1 eq, 3HCl), HCHO (33.06 mg, 407.43 umol, 30.33 uL, 37% purity, 1.5 eq), AcOH (32.62 mg, 543.24 umol, 31.07 uL, 2 eq) in MeOH (5 mL) was stirred at 25° C. After 10 mins NaBH3CN (25.60 mg, 407.43 umol, 1.5 eq) was added at 25° C. for 12 hr. The reaction mixture was concentrated under reduced pressure to remove MeOH. The crude product was purified by reversed-phase HPLC (column: Phenomenex Luna C18 100*30 mm*5 um; mobile phase: [water(FA)-ACN]; B %: 1%-15%, 8 min). Compound methyl 8-fluoro-2-[(8-methyl-8-azabicyclo[3.2.1]octan-3-yl)methyl]-3,4-dihydro-1H-isoquinoline-6-carboxylate (70 mg, 200.04 umol, 73.65% yield, 99% purity) was obtained as colourless liquid. MS(ESI): 347.1 [M+H]+

To a solution of methyl 8-fluoro-2-[(8-methyl-8-azabicyclo[3.2.1]octan-3-yl)methyl]-3,4-dihydro-1H-isoquinoline-6-carboxylate(70 mg, 200.04 umol, 99% purity, 1 eq) in MeOH (5 mL) was added KOH (33.67 mg, 600.11 umol, 3 eq) and hydroxylamine (264.29 mg, 4.00 mmol, 50% purity, 20 eq). The mixture was stirred at 25° C. for 12 hr. The reaction mixture was concentrated under reduced pressure to remove MeOH. The crude product was purified by reversed-phase HPLC (column: Waters Atlantis T3 150*30 mm*5 um; mobile phase: [water (TFA)-ACN]; B %: 0%-15%, 10 min). 8-fluoro-N-hydroxy-2-(((1R,5S)-8-methyl-8-azabicyclo[3.2.1]octan-3-yl)methyl)-1,2,3,4-tetrahydroisoquinoline-6-carboxamide (482) (28.67 mg, 61.51 umol, 30.75% yield, 99% purity, TFA) was obtained as a red solid.

To a solution of hydroxylamine (572.05 mg, 8.66 mmol, 50% purity, 20 eq) and methyl 8-fluoro-2-[[(1S,5R)-8-methyl-8-azabicyclo[3.2.1]octan-3-yl]methyl]-3,4-dihydro-1H-isoquinoline-6-carboxylate (150.00 mg, 432.98 umol, 1 eq) in MeOH (5 mL) was added KOH (48.58 mg, 865.96 umol, 2 eq). The mixture was stirred at 25° C. for 12 hr. The mixture was concentrated under reduced pressure. The residue was purified by prep-HPLC (column: Waters Atlantis T3 150*30 mm*5 um; mobile phase: [water (TFA)-ACN]; B %: 0%-10%, 10 min). The product 8-fluoro-2-[[(1S,5R)-8-methyl-8-azabicyclo[3.2.1]octan-3-yl]methyl]-3,4-dihydro-1H-isoquinoline-6-carbohydroxamic acid (483) (46.41 mg, 100.07 umol, 23.11% yield, 99.5% purity, TFA) was obtained as a yellow solid.

| | | |
|---|---|---|
| 482 | 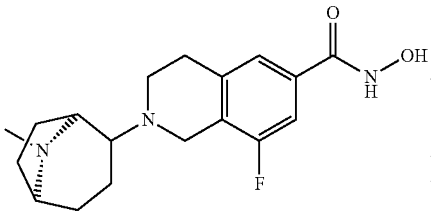<br>8-fluoro-N-hydroxy-2-(((1R,5S)-8-methyl-8-azabicyclo[3.2.1]octan-3-yl)methyl)-1,2,3,4-tetrahydroisoquinoline-6-carboxamide | 1H NMR (400 MHz, METHANOL-d4) δ = 7.52 (d, J = 3.1 Hz, 1H), 7.44 (dd, J = 3.8, 10.2 Hz, 1H), 4.56 - 4.42 (m, 2H), 4.02 - 3.88 (m, 2H), 3.66 - 3.48 (m, 3H), 3.31 - 3.22 (m, 3H), 2.81 (s, 3H), 2.65 - 2.35 (m, 4H), 2.22 - 2.03 (m, 4H), 1.89 - 1.78 (m, 1H). MS(ESI): 348.2[M + H]+ Note: absolute stereochemistry is unknown |
| 483 | 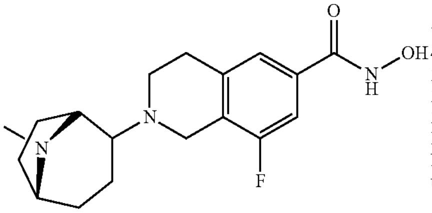<br>8-fluoro-2-[[(1S,5R)-8-methyl-8-azabicyclo[3.2.1]octan-3-yl]methyl]-3,4-dihydro-1H-isoquinoline-6-carbohydroxamic acid | 1H NMR (400 MHz, METHANOL-d4) δ = 7.53 (s, 1H), 7.45 (d, J = 10.1 Hz, 1H), 4.55 (br s, 2H), 3.98 (br s, 2H), 3.64 (br s, 2H), 3.29 - 3.26 (m, 4H), 2.81 (s, 3H), 2.66 - 2.58 (m, 1H), 2.44 - 2.34 (m, 2H), 2.22 - 2.08 (m, 4H), 1.89 - 1.79 (m, 2H). MS(ESI): 348.1 [M + H]+ Note: absolute stereochemistry is unknown. |

8-fluoro-2-[(2-methyl-2-azabicyclo[2.1.1]hexan-4-yl)methyl]-3,4-dihydro-1H-isoquinoline-6-carbohydroxamic acid (490)

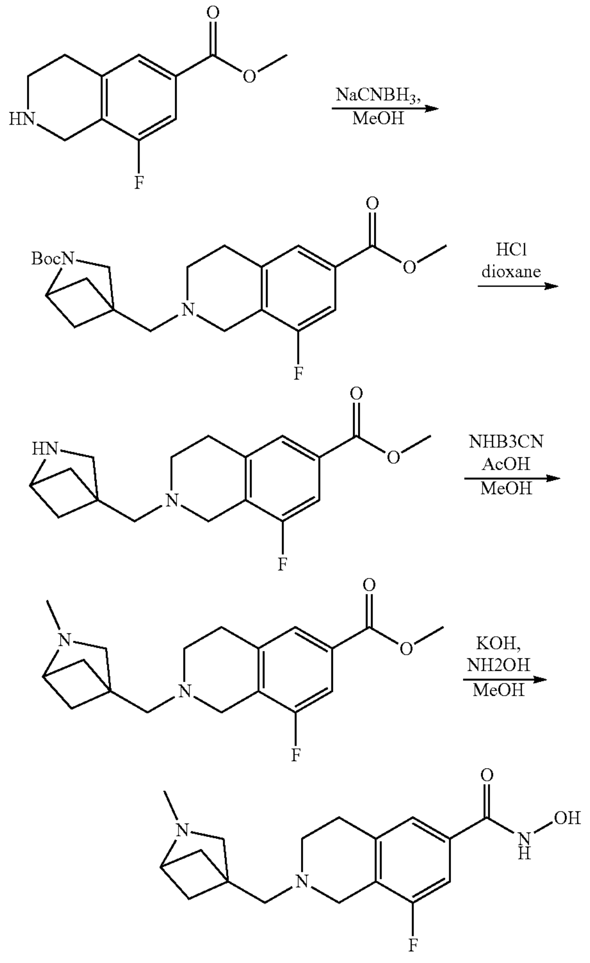

490

To a solution of methyl 8-fluoro-1,2,3,4-tetrahydroisoquinoline-6-carboxylate (49.52 mg, 236.68 umol, 1 eq), tert-butyl 4-formyl-2-azabicyclo[2.1.1]hexane-2-carboxylate (50 mg, 236.68 umol, 1 eq) in MeOH (2 mL) was added AcOH (28.43 mg, 473.36 umol, 27.07 uL, 2 eq) and NaBH3CN (19.34 mg, 307.68 umol, 1.3 eq). The mixture was stirred at 60° C. for 5 hr. The mixture was concentrated under reduced pressure. The residue was purified by prep-TLC (SiO2, Petroleum ether: Ethyl acetate=1:1). Compound methyl 2-[(2-tert-butoxycarbonyl-2-azabicyclo[2.1.1]hexan-4-yl)methyl]-8-fluoro-3,4-dihydro-1H-isoquinoline-6-carboxylate (50 mg, 121.15 umol, 51.19% yield, 98% purity) was obtained as a colorless oil. MS(ESI): 405.1 [M+H]+

The solution of methyl 2-[(2-tert-butoxycarbonyl-2-azabicyclo[2.1.1]hexan-4-yl)methyl]-8-fluoro-3,4-dihydro-1H-isoquinoline-6-carboxylate (180.00 mg, 436.12 umol, 98% purity, 1 eq) in HCl/dioxane (4 M, 109.03 uL, 1 eq) and was stirred at 25° C. for 1 hr. The mixture was concentrated under reduced pressure to give residue. The crude product methyl 2-(2-azabicyclo[2.1.1]hexan-4-ylmethyl)-8-fluoro-3,4-dihydro-1H-isoquinoline-6-carboxylate (180 mg, crude) as white solid was used into the next step without further purification.

To a solution of methyl 2-(2-azabicyclo[2.1.1]hexan-4-ylmethyl)-8-fluoro-3,4-dihydro-1H-isoquinoline-6-carboxylate (180 mg, 591.41 umol, 1 eq) in MeOH (5 mL) was added formaldehyde (47.99 mg, 591.41 umol, 44.03 uL, 37% purity, 1 eq) and NaBH3CN (48.31 mg, 768.83 umol, 1.3 eq) and AcOH (71.03 mg, 1.18 mmol, 67.65 uL, 2 eq). The mixture was stirred at 60° C. for 16 hr. The mixture was concentrated under reduced pressure. Compound methyl 8-fluoro-2-[(2-methyl-2-azabicyclo[2.1.1]hexan-4-yl)methyl]-3,4-dihydro-1H-isoquinoline-6-carboxylate (170 mg, 496.57 umol, 83.96% yield, 93% purity) was obtained as a yellow oil. MS(ESI): 319.1 [M+H]+

To a solution of methyl 8-fluoro-2-[(2-methyl-2-azabicyclo[2.1.1]hexan-4-yl)methyl]-3,4-dihydro-1H-isoquinoline-6-carboxylate (170 mg, 496.57 umol, 93% purity, 1 eq),in MeOH (4 mL) was added hydroxylamine (656.06 mg, 9.93 mmol, 50% purity, 20 eq) and KOH (55.72 mg, 993.14 umol, 2 eq). The mixture was stirred at 25° C. for 16 hr. The mixture was concentrated under reduced pressure. The residue was purified by prep-HPLC (column: Welch Xtimate C18 150*25 mm*5 um; mobile phase: [water (TFA)-ACN]; B %: 0%-10%, 10 min). Compound 8-fluoro-2-[(2-methyl-2-azabicyclo[2.1.1]hexan-4-yl)methyl]-3,4-dihydro-1H-isoquinoline-6-carbohydroxamic acid (41.81 mg, 96.28 umol, 19.39% yield, 99.8% purity, TFA) was obtained as a yellow gum. MS(ES+): 320.2 $[M+H]^+$; 1H NMR (400 MHz, METHANOL-d4) δ=7.48 (s, 1H), 7.40 (bd, J=10.3 Hz, 1H), 4.43 (bd, J=5.4 Hz, 2H), 4.21 (s, 1H), 3.87 (bd, J=9.9 Hz, 1H), 3.66 (bd, J=6.4 Hz, 2H), 3.57-3.45 (m, 2H), 3.30-3.21 (m, 3H), 3.03 (s, 3H), 2.38 (bdd, J=8.7, 16.1 Hz, 2H), 2.18 (bt, J=10.1 Hz, 1H), 1.99-1.87 (m, 1H)

The following compounds were prepared in a manner analogous to that used for preparing compounds of Formula (I) above. Although certain compound pairs are designated as having absolute stereochemistry as each stereoisomer was prepared and isolated, the absolute stereochemistry of each is unknown.

| Compound | Structure/Name | Characterization |
|---|---|---|
| 182 | 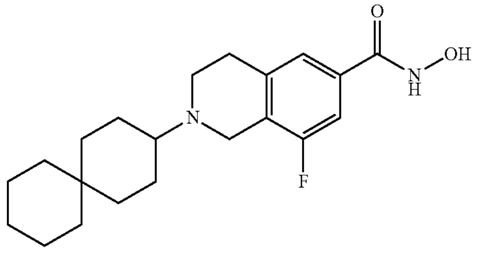 [SMILES: O=C(NO)c1cc(F)c2c(c1)CCN(C1CCC3(CCCCC3)CC1)C2] | $^1$H NMR (400 MHz, DMSO-d6) δ 7.38 (s, 1 H) 7.3 (d, J = 10.1, 1H) 3.88 - 3.93 (m, 2 H) 3.12 - 3.22 (m, 1 H) 2.80 - 2.92(m, 2 H) 2.70 - 2.80 (m, 2 H) 2.49 - 2.65 (m, 2 H) 1.77 - 1.88 (m, 2 H) 1.55 - 1.67 (m, 2 H) 1.43 - 1.52 (m, 8 H) 1.23 - 1.31 (m, 2 H) 1.09 - 1.22 (m, 2 H). MS (ESI): 361.1[M + H]+. |

-continued

| Compound | Structure/Name | Characterization |
|---|---|---|
| | 8-fluoro-2-spiro[5.5]undecan-3-yl-3,4-dihydro-1H-isoquinoline-6-carbohydroxamic acid | |
| 190 | 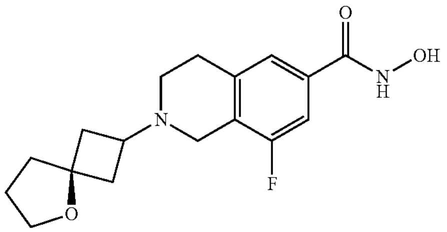 8-fluoro-N-hydroxy-2-(5-oxaspiro[3.4]octan-2-yl)-1,2,3,4-tetrahydroisoquinoline-6-carboxamide | MS (ESI): 321 [M + H]+. 1H NMR (400 MHz, DMSO-d6) δ 1.84 (d, J = 3.5Hz, 4H), 1.91 − 2.03 (m, 2H), 2.19 − 2.30 (m, 2H), 2.57 (q, J = 5.4 Hz, 3H), 2.86 (t, J = 5.8 Hz, 2H), 3.47 (s, 2H), 3.67 (s, 2H), 7.33 (d, J = 10.5Hz, 1H), 7.42 (s, 1H), 9.10 (s, 1H), 11.24 (s, 1H). Absolute stereochemistry is unknown |
| 191 | 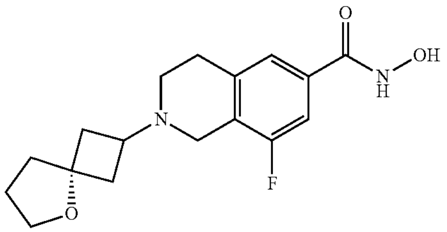 8-fluoro-N-hydroxy-2-(5-oxaspiro[3.4]octan-2-yl)-1,2,3,4-tetrahydroisoquinoline-6-carboxamide | MS (ESI): 321 [M + H]+. 1H NMR (400 MHz, DMSO-d6) δ 1.87 (s, 2H), 2.14 (d, J = 40.8 Hz, 2H), 2.86 (d, J = 4.5Hz, 3H), 3.27 (s, 3H), 3.82 (s, 3H), 4.03 (d, J = 39.5Hz, 2H), 4.39 (s, 2H), 4.87 (s, 1H), 7.60 (d, J = 4.5Hz, 1H), 7.84 (q, J = 11.4, 7.6 Hz, 1H), 8.03 (dt, J = 18.4, 8.2 Hz, 2H), 10.20 (s, 1H). Absolute stereochemistry is unknown |
| 192 | 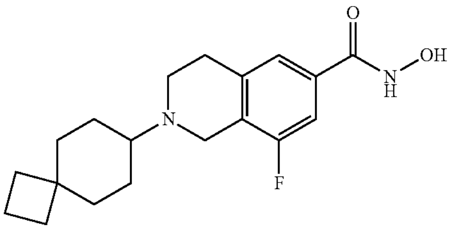 [SMILES: O=C(NO)c1cc(F)c2c(c1)CCN(C1CCC3(CCC3)CC1)C2] 8-fluoro-2-spiro[3.5]nonan-7-yl-3,4-dihydro-1H-isoquinoline-6-carbohydroxamic acid | 1H NMR (400 MHz, METHANOL-d4) δ = 7.53 (s, 1H), 7.45 (d, J = 10.1 , 1H), 4.60 − 4.48 (m, 2H), 3.88 − 3.75 (m, 1H), 3.46 − 3.36 (m, 2H), 3.31 − 3.21 (m, 2H), 2.03 (br d, J = 11.6 Hz, 4H), 1.94 − 1.86 (m, 4H), 1.81 − 1.76 (m, 2H), 1.72 − 1.60 (m, 2H), 1.51 − 1.41 (m, 2H). MS(ESI): 333.1 [M + H]+ |
| 193 | 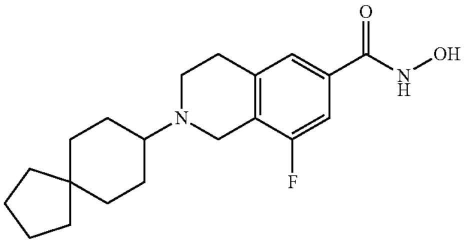 [SMILES: O=C(NO)c1cc(F)c2c(c1)CCN(C1CCC3(CCCC3)CC1)C2] 8-fluoro-2-spiro[4.5]decan-8-yl-3,4-dihydro-1H-isoquinoline-6-carbohydroxamic acid | 1H NMR (400 MHz, METHANOL-d4) δ ppm 7.70 (s, 1 H) 7.56 (d, J = 10.1 Hz, 1 H) 4.33 (s, 2 H) 3.50 − 3.39 (m, 2 H) 3.11 − 3.18 (m, 3 H) 2.11 − 2.05(m, 2 H) 1.58 − 1.71 (m, 8 H) 1.47 − 1.53 (m, 2 H) 1.31 − 1.43 (m, 4 H). MS (ESI): 347.2 [M + H]+. |

-continued

| Compound | Structure/Name | Characterization |
|---|---|---|
| 194 | 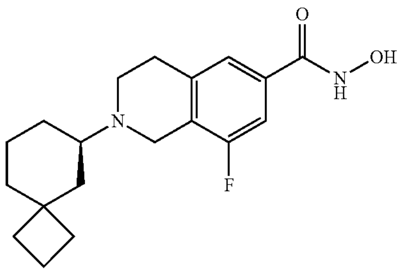 [SMILES: O=C(NO)c1cc(F)c2c(c1)CCN([C@@H]1CCCC3(CCC3)C1)C2] 8-fluoro-2-[(8R)-spiro[3.5]nonan-8-yl]-3,4-dihydro-1H-isoquinoline-6-carbohydroxamic acid | 1H NMR (400 MHz, METHANOL-d4) δ ppm 7.56 (s, 1 H) 7.47 (d, J = 10.01 Hz, 1 H) 4.53 - 4.68 (m, 2 H) 3.81 - 3.92 (m, 1 H) 3.41 - 3.52 (m, 4 H) 1.86 - 2.05 (m, 10 H) 1.48 - 1.65 (m, 3 H) 1.30 - 1.36 (m, 1 H). MS (ESI): 333.2 [M + H]+. Absolute stereochemistry is unknown. |
| 195 | 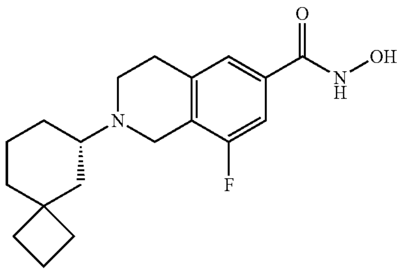 [SMILES: O=C(NO)c1cc(F)c2c(c1)CCN([C@H]1CCCC3(CCC3)C1)C2] 8-fluoro-2-[(8S)-spiro[3.5]nonan-8-yl]-3,4-dihydro-1H-isoquinoline-6-carbohydroxamic acid | 1H NMR (400 MHz, METHANOL-d4) δ ppm 7.56 (s, 1 H) 7.47 (d, J = 10.01 Hz, 1 H) 4.50 - 4.64 (m, 2 H) 3.78 - 3.92 (m, 1 H) 3.39 - 3.50 (m, 2 H) 3.26 - 3.32 (m, 2 H) 2.21 - 2.33 (m, 1 H) 2.07 - 2.18 (m, 1 H) 1.87 - 2.01 (m, 8 H) 1.49 - 1.67 (m, 3 H) 1.27 - 1.35 (m, 1 H). MS (ESI): 333.2 [M + H]+. Absolute stereochemistry is unknown. |
| 299 | 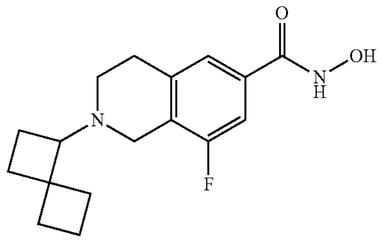 [SMILES: O=C(NO)c1cc(F)c2c(c1)CCN(C1CCC13CCC3)C2] 8-fluoro-2-spiro[3.3]heptan-3-yl-3,4-dihydro-1H-isoquinoline-6-carbohydroxamic acid | 1H NMR (400 MHz, METHANOL-d4) δ = 7.54 (s, 1H), 7.46 (d, J = 10.0 Hz, 1H), 4.49 (bd, J = 16 Hz, 1H), 4.43 - 4.11 (m, 1H), 4.09 - 3.70 (m, 1H), 3.64 (t, J = 8.4 Hz, 1H), 3.60 - 3.33 (m, 2H), 2.53 - 2.41 (m, 1H), 2.40 - 2.28 (m, 2H), 2.22 - 1.88 (m, 8H). MS(ESI): 305.1 [M + H]+. |
| 300 | 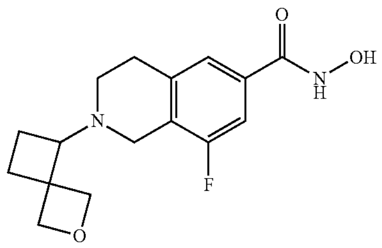 [SMILES: O=C(NO)c1cc(F)c2c(c1)CCN(C1CCC13COC3)C2] 8-fluoro-2-(2-oxaspiro[3.3]heptan-7-yl)-3,4-dihydro-1H-isoquinoline-6-carbohydroxamic acid | 1H NMR (400 MHz, METHANOL-d4) δ ppm 7.49 (s, 1 H) 7.42 (d, J = 10.0 Hz, 1 H) 5.10 (d, J = 6 Hz, 1 H) 4.64 - 4.69 (m, 2 H) 4.58 - 4.63 (m, 1 H) 3.72 (s, 2 H) 2.99 - 3.11 (m, 3 H) 2.88 - 2.95 (m, 1 H) 2.66 - 2.73 (m, 1 H) 2.00 - 2.08 (m, 2 H) 1.90 - 1.99 (m, 1 H) 1.65 - 1.62 (m, 1 H)MS (ESI): 307.2 [M + H]+. |

-continued

| Compound | Structure/Name | Characterization |
|---|---|---|
| 302 | 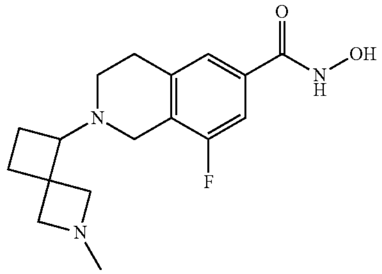 [SMILES: CN1CC2(CCC2N2CCc3cc(C(=O)NO)cc(F)c3C2)C1] 8-fluoro-2-(2-methyl-2-azaspiro[3.3]heptan-7-yl)-3,4-dihydro-1H-isoquinoline-6-carbohydroxamic acid | 1H NMR (400 MHz, METHANOL-d4) δ = 7.48 (s, 1H), 7.40 (d, J = 10.1 Hz, 1H), 4.66 – 4.23 (m, 2H), 4.22 – 3.91 (m, 4H), 3.57 – 3.45 (m, 1H), 3.28 – 3.08 (m, 4H), 2.99 (s, 3H), 2.40 – 2.30 (m, 1H), 2.28 – 2.16 (m, 2H), 2.14 – 1.98 (m, 1H). MS(ESI): 320.1 [M + H]+. |
| 303 | 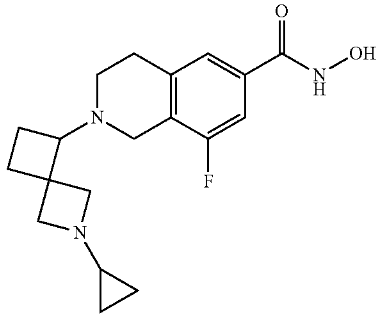 [SMILES: O=C(NO)c1cc(F)c2c(c1)CCN(C1CCC13CN(C1CC1)C3)C2] 2-(2-cyclopropyl-2-azaspiro[3.3]heptan-7-yl)-8-fluoro-3,4-dihydro-1H-isoquinoline-6-carbohydroxamic acid | 1H NMR (400 MHz, METHANOL-d4) δ = 7.51 (s, 1H), 7.43 (d, J = 10.1 Hz, 1H), 4.56 (bd, J = 11.5Hz, 1H), 4.37 – 4.36 (m, 1H), 4.32 (bd, J = 13.0 Hz, 2H), 4.19 (bd, J = 11.2 Hz, 1H), 3.86 – 3.74 (m, 1H), 3.58 – 3.49 (m, 1H), 3.45 – 3.33 (m, 2H), 3.31 – 3.18 (m, 2H), 3.16 – 3.14(m, 1H), 2.46 – 2.39 (m, 1H), 2.37 – 2.31 (m, 1H), 2.29 – 2.22 (m, 2H), 0.97 – 0.92 (m, 4H). MS(ESI): 346.0 [M + H]+. |
| 304 | 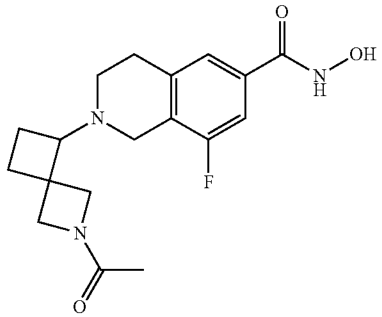 [SMILES: CC(=O)N1CC2(CCC2N2CCc3cc(C(=O)NO)cc(F)c3C2)C1] 2-(2-acetyl-2-azaspiro[3.3]heptan-7-yl)-8-fluoro-3,4-dihydro-1H-isoquinoline-6-carbohydroxamic acid | 1H NMR (400 MHz, METHANOL-d4) δ = 7.55 (s, 1H), 7.46 (d, J = 10.1 Hz, 1H), 4.54 – 4.37 (m, 2H), 4.35 – 4.27 (m, 2H), 4.15 – 3.96 (m, 2H), 3.95 – 3.84 (m, 1H), 3.54 (bs, 2H), 3.32 – 3.23 (m, 2H), 2.41 (bt, J = 7.8 Hz, 1H), 2.25 – 2.12 (m, 3H), 1.94 (d, J = 8 Hz, 3H). MS(ESI): 348.1 [M + H]+. |
| 314 | 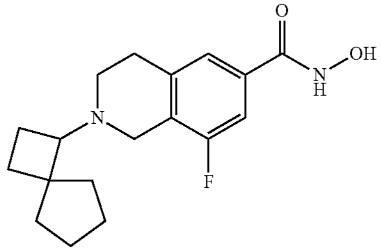 [SMILES: O=C(NO)c1cc(F)c2c(c1)CCN(C1CCC13CCCC3)C2] 8-fluoro-2-spiro[3.4]octan-3-yl-3,4-dihydro-1H-isoquinoline-6-carbohydroxamic acid | 1H NMR (400 MHz, METHANOL-d4) δ = 7.38 (s, 1H), 7.28 (d, J = 10.0 Hz, 1H), 3.62 (bd, J = 16.0 Hz, 1H), 3.41 (bd, J = 16.0 Hz, 1H), 2.99 – 2.92 (m, 2H), 2.90 – 2.85 (m, 1H), 2.72 – 2.66 (m, 1H), 2.58 – 2.51 (m, 1H), 2.11 – 2.05 (m, 1H), 1.85 – 1.74 (m, 3H), 1.71 – 1.65 (m, 4H), 1.64 – 1.56 (m, 4H). MS(ESI): 319.0 [M + H]+. |

-continued

| Compound | Structure/Name | Characterization |
| --- | --- | --- |
| 315 | 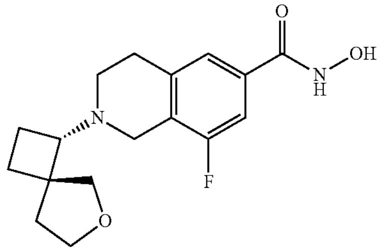 [SMILES: O=C(NO)c1cc(F)c2c(c1)CCN([C@H]1CC[C@@]13CCOC3)C2] 8-fluoro-2-[(3S,4R)-6-oxaspiro[3.4]octan-3-yl]-3,4-dihydro-1H-isoquinoline-6-carbohydroxamic acid | 1H NMR (400 MHz, METHANOL-d4) δ = 7.53 (s, 1H), 7.45 (d, J = 10.1 Hz, 1H), 4.63 - 4.35 (m, 3H), 4.10 - 4.01 (m, 1H), 3.96 - 3.90 (m, 1H), 3.85-3.78 (m, 1H), 3.67 - 3.45 (m, 3H), 3.28 (br t, J = 6.0 Hz, 2H), 2.49 - 2.40 (m, 1H), 2.34 - 2.25 (m, 1H), 2.24 - 2.18 (m, 1H), 2.17 (s, 3H). MS(ESI): 321.0 [M + H]+. Absolute stereochemistry is unknown. |
| 316 | 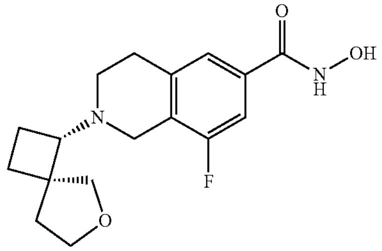 [SMILES: O=C(NO)c1cc(F)c2c(c1)CCN([C@H]1CC[C@]13CCOC3)C2] 8-fluoro-2-[(3S,4S)-6-oxaspiro[3.4]octan-3-yl]-3,4-dihydro-1H-isoquinoline-6-carbohydroxamic acid | 1H NMR (400 MHz, METHANOL-d4) δ = 7.54 (s, 1H), 7.46 (d, J = 10.1 Hz, 1H), 4.55 - 4.31 (m, 2H), 4.21 - 4.01 (m, 1H), 4.01 - 3.92 (m, 2H), 3.82 - 3.80 (m, 1H), 3.67 (d, J = 9.6 Hz, 1H), 3.63 - 3.40 (m, 2H), 3.31 - 3.09 (m, 2H), 2.47 - 2.22 (m, 3H), 2.16 - 2.10 (m, 1H), 2.05 - 1.92 (m, 2H). MS(ESI): 321.0 [M + H]+. Absolute stereochemistry is unknown. |
| 317 | 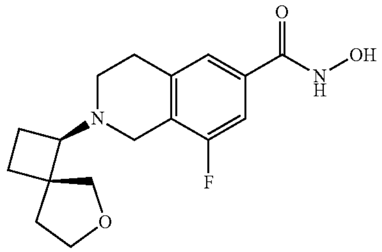 [SMILES: O=C(NO)c1cc(F)c2c(c1)CCN([C@@H]1CC[C@@]13CCOC3)C2] 8-fluoro-2-[(3R,4R)-6-oxaspiro[3.4]octan-3-yl]-3,4-dihydro-1H-isoquinoline-6-carbohydroxamic acid | 1H NMR (400 MHz, METHANOL-d4) δ = 7.54 (s, 1H), 7.46 (d, J = 10.1 Hz, 1H), 4.56 - 4.31 (m, 2H), 4.21 - 4.01 (m, 1H), 4.01 - 3.93 (m, 2H), 3.82 - 3.80 (m, 1H), 3.67 (d, J = 9.6 Hz, 1H), 3.63 - 3.38 (m, 2H), 3.31 - 3.17 (m, 2H), 2.46 - 2.22 (m, 3H), 2.16 - 2.10 (m, 1H),2.05 - 1.91 (m, 2H). MS(ESI): 321.0 [M + H]+. Absolute stereochemistry is unknown. |
| 318 | 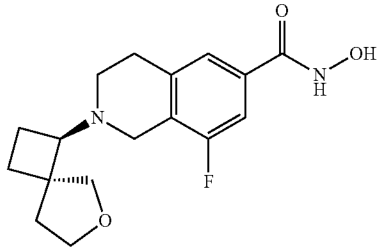 [SMILES: O=C(NO)c1cc(F)c2c(c1)CCN([C@@H]1CC[C@]13CCOC3)C2] 8-fluoro-2-[(3R,4S)-6-oxaspiro[3.4]octan-3-yl]-3,4-dihydro-1H-isoquinoline-6-carbohydroxamic acid | 1H NMR (400 MHz, METHANOL-d4) δ = 7.55 (s, 1H), 7.46 (d, J = 10.1 Hz, 1H), 4.64 - 4.39 (m, 3H), 4.10 - 4.01 (m, 1H), 3.96 - 3.89 (m, 1H), 3.83 - 3.76 (m, 1H), 3.67 - 3.57(m, 2H), 3.56 - 3.44 (m, 1H), 3.28 (br t, J = 6.0 Hz, 2H), 2.49 - 2.41 (m, 1H), 2.33 - 2.24 (m, 1H), 2.24 - 2.18 (m, 1H), 2.15 - 1.99 (m, 3H). MS(ESI): 321.0 [M + H]+. Absolute stereochemistry is unknown. |

-continued

| Compound | Structure/Name | Characterization |
|---|---|---|
| 319 | 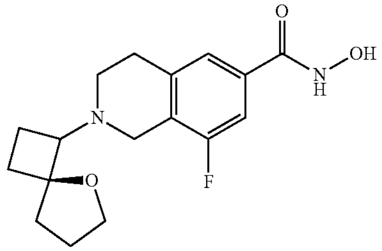 [SMILES: O=C(NO)c1cc(F)c2c(c1)CCN(C1CC[C@@]13CCCO3)C2] 8-fluoro-2-[(4R)-5-oxaspiro[3.4]octan-3-yl]-3,4-dihydro-1H-isoquinoline-6-carbohydroxamic acid | 1H NMR (400 MHz, METHANOL-d4) δ = 7.55 (s, 1H), 7.47 (d, J = 10.1 Hz, 1H), 4.57 – 4.36 (m, 2H), 4.03 (bt, J = 9.1 Hz, 1H), 3.96 – 3.88 (m, 2H), 3.69 – 3.46 (m, 2H), 3.32 – 3.22 (m, 2H), 2.32 – 2.25 (m, 1H), 2.14 – 2.10 (m, 4H), 2.02 – 1.96 (m, 1H), 1.87 – 1.77 (m, 2H). MS(ESI): 321.0 [M + H]+. Absolute stereochemistry is unknown. |
| 320 | 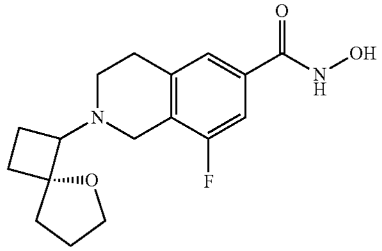 [SMILES: O=C(NO)c1cc(F)c2c(c1)CCN(C1CC[C@]13CCCO3)C2] 8-fluoro-2-[(4S)-5-oxaspiro[3.4]octan-3-yl]-3,4-dihydro-1H-isoquinoline-6-carbohydroxamic acid | 1H NMR (400 MHz, METHANOL-d4) δ = 7.56 (s, 1H), 7.47 (d, J = 10.1 Hz, 1H), 4.53 – 4.34 (m, 2H), 4.02 (bd, J = 9.4 Hz, 1H), 3.95 – 3.88 (m, 2H), 3.66 – 3.45 (m, 2H), 3.31 – 3.25 (m, 2H), 2.33 – 2.25 (m, 1H), 2.18 – 2.09 (m, 4H), 2.03 – 1.97 (m, 1H), 1.88 – 1.76 (m, 2H). MS(ESI): 321.0 [M + H]+. Absolute stereochemistry is unknown. |
| 329 | 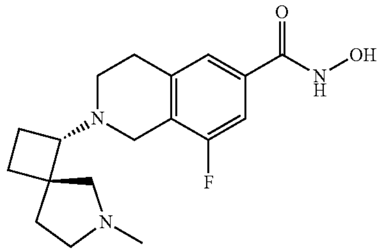 [SMILES: CN1CC[C@@]2(CC[C@@H]2N2CCc3cc(C(=O)NO)cc(F)c3C2)C1] 8-fluoro-2-[(3S,4S)-6-methyl-6-azaspiro[3.4]octan-3-yl]-3,4-dihydro-1H-isoquinoline-6-carbohydroxamic acid | 1H NMR (400 MHz, METHANOL-d4) δ = 7.48 (s, 1H), 7.39 (d, J = 10.1 Hz, 1H), 4.23 – 4.15 (m,1H), 4.10 – 3.97 (m, 1H), 3.95 – 3.82 (m, 1H), 3.80 – 3.58 (m, 2H), 3.52 – 3.34 (m, 2H), 3.27 – 3.09 (m, 4H), 3.04 (s, 3H), 2.54 – 2.22 (m, 4H), 2.16 (bs, 1H), 2.01 – 1.84 (m, 1H). MS(ESI): 334.1 [M + H]+. Absolute stereochemistry is unknown. |
| 330 | 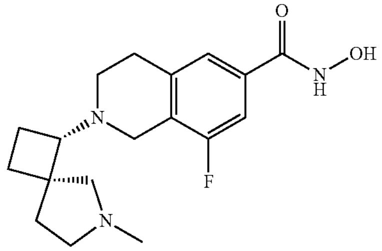 [SMILES: CN1CC[C@]2(CC[C@@H]2N2CCc3cc(C(=O)NO)cc(F)c3C2)C1] 8-fluoro-2-[(3S,4R)-6-methyl-6-azaspiro[3.4]octan-3-yl]-3,4-dihydro-1H-isoquinoline-6-carbohydroxamic acid | 1H NMR (400 MHz, METHANOL-d4) δ = 7.50 (s, 1H), 7.42 (d, J = 10.1 Hz, 1H), 4.44 – 4.36 (m, 1H), 4.28 – 4.18 (m, 1H), 4.07 – 3.90 (m, 2H), 3.89 – 3.74 (m, 1H), 3.55 – 3.35 (m, 3H), 3.29 – 3.09 (m, 3H), 3.00 (s, 3H), 2.47 – 2.26 (m, 4H), 2.14 – 1.96 (m, 2H). MS(ESI): 334.1 [M + H]+. Absolute stereochemistry is unknown. |

-continued

| Compound | Structure/Name | Characterization |
|---|---|---|
| 331 | 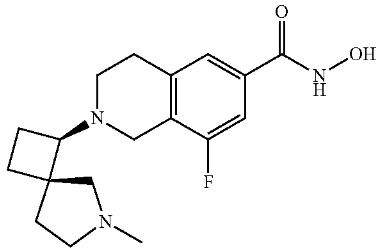 [SMILES: CN1CC[C@@]2(CC[C@H]2N2CCc3cc(C(=O)NO)cc(F)c3C2)C1] 8-fluoro-2-[(3R,4S)-6-methyl-6-azaspiro[3.4]octan-3-yl]-3,4-dihydro-1H-isoquinoline-6-carbohydroxamic acid | 1H NMR (400 MHz, METHANOL-d4) δ = 7.48 (s, 1H), 7.39 (d, J = 10.1 Hz, 1H), 4.25 − 4.13 (m, 1H), 4.11 − 4.01 (m, 1H), 3.97 − 3.80 (m, 1H), 3.79 − 3.63 (m, 2H), 3.52 − 3.38 (m, 1H), 3.30 − 3.08 (m, 5H), 3.04 (s, 3H), 2.57 − 2.40 (m, 1H), 2.38 − 2.25 (m, 2H), 2.22 − 2.10 (m, 2H), 2.02 − 1.84 (m, 1H). MS(ESI): 334.1 [M + H]+. Absolute stereochemistry is unknown. |
| 332 | 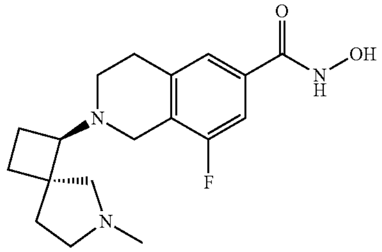 [SMILES: CN1CC[C@]2(CC[C@H]2N2CCc3cc(C(=O)NO)cc(F)c3C2)C1] 8-fluoro-2-[(3R,4R)-6-methyl-6-azaspiro[3.4]octan-3-yl]-3,4-dihydro-1H-isoquinoline-6-carbohydroxamic acid | 1H NMR (400 MHz, METHANOL-d4) δ = 7.51 (s, 1H), 7.42 (bd, J = 10.1 Hz, 1H), 4.39 − 4.28 (m, 1H), 4.24 − 4.12 (m,1H),, 4.03 − 3.71 (m, 3H), 3.51 − 3.37 (m, 2H), 3.31 − 3.11 (m, 4H), 3.00 (bs, 3H), 2.47 − 2.26 (m, 4H), 2.14 − 1.95 (m, 2H). MS(ESI): 334.1 [M + H]+. Absolute stereochemistry is unknown. |
| 339 | 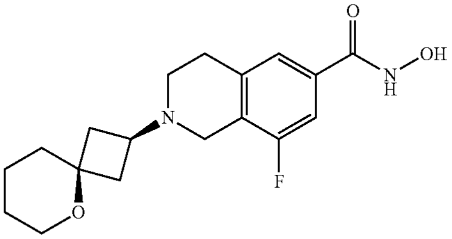 [SMILES: O=C(NO)c1cc(F)c2c(c1)CCN([C@H]1C[C@]3(CCCCO3)C1)C2] 8-fluoro-2-(5-oxaspiro[3.5]nonan-2-yl)-3,4-dihydro-1H-isoquinoline-6-carbohydroxamic acid | 1H NMR (400 MHz, METHANOL-d4) δ = 7.38 (s, 1H), 7.28 (d, J = 10.1 Hz, 1H), 3.66 (t, J = 5.2 Hz, 2H), 3.60 (s, 2H), 3.15 − 3.01 (m, 1H), 2.97 (t, J = 5.8 Hz, 2H), 2.70 (t, J = 6 Hz, 2H), 2.43 − 2.35 (m, 2H), 1.91 − 1.83 (m, 2H), 1.63 − 1.60 (m, 4H), 1.59 − 1.50 (m, 2H). MS(ESI): 335.1 [M + H]+. Absolute stereochemistry is unknown. |
| 340 | 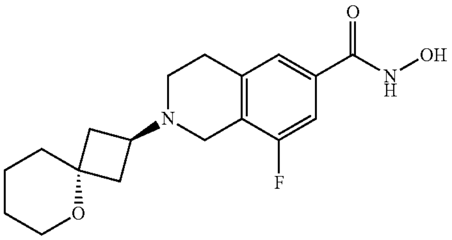 [SMILES: O=C(NO)c1cc(F)c2c(c1)CCN([C@H]1C[C@@]3(CCCCO3)C1)C2] 8-fluoro-2-(5-oxaspiro[3.5]nonan-2-yl)-3,4-dihydro-1H-isoquinoline-6-carbohydroxamic acid | 1H NMR (400 MHz, METHANOL-d4) δ = 7.37 (s, 1H), 7.28 (d, J = 10.1 Hz, 1H), 3.62 − 3.57 (m, 4H), 3.62 − 3.55 (m, 2H), 2.73 − 2.64 (m, 3H), 2.40 − 2.35 (m,2H), 1.98 − 1.90 (m, 2H), 1.72 − 1.65 (m, 2H), 1.65 − 1.60 (m, 2H), 1.56 − 1.48 (m, 2H). MS(ESI): 335.1 [M + H]+. Absolute stereochemistry is unknown. |

-continued

| Compound | Structure/Name | Characterization |
| --- | --- | --- |
| 348 | 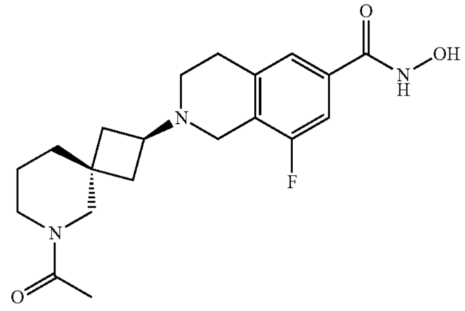 [SMILES: CC(=O)N1CCC[C@]2(C1)C[C@H](N1CCc3cc(C(=O)NO)cc(F)c3C1)C2] 2-(6-acetyl-6-azaspiro[3.5]nonan-2-yl)-8-fluoro-3,4-dihydro-1H-isoquinoline-6-carbohydroxamic acid | 1H NMR (400 MHz, METHANOL-d4) δ ppm 7.41 (s, 1 H) 7.28 (d, J = 10.1 Hz, 1H) 3.46 - 3.58 (m, 6 H) 3.04 - 3.11 (m, 1 H) 2.93 - 3.00 (m, 2 H) 2.65 - 2.71 (m, 2 H) 2.12 - 2.18 (m, 5 H) 1.55 - 1.69 (m, 6 H). MS (ESI): 376.2 [M + H]+. Absolute stereochemistry is unknown. |
| 349 | 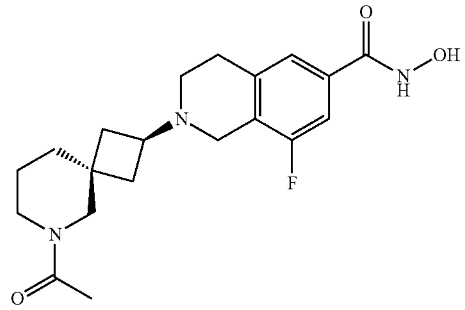 [SMILES: CC(=O)N1CCC[C@]2(C1)C[C@@H](N1CCc3cc(C(=O)NO)cc(F)c3C1)C2] 2-(6-acetyl-6-azaspiro[3.5]nonan-2-yl)-8-fluoro-3,4-dihydro-1H-isoquinoline-6-carbohydroxamic acid | 1H NMR (400 MHz, METHANOL-d4) δ ppm 7.42 (s, 1 H) 7.36 (d, J = 10.1 Hz, 1 H) 3.46 - 3.58 (m, 6 H) 3.04 - 3.11 (m, 1 H) 2.93 - 3.00 (m, 2 H) 2.65 - 2.71 (m, 2 H) 2.12 - 2.18 (m, 5 H) 1.55 - 1.69 (m, 6 H). MS (ESI): 376.2 [M + H]+. Absolute stereochemistry is unknown. |
| 355 | 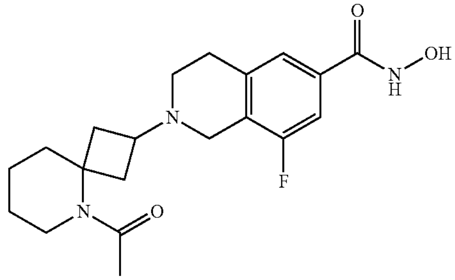 [SMILES: CC(=O)N1CCCCC12CC(N1CCc3cc(C(=O)NO)cc(F)c3C1)C2] 2-(5-acetyl-5-azaspiro[3.5]nonan-2-yl)-8-fluoro-3,4-dihydro-1H-isoquinoline-6-carbohydroxamic acid | 1H NMR (400 MHz, METHANOL-d4) δ ppm 7.55 (s, 1 H) 7.47 (m, J = 10.1 Hz, 1 H) 3.65 - 3.73 (m, 1 H) 3.49 - 3.57 (m, 1 H) 3.40 - 3.46 (m, 2 H) 3.25 - 3.31 (m, 3 H) 2.85 - 2.96 (m, 2 H) 2.54 - 2.68 (m, 2 H) 2.07 - 2.15 (m, 3 H) 1.71 - 1.89 (m, 5 H) 1.47 - 1.66 (m, 3 H). MS (ESI): 376.1 [M + H]+. |
| 359 | 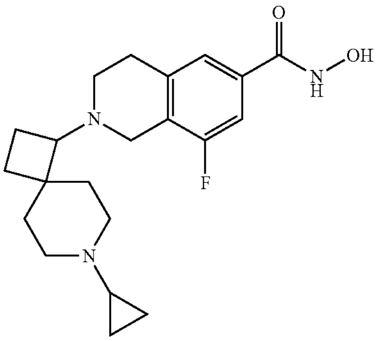 [SMILES: O=C(NO)c1cc(F)c2c(c1)CCN(C1CCC13CCN(C1CC1)CC3)C2] 2-(7-cyclopropyl-7-azaspiro[3.5]nonan-3-yl)-8-fluoro-3,4-dihydro-1H-isoquinoline-6-carbohydroxamic acid | 1H NMR (400 MHz, METHANOL-d4) δ = 7.49 (s, 1H), 7.41 (d, J = 10.1 Hz, 1H), 4.29 - 4.12 (m, 2H), 3.72 - 3.64 (m, 1H), 3.62 - 3.54 (m, 2H), 3.41 - 3.33 (m, 2H), 3.22 - 3.11 (m, 4H), 3.09 - 2.92(m, 1H), 2.49 - 2.39 (m, 1H), 2.32 - 2.22 (m, 2H), 2.15 - 1.98 (m, 4H), 1.81 - 1.73 (m, 1H), 1.07 - 1.01 (m, 2H), 1.00 - 0.96 (m, 2H). MS(ESI): 374.1 [M + H]+. |

-continued

| Compound | Structure/Name | Characterization |
|---|---|---|
| 360 | 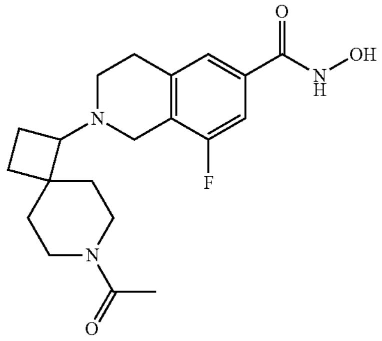 [SMILES: CC(=O)N1CCC2(CCC2N2CCc3cc(C(=O)NO)cc(F)c3C2)CC1] 2-(7-acetyl-7-azaspiro[3.5]nonan-3-yl)-8-fluoro-3,4-dihydro-1H-isoquinoline-6-carbohydroxamic acid | 1H NMR (400 MHz, METHANOL-d4) δ = 7.52 (s, 1H), 7.47 (d, J = 10.2 Hz, 1H), 4.70 - 4.49 (m, 2H), 4.01 - 3.84 (m, 1H), 3.78 - 3.63 (m, 2H), 3.55 - 3.43 (m, 1H), 3.39 - 3.34 (m, 1H), 3.31 - 3.24 (m, 2H), 3.10 - 2.77 (m, 1H), 2.64 - 2.39 (m, 2H), 2.38 - 2.29 (m, 1H), 2.15 (d, J = 11.6 Hz, 3H), 2.12 - 1.96 (m, 2H), 1.91 - 1.69 (m, 4H). MS(ESI): 376.1 [M + H]+. |
| 362 | 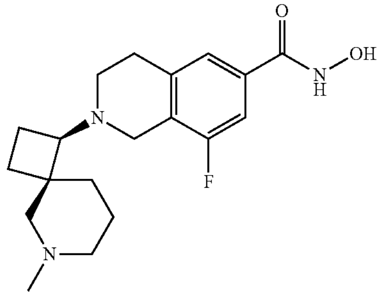 [SMILES: CN1CCC[C@@]2(CC[C@H]2N2CCc3cc(C(=O)NO)cc(F)c3C2)C1] 8-fluoro-2-[(3R,4R)-6-methyl-6-azaspiro[3.5]nonan-3-yl]-3,4-dihydro-1H-isoquinoline-6-carbohydroxamic acid | 1H NMR (400 MHz, METHANOL-d4) δ ppm 7.40 (s, 1 H), 7.32 (d, J = 10.2 Hz, 1 H) 3.85 - 4.21 (m, 3 H), 3.45 - 3.34 (m, 1 H), 3.04 - 3.18 (m, 6 H), 3.05 - 2.93 (m,1 H), 2.80 (s, 3 H), 2.29 - 2.37 (m, 1 H) , 2.14 - 2.23 (m, 1 H) 2.12 - 2.01 (m, 1 H) , 1.98 - 1.86 (m, 1 H), 1.82 - 1.89 (m, 2 H), 1.73 - 1.81 (m, 1 H)1.61 - 1.70 (m, 1 H). MS(ESI): 348.0 [M + H]+. Absolute stereochemistry is unknown. |
| 363 | 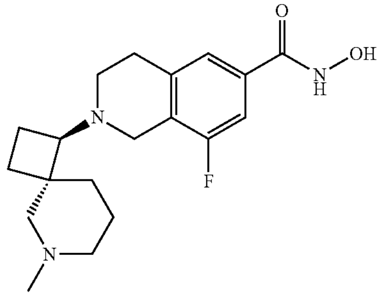 [SMILES: CN1CCC[C@]2(CC[C@H]2N2CCc3cc(C(=O)NO)cc(F)c3C2)C1] 8-fluoro-2-[(3R,4S)-6-methyl-6-azaspiro[3.5]nonan-3-yl]-3,4-dihydro-1H-isoquinoline-6-carbohydroxamic acid | 1H NMR (400 MHz, METHANOL-d4) δ ppm 7.40 (s, 1 H), 7.32 (d, J = 10.1 Hz, 1 H), 4.20 - 4.27 (m, 1 H), 4.11 - 4.02 (m, 1 H) , 3.58 - 3.48 (m, 1 H), 3.47 - 3.42 (m, 1 H), 3.40 - 3.32 (m, 2 H), 3.22 - 3.23 (m, 4 H) , 3.21 - 3.12 (m, 1 H), 2.80 (s, 3 H) , 2.33 - 2.42 (m, 1 H), 2.22 - 2.31 (m, 1 H), 2.18 - 2.10(m,1 H), 1.98 - 1.93 (m, 1 H), 1.77 - 1.90 (m, 3 H), 1.65 - 1.74 (m, 1 H). MS(ESI): 348.0 [M + H]+. Absolute stereochemistry is unknown. |
| 364 | 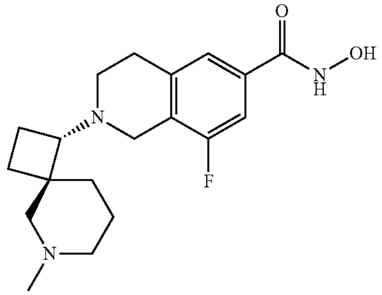 [SMILES: CN1CCC[C@@]2(CC[C@@H]2N2CCc3cc(C(=O)NO)cc(F)c3C2)C1] 8-fluoro-2-[(3S,4R)-6-methyl-6-azaspiro[3.5]nonan-3-yl]-3,4-dihydro-1H-isoquinoline-6-carbohydroxamic acid | 1H NMR (400 MHz, METHANOL-d4) δ = 7.44 (s, 1H), 7.35 (d, J = 10.0 Hz, 1H), 4.03 - 3.93 (m, 1H), 3.90 - 3.75 (m, 2H), 3.49 - 3.41 (m, 1H), 3.29 - 3.19 (m, 2H), 3.16 - 3.01 (m, 4H), 3.01 - 2.96(m, 1H), 2.94 (s, 3H), 2.38 - 2.29 (m, 1H), 2.27 - 2.16 (m, 1H), 2.13 - 2.04 (m, 1H), 2.03 - 1.94 (m, 1H), 1.91 - 1.86 (m, 2H), 1.78 - 1.66 (m, 2H). MS(ESI): 348.2 [M + H]+. Absolute stereochemistry is unknown. |

-continued

| Compound | Structure/Name | Characterization |
|---|---|---|
| 365 | 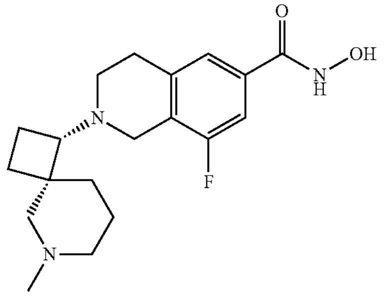 [SMILES: CN1CCC[C@]2(CC[C@@H]2N2CCc3cc(C(=O)NO)cc(F)c3C2)C1] 8-fluoro-2-[(3S,4S)-6-methyl-6-azaspiro[3.5]nonan-3-yl]-3,4-dihydro-1H-isoquinoline-6-carbohydroxamic acid | 1H NMR (400 MHz, METHANOL-d4) δ = 7.45 (s, 1H), 7.37 (d, J = 10.1 Hz, 1H), 4.09 − 3.98 (m, 1H), 3.94 − 3.83 (m, 2H), 3.51 − 3.42 (m, 1H), 3.28 − 3.21 (m, 2H), 3.18 − 3.05 (m, 4H), 3.04 − 2.98 (m, 1H), 2.94 (s, 3H), 2.40 − 2.31 (m, 1H), 2.29 − 2.20 (m, 1H), 2.16 − 2.08 (m, 1H), 2.04 − 1.96(m, 1H), 1.94 − 1.84 (m, 2H), 1.78 − 1.66 (m, 2H). MS(ESI): 348.2 [M + H]+. Absolute stereochemistry is unknown. |
| 387 | 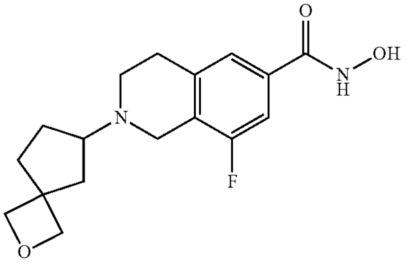 [SMILES: O=C(NO)c1cc(F)c2c(c1)CCN(C1CCC3(COC3)C1)C2] 8-fluoro-2-(2-oxaspiro[3.4]octan-6-yl)-3,4-dihydro-1H-isoquinoline-6-carbohydroxamic acid | 1H NMR (400 MHz, METHANOL-d4) δ = 7.58 (s, 1H), 7.48 (d, J = 10.1 Hz, 1H), 4.86 (br s, 2H), 4.77 − 4.63 (m, 2H), 4.18 − 4.10 (m, 1H), 3.96 − 3.91 (m, 2H), 3.81 − 3.74 (m, 2H), 3.67 (dd, J = 2.9, 11.4 Hz, 1H), 3.51 (dd, J = 1.8, 11.4 Hz, 1H), 2.45 − 2.34 (m, 2H), 2.10 − 2.01 (m, 1H), 1.95 − 1.85 (m, 2H), 1.80 − 1.75 (m, 1H). MS(ESI): 321.0 [M + H]+. |
| 390 | 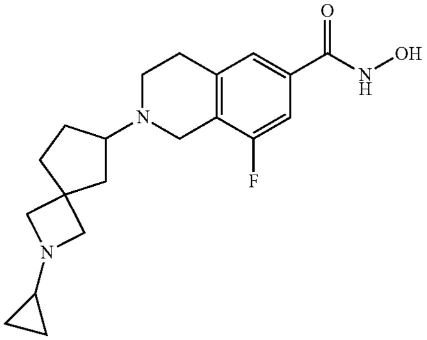 [SMILES: O=C(NO)c1cc(F)c2c(c1)CCN(C1CCC3(C1)CN(C1CC1)C3)C2] 2-(2-cyclopropyl-2-azaspiro[3.4]octan-6-yl)-8-fluoro-3,4-dihydro-1H-isoquinoline-6-carbohydroxamic acid | 1H NMR (400 MHz, METHANOL-d4) δ = 7.51 (s, 1H), 7.37 (d, J = 10.0 Hz, 1H), 4.33 − 3.99 (m, 2H), 3.97 − 3.76 (m, 2H), 3.73 − 3.57 (m, 2H), 3.48 − 3.39 (m, 2H), 2.79 − 2.68 (m, 1H), 2.48 − 2.28 (m, 2H), 2.09 − 1.77 (m, 5H), 1.25 − 1.18 (m, 2H), 0.92 − 0.77 (m, 4H). MS(ESI): 360.2[H + H]+ |
| 402 | 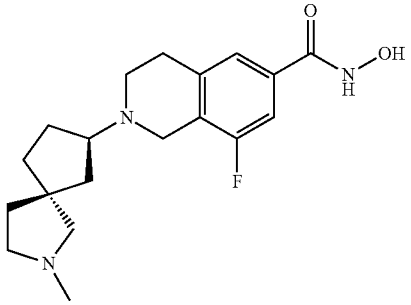 [SMILES: CN1CC[C@]2(CC[C@@H](N3CCc4cc(C(=O)NO)cc(F)c4C3)C2)C1] 8-fluoro-2-[(5S,8R)-2-methyl-2-azaspiro[4.4]nonan-8-yl]-3,4-dihydro-1H-isoquinoline-6-carbohydroxamic acid | 1H NMR (400 MHz, METHANOL-d4) δ = 7.54 (s, 1H), 7.46 (d, J = 10.0 Hz, 1H), 4.56 (br s, 2H), 3.93 −3.88 (m, 1H), 3.80 − 3.58 (m, 4H), 3.31 − 3.05 (m, 4H), 2.99 (s, 3H), 2.60 − 2.47 (m, 1H), 2.43 − 2.06 (m, 6H), 2.00 −1.92 (m, 1H). MS(ESI): 348.0 [M + H]+. Absolute stereochemistry is unknown. |

-continued

| Compound | Structure/Name | Characterization |
| --- | --- | --- |
| 403 | 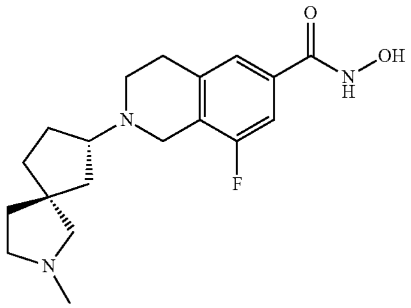 [SMILES: CN1CC[C@]2(CC[C@H](N3CCc4cc(C(=O)NO)cc(F)c4C3)C2)C1] 8-fluoro-2-[(5S,8S)-2-methyl-2-azaspiro[4.4]nonan-8-yl]-3,4-dihydro-1H-isoquinoline-6-carbohydroxamic acid | 1H NMR (400 MHz, METHANOL-d4) δ = 7.54 (s, 1H), 7.46 (d, J = 10.1Hz, 1H), 4.63 - 4.48 (m, 2H), 4.02 - 3.93 (m, 1H), 3.83 - 3.57 (m, 4H), 3.32 - 3.14 (m, 4H), 2.99 (s, 3H), 2.51 - 2.37 (m, 2H), 2.19 - 1.88 (m, 6H). MS(ESI): 348.0 [M + H]+. Absolute stereochemistry is unknown. |
| 404 | 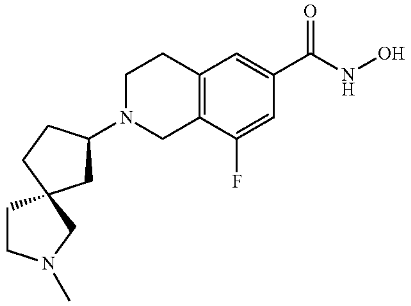 [SMILES: CN1CC[C@@]2(CC[C@@H](N3CCc4cc(C(=O)NO)cc(F)c4C3)C2)C1] 8-fluoro-2-[(5R,8R)-2-methyl-2-azaspiro[4.4]nonan-8-yl]-3,4-dihydro-1H-isoquinoline-6-carbohydroxamic acid | 1H NMR (400 MHz, METHANOL-d4) δ = 7.54 (s, 1H), 7.46 (d, J = 10.2 Hz, 1H), 4.63 - 4.48 (m, 2H), 4.01 - 3.90 (m, 1H), 3.83 - 3.56 (m, 4H), 3.32 - 3.21 (m, 3H), 3.15 - 3.02 (m, 1H), 2.99 (s, 3H), 2.55 - 2.43 (m, 2H),2.42 - 2.37 (m, 1H), 2.32 - 2.07 (m, 4H), 2.00 - 1.92 (m, 2H). MS(ESI): 348.2 [M + H]+. Absolute stereochemistry is unknown. |
| 405 | 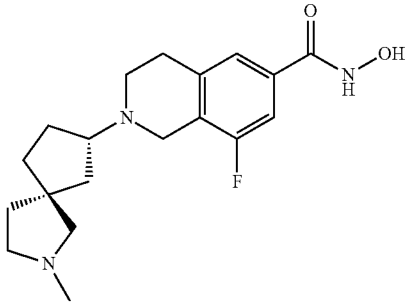 [SMILES: CN1CC[C@@]2(CC[C@H](N3CCc4cc(C(=O)NO)cc(F)c4C3)C2)C1] 8-fluoro-2-[(5R,8S)-2-methyl-2-azaspiro[4.4]nonan-8-yl]-3,4-dihydro-1H-isoquinoline-6-carbohydroxamic acid | 1H NMR (400 MHz, METHANOL-d4) = 7.54 (s, 1H), 7.46 (d, J = 10.1 Hz, 1H), 4.57 (bs, 2H), 4.02 - 3.93 (m, 1H), 3.86 - 3.55 (m, 4H), 3.32 - 3.23 (m, 3H), 3.22 - 3.12 (m, 1H), 2.99 (s, 3H), 2.50 - 2.36 (m, 2H), 2.20 - 2.00 (m, 5H), 1.97 - 1.80 (m, 1H). MS(ESI): 348.2 [M + H]+. Absolute stereochemistry is unknown. |
| 414 | 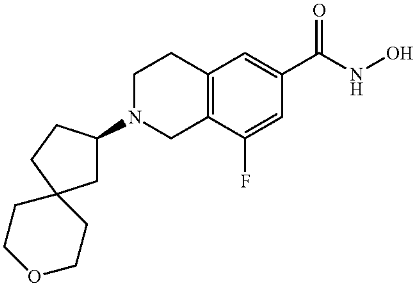 [SMILES: O=C(NO)c1cc(F)c2c(c1)CCN([C@@H]1CCC3(CCOCC3)C1)C2] 8-fluoro-2-(8-oxaspiro[4.5]decan-3-yl)-3,4-dihydro-1H-isoquinoline-6-carbohydroxamic acid | 1H NMR (400 MHz, METHANOL-d4) δ = 7.56 (s, 1H), 7.47 (d, J = 10.1 Hz, 1H), 4.78 - 4.64 (m, 1H), 4.52 - 4.34 (m, 1H), 4.01 - 3.85 (m, 2H), 3.79 - 3.63 (m, 4H), 3.30 (br s, 2H), 2.42 - 2.34 (m, 2H), 2.06 - 1.96 (m, 1H), 1.89 - 1.67 (m, 5H), 1.63 - 1.56 (m, 3H). MS(ESI): 349.0 [M + H]+. Absolute stereochemistry is unknown. |

-continued

| Compound | Structure/Name | Characterization |
|---|---|---|
| 415 | 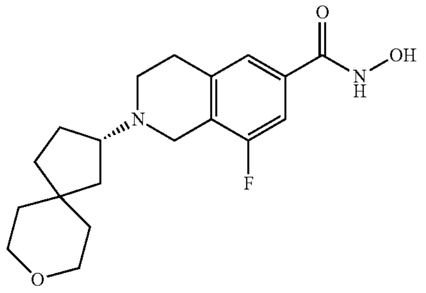 [SMILES: O=C(NO)c1cc(F)c2c(c1)CCN([C@H]1CCC3(CCOCC3)C1)C2] 8-fluoro-2-[(3S)-8-oxaspiro[4.5]decan-3-yl]-3,4-dihydro-1H-isoquinoline-6-carbohydroxamic acid | 1H NMR (400 MHz, METHANOL-d4) δ = 7.55 (s, 1H), 7.47 (d, J = 10.1 Hz, 1H), 4.82 - 4.61 (m, 1H), 4.57 - 4.34 (m, 1H), 4.02 - 3.84 (m, 2H), 3.75 - 3.67 (m, 4H), 3.40 - 3.25 (m, 2H), 2.44 - 2.33 (m, 2H), 2.06 - 1.95 (m, 1H), 1.94 - 1.65 (m, 5H), 1.64 - 1.54 (m, 3H). MS(ESI): 349.0 [M + H]+. Absolute stereochemistry is unknown. |
| 604 | 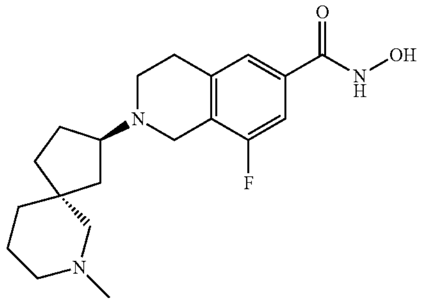 8-fluoro-2-[(3R,5R)-7-methyl-7-azaspiro[4.5]decan-3-yl]-3,4-dihydro-1H-isoquinoline-6-carbohydroxamic acid | 1H NMR (400 MHz, METHANOL-d4) δ = 7.55 (s, 1H), 7.47 (d, J = 10.1 Hz, 1H), 4.69 - 4.45 (m, 2H), 3.98 - 3.87 (m, 1H), 3.85 - 3.55 (m, 2H), 3.54 - 3.39 (m, 2H), 3.40 - 3.24 (m, 2H), 3.05 - 2.91 (m, 1H), 2.89 (s, 4H), 2.65 - 2.46 (m, 1H), 2.38 - 2.21 (m, 1H), 2.14 - 2.06 (m, 1H), 1.99 - 1.79 (m, 6H), 1.68 - 1.60 (m, 1H). MS(ESI): 349.0 [M + H]+. Absolute stereochemistry is unknown. |
| 605 | 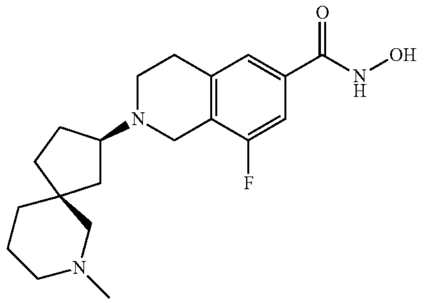 [SMILES: CN1CCC[C@@]2(CC[C@@H](N3CCc4cc(C(=O)NO)cc(F)c4C3)C2)C1] 8-fluoro-2-[(3R,5S)-7-methyl-7-azaspiro[4.5]decan-3-yl]-3,4-dihydro-1H-isoquinoline-6-carbohydroxamic acid | 1H NMR (400 MHz, METHANOL-d4) δ = 7.53 (s, 1H), 7.46 (d, J = 10.1 Hz, 1H), 4.70 - 4.42 (m, 2H),, 4.01 - 3.87 (m, 1H), 3.80 - 3.53 (m, 2H), 3.52 - 3.39 (m, 2H), 3.32 - 3.26 (m, 2H), 3.04 - 2.91 (m, 2H), 2.89 (s, 3H), 2.49 - 2.42 (m, 1H), 2.24 - 1.73 (m, 8H), 1.60 - 1.46 (m, 1H). MS(ESI): 362.1 [M + H]+. Absolute stereochemistry is unknown. |
| 425 | 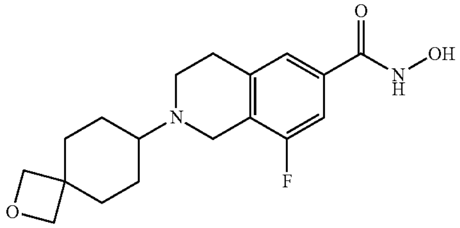 [SMILES: O=C(NO)c1cc(F)c2c(c1)CCN(C1CCC3(CC1)COC3)C2] 8-fluoro-2-(2-oxaspiro[3.5]nonan-7-yl)-3,4-dihydro-1H-isoquinoline-6-carbohydroxamic acid | 1H NMR (400 MHz, METHANOL-d4) δ ppm 7.38 (s, 1 H) 7.29 (d, J = 10.1 Hz, 1 H) 4.51 (s, 2 H) 4.38 (s, 2 H) 3.82 (s, 2 H) 2.94 - 2.98 (m, 2 H) 2.86 - 2.90 (m, 2 H) 2.51 - 2.59 (m, 1 H) 2.26 (br d, J = 13.01 Hz, 2 H) 1.92 - 1.98 (m, 2 H) 1.56 (br d, J = 3.00 Hz, 2 H) 1.36 - 1.44 (m, 2 H). MS (ESI): 335.3 [M + H]+. |

-continued

| Compound | Structure/Name | Characterization |
|---|---|---|
| 441 | 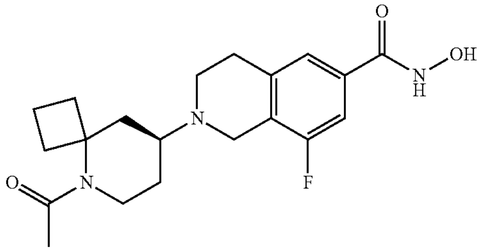 [SMILES: CC(=O)N1CC[C@H](N2CCc3cc(C(=O)NO)cc(F)c3C2)CC12CCC2] 2-[(8S)-5-acetyl-5-azaspiro[3.5]nonan-8-yl]-8-fluoro-3,4-dihydro-1H-isoquinoline-6-carbohydroxamic acid | 1H NMR (400 MHz, METHANOL-d4) δ = 7.56 (s, 1H), 7.48 (d, J = 10.4 Hz, 1H), 4.74 - 4.53 (m, 2H), 4.09 - 3.79 (m, 3H), 3.54 - 3.42 (m, 1H), 3.30 - 3.32 (m, 2H), 3.15 - 3.12 (m, 1H), 2.91 - 2.77 (m, 1H), 2.62 - 2.47 (m, 1H), 2.33 - 2.18 (m, 3H), 2.13 (s, 3H), 2.11 - 2.03 (m, 1H), 1.97 - 1.96 (m, 1H), 1.81 - 1.78 (m, 2H), 1.71 - 1.66 (m, 1H). MS(ESI): 376.3 [M + H]+. Absolute stereochemistry is unknown. |
| 442 | 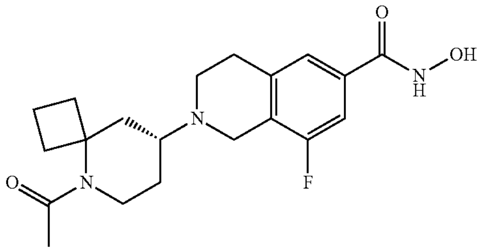 [SMILES: CC(=O)N1CC[C@@H](N2CCc3cc(C(=O)NO)cc(F)c3C2)CC12CCC2] 2-[(8R)-5-acetyl-5-azaspiro[3.5]nonan-8-yl]-8-fluoro-3,4-dihydro-1H-isoquinoline-6-carbohydroxamic acid | 1H NMR (400 MHz, METHANOL-d4) δ = 7.51 (s, 1H), 7.44 (d, J = 10.3 Hz, 1H), 4.61 (b s, 2H), 4.06 - 3.42 (m, 4H), 3.30 - 3.24 (m, 2H), 3.21 - 3.03 (m, 1H), 2.80 - 2.78 (m, 1H), 2.52 - 2.50 (m, 1H), 2.36 - 2.15 (m, 3H), 2.11 (s, 3H), 2.08 - 1.92 (m, 2H), 1.90 - 1.60 (m, 3H). MS(ESI): 376.2 [M + H]+. Absolute stereochemistry is unknown |
| 443 | 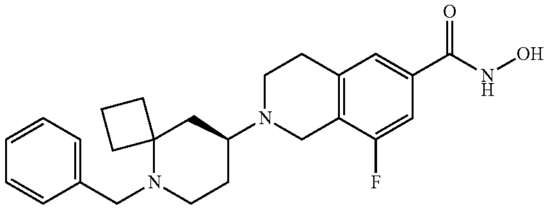 [SMILES: O=C(NO)c1cc(F)c2c(c1)CCN([C@H]1CCN(Cc3ccccc3)C3(CCC3)C1)C2] 2-[(8S)-5-benzyl-5-azaspiro[3.5]nonan-8-yl]-8-fluoro-3,4-dihydro-1H-isoquinoline-6-carbohydroxamic acid | 1H NMR (400 MHz, METHANOL-d4) δ = 7.67 - 7.57 (m, 2H), 7.57 - 7.48 (m, 4H), 7.45 (d, J = 10.1 Hz, 1H), 4.68 (br s, 2H), 4.61 - 4.43 (m, 1H), 4.35 - 4.34 (m, 1H), 4.04 - 3.82 (m, 1H), 3.74 (br s, 2H), 3.34 - 3.32 (m, 2H), 3.29 - 3.11 (m, 2H), 2.77 (br d, J = 12.4 Hz, 2H), 2.64 - 2.20 (m, 6H), 2.08 - 2.07 (m, 2H), 2.11 - 1.99 (m, 1H). MS(ESI): 424.4 [M + H]+. Absolute stereochemistry is unknown. |
| 444 | 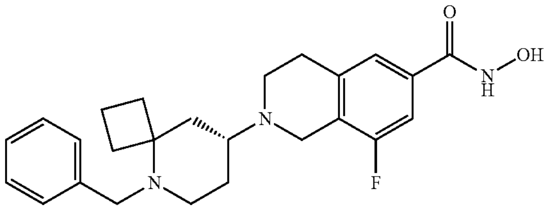 [SMILES: O=C(NO)c1cc(F)c2c(c1)CCN([C@@H]1CCN(Cc3ccccc3)C3(CCC3)C1)C2] 2-[(8R)-5-benzyl-5-azaspiro[3.5]nonan-8-yl]-8-fluoro-3,4-dihydro-1H-isoquinoline-6-carbohydroxamic acid | 1H NMR (400 MHz, METHANOL-d4) δ = 7.68 - 7.60 (m, 2H), 7.59 - 7.51 (m, 4H), 7.47 (d, J = 10.1 Hz, 1H), 4.65 (br s, 2H), 4.59 - 4.42 (m, 1H), 4.36 (br d, J = 13.1 Hz, 1H), 3.95 - 3.81 (m, 1H), 3.77 - 3.61 (m, 2H), 3.34 - 3.33 (m, 2H), 3.29 - 3.12 (m, 2H), 2.76 - 2.74 (m, 2H), 2.65 - 2.25 (m, 6H), 2.14 - 1.99 (m, 2H). MS(ESI): 424.3 [M + H]+. Absolute stereochemistry is unknown. |

-continued

| Compound | Structure/Name | Characterization |
|---|---|---|
| 449 | 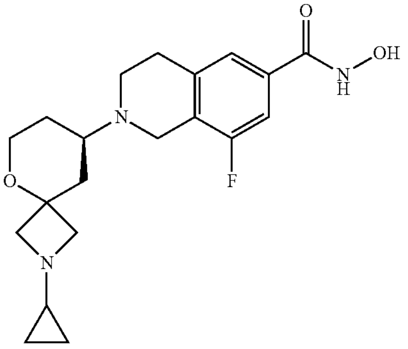 [SMILES: O=C(NO)c1cc(F)c2c(c1)CCN([C@@H]1CCOC3(C1)CN(C1CC1)C3)C2] 2-[(8S)-2-cyclopropyl-5-oxa-2-azaspiro[3.5]nonan-8-yl]-8-fluoro-3,4-dihydro-1H-isoquinoline-6-carbohydroxamic acid | 1H NMR (400 MHz, METHANOL-d4) δ = 7.61 (s, 1H), 7.46 (d, J = 10.3 Hz, 1H), 5.08 – 4.96 (m, 2H), 4.44 (bs, 1H), 4.32 – 4.15 (m, 4H), 4.00 – 3.96 (m, 1H), 3.86 – 3.84 (m, 1H), 3.59 – 3.47 (m, 4H), 2.85 – 2.72 (m, 2H), 2.43 – 2.29 (m, 3H), 0.90 (bd, J = 6.0 Hz, 4H). MS(ESI): 376.1 [M + H]+. Absolute stereochemistry is unknown. |
| 463 | 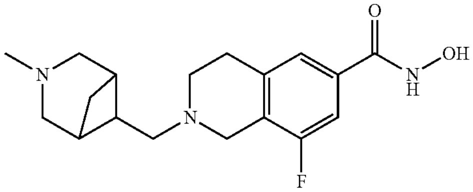 [SMILES: CN1CC2CC(C1)C2CN1CCc2cc(C(=O)NO)cc(F)c2C1] 8-fluoro-2-[(3-methyl-3-azabicyclo[3.1.1]heptan-6-yl)methyl]-3,4-dihydro-1H-isoquinoline-6-carbohydroxamic acid | 1H NMR (400 MHz, METHANOL-d4) δ ppm 7.53 (s, 1 H) 7.45 (d, J = 10.26 Hz, 1 H) 4.59 (br s, 2 H) 3.83 – 3.81 (m, 2 H) 3.68 (br s, 2 H) 3.60 (br d, J = 6.63 Hz, 2 H) 3.51 – 3.49 (m, 2 H) 3.28 – 3.32 (m, 2 H) 2.93 – 3.05 (m, 4 H) 2.73 – 2.81 (m, 2 H) 2.32 – 2.42 (m, 1 H) 1.89 – 1.98 (m, 1 H). MS (ESI): 334.1 [M + H]+. |
| 464 | 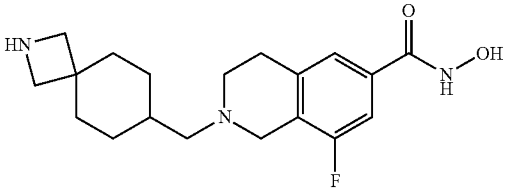 [SMILES: O=C(NO)c1cc(F)c2c(c1)CCN(CC1CCC3(CC1)CNC3)C2] 2-(2-azaspiro[3.5]nonan-7-ylmethyl)-8-fluoro-3,4-dihydro-1H-isoquinoline-6-carbohydroxamic acid | 1H NMR (400 MHz, METHANOL-d4) δ = 7.50 (s, 1H), 7.42 (d, J = 10.3 Hz, 1H), 4.72 – 4.33 (m, 2H), 3.85 (s, 2H), 3.78 (s, 2H), 3.74 – 3.43 (m, 2H), 3.29 – 3.27 (m, 2H), 3.22 (d, J = 7.0 Hz, 2H), 2.13 (br d, J = 13.4 Hz, 2H), 2.01 – 1.98 (m, 1H), 1.87 (br d, J = 11.8 Hz, 2H), 1.64 (dt, J = 3.2, 13.2 Hz, 2H), 1.22 – 1.07 (m, 2H). MS(ESI): 348.1 [M + H]+. |
| 465 | 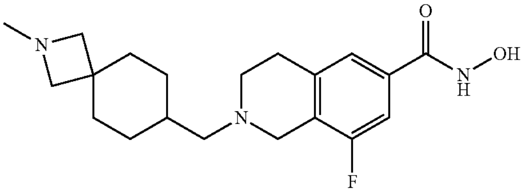 [SMILES: CN1CC2(CCC(CN3CCc4cc(C(=O)NO)cc(F)c4C3)CC2)C1] 8-fluoro-2-[(2-methyl-2-azaspiro[3.5]nonan-7-yl)methyl]-3,4-dihydro-1H-isoquinoline-6-carbohydroxamic acid | 1H NMR (400 MHz, METHANOL-d4) δ = 7.53 (s, 1H), 7.46 (d, J = 11.13 Hz, 1 H), 4.61 – 4.42 (m, 2H), 4.13 (br d, J = 10.5Hz, 1H), 4.00 (br d, J = 10.0 Hz, 1H), 3.80 (br t, J = 11.7 Hz, 2H), 3.72 – 3.46 (m, 2H), 3.28 – 3.27 (m, 2H), 3.21 (d, J = 7.0 Hz, 2H), 2.93 (s, 3H), 2.17 – 2.06 (m, 2H), 2.05 – 1.98 (m, 1H), 1.93 – 1.82 (m, 2H), 1.71 – 1.63 (m, 2H), 1.22 – 1.07 (m, 2H). MS(ESI): 362.2 [M + H]+. |
| 466 | 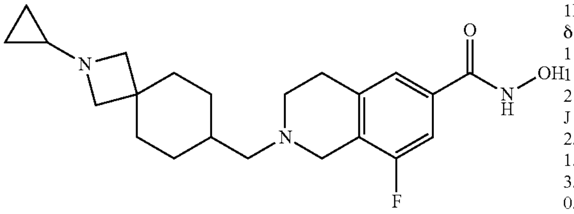 | 1H NMR (400 MHz, METHANOL-d4) δ ppm 7.54 (s, 1 H) 7.46 (d, J = 11.13 Hz, 1 H) 4.41 – 4.66 (m, 2 H) 4.06 – 4.19 (m, 1 H) 3.93 – 4.02 (m, 3 H) 3.48 – 3.78 (m, 2 H) 3.30 – 3.29 (m, 2 H) 3.23 (d, J = 6.88 Hz, 2 H) 3.02 – 3.10 (m, 1 H) 2.09 – 2.18 (m, 2 H) 1.97 – 2.06 (m, 1 H) 1.83 – 1.94 (m, 2 H) 1.70 (td, J = 13.26, 3.25 Hz, 2 H) 1.10 – 1.26 (m, 2 H) 0.86 – 0.95 (m, 4 H). MS (ESI): 388.2 [M + H]+. |

-continued

| Compound | Structure/Name | Characterization |
|---|---|---|
| | 2-[(2-cyclopropyl-2-azaspiro[3.5]nonan-7-yl)methyl]-8-fluoro-3,4-dihydro-1H-isoquinoline-6-carbohydroxamic acid | |
| 467 | 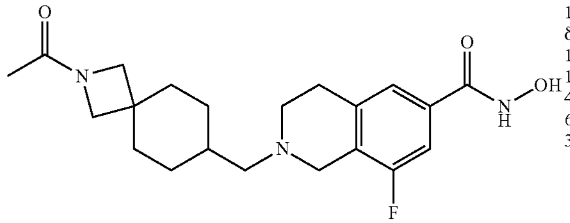 2-[(2-acetyl-2-azaspiro[3.5]nonan-7-yl)methyl]-8-fluoro-3,4-dihydro-1H-isoquinoline-6-carbohydroxamic acid | 1H NMR (400 MHz, METHANOL-d4) δ = 7.54 (s, 1H), 7.46 (d, J = 10.0 Hz, 1H), 3.91 (s, 1H), 3.86 (s, 1H), 3.67 (s, 1H), 3.62 (s, 1H), 3.23 (br d, J = 7.0 Hz, 4H), 2.03 – 1.96 (m, 4H), 1.88 – 1.82 (m, 6H), 1.69 – 1.57 (m, 3H), 1.23 – 1.10 (m, 3H). MS(ESI): 390.1 [M + H]+. |
| 468 | 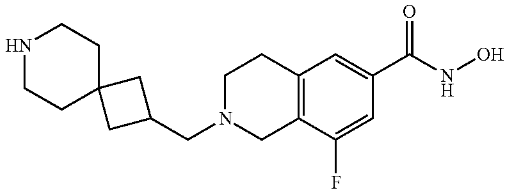 [SMILES: O=C(NO)c1cc(F)c2c(c1)CCN(CC1CC3(CCNCC3)C1)C2] 2-(7-azaspiro[3.5]nonan-2-ylmethyl)-8-fluoro-3,4-dihydro-1H-isoquinoline-6-carbohydroxamic acid | 1H NMR (400 MHz, METHANOL-d4) δ = 7.53 (s, 1H), 7.45 (d, J = 10.0 Hz, 1H), 4.62 – 4.39 (m, 2H), 3.76 – 3.51 (m, 2H), 3.48 (bd, J = 7.1 Hz, 2H), 3.29 – 3.27(m, 2H), 3.22 – 3.17 (m, 2H), 3.12 – 3.07 (m, 2H), 2.93 – 2.90 (m, 1H), 2.30 – 2.23 (m, 2H), 1.99 – 1.93 (m, 2H), 1.85 – 1.79 (m, 4H). MS(ESI): 348.1 [M + H]+. |
| 470 | 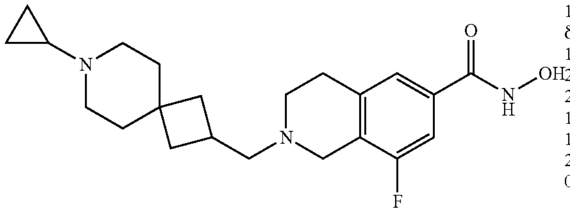 2-[(7-cyclopropyl-7-azaspiro[3.5]nonan-2-yl)methyl]-8-fluoro-3,4-dihydro-1H-isoquinoline-6-carbohydroxamic acid | 1H NMR (400 MHz, METHANOL-d4) δ = 7.52 (s, 1H), 7.44 (d, J = 10.0 Hz, 1H), 4.60 – 4.36 (m, 2H), 3.66 – 3.55 (m, 2H), 3.52 (b s, 1H), 3.47 (d, J = 7.3 Hz, 2H), 3.29 – 3.19 (m, 3H), 3.16 – 3.07 (m, 1H), 2.97 – 2.87 (m, 1H), 2.84 – 2.78 (m, 1H), 2.39 (b d, J = 1.4 Hz, 1H), 2.22 – 2.10 (m, 2H), 1.95 – 1.72 (m, 6H), 0.99 – 0.95 (m, 4H). MS(ESI): 388.2 [M + H]+. |
| 471 | 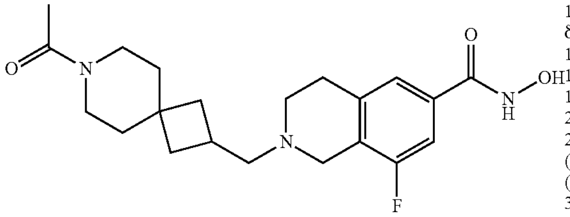 2-[(7-acetyl-7-azaspiro[3.5]nonan-2-yl)methyl]-8-fluoro-3,4-dihydro-1H-isoquinoline-6-carbohydroxamic acid | 1H NMR (400 MHz, METHANOL-d4) δ = 7.36 (s, 1H), 7.27 (d, J = 10.0 Hz, 1H), 3.65 – 3.64 (m, 2H), 3.57 – 3.52 (m, 1H), 3.46 – 3.45 (m, 2H), 3.41 – 3.36 (m, 1H), 2.99 – 2.93 (m, 2H), 2.80 – 2.75 (m, 2H), 2.70 (bs, 1H), 2.69 (s, 2H), 2.15 – 2.09 (m, 2H), 2.08 (s, 3H), 1.74 – 1.69 (m, 1H), 1.67 – 1.63 (m, 1H), 1.62 – 1.55 (m, 3H), 1.52 – 1.47 (m, 1H). MS(ESI): 390.2 [M + H]+. |
| 472 | 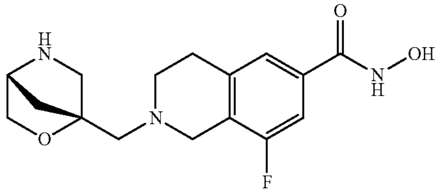 [SMILES: O=C(NO)c1cc(F)c2c(c1)CCN(C[C@@]13CN[C@@H](CO1)C3)C2] 8-fluoro-2-[[(1R,4R)-2-oxa-5-azabicyclo[2.2.1]heptan-1-yl]methyl]-3,4-dihydro-1H-isoquinoline-6-carbohydroxamic acid | 1H NMR (400 MHz, METHANOL-d4) δ = 7.49 (s, 1H), 7.42 (d, J = 10.0 Hz, 1H), 4.67 – 4.56 (m, 2H), 4.54 (bs, 1H), 4.24 – 4.17 (m, 1H), 4.14 – 4.08 (m, 1H), 3.96 – 3.87 (m, 2H), 3.72 (bs, 2H), 3.64 (bd, J = 11.3 Hz, 1H), 3.48 (bd, J = 11.3 Hz, 1H), 3.28 (bs, 2H), 2.44 – 2.43(m, 1H), 2.24 – 2.23(m, 1H). MS(ESI): 322.1 [M + H]+. |

-continued

| Compound | Structure/Name | Characterization |
| --- | --- | --- |
| 474 | 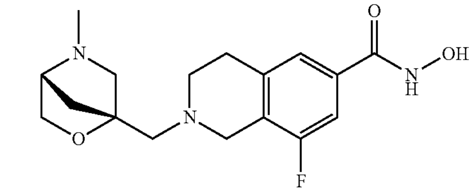 [SMILES: CN1C[C@@]2(CN3CCc4cc(C(=O)NO)cc(F)c4C3)C[C@@H]1CO2] 8-fluoro-2-[[(1S,4R)-5-methyl-2-oxa-5-azabicyclo[2.2.1]heptan-1-yl]methyl]-3,4-dihydro-1H-isoquinoline-6-carbohydroxamic acid | 1H NMR (400 MHz, METHANOL-d4) δ = 7.47 (s, 1H), 7.38 (d, J = 10.3 Hz, 1H), 4.43 - 4.18 (m, 4H), 4.12 - 4.05 (m, 1H), 4.01 - 3.71 (m, 1H), 3.65 - 3.38 (m, 5H), 3.16 (br t, J = 5.7 Hz, 2H), 3.03 (s, 3H), 2.39 (br s, 2H). MS(ESI): 336.1 [M + H]+. |
| 484 | 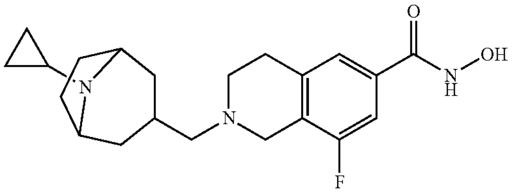 [SMILES: O=C(NO)c1cc(F)c2c(c1)CCN(CC1CC3CCC(C1)N3C1CC1)C2] 2-[(8-cyclopropyl-8-azabicyclo[3.2.1 ]octan-3-yl)methyl]-8-fluoro-3,4-dihydro-1H-isoquinoline-6-carbohydroxamic acid | 1H NMR (400 MHz, METHANOL-d4) δ = 7.49 (s, 1H), 7.40 (d, J = 10.1 Hz, 1H), 4.38 - 4.33 (m, 2H), 4.01 - 4.00 (m, 2H), 3.52 - 3.47 (m, 2H), 3.17 - 3.15 (m, 2H), 3.11 - 3.10 (m, 2H), 2.74 - 2.71 (m, 1H) 2.69 - 2.68 (m, 1H), 2.38 - 2.23 (m, 2H), 2.22 - 2.02 (m, 2H). 2.02 - 2.00 (m, 2H) 1.78 - 1.76 (m, 2H) 1.13 - 1.10 (m, 2H) 1.08 - 1.03 (m, 2H). MS (ESI): 374.2 [M + H]+. |
| 486 | 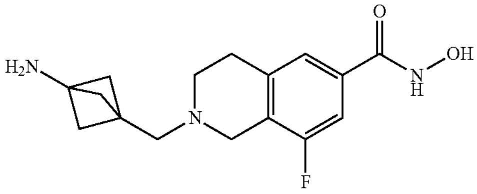 [SMILES: NC12CC(CN3CCc4cc(C(=O)NO)cc(F)c4C3)(C1)C2] 2-[(3-amino-1-bicyclo[1.1.1]pentanyl)methyl]-8-fluoro-3,4-dihydro-1H-isoquinoline-6-carbohydroxamic acid | 1H NMR (400 MHz, METHANOL-d4) δ = 7.52 (s, 1H), 7.44 (d, J = 10.3 Hz, 1H), 4.51 (br s, 2H), 3.64 - 3.60 (m, 2H), 3.60 (br s, 2H), 3.27 - 3.25 (m, 2H), 2.32 (s, 6H). MS(ESI): 306.2 [M + H]+. |
| 487 | 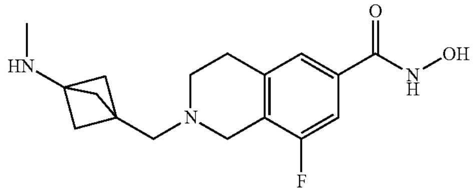 [SMILES: CNC12CC(CN3CCc4cc(C(=O)NO)cc(F)c4C3)(C1)C2] 8-fluoro-2-[[3-(methylamino)-1-bicyclo[1.1.1]pentanyl]methyl]-3,4-dihydro-1H-isoquinoline-6-carbohydroxamic acid | 1H NMR (400 MHz, METHANOL-d4) δ = 7.52 (s, 1H), 7.43 (d, J = 10.1 Hz, 1H), 4.41 -4.38(m, 2H), 3.61 - 3.43 (m, 4H), 3.24 - 3.23(m, 2H), 2.70 (s, 3H), 2.31 (s, 6H). MS(ESI): 320.0 [M + H]+. |
| 491 | 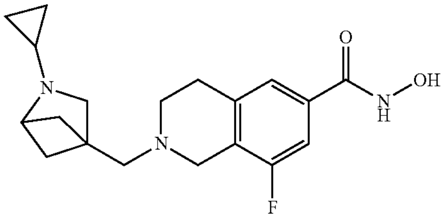 [SMILES: O=C(NO)c1cc(F)c2c(c1)CCN(CC13CC(C1)N(C1CC1)C3)C2] 2-[(2-cyclopropyl-2-azabicyclo[2.1.1]hexan-4-yl)methyl]-8-fluoro-3,4-dihydro-1H-isoquinoline-6-carbohydroxamic acid | 1H NMR (400 MHz, METHANOL-d4) δ = 7.50 (s, 1H), 7.42 (d, J = 10.0 Hz, 1H), 4.37 - 4.34 (m, 3H), 3.80 - 3.67(m, 2H), 3.59 - 3.57(s, 2H), 3.46 - 3.41 (m, 2H), 3.23 (br t, J = 5.9 Hz, 2H), 3.06 - 3.04(m, 1H), 2.40 - 2.38(m, 2H), 1.41 (t, J = 7.3 Hz, 2H), 1.10 - 1.03 (m, 4H). MS(ESI): 346.0 [M + H]+. |

-continued

| Compound | Structure/Name | Characterization |
|---|---|---|
| 493 | 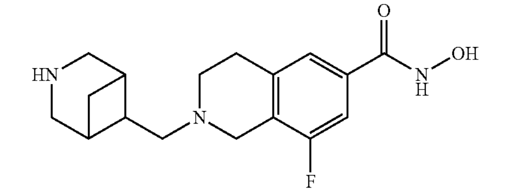 [SMILES: O=C(NO)c1cc(F)c2c(c1)CCN(CC1C3CNCC1C3)C2] | MS(ESI): 320.1 [M + H]+. |
| 494 | 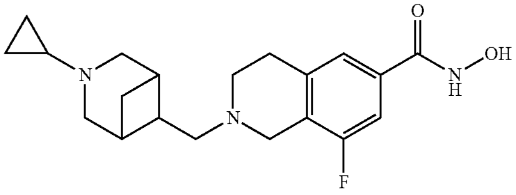 [SMILES: O=C(NO)c1cc(F)c2c(c1)CCN(CC1C3CC1CN(C1CC1)C3)C2]<br>2-[(3-cyclopropyl-3-azabicyclo[3.1.1]heptan-6-yl)methyl]-8-fluoro-3,4-dihydro-1H-isoquinoline-6-carbohydroxamic acid | 1H NMR (400 MHz, METHANOL-d4) δ = 7.53 (s, 1H), 7.45 (d, J = 10.1 Hz, 1H), 4.61 (br s, 2H), 4.01 - 3.88 (m, 2H), 3.84 - 3.65 (m, 6H), 3.18 - 2.84 (m, 2H), 2.78 (br s, 3H), 2.59 - 2.28(m, 2H), 2.40 - 2.23 (m, 1H), 1.94 - 1.77 (m, 1H), 1.14 - 1.07 (m, 2H), 1.00 - 0.94 (m, 2H). MS(ESI): 360.0 [M + H]+. |
| 505 | 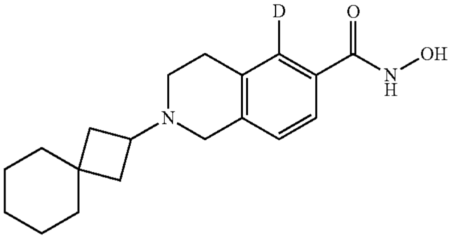<br>N-hydroxy-2-(spiro[3.5]nonan-2-yl)-1,2,3,4-tetrahydroisoquinoline-5-d-6-carboxamide | MS (ESI): 316 [M + H]+. |

N-hydroxy-7-methyl-2-(spiro[3.5]nonan-2-yl)-1,2,3,4-tetrahydroquinoline-6-carboxamide (AAA)

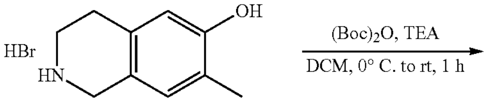

Ab

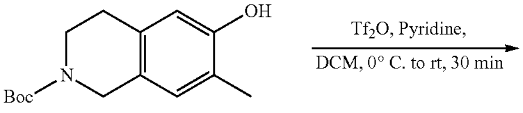

Ac

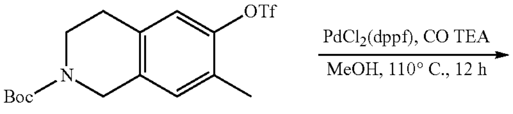

Ad

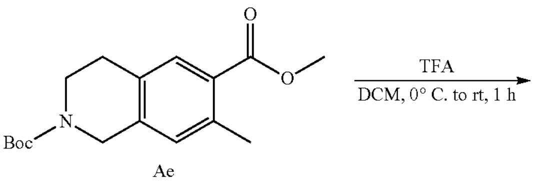

Ae

-continued

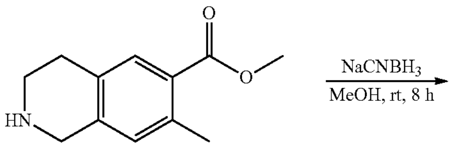

Af

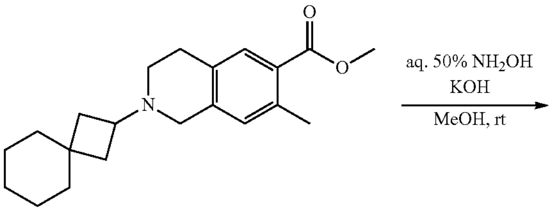

Ag

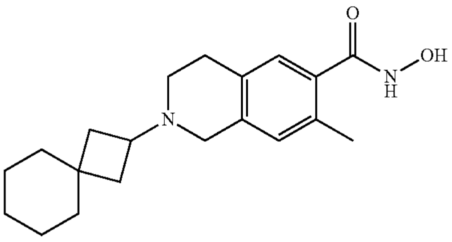

AAA

To an ice cold solution of 7-methyl-1,2,3,4-tetrahydroisoquinolin-6-ol hydrobromide (Ab. 800 mg, 3.28 mmol, 1.0 equiv.) in DCM (8.0 mL) was added $Et_3N$ (0.7 mL, 5.213 mmol, 1.6 equiv.) dropwise followed by Boc-anhydride (1.4 mL, 5.213 mmol, 1.6 equiv.). The reaction was allowed to attain room temperature and stirred for 1 h following which EtOAc (5.0 mL) was added and the organic layer was extracted three times. The organic layer was then dried over $Na_2SO_4$, concentrated and subjected to column chromatography (Hex:EtOAc, 100/0 to 93/7) to furnish tert-butyl 6-hydroxy-7-methyl-3,4-dihydroisoquinoline-2(1H)-carboxylate (Ac, 0.86 g, 3.804 mmol, 99%) as a white solid. MS (ESI): 208 $[M-56]^+$ To an ice cold solution of tert-butyl 6-hydroxy-7-methyl-3,4-dihydroisoquinoline-2(H)-carboxylate (Ac. 590 mg, 2.240 mmol, 1.0 equiv.) in DCM (6.0 mL) was added pyridine (0.5 mL, 6.720 mmol, 3.0 equiv.) dropwise followed by triflic anhydride (0.6 mL, 3.36 mmol, 1.5 equiv.). The reaction was allowed to stir for 0.5 h at the same temperature following which water (5.0 mL) was added and the organic layer was extracted three times. The organic layer was then dried over $Na_2SO_4$, concentrated and used for the next step without further purification. MS (ESI): 395 $[M+H]^+$ To a solution of tert-butyl 7-methyl-6-(((trifluoromethyl)sulfonyl)oxy)-3,4-dihydroisoquinoline-2(1H)-carboxylate (Ad, 780.0 mg, 1.970 mmol, 1.0 equiv.) in MeOH (12.0 mL) was added $Et_3N$ (0.8 mL, 5.910 mmol, 3.0 equiv.) dropwise and the reaction was purged with $N_2$ for 10 minutes and $PdCl_2$(dppf) (146.1 mg, 0.197 mmol, 0.1 equiv.) was added. The reaction was then heated to 110° C. for 12h under CO pressure (20 mbar) in an autoclave. The reaction mixture was allowed to attain room temperature and filtered through a pad of celite. The organic layer evaporated and then purified by flash chromatography to give ester 2-(tert-butyl) 6-methyl 7-methyl-3,4-dihydroisoquinoline-2,6(1H)-dicarboxylate (Ae, 456.0 mg, 1.494 mmol, 76%) as a colourless liquid. MS (ESI): 306 $[M+H]^+$ To a solution of 2-(tert-butyl) 6-methyl 7-methyl-3,4-dihydroisoquinoline-2,6(1H)-dicarboxylate (Ae, 456.0 mg, 1.026 mmol) in DCM (5.0 mL) was added TFA (1.1 mL, 15.100 mmol, 10.0 equiv.) at 0° C. and the reaction was allowed to stir at room temperature. After 1 h, the volatile organics were evaporated to furnish the TFA salt as a yellow solid (412.0 mg, 1.43 mmol, 95%) which was used in the further reaction without any purification. MS (ESI): 206 $[M+H]^+$ To a solution of 6-(methoxycarbonyl)-7-methyl-1,2,3,4-tetrahydroisoquinolin-2-ium 2,2,2-trifluoroacetate (Af, 412.0 mg, 1.024 mmol, 1.0 equiv.) in MeOH (5.0 mL) was added $NaHCO_3$ (177.7 mg, 2.115 mmol, 1.5 equiv.) and ketone Q (233.8 mg, 1.69 mmol, 1.2 equiv.) and the reaction stiffed for 1 hour at room temperature. $NaCNBH_3$ (221.4 mg, 3.525 mmol, 2.5 equiv.) was added to the reaction mixture and the reaction allowed to stir for 8 h. The volatile organics were evaporated, and the reaction diluted with water (6.0 mL). The resultant mixture was extracted twice with EtOAc (2×8.0 mL) and the organic layer was combined, dried over $Na_2SO_4$ and concentrated in vacuo. The crude was then purified by column chromatography to yield methyl 7-methyl-2-(spiro[3.5]nonan-2-yl)-1,2,3,4-tetrahydroisoquinoline-6-carboxylate (Ag, 212.0 mg, 0.647 mmol, 46%) as a colourless oil. MS (ESI): 327 $[M+H]^+$ Compound AAA (53.8 mg, 0.164 mmol, 74%) was prepared from Ag in a manner analogous to that used for preparation of the above compounds of Formula (I). MS (ESI): 329 $[M+H]^+$. $^1H$ NMR (400 MHz, DMSO-$d_6$) δ 10.85 (s, 1H), 10.19 (s, 1H), 9.09 (s, 1H), 7.13 (d, J=37.9 Hz, 2H), 4.45 (d, J=15.6 Hz, 1H), 4.09 (dd, J=15.8, 8.0 Hz, 1H), 3.77 (q, J=8.3 Hz, 1H), 3.57 (d, J=10.6 Hz, 1H), 3.19-2.96 (m, 3H), 2.30 (s, 3H), 2.17 (td, J=11.8, 11.4, 7.3 Hz, 2H), 2.01-1.87 (m, 2H), 1.50-1.29 (m, 8H).

The following compound was prepared in a manner analogous to that used for preparing compound AAA.

| Compound | Structure/Name | Characterization |
| --- | --- | --- |
| BBB | 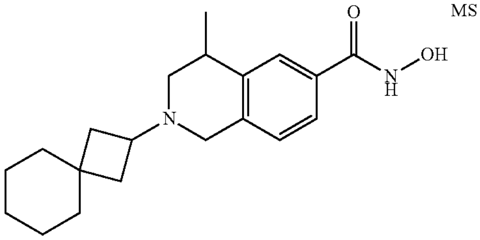 N-hydroxy-5-methyl-2-(spiro[3.5]nonan-2-yl)-1,2,3,4-tetrahydroisoquinoline-6-carboxamide | MS (ESI): 329 $[M + H]^+$ |

Compounds of Formula (II) were prepared following the synthetic schemes and procedures described in detail below.

General Scheme

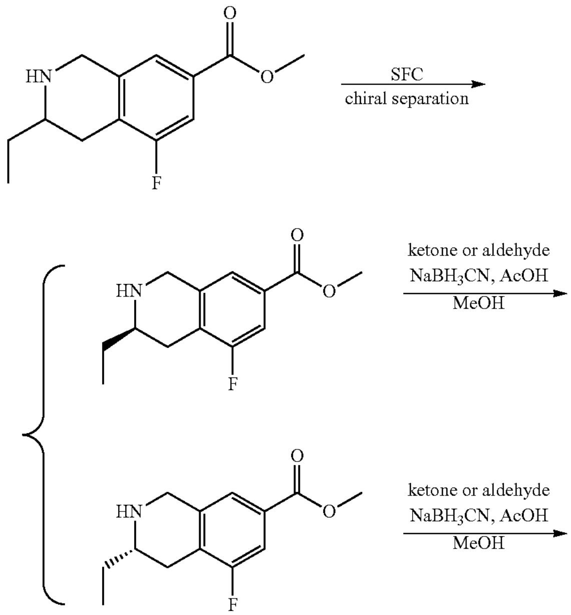

-continued

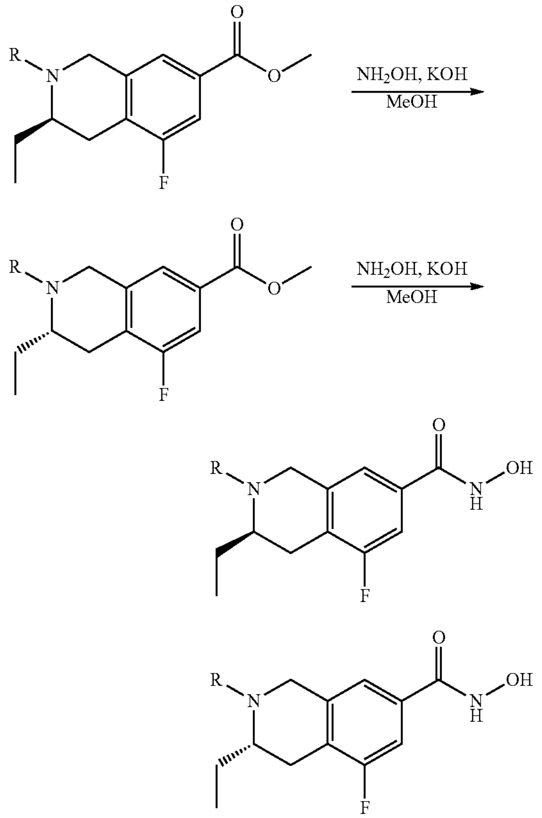

In general, certain compounds of Formula (II) are prepared via chiral separation of the above fluorinated tetrahydroisoquinoline, then reductive amination followed by conversion of the ester to the hydroxamic acid employing reaction methods well known to one of ordinary skill in the art and as described in more detail below.

2-(((3r,5r,7r)-adamantan-1-yl)methyl)-5-fluoro-N-hydroxy-1,2,3,4-tetrahydroisoquinoline-7-carboxamide 113

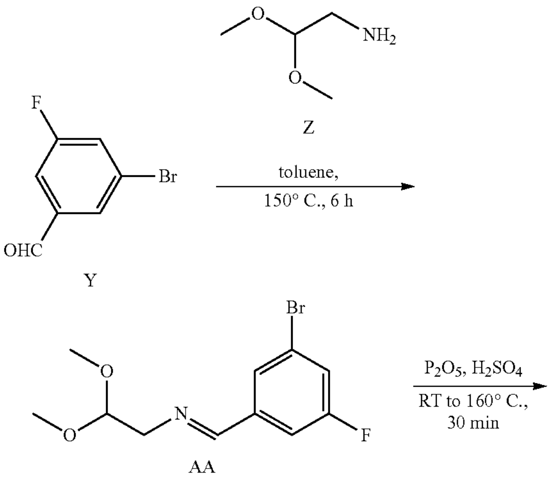

-continued

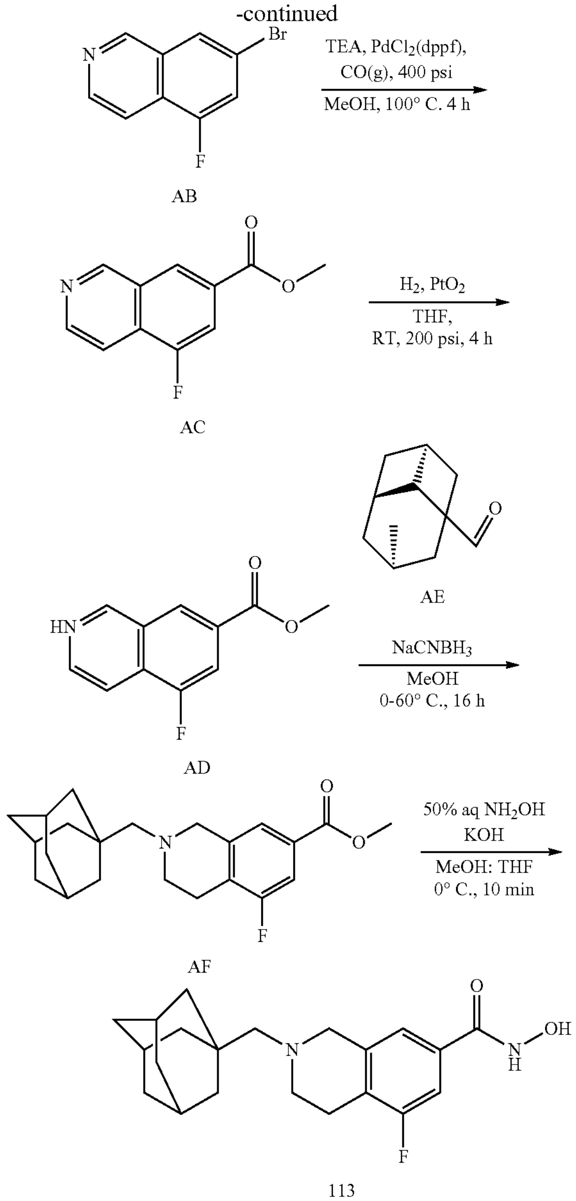

(E)-1-(3-bromo-5-fluorophenyl)-N(2,2-dimethoxyethyl) methanimine (AA): A stirred solution of 3-bromo-5-fluorobenzaldehyde (Y, 5.0 g. 24.293 mmol, 1.0 equiv.) and 2,2-dimethoxyethan-1-amine (Z, 3.103 g, 29.555 mmol, 1.2 equiv.) in toluene (50 mL) was refluxed using Dean-Stark apparatus at 120° C. for 6 h. Completion of reaction was monitored by TLC. The reaction the mixture was then concentrated under vacuum. The solid residue was triturated with pentane to give (E)-1-(3-bromo-5-fluorophenyl)-N-(2,2-dimethoxyethyl)methanimine (AA, 7.5 g, 25.850 mmol, 91%) was used as such in the next step. MS (ESI): 290 $[M+H]^+$.

7-bromo-5-fluoroisoquinolinemethanimine (AB): Phosphorous pentoxide (10.0 g) and concentrated sulfuric acid (3 mL) were mixed and stirred until thick brown coloured gum was formed. Next, (E)-1-(3-bromo-5-fluorophenyl)-N-(2,2-dimethoxyethyl)methanimine (AA, 7.5 g, 25.85 mmol) was dissolved in cold (5° C.) concentrated sulfuric acid (30 mL) and added slowly to the mixture of Phosphorous pentoxide and concentrated sulfuric acid prepared above. The resulting dark coloured reaction mixture was vigorously stirred and heated at 160° C. for 30 minutes. After cooling to room temperature, the dark brown viscous reaction mixture was carefully poured into ice water (500 mL) with vigorous stirring. The pH was adjusted to 7 using 1N NaOH and the black tarry precipitate were filtered. The pH was then further increased to 9 using 1N NaOH. This basic aqueous phase was extracted with EtOAc (3×500 mL). The combined organic layers were washed with brine dried over $MgSO_4$ and evaporated to afford 7 g of brown oil. The crude product was purified by Prep. HPLC to afford 7-bromo-5-fluoroisoquinoline (AB, 1.5 g, 6.6371 mmol, 38%). MS (ESI): 227 $[M+H]^+$.

methyl 5-fluoroisoquinoline-7-carboxylate (AC): To a stirred solution of 7-bromo-5-fluoroisoquinoline (AB, 1.1 g, 4.8672 mmol, 1 equiv.) in a methanol (20 mL), were added TEA (3.3 mL, 24.336 mmol, 5 equiv.) and $PdCl_2$(dppf) (177 mg, 0.2433 mmol, 0.05 equiv.) under nitrogen. The reaction mixture was heated to 100° C. under (400 psi) carbon monoxide for 4 h. Reaction was monitored by TLC. The reaction mixture was filtered through celite, washed with methanol (50 mL) and combined filtrate was concentrated under vacuum and the resulting residue was purified by combi flash chromatography eluting with 42% EtOAc: hexane to afford methyl 7-fluoroisoquinoline-5-carboxylate (AC, 770 mg, 3.7551 mmol, 73%) as a solid. MS (ESI): 206 $[M+H]^+$.

methyl 5-fluoro-1,2,3,4-tetrahydroisoquinoline-7-carboxylate (AD): To a stirred solution of methyl 7-fluoroisoquinoline-5-carboxylate (AC, 770 mg, 3.75 mmol) in THF (15 mL) were added 1N HCl (2.0 mL) and $PtO_2$ (300 mg) at room temperature. The resulting mixture was stiffed at room temperature under H2 gas (200 psi) for 4 h. Reaction was monitored by TLC. Reaction mixture was then filtered through celite washed with THF (30 mL) and combined filtrate was concentrated to afford methyl 5-fluoro-1,2,3,4-tetrahydroisoquinoline-7-carboxylat (AD, 581 mg, 2.78 mmol, 74%) as brown solid. MS (ESI): 210 $[M+H]^+$.

methyl 2-(((3r,5r,7r)-adamantan-1-yl)methyl)-5-fluoro-1,2,3,4 tetrahydroisoquinoline-7-carboxylate (AF): To a stirred solution of methyl 5-fluoro-1,2,3,4-tetrahydroisoquinoline-7-carboxylat (AD, 200 mg, 0.9559 mmol, 1.0 equiv.) in methanol (10 mL) were added acetic acid (cat.), adamantane-1-carbaldehyde (AE, 313 mg, 1.9118 mmol, 2.0 equiv.) and $NaCNBH_3$ (118 mg, 1.9118 mmol, 2.0 equiv.) at 0° C. Reaction mixture was stirred at 60° C. for 16 h. Reaction was monitored by TLC. The reaction was quenched with sodium bicarbonate solution (50 mL) and extracted with EtOAc (3×50 mL). The combined organic layers were dried over anhydrous $Na_2SO_4$ and concentrated under reduced pressure to obtain the crude material. It was purified by silica gel column. Compound was eluted at 3.4% EtOAc in hexane to afford methyl2-(((3r,5r,7r)-adamantan-1-yl)methyl)-5-fluoro-1,2,3,4-tetrahydroisoquinoline-7-carboxylate (AF, 45 mg, 0.1256 mmol, 13%). MS (ESI): 358 $[M+H]^+$.

2-(((3r,5r,7r)-adamantan-1-yl)methyl)-5-fluoro-N-hydroxy-1,2,3,4-tetrahydroisoquinoline-7-carboxamide (113): To a solution of methyl2-(((3r,5r,7r)-adamantan-1-yl)methyl)-5-fluoro-1,2,3,4-tetrahydroisoquinoline-7-carboxylate (AF, 40 mg, 0.1120 mmol, 1.0 equiv.) in MeOH (1 mL) were added $NH_2OH$ (0.1 mL, 1.6806 mmol, 50% aqueous solution, 15.0 equiv.) and KOH (18 mg, 0.336 mmol, 3.0 equiv.) at 0° C. The reaction was stirred for 10 min at room temperature. Completion of reaction was monitored by TLC and LCMS analysis. The reaction mixture was concentrated and purified by prep. HPLC. Mobile phase (A: 5 mM ammonium acetate+0.1% $NH_3$ in water, B: 100% ACN) to afford 2-(((3r,5r,7r)-adamantan-1-yl)methyl)-5-fluoro-N-hydroxy-1,2,3,4-tetrahydroisoquinoline-7-carboxamide (113, 4.1 mg, 0.011 mmol, 10.22% yield). $^1$H NMR (400 MHz, Methanol-d4) δ 7.27-7.25 (m, 2H), 3.70 (s, 2H), 2.81 (dt, J=9.3, 4.6 Hz, 4H), 2.17 (s, 2H), 1.95 (s, 3H), 1.75 (d, J=12.3 Hz, 3H), 1.68 (d, J=12.4 Hz, 3H), 1.59 (d, J=2.8 Hz, 6H). MS (ESI): 359 $[M+H]^+$.

The following compounds were prepared in a manner analogous to that used for preparing compound 113. Although compounds 214 and 215 are designated as the (S) and (R) enantiomers as each enantiomer was prepared and isolated, the absolute stereochemistry of each is unknown.

| Compound | Structure/Name | Characterization |
|---|---|---|
| 214 | 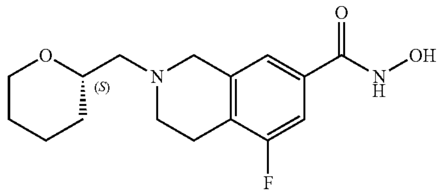 (S)-5-fluoro-N-hydroxy-2-((tetrahydro-2H-pyran-2-yl)methyl)-1,2,3,4-tetrahydroisoquinoline-7-carboxamide | $^1$H NMR (400 MHz, DMSO-$d_6$) δ 7.33 (d, J = 10.2 Hz, 2H), 3.85 (s, 1H), 3.79-3.60 (m, 2H), 3.57-3.45 (m, 1H), 2.74 (d, J = 3.3 Hz, 2H), 2.45 (dd, J = 12.9, 4.6 Hz, 2H), 1.78 (d, J = 10.5 Hz, 1H), 1.61 (d, J = 13.0 Hz, 1H), 1.55-1.36 (m, 3H), 1.21 (s, 1H). MS (ESI): 309 $[M + H]^+$ Note: absolute stereochemistry is unknown |
| 215 | 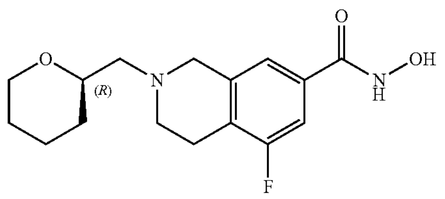 (R)-5-fluoro-N-hydroxy-2-((tetrahydro-2H-pyran-2-yl)methyl)-1,2,3,4-tetrahydroisoquinoline-7-carboxamide | $^1$H NMR (400 MHz, DMSO-$d_6$) δ 9.49 (s, 1H), 7.34 (s, 2H), 3.87 (dt, J = 11.2, 2.2 Hz, 1H), 3.78-3.57 (m, 2H), 3.57-3.47 (m, 1H), 3.38 (d, J = 3.2 Hz, 1H), 2.79-2.67 (m, 3H), 2.46 (dd, J = 13.0, 4.6 Hz, 2H), 1.82-1.71 (m, 1H), 1.61 (d, J = 13.3 Hz, 1H), 1.55-1.33 (m, 3H), 1.21 (tt, J = 12.9, 5.9 Hz, 1H). MS (ESI): 309 $[M + H]^+$ Note: absolute stereochemistry is unknown |

-continued

| Compound | Structure/Name | Characterization |
| --- | --- | --- |
| 213 | 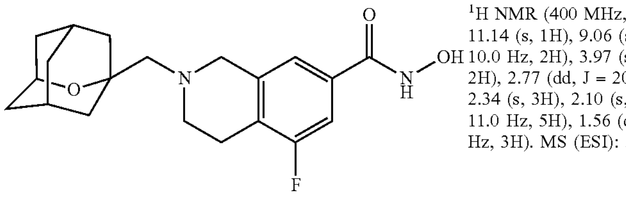 2-(((1r,3s,5R,7S)-2-oxaadamantan-1-yl)methyl)-5-fluoro-N-hydroxy-1,2,3,4-tetrahydroisoquinoline-7-carboxamide | $^1$H NMR (400 MHz, DMSO-$d_6$) δ 11.14 (s, 1H), 9.06 (s, 1H), 7.32 (d, J = 10.0 Hz, 2H), 3.97 (s, 1H), 3.70 (s, 2H), 2.77 (dd, J = 20.5, 5.6 Hz, 4H), 2.34 (s, 3H), 2.10 (s, 2H), 1.81 (d, J = 11.0 Hz, 5H), 1.56 (dd, J = 22.5, 12.4 Hz, 3H). MS (ESI): 361 [M + H]$^+$ |

(S)-3-ethyl-5-fluoro-N-hydroxy-2-(oxetan-3-ylmethyl)-1,2,3,4-tetrahydroisoquinoline-7-carboxamide (216) and (R)-3-ethyl-5-fluoro-N-hydroxy-2-(oxetan-3-ylmethyl)-1,2,3,4-tetrahydroisoquinoline-7-carboxamide (217)

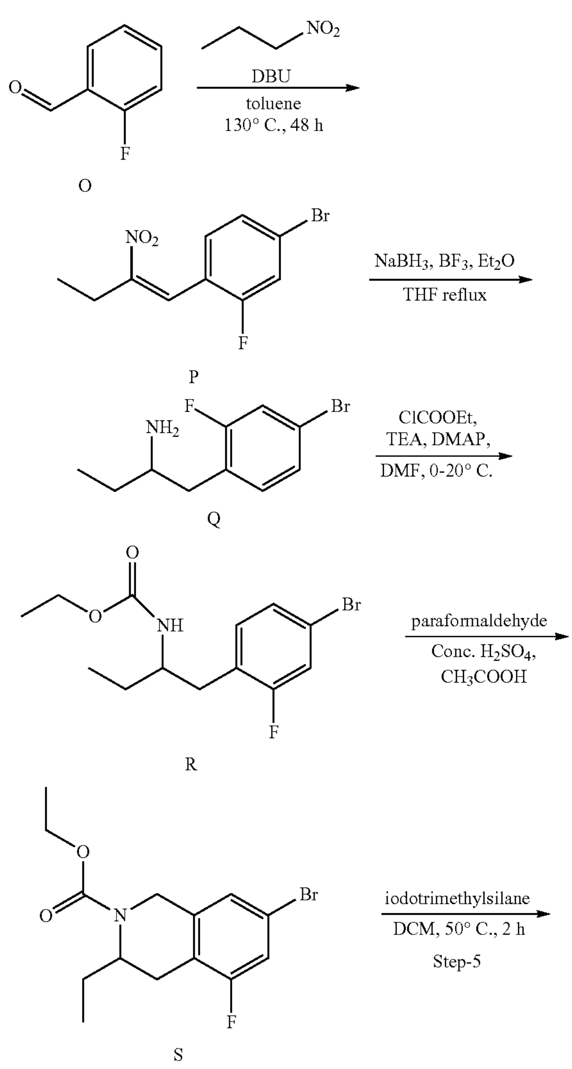

-continued

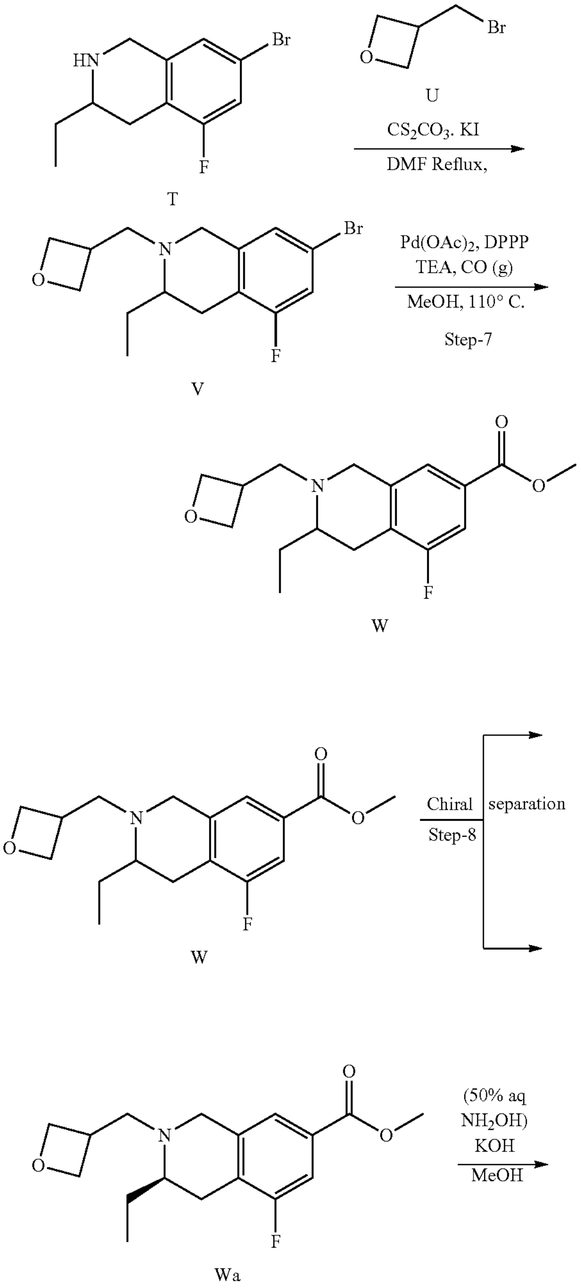

-continued

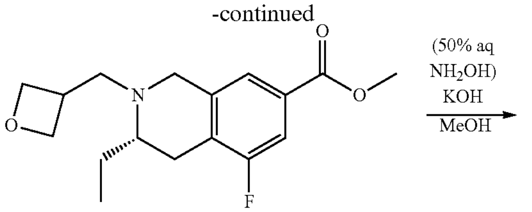

Wb

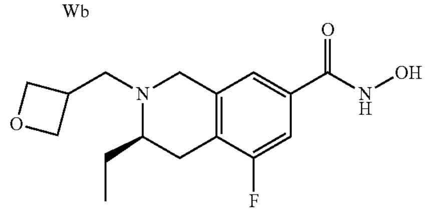

217

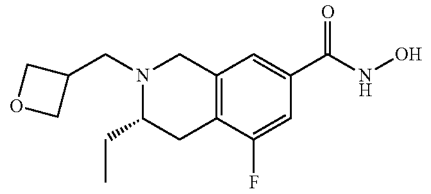

216

To a mixture of 4-bromo-2-fluorobenzaldehyde (0, 12.0 g, 59.11 mmol, 1.0 equiv.), 1-nitro propane (15.79 g, 177.33 mmol, 3.0 equiv.), DBU (13.49 g, 88.66 mmol, 1.5 equiv.) in Toluene (12 mL) stirred and heated at 130° C. for 48 h. Completion of reaction was confirmed by TLC. Reaction mixture was poured in to water (100 mL) and extracted with EtOAc (100 mL×2). The organic layer combined, dried and evaporated to give Crude. The material was purified by column chromatography using EtOAc/hexane to give (Z)-4-bromo-2-fluoro-1-(2-nitrobut-1-en-1-yl)benzene (P, 6.0 g, 21.89 mmol, 37.04%) MS (ESI): 275 $[M+H]^+$ Sodium borohydride (3.93 g, 104.01 mmol, 4.75 equiv.) in THF (40 mL) was placed in the flask followed by sequential addition of $BF_3$-$Et_2O$ (18.64 g, 131.38 mmol, 6.0 equiv.) at 0° C. After the addition, the ice bath was removed and the contents were stirred at room temperature for 15 min. The solution of (Z)-4-bromo-2-fluoro-1-(2-nitrobut-1-en-1-yl)benzene (P. 6.0 g, 21.89 mmol, 1.0 equiv.) in THF (60 mL) was then injected dropwise into the reaction flask via a syringe and the reaction mixture refluxed on an oil bath for 5.5 h. After cooling to room temperature, the reaction was quenched by careful addition of ice water (60 mL), the mixture acidified (N HCl, 60 mL), and then heated at 80-85° C. (oil bath) for 2 h. After cooling to room temperature, the acidic layer was washed with ether (2×15 mL). The organic layer separated gave wash of 1N NaOH (100 mL) and Brine (100 mL). organic layer dried, concentrated to give 1-(4-bromo-2-fluorophenyl)butan-2-amine (Q, 2.4 g, 9.75 mmol, 44.54%) MS (ESI): 247 $[M+H]^+$ To a mixture of 1-(4-bromo-2-fluorophenyl)butan-2-amine (Q, 2.5 g, 10.15 mmol, 1.0 equiv), TEA (4.2 mL, 30.47 mmol, 3.0 equiv.), DMAP (0.123 g, 1.01 mmol, 0.1 equiv.) in DMF (20 mL) added Ethyl chloroformate (0.461 g, 12.18 mmol, 1.2 equiv.) at 0° C. and stirred at 25° C. for 1.5 h. Completion of reaction was confirmed by TLC. Reaction mixture was poured in to chilled water (100 mL) and extracted with EtOAc (100 mL×2). The organic layer combined, dried and evaporated to give Crude. The material was purified by column chromatography using EtOAc/hexane to give ethyl (1-(4-bromo-2-fluorophenyl)butan-2-yl)carbamate (R, 1.5 g, 4.7 mmol, 46%) MS (ESI): 320 $[M+H]^+$ To a mixture of ethyl (1-(4-bromo-2-fluorophenyl)butan-2-yl)carbamate (R, 1.5 g, 4.71 mmol, 1.0 equiv.), p-formaldehyde (0.226 g, 7.54 mmol, 1.6 equiv.) in glacial acetic acid (10.76 g, 179.24 mmole, 38 equiv.) added sulfuric acid (7.0 mL, 132.07 mmole, 28 equiv.) at room temperature. The resulting reaction mixture was stiffed at room temperature for 18 h. Completion of reaction was confirmed by TLC. Reaction mixture was poured in to water (100 mL) and extracted with EtOAc (100 mL×2). The organic layer was washed with saturated $NaHCO_3$solution (50 mL), dried and evaporated to give ethyl 7-bromo-3-ethyl-5-fluoro-3,4-dihydroisoquinoline-2(1H)-carboxylate (S, 1.2 g, 3.63 mmol, 77%) MS (ESI): 331 $[M+H]^+$ To a mixture of ethyl 7-bromo-3-ethyl-5-fluoro-3,4-dihydroisoquinoline-2(1H)-carboxylate (S, 1.2 g, 3.63 mmol, 1.0 equiv.) in DCM (30 mL) added iodotrimethylsilane (2.90 g, 14.54 mmole, 4.0 equiv.) at room temperature. The resulting reaction mixture was stirred at 50° C. for 2 h. The reaction mixture was cooled to room temperature and anhydrous methanol (6 mL) was added. The reaction mixture was stirred for addition 10 min. The volatile was removed under reduced pressure. The residue was treated with diethyl ether (5 mL) and filtered. The solid was washed with ether (10 mL), dried under vacuum to provide 7-bromo-3-ethyl-5-fluoro-1,2,3,4-tetrahydroisoquinoline (T, 0.9 g, 3.48 mmol, 95%) MS (ESI): 259 $[M+H]^+$ To a mixture of 7-bromo-3-ethyl-5-fluoro-1,2,3,4-tetrahydroisoquinoline (T, 0.9 g, 3.48 mmol, 1.0 equiv.), cesium carbonate (2.26 g, 6.97 mmol, 2.0 equiv.), potassium iodide (0.289 g, 1.74 mmol, 0.5 equiv.) in DMF (9 mL) added 3-(bromomethyl)oxetane (U, 1.05 g, 6.97 mmole, 2.0 equiv.) at room temperature. The resulting reaction mixture was stirred at 100° C. for 24 h. The reaction mixture was cooled to room temperature and poured in to water (100 mL), extracted with Ethyl acetate (50 mL×2). The organic layer combined, evaporated to give crude product. The material was purified by column chromatography using Ethyl acetate/hexane to give 7-bromo-3-ethyl-5-fluoro-2-(oxetan-3-ylmethyl)-1,2,3,4-tetrahydroisoquinoline (V, 0.35 g, 1.06 mmol, 30%) MS (ESI): 329 $[M+H]^+$ To a stirred solution of 7-bromo-3-ethyl-5-fluoro-2-(oxetan-3-ylmethyl)-1,2,3,4-tetrahydroisoquinoline (V, 0.35 g, 1.06 mmol, 1.0 equiv.) in dry methanol (10 mL) was degassed with $N_2$ gas for 10 min. Palladium acetate (0.036 g, 0.160 mmol, 0.15 equiv.), DPPP (0.088 g, 0.21 mmol, 0.2 equiv.), TEA (0.5 ml, 3.20 mmol, 3.0 equiv.) were added to the above reaction mixture. The reaction mixture was stirred under an atmosphere of CO (250 psi) at 120° C. for 1 hr. The mixture was cooled to RT and the solids were removed by filtration. The filtrate was concentrated in vacuum and the residue was purified by Column chromatography (30%-50% EtOAc/Haxane) to provide methyl 3-ethyl-5-fluoro-2-(oxetan-3-ylmethyl)-1,2,3,4-tetrahydroisoquinoline-7-carboxylate (W, 0.05 g, 0.162 mmol, 15%). The 50 mg of racemic compound was purified on Shimadzu LC-20AP and UV detector. The column used was CHIRALPAK IB-N (250*21.0) mm, 5 micron, column flow was 20.0 ml/min. Mobile phase were used (A) 0.1% DEA in n-Hexane and (B) 0.1% DEA IN IPA:MEOH (50:50). (Fr-1 (Wa): 20 mg LCMS-98%, Fr-2 (Wb): 32 mg LCMS-96%). MS (ESI): 308 $[M+H]^+$ To a solution of methyl (3R,10bS)-10-fluoro-3-methyl-1,2,3,5,6,10b-hexahydropyrrolo[2,1-a]isoquinoline-8-carboxylate (Wb, 0.033 g, 0.107 mmol, 1.0 equiv.) in methanol (1.5 ml) added the $NH_2OH$ (0.141 ml, 2.14 mmol, 50.00% aqueous solution, 20.0 equiv.) and KOH (18 mg, 0.32 mmol, 3.0 equiv.) at 0° C. stirred at room temperature for 1 hr. Completion of reaction was confirmed by TLC. Reaction mixture was evaporated to dryness; the crude material was purified by Prep HPLC purification using (A) 5 mM ammonium bicarbonate+0.1% formic acid in water (2) 100% acetonitrile. The solvents were lyophilized to give (S)-3-ethyl-5-fluoro-N-hydroxy-2-(oxetan-3-ylmethyl)-1,2,3,4-tetrahydroisoquinoline-7-carboxamide (216, 2.7 mg, 0.162 mmol, 1.5%).

The same procedure was used to obtain compound 217. Although compounds 216 and 217 are designated as the (S) and (R) enantiomers as each enantiomer was prepared and isolated, the absolute stereochemistry of each is unknown.

3-benzyl-5-fluoro-N-hydroxy-2-methyl-1,2,3,4-tetrahydroisoquinoline-7-carboxamide (218)

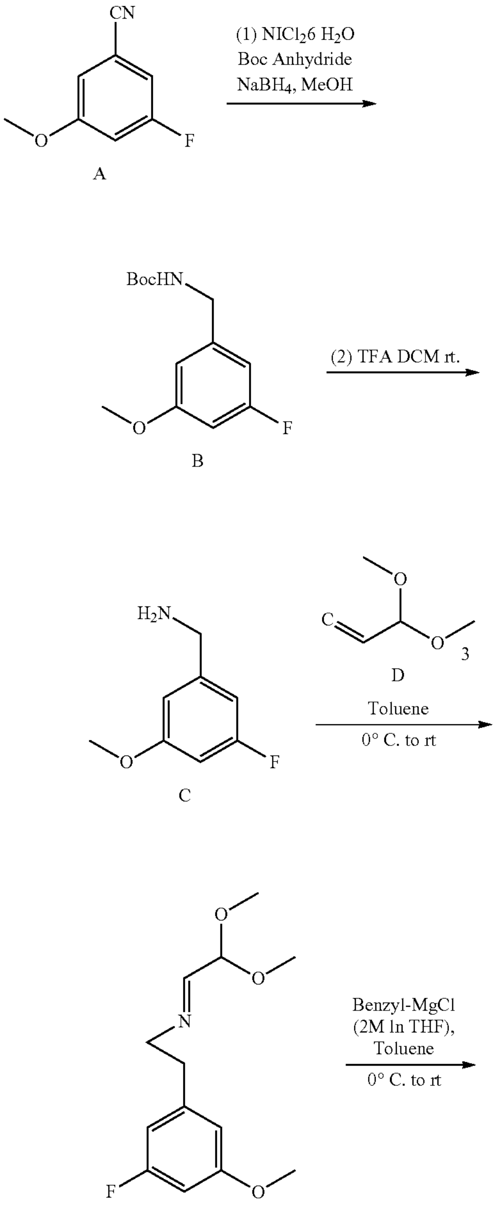

A B C D E

-continued

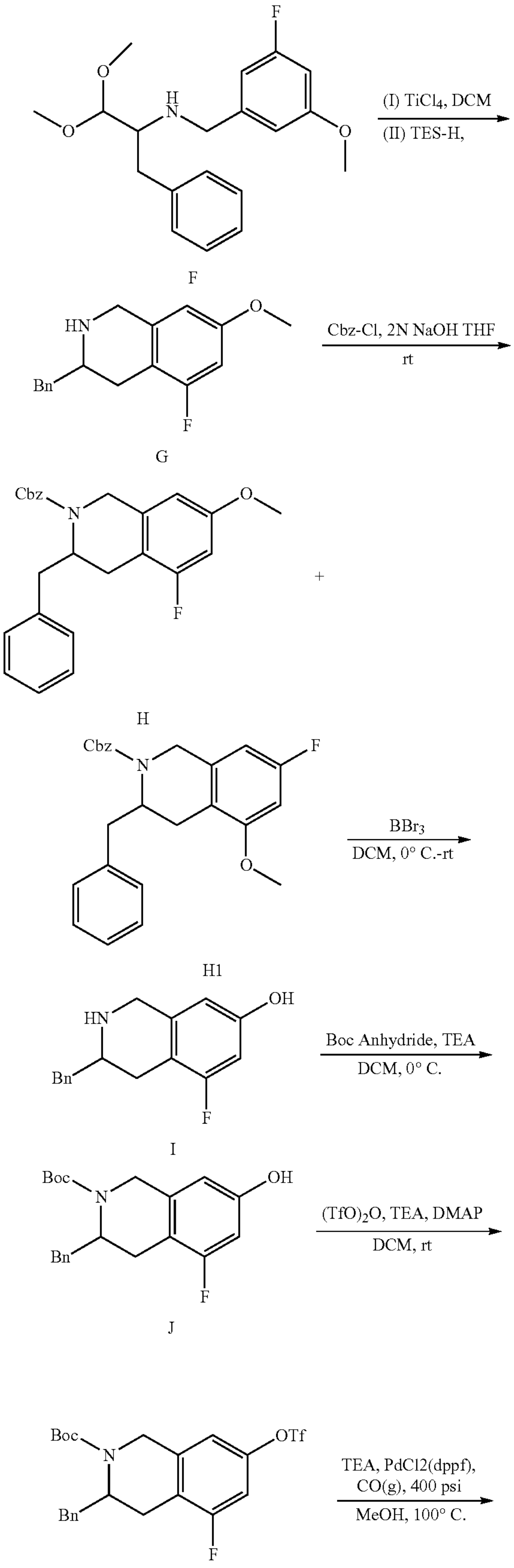

F G H + H1 I J K

-continued

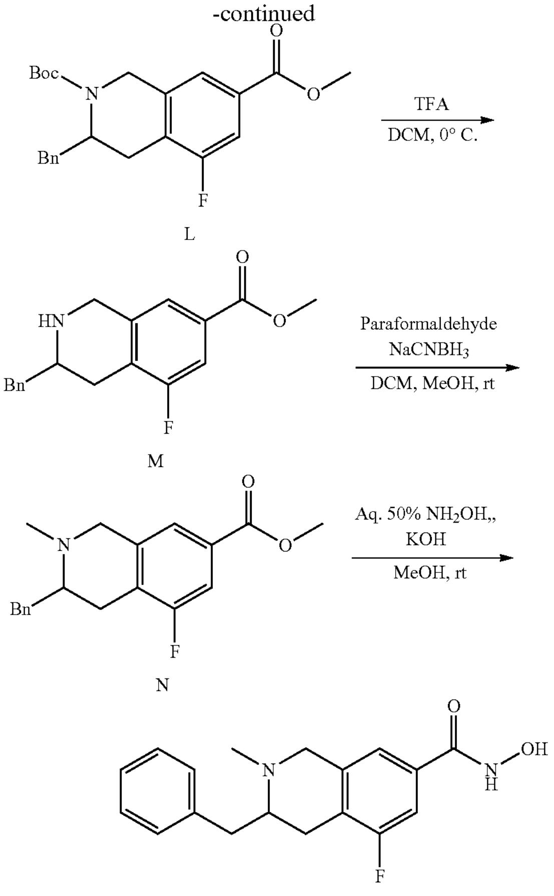

L

M

N

218

To a stirred solution of 3-fluoro-5-methoxybenzonitrile (A, 10 g, 66.181 mmol, 1.0 equiv.) in methanol (200 ml) was added $NiCl_2 \cdot 6H_2O$ (7.86 g, 33.090 mmol, 0.5 equiv.) at 0° C. and stirred for 10 min. Boc anhydride (15.86 g, 72.379 mmol, 1.0 equiv.) was added drop wise followed by sodium borohydride (7.5 g, 198.54 mmol, 3.0 equiv.) portion wise at 0° C. Reaction mixture was allowed to room temperature and stirred for 16 h. Reaction was monitored by TLC and LCMS. The reaction mixture was filtered through celite washed with methanol and filtrate was concentrated under vacuum. The residue was partitioned between water (500 mL) and ethyl acetate (500 mL). The organic layer was concentrated and the residue was purified by using column chromatography using 15% EtOAc/hexane to afford tert-butyl (3-fluoro-5-methoxybenzyl) carbamate (B, 6.9 g, 27.051 mmol. 40.85%) as white solid.

MS (ESI): 200.3 $[M-56]^+$

To a stirred solution of tert-butyl (3-fluoro-5-methoxybenzyl)carbamate (B, 6.9 g. 27.051 mmol, 1.0 equiv.) in DCM (60 ml) and added TFA (21 ml, 3.0 vol) dropwise at 0° C. Reaction mixture was stirred at 0° C. for 3 h. Reaction was monitored by TLC and LCMS. Reaction mixture was concentrated and residue was dumped in solution of potassium carbonate solution (100 ml) and extracted with EtOAc (200 ml) to afford 3-fluoro-5-methoxyphenyl) methanamine (C, 3.0 g, 19.346 mmol, 71.53%) MS (ESI): 156.1 $[M+H]^-$ To a stirred solution of 3-fluoro-5-methoxyphenyl) methanamine (C. 3.0 g, 19.53, 1.0 equiv.) in toluene (30 ml) was added 2,2-Dimethoxyacetaldehyde solution (60% in water) (D, 3.38 ml. 1.0 equiv.) at rt. Reaction mixture was stirred at room temperature for 2h. Reaction was monitored by TLC. Reaction mixture was poured in to water (100 mL), Ethyl acetate (100 mL). Organic layer dried over $Na_2SO_4$ and concentrated to afford (E)-N-(3-fluoro-5-methoxybenzyl)-2, 2-dimethoxyethan-1-imine (E, 4.52 g, 18.73 mmol, 95.94%). It was used as such for the next step with out analysis.

To a stirred solution of (E)-N-(3-fluoro-5-methoxybenzyl)-2,2-dimethoxyethan-1-imine (E, 15.8 g, 65.48 mmol, 1.0 equiv) in 180 ml toluene. A solution of benzyl magnesium chloride (2M in THF) (81 mL, 163.72 mmol, 2.5 equiv) drop wise added under nitrogen atmosphere at 0° C. and reaction mixture was stirred for 3 h. reaction was monitored by TLC and LCMS. The residue was partitioned between water (100 mL) and ethyl acetate (500 mL). The organic layer was concentrated. The residue was purified by using column chromatography using 30% EtOAc/hexane to afford As a N-(3-fluoro-5-methoxybenzyl)-1,1-dimethoxy-3-phenylpropan-2-amine (F, 16.7 g, 50.08 mmol, 76.49%) MS (ESI): 334.3 $[M+H]^+$ To a stirred solution of N-(3-fluoro-5-methoxybenzyl)-1, 1-dimethoxy-3-phenylpropan-2-amine (F, 16.7 g, 50.12 mmol, 1.0 equiv) in DCM(160 mL). Titanium tetrachloride (38.02 g, 200.49 mmol, 4.0 equiv) was added dropwise to above solution at room temperature and stirred for 3 h. Completion of SM was confirmed by TLC. Triethyl silane hydride (23.31 g, 200.49 mmol, 4.0 equiv.) was added dropwise to above cyclized reaction mixture at 0° C. The resulting reaction mixture was stirred at room temperature for 18 h. Completion of reaction was confirmed by TLC and LCMS. The residue was poured in to water (100 mL) and extracted with Ethyl acetate (100 mL×3). The organic layer was dried over $Na_2SO_4$, evaporated to dryness to give 3-benzyl-5-fluoro-7-methoxy-1,2,3,4-tetrahydroisoquinoline with other regioisomer. (G, 11.15 g, 41.09 mmol, 81.98%) The residue was used for next step without any purification. MS (ESI): 272 $[M+H]^+$ To a mixture of 3-benzyl-5-fluoro-7-methoxy-1,2,3,4-tetrahydroisoquinoline with other regioisomer (G, 11.0 g, 50.12 mmol, 1.0 equiv) in THF (800 mL) added 2N NaOH solution (150 mL) benzylchloroformate (38.2 g, 200.49 mmol, 1.2 equiv.). After stirring 1 h, the biphasic mixture was separated and the aqeuous phase was extracted with EtOAc (150 mL). The combined organics were dried, filtered and concentrated to provide the crude product. The residue contain both regioisomers which was purified by column chromatography using Ethyl acetate/hexane to give benzyl 3-benzyl-5-fluoro-7-methoxy-3,4-dihydroisoquinoline-2(1H)-carboxylate (H, 7.0 g, 17.26 mmol, 81.98%) MS (ESI): 406 $[M+H]^+$ To a solution of benzyl 3-benzyl-5-fluoro-7-methoxy-3, 4-dihydroisoquinoline-2(1H)-carboxylate (H, 2.5 g, 6.16 mmol, 1.0 eq.) in dichloromethane(25 mL) added 1M $BBr_3$ in DCM (7.4 mL, 4.41 mmol, 2.5 eq.) at 0° C., stirred at room temperature for 24 hrs. N-benzylated product observed in LCMS. Another 2.5 equiv. of 1M $BBr_3$ in DCM was added dropwise then reaction mixture was stirred for 24 hrs. Formation of product was confirmed by LCMS. Chilled ice (20 mL) was added to reaction mixture, solid became ppt out. Solid was filtered through Buchner funnel, gave wash of chilled DCM (15 mL). Solid was taken up 5% methanol in DCM (150 mL) and gave wash of saturated bicarbonate solution(100 mL). Organic layer separated, dried and evaporated to dryness to give 3-benzyl-5-fluoro-1,2,3,4-tetrahydroisoquinolin-7-ol (I, 1.1 g, 4.27 mmol, 69%).MS (ESI): 258 $[M+H]^+$ To a mixture of 3-benzyl-5-fluoro-1,2,3,4-tetrahydroisoquinolin-7-ol (I, 1.1 g, 4.27 mmol, 1.0 eq.), TEA (1.8 mL, 12.82 mmol, 3.0 equiv.) in dichloromethane (25 mL) added Boc anhydride (1.11 mL, 5.12 mmol, 3.0 eq.) at 25° C., stirred at room temperature for 18 h. Formation of product was confirmed on TLC. The residue was poured in to water (60 mL) and extracted DCM (60 mL×2). The combined organic layer was dried over $Na_2SO_4$, evaporated to give tert-butyl 3-benzyl-5-fluoro-7-hydroxy-3,4-dihydroisoquinoline-2(1H)-carboxylate (J, 1.1 g, 3.08 mmol, 72%). MS (ESI): 358 $[M+H]^+$ To a stirred solution of tert-butyl 3-benzyl-5-fluoro-7-hydroxy-3,4-dihydroisoquinoline-2(1H)-carboxylate (J, 1.1 g, 3.08 mmol, 1.0 equiv.) in dry DCM (12 mL) was added TEA (1.072 mL, 7.69 mmol, 1.5 equiv.) and 4-dimethylamino)pyridine (38 mg, 0.307 mmol, 0.1 equiv.). After about 20 minutes, Triflic anhydride (1.302 g, 1.91 mmol, 1.5 equiv.) was added dropwise. Upon complete addition, the solution was stirred at room temperature for 4 hrs and monitored with TLC and LC-MS. After 4 hours, the reaction mixture was poured in to water (120 ml) and extracted with DCM (75 ml×2). Organic layer dried with sodium sulfate, evaporate under reduced pressure and the crude was used for next step without any further purification to give 6-fluoro-2,2-dimethyl-1,2,3,5,10,10a-hexahydropyrrolo[1,2-b]isoquinolin-8-trifluoromethane sulfonate. (K, 1.2 g, 2.45 mmol, 79%). MS (ESI): 490$[M+H]^+$ To a stirred solution of tert-butyl 3-benzyl-5-fluoro-7-(((trifluoromethyl)sulfonyl)oxy)-3,4-dihydroisoquinoline-2 (1H)-carboxylate (K, 1.2 g, 2.45 mmol, 1.0 equiv.) in dry methanol (15 mL) was degassed with $N_2$ gas for 10 min. $PdCl_2dppf$ (0.179 g, 0.245 mmol, 0.1 equiv.), TEA (1.70 mL, 12.26 mmol, 5.0 equiv.) were added to the above reaction mixture. The reaction mixture was stirred under an atmosphere of CO (250 psi) at 100° C. for 16 hr. The mixture was cooled to RT and the solids were removed by filtration. The filtrate was concentrated in vacuo and the residue was purified by column chromatography using(EtOAc/Haxane) to provide 2-(tert-butyl) 7-methyl 3-benzyl-5-fluoro-3,4-dihydroisoquinoline-2,7(1H)-dicarboxylate (L, 0.6 g, 1.50 mmol, 61.47%).MS (ESI): 400$[M+H]^+$ To a solution of 2-(tert-butyl) 7-methyl 3-benzyl-5-fluoro-3,4-dihydroisoquinoline-2,7(1H)-dicarboxylate (L, 0.5 g, 1.25 mmol, 1.0 equiv.) in DCM (5 mL) added the TFA (0.109 g, 12.51 mmole, 10 equiv.) at 0° C. and stirred at room temperature for 16 hr. Completion of reaction was confirmed by TLC. Reaction mixture poured in saturated bicarbonate solution (100 mL) and extracted with DCM (100 mL×3). Organic layer was separated dried over sodium sulfate, evaporated to dryness to give methyl 3-benzyl-5-fluoro-1,2,3,4-tetrahydroisoquinoline-7-carboxylate (M, 0.34 g, 1.13 mmol, 90.84%). MS (ESI): 300 $[M+H]^+$ To a mixture of methyl 3-benzyl-5-fluoro-1,2,3,4-tetrahydroisoquinoline-7-carboxylate (M, 0.15 g, 0.50 mmol, 1.0 equiv.), p-formaldehyde (0.15 g, 5.014 mmol, 10 equiv.) in methanol (3 mL) was stirred at room temperature for 30 min. Sodium cyanoborohydride (0.063 g, 1.002 mmol, 2.0 equiv.) was added and stirred for 18 h. Upon completion of reaction concentrated under reduce pressure and to get crude mixture which was then purified by column chromatography using EtOAc: hexanes (1:9) to obtain methyl 3-benzyl-5-fluoro-2-methyl-1,2,3,4-tetrahydroisoquinoline-7-carboxylate (N, 0.08 g, 0.255 mmol, 64%). MS (ESI): 314 $[M+H]^+$ To a solution of methyl 3-benzyl-5-fluoro-2-methyl-1,2,3,4-tetrahydroisoquinoline-7-carboxylate (N, 17 mg, 0.054 mmol, 1.0 equiv.) in methanol (1.0 mL) added the $NH_2OH$ (0.07 mL, 1.08 mmol, 50.00% aqueous solution, 20.0 equiv.) and KOH (9.14 mg, 0.162 mmol, 3.0 equiv.) at 0° C. stirred at room temperature for 1 hr. Completion of reaction was confirmed by TLC. Reaction mixture was evaporated to dryness; the crude material was purified by Prep HPLC purification using (A) 5 mM ammonium bicarbonate+0.1% ammonia in water (2) 100% acetonitrile. The solvents were lyophilized to give 3-benzyl-5-fluoro-N-hydroxy-2-methyl-1,2,3,4-tetrahydroisoquinoline-7-carboxamide (218, 2.5 mg, 0.0079 mmol, 14%). MS (ESI): 315 $[M+H]^+$.

(R)-3-ethyl-5-fluoro-N-hydroxy-2-(2-methyl-2-azaspiro[3.3]heptan-6-yl)-1,2,3,4-tetrahydroisoquinoline-7-carboxamide (584) and (S)-3-ethyl-5-fluoro-N-hydroxy-2-(2-methyl-2-azaspiro[3.3]heptan-6-yl)-1,2,3,4-tetrahydroisoquinoline-7-carboxamide (585)

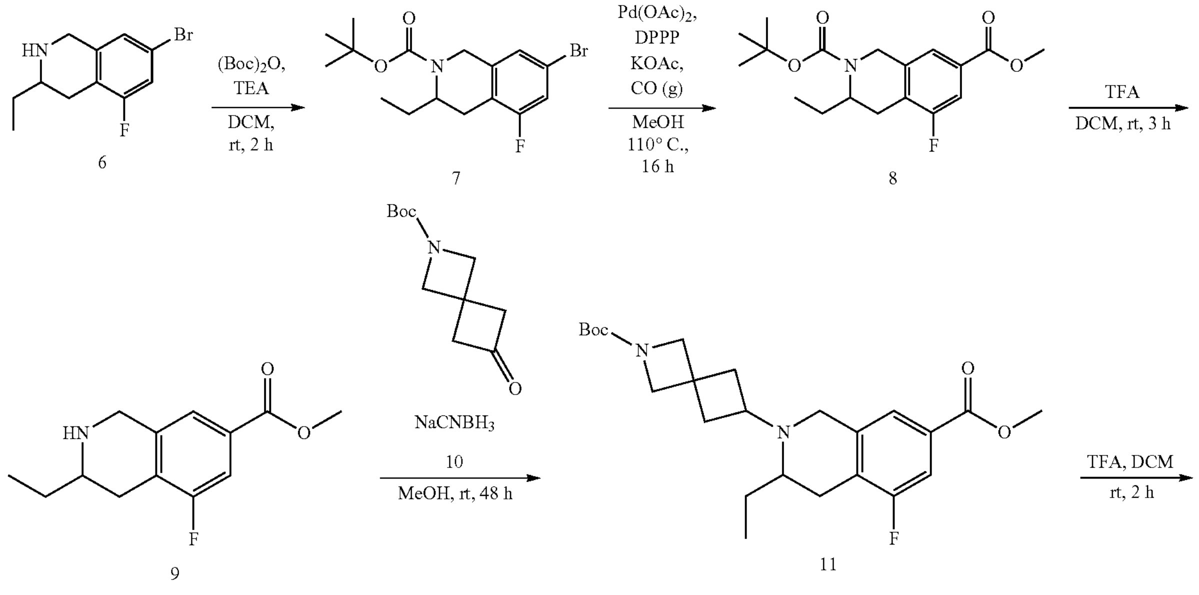

-continued

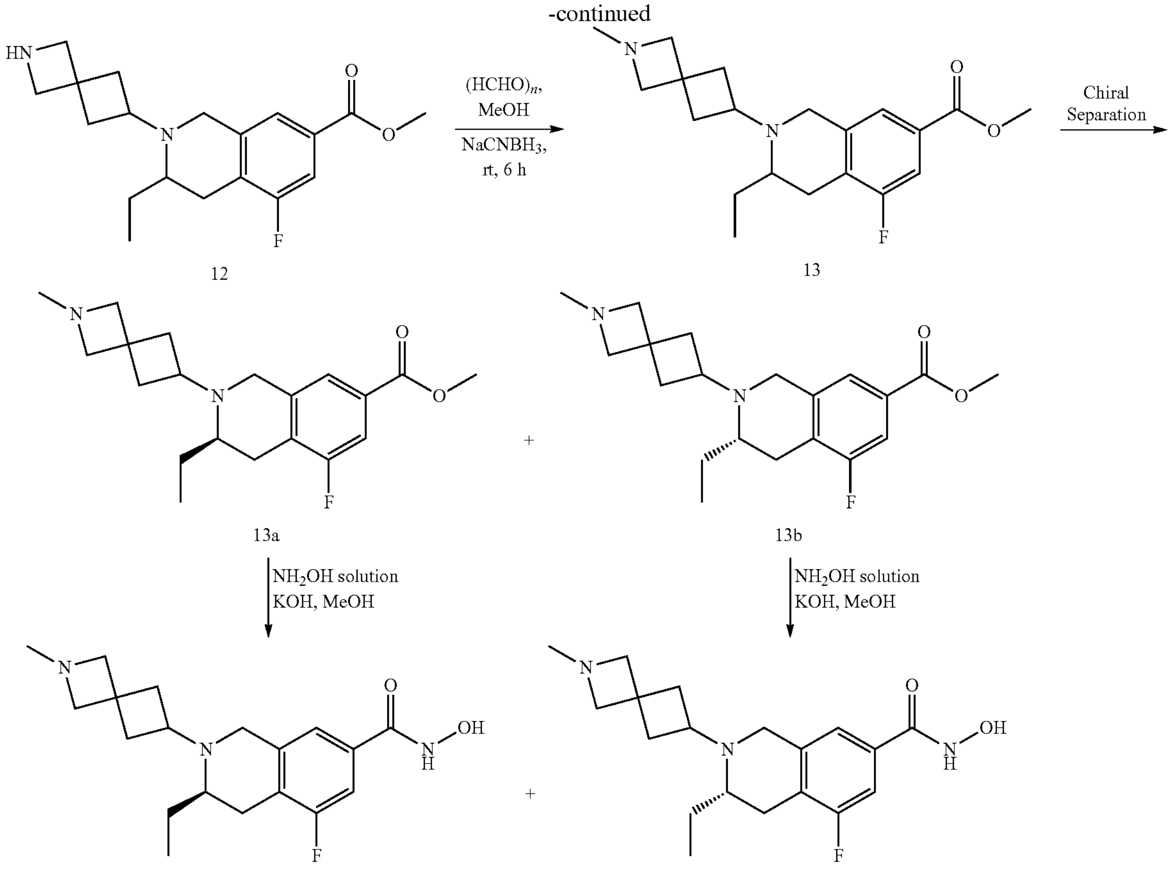

12, 13, 13a, 13b, 584, 585

To a solution of 7-bromo-3-ethyl-5-fluoro-1,2,3,4-tetrahydroisoquinoline (6, 11.5 g, 44.55 mmol, 1.0 equiv.) in DCM (110 mL) was added TEA (18.6 mL, 133.65 mmol, 3.0 equiv.) And BOC-anhydride (12.3 mL, 53.4613 mmol, 1.2 equiv.) at 0° C. The resulting reaction mixture was stirred at room temperature for 2 h. Completion of reaction was monitored by TLC. The reaction mixture was then added to water (250 mL) and extracted with DCM (250×2). The organic layer combined, dried and evaporated. The residue was purified by column chromatography using EtOAc/hexane to give tert-butyl 7-bromo-3-ethyl-40W 5-fluoro-3,4-dihydroisoquinoline-2(1H)-carboxylate (7, 10.5 g, 29.3091 mmol, 66%) MS (ESI): 302 [M-Bu]$^+$ To a solution of tert-butyl 7-bromo-3-ethyl-5-fluoro-3,4-dihydroisoquinoline-2(1H)-carboxylate (7, 5.5 g, 15.352 mmol, 1.0 equiv.) in methanol (55 mL) degassed with nitrogen, was added KOAc (7.53 g, 76.76 mmol, 5 equiv.), Pd(OAc)$_2$ (0.51 g, 2.3028 mmol, 0.15 equiv.) and DPPP (1.26 g, 3.0704 mmol, 0.2 equiv.) at room temperature under nitrogen. The resulting reaction mixture was stirred at 110° C. under CO atmosphere (400 psi) for 16 h. The reaction mixture was cooled to room temperature, filtered through a pad of celite, and concentrated to remove solvents. Added water (50 mL) and extracted with EtOAc (60 mL×2). The organic layer combined, dried and evaporated. The residue was purified by column chromatography using EtOAc/hexane to give 2-(tert-butyl) 7-methyl 3-ethyl-5-fluoro-3,4-dihydroisoquinoline-2,7(1H)-dicarboxylate (8, 4.3 g, 12.745 mmol, 70% yield) MS (ESI): 281 [M-Bu]$^+$ To a stirred solution of 2-(tert-butyl) 7-methyl 3-ethyl-5-fluoro-3,4-dihydroisoquinoline-2,7(1H)-dicarboxylate (8, 4.3 g, 12.745 mmol, 1.0 equiv.) in DCM (40 mL) were trifluoro acetic acid (9.75 mL, 127.45 mmol, 10.0 equiv.) at 0° C. The reaction mixture was stirred at room temperature for 3 h. Completion of reaction was monitored by TLC. The reaction mass was washed with sat. $NaHCO_3$ (40 mL) extracted with DCM (40 mL×2). The combine organic layer dried over $Na_2SO_4$, concentrated in vacuo to get methyl 3-ethyl-5-fluoro-1,2,3,4-tetrahydroisoquinoline-7-carboxylate (9, 2 g, 8.4292 mmol, 66% yield) as solid. MS (ESI): 238 [M+H]$^+$ To a solution of methyl 3-ethyl-5-fluoro-1,2,3,4-tetrahydroisoquinoline-7-carboxylate (9,400 mg, 1.6858 mmol, 1 equiv.) in MeOH (4.0 mL), tert-butyl 6-oxo-2-azaspiro[3.3]heptane-2-carboxylate (10, 427.38 mg, 2.023 mmol, 1.2 equiv.) was added and stirred for 15 min. $NaCNBH_3$ (261.29 mg, 4.2145 mmol, 2.5 equiv.) was added and the resulting reaction mixture was stirred at room temperature for 48 h. The reaction mass was diluted with water (30 mL) and extracted with ethyl acetate (3×30 mL). The combined organic layer was then dried over $Na_2SO_4$, concentrated and the residual mass was purified by silica gel column chromatography. Compound was eluted at 75% EtOAc in hexanes to give methyl 2-(2-(tert-butoxycarbonyl)-2-azaspiro[3.3]heptan-6-yl)-3-ethyl-5-fluoro-1,2,3,4-tetrahydroisoquinoline-7-carboxylate (11, 500 mg, 1.1559 mmol, 68.6%). MS (ESI): 433 [M+H]$^+$ To a solution of methyl 2-(2-(tert-butoxycarbonyl)-2-azaspiro[3.3]heptan-6-yl)-3-ethyl-5-fluoro-1,2,3,4-tetrahydroisoquinoline-7-carboxylate (11, 500 mg, 1.1559 mmol, 1.0 equiv.) in DCM (5.0 mL) was added TFA (0.94 mL, 11.5596 mmol, 10.0 equiv.) at 0° C. and the reaction allowed to stir at room temperature for 2 h. the reaction mixture was extracted three times using $NaHCO_3$. The organic layer was collected, dried over $Na_2SO_4$, and concentrated. To get crude methyl 3-ethyl-5-fluoro-2-(2-azaspiro[3.3]heptan-6-yl)-1,2,3,4-tetrahydroisoquinoline-7-carboxylate (12, 375 mg, 1.1280 mmol, 97.59%). MS (ESI): 333 $[M+H]^+$ To a solution of methyl 3-ethyl-5-fluoro-2-(2-azaspiro[3.3]heptan-6-yl)-1,2,3,4-tetrahydroisoquinoline-7-carboxylate (12, 375 mg, 1.1280 mmol, 1.0 equiv.) in MeOH (5.0 mL) was added paraformaldehyde (338 mg, 11.28 mmol, 10 equiv.) The reaction was then stirred at room temperature for 30 mins followed by the addition of $NaCNBH_3$ (209.8 mg, 3.384 mmol, 3.0 equiv.). The mixture was then allowed to stir for 6 h. The volatiles were evaporated, the reaction mass basify with NaHCO3Solution (30 mL) and extracted with DCM (3×30 mL). The combined organic layer was then dried over $Na_2SO_4$, concentrated and the residual mass was purified by silica gel column chromatography. Compound was eluted at 92% EtOAc in hexanes to give methyl 3-ethyl-5-fluoro-2-(2-methyl-2-azaspiro[3.3]heptan-6-yl)-1,2,3,4-tetrahydroisoquinoline-7-carboxylate (13, 140 mg, 0.4040 mmol, 38.8%) MS (ESI): 347 $[M+H]^+$ 98 mg of racemic compound (13) was purified on Shimadzu LC-20AP with UV detector. The column was used Chiralpak IG (250×21.0) mm, 5 micron, column flow was 10.0 mL/min and ABPR was 100 bar. Mobile phase were used (A) Liquid Carbon dioxide (Liq. CO2) and (B) 0.1% DEA in Methanol. Two fractions were collected. Fr-1 (13a): (40 mg, 0.1155 mmol, 41%). Fr-2(13b): (50 mg, 0.1443 mmol, 51%). MS (ESI): 347 $[M+H]^+$ To a solution of methyl (R)-3-ethyl-5-fluoro-2-(2-methyl-2-azaspiro[3.3]heptan-6-yl)-1,2,3,4-tetrahydroisoquinoline-7-carboxylate (13a, 40 mg, 0.1154 mmol, 1.0 equiv.) in MeOH (1 mL), added the $NH_2OH$ (0.15 mL, 2.3091 mmol, 50% aqueous solution, 20.0 equiv.) and KOH (12.92 mg, 0.2308 mmol, 2.0 equiv.) at 0° C. to room temperature and reaction was stirred for 10 min. Completion of reaction was monitored by TLC and LCM. Reaction mixture was evaporate. The crude compound was purified by Prep. HPLC method using 5 mM ABC+0.1% TFA in water and 100% $CH_3CN$ as a mobile phase to give methyl (R)-3-ethyl-5-fluoro-2-(2-methyl-2-azaspiro[3.3]heptan-6-yl)-1,2,3,4-tetrahydroisoquinoline-7-carboxylate (584) (10.09 mg, 0.02903 mmol, 25%). $^1H$ NMR (400 MHz, DMSO-d6) δ 11.36 (s, 1H), 10.36 (s, 1H), 9.87 (s, 1H), 9.22 (s, 1H), 7.57-7.52 (m, 2H), 4.54 (bs, 1H), 4.20 (bs, 2H), 4.10 (bs, 1H), 3.98 (bs, 3H), 3.76 (bs, 1H), 3.03 (bs, 1H), 2.91 (bs, 1H), 2.78 (d, J=4.0 Hz, 3H), 1.76 (bs, 1H), 1.46 (bs, 1H), 0.97 (bs, 3H). MS (ESI): 348 $[M+H]^+$ (S)-3-ethyl-5-fluoro-N-hydroxy-2-(2-methyl-2-azaspiro[3.3]heptan-6-yl)-1,2,3,4-tetrahydroisoquinoline-7-carboxamide (585): (12.78 mg, 0.0367 mmol. 25%) $^1H$ NMR (400 MHz, DMSO-d6) δ 11.35 (s, 1H), 10.54 (d, 1H), 9.97 (s, $^1H$), 9.22 (s, 1H), 7.57-7.52 (n, 2H), 4.52 (s, 1H), 4.21 (bs, 2H), 4.10 (bs, 1H), 3.97 (bs, 3H), 3.77 (bs, 1H), 3.03 (bs, 1H), 2.91 (bs, 1H), 2.77 (d, J=4.0 Hz, 3H), 1.75 (bs, 1H), 1.39 (bs, 1H), 0.97 (t, J=8.0 Hz, 3H). MS (ESI): 348 $[M+H]^+$ Although compounds 584 and 585 are designated as the (S) and (R) enantiomers as each enantiomer was prepared and isolated, the absolute stereochemistry of each is unknown.

8-fluoro-2-[spiro[3.4]octan-7-yl]-3,4-dihydro-1H-isoquinoline-6-carbohydroxamic acid

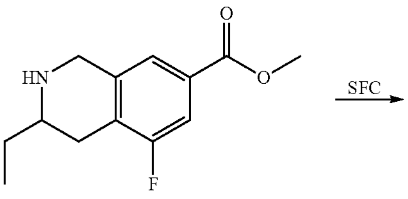

1

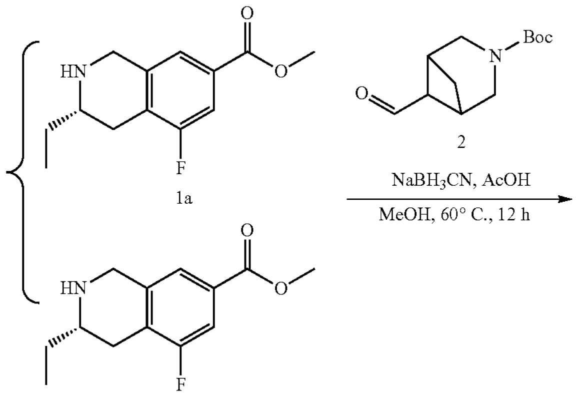

1a

1b

2

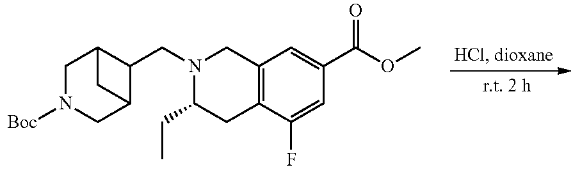

3

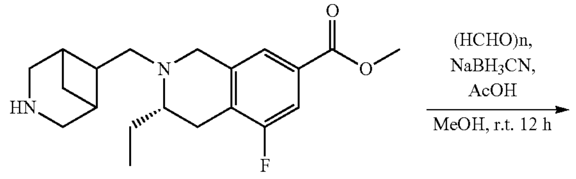

4

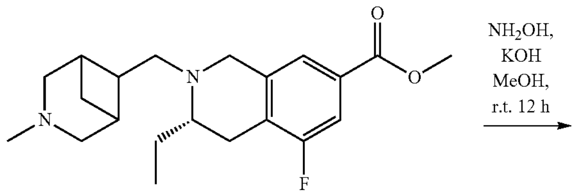

5

-continued

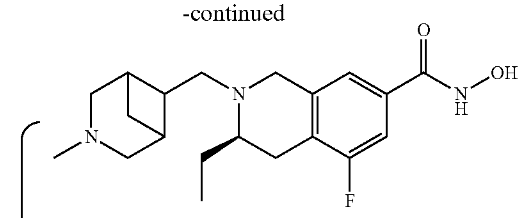

530

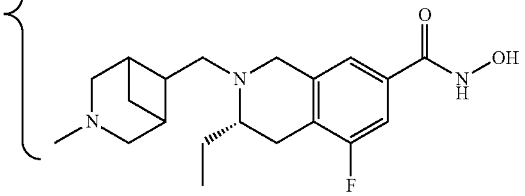

531

Preparation and separation of enantiomers of 8-fluoro-2-[spiro[3.4]octan-7-yl]-3,4-dihydro-1H-isoquinoline-6-carbohydroxamic acid (530 and 531) were achieved according to the reaction scheme above. Although compounds 284 and 285 are designated as the (S) and (R) enantiomers as each enantiomer was prepared and isolated, the absolute stereochemistry of each is unknown.

| Compound | Structure/Name | Characterization |
|---|---|---|
| 530 | 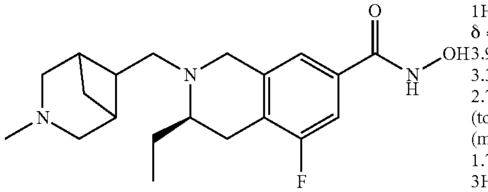 (3R)-3-ethyl-5-fluoro-2-[(3-methyl-3-azabicyclo[3.1.1]heptan-6-yl)methyl]-3,4-dihydro-1H-isoquinoline-7-carbohydroxamic acid | 1H NMR (400 MHz, METHANOL-d4) δ = 7.55-7.48 (m, 2H), 4.57 (bs, 2H), 3.90-3.68 (m, 3H), 3.53-3.42 (m, 4H), 3.37-3.33 (m, 2H),2.94 (s, 3H), 2.85-2.78(m, 1H), 2.79-2.70 (m, 2H), 2.34 (td, J = 5.7, 11.0 Hz, 1H), 2.08-1.97 (m, 1H), 1.90 (bd, J = 10.8 Hz, 1H), 1.75-1.63 (m, 1H), 1.13 (t, J = 7.4 Hz, 3H). MS(ESI): 362.2 [M + H]+. Absolute stereochemistry is unknown. |
| 531 | 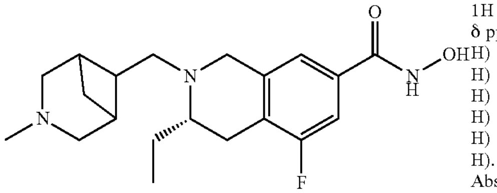 (3S)-3-ethyl-5-fluoro-2-[(3-methyl-3-azabicyclo[3.1.1]heptan-6-yl)methyl]-3,4-dihydro-1H-isoquinoline-7-carbohydroxamic acid | 1H NMR (400 MHz, METHANOL-d4) δ ppm 7.48-7.58 (m, 2 H) 4.60 (br s, 2 H) 3.90-4.10 (m, 2 H) 3.72-3.90 (m, 2 H) 3.62-3.71 (m, 1 H) 3.41-3.61 (m, 3 H) 3.06-3.15 (m, 1 H) 2.97-3.03 (m, 3 H) 2.43-2.70 (m, 4 H) 1.97-2.07 (m, 1 H) 1.70-1.90 (m, 2 H) 0.87-1.35 (m, 3 H). MS (ESI): 362.1 [M + H]+. Absolute stereochemistry is unknown. |

(3R)-3-ethyl-5-fluoro-2-[[(2R)-tetrahydropyran-2-yl]methyl]-3,4-dihydro-1H-isoquinoline-7-carbohydroxamic acid (230) and (3S)-3-ethyl-5-fluoro-2-[[(2R)-tetrahydropyran-2-yl]methyl]-3,4-dihydro-1H-isoquinoline-7-carbohydroxamic acid (231)

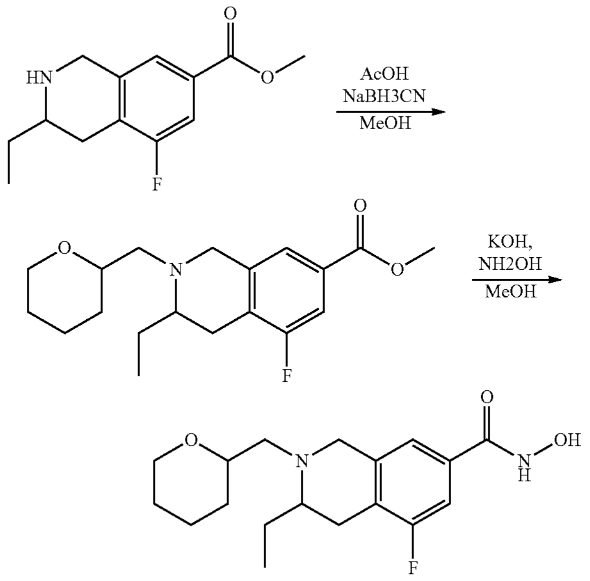

230/231

To a solution of methyl (3S)-3-ethyl-5-fluoro-1,2,3,4-tetrahydroisoquinoline-7-carboxylate (300 mg, 1.26 mmol, 1 eq) in MeOH (3 mL) was added AcOH (227.79 mg, 3.79 mmol, 216.94 uL, 3 eq) and tetrahydropyran-2-carbaldehyde (144.32 mg, 1.26 mmol, 1 eq) NaBH3CN (119.18 mg, 1.90 mmol, 1.5 eq).The mixture was stiffed at 25-60° C. for 12 hr. The reaction mixture was concentrated under reduced pressure to remove solvent. The residue was purified by prep-HPLC column: Phenomenex Luna C18 100*30 mm*5 um; mobile phase: [water(FA)-ACN]; B %: 14%-44%, 10 min to give the desired compound (250 mg) which was further separated by SFC (condition: column: DAICEL CHIRALPAK AD (250 mm*30 mm, 10 um); mobile phase: [0.1% $NH_3$ H2O ETOH]; B %: 10%-10%, 2; 30 min, to give: Methyl (3S)-3-ethyl-5-fluoro-2-[[(2S)-tetrahydropyran-2-yl]methyl]-3,4-dihydro-1H-isoquinoline-7-carboxylate (105 mg, 297.40 umol, 23.52% yield, 95% purity) was obtained as a white solid. Methyl (3S)-3-ethyl-5-fluoro-2-[[(2R)-tetrahydropyran-2-yl]methyl]-3,4-dihydro-1H-isoquinoline-7-carboxylate (105 mg, 297.40 umol, 23.52% yield, 95% purity) was obtained as a white solid. MS (ESI): 336.2[M+H]$^+$; 1H NMR (400 MHz, METHANOL-d4) δ ppm 7.63-7.71 (m, 1H) 7.53-7.62 (m, 1H) 4.27-4.41 (m, 2H) 3.97 (td, J=11.41, 2.81 Hz, 1H) 3.85-3.87 (m, 3H) 3.63-3.70 (m, 1H) 3.36-3.51 (m, 2H) 2.98-3.16 (m, 2H) 2.82-2.90 (m, 2H) 1.78-1.85 (m, 2H) 1.49-1.59 (m, 5H) 1.19-1.26 (m, 1H) 1.00-1.07 (m, 3H)

To a solution of methyl (3S)-3-ethyl-5-fluoro-2-[[(2R)-tetrahydropyran-2-yl]methyl]-3,4-dihydro-1H-isoquinoline-7-carboxylate(100.00 mg, 298.14 umol, 1 eq) in MeOH (2 mL) was added KOH (33.45 mg, 596.28 umol, 2 eq) and hydroxylamine (393.90 mg, 5.96 mmol, 50% purity, 20 eq). The mixture was stirred at 25° C. for 12 hr. The reaction mixture was concentrated under reduced pressure to remove solvent. The residue was purified by prep-HPLC column: Welch Xtimate C18 150*25 mm*5 um; mobile phase: [water(TFA)-ACN]; B %: 3%-33%, 10 min. Compound (3S)-3-ethyl-5-fluoro-2-[[(2R)-tetrahydropyran-2-yl]methyl]-3,4-dihydro-1H-isoquinoline-7-carbohydroxamic acid (231) (21 mg, 45.69 umol, 15.33% yield, 98% purity, TFA) was obtained as a white solid.

To a solution of methyl (3R)-3-ethyl-5-fluoro-2-[[(2R)-tetrahydropyran-2-yl]methyl]-3,4-dihydro-1H-isoquinoline-7-carboxylate (100 mg, 298.14 umol, 1 eq) in MeOH (3 mL) was added KOH (33.46 mg, 596.28 umol, 2 eq) and hydroxylamine (393.90 mg, 5.96 mmol, 50% purity, 20 eq). The mixture was stirred at 25° C. for 12 hr. The reaction mixture was concentrated under reduced pressure to remove solvent. The residue was purified by prep-HPLC column: Welch Xtimate C18 150*25 mm*5 um; mobile phase: [water (TFA)-ACN]; B %: 2%-32%, 10 min. (R)-3-ethyl-5-fluoro-N-hydroxy-2-(((R)-tetrahydro-2H-pyran-2-yl)methyl)-1,2,3,4-tetrahydroisoquinoline-7-carboxamide (230) (42 mg, 91.38 umol, 30.65% yield, 98% purity, TFA) was obtained as a white solid.

| | | |
|---|---|---|
| 230 | 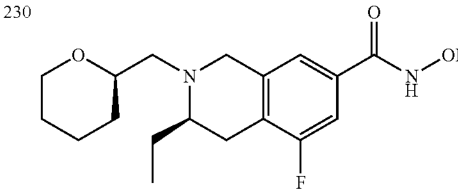 (R)-3-ethyl-5-fluoro-N-hydroxy-2-(((R)-tetrahydro-2H-pyran-2-yl)methyl)-1,2,3,4-tetrahydroisoquinoline-7-carboxamide | 1H NMR (400 MHz, METHANOL-d4) δ ppm 7.51-7.48 (m, 2 H) 4.67 (br s, 2 H) 4.07-4.01 (m, 1 H) 3.75-3.91 (m, 2 H) 3.53-3.62 (m, 1 H) 3.38-3.49 (m, 1 H) 3.22-3.30 (m, 1 H) 3.01-3.18 (m, 2 H) 1.88-2.05 (m, 2 H) 1.59-1.72 (m, 5 H) 1.26-1.38 (m, 1 H) 1.13-1.08 (m, 3 H). MS (ESI): 337.2 [M + H]+. Absolute stereochemistry is unknown. |
| 231 | 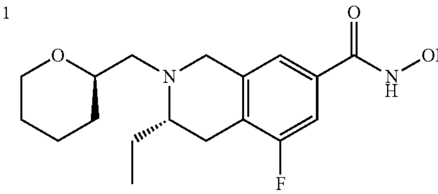 (3S)-3-ethyl-5-fluoro-2-[[(2R)-tetrahydropyran-2-yl]methyl]-3,4-dihydro-1H-isoquinoline-7-carbohydroxamic acid | 1H NMR (400 MHz, METHANOL-d4) δ ppm 7.48-7.60 (m, 2 H) 4.57-4.72 (m, 2 H) 4.09-4.00 (m, 1 H) 3.73-3.88 (m, 2 H) 3.60-3.52 (m, 1 H) 3.37-3.29 (m, 1 H) 3.19-3.28 (m, 1 H) 2.85-3.14 (m, 2 H) 1.87-2.00 (m, 2 H) 1.72-1.86 (m, 1 H) 1.57-1.69 (m, 4 H) 1.26-1.38 (m, 1 H) 1.11-1.20 (m, 3 H)MS (ESI): 337.2 [M + H]+. Absolute stereochemistry is unknown. |

(3S)-3-ethyl-5-fluoro-2-(2-oxatricyclo[3.3.1.13,7]decan-1-ylmethyl)-3,4-dihydro-1H-isoquinoline-7-carbohydroxamic acid (510)

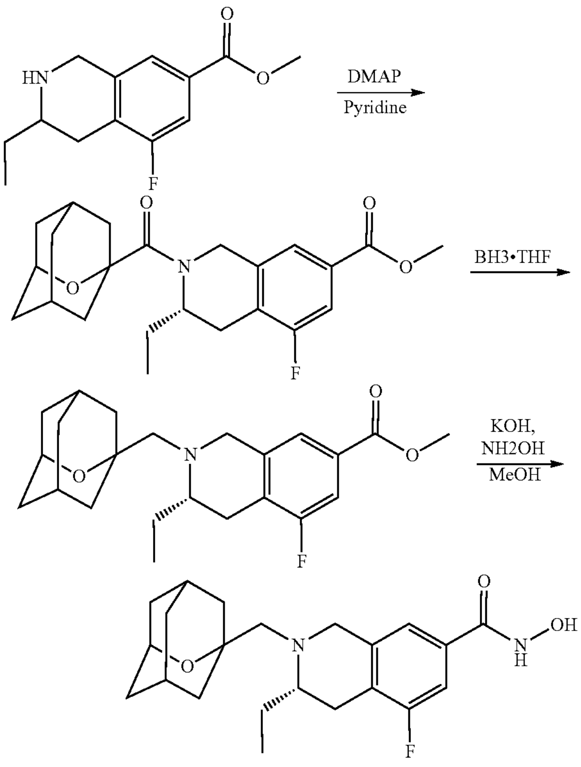

510

To a solution of 2-oxatricyclo[3.3.1.13,7]decane-1-carbonyl chloride (400 mg, 1.99 mmol, 1 eq) and methyl (3S)-3-ethyl-5-fluoro-1,2,3,4-tetrahydroisoquinoline-7-carboxylate (472.97 mg, 1.99 mmol, 1 eq) in PYRIDINE (5 mL) was added DMAP (0.2 mg, 1.64 umol, 8.21e-4 eq). The mixture was stirred at 60° C. for 16 hr. The mixture was concentrated under reduced pressure. The residue was purified by column chromatography (SiO2, Ethyl acetate/Petroleum ether/=0/1 to 1/90). The product methyl (3S)-3-ethyl-5-fluoro-2-(2-oxatricyclo[3.3.1.13,7]decane-1-carbonyl)-3,4-dihydro-1H-isoquinoline-7-carboxylate (200 mg, 497.17 umol, 24.94% yield, 99.8% purity) was obtained as a white solid. MS(ESI): 402.0 [M+H]+

To a solution of methyl (3S)-3-ethyl-5-fluoro-2-(2-oxatricyclo[3.3.1.13,7]decane-1-carbonyl)-3,4-dihydro-1H-isoquinoline-7-carboxylate (160 mg, 362.67 umol, 91% purity, 1 eq) in THF (4 mL) was added BH3·THF (1 M, 725.33 uL, 2 eq) at 25° C. Then the mixture was stirred at 65° C. for 12 hr. The reaction mixture was concentrated under reduced pressure to remove MeOH. The crude product was purified by reversed-phase HPLC(column: Phenomenex luna C18 150*25 mm*10 um; mobile phase: [water(FA)-ACN]; B %: 17%-34%, 10.5 min). Compound methyl (3S)-3-ethyl-5-fluoro-2-(2-oxatricyclo[3.3.1.13,7]decan-1-ylmethyl)-3,4-dihydro-1H-isoquinoline-7-carboxylate (95 mg, 242.72 umol, 66.93% yield, 99% purity) was obtained as colourless liquid. MS(ESI): 388.4[M+H]+

To a solution of hydroxylamine (343.26 mg, 5.20 mmol, 50% purity, 20.97 eq) and methyl (3S)-3-ethyl-5-fluoro-2-(2-oxatricyclo[3.3.1.13,7]decan-1-ylmethyl)-3,4-dihydro-1H-isoquinoline-7-carboxylate (96 mg, 247.75 umol, 1 eq) in MeOH (5 mL) was added KOH (14.58 mg, 259.81 umol, 1.05 eq).The mixture was stirred at 25° C. for 12 hr. The mixture was concentrated under reduced pressure. The residue was purified by prep-HPLC (column: Welch Xtimate C18 150*25 mm*5 um; mobile phase: [water(TFA)-ACN]; B %: 15%-45%, 10 min). The product (3S)-3-ethyl-5-fluoro-2-(2-oxatricyclo[3.3.1.13,7]decan-1-ylmethyl)-3,4-dihydro-1H-isoquinoline-7-carbohydroxamic acid (19.09 mg, 36.43 umol, 14.71% yield, 95.9% purity, TFA) was obtained as a yellow gum.

(3R)-3-ethyl-5-fluoro-2-(2-oxatricyclo[3.3.1.13,7]decan-1-ylmethyl)-3,4-dihydro-1H-isoquinoline-7-carbohydroxamic acid (509) was prepared in an analogous manner.

| | | |
|---|---|---|
| 509 | 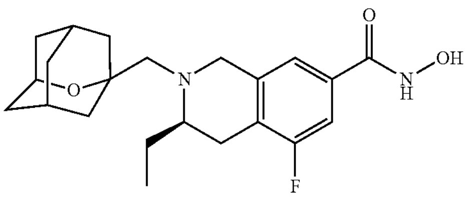 (3R)-3-ethyl-5-fluoro-2-(2-oxatricyclo[3.3.1.13,7]decan-1-ylmethyl)-3,4-dihydro-1H-isoquinoline-7-carbohydroxamic acid | 1H NMR (400 MHz, METHANOL-d4) δ = 7.55-7.49 (m, 2H), 4.71 (br s, 2H), 4.21 (br s, 1H), 3.81-3.70 (m, 1H), 3.27-3.18 (m, 1H), 2.93-2.88 (m, 1H), 2.82-2.78 (m, 1H), 2.25-2.15 (m, 2H), 2.09-1.91 (m, 6H), 1.89-1.61 (m, 7H), 1.15-1.08 (m, 3H). MS(ESI): 389.0 [M + H]+. Absolute stereochemistry is unknown. |
| 510 | 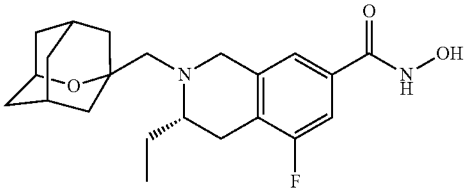 (3S)-3-ethyl-5-fluoro-2-(2-oxatricyclo[3.3.1.13,7]decan-1-ylmethyl)-3,4-dihydro-1H-isoquinoline-7-carbohydroxamic acid | 1H NMR (400 MHz, METHANOL-d4) δ = 7.55-7.50 (m, 2H), 4.70 (br s, 2H), 4.21 (br s, 1H), 3.78-3.71 (m, 1H), 3.27-3.18 (m, 1H), 2.93-2.88 (m, 1H), 2.82-2.78 (m, 1H), 2.25-2.18 (m, 2H), 2.07-1.91 (m, 6H), 1.87-1.64 (m, 7H), 1.15-1.08 (m, 3H). MS(ESI): 389.0 [M + H]+. Absolute stereochemistry is unknown. |

(3S)-3-ethyl-5-fluoro-2-(spiro[3.5]nonan-2-ylmethyl)-3,4-dihydro-1H-isoquinoline-7-carbohydroxamic acid (522)

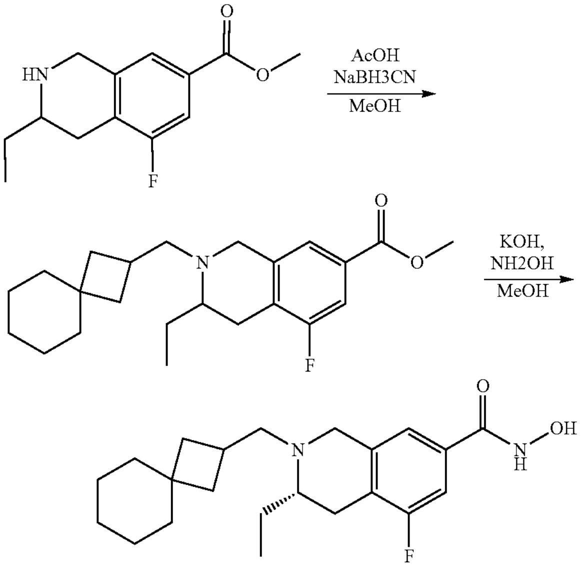

522

To a solution of methyl (3S)-3-ethyl-5-fluoro-1,2,3,4-tetrahydroisoquinoline-7-carboxylate (550 mg, 2.32 mmol, 1 eq), spiro[3.5]nonane-2-carbaldehyde (352.88 mg, 2.32 mmol, 1 eq) in MeOH (10 mL) was added AcOH (278.41 mg, 4.64 mmol, 265.15 uL, 2 eq) and NaBH3CN (218.51 mg, 3.48 mmol, 1.5 eq) at 25° C. The mixture was stiffed at 60° C. for 12 hr. The mixture was concentrated under reduce pressure. The residue was purified by flash silica gel chromatography (12 g Silica Flash Column, Eluent of 0-30% Petroleum ether: Ethyl acetate@ 40 mL/min). Compound methyl (3S)-3-ethyl-5-fluoro-2-(spiro[3.5]nonan-2-ylmethyl)-3,4-dihydro-1H-isoquinoline-7-carboxylate (336 mg, 890.60 umol, 38.42% yield, 99% purity) was obtained as a colorless oil. MS(ESI): 474.3 [M+H]+

To a solution of methyl (3S)-3-ethyl-5-fluoro-2-(spiro[3.5]nonan-2-ylmethyl)-3,4-dihydro-1H-isoquinoline-7-carboxylate (336 mg, 890.60 umol, 99% purity, 1 eq) in MeOH (10 mL) was added KOH (99.93 mg, 1.78 mmol, 2 eq) and HYDROXYLAMINE (1.18 g, 17.81 mmol, 50% purity, 20 eq).The mixture was stirred at 25° C. for 16 hr. The mixture was concentrated under reduce pressure. The residue was purified by prep-HPLC (column: Welch Xtimate C18 150*25 mm*5 um; mobile phase: [water(TFA)-ACN]; B %: 25%-55%, 10 min). Compound (3S)-3-ethyl-5-fluoro-2-(spiro[3.5]nonan-2-ylmethyl)-3,4-dihydro-1H-isoquinoline-7-carbohydroxamic acid (147 mg, 389.00 umol, 43.68% yield, 99.1% purity) was obtained as a white solid.

(3R)-3-ethyl-5-fluoro-2-(spiro[3.5]nonan-2-ylmethyl)-3,4-dihydro-1H-isoquinoline-7-carbohydroxamic acid (521) was prepared in an analogous manner.

| | | |
|---|---|---|
| 521 | 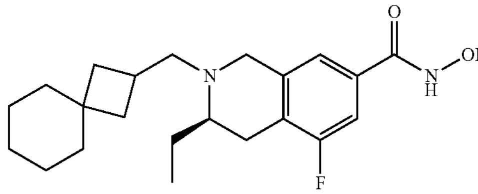 (3R)-3-ethyl-5-fluoro-2-(spiro[3.5]nonan-2-ylmethyl)-3,4-dihydro-1H-isoquinoline-7-carbohydroxamic acid | 1H NMR (400 MHz, METHANOL-d4) δ = 7.57-7.48 (m, 2H), 4.66-4.41 (m, 2H), 3.80-3.62 (m, 1H), 3.26 (bd, J = 5.5 Hz, 1H), 3.20-3.00 (m, 2H), 2.80-2.66 (m, 1H), 2.16-2.06 (m, 2H), 1.96 (bdd, J = 2.4, 4.9 Hz, 1H), 1.77-1.67 (m, 1H), 1.63-1.37 (m, 13H), 1.13 (t, J = 7.4 Hz, 3H). MS(ESI): 375.2 $[M + H]^+$. Absolute stereochemistry is unknown. |
| 522 | 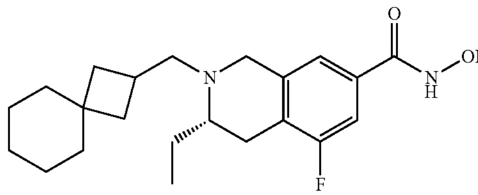 (3S)-3-ethyl-5-fluoro-2-(spiro[3.5]nonan-2-ylmethyl)-3,4-dihydro-1H-isoquinoline-7-carbohydroxamic acid | 1H NMR (400 MHz, METHANOL-d4) δ = 7.55-7.48 (m, 2H), 4.63-4.35 (m, 2H), 3.83-3.63 (m, 1H), 3.32-3.12 (m, 2H), 3.06 (dd, J = 7.0, 18.5 Hz, 1H), 2.83-2.63 (m, 1H), 2.16-2.05 (m, 2H), 2.03-1.92 (m, 1H), 1.76-1.65 (m, 1H), 1.65-1.45 (m, 7H), 1.45-1.36 (m, 6H), 1.13 (t, J = 7.4 Hz, 3H). MS(ESI): 375.1 $[M + H]^+$. Absolute stereochemistry is unknown. |

(3S)-3-ethyl-5-fluoro-2-[(2-methyl-2-azabicyclo [2.1.1]hexan-4-yl)methyl]-3,4-dihydro-1H-isoquinoline-7-carbohydroxamic acid (535)

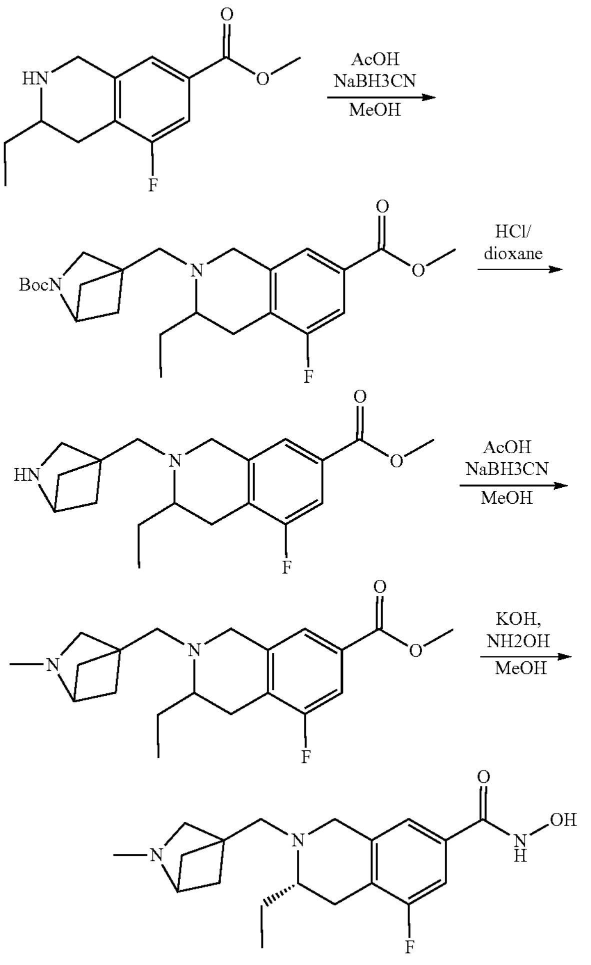

535

To a solution of methyl (3S)-3-ethyl-5-fluoro-1,2,3,4-tetrahydroisoquinoline-7-carboxylate (314.48 mg, 1.33 mmol, 1 eq) and tert-butyl 4-formyl-2-azabicyclo[2.1.1] hexane-2-carboxylate (280 mg, 1.33 mmol, 1 eq) in MeOH (3 mL) was added NaBH3CN (124.93 mg, 1.99 mmol, 1.5 eq) and AcOH (159.18 mg, 2.65 mmol, 151.60 uL, 2 eq).The mixture was stirred at 60° C. for 12 hr. The mixture was concentrated under reduced pressure. The product methyl (3S)-2-[(2-tert-butoxycarbonyl-2-azabicyclo[2.1.1]hexan-4-yl)methyl]-3-ethyl-5-fluoro-3,4-dihydro-1H-isoquinoline-7-carboxylate (120 mg, 163.69 umol, 12.35% yield, 59% purity) was obtained as a yellow solid. MS(ESI): 433.0 [M+H]+

To a solution of methyl (3S)-2-[(2-tert-butoxycarbonyl-2-azabicyclo[2.1.1]hexan-4-yl)methyl]-3-ethyl-5-fluoro-3,4-dihydro-1H-isoquinoline-7-carboxylate (120 mg, 163.69 umol, 59% purity, 1 eq) in dioxane (3 mL) was added HCl/dioxane (4 M, 1.66 mL, 40.45 eq). The mixture was stirred at 25° C. for 2 hr. The mixture was concentrated under reduced pressure. The crude product EC2819-31-P1 was used into the next step without further purification. The crude product methyl (3S)-2-(2-azabicyclo[2.1.1]hexan-4-ylmethyl)-3-ethyl-5-fluoro-3,4-dihydro-1H-isoquinoline-7-carboxylate (120 mg, crude) was obtained as a yellow solid, and was used into the next step without further purification.

To a solution of methyl (3S)-2-(2-azabicyclo[2.1.1] hexan-4-ylmethyl)-3-ethyl-5-fluoro-3,4-dihydro-1H-isoquinoline-7-carboxylate (120 mg, 270.75 umol, 75% purity, 1 eq) in MeOH (3 mL) was added HCHO (47.35 mg, 1.58 mmol, 43.44 uL, 5.82 eq) and AcOH (47.35 mg, 788.48 umol, 45.10 uL, 2.91 eq) and NaBH3CN (37.17 mg, 591.48 umol, 2.18 eq). The mixture was stirred at 25° C. for 12 hr. The mixture was concentrated under reduced pressure. The residue was purified by prep-HPLC (column: Welch Xtimate C18 150*25 mm*5 um; mobile phase: [water(FA)-ACN]; B %: 0%-25%, 10 min). The product methyl (3S)-3-ethyl-5-fluoro-2-[(2-methyl-2-azabicyclo[2.1.1]hexan-4-yl) methyl]-3,4-dihydro-1H-isoquinoline-7-carboxylate (60 mg, 172.67 umol, 63.78% yield, 99.7% purity) was obtained as a yellow solid. MS(ESI): 347.0 [M+H]+

To a solution of methyl (3S)-3-ethyl-5-fluoro-2-[(2-methyl-2-azabicyclo[2.1.1]hexan-4-yl)methyl]-3,4-dihydro-1H-isoquinoline-7-carboxylate (60 mg, 173.19 umol, 1 eq) and hydroxylamine (228.82 mg, 3.46 mmol, 50% purity, 20 eq) in MeOH (3 mL) was added KOH (29.15 mg, 519.57 umol, 3 eq).The mixture was stirred at 25° C. for 12 hr. The mixture was concentrated under reduced pressure. The residue was purified by prep-HPLC (column: Waters Atlantis T3 150*30 mm*5 um; mobile phase: [water(TFA)-ACN]; B %: 0%-20%, 10 min). The product (3S)-3-ethyl-5-fluoro-2-[(2-methyl-2-azabicyclo[2.1.1]hexan-4-yl) methyl]-3,4-dihydro-1H-isoquinoline-7-carbohydroxamic acid (30.78 mg, 65.57 umol, 37.86% yield, 98.3% purity, TFA) was obtained as a yellow oil.

(3R)-3-ethyl-5-fluoro-2-[(2-methyl-2-azabicyclo[2.1.1] hexan-4-yl)methyl]-3,4-dihydro-1H-isoquinoline-7-carbohydroxamic acid (534) was prepared in an analogous manner.

| | | |
|---|---|---|
| 534 | 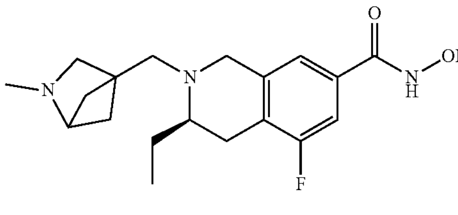<br>(3R)-3-ethyl-5-fluoro-2-[(2-methyl-2-azabicyclo[2.1.1]hexan-4-yl)methyl]-3,4-dihydro-1H-isoquinoline-7-carbohydroxamic acid | 1H NMR (400 MHz, METHANOL-d4) δ = 7.48 (s, 1H), 7.44 (d, J = 9.9 Hz, 1H), 4.46-4.27 (m, 2H), 4.17 (s, 1H), 3.81 (b dd, J = 9.8, 15.4 Hz, 1H), 3.50 (b d, J = 16.3 Hz, 2H), 3.36-3.32 (m, 1H), 3.26-3.15 (m, 2H), 3.01 (s, 3H), 2.89 (b dd, J = 7.3, 18.3 Hz, 1H), 2.36-2.22 (m, 2H), 2.11 (b t, J = 10.1 Hz, 1H), 1.94-1.81 (m, 2H), 1.69-1.56 (m, 1H), 1.09 (t, J = 7.3 Hz, 3H). MS(ES[+]): 348.2 [M + H]+. Absolute stereochemistry is unknown. |

-continued

| | | |
|---|---|---|
| 535 | 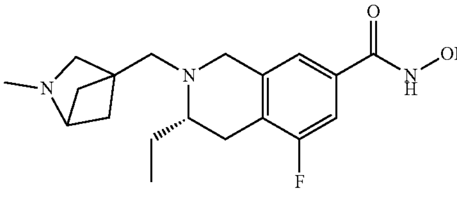 (3S)-3-ethyl-5-fluoro-2-[(2-methyl-2-azabicyclo[2.1.1]hexan-4-yl)methyl]-3,4-dihydro-1H-isoquinoline-7-carbohydroxamic acid | 1H NMR (400 MHz, METHANOL-d4) δ = 7.52-7.43 (m, 2H), 4.46-4.37 (m, 1H), 4.35-4.28 (m, 1H), 4.19 (s, 1H), 3.87-3.78 (m, 1H), 3.58-3.45 (m, 2H), 3.30 (br s, 1H), 3.26-3.17 (m, 2H), 3.03 (s, 3H), 2.96-2.84 (m, 1H), 2.37-2.24 (m, 2H), 2.13 (t, J = 10.1 Hz, 1H), 1.94-1.83 (m, 2H), 1.70-1.57 (m, 1H), 1.10 (t, J = 7.4 Hz, 3H). MS(ESI): 348.0 [M + H]+. Absolute stereochemistry is unknown. |

(3R)-3-ethyl-5-fluoro-2-[[(1R,4R)-5-methyl-2-oxa-5-azabicyclo[2.2.1]heptan-1-yl]methyl]-3,4-dihydro-1H-isoquinoline-7-carbohydroxamic acid (554)

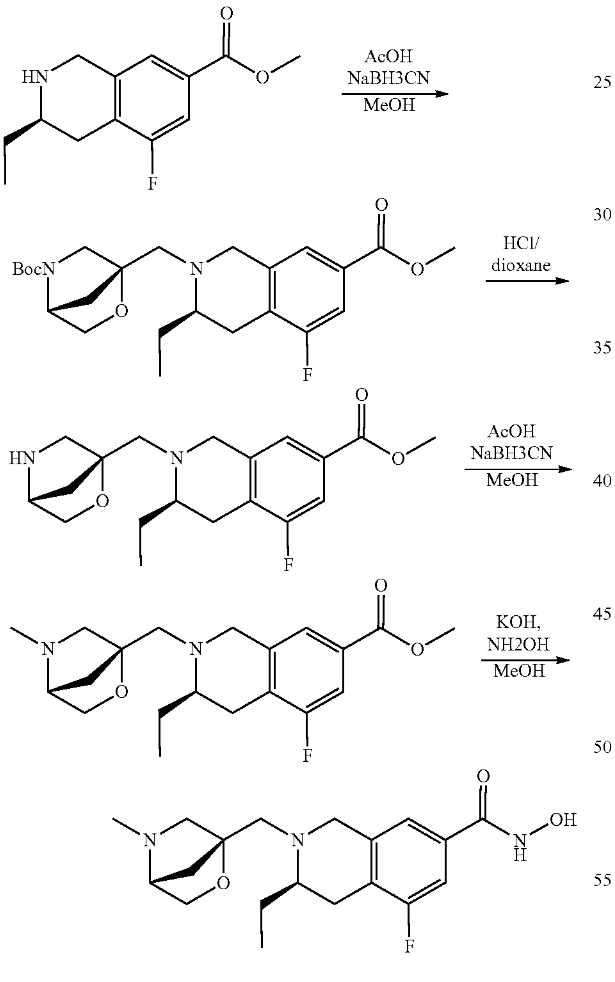

To a solution of tert-butyl (1R,4R)-1-formyl-2-oxa-5-azabicyclo[2.2.1]heptane-5-carboxylate (300 mg, 1.32 mmol, 1 eq), methyl (3R)-3-ethyl-5-fluoro-1,2,3,4-tetrahydroisoquinoline-7-carboxylate (313.22 mg, 1.32 mmol, 1 eq) in MeOH (3 mL) was added NaBH3CN (124.44 mg, 1.98 mmol, 1.5 eq) and AcOH (158.55 mg, 2.64 mmol, 151.00 uL, 2 eq).The mixture was stirred at 60° C. for 16 hr. The reaction mixture was concentrated under reduced pressure to remove solvent. The residue was purified by prep-HPLC (column: Waters xbridge 150*25 mm 10 um; mobile phase: [water(NH4HCO3)-ACN]; B %: 60%-90%, 11 min). Compound tert-butyl (1S,4R)-1-[[(3R)-3-ethyl-5-fluoro-7-methoxycarbonyl-3,4-dihydro-1H-isoquinolin-2-yl]methyl]-2-oxa-5-azabicyclo[2.2.1]heptane-5-carboxylate (70 mg, 152.95 umol, 11.59% yield, 98% purity) was obtained as a yellow solid. MS(ESI)=449.2[M+H]+

To a solution of tert-butyl (1S,4R)-1-[[(3R)-3-ethyl-5-fluoro-7-methoxycarbonyl-3,4-dihydro-1H-isoquinolin-2-yl]methyl]-2-oxa-5-azabicyclo[2.2.1]heptane-5-carboxylate (70 mg, 156.07 umol, 1 eq) in dioxane (1 mL) was added HCl/dioxane (4 M, 39.02 uL, 1 eq). The mixture was stirred at 25° C. for 2 hr. The reaction mixture was concentrated under reduced pressure to remove solvent. The crude product was used into the next step without further purification. Compound methyl (3R)-3-ethyl-5-fluoro-2-[[(1R,4R)-2-oxa-5-azabicyclo[2.2.1]heptan-1-yl]methyl]-3,4-dihydro-1H-isoquinoline-7-carboxylate (70 mg, 133.55 umol, 85.57% yield, 80% purity, 2Cl) was obtained as a yellow solid. MS(ESI)=349.2[M+H]+

To a solution of methyl (3R)-3-ethyl-5-fluoro-2-[[(1R,4R)-2-oxa-5-azabicyclo[2.2.1]heptan-1-yl]methyl]-3,4-dihydro-1H-isoquinoline-7-carboxylate (70.00 mg, 200.91 umol, 1 eq) in MeOH (2 mL) was added HCHO (48.91 mg, 602.74 umol, 44.87 uL, 37% purity, 3 eq) and AcOH (24.13 mg, 401.82 umol, 22.98 uL, 2 eq) NaBH3CN (18.94 mg, 301.37 umol, 1.5 eq). The mixture was stirred at 25° C. for 12 hr. The reaction mixture was concentrated under reduced pressure to remove solvent. The residue was purified by prep-HPLC (column: Welch Xtimate C18 150*25 mm*5 um; mobile phase: [water(FA)-ACN]; B %: 0%-25%, 10 min). Compound methyl (3R)-3-ethyl-5-fluoro-2-[[(1R,4R)-5-methyl-2-oxa-5-azabicyclo[2.2.1]heptan-1-yl]methyl]-3,4-dihydro-1H-isoquinoline-7-carboxylate (60 mg, 148.99 umol, 74.16% yield, 90% purity) was obtained as a yellow solid. MS(ESI)=363.1[M+H]+

To a solution of methyl (3R)-3-ethyl-5-fluoro-2-[[(1R,4R)-5-methyl-2-oxa-5-azabicyclo[2.2.1]heptan-1-yl]methyl]-3,4-dihydro-1H-isoquinoline-7-carboxylate (60.00 mg, 148.99 umol, 90% purity, 1 eq) in MeOH (3 mL) was added KOH (16.72 mg, 297.98 umol, 2 eq) and hydroxylamine (196.85 mg, 2.98 mmol, 50% purity, 20 eq) at 25° C. The mixture was stirred at 25° C. for 16 hr. The reaction mixture was concentrated under reduced pressure to remove solvent. The residue was purified by prep-HPLC (column: Waters Atlantis T3 150*30 mm*5 um; mobile phase: [water (TFA)-ACN]; B %: 0%-20%, 10 min). Compound (3R)-3-ethyl-5-fluoro-2-[[(1R,4R)-5-methyl-2-oxa-5-azabicyclo[2.2.1]heptan-1-yl]methyl]-3,4-dihydro-1H-isoquinoline-7-carbohydroxamic acid (35 mg, 70.37 umol, 47.23% yield, 96% purity, TFA) was obtained as a yellow solid.

Compounds 552, 553, and 555 were prepared in an analogous manner.

554

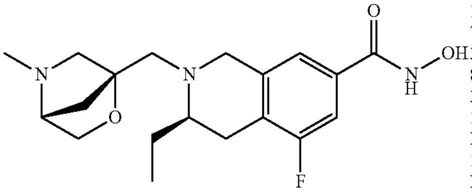

(3R)-3-ethyl-5-fluoro-2-[[(1R,4R)-5-methyl-2-oxa-5-azabicyclo[2.2.1]heptan-1-yl]methyl]-3,4-dihydro-1H-isoquinoline-7-carbohydroxamic acid 1H NMR (400 MHz, METHANOL-d4) δ = 7.48-7.39 (m, 2H), 4.56-4.40 (m, 3H), 4.32-4.14 (m, 1H), 4.07 (bd, J = 8.9 Hz, 1H), 3.85-3.54 (m, 3H), 3.51-3.31 (m, 2H), 3.24 (bdd, J = 4.8, 18.6 Hz, 1H), 2.99 (s, 3H), 2.87 (bdd, J = 7.7, 18.6 Hz, 1H), 2.42 (bs, 2H), 1.96-1.84 (m, 1H), 1.71-1.59 (m, 1H), 1.09 (t, J = 7.4 Hz, 3H).
19F NMR (376 MHz, METHANOL-d4) δ =-77.06 (s, 3F),-118.47 (br s, 1F)
MS(ESI): 364.2 [M + H]+.
Absolute stereochemistry is unknown.

552

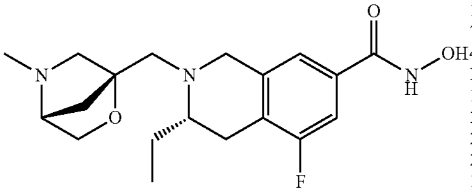

(3S)-3-ethyl-5-fluoro-2-[[(1R,4R)-5-methyl-2-oxa-5-azabicyclo[2.2.1]heptan-1-yl]methyl]-3,4-dihydro-1H-isoquinoline-7-carbohydroxamic acid 1H NMR (400 MHz, METHANOL-d4) δ = 7.42-7.35 (m, 2H), 4.37 (br s, 1H), 4.29 (br s, 2H), 4.03 (dd, J = 1.6, 10.1 Hz, 1H), 3.46-3.35 (m, 2H), 3.33 (d, J = 1.6 Hz, 3H), 3.14 (br d, J = 14.8 Hz, 1H), 3.07 (br d, J = 3.9 Hz, 1H), 3.01 (s, 3H), 2.74 (br dd, J = 7.1, 18.0 Hz, 1H), 2.42-2.31 (m, 1H), 2.25 (br d, J = 11.0 Hz, 1H), 1.82-1.71 (m, 1H), 1.58-1.46 (m, 1H), 1.06 (t, J = 7.4 Hz, 3H). MS(ESI): 364.0 [M + H]+.
Absolute stereochemistry is unknown.

553

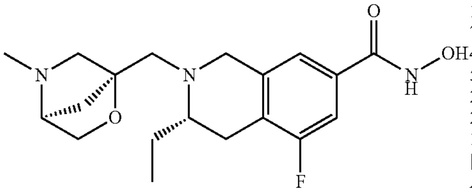

(3S)-3-ethyl-5-fluoro-2-[[(1S,4S)-5-methyl-2-oxa-5-azabicyclo[2.2.1]heptan-1-yl]methyl]-3,4-dihydro-1H-isoquinoline-7-carbohydroxamic acid 1H NMR (400 MHz, METHANOL-d4) δ = 7.53-7.42 (m, 2H), 4.72-4.40 (m, 4H), 4.36-4.04 (m, 2H), 3.93-3.36 (m, 5H), 3.27-3.15 (m, 1H), 3.01 (s, 3H), 2.97-2.81 (m, 1H), 2.58-2.34 (m, 2H), 2.04-1.84 (m, 1H), 1.79-1.61 (m, 1H), 1.22-1.05 (m, 3H). MS(ESI): 364.1 [M + H]+.
Absolute stereochemistry is unknown.

555

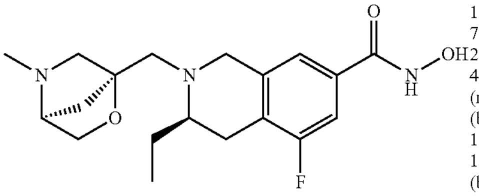

(3R)-3-ethyl-5-fluoro-2-[[(1S,4S)-5-methyl-2-oxa-5-azabicyclo[2.2.1]heptan-1-yl]methyl]-3,4-dihydro-1H-isoquinoline-7-carbohydroxamic acid 1H NMR (400 MHz, METHANOL-d4) δ = 7.54-7.44 (m, 2H), 4.72-4.54 (m, 2H), 4.45 (bs, 1H), 4.34-4.15 (m, 1H), 4.08 (bd, J = 10.1 Hz, 1H), 3.99-3.67 (m, 3H), 3.49 (bd, J = 14.1 Hz, 1H), 3.31 (bs, 2H), 3.01 (s, 3H), 2.91 (bdd, J = 8.6, 18.4 Hz, 1H), 2.55-2.35 (m, 2H), 2.00-1.86 (m, 1H), 1.78-1.63 (m, 1H), 1.11 (br t, J = 7.3 Hz, 3H). MS(ESI): 364.2 [M + H]+.
Absolute stereochemistry is unknown.

(3S)-3-ethyl-5-fluoro-2-[(&-methyl4l-azabicyclo [3.2.1]octan-3-yl)methyl]-3,4-dihydro-1H-isoquinoline-7-carbohydroxamic acid (570); (R)-3-ethyl-5-fluoro-N-hydroxy-2-(((1R,3r,5S)-8methyl-8-azabicyclo[3.2.1]octan-3-yl)methyl)-1,2,3,4-tetrahydroisoquinoline-7-carboxamide (572); (S)-3-ethyl-5-fluoro-N-hydroxy-2-(((1R,3s,5S)-8-methyl-8-azabicyclo[3.2.1]octan-3-yl)methyl)-1,2,3,4-tetrahydroisoquinoline-7-carboxamide (573)

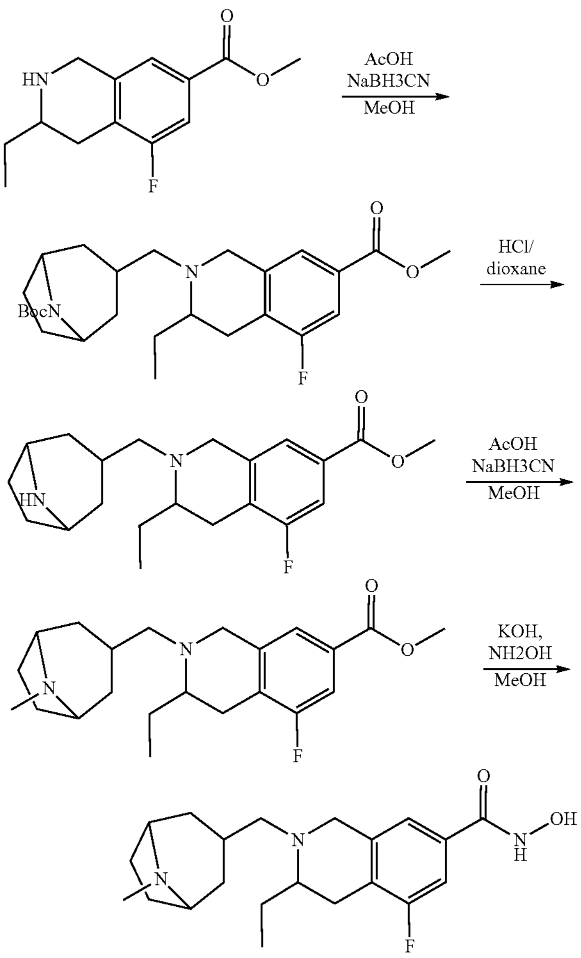

570-573

To a solution of tert-butyl 3-formyl-8-azabicyclo[3.2.1] octane-8-carboxylate (1 g, 4.18 mmol, 1 eq), methyl (3S)-3-ethyl-5-fluoro-1,2,3,4-tetrahydroisoquinoline-7-carboxylate (991.47 mg, 4.18 mmol, 1 eq) in MeOH (3 mL) was added AcOH (501.88 mg, 8.36 mmol, 477.98 uL, 2 eq) and NaBH3CN (393.90 mg, 6.27 mmol, 1.5 eq) at 25° C. The mixture was stirred at 60° C. for 16 hr. The mixture was concentrated under reduce pressure. The residue was purified by prep-HPLC (column: Phenomenex Luna C18 200*40 mm*10 um; mobile phase: [water (FA)-ACN]; B %: 25%-55%, 10 min). [Result]Compound methyl (3S)-2-[(8-tert-butoxycarbonyl-8-azabicyclo[3.2.1]octan-3-yl)methyl]-3-ethyl-5-fluoro-3,4-dihydro-1H-isoquinoline-7-carboxylate (480 mg, 896.26 umol, 21.45% yield, 86% purity) was obtained as a yellow gum. MS(ESI): 461.1 [M+H]+

To a solution of methyl (3S)-2-[(8-tert-butoxycarbonyl-8-azabicyclo[3.2.1]octan-3-yl)methyl]-3-ethyl-5-fluoro-3,4-dihydro-1H-isoquinoline-7-carboxylate (480 mg, 896.26 umol, 86% purity, 1 eq) in dioxane (5 mL) was added HCl/dioxane (4 M, 672.20 uL, 3 eq).The mixture was stirred at 25° C. for 1.5 hr. The mixture was concentrated under reduce pressure. The crude product methyl(3S)-2-(8-azabicyclo[3.2.1]octan-3-ylmethyl)-3-ethyl-5-fluoro-3,4-dihydro-1H-isoquinoline-7-carboxylate (730 mg, crude, 2HCl) was obtained as a light yellow oil and was used into the next step without further purification.

To a solution of methyl (3S)-2-(8-azabicyclo[3.2.1]octan-3-ylmethyl)-3-ethyl-5-fluoro-3,4-dihydro-1H-isoquinoline-7-carboxylate (730 mg, 1.68 mmol, 1 eq, 2HCl), HCHO (273.38 mg, 3.37 mmol, 250.81 uL, 37% purity, 2 eq) in MeOH (10 mL) was added AcOH (202.30 mg, 3.37 mmol, 192.67 uL, 2 eq) and NaBH3CN (158.78 mg, 2.53 mmol, 1.5 eq). The mixture was stirred at 25° C. for 12 hr. The mixture was concentrated under reduce pressure. The residue was purified by prep-HPLC (column: Phenomenex luna C18 150*25 mm*10 um; mobile phase: [water(FA)-ACN]; B %: 0%-20%, 10.5 min). Compound methyl (3S)-3-ethyl-5-fluoro-2-[(8-methyl-8-azabicyclo[3.2.1]octan-3-yl)methyl]-3,4-dihydro-1H-isoquinoline-7-carboxylate (240 mg, 640.87 umol, 38.05% yield, 100% purity) was obtained as light-yellow oil. MS(ESI): 375.3[M+H]+

To a solution of methyl (3S)-3-ethyl-5-fluoro-2-[(8-methyl-8-azabicyclo[3.2.1]octan-3-yl)methyl]-3,4-dihydro-1H-isoquinoline-7-carboxylate (100 mg, 267.03 umol, 1 eq) in MeOH (5 mL) was added HYDROXYLAMINE (352.80 mg, 5.34 mmol, 50% purity, 20 eq) and KOH (22.47 mg, 400.54 umol, 1.5 eq). The mixture was stirred at 25° C. for 12 hr. The mixture was concentrated under reduce pressure. The residue was purified by prep-HPLC (column: Waters Atlantis T3 150*30 mm*5 um; mobile phase: [water(TFA)-ACN]; B %: 0%-30%, 10 min). Compound (3S)-3-ethyl-5-fluoro-2-[(8-methyl-8-azabicyclo[3.2.1]octan-3-yl)methyl]-3,4-dihydro-1H-isoquinoline-7-carbohydroxamic acid (570) (46.45 mg, 123.51 umol, 46.25% yield, 99.84% purity) was obtained as a yellow gum.

(3R)-3-ethyl-5-fluoro-2-[(8-methyl-8-azabicyclo[3.2.1] octan-3-yl)methyl]-3,4-dihydro-1H-isoquinoline-7-carbohydroxamic acid (571) was prepared in an analogous manner.

To a solution of methyl (3R)-3-ethyl-5-fluoro-2-[(8-methyl-8-azabicyclo[3.2.1]octan-3-yl)methyl]-3,4-dihydro-1H-isoquinoline-7-carboxylate (300 mg, 793.08 umol, 99% purity, 1 eq) in MeOH (3 mL) was added KOH (88.99 mg, 1.59 mmol, 2 eq) and hydroxylamine (1.05 g, 15.86 mmol, 50% purity, 20 eq). The mixture was stirred at 25° C. for 16 hr. The reaction mixture was concentrated under reduced pressure to remove solvent. The residue was purified by prep-HPLC (column: Waters Atlantis T3 150*30 mm*5 um; mobile phase: [water(TFA)-ACN]; B %: 0%-30%, 10 min). (R)-3-ethyl-5-fluoro-N-hydroxy-2-(((1R,3r,5S)-8-methyl-8-azabicyclo[3.2.1]octan-3-yl)methyl)-1,2,3,4-tetrahydroisoquinoline-7-carboxamide (572) (174 mg, 351.91 umol, 44.37% yield, 99% purity, TFA) was obtained as a white solid.

To a solution of methyl (3S)-3-ethyl-5-fluoro-2-[(8-methyl-8-azabicyclo[3.2.1]octan-3-yl)methyl]-3,4-dihydro-1H-isoquinoline-7-carboxylate (80 mg, 213.62 umol, 1 eq) in MeOH (2 mL) was added KOH (23.97 mg, 427.25 umol, 2 eq) and hydroxylamine (282.24 mg, 4.27 mmol, 50% purity, 20 eq). The mixture was stirred at 25° C. for 12 hr. The reaction mixture was concentrated under reduced pressure to remove solvent. The residue was purified by prep-HPLC column: Waters Atlantis T3 150*30 mm*5 um; mobile phase: [water (TFA)-ACN]; B %: 0%-15%, 10 min. (S)-3-ethyl-5-fluoro-N-hydroxy-2-(((1R,3s,5S)-8-methyl-8-azabicyclo[3.2.1]octan-3-yl)methyl)-1,2,3,4-tetrahydroisoquinoline-7-carboxamide (573) (13 mg, 26.03 umol, 12.18% yield, 98% purity, TFA) was obtained as a yellow solid.

| | | |
|---|---|---|
| 570 | 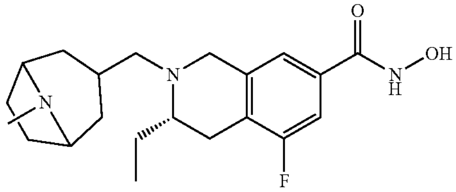 (3S)-3-ethyl-5-fluoro-2-[(8-methyl-8-azabicyclo[3.2.1]octan-3-yl)methyl]-3,4-dihydro-1H-isoquinoline-7-carbohydroxamic acid | $^{1}$H NMR (400 MHz, METHANOL-d4) δ ppm 7.43-7.53 (m, 2 H) 4.38-4.50 (m, 2 H) 3.87-3.94 (m, 2 H) 3.59-3.71 (m, 1 H) 3.19-3.27 (m, 2 H) 2.93-3.07 (m, 2 H) 2.80 (s, 3 H) 2.36-2.48 (m, 5 H) 1.90-2.12 (m, 5 H) 1.58-1.67 (m, 1 H) 1.12 (t, J=7.32 Hz, 3 H)MS (ESI): 376.3 [M + H]+. Absolute stereochemistry is unknown. |
| 571 | 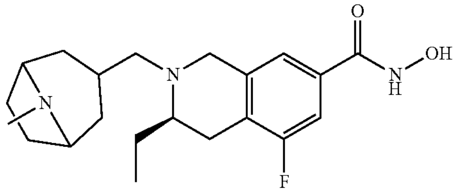 (3R)-3-ethyl-5-fluoro-2-[(8-methyl-8-azabicyclo[3.2.1]octan-3-yl)methyl]-3,4-dihydro-1H-isoquinoline-7-carbohydroxamic acid | $^{1}$H NMR (400 MHz, METHANOL-d4) δ ppm 7.43-7.53 (m, 2 H) 4.38-4.50 (m, 2 H) 3.87-3.94 (m, 2 H) 3.59-3.71 (m, 1 H) 3.19-3.27 (m, 2 H) 2.93-3.07 (m, 2 H) 2.80 (s, 3 H) 2.36-2.48 (m, 5 H) 1.90-2.12 (m, 5 H) 1.58-1.67 (m, 1 H) 1.12 (t, J=7.32 Hz, 3 H)MS (ESI): 376.3 [M + H]+. Absolute stereochemistry is unknown. |
| 572 | 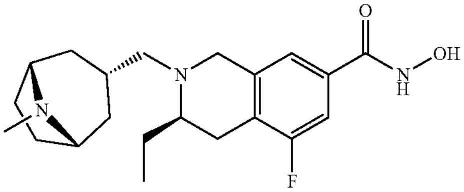 (R)-3-ethyl-5-fluoro-N-hydroxy-2-(((1R,3r,5S)-8-methyl-8-azabicyclo[3.2.1]octan-3-yl)methyl)-1,2,3,4-tetrahydroisoquinoline-7-carboxamide | $^{1}$H NMR (400 MHz, METHANOL-d4) δ = 7.54 (s, 1H), 7.48 (d, J = 9.9 Hz, 1H), 4.62 (bs, 2H), 3.95 (bdd, J = 3.6, 7.2 Hz, 2H), 3.79 (bd, J = 4.8 Hz, 1H), 3.28 (bd, J = 4.9 Hz, 1H), 3.22-3.14 (m, 1H), 3.11-2.97 (m, 2H), 2.79 (s, 3H), 2.51 (bdd, J = 5.8, 11.1 Hz, 1H), 2.41-2.29 (m, 2H), 2.21-2.10 (m, 3H), 2.05-1.93 (m, 2H), 1.88-1.76 (m, 2H), 1.75-1.65 (m, 1H), 1.12 (t, J = 7.4 Hz, 3H). MS(ESI): 376.2 [M + H]+. Absolute stereochemistry is unknown. |
| 573 | 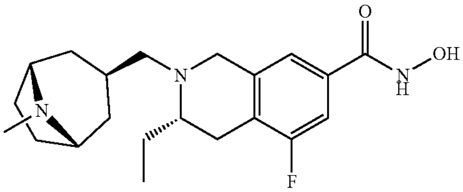 (S)-3-ethyl-5-fluoro-N-hydroxy-2-(((1R,3s,5S)-8-methyl-8-azabicyclo[3.2.1]octan-3-yl)methyl)-1,2,3,4-tetrahydroisoquinoline-7-carboxamide | $^{1}$H NMR (400 MHz, METHANOL-d4) δ = 7.55 (s, 1H), 7.52-7.45 (m, 1H), 4.64 (br s, 2H), 3.97 (br dd, J = 3.8, 7.4 Hz, 2H), 3.81 (br d, J = 5.6 Hz, 1H), 3.32 (br s, 1H), 3.26-3.16 (m, 1H), 3.12-2.98 (m, 2H), 2.80 (s, 3H), 2.60-2.49 (m, 1H), 2.43-2.30 (m, 2H), 2.23-2.12 (m, 3H), 2.07-1.96 (m, 2H), 1.88-1.77 (m, 2H), 1.75-1.64 (m, 1H), 1.13 (t, J = 7.4 Hz, 3H). MS(ESI): 376.1 [M + H]+. Absolute stereochemistry is unknown. |

(3R)-3-ethyl-5-fluoro-2-(7-methyl-7-azaspiro[3.5]nonan-2-yl)-3,4-dihydro-1H-isoquinoline-7-carbohydroxamic acid (594)

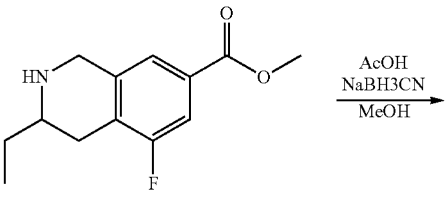

-continued

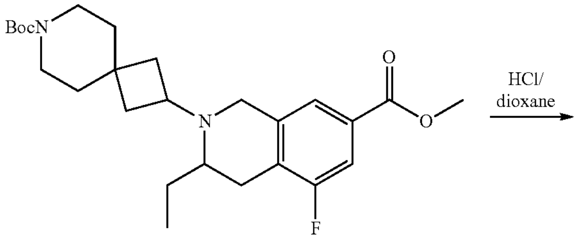

-continued

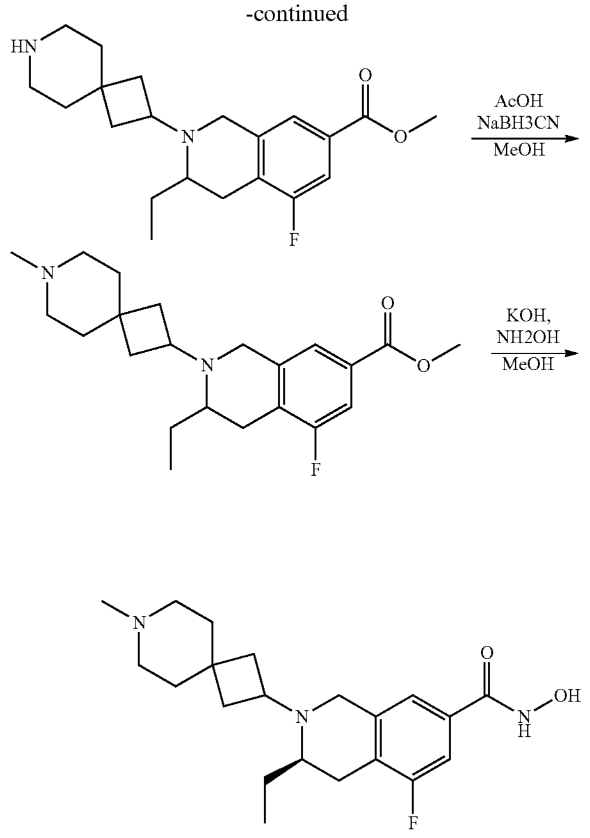

594

To a solution of methyl (3R)-3-ethyl-5-fluoro-1,2,3,4-tetrahydroisoquinoline-7-carboxylate (991.47 mg, 4.18 mmol, 1 eq) in MeOH (10 mL) was added tert-butyl 2-oxo-7-azaspiro[3.5]nonane-7-carboxylate (1 g, 4.18 mmol, 1 eq), AcOH (501.88 mg, 8.36 mmol, 477.98 uL, 2 eq) and stirred at 25° C. for 2 hr, then was added NaBH3CN (341.38 mg, 5.43 mmol, 1.3 eq).The mixture was stirred at 25° C. for 16 hr. The mixture was concentrated under reduced pressure. The residue was purified by flash silica gel chromatography (ISCO®; 25 g SepaFlash® Silica Flash Column, Eluent of 0-60% Ethylacetate/Petroleum ether gradient @ 60 mL/min). Compound methyl (3R)-2-(7-tertbutoxycarbonyl-7-azaspiro[3.5]nonan-2-yl)-3-ethyl-5-fluoro-3,4-dihydro-1H-isoquinoline-7-carboxylate (1.3 g, 2.68 mmol, 64.17% yield, 95% purity) was obtained as a colorless oil. MS(ESI): 461.8 [M+H]+

To a solution of methyl (3R)-2-(7-tert-butoxycarbonyl-7-azaspiro[3.5]nonan-2-yl)-3-ethyl-5-fluoro-3,4-dihydro-1H-isoquinoline-7-carboxylate (1.3 g, 2.68 mmol, 95% purity, 1 eq) in HCl/dioxane (4 M, 10 mL, 14.92 eq) was stirred at 25° C. for 2 hr. The mixture was concentrated under reduced pressure. The crude product methyl (3R)-2-(7-azaspiro[3.5]nonan-2-yl)-3-ethyl-5-fluoro-3,4-dihydro-1H-isoquinoline-7-carboxylate (1.1 g, crude, HCl) as white solid was used into the next step without further purification. MS(ESI): 361.3 [M+H]+

To a solution of methyl (3R)-2-(7-azaspiro[3.5]nonan-2-yl)-3-ethyl-5-fluoro-3,4-dihydro-1H-isoquinoline-7-carboxylate (300 mg, 832.26 umol, 1 eq) in MeOH (10 mL) was added formaldehyde (67.54 mg, 832.26 umol, 61.96 uL, 37% purity, 1 eq) and AcOH (99.96 mg, 1.66 mmol, 95.20 uL, 2 eq) the mixture was stirred at 25° C. for 2 hr and then was added NaBH3CN (67.99 mg, 1.08 mmol, 1.3 eq). The mixture was stirred at 25° C. for 16 hr. The mixture was concentrated under reduced pressure. The residue was purified by prep-TLC (SiO2, Petroleum ether:Ethyl acetate=1:1). Compound methyl (3R)-3-ethyl-5-fluoro-2-(7-methyl-7-azaspiro[3.5]nonan-2-yl)-3,4-dihydro-1H-isoquinoline-7-carboxylate (130 mg, 336.72 umol, 40.46% yield, 97% purity) was obtained as a colorless oil. MS(ESI): 375.2 [M+H]+

To a solution of methyl (3R)-3-ethyl-5-fluoro-2-(7-methyl-7-azaspiro[3.5]nonan-2-yl)-3,4-dihydro-1H-isoquinoline-7-carboxylate (130 mg, 336.72 umol, 97% purity, 1 eq) in MeOH (5 mL) was added hydroxylamine (444.88 mg, 6.73 mmol, 50% purity, 20 eq) and KOH (37.78 mg, 673.45 umol, 2 eq).The mixture was stirred at 25° C. for 3 hr. The mixture was concentrated under reduced pressure. The residue was purified by prep-HPLC (column: Welch Xtimate C18 150*25 mm*5 um; mobile phase: [water (TFA)-ACN]; B %: 0%-20%, 10 min). Compound (3R)-3-ethyl-5-fluoro-2-(7-methyl-7-azaspiro[3.5]nonan-2-yl)-3,4-dihydro-1H-isoquinoline-7-carbohydroxamic acid (40.52 mg, 107.42 umol, 31.90% yield, 99.542% purity) was obtained as a white solid.

(3S)-3-ethyl-5-fluoro-2-(7-methyl-7-azaspiro[3.5]nonan-2-yl)-3,4-dihydro-1H-isoquinoline-7-carbohydroxamic acid (595) was prepared in an analogous manner.

| | | |
|---|---|---|
| 594 | 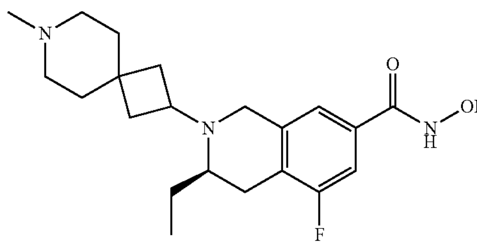<br>(3R)-3-ethyl-5-fluoro-2-(7-methyl-7-azaspiro[3.5]nonan-2-yl)-3,4-dihydro-1H-isoquinoline-7-carbohydroxamic acid | $^1$H NMR (400 MHz, METHANOL-d4) δ = 7.53-7.46 (m, 2H), 4.44(s, 2H), 4.02 (bs, 1H), 3.74 (bs, 1H), 3.48-3.37 (m, 2H), 3.27-3.08 (m, 2H), 3.07-2.92 (m, 2H), 2.85 (s, 3H), 2.55(s, 1H), 2.38-2.23 (m, 3H), 2.10-2.01 (m, 1H), 1.98-1.89 (m, 3H), 1.88-1.78 (m, 1H), 1.65(s, 1H), 1.09 (m, 3H). MS(ESI): 376.2 [M + H]+.<br>Absolute stereochemistry is unknown. |

-continued

| | | |
|---|---|---|
| 595 | 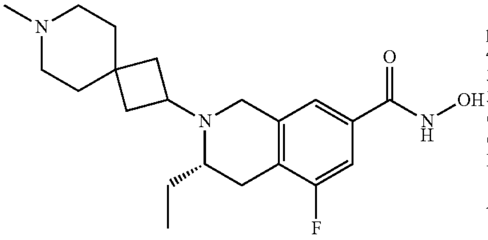<br>(3S)-3-ethyl-5-fluoro-2-(7-methyl-7-azaspiro[3.5]nonan-2-yl)-3,4-dihydro-1H-isoquinoline-7-carbohydroxamic acid | $^1$H NMR (400 MHz, METHANOL-d4) δ ppm 7.48-7.56 (m, 2 H) 4.44 (s, 2 H) 4.04 (s, 1 H) 3.69-3.84 (m, 1 H) 3.39-3.48 (m, 2 H) 3.12-3.25 (m, 2 H) 2.94-3.06 (m, 2 H) 2.88 (s, 3 H) 2.51-2.61 (m, 1 H) 2.25-2.38 (m, 3 H) 2.03-2.14 (m, 1 H) 1.82-1.97 (m, 4 H) 1.58 (s, 1 H) 1.11 (m, 3 H) MS (ESI): 376.1 [M + H]+.<br>Absolute stereochemistry is unknown. |

The following compounds were prepared in a manner analogous to that used for preparing compounds of Formula (II) above. Although certain compounds are designated as having absolute stereochemistry as each stereoisomer was prepared and isolated, the absolute stereochemistry of each is unknown.

| Compound | Structure/Name | Characterization |
|---|---|---|
| 228 | 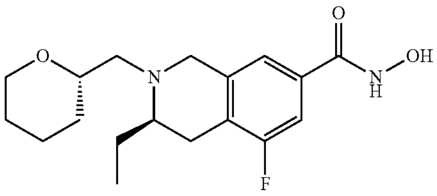<br>(3R)-3-ethyl-5-fluoro-2-[[(2S)-tetrahydropyran-2-yl]methyl]-3,4-dihydro-1H-isoquinoline-7-carbohydroxamic acid | 1H NMR (400 MHz, METHANOL-d4) δ = 7.49-7.38 (m, 2H), 4.65 (br s, 2H), 4.05-3.98 (m, 1H), 3.90-3.67 (m, 2H), 3.62-3.37 (m, 2H), 3.06-2.98 (m, 1H), 2.96-2.88(m,2H) 2.09-1.86 (m, 2H), 1.75-1.53 (m, 5H), 1.38-1.21 (m, 1H), 1.11-1.09 (m, 3H). MS(ESI): 337.2 [M + H]+.<br>Absolute stereochemistry is unknown. |
| 229 | 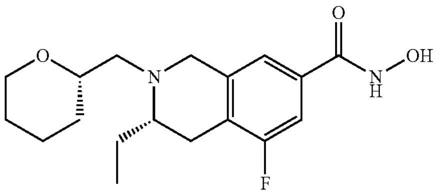<br>(3R)-3-ethyl-5-fluoro-2-[[(2R)-tetrahydropyran-2-yl]methyl]-3,4-dihydro-1H-isoquinoline-7-carbohydroxamic acid | 1H NMR (400 MHz, METHANOL-d4) δ = 7.57-7.46 (m, 2H), 4.68-4.58 (m, 2H), 4.08-3.98 (M, 1H), 3.82-3.68 (m, 2H), 3.62-3.52 (m, 1H), 3.27-3.15 (m, 2H), 3.02-2.85 (m, 2H), 1.96-1.85 (m, 2H), 1.84-1.74 (m, 1H), 1.64-1.55 (m, 4H), 1.35-1.23 (m, 1H), 1.12-1.08 (M, 3H). MS(ESI): 337.1 [M + H]+.<br>Absolute stereochemistry is unknown. |
| 232 | 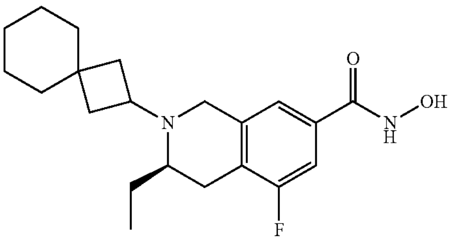<br>(3R)-3-ethyl-5-fluoro-2-spiro[3.5]nonan-2-yl-3,4-dihydro-1H-isoquinoline-7-carbohydroxamic acid | 1H NMR (400 MHz, METHANOL-d4) δ = 7.55-7.46 (m, 2H), 4.66-4.45 (m, 1H), 4.37-4.19 (m, 1H), 4.07-3.59 (m, 2H), 3.27-2.96 (m, 2H), 2.32 (b s, 2H), 2.07-1.85 (m, 3H), 1.58-1.39 (m, 11H), 1.08 (b s, 3H). MS(ESI): 361.2 [M + H]+.<br>Absolute stereochemistry is unknown. |

-continued

| Compound | Structure/Name | Characterization |
| --- | --- | --- |
| 233 | 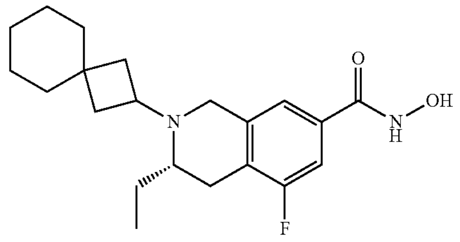 (3S)-3-ethyl-5-fluoro-2-spiro[3.5]nonan-2-yl-3,4-dihydro-1H-isoquinoline-7-carbohydroxamic acid | 1H NMR (400 MHz, METHANOL-d4) δ = 7.53-7.46 (m, 2H), 4.65-4.20 (m, 2H), 4.04-3.59 (m, 2H), 3.24-2.98 (m, 2H), 2.32 (br s, 2H), 2.08-1.99 (m, 2H), 1.91-1.88 (m, 1H), 1.59-1.46 (m, 7H), 1.42 (br s, 4H), 1.08-1.01 (m, 3H). MS(ESI): 361.1 [M + H]+. Absolute stereochemistry is unknown. |
| 507 | 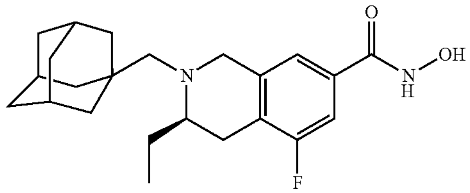 (3R)-2-(1-adamantylmethyl)-3-ethyl-5-fluoro-3,4-dihydro-1H-isoquinoline-7-carbohydroxamic acid | 1H NMR (400 MHz, METHANOL-d4) δ = 7.54 (s, 1H), 7.49-7.40 (m, 1H), 4.76-4.68 (m, 1H), 4.49-4.40 (m, 1H), 3.78-3.61 (m, 1H), 3.41-3.32 (m, 1H), 3.14-3.03 (m, 1H), 2.98-2.86 (m, 1H), 2.59-2.49 (m, 1H), 2.06 (br s, 3H), 1.94-1.86 (m, 1H), 1.77-1.62 (m, 10H), 1.67-1.62 (m, 3H), 1.13-1.12 (m, 3H). MS(ESI): 387.2 [M + H]+. Absolute stereochemistry is unknown. |
| 508 | 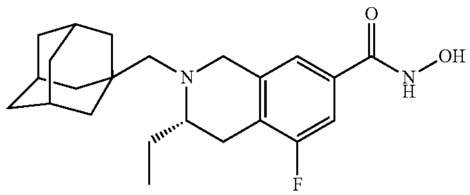 (3S)-2-(1-adamantylmethyl)-3-ethyl-5-fluoro-3,4-dihydro-1H-isoquinoline-7-carbohydroxamic acid | 1H NMR (400 MHz, METHANOL-d4) δ ppm 7.57 (s, 1 H) 7.52-7.48 (m, 1 H) 4.76-4.70 (m, 1 H) 4.48-4.45 (m, 1 H) 3.70-3.78 (m, 1 H) 3.35-3.42 (m, 1 H) 3.09-3.16 (m, 1 H) 2.96-2.88 (m, 1 H) 2.59-2.52 (m, 1 H) 2.09 (br s, 3 H) 1.92-1.88 (m, 1 H) 1.82-1.75 (m, 3 H) 1.78-1.65 (m, 7 H) 1.64-1.71 (m, 3 H) 1.16-1.08 (m, 3 H)MS (ESI): 387.2 [M + H]+. Absolute stereochemistry is unknown. |
| 517 | 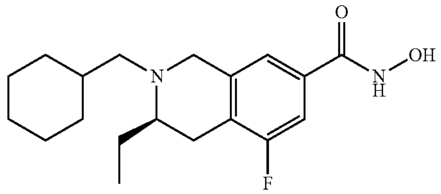 (3R)-2-(cyclohexylmethyl)-3-ethyl-5-fluoro-3,4-dihydro-1H-isoquinoline-7-carbohydroxamic acid | 1H NMR (400 MHz, METHANOL-d4) δ = 7.52 (s, 1H), 7.48-7.38 (m, 1H), 4.60-4.52 (m, 2H), 3.78 (bs, 1H), 3.30-3.21 (m, 1H), 3.17-2.99 (m, 2H), 2.87 (bs, 1H), 1.95 (bs, 3H), 1.85-1.67 (m, 6H), 1.44-1.32 (m, 2H), 1.30-1.21 (m, 1H), 1.12-1.08 (m, 3H), 1.09-1.02 (m, 1H). MS(ESI): 335.4 [M + H]+. Absolute stereochemistry is unknown. |
| 518 | 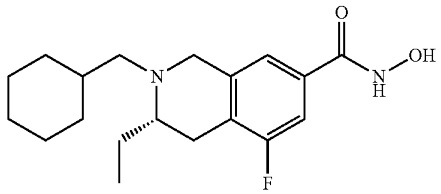 (3S)-2-(cyclohexylmethyl)-3-ethyl-5-fluoro-3,4-dihydro-1H-isoquinoline-7-carbohydroxamic acid | 1H NMR (400 MHz, METHANOL-d4) δ ppm 7.47-7.58 (m, 2 H) 4.56-4.63 (m, 1 H) 3.70-3.84 (m, 1 H) 3.22-3.32 (m, 2 H) 3.04-3.20 (m, 2 H) 2.81-2.99 (m, 1 H) 1.71-1.99 (m, 8 H) 1.34-1.47 (m, 2 H) 1.24-1.33 (m, 1 H) 1.06-1.18 (m, 5 H)MS (ESI): 335.2 [M + H]+. Absolute stereochemistry is unknown. |

-continued

| Compound | Structure/Name | Characterization |
| --- | --- | --- |
| 523 | 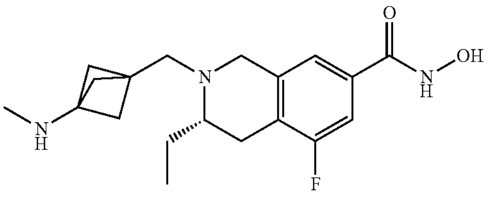 (3S)-3-ethyl-5-fluoro-2-[[3-(methylamino)-1-bicyclo[1.1.1]pentanyl]methyl]-3,4-dihydro-1H-isoquinoline-7-carbohydroxamic acid | 1H NMR (400 MHz, METHANOL-d4) δ = 7.56 (s, 1H), 7.51 (d, J = 9.8 Hz, 1H), 4.65-4.48 (m, 2H), 3.83-3.73 (m, 1H), 3.65-3.58 (m, 1H), 3.54-3.42 (m, 1H), 3.29-3.19 (m, 1H), 3.02-2.97 (m, 1H), 2.70 (s, 3H), 2.35-2.29 (m, 6H), 2.04-1.93 (m, 1H), 1.75-1.63 (m, 1H), 1.13 (t, J = 7.4 Hz, 3H) MS(ESI): 348.3 [M + H]+. Absolute stereochemistry is unknown. |
| 524 | 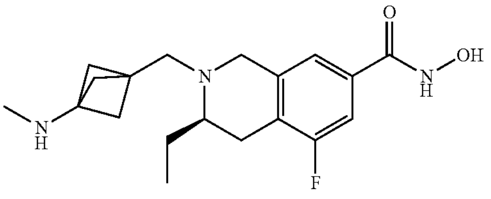 (3R)-3-ethyl-5-fluoro-2-[[3-(methylamino)-1-bicyclo[1.1.1 ]pentanyl]methyl]-3,4-dihydro-1H-isoquinoline-7-carbohydroxamic acid | 1H NMR (400 MHz, METHANOL-d4) δ = 7.47-7.56 (m, 2 H), 4.59-4.48 (m, 2 H), 3.82-3.72 (m, 1 H), 3.68-3.15 (m, 3 H), 2.69-2.52 (m, 1 H),2.50-2.42(m, 1 H) 2.36-2.29 (m, 6 H), 2.27-2.27 (m, 1 H), 2.06-1.96 (m, 1 H), 1.76-1.64 (m, 2 H), 1.13 (t, J = 7.4 Hz, 3 H). MS(ESI): 348.2 [M + H]+. Absolute stereochemistry is unknown. |
| 525 | 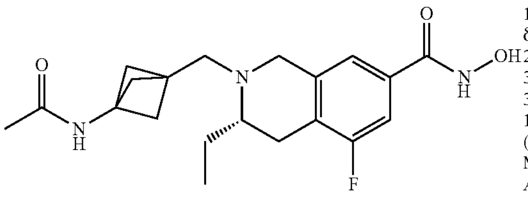 N-[3-[[(3S)-3-ethyl-5-fluoro-7-(hydroxycarbamoyl)-3,4-dihydro-1H-isoquinolin-2-yl]methyl]-1-bicyclo[1.1.1]pentanyl]acetamide | 1H NMR (400 MHz, METHANOL-d4) δ = 7.60-7.43 (m, 2H), 4.56-4.48 (m, 2H), 3.80 (br s, 1H), 3.57-3.55 (m, 1H), 3.32-3.28 (m, 1H), 3.27-3.18 (m, 1H), 3.02-2.98 (m, 1H), 2.24 (s, 6H), 1.95-1.88 (m, 1H), 1.89 (s, 3H), 1.77-1.62 (m, 1H), 1.11 (t, J = 7.4 Hz, 3H). MS(ESI): 376.4 [M + H]+. Absolute stereochemistry is unknown. |
| 527 | 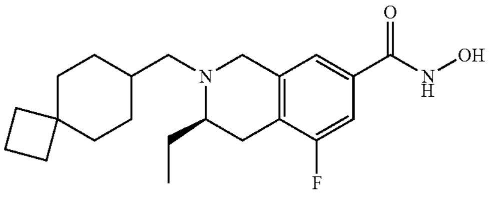 (3R)-3-ethyl-5-fluoro-2-(spiro[3.5]nonan-7-ylmethyl)-3,4-dihydro-1H-isoquinoline-7-carbohydroxamic acid | 1H NMR (400 MHz, METHANOL-d4) δ = 7.58-7.48 (m, 2H), 4.72-4.51 (m, 2H), 3.84-3.71 (m, 1H), 3.30-3.23 (m, 1H), 3.18-2.99 (m, 2H), 2.96-2.76 (m, 1H), 2.00-1.85 (m, 5H), 1.83-1.71 (m, 7H), 1.65-1.50 (m, 1H), 1.47-1.29 (m, 2H), 1.26-1.04 (m, 5H). MS(ESI): 375.0 [M + H]+. Absolute stereochemistry is unknown. |
| 528 | 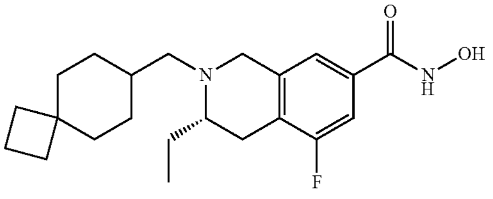 (3S)-3-ethyl-5-fluoro-2-(spiro[3.5]nonan-7-ylmethyl)-3,4-dihydro-1H-isoquinoline-7-carbohydroxamic acid | 1H NMR (400 MHz, METHANOL-d4) δ = 7.61-7.44 (m, 2H), 4.79-4.48 (m, 2H), 3.91-3.65 (m, 1H), 3.32-3.20 (m, 1H), 3.19-2.77 (m, 3H), 1.93-1.84 (m, 5H), 1.78 (dt, J = 6.8, 14.3 Hz, 7H), 1.68-1.50 (m, 1H), 1.46-1.33 (m, 2H), 1.22-1.07 (m, 5H). MS(ESI): 375.3 [M + H]+. Absolute stereochemistry is unknown. |

-continued

| Compound | Structure/Name | Characterization |
|---|---|---|
| 529 | 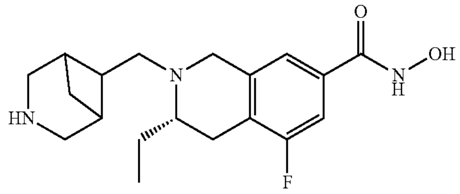 (3S)-2-(3-azabicyclo[3.1.1]heptan-6-ylmethyl)-3-ethyl-5-fluoro-3,4-dihydro-1H-isoquinoline-7-carbohydroxamic acid | 1H NMR (400 MHz, METHANOL-d4) δ = 7.56 (s, 1H), 7.44 (d, J = 9.9 Hz, 1H) 4.57 (br s, 2H), 3.84 (br d, J = 5.5 Hz, 1H), 3.56-3.32 (m, 6H), 3.30-3.19 (m, 1H), 3.09-3.07 (m, 1H), 2.90-2.89 (m, 1H), 2.77-2.64 (m, 2H), 2.42-2.33 (m, 1H), 2.09-1.96 (m, 1H), 1.82-1.65 (m, 2H), 1.12-1.10(m, 3H). MS(ESI): 348.2 [M + H]+. Absolute stereochemistry is unknown. |
| 549 | 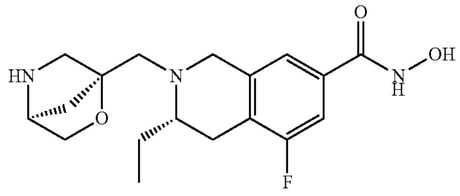 (3S)-3-ethyl-5-fluoro-2-[[(1S,4S)-2-oxa-5-azabicyclo[2.2.1]heptan-1-yl]methyl]-3,4-dihydro-1H-isoquinoline-7-carbohydroxamic acid | 1H NMR (400 MHz, METHANOL-d4) δ = 7.53-7.45 (m, 2H), 4.67-4.55 (m, 2H), 4.53-4.48 (m, 1H), 4.20-4.13 (m, 1H), 4.13-4.07 (m, 1H), 3.85-3.69 (m, 2H), 3.58-3.47 (m, 2H), 3.44-3.38 (m, 1H), 3.31-3.25 (m, 1H), 2.99-2.88 (m, 1H), 2.47-2.38 (m, 1H), 2.15 (bd, J = 11.3 Hz, 1H), 2.02-1.89 (m, 1H), 1.79-1.65 (m, 1H), 1.13 (t, J = 7.4 Hz, 3H). MS(ESI): 350.1 [M + H]+. Absolute stereochemistry is unknown. |
| 576 | 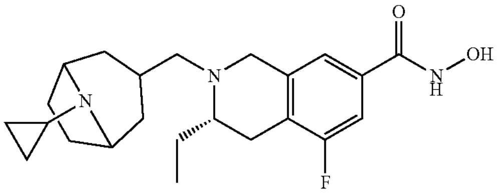 (3S)-2-[(8-cyclopropyl-8-azabicyclo[3.2.1]octan-3-yl)methyl]-3-ethyl-5-fluoro-3,4-dihydro-1H-isoquinoline-7-carbohydroxamic acid | 1H NMR (400 MHz, METHANOL-d4) δ = 7.58-7.52 (m, 1H), 7.50-7.46 (m, 1H), 4.66-4.54 (m, 2H), 4.20-4.07 (m, 2H), 3.79 (s, 1H), 3.29- (m, 1H), 3.17-3.09 (m, 1H), 3.08-3.02 (m, 1H), 2.85 (bs, 1H), 2.62-2.36 (m, 4H), 2.26-2.13 (m, 3H), 2.09-1.91 (m, 3H), 1.88-1.79 (m, 1H), 1.74-1.65 (m, 1H), 1.17-1.08 (m, 5H), 0.99 (bd, J = 6.1 Hz, 2H). MS(ESI):402.2 [M + H]+ Absolute stereochemistry is unknown. |
| 580 | 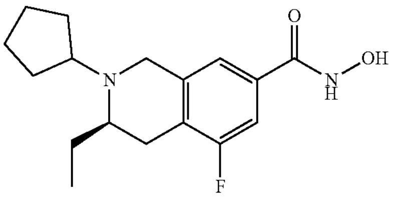 (3R)-2-cyclopentyl-3-ethyl-5-fluoro-3,4-dihydro-1H-isoquinoline-7-carbohydroxamic acid | 1H NMR (400 MHz, METHANOL-d4) δ = 7.60-7.43 (m, 2H), 4.75-4.57 (m, 1H), 4.54-4.34 (m, 1H), 4.01-3.69 (m, 2H), 3.29-3.04 (m, 2H), 2.37-2.11 (m, 2H), 2.04-1.51 (m, 8H), 1.08 (bs, 3H). MS(ESI): 307.2 [M + H]+. Absolute stereochemistry is unknown. |
| 581 | 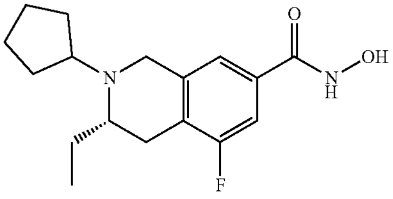 (3S)-2-cyclopentyl-3-ethyl-5-fluoro-3,4-dihydro-1H-isoquinoline-7-carbohydroxamic acid | 1H NMR (400 MHz, METHANOL-d4) δ = 7.50 (br s, 2H), 4.73-4.60 (m, 1H), 4.51-4.37 (m, 1H), 3.96-3.70 (m, 2H), 3.29-3.21 (m, 1H), 3.19-3.12 (m, 1H), 2.28-2.02 (m, 2H), 2.09-1.83 (m, 4H), 1.83-1.66 (m, 4H), 1.08 (br s, 3H). MS(ESI): 307.2 [M + H]+. Absolute stereochemistry is unknown. |

-continued

| Compound | Structure/Name | Characterization |
|---|---|---|
| 582 | 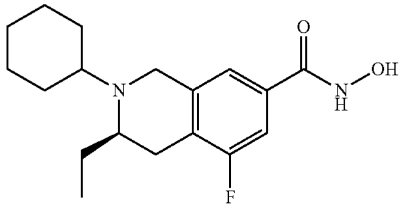 (3R)-2-cyclohexyl-3-ethyl-5-fluoro-3,4-dihydro-1H-isoquinoline-7-carbohydroxamic acid | 1H NMR (400 MHz, METHANOL-d4) δ = 7.61-7.40 (m, 2H), 4.65-4.29 (m, 2H), 4.14-3.75 (m, 1H), 3.53-3.40 (m, 1H), 3.28-2.97 (m, 2H), 2.45-2.20 (m, 1H), 2.11 (br s, 1H), 2.06-1.94 (m, 3H), 1.74 (bd, J = 12.8 Hz, 2H), 1.61-1.35 (m, 4H), 1.33-1.19 (m, 1H), 1.10 (bs, 3H). MS(ESI): 321.2 [M + H]+. Absolute stereochemistry is unknown. |
| 583 | 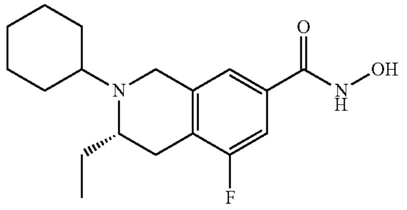 (3S)-2-cyclohexyl-3-ethyl-5-fluoro-3,4-dihydro-1H-isoquinoline-7-carbohydroxamic acid | 1H NMR (400 MHz, METHANOL-d4) δ = 7.61-7.45 (m, 2H), 4.58-4.38 (m, 2H), 4.13-3.78 (m, 1H), 3.58-3.48 (m, 1H), 3.27-3.18(m, 1H), 3.17-2.97 (m, 1H), 2.44-2.24 (m, 1H), 2.16-2.04 (m, 1H), 1.98 (br d, J = 6.5 Hz, 3H), 1.82-1.57 (m, 3H), 1.52-1.37 (m, 3H), 1.34-1.21 (m, 1H), 1.16-1.03 (m, 3H). MS(ESI): 321.1 [M + H]+. Absolute stereochemistry is unknown. |
| 590 | 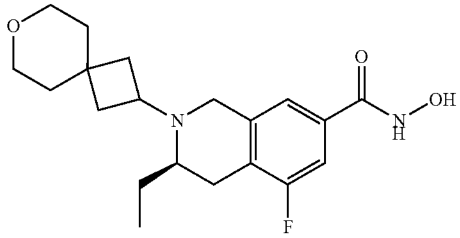 (3R)-3-ethyl-5-fluoro-2-(7-oxaspiro[3.5]nonan-2-yl)-3,4-dihydro-1H-isoquinoline-7-carbohydroxamic acid | 1H NMR (400 MHz, METHANOL-d4) δ = 7.54-7.45 (m, 2H), 4.68-4.18 (m, 2H), 4.13-3.68 (m, 2H), 3.66-3.58 (m, 2H), 3.61-3.55 (m, 2H), 3.26-2.99 (m, 2H), 2.43 (br s, 2H), 2.21-2.10 (m, 2H), 1.99-1.86 (m, 1H), 1.74-1.51 (m, 5H), 1.09 (m, 3H). MS(ESI): 363.2 [M + H]+. Absolute stereochemistry is unknown. |
| 591 | 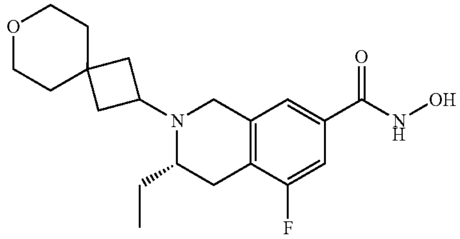 (3S)-3-ethyl-5-fluoro-2-(7-oxaspiro[3.5]nonan-2-yl)-3,4-dihydro-1H-isoquinoline-7-carbohydroxamic acid | 1H NMR (400 MHz, METHANOL-d4) δ ppm 7.48-7.57 (m, 2 H) 4.64 (m, 2 H) 4.02 (s, 1 H) 3.80(s, 1 H) 3.56-3.69 (m, 4 H) 3.10-3.29 (m, 2 H) 2.46 (s, 2 H) 2.2(s, 2 H) 1.88-2.03 (s, 1 H) 1.57-1.78 (m, 5 H) 1.06-1.17 (m, 3 H)MS (ESI): 363.1 [M + H]+. Absolute stereochemistry is unknown. |
| 592 | 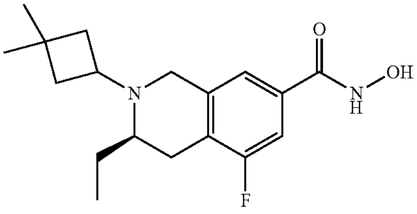 (3R)-2-(3,3-dimethylcyclobutyl)-3-ethyl-5-fluoro-3,4-dihydro-1H-isoquinoline-7-carbohydroxamic acid | 1H NMR (400 MHz, METHANOL-d4) δ = 7.54-7.45 (m, 2H), 4.64-4.17 (m, 2H), 4.11-3.59 (m, 2H), 3.26-2.97 (m, 2H), 2.34-2.12 (m, 4H), 1.93 (s, 1H), 1.70-1.39 (m, 1H), 1.21 (s, 6H), 1.08 (m, 3H) MS(ESI): 321.2 [M + H]+. Absolute stereochemistry is unknown. |

-continued

| Compound | Structure/Name | Characterization |
|---|---|---|
| 593 | 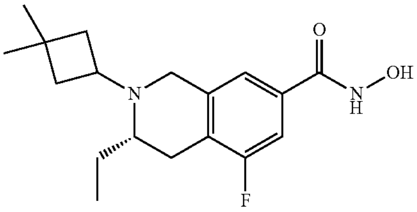 (3S)-2-(3,3-dimethylcyclobutyl)-3-ethyl-5-fluoro-3,4-dihydro-1H-isoquinoline-7-carbohydroxamic acid | 1H NMR (400 MHz, METHANOL-d4) δ ppm 7.52 (br d, J=7.88 Hz, 2 H) 4.54(s, 1 H) 4.28(s, 1 H) 3.64-4.09 (m, 2 H) 3.07-3.27 (m, 2 H) 2.28(s, 2 H) 2.14 (s, 2 H) 1.96 (s, 1 H) 1.41-1.67 (m, 1 H) 1.18-1.29 (m, 6 H) 1.10 (m, 3 H)MS (ESI): 321.2 [M + H]+. Absolute stereochemistry is unknown. |
| 596 | 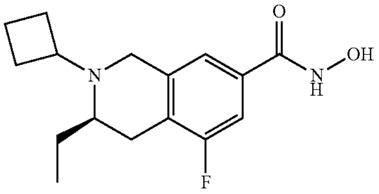 (3R)-2-cyclobutyl-3-ethyl-5-fluoro-3,4-dihydro-1H-isoquinoline-7-carbohydroxamic acid | 1H NMR (400 MHz, METHANOL-d4) δ = 7.54-7.43 (m, 2H), 4.54 (s, 1H), 4.32 (s, 1H), 4.12-3.87 (m, 1H), 3.83-3.59 (m, 1H), 3.26-2.98 (m, 2H), 2.47-2.28 (m, 4H), 1.90 (b d, J = 7.0 Hz, 3H), 1.70-1.41 (m, 1H), 1.09 (m, 3H) MS(ESI): 293.1 [M + H]+. Absolute stereochemistry is unknown. |
| 597 | 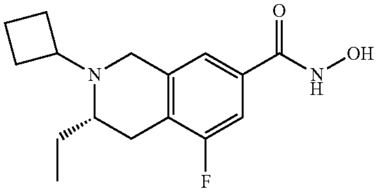 (3S)-2-cyclobutyl-3-ethyl-5-fluoro-3,4-dihydro-1H-isoquinoline-7-carbohydroxamic acid | 1H NMR (400 MHz, METHANOL-d4) δ = 7.55-7.48 (m, 2H), 4.74 (s, 1H), 4.32(s, 1H), 4.09-3.89 (m, 1H), 3.85-3.65 (m, 1H), 3.26-3.07 (m, 2H), 2.43-2.34 (m, 4H), 1.92 (br d, J = 7.1 Hz, 3H), 1.68-1.48 (m, 1H), 1.10 (m,3H). MS(ESI):293.1 [M + H]+. Absolute stereochemistry is unknown. |
| 598 | 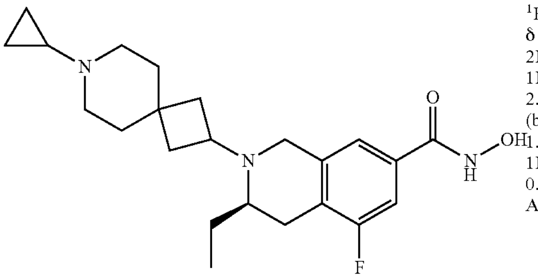 (3R)-2-(7-cyclopropyl-7-azaspiro[3.5]nonan-2-yl)-3-ethyl-5-fluoro-3,4-dihydro-1H-isoquinoline-7-carbohydroxamic acid | $^1$H NMR (400 MHz, METHANOL-d4) δ = 7.53-7.46 (m, 2H), 4.63-4.27 (m, 2H), 4.03 (bs, 1H), 3.75 (bd, J = 1.0 Hz, 1H), 3.55 (bs, 2H), 3.28-3.05 (m, 4H), 2.86-2.76 (m, 1H), 2.59 (S, 1H), 2.33 (bs, 3H), 2.16-2.02 (m, 1H), 2.00-1.87 (m, 3H), 1.82 (bd, J = 10.6 Hz, 1H), 1.54(s, 1H), 1.09 (m, 3H), 1.02-0.90 (m, 4H). MS(ESI): 402.2 [M + H]+. Absolute stereochemistry is unknown. |
| 599 | 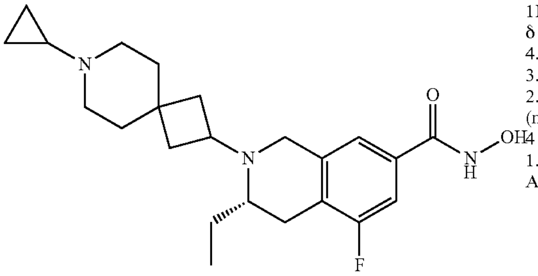 | 1H NMR (400 MHz, METHANOL-d4) δ ppm 7.49-7.55 (m, 2 H) 4.46 (s, 2 H) 4.04 (br d, J=3.88 Hz, 1 H) 3.76 (s, 1 H) 3.56 (s, 2 H) 3.13-3.27 (m, 4 H) 2.79-2.87 (m, 1 H) 2.61 (s, 1 H) 2.28-2.40 (m, 3 H) 2.04-2.15 (m, 1 H) 1.94 (br s, 4 H) 1.58 (s, 1 H) 1.11 (m, 3 H) 0.97-1.02 (m, 4 H)MS (ESI):402.2 [M + H]+. Absolute stereochemistry is unknown. |

-continued

| Compound | Structure/Name | Characterization |
|---|---|---|
| | 3S)-2-(7-cyclopropyl-7-azaspiro[3.5]nonan-2-yl)-3-ethyl-5-fluoro-3,4-dihydro-1H-isoquinoline-7-carbohydroxamic acid | |
| 600 | 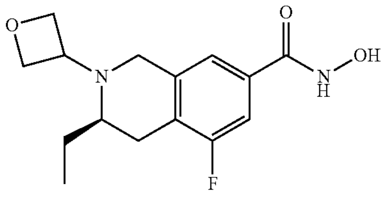 (3R)-3-ethyl-5-fluoro-2-(oxetan-3-yl)-3,4-dihydro-1H-isoquinoline-7-carbohydroxamic acid | 1H NMR (400 MHz, METHANOL-d4) δ = 7.49 (t, J = 4.3 Hz, 2H), 4.96-4.90 (m, 2H), 4.88 (s, 2H), 4.77-4.69 (m, 1H), 4.52-4.38 (m, 2H), 3.75-3.66 (m, 1H), 3.28-3.19 (m, 1H), 3.11-3.02 (m, 1H), 1.91-1.79 (m, 1H), 1.58-1.44 (m, 1H), 1.08 (m, 3H). MS(ESI): 295.1 [M + H]+. Absolute stereochemistry is unknown. |
| 601 | 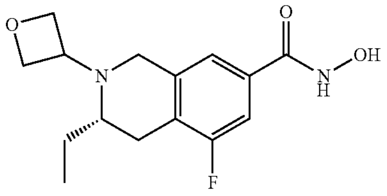 (3S)-3-ethyl-5-fluoro-2-(oxetan-3-yl)-3,4-dihydro-1H-isoquinoline-7-carbohydroxamic acid | 1H NMR (400 MHz, METHANOL-d4) δ ppm 7.57-7.45 (m, 2 H) 4.94-4.78 (m, 3 H) 4.76-4.68 (m, 2 H) 4.66-4.42 (m, 2 H) 3.7-3.54(m,1H) 3.40-3.28 (m, 1 H) 3.21-3.12 (m, 1 H) 1.87 (s, 1H) 1.62-1.50 (m, 1 H) 1.32-1.02 (m, 3 H). MS (ESI):295.1 [M + H]+ Absolute stereochemistry is unknown. |
| 602 | 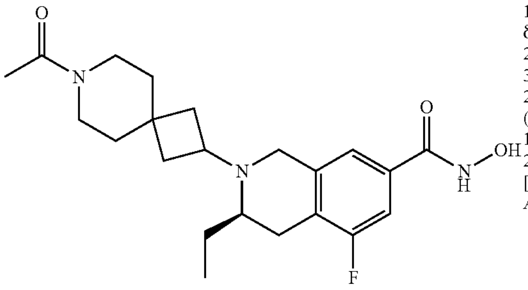 (3R)-2-(7-acetyl-7-azaspiro[3.5]nonan-2-yl)-3-ethyl-5-fluoro-3,4-dihydro-1H-isoquinoline-7-carbohydroxamic acid | 1H NMR (400 MHz, METHANOL-d4) δ = 7.54-7.46 (m, 2H), 4.67-4.20 (m, 2H), 4.15-3.65 (m, 2H), 3.57-3.47 (m, 3H), 3.46-3.42 (m, 1H), 3.20 (b s, 1H), 2.42 (b s, 2H), 2.23-2.12 (m, 2H), 2.08 (m, 3H), 2.03 (s, 2H), 1.98-1.87 (m, 1H), 1.72-1.65 (m, 2H), 1.64-1.57 (m, 2H), 1.09 (m, 3H). MS(ESI): 404.2 [M + H]+. Absolute stereochemistry is unknown. |
| 603 | 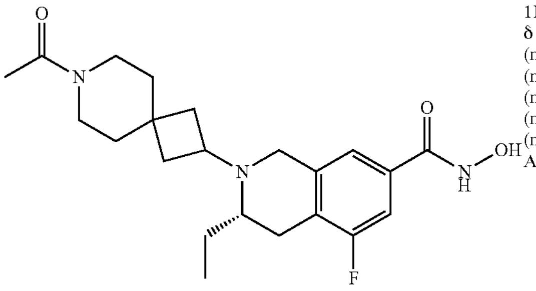 (3S)-2-(7-acetyl-7-azaspiro[3.5]nonan-2-yl)-3-ethyl-5-fluoro-3,4-dihydro-1H-isoquinoline-7-carbohydroxamic acid | 1H NMR (400 MHz, METHANOL-d4) δ ppm 7.47-7.58 (m, 2 H) 4.25-4.69 (m, 2 H) 3.66-4.17 (m, 2 H) 3.43-3.58 (m, 4 H) 3.07-3.28 (m, 2 H) 2.42-2.62 (m, 2H) 2.13-2.53 (m, 5 H) 1.88-2.00 (m, 1H) 1.53-1.78 (m, 5 H) 1.05-1.17 (m, 3H) MS (ESI):404.1 [M + H]+. Absolute stereochemistry is unknown. |

Compounds of Formula (I) and (IV) were prepared following the synthetic schemes and procedures described in detail below.

4-((2-Azaspiro[4.5]decan-2-yl)methyl)-3-fluoro-N-hydroxybenzamide (75)

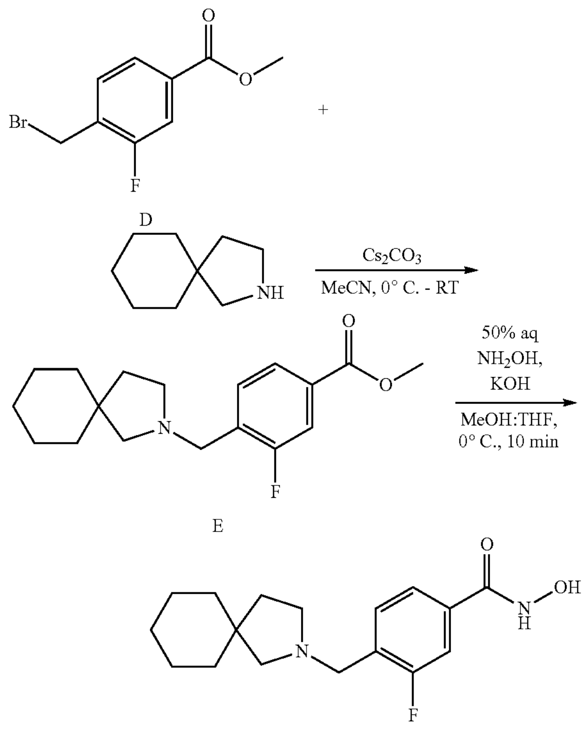

D

E

75

To a stirred solution of methyl 4-(bromomethyl)-3-fluorobenzoate (D, 150 mg, 0.6098 mmol, 1 eqiv) in acetonitrile (5 mL) was added $Cs_2CO_3$ (397 mg, 1.2196 mmol, 2.0 eqiv) and 2-azaspiro[4.5]decane (84 mg, 0.6098 mmol, 1 equiv) at room temperature. The reaction was stirred at room temperature for 2h, then quenched with water (10 mL) and extracted with ethyl acetate (10 mL×3). The combined organic phases were washed with brine (10 mL), dried over anhydrous sodium sulphate, filtered and concentrated in vacuo. The residue was purified by a flash silica gel column chromatography. The product was eluted at 5% EtOAc in hexane to give 4-((2-azaspiro[4.5]decan-2-yl)methyl)-3-fluorobenzoate (E) as a colorless oil (110 mg, 0.3604 mmol, 59%). $^1$H NMR (400 MHz, $CDCl_3$) δ 7.81 (dd, J=8.0, 1.7 Hz, 1H), 7.69 (dd, J=10.4, 1.7 Hz, 1H), 7.55 (s, 1H), 3.93 (s, 3H), 3.71 (s, 2H), 2.62 (s, 2H), 2.39 (s, 2H), 1.41 (d, J=18.8 Hz, 12H), 1.27 (t, J=3.5 Hz, 1H). MS (ESI): 305 $[M+H]^+$ To a stirred solution of methyl 4-((2-azaspiro[4.5]decan-2-yl)methyl)-3-fluorobenzoate (E, 110 mg, 0.3604 mmol, 1.0 equiv.) in methanol (1 mL) were added $NH_2OH$ (50% aq.) (0.4 mL, 7.2 mmol, 20.0 equiv) and KOH (40 mg, 0.72 mmol, 2.0 equiv) at 0° C. The reaction was stirred at 0° C. for 10 min then quenched with a saturated solution of $NaHCO_3$ (2 mL). A white compound was precipitated, filtered and washed with n-hexane to obtain the title compound (75) as an off-white solid (55 mg, 0.1795 mmol, 50%). $^1$H NMR (400 MHz, DMSO-d6) δ 11.17 (s, 1H), 9.17 (s, 1H), 7.56 (d, J=7.8 Hz, 1H), 7.52-7.39 (m, 2H), 3.59 (s, 2H), 2.30 (s, 2H), 1.50 (t, J=6.8 Hz, 2H), 1.34 (d, J=13.5 Hz, 10H). MS (ESI): 306.38 $[M+H]^+$ The following compounds were prepared in a manner analogous to that used for preparing compound 75. Although compound pairs 237/238 are designated as the (S) and (R) enantiomers as each enantiomer was prepared and isolated, the absolute stereochemistry of each is unknown.

| Compound | Structure/Name | Characterization |
| --- | --- | --- |
| 237 | 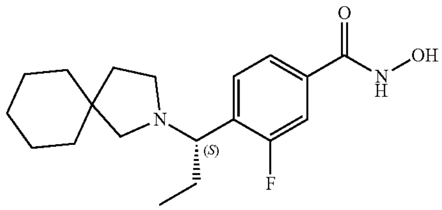 | LC-MS: m/z 335.1 [M + H]<br>$^{19}$F NMR(400 MHz, DMSO-d6): δ-119.55<br>Note: absolute stereochemistry is unknown |
| 238 | 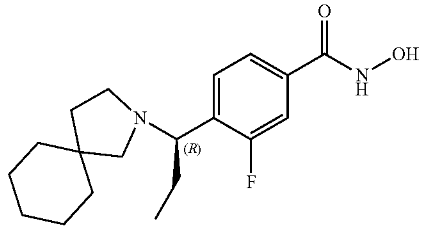 | LC-MS: m/z 335.1 [M + H]<br>$^{19}$F NMR{400 MHz, DMSO-d6): δ-119.54<br>Note: absolute stereochemistry is unknown |

Compounds of Formula (VI) were prepared following the synthetic schemes and procedures described in detail below.

(R)-3-fluoro-N-hydroxy-5-((2-methyl-2-azaspiro[5.5]undecan-3-y)methyl)benzamide (170) and (S)-3-fluoro-N-hydroxy-5-((2-methyl-2-azaspiro[5.5]undecan-3-yl)methyl)benzamide (171)

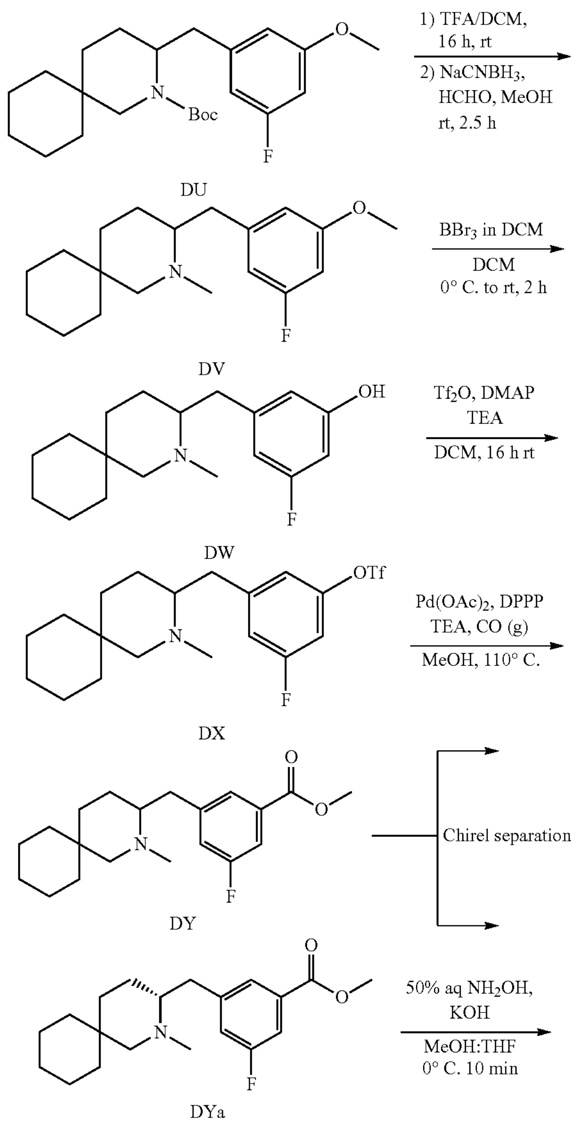

DU DV DW DX DY DYa

-continued

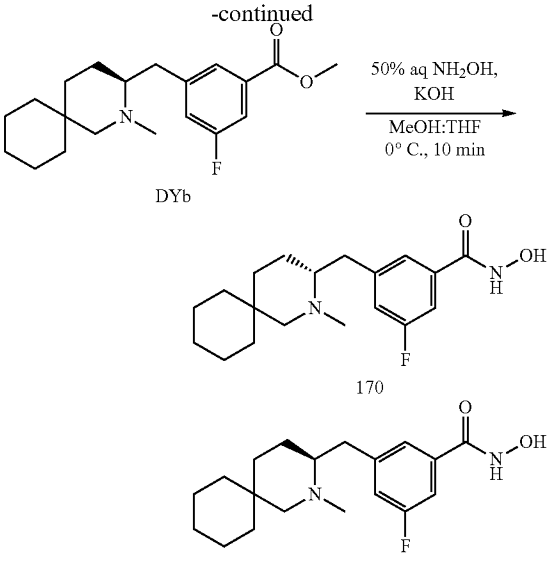

DYb 170 171

3-(3-fluoro-5-methoxybenzyl)-2-methyl-2-azaspiro[5.5]undecane (DV): To a stirred solution of tert-butyl 3-(3-fluoro-5-methoxybenzyl)-2-azaspiro[5.5]undecane-2-carboxylate (DU. 1.3 g, 3.325 mmol, 1.0 equiv.) in DCM (15 mL) was added TFA (1.4 ml, 13.299 mmol, 4.0 equiv.) at 0° C. The reaction mixture was stirred at 0° C. for 16 h and was monitored by TLC and LCMS. Upon completion of reaction, it was concentrated under reduced pressure to get crude mixture. It was dissolved in methanol (15 mL) and p-formaldehyde (1.4 g, 44.61 mmol, 10 equiv.) was added to it at 0 T. The reaction mixture was stirred at 0° C. for 30 min following which sodium cyanoborohydride (596 mg, 9.6218 mmol, 2.0 equiv.) was added. The reaction mixture was stirred at room temperature for 6 h. Upon completion of reaction concentrated under reduce pressure and to get crude mixture which was then purified by silica gel column chromatography using EtOAc:hexanes (1:9) to obtain 3-(3-fluoro-5-methoxybenzyl)-2-methyl-2-azaspiro[5.5]undecane (DV, (670 mg, 2.1967 mmol, 66%) as solid. MS (ESI): 306 [M+H]$^+$ Although compounds 170 and 171 are designated as the (S) and (R) enantiomers as each enantiomer was prepared and isolated, the absolute stereochemistry of each is unknown. Compounds 274-276 were prepared in a manner analogous to that used to prepare compounds 170 and 171. Although compounds 274 and 275 are designated as the (S) and (R) enantiomers as each enantiomer was prepared and isolated, the absolute stereochemistry of each is unknown.

| | | |
|---|---|---|
| 274 | 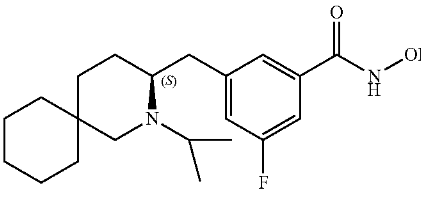<br>R)-3-fluoro-N-hydroxy-5-((2-isopropyl-2-azaspiro[5.5]undecan-3-yl)methyl)benzamide | $^1$H NMR (400 MHz, DMSO-$d_6$) δ 11.26 (s, 1H), 9.11 (s, 1H), 7.43 (s, 1H), 7.38-7.29 (m, 1H), 7.24 (d, J = 9.4 Hz, 1H), 3.26 (dd, J = 8.0, 4.9 Hz, 1H), 2.98 (d, J = 10.9 Hz, 1H), 2.59 (t, J = 11.2 Hz, 3H), 1.84 (d, J = 11.5 Hz, 1H), 1.25 (d, J = 75.0 Hz, 14H), 1.06 (d, J = 6.5 Hz, 3H), 0.89 (d, J = 6.4 Hz, 4H). MS (ESI): 363 [M + H]$^+$<br>Note: absolute stereochemistry is unknown |

-continued

| | | |
|---|---|---|
| 275 | 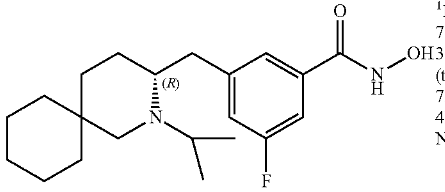 (R)-3-fluoro-N-hydroxy-5-((2-isopropyl-2-azaspiro[5.5]undecan-3-yl)methyl)benzamide | $^1$H NMR (400 MHz, DMSO-$d_6$) δ 11.26 (s, 1H), 9.11 (s, 1H), 7.43 (s, 1H), 7.38-7.29 (m, 1H), 7.24 (d, J = 9.4 Hz, 1H), 3.26 (dd, J = 8.0, 4.9 Hz, 1H), 2.98 (d, J = 10.9 Hz, 1H), 2.59 (t, J = 11.2 Hz, 3H), 1.84 (d, J = 11.5 Hz, 1H), 1.25 (d, J = 75.0 Hz, 14H), 1.06 (d, J = 6.5 Hz, 3H), 0.89 (d, J = 6.4 Hz, 4H). MS (ESI): 363 [M + H]$^+$ Note: absolute stereochemistry is unknown |
| 276 | 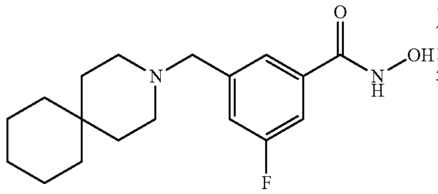 3-((3-azaspiro[5.5]undecan-3-yl)methyl)-5-fluoro-N-hydroxybenzamide | $^1$H NMR (400 MHz, DMSO-$d_6$) δ 11.28 (s, 1H), 9.05 (s, 1H), 7.53 (s, 1H), 7.38 (d, J = 9.5 Hz, 1H), 7.21 (d, J = 9.8 Hz, 1H), 3.48 (s, 2H), 2.31 (d, J = 5.8 Hz, 4H), 1.39 (dd, J = 12.0, 5.7 Hz, 10H), 1.29 (s, 4H). MS (ESI): 321 [M + H]$^+$ |

Biological Assay Data and Procedures

Caliper Endpoint Assay for HDAC Enzymatic Activity

HDAC reactions were assembled in 384 well plates (Greiner) in a total volume of 20 µL as follows: HDAC proteins (and their regulatory subunit, if applicable) were pre-diluted in the assay buffer comprising: 100 mM HEPES, pH 7.5, 0.1% BSA, 0.01% Triton X-100, 25 mM KCl and dispensed into a 384 well plate (10 µL per well). An example of enzyme concentrations used in each assay is listed in the table below.

| Assay | Expression Construct | Regulatory subunit | [Enzyme] nM | Substrate Peptide | Substrate Conc (µM) | Incubation Time (hr) |
|---|---|---|---|---|---|---|
| HDAC6 | Full length Human HDAC6 with C-terminal FLAG-tag, expressed in baculovirus expression system. | None | 60 | FAM-RHKK(Ac)-NH2 | 1 | 5 |
| HDAC8 | Full length Human HDAC8 with N-terminal HIS-tag, expressed in baculovirus expression system. | None | 5 | FAM-RHKK(TFAc)-NH2 | 1 | 3 |

Test compounds were serially pre-diluted in 100% DMSO using 3-fold dilution steps and added to the protein samples by acoustic dispensing (Labcyte Echo). Concentration of DMSO was equalized to 1% in all samples. Final compound concentration in assays typically ranged from 100 µM to 0.00056 µM for a 12-point concentration-response format. Reference compounds such as TSA (trichostatin A) and MS-275, were tested in an identical manner.

Control samples (0%-inhibition in the absence of inhibitor, DMSO only) and 100%-inhibition (in the absence of enzyme) were assembled in replicates of four (for each caliper sipper) and used to calculate the %-inhibition in the presence of compounds. At this step compounds were pre-incubated with enzyme for 30 minutes at room temperature (20-23° C.). The reactions were initiated by addition of 10 µL of the FAM-labeled substrate peptide (see table above) pre-diluted in the same assay buffer. Final concentration of substrate peptide was 1 µM. The reactions were allowed to proceed at room temperature (20-23° C.). Typical incubation times for each HDAC, based on pre-determined enzyme progress curves, vary and are listed in table above.

Following incubation, the reactions were quenched by addition of 50 µL of termination buffer (100 mM HEPES, pH7.5, 0.01% Triton X-100, 0.05% SDS). Terminated plates were analyzed on a microfluidic electrophoresis instrument (Caliper LabChip® 3000, Caliper Life Sciences/Perkin Elmer) which enables electrophoretic separation of deacetylated product from acetylated substrate. A change in the relative intensity of the peptide substrate and product is the parameter measured. Activity in each test sample was determined as the product to sum ratio (PSR): P/(S+P), where P is the peak height of the product, and S is the peak height of the substrate. Percent inhibition ($P_{inh}$) is determined using the following equation: $P_{inh}$=($PSR_{0\%inh}$−$PSR_{compound}$)/($PSR_{0\%inh}$−$PSR_{100\%inh}$)*100, in which: $PSR_{compound}$ is the product/sum ratio in the presence of compound, $PSR_{0\%inh}$ is the product/sum ratio in the absence of compound and the $PSR_{100\%inh}$ is the product/sum ratio in the absence of the enzyme. To determine the $IC_{50}$ of compounds (50%-inhibition) the %-inh data ($P_{inh}$ versus compound concentration) were fitted by a 4 parameter sigmoid dose-response model using XLfit software (IDBS).

Exemplary compounds were evaluated for inhibitory activity of a panel of HDAC paralogs. The results in Table 1 demonstrate that compounds of the disclosure have potent activity against HDAC6, and many compounds selectively inhibit HDAC6 over the Class I HDAC paralog HDAC8. $IC_{50}$ ranges: A: 0.001-0.1 μM; B: >0.1-1 μM; C: >1-10 μM; D: >10-100 μM; E: >100 μM. Selectivity ranges (ratio of HDAC8 $IC_{50}$/HDAC6 $IC_{50}$): I: 0.1-1; II: >1-10; III: >10-100; IV: >100-1000; V: >1000

TABLE 1

In vitro enzymatic $IC_{50}$ values for exemplary compounds

| Compound | HDAC6 IC50: (μM) | HDAC8 IC50: (μM) | Selectivity (6 v 8) (fold) |
|---|---|---|---|
| 1 | A | D | IV |
| 2 | A | C | III |
| 3 | A | C | IV |
| 4 | A | D | IV |
| 7 | A | C | IV |
| 8 | B | D | IV |
| 9 | A | D | IV |
| 13 | B | D | IV |
| 14 | A | D | IV |
| 15 | A | D | IV |
| 16 | A | D | IV |
| 19 | A | C | IV |
| 20 | A | D | IV |
| 21 | B | C | III |
| 24 | A | C | IV |
| 25 | A | D | IV |
| 26 | A | C | III |
| 27 | A | D | IV |
| 28 | A | C | IV |
| 30 | A | C | IV |
| 31 | A | C | IV |
| 32 | A | C | IV |
| 33 | A | C | IV |
| 34 | A | D | V |
| 45 | A | B | IV |
| 46 | A | B | III |
| 47 | A | B | III |
| 48 | A | C | III |
| 49 | B | C | III |
| 50 | A | C | III |
| 51 | A | B | III |
| 52 | A | B | III |
| 53 | A | B | III |
| 54 | A | B | III |
| 56 | A | B | III |
| 57 | A | B | III |
| 58 | A | B | III |
| 59 | A | B | III |
| 60 | B | C | II |
| 61 | B | C | II |
| 62 | A | B | III |
| 63 | A | B | III |
| 64 | A | C | IV |
| 67 | A | C | III |
| 68 | A | C | III |
| 69 | A | C | III |
| 70 | A | C | III |
| 71 | A | C | III |
| 72 | A | B | III |
| 73 | A | C | III |
| 74 | B | C | III |
| 75 | A | C | III |
| 77 | A | C | III |
| 78 | C | B | I |
| 79 | A | C | IV |
| 80 | B | C | III |
| 89 | C | C | II |
| 90 | C | C | II |
| 93 | A | C | IV |
| 94 | B | C | III |
| 106 | B | C | III |
| 107 | A | D | IV |
| 108 | A | D | IV |
| 109 | A | D | IV |
| 110 | A | D | IV |
| 111 | A | D | IV |
| 112 | A | E | V |

TABLE 1-continued

In vitro enzymatic $IC_{50}$ values for exemplary compounds

| Compound | HDAC6 IC50: (μM) | HDAC8 IC50: (μM) | Selectivity (6 v 8) (fold) |
|---|---|---|---|
| 113 | A | C | III |
| 114 | A | B | III |
| 115 | B | C | III |
| 116 | A | B | III |
| 117 | A | B | II |
| 118 | A | C | IV |
| 119 | B | D | III |
| 120 | A | C | IV |
| 121 | B | D | III |
| 122 | B | C | III |
| 123 | B | C | III |
| 124 | A | C | IV |
| 125 | A | C | III |
| 126 | B | C | III |
| 127 | A | C | IV |
| 128 | B | C | III |
| 129 | D | E | V |
| 130 | D | E | V |
| 131 | B | C | III |
| 132 | A | C | IV |
| 133 | B | C | III |
| 134 | A | C | IV |
| 135 | B | C | III |
| 136 | A | C | IV |
| 137 | B | D | IV |
| 138 | B | D | III |
| 139 | A | C | III |
| 140 | C | D | II |
| 143 | B | C | III |
| 144 | B | D | III |
| 145 | A | D | IV |
| 146 | B | D | III |
| 147 | A | C | III |
| 148 | C | C | II |
| 149 | B | C | II |
| 151 | A | C | III |
| 152 | A | C | IV |
| 153 | B | C | III |
| 154 | B | C | III |
| 155 | A | B | II |
| 156 | B | C | II |
| 157 | A | C | IV |
| 158 | A | C | III |
| 159 | B | C | III |
| 160 | B | B | II |
| 161 | B | C | II |
| 162 | B | C | II |
| 164 | C | C | II |
| 165 | B | C | III |
| 166 | B | C | III |
| 167 | A | C | III |
| 168 | B | C | III |
| 169 | A | C | III |
| 170 | A | C | III |
| 171 | A | C | III |
| 172 | A | C | III |
| 173 | A | C | III |
| 174 | A | D | IV |
| 175 | A | D | IV |
| 176 | A | D | V |
| 177 | A | D | IV |
| 178 | A | E | V |
| 179 | A | E | V |
| 182 | A | D | IV |
| 183 | A | E | V |
| 184 | A | C | IV |
| 185 | A | D | IV |
| 188 | A | D | IV |
| 189 | A | D | IV |
| 190 | A | C | IV |
| 191 | A | D | IV |
| 192 | A | D | V |
| 193 | A | D | V |
| 194 | A | D | V |

TABLE 1-continued

In vitro enzymatic $IC_{50}$ values for exemplary compounds

| Compound | HDAC6 IC50: (μM) | HDAC8 IC50: (μM) | Selectivity (6 v 8) (fold) |
|---|---|---|---|
| 195 | A | D | IV |
| 197 | A | D | IV |
| 198 | A | D | IV |
| 199 | A | D | IV |
| 607 | A | D | IV |
| 201 | A | D | V |
| 213 | A | B | III |
| 214 | A | C | III |
| 215 | A | B | II |
| 216 | A | E | V |
| 217 | A | D | IV |
| 228 | A | C | III |
| 229 | B | C | III |
| 230 | A | C | III |
| 231 | A | C | IV |
| 232 | B | D | IV |
| 233 | A | D | IV |
| 237 | B | C | II |
| 238 | B | C | III |
| 274 | D | C | I |
| 275 | C | C | I |
| 276 | D | C | I |
| 289 | A | C | IV |
| 290 | A | C | IV |
| 291 | A | C | IV |
| 292 | A | D | IV |
| 299 | A | D | IV |
| 300 | A | C | IV |
| 301 | A | C | IV |
| 302 | A | C | IV |
| 303 | A | C | III |
| 304 | A | C | IV |
| 314 | A | C | IV |
| 315 | A | D | IV |
| 316 | A | D | V |
| 317 | A | D | IV |
| 318 | A | D | V |
| 319 | A | C | IV |
| 320 | A | D | IV |
| 329 | A | C | III |
| 330 | A | D | IV |
| 331 | A | D | IV |
| 332 | B | C | III |
| 339 | A | D | IV |
| 340 | A | D | V |
| 341 | A | D | IV |
| 342 | A | C | IV |
| 343 | A | D | IV |
| 344 | A | D | IV |
| 345 | A | C | IV |
| 346 | A | C | IV |
| 348 | A | D | IV |
| 349 | A | D | IV |
| 352 | A | E | V |
| 353 | A | D | IV |
| 355 | A | D | V |
| 357 | A | C | IV |
| 358 | A | C | IV |
| 359 | B | C | III |
| 360 | A | D | IV |
| 362 | B | D | III |
| 363 | A | D | IV |
| 364 | A | D | IV |
| 365 | A | D | IV |
| 383 | A | D | V |
| 384 | A | D | V |
| 387 | A | D | IV |
| 388 | A | D | IV |
| 389 | A | E | V |
| 390 | B | D | III |
| 391 | A | D | IV |
| 402 | A | C | IV |
| 403 | A | D | V |
| 404 | A | D | IV |

TABLE 1-continued

In vitro enzymatic $IC_{50}$ values for exemplary compounds

| Compound | HDAC6 IC50: (μM) | HDAC8 IC50: (μM) | Selectivity (6 v 8) (fold) |
|---|---|---|---|
| 405 | A | E | V |
| 416 | A | D | IV |
| 417 | A | D | IV |
| 418 | A | C | IV |
| 419 | A | D | IV |
| 425 | A | D | V |
| 426 | A | E | V |
| 427 | A | D | V |
| 429 | A | D | IV |
| 430 | A | C | IV |
| 435 | A | C | IV |
| 436 | A | C | IV |
| 437 | A | D | IV |
| 438 | A | C | IV |
| 439 | A | D | IV |
| 440 | A | C | IV |
| 441 | A | C | IV |
| 442 | A | D | IV |
| 443 | A | D | IV |
| 444 | A | D | IV |
| 445 | A | D | IV |
| 446 | A | D | V |
| 449 | C | D | III |
| 451 | A | C | IV |
| 452 | B | D | III |
| 453 | A | D | IV |
| 454 | A | D | IV |
| 461 | A | C | V |
| 463 | A | D | IV |
| 464 | A | D | V |
| 465 | A | D | V |
| 466 | A | D | V |
| 467 | A | D | IV |
| 468 | A | D | V |
| 469 | A | C | IV |
| 470 | A | D | IV |
| 471 | A | D | IV |
| 472 | A | C | IV |
| 474 | A | C | IV |
| 475 | A | D | IV |
| 482 | A | C | IV |
| 483 | A | C | IV |
| 484 | A | C | IV |
| 486 | A | D | IV |
| 487 | A | C | IV |
| 490 | A | C | IV |
| 491 | A | D | IV |
| 493 | A | D | IV |
| 494 | A | C | III |
| 504 | B | D | IV |
| 505 | A | D | IV |
| 506 | E | D | V |
| 507 | B | C | III |
| 508 | A | C | III |
| 509 | A | C | III |
| 510 | A | C | IV |
| 517 | A | C | III |
| 518 | A | C | IV |
| 521 | A | B | III |
| 522 | A | B | III |
| 523 | A | D | IV |
| 524 | A | C | III |
| 525 | A | C | III |
| 527 | A | C | III |
| 528 | A | C | III |
| 529 | A | D | IV |
| 530 | B | D | III |
| 531 | A | E | V |
| 534 | B | D | IV |
| 535 | A | C | IV |
| 549 | A | D | IV |
| 552 | A | D | IV |
| 553 | A | D | IV |
| 554 | A | C | IV |

TABLE 1-continued

In vitro enzymatic $IC_{50}$ values for exemplary compounds

| Compound | HDAC6 IC50: (μM) | HDAC8 IC50: (μM) | Selectivity (6 v 8) (fold) |
|---|---|---|---|
| 555 | E | E | V |
| 570 | A | D | V |
| 571 | B | C | III |
| 572 | A | C | III |
| 573 | A | C | IV |
| 576 | A | C | IV |
| 580 | B | D | III |
| 581 | B | D | III |
| 582 | B | D | III |
| 583 | B | D | III |
| 584 | B | D | IV |
| 585 | B | C | III |
| 590 | B | D | III |
| 591 | A | D | IV |
| 592 | B | D | IV |
| 593 | B | D | IV |
| 594 | A | E | V |
| 595 | B | D | IV |
| 596 | A | D | IV |
| 597 | B | D | IV |
| 598 | B | D | IV |
| 599 | B | D | IV |
| 600 | A | C | IV |
| 601 | A | D | IV |
| 602 | B | D | III |
| 603 | B | D | IV |
| 607 | A | D | IV |
| AAA | E | D | V |
| BBB | E | D | V |
| TSA | A | B | IV |

Ames Screening of Exemplary Compounds for Mutagenicity in Bacteria

Figure 1A:
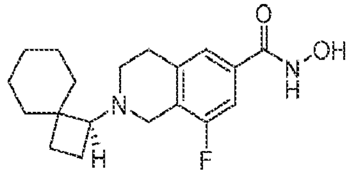
Figure 1A:
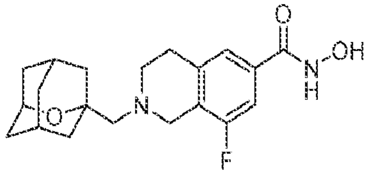
Figure 1A:
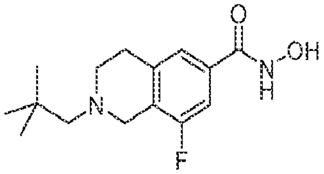
Figure 1A:
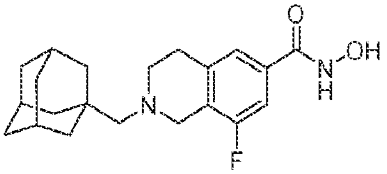
Figure 1A:
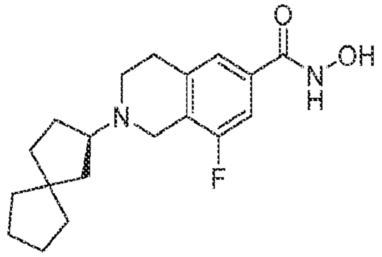
Figure 1A:
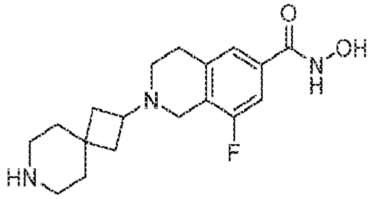
Figure 1A:
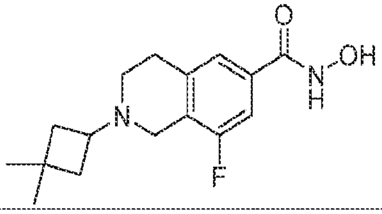
Figure 1A:
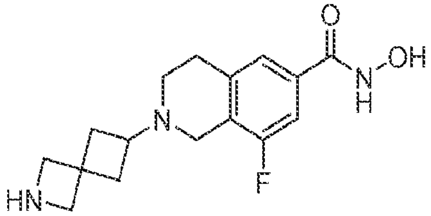
Figure 1A:
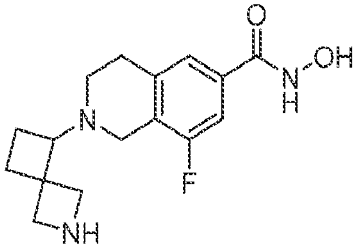
Figure 1A:
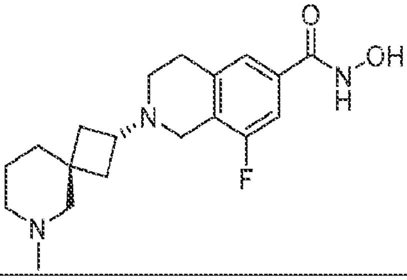
Figure 1A:
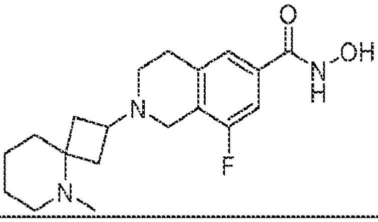
Figure 1A:
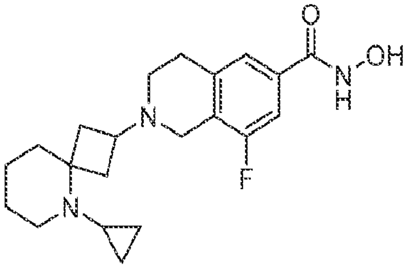
Figure 1A:
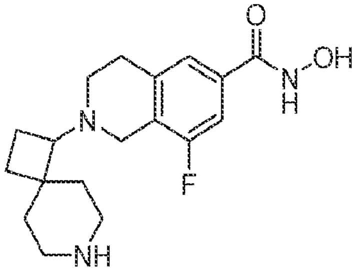
Figure 1A:
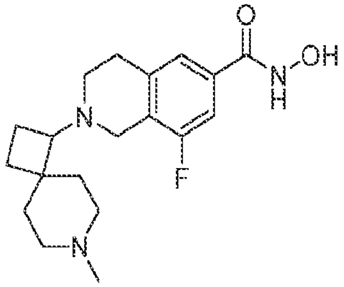
Figure 1A:
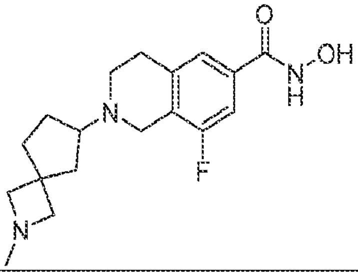
Figure 1A:
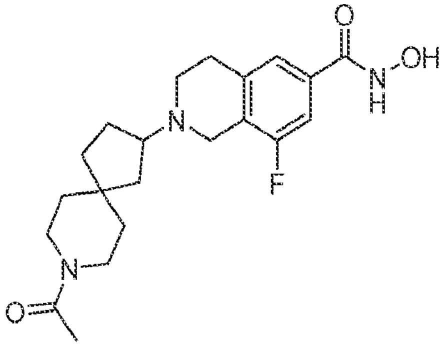
Figure 1A:
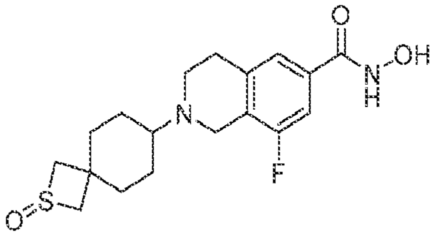
Figure 1A:
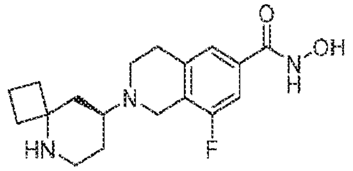
Figure 1A:
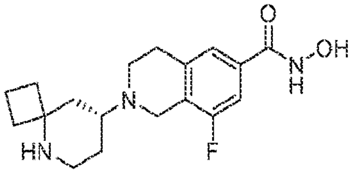
Figure 1A:
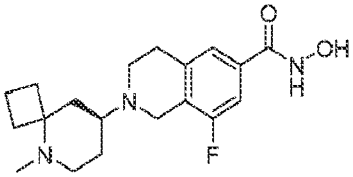
Figure 1A:
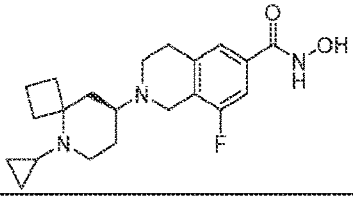
Figure 1A:
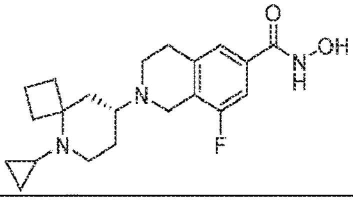
Figure 1A:
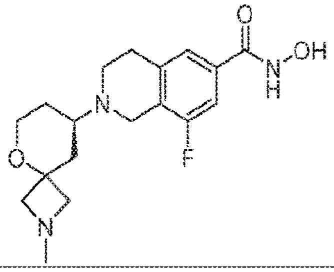
Figure 1A:
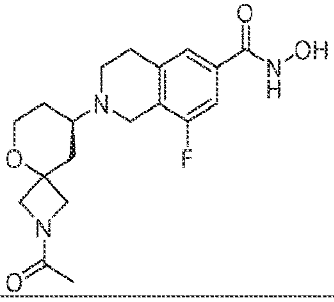
Figure 1A:
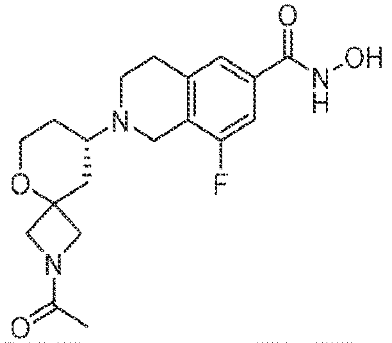
Figure 1A:
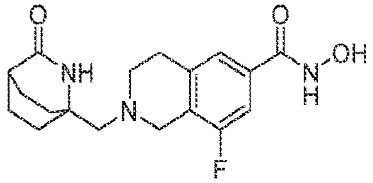
Figure 1A:
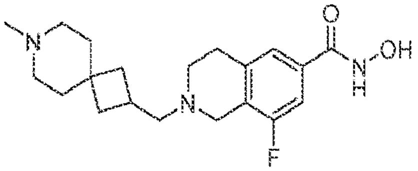
Figure 1A:
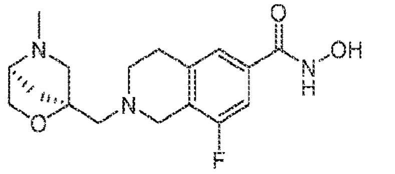
Figure 1A:
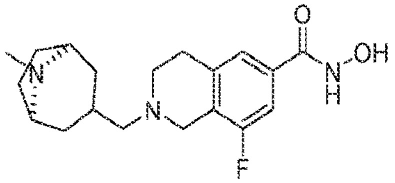
Figure 1A:
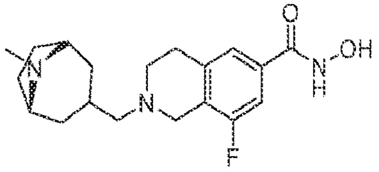
Figure 1A:
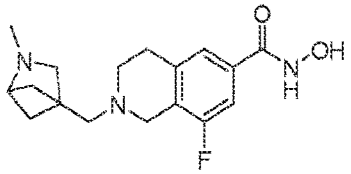
Figure 1B:
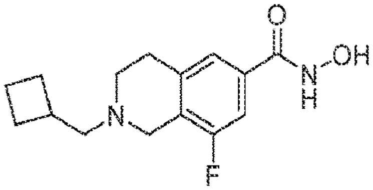
FIG. 1B is a chart of exemplary compounds of Formula (I) assayed as non-negative using the microplate Ames fluctuation assay (A), the microAmes protocol (B), or the standard Ames reverse mutation assay (C).
Figure 1B:
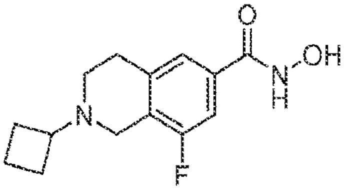
Figure 1B:
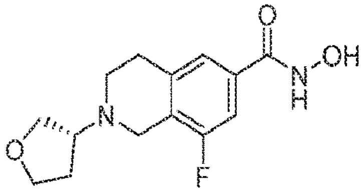
Figure 1B:
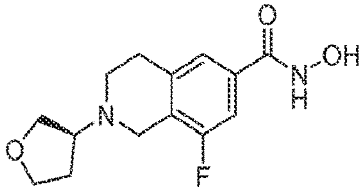
Figure 1B:
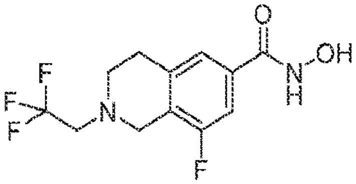
Figure 1B:
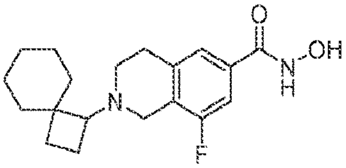
Figure 1B:
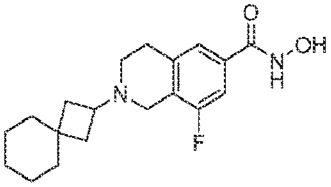
Figure 1B:
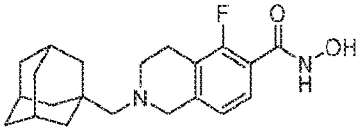
Figure 1B:
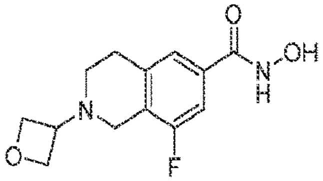
Figure 1B:
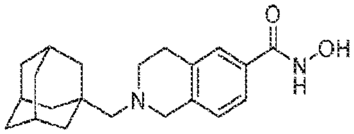
Figure 1B:
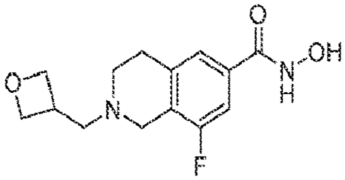
Figure 1B:
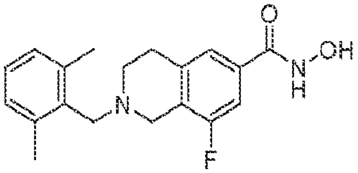
Figure 1B:
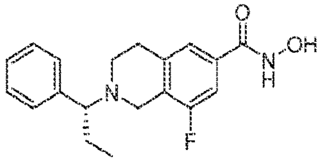
Figure 1B:
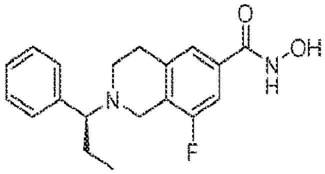
Figure 1B:
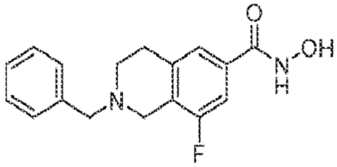
Figure 1B:
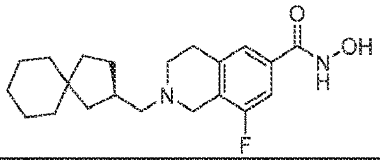
Figure 1B:
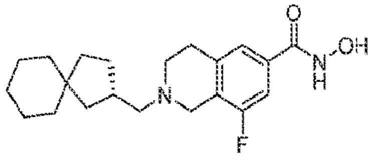
Figure 1B:
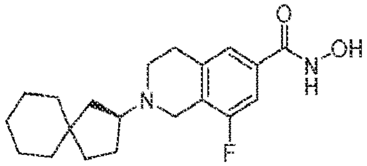
Figure 1B:
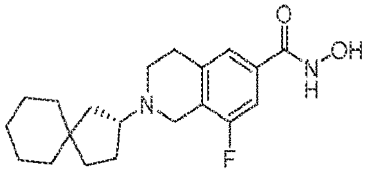
Figure 1B:
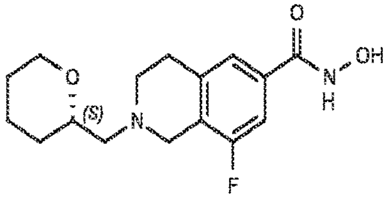
Figure 1B:
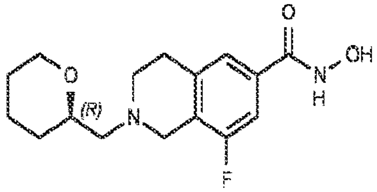
Figure 1B:
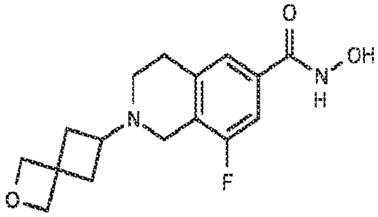
Figure 1B:
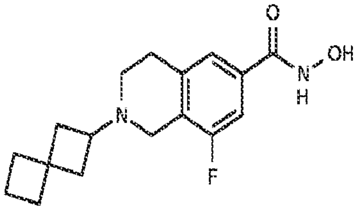
Figure 1B:
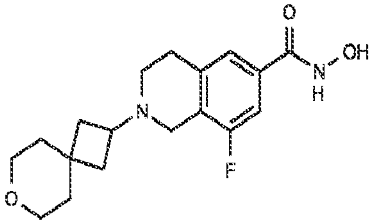
Figure 1B:
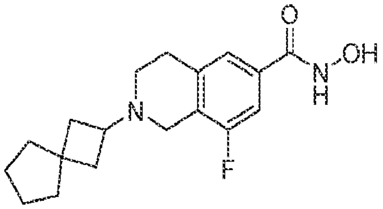
Figure 1B:
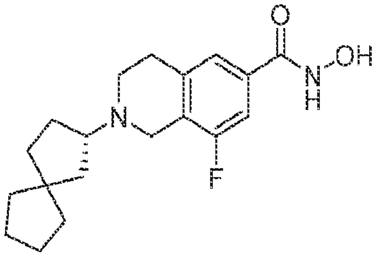
Figure 1B:
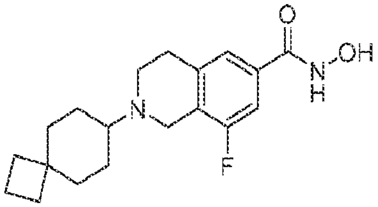
Figure 1B:
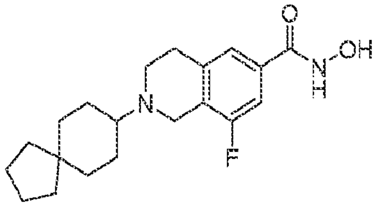
Figure 1B:
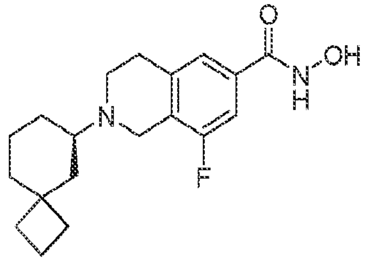
Figure 1B:
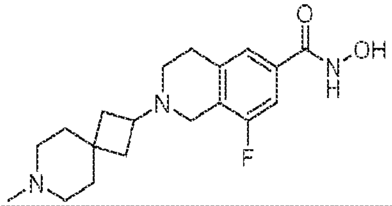
Figure 1B:
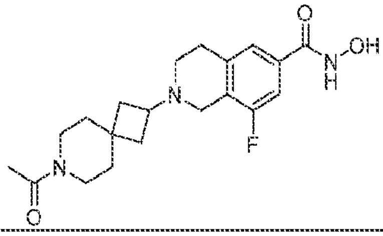
Figure 1B:
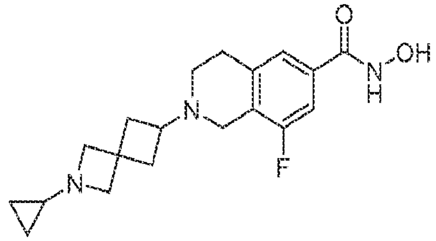
Figure 1B:
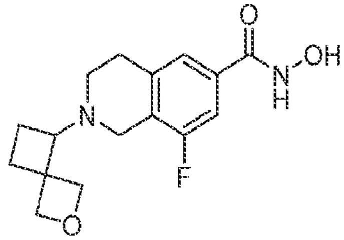
Figure 1B:
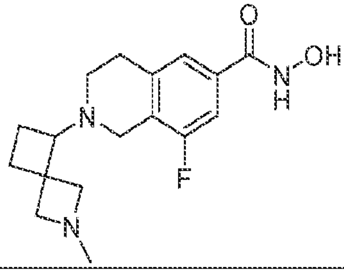
Figure 1B:
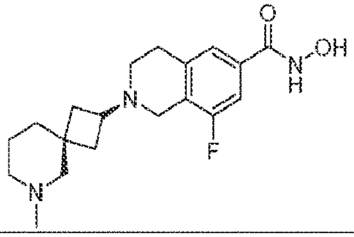
Figure 1B:
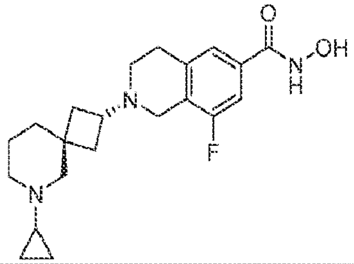
Figure 1B:
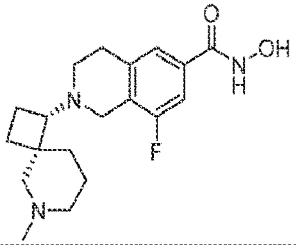
Figure 1B:
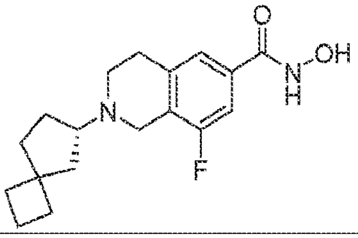
Figure 1B:
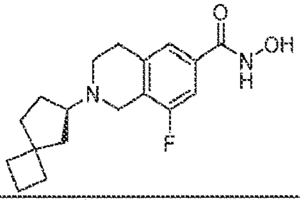
Figure 1B:
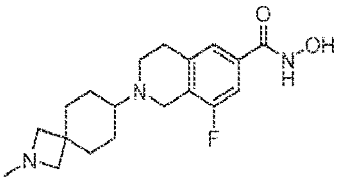
Figure 1B:
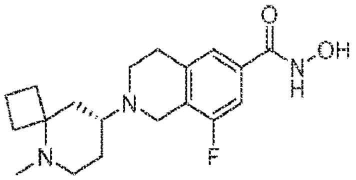
Figure 1B:
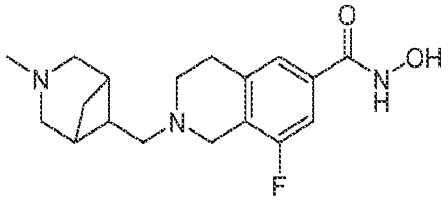
Figure 1B:
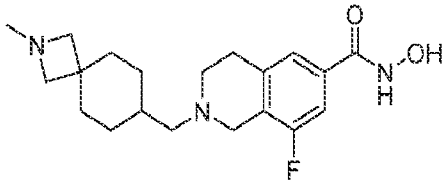
Figure 1B:
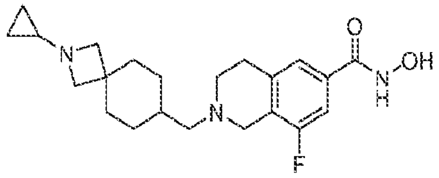
Figure 1B:
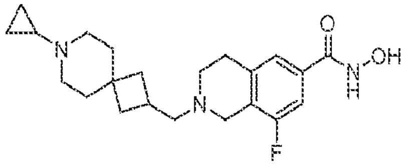
Figure 1B:
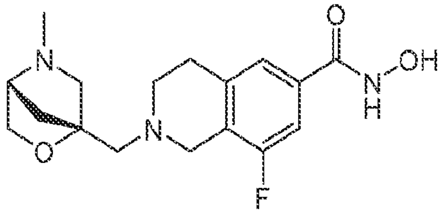
Figure 1B:
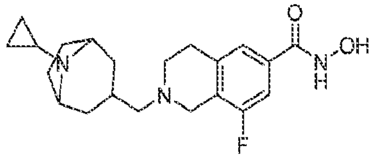
Figure 1B:
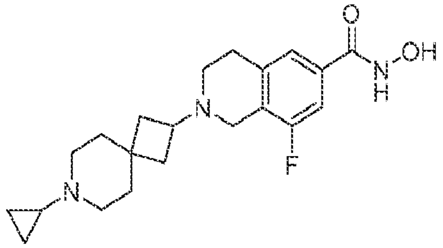
Figure 2A:
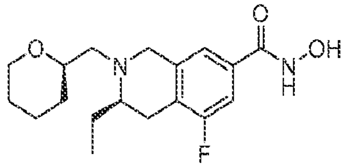
FIG. 2A is a chart of exemplary compounds of Formula (II) assayed as negative using the microplate Ames fluctuation assay (A) or the microAmes protocol (B).
Figure 2A:
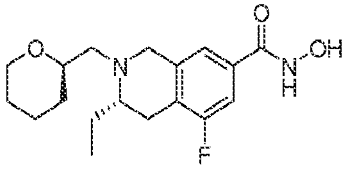
Figure 2A:
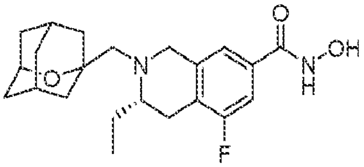
Figure 2A:
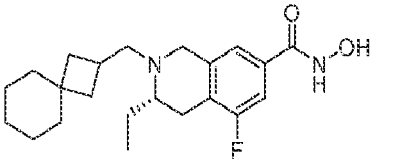
Figure 2A:
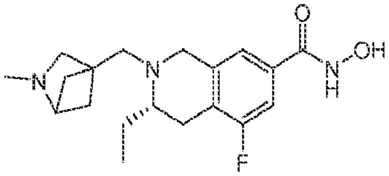
Figure 2A:
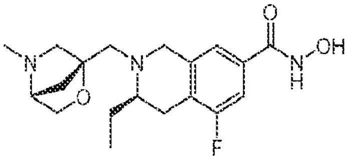
Figure 2A:
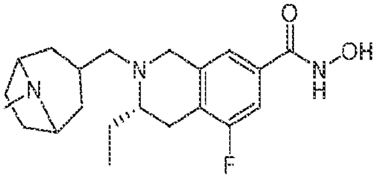
Figure 2A:
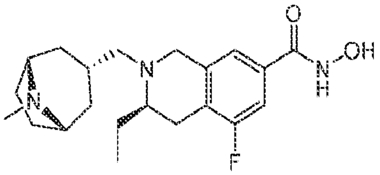
Figure 2A:
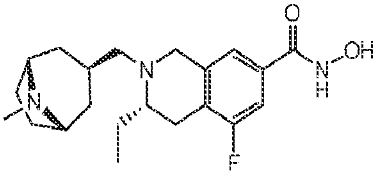
Figure 2A:
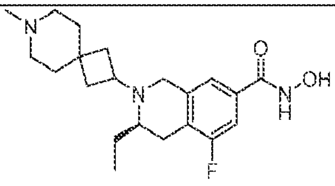
Figure 2B:
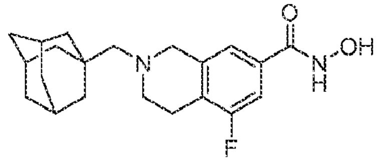
FIG. 2B is a chart of exemplary compounds of Formula (II) assayed as non-negative using the microplate Ames fluctuation assay (A) or the microAmes protocol (B).
Figure 2B:
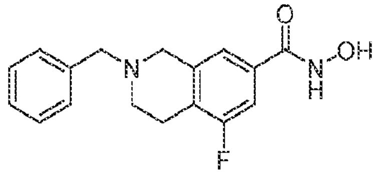
Figure 2B:
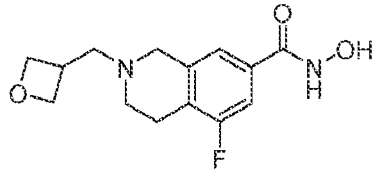
Figure 2B:
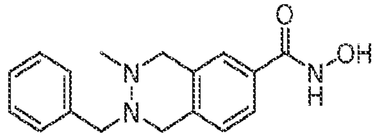
Figure 2B:
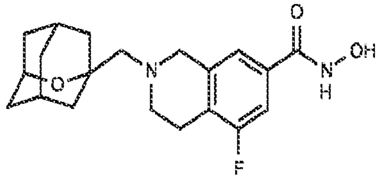
Figure 2B:
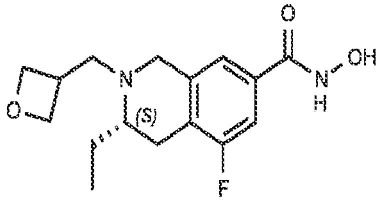
Figure 2B:
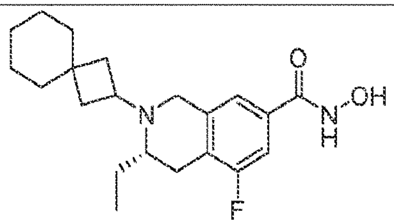
Figure 2B:
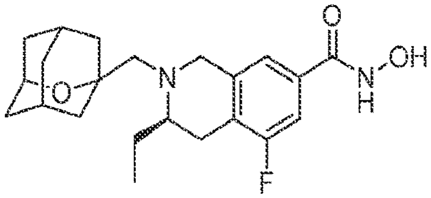
Figure 2B:
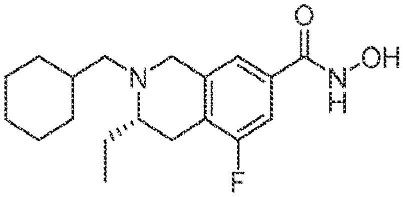
Figure 2B:
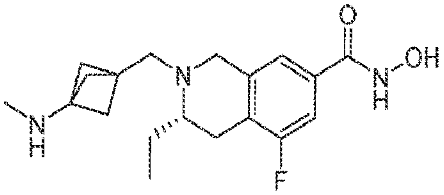
Figure 2B:
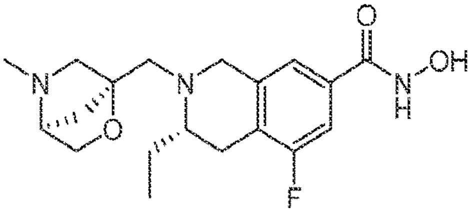
Figure 2B:
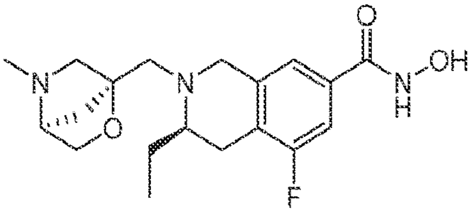
Figure 2B:
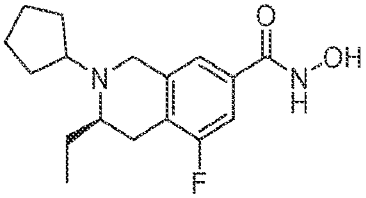
Figure 2B:
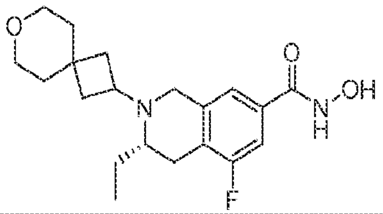
Figure 2B:
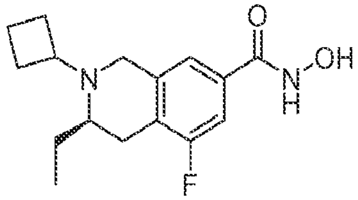
Figure 2B:
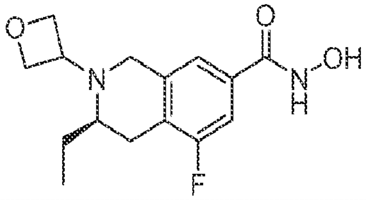
Figure 2B:
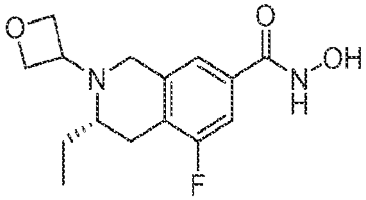
Figure 3A:
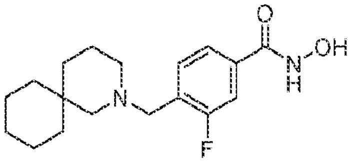
FIG. 3A is a chart of additional compounds assayed as negative using the microplate Ames fluctuation assay (A) or the microAmes protocol (B).
Figure 3A:
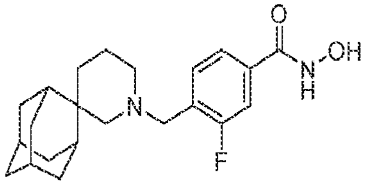
Figure 3B:
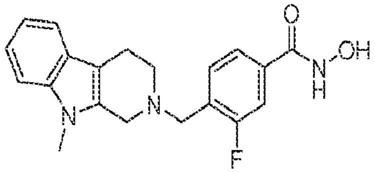
FIG. 3B is a chart of additional compounds assayed as non-negative using the microplate Ames fluctuation assay (A) or the microAmes protocol (B).
Figure 3B:
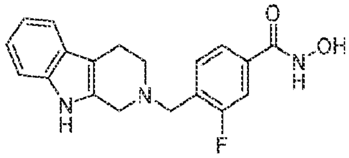
Figure 3B:
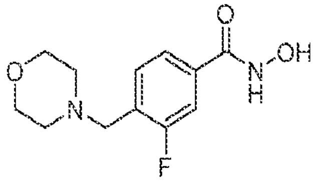
Figure 3B:
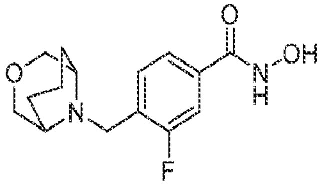
Figure 3B:
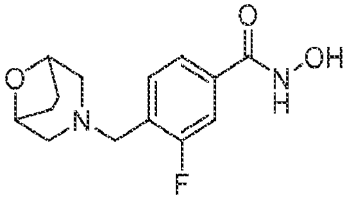
Figure 3B:
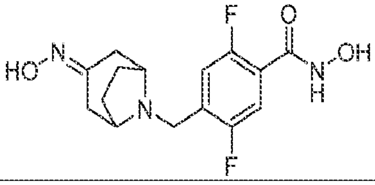
Figure 3B:
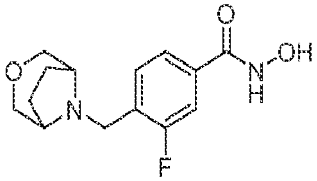
Figure 3B:
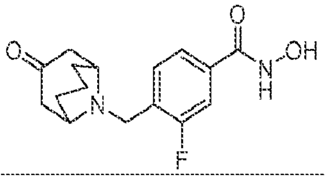
Figure 3B:
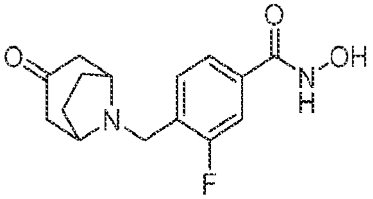
Figure 3B:
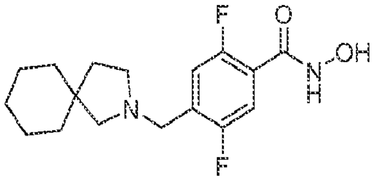
Figure 3B:
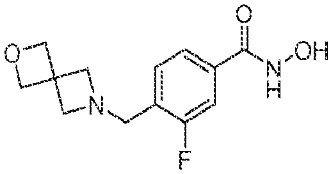
Figure 3B:
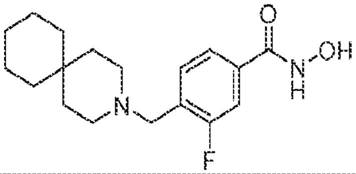
Figure 3B:
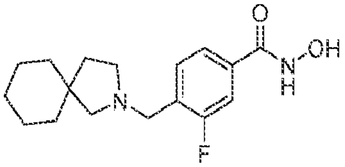
Figure 3B:
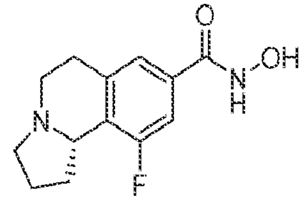
Figure 3B:
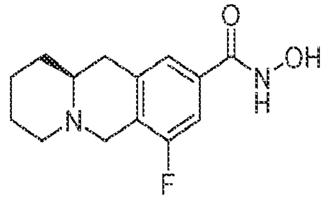
Figure 3B:
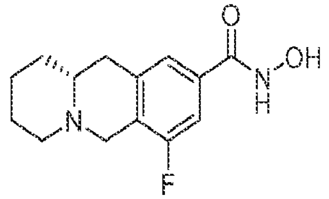
Figure 3B:
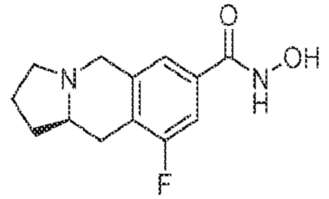
Figure 3B:
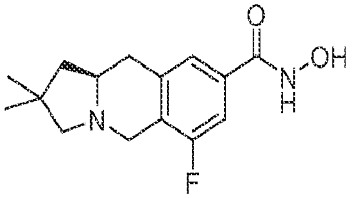
Figure 3B:
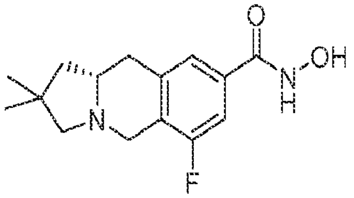
Figure 3B:
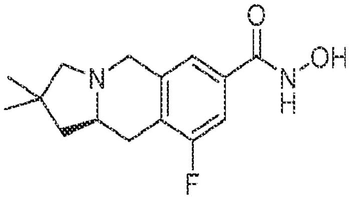
Figure 3B:
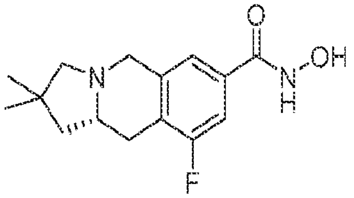
Figure 3B:
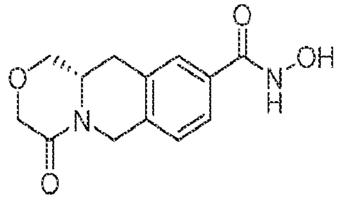
Figure 3B:
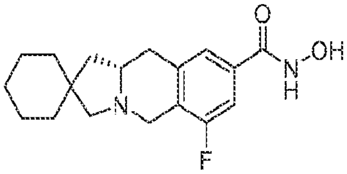
Figure 3B:
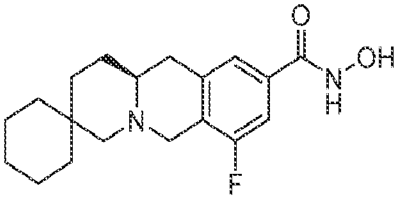
Figure 3B:
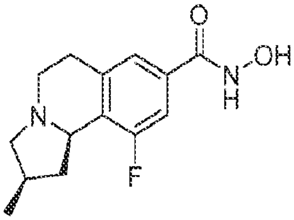
Figure 3B:
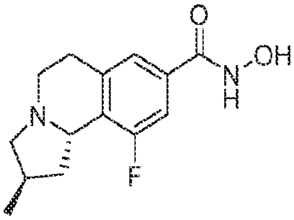
Figure 3B:
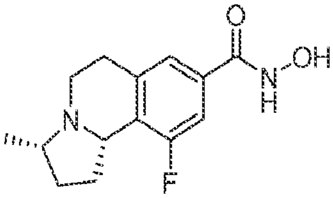
Figure 3B:
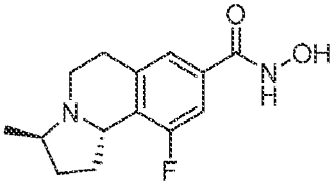
Figure 3B:
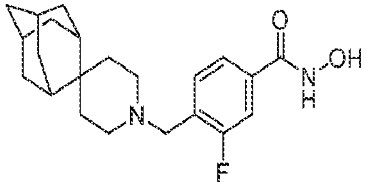
Figure 3B:
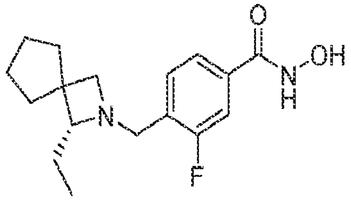
Figure 3B:
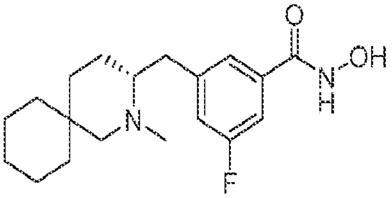
Figure 3B:
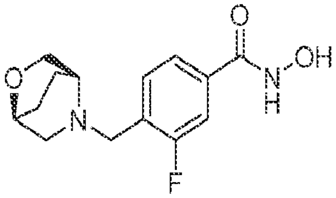
Figure 3B:
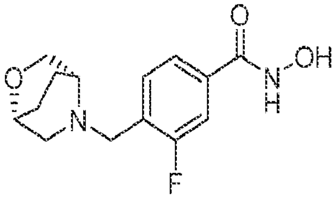
Figure 3B:
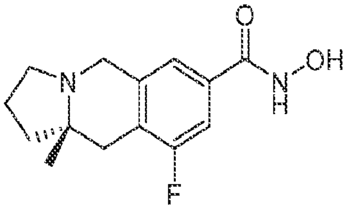
Figure 3B:
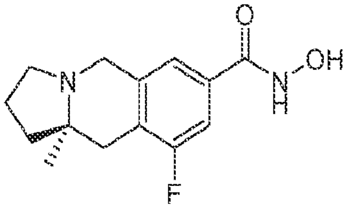
Figure 3B:
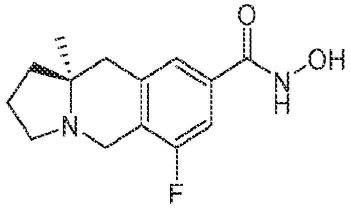
Figure 3B:
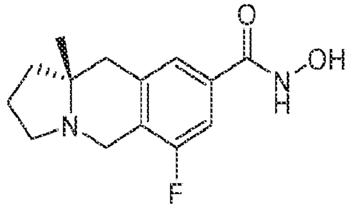
Figure 3B:
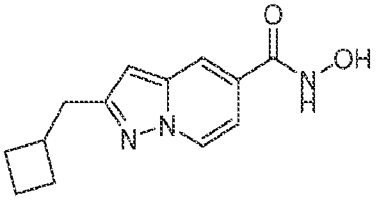
Figure 3B:
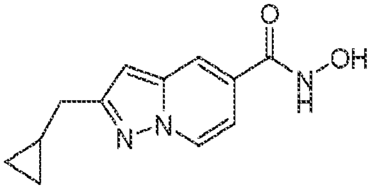
Figure 3B:
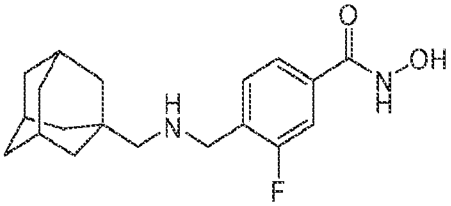
Figure 3B:
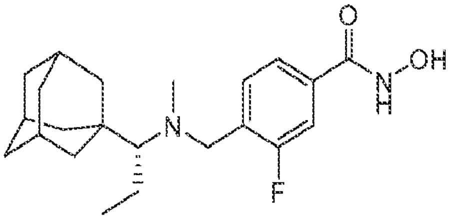
Figure 3B:
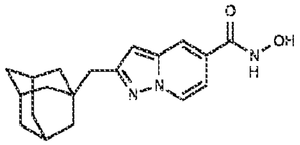
Figure 3B:
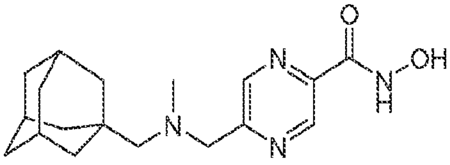
Figure 3B:
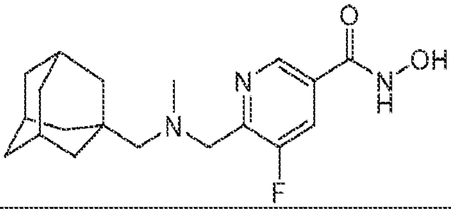
Figure 3B:
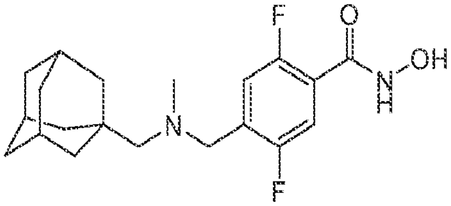
Figure 3B:
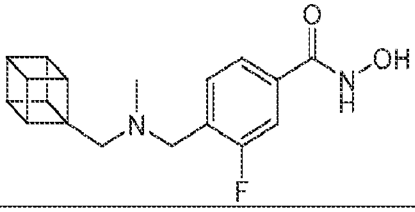
Figure 3B:
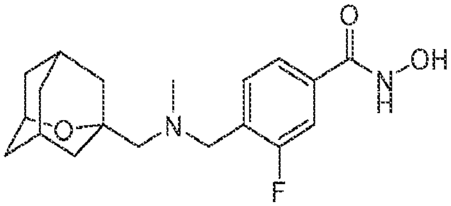
Figure 3B:
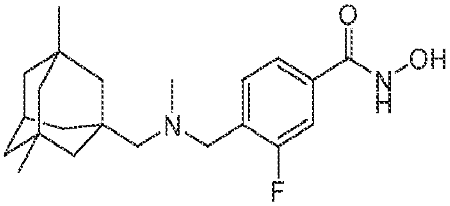
Figure 3B:
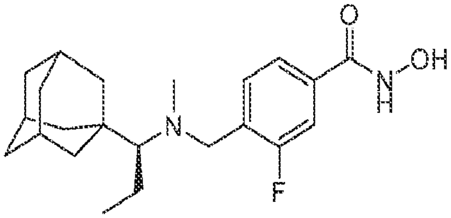

The bacterial reverse mutation test, commonly called the Ames test, is a standard in vitro bioassay typically performed on different strains of *Salmonella typhimurium/E. coli* and used for ascertaining the mutagenic potential of a sample. ICH S2A and ICH S2B Guidances (ICH=International Conference on Harmonisation of Technical Requirements for Registration of Pharmaceuticals for Human Use) recommend using this set of bacterial strains: *S. typhimurium* TA98, *S. typhimurium* TA100, *S. typhimurium* TA1535, *S. typhimurium* TA1537 or TA97 or TA97a, and *S. typhimurium* TA102 or *Escherichia coli* WP2 uvrA or *Escherichia coli* WP2 uvrA (pKM101). For this class of compounds (hydroxamates), we previously identified one strain as most sensitive (*S. typhimurium* TA1537 or TA97 or TA97a) so further evaluation of all compounds was performed with this strain, using one of three different protocols described below and designated in the Figures as A, B or C (see FIGS. 1A-3B).

A: Microplate Ames Fluctuation Assay

The Ames reverse mutation assay using the microplate fluctuation protocol was performed by Eurofins (St. Charles MO, USA). Compounds were assessed at four concentrations (5, 10, 50 and 100 μM) in *S. typhimurium* strain TA1537 (hisC3076) to detect frameshift mutations in the absence and presence of S9 (rat liver homogenate) metabolic activation. In 48 wells of a 384-well plate, overnight cultures of the tester stain (TA1537) are incubated in minimal medium (lacking histidine) containing the compound at each concentration, a vehicle control (DMSO) or a positive control with and without S9 at 37° C. for 96 hrs. The optical densities of each well at OD430 and OD570 are then recorded. Wells with an OD430/OD570 ratio of greater than 1.0 display bacteria growth due to the reversion of the histidine mutation and are recorded as positive counts. The positive counts between the treatment (in the presence of test compound) and the vehicle control (in the absence of test compound) are compared using the one-tailed Fisher's exact test. Compounds with p-values<0.05 are considered significantly different than the vehicle control and are reported as positive ('Pos'). A compound is reported as negative ('Neg') if the p-value (comparing positive counts in the treatment and vehicle control conditions) is >0.05 in at least three consecutive concentrations below the lowest bacteriotoxic concentration. Bacteriotoxicity was measured at eight concentrations (0.6-100 μM) in the absence of S9 metabolic activation in triplicate wells. A compound is considered bacteriotoxic ('Bac') if the OD650 reading is ≤60% that measured in the vehicle control wells. A compound is reported as 'Equivocal' if it only partially satisfies the above criteria or if there is a dose-related increase in the number of revertants that does not reach positivity threshold.

B: MicroAmes Assay

The Ames reverse mutation assay using the microAmes protocol was performed by BioReliance (Rockville MD, USA) and Charles River Labs (Skokie IL, USA). Compounds were assessed at ten concentrations (0.0075, 0.025, 0.075, 0.25, 0.75, 2.50, 7.50, 25.0, 75.0 and 250 μg/well) at BioReliance or six concentrations (0.25, 2.5, 12.5, 25, 75 and 250 μg/well) at Charles River Labs. Compounds were evaluated for mutagenic effect in *S. typhimurium* strain TA97a (hisD6610) to detect frameshift mutations in the absence and presence of S9 (rat liver homogenate) metabolic activation. Test compound, vehicle control (DMSO) or positive control were combined with a mixture of the tester strain (TA97a), S9 mix or buffer, and selective top agar (maintained at 45±2° C.) into duplicate wells of a 24-well plate. After the agar solidified in each well the plates are inverted and incubated for 48-72 hrs at 37° C. The revertant colony count per well is determined and compared to the vehicle control wells. A compound is reported as positive ('Pos') if the increase in the mean revertants is ≥2 times the number of revertants in the vehicle control wells. A dose is considered bacteriotoxic ('Bac') if it causes a >50% reduction in the mean number of revertants per well. A compound is reported as negative ('Neg') if the mean number of revertants is <2 times that of the vehicle control in at least three concentrations below the lowest bacteriotoxic concentration. A compound is reported as 'Equivocal' if it only partially satisfies the above criteria or if there is a dose-related increase in the number of revertants that does not reach positivity threshold.

C: Ames Assay

The standard Ames reverse mutation assay was performed by Aptuit (Verona, Italy). Compounds were assessed at seven concentrations (5, 15, 50, 150, 500, 1500 and 5000 pg/plate) in *S. typhimurium* bacteria strains (TA1535, TA1537, TA98 and TA100) and *E. coli* WP2 uvrA (pKM101) bacteria strain. Assays were performed in the presence and absence of S9 (rat liver homogenate) metabolic activation. A 0.1 ml aliquot of the appropriate bacterial suspension (at 1.2×109 cells/ml) of was mixed with minimal media-top agar maintained at 46±2° C., then test compound, vehicle control (DMSO) or a positive control, and either S9 mix or buffer were added and poured over a minimal agar plate (100 mm2). The plates are then incubated in the dark for 66 hrs at 37° C. A compound is reported as positive ('Pos') if any of these criteria are met: an increase in the mean revertants is ≥2 times that of the vehicle control for any one of the strains TA98, TA100 or WP2 uvrA (pKM101)

or ≥3 times that of the vehicle control for either TA1535 and/or TA1537. Plates were also inspected for bacteriotoxicity. A concentration is considered bacteriotoxic ('Bac') if the background is reduced >30% from the vehicle control. A compound is reported as negative ('Neg') if the mean number of revertants is <2 times that of the vehicle control for strains TA98, TA100 or WP2 uvrA (pKM101) or if the mean number of revertants is <3 times that of the vehicle control for strains TA1535 and/or TA1537. A compound is reported as 'Equivocal' if it only partially satisfies the above criteria or if there is a dose-related increased in the number of revertants that does not reach positivity threshold.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A compound of Formula (II):

(II)

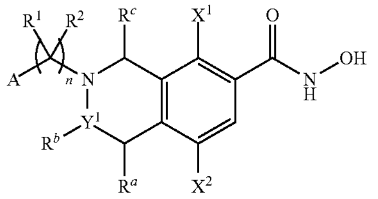

or a pharmaceutically acceptable salt thereof, wherein:

$X^1$ is hydrogen;

$X^2$ is fluoro;

$Y^1$ is $CR^x$;

A is a 3-6 membered monocyclic cycloalkyl or heterocyclyl, a 5-10 membered bridged cycloalkyl or bridged heterocyclyl, or a 7-10 membered spirocyclic ring system optionally comprising a heterocycle;

each $R^1$ is hydrogen;

each $R^2$ is hydrogen;

$R^x$ is hydrogen;

$R^a$ is hydrogen;

$R^b$ is unsubstituted $C_{1-4}$ alkyl;

$R^c$ is hydrogen; and n is 0 or 1.

2. The compound of claim 1, or a pharmaceutically acceptable salt thereof, wherein each A is a 4-6 membered monocyclic cycloalkyl or heterocyclyl, a 5-10 membered bridged cycloalkyl or bridged heterocyclyl, or a 7-10 membered spirocyclic ring system optionally comprising a heterocycle.

3. The compound of claim 2, or a pharmaceutically acceptable salt thereof, wherein A is a 4-6 membered monocyclic cycloalkyl or heterocyclyl.

4. The compound of claim 3, or a pharmaceutically acceptable salt thereof, wherein A is cyclopropyl, cyclobutyl,

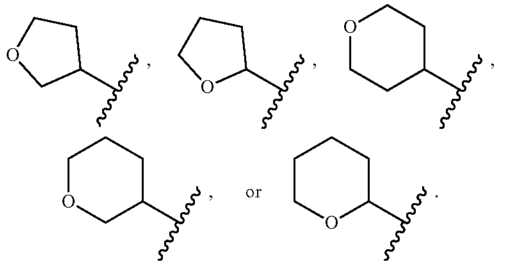

, , , or .

5. The compound of claim 2, or a pharmaceutically acceptable salt thereof, wherein A is a 5-10 membered bridged cycloalkyl or bridged heterocyclyl.

6. The compound of claim 5, or a pharmaceutically acceptable salt thereof, wherein A is

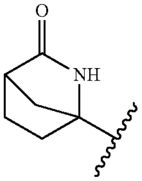,
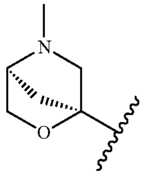,
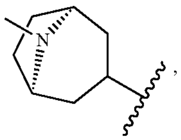,
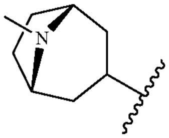
or
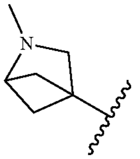.

7. The compound of claim 2, or a pharmaceutically acceptable salt thereof, wherein A is a 7-10 membered spirocyclic ring system optionally comprising a heterocycle.

8. The compound of claim 7, or a pharmaceutically acceptable salt thereof, wherein A is

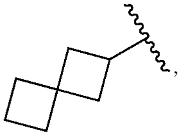,
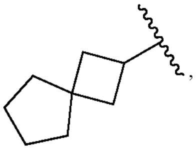,
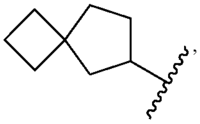,
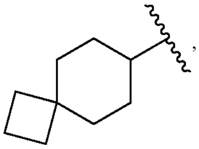,
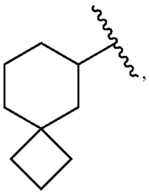,
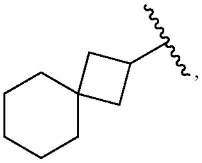,
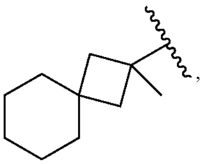,
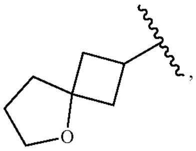,
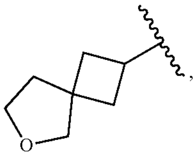,
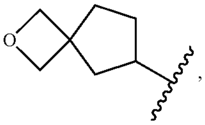, -continued

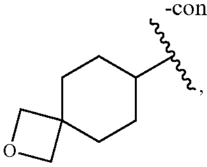,
or
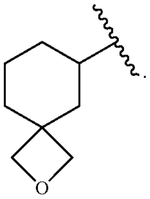.

9. A compound of Formula (II):

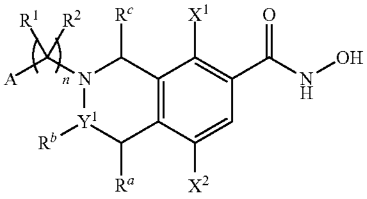

(II)

or a pharmaceutically acceptable salt thereof, wherein:

$X^1$ is hydrogen;

$X^2$ is fluoro;

$Y^1$ is $CR^x$;

A is a 4-6 membered monocyclic cycloalkyl or heterocyclyl, a 5-10 membered bridged cycloalkyl or bridged heterocyclyl, or a 7-10 membered spirocyclic ring system optionally comprising a heterocycle;

each $R^1$ is hydrogen;

each $R^2$ is hydrogen;

$R^x$ is hydrogen;

$R^a$ is hydrogen;

$R^b$ is unsubstituted ethyl;

$R^c$ is hydrogen; and n is 1.

10. The compound of claim 9, or a pharmaceutically acceptable salt thereof, wherein A is a 4-6 membered monocyclic cycloalkyl or heterocyclyl.

11. The compound of claim 10, or a pharmaceutically acceptable salt thereof, wherein A is cyclopropyl, cyclobutyl,

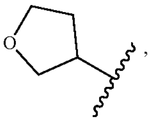,
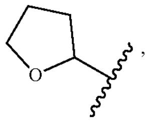,
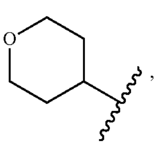,
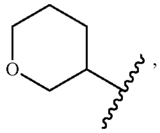,
or
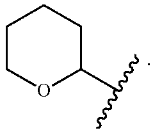.

12. The compound of claim 10, wherein the compound is

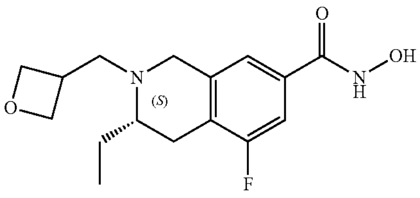
or

-continued

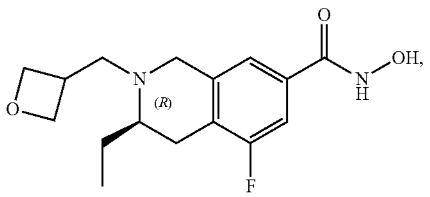

or a pharmaceutically acceptable salt thereof.

13. The compound of claim 10, wherein the compound is

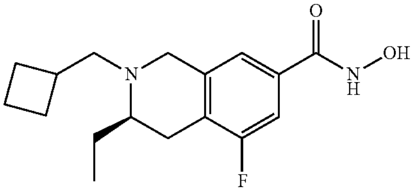

or

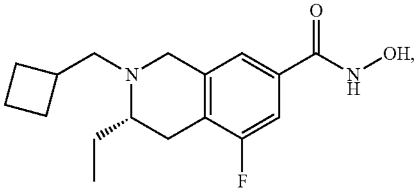

or a pharmaceutically acceptable salt thereof.

14. The compound of claim 10, wherein the compound is

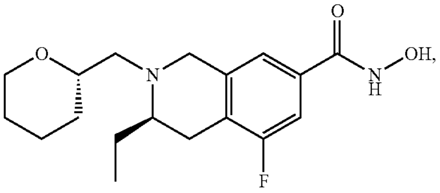

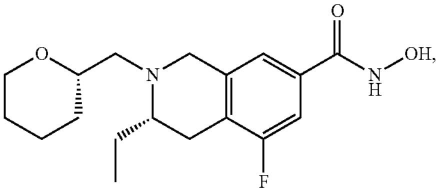

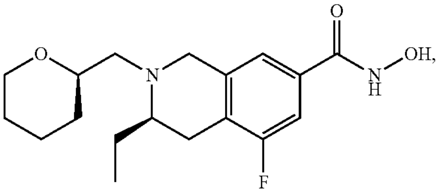

or

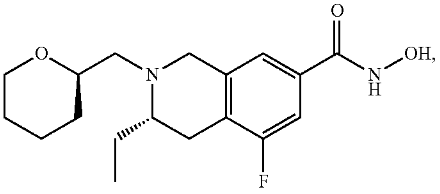

or a pharmaceutically acceptable salt thereof.

15. The compound of claim 9, or a pharmaceutically acceptable salt thereof, wherein A is a 5-10 membered bridged cycloalkyl or bridged heterocyclyl.

16. The compound of claim 15, or a pharmaceutically acceptable salt thereof, wherein A is

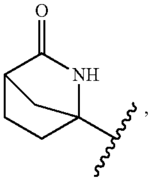

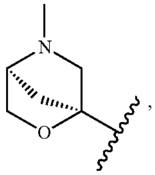

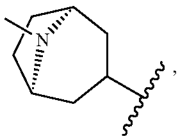

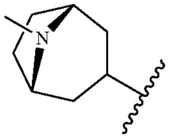

or

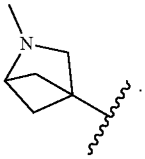

17. The compound of claim 9, or a pharmaceutically acceptable salt thereof, wherein A is a 7-10 membered spirocyclic ring system optionally comprising a heterocycle.

18. The compound of claim 17, or a pharmaceutically acceptable salt thereof, wherein A is

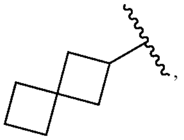

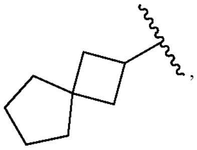

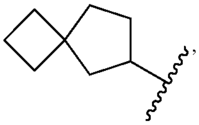

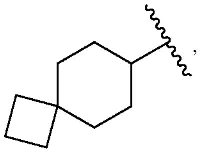

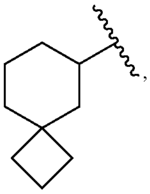

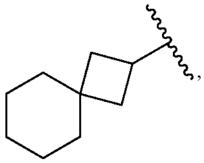

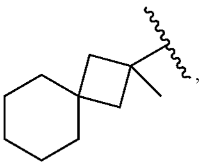

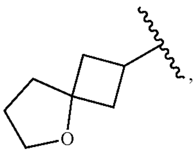

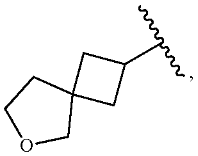

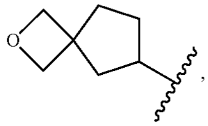

-continued

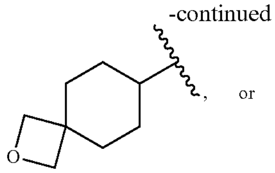

, or

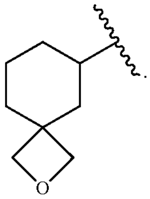

.

19. The compound of claim 17, wherein the compound is

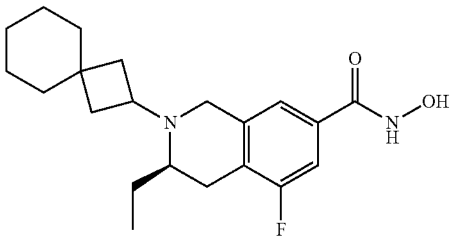

or

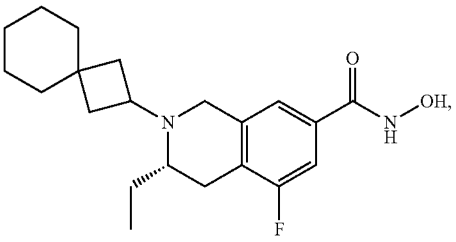

, or a pharmaceutically acceptable salt thereof.

20. A compound of Formula (II):

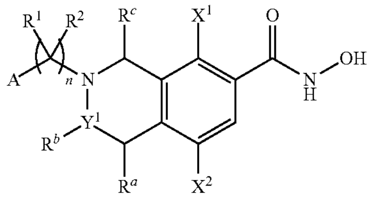

(II)

or a pharmaceutically acceptable salt thereof, wherein:

$X^1$ is hydrogen;

$X^2$ is fluoro;

$Y^1$ is $CR^x$;

A is a 4-6 membered monocyclic cycloalkyl or heterocyclyl comprising an oxygen heteroatom, or a 7-10 membered spirocyclic ring system optionally comprising a heterocycle comprising an oxygen heteroatom;

each $R^1$ is hydrogen;

each $R^2$ is hydrogen;

$R^x$ is hydrogen;

$R^a$ is hydrogen;

$R^b$ is unsubstituted ethyl;

$R^c$ is hydrogen; and n is 1.

* * * * *